US009694016B2

(12) United States Patent
Aversa et al.

(10) Patent No.: US 9,694,016 B2
(45) Date of Patent: Jul. 4, 2017

(54) BIARYL AMIDE COMPOUNDS AS KINASE INHIBITORS

(71) Applicant: Novartis AG, Basel (CH)

(72) Inventors: Robert John Aversa, Watertown, MA (US); Paul Andrew Barsanti, Pleasant Hill, CA (US); Matthew Burger, Belmont, MA (US); Michael Patrick Dillon, Boston, MA (US); Alan Dipesa, Bronx, NY (US); Cheng Hu, San Mateo, CA (US); Yan Lou, Pleasanton, CA (US); Gisele Nishiguchi, Arlington, MA (US); Yue Pan, Lexington, MA (US); Valery Polyakov, Moraga, CA (US); Savithri Ramurthy, Arlington, MA (US); Alice Rico, Castro Valley, CA (US); Lina Setti, Fremont, CA (US); Aaron Smith, Fremont, CA (US); Sharadha Subramanian, San Ramon, CA (US); Benjamin Taft, Oakland, CA (US); Huw Tanner, San Francisco, CA (US); Lifeng Wan, Union City, CA (US); Naeem Yusuff, Cambridge, MA (US)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 14/774,431

(22) PCT Filed: Mar. 13, 2014

(86) PCT No.: PCT/US2014/026107
§ 371 (c)(1),
(2) Date: Sep. 10, 2015

(87) PCT Pub. No.: WO2014/151616
PCT Pub. Date: Sep. 25, 2014

(65) Prior Publication Data
US 2016/0038504 A1 Feb. 11, 2016

Related U.S. Application Data

(60) Provisional application No. 61/783,558, filed on Mar. 14, 2013.

(51) Int. Cl.
C07D 413/14 (2006.01)
C07D 403/14 (2006.01)
(Continued)

(52) U.S. Cl.
CPC ...... A61K 31/5377 (2013.01); A61K 31/5375 (2013.01); A61K 31/541 (2013.01); A61K 45/06 (2013.01); C07D 213/74 (2013.01); C07D 213/75 (2013.01); C07D 213/81 (2013.01); C07D 213/82 (2013.01); C07D 213/84 (2013.01); C07D 233/88 (2013.01); C07D 237/20 (2013.01); C07D 237/22 (2013.01); C07D 239/42 (2013.01); C07D 239/47 (2013.01); C07D 239/48 (2013.01); C07D 241/20 (2013.01); C07D 263/58 (2013.01); C07D 277/42 (2013.01); C07D 401/04 (2013.01); C07D 401/12 (2013.01); C07D 401/14 (2013.01); C07D 403/04 (2013.01); C07D 403/12 (2013.01); C07D 405/04 (2013.01); C07D 405/12 (2013.01); C07D 405/14 (2013.01); C07D 409/14 (2013.01); C07D 413/04 (2013.01); C07D 413/12 (2013.01); C07D 413/14 (2013.01);
(Continued)

(58) Field of Classification Search
CPC .. C07D 413/14; C07D 403/12; C07D 403/14; C07D 401/04
See application file for complete search history.

(56) References Cited

U.S. PATENT DOCUMENTS 3,707,475 A 12/1972 Lombardino et al.
5,717,100 A 2/1998 Selnick et al.
(Continued)

FOREIGN PATENT DOCUMENTS

DE 2155558 A1 6/1972
DE 3029376 A1 3/1982
(Continued)

OTHER PUBLICATIONS

Al-Ali et al., Chemical interrogation of the neuronal kinome using a primary cell-based screening assay. ACS Chem Biol. May 17, 2013;8(5)1027-36.
Andreyev et al., Kirsten ras mutations in patients with colorectal cancer: the multicenter "Rascal" study. J Natl Cancer Inst. May 6, 1998;90(9):675-84.
Babchia et al., The PI3K/Akt and mTOR/P70S6K signaling pathways in human uveal melanoma cells: interaction with B-Raf/ERK. Invest Ophthalmol Vis Sci. Jan. 2010;51(1):421-9.
Banker, Modern Pharmaceutics. Marcel Dekker. New York. 1996. 3 pages.
(Continued)

Primary Examiner — Rebecca Anderson
(74) Attorney, Agent, or Firm — Scott W. Reid

(57) ABSTRACT

The present invention provides compounds of Formula (I) as described herein, and salts thereof, and therapeutic uses of these compounds for treatment of disorders associated with Raf kinase activity. The invention further provides pharmaceutical compositions comprising these compounds, and compositions comprising these compounds and a therapeutic co-agent.

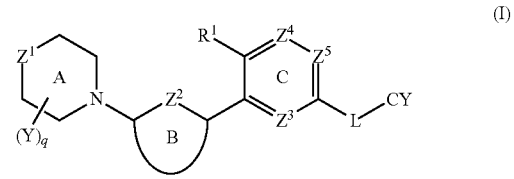

(I)

8 Claims, No Drawings

(51) Int. Cl.

| | |
|---|---|
| *C07D 403/12* | (2006.01) |
| *C07D 401/04* | (2006.01) |
| *A61K 31/5377* | (2006.01) |
| *C07D 413/04* | (2006.01) |
| *A61K 31/541* | (2006.01) |
| *A61K 45/06* | (2006.01) |
| *C07D 213/74* | (2006.01) |
| *C07D 237/20* | (2006.01) |
| *C07D 239/42* | (2006.01) |
| *C07D 239/47* | (2006.01) |
| *C07D 239/48* | (2006.01) |
| *C07D 277/42* | (2006.01) |
| *C07D 401/12* | (2006.01) |
| *C07D 403/04* | (2006.01) |
| *C07D 413/12* | (2006.01) |
| *C07D 417/12* | (2006.01) |
| *C07D 493/10* | (2006.01) |
| *C07D 401/14* | (2006.01) |
| *C07D 405/14* | (2006.01) |
| *C07D 213/75* | (2006.01) |
| *C07D 233/88* | (2006.01) |
| *C07D 405/04* | (2006.01) |
| *C07D 405/12* | (2006.01) |
| *C07D 241/20* | (2006.01) |
| *C07D 471/04* | (2006.01) |
| *C07D 487/04* | (2006.01) |
| *C07D 263/58* | (2006.01) |
| *C07D 491/107* | (2006.01) |
| *C07D 493/04* | (2006.01) |
| *C07D 495/04* | (2006.01) |
| *C07D 498/08* | (2006.01) |
| *C07D 513/04* | (2006.01) |
| *A61K 31/5375* | (2006.01) |
| *C07D 213/81* | (2006.01) |
| *C07D 213/82* | (2006.01) |
| *C07D 213/84* | (2006.01) |
| *C07D 237/22* | (2006.01) |
| *C07D 409/14* | (2006.01) |
| *C07D 491/048* | (2006.01) |

(52) U.S. Cl.
CPC ......... *C07D 417/12* (2013.01); *C07D 471/04* (2013.01); *C07D 487/04* (2013.01); *C07D 491/048* (2013.01); *C07D 491/107* (2013.01); *C07D 493/04* (2013.01); *C07D 493/10* (2013.01); *C07D 495/04* (2013.01); *C07D 498/08* (2013.01); *C07D 513/04* (2013.01)

(56) References Cited

U.S. PATENT DOCUMENTS

| | | | |
|---|---|---|---|
| 6,211,177 | B1 | 4/2001 | Sperl et al. |
| 6,248,771 | B1 | 6/2001 | Shenoy et al. |
| 6,268,391 | B1 | 7/2001 | Dickerson et al. |
| 6,358,932 | B1 | 3/2002 | Monia |
| 6,399,603 | B1 | 6/2002 | Jacobs et al. |
| 6,417,194 | B1 | 7/2002 | Fox et al. |
| 6,458,813 | B1 | 10/2002 | Mantlo et al. |
| 6,465,493 | B1 | 10/2002 | Burgess et al. |
| 6,608,053 | B2 | 8/2003 | Hayakawa et al. |
| 7,071,216 | B2 | 7/2006 | Renhowe et al. |
| 7,423,150 | B2 | 9/2008 | Costales et al. |
| 7,531,553 | B2 | 5/2009 | Di Pietro et al. |
| 8,129,394 | B2 | 3/2012 | Huang et al. |
| 8,242,260 | B2 | 8/2012 | Costales et al. |
| 8,299,108 | B2 | 10/2012 | Amiri et al. |
| 8,415,382 | B2 | 4/2013 | Costales et al. |
| 8,563,553 | B2 | 10/2013 | Costales et al. |
| 2001/0014679 | A1 | 8/2001 | Tang et al. |
| 2003/0166633 | A1 | 9/2003 | Gaster et al. |
| 2004/0053973 | A1 | 3/2004 | Ohkawa et al. |
| 2004/0063946 | A1 | 4/2004 | Ohkawa et al. |
| 2004/0087626 | A1 | 5/2004 | Renhowe et al. |
| 2004/0122237 | A1 | 6/2004 | Amiri et al. |
| 2005/0192287 | A1 | 9/2005 | Costales et al. |
| 2005/0282805 | A1 | 12/2005 | Hangeland et al. |
| 2009/0005359 | A1 | 1/2009 | Cossrow et al. |
| 2009/0298815 | A1 | 12/2009 | Adams et al. |
| 2013/0096149 | A1 | 4/2013 | Madera et al. |
| 2013/0210818 | A1 | 8/2013 | Huang et al. |
| 2013/0224195 | A1 | 8/2013 | Costales et al. |
| 2014/0011825 | A1 | 1/2014 | Costales et al. |
| 2014/0178360 | A1 | 6/2014 | Kuo et al. |
| 2014/0275003 | A1 | 9/2014 | Barsanti et al. |
| 2016/0075727 | A1 | 3/2016 | Burger et al. |

FOREIGN PATENT DOCUMENTS

| | | |
|---|---|---|
| EP | 0149884 B1 | 12/1992 |
| EP | 1232153 B1 | 11/2004 |
| EP | 1721905 A1 | 11/2006 |
| GB | 2306108 A | 4/1997 |
| JP | 02-188579 A | 7/1990 |
| JP | 03-157383 A | 7/1991 |
| JP | 2000-302680 A2 | 1/2000 |
| JP | 2007-246520 A | 9/2007 |
| WO | 9808845 A1 | 3/1998 |
| WO | 0042012 A1 | 7/2000 |
| WO | 0059506 A1 | 10/2000 |
| WO | 0062778 A1 | 10/2000 |
| WO | 0138324 A2 | 5/2001 |
| WO | 0152845 A1 | 7/2001 |
| WO | 0152846 A1 | 7/2001 |
| WO | 0162756 A1 | 8/2001 |
| WO | 0166539 A1 | 9/2001 |
| WO | 0166540 A1 | 9/2001 |
| WO | 0172737 A1 | 10/2001 |
| WO | 01/96308 A1 | 12/2001 |
| WO | 0239954 A2 | 5/2002 |
| WO | 0242273 A2 | 5/2002 |
| WO | 0244156 A2 | 6/2002 |
| WO | 02064136 A2 | 8/2002 |
| WO | 02076960 A1 | 10/2002 |
| WO | 02094808 A1 | 11/2002 |
| WO | 03047577 A2 | 6/2003 |
| WO | 03082272 A1 | 10/2003 |
| WO | 03087304 A2 | 10/2003 |
| WO | 2004002948 A1 | 1/2004 |
| WO | 2004026859 A1 | 4/2004 |
| WO | 2004026863 A1 | 4/2004 |
| WO | 2004085425 A1 | 10/2004 |
| WO | 2005034869 A2 | 4/2005 |
| WO | 2005047266 A1 | 5/2005 |
| WO | 2005103028 A1 | 11/2005 |
| WO | 2005105814 A1 | 11/2005 |
| WO | 2005116000 A1 | 12/2005 |
| WO | 2005123050 A2 | 12/2005 |
| WO | 2006005914 A1 | 1/2006 |
| WO | 2006005915 A1 | 1/2006 |
| WO | 2006005918 A1 | 1/2006 |
| WO | 2006026306 A1 | 3/2006 |
| WO | 2006038734 A1 | 4/2006 |
| WO | 2006044509 A2 | 4/2006 |
| WO | 2007118149 A2 | 10/2007 |
| WO | 2008071605 A2 | 6/2008 |
| WO | 2009001132 A1 | 12/2008 |
| WO | 2009003998 A1 | 1/2009 |
| WO | 2009006389 A2 | 1/2009 |
| WO | 2009007749 A2 | 1/2009 |
| WO | 2009012283 A1 | 1/2009 |
| WO | 2009014637 A2 | 1/2009 |
| WO | 2009030952 A2 | 3/2009 |
| WO | 2009032667 A1 | 3/2009 |
| WO | 2009047163 A1 | 4/2009 |
| WO | 2009106885 A1 | 9/2009 |
| WO | 2009115572 A2 | 9/2009 |
| WO | 2009137391 A2 | 11/2009 |

(56) References Cited

FOREIGN PATENT DOCUMENTS

| WO | 2009152356 A2 | 12/2009 |
|---|---|---|
| WO | 2010010154 A1 | 1/2010 |
| WO | 2010048149 A2 | 4/2010 |
| WO | 2010071837 A1 | 6/2010 |
| WO | 2011026911 A1 | 3/2011 |
| WO | 2011059610 A1 | 5/2011 |
| WO | 2011081205 A1 | 7/2011 |
| WO | 2011139107 A2 | 11/2011 |
| WO | 2012034363 A1 | 3/2012 |
| WO | 2012109075 A1 | 8/2012 |
| WO | 2013022766 A1 | 2/2013 |
| WO | 2013033167 A1 | 3/2013 |
| WO | 2013041652 A1 | 3/2013 |
| WO | 2013164769 A1 | 11/2013 |
| WO | 2013171640 A1 | 11/2013 |
| WO | 2014008214 A1 | 1/2014 |
| WO | 2014058691 A1 | 4/2014 |
| WO | 2014151616 A1 | 9/2014 |
| WO | 2016/038582 A1 | 3/2016 |
| WO | 2016/038583 A1 | 3/2016 |

OTHER PUBLICATIONS

Bos, Ras oncogenes in human cancer: a review. Cancer Res. Sep. 1, 1989;49(17):4682-9.
Brose et al., BRAF and RAS mutations in human lung cancer and melanoma. Cancer Res. Dec. 1, 2002;62(23):6997-7000.
Davies et al., Mutations of the BRAF gene in human cancer. Nature. Jun. 27, 2002;417(6892):949-54.
De Bono et al., Therapeutics targeting signal transduction for patients with colorectal carcinoma. Br Med Bull. 2002;64:227-54.
Gopalsamy et al., Hit to lead optimization of pyrazolo[1,5-a]pyrimidines as B-Raf kinase inhibitors. Bioorg & Med Chem Lett. Oct. 2009;19(24):6890-2.
Hatzivassiliou et al., RAF inhibitors prime wild-type RAF to activate the MAPK pathway and enhance growth. Nature. Mar. 18, 2010;464:431-5. (Includes Methods page and Supplementary Information).
Hoshino et al., Constitutive activation of the 41-/43-kDa mitogen-activated protein kinase signaling pathway in human tumors. Oncogene. Jan. 21, 1999;18(3):813-22.
Kawasaki et al., The second messenger phosphatidylinositol-5-phosphate facilitates antiviral innate immune signaling. Cell Host & Microbe. Aug. 14, 2013;14(2):148-58.
Lambert et al., Targeting the PI3K and MAPK pathways to treat Kaposi's-sarcoma-associated herpes virus infection and pathogenesis. Expert Opin Ther Targets. May 2007;11(5):589-99.
Martin et al., Inhibition of PIKfyve by YM-201636 dysregulates autophagy and leads to apoptosisindependent neuronal cell death. PLoS One. Mar. 2013;8(3):1-14.
Moore et al., Phase I study of the raf-1 kinase inhibitor BAY 43-9006 in patients with advanced refractory solid tumors. Proceedings of the American Society of Clinical Oncology. 2002;21. Abstract 1816. <http://www.asco.org/portal/site/ASCO/template.RAW/menuitem.34d60f5624ba07fd506fe . . . > Last accessed Dec. 3, 2008. 2 pages.
Patani et al., Bioisosterism: A Rational Approach in Drug Design. Chem Rev. Dec. 19, 1996;96(8):3147-3176.
Pollock et al., High frequency of BRAF mutations in nevi. Nat Genet. Jan. 2003;33(1):19-20.
Rowinsky et al., Ras protein farnesyltransferase: A strategic target for anticancer therapeutic development. J Clin Oncol. Nov. 1999;17(11):3631-52.
Scharovsky et al., Inhibition of ras oncogene: a novel approach to antineoplastic therapy. J Biomed Sci. Jul.-Aug. 2000;7(4):292-8.
Strumberg et al., Final results of a phase I pharmacokinetic and pharmacodynamic study of the raf kinase inhibitor BAY 43-9006 in patients with solid tumors. Proceedings of the American Society of Clinical Oncology. 2002;21. Abstract 121. <http://www.asco.org/portal/site/ACSO/template.RAW/menuitem.34d60f5624ba07fd506fe . . . > Last accessed Dec. 3, 2008. 2 pages.
Wenglowsky et al., Pyrazolopyridine inhibitors of B-RafV600E. Part 4: Rational design and kinase selectivity profile of cell potent type II inhibitors. Bioorg Med Chem Lett. Oct. 1, 2012;22(19):6237-41.
Wolff, Burger's Medicinal Chemistry and Drug Discovery. 5th Edition. vol. 1: Principles and Practice. John Wiley & Sons. 1995:975.
Yuen et al., Similarity of the phenotypic patterns associated with BRAF and KRAS mutations in colorectal neoplasia. Cancer Res. Nov. 15, 2002;62(22):6451-5.
Zuccotto et al., Through the "Gatekeeper Door": Exploring the active kinase conformation. J Med Chem. Apr. 8, 2010;53(7):2681-94.
CAS Registry No. 730972-83-5, STN Entry Date Aug. 23, 2004.
CAS Registry No. 867157-50-4, STN Entry Date Nov. 10, 2005.
Deng et al., Knowledge-based design of target-focused libraries using protein-ligand interaction constraints. J Med Chem. Jan. 26, 2006;49(2):490-500.
Jensen, A note on the term "Chalcogen." Journal of Chemical Education, Sep. 1997;74(9):1063-4.
Kim et al., Synthesis and biological evaluation of 4(5)-(6-alkylpyridin-2-yl)imidazoles as transforming growth factor-beta type 1 receptor kinase inhibitors. J Med Chem. Jun. 28, 2007;50(13):3143-7. Epub Jun. 7, 2007.
Kim et al., Synthesis of heteroaryl substituted imidazole derivatives. Bull Korean Chem Soc. 2000;21(3):345-7.
Krayushkin et al., Photochromic dihetarylethenes 7, synthesis . . . Russian Chemical Bulletin. International Edition. Jan. 2001;50(1):116-21.
Revesz et al., SAR of 2,6-diamino-3,5-difluoropyridinyl substituted heterocycles as novel p38MAP kinase inhibitors. Bioorg Med Chem Lett. Aug. 19, 2002;12(16):2109-12. PubMed PMID: 12127515.
Tsai et al., Discovery of a selective inhibitor of oncogenic B-Raf kinase with potent antimelanoma activity. Proc Natl Acad Sci U S A. Feb. 26, 2008;105(8):3041-6.
White et al., Chemiluminescence in liquid solutions: The chemiluminescence of lophine and its derivatives. Photochemistry and Photobioloby. 1965;4:1129-55.
Wolin et al., Dual binding site inhibitors of B-RAF kinase. Bioorganic & Medicinal Chemistry Letters. Apr. 2008;18:2825-9.
Pearce et al., Failure modes in anticancer drug discovery and development, Cancer Drug Design and Discovery Edited by Stephen Neidle, Chapter 18, pp. 424-35 (2008).
Johnson et al., Relationships between drug activity in NCI preclinical in vitro and in vivo models and early clinical trials, Br J Cancer. May 18, 2001;84(10):1424-31.
Simone, Oncology: Introduction, Cecil Textbook of Medicine, 20th Edition, vol. 1, pp. 1004-1010, 1996.
Gura, Systems for identifying new drugs are often faulty, Science. Nov. 7, 1997;278(5340):1041-2.

BIARYL AMIDE COMPOUNDS AS KINASE INHIBITORS

This application is a U.S. National Phase filing of International Application No. PCT/US2014/026107 filed 13 Mar. 2014, which claims priority to U.S. Application No. 61/783,558 filed 14 Mar. 2013, the contents of which are incorporated herein by reference in its entirety.

FIELD OF THE INVENTION

The invention provides compounds that inhibit Raf kinases, and are accordingly useful for treating certain disorders associated with excessive Raf kinase activity, including cell proliferation disorders such as cancers. The invention further provides pharmaceutical compositions containing these compounds and methods of using these compounds to treat conditions including cancer.

BACKGROUND

Protein Kinases are involved in very complex signaling cascades that regulate most cellular functions, including cell survival and proliferation. These signaling pathways have been heavily studied, particularly in the context of disorders caused by dysregulated cellular function, such as cancer. The mitogen-activated protein kinase (MAPK) cascade has been studied extensively, for example, and kinases in this pathway (e.g., RAS, RAF, MEK, and ERK) have been exploited as target sites for drug discovery. Mutated B-Raf is found in a significant fraction of malignancies (over 30% of all tumors and 40% of melanomas), and several drug candidates that inhibit a common B-Raf mutant (V600E, an activating mutation found in many cancers, particularly in cutaneous malignant melanoma, thyroid cancer, colorectal cancer, and ovarian cancer) have been reported, including GDC-0879, PLX4032, and PLX4720, while other inhibitors targeting C-Raf or B-Raf (or both) include sorafenib, XL281 RAF265, and BAY43-9006. These examples demonstrate that compounds that inhibit B-Raf or C-Raf are useful to treat various cancers.

The MAPK signaling cascade includes RAS, Raf, MEK and ERK kinases, each of which is actually a group of related proteins. Because they function collectively as a signal transduction cascade, the number of distinct kinases and their varying substrate specificities create a complex and highly branched pathway. Roskoski, *Biochem. Biophys. Res. Comm.*, 399, 313-17 (2010). Raf, for example, consists of monomers referred to as A-Raf, B-Raf, and C-Raf (also called Raf-1), each of which functions primarily as a dimer. The RAF complex includes heterodimers as well as homodimers of these three species, bringing the total number of dimeric species in the Raf group to six, and each of these has a number of sites where phosphorylation at serine, threonine or tyrosine can cause either activation or inhibition. Matalanas, et al., *Genes and Cancer* 2:232 (2011, published online 10 May 2011). Due to the complexity of the pathway and its regulation, it has been reported that inhibitors of B-Raf can cause paradoxical activation of the pathway, apparently due to conformational effects on the kinase domain of Raf that affect dimerization, membrane localization, and interaction with RAS-GTP. Hatzivassiliou, et al., *Nature*, vol. 464, 431-36 (18 Mar. 2010). In particular, ATP-competitive inhibitors can exhibit opposing effects on the signaling pathway, as either inhibitors or activators, depending on the cellular context. As a result, B-Raf inhibitors effective against tumors having the activating B-Raf mutation V600E may not be as effective as expected in tumors having wild-type B-Raf or KRas mutations. Id.

SUMMARY OF THE INVENTION

The present invention provides novel inhibitors of Raf kinases, including A-Raf, B-Raf and/or C-Raf, and use of these compounds to treat disorders associated with excessive or undesired levels of Raf activity, such as certain cancers. The compounds of the invention minimize undesired pathway activation effects, and thus can be more efficacious and more predictable in vivo than the B-Raf inhibitors that cause paradoxical pathway activation even when they have similar in vitro potency. The compounds of the invention bind in a DFG-out mode, making them type 2 inhibitors, which have been reported to be less prone to induce paradoxical activation. They are also quite different in structure from known type 2 inhibitors like sorafenib and RAF265. *J. Med. Chem.* 2012, vol. 55, 3452-78. The compounds are thus suited for treatment of BRaf wild-type and KRas mutant tumors, as well as B-Raf V600E mutant tumors.

In one aspect, the invention provides compounds of the formula (I):

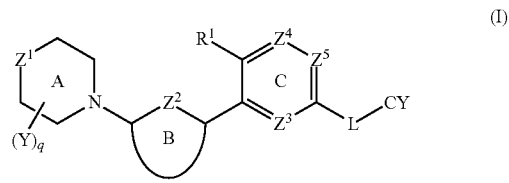

as further described herein, including the pharmaceutically acceptable salts of these compounds. The compounds of Formula (I) are inhibitors of Raf kinases as shown by data herein, and are accordingly useful to treat conditions such as melanoma, breast cancer, sarcoma, GI tumors such as gastrointestinal stromal tumors, ovarian cancer, sarcoma, GI tumors such as gastrointestinal stromal tumors, and other malignancies associated with excessive Raf pathway activity, particularly in cancers driven by Ras mutations. In addition, the compounds of the invention exhibit low levels of paradoxical activation of the Raf pathway.

In another aspect, the invention provides pharmaceutical compositions comprising a compound of Formula (I) admixed with at least one pharmaceutically acceptable carrier or excipient, optionally admixed with two or more pharmaceutically acceptable carriers or excipients. In addition, the invention includes combinations of a compound of Formula (I) with a co-therapeutic agent, optionally including one or more pharmaceutically acceptable carriers, and methods of treatment using a compound of Formula (I) in combination with a co-therapeutic agent. Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like.

In another aspect, the invention provides a method to treat a condition characterized by excessive or undesired levels of activity of Raf, especially B-Raf and/or C-Raf, which comprises administering to a subject in need of such treatment an effective amount of a compound of Formula (I) or any subgenus thereof as described herein, or a pharmaceutical composition comprising such compound. The subject can be a mammal, and is preferably a human. Conditions treatable by the compounds and methods described herein include various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. The invention thus includes compounds of Formula (I) and the subgenera thereof that are disclosed herein, including each species disclosed herein, for use in therapy, particularly for use to treat cancers such as melanoma, breast cancer, lung cancer, liver cancer, sarcoma, GI tumors such as gastrointestinal stromal tumors, sarcoma, GI tumors such as gastrointestinal stromal tumors, ovarian cancer, colorectal cancer, thyroid cancer, and pancreatic cancer. The invention also includes use of such compounds for manufacture of a medicament for treating these conditions.

The invention includes compounds of Formula (I) and the subgenera of Formula (I) described herein, and all stereoisomers (including diastereoisomers and enantiomers), tautomers and isotopically enriched versions thereof (including deuterium substitutions), as well as pharmaceutically acceptable salts of these compounds. In particular, where a heteroaryl ring containing N as a ring atom is optionally substituted with hydroxyl, e.g., a 2-hydroxypyridine ring, tautomers where the hydroxyl is depicted as a carbonyl (e.g., 2-pyridone) are included. Compounds of the present invention also comprise polymorphs of compounds of formula I (or sub-formulae thereof) and salts thereof.

DETAILED DESCRIPTION

The following definitions apply unless otherwise expressly provided.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety having up to 20 carbon atoms. Unless otherwise provided, alkyl refers to hydrocarbon moieties having 1 to 10 carbon atoms, 1 to 6 carbon atoms, or 1 to 4 carbon atoms. Typically, alkyl groups have 1-6 carbon atoms. "Lower alkyl" refers to alkyl groups having 1-4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, or 1-4 substituents, up to the number of hydrogens present on the unsubstituted alkyl group. Suitable substituents for alkyl groups, if not otherwise specified, may be selected from halogen, CN, oxo, hydroxy, substituted or unsubstituted $C_{1-4}$ alkoxy, substituted or unsubstituted $C_{3-6}$ cycloalkyl, substituted or unsubstituted $C_{3-6}$ heterocloalkyl, substituted or unsubstituted phenyl, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, COO($C_{1-4}$ alkyl), —O(C=O)—$C_{1-4}$ alkyl, —NHC(=O)$C_{1-4}$ alkyl and —NHC(=O)O$C_{1-4}$ alkyl groups; wherein the substituents for substituted $C_{1-4}$ alkoxy, substituted $C_{3-6}$ cycloalkyl, $C_{3-6}$ heterocycloalkyl, and substituted phenyl are up to three groups selected from halo, $C_{1-4}$ alkyl, $C_{1-4}$ haloalkyl, $C_{1-4}$ alkoxy, amino, hydroxy, and CN. Preferred substituents for alkyl groups include halogen, CN, oxo, hydroxy, $C_{1-4}$ alkoxy, $C_{3-6}$ cycloalkyl, phenyl, amino, ($C_{1-4}$ alkyl)amino, alkyl)amino, $C_{1-4}$ alkylthio, $C_{1-4}$ alkylsulfonyl, —C(=O)—$C_{1-4}$ alkyl, COOH, —COO($C_{1-4}$ alkyl), —O(C=O)—$C_{1-4}$ alkyl, —NHC(=O) $C_{1-4}$ alkyl and —NHC(=O)O $C_{1-4}$ alkyl groups.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the substituents described as suitable and preferred for alkyl groups.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g, trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-10, or 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable and preferred substituents are selected from the substituents listed above for alkyl groups, except that hydroxyl and amino are not normally present on the carbon that is directly attached to the oxygen of the substituted 'alkyl-O' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are selected from the suitable or preferred substituents named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, provided the ring atom of the cycloalkyl group that is connected to the molecular formula of interest is not an aromatic ring atom. Unless otherwise provided, cycloalkyl refers to cyclic hydrocarbon groups having between 3 and 9 ring carbon atoms or between 3 and 7 ring carbon atoms. Preferably, cycloalkyl groups are saturated monocyclic rings having 3-7 ring atoms unless otherwise specified.

A substituted cycloalkyl is a cycloalkyl group substituted by one, or two, or three, or more than three substituents, up to the number of hydrogens on the unsubstituted group. Typically, a substituted cycloalkyl will have 1-4 or 1-2 substituents. Suitable substituents, unless otherwise specified, are independently selected from the group consisting of halogen, hydroxyl, thiol, cyano, nitro, oxo, $C_{1-4}$-alkylimino, $C_{1-4}$-alkoximino, hydroxyimino, $C_{1-4}$-alkyl, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, $C_{1-4}$-alkylcarbonyl, carboxy, $C_{1-4}$-alkoxycarbonyl, amino, $C_{1-4}$-alkylamino, di-$C_{1-4}$-alkylamino, $C_{1-4}$-alkylaminocarbonyl, di-$C_{1-4}$-alkylaminocarbonyl, $C_{1-4}$-alkylcarbonylamino, $C_{1-4}$-alkylcarbonyl($C_{1-4}$-alkyl) amino, $C_{1-4}$-alkylsulfonyl, $C_{1-4}$-alkylsulfamoyl, and $C_{1-4}$-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups herein. Preferred substituents include $C_{1-4}$ alkyl and the substituent groups listed above as preferred substituents for alkyl groups.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "cycloalkyl". When used in these terms, the cycloalkyl is typically a monocyclic 3-7 carbon ring, that is unsubstituted or substituted with 1-2 groups. When optionally substituted, the substituents are typically selected from $C_{1-4}$ alkyl and those set forth above as suitable or preferred substituents for alkyl groups.

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group.

A substituted aryl is an aryl group substituted by 1-5 (such as one, or two, or three) substituents independently selected from the group consisting of hydroxyl, thiol, cyano, nitro, $C_{1-4}$-alkyl, $C_{2-4}$-alkenyl, $C_{2-4}$-alkynyl, $C_{1-4}$-alkoxy, $C_{1-4}$-thioalkyl, $C_{2-4}$-alkenyloxy, $C_{2-4}$-alkynyloxy, halogen, $C_{1-4}$-alkylcarbonyl, carboxy, $C_{1-4}$-alkoxycarbonyl, amino, $C_{1-4}$-alkylamino, di-$C_{1-4}$-alkylamino, $C_{1-4}$-alkylaminocarbonyl, di-$C_{1-4}$-alkylaminocarbonyl, $C_{1-4}$-alkylcarbonylamino, $C_{1-4}$-alkylcarbonyl($C_{1-4}$-alkyl)amino, $C_{1-4}$-alkylsulfonyl, sulfamoyl, $C_{1-4}$-alkylsulfamoyl, and $C_{1-4}$-alkylaminosulfonyl where each of the afore-mentioned hydrocarbon groups (e.g., alkyl, alkenyl, alkynyl, alkoxy residues) may be further substituted by one or more groups independently selected at each occurrence from the groups listed above as suitable substituents for alkyl groups. Preferred substituents for a substituted aryl group are $C_{1-4}$ alkyl, halogen, CN, hydroxy, substituted or unsubstituted $C_{1-4}$ alkyl, substituted or unsubstituted $C_{1-4}$ alkoxy, substituted or unsubstituted $C_{3-6}$ cycloalkyl, substituted or unsubstituted $C_{3-6}$ heterocycloalkyl, amino, ($C_{1-4}$ alkyl)amino, di($C_{1-4}$ alkyl)amino, $C_{1-4}$ alkylthio, $C_{1-4}$ alkylsulfonyl, —C(=O)—$C_{1-4}$ alkyl, COOH, COO($C_{1-4}$ alkyl), —O(C=O)—$C_{1-4}$ alkyl, —NHC(=O)$C_{1-4}$ alkyl and —NHC(=O)O$C_{1-4}$ alkyl groups; wherein the substituents for substituted $C_{1-4}$ alkoxy, substituted $C_{3-6}$ cycloalkyl, $C_{3-6}$ heterocycloalkyl, and substituted alkyl are up to three groups selected from halo, oxo, $C_{1-4}$ alkyl, $C_{1-4}$ haloalkyl, $C_{1-4}$ alkoxy, amino, hydroxy, and CN.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" or "heterocycloalkyl" refers to a heterocyclic radical that is saturated or partially unsaturated but not aromatic, and can be a monocyclic or a polycyclic ring, including a bicyclic, tricyclic or spirocyclic ring system; and has 3 to 14, more commonly 4 to 10, and most preferably 5 to 7 ring atoms; wherein one or more, preferably one to four, especially one or two ring atoms are heteroatoms independently selected from O, S and N (the remaining ring atoms therefore being carbon). Even though described as, e.g., a $C_{5-6}$ atom ring, a heterocycle contains at least one heteroatom as a ring atom and has the total number of ring atoms stated, e.g. 5 or 6 in this example. Preferably, a heterocyclyl group has one or two such heteroatoms as ring atoms, and preferably the heteroatoms are not directly connected to each other. The bonding ring (i.e. the ring connecting to the Formula of interest) preferably has 4 to 12, especially 5 to 7 ring atoms. The heterocyclic group can be fused to an aromatic ring, provided the atom of the heterocyclic group attached to the Formula of interest is not aromatic. The heterocyclic group can be attached to the Formula of interest via a heteroatom (typically nitrogen) or a carbon atom of the heterocyclic group. The heterocyclyl can comprise fused or bridged rings as well as spirocyclic ring systems (e.g., 2-oxa-6-azaspiro[3.3]heptane), and only one ring of a polycyclic heterocyclic group needs to contain a heteroatom as a ring atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-5 (such as one, or two, or three) substituents selected from the substituents described above as suitable or preferred for a cycloalkyl group.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms as ring members; the heteroatoms are selected from N, O and S. Typically, the heteroaryl is a 5-10 membered ring system, e.g., a 5-6 membered monocyclic or an 8-10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, 1- or 2-tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings, where the radical or point of attachment to the Formula of interest is on a heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or I-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroaryl groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents, typically 1, 2 or 3 substituents, selected from the substituents described above as suitable or preferred for an aryl group.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Various embodiments of the invention are described herein. It will be recognized that features specified in each embodiment may be combined with other specified features to provide further embodiments of the present invention. The following enumerated embodiments are representative of the invention:

1. In certain embodiments, the invention provides a compound of Formula (I)

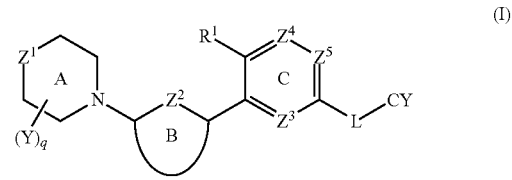

or a pharmaceutically acceptable salt thereof, wherein:
$Z^1$ is O, S, S(=O) or $SO_2$;
$Z^2$ is N, S or $CR^a$, where $R^a$ is H, halo, $C_{1-4}$ alkyl or $C_{1-4}$ haloalkyl;
$R^1$ is CN, halo, OH, $C_{1-4}$ alkoxy, or $C_{1-4}$ alkyl that is optionally substituted with one to three groups selected from halo, $C_{1-4}$ alkoxy, CN, and hydroxyl;
Ring B is selected from phenyl, pyridine, pyrimidine, pyrazine, pyridazine, pyridone, pyrimidone, pyrazinone, pyridazinone, and thiazole, each of which is optionally substituted with up to two groups selected from halo, OH, CN, $C_{1-4}$ alkyl, $C_{2-4}$ alkenyl, —O—($C_{1-4}$alkyl), $NH_2$, NH—($C_{1-4}$alkyl), —N($C_{1-4}$ alkyl)$_2$, —$SO_2R^2$, $NHSO_2R^2$, NHC(O)$R^2$, $NHCO_2R^2$, $C_{3-6}$ cycloalkyl, 5-6 membered heteroaryl, —O—$C_{3-6}$ cycloalkyl, —O-(5-6-membered heteroaryl), $C_{4-8}$ heterocycloalkyl, and —O-(4-8 membered heterocycloalkyl), where each heterocycloalkyl and heteroaryl contains up to three heteroatoms selected from N, O and S as ring members,
where each $C_{1-4}$ alkyl, $C_{2-4}$ alkenyl, $C_{3-6}$ cycloalkyl, 5-6 membered heteroaryl, and 4-8 membered heterocycloalkyl is each optionally substituted with up to three groups selected from oxo, hydroxyl, halo, $C_{1-4}$ alkyl, $C_{1-4}$ haloalkyl, $C_{1-4}$ alkoxy, and —$(CH_2)_{1-2}Q$ where Q is OH, $C_{1-4}$ alkoxy, —CN, $NH_2$, —$NHR^3$, —$N(R^3)_2$, —$SO_2R^3$, $NHSO_2R^3$, $NHC(O)OR^3$, or $NHC(O)R^3$; each $R^2$ and $R^3$ is independently $C_{1-4}$ alkyl; and
Ring B is optionally fused to a 5-6 membered aromatic or nonaromatic ring containing up to two heteroatoms selected from N, O and S, where the 5-6 membered ring can be substituted with halo, $C_{1-4}$ alkyl, $C_{1-4}$ haloalkyl, or $C_{1-4}$ alkoxy, and optionally, if the fused ring is non-aromatic the substituent options can further include oxo;
each Y is independently selected from $C_{1-4}$ alkyl, $C_{1-4}$ alkoxy, CN, halo, oxo, —$(CH_2)_pOR^4$, —$(CH_2)_pN(R^4)_2$, —$(CH_2)_pNHC(O)R^4$, —$(CH_2)_pNHCOO(C_{1-4}$ alkyl), and imidazole,
or two Y groups on Ring A are optionally taken together to form a ring fused to or bridging Ring A, where said fused or bridging ring optionally contains a heteroatom selected from N, O and S as a ring member, and is optionally substituted with up to two groups selected from $C_{1-4}$ alkyl, $C_{1-4}$ alkoxy, CN, halo, oxo, $-(CH_2)_pOR^4$, $-(CH_2)_pN(R^4)_2$, $-(CH_2)_pNHC(O)R^4$, and $-(CH_2)_pNHCOO(C_{1-4}$ alkyl);

each $R^4$ is independently H or $C_{1-4}$ alkyl;

each p is independently 0, 1, or 2;

q is 0, 1 or 2;

$Z^3$, $Z^4$, and $Z^5$ are independently selected from CH and N and optionally NO;

L is $-C(=O)-NR^4-[CY]$ or $-NR^4-C(=O)-[CY]$, where [CY] indicates which atom of L is attached to CY; and CY is an aromatic ring selected from phenyl, pyridine, pyrimidine, pyrazine, pyridazine, pyridone, thiazole, isothiazole, oxazole, pyrazole, and isoxazole, wherein the ring is optionally fused to a thiophene, imidazole, oxazolone, or pyrrole ring;

and CY is substituted with up to two groups selected from halo, CN, $R^5$, $OR^5$, $SO_2R^5$, $-S(=NH)(=O)R^5$, OH, $NH_2$, $NHR^5$, and $-N(R^5)_2$, wherein each $R^5$ is independently $C_{1-4}$ alkyl, $C_{2-4}$ alkenyl, $C_{4-6}$ heterocyclyl, 5-membered heteroaryl containing up to three heteroatoms selected from N, O and S as ring members, or $C_{3-8}$ cycloalkyl, and $R^5$ is optionally substituted with up to four groups selected from oxo, halo, CN, $R^6$, OH, $OR^6$, $SO_2R^6$, $NH_2$, $NHR^6$, $N(R^6)_2$, $NHSO_2R^6$, $NHCOOR^6$, $NHC(=O)R^6$, $-CH_2OR^7$, $-CH_2N(R^7)_2$, wherein each $R^6$ is independently $C_{1-4}$ alkyl, and each $R^7$ is independently H or $C_{1-4}$ alkyl;

and two $R^4$, $R^5$, $R^6$, or $R^7$ on the same nitrogen atom can be taken together to form a 5-6 membered heterocyclic ring optionally containing an additional N, O or S as a ring member and optionally substituted with up to two groups selected from $C_{1-4}$ alkyl, oxo, halo, OH, and $C_{1-4}$ alkoxy.

In certain embodiments, the compound is a compound of the formula (I):

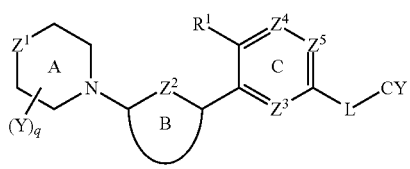

(I)

or a pharmaceutically acceptable salt thereof, wherein:

$Z^1$ is O, S, S(=O) or $SO_2$;

$Z^2$ is N, S or $CR^a$, where $R^a$ is H, $C_{1-4}$ alkyl or $C_{1-4}$ haloalkyl;

$R^1$ is CN, halo, OH, $C_{1-4}$ alkoxy, or $C_{1-4}$ alkyl that is optionally substituted with one to three groups selected from halo, $C_{1-4}$ alkoxy, CN, and hydroxyl;

Ring B is selected from phenyl, pyridine, pyrimidine, pyrazine, pyridone, pyrimidone, pyrazinone, pyridazinone, and thiazole, each of which is optionally substituted with up to two groups selected from halo, OH, CN, $C_{1-4}$ alkyl, $C_{2-4}$ alkenyl, $-O-(C_{1-4}$alkyl), $NH_2$, $NH-(C_{1-4}$alkyl), $-N(C_{1-4}$ alkyl)$_2$, $-SO_2R^2$, $NHSO_2R^2$, $NHC(O)R^2$, $NHCO_2R^2$, $C_{3-6}$ cycloalkyl, 5-6 membered heteroaryl, $-O-C_{3-6}$ cycloalkyl, $-O$-(5-6-membered heteroaryl), $C_{4-8}$ heterocycloalkyl, and $-O$-(4-8 membered heterocycloalkyl), where each heterocycloalkyl and heteroaryl contains up to three heteroatoms selected from N, O and S as ring members, where each $C_{1-4}$ alkyl, $C_{2-4}$ alkenyl, $C_{3-6}$ cycloalkyl, 5-6 membered heteroaryl, and 4-8 membered heterocycloalkyl is each optionally substituted with up to three groups selected from oxo, hydroxyl, halo, $C_{1-4}$ alkyl, $C_{1-4}$ haloalkyl, $C_{1-4}$ alkoxy, and $-(CH_2)_{1-2}Q$ where Q is OH, $C_{1-4}$ alkoxy, $-CN$, $NH_2$, $-NHR^3$, $-N(R^3)_2$, $-SO_2R^3$, $NHSO_2R^3$, $NHC(O)OR^3$, or $NHC(O)R^3$;

each $R^2$ and $R^3$ is independently $C_{1-4}$ alkyl; and

Ring B is optionally fused to a 5-6 membered aromatic or nonaromatic ring containing up to two heteroatoms selected from N, O and S, where the 5-6 membered ring can be substituted with halo, $C_{1-4}$ alkyl, $C_{1-4}$ haloalkyl, or $C_{1-4}$ alkoxy;

each Y is independently selected from $C_{1-4}$ alkyl, $C_{1-4}$ alkoxy, CN, halo, oxo, $-(CH_2)_pOR^4$, $-(CH_2)_pN(R^4)_2$, $-(CH_2)_pNHC(O)R^4$, $-(CH_2)_pNHCOO(C_{1-4}$ alkyl), or two Y groups on Ring A are optionally taken together to form a ring fused to or bridging Ring A, where said fused or bridging ring optionally contains a heteroatom selected from N, O and S as a ring member, and is optionally substituted with up to two groups selected from $C_{1-4}$ alkyl, $C_{1-4}$ alkoxy, CN, halo, oxo, $-(CH_2)_pOR^4$, $-(CH_2)_pN(R^4)_2$, $-(CH_2)_pNHC(O)R^4$, and $-(CH_2)_pNHCOO(C_{1-4}$ alkyl);

each $R^4$ is independently H or $C_{1-4}$ alkyl;

each p is independently 0, 1, or 2;

q is 0, 1 or 2;

$Z^3$, $Z^4$, and $Z^5$ are independently selected from CH and N;

L is $-C(=O)-NH-[CY]$ or $-NH-C(=O)-[CY]$, where [CY] indicates which atom of L is attached to CY; and CY is an aromatic ring selected from phenyl, pyridine, pyrimidine, pyrazine, pyridazine, pyridone, thiazole, isothiazole, oxazole, pyrazole, and isoxazole, wherein the ring is optionally fused to a thiophene, imidazole, oxazolone, or pyrrole ring;

and CY is substituted with up to two groups selected from halo, CN, $R^5$, $OR^5$, $SO_2R^5$, OH, $NH_2$, $NHR^5$, and $-N(R^5)_2$, wherein each $R^5$ is independently $C_{1-4}$ alkyl, $C_{4-6}$ heterocyclyl, or $C_{3-8}$ cycloalkyl, and $R^5$ is optionally substituted with up to three groups selected from oxo, halo, CN, $R^6$, OH, $OR^6$, $SO_2R^6$, $NH_2$, $NHR^6$, $N(R^6)_2$, $NHSO_2R^6$, $NHCOOR^6$, $NHC(=O)R^6$, $-CH_2OR^7$, $-CH_2N(R^7)_2$, wherein each $R^6$ is independently $C_{1-4}$ alkyl, and each $R^7$ is independently H or $C_{1-4}$ alkyl;

and two $R^4$, $R^5$, $R^6$, or $R^7$ on the same nitrogen atom can be taken together to form a 5-6 membered heterocyclic ring optionally containing an additional N, O or S as a ring member and optionally substituted with up to two groups selected from $C_{1-4}$ alkyl, oxo, halo, OH, and $C_{1-4}$ alkoxy.

2. A compound according to embodiment 1 or a pharmaceutically acceptable salt thereof, wherein $Z^1$ is O.

3 (a). A compound according to embodiment 1 or embodiment 2 or a pharmaceutically acceptable salt thereof, wherein $Z^2$ is CH.

3 (b). In an alternative, a compound according to embodiment 1 or embodiment 2 or a pharmaceutically acceptable salt thereof, wherein, $Z^2$ is N.

4. A compound according to any one of embodiments 1 to 3 or a pharmaceutically acceptable salt thereof, wherein CY is selected from phenyl, pyridine, pyrimidine, pyrazine, pyridazine, pyridone, thiazole, isothiazole, oxazole, and isoxazole, each of which is optionally substituted as described for embodiment 1. In some of these embodiments, CY is phenyl or 4-pyridinyl.

5. A compound according to any of the preceding embodiments or a pharmaceutically acceptable salt thereof, wherein $R^1$ is methyl or $CF_3$.

6. A compound according to any of the preceding embodiments or a pharmaceutically acceptable salt thereof, wherein Ring B is pyridine or pyrimidine or pyridone.

7. A compound according to any of the preceding embodiments or a pharmaceutically acceptable salt thereof, wherein CY is phenyl or pyridin-4-yl, and is optionally substituted with one or two groups selected from methyl, ethyl, isopropyl, $CF_3$, —$CHF_2$, $CH_2F$, $CF_2CH_3$, $CH_2CF_3$, 1-piperazinyl, 4-methyl-1-piperazinyl, 4-ethyl-1-piperazinyl, cyclopropyl, 1-cyanocyclopropyl, —$CH_2CN$, —$CHMeCN$, —$CMe_2CN$, OMe, OEt, F, Cl, —$SO_2Me$, —$SO_2NMe_2$, —$CH_2NH_2$, —$CH_2NMe_2$, —$CH_2NHMe$, and —$CH_2OMe$. In some of these embodiments, CY has one or two substituents at ring atom 3 or ring atom 5 relative to the point of attachment of CY to L.

8. A compound according to any of the preceding embodiments or a pharmaceutically acceptable salt thereof, wherein CY is substituted with at least one group selected from $CF_3$, $OCF_3$, t-butyl, —$C(Me)_2CN$, and —$SO_2Me$.

In some embodiments, CY is substituted with —$CF(Me)_2$ or —$CHF_2$.

In some of these embodiments, CY has one or two substituents at ring atom 3 or ring atom 5 relative to the point of attachment of CY to L.

9. A compound according to any of the preceding embodiments or a pharmaceutically acceptable salt thereof, wherein $Z^4$ is CH.

10. A compound according to any of embodiments 1-8 or a pharmaceutically acceptable salt thereof, wherein $Z^4$ is N.

11. A compound according to any of the preceding embodiments or a pharmaceutically acceptable salt thereof, wherein L is —C(=O)—NH—[CY], where [CY] indicates which atom of L is attached to ring CY.

12. A compound according to any of embodiments 1-10 or a pharmaceutically acceptable salt thereof, wherein L is —NH—C(=O)—[CY], where [CY] indicates which atom of L is attached to ring CY.

13. A compound according to any of the preceding embodiments or a pharmaceutically acceptable salt thereof, wherein $Z^3$ is N.

14. A compound of any of the preceding embodiments, wherein ring B is selected from

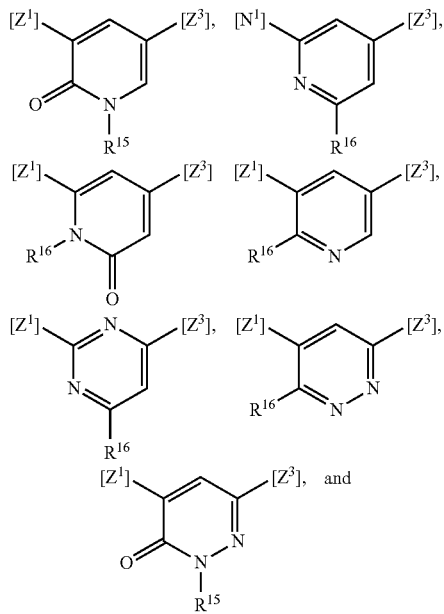

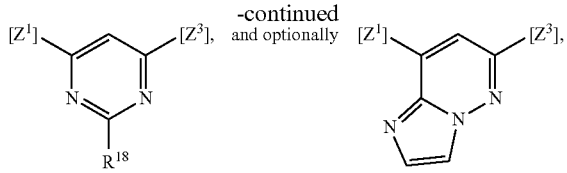

wherein $[Z^1]$ indicates where the ring containing $Z^1$ is attached to ring B, and $[Z^3]$ indicates where the ring containing $Z^3$ is attached to ring B, and $R^{15}$, $R^{16}$, $R^{17}$ and $R^{18}$ are each selected from CN, halo, $R^{20}$, —$N(R^{20})_2$, —$OR^{20}$, and $C_{4-8}$ heterocycloalkyl optionally substituted with up to two groups selected from hydroxyl, $C_{1-4}$ alkyl, oxo, and halo; where each $R^{20}$ is independently H or $C_{1-4}$ alkyl optionally substituted with up to three groups independently selected from halo, oxo, $C_{1-4}$ alkoxy, hydroxyl, amino, and CN.

15. A compound of any of the preceding embodiments, wherein q is 0.

16. A compound of any of the preceding embodiments, wherein ring B is selected from

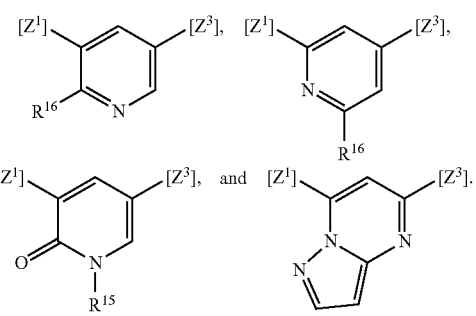

17. A compound of any of the preceding embodiments, wherein $Z^3$ and $Z^5$ are both CH.

18. A compound of any of the preceding embodiments wherein $Z^4$ is N and $R^1$ is methyl.

19. A compound of any of embodiments 1-17, wherein $Z^4$ is CH and $R^1$ is methyl.

20. A compound of any of the preceding embodiments, wherein L is —NH—C(=O)—[CY] and CY is phenyl or 4-pyridinyl, and CY is substituted with one or two groups selected from halo, $CF_3$, $CF_2H$, $CFH_2$, $CFMe_2$, and —$CH_2NMe_2$.

21. A compound of embodiment 1, which is selected from the compounds of Examples 1-1175 and compounds in Table A and the pharmaceutically acceptable salts thereof.

22. A pharmaceutical composition comprising a compound of any of the preceding embodiments or a pharmaceutically acceptable salt thereof and one or more pharmaceutically acceptable carriers.

23. A combination comprising a therapeutically effective amount of a compound according to any one of embodiments 1 to 21 or a pharmaceutically acceptable salt thereof and one or more therapeutically active co-agents.

24. A method of treating a proliferative disorder, comprising administering to a subject in need thereof a therapeutically effective amount of a compound of any of embodiments 1-21 or a pharmaceutically acceptable salt thereof. In some embodiments, the proliferative disorder is a cancer, e.g., a condition selected from solid tumors, melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer.
25. A compound according to any one of embodiments 1 to 21 or a pharmaceutically acceptable salt thereof, for use as a medicament.
26. A compound according to any one of embodiments 1 to 21 or a pharmaceutically acceptable salt thereof, for use in the treatment of cancer. In some embodiments, the cancer is selected from solid tumors, melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer.
27. Use of a compound according to any one of embodiments 1 to 21 or a pharmaceutically acceptable salt thereof in the manufacture of a medicament for the treatment of cancer. In some embodiments, the cancer is selected from solid tumors, melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer.

Each of the Example compounds having a measured IC-50 (B-Raf) of less than or equal to 0.01 µM, and a measured IC-50 (c-Raf) of less than 0.005 µM as shown in Table 2 is a preferred compound of the invention. The compounds of Examples having a measured IC-50 (B-Raf) of less than or equal to 0.01 µM and measured IC-50 (c-Raf) less than or equal to 0.002 µM according to Table 2 are especially preferred. Thus the use of any one of these compounds for treatment of a condition selected from melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer is an embodiment of the invention.

Unless otherwise specified, in any of the foregoing enumerated embodiments, Ring A can be unsubstituted morpholine or a substituted morpholine derivative as described for Formula (I) above. In specific embodiments, Ring A is selected from the following morpholinic groups

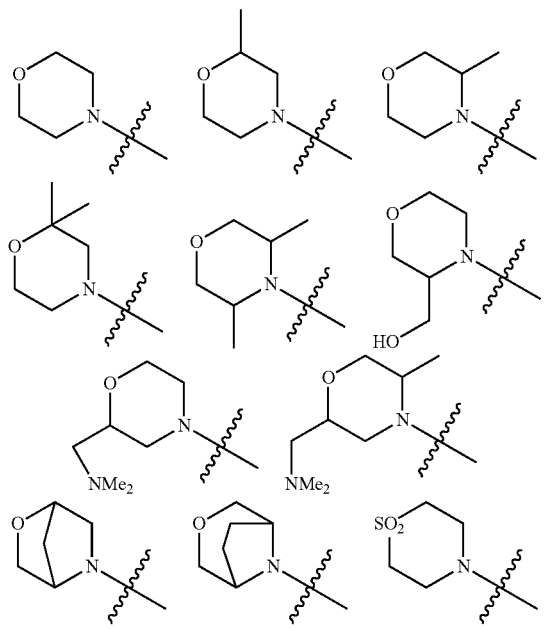

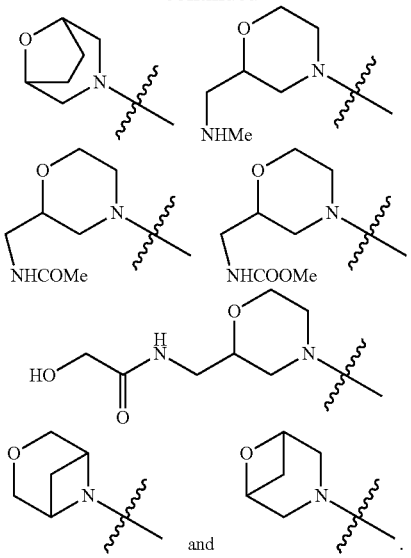

In certain embodiments, Ring A is unsubstituted morpholine.

In the foregoing enumerated embodiments, unless otherwise stated, Ring B is selected from phenyl, pyridine, pyrimidine, pyrazine, pyridone, pyrimidone, pyrazinone, pyridazinone, and thiazole. In certain of these embodiments, Ring B is selected from pyrazine, pyridazine, pyridone, pyrimidone, pyrazinone, and pyridazinone. Ring B in any of these embodiments can be substituted as described above for Formula (I); in some embodiments, Ring B is a six-membered ring that is substituted at positions 1, 3 and 5, where the N of ring A is at position 1 and $Z^2$ is at position 6. Where Ring B includes an oxo group (pyridone, pyridazinone, pyrazinone), oxo is sometimes at position 2 using this numbering. In some embodiments, Ring B is substituted by a group selected from methyl, ethyl, isopropyl, amino, hydroxyl, —NHMe, —NHEt, —NMe$_2$, —NHSO$_2$Me, —NH—CH$_2$CH$_2$OH, 4-tetrahydropyranyl, —O-4-tetrahydropyranyl, 1-pyrrolidinyl, 1-morpholinyl, —NH—CH(CH$_2$OH)$_2$, 1-pyrrolidin-2-one, 4-morpholin-3-one, 2-oxa-6-aza[3.3]heptan-6-yl, —CH$_2$CH$_2$OH, CF$_3$, SO$_2$Me, 2-propenyl, —CH$_2$CN, and —CH$_2$CH$_2$NHCOOMe.

Preferably, Ring B is selected from pyridine, pyrimidine, pyrazine, pyridone, pyrimidone, pyrazinone, and pyridazinone, optionally substituted and/or fused as described for Formula (I). When Ring B is fused, the additional fused ring can be substituted as described, typically with up to two (0, 1 or 2) of the substituents described above.

Where Ring B is pyridone, it is preferably a 2-pyridone (pyridin-2-one), and optionally is N-alkylated with a C$_{1-4}$ alkyl, which may be substituted with one to three groups selected from OH, OMe, halo, and CN. In some embodiments, Ring B is substituted by a group selected from methyl, ethyl, isopropyl, amino, hydroxyl, —NHMe, —NHEt, —NMe$_2$, —NHSO$_2$Me, —NH—CH$_2$CH$_2$OH, 4-tetrahydropyranyl, —O-4-tetrahydropyranyl, 1-pyrrolidinyl, 1-morpholinyl, —NH—CH(CH$_2$OH)$_2$, 1-pyrrolidin-2-one, 4-morpholin-3-one, 2-oxa-6-aza[3.3]heptan-6-yl, 1-imidazolyl, 4-methyl-1,2,3-triazol-1-yl, 4-ethyl-1,2,3-triazol-1-yl, 4-isopropyl-1,2,3-triazol-1-yl, 4-(1-hydroxy-2-propyl)-1,2,3-triazol-1-yl, —CH$_2$CH$_2$OH, CF$_3$, SO$_2$Me, 2-propenyl, —CH$_2$CN, and —CH$_2$CH$_2$NHCOOMe.

Preferred embodiments of Ring B include

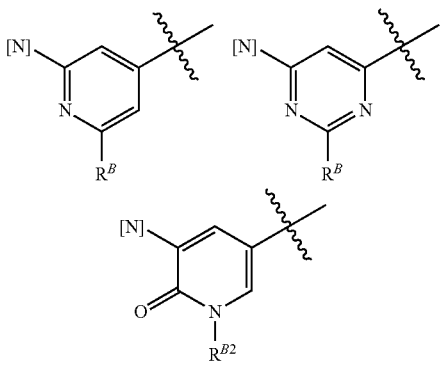

where [N] indicates the position attached to Ring A; $R^B$ is selected from amino, hydroxyl, —NHMe, —NHEt, —NMe$_2$, —NHSO$_2$Me, —NH—CH$_2$CH$_2$OH, —O-4-tetrahydropyranyl, 1-pyrrolidinyl, 1-morpholinyl, —NH—CH(CH$_2$OH)$_2$, 1-pyrrolidin-2-one, 4-morpholin-3-one, and 2-oxa-6-aza[3.3]heptan-6-yl; and $R^{B2}$ is selected from methyl, ethyl, isopropyl, —CH$_2$CH$_2$OH, 4-tetrahydropyranyl, CH$_2$CN, and —CH$_2$CH$_2$NHCOOMe.

In some of the foregoing embodiments, Ring C is phenyl or pyridine. When Ring C is pyridine, preferably $Z^4$ is N. Unless otherwise stated, $R^1$ is often methyl or CF$_3$. The presence of $R^1$, a substituent such as methyl rather than hydrogen, significantly affects the conformation of the compound, favoring a highly active conformation. The methyl group thereby enhances in vitro activity significantly.

In the enumerated embodiments where not otherwise specified, CY can be substituted with 1 or 2 groups selected from methyl, ethyl, isopropyl, CF$_3$, —CHF$_2$, CH$_2$F, CF$_2$CH$_3$, CH$_2$CF$_3$, 1-piperazinyl, 4-methyl-1-piperazinyl, 4-ethyl-1-piperazinyl, cyclopropyl, 1-cyanocyclopropyl, —CH$_2$CN, —CHMeCN, —CMe$_2$CN, OMe, OEt, F, Cl, —SO$_2$Me, —SO$_2$NMe$_2$, —CH$_2$NH$_2$, —CH$_2$NMe$_2$, —CH$_2$NHMe, and —CH$_2$OMe. It some of these embodiments, CY is phenyl or 4-pyridinyl, and at least one substituent is at position 3. In some embodiments, CY is a group of the formula

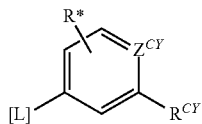

where [L] indicates which position is attached to L in Formula (I); $Z°$ is N or CH; R* is selected from methyl, ethyl, isopropyl, CF$_3$, —CHF$_2$, CH$_2$F, CF$_2$CH$_3$, CH$_2$CF$_3$, 1-piperazinyl, 4-methyl-1-piperazinyl, 4-ethyl-1-piperazinyl, cyclopropyl, 1-cyanocyclopropyl, —CH$_2$CN, —CHMeCN, —CMe$_2$CN, OMe, OEt, F, Cl, —SO$_2$Me, —SO$_2$NMe$_2$, —CH$_2$NH$_2$, —CH$_2$NMe$_2$, —CH$_2$NHMe, and —CH$_2$OMe; and $R^{CY}$ is selected from CF$_3$, OCF$_3$, t-butyl, —C(Me)$_2$CN, and —SO$_2$Me.

In certain embodiments, the compound of Formula (I) has this formula:

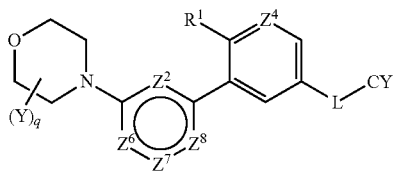

wherein $Z^2$ is N or CH;
$Z^4$ is N or CH;

$Z^6$ is C=O and $Z^7$ is NR$^Q$, where R$^Q$ is H or C$_{1-4}$ alkyl optionally substituted by OH, CN, OMe, SO$_2$Me, or 1-3 halogens;
or $Z^6$ is CH and $Z^7$ is C-Q;
$Z^8$ is CH or N (and preferably $Z^8$ and $Z^2$ are not both simultaneously N);
Q is selected from H, C$_{1-4}$ alkyl, C$_{1-4}$ haloalkyl, C$_{3-6}$ cycloalkyl, C$_{5-6}$ heteroaryl, C$_{4-7}$ heterocycloalkyl, including morpholine or any of the morpholinic groups shown above as options for Ring A, as well as 2-oxa-6-azaspiro[3.3]heptane, e.g.,

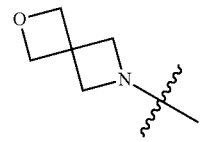 [SMILES: *N1CC2(COC2)C1]

and other spirocyclic systems; where the, C$_{1-4}$ alkyl, C$_{3-6}$ cycloalkyl, C$_{5-6}$ heteroaryl, or C$_{4-7}$ heterocycloalkyl is optionally substituted with a group selected from OH, NH$_2$, CN, OMe, SO$_2$Me, and NMe$_2$;
and R$_1$, Y, q, L, and CY are as defined for Formula (I) or any of the subgenera of Formula (I) described herein.

In a particular embodiment, the invention provides compounds of this formula:

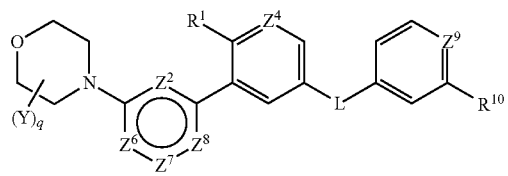

wherein:
Y is oxo, C$_{1-4}$ alkyl, or —CH$_2$T, where T is selected from hydroxyl, C$_{1-4}$ alkoxy, amino, C$_{1-4}$ alkylamino, di(C$_{1-4}$ alkyl)amino, —NHC(=O)(C$_{1-4}$ alkyl) and —NHC(=O)—O(C$_{1-4}$ alkyl);
q is 0, 1 or 2;
$Z^2$ is CH or N;
$Z^4$ is CH or N;
$Z^6$ is C=O, $Z^7$ is NR$^{20}$, and $Z^8$ is CH;
or $Z^6$ is N, $Z^7$ is CR$^{21}$, and $Z^8$ is CH;
or $Z^6$ is N, $Z^7$ is CR$^{22}$, and $Z^8$ is N, provided $Z^2$ and $Z^8$ are not both N;
$Z^9$ is N or CH;
$R^1$ is Me or CF$_3$;
L is —C(=O)NH— or —NH—C(=O)—;
$R^{10}$ is selected from C$_{1-4}$ alkyl, —O—C$_{1-3}$ alkyl, —SO$_2$—C$_{1-3}$ alkyl, and C$_{3-4}$ cycloalkyl, wherein each C$_{1-3}$ alkyl, —O—C$_{1-3}$ alkyl, —SO$_2$—C$_{1-3}$ alkyl, and C$_{3-4}$ cycloalkyl is optionally substituted with up to three groups selected from halo, CN, Me, CF$_3$, OH and OMe; and
$R^{20}$, $R^{21}$, and $R^{22}$ are each selected from H, C$_{1-4}$ alkyl and C$_{4-8}$ heterocycloalkyl, wherein the C$_{1-4}$ alkyl and C$_{4-8}$ heterocycloalkyl are each optionally substituted with 1-2 groups selected from C$_{1-4}$ alkyl, oxo, halo, and —(CH$_2$)$_{1-2}$Q wherein Q is OH, C$_{1-4}$ alkoxy, —CN, NH$_2$, —NHR$^3$, —N(R$^3$)$_2$, —SO$_2$R$^3$, NHSO$_2$R$^3$, or NHC(O)R$^3$;
or a pharmaceutically acceptable salt thereof.

In specific embodiments of these compounds, $Z^6$ is C=O, $Z^7$ is NR$^{20}$, and $Z^8$ is CH. In some such embodiments, L is —NH—C(=O)—; in alternative embodiments, L is —C(=O)NH—. In some of these embodiments, $Z^4$ is N; in alternative embodiments, $Z^4$ is CH. In some of these embodiments, $Z^9$ is N; in other embodiments, $Z^9$ is CH. In some of these embodiments, $R^{10}$ is trifluoromethyl. In preferred embodiments of these compounds, $R^1$ is methyl.

In another particular embodiment, the compound of Formula (I) is of this formula:

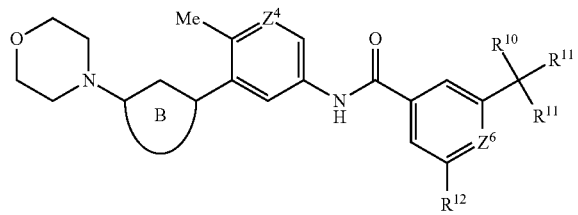

wherein $Z^4$ is CH or N;
$Z^6$ is CH or N;
$R^{10}$ is selected from F, CN, OH, —OMe, and —NMe$_2$;
each $R^{11}$ is independently selected from H, F, and Me;
$R^{12}$ is selected from H, halo, CF$_3$, and —CH$_2$R$^{13}$, where $R^{13}$ is selected from F, —OH, —OMe, NH$_2$, NHMe, NMe$_2$; and
Ring B is selected from

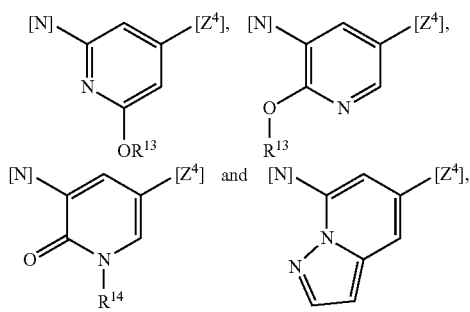

where [N] indicates the point of attachment of Ring B to the morpholine ring and [$Z^4$] indicates the point where Ring B is attached to the ring containing $Z^4$;
$R^{13}$ is selected from $C_{1-4}$ alkyl, tetrahydropyranyl, and $C_{1-4}$ haloalkyl, wherein the $C_{1-4}$ alkyl group is optionally substituted with up to three groups selected from halo, CN, —N(R$^{15}$)$_2$, and —OR$^{15}$;
$R^{14}$ is $C_{1-6}$ alkyl optionally substituted with up to three groups selected from halo, CN, —N(R$^{15}$)$_2$, and —OR$^{15}$; and
each $R^{15}$ is selected from H and Me,
including the pharmaceutically acceptable salts of these compounds.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$F, $^{32}$F, $^{35}$S, $^{36}$Cl, $^{125}$I respectively. The invention includes various isotopically labeled compounds as defined herein, for example those in which radioactive isotopes, such as $^3$H and $^{14}$C, or those in which non-radioactive isotopes, such as $^2$H and $^{13}$C, are present at levels significantly above the natural abundance for these isotopes. These isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by a Raf kinase such as B-Raf or C-Raf, or associated with activity of a kinase such as B-Raf or C-Raf, or (2) reduce or inhibit the activity of a kinase such as B-Raf or C-Raf in vivo.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of a kinase such as B-Raf or C-Raf, or at least partially reduce or alleviate a symptom or a condition associated with excessive Raf kinase activity.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions for compounds of Formula (I) are tablets or gelatin capsules comprising an active ingredient of Formula (I) together with at least one of the following pharmaceutically acceptable excipients:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in salt form, exhibit valuable pharmacological activities, e.g. they modulate or inhibit activity of A-Raf, B-Raf and/or C-Raf, as indicated by test data provided in the next sections, and are therefore indicated for therapy or for use as research chemicals, e.g. as tool compounds. These compounds are especially useful for treatment of cancers driven by mutations in the Raf/Raf/MEK/ERK pathway, including cancers characterized by an activating Raf mutation such as Raf V600E, including but not limited to melanoma (e.g., malignant melanoma), breast cancer, lung cancer (e.g., non-small cell lung cancer), sarcoma, GI tumors such as gastrointestinal stromal tumors, ovarian cancer, colorectal cancer, thyroid cancer, and pancreatic cancer.

Thus, as a further embodiment, the present invention provides the use of a compound of formula (I) or any of the embodiments within the scope of Formula (I) as described herein, in therapy. In a further embodiment, the therapy is for a disease which may be treated by inhibition of A-Raf, B-Raf or C-Raf. In another embodiment, the compounds of the invention are useful to treat cancers, including but not limited to melanoma, breast cancer, lung cancer, sarcoma, GI tumors such as gastrointestinal stromal tumors, ovarian cancer, colorectal cancer, thyroid cancer, and pancreatic cancer.

In another embodiment, the invention provides a method of treating a disease which is treatable by inhibition of A-Raf, B-Raf or C-Raf, or a combination thereof, comprising administration of a therapeutically effective amount of a compound of formula (I) or any of the embodiments within the scope of Formula (I) as described herein. In a further embodiment, the disease is selected from the afore-mentioned list, suitably melanoma, breast cancer, lung cancer, sarcoma, GI tumors such as gastrointestinal stromal tumors, ovarian cancer, colorectal cancer, thyroid cancer, and pancreatic cancer. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula (I) or any of the embodiments of such compounds described herein for the manufacture of a medicament. In a further embodiment, the medicament is for treatment of a disease which may be treated by inhibition of A-Raf, B-Raf or C-Raf. In another embodiment, the disease is a cancer, e.g., a cancer selected from the afore-mentioned list, including melanoma, breast cancer, lung cancer, sarcoma, GI tumors such as gastrointestinal stromal tumors, ovarian cancer, colorectal cancer, thyroid cancer, and pancreatic cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s) (co-therapeutic agents). Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like. The compound of the present invention may be administered separately, by the same or different route of administration, or together in the same pharmaceutical composition as the co-agent(s).

In one embodiment, the invention provides a product comprising a compound of formula (I) and at least one other therapeutic co-agent as a combined preparation for simultaneous, separate or sequential use in therapy. In one embodiment, the therapy is the treatment of a disease or condition mediated by B-Raf or C-Raf, such as cancer. Products provided as a combined preparation include a composition comprising the compound of formula (I) and the other therapeutic co-agent(s) together in the same pharmaceutical composition, or the compound of formula (I) and the other therapeutic co-agent(s) in separate form, e.g. in the form of a kit.

In one embodiment, the invention provides a pharmaceutical composition comprising a compound of formula (I) and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by B-Raf or C-Raf, wherein the medicament is prepared for administration with another therapeutic agent. The invention also provides the use of another therapeutic co-agent for treating a disease or condition, wherein the medicament is administered with a compound of formula (I).

The invention also provides a compound of formula (I) for use in a method of treating a disease or condition mediated by B-Raf or C-Raf, wherein the compound of formula (I) is prepared for administration with another therapeutic agent. The invention also provides another therapeutic co-agent for use in a method of treating a disease or condition mediated by B-Raf or C-Raf, wherein the other therapeutic co-agent is prepared for administration with a compound of formula (I). The invention also provides a compound of formula (I) for use in a method of treating a disease or condition mediated by B-Raf or C-Raf, wherein the compound of formula (I) is administered with another therapeutic co-agent. The invention also provides another therapeutic co-agent for use in a method of treating a disease or condition mediated by B-Raf or C-Raf, wherein the other therapeutic co-agent is administered with a compound of formula (I).

The invention also provides the use of a compound of formula (I) for treating a disease or condition mediated by B-Raf or C-Raf, wherein the patient has previously (e.g. within 24 hours) been treated with another therapeutic agent. The invention also provides the use of another therapeutic agent for treating a disease or condition mediated by B-Raf or C-Raf, wherein the patient has previously (e.g. within 24 hours) been treated with a compound of formula (I).

General Synthesis Methods

The following Schemes and Examples illustrate representative methods useful for making the compounds of Formula (I).

Compounds of Formula (I) where ring B is a pyrimidine can be prepared from known halopyrimidine intermediates, introducing ring C by a Suzuki or similar arylation reactions. The group -L-CY can be attached to Ring C before it is installed, or a protected amine can be present at the position corresponding to L for the Suzuki, and can be converted into the amide linker to form -L-CY after the Suzuki reaction.

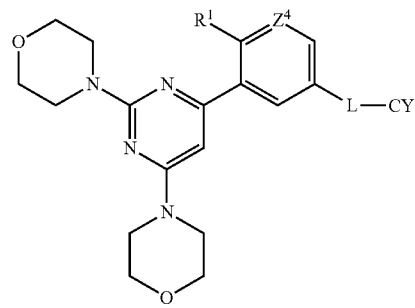

-continued

Scheme 1.

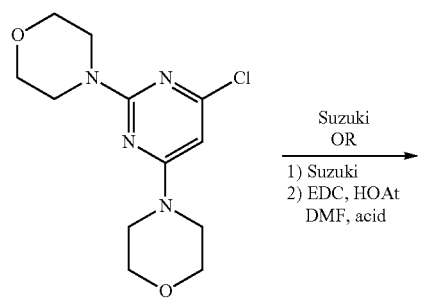

Compounds having different groups on Ring B, instead of two morpholine groups, can be prepared by using thioalkyl-substituted pyrimidines, as exemplified in the following scheme. A desired A-ring morpholine group (see Formula (I)) can be attached using nucleophilic aromatic substitution chemistry, and a Suzuki or similar arylation can be used to attach Ring C. The thioalkyl group can then be activated toward nucleophilic displacement by oxidation to an alkyl-sulfonyl group, which can be displaced by various nucleophilic groups.

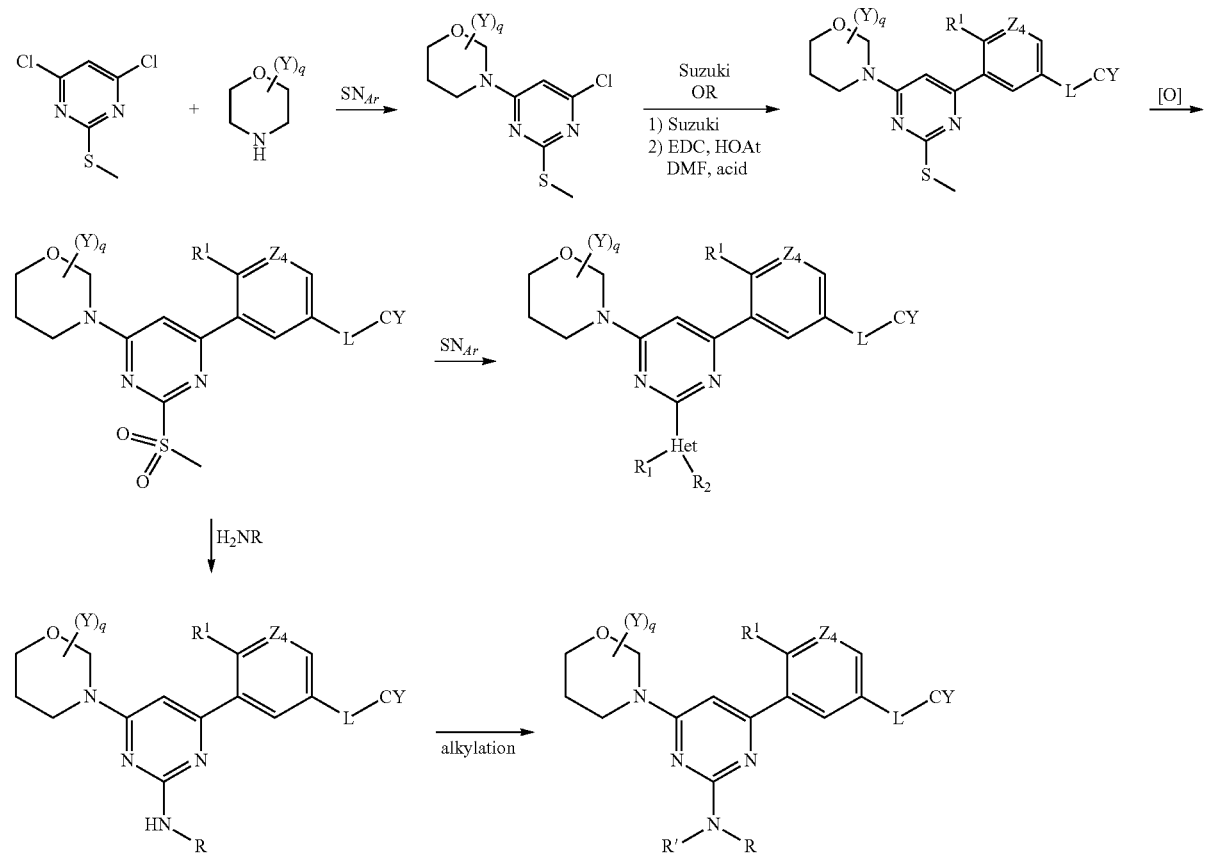

Scheme 2.

Alternatively, the oxidation can be done before the Suzuki reaction. This sequence can be used to install a heterocyclic or heteroaryl group on the B ring, or it can be used to introduce other nucleophiles such as alkoxy, amine or azide at this position. These can then be further modified as exemplified by amine alkylation (above) or, e.g., if azide is used as the nucleophile, a cycloaddition reaction can be used to make a heteroaryl substituent on Ring B as shown below.

Scheme 3.

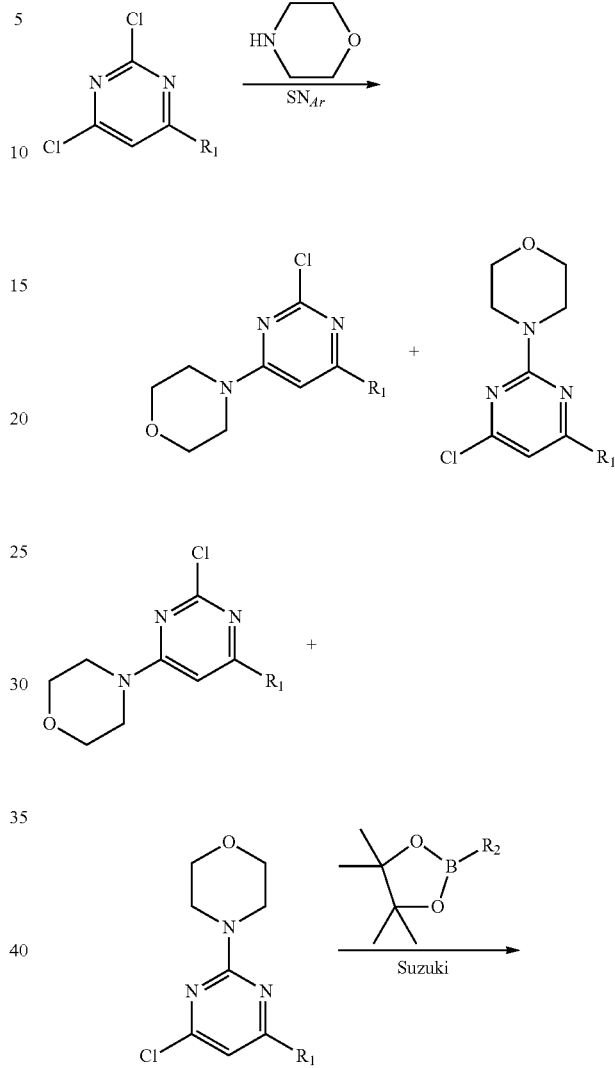

Other compounds of Formula (I) wherein Ring B is pyrimidine can be made from 2,4,6-trichloropyrimidine by starting with a Suzuki reaction to introduce one group ($R_1$), providing a mixture of isomeric products, as shown in Scheme 4. A morpholine A-ring can then be attached by aromatic nucleophilic substitution chemistry, followed by another Suzuki reaction.

Scheme 4.

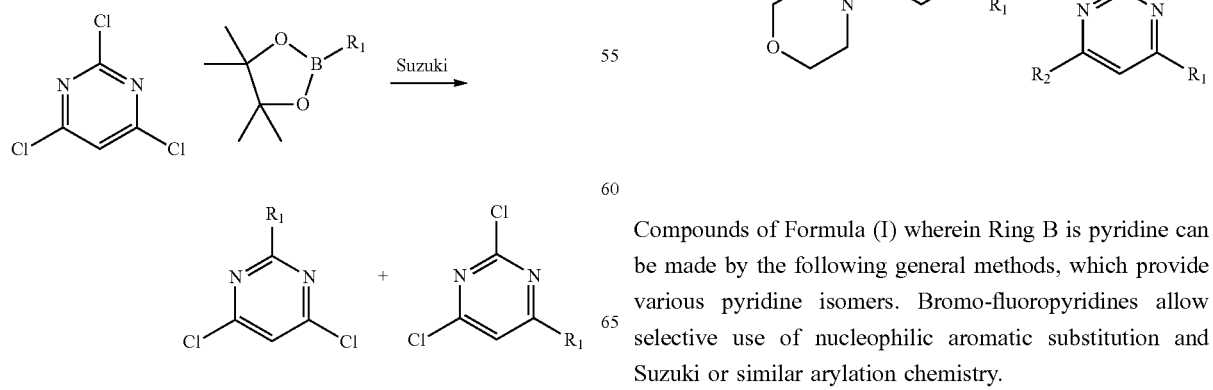

Compounds of Formula (I) wherein Ring B is pyridine can be made by the following general methods, which provide various pyridine isomers. Bromo-fluoropyridines allow selective use of nucleophilic aromatic substitution and Suzuki or similar arylation chemistry.

Scheme 5a.

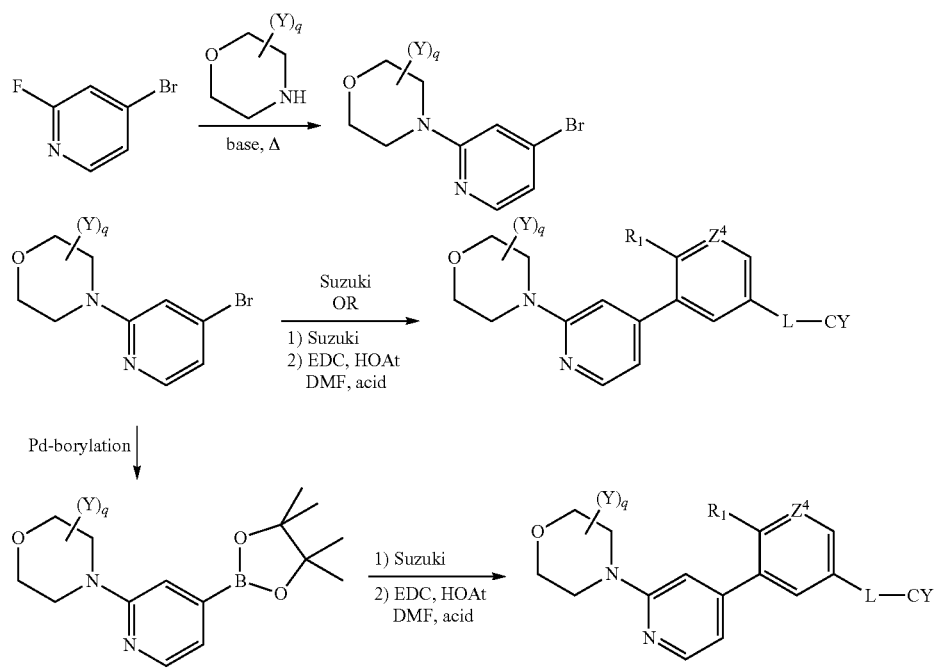

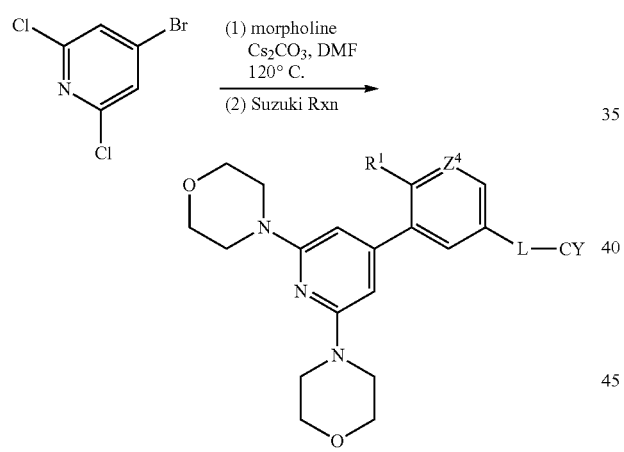

Scheme 5b.

Various other substituent groups can be introduced onto pyridinyl B-ring compounds by introducing only one optionally substituted morpholine on a 2,4,6-trihalopyridine, then sequentially replacing the other two halogens with suitable groups as illustrated in the following schemes. Scheme 6 illustrates introduction of an aryl or heteroaryl group on the B ring, using Suzuki chemistry; Scheme 7 illustrates use of aromatic nucleophilic substitution chemistry to introduce other nucleophilic substituents such as amines, alkoxy groups, and alkylthio groups.

Scheme 6.

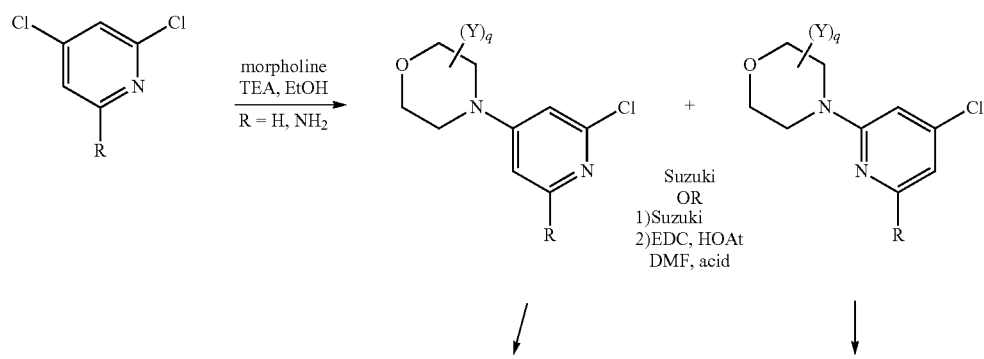

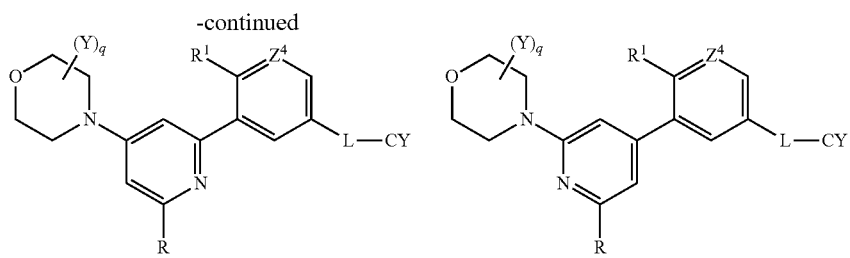
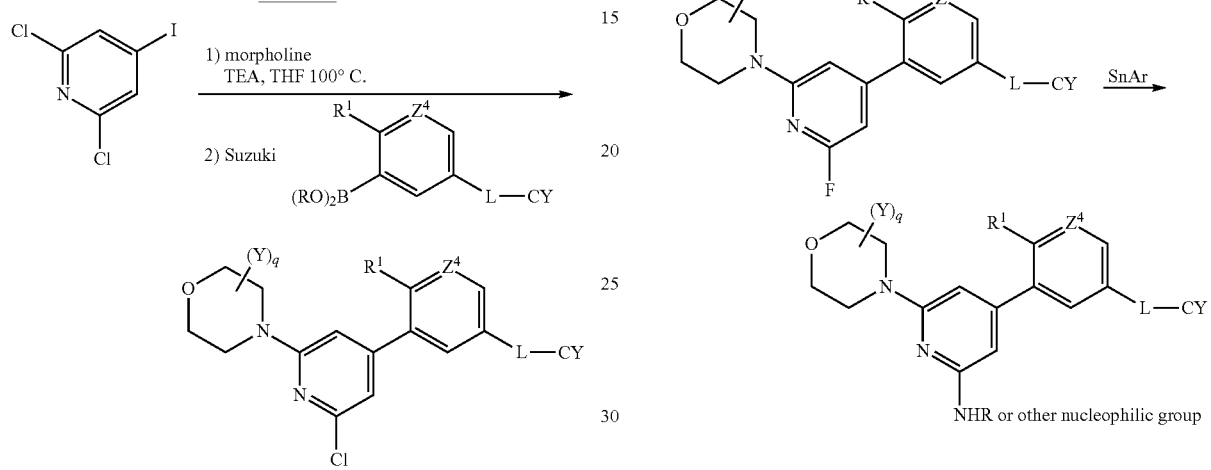
The following schemes illustrate additional routes to make compounds where ring B is pyridine, as demonstrated by the Examples below.
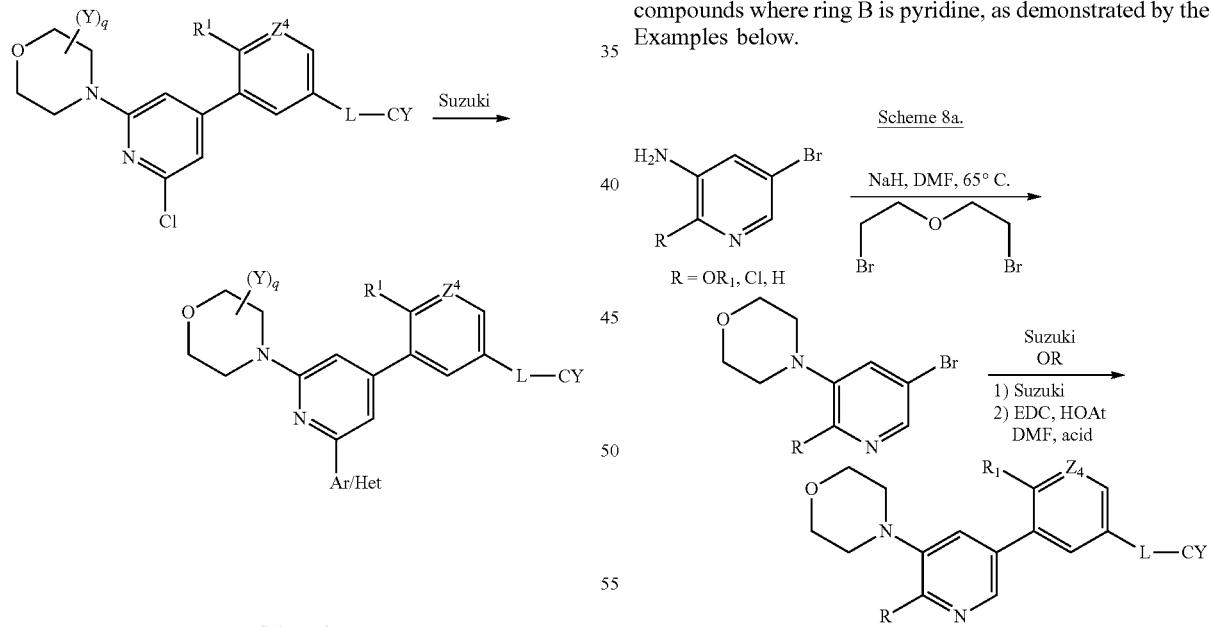
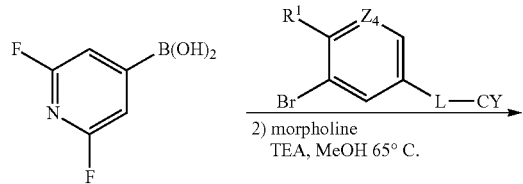
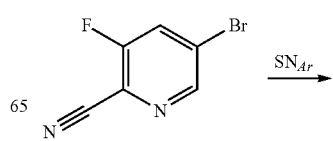

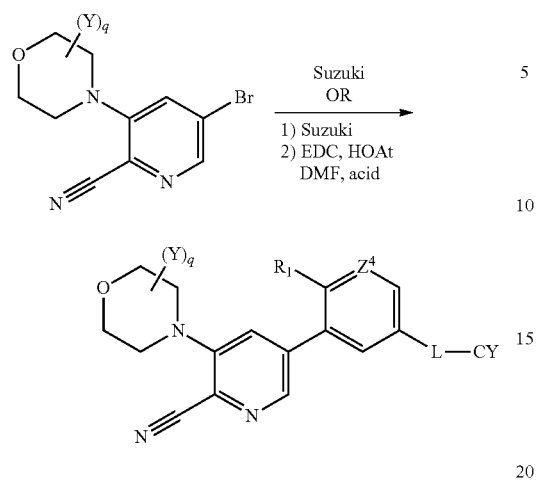
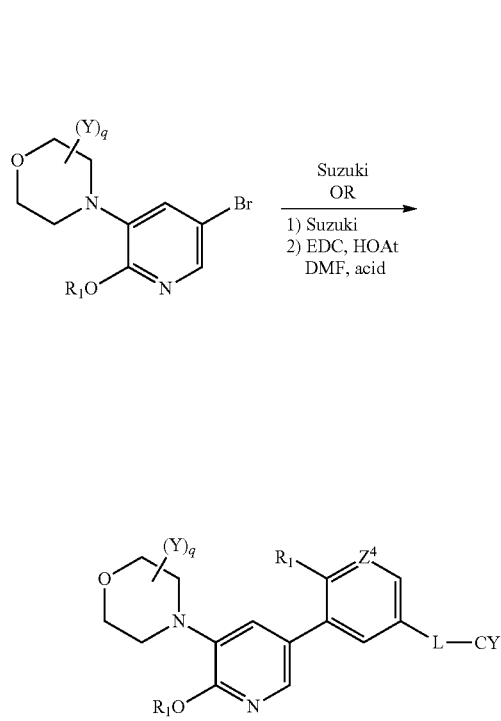
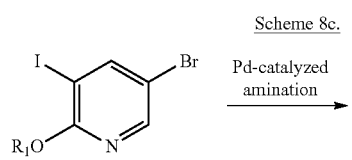
Scheme 8c.
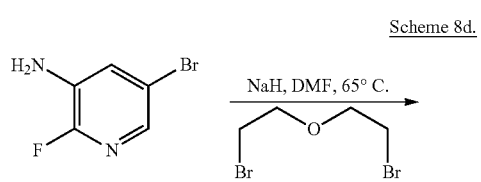
Scheme 8d.
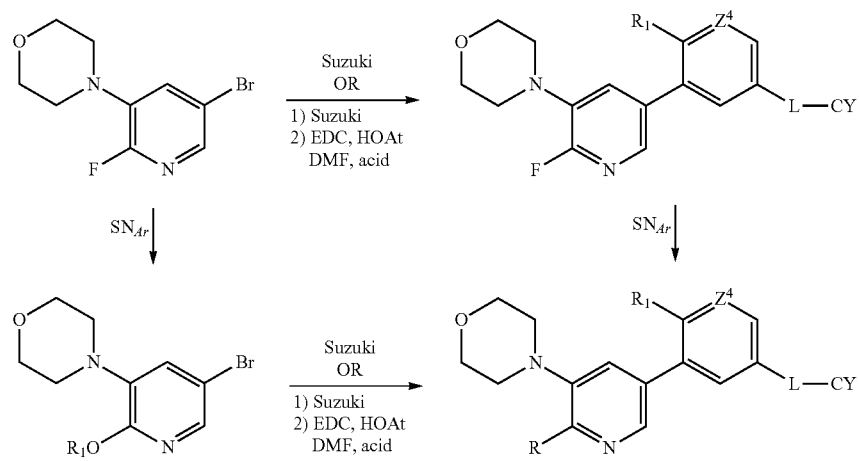

The following scheme illustrates a general route for synthesis of compound of Formula (I) wherein the B-ring is pyridone. The sequence also produces alkoxy-substituted pyridine B-ring compounds of Formula (I).

Scheme 9.

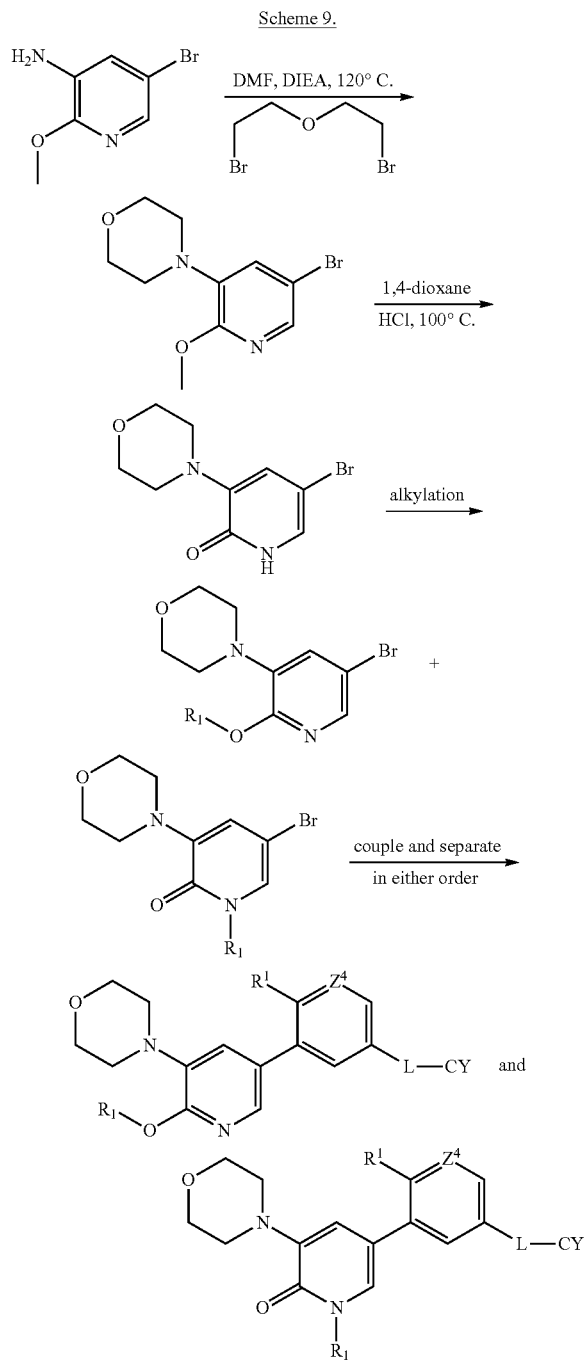

Compounds of Formula (I) wherein the B-ring is pyridazine can be made similarly, using known halogenated pyridazine starting materials with nucleophilic aromatic substitution reactions to attach Ring A (and/or other substituents on the B-ring), and Suzuki chemistry to attach Ring C.

Scheme 10.

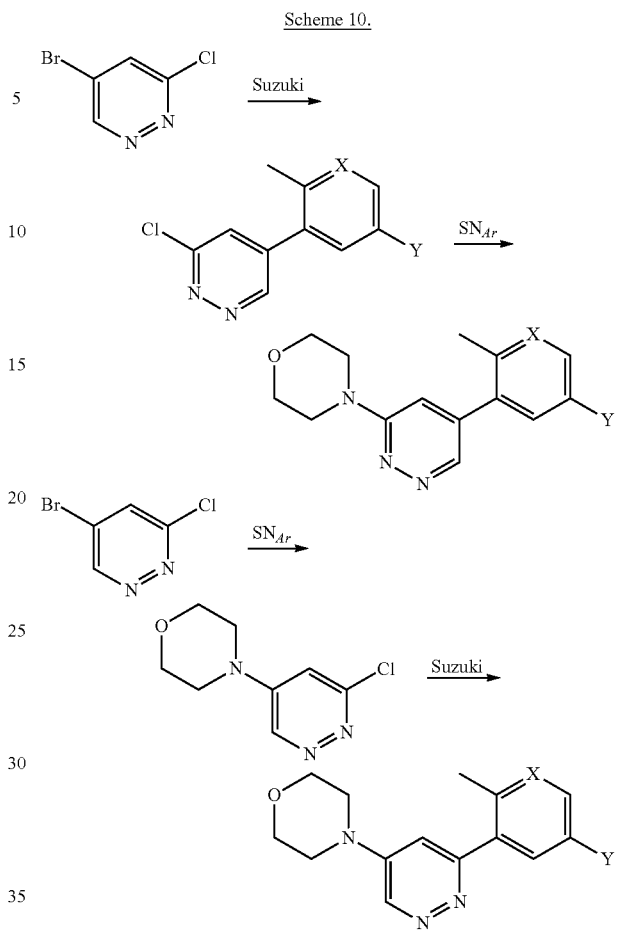

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralization of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Intermediates and final products can be worked up and/or purified according to standard methods, e.g. using chromatographic methods, distribution methods, (re-) crystallization, and the like.

Compounds of the invention and intermediates can also be converted into each other according to methods generally known to those skilled in the art.

Terms used herein have their ordinary meaning to those of skill in the art unless otherwise defined. The following abbreviations may be used herein:

| | |
|---|---|
| DAST | (diethylamino)sulfurtrifluoride |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| HOBt | Hydroxybenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$-DCM | Dichloro-(1,2-bis(diphenylphosphino)ethan)-Palladium(II)-dichloromothethane adduct |
| RT or rt | room temperature |
| TBDMSCl | tert-butyldimethylsilylchloride |
| TEA | Triethylamine |
| THF | tetrahydrofuran |

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Mass spectrometric analysis was performed on LCMS instruments: Waters System (Acuity UPLC and a Micromass ZQ mass spectrometer; Column: Acuity HSS C18 1.8-micron, 2.1×50 mm; gradient: 5-95% acetonitrile in water with 0.05% TFA over a 1.8 min period; flow rate 1.2 mL/min; molecular weight range 200-1500; cone Voltage 20 V; column temperature 50° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

Compounds of the invention can be prepared using methods known in the art, along with methods disclosed herein, starting with known materials.

The syntheses of certain intermediates are outlined here, followed by description of syntheses of examples of compounds of Formula (I).

Synthesis of 4-(2-cyanopropan-2-yl)picolinic acid

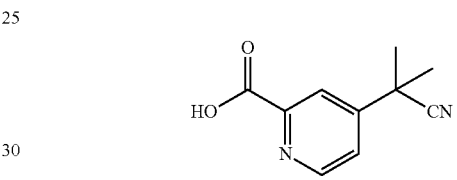

To a suspension of 4-chloropicolinic acid (1.0 equiv.) in THF (0.95 M) at rt was added isobutyronitrile (3.2 equiv.) and LiHMDS (1M solution in THF, 3.1 equiv.). The mixture was stirred at 100° C. for 10 min in the microwave. The cooled solution was quenched with sat. ammonium chloride and acidified with 6N HCl to pH=4. The solution was extracted with IPA/Chloroform (1:3) three times. The combined organic layer was washed with brine, dried over sodium sulfate, filtered and concentrated to give 4-(2-cyanopropan-2-yl)picolinic acid in 72% yield. $^1$H NMR (400 MHz, <dmso>) δ ppm 1.71 (s, 6H) 7.76 (dd, J=5.48, 1.96 Hz, 1H) 8.12 (d, J=1.57 Hz, 1H) 8.73 (d, J=5.09 Hz, 1H). LCMS m/z (M+H)=190.9, Rt=0.31 min.

Synthesis of 4-(2-hydroxypropan-2-yl)picolinic acid

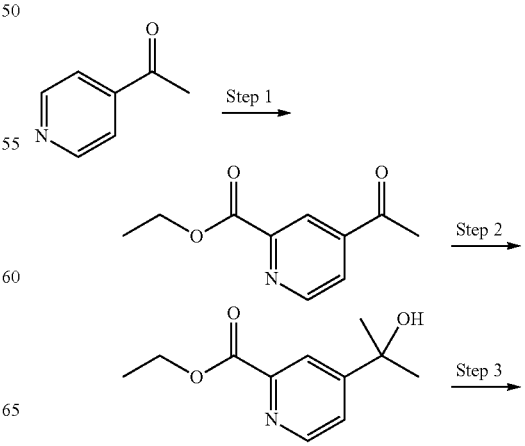

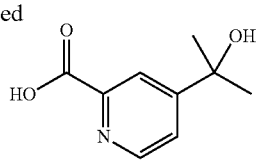

Step 1:

To a solution of ethyl 2-oxopropanoate (15 equiv.) at 0° C. was added dropwise $H_2O_2$ (10 equiv.). The cold mixture (still stirred at 0° C.) was cannulated into a mixture of 1-(pyridin-4-yl)ethanone (1.0 equiv.), $H_2SO_4$ (1.0 equiv.) and $FeSO_4 \cdot 7H_2O$ (10 equiv.) in DCM/water (15:1, 0.08 M) at rt over 3 h. The resulting reaction mixture was stirred at rt for additional 30 min. The aqueous layer was extracted with DCM and the combined organic DCM layers were washed with 5% sodium sulfite, brine, dried over sodium sulfate and concentrated. Purification via silica gel column chromatography (ISCO, 0-60% EtOAc/Heptane) gave ethyl 4-acetylpicolinate in 46% yield. LCMS m/z (M+H)=193.9, Rt=0.51 min.

Step 2:

Ethyl 4-acetylpicolinate (1.0 equiv.) was dissolved in THF (0.1 M) and the solution was cooled to −78° C. Methyllithium (1.2 equiv.) was added over the period of 5 min and the mixture was stirred at −78° C. for an additional 5 min. The reaction was poured into ice-water and extracted twice with ethyl acetate. The organic layer was washed with brine, dried over sodium sulfate, filtered and concentrated. The residue was purified via silica gel chromatography (ISCO, 0-100% ethyl acetate/heptanes) to give ethyl 4-(2-hydroxypropan-2-yl)picolinate in 47% yield. LCMS m/z (M+H)=210.2, Rt=0.43 min.

Step 3:

To a solution of ethyl 4-(2-hydroxypropan-2-yl)picolinate (1.0 equiv.) in THF (0.13 M) was added LiOH (3.0 equiv.). The mixture was stirred at rt for 4 hr. Concentrated to remove most of THF and the residue was neutralized with 6 N HCl to pH=3. Dilute the mixture with water and MeCN, then lyophilized give 4-(2-hydroxypropan-2-yl)picolinic acid containing 3.0 equiv. of LiCl. LCMS m/z (M+H)=181.9, Rt=0.18 min.

Synthesis of 4-(2-fluoropropan-2-yl)picolinic acid

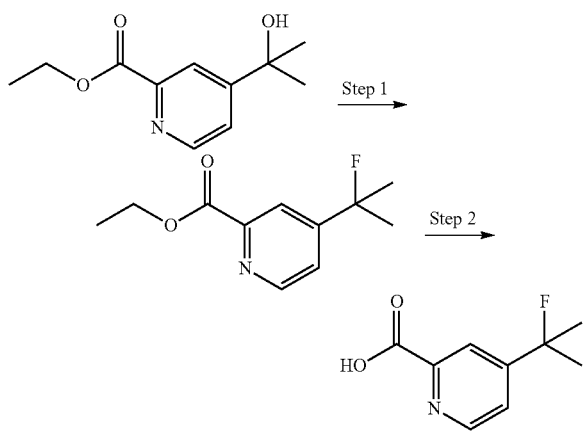

Step 1:

To a solution of ethyl 4-(2-hydroxypropan-2-yl)picolinate (1.0 equiv.) in DCM (0.1 M) at −78° C. was added DAST (1.2 equiv.). The mixture was stirred at −78° C. for 1 h and warmed up to rt and stirred at rt for 1 h. LC-Ms indicated completed conversion. An aqueous saturated $NaHCO_3$ solution was added and the mixture was stirred for 15 minutes, then the mixture was extracted with EtOAc. The organic layer was washed with brine, dried over sodium sulfate and concentrated to give ethyl 4-(2-fluoropropan-2-yl)picolinate in 98% yield. LCMS m/z (M+H)=211.9, Rt=0.69 min.

Step 2:

To a solution of ethyl 4-(2-fluoropropan-2-yl)picolinate (1.0 equiv.) in THF (0.19 M) was added LiOH (3.8 equiv.). The mixture was stirred at rt for 4 hr. Concentrated to remove most of THF and the residue was neutralized with 6 N HCl to pH=3 and extracted with EtOAc. The organic layer was washed with brine, dried over sodium sulfate and concentrated to yield 4-(2-fluoropropan-2-yl)picolinic acid in 71% yield. LCMS m/z (M+H)=183.9, Rt=0.32 min.

Synthesis of 4-(1,1-difluoroethyl)picolinic acid

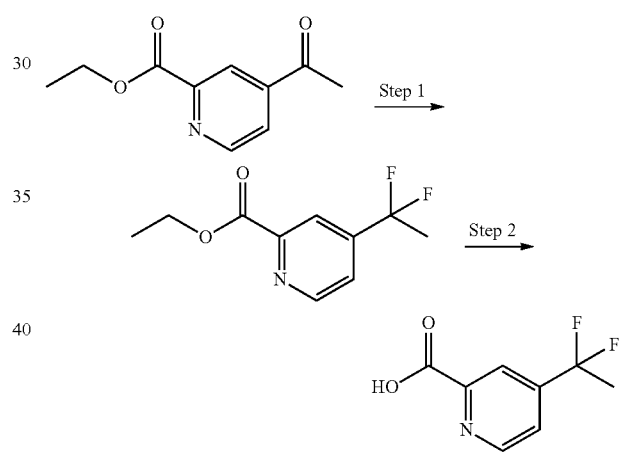

Step 1:

A solution of ethyl 4-acetylpicolinate (1.0 equiv.) in 1.0 equiv. of DeoxoFluor (50% in toluene) was stirred for 12 h at 85° C. The reaction mixture was then added to a NaCl(sat) solution. The aqueous mixture was extracted with EtOAc. The organics were dried, and the resulting material was purified by column chromatography utilizing an ISCO system (heptane-EtOAc) to yield ethyl 4-(1,1-difluoroethyl)picolinate in 72% yield. LCMS m/z (M+H)=216.1, Rt=0.70 min.

Step 2:

To a solution of ethyl 4-(1,1-difluoroethyl)picolinate (1.0 equiv.) in THF (0.2 M) was added LiOH (3.9 equiv.). The mixture was stirred at rt for 4 hr. Concentrated to remove most of THF and the residue was neutralized with 6N HCl to pH=3 and extracted with EtOAc. The organic layer was washed with brine, dried with sodium sulfate and concentrated to yield 4-(1,1-difluoroethyl)picolinic acid in 86% yield. LCMS m/z (M+H)=187.9, Rt=0.41 min.

Synthesis of 3-(S-methylsulfonimidoyl)benzoic acid

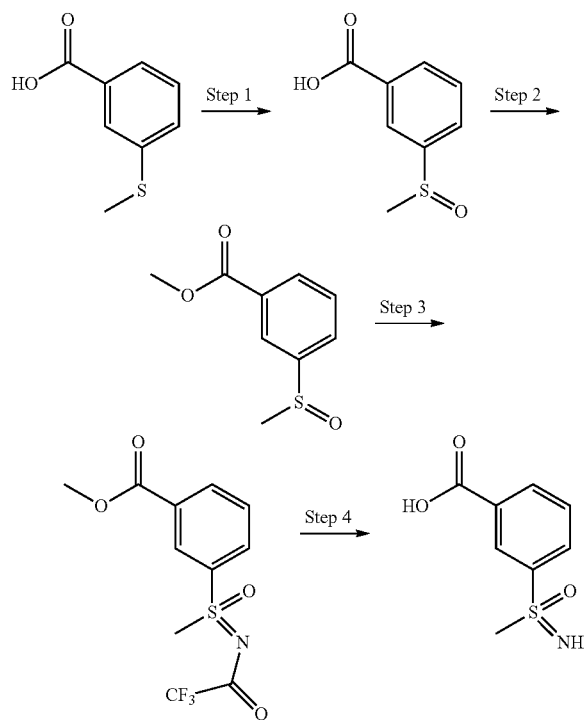

Step 1:

A solution of NaIO$_4$ (1.0 equiv.) in Water (0.11 M) was prepared and then added dropwise to a stirred solution of 3-(methylthio)benzoic acid (1.0 equiv.) in MeOH (0.11 M) at 0° C. After the addition was complete the mixture was allowed to warm to 25° C. and stirred for 1 h. LCMS shows about 20% complete, clean conversion to product. Stirring was continued at 25° C. overnight. The reaction mixture was filtered, the filter cake washed with MeOH. The filtrate was concentrated to a peach solid and 3-(methylsulfinyl)benzoic acid was obtained in quantitative yield. LCMS (m/z) (M+H)=185.1, Rt=0.35 min.

Step 2:

To solution of 3-(methylsulfinyl)benzoic acid (1.0 equiv.) in THF (0.2 M) at 25° C. was added CDI (1.2 equiv.) and the mixture was stirred for 15 min. MeOH (8.0 equiv.) was then added and the reaction was briefly warmed to near reflux and then allowed to cool back to room temperature. LCMS shows about near complete, clean conversion to product. The reaction mixture was poured onto a mix of saturated aqueous sodium bicarbonate and brine and extracted two times with ethyl acetate. The combined organics were washed with brine, dilute HCl, and brine again, and then dried over magnesium sulfate, filtered, and concentrated. The crude reside was purified by Grace flash column chromatography over silica gel eluting with heptane and 0-100% EtOAc gradient. Product fractions elute around 75% EtOAc and were concentrated to give methyl 3-(methylsulfinyl) benzoate as a pale yellow oil in 70% yield. $^1$H NMR (400 MHz, <cdcl3>) δ ppm 2.76 (s, 3H) 3.96 (s, 3H) 7.65 (t, J=7.83 Hz, 1H) 7.90 (d, J=7.83 Hz, 1H) 8.18 (d, J=7.83 Hz, 1H) 8.28 (s, 1H). LCMS (m/z) (M+H)=198.9, Rt=0.47 min.

Step 3:

To solution of methyl 3-(methylsulfinyl)benzoate (1.0 equiv.) in DCM (0.1 M) at 25° C. under Ar were added 2,2,2-trifluoroacetamide (2.0 equiv.), MgO (4.0 equiv.), rhodium(II) acetate dimer (0.05 equiv.), and diacetoxyiodobenzene (1.5 equiv.) and the mixture was stirred overnight. LCMS shows near complete consumption of starting material and clean conversion to product (M+1=310, R$_t$=0.76). The reaction mixture was filtered through Celite, washing with DCM, and concentrated. The residue was purified by Grace flash column chromatography over silica gel, eluting with heptane and 0-75% EtOAc gradient. Product fractions elute around 40% EtOAc and were concentrated to give methyl 3-(S-methyl-N-(2,2,2-trifluoroacetyl)sulfonimidoyl) benzoate in 90% yield as a colorless oil. $^1$H NMR (400 MHz, <cdcl3>) δ ppm 3.50 (s, 3H) 4.00 (s, 3H) 7.78 (t, J=8.02 Hz, 1H) 8.17-8.23 (m, 1H) 8.41 (d, J=7.83 Hz, 1H) 8.63 (s, 1H). LCMS (m/z) (M+H)=310.0, Rt=0.76 min.

Step 4:

To a stirred solution of methyl 3-(S-methyl-N-(2,2,2 trifluoroacetyl)sulfonimidoyl)benzoate (1.0 equiv.) in THF and MeOH (2:1, 0.09 M) at 25° C. was added LiOH (2 M aq.) (3.5 equiv.) and the mixture was stirred for 3 h. LCMS shows complete consumption of starting material and clean conversion to product. Most of the THF/MeOH was removed by concentration and then the mixture was acidified using 1 M HCl. Product could not be extracted from the aqueous with organic solvents, so the acidic aqueous layer was diluted with some acetonitrile and then lyophilized to give 3-(S-methylsulfonimidoyl)benzoic acid as a white solid which likely contains approx. 3.5 eq of LiCl. This calculates to a 99% calculated yield of desired product. LCMS (m/z) (M+H)=199.9, Rt=0.25 min

Synthesis of 3-(2,2,2-trifluoro-1-hydroxyethyl)benzoic acid

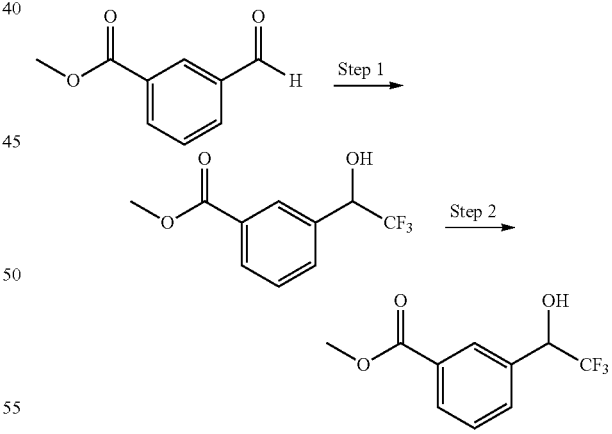

Step 1:

Trimethyl(trifluoromethyl)silane (1.3 quiv.) and cesium fluoride (0.1 equiv.) were added to a solution of methylformylbenzoate (1.0 equiv.) in THF (0.3 M) at room temperature under nitrogen and the mixture was sonicated for 30 min to initiate the reaction, which was indicated by the appearance of a pale yellow colour. The mixture was stirred at room temp for 5 h, after which HCl(aq) (1 M) was added and the mixture stirred for a further 15 min. The mixture was then extracted with EtOAc, washed (saturated NaHCO$_3$, brine), dried (MgSO$_4$) and evaporated in vacuo. The product was purified by ISCO and eluted with 0 to 70% ethyl acetate in heptane to give methyl 3-(2,2,2-trifluoro-1-hydroxyethyl) benzoate in 81% yield. LCMS (m/z) (M+H)=234.9, Rt=0.74 min.

Step 2:

Lithium hydroxide (5.0 equiv, 2M aqueous solution) was added to methyl 3-(2,2,2-trifluoro-1-hydroxyethyl)benzoate (1.0 equiv.) in Acetonitrile and Water (2:1, 0.001M) at 0° C. and then the mixture was brought to RT and stirred for 6 h. The mixture was acidified with 1N HCl and extracted with ethyl acetate to give 3-(2,2,2-trifluoro-1-hydroxyethyl)benzoic acid in 91% yield. LCMS (m/z) (M+H)=219.1, Rt=0.3 min.

Synthesis of
5-fluoro-2-(trifluoromethyl)pyridin-4-amine

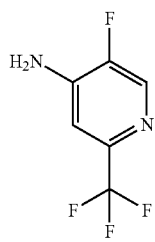

2-(trifluoromethyl)pyridin-4-amine (1.0 equiv.) was dissolved in ACN (0.06). Selectfluor (2.2 equiv.) was added and the reaction mixture was stirred at rt for 2 days. Sat. sodium bicarbonate solution added to quench reaction, partitioned with ethyl acetate, the organic phase was concentrated to dryness and purified by ISCO flash chromatograph (0-70% ethyl acetate in heptane) to yield 5-fluoro-2-(trifluoromethyl)pyridin-4-amine in 23% yield. $^1$H NMR (400 MHz, <cdcl3>) δ ppm 4.52 (br. s., 2H) 6.97-7.16 (m, 1H) 8.27 (d, J=2.35 Hz, 1H).

Synthesis of 2-(1,1-difluoroethyl)pyridin-4-amine

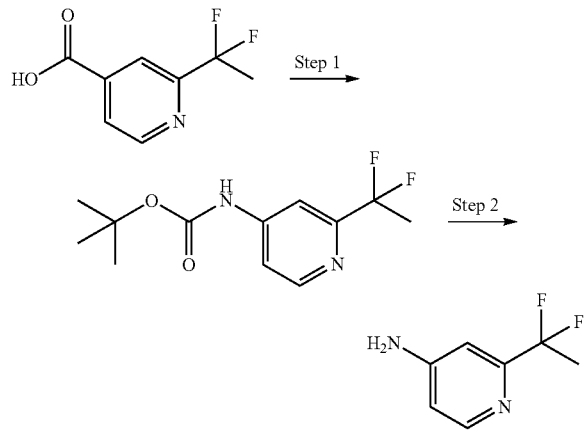

Step 1:

To a solution of 2-(1,1-difluoroethyl)isonicotinic acid (1.0 equiv.) in Dioxane (0.3 M) was added diphenyl phosphoryl azide (1.8 equiv.), t-butyl alcohol (6.0 equiv.), and TEA (1.8 equiv.). The rxn was degassed for 1 min, then heated at 110° C. for 3.0 hr. The dioxane was evaporated in vacuo, and the residue partioned between EtOAc and 10% citric acid. The organic layer was separated and the aqueous layer further extracted with EtOAc. The combined organics were dried over Na$_2$SO$_4$, filtered and concentrated. The crude was loaded onto silica gel and purified by column chromatography (ISCO, 0-50% EtOAc in Heptanes). Pure fractions were combined and concentrated to yield tert-butyl(2-(1,1-difluoroethyl)pyridin-4-yl)carbamate in 44% yield as a clear oil. LCMS (m/z) (M+H)=259, Rt=0.68.

Step 2:

To a solution of tert-butyl(2-(1,1-difluoroethyl)pyridin-4-yl)carbamate (1.0 equiv.) in DCM (0.25 M) was added TFA (10 equiv.) and allowed to stir at RT for 6 hrs. The volatiles were removed in vacuo, and the residue was taken up in DCM and pushed through a carbonate column to remove the TFA salt, the column was washed several times with DCM. The combined organics were concentrated to yield 2-(1,1-difluoroethyl)pyridin-4-amine in 54% yield. LCMS (m/z) (M+H)=158.9, R$_t$=0.29.

Synthesis of N-(4-methyl-3-(4,4,5,5-tetramethyl-1,3,2-dioxaborolan-2-yl)phenyl)-3-(trifluoromethyl)benzamide Intermediate A

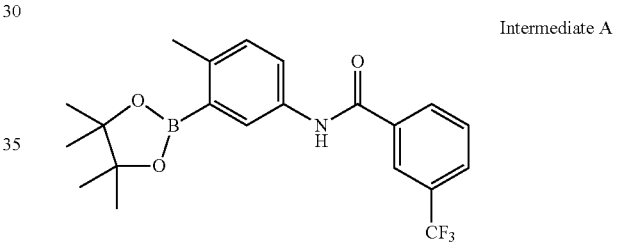

To a solution of 4-methyl-3-(4,4,5,5-tetramethyl-1,3,2-dioxaborolan-2-yl)aniline (1.0 equiv.) in THF (0.1 M) at 0° C. was added 3-trifluoromethylbenzoylchloride (1.0 equiv.) and the reaction was stirred at room temperature for 3 h. The solution was concentrated and dried under vacuo to give N-(4-methyl-3-(4,4,5,5-tetramethyl-1,3,2-dioxaborolan-2-yl)phenyl)-3-(trifluoromethyl)benzamide as a tan solid in 96% yield. LCMS (m/z) (M+H)=406.2, Rt=1.24 min.

Synthesis of N-(6-methyl-5-(4,4,5,5-tetramethyl-1,3,2-dioxaborolan-2-yl)pyridin-3-yl)-3-(trifluoromethyl)benzamide

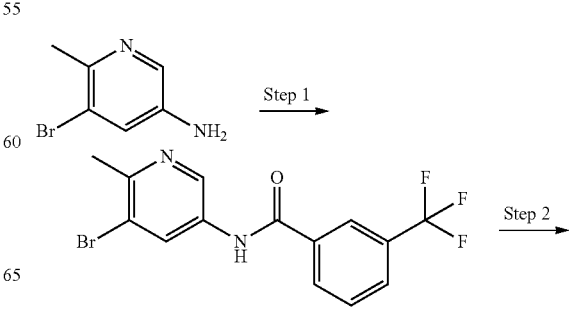

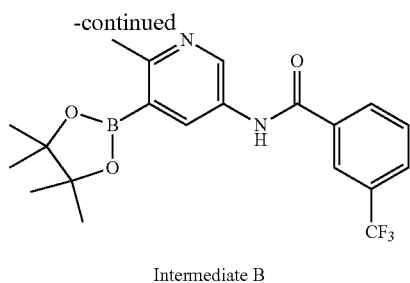

Intermediate B

Step 1:

To a 0.4 M solution of 5-bromo-6-methylpyridin-3-amine (1.00 equiv.) in DCM was added DIEA (1.00 equiv.) and 3-(trifluoromethyl)benzoyl chloride (1.00 equiv.). The mixture was stirred at ambient temperature for 3 hr. The reaction mixture was diluted with DCM, washed with saturated aqueous sodium bicarbonate, dried over sodium sulfate, filtered, and concentrated to give N-(5-bromo-6-methylpyridin-3-yl)-3-(trifluoromethyl)benzamide as an off-white solid in 98% yield. LCMS (m/z) (M+H)=359.0/361.0, Rt=0.86 min.

Step 2:

To a 0.27 M solution N-(5-bromo-6-methylpyridin-3-yl)-3-(trifluoromethyl)benzamide (1.00 equiv.) in 1,4-dioxane was added bis(pinacolato)diboron (1.50 equiv.), potassium acetate (2.00 equiv.) and PdCl$_2$(dppf).CH$_2$Cl$_2$ adduct (0.10 equiv.). The reaction was irradiated at 120° C. for 20 min. The cooled reaction mixture was diluted with ethyl acetate and filtered through Celite. The filtrate was concentrated to give N-(6-methyl-5-(4,4,5,5-tetramethyl-1,3,2-dioxaborolan-2-yl)pyridin-3-yl)-3-(trifluoromethyl)benzamide as a dark brown tacky solid in quantitative yield. LCMS (m/z) (M+H)=325.0, Rt=0.59 min.

Synthesis of 2-(2-cyanopropan-2-yl)-N-(4-methyl-3-(4,4,5,5-tetramethyl-1,3,2-dioxaborolan-2-yl)phenyl) isonicotinamide Step 1:

To a mixture of 2-fluoro-4-methylpyridine (1.0 equiv.) and isobutyronitrile (4.0 equiv.) was cannulated KHMDS (1.2 equiv.) in toluene. The mixture was heated to reflux for 1.5 hours at which time the reaction was cooled to RT, quenched with NH$_4$Cl (aq), extracted with EtOAc, dried over Na$_2$SO$_4$, filtered, and concentrated. The crude material was used in next step. LCMS (m/z) (M+H)=161.1, Rt=0.48 min.

Step 2:

To a solution of 2-methyl-2-(4-methylpyridin-2-yl)propanenitrile (1.0 equiv.) in water (0.38 M) was added potassium permanganate (6.0 equiv.). The mixture was heated at 60° C. for 1 hr. The mixture was cooled to rt, acidified with 2 M HCl to pH 4 and extracted with EtOAc. The organic layer was washed with brine, dried over Na$_2$SO$_4$ and concentrated. LC-MS showed the crude yellowish solid still contained 15% of diacid. Redissolved the crude in EtOAc and washed with acidic water (pH 4). The organic layer was washed with brine, dried over Na$_2$SO$_4$ and concentrated to yield off white solid. NO diacid left. Used as is in next step. LCMS (m/z) (M+H)=191.0, Rt=0.53 min.

Step 3:

EDC (1.3 equiv.) was added to a solution of 4-methyl-3-(4,4,5,5-tetramethyl-1,3,2-dioxaborolan-2-yl)aniline (1.0 equiv.), 2-(2-cyanopropan-2-yl)isonicotinic acid (1.2 equiv.), HOAt (1.3 equiv.) in DMF (0.19 M). The mixture was stirred at ambient temperature 3 hrs. The reaction mixture was diluted with water and extracted with ethyl acetate. The combined extracts were washed sequentially with 1M aqueous sodium hydroxide and brine, dried over sodium sulfate, filtered, and concentrated to yield 2-(2-cyanopropan-2-yl)-N-(4-methyl-3-(4,4,5,5-tetramethyl-1,3, 2-dioxaborolan-2-yl)phenyl)isonicotinamide in 97% yield. LCMS (m/z) (M+H)=406.2, Rt=1.10 min.

Synthesis of N-(4-methyl-3-(4,4,5,5-tetramethyl-1,3, 2-dioxaborolan-2-yl)phenyl)-3-(trifluoromethyl) benzamide

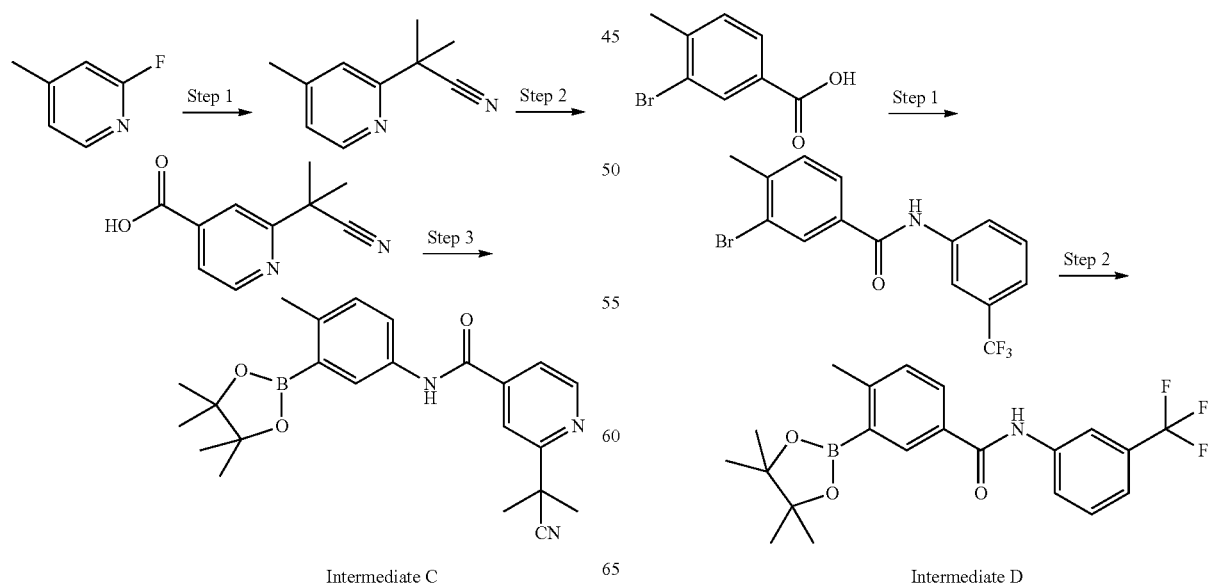

Intermediate C

Intermediate D

Step 1:

To a solution of 3-bromo-4-methylbenzoic acid (1.0 equiv.) in DMF (1.2M) was added EDC (1.0 equiv.) and HOBt (1.0 equiv.) followed by 3-trifluoromethylaniline (1.0 equiv.) and the reaction was stirred at ambient temperature for 48 h. The reaction mixture was partitioned between ethyl acetate and water. The separated organic layer was dried with sodium sulfate and concentrated under vacuo. The concentrated crude was purified via silica gel chromatography and eluted with 0 to 100% ethyl acetate in heptanes to give 3-bromo-4-methyl-N-(3-(trifluoromethyl)phenyl)benzamide in 83% yield. LCMS (m/z) (M+H)=358/360, Rt=1.1 min.

Step 2:

To 3-bromo-4-methyl-N-(3-(trifluoromethyl)phenyl)benzamide (1.0 equiv.) in a microwave vial equipped with a stir bar was added dioxane (0.5M) was added 4,4,4',4',5,5,5',5'-octamethyl-2,2'-bi(1,3,2-dioxaborolane) (3 equiv.) and potassium acetate (6 equiv.) and nitrogen was bubbled through the reaction mixture for 5 min. To it was added PdCl$_2$(dppf)-DCM adduct (0.1 equiv) and the vial was sealed and heated to 120° C. for 16 h. The reaction mixture was filtered and the filter paper was washed with dichloromethane and the filtrate was concentrated under vacuo. It was then loaded on celite and purified via silica gel chromatography eluting with 0-100% ethyl acetate in heptanes to afford N-(4-methyl-3-(4,4,5,5-tetramethyl-1,3,2-dioxaborolan-2-yl)phenyl)-3-(trifluoromethyl)benzamide in quantitative yield. LCMS (m/z) (M+H)=406.2, Rt=1.2 min.

Synthesis of N-(4-methyl-3-(4,4,5,5-tetramethyl-1,3,2-dioxaborolan-2-yl)phenyl)-2-(trifluoromethyl)isonicotinamide Intermediate E

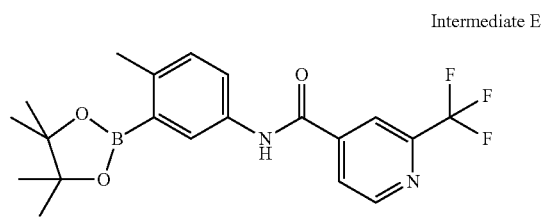 [SMILES: Cc1ccc(NC(=O)c2ccnc(C(F)(F)F)c2)cc1B1OC(C)(C)C(C)(C)O1]

To a mixture of 4-methyl-3-(4,4,5,5-tetramethyl-1,3,2-dioxaborolan-2-yl)aniline (1.0 equiv.) and 3-(trifluoromethyl)benzoic acid (1.1 equiv.) in DMF (0.27 M) was added HOAt (1.3 equiv.) and EDC (1.3 equiv.) After 3 h the reaction mixture was diluted with water and then extracted with EtOAc. The organic phase was washed sequentially with 1 M aqueous sodium hydroxide and brine and was then dried over sodium sulfate. The solution was concentrated and dried under vacuo to give N-(4-methyl-3-(4,4,5,5-tetramethyl-1,3,2-dioxaborolan-2-yl)phenyl)-2-(trifluoromethyl)isonicotinamide in 91% yield. LCMS (m/z) (M+H)= 407.1, Rt=1.13 min.

2-(tert-butyl)-N-(4-methyl-3-(4,4,5,5-tetramethyl-1,3,2-dioxaborolan-2-yl)phenyl)isonicotinamide Intermediate F

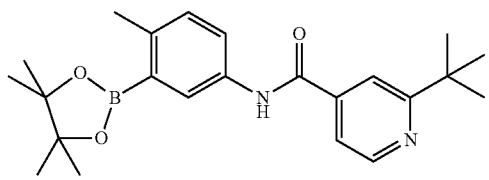

A solution of 5-amino-2-methylphenylboronic acid, pinacol ester (1.0 equiv.), 2-(tert-butyl)isonicotinic acid (1.0 equiv.), EDC (1.0 equiv.) and 1-hydroxy-7-azabenzotriazole (0.380 g, 1.0 equiv.) in DMF (0.3 M) was stirred at RT for 68 hr. The reaction mixture was then diluted with EtOAc and water, the organic layer was isolated and the aqueous layer was extracted twice with EtOAc. The combined organics were dried over MgSO$_4$, filtered and concentrated in vacuo to yield 2-(tert-butyl)-N-(4-methyl-3-(4,4,5,5-tetramethyl-1,3,2-dioxaborolan-2-yl)phenyl)isonicotinamide as a white solid in 91%. LCMS (m/z) (M+H)=395.1, Rt=0.71 min.

Synthesis of 2-(2-cyanopropan-2-yl)-N-(6-methyl-5-(4,4,5,5-tetramethyl-1,3,2-dioxaborolan-2-yl)pyridin-3-yl)isonicotinamide

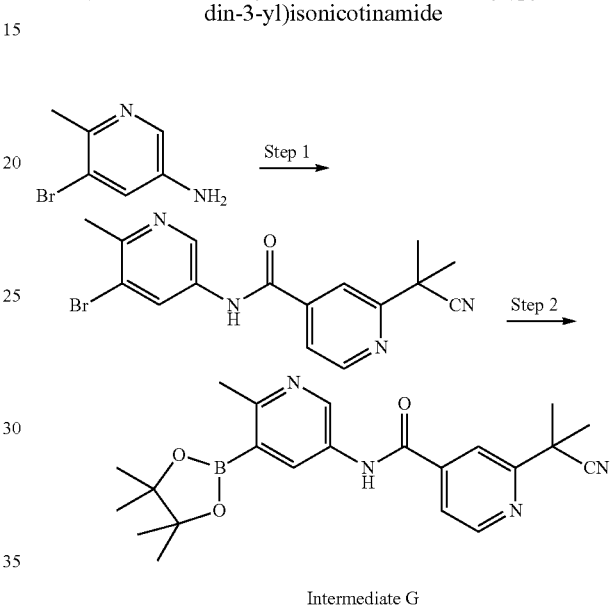

Intermediate G

Step 1:

EDC (1.3 equiv.) was added to a solution of 5-bromo-6-methylpyridin-3-amine (1.05 equiv), 2-(2-cyanopropan-2-yl)isonicotinic acid (1.0 equiv), HOAt (1.3 equiv) in DMF (0.17 M). The mixture was stirred at ambient temperature 3 hrs. The reaction mixture was diluted with water and extracted with ethyl acetate. The combined extracts were washed sequentially with 1M aqueous sodium hydroxide and brine, dried over sodium sulfate, filtered, and concentrated. The crude was purified by ISCO (50% EtOAc/Heptane). Combined fractions still contained 17% 5-bromo-6-methylpyridin-3-amine. Add 2-(2-cyanopropan-2-yl)isonicotinic acid (0.3 equiv), EDC (0.3 equiv), HOAt (0.3 equiv) in DMF (0.17 M). After stirred at rt overnight, the reaction mixture was diluted with water and extracted with ethyl acetate. The combined extracts were washed sequentially with 1M aqueous sodium hydroxide and brine, dried over sodium sulfate, filtered, and concentrated to yield N-(5-bromo-6-methylpyridin-3-yl)-2-(2-cyanopropan-2-yl)isonicotinamide in 71% over three steps. LCMS (m/z) (M+H)=359.0, Rt=0.73 min.

Step 2:

To a solution of N-(5-bromo-6-methylpyridin-3-yl)-2-(2-cyanopropan-2-yl)isonicotinamide (1.0 equiv.) in dioxane (0.18 M) was added potassium acetate (5.0 equiv.) and 4,4,4',4',5,5,5',5'-octamethyl-2,2'-bi(1,3,2-dioxaborolane) (1.5 equiv.). The solution was degassed with nitrogen and Pd(dppf)Cl$_2$-DCM was added. The reaction was then heated to 80° C. overnight. The mixture was concentrated and diluted with EtOAc, washed with H$_2$O, brine. The organic layer was dried over Na₂SO₄ and concentrated. The residue was then titrated in hexane. Filtered and the solid was collected to yield 2-(2-cyanopropan-2-yl)-N-(6-methyl-5-(4,4,5,5-tetramethyl-1,3,2-dioxaborolan-2-yl)pyridin-3-yl)isonicotinamide in 82% yield. LCMS (m/z) (M+H)=325.1, Rt=0.49 min. 1H NMR (400 MHz, <cdcl3>) δ ppm 1.27 (s, 6H), 1.32-1.40 (m, 12H), 1.82 (s, 6H), 2.75 (s, 3H), 7.69 (d, J=3.91 Hz, 1H), 7.86-7.95 (m, 1H), 7.98 (s, 1H), 8.28 (br. s., 1H), 8.79 (d, J=5.09 Hz, 1H), 8.89 (br. s., 1H).

Synthesis of Amine-substituted 4-Pyridinyl-Phenyl/3-Pyridinyl Amines as Intermediates

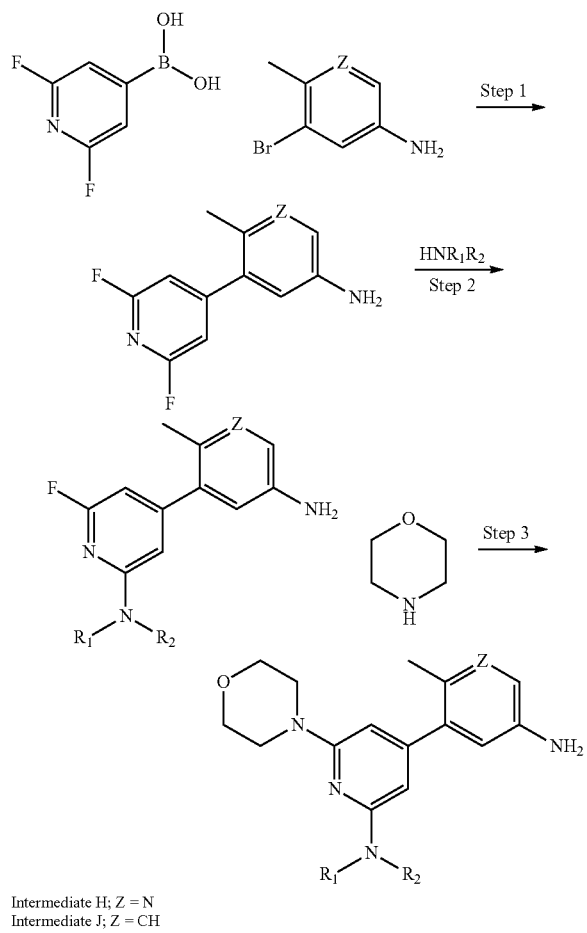

Intermediate H; Z = N
Intermediate J; Z = CH

Synthesis of 2-((5-amino-2-methyl-6'-morpholino-[3,4'-bipyridin]-2'-yl)amino)ethanol Step 1:
To a 0.3M solution of 5-bromo-6-methylpyridin-3-amine (1.00 equiv.) in DME was added (2,6-difluoropyridin-4-yl)boronic acid (1.30 equiv.), PdCl2(dppf).CH2Cl2 adduct (0.05 equiv.), and 2M aqueous sodium carbonate (3.00 equiv.). The reaction mixture was heated at 60° C. for 18 hrs in an oil bath. The cooled reaction mixture was partitioned between water and EtOAc (3×100 mL). The combined organics were washed with brine, dried over MgSO₄, filtered and concentrated. The crude was purified by flash chromatography over silica gel (ethyl acetate in heptane, 0-100% gradient) to give 2',6'-difluoro-2-methyl-[3,4'-bipyridin]-5-amine (90.0% yield) as an orange solid. ¹H NMR (400 MHz, <dmso>) δ ppm 2.27 (s, 3H) 5.31 (s, 2H) 6.84 (d, J=2.35 Hz, 1H), 7.23 (s, 2H) 7.94 (d, J=2.74 Hz, 1H). LCMS (m/z) (M+H)=222.1, Rt=0.41 min.

Step 2:
To a 0.35M suspension of 2',6'-difluoro-2-methyl-[3,4'-bipyridin]-5-amine (1.00 eq) and potassium carbonate (1.20 eq) in DMSO was added 2-aminoethanol (5.10 eq) drop wise. The reaction was mixture was heated to 35° C. for 18 hrs in an oil bath. The reaction was partition between water and EtOAc. The aqueous was further washed with EtOAc (3×75 mL). The combined organics were dried over MgSO₄, filtered, and concentrated to yield 2-((5-amino-6'-fluoro-2-methyl-[3,4'-bipyridin]-2'-yl)amino)ethanol (95%). No further purification was performed. LCMS (m/z) (M+H)= 263.0, Rt=0.38 min.

Step 3:
To a 0.5M suspension of 2-((5-amino-6'-fluoro-2-methyl-[3,4'-bipyridin]-2'-yl)amino)ethanol (1.00 equiv.) and potassium carbonate (1.20 eq) in DMSO was added morpholine (5 eq). The reaction mixture was irradiated at 150° C. for 30 min in the microwave. The cooled reaction mixture was partitioned between water and EtOAc (3×75 mL). The combined organics were washed with brine, dried over MgSO₄, filtered and concentrated. The crude was purified by flash chromatography over silica gel (MeOH in DCM 0-15% gradient) to give 2-((5-amino-2-methyl-6'-morpholino-[3,4'-bipyridin]-2'-yl)amino)ethanol (58.0% yield) as a tan solid. ¹H NMR (400 MHz, <dmso>) δ ppm 2.22 (s, 3H) 3.26-3.30 (m, 2H) 3.37 (t, J=4.50 Hz, 4H) 3.52 (q, J=6.00 Hz, 2H) 3.64-3.69 (m, 4H) 4.63 (t, J=5.48 Hz, 1H) 5.11 (s, 2H) 5.72-5.80 (m, 2H) 6.24 (t, J=5.48 Hz, 1H) 6.71 (d, J=2.35 Hz, 1H) 7.81 (d, J=2.74 Hz, 1H). LCMS (m/z) (M+H)= 330.1, Rt=0.32 min.

Synthesis of 3-(difluoromethyl)benzoic acid

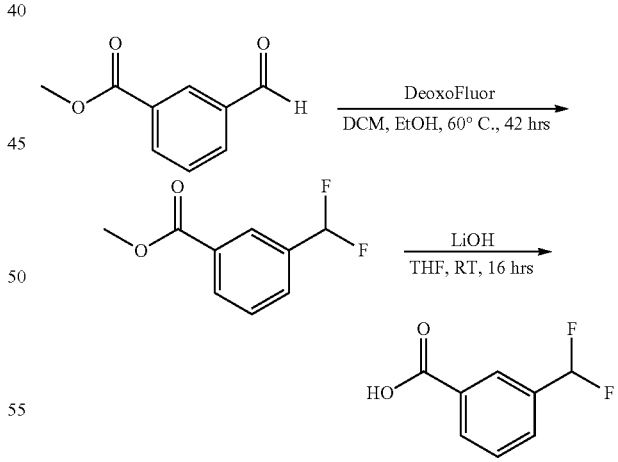

Step 1:
In a high pressure vial, a solution of methyl 3-formylbenzoate (1 equiv.) in DCM/EtOH (867:1, 0.40M) was added DeoxoFluor (2.0 equiv.). The reaction was purged with N₂, the vessel was sealed and heated at 60° C. After 18 hrs of stirring additional DeoxoFluor (2.0 equiv.) was added and allowed to stir for 42 hrs. The reaction was followed by TLC (25% EtOAc in heptanes). The reaction was partitioned between brine and EtOAc. The aqueous layer was further washed with EtOAc (3×) and the combined organics were dried over Na$_2$SO$_4$, filtered, and concentrated. The crude material was purified via flash chromatography over silica gel eluting with heptanes and 0-25% ethyl acetate gradient. Isolated methyl 3-(difluoromethyl)benzoate as a yellow oil in 62% yield. 1H NMR (400 MHz, <cdcl3>) δδ ppm 3.94 (s, 3H) 6.53-6.84 (m, 1H) 7.54 (t, J=7.83 Hz, 1H) 7.71 (d, J=7.83 Hz, 1H) 8.15 (d, J=7.83 Hz, 1H) 8.18 (s, 1H).

Step 2:

To a solution of methyl 3-(difluoromethyl)benzoate (1 equiv.) in THF (0.25M) was added 1M LiOH (2.5 equiv.) and allowed to stir at RT. Upon initial addition of LiOH, the solution turned from clear to a burnt orange, and after 2 hrs the solution is light yellow. The reaction stirred for 18 hrs at RT. The volatiles were removed in vacuo, and the aqueous phase was acidified to ~pH 3. A white precipitate was formed, filtered and dried. Isolated 3-(difluoromethyl)benzoic acid in 78% yield. LCMS (m/z) (M+H)=245.1, Rt=0.73). 1H NMR (400 MHz, <dmso>) δ ppm 6.97-7.30 (m, 1H) 7.63-7.71 (m, 1H) 7.83 (d, J=7.43 Hz, 1H) 8.06-8.16 (m, 1H)

Synthesis of 2-(1,1-difluoroethyl)isonicotinic acid

Step 1:

In a high pressure vial charged with a solution of 1-(4-methylpyridin-2-yl)ethanone (1.0 equiv.) and EtOH (0.1 equiv) in DCM (2.0M) was added DAST (2.5 equiv.). The reaction was heated to 30° C. and heated for 48 hrs. LCMS analysis indicated the formation of the desired product (MH+—157.9, Rt—0.54 min). The reaction was diluted with DCM and quenched with NaHCO3, slowly at 0° C. The phases were separated and the aqueous layer was washed with DCM (2×). The combined organics were dried over MgSO4, filtered, and concentrated. The crude material was purified via flash chromatography over silica gel eluting with heptanes and 0-100% ethyl acetate gradient. Isolated 2-(1,1-difluoroethyl)-4-methylpyridine in 27% yield. LCMS (m/z) (M+H)=157.9, Rt=0.54.

Step 2:

To a solution of 2-(1,1-difluoroethyl)-4-methylpyridine (1 equiv.) in water (2.0 M) was added KMnO$_4$ (3.0 equiv) and heated to 80° C. for 4 hrs. LCMS analysis indicated the formation of the desired product (MH$^+$—188.0, Rt—0.52 min). The reaction was acidified to pH 3 with 1M HCl. The white precipitate was filtered and dried. Isolated 2-(1,1-difluoroethyl)isonicotinic acid in 12% yield. LCMS (m/z) (M+H)=188.0, Rt=0.52). 1H NMR (400 MHz, <cd3od>) δδ ppm 2.01 (t, J=18.78 Hz, 3H) 8.00 (d, J=4.70 Hz, 1H) 8.16 (s, 1H) 8.80 (d, J=5.09 Hz, 1H).

Synthesis of 2-(difluoromethyl)isonicotinic acid

Procedure follows exactly as that of 2-(1,1-difluoroethyl)isonicotinic acid. Isolated 2-(difluoromethyl)isonicotinic acid in 23%. LCMS (m/z) (M+H)=174.0, Rt=0.48).

Synthesis of 3-(2-cyanopropan-2-yl)benzoic acid

Step 1:

To a vial with a stir bar was added methyl 3-bromobenzoate (1.0 equiv.) 4-isoxazoleboronic acid (1.2 equiv.), PdCl$_2$(dppf).CH$_2$Cl$_2$ adduct (0.1 equiv.), 1M KF (2.0) and DMSO (0.10 M). The reaction mixture was degassed with bubbling nitrogen and the vial capped and heated at 130° C.

for 18 hr. LCMS analysis indicated the formation of the desired product (MH+—176, Rt—0.62 min). The reaction mixture was diluted with a saturated solution of NH$_4$Cl and extracted with EtOAc (2×). The combined organics were washed with water and brine, dried over MgSO$_4$, filtered and concentrated. The crude material was purified via flash chromatography over silica gel eluting with heptanes and 0-100% ethyl acetate gradient. Isolated methyl 3-(cyanomethyl)benzoate in 69% yield. LCMS (m/z) (M+H)=176.1, Rt=0.62). 1H NMR (400 MHz, <cd3od>) δ ppm 3.92 (s, 3H), 3.99 (s, 2H), 7.49-7.55 (m, 1H), 7.62 (d, J=7.83 Hz, 1H), 7.99 (d, J=7.83 Hz, 1H), 8.04 (s, 1H).

Step 2:

To a solution of methyl 3-(cyanomethyl)benzoate (1.0 equiv.) in DMSO (0.50 M) was slowly added NaH (3 equiv.) at 0° C. and allowed to stir for 20 mins. To the mixture was added MeI (3.0 equiv.) and allowed to stir 18 hrs at RT. LCMS analysis indicated the formation of the desired product (MH+—204, Rt—0.78 min). Under ice-cooling, the reaction mixture was diluted with water and extracted with EtOAc. The organics were washed with water and brine, dried over MgSO$_4$, filtered, and concentrated. The crude material was purified via flash chromatography over silica gel eluting with heptanes and 0-50% ethyl acetate gradient. Isolated methyl 3-(2-cyanopropan-2-yl)benzoate in 63% yield. LCMS (m/z) (M+H)=204.1, Rt=0.78).

Step 3:

To a solution of methyl 3-(2-cyanopropan-2-yl)benzoate (1 equiv.) in THF (0.10 M) was added 1M LiOH (2.5 equiv.) and allowed to stir at RT for 18 hrs. LCMS analysis indicated the formation of the desired product (MH+—190, Rt—0.60 min). The volatiles were removed in vacuo, and the aqueous phase was acidified to ~pH3 with 1M HCl. A white precipitate was formed, filtered and dried. Isolated 3-(2-cyanopropan-2-yl)benzoic acid in 63% yield. LCMS (m/z) (M+H)=190.1, Rt=0.60. 1H NMR (400 MHz, <cd3od>) δ ppm 1.76 (s, 6H) 7.54 (t, J=7.83 Hz, 1H) 7.74-7.80 (m, 1H) 8.00 (d, J=7.43 Hz, 1H) 8.16-8.21 (m, 1H).

Synthesis of (R)-tert-butyl 2-(aminomethyl)morpholine-4-carboxylate

Step 1.

A solution of (5)-tert-butyl 2-(hydroxymethyl)morpholine-4-carboxylate (1.0 equiv.), tosyl chloride (1.10 equiv.), triethylamine (1.40 equiv.) and N,N-dimethylpyridin-4-amine (0.1 equiv.) in dichloromethane (0.1 M) at RT. The resulting mixture was stirred at RT for 2 hours. The reaction mixture was then diluted with water and the aqueous layer was separated and washed sequentially with NaOH (1 M), water, brine dried over sodium sulfate then concentrated in vaccuo to yield (S)-tert-butyl 2-((tosyloxy)methyl)morpholine-4-carboxylate as a pale yellow oil in 99% yield. LCMS (m/z) (M+H)=390.2, Rt=0.84 min.

Step 2.

To a solution of (5)-tert-butyl 2-((tosyloxy)methyl)morpholine-4-carboxylate (1.0 equiv.) in DMF (0.1 M) at RT was added sodium azide (2.00). The resulting mixture was heated to 60° C. for 24 h. The reaction then cooled to RT and partitioned between water and diethyl ether. The organic layer was separated then washed with water followed by brine then dried over sodium sulfate. The organic layer was then concentrated in vaccuo to yield (5)-tert-butyl 2-(azidomethyl)morpholine-4-carboxylates a white solid oil in 83% yield.

Step 3.

A solution of (S)-tert-butyl 2-(azidomethyl)morpholine-4-carboxylates (1.0 equiv.) in ethanol (0.1 M) was evacuated and back filled with argon (×3). To the solution was then added Pd/C (0.20 eq.) and the mixture was evacuated and back filled with hydrogen (×3). The mixture was then stirred at RT under a positive pressure of atmospheric hydrogen (balloon) for 24 h. The hydrogen gas was removed by evacuation and the reaction backfilled with argon. The reaction mixture was then filtered through a pad of celite and then concentrated in vaccuo to afford (R)-tert-butyl 2-(aminomethyl)morpholine-4-carboxylate as a white solid in 91% yield. LCMS (m/z) (M+H)=217.1, Rt=0.43 min.

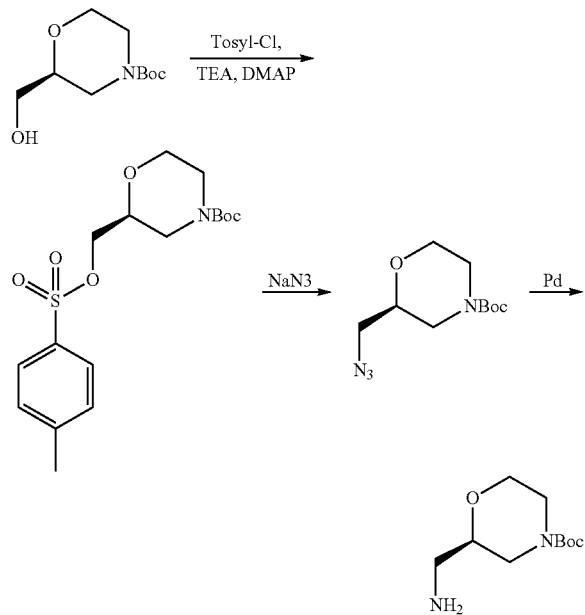

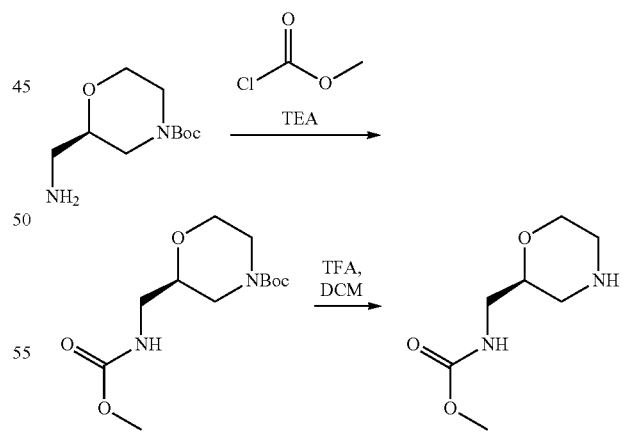

Synthesis of (S)-methyl(morpholin-2-ylmethyl)carbamate

Step 1.

To a solution of (R)-tert-butyl 2-(aminomethyl)morpholine-4-carboxylate (1.0 equiv.) and triethylamine (3.0 equiv.) in dichloromethane (0.1 M) was added methyl chloroformate (1.1 equiv.). The resulting mixture was stirred at RT for 45 min. After concentration, the residue was partitioned between EtOAc and water. The organic phase was washed with water and then with brine. After drying over sodium sulfate the solution was concentrated in vaccuo to give crude (R)-tert-butyl 2-(((methoxycarbonyl)amino)methyl)morpholine-4-carboxylate which was used in the next step without further purification. LCMS (m/z) (M+H)=175.1 (-Boc), Rt=0.63 min.

Step 2.

To a 4:1 solution of dichloromethane and TFA (0.1 M) was added (R)-tert-butyl 2-(((methoxycarbonyl)amino)methyl)morpholine-4-carboxylate. After 1 h the solution was then concentrated in vaccuo to give crude (S)-methyl (morpholin-2-ylmethyl)carbamate which was used in the next step without further purification. LCMS (m/z) (M+H)= 175.0, Rt=0.11 min.

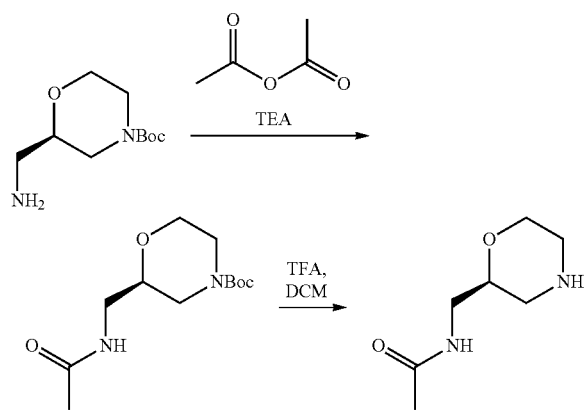

Synthesis of
(S)—N-(morpholin-2-ylmethyl)acetamide

Step 1.

To a solution of (R)-tert-butyl 2-(aminomethyl)morpholine-4-carboxylate (1.0 equiv.) and triethylamine (1.5 equiv.) in dichloromethane (0.1 M) was added acetic anhydride (1.1 equiv.). The resulting mixture was stirred at RT for 45 min. After concentration, the residue was partitioned between EtOAc and water. The organic phase was washed with water and then with brine. After drying over sodium sulfate the solution was concentrated in vaccuo to give crude (R)-tert-butyl 2-(acetamidomethyl)morpholine-4-carboxylate which was used in the next step without further purification. LCMS (m/z) (M+H)=159.1 (-Boc), Rt=0.53 min.

Step 2.

To a 4:1 solution of dichloromethane and TFA (0.1 M) was added (R)-tert-butyl 2-(acetamidomethyl)morpholine-4-carboxylate. After 1 h the solution was then concentrated in vacuo to give crude (S)—N-(morpholin-2-ylmethyl)acetamide which was used in the next step without further purification. LCMS (m/z) (M+H)=159.0, Rt=0.11 min.

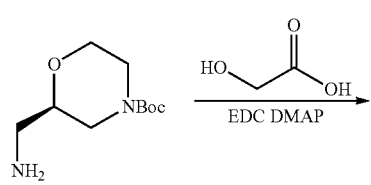

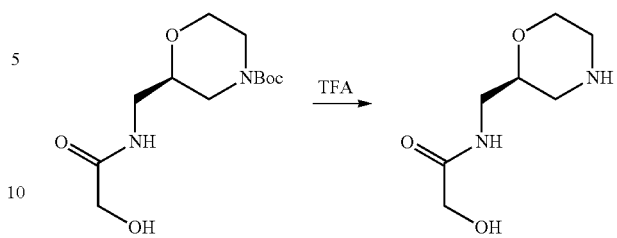

Synthesis of
(S)-2-hydroxy-N-(morpholin-2-ylmethyl)acetamide

Step 1.

A mixture of (R)-tert-butyl 2-(aminomethyl)morpholine-4-carboxylate (1.0 equiv.), 2-hydroxyacetic acid (1.80 equiv.), N1-((ethylimino)methylene)-N3,N3-dimethylpropane-1,3-diamine hydrochloride (2.0 equiv.), and N,N-dimethylpyridin-4-amine (0.20 equiv.) was stirred in DCM (0.1 M) at room temperature overnight. The reaction was quenched with water and washed (3x) with water. The combined aqueous fractions were then back-extracted with chloroform (4x) and the combined organics were dried over Na₂SO₄, filtered, and concentrated. The resulting oil was passed through a pad of SiO₂ gel using 5-50% MeOH/DCM and concentrated to yield (R)-tert-butyl 2-((2-hydroxyacetamido)methyl)morpholine-4-carboxylate as an oil. LCMS (m/z) (M+H)=175.1 (-Boc), Rt=0.55 min.

Step 2.

(R)-tert-butyl 2-((2-hydroxyacetamido)methyl)morpholine-4-carboxylate (1.0 equiv.) was dissolved in DCM:TFA (4:1, 0.5 M) and stirred at room temperature. After one hour the solution was concentrated to yield (S)-2-hydroxy-N-(morpholin-2-ylmethyl)acetamide. LCMS (m/z) (M+H)= 175.1, Rt=0.12 min.

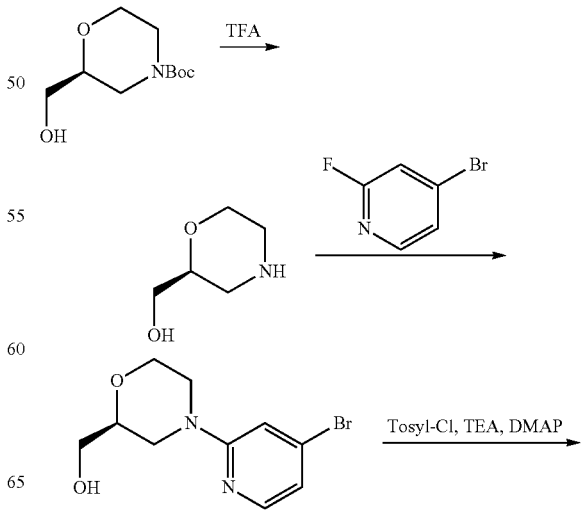

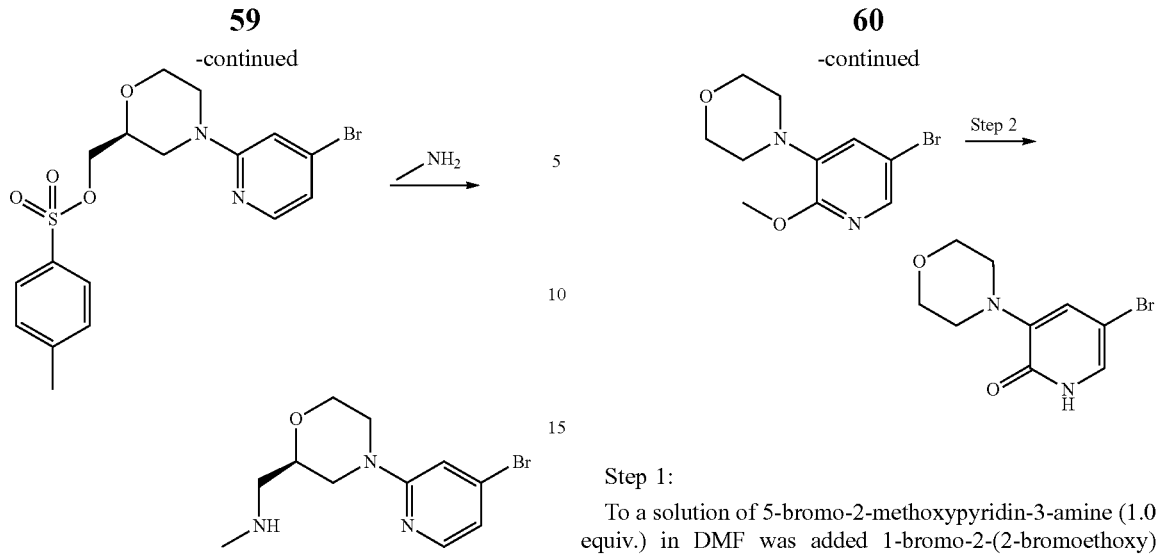

(R)-1-(4-(4-bromopyridin-2-yl)morpholin-2-yl)-N-methylmethanamine

Step 1.
To a 4:1 solution of dichloromethane and TFA (0.1 M) was added (S)-tert-butyl 2-(hydroxymethyl)morpholine-4-carboxylate. After 1 h the solution was then concentrated in vaccuo to give crude (S)-morpholin-2-ylmethanol which was used in the next step without further purification. LCMS (m/z) (M+H)=60.0, Rt=0.11 min.

Step 2.
Refer to standard.

Step 3.
A solution of (S)-(4-(4-bromopyridin-2-yl)morpholin-2-yl)methanol (1.0 equiv.), tosyl chloride (1.0 equiv.), triethylamine (1.40 equiv.) and N,N-dimethylpyridin-4-amine (0.1 equiv.) in dichloromethane (0.1 M) at RT. The resulting mixture was stirred at RT for 18 hours. The reaction mixture was then diluted with water and the aqueous layer was separated and washed sequentially with NaOH (1 M), water, brine dried over sodium sulfate then concentrated in vacuo to yield (S)-(4-(4-bromopyridin-2-yl)morpholin-2-yl)methyl 4-methylbenzenesulfonate in 56% yield. LCMS (m/z) (M+H)=427.1/429.0, Rt=0.77 min.

Step 4.
To a 2 M solution of methylamine in methanol was added (S)-(4-(4-bromopyridin-2-yl)morpholin-2-yl)methyl 4-methylbenzenesulfonate (1.0 eq). This solution was microwave heated at 80° C. After 1 h the solution was then concentrated in vacuo and water was added. The resulting suspension was sonicated and centrifuged. The water soluble portion was separated from the solids. The resulting aqueous solution of (R)-1-(4-(4-bromopyridin-2-yl)morpholin-2-yl)-N-methylmethanamine was used in the next step without further purification. LCMS (m/z) (M+H)=286.0/288.0, Rt=0.34 min.

Synthesis of 5-bromo-3-morpholinopyridin-2(1H)-one

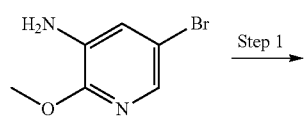

Step 1:
To a solution of 5-bromo-2-methoxypyridin-3-amine (1.0 equiv.) in DMF was added 1-bromo-2-(2-bromoethoxy) ethane (1.2 equiv.), followed by DIEA (3.0 equiv.). The solution was heated at 120° C. for 24 hours. Cooled to room temperature and partitioned between ethyl acetate and water. The organic phase was washed with brine, dried over sodium sulfate, filtered and concentrated. The crude material was purified via flash chromatography over silica gel eluting with heptanes and 0-25% ethyl acetate gradient). Isolated 4-(5-bromo-2-methoxypyridin-3-yl)morpholine as a yellow solid in 69% yield. LCMS (m/z) (M+H)=273.0/274.9, Rt=0.82 min. $^1$H NMR (400 MHz, <cdcl3>) δ ppm 2.90-3.18 (m, 4H) 3.76-3.91 (m, 4H) 3.97 (s, 3H) 7.14 (d, J=1.96 Hz, 1H) 7.84 (d, J=1.96 Hz, 1H).

Step 2:
To a solution of 4-(5-bromo-2-methoxypyridin-3-yl)morpholine (1.0 equiv.) in 1,4-dioxane (0.3 M) was added concentrated HCl (5 equiv.) and the solution was heated to 100° C. for 1 h. Upon cooling to room temperature, the solution was concentrated to dryness under vacuo, then dissolved in water and neutralized with solid sodium bicarbonate. The precipitate was filtered, washed with water and dried under vacuo to give 5-bromo-3-morpholinopyridin-2 (1H)-one as a beige solid in 93% yield. LCMS m/z (M+H)= 258.9/260.9, Rt=0.48 min.

Synthesis of 4-(6-chloropyrazin-2-yl)morpholine

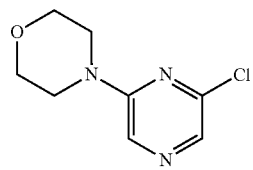 [SMILES: Clc1cncc(N2CCOCC2)n1]

To a solution of 2,6-dichloropyrazine (1.0 equiv.) in acetonitrile (0.3 M) was added morpholine (3.5 equiv.) and the reaction was stirred at room temperature for 20 h. The resulting precipitate was filtered off and the filtrate was concentrated under vacuo. The crude material was partitioned between water and ethyl acetate, the organic phase was dried with sodium sulfate, filtered and concentrated to afford 4-(6-chloropyrazin-2-yl)morpholine in 75% yield. LCMS m/z (M+H)=200.0, Rt=0.61 min.

Synthesis of 5-bromo-3-morpholinopyridin-2(1H)-one

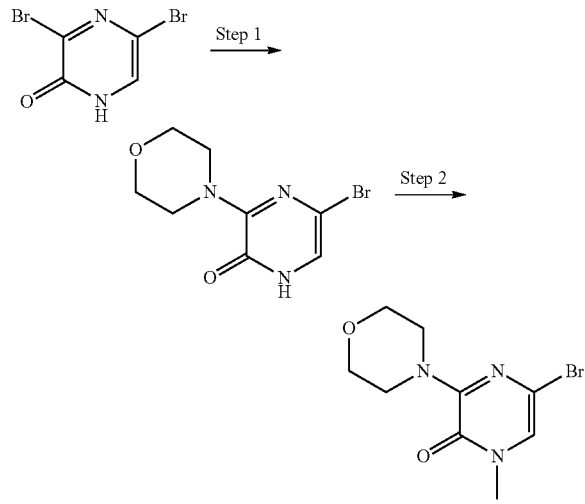

Step 1:
A solution of 3,5-dibromopyrazin-2(1H)-one (1.0 equiv.) in morpholine (5 equiv.) was heated to 100° C. for 24 h. Cooled to room temperature and filtered off the precipitate. The filtrate was partitioned between water and ethyl acetate. The organic phase was dried with sodium sulfate, filtered and concentrated. The crude material was purified via silica gel column chromatography eluting with ethyl acetate and heptanes (0-50%). The pure fractions were concentrated to yield 5-bromo-3-morpholinopyrazin-2(1H)-one as a white solid in 43% yield. LCMS m/z (M+H)=259.9, Rt=0.41 min.

Step 2:
To a solution of 5-bromo-3-morpholinopyrazin-2(1H)-one (1.0 equiv.) in DMF (0.1 M) was added potassium carbonate (2.0 equiv.) and iodomethane (1.0 equiv.) at 0° C. and the solution was allowed to warm to room temperature and stirred for 2 hours. Upon completion, the reaction was partitioned between water and ethyl acetate, the organic phase was washed with brine, dried with sodium sulfate, filtered and concentrated. The crude material was used for the next step without further purification. Isolated 5-bromo-1-methyl-3-morpholinopyrazin-2(1H)-one in 91% yield. LCMS m/z (M+H)=274/276, Rt=0.60 min. $^1$H NMR (400 MHz, <cdcl3>) δ ppm 3.42 (s, 3H) 3.66-3.83 (m, 4H) 3.85-4.00 (m, 4H), 6.77 (s, 1H).

Synthesis of 3-bromo-1-methyl-5-morpholinopyridin-2(1H)-one

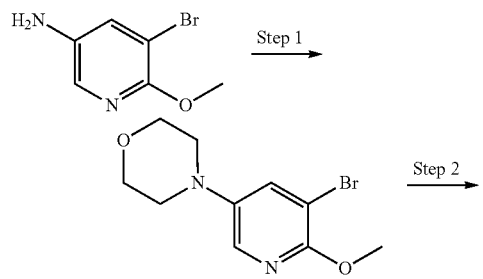

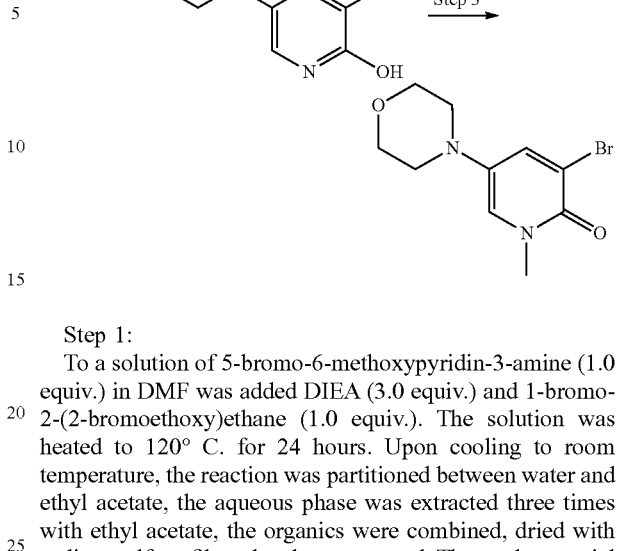

Step 1:
To a solution of 5-bromo-6-methoxypyridin-3-amine (1.0 equiv.) in DMF was added DIEA (3.0 equiv.) and 1-bromo-2-(2-bromoethoxy)ethane (1.0 equiv.). The solution was heated to 120° C. for 24 hours. Upon cooling to room temperature, the reaction was partitioned between water and ethyl acetate, the aqueous phase was extracted three times with ethyl acetate, the organics were combined, dried with sodium sulfate, filtered and concentrated. The crude material was purified via silica gel column chromatography eluting with 0-50% ethyl acetate in heptanes. The pure fractions were concentrated to yield 4-(5-bromo-6-methoxypyridin-3-yl)morpholine in 53% yield as an orange oil. LCMS m/z (M+H)=273/275, Rt=0.61 min. $^1$H NMR (400 MHz, <cdcl3>) δ ppm 2.93-3.18 (m, 4H) 3.80-4.05 (m, 7H) 7.50 (d, J=2.74 Hz, 1H) 7.74 (d, J=2.74 Hz, 1H).

Step 2:
A solution of 4-(5-bromo-6-methoxypyridin-3-yl)morpholine (1.0 equiv.) in 4M HCl in dioxane (20 equiv.) was heated to 110° C. for 24 hours. Upon cooling to room temperature, the reaction was neutralized with aqueous NaOH to pH~6 then extracted with ethyl acetate three times. The organic phase was dried with sodium sulfate, filtered and concentrated. Isolated 3-bromo-5-morpholinopyridin-2-ol as the desired product in 32% yield. LCMS (m/z) (M+H)=259.0/261.0, Rt=0.36 min.

Step 3:
To a solution of 3-bromo-5-morpholinopyridin-2-ol (1.0 equiv.) in DMF (0.1 M) was added potassium carbonate (2.0 equiv.) and iodomethane (1.0 equiv.). The solution was stirred at room temperature for 3 hours. Partitioned between water and ethyl acetate, the organic phase was washed with brine, dried with sodium sulfate, filtered and concentrated to dryness. Isolated 3-bromo-1-methyl-5-morpholinopyridin-2(1H)-one in 87% yield. LCMS (m/z) (M+H)=273.0/275.0, Rt=0.41 min.

Synthesis of 4-bromo-1-methyl-6-morpholinopyridin-2(1H)-one and 6-chloro-1-methyl-4-morpholinopyridin-2(1H)-one

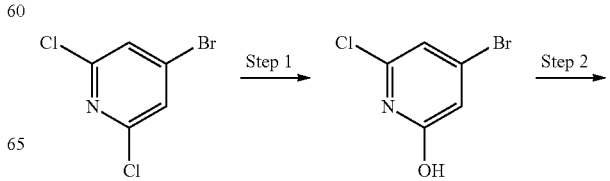

-continued

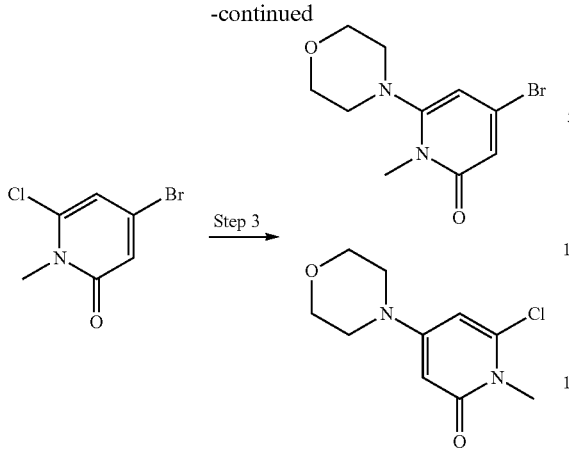

Synthesis of 6-chloro-2-methyl-4-morpholinopyridazin-3(2H)-one

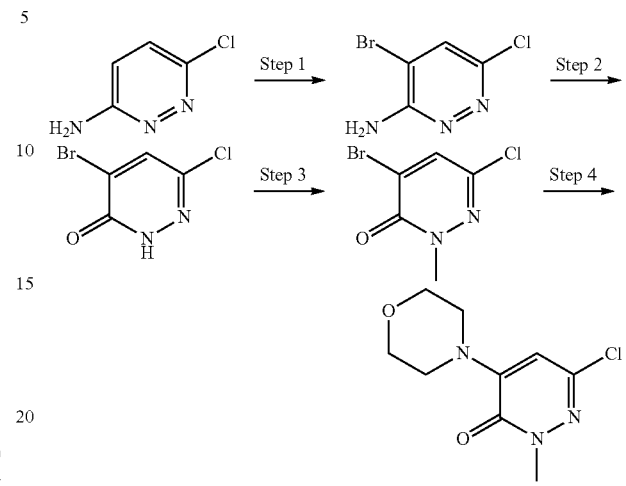

Step 1:

A solution of 4-bromo-2,6-dichloropyridine (1.0 equiv.) in dioxane and aqueous sodium hydroxide (15% by weight solution, 1:1 ratio, 0.55 M) was heated in the microwave for 30 min at 150° C. The solution was cooled to room temperature and neutralized with concentrated HCl (pH=~6) and extracted with ethyl acetate three times. The organic phase was dried with sodium sulfate, filtered and concentrated. The crude material was dried under vacuo to give 4-bromo-6-chloropyridin-2-ol as an off-white solid in 76% yield. LCMS (m/z) (M+H)=207.9/209.9, Rt=0.60 min.

Step 2:

To a solution of 4-bromo-6-chloropyridin-2-ol (1.0 equiv.) in DMF (0.16 M) was added potassium carbonate (2.0 equiv.) and iodomethane (1.2 equiv.) at room temperature. The solution was stirred for 2 hours, then partitioned between water and ethyl acetate. The aqueous phase was extracted with ethyl acetate two more times, the organic phase was washed with brine, dried with sodium sulfate, filtered and concentrated. The crude material was purified via silica gel column chromatography eluting with ethyl acetate and heptanes (0-50% ethyl acetate). The pure fractions were concentrated to yield 4-bromo-6-chloro-1-methylpyridin-2(1H)-one in 38% yield. LCMS (m/z) (M+H)=221.9/223.9, Rt=0.64 min.

Step 3:

To a solution of 4-bromo-6-chloro-1-methylpyridin-2(1H)-one (1.0 equiv.) in NMP (0.18 M) was added morpholine (1.1 equiv.) and DIEA (1.1 equiv). The solution was stirred at 100° C. for 4 hours. Upon cooling to room temperature, the solution was partitioned between water and ethyl acetate. The organic phase was washed with water, then brine, dried with sodium sulfate, filtered and concentrated. The crude material was purified via silica gel column chromatography eluting with ethyl acetate and heptanes (0-100% ethyl acetate then 90% ethyl acetate and 10% methanol). Isolated 4-bromo-1-methyl-6-morpholinopyridin-2(1H)-one in 51% yield and 6-chloro-1-methyl-4-morpholinopyridin-2(1H)-one in 15% yield. LCMS (m/z) (M+H)=273/274.9, Rt=0.53 min and LCMS (m/z) (M+H)=229.1/230.9, Rt=0.47 min respectively.

Step 1:

To a solution of 6-chloropyridazin-3-amine (1.0 equiv) in MeOH (1 M) at room temperature was added sodium bicarbonate (2.0 equiv.) and the resulting suspension was stirred at room temperature for 30 min before the dropwise addition of bromine (1.0 equiv.). The reaction mixture was stirred for 20 h. Upon concentration under vacuo, the crude residue was purified via silica gel column chromatography eluting with 100% heptanes to 80% ethyl acetate:heptanes to yield 4-bromo-6-chloropyridazin-3-amine in 50% yield. LCMS (m/z) (M+H)=207.8/209.8, Rt=0.47 min. $^1$H NMR (400 MHz, <cdcl3>) δ ppm 5.31-5.63 (m, 2H) 7.46-7.61 (m, 1H).

Step 2:

To a cooled solution (0-5° C.) of $NaNO_2$ (2.4 equiv.) in $H_2SO_4$ conc. (23 equiv.) was added 4-bromo-6-chloropyridazin-3-amine (1.0 equiv.) in acetic acid (0.25 M). The reaction mixture was stirred at 0° C. for 30 min before warming to room temperature and stirring for 1 hour. Water was added and stirred at room temperature for a further 4 hours. The reaction mixture was then extracted with ethyl acetate, dried over $MgSO_4$ and concentrated in vacuo to yield a brown oil. The oil was further purified by silica gel column chromatography eluting with 100% heptanes to 80% ethyl acetate/heptanes to yield 4-bromo-6-chloropyridazin-3(2H)-one as an off-white solid in 83% yield. LCMS (m/z) (M+H)=208.9/210.9, Rt=0.42 min. $^1$H NMR (400 MHz, <dmso>) δ ppm 8.08-8.32 (m, 1H) 13.25-13.71 (m, 1H).

Step 3:

To a solution of 4-bromo-6-chloropyridazin-3(2H)-one (1.0 equiv.) and $Cs_2CO_3$ (1.2 equiv.) in DMF (0.07 M) was added iodomethane (1.5 equiv.) drop-wise over 20 min. The resulting mixture was stirred for 3 h. The reaction mixture was then diluted with ammonium chloride, then extracted with ethyl acetate, dried over $MgSO_4$ and concentrated in vacuo to yield as a brown solid. The oil was further purified via silica gel column chromatography eluting with 100% heptanes to 80% ethyl acetate:heptanes to yield 4-bromo-6-chloro-2-methylpyridazin-3(2H)-one as an off-white solid in 79% yield. LCMS (m/z) (M+H)=222.9/224.9, Rt=0.54 min. $^1$H NMR (400 MHz, <cdcl3>) δ ppm 3.77-3.86 (m, 3H) 7.56-7.69 (m, 1H).

Step 4:

To a solution of 4-bromo-6-chloro-2-methylpyridazin-3(2H)-one (1.0 equiv.) in DMF (0.3 M) was added DIEA (1.0 equiv.) and morpholine (1.0 equiv.) at room temperature. The resulting mixture was heated to 120° C. for 5 h and 30 min. The reaction mixture was diluted with water, extracted with ethyl acetate, dried over MgSO$_4$ and concentrated in vacuo to yield. 6-chloro-2-methyl-4-morpholinopyridazin-3(2H)-one as an off-white solid in 97% yield. LCMS (m/z) (M+H)=230.0/232.0, Rt=0.63 min.

Synthesis of 4-(5-bromo-2-((tetrahydro-2H-pyran-4-yl)oxy)pyridin-3-yl)morpholine AND 5-bromo-3-morpholino-1-(tetrahydro-2H-pyran-4-yl)pyridin-2(1H)-one

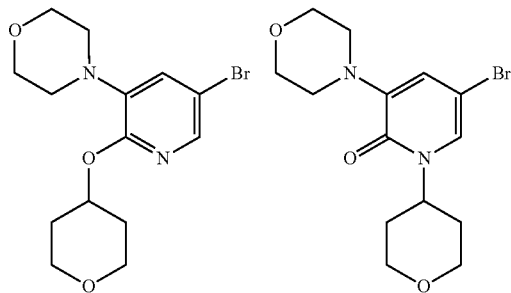

To a 0.45 M solution of triphenylphosphine (1.50 equiv.) in DMF was added DIAD (1.50 equiv.). The mixture was stirred at ambient temperature for 10 min. Tetrahydro-2H-pyran-4-ol (2.00 equiv.) was added, and the mixture was stirred for 15 min. 5-Bromo-3-morpholinopyridin-2(1H)-one (1.00 equiv.) was added. The mixture was stirred for 2 hr. The reaction mixture was diluted with water and extracted with ethyl acetate. The combined organics were washed with brine, dried over sodium sulfate, filtered and concentrated with silica gel. The material was purified by flash chromatography over silica gel (heptanes with 0-100% ethyl acetate gradient) to give both the O-alkylated isomer (88% yield) and the N-alkylated isomer (11% yield).

4-(5-bromo-2-((tetrahydro-2H-pyran-4-yl)oxy)pyridin-3-yl)morpholine: $^1$H NMR (400 MHz, <cdcl3>) δ ppm 1.82 (td, J=8.51, 4.30 Hz, 2H) 2.09 (dt, J=8.99, 4.33 Hz, 2H) 3.02-3.17 (m, 4H) 3.56-3.73 (m, 2H) 3.77-3.89 (m, 4H) 3.90-4.03 (m, 2H) 5.29 (dt, J=8.01, 3.99 Hz, 1H) 7.13 (d, J=2.10 Hz, 1H) 7.78 (d, J=2.20 Hz, 1H). LCMS (m/z) (M+H)=343.0/345.0, Rt=0.92 min.

5-bromo-3-morpholino-1-(tetrahydro-2H-pyran-4-yl)pyridin-2(1H)-one: $^1$H NMR (400 MHz, <cdcl3>) δ ppm 1.26 (s, 2H) 1.72-1.96 (m, 4H) 3.08-3.24 (m, 4H) 3.47-3.67 (m, 2H) 3.79-3.95 (m, 4H) 4.04-4.19 (m, 2H) 5.14 (s, 1H) 6.64 (d, J=2.40 Hz, 1H) 7.13 (d, J=2.40 Hz, 1H). LCMS (m/z) (M+H)=342.9/344.9, Rt=0.63 min.

Synthesis of 4-(5-bromo-2-isopropoxypyridin-3-yl)morpholine AND 5-bromo-1-isopropyl-3-morpholinopyridin-2(1H)-one

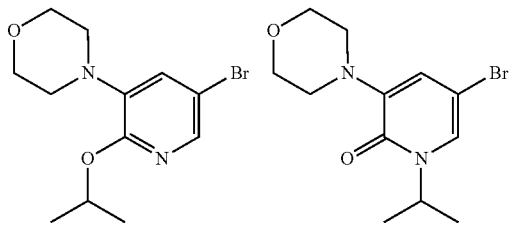

A 0.3 M solution of 5-bromo-3-morpholinopyridin-2(1H)-one (1.00 equiv.) in DMF was treated with sodium hydride (1.20 equiv.). The mixture was stirred for 20 min at ambient temperature. 2-bromopropane (1.20 equiv.) was added. The mixture was stirred at 70° C. for 18 hr. The cooled reaction mixture was diluted with water and extracted with ethyl acetate. The combined extracts were washed with brine, dried over sodium sulfate, filtered, and concentrated. The crude material was purified by flash chromatography over silica gel (heptanes with 20-100% ethyl acetate gradient) to give both the O-alkylated isomer (56% yield) and the N-alkylated isomer (26% yield).

4-(5-bromo-2-isopropoxypyridin-3-yl)morpholine: $^1$H NMR (400 MHz, <cdcl3>) δ ppm 1.39 (d, J=6.16 Hz, 6H) 3.04-3.15 (m, 4H) 3.82-3.93 (m, 4H) 5.24-5.44 (m, 1H) 7.12 (d, J=2.10 Hz, 1H) 7.82 (d, J=2.15 Hz, 1H). LCMS (m/z) (M+H)=301.0/303.0, Rt=0.99 min.

5-bromo-1-isopropyl-3-morpholinopyridin-2(1H)-one: $^1$H NMR (400 MHz, <cdcl3>) δ ppm 1.30-1.40 (m, 6H) 3.12-3.21 (m, 4H) 3.82-3.93 (m, 4H) 5.19-5.33 (m, 1H) 6.62 (d, J=2.35 Hz, 1H) 7.11 (d, J=2.35 Hz, 1H). LCMS (m/z) (M+H)=301.0/303.0, Rt=0.70 min.

Synthesis of tert-butyl(2-(5-bromo-3-morpholino-2-oxopyridin-1(2H)-yl)ethyl)carbamate

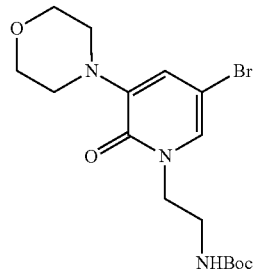 [SMILES: CC(C)(C)OC(=O)NCCn1cc(Br)cc(N2CCOCC2)c1=O]

A 0.3 M solution of 5-bromo-3-morpholinopyridin-2(1H)-one (1.00 equiv.) in DMF was treated with sodium hydride (1.20 equiv.). The mixture was stirred for 15 min at ambient temperature. Tert-butyl(2-bromoethyl)carbamate (1.20 equiv.) was added. The mixture was stirred at 60° C. for 3 hr. The cooled reaction mixture was diluted with water and extracted with ethyl acetate. The combined organics were washed with saturated aqueous sodium bicarbonate, dried over sodium sulfate, filtered, and concentrated to give tert-butyl(2-(5-bromo-3-morpholino-2-oxopyridin-1(2H)-yl)ethyl)carbamate. LCMS (m/z) (M+H)=402.1/404.1, Rt=0.78 min.

Method 1:

To a solution of the starting pyridone or pyrazinone (1.0 equiv.) in DMF (0.1-0.2 M) was added the electrophile (1.0-1.5 equiv.) followed by potassium carbonate or cesium carbonate (1.0-2.0 equiv.). The solution was stirred at room temperature (or alternatively heated up to 80° C.) for 2-24 hours. Upon cooling to room temperature, the solution was partitioned between water and ethyl acetate, the organic phase was washed with water, then brine, dried over sodium sulfate, filtered and concentrated under vacuo. The crude material was a mixture of N-alkyl and O-alkyl products. The material could be used for the next step without further purification as a mixture of isomers or it could be purified via silica gel column chromatography eluting with 0-100% ethyl acetate in heptanes.

Synthesis of 5-bromo-1-methyl-3-morpholinopyridin-2(1H)-one AND 4-(5-bromo-2-methoxypyridin-3-yl)morpholine

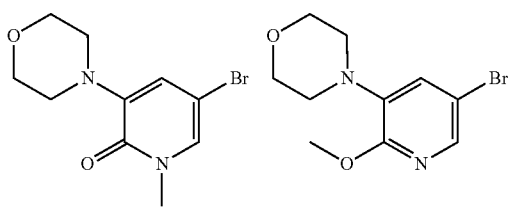

To a solution of 5-bromo-3-morpholinopyridin-2(1H)-one (1.0 equiv.) in DMF (0.2 M) was added potassium carbonate (2.0 equiv.), followed by iodomethane (1.0 equiv.). The solution was stirred at room temperature for 3 hours. The solution was partitioned between water and ethyl acetate, the organic phase was washed with brine, dried with sodium sulfate, filtered and concentrated. The crude material was a mixture of N-methylated and O-methylated products (90:10). The material could be used for the next step without further purification as a mixture of isomers or it could be purified via silica gel column chromatography eluting with 0-100% ethyl acetate in heptanes to afford 5-bromo-1-methyl-3-morpholinopyridin-2(1H)-one in 71% yield LCMS (m/z) (M+H)=273/275, Rt=0.55 min and 4-(5-bromo-2-methoxypyridin-3-yl)morpholine in 10% yield. LCMS (m/z) (M+H)=273/275, Rt=0.82 min.

The intermediates listed below were prepared using methods similar to those described for the preparation of 5-bromo-1-methyl-3-morpholinopyridin-2(1H)-one AND 4-(5-bromo-2-methoxypyridin-3-yl)morpholine (Method 1) using the appropriate starting materials.

Synthesis of 5-bromo-1-(2-hydroxyethyl)-3-morpholinopyridin-2(1H)-one and 2-((5-bromo-3-morpholinopyridin-2-yl)oxy)ethanol

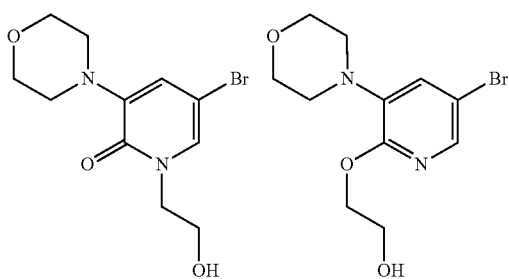

Method 1 was followed using 5-bromo-3-morpholinopyridin-2(1H)-one (1.0 equiv.), 2-iodoethanol (1.0 equiv.) and potassium carbonate (2.0 equiv.) at room temperature to give 5-bromo-1-(2-hydroxyethyl)-3-morpholinopyridin-2(1H)-one and 2-((5-bromo-3-morpholinopyridin-2-yl)oxy)ethanol as a mixture of two isomers (~5:1 ratio). LCMS (m/z) (M+H)=303/305, Rt=0.47 min and 0.62 min.

Synthesis of 5-bromo-1-(2-(methylsulfonyl)ethyl)-3-morpholinopyridin-2(1H)-one

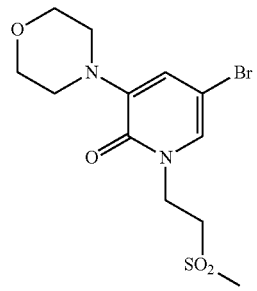 [SMILES: CS(=O)(=O)CCn1cc(Br)cc(N2CCOCC2)c1=O]

Method 1 was followed using 5-bromo-3-morpholinopyridin-2(1H)-one (1.0 equiv.), (methylsulfonyl)ethene (1.2 equiv.) and cesium carbonate (1.2 equiv.) at room temperature to give 5-bromo-1-(2-(methylsulfonyl)ethyl)-3-morpholinopyridin-2(1H)-one in 98% yield. $^1$H NMR (400 MHz, <cdcl3>) δ ppm 2.92 (s, 3H) 3.09-3.23 (m, 4H) 3.53 (t, J=6.65 Hz, 2H) 3.78-3.96 (m, 4H) 4.32 (t, J=6.65 Hz, 2H) 6.69 (s, 1H) 7.23 (d, J=2.35 Hz, 1H). LCMS (m/z) (M+H)=365.1/366.9, Rt=0.57 min.

Synthesis of 5-bromo-1-ethyl-3-morpholinopyridin-2(1H)-one and 4-(5-bromo-2-ethoxypyridin-3-yl)morpholine

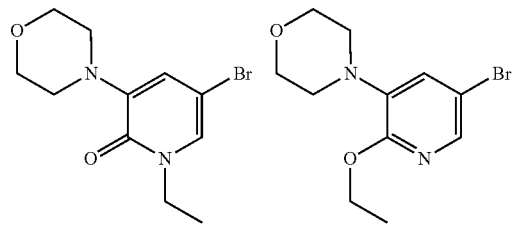

Method 1 was followed using 5-bromo-3-morpholinopyridin-2(1H)-one (1.0 equiv.), iodoethane (1.0 equiv.) and cesium carbonate (1.0 equiv.) at 50° C. to afford a mixture of 5-bromo-1-ethyl-3-morpholinopyridin-2(1H)-one and 4-(5-bromo-2-ethoxypyridin-3-yl)morpholine in about 2:1 ratio. LCMS (m/z) (M+H)=286.9/288.9, Rt=0.62 min and 0.88 min.

Synthesis of 2-(5-bromo-3-morpholino-2-oxopyridin-1(2H)-yl)acetonitrile and 2-((5-bromo-3-morpholinopyridin-2-yl)oxy)acetonitrile

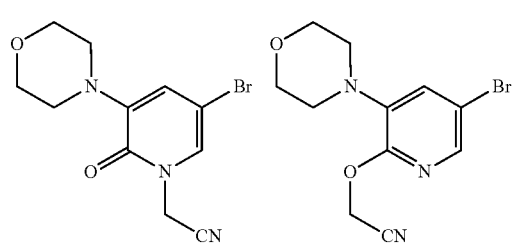

Method 1 was followed using 5-bromo-3-morpholinopyridin-2(1H)-one (1.0 equiv.), 2-bromoacetonitrile (1.2 equiv.) and potassium carbonate (1.0 equiv.) at 80° C. and the isomers were purified via silica gel column chromatography (0-50% ethyl acetate and heptanes). Isolated 2-(5-bromo-3-morpholino-2-oxopyridin-1(2H)-yl)acetonitrile in 61% yield. LCMS (m/z) (M+H)=298/299.8, Rt=0.60 min. And 2-((5-bromo-3-morpholinopyridin-2-yl)oxy)acetonitrile in 12% yield. LCMS (m/z) (M+H)=298/299.8, Rt=0.82 min.

Synthesis of 2-(5-bromo-3-morpholino-2-oxopyridin-1(2H)-yl)propanenitrile and 2-((5-bromo-3-morpholinopyridin-2-yl)oxy)propanenitrile

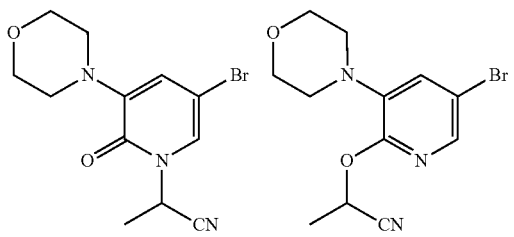

Method 1 was followed using 5-bromo-3-morpholinopyridin-2(1H)-one (1.0 equiv.), 2-bromopropanenitrile (1.2 equiv.) and potassium carbonate (1.0 equiv.) at 80° C. and the isomers were purified via silica gel column chromatography (0-50% ethyl acetate and heptanes). Isolated 2-(5-bromo-3-morpholino-2-oxopyridin-1(2H)-yl)propanenitrile in 50% yield. LCMS (m/z) (M+H)=312/314, Rt=0.63 min. And 2-((5-bromo-3-morpholinopyridin-2-yl)oxy)propanenitrile in 39% yield. LCMS (m/z) (M+H)=312/314, Rt=0.84 min.

Synthesis of (R)-2-(5-bromo-3-morpholino-2-oxopyridin-1(2H)-yl)propanenitrile and (S)-2-(5-bromo-3-morpholino-2-oxopyridin-1(2H)-yl)propanenitrile

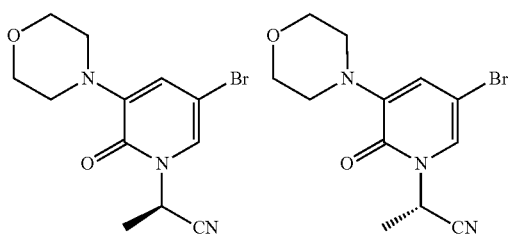

2-(5-bromo-3-morpholino-2-oxopyridin-1(2H)-yl)propanenitrile was further purified via chiral HPLC (SFC, Methanol, AD-column) to give: Peak 1 (Rt=1.13 min, 99% ee) and Peak 2 (Rt=1.74 min, 95% ee).

Synthesis of (R)-2-((5-bromo-3-morpholinopyridin-2-yl)oxy)propanenitrile and (S)-2-((5-bromo-3-morpholinopyridin-2-yl)oxy)propanenitrile

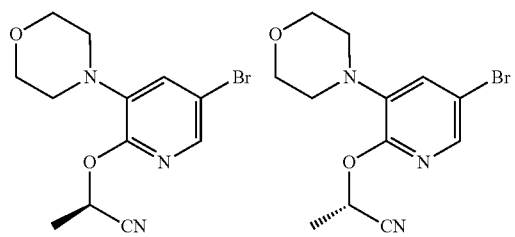

2-((5-bromo-3-morpholinopyridin-2-yl)oxy)propanenitrile was further purified via chiral HPLC (Heptanes/ethanol 95:5, AD-H column) to give: Peak 1 (Rt=4.808 min, 99% ee) and Peak 2 (Rt=7.274 min, 99% ee).

Method 2:

To a solution of the aryl halide (1.0 equiv.) and the boronic ester (Intermediate A-G, 1.0-1.2 equiv.) in DME and 2M sodium carbonate (3:1, 0.1 M) was added PdCl$_2$(dppf)-DCM adduct (0.1-0.5 equiv.) in a microwave vial equipped with a stir bar. The reaction was heated to 120° C. for 10-20 min in the microwave. The solution was partitioned between ethyl acetate and water, the organic phase was dried with sodium sulfate or magnesium sulfate, filtered and concentrated. The crude material was purified via preparative reverse HPLC. Upon lyophilization, the TFA salt of the product was obtained.

Compounds of Formula (I) were prepared by the synthetic schemes shown above, using the intermediates depicted above and analogs made similarly. Other compounds of the invention can be made by the same methods, based on the Examples described herein and known starting materials, in combination with methods known in the art.

Synthesis of 2-(difluoromethyl)isonicotinic acid

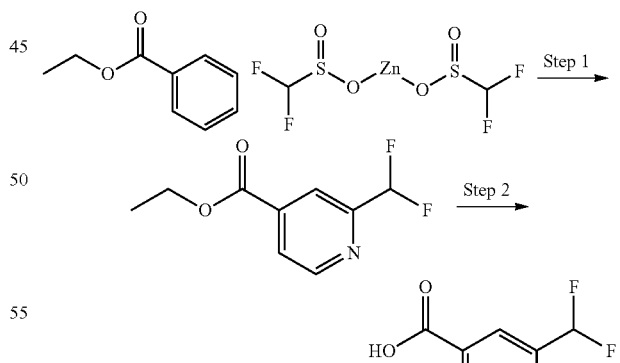

Step 1:

To a solution of ethyl isonicotinate (1.0 eq) and bis(((difluoromethyl)sulfinyl)oxy)zinc (2.7 eq) in DCM/Water (1:0.4) was cooled to 0° C. followed by the slow addition of t-butylhydroperoxide (6M in decane) (5 eq) with vigorous stirring. The reaction was warmed to RT and stirred for 18 hrs. TLC (4:1 EtOAc in Heptanes) indicates compete consumption of SM. The reaction was partitioned between DCM and NaHCO$_3$(sat). The organic phase was separated and the aqueous layer was extracted with DCM (3×). The combined organics were dried over MgSO$_4$, filtered and concentrated. The crude was loaded onto silica gel and purified via ISCO (0-30% EtOAc in heptanes). Pure fractions were combined and concentrated to yield ethyl 2-(difluoromethyl)isonicotinate in 95% as a colorless oil. $^1$H NMR (400 MHz, <cdcl3>) δ ppm 1.44 (t, J=7.24 Hz, 3H) 4.46 (q, J=7.30 Hz, 2H) 6.70 (t, J=55.60 Hz, 1H) 7.98 (d, J=4.70 Hz, 1H) 8.19 (s, 1H) 8.82 (d, J=5.09 Hz, 1H).

Step 2:

To a solution of 2-(difluoromethyl)isonicotinate (1 eq) in THF (0.25 M) was added 2M LiOH (2.5 eq) and allowed to stir at RT. Upon initial addition of LiOH, the solution turned from clear to burnt orange. After 2 hrs of stirring, the solution is light yellow in color. The reaction stirred for 18 hrs. The volatiles were removed in vacuo, and the aqueous phase was acidified to ~pH 3. A white ppt formed and was filtered and dried. Some product remained in the aqueous layer which was extracted with BuOH (2×). The organics were dried over MgSO$_4$, filtered, concentrated and dried on the high-vacuum for 2 days to yield 2-(difluoromethyl)isonicotinic acid in 99% as a white solid. $^1$H NMR (400 MHz, <dmso>) δ ppm 7.05 (t, J=54.00 Hz, 1H) 7.97 (d, J=4.70 Hz, 1H) 8.05 (s, 1H) 8.82 (d, J=4.70 Hz, 1H)

Synthesis of 2-(2-fluoropropan-2-yl)isonicotinic acid

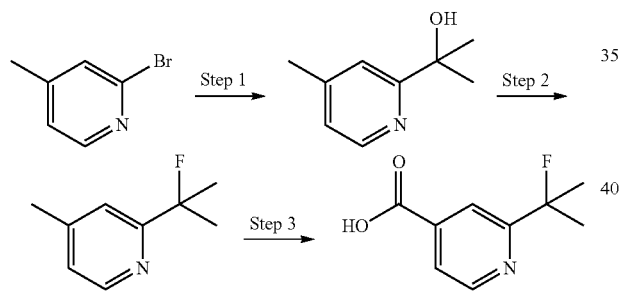

Step 1:

To a solution of 2-bromo-4-methylpyridine (1.0 equiv) in toluene (0.3 M) at −78° C. was slowly added n-BuLi (1.15 equiv) and the mixture was allowed to stir for 45 min. Acetone (3 equiv) was then added, and the reaction was allowed to warm to 25° C. over 30 min. The reaction was quenched with saturated aqueous ammonium chloride and extracted three times with ethyl acetate The combined organics were washed with brine, dried over magnesium sulfate, filtered and concentrated. The crude residue was purified via flash chromatography over silica gel eluting with heptanes and 0-50% ethyl acetate gradient. Isolated 2-(4-methylpyridin-2-yl)propan-2-ol as a pale yellow oil in 72% yield. LCMS (m/z) (M+H)=151.9, Rt=0.28 min.

Step 2:

To a solution of 2-(4-methylpyridin-2-yl)propan-2-ol (1.0 equiv.) in DCM (0.2 M) at −78° C. was added DAST (1.4 equiv.). The reaction was allowed to warm to 0° C. over 30 min and then slowly quenched with saturated aqueous sodium bicarbonate and extracted two times with DCM. The combined organics were washed with brine, dried over magnesium sulfate, filtered and concentrated. The crude residue was purified via flash chromatography over silica gel eluting with pentane and 0-20% diethyl ether gradient. Isolated 2-(2-fluoropropan-2-yl)-4-methylpyridine as a pale yellow oil in 61% yield. LCMS (m/z) (M+H)=153.9, Rt=0.32 min.

Step 3:

To a solution of 2-(2-fluoropropan-2-yl)-4-methylpyridine (1.0 equiv.) in water (0.2 M) was added KMnO$_4$ (3.0 equiv) and the reaction heated to 80° C. for 1.5 hrs. More KMnO$_4$ (1.5 equiv) was added and the reaction heated at 80° C. for an additional 1.5 hrs. The reaction was cooled to room temperature, acidified to pH 3 with 1 M HCl, and then extracted three times with ethyl acetate. The combined organics were dried over magnesium sulfate, filtered and concentrated. Isolated 2-(2-fluoropropan-2-yl)isonicotinic acid as a white solid in 43% yield. LCMS (m/z) (M+H)=184.0, Rt=0.45. $^1$H NMR (400 MHz, <dmso>) δ ppm 1.65 (s, 3H) 1.70 (s, 3H) 7.76 (dd, J=5.09, 1.57 Hz, 1H) 7.93 (s, 1H) 8.75 (d, J=5.09 Hz, 1H)

Synthesis of 3-(1,3,4-oxadiazol-2-yl)benzoic acid

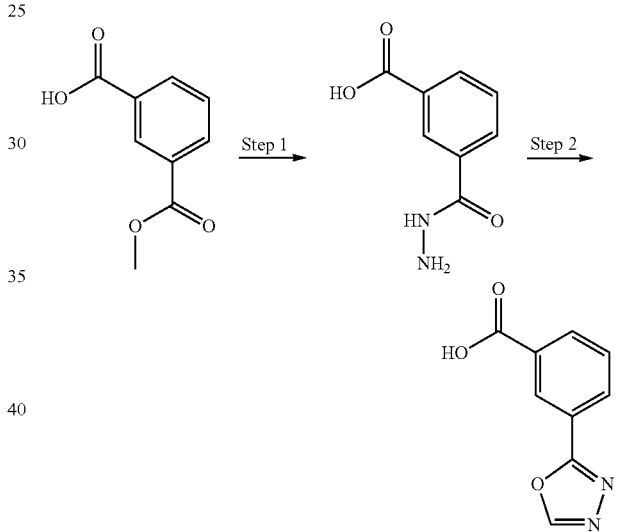

Step 1:

Monomethyl isophthalate (1.0 equiv) and hydrazine hydrate (4 equiv) were combined in MeOH (1.0 M) and heated to reflux for 4 h. More hydrazine hydrate (4 equiv) was added and the reaction was continued refluxing for another 3 h. The mixture was cooled and concentrated, providing 3-(hydrazinecarbonyl)benzoic acid which was used without further purification. LCMS (m/z) (M+H)=181.0, Rt=0.27 min.

Step 2:

A mixture of 3-(hydrazinecarbonyl)benzoic acid (1.0 equiv), triethyl orthoformate (12 equiv), and TsOH.H$_2$O (0.1 equiv) was heated at 60° C. overnight, and then further heated to 120° C. for 1.5 h. The mixture was cooled to room temp and poured onto water. The precipitated solid was filtered, washed with water, and dried to give 3-(1,3,4-oxadiazol-2-yl)benzoic acid as a white solid in 61% yield. LCMS (m/z) (M+H)=191.0, Rt=0.44 min. $^1$H NMR (400 MHz, <dmso>) δ ppm 7.74 (t, J=7.83 Hz, 1H) 8.16 (d, J=7.83 Hz, 1H) 8.25 (d, J=7.43 Hz, 1H) 8.51 (s, 1H) 9.38 (s, 1H) 13.39 (br. s., 1H)

Synthesis of 1-ethyl-6-oxo-5-(trifluoromethyl)-1,6-dihydropyridine-3-carboxylic acid

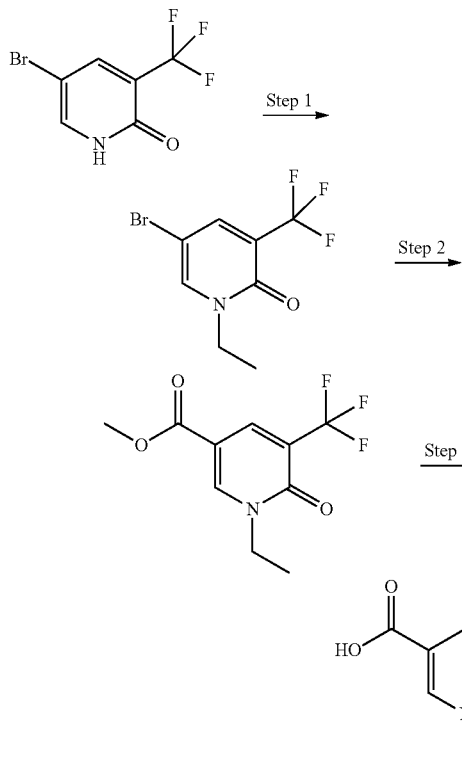

Step 1:

In a round bottom flask equipped with a stir bar and purged with nitrogen was added 5-bromo-3-(trifluoromethyl)pyridin-2-ol (1.0 equiv.), potassium carbonate (2.0 equiv.) and DMF (0.2 M). The mixture was stirred at room temperature and iodoethane (1.2 equiv.) was added via syringe. The mixture was warmed to 30° C. for 4 hours at which time LCMS indicated full conversion. The reaction was worked up by partitioning between water and ethyl acetate, the aqueous phase was extracted 3 more times with ethyl acetate, the organics were combined, washed with brine, dried with sodium sulfate, filtered and concentrated to yield 5-bromo-1-ethyl-3-(trifluoromethyl)pyridin-2(1H)-one (83%). $^1$H NMR (400 MHz, <cdcl3>) δ ppm 1.32-1.50 (m, 3H) 4.04 (q, J=7.17 Hz, 2H) 7.63 (br. s., 1H) 7.78 (br. s., 1H). LCMS (m/z) (M+H)=269.1/271.1, Rt=0.72 min Step 2:

In a 2.0 mL microwave tube was added 5-bromo-1-ethyl-3-(trifluoromethyl)pyridin-2(1H)-one (1.0 equiv.), PdCl$_2$ (dppf).CH$_2$Cl$_2$ adduct (0.1 equiv.), Mo(CO)$_6$ (1.0 equiv.), methanol (10.0 equiv.) and THF (0.4 M). The mixture was capped and stirred while DBU (3.0 equiv) was added, fizzing occurred and the tube was vented and subsequently heated in the microwave at 120° C. for 20 min at which time LCMS indicated full conversion to product (M+H=250). The reaction was filtered through Celite, concentrated, and purified via ISCO to yield methyl 1-ethyl-6-oxo-5-(trifluoromethyl)-1,6-dihydropyridine-3-carboxylate (52% yield). LCMS (m/z) (M+H)=250.0, Rt=0.69 min.

Step 3:

To a solution of methyl 1-ethyl-6-oxo-5-(trifluoromethyl)-1,6-dihydropyridine-3-carboxylate (1.0 equiv.) in THF (0.25 M) was added lithium hydroxide (1.0 M, 3.0 equiv.) and allowed to stir at RT. Upon initial addition of LiOH, the solution turned from clear to burnt orange. The rxn stirred overnight at which time LCMS indicated conversion to M+H=236. The volatiles were removed in vacuo, and the aqueous phase was acidified to ~pH 3. A tan ppt formed and was filtered and dried. A significant amount of the product remained in the aqueous layer so it was extracted 3× with EtOAc, dried, filtered and concentrated. The solids were combined to yield 1-ethyl-6-oxo-5-(trifluoromethyl)-1,6-dihydropyridine-3-carboxylic acid (97% yield). $^{13}$C NMR (400 MHz, <cdcl3>) δ ppm 166.2, 160.1, 148.3, 140.0, 125.5, 122.8, 110.6, 47.4, 14.7. LCMS (m/z) (M+H)=236.0, Rt=0.53 min.

Synthesis of 2-(1,1-difluoropropyl)isonicotinic acid

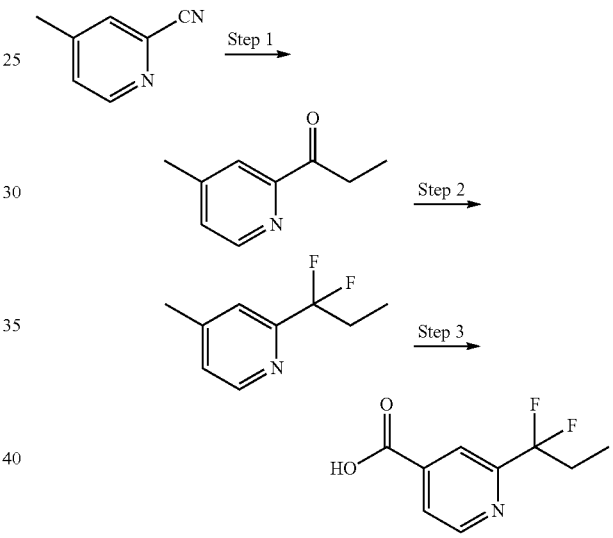

Step 1:

To a flame dried flask and 2-cyano-4-methylpyridine (1.0 equiv.) in THF (0.5 M) at −78° C. was added 3M ethylmagnesiumbromide in diethyl ether (1.2 equiv.) and the mixture was stirred at that temperature for 20 mins and then warmed to room temperature. The reaction mixture was acidified with aqueous citric acid and then partitioned between ethyl acetate and water. The separated organic layer was dried with sodium sulfate and concentrated under vacuo. The concentrated crude was purified via silica gel chromatography and eluted with 0 to 100% ethyl acetate in heptanes to give 1-(4-methylpyridinyl-2-yl)propan-1-one in 78% yield. LCMS m/z (M+H)=150.1, Rt=0.35 min.

Step 2:

To 1-(4-methylpyridinyl-2-yl)propan-1-one (1 eq) in DCM (0.46 M) was added DAST (3 eq) and ethanol (0.8 eq) and the mixture was refluxed under nitrogen atmosphere. After 5 h another portion of ethanol (0.8 eq) was added and the mixture was refluxed for 16 h. The reaction mixture was partitioned between ethyl acetate and saturated sodium bicarbonate solution and the separated organic layer was dried with sodium sulfate and concentrated under vacuo. The concentrated crude was purified via silica gel chromatography and eluted with 0 to 100% ethyl acetate in heptanes to give 2-(1,1-difluoropropyl)-4-methylpyridine in 70% yield. LCMS m/z (M+H)=172.1, Rt=0.68 min.

Step 3:

To 2-(1,1-difluoropropyl)-4-methylpyridine (1 eq) in water (0.36M) was added potassium permanganate (3 eq) and the mixture was heated to 80° C. for 6 h. To the reaction mixture was added another portion of potassium permanganate (1.5 eq) and after 1 h the reaction mixture was cooled to ambient temperature and was then acidified with 6N HCl and the product was extracted with ethyl acetate and the separated organic layer was dried with sodium sulfate and concentrated under vacuo to give 2-(1,1-difluoropropyl)isonicotinic acid in 23% yield. LCMS m/z (M+H)=202.1, Rt=0.64 min.

Synthesis of 2-(2-hydroxypropan-2-yl)isonicotinic acid

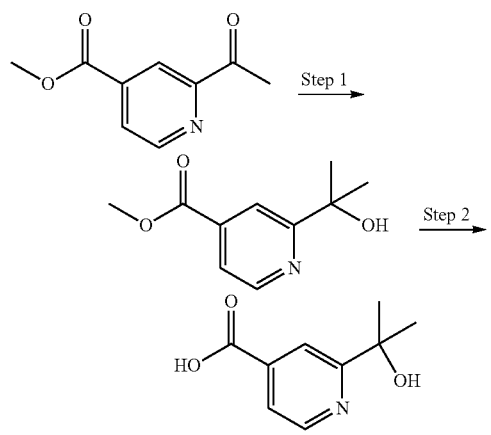

Step 1:

To a solution of methyl-2-acetylisonicotinate (1.0 equiv.) in THF (0.089M) at −78° C. was added 3M solution of methyl magnesiumbromide in diethyl ether (6 eq) drop-wise over 10 min. The reaction mixture was quenched with water at that temperature and brought to ambient temperature. The reaction mixture was partitioned between ethyl acetate and water. The separated organic layer was dried with sodium sulfate and concentrated under vacuo. The concentrated crude was purified via silica gel chromatography and eluted with 0 to 100% ethyl acetate in heptanes to give methyl 2-(2-hydroxypropan-2-yl)isonicotinate in 38% yield. LCMS m/z (M+H)=196 Rt=0.3 min.

Step 2:

To methyl 2-(2-hydroxypropan-2-yl)isonicotinate (1.0 equiv.) in THF (0.3 M) was added 2M Lithium hydroxide (2 eq) and the reaction mixture was stirred at ambient temperature for 1 h. The reaction mixture was concentrated and to it was added 6M HCl (2 eq) (pH=4) and then extracted with 3:1 chloroform:IPA mixture and the separated organic layer was dried with sodium sulfate and concentrated under vacuo to give 2-(2-hydroxypropan-2-yl)isonicotinic acid in 91% yield. LCMS (m/z) (M+H)=182, Rt=0.12 min. 1H NMR (400 MHz, <dmso>) δ ppm 1.40 (d, J=5.09 Hz, 16H) 5.08-5.23 (m, 1H) 7.15-7.29 (m, 1H) 7.67-7.78 (m, 1H) 8.28-8.43 (m, 1H).

Synthesis of 6-cyclopropylpyridazine-4-carboxylic acid

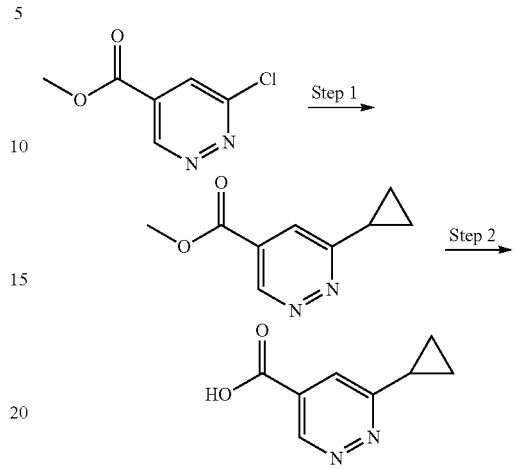

Step 1:

To a dry round bottom flask was added a solution of ZnCl$_2$ (0.5 M in THF) (1.50 equiv.) followed by cyclopropylmagnesium bromide (0.5 M in THF) (1.50 equiv.) at room temperature under Argon. The resulting solution was stirred for 30 min before the addition of methyl 6-chloropyridazine-4-carboxylate (1.0 equiv.), PdCl$_2$(dppf)-DCM (0.05 equiv.), and zinc dust (0.15 equiv.). The resulting mixture was then heated to 55° C. overnight. LCMS indicated 90% conversion and the reaction was cooled, quenched with H$_2$O, filtered through Celite, extracted with EtOAc (3×), dried, concentrated, and purified on a ISCO SiO$_2$ cartridge using 0-100% EtOAc/Heptanes to yield methyl 6-cyclopropylpyridazine-4-carboxylate (39% yield). 1H NMR (400 MHz, <cdcl3>) δ ppm 1.12-1.34 (m, 4H) 2.11-2.36 (m, 1H) 4.01 (s, 3H) 7.73 (d, J=1.96 Hz, 1H) 9.43 (d, J=1.96 Hz, 1H). LCMS (m/z) (M+H)=178.9, Rt=0.46 min.

Step 2:

To a solution of methyl 6-cyclopropylpyridazine-4-carboxylate (1.0 equiv.) in THF (0.25 M) was added lithium hydroxide (1.0 M, 3.0 equiv.) and allowed to stir at room temperature. The rxn stirred overnight at which time LCMS indicated conversion to M+H=165. The volatiles (THF) were removed in vacuo, and the aqueous phase was acidified to ~pH 3-4 with HCl. The reaction was diluted with H$_2$O and brine, extracted with EtOAc (3×), dried over MgSO$_4$, filtered, and concentrated to yield 6-cyclopropylpyridazine-4-carboxylic acid (83% yield). LCMS (m/z) (M+H)=164.8, Rt=0.27 min.

Synthesis of 2-cyclopropylisonicotinic acid

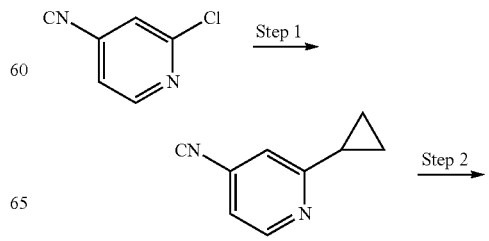

77

-continued

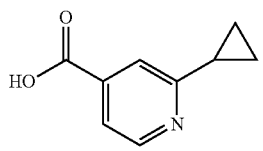

Step 1:

To an oven dried round-bottomed flask was added a solution of zinc chloride (0.5 M in THF, 1.5 equiv.) followed by cyclopropylmagnesium bromide (0.5 M in THF, 1.5 equiv.) at room temperature and the resulting solution was stirred at room temperature for 30 min before the portion-wise sequential addition of 2-chloroisonicotinonitrile (1.0 equiv.), dppf (0.12 equiv.) and Pd$_2$(dba)$_3$ (0.06 equiv.) at room temperature. The resulting mixture was heated to 60° C. for 23 hours. At this point, LC/MS indicated complete consumption of the starting material and formation of the desired product. The reaction mixture was quenched by the addition of ammonium chloride and diluted with diethyl ether. Extracted with ethyl acetate three times, the combined organics were dried over magnesium sulfate and concentrated in vacuo to yield a brown oil. The oil was further purified by flash column chromatography eluting with 100% heptanes to 50% ethyl acetate:heptanes to yield 2-cyclopropylisonicotinonitrile as the desired product as a yellow oil in 75% yield. LCMS (m/z) (M+H)=145.0, Rt=0.53 min.

Step 2:

To a solution of 2-cyclopropylisonicotinonitrile (1.0 equiv.) in ethanol and water (2:3, 1.7 M) was added sodium hydroxide (2.0 equiv.). The resulting mixture was then heated to 80° C. for 90 min. Cooled to room temperature and concentrated under vacuo. The residue was diluted with water and 2M HCl to pH=5. The aqueous layer was separated and extracted with ethyl acetate three times. The combined organics were then dried over magnesium sulfate, filtered, and concentrated under vacuo to yield 2-cyclopropylisonicotinic acid as a white solid in 99% yield. LCMS (m/z) (M+H)=164.0, Rt=0.26 min.

Synthesis of 2-(oxetan-3-yl)isonicotinic acid

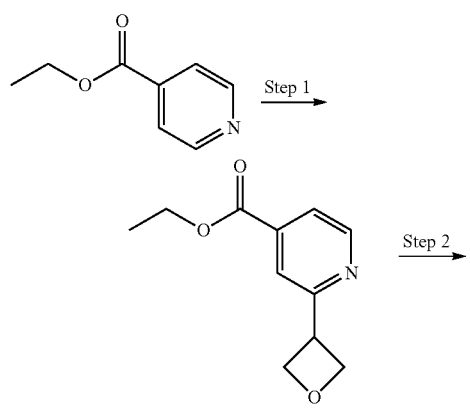

78

-continued

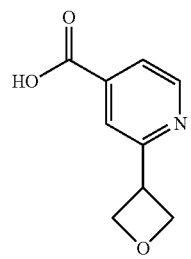

Step 1:

To a solution of ethyl isonicotinate (1.0 equiv.) in DMSO (0.1M) was added sulphuric acid (2.0 equiv.), iron(II) sulfate heptahydrate (0.3 equiv.), 3-iodooxetane (2.0 equiv.). Heated to 40° C. and then added hydrogen peroxide (30% in water, 3.0 equiv.). After 2 min, another 0.3 equiv. of iron (II) sulfate heptahydrate was added and stirred for 30 min. After 30 min, added additional hydrogen peroxide (3.0 equiv.) and iron (II) sulfate heptahydrate (0.3 equiv.) and stirred for 15 min at 40° C. After 2 hours, LC/MS indicated complete conversion to product. Quenched by the addition of 1M NaOH and diluted with diethyl ether. Extracted three more times with diethyl ether, the organics were combined, dried over magnesium sulfate, filtered and concentrated in vacuo to yield an orange oil. This material was further purified via flash column chromatography eluting with 100% heptanes to 20% ethyl acetate:heptanes to 80% ethyl acetate:heptanes to yield ethyl 2-(oxetan-3-yl)isonicotinate as a colorless oil in 14% yield. LCMS (m/z) (M+H)=208.1, Rt=0.48 min.

Step 2:

To a solution of ethyl 2-(oxetan-3-yl)isonicotinate (1.0 equiv.) in THF and Water (1:1, 0.45 M) was added lithium hydroxide (2.0 equiv.) at room temperature. The mixture was stirred for 4 hours at rt. The reaction was quenched with 2M HCl and diluted with ethyl acetate. The organic phase was dried over magnesium sulfate, filtered and concentrated under vacuo to yield 2-(oxetan-3-yl)isonicotinic acid as an off-white solid in 41% yield. LCMS (m/z) (M+H)=180.0, Rt=0.22.

Synthesis of 6-(trifluoromethyl)pyridazine-4-carboxylic acid

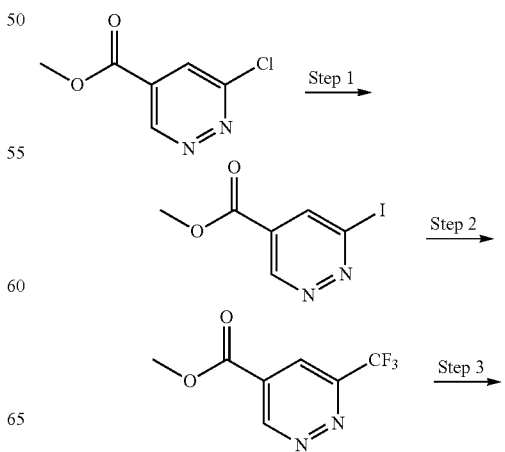

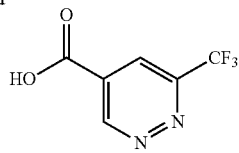

Step 1:

To a solution of methyl 6-chloropyridazine-4-carboxylate (1.0 equiv.) in HI (57% w/w in water) (1.35 M) was added NaI (1.3 equiv.). The reaction was heated at 40° C. for 20 hrs. The reaction mixture was cooled to room temperature, neutralized with sat. NaHCO₃ and extracted with EtOAc. The combined organic solution was washed with sat NH₄Cl, brine, dried and concentrated in vacuo to give methyl 6-iodopyridazine-4-carboxylate in 87% yield. LCMS (m/z) (M+H)=264.9, Rt=0.48 min.

Step 2:

To a mixture of methyl 6-iodopyridazine-4-carboxylate (1.0 equiv.) and [(phen)CuCF₃] (1.5 equiv.) at rt was added DMF (0.28 M). The mixture was stirred at rt overnight, diluted with ether and filtered through Celite. The organics were washed with H₂O, Brine and dried over Na₂SO₄ and concentrated to yield methyl 6-(trifluoromethyl)pyridazine-4-carboxylate in 99% yield. LCMS (m/z) (M+H)=206.9, Rt=0.53 min.

Step 3:

To a solution of methyl 6-(trifluoromethyl)pyridazine-4-carboxylate (1.0 equiv.) in THF/water (1:1, 0.20 M) was added LiOH (6.0 equiv.). After it stirred at rt for 3 hr, the mixture was concentrated to remove most of THF and the residue was diluted with EtOAc and neutralized with 6N HCl to pH=2. The organic layer was washed with brine, dried with Na₂SO₄, filtered and concentrated to yield 6-(trifluoromethyl)pyridazine-4-carboxylic acid in 69% yield. LCMS (m/z) (M+H)=192.8, Rt=0.37 min. 1H NMR (400 MHz, <dmso>) δ ppm 8.42 (d, J=1.57 Hz, 1H), 9.81 (d, J=1.57 Hz, 1H).

Synthesis of 2-(1-cyanocyclopropyl)isonicotinic acid

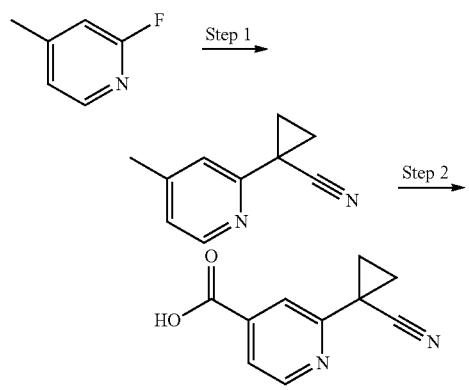

Step 1:

To a mixture of cyclopropanecarbonitrile (4.0 equiv.) and 2-fluoro-4-methylpyridine (1.0 equiv.) was added KHMDS in PhMe (1.3 equiv.) to give a dark suspension. The mixture was heated to reflux for 1.5 hours at which time the reaction was cooled to RT, quenched with NH₄Cl (aq), extracted with EtOAc (3×), dried over Na₂SO₄, filtered, and concentrated to yield 1-(4-methylpyridin-2-yl)cyclopropanecarbonitrile in 38% yield. LCMS (m/z) (M+H)=158.8, Rt=0.43 min. The crude material was used in next step.

Step 2:

To a solution of 1-(4-methylpyridin-2-yl)cyclopropanecarbonitrile (1.0 equiv.) in water (0.16 M) was added potassium permanganate (6.0 equiv.). The mixture was heated at 60° C. for 4 hr. The mixture was cooled to rt, acidified with 2 M HCl to pH=4 and extracted with EtOAc. The organic layer was washed with brine, dried over Na₂SO₄ and concentrated to yield 2-(1-cyanocyclopropyl)isonicotinic acid in 34% yield. LCMS (m/z) (M+H)=189.1, Rt=0.53 min.

Synthesis of 6-(1-cyanocyclopropyl)pyridazine-4-carboxylic acid

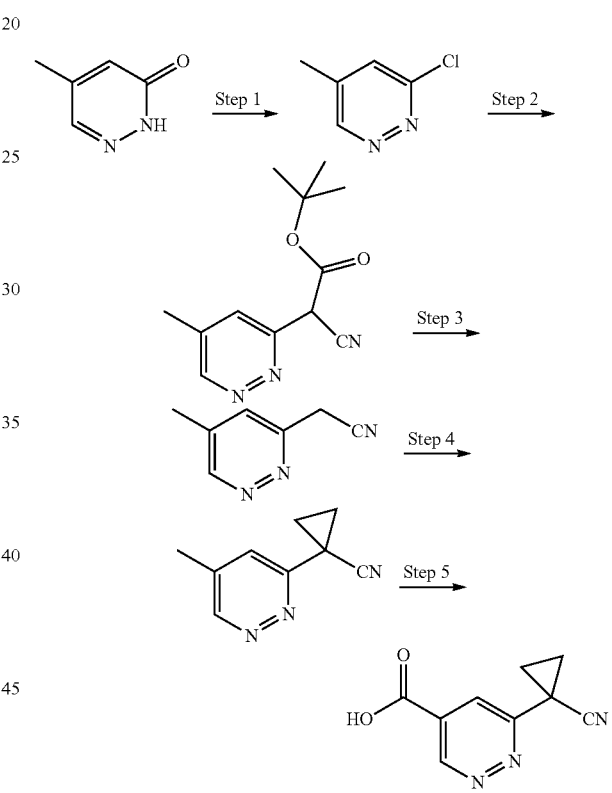

Step 1:

A solution of 5-methylpyridazin-3(2H)-one (1.0 equiv.) in POCl₃ (2.3 M) was heated at 90° C. for 2 h. The reaction mixture was poured into crushed ice and neutralized with sodium bicarbonate. After three extractions with EtOAc, the combined organic phase was washed with brine and then dried over sodium sulfate. After concentration, the crude material was purified via normal phase chromatography eluting with 30% EtOAc in heptanes. 3-chloro-5-methylpyridazine was isolated in 93% yield. LCMS (m/z) (M+H)= 128.9, Rt=0.37 min.

Step 2:

To a solution of tert-butyl 2-cyanoacetate (1.0 equiv.) in THF (0.25 M) in a flame dried flask under Ar and cooled in an ice-water bath was added sodium hydride (2.7 eq). After 30 min, 3-chloro-5-methylpyridazine in THF (2 M) was added dropwise. After several min, the solution was warmed to room temperature and then microwave heated at 120° C. for 60 min. The reaction mixture was then partitioned between water and EtOAc. The organic phase was then washed with water and brine and then dried over sodium sulfate. After concentration, the crude material was purified via normal phase chromatography. tert-butyl 2-cyano-2-(5-methylpyridazin-3-yl)acetate was isolated in 44% yield. LCMS (m/z) (M+H)=178.1, Rt=0.90 min.

Step 3:
To a solution of tert-butyl 2-cyano-2-(5-methylpyridazin-3-yl)acetate (1.0 equiv.) in DCM (0.1 M) was added 2,2,2-trifluoroacetic acid (24 eq). After 1 h 45 min, the reaction mixture was concentrated and was then purified via normal phase chromatography. Product eluted at 90% EtOAc in heptanes. 2-(5-Methylpyridazin-3-yl)acetonitrile was isolated in 81% yield. LCMS (m/z) (M+H)=134.0, Rt=0.25 min.

Step 4:
In a flame dried flask under Ar, 2-(5-methylpyridazin-3-yl)acetonitrile was dissolved in DMF (0.1 M) and then cooled in an ice-water bath. Sodium hydride (3 eq) was added. After 30 min, 1,2-dibromoethane (1 eq) was added. After 2 h, the reaction mixture was warmed to room temperature and was then poured into water. The product was extracted with three portions of EtOAc. The combined organics were washed with brine and dried over sodium sulfate. The organics were concentrated and were then purified via normal phase chromatography. Product eluted at 20% EtOAc in heptanes. 1-(5-Methylpyridazin-3-yl)cyclopropanecarbonitrile was isolated in 65% yield. LCMS (m/z) (M+H)=160.2, Rt=0.40 min.

Step 5:
To a solution of 1-(5-methylpyridazin-3-yl)cyclopropanecarbonitrile (1.0 equiv.) in pyridine (0.38 M) under Ar was added selenium dioxide (4 eq). After heating at 90° C. for 2 days, the reaction mixture was cooled in an ice bath and water was added. After washing with ethyl acetate, the aqueous phase was acidified to pH 3 with 6 N HCl and then extracted with ethyl acetate. The combined organics were dried over Na$_2$SO$_4$ and concentrated to give 6-(1-cyanocyclopropyl)pyridazine-4-carboxylic acid in 36% yield. LCMS (m/z) (M+H)=190.2, Rt=0.36 min.

Synthesis of
3-(2-(methylsulfonyl)propan-2-yl)benzoic acid

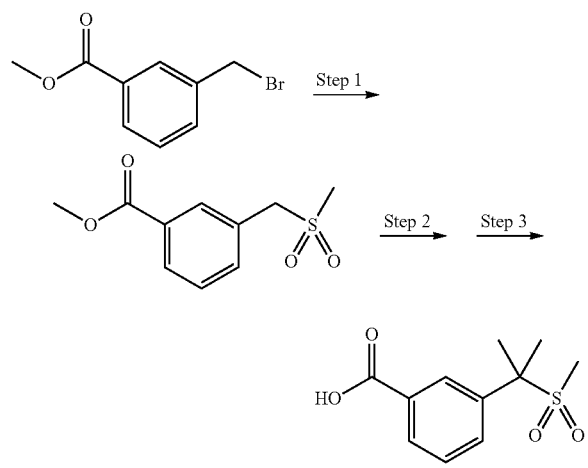

Step 1:
To methyl 3-(bromomethyl)benzoate (1.0 equiv.) in THF (0.44M) at rt was added sodium methanesulfonate (2.0 equiv.). The mixture was stirred at rt for 18 h. The reaction mixture was poured onto ice-water. The solid was collected by filtration and dried overnight under vacuo to give methyl 3-((methylsulfonyl)methyl)benzoate in 95% yield. LCMS m/z (M+H)=229.2, Rt=0.52 min.

Step 2:
To methyl 3-((methylsulfonyl)methyl)benzoate (1.0 equiv.) in THF (0.16M) at rt was added sodium t-butoxide (3.0 equiv.) and 2.0 M methyl iodide in diethyl ether (2.2 equiv.). The reaction mixture was stirred at rt for 18 h. The reaction mixture was partitioned between ethyl acetate and water. The separated organic layer was dried with sodium sulfate and concentrated under vacuo. The concentrated crude was purified via silica gel chromatography and eluted with 0 to 50% ethyl acetate in heptanes to give methyl 3-(2-(methylsulfonyl)propan-2-yl)benzoate in 70% yield. LCMS m/z (M+H)=257.2, Rt=0.60 min.

Step 3:
To methyl 3-(2-(methylsulfonyl)propan-2-yl)benzoate (1.0 equiv.) in 10:1 mixture of THF and water (0.5M) at rt was added lithium hydroxide. The reaction mixture was stirred at rt for 1 h then concentrated. The residue was dissolved in water then acidified with 1.0N HCl to pH=3. The precipitate was collected by filtration and dried under vacuo to give 3-(2-(methylsulfonyl)propan-2-yl)benzoic acid in 95% yield. LCMS m/z (M+H)=243.2, Rt=0.54 min.

Synthesis of
6-(2-fluoropropan-2-yl)pyridazine-4-carboxylic acid

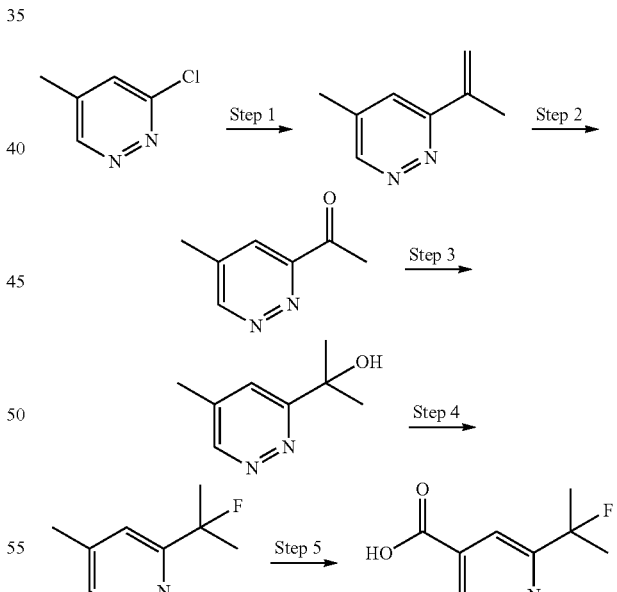

Step 1:
To 3-chloro-5-methylpyridazine (1.0 equiv.) in DME (0.5M) at rt was added 4,4,5,5-tetramethyl-2-(prop-1-en-2-yl)-1,3,2-dioxaborolane (1.4 equiv.), 2.0 M sodium carbonate (3.0 equiv.), Pd(PPh$_3$)$_4$ (0.02 equiv.). The mixture was stirred at 70° C. for 18 h then cooled to ambient temperature. The reaction mixture was partitioned between ethyl acetate and water. The separated organic layer was dried with sodium sulfate and concentrated under vacuo. The concentrated crude was purified via silica gel chromatography and eluted with 0 to 30% ethyl acetate in heptanes to give 5-methyl-3-(prop-1-en-2-yl)pyridazine in 58% yield. LCMS m/z (M+H)=134.8, Rt=0.44 min.

Step 2:

To 5-methyl-3-(prop-1-en-2-yl)pyridazine in dichloromethane (0.5M) at −78° C. was bubbled with ozone for 10 min. The reaction mixture was warmed to rt then concentrated. The concentrated crude was purified via silica gel chromatography and eluted with 0 to 50% ethyl acetate in heptanes to give 1-(5-methylpyridazin-3-yl)ethanone in 50% yield. LCMS m/z (M+H)=136.8, Rt=0.36 min.

Step 3:

To 1-(5-methylpyridazin-3-yl)ethanone (1.0 equiv.) in THF (0.5M) at −0° C. was added 3.0 M methylmagnesiumbromide in diethyl ether (1.1 eq) and the mixture was stirred at that temperature for 2 h. The reaction mixture was acidified with aqueous citric acid and then partitioned between ethyl acetate and water. The separated organic layer was dried with sodium sulfate and concentrated under vacuo. The concentrated crude was purified via silica gel chromatography and eluted with 0 to 40% ethyl acetate in heptanes to give 2-(5-methylpyridazin-3-yl)propan-2-ol in 49% yield. LCMS m/z (M+H)=152.9, Rt=0.76 min.

Step 4:

To 2-(5-methylpyridazin-3-yl)propan-2-ol (1 equiv.) in DCM (0.46M) at −15° C. was added DAST (1.2 equiv.) and the mixture was stirred at that temperature for 1 h under argon atmosphere. The reaction mixture was neutralized with saturated sodium bicarbonate solution to pH=8 and partitioned between water and dichloromethane. The separated organic layer was dried with sodium sulfate and concentrated under vacuo. The concentrated crude was purified via silica gel chromatography and eluted with 0 to 50% ethyl acetate in heptanes to give 3-(2-fluoropropan-2-yl)-5-methylpyridazine in 52% yield. LCMS m/z (M+H)=154.8, Rt=0.42 min.

Step 5:

To 3-(2-fluoropropan-2-yl)-5-methylpyridazine (1 equiv.) in pyridine (0.38 M) was added selenium dioxide (2.5 equiv.) and the mixture was heated to 70° C. for 18 h. The reaction mixture was cooled to ambient temperature and concentrated. The concentrated crude was dissolved in water and then acidified with 1N HCl to pH=3. The mixture was partitioned between ethyl acetate and water. The separated organic layer was dried with sodium sulfate and concentrated under vacuo to give 2-(1,1-difluoropropyl)isonicotinic acid in 89% yield. LCMS m/z (M+H)=184.9, Rt=0.63 min.

Synthesis of
6-(2-cyanopropan-2-yl)pyridazine-4-carboxylic acid

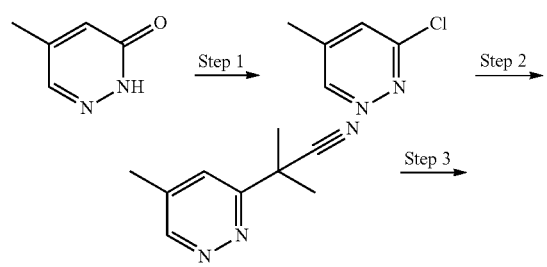

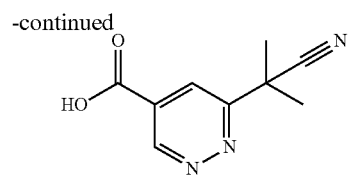

Step 1:

A solution of 5-methylpyridazin-3(2H)-one (1.0 equiv.) in POCl₃ (2 M) was heated up to 90° C. for 2 h. After completion of the reaction (TLC monitoring), reaction mass was poured into crushed ice and pH was neutralized by using solid NaHCO₃. The compound was extracted with EtOAc (3×); combined organics were washed with brine and dried over anhydrous Na₂SO₄. The solvent was evaporated and crude residue was purified over silica gel by using eluents 30% EtOAc:hexanes to afford 3-chloro-5-methylpyridazine as yellowish liquid in 93% yield. ¹H-NMR (400 MHz, CDCl₃): δ 8.96 (s, 1H), 7.36 (s, 1H) and 2.39 (s, 3H). LCMS m/z (M+H)=129.13.

Step 2:

A solution of LDA (2M in THF, 2.5 equiv.) in THF (1 M) was cooled up to −78° C. followed by the drop wise addition of isobutyronitrile (2.5 equiv.). The resulting reaction mixture was stirred at 0° C. for 30 minutes and again cooled up to −78° C. followed by the addition of a solution of 3-chloro-5-methylpyridazine (1.0 equiv.) in THF. The resulting reaction mixture temperature was slowly raised up to room temperature and left for stirring for 16 h. After completion of the reaction (TLC monitoring), reaction mass was quenched with saturated solution of NH₄Cl followed by the extraction with EtOAc (3×). The combined organics were washed with brine, dried over anhydrous Na₂SO₄. The solvent was evaporated and crude residue was purified over silica gel by using eluents 50% EtOAc: hexanes to afford 2-methyl-2-(5-methylpyridazin-3-yl)propanenitrile as the desired product as off-white low melting solid (76%). ¹H-NMR (400 MHz, CDCl₃): δ 9.01 (s, 1H), 7.61 (s, 1H), 2.42 (s, 3H) and 1.87 (s, 6H). LCMS m/z (M+H)=162.42.

Step 3:

To a solution of 2-methyl-2-(5-methylpyridazin-3-yl)propanenitrile (1.0 equiv.) in pyridine (1.2 M) was added SeO₂ (2.5 equiv.). The resulting reaction mass was stirred at 90° C. for 24 h. After completion of the reaction (TLC monitoring), reaction mixture was cooled up to room temperature and poured into crushed ice followed by the extraction with EtOAc (2×). The organics were discarded and the pH of the aqueous layer was adjusted up to 3-4 by using 6N HCl followed by the extraction with EtOAc (3×). The combined organics were washed with brine, dried over anhydrous Na₂SO₄, filtered and evaporated under reduced pressure. The crude compound was finally triturated with n-pentane to get 6-(2-cyanopropan-2-yl)pyridazine-4-carboxylic acid as the desired product as light yellow solid (51%). ¹H-NMR (400 MHz, DMSO-d₆): δ 9.55 (s, 1H), 8.21 (s, 1H) and 1.82 (s, 6H). LCMS m/z (M+H)=192.28.

Synthesis of
4-(5-bromo-2-ethoxypyridin-3-yl)morpholine

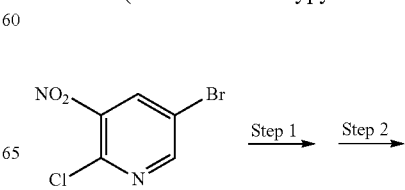

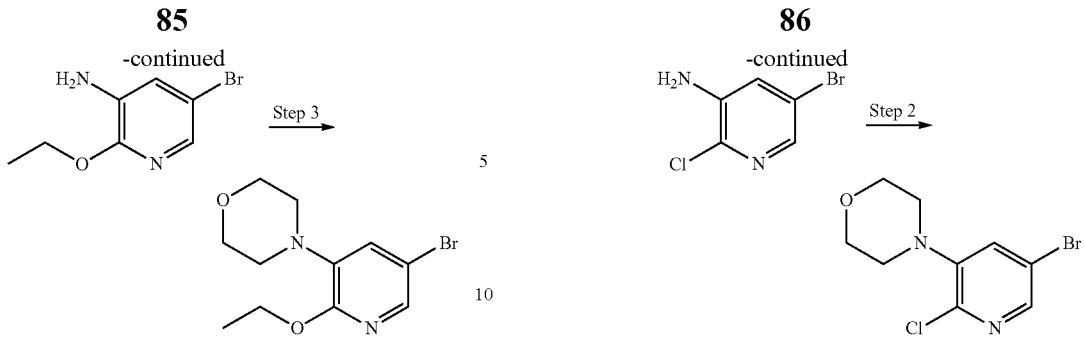

Step 1:

To a solution of 5-bromo-2-chloro-3-nitropyridine (1.0 equiv) in EtOH (0.25 M) at 25° C. was added sodium ethoxide (21 wt % solution in EtOH, 1.2 equiv) and the mixture was heated to 75° C. for 1 h. The reaction was poured onto a 1:1 mix of 1 M citric acid and water and the ethanol was removed by concentration. The residue was extracted with three times with ethyl acetate. The combined organics were washed with brine, dried over magnesium sulfate, filtered and concentrated. Isolated 5-bromo-2-ethoxy-3-nitropyridine as a brown oil which was used without further purification. LCMS (m/z) (M+H)=246.8/248.8, Rt=0.95 min.

Step 2:

To a solution of 5-bromo-2-ethoxy-3-nitropyridine (1.0 equiv) in MeOH and DCM (1:10; 0.3 M) at 25° C. were added zinc (5.5 equiv) and ammonium chloride (5 equiv) and the mixture was heated to 75° C. and stirred for 4 hours. The reaction was cooled to room temperature and filtered through a short plug of Celite, washing with DCM, and then concentrated. The residue was taken up in ethyl acetate, washed with water and brine and then dried over magnesium sulfate, filtered and concentrated. The crude residue was purified via flash chromatography over silica gel eluting with heptanes and 0-50% ethyl acetate gradient. Isolated 5-bromo-2-ethoxypyridin-3-amine as a brown solid in 79% yield. LCMS (m/z) (M+H)=216.9/218.9, Rt=0.75 min.

Step 3:

To a solution of 5-bromo-2-ethoxypyridin-3-amine (1.0 equiv.) in DMF (0.5 M) at 0° C. was slowly added NaH (1.5 equiv.) and the mixture was allowed to warm to room temperature over 15 min followed by the addition of bis(2-bromoethyl) ether (4 equiv.). The mixture was heated to 90° C. and stirred for 48 hours. The mixture was poured onto ice water and extracted three times with ethyl acetate. The combined organics were washed with water, brine, dried over magnesium sulfate, filtered and concentrated. The crude residue was purified via flash chromatography over silica gel eluting with heptanes and 0-25% acetone gradient. Isolated 4-(5-bromo-2-ethoxypyridin-3-yl)morpholine as an orange solid in 76% yield. LCMS (m/z) (M+H)=286.9/288.9, Rt=0.93 min.

Synthesis of
4-(5-bromo-2-chloropyridin-3-yl)morpholine

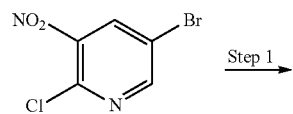

Step 1:

To a solution of 5-bromo-2-chloro-3-nitropyridine (1.0 equiv) in MeOH and DCM (1:10; 0.45 M) at 25° C. were added zinc (5.5 equiv) and ammonium chloride (5 equiv) and the mixture was heated to 65° C. and stirred for 5 hours. More zinc (2.5 equiv) and ammonium chloride (2.5 equiv) was added and the mixture was stirred at 65° C. for an additional 3 hours. The reaction was cooled to room temperature and filtered through a short plug of Celite. The filtrate was washed with water and brine and then dried over magnesium sulfate, filtered and concentrated. Isolated 5-bromo-2-chloropyridin-3-amine as an off-white solid in 35% yield which was used without further purification. LCMS (m/z) (M+H)=206.8/208.8, Rt=0.62 min.

Step 2:

To a solution of 5-bromo-2-chloropyridin-3-amine (1.0 equiv.) in DMF (0.2 M) at 0° C. was slowly added NaH (1.5 equiv.) and the mixture was allowed to warm to room temperature over 15 min followed by the addition of bis(2-bromoethyl) ether (3 equiv.). The mixture was heated to 80° C. and stirred for 2 hours. The mixture was poured onto water and extracted three times with ethyl acetate. The combined organics were washed with water, brine, dried over magnesium sulfate, filtered and concentrated. The crude residue was purified via flash chromatography over silica gel eluting with heptanes and 0-50% acetone gradient. Isolated 4-(5-bromo-2-chloropyridin-3-yl)morpholine as a yellow solid in 71% yield. LCMS (m/z) (M+H)=276.9/278.9, Rt=0.81 min.

Synthesis of
4-(5-bromo-2-fluoropyridin-3-yl)morpholine

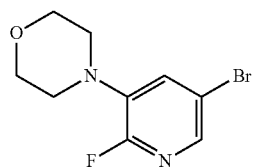 [SMILES: Fc1ncc(Br)cc1N1CCOCC1]

To an ice-bath cooled solution of NaH (60% in mineral oil, 3.0 equiv.) in DMF (1.4 M) was added 3-amino-5-bromo-2-fluoropyridine (1.0 equiv.). The mixture was allowed to warm to room temperature over 15 min and then treated with bis(2-bromoethyl) ether (1.5 equiv.). The mixture was heated to 80° C. and stirred for 35 min. The cooled reaction mixture was poured into four volumes of water. The resulting precipitate was collected by vacuum filtration. The filter cake was rinsed twice with water and twice with heptanes. The tan solid was dried under high vacuum to give 4-(5-bromo-2-fluoropyridin-3-yl)morpholine in 83% yield. LCMS (m/z) (M+H)=260.9/262.9, Rt=0.74 min.

Synthesis of 4-(5-bromopyridin-3-yl)morpholine

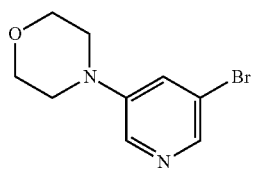

To a solution of 3-amino-5-bromopyridine (1.0 equiv.) in DMF (0.6 M) at 0° C. was slowly added NaH (1.5 equiv.) and the mixture was allowed to warm to room temperature over 15 min followed by the addition of bis(2-bromoethyl) ether (3 equiv.). The mixture was heated to 80° C. and stirred for 18 hours. The mixture was poured onto water and extracted three times with DCM. The combined organics were washed with water, brine, dried over magnesium sulfate, filtered and concentrated. The crude residue was purified via flash chromatography over silica gel eluting with heptanes and 0-75% ethyl acetate gradient. Isolated 4-(5-bromopyridin-3-yl)morpholine as a yellow solid in 40% yield. LCMS (m/z) (M+H)=242.9/244.9, Rt=0.39 min.

Synthesis of 5-bromo-3-morpholinopicolinonitrile

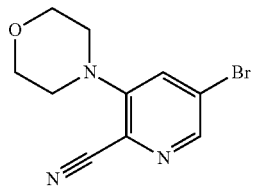 [SMILES: N#Cc1ncc(Br)cc1N1CCOCC1]

A solution of 5-bromo-3-fluoropicolinonitrile (1.0 equiv.) in acetonitrile (0.5 M) was treated with morpholine (1.1 equiv.), and DIEA (2.0 equiv.). The mixture was stirred at 90° C. for 22 hr. The cooled reaction mixture was diluted with water (12 mL) and filtered. The precipitate was air-dried to give 5-bromo-3-morpholinopicolinonitrile as a yellow crystalline solid in 87% yield. LCMS (m/z) (M+H)= 267.9/269.9, Rt=0.79 min.

Synthesis of 5-bromo-N,N-dimethyl-3-morpholinopyridin-2-amine

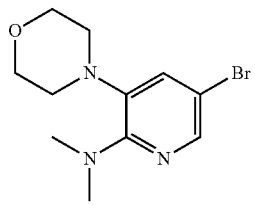 [SMILES: CN(C)c1ncc(Br)cc1N1CCOCC1]

To a solution of 4-(5-bromo-2-fluoropyridin-3-yl)morpholine (1.0 equiv.) in DMF (0.3 M) was added dimethylamine, 5.6M in ethanol (4.0 equiv.). The reaction mixture was stirred at 90° C. overnight. The cooled reaction mixture was partially concentrated in vacuo. Four volumes of water were added. The mixture was stirred for 1 hr and filtered. The pinkish solid was air-dried to give 5-bromo-N,N-dimethyl-3-morpholinopyridin-2-amine in 69% yield. LCMS (m/z) (M+H)=285.8/287.8, Rt=0.50 min.

Synthesis of 4-(5-bromo-2-(difluoromethoxy)pyridin-3-yl)morpholine

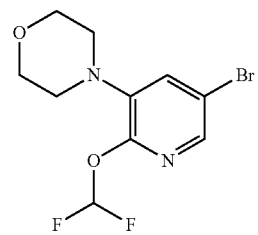 [SMILES: FC(F)Oc1ncc(Br)cc1N1CCOCC1]

To a solution of 5-bromo-3-morpholinopyridin-2-ol (1.0 equiv) in DMF (0.38 M) was added sodium 2-chloro-2,2-difluoroacetate (2 equiv.) and sodium hydroxide (1.1 equiv.) and the reaction was heated to 55° C. for 16 h. The reaction mixture was further heated to 90° C. for 16 h. The reaction mixture was partitioned between water and ethyl acetate, and the organic phase was dried with sodium sulfate, filtered and concentrated. The crude material was redissolved in DCM and a few drops of methanol and filtered. The filtrate was concentrated and purified via flash column chromatography over silica gel eluting with heptane and 0 to 100% ethyl acetate gradient. Isolated 4-(5-bromo-2-(difluoromethoxy)pyridin-3-yl)morpholine. $^1$H NMR (500 MHz, DMSO-d6) δ 2.95-3.14 (m, 4H), 3.54-3.93 (m, 4H), 7.58 (d, J=2.2 Hz, 1H), 7.74 (t, J=72.4 Hz, 1H), 7.95 (d, J=2.1 Hz, 1H), LCMS (m/z) (M+H)=308.9/310.9, Rt=0.87 min.

Synthesis of 8-(5-bromo-2-((tetrahydro-2H-pyran-4-yl)oxy)pyridin-3-yl)-3-oxa-8-azabicyclo[3.2.1]octane

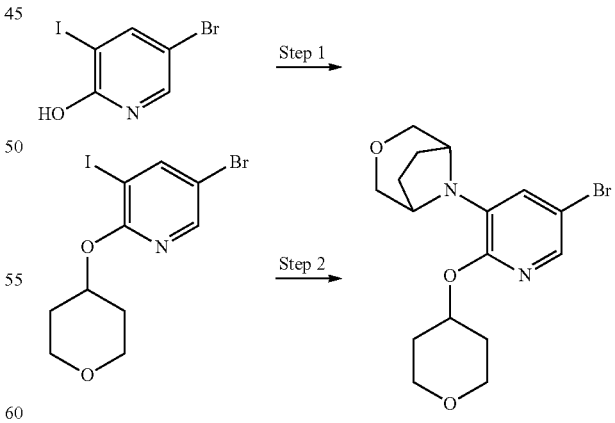

Step 1:
To a solution of 5-bromo-3-iodo-2-hydroxypyridine (1.0 equiv.) in THF (0.18 M) at 25° C. were added 4-hydroxytetrahydropyran (1.2 equiv.), PPh$_3$ (1.25 equiv.) and DIAD (1.2 equiv.) and the mixture was stirred for 2 hours. More 4-hydroxytetrahydropyran (1.2 equiv.), PPh$_3$ (1.25 equiv.), and DIAD (1.2 equiv.) was added, and the reaction was stirred for another 2 hours. The reaction mixture was concentrated, and the crude residue was purified via flash chromatography over silica gel eluting with heptanes and 0-20% ethyl acetate gradient. Isolated 5-bromo-3-iodo-2-((tetrahydro-2H-pyran-4-yl)oxy)pyridine as a colorless oil in 55% yield. LCMS (m/z) (M+H)=384.0/386.0, Rt=0.88 min.

Step 2:

To a solution of 5-bromo-3-iodo-2-((tetrahydro-2H-pyran-4-yl)oxy)pyridine (1.0 equiv.) in toluene (0.15 M) in a microwave vial was added 3-oxa-8-azabicyclo[3.2.1]octane (1.3 equiv.), NaOtBu (3 equiv.), and Xantphos (0.1 equiv.) and the mixture was degassed with Ar. Pd(dba)$_2$ (0.05 equiv) was added, and the mixture was degassed again and then sealed and heated at 90° C. for 18 hours. The mixture was poured onto saturated aqueous sodium bicarbonate and extracted three times with ethyl acetate. The combined organics were washed with brine, dried over magnesium sulfate, filtered and concentrated. The crude residue was purified via flash chromatography over silica gel eluting with heptanes and 0-30% ethyl acetate gradient. Isolated 8-(5-bromo-2-((tetrahydro-2H-pyran-4-yl)oxy)pyridin-3-yl)-3-oxa-8-azabicyclo[3.2.1]octane as a pale yellow solid in 67% yield. LCMS (m/z) (M+H)=369.1/371.1, Rt=0.95 min.

Synthesis of 5-bromo-2-ethoxy-3-iodopyridine

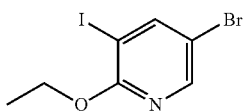

To a solution of 5-bromo-2-ethoxypyridin-3-amine (1.0 equiv.) in a mixture of concentrated HCl and water (1:1.3, 0.2 M) at 0° C. was slowly added NaNO2 (1.4 equiv.) and the mixture was stirred for 30 min. A 0.3 M solution of KI in water (3 equiv.) was slowly added to the mixture, which was then allowed to warm to 25° C. and stirred for 30 min. The mixture was poured into a separatory funnel and extracted three times with ethyl acetate. The combined organics were washed with saturated aqueous sodium sulfite, saturated aqueous sodium bicarbonate, dried over magnesium sulfate, filtered, and concentrated. The crude residue was purified via flash chromatography over silica gel eluting with heptanes and 0-15% ethyl acetate gradient. Isolated 5-bromo-2-ethoxy-3-iodopyridine as a white solid in 71% yield. LCMS (m/z) (M+H)=327.9/329.9, Rt=1.10 min.

Method 4:

To a solution of the starting iodide (1.0 equiv.) in toluene (0.15 M) in a microwave vial was added the amine (1.3 equiv.), NaOtBu (3 equiv.), and Xantphos (0.1 equiv.) and the mixture was degassed with Ar. Pd(dba)$_2$ (0.05 equiv) was added, and the mixture was degassed again and then sealed and heated at 90° C. for 18 hours. The mixture was poured onto saturated aqueous sodium bicarbonate and extracted three times with ethyl acetate. The combined organics were washed with brine, dried over magnesium sulfate, filtered and concentrated. The crude residue was purified via flash chromatography over silica gel eluting with heptanes and 0-30% ethyl acetate gradient.

Synthesis of 8-(5-bromo-2-ethoxypyridin-3-yl)-3-oxa-8-azabicyclo[3.2.1]octane

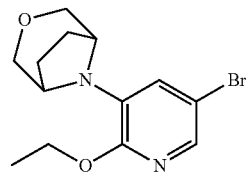 [SMILES: CCOc1ncc(Br)cc1N1C2CCC1COC2]

Method 4 was followed using 5-bromo-2-ethoxy-3-iodopyridine and 3-oxa-8-azabicyclo[3.2.1]octane to give 8-(5-bromo-2-ethoxypyridin-3-yl)-3-oxa-8-azabicyclo [3.2.1]octane as a pale orange oil in 46% yield. LCMS (m/z) (M+H)=312.9/314.9, Rt=0.97 min.

Synthesis of (S)-4-(5-bromo-2-ethoxypyridin-3-yl)-3-methylmorpholine

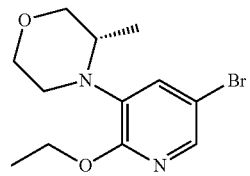 [SMILES: CCOc1ncc(Br)cc1N1CCOC[C@@H]1C]

Method 4 was followed using 5-bromo-2-ethoxy-3-iodopyridine and (S)-3-methylmorpholine to give (S)-4-(5-bromo-2-ethoxypyridin-3-yl)-3-methylmorpholine as a pale orange oil in 12% yield. LCMS (m/z) (M+H)=300.9/302.9, Rt=0.91 min.

Synthesis of (R)-4-(5-bromo-2-ethoxypyridin-3-yl)-3-methylmorpholine

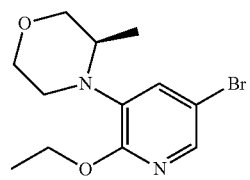 [SMILES: CCOc1ncc(Br)cc1N1CCOC[C@H]1C]

Method 4 was followed using 5-bromo-2-ethoxy-3-iodopyridine and (R)-3-methylmorpholine to give (R)-4-(5-bromo-2-ethoxypyridin-3-yl)-3-methylmorpholine as a pale yellow oil in 17% yield. LCMS (m/z) (M+H)=300.9/302.9, Rt=0.92 min.

Synthesis of 4-(5-bromo-2-methoxypyridin-3-yl)morpholine

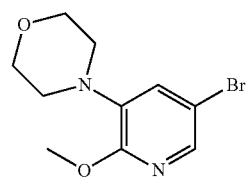

To a solution of 4-(5-bromo-2-fluoropyridin-3-yl)morpholine (1.0 equiv.) in dioxane (0.13 M) at 25° C. was added NaOMe (5 equiv.) and the reaction was heated to 105° C. and stirred for 2 hours. The reaction was cooled to room temperature, poured onto water, and extracted three times with ethyl acetate. The combined organics were washed with water, brine, dried over magnesium sulfate and concentrated. Isolated 4-(5-bromo-2-methoxypyridin-3-yl)morpholine as a pale orange solid in 95% yield which was used without further purification. LCMS (m/z) (M+H)=272.9/274.9, Rt=0.78 min.

Synthesis of 4-(5-bromo-2-((tetrahydro-2H-pyran-4-yl)oxy)pyridin-3-yl)morpholine

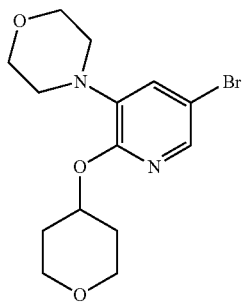 [SMILES: Brc1cnc(OC2CCOCC2)c(N2CCOCC2)c1]

To a solution of 4-hydroxytetrahydropyran (2 equiv.) in dioxane (0.2 M) at 25° C. was added NaH (2.1 equiv.) and the reaction was stirred for 30 min. 4-(5-bromo-2-fluoropyridin-3-yl)morpholine (1.0 equiv.) was then added and the reaction was heated to 105° C. and stirred for 5 h. The reaction was cooled to room temperature, poured onto water, and extracted three times with ethyl acetate. The combined organics were dried over sodium sulfate, filtered, and concentrated. The crude residue was purified by flash chromatography over silica gel eluting with heptane and 50-100% ethyl acetate gradient. Isolated 4-(5-bromo-2-((tetrahydro-2H-pyran-4-yl)oxy)pyridin-3-yl)morpholine as a light yellow oil in 83% yield. LCMS (m/z) (M+H)=343.0/344.9, Rt=0.86 min.

Synthesis of 4-(5-bromo-2-(2,2-difluoroethoxy)pyridin-3-yl)morpholine

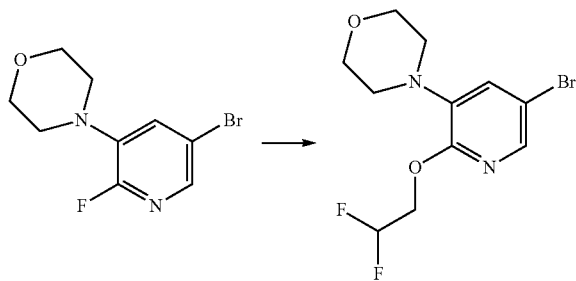 [SMILES: Fc1ncc(Br)cc1N1CCOCC1 ; FC(F)COc1ncc(Br)cc1N1CCOCC1]

To a solution of 2,2-difluroethanol (2.0 equiv.) in dioxane (0.13 M) was added sodium hydride (2.0 equiv.) under nitrogen. The reaction was stirred for 15 min at room temperature, then 4-(5-bromo-2-fluoropyridin-3-yl)morpholine (1.0 equiv.) was added. The solution was allowed to stir at room temperature overnight. The mixture was partitioned between water and ethyl acetate, and the organic phase was dried over sodium sulfate, filtered and concentrated. The crude material was used for the next step without further purification. LCMS (m/z) (M+H)=322.9/324.9, Rt=0.89 min.

Synthesis of 4-(2-methoxy-5-(4,4,5,5-tetramethyl-1,3,2-dioxaborolan-2-yl)pyridin-3-yl)morpholine

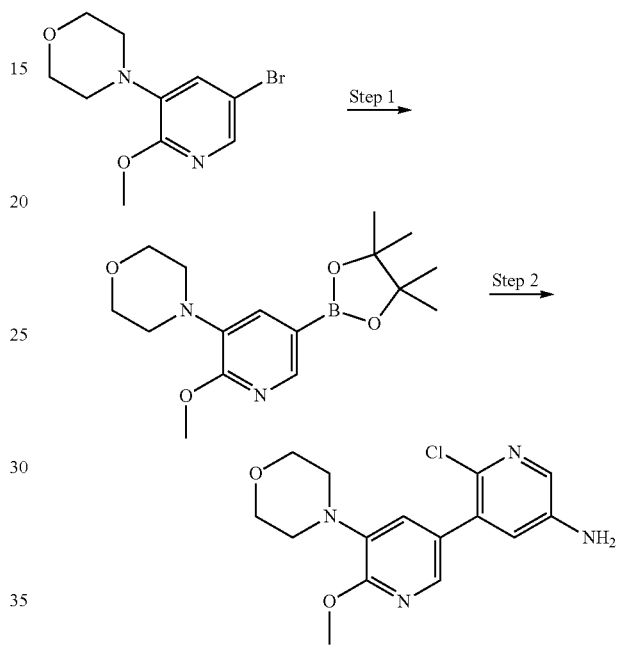

Step 1:

To a solution of 4-(5-bromo-2-methoxypyridin-3-yl)morpholine (1.0 equiv.) in 1,4-dioxane (0.15 M) was added bis(pinacolato)diboron (1.5 equiv.), PdCl$_2$(dppf).CH$_2$Cl$_2$ adduct (0.1 equiv.), and 2M aqueous sodium carbonate (3.0 equiv.). The reaction mixture was irradiated at 120° C. for 18 min in the microwave. The cooled reaction mixture was diluted with DCM and filtered. The filtrate was concentrated to give crude 4-(2-methoxy-5-(4,4,5,5-tetramethyl-1,3,2-dioxaborolan-2-yl)pyridin-3-yl)morpholine (assumed 100% yield) as a brown residue which was used without further purification. LCMS (m/z) (M+H)=321.0, Rt=0.81 min.

Step 2:

To a solution of 4-(2-methoxy-5-(4,4,5,5-tetramethyl-1,3,2-dioxaborolan-2-yl)pyridin-3-yl)morpholine (1.0 equiv.) in DME (0.15 M) was added 5-bromo-6-chloropyridin-3-amine (1.0 equiv.), PdCl$_2$(dppf).CH$_2$Cl$_2$ adduct (0.1 equiv.), and 2M aqueous sodium carbonate (3.0 equiv.). The reaction mixture was irradiated at 120° C. for 15 min in the microwave. The cooled reaction mixture was diluted with 2:1 DCM:MeOH and filtered. The filtrate was concentrated and purified by flash chromatography over silica gel eluting with heptane and 50-100% ethyl acetate gradient. Isolated 2-chloro-6'-methoxy-5'-morpholino-[3,3'-bipyridin]-5-amine as a brown residue in 73% yield. LCMS (m/z) (M+H)=321.0, Rt=0.60 min.

Method 5:

A solution of the aryl bromide (1.0 equiv.) and the boronic ester (1.2 equiv.) in DME (0.15 M) and 2 M aqueous sodium carbonate (3 equiv.) was purged with Ar for 5 min. PdCl₂(dppf).CH₂Cl₂ adduct (0.05 equiv.) was then added, and the mixture was purged with Ar again and then heated at 100° C. for 1 h. The mixture was poured onto water and extracted three times with ethyl acetate. The combined organics were washed with brine, dried over magnesium sulfate, filtered and concentrated. The crude residue was purified via flash chromatography over silica gel eluting with either heptane and 0-100% ethyl acetate gradient or DCM and 0-15% methanol gradient, or in other cases the crude residue was used without further purification.

Synthesis of 3-(6-ethoxy-5-morpholinopyridin-3-yl)-4-methylaniline

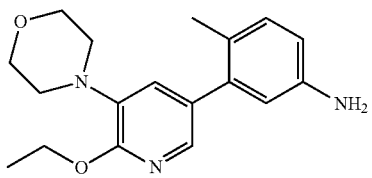

Method 5 was followed using 4-(5-bromo-2-ethoxypyridin-3-yl)morpholine and 5-amino-2-methylphenylboronic acid, pinacol ester. The crude residue was purified via flash chromatography over silica gel eluting with heptane and 0-100% ethyl acetate gradient. Isolated 3-(6-ethoxy-5-morpholinopyridin-3-yl)-4-methylaniline as a pale yellow oil in 91% yield. LCMS (m/z) (M+H)=314.1, Rt=0.60 min.

Synthesis of 6'-ethoxy-2-methyl-5'-morpholino-[3,3'-bipyridin]-5-amine

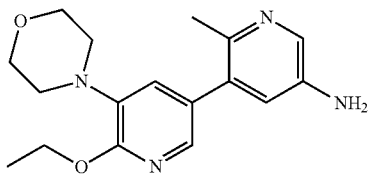 [SMILES: CCOc1ncc(-c2cc(N)ccc2C)cc1N1CCOCC1]

Method 5 was followed using 4-(5-bromo-2-ethoxypyridin-3-yl)morpholine and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 6'-ethoxy-2-methyl-5'-morpholino-[3,3'-bipyridin]-5-amine as a light brown solid in 96% yield. LCMS (m/z) (M+H)=315.1, Rt=0.52 min.

Synthesis of 3-(6-ethoxy-5-morpholinopyridin-3-yl)-4-methylbenzoic acid

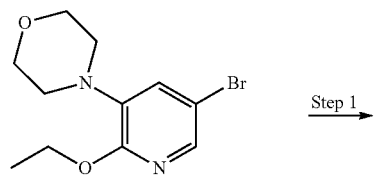 Step 1

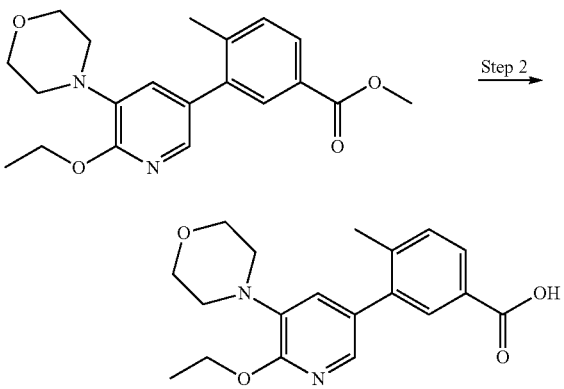 Step 2

Step 1:
Method 5 was followed using 4-(5-bromo-2-ethoxypyridin-3-yl)morpholine and methyl 4-methyl-3-(4,4,5,5-tetramethyl-1,3,2-dioxaborolan-2-yl)benzoate. The crude residue was purified via flash chromatography over silica gel eluting with heptane and 0-100% ethyl acetate gradient. Isolated methyl 3-(6-ethoxy-5-morpholinopyridin-3-yl)-4-methylbenzoate as a white solid in 57% yield. LCMS (m/z) (M+H)=357.1, Rt=1.01 min.

Step 2:
To a stirred solution of methyl 3-(6-ethoxy-5-morpholinopyridin-3-yl)-4-methylbenzoate (1.0 equiv.) in THF/MeOH (2:1, 0.1 M) was added 2.0 M aqueous LiOH (6 equiv.) and the mixture was heated at 45° C. for 2 h. The mixture was cooled to room temperature and acidified with 1 M HCl. The mixture was extracted three times with ethyl acetate. The combined organics were dried over magnesium sulfate, filtered, and concentrated. Isolated 3-(6-ethoxy-5-morpholinopyridin-3-yl)-4-methylbenzoic acid as a pale orange solid which was used without further purification. LCMS (m/z) (M+H)=343.1, Rt=0.81 min.

Synthesis of N-(6'-fluoro-2-methyl-5'-morpholino-[3,3'-bipyridin]-5-yl)-3-(trifluoromethyl)benzamide

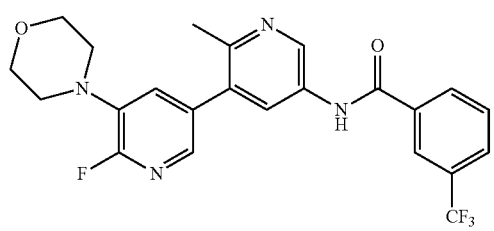 [SMILES: Cc1ncc(NC(=O)c2cccc(C(F)(F)F)c2)cc1-c1cnc(F)c(N2CCOCC2)c1]

Method 5 was followed using 4-(5-bromo-2-fluoropyridin-3-yl)morpholine and N-(6-methyl-5-(4,4,5,5-tetramethyl-1,3,2-dioxaborolan-2-yl)pyridin-3-yl)-3-(trifluoromethyl)benzamide. The crude residue was purified via flash chromatography over silica gel eluting with DCM and 0-15% methanol gradient. Isolated N-(6'-fluoro-2-methyl-5'-morpholino-[3,3'-bipyridin]-5-yl)-3-(trifluoromethyl)benzamide as a light brown solid in 100% yield. LCMS (m/z) (M+H)=461.1, Rt=0.75 min.

Synthesis of 6'-fluoro-2-methyl-5'-morpholino-[3,3'-bipyridin]-5-amine

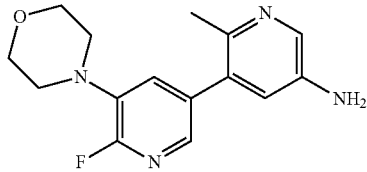 [SMILES: Cc1ncc(N)cc1-c1cnc(F)c(N2CCOCC2)c1]

Method 5 was followed using 4-(5-bromo-2-fluoropyridin-3-yl)morpholine and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 6'-fluoro-2-methyl-5'-morpholino-[3,3'-bipyridin]-5-amine as a light brown oil in 100% yield. LCMS (m/z) (M+H)=289.0, Rt=0.45 min.

Synthesis of 5'-amino-2'-methyl-5-morpholino-[3,3'-bipyridine]-6-carbonitrile

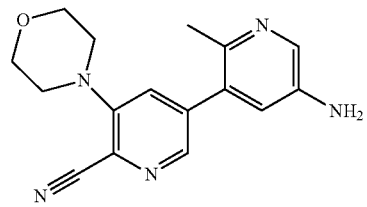 [SMILES: Cc1ncc(N)cc1-c1cnc(C#N)c(N2CCOCC2)c1]

Method 5 was followed using 5-bromo-3-morpholinopicolinonitrile and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 5'-amino-2'-methyl-5-morpholino-[3,3'-bipyridine]-6-carbonitrile as a tan solid. LCMS (m/z) (M+H)=296.0, Rt=0.46 min.

Synthesis of N6',N6',2-trimethyl-5'-morpholino-[3,3'-bipyridine]-5,6'-diamine

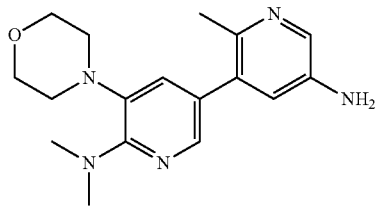 [SMILES: Cc1ncc(N)cc1-c1cnc(N(C)C)c(N2CCOCC2)c1]

Method 5 was followed using 5-bromo-N,N-dimethyl-3-morpholinopyridin-2-amine and 6-methyl-5-(4,4,5,5-tetramethyl-1,3,2-dioxaborolan-2-yl)pyridin-3-amine The crude residue was purified via flash chromatography over silica gel eluting with ethyl acetate and 0-5% methanol Isolated N6',N6',2-trimethyl-5'-morpholino-[3,3'-bipyridine]-5,6'-diamine as a brown residue in 69% yield. LCMS (m/z) (M+H)=314.1, Rt=0.32 min.

Synthesis of 5'-(3-oxa-8-azabicyclo[3.2.1]octan-8-yl)-2-methyl-6'-((tetrahydro-2H-pyran-4-yl)oxy)-[3,3'-bipyridin]-5-amine

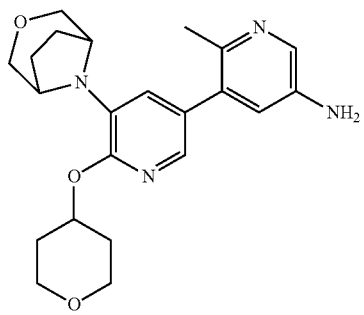 [SMILES: Cc1ncc(N)cc1-c1cnc(OC2CCOCC2)c(N2C3CCC2COC3)c1]

Method 5 was followed using 8-(5-bromo-2-((tetrahydro-2H-pyran-4-yl)oxy)pyridin-3-yl)-3-oxa-8-azabicyclo[3.2.1]octane and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 5'-(3-oxa-8-azabicyclo[3.2.1]octan-8-yl)-2-methyl-6'-((tetrahydro-2H-pyran-4-yl)oxy)-[3,3'-bipyridin]-5-amine as a light brown oil in 98% yield. LCMS (m/z) (M+H)=397.0, Rt=0.56 min.

Synthesis of 2-methyl-5'-morpholino-6-((tetrahydro-2H-pyran-4-yl)oxy)-[3,3'-bipyridin]-5-amine

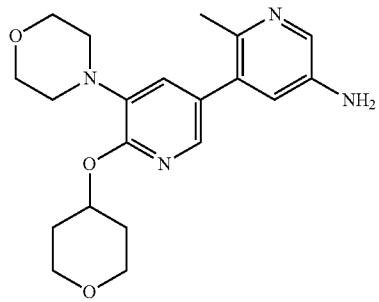 [SMILES: Cc1ncc(N)cc1-c1cnc(OC2CCOCC2)c(N2CCOCC2)c1]

Method 5 was followed using 4-(5-bromo-2-((tetrahydro-2H-pyran-4-yl)oxy)pyridin-3-yl)morpholine and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 2-methyl-5'-morpholino-6'-((tetrahydro-2H-pyran-4-yl)oxy)-[3,3'-bipyridin]-5-amine as a brown residue in 46% yield. LCMS (m/z) (M+H)=371.1, Rt=0.51 min.

Synthesis of 4-methyl-3-(5-morpholino-6-((tetrahydro-2H-pyran-4-yl)oxy)pyridin-3-yl)aniline

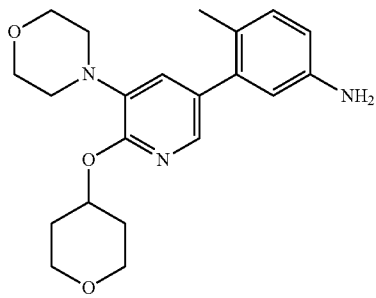 [SMILES: Cc1ccc(N)cc1-c1cnc(OC2CCOCC2)c(N2CCOCC2)c1]

Method 5 was followed using 4-(5-bromo-2-((tetrahydro-2H-pyran-4-yl)oxy)pyridin-3-yl)morpholine and 4-methyl-3-(4,4,5,5-tetramethyl-1,3,2-dioxaborolan-2-yl)aniline (1.15 equiv.). The crude residue was purified via flash chromatography over silica gel eluting with DCM and 0-15% methanol gradient. Isolated 4-methyl-3-(5-morpholino-6-((tetrahydro-2H-pyran-4-yl)oxy)pyridin-3-yl)aniline as a brown residue in 76% yield. LCMS (m/z) (M+H)= 370.2, Rt=0.59 min.

Synthesis of 5'-(3-oxa-8-azabicyclo[3.2.1]octan-8-yl)-6'-ethoxy-2-methyl-[3,3'-bipyridin]-5-amine

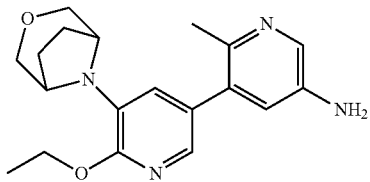 [SMILES: CCOc1ncc(-c2cc(N)cnc2C)cc1N1C2CCC1COC2]

Method 5 was followed using 8-(5-bromo-2-ethoxypyridin-3-yl)-3-oxa-8-azabicyclo[3.2.1]octane and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 5'-(3-oxa-8-azabicyclo[3.2.1]octan-8-yl)-6'-ethoxy-2-methyl-[3,3'-bipyridin]-5-amine as a light brown oil in 92% yield. LCMS (m/z) (M+H)=341.0, Rt=0.58 min.

Synthesis of (S)-6'-ethoxy-2-methyl-5'-(3-methylmorpholino)-[3,3'-bipyridin]-5-amine

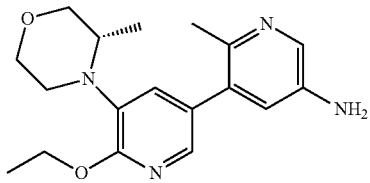 [SMILES: CCOc1ncc(-c2cc(N)cnc2C)cc1N1CCOC[C@@H]1C]

Method 5 was followed using (S)-4-(5-bromo-2-ethoxypyridin-3-yl)-3-methylmorpholine and 6-methyl-5-(4,4,5,5-tetramethyl-1,3,2-dioxaborolan-2-yl)pyridin-3-amine. The crude residue used without further purification. Isolated (S)-6-ethoxy-2-methyl-5-(3-methylmorpholino)-[3,3'-bipyridin]-5-amine as a light brown oil. LCMS (m/z) (M+H)= 329.1.0, Rt=0.53 min.

Synthesis of (R)-6'-ethoxy-2-methyl-5'-(3-methylmorpholino)-[3,3'-bipyridin]-5-amine

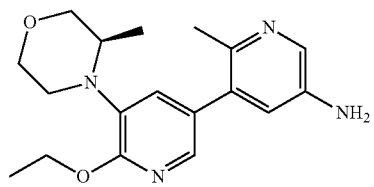 [SMILES: CCOc1ncc(-c2cc(N)cnc2C)cc1N1CCOC[C@H]1C]

Method 5 was followed using (R)-4-(5-bromo-2-ethoxypyridin-3-yl)-3-methylmorpholine and 6-methyl-5-(4,4,5,5-tetramethyl-1,3,2-dioxaborolan-2-yl)pyridin-3-amine. The crude residue was purified via flash chromatography over silica gel eluting with heptane and 0-100% ethyl acetate gradient. Isolated (R)-6'-ethoxy-2-methyl-5'-(3-methylmorpholino)-[3,3'-bipyridin]-5-amine as a pale yellow solid. LCMS (m/z) (M+H)=329.1.0, Rt=0.53 min.

Synthesis of 6'-chloro-2-methyl-5'-morpholino-[3,3'-bipyridin]-5-amine

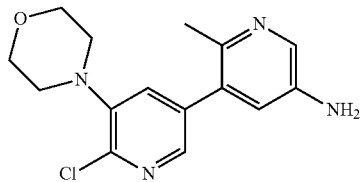 [SMILES: Cc1ncc(N)cc1-c1cnc(Cl)c(N2CCOCC2)c1]

Method 5 was followed using 4-(5-bromo-2-chloropyridin-3-yl)morpholine and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 6'-chloro-2-methyl-5'-morpholino-[3,3'-bipyridin]-5-amine as a pale yellow foam in 100% yield. LCMS (m/z) (M+H)=305.0, Rt=0.47 min.

Synthesis of 2-methyl-5'-morpholino-[3,3'-bipyridin]-5-amine

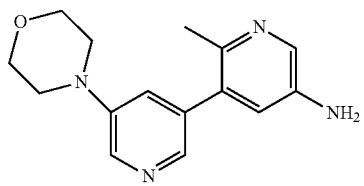 [SMILES: Cc1ncc(N)cc1-c1cncc(N2CCOCC2)c1]

Method 5 was followed using 4-(5-bromopyridin-3-yl)morpholine and 6-methyl-5-(4,4,5,5-tetramethyl-1,3,2-dioxaborolan-2-yl)pyridin-3-amine. The crude residue was purified via flash chromatography over silica gel eluting with DCM and 0-15% methanol gradient. Isolated 2-methyl-5'-morpholino-[3,3'-bipyridin]-5-amine as a light brown oil in 69% yield. LCMS (m/z) (M+H)=271.0, Rt=0.27 min.

6'-methoxy-2-methyl-5'-morpholino-[3,3'-bipyridin]-5-amine

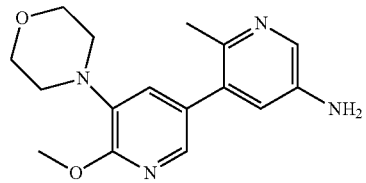 [SMILES: COc1ncc(-c2cc(N)cnc2C)cc1N1CCOCC1]

¹H NMR (400 MHz, <cd3od>) δ ppm 2.40 (s, 3H) 3.05-3.18 (m, 4H) 3.84-3.95 (m, 4H) 4.05 (s, 3H) 6.89 (br. s., 1H) 7.02 (d, J=1.96 Hz, 1H) 7.76 (d, J=1.96 Hz, 1H) 8.04 (d, J=2.74 Hz, 1H). LCMS (m/z) (M+H)=301.0, Rt=0.45 min.

Synthesis of 2-((5'-amino-2'-methyl-5-morpholino-[3,3'-bipyridin]-6-yl)oxy)ethanol

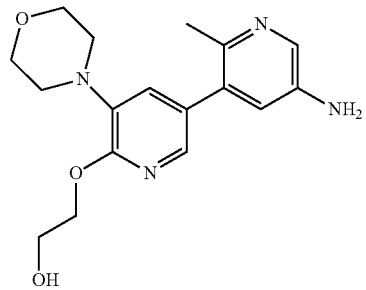 [SMILES: Cc1ncc(N)cc1-c1cnc(OCCO)c(N2CCOCC2)c1]

To a solution of ethylene glycol (5 equiv.) in dioxane (0.1 M) at 25° C. was added NaH (5 equiv) and the reaction was stirred for 15 min 6'-fluoro-2-methyl-5'-morpholino-[3,3'-bipyridin]-5-amine (1.0 equiv.) was then added and the reaction was heated to 105° C. and stirred for 24 h. More ethylene glycol (5 equiv.) and NaH (5 equiv) was added and the mixture was stirred at 105° C. for an additional 24 h. The reaction was cooled to room temperature, poured onto water, and extracted three times with ethyl acetate. The combined organics were washed with brine, dried over magnesium sulfate and concentrated. Isolated 2-((5'-amino-2'-methyl-5-morpholino-[3,3'-bipyridin]-6-yl)oxy)ethanol as a light brown oil in 95% yield which was used without further purification. LCMS (m/z) (M+H)=331.1 Rt=0.39 min.

Method 6:

To a solution of the amine (1.0 equiv) and the acid (1.1 equiv.) in DMA (0.15 M) at 25° C. were added HOAT (1.3 equiv.), i-Pr₂NEt (3 equiv.), and EDC (1.3 equiv) and the mixture was stirred for 4 h at 25° C. The mixture was poured onto water and extracted three times with ethyl acetate. The combined organics were washed with water, brine, dried over magnesium sulfate, filtered and concentrated. The crude residue was used without further purification.

Method 7:

Synthesis of 5'-amino-2'-chloro-1-methyl-5-morpholino-[3,3'-bipyridin]-6(1H)-one

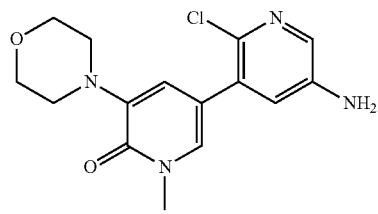 [SMILES: Cn1cc(-c2cc(N)cnc2Cl)cc(N2CCOCC2)c1=O]

To a 0.15M solution of 1-methyl-3-morpholino-5-(4,4,5,5-tetramethyl-1,3,2-dioxaborolan-2-yl)pyridin-2(1H)-one (1.00 equiv.) in DME was added 5-bromo-6-chloropyridin-3-amine (1.00 equiv.), PdCl₂(dppf).CH₂Cl₂ adduct (0.10 equiv.), and 2M aqueous sodium carbonate (3.00 equiv.). The reaction mixture was irradiated at 120° C. for 15 min in the microwave. The cooled reaction mixture was diluted with 2:1 DCM:MeOH and filtered. The filtrate was concentrated and purified by flash chromatography over silica gel (ethyl acetate with 0-10% methanol gradient) to give 5'-amino-2'-chloro-1-methyl-5-morpholino-[3,3'-bipyridin]-6(1H)-one (56.6% yield) as a brown residue. LCMS (m/z) (M+H)=321.0, Rt=0.45 min.

Synthesis of 5-(5-amino-2-fluorophenyl)-1-methyl-3-morpholinopyridin-2(1H)-one

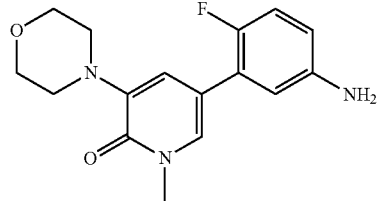 [SMILES: Cn1cc(-c2cc(N)ccc2F)cc(N2CCOCC2)c1=O]

Following the preparation in Method 7 using the appropriate starting materials gave 5-(5-amino-2-fluorophenyl)-1-methyl-3-morpholinopyridin-2(1H)-one (52.2% yield) as a brown residue. LCMS (m/z) (M+H)=304.0, Rt=0.40 min.

Synthesis of 5-(5-amino-2-chlorophenyl)-1-methyl-3-morpholinopyridin-2(1H)-one

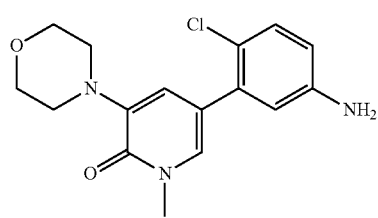 [SMILES: Cn1cc(-c2cc(N)ccc2Cl)cc(N2CCOCC2)c1=O]

Following the preparation in Method 7 using the appropriate starting materials gave 5-(5-amino-2-chlorophenyl)-1-methyl-3-morpholinopyridin-2(1H)-one (52.1% yield) as a brown residue. LCMS (m/z) (M+H)=320.1, Rt=0.46 min.

Synthesis of 4-amino-2-(1-methyl-5-morpholino-6-oxo-1,6-dihydropyridin-3-yl)benzonitrile

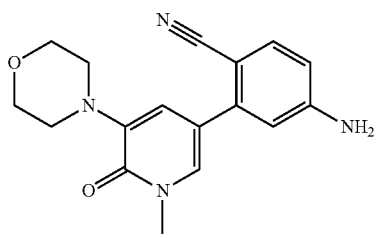 [SMILES: Cn1cc(-c2cc(N)ccc2C#N)cc(N2CCOCC2)c1=O]

Following the preparation in Method 7 using the appropriate starting materials gave 4-amino-2-(1-methyl-5-morpholino-6-oxo-1,6-dihydropyridin-3-yl)benzonitrile (63.4% yield) as a tan solid. LCMS (m/z) (M+H)=310.9, Rt=0.56 min.

Method 8:

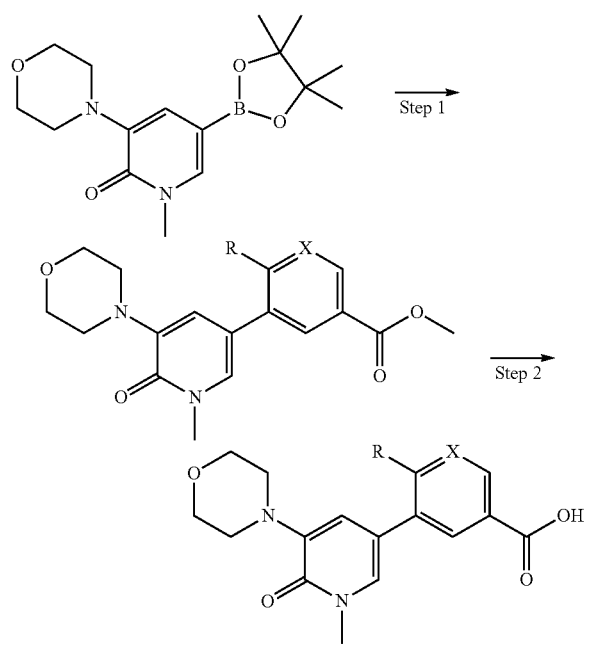

X = CH or N
R = Cl or Me when X = CH

Synthesis of 2-chloro-1'-methyl-5'-morpholino-6'-oxo-1',6'-dihydro-[3,3'-bipyridine]-5-carboxylic acid

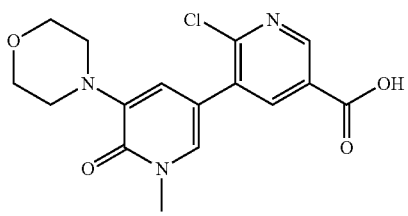 [SMILES: Cn1cc(-c2cc(C(=O)O)cnc2Cl)cc(N2CCOCC2)c1=O]

Step 1:
To a 0.15M solution of 1-methyl-3-morpholino-5-(4,4,5,5-tetramethyl-1,3,2-dioxaborolan-2-yl)pyridin-2(1H)-one (1.00 equiv.) in DME was added methyl 5-bromo-6-chloronicotinate (1.00 equiv.), PdCl$_2$(dppf).CH$_2$Cl$_2$ adduct (0.10 equiv.), and 2M aqueous sodium carbonate (3.00 equiv.). The reaction mixture was irradiated at 120° C. for 15 min in the microwave. The cooled reaction mixture was diluted with 2:1 DCM:MeOH and filtered. The filtrate was concentrated and purified by flash chromatography over silica gel (ethyl acetate with 0-10% methanol gradient) to give methyl 2-chloro-1'-methyl-5'-morpholino-6'-oxo-1',6'-dihydro-[3,3'-bipyridine]-5-carboxylate (29.0% yield) as a yellow solid. LCMS (m/z) (M+H)=364.1, Rt=0.62 min.

Step 2:
To a 0.23M solution of methyl 2-chloro-1'-methyl-5'-morpholino-6'-oxo-1',6'-dihydro-[3,3'-bipyridine]-5-carboxylate (1.00 equiv.) in THF was added 2.0M aqueous lithium hydroxide (3.00 equiv.). The mixture was stirred at ambient temperature for 1.5 hr. The reaction mixture was acidified to pH 3 with aqueous HCl and concentrated to give crude 2-chloro-1'-methyl-5'-morpholino-6'-oxo-1',6'-dihydro-[3,3'-bipyridine]-5-carboxylic acid as a yellow solid (assumed 100% yield). LCMS (m/z) (M+H)=350.0, Rt=0.52 min.

Synthesis of 2-chloro-1'-methyl-5'-morpholino-6'-oxo-1',6'-dihydro-[3,3'-bipyridine]-5-carboxylic acid

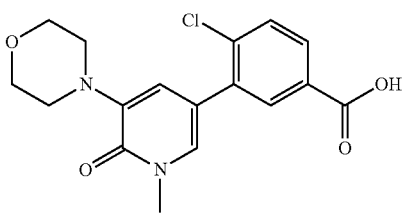 [SMILES: Cn1cc(-c2cc(C(=O)O)ccc2Cl)cc(N2CCOCC2)c1=O]

Following the preparation of Method 8 using the appropriate starting materials gave 4-chloro-3-(1-methyl-5-morpholino-6-oxo-1,6-dihydropyridin-3-yl)benzoic acid as a yellow solid (assumed 100% yield). LCMS (m/z) (M+H)= 349.1, Rt=0.61 min.

Synthesis of 4-methyl-3-(1-methyl-5-morpholino-6-oxo-1,6-dihydropyridin-3-yl)benzoic acid

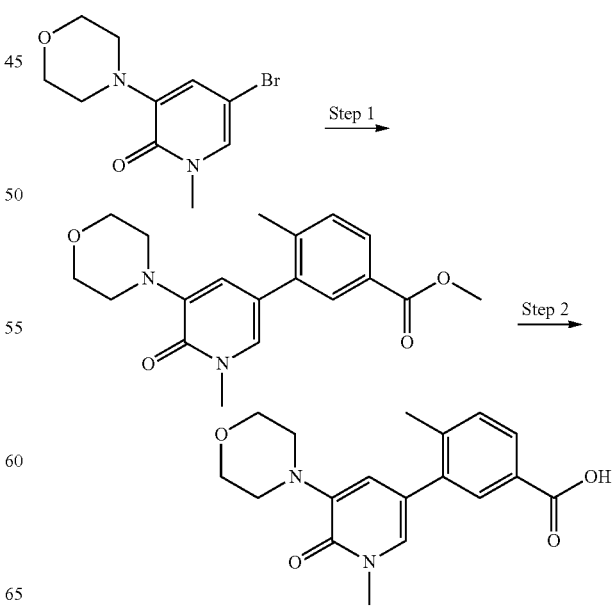

Step 1:

To a solution of 5-bromo-1-methyl-3-morpholinopyridin-2(1H)-one (1.0 equiv.) in DME (0.18 M) was added methyl 4-methyl-3-(4,4,5,5-tetramethyl-1,3,2-dioxaborolan-2-yl)benzoate (1.5 equiv.), PdCl$_2$(dppf).CH$_2$Cl$_2$ adduct (0.10 equiv.), and 2M aqueous sodium carbonate (3.00 equiv.). The reaction was heated to 90 C for 2 hours. Cooled to room temperature, partitioned between water and ethyl acetate, the organic phase was dried with sodium sulfate, filtered and concentrated. The crude material was purified via silica gel column chromatography eluting with 0-100% ethyl acetate in heptanes followed by 10% methanol in ethyl acetate. The pure fractions were concentrated to yield methyl 4-methyl-3-(1-methyl-5-morpholino-6-oxo-1,6-dihydropyridin-3-yl)benzoate in 76% yield. LCMS (m/z) (M+H)=343.2, Rt=0.70 min.

Step 2:

To a solution of methyl 4-methyl-3-(1-methyl-5-morpholino-6-oxo-1,6-dihydropyridin-3-yl)benzoate (1.0 equiv.) in THF was added lithium hydroxide (2M solution, 3.0 equiv.). The reaction was stirred at room temperature overnight. Acidified with 1N HCl to pH=2 and extracted with ethyl acetate. The organic phase was separated, and the precipitate was filtered off to yield 4-methyl-3-(1-methyl-5-morpholino-6-oxo-1,6-dihydropyridin-3-yl)benzoic acid as the desired product in 91% yield. LCMS (m/z) (M+H)=329.1, Rt=0.60 min.

Synthesis of N-(6'-fluoro-2-methyl-5'-morpholino-[3,3'-bipyridin]-5-yl)-2-isopropylisonicotinamide

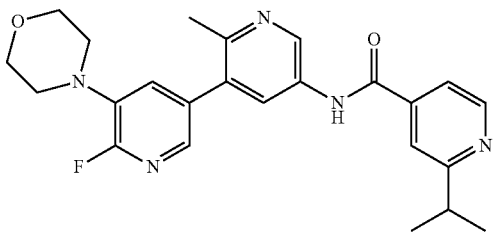 [SMILES: Cc1ncc(NC(=O)c2ccnc(C(C)C)c2)cc1-c1cnc(F)c(N2CCOCC2)c1]

Method 6 was followed using 6'-fluoro-2-methyl-5'-morpholino-[3,3'-bipyridin]-5-amine and 2-isopropylisonicotinic acid. Isolated N-(6'-fluoro-2-methyl-5'-morpholino-[3,3'-bipyridin]-5-yl)-2-isopropylisonicotinamide as a light brown oil. LCMS (m/z) (M+H)=436.3, Rt=0.52 min.

Synthesis of N-(6'-fluoro-2-methyl-5'-morpholino-[3,3'-bipyridin]-5-yl)-2-(trifluoromethyl)isonicotinamide

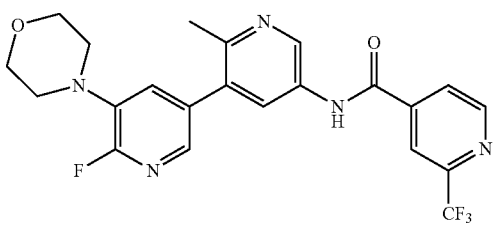 [SMILES: Cc1ncc(NC(=O)c2ccnc(C(F)(F)F)c2)cc1-c1cnc(F)c(N2CCOCC2)c1]

Method 6 was followed using 6'-fluoro-2-methyl-5'-morpholino-[3,3'-bipyridin]-5-amine and 2-(trifluoromethyl)pyridine-4-carboxylic acid. Isolated N-(6'-fluoro-2-methyl-5'-morpholino-[3,3'-bipyridin]-5-yl)-2-(trifluoromethyl)isonicotinamide as a light brown oil. LCMS (m/z) (M+H)=462.2, Rt=0.65 min.

Synthesis of 6'-chloro-3'-fluoro-2-methyl-2'-morpholino-[3,4'-bipyridin]-5-amine

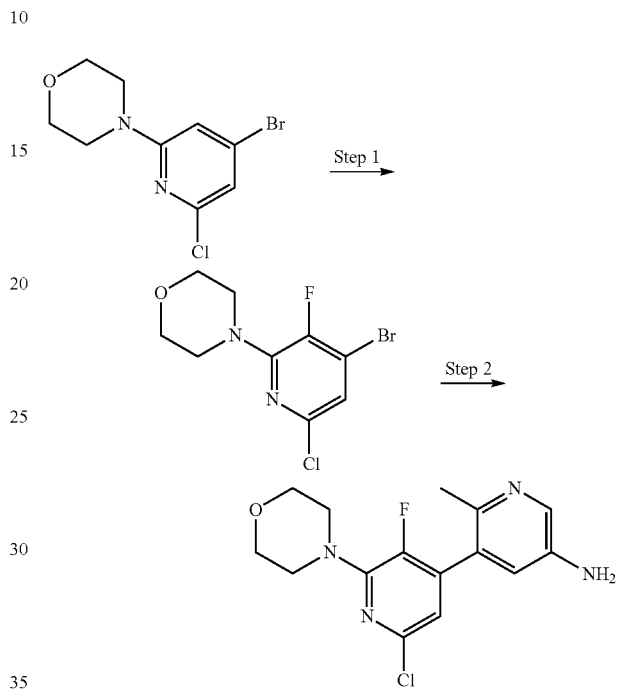

Step 1:

4-(4-bromo-6-chloropyridin-2-yl)morpholine (1.0 equiv.) was dissolved in acetonitrile (0.1 M). Selectfluor (1.1 equiv.) was added at rt and stirred for 18 hours. The reaction was diluted with ethyl acetate and washed with water, brine, dried over sodium sulfate, filtered and concentrated. The residue was purified by silica gel chromatography (ISCO, 0-10% ethyl acetate/heptanes) to give 4-(4-bromo-6-chloro-3-fluoropyridin-2-yl)morpholine in 42% yield and 4-(4-bromo-6-chloro-5-fluoropyridin-2-yl)morpholine in 14% yield. LCMS (m/z) (M+H)=294.7, Rt=0.95 and 0.99 min.

Step 2:

To a solution of 4-(4-bromo-6-chloro-3-fluoropyridin-2-yl)morpholine (1.0 equiv.) and 6-methyl-5-(4,4,5,5-tetramethyl-1,3,2-dioxaborolan-2-yl)pyridin-3-amine (1.7 equiv.) in DME (0.04 M) and sodium carbonate (2M, 3.0 equiv.) was added Pd(PPh$_3$)$_4$ (0.03 equiv.) and the reaction was heated at 100° C. for 2 hours. The mixture was poured onto ice water and extracted with ethyl acetate. The combined organics were washed with brine, dried over magnesium sulfate, filtered and concentrated. The mixture was purified via silica gel chromatography (10% methanol:ethyl acetate:heptanes) to give 6'-chloro-3'-fluoro-2-methyl-2'-morpholino-[3,4'-bipyridin]-5-amine as a yellow solid in 39% yield. $^1$H NMR (400 MHz, <cdcl3>) δ ppm 2.32 (s, 3H) 3.52-3.59 (m, 4H) 3.66 (br. s., 2H) 3.80-3.85 (m, 4H) 6.63 (d, J=3.91 Hz, 1H) 6.79-6.84 (m, 1H) 8.08 (d, J=2.74 Hz, 1H)

Synthesis of 2'-chloro-3'-fluoro-2-methyl-6'-morpholino-[3,4'-bipyridin]-5-amine

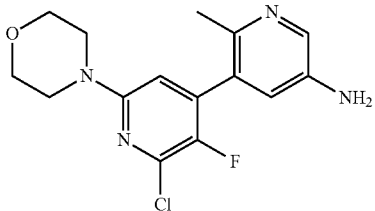 [SMILES: Cc1ncc(N)cc1-c1cc(N2CCOCC2)nc(Cl)c1F]

To a solution of 4-(4-bromo-6-chloro-5-fluoropyridin-2-yl)morpholine (1.0 equiv.) and 6-methyl-5-(4,4,5,5-tetramethyl-1,3,2-dioxaborolan-2-yl)pyridin-3-amine (1.4 equiv.) in DME (0.02 M)) and Na₂CO₃ (2 M aq.) (3.0 equiv.) was added Pd(PPh₃)₄ and heated (thermally) at 100° C. for 2 h. LCMS shows complete consumption of starting material with fairly clean conversion to desired product. The mixture was poured onto ice-water and extracted with EtOAc (3×). The combined organics were washed with brine, dried (MgSO₄) and concentrated. The mixture was adsorbed onto Celite and purified by ISCO flash column chromatography (silica gel, 10% methanol in EtOAc:heptane). Product fractions eluted around 40% EtOAc and were concentrated to give 2'-chloro-3'-fluoro-2-methyl-6'-morpholino-[3,4'-bipyridin]-5-amine in 77% yield as a pale yellow solid. LCMS (m/z) (M+H)=322.9, Rt=0.62 min.

Synthesis of 2-((4-(5-amino-2-methylphenyl)-3-fluoro-6-morpholinopyridin-2-yl)amino)ethanol

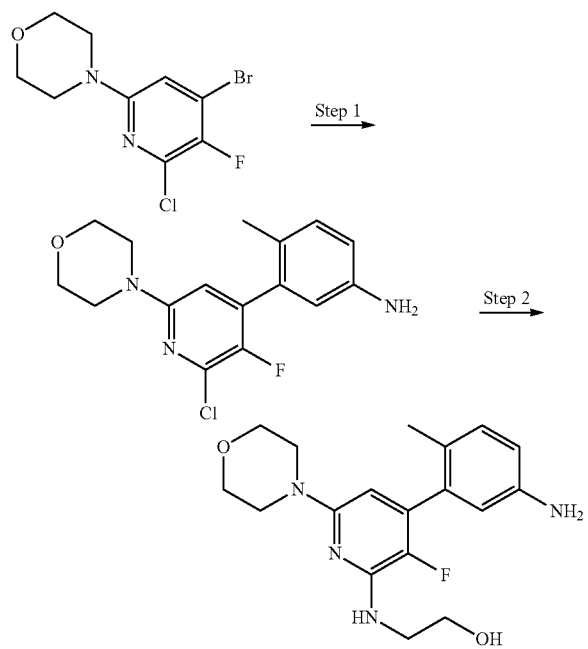

Step 1:
To a solution of 4-(4-bromo-6-chloro-5-fluoropyridin-2-yl)morpholine (1.0 equiv.) and 4-methyl-3-(4,4,5,5-tetramethyl-1,3,2-dioxaborolan-2-yl)aniline (1.2 equiv.) in DME (0.1 M) and Na₂CO₃ (2 M aq.) (3.0 equiv.) was added Pd(PPh₃)₄ and heated (thermally) at 100° C. for 2 h. LCMS shows complete consumption of starting material with fairly clean conversion to desired product. The mixture was poured onto ice-water and extracted with EtOAc (3×). The combined organics were washed with brine, dried (MgSO₄) and concentrated. The mixture was adsorbed onto Celite and purified by ISCO flash column chromatography (silica gel, 10% methanol in EtOAc:heptane). Product fractions eluted around 40% EtOAc and were concentrated to give 3-(2-chloro-3-fluoro-6-morpholinopyridin-4-yl)-4-methylaniline in 87% yield. LCMS (m/z) (M+H)=322, Rt=0.62 min.

Step 2:
In a microwave vial was added 3-(2-chloro-3-fluoro-6-morpholinopyridin-4-yl)-4-methylaniline (1.0 equiv.), 2-aminoethanol (50 equiv.), DIPEA (2.0 equiv.) in NMP (0.2). The vial was sealed with a crimp top. The reaction was then heated to 250° C. for 30 min heated by microwave. LC-MS showed completion of the reaction. The reaction mixture was diluted with ethyl acetate, washed with water, brine then dried over sodium sulfate. Concentrated to yield crude. Purified by 10% methanol in ethyl acetate to yield 2-((4-(5-amino-2-methylphenyl)-3-fluoro-6-morpholinopyridin-2-yl)amino)ethanol in 43% yield. LCMS (m/z) (M+H)=347.0, Rt=0.50 min.

Example 1: Synthesis of N-(4-methyl-3-(6-morpholinopyrimidin-4-yl)phenyl)-3-(trifluoromethyl)benzamide

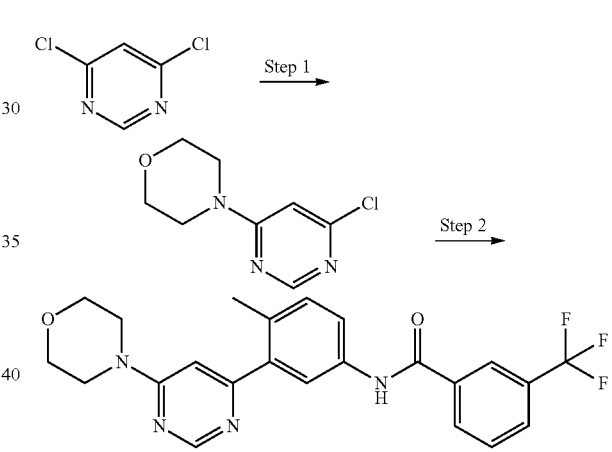

Step 1.
To a solution of 4,6-dichloropyrimidine (1.0 equiv.) in EtOH (0.44 M) was added morpholine (1.0 equiv.) followed by triethylamine (1.10 equiv.). The resulting mixture was stirred at RT for 16 hours. The reaction mixture was then concentrated in vacuo and dried under high vacuum over 20 h to yield 4-(6-chloropyrimidin-4-yl)morpholine as a white solid in 93% yield. LCMS (m/z) (M+H)=200.0/201.8, Rt=0.35 min. ¹H NMR (400 MHz, <cdcl3>) δ ppm 3.53-3.71 (m, 4H) 3.72-3.83 (m, 4H) 6.51 (s, 1H) 8.39 (s, 1H) 11.75 (br. s., 1H).

Step 2.
To a solution of 4-(6-chloropyrimidin-4-yl)morpholine (1.0 equiv.) and Intermediate A (1.1 equiv.) in DME and 2M sodium carbonate (3:1, 0.2 M) was added PdCl₂(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(4-methyl-3-(6-morpholinopyrimidin-4-yl)phenyl)-3-(trifluoromethyl)benzamide was isolated as the TFA salt in 52% yield. ¹H NMR (400 MHz, <cd3od>) δ ppm 2.28 (s, 3H) 3.67-4.02 (m, 8H) 7.09 (s, 1H) 7.35 (d, J=8.22 Hz, 1H) 7.65 (s, 2H) 7.78-7.84

(m, 1H) 7.92 (d, J=2.35 Hz, 1H) 8.16 (s, 2H) 8.64 (s, 1H). LCMS (m/z) (M+H)=443.2, Rt=0.77 min.

The compounds listed below were prepared using methods similar to those described for the preparation of Example 1 using the appropriate starting materials.

Example 2: 2-(2-cyanopropan-2-yl)-N-(4-methyl-3-(6-morpholinopyrimidin-4-yl)phenyl)isonicotinamide

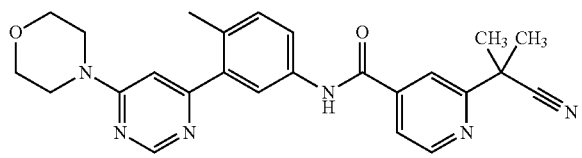 [SMILES: Cc1ccc(NC(=O)c2ccnc(C(C)(C)C#N)c2)cc1-c1cc(N2CCOCC2)ncn1]

1H NMR (400 MHz, <dmso>) δ ppm 1.70-1.81 (m, 6H) 2.30 (s, 3H) 3.67-3.92 (m, 8H) 7.11-7.22 (m, 1H) 7.34-7.45 (m, 1H) 7.73-7.83 (m, 1H) 7.83-7.92 (m, 2H) 7.99 (s, 1H) 8.73-8.86 (m, 2H) 10.70 (s, 1H). LCMS (m/z) (M+H)=443.2, Rt=0.64 min.

Example 3: Synthesis of N-(4-methyl-3-(2-morpholino-6-(3-oxomorpholino)pyrimidin-4-yl)phenyl)-3-(trifluoromethyl)benzamide

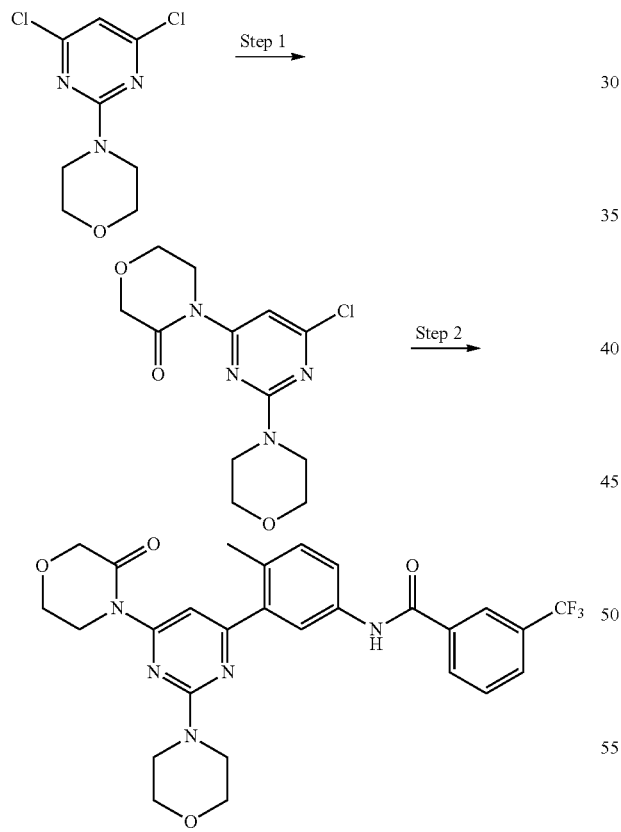

Step 1.

To a solution 4-(4,6-dichloropyrimidin-2-yl)morpholine (1.0 equiv.), morpholin-3-one (1.2 equiv.), tribasic potassium phosphate (4.00 equiv), (9,9-dimethyl-9H-xanthene-4,5-diyl)bis(diphenylphosphine) (0.16 equiv) and Pd$_2$(dba)$_3$·HCCl$_3$ (20 mol %) in dioxane (0.5 M) was heated to 100° C. for 90 min. The reaction mixture was then cooled to room temperature and diluted with EtOAc (20 ml) and water (20 ml). The aqueous layer was separated and extracted with EtOAc (×2, 20 ml). The combined organic layer was dried over magnesium sulfate, filtered and concentrated in vacuo. The compound was utilized in the subsequent reactions without further purification. LCMS (m/z) (M+H)=299.2/300.9, Rt=0.77 min.

Step 2.

To a solution of 4-(6-chloro-2-morpholinopyrimidin-4-yl)morpholin-3-one (1.0 equiv.) and Intermediate A (1.1 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(4-methyl-3-(1-methyl-5-morpholino-6-oxo-1,6-dihydropyridin-3-yl)phenyl)-3-(trifluoromethyl)benzamide was isolated as the TFA salt in 19% yield. LCMS (m/z) (M+H)=542.4, Rt=1.04 min. $^1$H NMR (400 MHz, <dmso>) δ ppm 2.36 (s, 3H) 3.56-3.81 (m, 8H) 4.01 (d, J=5.09 Hz, 4H) 4.28 (s, 5H) 7.31 (d, J=8.22 Hz, 1H) 7.72-7.82 (m, 2H) 7.85 (d, J=1.96 Hz, 1H) 7.97 (d, J=7.83 Hz, 1H) 8.20-8.35 (m, 2H) 10.53 (s, 1H).

The compounds listed below were prepared using methods similar to those described for the preparation of Example 3 using the appropriate starting materials.

Example 4: 4-methyl-3-(2-morpholino-6-(3-oxomorpholino)pyrimidin-4-yl)-N-(3-(trifluoromethyl)phenyl)benzamide

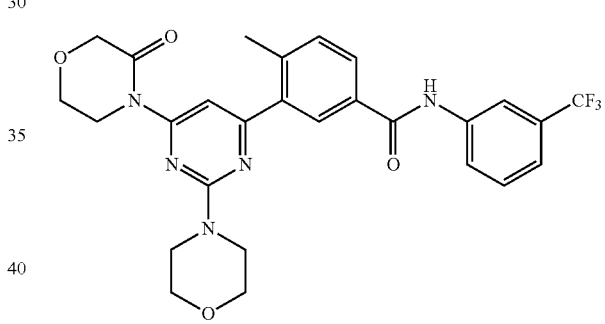

$^1$H NMR (400 MHz, <dmso>) δ ppm 2.45 (s, 3H) 3.69 (d, J=4.70 Hz, 5H) 3.74 (d, J=4.70 Hz, 5H) 4.01 (d, J=5.09 Hz, 3H) 4.29 (s, 2H) 7.36-7.54 (m, 3H) 7.60 (t, J=8.02 Hz, 2H) 7.93-8.02 (m, 2H) 8.05 (d, J=8.22 Hz, 1H) 8.24 (s, 1H) 10.55 (s, 1H) LCMS (m/z) (M+H)=542.3, Rt=1.08 min.

Example 5: N-(6-methyl-5-(2-morpholino-6-(3-oxomorpholino)pyrimidin-4-yl)pyridin-3-yl)-3-(trifluoromethyl)benzamide

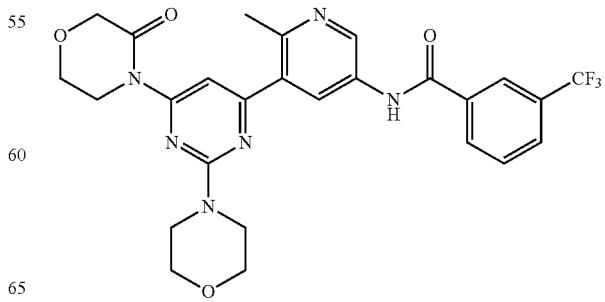

$^1$H NMR (400 MHz, <dmso>) δ ppm 3.61-3.72 (m, 6H) 3.75 (d, J=4.70 Hz, 5H) 3.88-4.08 (m, 9H) 4.29 (s, 3H) 7.41-7.51 (m, 4H) 7.51-7.58 (m, 3H) 7.77-7.88 (m, 3H) 8.01 (t, J=6.46 Hz, 3H) 8.22-8.32 (m, 4H) 9.01 (dd, J=4.30, 2.35 Hz, 2H) 10.83 (s, 1H) 10.88 (s, 1H), LCMS (m/z) (M+H)= 543.3, Rt=0.78 min.

Example 6: Synthesis of N-(3-(6-(1,1-dioxidothio-morpholino)-2-morpholinopyrimidin-4-yl)-4-methyl-phenyl)-3-(trifluoromethyl)benzamide

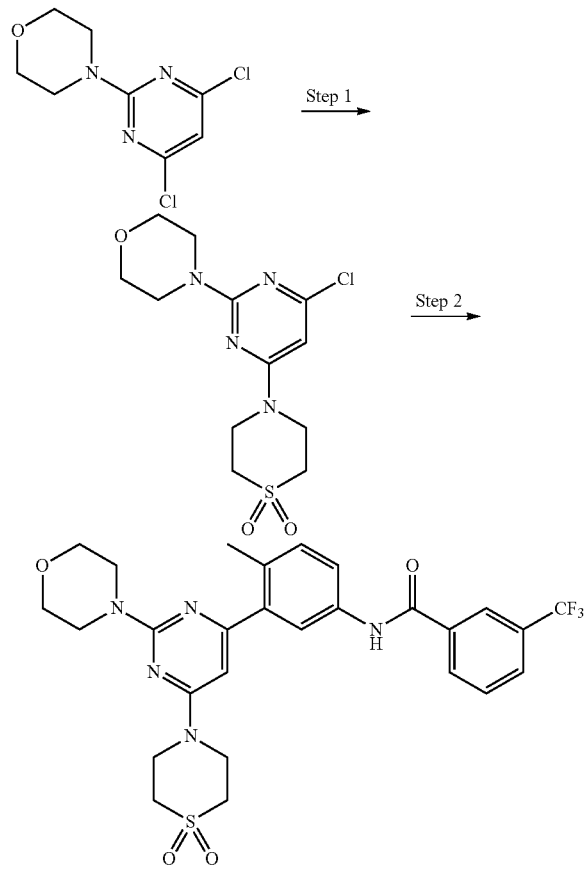

Step 1.
To a solution of 4-(4,6-dichloropyrimidin-2-yl)morpholine (1.0 equiv.) in EtOH:THF (1:1, 0.25 M) was added thiomorpholine 1,1-dioxide (1.0 equiv.) in one portion. The resulting mixture was heated to 100° C. for 42 h. The resulting mixture was then cooled to RT and concentrated in vacuo to yield an off white solid in The reaction mixture was then concentrated in vacuo and dried under high vacuum over 20 h to yield 4-(6-chloropyrimidin-4-yl)morpholine as a white solid in 97% yield. LCMS (m/z) (M+H)=333.0/334.9, Rt=0.68 min.

Step 2.
To a solution of 4-(6-chloro-2-morpholinopyrimidin-4-yl) thiomorpholine 1,1-dioxide (1.0 equiv.) and Intermediate A (1.1 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(3-(6-(1,1-dioxidothiomorpholino)-2-morpholinopyrimidin-4-yl)-4-methylphenyl)-3-(trifluoromethyl)benzamide was isolated as the TFA salt in 35% yield. LCMS (m/z) (M+H)=576.3, Rt=0.79 min, $^1$H NMR (400 MHz, <dmso>) δ ppm 2.33 (s, 3H) 2.54 (s, 1H) 3.21 (br. s., 4H) 3.70 (d, J=10.56 Hz, 8H) 4.16 (br. s., 4H) 6.56 (br. s., 1H) 7.32 (d, J=7.83 Hz, 1H) 7.67-7.87 (m, 3H) 7.98 (d, J=7.83 Hz, 1H) 8.21-8.44 (m, 2H) 10.55 (br. s., 1H).

The compounds listed below were prepared using methods similar to those described for the preparation of Example 6 using the appropriate starting materials.

Example 7: Synthesis of 3-(6-(1,1-dioxidothiomor-pholino)-2-morpholinopyrimidin-4-yl)-4-methyl-N-(3-(trifluoromethyl)phenyl)benzamide

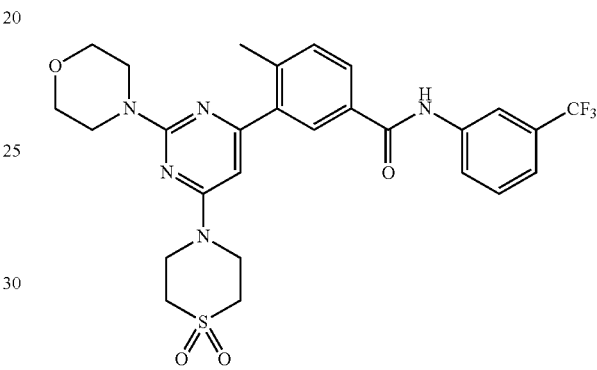

LCMS (m/z) (M+H)=576.3, Rt=0.78 min, $^1$H NMR (400 MHz, <dmso>) δ ppm 2.44 (s, 3H) 3.08-3.30 (m, 4H) 3.41-3.88 (m, 46H) 4.15 (br. s., 4H) 6.49-6.68 (m, 1H) 7.39-7.52 (m, 2H) 7.56-7.66 (m, 1H) 7.91-8.00 (m, 1H) 8.01 (d, J=1.57 Hz, 1H) 8.06 (d, J=8.22 Hz, 1H) 8.25 (s, 1H) 10.40-10.60 (m, 1H).

Example 8: Synthesis of N-(3-(2-(1,1-dioxidothio-morpholino)-6-morpholinopyrimidin-4-yl)-4-methyl-phenyl)-3-(trifluoromethyl)benzamide

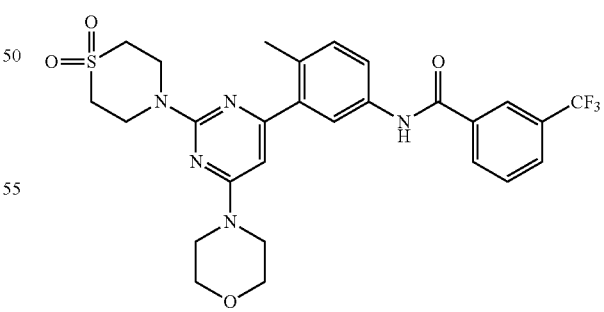

LCMS (m/z) (M+H)=576.3, Rt=0.78 min, $^1$H NMR (400 MHz, <dmso>) δ ppm 2.32 (s, 3H) 2.54 (s, 2H) 3.20 (br. s., 4H) 3.69 (br. s., 8H) 4.01-4.30 (m, 4H) 6.45 (br. s., 1H) 7.32 (d, J=8.22 Hz, 1H) 7.71-7.80 (m, 2H) 7.82 (d, J=4.30 Hz, 1H) 7.98 (d, J=7.43 Hz, 1H) 8.27 (d, J=8.22 Hz, 1H) 8.30 (s, 1H) 10.55 (s, 1H).

Example 9: Synthesis of 3-(2-(1,1-dioxidothiomorpholino)-6-morpholinopyrimidin-4-yl)-4-methyl-N-(3-(trifluoromethyl)phenyl)benzamide

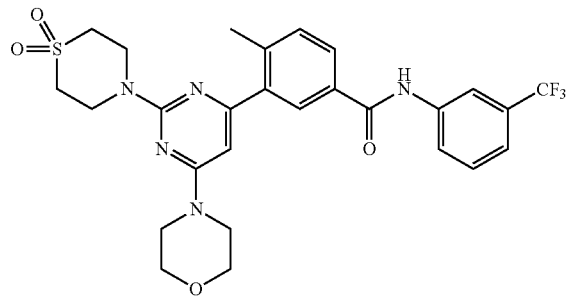 [SMILES: Cc1ccc(C(=O)Nc2cccc(C(F)(F)F)c2)cc1-c1cc(N2CCOCC2)nc(N2CCS(=O)(=O)CC2)n1]

LCMS (m/z) (M+H)=576.3, Rt=0.80 min, $^1$H NMR (400 MHz, <dmso>) δ ppm 2.43 (s, 3H) 2.54 (s, 2H) 3.04-3.23 (m, 4H) 3.68 (br. s., 10H) 4.20 (br. s., 4H) 6.46 (br. s., 1H) 7.26-7.53 (m, 2H) 7.60 (t, J=7.83 Hz, 1H) 7.98 (d, J=7.83 Hz, 1H) 8.00 (s, 1H) 8.06 (d, J=8.22 Hz, 1H) 8.25 (s, 1H) 10.52 (s, 1H).

Example 10: Synthesis of N-(3-(2,6-dimorpholinopyrimidin-4-yl)-4-methylphenyl)-3-(trifluoromethyl)benzamide

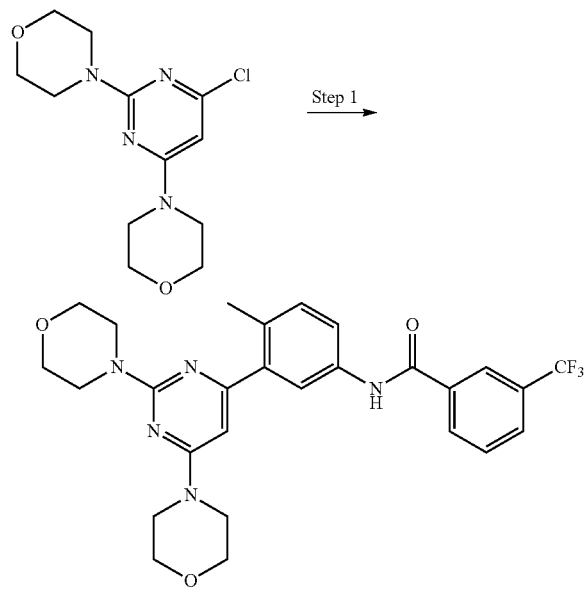

Step 1.

To a solution of 4,4'-(6-chloropyrimidine-2,4-diyl)dimorpholine (1.0 equiv.) and Intermediate A (1.1 equiv.) in DME and 2M sodium carbonate (3:1, 0.2 M) was added PdCl$_2$ (dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(3-(2,6-dimorpholinopyrimidin-4-yl)-4-methylphenyl)-3-(trifluoromethyl)benzamide was isolated as the TFA salt in 37% yield. LCMS (m/z) (M+H)=528.3, Rt=0.80 min, $^1$H NMR (400 MHz, <dmso>) δ ppm 2.21-2.35 (m, 3H) 3.68 (br. s., 8H) 3.71 (d, J=4.30 Hz, 8H) 6.50 (br. s., 1H) 7.34 (d, J=8.22 Hz, 1H) 7.70-7.89 (m, 3H) 7.97 (d, J=7.83 Hz, 1H) 8.26 (d, J=7.83 Hz, 1H) 8.29 (s, 1H) 10.59 (br. s., 1H).

The compounds listed below were prepared using methods similar to those described for the preparation of Example 10 using the appropriate starting materials.

Example 11: 3-(2,6-dimorpholinopyrimidin-4-yl)-4-methyl-N-(3-(trifluoromethyl)phenyl)benzamide

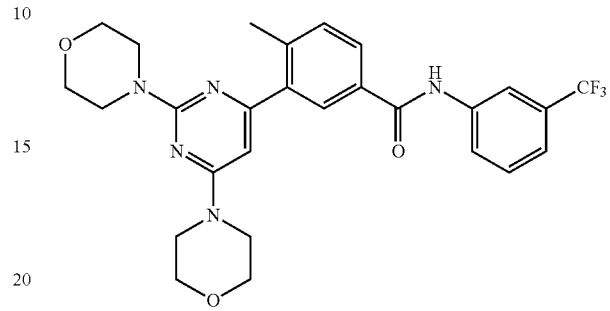

LCMS (m/z) (M+H)=528.3, Rt=0.80 min. $^1$H NMR (400 MHz, <dmso>) δ ppm 2.29-2.37 (m, 3H) 3.42-3.72 (m, 19H) 3.84 (br. s., 8H) 7.35-7.50 (m, 2H) 7.54 (t, J=8.02 Hz, 1H) 7.95 (s, 2H) 8.00 (d, J=8.22 Hz, 1H) 8.18 (s, 1H) 10.47 (s, 1H).

Example 12: N-(5-(2,6-dimorpholinopyrimidin-4-yl)-6-methylpyridin-3-yl)-3-(trifluoromethyl)benzamide

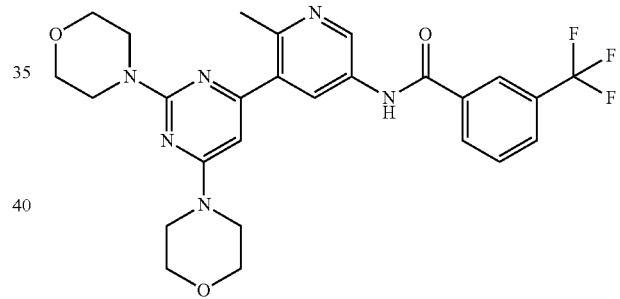

$^1$H NMR (400 MHz, <dmso>) δ ppm 10.86 (s, 1H), 8.99 (d, J=2.3 Hz, 1H), 8.24-8.40 (m, 3H), 8.01 (d, J=7.8 Hz, 1H), 7.75-7.89 (m, 1H), 6.51 (br. s., 1H), 3.68 (d, J=6.6 Hz, 16H), 2.56 (s, 3H). LCMS (m/z) (M+H)=529.4, Rt=0.70 min.

Example 13: Synthesis of N-(3-(4,6-dimorpholinopyrimidin-2-yl)-4-methylphenyl)-3-(trifluoromethyl)benzamide

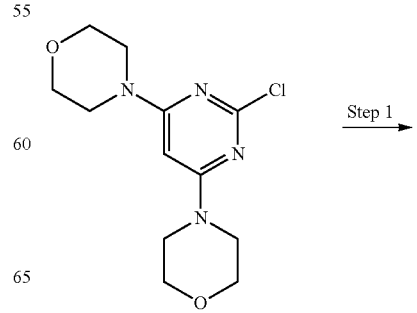

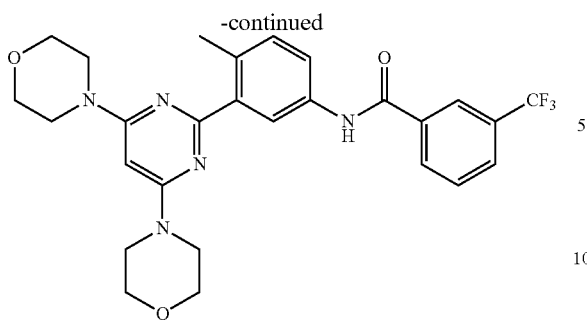

To a solution of 4,4'-(2-chloropyrimidine-4,6-diyl)dimorpholine (1.0 equiv.) and Intermediate A (1.1 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, N-(3-(4,6-dimorpholinopyrimidin-2-yl)-4-methylphenyl)-3-(trifluoromethyl)benzamide was isolated as the TFA salt in 35% yield. LCMS (m/z) (M+H)=528.3, Rt=0.82 min, $^1$H NMR (400 MHz, <dmso>) δ ppm 2.35-2.45 (m, 3H) 3.40-3.63 (m, 9H) 3.66 (d, J=4.30 Hz, 9H) 5.97 (s, 1H) 7.26 (d, J=8.22 Hz, 1H) 7.69-7.84 (m, 2H) 7.95 (d, J=7.83 Hz, 1H) 8.04 (d, J=2.35 Hz, 1H) 8.21-8.31 (m, 2H) 10.49 (s, 1H).

The compounds listed below were prepared using methods similar to those described for the preparation of Example 13 using the appropriate starting materials.

Example 14: Synthesis of 3-(4,6-dimorpholinopyrimidin-2-yl)-4-methyl-N-(3-(trifluoromethyl)phenyl)benzamide

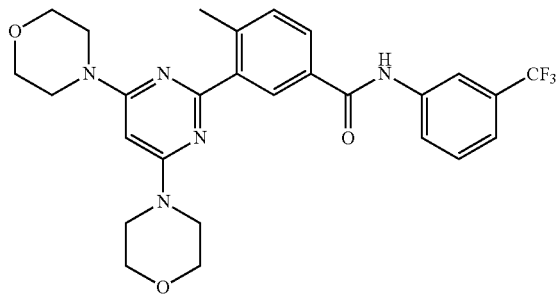 [SMILES: Cc1ccc(C(=O)Nc2cccc(C(F)(F)F)c2)cc1-c1nc(N2CCOCC2)cc(N2CCOCC2)n1]

LCMS (m/z) (M+H)=528.3, Rt=0.84 min, $^1$H NMR (400 MHz, <dmso>) δ ppm 2.51-2.62 (m, 4H) 3.58 (d, J=4.30 Hz, 9H) 3.62-3.77 (m, 9H) 5.96 (s, 1H) 7.30-7.47 (m, 2H) 7.51-7.65 (m, 2H) 7.92 (dd, J=8.02, 1.76 Hz, 1H) 8.03 (d, J=8.22 Hz, 1H) 8.16-8.34 (m, 2H) 10.53 (s, 1H).

Example 15: Synthesis of 2-(2-cyanopropan-2-yl)-N-(3-(2,6-dimorpholinopyrimidin-4-yl)-4-methylphenyl)isonicotinamide

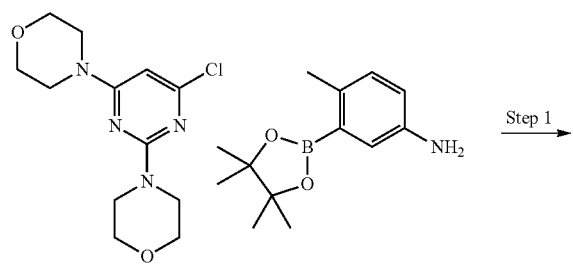

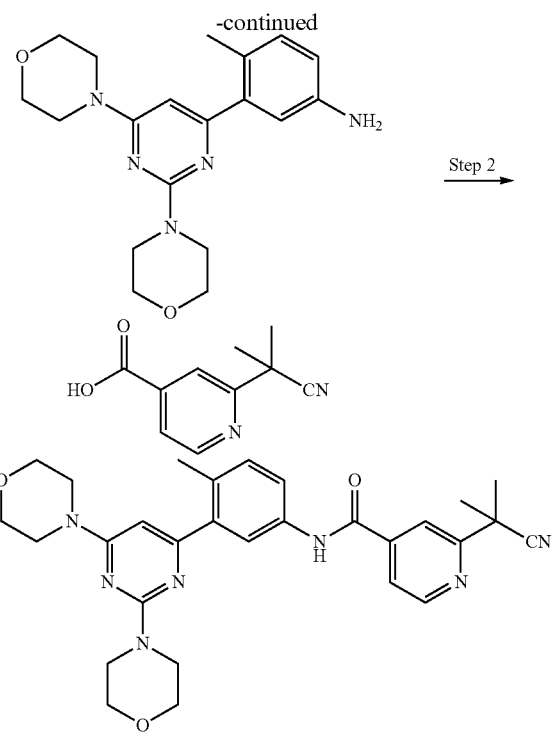

Step 1.

To a solution of 4,4'-(6-chloropyrimidine-2,4-diyl)dimorpholine (1.0 equiv.) and 4-methyl-3-(4,4,5,5-tetramethyl-1,3,2-dioxaborolan-2-yl)aniline (1.5 equiv.) in DME and 2M sodium carbonate (3:1, 0.2 M) was added PdCl$_2$(dppf)-DCM adduct (0.100 equiv.) in a microwave vial equipped with a stir bar. The reaction was heated to 120° C. for 20 min in the microwave. The reaction mixture gas quenched with water and the aqueous layer was separated and extracted with EtOAc (×3). The combined organic layer was dried over magnesium sulfate, filtered and concentrated in vacuo. The material was purified via silica gel column chromatography eluting with 100% DCM to 10% MeOH/DCM to afford 3-(2,6-dimorpholinopyrimidin-4-yl)-4-methylaniline in 96% yield. LCMS (m/z) (M+H)=356.2, Rt=0.44 min.

Step 2.

To a solution of 3-(2,6-dimorpholinopyrimidin-4-yl)-4-methylaniline (1.0 equiv.) in DMF (0.10 M) was added 2-(2-cyanopropan-2-yl)isonicotinic acid (1.2 equiv.), EDC-HCl (1.2 equiv.) and aza-HOBt (1.2 equiv.). The reaction was stirred at room temperature for 6 hours. Upon completion, the solution was filtered through a HPLC filter and purified via reverse phase preparative HPLC. Upon lyophilization of the pure fractions, 2-(2-cyanopropan-2-yl)-N-(3-(2,6-dimorpholinopyrimidin-4-yl)-4-methylphenyl)isonicotinamide was isolated as the TFA salt in 40% yield. $^1$H NMR (400 MHz, <cd3od>) δ ppm 1.81 (s, 6H) 2.38 (s, 3H) 3.79 (s, 13H) 3.89 (br. s., 3H) 6.57 (s, 1H) 7.43 (d, J=8.41 Hz, 1H) 7.65 (dd, J=8.27, 2.30 Hz, 1H) 7.81 (dd, J=5.04, 1.57 Hz, 1H) 7.97 (d, J=2.25 Hz, 1H) 8.04-8.10 (m, 1H) 8.78 (dd, J=5.04, 0.78 Hz, 1H). LCMS (m/z) (M+H)=528.3, Rt=0.69 min.

The compounds listed below were prepared using methods similar to those described for the preparation of Example 15 using the appropriate starting materials.

Example 16: 3-(2-cyanopropan-2-yl)-N-(3-(2,6-dimorpholinopyrimidin-4-yl)-4-methylphenyl)benzamide

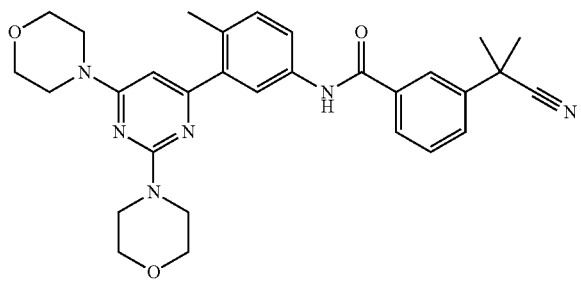 [SMILES: Cc1ccc(NC(=O)c2cccc(C(C)(C)C#N)c2)cc1-c1cc(N2CCOCC2)nc(N2CCOCC2)n1]

¹H NMR (400 MHz, <cd3od>) δ ppm 1.79 (s, 7H) 2.38 (s, 3H) 3.80 (s, 13H) 6.58 (s, 1H) 7.41 (d, J=8.36 Hz, 1H) 7.53-7.68 (m, 2H) 7.78 (ddd, J=7.92, 2.05, 1.03 Hz, 1H) 7.86-7.99 (m, 2H) 8.10 (t, J=1.71 Hz, 1H). LCMS (m/z) (M+H)=527.3, Rt=0.75 min.

Example 17: 2-chloro-3-(1-cyanocyclopropyl)-N-(3-(2,6-dimorpholinopyrimidin-4-yl)-4-methylphenyl)benzamide

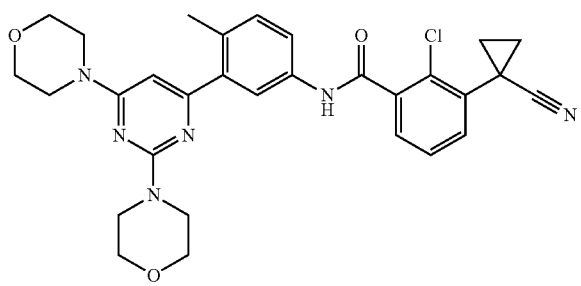 [SMILES: Cc1ccc(NC(=O)c2cccc(C3(C#N)CC3)c2Cl)cc1-c1cc(N2CCOCC2)nc(N2CCOCC2)n1]

¹H NMR (400 MHz, <cd3od>) δ ppm 1.31-1.41 (m, 2H) 1.65-1.76 (m, 2H) 2.26 (s, 3H) 3.69 (s, 17H) 6.47 (s, 1H) 7.30 (d, J=8.36 Hz, 1H) 7.35-7.41 (m, 1H) 7.44-7.50 (m, 2H) 7.53 (dd, J=7.65, 1.74 Hz, 1H) 7.87 (d, J=2.30 Hz, 1H). LCMS (m/z) (M+H)=560.2, Rt=0.72 min.

Example 18: 5-(dimethylamino)-N-(3-(2,6-dimorpholinopyrimidin-4-yl)-4-methylphenyl)nicotinamide

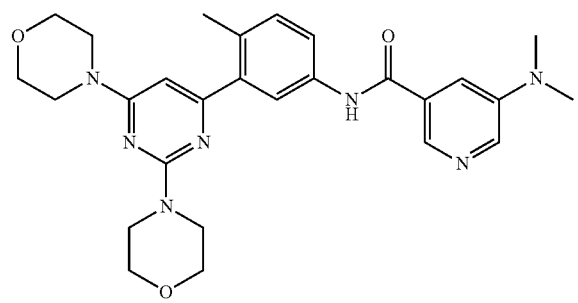 [SMILES: Cc1ccc(NC(=O)c2cncc(N(C)C)c2)cc1-c1cc(N2CCOCC2)nc(N2CCOCC2)n1]

¹H NMR (400 MHz, <cd3od>) δ ppm 2.38 (s, 3H) 3.17 (s, 6H) 3.71-3.99 (m, 16H) 6.56 (s, 1H) 7.43 (d, J=8.36 Hz, 1H) 7.67 (dd, J=8.31, 2.30 Hz, 1H) 7.95 (d, J=2.35 Hz, 1H) 8.03 (dd, J=2.86, 1.54 Hz, 1H) 8.26 (d, J=2.84 Hz, 1H) 8.44 (d, J=1.22 Hz, 1H). LCMS (m/z) (M+H)=504.3, Rt=0.53 min.

Example 19: 5-(tert-butyl)-N-(3-(2,6-dimorpholinopyrimidin-4-yl)-4-methylphenyl)nicotinamide

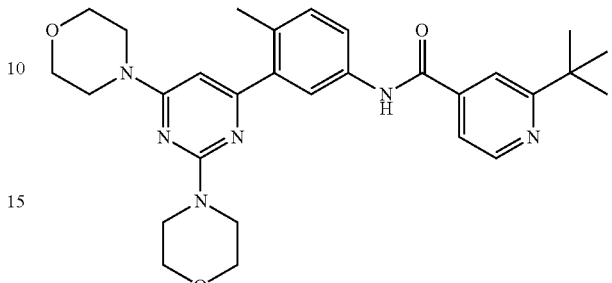

¹H NMR (400 MHz, <cd3od>) δ ppm 1.40-1.48 (m, 9H) 2.38 (s, 3H) 3.80 (s, 13H) 6.58 (s, 1H) 7.43 (d, J=8.41 Hz, 1H) 7.62-7.68 (m, 1H) 7.72 (d, J=5.28 Hz, 1H) 7.97 (d, J=2.15 Hz, 2H) 8.69 (d, J=5.18 Hz, 1H). LCMS (m/z) (M+H)=517.3, Rt=0.60 min.

Example 20: 3-((dimethylamino)methyl)-N-(3-(2,6-dimorpholinopyrimidin-4-yl)-4-methylphenyl)-5-(trifluoromethyl)benzamide

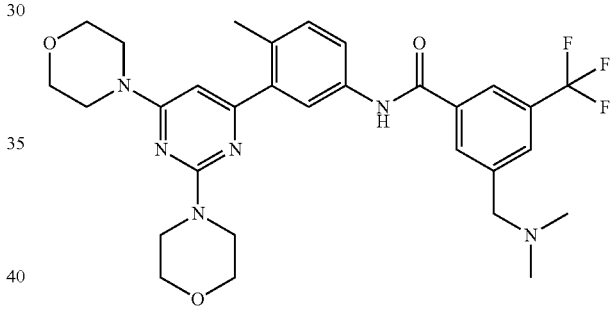

¹H NMR (400 MHz, <cd3od>) δ ppm 2.38 (s, 3H) 2.92 (s, 6H) 3.68-3.98 (m, 16H) 4.51 (s, 2H) 6.53 (s, 1H) 7.42 (d, J=8.41 Hz, 1H) 7.66-7.73 (m, 1H) 7.93 (d, J=2.15 Hz, 1H) 8.12 (s, 1H) 8.38 (s, 1H) 8.43 (s, 1H). LCMS (m/z) (M+H)=585.3, Rt=0.61 min.

Example 21: N-(3-(2,6-dimorpholinopyrimidin-4-yl)-4-methylphenyl)-3-(4-ethylpiperazin-1-yl)-5-(trifluoromethyl)benzamide

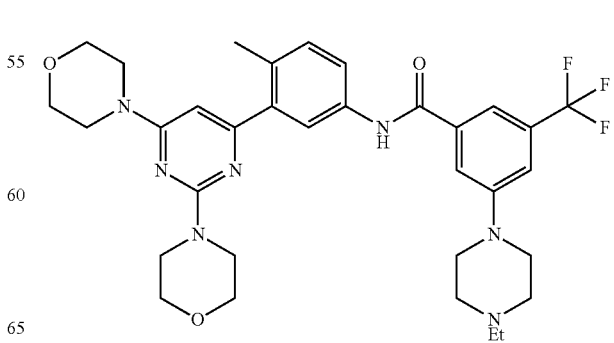

¹H NMR (400 MHz, <cd3od>) δ ppm 1.41 (t, J=7.34 Hz, 3H) 2.38 (s, 3H) 3.70-3.93 (m, 15H) 6.52 (s, 1H) 7.40 (d, J=8.36 Hz, 1H) 7.52 (s, 1H) 7.66 (dd, J=8.39, 1.98 Hz, 1H) 7.79 (s, 1H) 7.82 (d, J=2.01 Hz, 1H) 7.91 (d, J=2.25 Hz, 1H). LCMS (m/z) (M+H)=640.3, Rt=0.66 min.

Example 22: N-(3-(2,6-dimorpholinopyrimidin-4-yl)-4-methylphenyl)-3-(trifluoromethoxy)benzamide

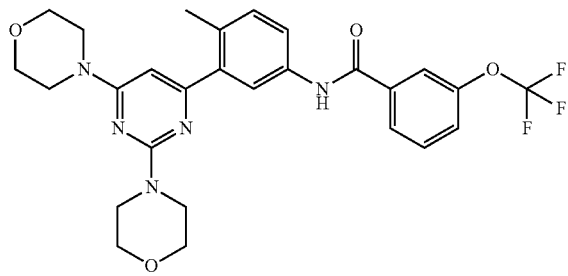 [SMILES: Cc1ccc(NC(=O)c2cccc(OC(F)(F)F)c2)cc1-c1cc(N2CCOCC2)nc(N2CCOCC2)n1]

¹H NMR (400 MHz, <cd3od>) δ ppm 2.38 (s, 3H) 3.72-3.94 (m, 15H) 6.57 (s, 1H) 7.42 (d, J=8.36 Hz, 1H) 7.51-7.57 (m, 1H) 7.60-7.69 (m, 2H) 7.87 (s, 1H) 7.94-8.00 (m, 1H). LCMS (m/z) (M+H)=544.3, Rt=0.84 min.

Example 23: N-(3-(2,6-dimorpholinopyrimidin-4-yl)-4-methylphenyl)-3-(methylsulfonyl)benzamide

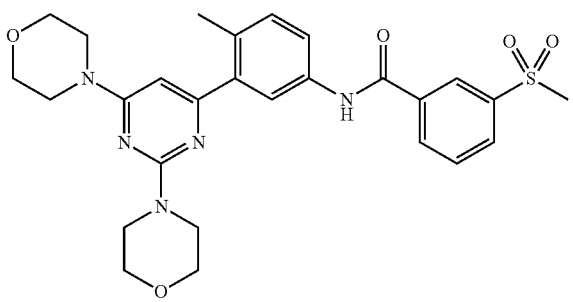 [SMILES: Cc1ccc(NC(=O)c2cccc(S(C)(=O)=O)c2)cc1-c1cc(N2CCOCC2)nc(N2CCOCC2)n1]

¹H NMR (400 MHz, <cd3od>) δ ppm 2.38 (s, 3H) 3.19 (s, 3H) 3.65-4.06 (m, 16H) 6.58 (s, 1H) 7.42 (d, J=8.22 Hz, 1H) 7.65 (dd, J=8.41, 2.15 Hz, 1H) 7.81 (t, J=7.83 Hz, 1H) 7.97 (d, J=2.35 Hz, 1H) 8.19 (d, J=7.83 Hz, 1H) 8.28 (d, J=7.83 Hz, 1H) 8.51 (s, 1H). LCMS (m/z) (M+H)=538.3, Rt=0.64 min.

Example 24: 3-(tert-butyl)-N-(3-(2,6-dimorpholinopyrimidin-4-yl)-4-methylphenyl)isoxazole-5-carboxamide

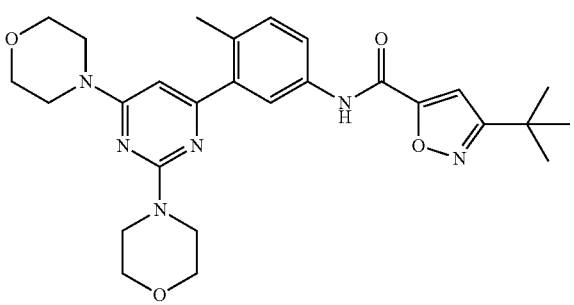 [SMILES: Cc1ccc(NC(=O)c2cc(C(C)(C)C)no2)cc1-c1cc(N2CCOCC2)nc(N2CCOCC2)n1]

¹H NMR (400 MHz, <cd3od>) δ ppm 1.42 (s, 9H) 2.37 (s, 3H) 3.80 (m, 16H) 6.52 (s, 1H) 7.10 (s, 1H) 7.42 (d, J=5.28 Hz, 1H) 7.71 (d, J=5.28 Hz, 1H) 7.92 (s, 1H). LCMS (m/z) (M+H)=507.3, Rt=0.79 min.

Example 25: 5-(tert-butyl)-N-(3-(2,6-dimorpholinopyrimidin-4-yl)-4-methylphenyl)isoxazole-3-carboxamide

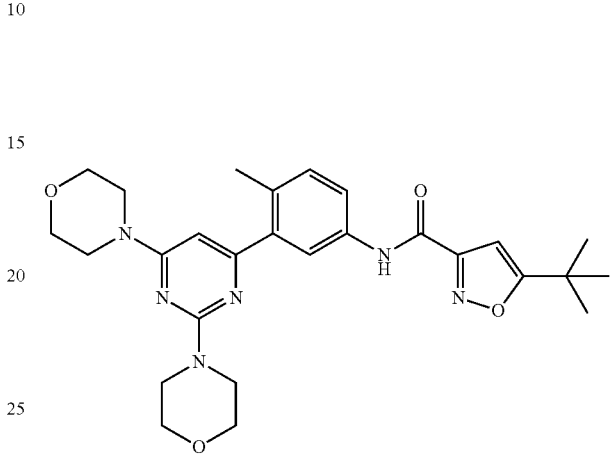

¹H NMR (400 MHz, <cd3od>) δ ppm 1.39 (s, 9H) 2.30 (s, 3H) 3.80 (m, 16H) 6.52 (m, 2H) 7.40 (d, J=5.28 Hz, 1H) 7.71 (d, J=5.28 Hz, 1H) 7.87 (s, 1H). LCMS (m/z) (M+H)=507.3, Rt=0.84 min.

Example 26 N-(3-(2,6-dimorpholinopyrimidin-4-yl)-4-methylphenyl)-2-(trifluoromethyl)thiazole-4-carboxamide

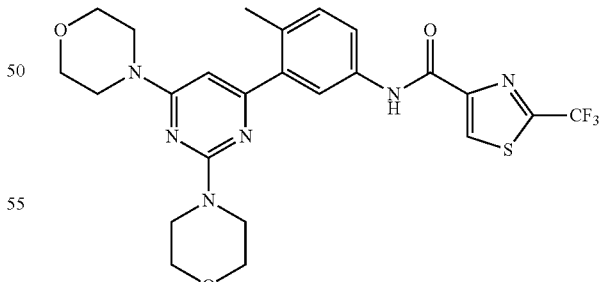

LCMS (m/z) (M+H)=535.2, Rt=0.78 min. 1H NMR (400 MHz, <cd3od>) δ ppm 2.37 (s, 3H) 3.71-4.00 (m, 16H) 6.57 (s, 1H) 7.42 (d, J=8.22 Hz, 1H) 7.77 (dd, J=8.22, 2.35 Hz, 1H) 7.92 (d, J=1.96 Hz, 1H) 8.70 (s, 1H).

Example 27 N-(4-methyl-3-(2-(methylsulfonyl)-6-morpholinopyrimidin-4-yl)phenyl)-3-(trifluoromethyl)benzamide

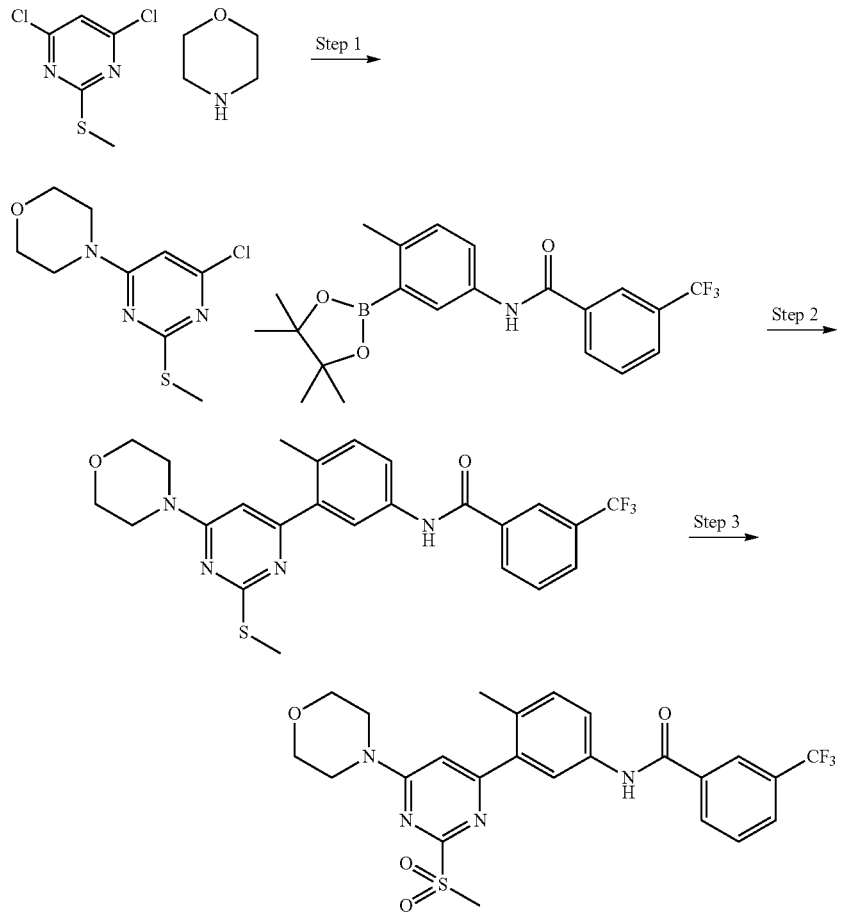

Step 1.

To a solution of 4,6-dichloro-2-(methylthio)pyrimidine (1.0 equiv.) and triethylamine (0.8 equiv.) in EtOH (0.256 M) at RT was added morpholine (1.0 equiv.) in one portion. The resulting mixture was stirred at RT for 6 hours; a precipitate formed during this time. LCMS analysis indicated the formation of the desired product. The precipitate was filtered and washed with EtOH. Isolated 4-(6-chloro-2-(methylthio)pyrimidin-4-yl)morpholine as a white solid in 76% yield. LCMS (m/z) (M+H)=245.1, Rt=0.73 min.

Step 2.

To a solution of 4-(6-chloro-2-(methylthio)pyrimidin-4-yl)morpholine (1.0 equiv.), N-(4methyl-3-(4,4,5,5-tetramethyl-1,3,2-dioxaborolan-2-yl)phenyl)-3-(trifluoromethyl)benzamide (1.05 equiv.) in DME/2M sodium carbonate (3:1, 0.20M) was added PdCl$_2$(dppf).CH$_2$C$_{12}$ adduct (0.1 equiv.). The reaction was purged with N$_2$ for 5 mins, the vial was sealed and subjected to microwave irradiation for 10 min at 120° C. LCMS shows complete formation of desired product. The reaction was partitioned between water and EtOAc. The aqueous layer was further washed EtOAc (2×100 mL). The combined organics were dried over MgSO$_4$, filtered and concentrated. The crude material was purified via flash chromatography over silica gel eluting with heptanes and 0-60% ethyl acetate gradient. Isolated N-(4-methyl-3-(2-(methylthio)-6-morpholinopyrimidin-4-yl)phenyl)-3-(trifluoromethyl)benzamide as a white solid in 60% yield. LCMS (m/z) (M+H)=489.1, Rt=0.81 min.

Step 3.

To a solution of N-(4-methyl-3-(2-(methylthio)-6-morpholinopyrimidin-4-yl)phenyl)-3-(trifluoromethyl)benzamide (1.0 equiv.) in DCM (0.1 M) was added m-CPBA (2.2 equiv.) portion wise. The reaction was stirred at RT for 4 hours. After which time LCMS shows complete oxidation to desired product. The reaction was diluted with DCM and washed with 0.5M Na$_2$CO$_3$. The resulting emulsion was filtered through a pad of celite and the cake was washed with DCM. The organics were dried over MgSO$_4$, filtered and concentrated. The material was purified via preparative reverse phase HPLC. Upon lyophilization of the pure fractions, N-(4-methyl-3-(2-(methylsulfonyl)-6-morpholinopyrimidin-4-yl)phenyl)-3-(trifluoromethyl)benzamide was isolated as the TFA salt in 33% yield. LCMS (m/z) (M+H)= 521.2, Rt=0.97 min. 1H NMR (400 MHz, <dmso>) δ ppm 2.36 (s, 3H) 3.68-3.81 (m, 9H) 4.03 (br. s., 2H) 7.14 (s, 1H) 7.35 (d, J=9.00 Hz, 1H) 7.76-7.82 (m, 1H) 7.82-7.87 (m, 2H) 7.98 (d, J=7.83 Hz, 1H) 8.28 (d, J=7.83 Hz, 1H) 8.31 (s, 1H) 10.57 (s, 1H).

Example 28 Synthesis of N-(3-(2-(ethylamino)-6-morpholinopyrimidin-4-yl)-4-methylphenyl)-3-(trifluoromethyl)benzamide

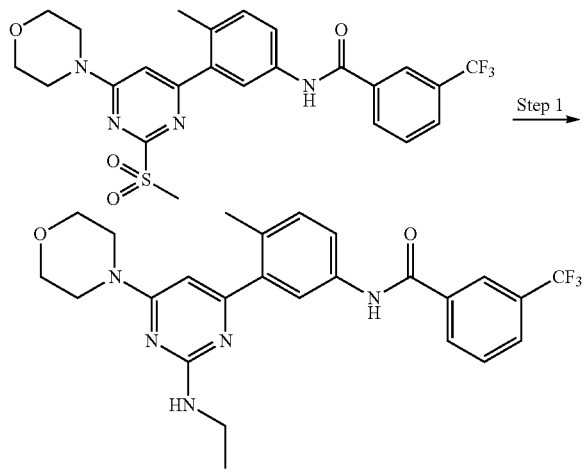

Step 1.
To a solution of N-(4-methyl-3-(2-(methylsulfonyl)-6-morpholinopyrimidin-4-yl)phenyl)-3-(trifluoromethyl)benzamide (1.0 equiv.) and 2-oxa-6-azaspiro[3.3]heptane (1.0 equiv.) in THF (0.20M) was added triethylamine (3.5 equiv.) and the allowed to stir at 75° C. for 48 hours. LCMS analysis indicated formation of the desired product. The volatiles were removed in vacuo. The crude material was purified via preparative reverse phase HPLC. Upon lyophilization of the pure fractions, N-(3-(2-(ethylamino)-6-morpholinopyrimidin-4-yl)-4-methylphenyl)-3-(trifluoromethyl)benzamide was isolated as the TFA salt in 21% yield. 1H NMR (400 MHz, <cd3od>) δ ppm 1.28 (t, J=7.24 Hz, 3H) 2.38 (s, 3H) 3.52 (q, J=6.65 Hz, 2H) 3.80 (br. s., 6H) 4.05 (br. s., 2H) 6.50 (s, 1H) 7.41 (d, J=8.61 Hz, 1H) 7.66 (dd, J=8.22, 2.35 Hz, 1H) 7.72-7.78 (m, 1H) 7.91 (d, J=7.83 Hz, 1H) 7.96 (d, J=2.35 Hz, 1H) 8.21 (d, J=7.83 Hz, 1H) 8.26 (s, 1H). LCMS (m/z) (M+H)=486.3, Rt=0.86 min.

The compounds listed below were prepared using methods similar to those described for the preparation of Example 28 using the appropriate starting materials.

Example 29 N-(4-methyl-3-(6-morpholino-2-(2-oxa-6-azaspiro[3.3]heptan-6-yl)pyrimidin-4-yl)phenyl)-3-(trifluoromethyl)benzamide

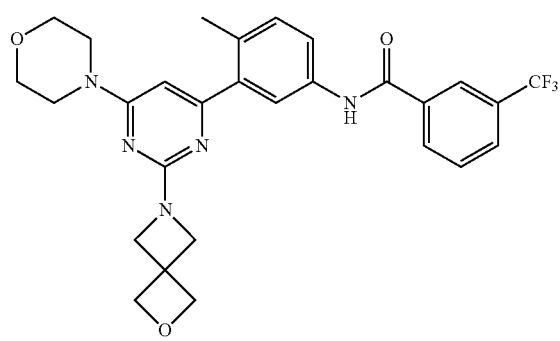 [SMILES: Cc1ccc(NC(=O)c2cccc(C(F)(F)F)c2)cc1-c1cc(N2CCOCC2)nc(N2CC3(COC3)C2)n1]

LCMS (m/z) (M+H)=540.3, Rt=0.81 min. 1H NMR (400 MHz, <cd3od>) δ ppm 2.36 (s, 3H) 3.69-3.83 (m, 12H) 4.44 (s, 4H) 6.51 (s, 1H) 7.41 (d, J=8.61 Hz, 1H) 7.63 (dd, J=8.22, 2.35 Hz, 1H) 7.72-7.78 (m, 1H) 7.92 (d, J=7.83 Hz, 1H) 7.95 (d, J=1.96 Hz, 1H) 8.21 (d, J=7.83 Hz, 1H) 8.26 (s, 1H).

Example 30 N-(4-methyl-3-(2-(methylamino)-6-morpholinopyrimidin-4-yl)phenyl)-3-(trifluoromethyl)benzamide

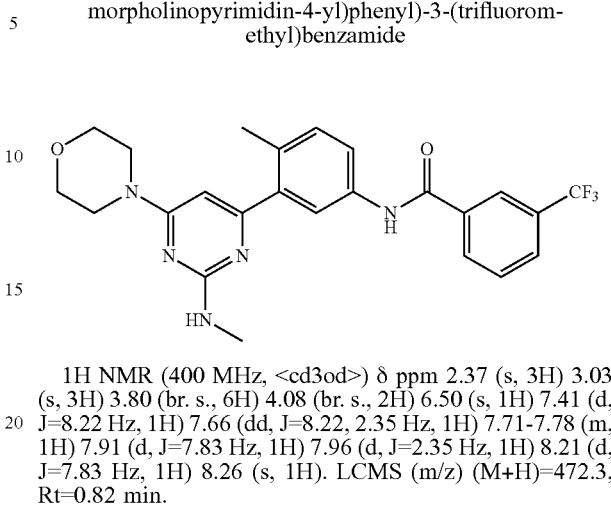

1H NMR (400 MHz, <cd3od>) δ ppm 2.37 (s, 3H) 3.03 (s, 3H) 3.80 (br. s., 6H) 4.08 (br. s., 2H) 6.50 (s, 1H) 7.41 (d, J=8.22 Hz, 1H) 7.66 (dd, J=8.22, 2.35 Hz, 1H) 7.71-7.78 (m, 1H) 7.91 (d, J=7.83 Hz, 1H) 7.96 (d, J=2.35 Hz, 1H) 8.21 (d, J=7.83 Hz, 1H) 8.26 (s, 1H). LCMS (m/z) (M+H)=472.3, Rt=0.82 min.

Example 31 N-(3-(2-((2-hydroxyethyl)amino)-6-morpholinopyrimidin-4-yl)-4-methylphenyl)-3-(trifluoromethyl)benzamide

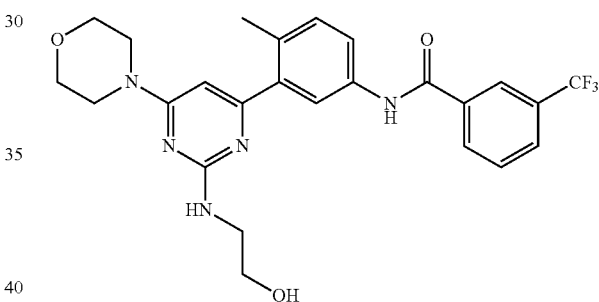

1H NMR (400 MHz, <cd3od>) δ ppm 2.02-2.26 (m, 2H) 2.38 (s, 3H) 3.62-3.85 (m, 9H) 4.04 (br. s., 2H) 4.56 (br. s., 1H) 6.52 (s, 1H) 7.41 (d, J=8.22 Hz, 1H) 7.66 (dd, J=8.22, 2.35 Hz, 1H) 7.72-7.78 (m, 1H) 7.92 (d, J=7.83 Hz, 1H) 7.94 (d, J=1.96 Hz, 1H) 8.21 (d, J=7.83 Hz, 1H) 8.26 (s, 1H). LCMS (m/z) (M+H)=502.3, Rt=0.77 min.

Example 32 N-(3-(2-(3-hydroxypyrrolidin-1-yl)-6-morpholinopyrimidin-4-yl)-4-methylphenyl)-3-(trifluoromethyl)benzamide

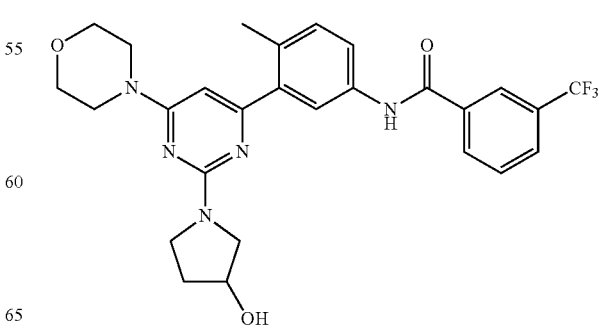

1H NMR (400 MHz, <cd3od>) δ ppm 2.02-2.27 (m, 2H) 2.38 (s, 3H) 3.63-3.87 (m, 10H) 4.05 (br. s., 2H) 4.56 (br. s., 1H) 6.52 (s, 1H) 7.41 (d, J=8.61 Hz, 1H) 7.66 (dd, J=8.41, 2.15 Hz, 1H) 7.72-7.78 (m, 1H) 7.92 (d, J=7.83 Hz, 1H) 7.94 (d, J=2.35 Hz, 1H) 8.21 (d, J=7.83 Hz, 1H) 8.26 (s, 1H). LCMS (m/z) (M+H)=528.3, Rt=0.79 min.

Example 33 N-(3-(2-(1H-imidazol-1-yl)-6-morpholinopyrimidin-4-yl)-4-methylphenyl)-3-(trifluoromethyl)benzamide

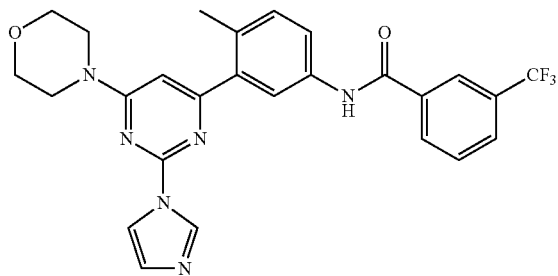 [SMILES: Cc1ccc(NC(=O)c2cccc(C(F)(F)F)c2)cc1-c1cc(N2CCOCC2)nc(-n2ccnc2)n1]

1H NMR (400 MHz, <cd3od>) δ ppm 2.46 (s, 3H) 3.78-3.93 (m, 8H) 6.99 (s, 1H) 7.36 (d, J=8.22 Hz, 1H) 7.60 (s, 1H) 7.63 (dd, J=8.22, 2.35 Hz, 1H) 7.71-7.78 (m, 1H) 7.91 (d, J=7.83 Hz, 1H) 7.99 (d, J=1.96 Hz, 1H) 8.22 (d, J=7.83 Hz, 1H) 8.27 (s, 1H) 8.36 (s, 1H) 9.61 (s, 1H). LCMS (m/z) (M+H)=509.4, Rt=0.84 min.

Example 34 Synthesis of N-(3-(2-(2-hydroxyethoxy)-6-morpholinopyrimidin-4-yl)-4-methylphenyl)-3-(trifluoromethyl)benzamide

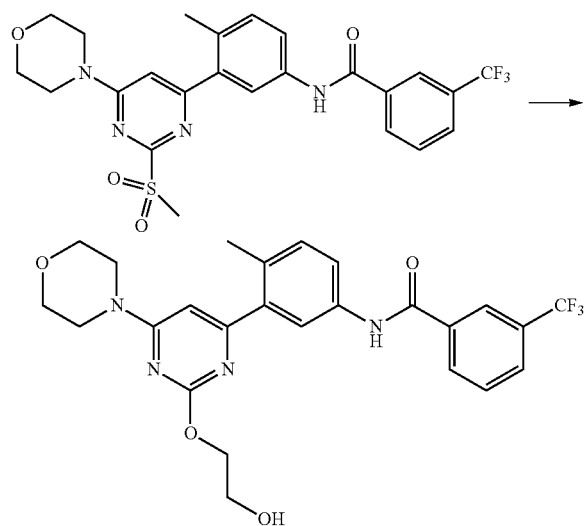

To a solution of N-(4-methyl-3-(2-(methylsulfonyl)-6-morpholinopyrimidin-4-yl)phenyl)-3-(trifluoromethyl)benzamide (1.0 equiv.) and ethylene glycol (1.0 equiv.) in acetonitrile (0.10M) was added potassium carbonate (1.0 equiv.) and the allowed to stir at 120° C. for 24 hours. LCMS analysis indicated formation of the desired product. The volatiles were removed in vacuo. The crude material was purified via preparative reverse phase HPLC. Upon lyophilization of the pure fractions, N-(4-methyl-3-(2-(methylsulfonamido)-6-morpholinopyrimidin-4-yl)phenyl)-3-(trifluoromethyl)benzamide was isolated as the TFA salt in 6% yield. LCMS (m/z) (M+H)=536.3, Rt=0.80 min, 1H NMR (400 MHz, <cd3od>) δ ppm 2.37 (s, 3H) 3.79-3.85 (m, 4H) 3.86-3.97 (m, 6H) 4.60-4.65 (m, 2H) 6.78 (s, 1H) 7.41 (d, J=8.22 Hz, 1H) 7.67 (dd, J=8.22, 2.35 Hz, 1H) 7.74 (t, J=7.83 Hz, 1H) 7.91 (d, J=8.22 Hz, 1H) 7.94 (d, J=1.96 Hz, 1H) 8.21 (d, J=7.83 Hz, 1H) 8.26 (s, 1H). LCMS (m/z) (M+H)=503.1, Rt=0.73 min.

The compounds listed below were prepared using methods similar to those described above using the appropriate starting materials.

Example 35 N-(4-methyl-3-(2-(methylsulfonamido)-6-morpholinopyrimidin-4-yl)phenyl)-3-(trifluoromethyl)benzamide

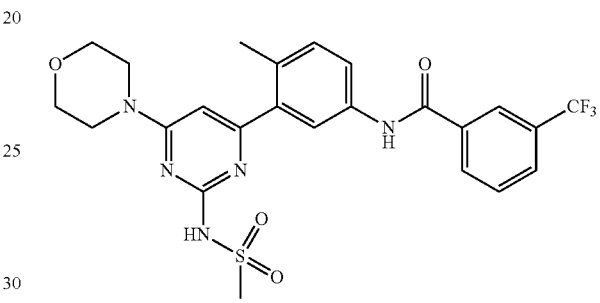

LCMS (m/z) (M+H)=536.3, Rt=0.80 min. 1H NMR (400 MHz, <cd3od>) δ ppm 2.37 (s, 3H) 3.23 (s, 3H) 3.76-3.83 (m, 4H) 3.86 (br. s., 4H) 6.50 (s, 1H) 7.38 (d, J=8.22 Hz, 1H) 7.68-7.78 (m, 2H) 7.84 (d, J=2.35 Hz, 1H) 7.91 (d, J=7.83 Hz, 1H) 8.21 (d, J=7.83 Hz, 1H) 8.26 (s, 1H).

Example 36 Synthesis of N-(4-methyl-3-(6-morpholino-2-(2-oxopyrrolidin-1-yl)pyrimidin-4-yl)phenyl)-3-(trifluoromethyl)benzamide

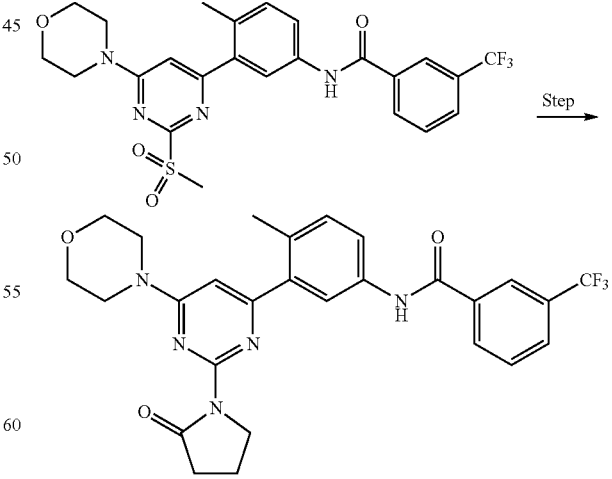

To a solution of N-(4-methyl-3-(2-(methylsulfonyl)-6-morpholinopyrimidin-4-yl)phenyl)-3-(trifluoromethyl)benzamide (1.0 equiv.) and pyrrolidin-2-one (2.0 equiv.) in dioxane (0.10M) was added cesium carbonate (1.0 equiv.)

and the allowed to stir at 120° C. for 24 hours. LCMS analysis indicated formation of the desired product. The volatiles were removed in vacuo. The crude material was purified via preparative reverse phase HPLC. Upon lyophilization of the pure fractions, N-(4-methyl-3-(6-morpholino-2-(2-oxopyrrolidin-1-yl)pyrimidin-4-yl)phenyl)-3-(trifluoromethyl)benzamide was isolated as the TFA salt in 12% yield. LCMS (m/z) (M+H)=526.3, Rt=0.83 min. 1H NMR (400 MHz, <cd3od>) δ ppm 2.25 (quin, J=7.73 Hz, 2H) 2.47 (s, 3H) 2.81 (t, J=8.02 Hz, 2H) 3.82-3.87 (m, 8H) 4.15 (t, J=7.43 Hz, 2H) 7.03 (s, 1H) 7.47 (d, J=8.61 Hz, 1H) 7.71 (dd, J=8.41, 2.15 Hz, 1H) 7.75 (t, J=7.83 Hz, 1H) 7.92 (d, J=7.83 Hz, 1H) 8.11 (d, J=2.35 Hz, 1H) 8.22 (d, J=7.83 Hz, 1H) 8.27 (s, 1H).

Example 37 Synthesis of N-(3-(2-(4-(2-hydroxypropan-2-yl)-1H-1,2,3-triazol-1-yl)-6-morpholinopyrimidin-4-yl)-4-methylphenyl)-3-(trifluoromethyl) benzamide

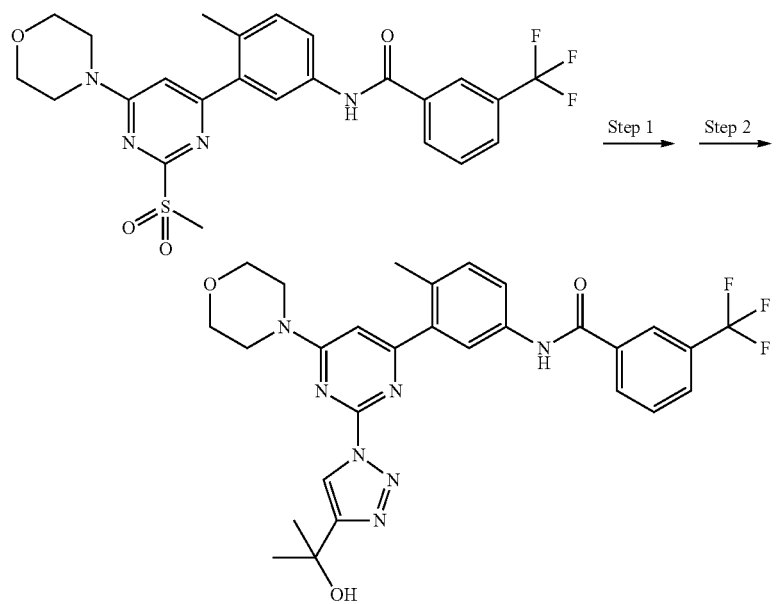

Step 1.

A solution of N-(4-methyl-3-(2-(methylsulfonyl)-6-morpholinopyrimidin-4-yl)phenyl)-3-(trifluoromethyl)benzamide (1.0 equiv.) and Sodium azide in DMF (0.2 M) was heated at 90° C. for 3 hours. The reaction mixture was then cooled to room temperature and quenched with water then the aqueous layer was separated and extracted with EtOAc (×2). The combined organic layer was dried over sodium sulfate, filtered and concentrated in vacuo to afford N-(3-(2-azido-6-morpholinopyrimidin-4-yl)-4-methylphenyl)-3-(trifluoromethyl)benzamide. The compound was utilized in the subsequent reaction without further purification. LCMS (m/z) (M+H)=484.0/485.1, Rt=0.96 min.

Step 2.

To a mixture of N-(3-(2-azido-6-morpholinopyrimidin-4-yl)-4-methylphenyl)-3-(trifluoromethyl)benzamide (1.0 equiv.), 2-methylbut-3-yn-2-ol (5.0 equiv.) and triethylamine (2.0 equiv.) in dioxane (0.25 M) was added Copper (I) Oxide on carbon (0.2 equiv.). The resulting mixture was heated to 90° C. for 3 hours. The reaction mixture was then cooled to room temperature and filtered, concentrated in vacuo. The crude material was purified via preparative reverse phase HPLC. Upon lyophilization of the pure fractions, N-(3-(2-(4-(2-hydroxypropan-2-yl)-1H-1,2,3-triazol-1-yl)-6-morpholinopyrimidin-4-yl)-4-methylphenyl)-3-(trifluoromethyl)benzamide was isolated as the TFA salt in 14% yield. 1H NMR (400 MHz, <cd3od>) δ ppm 1.66 (s, 6H) 2.55 (s, 3H) 2.66 (s, 1H) 3.71-4.06 (m, 8H) 6.99 (s, 1H) 7.43 (d, J=7.83 Hz, 1H) 7.47-7.61 (m, 2H) 7.92-8.02 (m, 2H) 8.11 (d, J=1.96 Hz, 1H) 8.17 (s, 1H) 8.62 (s, 1H). LCMS (m/z) (M+H)=568.3, Rt=0.96 min.

Example 38 Synthesis of N-(3-(2-amino-6-morpholinopyrimidin-4-yl)-4-methylphenyl)-3-(trifluoromethyl)benzamide

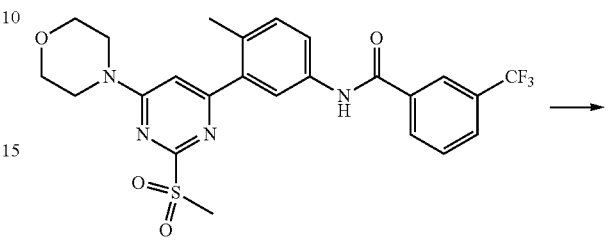

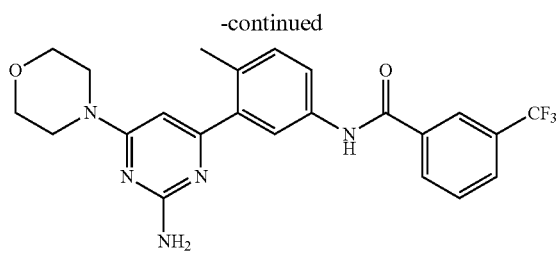

To a solution of N-(4-methyl-3-(2-(methylsulfonyl)-6-morpholinopyrimidin-4-yl)phenyl)-3-(trifluoromethyl)benzamide (1.0 equiv.) in DMSO (0.05M) was added ammonium acetate (2 equiv.) in a microwave vial equipped with a stir bar. The reaction was heated to 100° C. for 15 min in the microwave. The crude material was purified via preparative reverse phase HPLC. Upon lyophilization of the pure fractions, N-(3-(2-amino-6-morpholinopyrimidin-4-yl)-4-methylphenyl)-3-(trifluoromethyl)benzamide was isolated as the TFA salt in 23% yield. LCMS (m/z) (M+H)=458.0, Rt=0.79 min. 1H NMR (400 MHz, <cd3od>) δ ppm 2.48 (s, 3H) 3.79 (br. s., 8H) 6.57 (s, 1H) 7.45 (d, J=7.83 Hz, 1H)

7.54-7.60 (m, 2H) 7.94 (d, J=8.61 Hz, 1H) 8.03 (d, J=1.57 Hz, 1H) 8.08 (dd, J=8.02, 1.76 Hz, 1H) 8.17 (s, 1H).

Example 39 Synthesis of N-(3-(2-((1,3-dihydroxypropan-2-yl)amino)-6-morpholinopyrimidin-4-yl)-4-methylphenyl)-3-(trifluoromethyl)benzamide

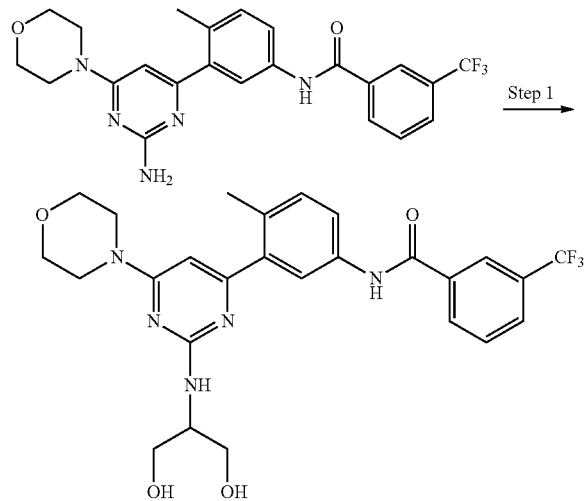

To a solution of N-(4-methyl-3-(2-(methylsulfonyl)-6-morpholinopyrimidin-4-yl)phenyl)-3-(trifluoromethyl)benzamide (1.0 equiv.) and 2-aminopropane-1,3-diol (1.0 equiv.) in DMF (0.05M) was added 60% sodium hydride (1.0 equiv.) at 0° C. The reaction was allowed to warm to room temperature and stir for 24 hours. LCMS analysis indicated the formation of the desired product. The crude material was purified via preparative reverse phase HPLC. Upon lyophilization of the pure fractions, N-(3-(2-((1,3-dihydroxypropan-2-yl)amino)-6-morpholinopyrimidin-4-yl)-4-methylphenyl)-3-(trifluoromethyl)benzamide was isolated as the TFA salt in 28% yield. LCMS (m/z) (M+H)=532.1, Rt=0.68 min. 1H NMR (400 MHz, <cd3od>) δ ppm 2.45 (s, 3H) 3.64-3.71 (m, 1H) 3.79 (s, 10H) 3.85-3.91 (m, 1H) 4.53-4.59 (m, 1H) 4.63-4.69 (m, 1H) 6.67 (s, 1H) 7.44 (d, J=7.43 Hz, 1H) 7.51 (d, J=7.83 Hz, 1H) 7.56 (t, J=8.02 Hz, 1H) 7.93 (d, J=8.22 Hz, 1H) 7.96-8.01 (m, 3H) 8.16 (s, 1H).

Step 2.

To a solution of 4-(6-chloro-2-(methylthio)pyrimidin-4-yl)morpholine (1.0 equiv.) in DCM (0.10 M) was added mCPBA (2.2 equiv.) portion-wise. The reaction was stirred at RT for 3 hours. After which time LCMS shows complete oxidation to desired product. The reaction was diluted with DCM (150 mL) and washed with 0.5M Na₂CO₃. The organics were dried over MgSO₄, filtered and concentrated. Isolated 4-(6-chloro-2-(methylsulfonyl)pyrimidin-4-yl)morpholine in 100% yield. LCMS (m/z) (M+H)=277.9, Rt=0.49 min.

Step 3.

To a solution of 4-(6-chloro-2-(methylsulfonyl)pyrimidin-4-yl)morpholine (1.0 equiv) in dioxane (0.20M) was added ethane-1,2-diol (90 equiv.). To this stirring solution was added 60% NaH (1.0 equiv.) at 0° C. The reaction was allowed to warm to room temperature stirring for 24 hours. LCMS analysis indicated the formation of the desired product. The reaction was partitioned between NH₄Cl and EtOAc. The organics were washed with brine, water, then dried over MgSO₄ filtered and concentrated. Isolated 2-((4-chloro-6-morpholinopyrimidin-2-yl)oxy)ethanol in 75% yield. LCMS (m/z) (M+H)=260.0, Rt=0.49 min. ¹H NMR (400 MHz, <cdcl3>) δ ppm 3.71-3.82 (m, 8H) 3.91-3.98 (m, 2H) 4.40-4.47 (m, 2H) 6.18-6.24 (m, 1H).

Example 40 N-(3-(2-(2-hydroxyethoxy)-6-morpholinopyrimidin-4-yl)-4-methylphenyl)-3-(trifluoromethyl)benzamide

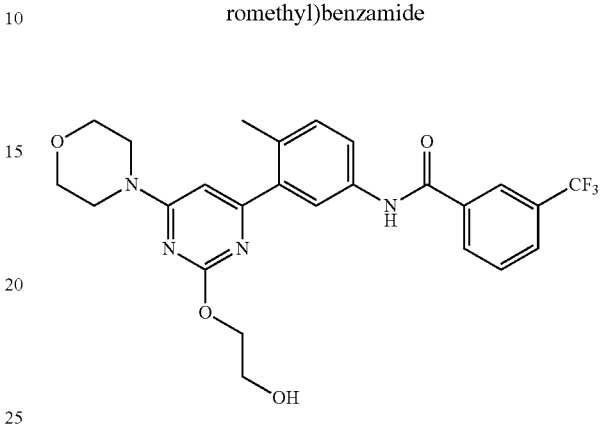

To a solution of 2-((4-chloro-6-morpholinopyrimidin-2-yl)oxy)ethanol (1.0 equiv.) and N-(4-methyl-3-(4,4,5,5-tetramethyl-1,3,2-dioxaborolane-2-yl)phenyl)-3-(trifluoromethyl)benxamide (1.2 equiv.) in DME and 2M sodium carbonate (3:1, 0.2 M) was added PdCl₂(dppf)-DCM adduct (0.1 equiv.) in a microwave vial equipped with a stir bar. The reaction was heated to 120° C. for 20 min in the microwave. The reaction was partitioned between water and ethyl acetate, the organic phase was washed with brine, was dried with sodium sulfate, filtered and concentrated. The crude material was purified via preparative reverse phase HPLC. Upon lyophilization of the pure fractions, N-(3-(2-(2-hydroxyethoxy)-6-morpholinopyrimidin-4-yl)-4-methylphenyl)-3-(trifluoromethyl)benzamide was isolated as the TFA salt in 18% yield. 1H NMR (400 MHz, <cd3od>) δ ppm 2.37 (s, 3H) 3.79-3.85 (m, 4H) 3.86-3.97 (m, 6H) 4.60-4.65 (m, 2H) 6.78 (s, 1H) 7.41 (d, J=8.22 Hz, 1H) 7.67 (dd, J=8.22, 2.35 Hz, 1H) 7.74 (t, J=7.83 Hz, 1H) 7.91 (d, J=8.22 Hz, 1H) 7.94 (d, J=1.96 Hz, 1H) 8.21 (d, J=7.83 Hz, 1H) 8.26 (s, 1H). LCMS (m/z) (M+H)=503.1, Rt=0.73 min.

Example 42 and Example 43: Synthesis of N-(4-methyl-3-(2-morpholino-6-(prop-1-en-2-yl)pyrimidin-4-yl)phenyl)-3-(trifluoromethyl)benzamide and N-(4-methyl-3-(4-morpholino-6-(prop-1-en-2-yl)pyrimidin-2-yl)phenyl)-3-(trifluoromethyl)benzamide

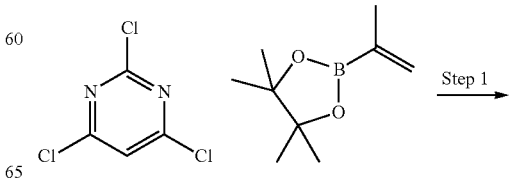

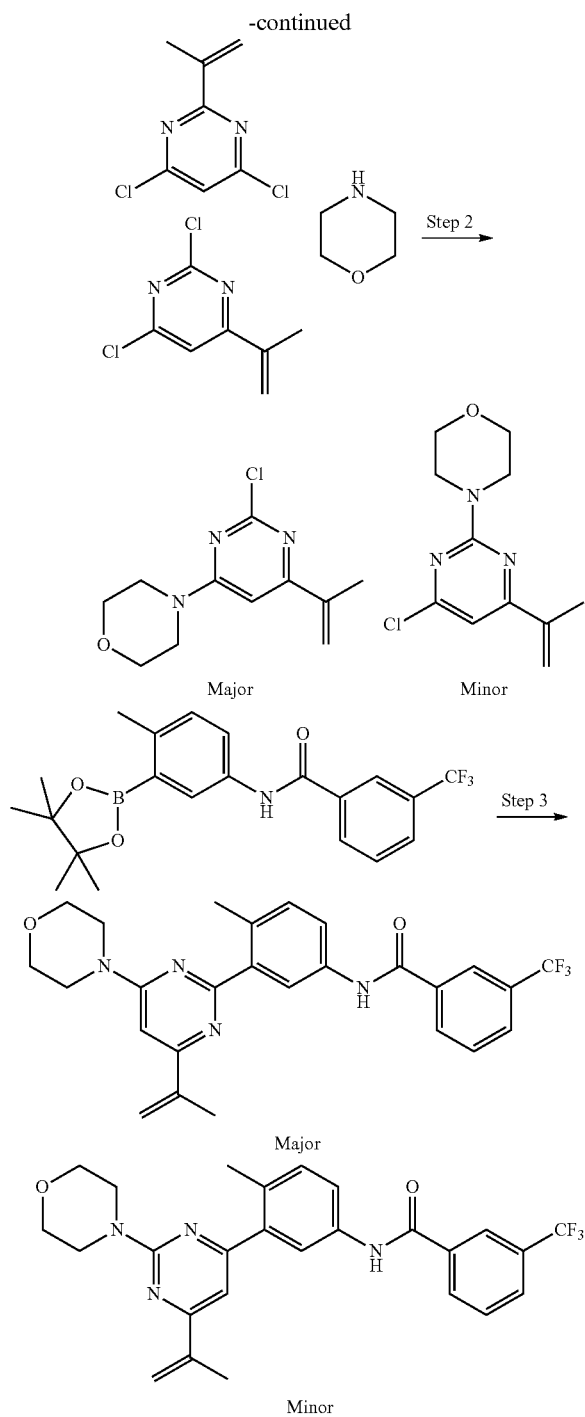

utilized in the subsequent reactions without further purification. LCMS (m/z) (M+H)=189.0/191.1, Rt=0.92 min two overlapping.

Step 2.

To a solution of 2,4-dichloro-6-(prop-1-en-2-yl)pyrimidine and 4,6-dichloro-2-(prop-1-en-2-yl)pyrimidine (total 1.0 equiv.) in t-Butanol (0.2 M) was added morpholine (1.0 equiv.) followed by N,N-diisopropylethylamine (1.20 equiv.). The resulting mixture was heated to 120 at ° C. for 45 min. The reaction mixture was then cooled to RT, concentrated in vacuo and utilized in the subsequent reactions without further purification. LCMS Major (m/z) (M+H)=240.1/242.1, Rt=0.74 min and Minor (m/z) (M+H)= 240.1/242.1, 0.94 min.

Step 3.

To a solution of 4-(2-chloro-6-(prop-1-en-2-yl)pyrimidin-4-yl)morpholine and 4-(4-chloro-6-(prop-1-en-2-yl)pyrimidin-2-yl)morpholine (total 1.0 equiv.) and Intermediate A (1.1 equiv.) in dioxane and 2M sodium carbonate (4:1, 0.17 M) was added $PdCl_2$(dppf)-DCM adduct (0.150 equiv.) in a microwave vial equipped with a stir bar. The reaction was heated to 120° C. for 20 min in the microwave. The organic phase was dried with sodium sulfate, filtered and concentrated. The crude material was purified via preparative reverse phase HPLC. Upon lyophilization of the pure fractions, two regioisomers were isolated in order of elution, major N-(4-methyl-3-(4-morpholino-6-(prop-1-en-2-yl)pyrimidin-2-yl)phenyl)-3-(trifluoromethyl)benzamide as the TFA salt in 4% yield. 1H NMR (400 MHz, <dmso>) δ ppm 2.13 (s, 3H) 3.30 (s, 3H) 3.69 (s, 8H) 5.38 (s, 1H) 6.15 (d, J=0.78 Hz, 1H) 6.83 (s, 1H) 7.26 (d, J=8.61 Hz, 1H) 7.72-7.84 (m, 2H) 7.95 (d, J=7.83 Hz, 1H) 8.16 (d, J=2.35 Hz, 1H) 8.22-8.34 (m, 2H) 10.48 (s, 1H). LCMS (m/z) (M+H)=483.2, Rt=0.87 min and minor N-(4-methyl-3-(2-morpholino-6-(prop-1-en-2-yl)pyrimidin-4-yl)phenyl)-3-(trifluoromethyl)benzamide 2% as the TFA salt in 2% yield. 1H NMR (400 MHz, <dmso>) δ ppm 2.11 (s, 3H) 2.35 (s, 3H) 3.75 (d, J=4.70 Hz, 8H) 5.45 (s, 1H) 6.12 (s, 1H) 6.99 (s, 1H) 7.30 (d, J=8.22 Hz, 1H) 7.73-7.87 (m, 3H) 7.95 (s, 1H) 8.21-8.35 (m, 2H) 10.49 (s, 1H). LCMS (m/z) (M+H)= 483.2, Rt=1.22 min.

Example 44: Synthesis of N-(3-(4-isopropyl-6-morpholinopyrimidin-2-yl)-4-methylphenyl)-3-(trifluoromethyl)benzamide

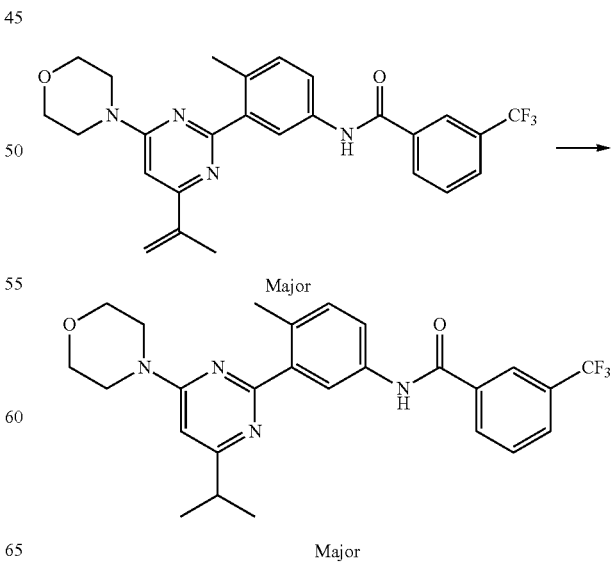

Step 1.

To a solution of 2,4,6-trichloropyrimidine (1.0 equiv.) and 4,4,5,5-tetramethyl-2-(prop-1-en-2-yl)-1,3,2-dioxaborolane (1.05 equiv.) in dioxane and 2M sodium carbonate (3:1, 0.31 M) was added $PdCl_2$(dppf)-DCM adduct (0.05 equiv.). The reaction mixture was heated to 110° C. for 45 min. The reaction mixture was then cooled to room temperature and diluted with EtOAc and water. The aqueous layer was separated and extracted with EtOAc (×2). The combined organic layer was dried over sodium sulfate, filtered and concentrated in vacuo. The mixture of regioisomers was A solution of N-(4-methyl-3-(4-morpholino-6-(prop-1-en-2-yl)pyrimidin-2-yl)phenyl)-3-(trifluoromethyl)benzamide in Methanol (0.083 M) was evacuated and back filled with argon (×3). To the solution was then added Pd/C (1.00 eq.) and the mixture was evacuated and back filled with hydrogen (×3). The mixture was then stirred at RT under a positive pressure of atmospheric hydrogen (balloon) for 2 h. The hydrogen gas was removed by evacuation and the reaction backfilled with argon. The reaction mixture was then concentrated in vacuo. The crude material was purified via preparative reverse phase HPLC. Upon lyophilization of the pure fractions N-(3-(4-isopropyl-6-morpholinopyrimidin-2-yl)-4-methylphenyl)-3-(trifluoromethyl)benzamide as the TFA salt in 30% yield. 1H NMR (400 MHz, <dmso>) δ ppm 1.29 (d, J=6.65 Hz, 6H) 2.38 (br. s., 3H) 2.91-3.07 (m, 1H) 3.71 (br. s., 8H) 7.27-7.47 (m, 1H) 7.74-7.88 (m, 2H) 7.93-8.01 (m, 1H) 8.06 (s, 1H) 8.28 (s, 2H) 10.54-10.70 (m, 1H). LCMS (m/z) (M+H)=485.4, Rt=0.85 min.

Example 45: Synthesis of N-(3-(6-isopropyl-2-morpholinopyrimidin-4-yl)-4-methylphenyl)-3-(trifluoromethyl)benzamide

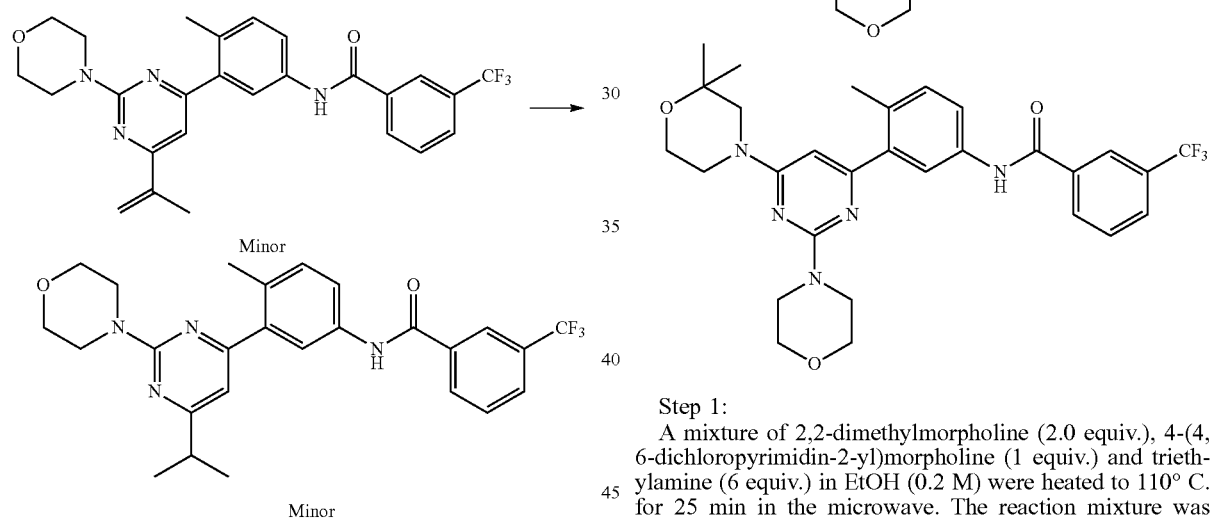

Minor

Minor

A solution of N-(4-methyl-3-(2-morpholino-6-(prop-1-en-2-yl)pyrimidin-4-yl)phenyl)-3-(trifluoromethyl)benzamide in Methanol (0.083 M) was evacuated and back filled with argon (×3). To the solution was then added Pd/C (1.00 eq.) and the mixture was evacuated and back filled with hydrogen (×3). The mixture was then stirred at RT under a positive pressure of atmospheric hydrogen (balloon) for 2 h. The hydrogen gas was removed by evacuation and the reaction backfilled with argon. The reaction mixture was then concentrated in vacuo. The crude material was purified via preparative reverse phase HPLC. Upon lyophilization of the pure fractions N-(3-(6-isopropyl-2-morpholinopyrimidin-4-yl)-4-methylphenyl)-3-(trifluoromethyl)benzamide was obtained as the TFA salt in 43% yield. 1H NMR (400 MHz, <dmso>) δ ppm 1.22 (d, J=6.65 Hz, 6H) 2.34 (s, 3H) 2.86 (dt, J=13.69, 6.85 Hz, 1H) 3.62-3.79 (m, 8H) 6.70 (s, 1H) 7.29 (d, J=8.22 Hz, 1H) 7.74-7.84 (m, 3H) 7.95 (d, J=7.83 Hz, 1H) 8.21-8.33 (m, 2H) 10.49 (s, 1H). LCMS (m/z) (M+H)=485.4, Rt=1.09 min.

Example 46 Synthesis of N-(3-(6-(2,2-dimethylmorpholino)-2-morpholinopyrimidin-4-yl)-4-methylphenyl)-3-(trifluoromethyl)benzamide

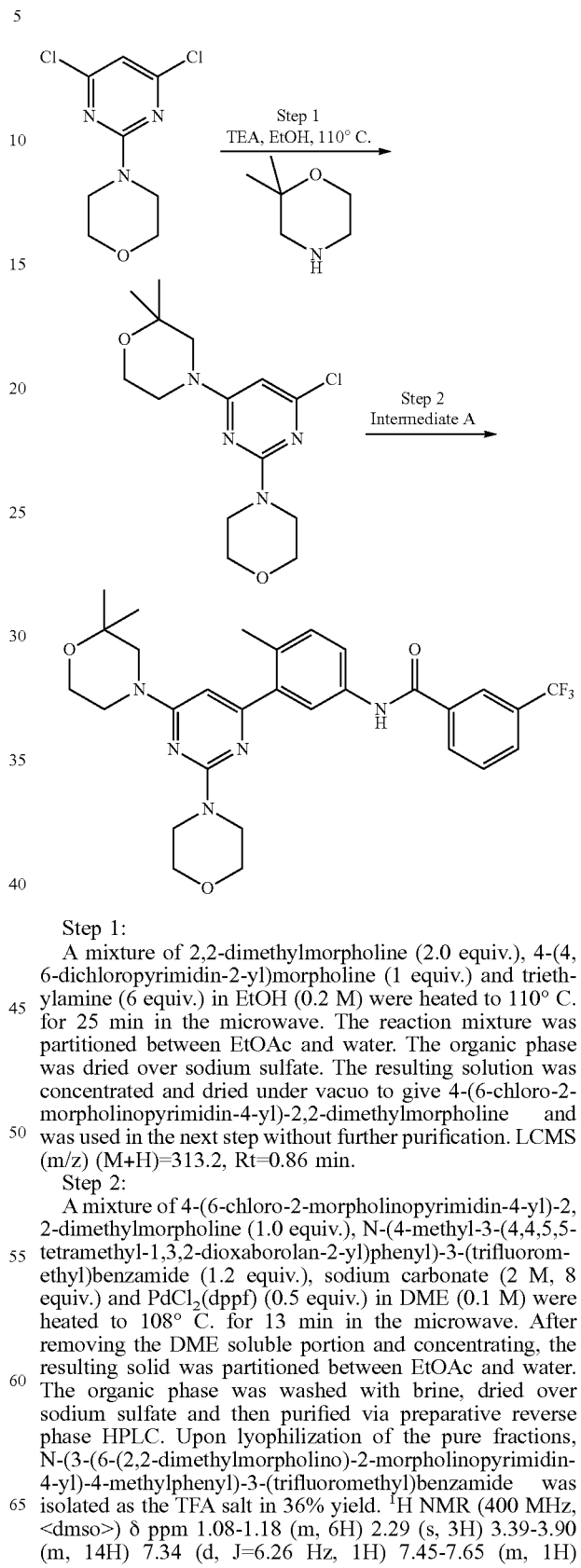

Step 1:

A mixture of 2,2-dimethylmorpholine (2.0 equiv.), 4-(4,6-dichloropyrimidin-2-yl)morpholine (1 equiv.) and triethylamine (6 equiv.) in EtOH (0.2 M) were heated to 110° C. for 25 min in the microwave. The reaction mixture was partitioned between EtOAc and water. The organic phase was dried over sodium sulfate. The resulting solution was concentrated and dried under vacuo to give 4-(6-chloro-2-morpholinopyrimidin-4-yl)-2,2-dimethylmorpholine and was used in the next step without further purification. LCMS (m/z) (M+H)=313.2, Rt=0.86 min.

Step 2:

A mixture of 4-(6-chloro-2-morpholinopyrimidin-4-yl)-2,2-dimethylmorpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine, dried over sodium sulfate and then purified via preparative reverse phase HPLC. Upon lyophilization of the pure fractions, N-(3-(6-(2,2-dimethylmorpholino)-2-morpholinopyrimidin-4-yl)-4-methylphenyl)-3-(trifluoromethyl)benzamide was isolated as the TFA salt in 36% yield. ¹H NMR (400 MHz, <dmso>) δ ppm 1.08-1.18 (m, 6H) 2.29 (s, 3H) 3.39-3.90 (m, 14H) 7.34 (d, J=6.26 Hz, 1H) 7.45-7.65 (m, 1H)

7.70-7.88 (m, 3H) 7.92-8.03 (m, 1H) 8.18-8.36 (m, 2H) 10.58 (br. s., 1H). LCMS (m/z) (M+H)=556.4, Rt=0.87 min.

The compounds listed below were prepared using methods similar to those described above using the appropriate starting materials.

Example 47: N-(4-methyl-3-(2-morpholino-6-(2-oxa-6-azaspiro[3.3]heptan-6-yl)pyrimidin-4-yl)phenyl)-3-(trifluoromethyl)benzamide

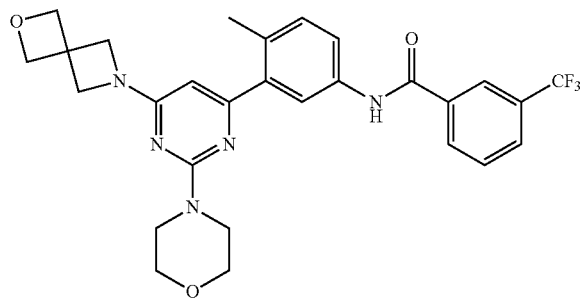 [SMILES: Cc1ccc(NC(=O)c2cccc(C(F)(F)F)c2)cc1-c1cc(N2CC3(COC3)C2)nc(N2CCOCC2)n1]

LCMS (m/z) (M+H)=540.2, Rt=0.79 min.

Example 48: (R)—N-(3-(6-(3-(hydroxymethyl)morpholino)-2-morpholinopyrimidin-4-yl)-4-methylphenyl)-3-(trifluoromethyl)benzamide

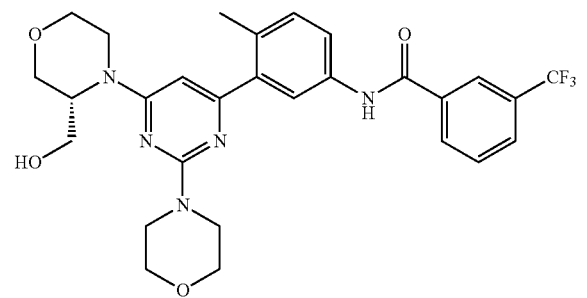 [SMILES: Cc1ccc(NC(=O)c2cccc(C(F)(F)F)c2)cc1-c1cc(N2CCOC[C@H]2CO)nc(N2CCOCC2)n1]

¹H NMR (400 MHz, <dmso>) δ ppm 2.29 (s, 3H) 3.16 (br. s., 1H) 3.36-3.55 (m, 3H) 3.68 (d, J=7.43 Hz, 10H) 3.85-4.04 (m, 3H) 6.43 (br. s., 1H) 7.34 (d, J=6.65 Hz, 1H) 7.69-7.88 (m, 3H) 7.97 (d, J=7.83 Hz, 1H) 8.20-8.35 (m, 2H) 10.57 (br. s., 1H). LCMS (m/z) (M+H)=558.3, Rt=0.75 min.

Example 49: N-(3-(6-(3-oxa-8-azabicyclo[3.2.1]octan-8-yl)-2-morpholinopyrimidin-4-yl)-4-methylphenyl)-3-(trifluoromethyl)benzamide

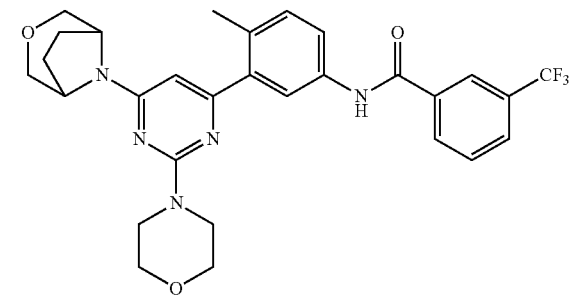 [SMILES: Cc1ccc(NC(=O)c2cccc(C(F)(F)F)c2)cc1-c1cc(N2C3CCC2COC3)nc(N2CCOCC2)n1]

¹H NMR (400 MHz, <dmso>) δ ppm 1.82-2.06 (m, 4H) 2.31 (s, 3H) 3.58-3.73 (m, 14H) 7.33 (br. s., 1H) 7.45-7.67 (m, 1H) 7.71-7.88 (m, 3H) 7.91-8.02 (m, 1H) 8.16-8.39 (m, 2H) 10.55 (br. s., 1H). LCMS (m/z) (M+H)=554.3, Rt=0.85 min.

Example 50: N-(4-methyl-3-(2-morpholino-6-(1,4-oxazepan-4-yl)pyrimidin-4-yl)phenyl)-3-(trifluoromethyl)benzamide

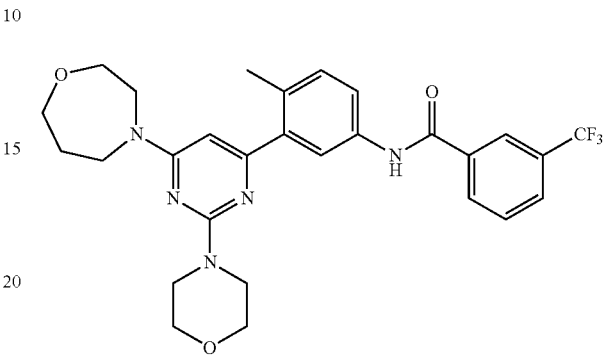

¹H NMR (400 MHz, <dmso>) δ ppm 1.85 (br. s., 2H) 2.30 (s, 3H) 3.58-3.80 (m, 16H) 7.35 (br. s., 1H) 7.44-7.69 (m, 1H) 7.72-7.90 (m, 3H) 7.97 (d, J=7.83 Hz, 1H) 8.18-8.36 (m, 2H) 10.57 (br. s., 1H). LCMS (m/z) (M+H)=542.3, Rt=0.85 min.

Example 51: N-(3-(6-(2-oxa-5-azabicyclo[2.2.1]heptan-5-yl)-2-morpholinopyrimidin-4-yl)-4-methylphenyl)-3-(trifluoromethyl)benzamide

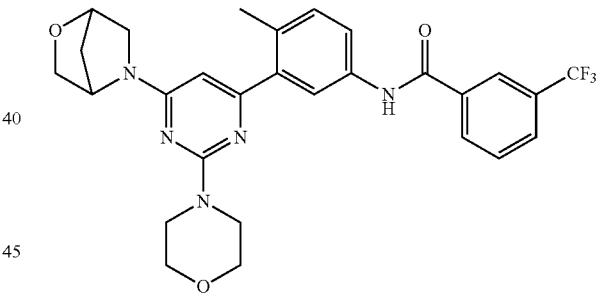

LCMS (m/z) (M+H)=540.4, Rt=0.79 min.

Example 52: N-(3-(6-(8-oxa-3-azabicyclo[3.2.1]octan-3-yl)-2-morpholinopyrimidin-4-yl)-4-methylphenyl)-3-(trifluoromethyl)benzamide

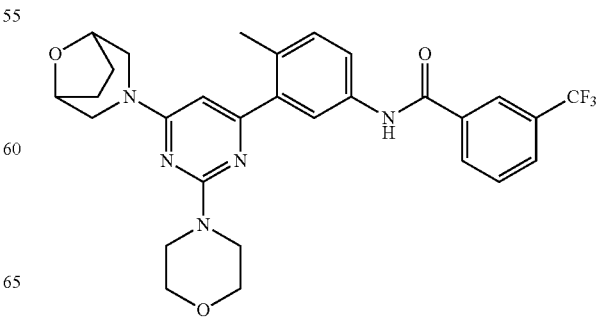

¹H NMR (400 MHz, <dmso>) δ ppm 1.58-1.72 (m, 2H) 1.74-1.92 (m, 2H) 2.29 (s, 3H) 2.94-3.29 (m, 2H) 3.68 (d, J=7.04 Hz, 8H) 4.42 (br. s., 2H) 7.33 (d, J=7.04 Hz, 1H) 7.46-7.68 (m, 1H) 7.70-7.86 (m, 3H) 7.97 (d, J=7.83 Hz, 1H) 8.19-8.34 (m, 2H) 10.56 (br. s., 1H). LCMS (m/z) (M+H)=554.4, Rt=0.83 min.

Example 53: (R)—N-(4-methyl-3-(6-(2-methylmorpholino)-2-morpholinopyrimidin-4-yl)phenyl)-3-(trifluoromethyl)benzamide

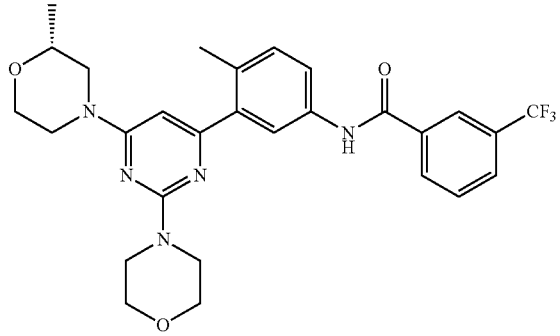 [SMILES: Cc1ccc(NC(=O)c2cccc(C(F)(F)F)c2)cc1-c1cc(N2CCO[C@H](C)C2)nc(N2CCOCC2)n1]

¹H NMR (400 MHz, <dmso>) δ ppm 1.00-1.26 (m, 3H) 2.29 (s, 3H) 3.41-3.57 (m, 2H) 3.68 (d, J=8.61 Hz, 8H) 3.89 (d, J=10.96 Hz, 1H) 7.32 (br. s., 1H) 7.42-7.66 (m, 1H) 7.70-7.87 (m, 3H) 7.92-8.02 (m, 1H) 8.19-8.33 (m, 2H) 10.54 (br. s., 1H). LCMS (m/z) (M+H)=542.3, Rt=0.85 min.

Example 54: (S)—N-(4-methyl-3-(6-(2-methylmorpholino)-2-morpholinopyrimidin-4-yl)phenyl)-3-(trifluoromethyl)benzamide

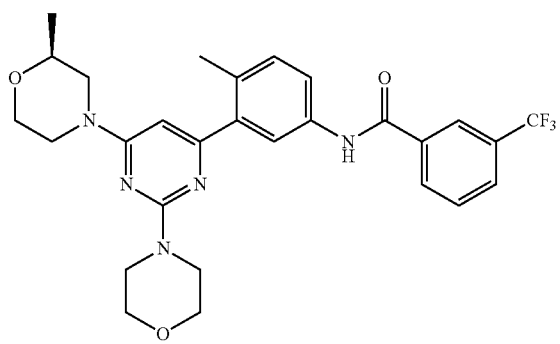 [SMILES: Cc1ccc(NC(=O)c2cccc(C(F)(F)F)c2)cc1-c1cc(N2CCO[C@@H](C)C2)nc(N2CCOCC2)n1]

¹H NMR (400 MHz, <dmso>) δ ppm 1.13 (d, J=6.26 Hz, 3H) 2.29 (s, 3H) 2.52 (s, 2H) 3.41-3.61 (m, 2H) 3.68 (d, J=9.39 Hz, 8H) 3.90 (d, J=10.17 Hz, 1H) 7.33 (d, J=6.26 Hz, 1H) 7.42-7.62 (m, 1H) 7.69-7.88 (m, 3H) 7.93-8.03 (m, 1H) 8.20-8.35 (m, 2H) 10.57 (br. s., 1H). LCMS (m/z) (M+H)=542.4, Rt=0.85 min.

Example 55: N-(3-(6-(3-oxa-8-azabicyclo[3.2.1]octan-8-yl)-2-morpholinopyrimidin-4-yl)-4-methylphenyl)-3-(trifluoromethyl)benzamide

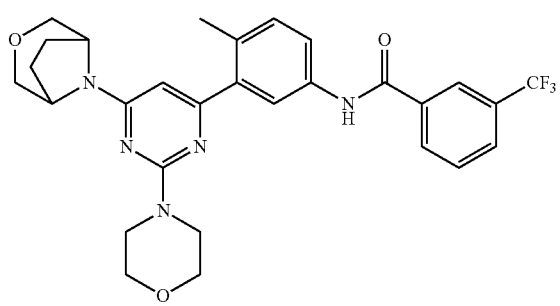 [SMILES: Cc1ccc(NC(=O)c2cccc(C(F)(F)F)c2)cc1-c1cc(N2C3CCC2COC3)nc(N2CCOCC2)n1]

¹H NMR (400 MHz, <dmso>) δ ppm 1.82-2.06 (m, 4H) 2.31 (s, 3H) 3.58-3.73 (m, 14H) 7.33 (br. s., 1H) 7.45-7.67 (m, 1H) 7.71-7.88 (m, 3H) 7.91-8.02 (m, 1H) 8.16-8.39 (m, 2H) 10.55 (br. s., 1H). LCMS (m/z) (M+H)=554.3, Rt=0.79 min.

Example 56: Synthesis of N-(4-methyl-3-(2-morpholino-6-((tetrahydro-2H-pyran-4-yl)oxy)pyrimidin-4-yl)phenyl)-3-(trifluoromethyl)benzamide

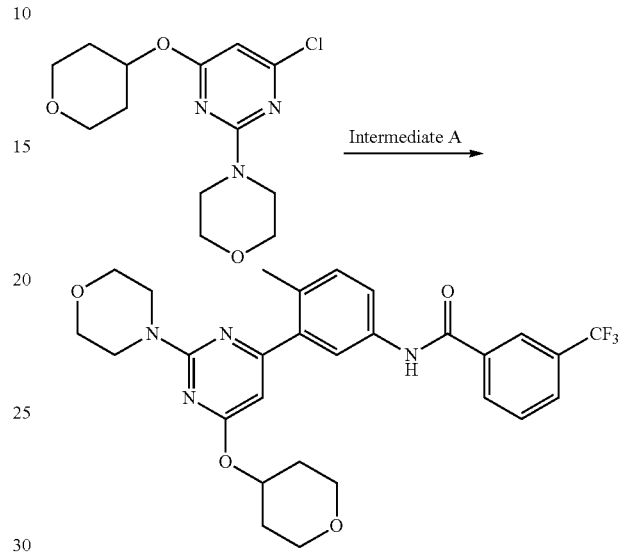

A mixture of 4-(4-chloro-6-((tetrahydro-2H-pyran-4-yl)oxy)pyrimidin-2-yl)morpholine (prepared according to WO2007/084786) (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl₂(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine, dried over sodium sulfate and then purified via preparative reverse phase HPLC. Upon lyophilization of the pure fractions, N-(3-(6-(2,2-dimethylmorpholino)-2-morpholinopyrimidin-4-yl)-4-methylphenyl)-3-(trifluoromethyl)benzamide was isolated as the TFA salt in 44% yield. ¹H NMR (400 MHz, <dmso>) δ ppm 1.59-1.71 (m, 2H) 1.95-2.09 (m, 2H) 2.35 (s, 3H) 3.64-3.72 (m, 10H) 3.80-3.91 (m, 2H) 5.24 (dt, J=8.71, 4.45 Hz, 1H) 6.18 (s, 1H) 7.27 (d, J=8.22 Hz, 1H) 7.72-7.87 (m, 3H) 7.96 (d, J=7.43 Hz, 1H) 8.18-8.38 (m, 2H) 10.45 (s, 1H). LCMS (m/z) (M+H)=543.3, Rt=0.96 min.

Example 57: Synthesis of N-(4-methyl-3-(5-methyl-2,6-dimorpholinopyrimidin-4-yl)phenyl)-3-(trifluoromethyl)benzamide

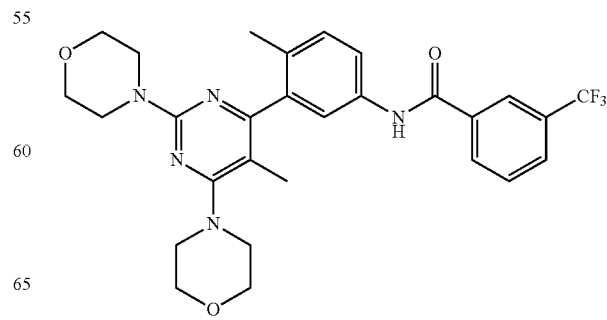

Step 1.

To a solution of 4-(4,6-dichloro-5-methylpyrimidin-2-yl) morpholine in EtOH (0.15 M) was added morpholine (2.0 equiv.) followed by triethylamine (4.00 equiv.). The resulting mixture was heated under microwave irradiation at 125° C. for 50 min (2×25 min). The reaction mixture was then concentrated in vacuo to yield 4,4'-(6-chloro-5-methylpyrimidine-2,4-diyl)dimorpholine as a white solid in 96% yield which was utilized without further purification in the subsequent reaction. LCMS (m/z) (M+H)=299.1, Rt=0.85 min.

Step 2.

To a solution of 4,4'-(6-chloro-5-methylpyrimidine-2,4-diyl)dimorpholine (1.0 equiv.) and Intermediate A (1.20 equiv.) in DME and 2M sodium carbonate (3:1, 0.2 M) was added PdCl$_2$(dppf)-DCM adduct (0.500 equiv.) in a microwave vial equipped with a stir bar. The reaction was heated to 110° C. for 10 min under microwave irradiation. The organic phase was dried with sodium sulfate, filtered and concentrated. The crude material was purified via preparative reverse phase HPLC. Upon lyophilization of the pure fractions, N-(4-methyl-3-(5-methyl-2,6-dimorpholinopyrimidin-4-yl)phenyl)-3-(trifluoromethyl)benzamide was isolated as the TFA salt in 6% yield. $^1$H NMR (400 MHz, <dmso>) δ ppm 1.81 (s, 3H) 2.10 (br. s., 3H) 3.63 (br. s., 11H) 3.70 (d, J=3.91 Hz, 5H) 7.30 (br. s., 1H) 7.65-7.82 (m, 2H) 7.95 (d, J=7.43 Hz, 1H) 8.15-8.35 (m, 3H) 10.48 (br. s., 1H). LCMS (m/z) (M+H)=542.2, Rt=0.85 min.

Example 58: Synthesis of N-(6-methyl-5-(6-morpholinopyridazin-4-yl)pyridin-3-yl)-3-(trifluoromethyl)benzamide

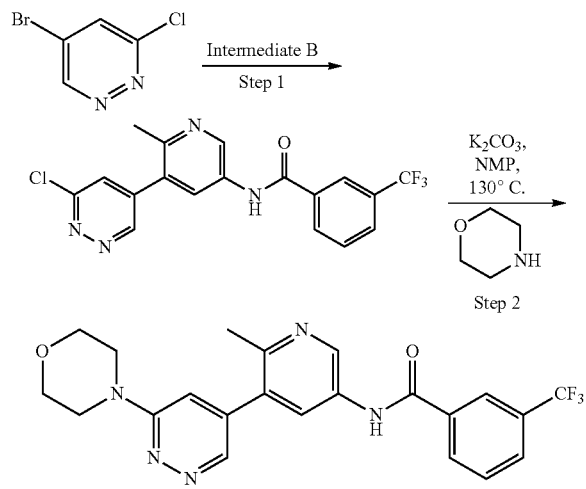

Step 1:

A mixture of 5-bromo-3-chloropyridazine (1.0 equiv.), N-(6-methyl-5-(4,4,5,5-tetramethyl-1,3,2-dioxaborolan-2-yl)pyridin-3-yl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over sodium sulfate. After concentration, the crude material was purified via preparative reverse phase HPLC. Volatiles were removed by rotary evaporation and the remaining aqueous solution was basified with sodium bicarbonate. This solution was extracted with EtOAc, washed with brine and dried over sodium sulfate. The solution was concentrated and dried under vacuo to give crude N-(5-(6-chloropyridazin-4-yl)-6-methylpyridin-3-yl)-3-(trifluoromethyl)benzamide and was used in the next step without further purification. LCMS (m/z) (M+H)=393.1, Rt=0.73 min.

Step 2:

A mixture of N-(5-(6-chloropyridazin-4-yl)-6-methylpyridin-3-yl)-3-(trifluoromethyl)benzamide (1.0 equiv.), morpholine (5 equiv.) and potassium carbonate (10 equiv.) in NMP (0.15 M) were heated to 130° C. for 18 h in an oil bath. The reaction mixture was centrifuged and the soluble portion was removed from solids. The soluble portion was purified via preparative reverse phase HPLC. Upon lyophilization of the pure fractions, N-(6-methyl-5-(6-morpholinopyridazin-4-yl)pyridin-3-yl)-3-(trifluoromethyl)benzamide was isolated as the TFA salt in 1% yield. LCMS (m/z) (M+H)=444.2, Rt=0.63 min.

Example 59: Synthesis of N-(4-methyl-3-(5-morpholinopyridazin-3-yl)phenyl)-3-(trifluoromethyl)benzamide

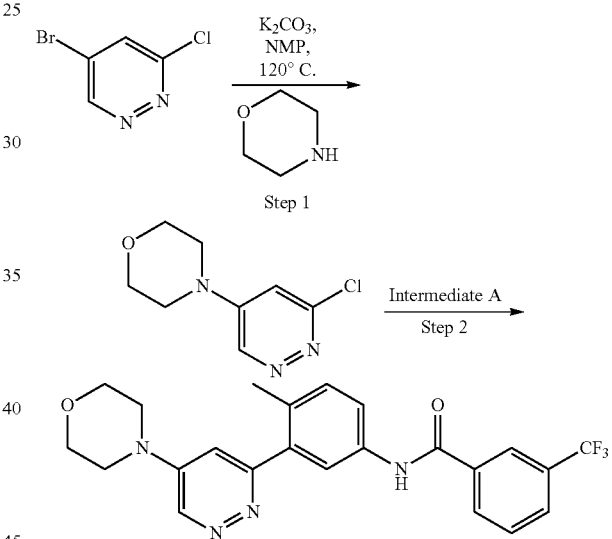

Step 1:

A mixture of 5-bromo-3-chloropyridazine (1.0 equiv.), morpholine (1 equiv.) and potassium carbonate (6 equiv.) in NMP (0.2 M) were heated to 110° C. for 4 hours in an oil bath. The reaction mixture was partitioned between EtOAc and water. The organic phase was dried over sodium sulfate, concentrated and purified by normal phase chromatography. The combined fractions were concentrated and dried under vacuo to give crude 4-(6-chloropyridazin-4-yl)morpholine and was used in the next step without further purification. LCMS (m/z) (M+H)=200.0, Rt=0.34 min.

Step 2:

A mixture of 4-(6-chloropyridazin-4-yl)morpholine (1.0 equiv.), N-(4-methyl-3-(4,4,5,5-tetramethyl-1,3,2-dioxaborolan-2-yl)phenyl)-3-(trifluoromethyl)benzamide (1.0 equiv.), sodium carbonate (2 M, 10 equiv.) and PdCl$_2$(dppf) (0.5 equiv.) in DME (0.1 M) were heated to 110° C. for 15 min in the microwave. After removing the DME soluble portion and concentrating, the resulting solid was partitioned between EtOAc and water. The organic phase was washed with brine, dried over sodium sulfate and then purified via preparative reverse phase HPLC. Upon lyophilization of the pure fractions, N-(4-methyl-3-(5-morpholinopyridazin-3-yl)phenyl)-3-(trifluoromethyl)benzamide was isolated as the TFA salt in 14% yield. ¹H NMR (400 MHz, <dmso>) δ ppm 2.37 (s, 3H) 3.73-3.86 (m, 8H) 7.46 (d, J=7.83 Hz, 1H) 7.51 (d, J=2.35 Hz, 1H) 7.55-7.69 (m, 2H) 8.01-8.10 (m, 2H) 8.14 (d, J=8.22 Hz, 1H) 8.21 (s, 1H) 9.07 (d, J=2.74 Hz, 1H) 10.60 (s, 1H). LCMS (m/z) (M+H)=443.1, Rt=0.74 min.

The compound listed below were prepared using methods similar to those described above using the appropriate starting materials.

Example 60: N-(6-methyl-5-(5-morpholinopyridazin-3-yl)pyridin-3-yl)-3-(trifluoromethyl)benzamide

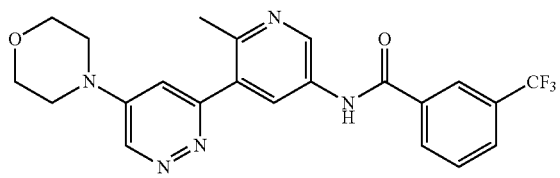 [SMILES: Cc1ncc(NC(=O)c2cccc(C(F)(F)F)c2)cc1-c1cc(N2CCOCC2)cnn1]

¹H NMR (400 MHz, <dmso>) δ ppm 2.46 (s, 3H) 3.73-3.90 (m, 9H) 7.55 (br. s., 1H) 7.76-7.88 (m, 1H) 8.01 (d, J=7.83 Hz, 1H) 8.28 (d, J=7.83 Hz, 1H) 8.32 (s, 1H) 8.38 (d, J=2.35 Hz, 1H) 8.95 (d, J=1.96 Hz, 1H) 9.07 (d, J=3.13 Hz, 1H) 10.87 (s, 1H). LCMS (m/z) (M+H)=444.0, Rt=0.62 min.

Example 61: N-(4-methyl-3-(2-morpholino-6-(trifluoromethyl)pyrimidin-4-yl)phenyl)-3-(trifluoromethyl)benzamide

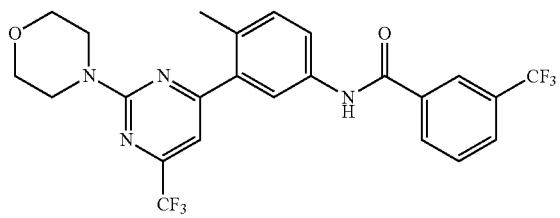 [SMILES: Cc1ccc(NC(=O)c2cccc(C(F)(F)F)c2)cc1-c1cc(C(F)(F)F)nc(N2CCOCC2)n1]

¹H NMR (400 MHz, <dmso>) δ ppm 2.40 (s, 3H) 3.65-3.85 (m, 8H) 7.19 (s, 1H) 7.35 (d, J=8.22 Hz, 1H) 7.75-7.83 (m, 1H) 7.87 (dd, J=8.22, 1.96 Hz, 1H) 7.91 (d, J=1.96 Hz, 1H) 7.97 (d, J=7.43 Hz, 1H) 8.22-8.34 (m, 2H) 10.54 (s, 1H). LCMS (m/z) (M+H)=511.2, Rt=1.23 min.

Example 62: Synthesis of N-(4-methyl-3-(2-morpholinopyridin-4-yl)phenyl)-3-(trifluoromethyl)benzamide

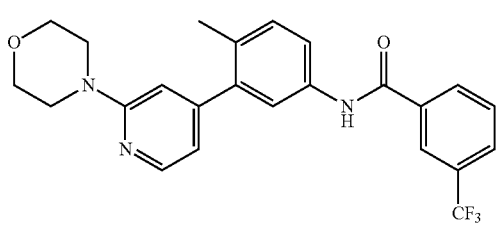 [SMILES: Cc1ccc(NC(=O)c2cccc(C(F)(F)F)c2)cc1-c1ccnc(N2CCOCC2)c1]

Synthesis of 4-(4-bromopyridin-2-yl)morpholine

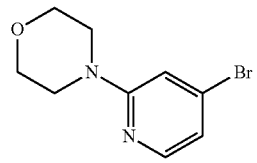 [SMILES: Brc1ccnc(N2CCOCC2)c1]

To a solution of triethylamine (1.0 equiv.) and 2-fluoro-4-bromopyridine (1.0 equiv.) at RT was added morpholine (1.0 equiv) in one portion, the resulting mixture was then heated in an oil bath at 100° C. for 66 hr. LCMS analysis indicated the formation of the desired product (m/z=244.9, Rt=0.36 min). The reaction mixture was concentrated in vacuo to yield 4-(4-bromopyridin-2-yl)morpholine as a light brown solid, (>100%, TEA impurity). LCMS (m/z) (M+H)=244.9, Rt=0.36 min. ¹H NMR (400 MHz, <dmso>) δ ppm 3.39-3.55 (m, 4H) 3.59-3.75 (m, 4H) 6.87 (dd, J=5.28, 1.37 Hz, 1H) 7.05 (d, J=1.17 Hz, 1H) 8.00 (d, J=5.48 Hz, 1H).

Synthesis of 4-(4-(4,4,5,5-tetramethyl-1,3,2-dioxaborolan-2-yl)pyridin-2-yl)morpholine

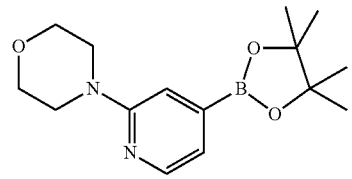 [SMILES: CC1(C)OB(c2ccnc(N3CCOCC3)c2)OC1(C)C]

4-(4-bromopyridin-2-yl)morpholine (1.10 equiv), bis(pinacolato)diboron (1.0 equiv.), potassium acetate (4.0 equiv), and PdCl₂(dppf)CH₂Cl₂ (0.05 equiv.) were added to a rb flask which was purged with nitrogen. DMF (0.20 M) was added and the mixture was heated to 80° C. overnight. The reaction was cooled to rt, quenched with water, and the product was extracted into EtOAc (3x). The combined organics were dried over Na₂SO₄, filtered, and concentrated. The crude was loaded onto silica gel and purified via ISCO to yield 4-(4-(4,4,5,5-tetramethyl-1,3,2-dioxaborolan-2-yl)pyridin-2-yl)morpholine as a light brown foam (56%). 1H NMR (400 MHz, <cdcl3>) δ ppm 1.33 (s, 12H) 3.49-3.55 (m, 4H) 3.79-3.83 (m, 4H) 6.98 (d, J=4.70 Hz, 1H) 7.03 (s, 1H) 8.21 (d, J=4.70 Hz, 1H).

Synthesis of 2-methyl-2'-morpholino-[3,4'-bipyridin]-5-amine

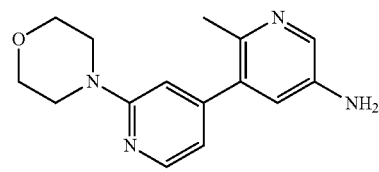 [SMILES: Cc1ncc(N)cc1-c1ccnc(N2CCOCC2)c1]

To a solution of 5-bromo-6-methylpyridin-3-amine (1.0 equiv.) and 4-(4-(4,4,5,5-tetramethyl-1,3,2-dioxaborolan-2-yl)pyridin-2-yl)morpholine (1.7 equiv.) in DME and 2M sodium carbonate (4:1, 0.14 M) was added PdCl₂(dppf)-

DCM adduct (0.1 equiv.) in a microwave vial equipped with a stir bar. The reaction was heated to 110° C. for 15 min in the microwave. The cooled reaction mixture was partitioned between water and ethyl acetate. The organic phase was dried with sodium sulfate, filtered and concentrated. The crude material was purified by flash chromatography over silica gel (DCM with a 0-20% methanol gradient). The pure fractions were concentrated in vacuo to afford 2-methyl-2'-morpholino-[3,4'-bipyridin]-5-amine in quantitative yield. LCMS (m/z) (M+H)=271.1, Rt=0.26 min.

Synthesis of N-(4-methyl-3-(2-morpholinopyridin-4-yl)phenyl)-3-(trifluoromethyl)benzamide To a solution of 4-(4-bromopyridin-2-yl)morpholine (1.0 equiv.) and Intermediate A (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 20 min in the microwave. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(4-methyl-3-(2-morpholinopyridin-4-yl)phenyl)-3-(trifluoromethyl)benzamide was isolated as the TFA salt in 16% yield. LCMS (m/z) (M+H)=442.3, Rt=0.76 min. 1H NMR (400 MHz, <dmso>) δ ppm 2.25 (s, 3H) 3.44-3.59 (m, 5H) 3.64-3.87 (m, 22H) 6.82 (d, J=5.48 Hz, 1H) 7.00 (s, 1H) 7.27-7.41 (m, 1H) 7.67-7.82 (m, 3H) 7.90-8.03 (m, 1H) 8.17 (d, J=5.48 Hz, 1H) 8.26 (d, J=7.83 Hz, 1H) 8.30 (s, 1H) 10.40-10.61 (m, 1H).

The compounds listed below were prepared using methods similar to those described for the preparation of Example 62 using the appropriate starting materials.

Example 63: 4-Methyl-3-(2-morpholinopyridin-4-yl)-N-(3-(trifluoromethyl)phenyl)benzamide

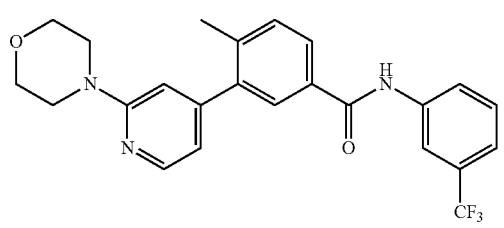 [SMILES: Cc1ccc(C(=O)Nc2cccc(C(F)(F)F)c2)cc1-c1ccnc(N2CCOCC2)c1]

1H NMR (400 MHz, <dmso>) δ ppm 2.28-2.38 (m, 3H) 3.50-3.58 (m, 5H) 3.61-3.93 (m, 36H) 6.83 (d, J=5.09 Hz, 1H) 6.97 (br. s., 1H) 7.37-7.69 (m, 6H) 7.89 (d, J=1.57 Hz, 1H) 7.96 (dd, J=7.83, 1.57 Hz, 1H) 8.06 (d, J=8.22 Hz, 1H) 8.20 (d, J=5.48 Hz, 1H) 8.23 (s, 1H) 10.50 (s, 1H). LCMS (m/z) (M+H)=442.3, Rt=0.79 min.

Example 64: 4-methyl-3-(4-morpholinopyridin-2-yl)-N-(3-(trifluoromethyl)phenyl)benzamide

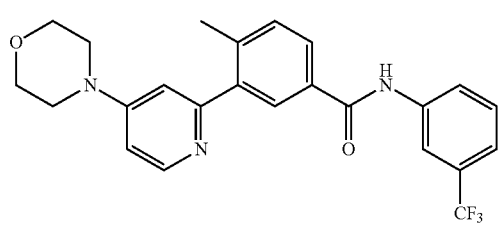 [SMILES: Cc1ccc(C(=O)Nc2cccc(C(F)(F)F)c2)cc1-c1cc(N2CCOCC2)ccn1]

1H NMR (400 MHz, <dmso>) δ ppm 2.36 (s, 3H) 2.54 (s, 1H) 7.27 (dd, J=7.24, 2.54 Hz, 1H) 7.32 (d, J=2.74 Hz, 1H) 7.48 (d, J=7.83 Hz, 1H) 7.56-7.65 (m, 2H) 8.03-8.10 (m, 2H) 8.14 (dd, J=8.02, 1.76 Hz, 1H) 8.23 (s, 1H) 8.36 (d, J=7.04 Hz, 1H) 10.50-10.65 (m, 1H) 13.75 (br. s., 1H). LCMS (m/z) (M+H)=442.3, Rt=0.74 min.

Example 65: N-(3-(2,6-dimorpholinopyridin-4-yl)-4-methylphenyl)-3-(trifluoromethyl)benzamide

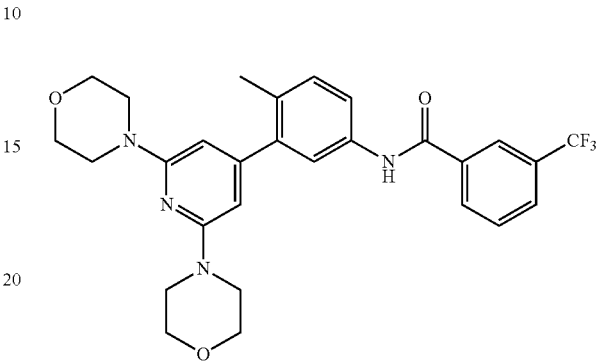

1H NMR (400 MHz, <dmso>) δ ppm 2.14-2.27 (m, 3H) 3.28-3.51 (m, 8H) 3.54-3.82 (m, 8H) 5.97-6.12 (m, 2H) 7.21-7.33 (m, 1H) 7.56-7.63 (m, 2H) 7.68-7.74 (m, 1H) 7.78 (t, J=7.83 Hz, 1H) 7.96 (d, J=7.83 Hz, 1H) 8.17-8.27 (m, 1H) 8.29 (s, 1H) 10.36-10.50 (m, 1H), LCMS (m/z) (M+H)= 527.4, Rt=1.04 min.

Example 66: 2-(2-cyanopropan-2-yl)-N-(4-methyl-3-(2-morpholinopyridin-4-yl)phenyl)isonicotinamide

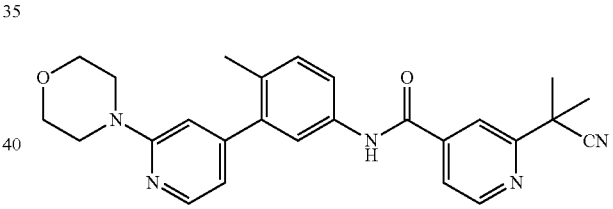

1H NMR (400 MHz, <dmso>) δ ppm 2.25 (s, 3H) 3.45-3.61 (m, 4H) 3.67-3.79 (m, 4H) 6.81 (d, J=5.48 Hz, 1H) 6.98 (br. s., 1H) 7.35 (d, J=8.22 Hz, 1H) 7.69 (s, 1H) 7.73 (dd, J=8.22, 1.96 Hz, 1H) 7.86 (dd, J=5.09, 1.17 Hz, 1H) 8.00 (s, 1H) 8.17 (d, J=5.87 Hz, 1H) 8.81 (d, J=5.09 Hz, 1H) 10.60 (s, 1H), LCMS (m/z) (M+H)=442.4, Rt=0.67 min.

Example 67: N-(4-methyl-3-(2-morpholinopyridin-4-yl)phenyl)pyridazine-3-carboxamide

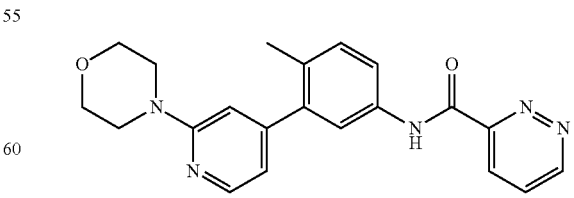

1H NMR (400 MHz, <dmso>) δ ppm 2.17-2.34 (m, 3H) 3.49-3.65 (m, 4H) 3.69-3.82 (m, 4H) 6.88 (d, J=5.48 Hz, 1H) 7.09 (s, 1H) 7.27-7.44 (m, 1H) 7.86-7.95 (m, 2H) 7.98 (dd, J=8.61, 5.09 Hz, 1H) 8.13-8.22 (m, 1H) 8.27-8.37 (m, 1H)

9.38-9.55 (m, 1H) 11.03-11.24 (m, 1H), LCMS (m/z) (M+H)=376.3.0, Rt=0.56 min.

Example 68: N-(4-methyl-3-(2-morpholinopyridin-4-yl)phenyl)-3-(methylsulfonyl)benzamide

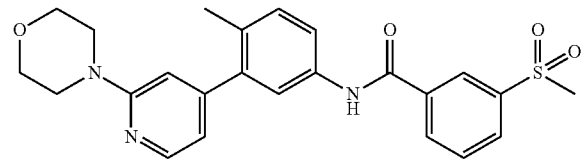

1H NMR (400 MHz, <dmso>) δ ppm 2.17-2.30 (m, 3H) 3.23-3.35 (m, 3H) 3.52-3.64 (m, 4H) 3.69-3.85 (m, 4H) 6.85 (d, J=5.48 Hz, 1H), 7.06 (br. s., 1H) 7.35 (d, J=8.22 Hz, 1H) 7.65-7.79 (m, 2H) 7.79-7.89 (m, 1H) 8.09-8.20 (m, 2H) 8.29 (d, J=7.83 Hz, 1H) 8.43-8.53 (m, 1H) 10.50-10.65 (m, 1H), LCMS (m/z) (M+H)=452.1, Rt=0.61 min.

Example 69: 2-(tert-butyl)-N-(4-methyl-3-(2-morpholinopyridin-4-yl)phenyl)isonicotinamide

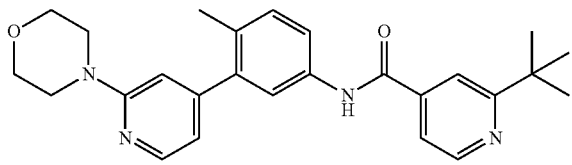 [SMILES: Cc1ccc(NC(=O)c2ccnc(C(C)(C)C)c2)cc1-c1ccnc(N2CCOCC2)c1]

1H NMR (400 MHz, <dmso>) δ ppm 1.29-1.42 (m, 9H) 2.25 (s, 3H) 3.51-3.65 (m, 4H) 3.69-3.81 (m, 4H) 6.85 (d, J=5.48 Hz, 1H) 6.95-7.13 (m, 1H) 7.35 (d, J=8.22 Hz, 1H) 7.59-7.78 (m, 3H) 7.86 (s, 1H) 8.16 (d, J=5.48 Hz, 1H) 8.72 (d, J=5.09 Hz, 1H) 10.52 (s, 1H), LCMS (m/z) (M+H)=431.3, Rt=0.54 min.

Example 70: N-(4-methyl-3-(2-morpholinopyridin-4-yl)phenyl)pyrazine-2-carboxamide

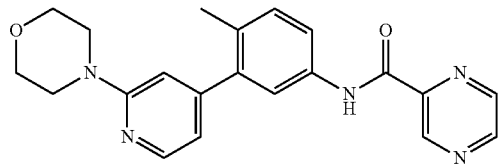 [SMILES: Cc1ccc(NC(=O)c2cnccn2)cc1-c1ccnc(N2CCOCC2)c1]

1H NMR (400 MHz, <dmso>) δ ppm 2.18-2.31 (m, 3H) 3.48-3.65 (m, 4H) 3.68-3.83 (m, 4H) 6.85 (d, J=5.48 Hz, 1H) 6.95-7.13 (m, 1H), 7.27-7.39 (m, 1H) 7.79-7.92 (m, 2H) 8.05-8.22 (m, 1H) 8.81 (dd, J=2.35, 1.57 Hz, 1H) 8.94 (d, J=2.35 Hz, 1H) 9.23-9.37 (m, 1H) 10.79 (s, 1H), LCMS (m/z) (M+H)=376.2, Rt=0.57 min.

Example 71: N-(4-methyl-3-(2-morpholinopyridin-4-yl)phenyl)pyrimidine-5-carboxamide

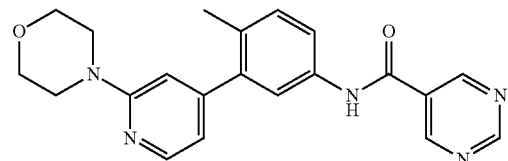

1H NMR (400 MHz, <dmso>) δ ppm 2.19-2.28 (m, 3H) 3.49-3.63 (m, 4H) 3.68-3.81 (m, 4H) 6.85 (d, J=5.48 Hz, 1H) 6.97-7.12 (m, 1H) 7.32-7.41 (m, 1H) 7.65-7.78 (m, 2H) 8.11 (dd, J=5.28, 2.15 Hz, 1H) 8.17 (d, J=5.48 Hz, 1H) 9.50 (dd, J=5.48, 0.78 Hz, 1H) 9.64 (d, J=0.78 Hz, 1H) 10.68-10.86 (m, 1H), LCMS (m/z) (M+H)=376.2, Rt=0.52 min.

Example 72: N-(4-methyl-3-(2-morpholinopyridin-4-yl)phenyl)pyridazine-4-carboxamide

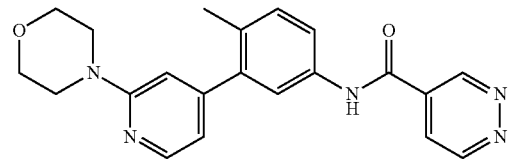 [SMILES: Cc1ccc(NC(=O)c2ccnnc2)cc1-c1ccnc(N2CCOCC2)c1]

1H NMR (400 MHz, <dmso>) δ ppm 2.19-2.29 (m, 3H) 3.58 (d, J=3.91 Hz, 4H) 3.67-3.82 (m, 4H) 6.83 (d, J=5.09 Hz, 1H) 7.03 (br. s., 1H), 7.29-7.42 (m, 1H) 7.64-7.76 (m, 2H) 8.10-8.24 (m, 1H) 9.27 (s, 2H) 9.37 (s, 1H) 10.66 (s, 1H), LCMS (m/z) (M+H)=376.2, Rt=0.50 min.

Example 73: N-(4-methyl-3-(2-morpholinopyridin-4-yl)phenyl)-2-(methylsulfonyl)isonicotinamide

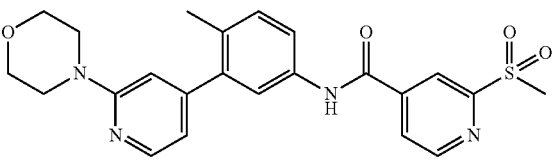 [SMILES: Cc1ccc(NC(=O)c2ccnc(S(C)(=O)=O)c2)cc1-c1ccnc(N2CCOCC2)c1]

1H NMR (400 MHz, <dmso>) δ ppm 2.18-2.34 (m, 3H) 3.35 (s, 3H) 3.47-3.63 (m, 4H) 3.69-3.84 (m, 4H) 6.72-6.88 (m, 1H) 6.95-7.07 (m, 1H) 7.37 (d, J=8.22 Hz, 1H) 7.72 (s, 1H) 7.76 (dd, J=8.22, 2.35 Hz, 1H) 8.17 (d, J=5.48 Hz, 1H) 8.20-8.26 (m, 1H) 8.53 (s, 1H) 8.94-9.05 (m, 1H) 10.75-10.90 (m, 1H), LCMS (M+H)=453.3, Rt=0.57 min.

Example 74: 3-(4-ethylpiperazin-1-yl)-N-(4-methyl-3-(2-morpholinopyridin-4-yl)phenyl)-5-(trifluoromethyl)benzamide

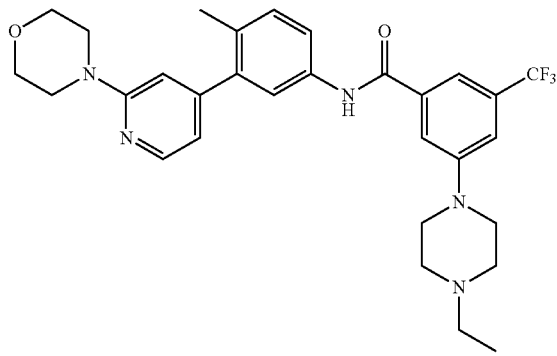 [SMILES: CCN1CCN(c2cc(C(=O)Nc3ccc(C)c(-c4ccnc(N5CCOCC5)c4)c3)cc(C(F)(F)F)c2)CC1]

1H NMR (400 MHz, <dmso>) δ ppm 1.27 (t, J=7.24 Hz, 4H) 2.24 (s, 3H) 2.54 (s, 1H) 3.13 (d, J=8.22 Hz, 5H) 3.18-3.28 (m, 3H) 3.44-3.56 (m, 6H) 3.61 (d, J=6.26 Hz, 3H) 3.66-3.81 (m, 6H) 4.11 (d, J=8.61 Hz, 3H) 6.76 (d, J=5.09 Hz, 1H) 6.89 (s, 1H) 7.33 (d, J=8.61 Hz, 1H) 7.52 (s, 1H) 7.65 (d, J=1.96 Hz, 1H) 7.73 (s, 2H) 7.75-7.81 (m, 2H) 8.18 (d, J=5.48 Hz, 1H) 9.72 (br. s., 1H) 10.42 (s, 1H), LCMS (m/z) (M+H)=554.4, Rt=0.61 min.

Example 75: 3-(difluoromethyl)-N-(4-methyl-3-(2-morpholinopyridin-4-yl)phenyl)benzamide

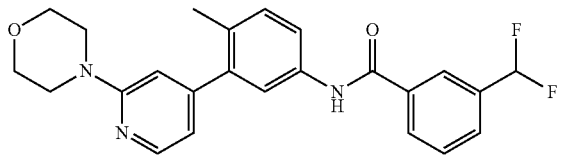 [SMILES: Cc1ccc(NC(=O)c2cccc(C(F)F)c2)cc1-c1ccnc(N2CCOCC2)c1]

1H NMR (400 MHz, <dmso>) δ ppm 2.54 (s, 1H) 3.46-3.63 (m, 4H) 3.66-3.82 (m, 4H) 6.84 (d, J=5.09 Hz, 1H) 7.01 (s, 1H) 7.03 (br. s., 1H), 7.15 (s, 1H) 7.28 (s, 1H) 7.33 (d, J=8.22 Hz, 1H) 7.62-7.84 (m, 4H) 8.06-8.20 (m, 3H) 10.46 (s, 1H), LCMS (m/z) (M+H)=424.1, Rt=0.73 min.

Example 76: N-(3-(2-(dimethylamino)-6-morpholinopyridin-4-yl)-4-methylphenyl)-3-(trifluoromethyl)benzamide

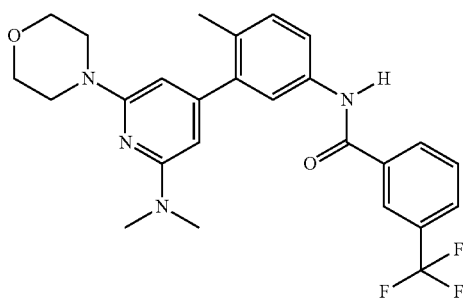 [SMILES: Cc1ccc(NC(=O)c2cccc(C(F)(F)F)c2)cc1-c1cc(N(C)C)nc(N2CCOCC2)c1]

1H NMR (400 MHz, DMSO-d$_6$) δ ppm 2.21 (s, 3H) 2.99 (s, 6H) 3.30-3.49 (m, 4H) 5.89 (d, J=19.95 Hz, 2H) 7.12-7.32 (m, 1H) 7.63-7.84 (m, 2H) 7.90-8.04 (m, 1H) 8.17-8.35 (m, 2H) 10.30-10.53 (m, 1H). LCMS (m/z) (M+H) 485.4, Rt=0.93 min.

Example 77: N-(2-methyl-2',6'-dimorpholino-[3,4'-bipyridin]-5-yl)-3-(trifluoromethyl)benzamide

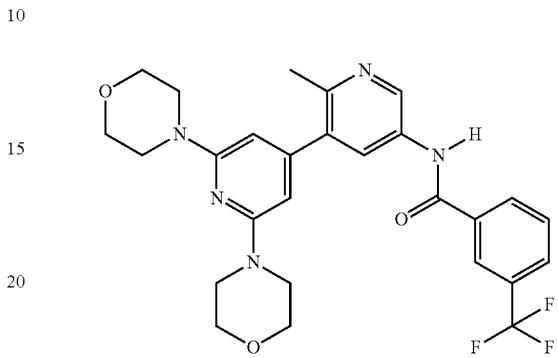

1H NMR (400 MHz, DMSO-d$_6$) δ 2.13-2.32 (m, 1H) 2.54-2.66 (m, 2H) 3.54-3.70 (m, 9H) 7.65-8.11 (m, 4H) 7.83-8.02 (m, 3H) 8.26 (s, 3H) 8.76-8.94 (m, 1H) 10.53-10.79 (m, 1H). LCMS (m/z) (M+H) 528.3, Rt=0.8 min.

Example 78: (S)—N-(3-(2-(2-(hydroxymethyl)morpholino)pyridin-4-yl)-4-methylphenyl)-3-(trifluoromethyl)benzamide

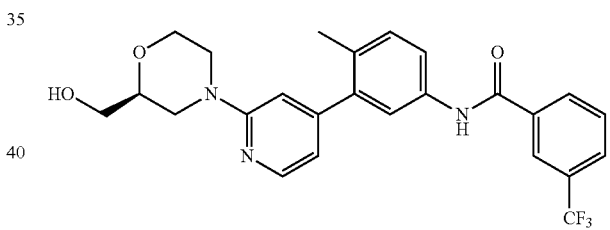

$^1$H NMR (400 MHz, <cd3od>) δ ppm 2.33 (s, 3H) 3.13 (t, J=11.54 Hz, 1H) 3.60-3.73 (m, 3H) 3.77 (td, J=11.74, 2.74 Hz, 1H) 4.02 (d, J=13.30 Hz, 1H) 4.11 (d, J=12.91 Hz, 2H) 7.02 (d, J=6.26 Hz, 1H) 7.29 (s, 1H) 7.37 (d, J=8.61 Hz, 1H) 7.61 (dd, J=8.22, 2.35 Hz, 1H) 7.70-7.76 (m, 1H) 7.81 (d, J=2.35 Hz, 1H) 7.90 (d, J=7.83 Hz, 1H) 8.04 (d, J=6.26 Hz, 1H) 8.20 (d, J=7.83 Hz, 1H) 8.26 (s, 1H). LCMS (m/z) (M+H)=472.3, Rt=0.74 min.

Example 79: 2-(2-cyanopropan-2-yl)-N-(3-(2-((2R,5R)-2-((dimethylamino)methyl)-5-methylmorpholino)pyridin-4-yl)-4-methylphenyl)isonicotinamide

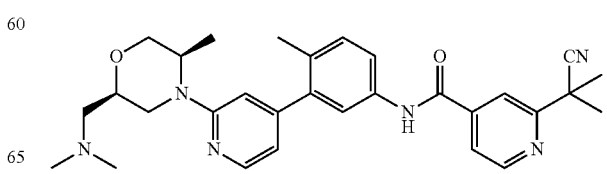

¹H NMR (400 MHz, <dmso>) δ ppm 1.18 (d, J=6.26 Hz, 3H) 1.75 (s, 6H) 2.23 (s, 3H) 2.81 (br. s., 6H) 3.11 (br. s., 1H) 3.43 (dd, J=13.69, 4.70 Hz, 1H) 3.52 (dd, J=11.74, 2.35 Hz, 1H) 3.70-3.80 (m, 1H) 3.91 (d, J=12.91 Hz, 1H) 4.04 (dd, J=11.93, 3.33 Hz, 1H) 4.22-4.31 (m, 1H) 4.37 (d, J=10.56 Hz, 1H) 6.70 (d, J=5.09 Hz, 1H) 6.75 (s, 1H) 7.33 (d, J=8.22 Hz, 1H) 7.62-7.76 (m, 2H) 7.80-7.88 (m, 1H) 7.99 (s, 1H) 8.19 (d, J=5.09 Hz, 1H) 8.80 (d, J=5.09 Hz, 1H) 10.56-10.66 (m, 1H). LCMS (m/z) (M+H)=513.5, Rt=0.59 min.

Example 80: 2-(2-cyanopropan-2-yl)-N-(3-(2-((2S,5S)-2-((dimethylamino)methyl)-5-methylmorpholino)pyridin-4-yl)-4-methylphenyl)isonicotinamide

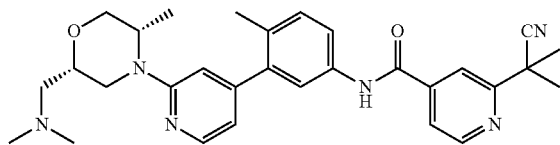 [SMILES: Cc1ccc(NC(=O)c2ccnc(C(C)(C)C#N)c2)cc1-c1ccnc(N2C[C@H](CN(C)C)OC[C@@H]2C)c1]

¹H NMR (400 MHz, <dmso>) δ ppm 1.14 (d, J=6.65 Hz, 3H) 1.75 (s, 6H) 2.22 (s, 3H) 2.75-2.89 (m, 7H) 3.23-3.36 (m, 2H) 3.79-3.85 (m, 2H) 3.92 (t, J=9.78 Hz, 1H) 4.11 (d, J=12.52 Hz, 1H) 4.40 (d, J=6.26 Hz, 1H) 6.68 (d, J=5.48 Hz, 1H) 6.74 (s, 1H) 7.32 (d, J=8.61 Hz, 1H) 7.64-7.72 (m, 2H) 7.84 (d, J=4.70 Hz, 1H) 7.98 (s, 1H) 8.18 (d, J=5.09 Hz, 1H) 8.79 (d, J=5.09 Hz, 1H) 10.57 (s, 1H). LCMS (m/z) (M+H)=513.4, Rt=0.57 min.

Example 81: 5-(dimethylamino)-N-(2-methyl-2'-morpholino-[3,4'-bipyridin]-5-yl)nicotinamide

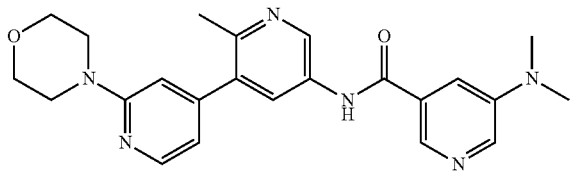 [SMILES: Cc1ncc(NC(=O)c2cncc(N(C)C)c2)cc1-c1ccnc(N2CCOCC2)c1]

¹H NMR (400 MHz, <dmso>) δ ppm 2.49 (s, 9H) 3.50-3.62 (m, 4H) 3.68-3.77 (m, 4H) 6.86 (d, J=5.48 Hz, 1H) 7.07 (s, 1H) 7.87 (br. s., 1H) 8.18 (d, J=2.35 Hz, 1H) 8.22 (d, J=5.48 Hz, 1H) 8.34 (d, J=2.74 Hz, 1H) 8.50 (s, 1H) 8.97 (d, J=2.35 Hz, 1H) 10.96 (s, 1H). LCMS (m/z) (M+H)=419.3, Rt=0.37 min.

Example 82: (R)-2-(2-cyanopropan-2-yl)-N-(4-methyl-3-(2-(3-methylmorpholino)pyridin-4-yl)phenyl)isonicotinamide

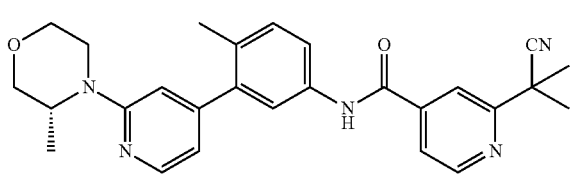 [SMILES: Cc1ccc(NC(=O)c2ccnc(C(C)(C)C#N)c2)cc1-c1ccnc(N2CCOC[C@H]2C)c1]

LCMS (m/z) (M+H)=456.3, Rt=0.66 min.

Example 83: (S)-2-(2-cyanopropan-2-yl)-N-(3-(2-(2-(hydroxymethyl)morpholino)pyridin-4-yl)-4-methylphenyl)isonicotinamide

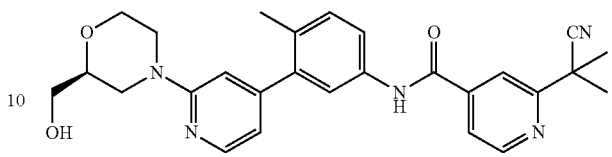

¹H NMR (400 MHz, <dmso>) δ ppm 1.75 (s, 6H) 2.23 (s, 3H) 2.76 (t, J=11.35 Hz, 1H) 2.99 (t, J=10.96 Hz, 1H) 3.36-3.66 (m, 4H) 3.96 (dd, J=11.54, 2.15 Hz, 1H) 4.07 (d, J=12.91 Hz, 1H) 4.19 (d, J=12.52 Hz, 1H) 6.81 (d, J=5.09 Hz, 1H) 6.99 (br. s., 1H) 7.34 (d, J=8.61 Hz, 1H) 7.68 (d, J=1.57 Hz, 1H) 7.72 (dd, J=8.41, 2.15 Hz, 1H) 7.85 (dd, J=5.09, 1.17 Hz, 1H) 7.99 (s, 1H) 8.15 (d, J=5.48 Hz, 1H) 8.80 (d, J=5.09 Hz, 1H) 10.59 (s, 1H). LCMS (m/z) (M+H)=472.1, Rt=0.63 min.

Example 84: (R)-2-(2-cyanopropan-2-yl)-N-(4-methyl-3-(2-(2-((methylamino)methyl)morpholino)pyridin-4-yl)phenyl)isonicotinamide

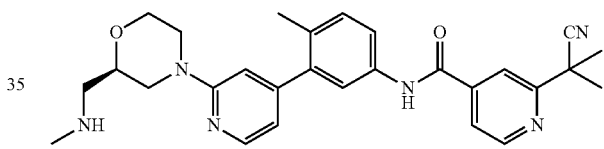

¹H NMR (400 MHz, <dmso>) δ ppm 1.75 (s, 7H) 2.22 (s, 3H) 2.58 (t, J=5.28 Hz, 3H) 2.62-2.73 (m, 2H) 2.87-2.99 (m, 1H) 3.00-3.22 (m, 2H) 3.76-3.87 (m, 2H) 4.01 (d, J=11.35 Hz, 1H) 4.11 (d, J=12.52 Hz, 1H) 4.26 (d, J=12.13 Hz, 1H) 6.72 (d, J=5.09 Hz, 1H) 6.81 (s, 1H) 7.33 (d, J=9.00 Hz, 1H) 7.61-7.72 (m, 2H) 7.84 (dd, J=5.09, 1.17 Hz, 1H) 7.98 (s, 1H) 8.19 (d, J=5.09 Hz, 1H) 8.80 (d, J=5.09 Hz, 1H) 10.57 (s, 1H). LCMS (m/z) (M+H)=485.3, Rt=0.60 min.

Example 85: (R)—N-(3-(2-(2-(acetamidomethyl)morpholino)pyridin-4-yl)-4-methylphenyl)-2-(2-cyanopropan-2-yl)isonicotinamide

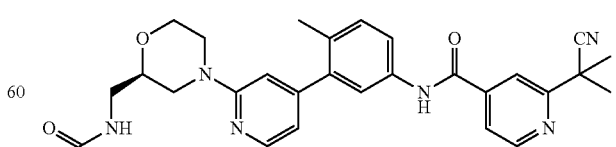

LCMS (m/z) (M+H)=513.2, Rt=0.64 min.

Example 86: (R)-methyl((4-(2-methyl-5-(3-(trifluoromethyl)benzamido)-[3,4'-bipyridin]-2'-yl)morpholin-2-yl)methyl)carbamate

LCMS (m/z) (M+H)=530.2, Rt=0.65 min.

Example 87: (R)—N-(2'-(2-((2-hydroxyacetamido)methyl)morpholino)-2-methyl-[3,4'-bipyridin]-5-yl)-3-(trifluoromethyl)benzamide

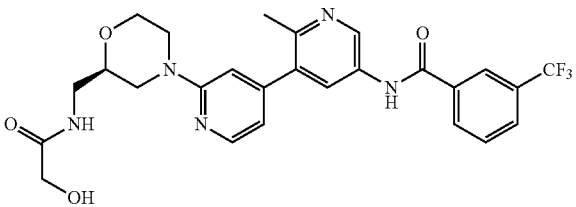 [SMILES: Cc1ncc(NC(=O)c2cccc(C(F)(F)F)c2)cc1-c1ccnc(N2CCO[C@H](CNC(=O)CO)C2)c1]

To a solution of (S)-2-hydroxy-N-(morpholin-2-ylmethyl)acetamide (1.0 equiv.) and N-(2'-fluoro-2-methyl-[3,4'-bipyridin]-5-yl)-3-(trifluoromethyl)benzamide (2.0 equiv.) in NMP (0.13 M) was added potassium carbonate (6.0 equiv.). The mixture was heated at 120° C. overnight. The reaction mixture was then filtered, and purified via reverse phase HPLC to yield (R)—N-(2'-(2-((2-hydroxyacetamido)methyl)morpholino)-2-methyl-[3,4'-bipyridin]-5-yl)-3-(trifluoromethyl)benzamide (5%, 99% purity by LC) as a white crystalline solid. LCMS (m/z) (M+H)=530.1, Rt=0.56 min.

Example 88: 2-(2-cyanopropan-2-yl)-N-(2-methoxy-2'-morpholino-[3,4'-bipyridin]-5-yl)isonicotinamide

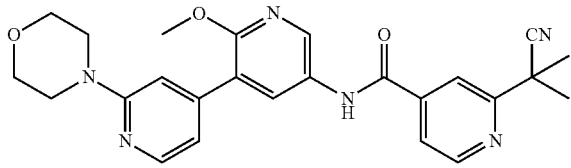 [SMILES: COc1ncc(NC(=O)c2ccnc(C(C)(C)C#N)c2)cc1-c1ccnc(N2CCOCC2)c1]

$^1$H NMR (400 MHz, <dmso>) δ ppm 1.75 (s, 6H) 3.53 (t, J=4.30 Hz, 4H) 3.67-3.76 (m, 4H) 3.90 (s, 3H) 6.98 (d, J=5.48 Hz, 1H) 7.15 (br. s., 1H) 7.88 (dd, J=4.89, 1.37 Hz, 1H) 8.02 (s, 1H) 8.11-8.23 (m, 2H) 8.58 (d, J=2.35 Hz, 1H) 8.82 (d, J=5.09 Hz, 1H) 10.73 (s, 1H). LCMS (m/z) (M+H)=459.2, Rt=0.69 min.

Example 89: 2-(1,1-difluoroethyl)-N-(2'-morpholino-2-oxo-1,2-dihydro-[3,4'-bipyridin]-5-yl)isonicotinamide

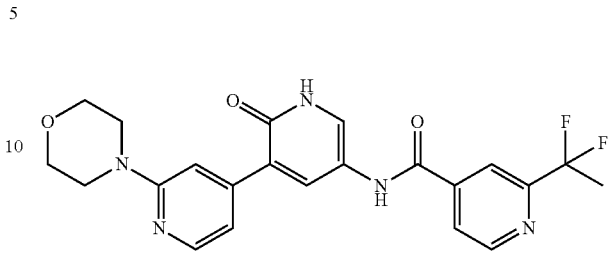

$^1$H NMR (400 MHz, <dmso>) δ ppm 1.94-2.12 (m, 3H) 3.54 (d, J=4.70 Hz, 4H) 3.68-3.79 (m, 4H) 7.19 (d, J=5.48 Hz, 1H) 7.56 (br. s., 1H) 8.00 (d, J=4.70 Hz, 1H) 8.04-8.15 (m, 3H) 8.17 (s, 1H) 8.88 (d, J=5.09 Hz, 1H) 10.54 (s, 1H). LCMS (m/z) (M+H)=442.2, Rt=0.60 min.

Example 90: N-(2'-morpholino-2-oxo-1,2-dihydro-[3,4'-bipyridin]-5-yl)-2-(trifluoromethyl)isonicotinamide

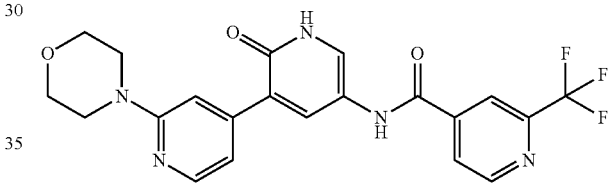

$^1$H NMR (400 MHz, <dmso>) δ ppm 3.53 (d, J=4.30 Hz, 4H) 3.68-3.77 (m, 4H) 7.17 (d, J=4.70 Hz, 1H) 7.52 (br. s., 1H) 8.00-8.14 (m, 3H) 8.17 (d, J=4.70 Hz, 1H) 8.34 (s, 1H) 9.00 (d, J=5.09 Hz, 1H) 10.59 (s, 1H). LCMS (m/z) (M+H)=446.2, Rt=0.61 min.

Example 91: 2-(2-cyanopropan-2-yl)-N-(2'-morpholino-2-oxo-1,2-dihydro-[3,4'-bipyridin]-5-yl)isonicotinamide

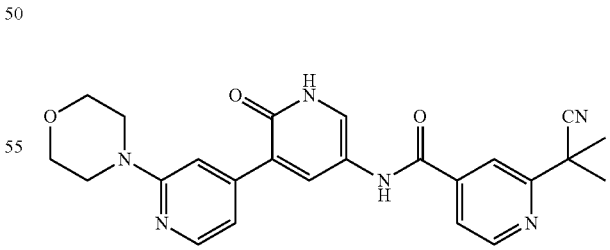

$^1$H NMR (400 MHz, <dmso>) δ ppm 1.75 (s, 6H) 3.69-3.79 (m, 4H) 7.05-7.21 (m, 1H) 7.50 (br. s., 1H) 7.84 (dd, J=5.09, 1.57 Hz, 1H) 7.99 (s, 1H) 8.03 (br. s., 1H) 8.06-8.15 (m, 2H) 8.81 (d, J=5.09 Hz, 1H) 10.45 (s, 1H). LCMS (m/z) (M+H)=445.2, Rt=0.59 min.

Example 92: N-(3-(6-amino-4-morpholinopyridin-2-yl)-4-methylphenyl)-3-(trifluoromethyl)benzamide

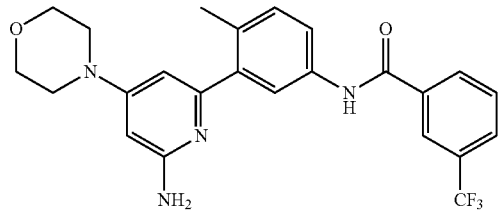

$^1$H NMR (400 MHz, <cd3od>) δ ppm 2.34 (s, 3H) 3.49-3.60 (m, 4H) 3.75-3.86 (m, 4H) 6.07 (d, J=2.35 Hz, 1H) 6.61 (d, J=2.35 Hz, 1H) 7.40 (d, J=8.61 Hz, 1H) 7.65 (dd, J=8.41, 2.15 Hz, 1H) 7.70-7.79 (m, 1H) 7.87-7.96 (m, 2H) 8.21 (d, J=7.83 Hz, 1H) 8.26 (s, 1H). LCMS (m/z) (M+H)= 447.2, Rt=0.87 min.

Example 93: N-(3-(2-amino-6-morpholinopyridin-4-yl)-4-methylphenyl)-3-(trifluoromethyl)benzamide

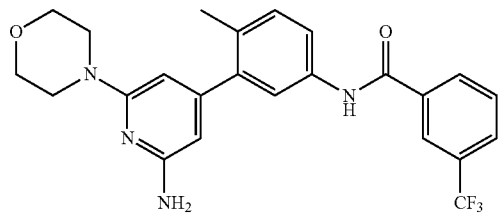

$^1$H NMR (400 MHz, <cd3od>) δ ppm 2.32 (s, 3H) 3.44-3.55 (m, 4H) 3.80-3.88 (m, 4H) 6.13-6.24 (m, 1H) 7.34 (d, J=8.22 Hz, 1H) 7.58 (dd, J=8.22, 2.35 Hz, 1H) 7.69-7.81 (m, 2H) 7.90 (d, J=7.83 Hz, 1H) 8.20 (d, J=7.83 Hz, 1H) 8.26 (s, 1H). LCMS (m/z) (M+H)=447.2, Rt=0.87 min.

Example 94: 1-ethyl-N-(4-methyl-3-(2-morpholinopyridin-4-yl)phenyl)-6-oxo-5-(trifluoromethyl)-1,6-dihydropyridine-3-carboxamide

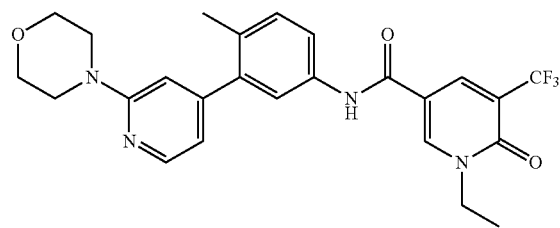 [SMILES: CCn1cc(C(=O)Nc2ccc(C)c(-c3ccnc(N4CCOCC4)c3)c2)cc(C(F)(F)F)c1=O]

1H NMR (400 MHz, <cd3od>) δ ppm 1.41 (t, J=7.24 Hz, 3H) 2.32 (s, 3H) 3.61-3.74 (m, 4H) 3.80-3.94 (m, 4H) 4.16 (q, J=7.04 Hz, 2H) 7.02 (d, J=5.87 Hz, 1H) 7.28 (s, 1H) 7.36 (d, J=8.61 Hz, 1H) 7.55 (dd, J=8.22, 1.96 Hz, 1H) 7.76 (d, J=1.96 Hz, 1H) 8.04 (d, J=6.26 Hz, 1H) 8.48 (s, 1H) 8.70 (d, J=2.74 Hz, 1H). LCMS (m/z) (M+H)=487.2, Rt=0.72 min.

Example 95: Synthesis of 2-(2-cyanopropan-2-yl)-N-(2-methyl-2'-morpholino-[3,4'-bipyridin]-5-yl)isonicotinamide

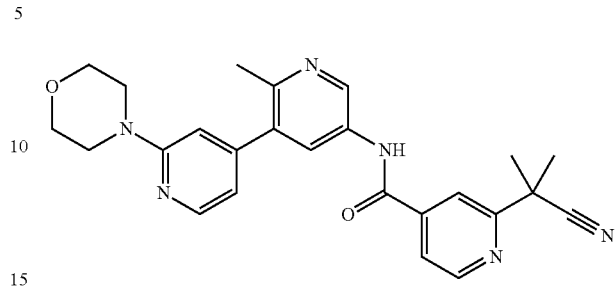

To a 0.2 M solution of 2-methyl-2'-morpholino-[3,4'-bipyridin]-5-amine (1.0 equiv.) in DMF was added 2-(2-cyanopropan-2-yl)isonicotinic acid (1.0 equiv.), EDC-HCl (1.1 equiv.) and aza-HOBt (1.1 equiv.). The reaction was stirred at room temperature for 4 hours. The solution was filtered through a syringe filter and purified via reverse phase preparative HPLC. Upon lyophilization of the pure fractions, 2-(2-cyanopropan-2-yl)-N-(2-methyl-2'-morpholino-[3,4'-bipyridin]-5-yl)isonicotinamide was isolated as the TFA salt in 51% yield. $^1$H NMR (400 MHz, <dmso>) δ ppm 1.75 (s, 6H) 2.47 (br. s., 3H) 3.45-3.63 (m, 4H) 3.64-3.79 (m, 4H) 6.84 (d, J=5.09 Hz, 1H) 7.03 (br. s., 1H) 7.87 (dd, J=5.09, 1.17 Hz, 1H) 8.02 (s, 1H) 8.14 (d, J=2.35 Hz, 1H) 8.20 (d, J=5.48 Hz, 1H) 8.83 (d, J=5.09 Hz, 1H) 8.92 (d, J=2.35 Hz, 1H) 10.90 (s, 1H); LCMS (m/z) (M+H)=443.2, Rt=0.50 min.

Synthesis of 3-bromo-4-(bromomethyl)benzoic acid

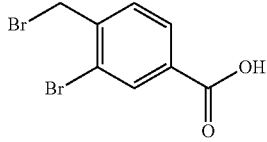

To a solution of 3-bromo-4-methylbenzoic acid (1.0 equiv.) and AIBN (0.05 equiv.) in trifluorotoluene (0.28 M) was added NBS (1.1 equiv.). The mixture was heated at 90° C. overnight. The reaction mixture was partitioned between EtOAc and H$_2$O. The organic layer was washed with NaCl (sat.), dried over MgSO$_4$, filtered, concentrated to yield 3-bromo-4-(bromomethyl)benzoic acid in 60% yield. LC/MS (m/z)=294.8 (MH$^+$), Rt=0.80 min.

Synthesis of 3-bromo-4-(hydroxymethyl)benzoic acid

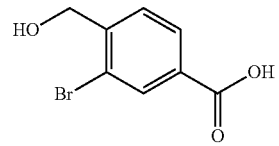 [SMILES: O=C(O)c1ccc(CO)c(Br)c1]

To a solution of yield 3-bromo-4-(bromomethyl)benzoic acid (1.0 equiv.) in Water (0.56 M) at 95° C. was added potassium carbonate K₂CO₃ (5.0 equiv.). The homogenous reaction mixture was stirred at 95° C. in an oil bath for 1 hr. The reaction mixture was COOLED OFF TO RT, neutralized with 6 M HCl. diluted with EtOAc and washed with brine. The organic layer was dried over Na₂SO₄, filtered and concentrated. The crude was used in next step. LC/MS (m/z)=294.8 (MH⁺), Rt=0.80 min.

Synthesis of 3-bromo-4-(hydroxymethyl)-N-(3-(trifluoromethyl)phenyl)benzamide

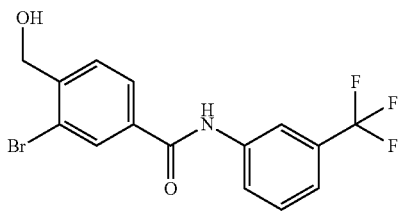 [SMILES: O=C(Nc1cccc(C(F)(F)F)c1)c1ccc(CO)c(Br)c1]

EDC (1.3 equiv.) was added to a solution of 3-bromo-4-(hydroxymethyl)benzoic acid (1.0 equiv), 3-(trifluoromethyl)aniline (1.1 equiv.), HOAt (1.3 equiv.) in DMF (0.43 M). The mixture was stirred at ambient temperature 3 hrs. The reaction mixture was diluted with water and extracted with ethyl acetate. The combined extracts were washed sequentially with 1M aqueous sodium hydroxide and brine, dried over sodium sulfate, filtered, and concentrated. The residue was purified by ISCO (50% EtOAc/Heptane) to yield 3-bromo-4-(hydroxymethyl)-N-(3-(trifluoromethyl)phenyl)benzamide in 35% yield. LC/MS (m/z)=374.0 (MH⁺), Rt=0.93 min.

The compounds listed below were prepared using methods similar to those described for the preparation of Example 95 using the appropriate starting materials.

Example 96: N-(2-methyl-2'-morpholino-[3,4'-bipyridin]-5-yl)-3-(trifluoromethyl)benzamide

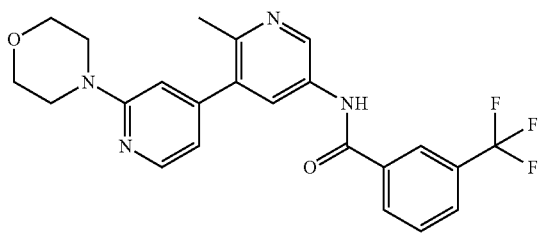 [SMILES: Cc1ncc(NC(=O)c2cccc(C(F)(F)F)c2)cc1-c1ccnc(N2CCOCC2)c1]

¹H NMR (400 MHz, <dmso>) δ ppm 2.47 (br. s., 3H) 3.49-3.59 (m, 4H) 3.67-3.75 (m, 4H) 6.85 (d, J=4.65 Hz, 1H) 7.03 (s, 1H) 7.81 (t, J=7.83 Hz, 1H) 8.00 (d, J=7.87 Hz, 1H) 8.18 (d, J=2.40 Hz, 1H) 8.21 (d, J=5.67 Hz, 1H) 8.27 (d, J=7.92 Hz, 1H) 8.32 (s, 1H) 8.96 (d, J=2.40 Hz, 1H) 10.82 (s, 1H). LCMS (m/z) (M+H)=443.3, Rt=0.61 min.

Example 97: 4-methoxy-N-(2-methyl-2'-morpholino-[3,4'-bipyridin]-5-yl)-3-trifluoromethyl)benzamide

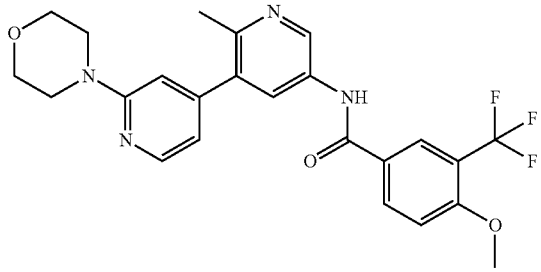 [SMILES: COc1ccc(C(=O)Nc2cnc(C)c(-c3ccnc(N4CCOCC4)c3)c2)cc1C(F)(F)F]

¹H NMR (400 MHz, <cd3od>) δ ppm 2.60 (s, 3H) 3.63-3.73 (m, 4H) 3.81-3.91 (m, 4H) 4.01 (s, 3H) 6.98-7.06 (m, 1H) 7.29 (s, 1H) 7.36 (d, J=8.22 Hz, 1H) 8.14 (d, J=5.87 Hz, 1H) 8.22-8.33 (m, 2H) 8.42 (d, J=2.35 Hz, 1H) 9.04 (d, J=2.35 Hz, 1H). LCMS (m/z) (M+H)=473.3, Rt=0.59 min.

Example 98: 4-fluoro-3-methoxy-N-(2-methyl-2'-morpholino-[3,4'-bipyridin]-5-yl)benzamide

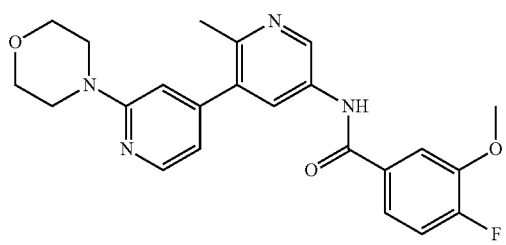 [SMILES: COc1cc(C(=O)Nc2cnc(C)c(-c3ccnc(N4CCOCC4)c3)c2)ccc1F]

¹H NMR (400 MHz, <cd3od>) δ ppm 2.59 (s, 3H) 3.62-3.73 (m, 4H) 3.81-3.91 (m, 4H) 3.97 (s, 3H) 7.01 (dd, J=6.06, 0.98 Hz, 1H) 7.20-7.33 (m, 2H) 7.60 (ddd, J=8.41, 4.11, 2.35 Hz, 1H) 7.73 (dd, J=8.02, 2.15 Hz, 1H) 8.14 (d, J=6.26 Hz, 1H) 8.39 (d, J=2.35 Hz, 1H) 9.02 (d, J=2.35 Hz, 1H). LCMS (m/z) (M+H)=423.3, Rt=0.51 min.

Example 99: 3-(difluoromethyl)-N-(2-methyl-2'-morpholino-[3,4'-bipyridin]-5-yl)benzamide

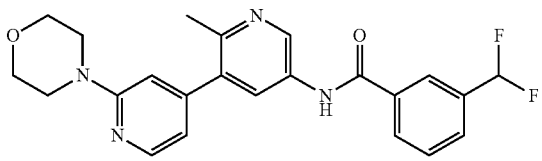 [SMILES: Cc1ncc(NC(=O)c2cccc(C(F)F)c2)cc1-c1ccnc(N2CCOCC2)c1]

1H NMR (400 MHz, <cd3od>) δ ppm 2.59 (s, 3H) 3.65-3.70 (m, 4H) 3.84-3.89 (m, 4H) 6.75 (s, 1H) 6.89 (s, 1H) 7.01 (s, 1H) 7.03 (d, J=3.13 Hz, 1H) 7.27 (s, 1H) 7.66-7.72 (m, 1H) 7.81 (d, J=7.83 Hz, 1H) 8.11-8.16 (m, 2H) 8.19 (s, 1H) 8.41 (d, J=2.35 Hz, 1H) 9.01 (d, J=2.35 Hz, 1H). LCMS (m/z) (M+H)=425.1, Rt=0.56 min.

Example 100: 2-(1,1-difluoroethyl)-N-(2-methyl-2'-morpholino-[3,4'-bipyridin]-5-yl)isonicotinamide

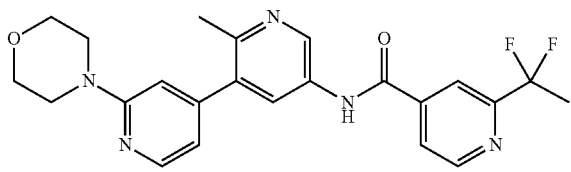 [SMILES: Cc1ncc(NC(=O)c2ccnc(C(C)(F)F)c2)cc1-c1ccnc(N2CCOCC2)c1]

1H NMR (400 MHz, <cd3od>) δ ppm 2.05 (t, J=18.78 Hz, 3H) 2.59 (s, 3H) 3.67-3.73 (m, 4H) 3.84-3.91 (m, 4H) 7.05 (dd, J=6.26, 1.17 Hz, 1H) 7.34 (s, 1H) 8.00 (d, J=3.91 Hz, 1H) 8.13 (d, J=6.26 Hz, 1H) 8.23 (s, 1H) 8.41 (d, J=2.35 Hz, 1H) 8.85 (d, J=5.09 Hz, 1H) 8.98 (d, J=2.35 Hz, 1H). LCMS (m/z) (M+H)=440.1, Rt=0.51 min.

Example 101: 3-(1,1-difluoroethyl)-N-(2-methyl-2'-morpholino-[3,4'-bipyridin]-5-yl)benzamide

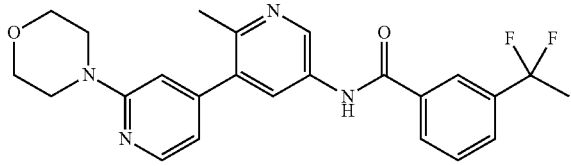 [SMILES: Cc1ncc(NC(=O)c2cccc(C(C)(F)F)c2)cc1-c1ccnc(N2CCOCC2)c1]

¹H NMR (400 MHz, <cd3od>) δ ppm 1.99 (t, J=18.39 Hz, 3H) 2.60 (s, 3H) 3.66-3.71 (m, 4H) 3.84-3.89 (m, 4H) 7.03 (dd, J=6.26, 1.17 Hz, 1H) 7.30 (s, 1H) 7.63-7.69 (m, 1H) 7.81 (d, J=7.43 Hz, 1H) 8.09 (d, J=7.83 Hz, 1H) 8.15 (d, J=6.26 Hz, 1H) 8.18 (s, 1H) 8.44 (d, J=2.35 Hz, 1H) 9.05 (d, J=2.35 Hz, 1H). LCMS (m/z) (M+H)=439.1, Rt=0.59 min.

Example 102: N-(2-methyl-2'-morpholino-[3,4'-bipyridin]-5-yl)-2-(methylsulfonyl)isonicotinamide

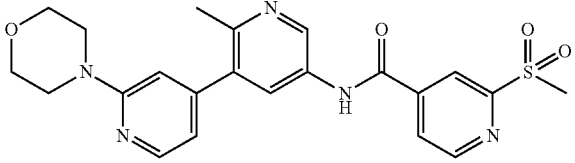 [SMILES: Cc1ncc(NC(=O)c2ccnc(S(C)(=O)=O)c2)cc1-c1ccnc(N2CCOCC2)c1]

1H NMR (400 MHz, <dmso>) δ ppm 3.27-3.42 (m, 3H) 3.48-3.64 (m, 4H) 3.67-3.84 (m, 4H) 6.90 (d, J=5.09 Hz, 1H) 7.12 (s, 1H) 8.10-8.34 (m, 3H) 8.57 (s, 1H) 8.99 (d, J=2.35 Hz, 1H) 9.04 (d, J=5.09 Hz, 1H) 11.19 (s, 1H), LCMS (m/z) (M+H)=454.2, Rt=0.40 min.

Example 103: N-(2-methyl-2'-morpholino-[3,4'-bipyridin]-5-yl)-3-(methylsulfonyl)benzamide

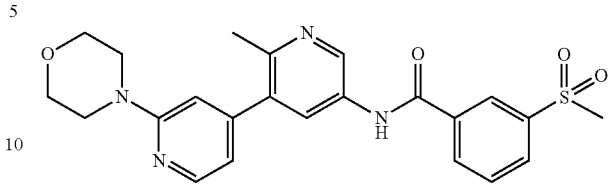

1H NMR (400 MHz, <dmso>) δ ppm 2.53 (s, 3H) 3.45-3.63 (m, 4H) 3.66-3.82 (m, 4H) 5.67 (br. s., 1H) 6.81-6.96 (m, 1H) 7.14 (s, 1H) 7.87 (t, J=7.83 Hz, 1H) 8.13-8.26 (m, 2H) 8.27-8.37 (m, 2H) 8.53 (s, 1H) 9.00-9.13 (m, 1H) 10.96-11.11 (m, 1H), LCMS (m/z) (M+H)=453.2, Rt=0.43 min.

Example 104: 2-(tert-butyl)-N-(2-methyl-2'-morpholino-[3,4'-bipyridin]-5-yl)isonicotinamide

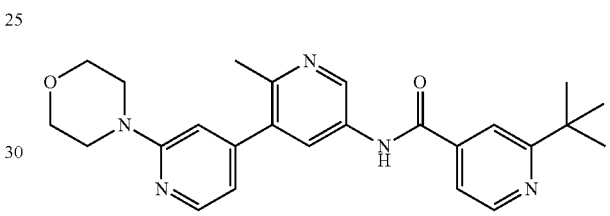

1H NMR (400 MHz, <dmso>) δ ppm 1.38 (s, 9H) 2.51-2.54 (m, 3H) 3.52-3.63 (m, 4H) 3.68-3.79 (m, 4H) 6.85-6.97 (m, 1H) 7.10-7.17 (m, 1H) 7.74 (dd, J=5.09, 1.57 Hz, 1H) 7.87-7.95 (m, 1H) 8.23 (d, J=5.48 Hz, 1H) 8.25-8.30 (m, 1H) 8.77 (d, J=5.09 Hz, 1H) 9.00-9.06 (m, 1H) 10.98 (s, 1H), LCMS (m/z) (M+H)=432.3, Rt=0.46 min.

Example 106: 2-(2-cyanopropan-2-yl)-N-(4-methyl-3-(2-morpholino-6-(tetrahydro-2H-pyran-4-yl)pyridin-4-yl)phenyl)isonicotinamide

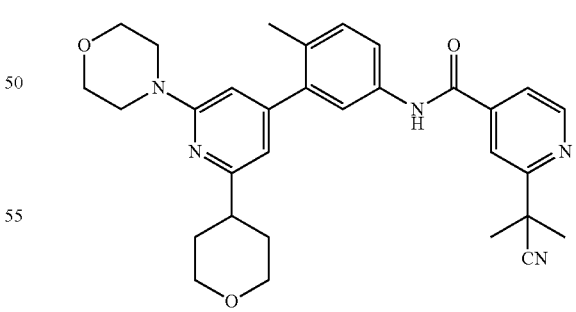

¹H NMR (400 MHz, <cd3od>) δ ppm 1.81 (s, 6H) 1.85-2.01 (m, 4H) 2.31 (s, 3H) 3.02-3.17 (m, 1H) 3.48-3.61 (m, 2H) 3.65-3.76 (m, 3H) 3.80-3.92 (m, 4H) 4.01-4.14 (m, 2H) 6.87 (s, 1H) 7.02 (s, 1H) 7.37 (d, J=8.22 Hz, 1H) 7.61 (dd, J=8.22, 1.96 Hz, 1H) 7.73-7.86 (m, 2H) 8.06 (s, 1H) 8.76 (d, J=5.09 Hz, 1H). LCMS (m/z) (M+H)=526.3, Rt=0.76 min.

Example 107: N-(4-methyl-3-(2-morpholino-6-(tetrahydro-2H-pyran-4-yl)pyridin-4-yl)phenyl)-3-(trifluoromethyl)benzamide

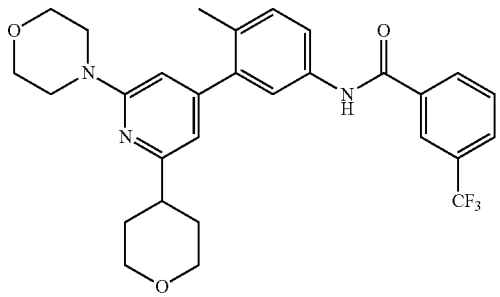 [SMILES: Cc1ccc(NC(=O)c2cccc(C(F)(F)F)c2)cc1-c1cc(C2CCOCC2)nc(N2CCOCC2)c1]

$^1$H NMR (400 MHz, <cd3od>) δ ppm 1.81-2.02 (m, 4H) 2.31 (s, 3H) 3.05-3.18 (m, 1H) 3.45-3.62 (m, 2H) 3.66-3.75 (m, 4H) 3.81-3.91 (m, 4H) 4.03-4.15 (m, 2H) 6.89 (s, 1H) 7.06 (s, 1H) 7.36 (d, J=8.22 Hz, 1H) 7.60 (dd, J=8.22, 2.35 Hz, 1H) 7.69-7.83 (m, 2H) 7.90 (d, J=7.83 Hz, 1H) 8.20 (d, J=7.83 Hz, 1H) 8.26 (s, 1H). LCMS (m/z) (M+H)=526.2, Rt=0.86 min.

Example 108: 4-(hydroxymethyl)-3-(2-morpholinopyridin-4-yl)-N-(3-(trifluoromethyl)phenyl)benzamide

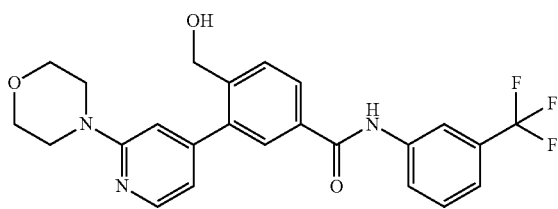 [SMILES: O=C(Nc1cccc(C(F)(F)F)c1)c1ccc(CO)c(-c2ccnc(N3CCOCC3)c2)c1]

The method used to prepare example 62 was followed using 3-bromo-4-(hydroxymethyl)-N-(3-(trifluoromethyl)phenyl)benzamide and 4-(4-(4,4,5,5-tetramethyl-1,3,2-dioxaborolan-2-yl)pyridin-2-yl)morpholine to afford 4-(hydroxymethyl)-3-(2-morpholinopyridin-4-yl)-N-(3-(trifluoromethyl)phenyl)benzamide in a 91% yield. $^1$H NMR (400 MHz, <cd3od>) δ ppm 3.61-3.73 (m, 4H), 3.83-3.90 (m, 4H), 4.63 (s, 2H), 7.09-7.15 (m, 1H), 7.39-7.47 (m, 2H), 7.53-7.60 (m, 1H), 7.75-7.82 (m, 1H), 7.91-7.99 (m, 2H), 8.04-8.13 (m, 2H), 8.14-8.19 (m, 1H). LC/MS (m/z)=458.1 (MH$^+$), R$_t$=0.73 min.

4-formyl-3-(2-morpholinopyridin-4-yl)-N-(3-(trifluoromethyl)phenyl)benzamide

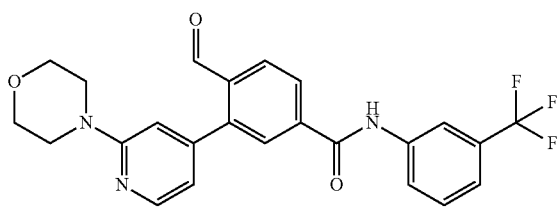 [SMILES: O=Cc1ccc(C(=O)Nc2cccc(C(F)(F)F)c2)cc1-c1ccnc(N2CCOCC2)c1]

MnO$_2$ (8.0 equiv.) was added into a solution of 4-(hydroxymethyl)-3-(2-morpholinopyridin-4-yl)-N-(3-(trifluoromethyl)phenyl)benzamide (1.0 equiv.) in DCM (0.05 M). The suspension was stirred at rt for 1 hr. The mixture was filtered over celite and concentrated to yield 4-formyl-3-(2-morpholinopyridin-4-yl)-N-(3-(trifluoromethyl)phenyl)benzamide in 100% yield. LC/MS (m/z)=456.1 (MH$^+$), R$_t$=0.76 min.

Example 109: 4-(difluoromethyl)-3-(2-morpholinopyridin-4-yl)-N-(3-(trifluoromethyl)phenyl)benzamide

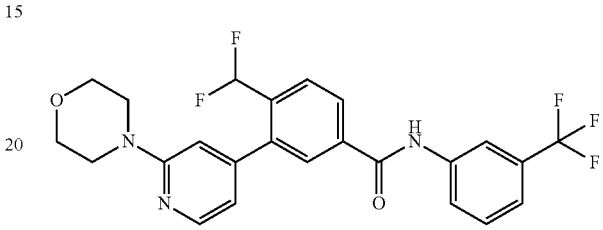

To a cooled solution of 4-formyl-3-(2-morpholinopyridin-4-yl)-N-(3-(trifluoromethyl)phenyl)benzamide (1.0 equiv.) in dry CH$_2$Cl$_2$ (0.05 M), (diethylamino)sulfur trifluoride (3.5 equiv.) was added under vigorous stirring. The resulting reaction mixture was stirred at 0° C. for 2 hrs. Quenched the reaction with sat NaHCO$_3$ and extracted with DCM. The organic layer was washed with Brine, filtered over Na$_2$SO$_4$ and concentrated. The crude was purified by prep HPLC to yield 4-(difluoromethyl)-3-(2-morpholinopyridin-4-yl)-N-(3-(trifluoromethyl)phenyl)benzamide in 12% yield. $^1$H NMR (400 MHz, <cd3od>) δ ppm 2.65 (s, 1H), 3.63-3.73 (m, 4H), 3.80-3.90 (m, 4H), 6.70-7.05 (m, 2H), 7.27 (s, 1H), 7.43-7.49 (m, 1H), 7.53-7.61 (m, 1H), 7.91-7.99 (m, 2H), 8.01-8.05 (m, 1H), 8.08-8.14 (m, 1H), 8.15-8.23 (m, 2H). LC/MS (m/z)=478.1 (MH$^+$), R$_t$=0.85 min.

Example 110: Synthesis of 4-(fluoromethyl)-3-(2-morpholinopyridin-4-yl)-N-(3-(trifluoromethyl)phenyl)benzamide

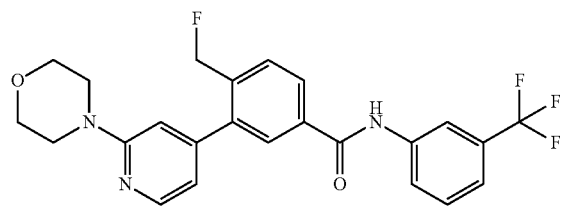 [SMILES: O=C(Nc1cccc(C(F)(F)F)c1)c1ccc(CF)c(-c2ccnc(N3CCOCC3)c2)c1]

To a cooled solution of 4-(difluoromethyl)-3-(2-morpholinopyridin-4-yl)-N-(3-(trifluoromethyl)phenyl)benzamide (1.0 equiv.) in dry CH$_2$Cl$_2$ (0.05 M), (diethylamino)sulfur trifluoride (3.5 equiv.) was added portionwise under vigorous stirring. The resulting reaction mixture was stirred at −78° C. for 3 hrs, Quenched the reaction with sat NaHCO$_3$ and extracted with DCM. The organic layer was washed with Brine, filtered over Na$_2$SO$_4$ and concentrated. The residue was purified by PREP HPLC to yield 4-(fluoromethyl)-3-(2-morpholinopyridin-4-yl)-N-(3-(trifluoromethyl)phenyl)benzamide in 16% yield. $^1$H NMR (400 MHz, <cd3od>) δ ppm 3.68 (d, J=5.09 Hz, 4H), 3.86 (d, J=5.09

Hz, 4H), 5.40 (s, 1H), 5.52 (s, 1H), 7.01-7.11 (m, 1H), 7.24-7.31 (m, 1H), 7.41-7.48 (m, 1H), 7.52-7.60 (m, 1H), 7.77-7.83 (m, 1H), 7.91-7.98 (m, 1H), 7.99-8.04 (m, 1H), 8.07-8.19 (m, 3H). LC/MS (m/z)=460.1 (MH$^+$), R$_f$=0.85 min.

Synthesis of 4-(2-chloropyridin-4-yl)morpholine

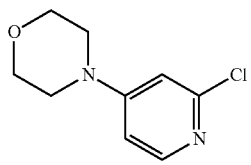 [SMILES: Clc1cc(N2CCOCC2)ccn1]

To a solution of triethylamine (1.0 equiv.) and 2,4-dichloropyridine (1.0 equiv.) at RT was added morpholine (1.0 equiv) in one portion, the resulting mixture was then stirred at RT for 45 hr. LCMS analysis indicated the formation of the desired product (M+H=199, Rt=0.29 min, major) and the undesired isomer (M+H=199, Rt=0.33 min, minor). The reaction mixture was concentrated in vacuo and purified via ISCO to yield 4-(2-chloropyridin-4-yl)morpholine as a light brown solid (28%). LCMS (m/z) (M+H)=299.0, Rt=0.29 min. 1H NMR (400 MHz, <cdcl3>) δ ppm 3.18-3.37 (m, 4H) 3.72-3.91 (m, 4H) 6.51-6.61 (m, 1H) 6.61-6.69 (m, 1H) 8.05 (d, J=6.26 Hz, 1H)

Example 111: N-(4-methyl-3-(4-morpholinopyridin-2-yl)phenyl)-3-(trifluoromethyl)benzamide

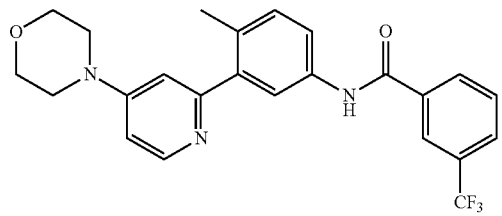 [SMILES: Cc1ccc(NC(=O)c2cccc(C(F)(F)F)c2)cc1-c1cc(N2CCOCC2)ccn1]

To a solution of 4-(2-chloropyridin-4-yl)morpholine (1.0 equiv.) and Intermediate A (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 20 min in the microwave. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(4-methyl-3-(4-morpholinopyridin-2-yl)phenyl)-3-(trifluoromethyl)benzamide was isolated as the TFA salt in 16% yield. $^1$H NMR (400 MHz, <dmso>) δ ppm 2.17-2.30 (m, 3H) 7.17-7.29 (m, 2H) 7.44 (d, J=8.22 Hz, 1H) 7.74-7.86 (m, 2H) 7.93 (d, J=1.96 Hz, 1H) 7.99 (d, J=7.83 Hz, 1H) 8.17-8.41 (m, 3H) 10.68 (s, 1H) 13.74 (br. s., 1H). LCMS (m/z) (M+H)=442.3, Rt=0.73 min.

Synthesis of 4,4'-(4-bromopyridine-2,6-diyl)dimorpholine

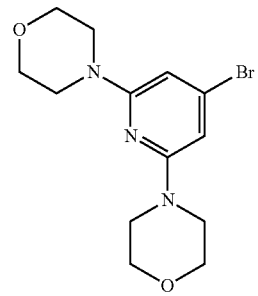 [SMILES: Brc1cc(N2CCOCC2)nc(N2CCOCC2)c1]

To a solution of Morpholine (5.0 equiv.) and 4-bromo-2,6-dichloropyridine (1.0 equiv.) in DMF (0.275 M) was added cesium carbonate (2.0 equiv.). The mixture was heated at 100° C. for 45 hours. LCMS analysis indicated formation of several products including the desired (M+H=288, Rt=0.87 min). The reaction mixture was then concentrated in vacuo to yield a glassy foam. Water was then added, and the mixture was extracted with ethyl acetate, and the combined extracts were washed with brine, dried over magnesium sulfate, filtered, and concentrated. The residue was chromatographed via ISCO to provide 4,4'-(4-bromopyridine-2,6-diyl)dimorpholine (44%, 80% purity by LC) as a white crystalline solid. LCMS (m/z) (M+H)=288.0, Rt=0.87 min.

Example 112: 3-(2,6-dimorpholinopyridin-4-yl)-4-methyl-N-(3-(trifluoromethyl)phenyl)benzamide

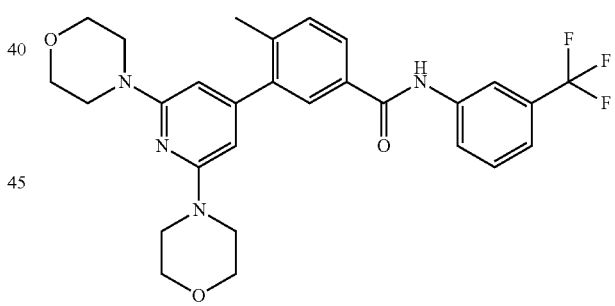

To a solution of 4-bromo-2,6-dichloropyridine (1.0 equiv.) and Intermediate D (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 20 min in the microwave. The reaction was quenched with water and extracted with ethyl acetate. The combined organic phase was dried with sodium sulfate, filtered and concentrated. The crude material was purified via preparative reverse phase HPLC. Upon lyophilization of the pure fractions, 3-(2,6-dimorpholinopyridin-4-yl)-4-methyl-N-(3-(trifluoromethyl)phenyl)benzamide was isolated as the TFA salt in 8% yield. LCMS (m/z) (M+H)=527.3, Rt=1.07 min. 1H NMR (400 MHz, <dmso>) δ ppm 1.27 (s, 2H) 2.31 (s, 3H) 3.53-3.71 (m, 16H) 6.08 (s, 2H) 7.30-7.72 (m, 6H) 7.80-7.98 (m, 2H) 8.22 (s, 2H) 10.44 (s, 1H).

Synthesis of 4-(6-chloro-4-iodopyridin-2-yl)morpholine

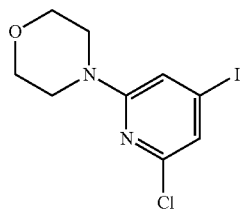 [SMILES: Clc1cc(I)cc(N2CCOCC2)n1]

To a solution of triethylamine (1.0 equiv.) and 2,6-dichloro-4-iodopyridine (1.0 equiv.) at RT was added morpholine (1.0 equiv) in one portion, the resulting mixture was then heated in an oil bath at 100° C. for 18 hours. LCMS analysis indicated the formation of the desired product (M+H=324.9/326.8, Rt=0.98 min). Water was then added, and the mixture was extracted with ethyl acetate, and the combined extracts were washed with brine, dried over magnesium sulfate, filtered, and concentrated. The residue was chromatographed via ISCO to yield 4-(6-chloro-4-iodopyridin-2-yl)morpholine as a light brown solid (63%). LCMS (m/z) (M+H)=324.9/326.8, Rt=0.98 min.

Synthesis of N-(3-(2-chloro-6-morpholinopyridin-4-yl)-4-methylphenyl)-3-(trifluoromethyl)benzamide

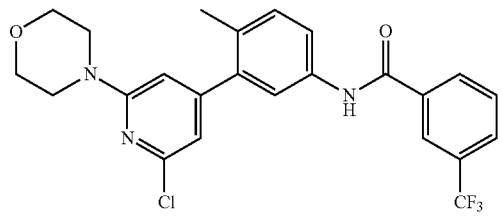

To a solution of 4-(6-chloro-4-iodopyridin-2-yl)morpholine (1.0 equiv.) and Intermediate A (1.2 equiv.) in DME and 2M sodium carbonate (3:1, 0.08 M) was added PdCl$_2$(dppf)-DCM adduct (0.1 equiv.) in a vial equipped with a stir bar. The reaction was heated to 80° C. for 18 hours. The reaction was quenched with water and extracted with ethyl acetate. The combined organic phase was dried with sodium sulfate, filtered and concentrated. The residue was chromatographed via ISCO to yield N-(3-(2-chloro-6-morpholinopyridin-4-yl)-4-methylphenyl)-3-(trifluoromethyl)benzamide as a light brown solid (>100%, 90% purity by UV). LCMS (m/z) (M+H)=476.0, Rt=1.16 min.

Example 113: N-(4-methyl-3-(2-(1-methyl-1H-pyrazol-4-yl)-6-morpholinopyridin-4-yl)-3-phenyl)-3-(trifluoromethyl)benzamide

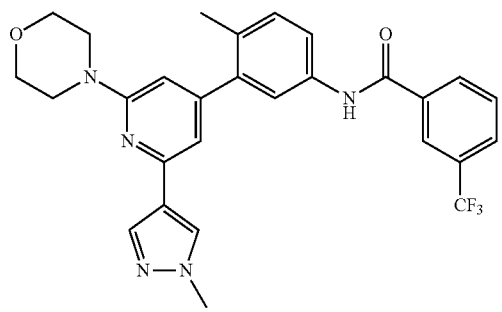 [SMILES: Cc1ccc(NC(=O)c2cccc(C(F)(F)F)c2)cc1-c1cc(-c2cnn(C)c2)nc(N2CCOCC2)c1]

To a solution of N-(3-(2-chloro-6-morpholinopyridin-4-yl)-4-methylphenyl)-3-(trifluoromethyl)benzamide (1.0 equiv.), 1-methyl-4-pyrazole-1H-boronic acid pinacol ester (2.0 equiv.), potassium fluoride (3.0 equiv.), and P(t-Bu)$_3$ (0.1 equiv./1.0 M in PhMe) in THF and water (1:1, 0.12 M) was added Pd$_2$(dba)$_3$ (0.1 equiv.) in a nitrogen purged microwave vial equipped with a stir bar. The reaction was heated to 80° C. for 2 hours. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(4-methyl-3-(2-(1-methyl-1H-pyrazol-4-yl)-6-morpholinopyridin-4-yl)phenyl)-3-(trifluoromethyl)benzamide was isolated as the TFA salt in 6% yield. 1H NMR (400 MHz, <cd3od>) δ ppm 2.33 (s, 3H) 3.64-3.69 (m, 4H) 3.82-3.88 (m, 4H) 3.96 (s, 3H) 6.79 (s, 1H) 7.08 (s, 1H) 7.35 (d, J=8.61 Hz, 1H) 7.62 (dd, J=8.41, 2.15 Hz, 1H) 7.70-7.77 (m, 2H) 7.90 (d, J=7.83 Hz, 1H) 8.04 (s, 1H) 8.18-8.24 (m, 2H) 8.26 (s, 1H). LCMS (m/z) (M+H)=522.1, Rt=0.89 min.

Synthesis of 3-(2-(3,6-dihydro-2H-pyran-4-yl)-6-morpholinopyridin-4-yl)-4-methylaniline

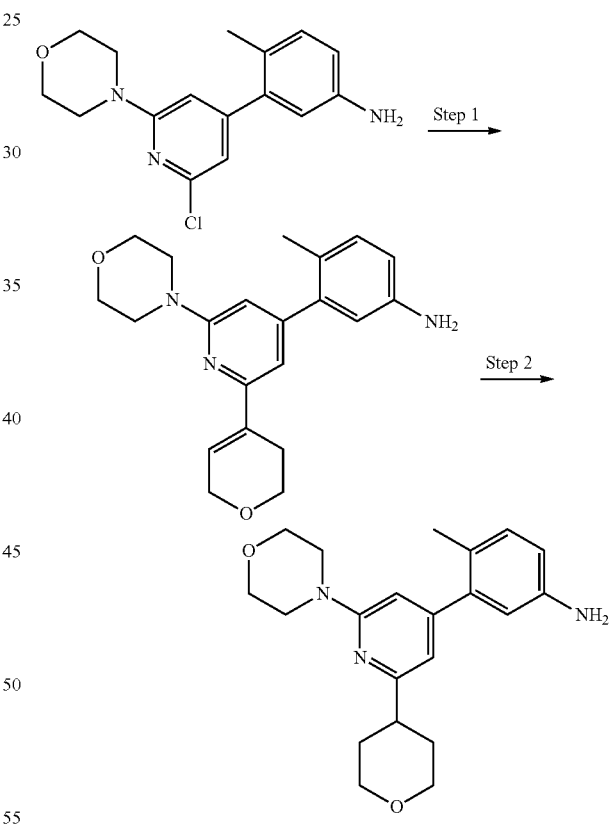

Step 1:
To a solution of 3-(2-chloro-6-morpholinopyridin-4-yl)-4-methylaniline (1.0 equiv.) and 2-(3,6-dihydro-2H-pyran-4-yl)-4,4,5,5-tetramethyl-1,3,2-dioxaborolane (1.2 equiv.) in DME and 2M sodium carbonate (3:1, 0.1 M) was added PdCl2(dppf)-DCM adduct (0.1 equiv.). The solution was heated to 100 C for 5 hours. Upon cooling to room temperature, the solution was partitioned between water and ethyl acetate, the organic phase was dried with sodium sulfate, filtered and concentrated. The crude material was purified via silica gel column chromatography eluting with 0-50% ethyl acetate and heptanes). The pure fractions were concentrated to yield 3-(2-(3,6-dihydro-2H-pyran-4-yl)-6-morpholinopyridin-4-yl)-4-methylaniline in 69% yield. LCMS (m/z) (M+H)=352.3, Rt=0.50 min.

Step 2:

To a solution of 3-(2-(3,6-dihydro-2H-pyran-4-yl)-6-morpholinopyridin-4-yl)-4-methylaniline (1.0 equiv.) in degassed ethanol (0.09 M) was added Pd/C (0.1 equiv.) and the solution was stirred under a hydrogen balloon for 1 h. Upon completion, the solution was filtered through Celite, and the filtrate was concentrated to dryness to give 4-methyl-3-(2-morpholino-6-(tetrahydro-2H-pyran-4-yl)pyridin-4-yl)aniline as desired product in 87% yield. LCMS (m/z) (M+H)=354.3, Rt=0.42 min.

Example 114: 3-(2-cyanopropan-2-yl)-N-(4-methyl-3-(2-morpholino-6-(tetrahydro-2H-pyran-4-yl)pyridin-4-yl)phenyl)benzamide

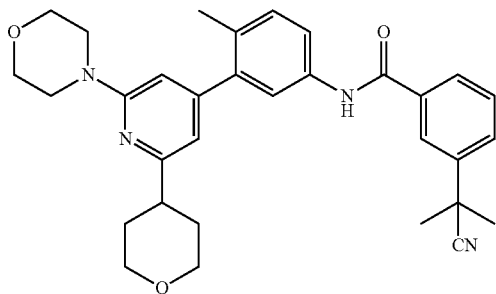 [SMILES: Cc1ccc(NC(=O)c2cccc(C(C)(C)C#N)c2)cc1-c1cc(C2CCOCC2)nc(N2CCOCC2)c1]

$^1$H NMR (400 MHz, <cd3od>) δ ppm 1.79 (s, 6H) 1.85-1.96 (m, 4H) 2.31 (s, 3H) 3.05-3.17 (m, 1H) 3.48-3.62 (m, 2H) 3.66-3.76 (m, 4H) 3.82-3.92 (m, 4H) 4.07 (d, J=11.35 Hz, 2H) 6.89 (s, 1H) 7.06 (s, 1H) 7.36 (d, J=8.22 Hz, 1H) 7.54-7.64 (m, 2H) 7.77 (d, J=5.09 Hz, 2H) 7.91 (d, J=7.83 Hz, 1H) 8.09 (s, 1H). LCMS (m/z) (M+H)=525.3, Rt=0.82 min.

Synthesis of N-(3-(2,6-difluoropyridin-4-yl)-4-methylphenyl)-3-(trifluoromethyl)benzamide

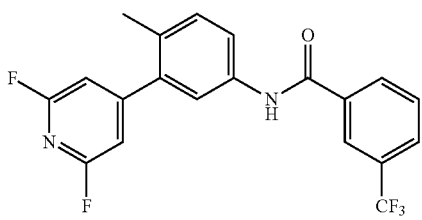 [SMILES: Cc1ccc(NC(=O)c2cccc(C(F)(F)F)c2)cc1-c1cc(F)nc(F)c1]

To a solution of (2,6-difluoropyridin-4-yl)boronic acid (1.5 equiv.) and Intermediate X (1.0 equiv.) in DME and 2M sodium carbonate (3:1, 0.2 M) was added PdCl$_2$(dppf)-DCM adduct (0.1 equiv.) in a vial equipped with a stir bar. The reaction was heated to 80° C. for 18 hours. The reaction was quenched with water and extracted with ethyl acetate. The combined organic phase was dried with sodium sulfate, filtered and concentrated. The residue was chromatographed via ISCO to yield N-(3-(2,6-difluoropyridin-4-yl)-4-methylphenyl)-3-(trifluoromethyl)benzamide as a light brown solid (37%). LCMS (m/z) (M+H)=393.0, Rt=1.09 min.

Synthesis of N-(3-(2-fluoro-6-morpholinopyridin-4-yl)-4-methylphenyl)-3-(trifluoromethyl)benzamide

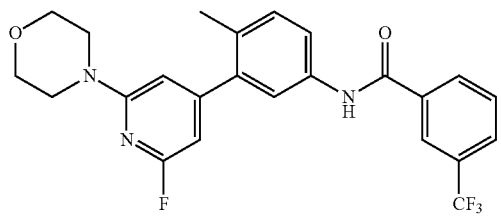

To a solution of triethylamine (3.0 equiv.) and N-(3-(2,6-difluoropyridin-4-yl)-4-methylphenyl)-3-(trifluoromethyl)benzamide (1.0 equiv.) at RT in MeOH (0.12 M) was added morpholine (2.0 equiv) in one portion, the resulting mixture was then heated at 55° C. for 8 hours. LCMS analysis indicated 90% conversion to the desired product (M+H=460.1, Rt=0.43 min/non-polar). Water was then added, and the mixture was extracted with ethyl acetate, and the combined extracts were washed with brine, dried over magnesium sulfate, filtered, and concentrated to yield N-(3-(2-fluoro-6-morpholinopyridin-4-yl)-4-methylphenyl)-3-(trifluoromethyl)benzamide as a light brown solid (>100%). LCMS (m/z) (M+H)=460.1, Rt=0.43 min/non-polar.

Example 115: N-(3-(2-((2-hydroxyethyl)amino)-6-morpholinopyridin-4-yl)-4-methylphenyl)-3-(trifluoromethyl)benzamide

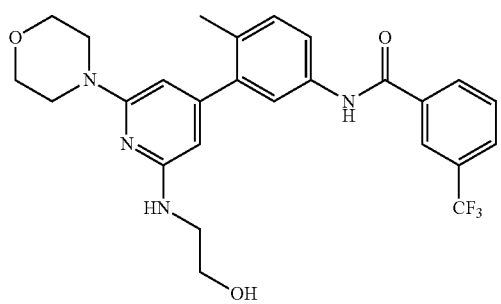 [SMILES: Cc1ccc(NC(=O)c2cccc(C(F)(F)F)c2)cc1-c1cc(NCCO)nc(N2CCOCC2)c1]

In a nitrogen purged microwave vial equipped with a stir bar N-(3-(2-fluoro-6-morpholinopyridin-4-yl)-4-methylphenyl)-3-(trifluoromethyl)benzamide (1.0 equiv.), in ethanolamine (276 equiv.) was heated to 180° C. for 15 minutes. The reaction was quenched with water and extracted with ethyl acetate. The combined organic phase was dried with sodium sulfate, filtered and concentrated. The crude material was purified via preparative reverse phase HPLC. Upon lyophilization of the pure fractions, N-(3-(2-((2-hydroxyethyl)amino)-6-morpholinopyridin-4-yl)-4-methylphenyl)-3-(trifluoromethyl)benzamide was isolated as the TFA salt in 27% yield. $^1$H NMR (400 MHz, <cd3od>) δ ppm 2.23 (s, 3H) 3.35-3.50 (m, 6H) 3.63-3.81 (m, 6H) 6.08-6.18 (m, 1H) 7.24 (d, J=8.22 Hz, 1H) 7.47 (dd, J=8.22, 2.35 Hz, 1H) 7.59-7.71 (m, 2H) 7.80 (d, J=7.83 Hz, 1H) 8.10 (d, J=7.83 Hz, 1H) 8.16 (s, 1H). LCMS (m/z) (M+H)=501.1, Rt=0.80 min.

Synthesis of 5-bromo-1-ethyl-3-(trifluoromethyl) pyridin-2(1H)-one

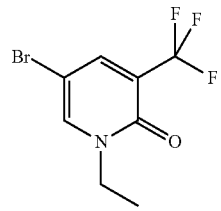

In a round bottom flask equipped with a stir bar and purged with nitrogen was added 5-bromo-3-(trifluoromethyl)pyridin-2-ol (1.0 equiv.), potassium carbonate (2.0 equiv.) and DMF (0.2 M). The mixture was stirred at room temperature and iodoethane (1.2 equiv.) was added via syringe. The mixture was warmed to 35° C. for 4 hours at which time LCMS indicated full conversion. The reaction was worked up by partitioning between water and ethyl acetate, the aqueous phase was extracted 3 more times with ethyl acetate, the organics were combined, washed with brine, dried with sodium sulfate, filtered and concentrated to yield 5-bromo-1-ethyl-3-(trifluoromethyl)pyridin-2(1H)-one (67%). $^1$H NMR (400 MHz, <cdcl3>) δ ppm 1.32-1.50 (m, 3H) 4.04 (q, J=7.17 Hz, 2H) 7.63 (br. s., 1H) 7.78 (br. s., 1H). LCMS (m/z) (M+H)=269.1/271.1, Rt=0.72 min

Example 116: 1-ethyl-N-(4-methyl-3-(1-methyl-5-morpholino-6-oxo-1,6-dihydropyridin-3-yl)phenyl)-6-oxo-5-(trifluoromethyl)-1,6-dihydropyridine-3-carboxamide

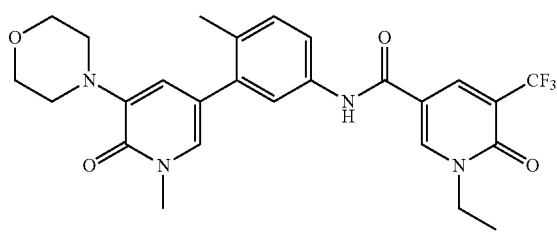 [SMILES: CCn1cc(C(=O)Nc2ccc(C)c(-c3cc(N4CCOCC4)c(=O)n(C)c3)c2)cc(C(F)(F)F)c1=O]

In a microwave tube was added 5-(5-amino-2-methylphenyl)-1-methyl-3-morpholinopyridin-2(1H)-one (1.0 equiv.), 5-bromo-1-ethyl-3-(trifluoromethyl)pyridin-2(1H)-one (2.0 equiv.), PdCl$_2$(dppf).CH$_2$Cl$_2$ adduct (0.1 equiv.), Mo(CO)6 (1.0 equiv.), and THF (0.3 M). The mixture was capped and stirred while DBU (3.0 equiv.) was added, fizzing occurred and the tube was subsequently heated in the microwave at 150° C. for 15 min at which time LCMS indicated full conversion to product (M+H=517). The reaction was filtered, concentrated, and purified via preparative HPLC to yield 1-ethyl-N-(4-methyl-3-(1-methyl-5-morpholino-6-oxo-1,6-dihydropyridin-3-yl)phenyl)-6-oxo-5-(trifluoromethyl)-1,6-dihydropyridine-3-carboxamide (15% yield). $^1$H NMR (400 MHz, <cd3od>) δ ppm 1.42 (t, J=7.24 Hz, 3H) 2.30 (s, 3H) 3.08-3.21 (m, 4H) 3.64 (s, 3H) 3.80-3.92 (m, 4H) 4.16 (q, J=7.04 Hz, 2H) 6.93 (d, J=1.96 Hz, 1H) 7.28 (d, J=8.22 Hz, 1H) 7.34 (d, J=1.96 Hz, 1H) 7.47-7.60 (m, 2H) 8.48 (d, J=1.96 Hz, 1H) 8.70 (d, J=2.35 Hz, 1H). LCMS (m/z) (M+H)=517.1, Rt=0.81 min.

Example 117: Synthesis of N-(4-methyl-3-(1-methyl-5-morpholino-6-oxo-1,6-dihydropyridin-3-yl)phenyl)-3-(trifluoromethyl)benzamide

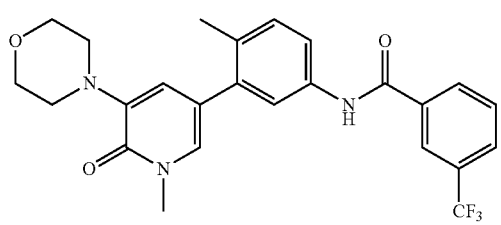

To a solution of 5-bromo-1-methyl-3-morpholinopyridin-2(1H)-one (1.0 equiv.) and Intermediate A (1.2 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 120° C. for 10 min in the microwave. The organic phase was dried with sodium sulfate, filtered and concentrated. The crude material was purified via preparative reverse phase HPLC. Upon lyophilization of the pure fractions, N-(4-methyl-3-(1-methyl-5-morpholino-6-oxo-1,6-dihydropyridin-3-yl)phenyl)-3-(trifluoromethyl)benzamide was isolated as the TFA salt in 11% yield. LCMS (m/z) (M+H)=472.2, Rt=0.87 min. $^1$H NMR (400 MHz, <cd3od>) δ ppm 2.30 (s, 3H) 3.13-3.21 (m, 4H) 3.64 (s, 3H) 3.81-3.92 (m, 4H) 7.01 (d, J=2.35 Hz, 1H) 7.29 (d, J=8.61 Hz, 1H) 7.39 (d, J=2.35 Hz, 1H) 7.57 (dd, J=8.22, 1.96 Hz, 1H) 7.62 (d, J=1.96 Hz, 1H) 7.69-7.77 (m, 1H) 7.89 (d, J=7.83 Hz, 1H) 8.19 (d, J=7.43 Hz, 1H) 8.25 (s, 1H).

The compounds listed below were prepared by methods similar to those described for the preparation of Example 117 using the corresponding aryl halide and intermediates (A-G).

Example 118: N-(4-methyl-3-(6-morpholinopyrazin-2-yl)phenyl)-3-(trifluoromethyl)benzamide

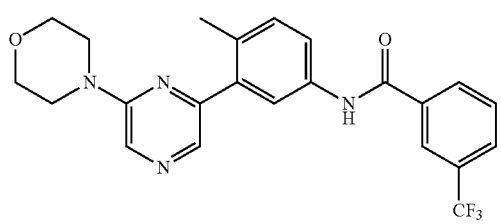 [SMILES: Cc1ccc(NC(=O)c2cccc(C(F)(F)F)c2)cc1-c1cncc(N2CCOCC2)n1]

$^1$H NMR (400 MHz, <cd3od>) δ ppm 2.40 (s, 3H) 3.60-3.73 (m, 4H) 3.75-3.88 (m, 4H) 7.33 (d, J=8.22 Hz, 1H) 7.59-7.78 (m, 2H) 7.81-7.96 (m, 2H) 8.02 (s, 1H) 8.14-8.40 (m, 3H). LCMS (m/z) (M+H)=443.2, Rt=0.93 min.

Example 119: N-(4-methyl-3-(4-methyl-6-morpholino-5-oxo-4,5-dihydropyrazin-2-yl)phenyl)-3-(trifluoromethyl)benzamide

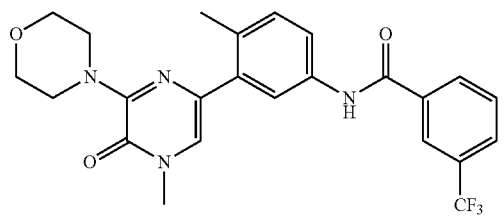

¹H NMR (400 MHz, <cd3od>) δ ppm 2.39 (s, 3H) 3.56 (s, 3H) 3.80 (s, 9H) 7.18 (s, 1H) 7.26 (d, J=8.22 Hz, 1H) 7.56 (dd, J=8.22, 2.35 Hz, 1H) 7.67-7.80 (m, 2H) 7.89 (d, J=7.83 Hz, 1H) 8.20 (d, J=7.83 Hz, 1H) 8.25 (s, 1H). LCMS (m/z) (M+H)=473.1, Rt=0.92 min.

Example 120: N-(4-methyl-3-(6-morpholino-5-oxo-4,5-dihydropyrazin-2-yl)phenyl)-3-(trifluoromethyl)benzamide

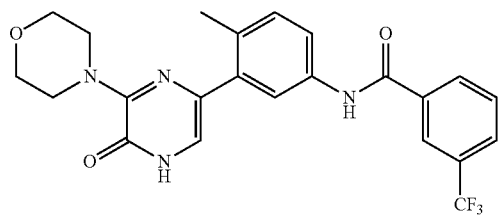

¹H NMR (400 MHz, <cd3od>) δ ppm 2.29 (s, 3H) 3.72 (d, J=4.70 Hz, 9H) 6.85 (s, 1H) 7.16 (d, J=8.22 Hz, 1H) 7.47 (dd, J=8.22, 2.35 Hz, 1H) 7.58-7.69 (m, 2H) 7.79 (d, J=7.83 Hz, 1H) 8.05-8.20 (m, 1H). LCMS (m/z) (M+H)=459.3, Rt=0.86 min.

Example 121: N-(6-methyl-5-(6-morpholino-5-oxo-4,5-dihydropyrazin-2-yl)pyridin-3-yl)-3-trifluoromethyl)benzamide

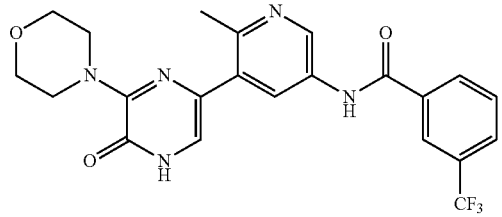

¹H NMR (400 MHz, <cd3od>) δ ppm 2.71 (s, 3H) 3.59-3.91 (m, 9H) 7.11 (s, 1H) 7.69 (t, J=7.83 Hz, 1H) 7.86 (d, J=7.83 Hz, 1H) 8.08-8.30 (m, 2H) 8.54 (d, J=2.35 Hz, 1H) 9.11 (d, J=1.96 Hz, 1H). LCMS (m/z) (M+H)=460.2, Rt=0.66 min.

Example 122: N-(3-(2-methoxy-5-morpholinopyridin-3-yl)-4-methylphenyl)-3-trifluoromethyl)benzamide

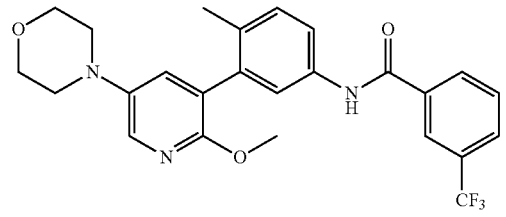 [SMILES: COc1ncc(N2CCOCC2)cc1-c1cc(NC(=O)c2cccc(C(F)(F)F)c2)ccc1C]

¹H NMR (400 MHz, <cd3od>) δ ppm 2.11 (s, 3H) 3.21 (dd, J=5.48, 3.91 Hz, 4H) 3.81-3.92 (m, 7H) 7.27 (d, J=8.22 Hz, 1H) 7.45 (d, J=2.74 Hz, 1H) 7.52-7.62 (m, 2H) 7.68-7.77 (m, 1H) 7.83-7.97 (m, 2H) 8.10-8.36 (m, 2H). LCMS (m/z) (M+H)=472.2, Rt=0.93 min.

Example 123: N-(4-methyl-3-(1-methyl-5-morpholino-2-oxo-1,2-dihydropyridin-3-yl)phenyl)-3-(trifluoromethyl)benzamide

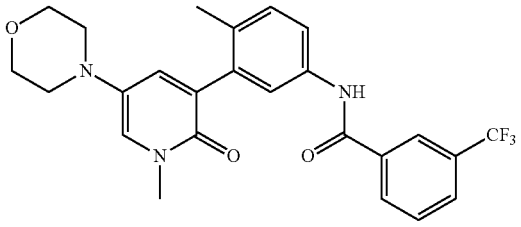 [SMILES: Cc1ccc(NC(=O)c2cccc(C(F)(F)F)c2)cc1-c1cc(N2CCOCC2)cn(C)c1=O]

¹H NMR (400 MHz, <cd3od>) δ ppm 2.17 (s, 3H) 2.87-3.06 (m, 4H) 3.63 (s, 3H) 3.74-3.87 (m, 4H) 7.14-7.30 (m, 2H) 7.43-7.63 (m, 3H) 7.67-7.77 (m, 1H) 7.88 (d, J=7.83 Hz, 1H) 8.12-8.28 (m, 1H). LCMS (m/z) (M+H)=472.3, Rt=0.80 min.

Example 124: N-(1',2-dimethyl-5'-morpholino-2'-oxo-1',2'-dihydro-[3,3'-bipyridin]-5-yl)-3-(trifluoromethyl)benzamide

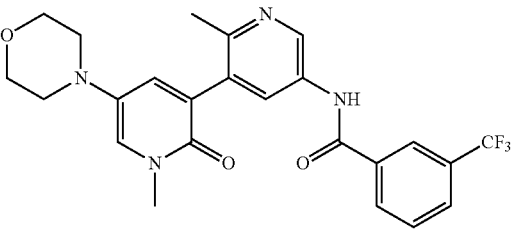 [SMILES: Cc1ncc(NC(=O)c2cccc(C(F)(F)F)c2)cc1-c1cc(N2CCOCC2)cn(C)c1=O]

¹H NMR (400 MHz, <cd3od>) δ ppm 2.61 (s, 3H) 2.92-3.08 (m, 4H) 3.67 (s, 3H) 3.77-3.92 (m, 4H) 7.42 (d, J=3.13 Hz, 1H) 7.68-7.83 (m, 2H) 7.96 (d, J=7.83 Hz, 1H) 8.17-8.37 (m, 2H) 8.47 (d, J=2.35 Hz, 1H) 9.37 (d, J=2.35 Hz, 1H). LCMS (m/z) (M+H)=473.2, Rt=0.63 min.

Example 125: N-(4-methyl-3-(5-morpholino-2-oxo-1,2-dihydropyridin-3-yl)phenyl)-3-(trifluoromethyl)benzamide

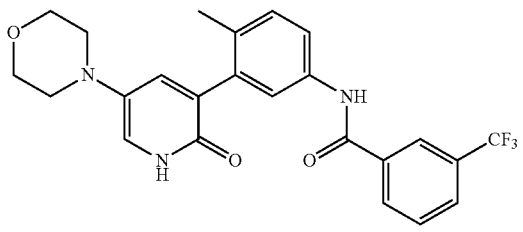 [SMILES: Cc1ccc(NC(=O)c2cccc(C(F)(F)F)c2)cc1-c1cc(N2CCOCC2)c[nH]c1=O]

¹H NMR (400 MHz, <cd3od>) δ ppm 2.11 (s, 3H) 2.84-2.98 (m, 4H) 3.66-3.79 (m, 4H) 6.93 (d, J=3.13 Hz, 1H) 7.18 (d, J=8.22 Hz, 1H) 7.39-7.55 (m, 3H) 7.57-7.68 (m, 1H) 7.79 (d, J=7.43 Hz, 1H) 8.02-8.22 (m, 1H). LCMS (m/z) (M+H)=458.2, Rt=0.78 min.

Example 126: N-(3-(6-methoxy-5-morpholinopyridin-3-yl)-4-methylphenyl)-3-(trifluoromethyl)benzamide

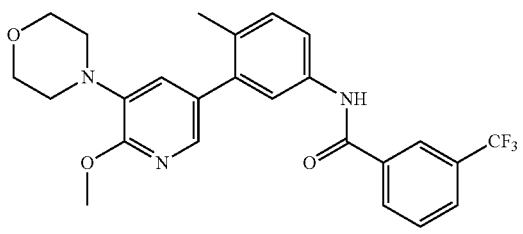 [SMILES: COc1ncc(-c2cc(NC(=O)c3cccc(C(F)(F)F)c3)ccc2C)cc1N1CCOCC1]

1H NMR (400 MHz, <cd3od>) δ ppm 2.27 (s, 3H) 3.04-3.22 (m, 4H) 3.81-3.93 (m, 4H) 4.04 (s, 3H) 7.27-7.34 (m, 2H) 7.61 (dd, J=4.11, 2.15 Hz, 2H) 7.68-7.76 (m, 1H) 7.80 (d, J=1.96 Hz, 1H) 7.88 (d, J=7.83 Hz, 1H) 8.20 (d, J=7.83 Hz, 1H) 8.25 (s, 1H). LCMS (m/z) (M+H)=472.4, Rt=1.04 min.

Example 127: N-(6'-methoxy-2-methyl-5'-morpholino-[3,3'-bipyridin]-5-yl)-3-(trifluoromethyl)benzamide

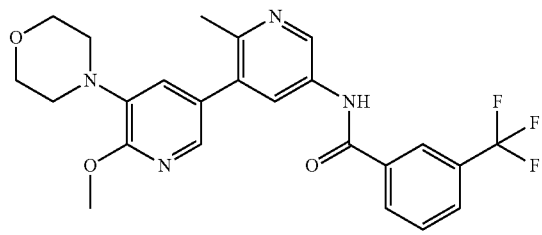 [SMILES: COc1ncc(-c2cc(NC(=O)c3cccc(C(F)(F)F)c3)cnc2C)cc1N1CCOCC1]

1H NMR (400 MHz, <cd3od>) δ ppm 2.67 (s, 3H) 3.09-3.18 (m, 4H) 3.80-3.91 (m, 4H) 4.05 (s, 3H) 7.31 (d, J=1.96 Hz, 1H) 7.78 (t, J=7.83 Hz, 1H) 7.88 (d, J=1.96 Hz, 1H) 7.96 (d, J=7.83 Hz, 1H) 8.28 (d, J=8.22 Hz, 1H) 8.34 (s, 1H) 8.43 (d, J=2.35 Hz, 1H) 9.32 (d, J=2.35 Hz, 1H). LCMS (m/z) (M+H)=473.3, Rt=0.72 min.

Example 128: 2-(2-cyanopropan-2-yl)-N-(3-(6-methoxy-5-morpholinopyridin-3-yl)-4-methylphenyl)isonicotinamide

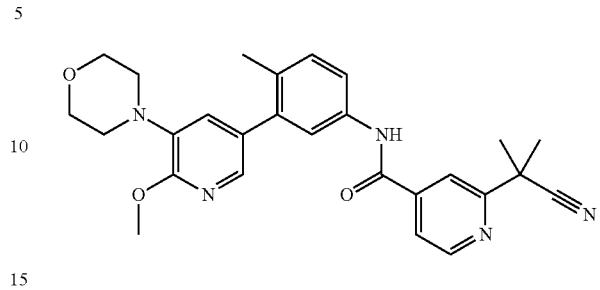

¹H NMR (400 MHz, <cd3od>) δ ppm 1.81 (s, 6H) 2.27 (s, 3H) 3.09-3.17 (m, 4H) 3.81-3.89 (m, 4H) 4.02 (s, 3H) 7.24 (d, J=1.96 Hz, 1H) 7.32 (d, J=8.22 Hz, 1H) 7.60 (d, J=1.96 Hz, 1H) 7.63 (dd, J=8.22, 2.35 Hz, 1H) 7.76 (d, J=1.96 Hz, 1H) 7.81 (dd, J=4.89, 1.37 Hz, 1H) 8.06 (s, 1H) 8.75 (d, J=5.09 Hz, 1H). LCMS (m/z) (M+H)=472.4, Rt=0.87 min.

Example 129: 2-(2-cyanopropan-2-yl)-N-(6'-methoxy-2-methyl-5'-morpholino-[3,3'-bipyridin]-5-yl)isonicotinamide

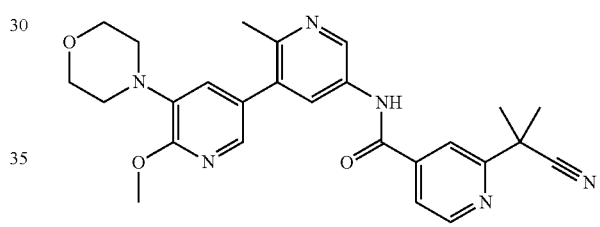

¹H NMR (400 MHz, <cd3od>) δ ppm 1.82 (s, 6H) 2.69 (s, 3H) 3.07-3.21 (m, 4H) 3.78-3.92 (m, 4H) 4.05 (s, 3H) 7.31 (d, J=1.96 Hz, 1H) 7.82-7.94 (m, 2H) 8.14 (s, 1H) 8.45 (d, J=2.35 Hz, 1H) 8.82 (d, J=5.09 Hz, 1H) 9.34 (d, J=2.35 Hz, 1H). LCMS (m/z) (M+H)=473.3, Rt=0.62 min.

Example 130: N-(2-methyl-5'-morpholino-6'-oxo-1'-(tetrahydro-2H-pyran-4-yl)-1',6'-dihydro-[3,3'-bipyridin]-5-yl)-3-(trifluoromethyl)benzamide

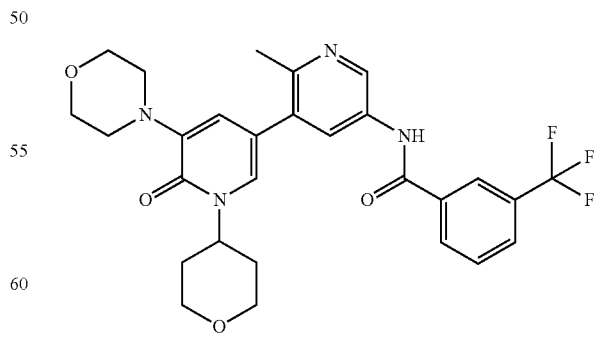

¹H NMR (400 MHz, <cd3od>) δ ppm 1.87 (dd, J=11.98, 2.15 Hz, 2H) 2.01 (qd, J=12.22, 4.52 Hz, 2H) 3.09-3.21 (m, 4H) 3.62 (td, J=11.77, 1.83 Hz, 2H) 3.79-3.91 (m, 4H) 4.10 (dd, J=11.27, 4.33 Hz, 2H) 5.19 (tt, J=12.06, 4.00 Hz, 1H)

6.94 (d, J=2.25 Hz, 1H) 7.55 (d, J=2.30 Hz, 1H) 7.74-7.83 (m, 1H) 7.96 (dd, J=7.87, 0.68 Hz, 1H) 8.27 (d, J=7.92 Hz, 1H) 8.34 (d, J=0.64 Hz, 1H) 8.40 (d, J=2.40 Hz, 1H) 9.22 (d, J=2.40 Hz, 1H). LCMS (m/z) (M+H)=543.1, Rt=0.70 min.

Example 131: N-(2-methyl-5'-morpholino-6'-((tetrahydro-2H-pyran-4-yl)oxy)-[3,3'-bipyridin]-5-yl)-3-(trifluoromethyl)benzamide

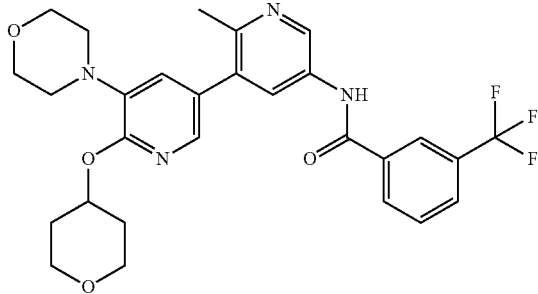 [SMILES: Cc1ncc(NC(=O)c2cccc(C(F)(F)F)c2)cc1-c1cnc(OC2CCOCC2)c(N2CCOCC2)c1]

¹H NMR (400 MHz, <cd3od>) δ ppm 1.77-1.91 (m, 2H) 2.06-2.20 (m, 2H) 2.71 (s, 3H) 3.12-3.22 (m, 4H) 3.67 (ddd, J=11.59, 8.22, 3.28 Hz, 2H) 3.81-3.91 (m, 4H) 3.92-4.03 (m, 2H) 5.45 (tt, J=7.92, 3.91 Hz, 1H) 7.33 (d, J=2.20 Hz, 1H) 7.74-7.82 (m, 1H) 7.87 (d, J=2.15 Hz, 1H) 7.93-8.00 (m, 1H) 8.29 (d, J=7.87 Hz, 1H) 8.35 (d, J=1.22 Hz, 1H) 8.50 (d, J=2.30 Hz, 1H) 9.40 (d, J=2.40 Hz, 1H). LCMS (m/z) (M+H)=543.1, Rt=0.80 min.

Example 132: N-(4-methyl-3-(5-morpholino-6-((tetrahydro-2H-pyran-4-yl)oxy)pyridin-3-yl)phenyl)-3-(trifluoromethyl)benzamide

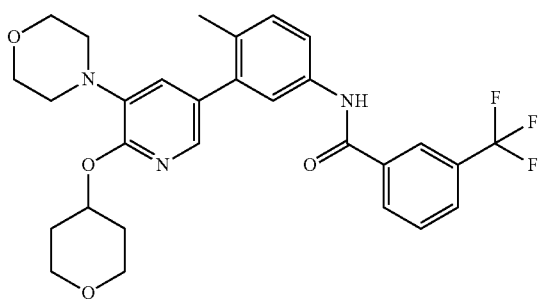 [SMILES: Cc1ccc(NC(=O)c2cccc(C(F)(F)F)c2)cc1-c1cnc(OC2CCOCC2)c(N2CCOCC2)c1]

¹H NMR (400 MHz, <cd3od>) δ 1.84 (dtd, J=12.67, 8.34, 8.34, 3.91 Hz, 2H) 2.03-2.20 (m, 2H) 2.27 (s, 3H) 3.06-3.22 (m, 4H) 3.67 (ddd, J=11.64, 8.31, 3.13 Hz, 2H) 3.78-3.91 (m, 4H) 3.92-4.04 (m, 2H) 5.39 (tt, J=7.83, 3.91 Hz, 1H) 7.24 (d, J=1.96 Hz, 1H) 7.30 (d, J=7.83 Hz, 1H) 7.56-7.66 (m, 2H) 7.68-7.78 (m, 2H) 7.88 (d, J=7.83 Hz, 1H) 8.20 (d, J=7.83 Hz, 1H) 8.25 (s, 1H). LCMS (m/z) (M+H)=542.1, Rt=1.06 min.

Example 133: N-(1'-isopropyl-2-methyl-5'-morpholino-6'-oxo-1',6'-dihydro-[3,3'-bipyridin]-5-yl)-3-(trifluoromethyl)benzamide

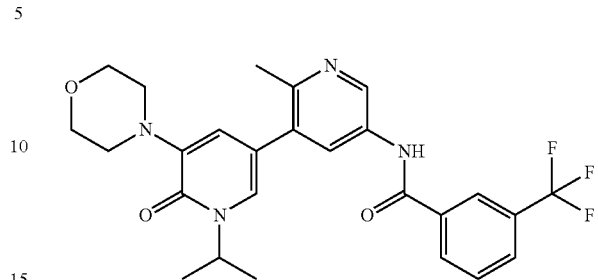

¹H NMR (400 MHz, <cd3od>) δ ppm 1.45 (d, J=6.80 Hz, 6H) 2.70 (s, 3H) 3.12-3.23 (m, 4H) 3.81-3.95 (m, 4H) 5.35 (quin, J=6.87 Hz, 1H) 6.95 (d, J=2.15 Hz, 1H) 7.56 (d, J=2.10 Hz, 1H) 7.80 (t, J=7.73 Hz, 1H) 7.98 (d, J=7.19 Hz, 1H) 8.30 (d, J=7.87 Hz, 1H) 8.36 (s, 1H) 8.41 (d, J=2.35 Hz, 1H) 9.26 (d, J=2.20 Hz, 1H). LCMS (m/z) (M+H)=501.3, Rt=0.78 min.

Example 134: N-(6'-isopropoxy-2-methyl-5'-morpholino-[3,3'-bipyridin]-5-yl)-3-(trifluoromethyl)benzamide

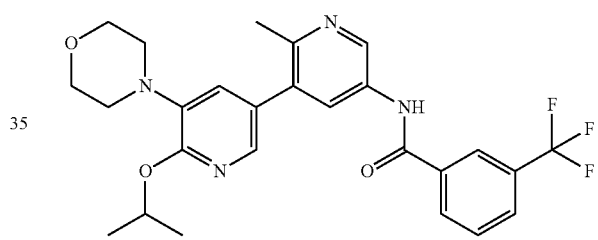

¹H NMR (400 MHz, <cd3od>) δ ppm 1.43 (d, J=6.16 Hz, 6H) 2.69 (s, 3H) 3.12-3.22 (m, 4H) 3.82-3.92 (m, 4H) 5.47 (quin, J=6.17 Hz, 1H) 7.30 (d, J=2.10 Hz, 1H) 7.76-7.84 (m, 1H) 7.87 (d, J=2.01 Hz, 1H) 7.98 (d, J=7.87 Hz, 1H) 8.30 (d, J=7.68 Hz, 1H) 8.36 (s, 1H) 8.43 (d, J=2.35 Hz, 1H) 9.31 (d, J=2.35 Hz, 1H). LCMS (m/z) (M+H)=501.3, Rt=0.90 min.

Example 135: N-(3-(1-isopropyl-5-morpholino-6-oxo-1,6-dihydropyridin-3-yl)-4-methylphenyl)-3-(trifluoromethyl)benzamide

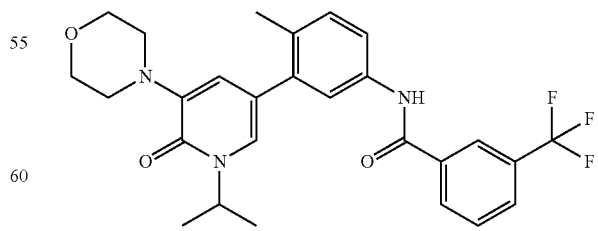

¹H NMR (400 MHz, <cd3od>) δ ppm 1.44 (d, J=6.80 Hz, 6H) 2.32 (s, 3H) 3.12-3.23 (m, 4H) 3.84-3.93 (m, 4H) 5.35 (quin, J=6.86 Hz, 1H) 6.98 (d, J=2.10 Hz, 1H) 7.32 (d, J=8.02 Hz, 1H) 7.39 (d, J=2.10 Hz, 1H) 7.58-7.66 (m, 2H)

7.71-7.79 (m, 1H) 7.91 (d, J=7.92 Hz, 1H) 8.23 (d, J=7.92 Hz, 1H) 8.28 (s, 1H). LCMS (m/z) (M+H)=500.3, Rt=1.02 min.

Example 136: N-(3-(6-isopropoxy-5-morpholinopyridin-3-yl)-4-methylphenyl)-3-(trifluoromethyl)benzamide

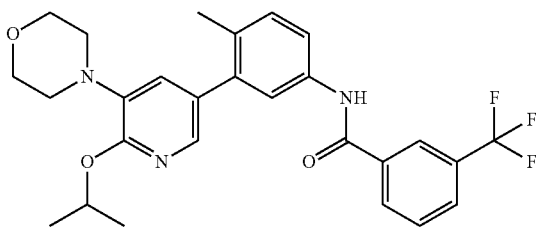 [SMILES: Cc1ccc(NC(=O)c2cccc(C(F)(F)F)c2)cc1-c1cnc(OC(C)C)c(N2CCOCC2)c1]

¹H NMR (400 MHz, <cd3od>) δ ppm 1.43 (d, J=6.16 Hz, 6H) 2.29 (s, 3H) 3.15-3.25 (m, 4H) 3.83-3.94 (m, 4H) 5.42 (spt, J=6.18 Hz, 1H) 7.27-7.35 (m, 2H) 7.59-7.66 (m, 2H) 7.70-7.77 (m, 1H) 7.79 (d, J=1.86 Hz, 1H) 7.90 (d, J=7.87 Hz, 1H) 8.22 (d, J=7.68 Hz, 1H) 8.27 (s, 1H). LCMS (m/z) (M+H)=500.4, Rt=1.17 min.

Example 137: 4-methyl-3-(1-methyl-5-morpholino-6-oxo-1,6-dihydropyridin-3-yl)-N-(3-(trifluoromethyl)phenyl)benzamide

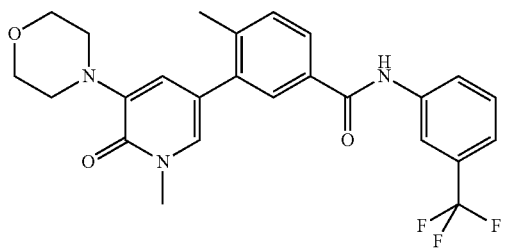 [SMILES: Cc1ccc(C(=O)Nc2cccc(C(F)(F)F)c2)cc1-c1cc(N2CCOCC2)c(=O)n(C)c1]

¹H NMR (400 MHz, <cd3od>) δ ppm 2.42 (s, 3H) 3.12-3.22 (m, 4H) 3.67 (s, 3H) 3.83-3.94 (m, 4H) 6.99 (d, J=2.25 Hz, 1H) 7.42 (d, J=2.25 Hz, 1H) 7.43-7.50 (m, 2H) 7.57 (t, J=8.02 Hz, 1H) 7.85 (d, J=2.01 Hz, 1H) 7.89 (dd, J=7.92, 2.01 Hz, 1H) 7.95 (d, J=8.22 Hz, 1H) 8.17 (s, 1H). LCMS (m/z) (M+H)=472.1, Rt=0.91 min.

Example 138: N-(1',2-dimethyl-5'-morpholino-6'-oxo-1',6'-dihydro-[3,3'-bipyridin]-5-yl)-3-(trifluoromethyl)benzamide

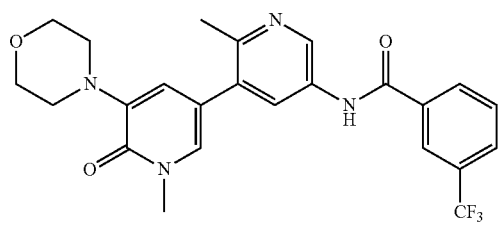 [SMILES: Cc1ncc(NC(=O)c2cccc(C(F)(F)F)c2)cc1-c1cc(N2CCOCC2)c(=O)n(C)c1]

¹H NMR (400 MHz, <cd3od>) δ ppm 2.71 (s, 3H) 3.12-3.21 (m, 4H) 3.65 (s, 3H) 3.82-3.90 (m, 4H) 6.96 (d, J=2.35 Hz, 1H) 7.53 (d, J=1.96 Hz, 1H) 7.74-7.83 (m, 1H) 7.96 (d, J=7.83 Hz, 1H) 8.28 (d, J=7.83 Hz, 1H) 8.34 (s, 1H) 8.45 (d, J=2.35 Hz, 1H) 9.27 (d, J=2.35 Hz, 1H). LCMS (m/z) (M+H)=473.3, Rt=0.64 min.

Example 139: 2-(tert-butyl)-N-(4-methyl-3-(1-methyl-5-morpholino-6-oxo-1,6-dihydropyridin-3-yl)phenyl)isonicotinamide

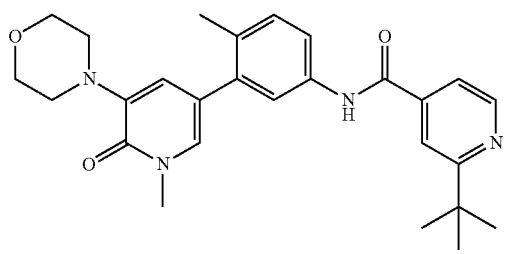 [SMILES: Cc1ccc(NC(=O)c2ccnc(C(C)(C)C)c2)cc1-c1cc(N2CCOCC2)c(=O)n(C)c1]

¹H NMR (400 MHz, <cd3od>) δ ppm 1.50 (s, 9H) 2.31 (s, 3H) 3.08-3.19 (m, 4H) 3.64 (s, 3H) 3.79-3.94 (m, 4H) 6.93 (d, J=1.96 Hz, 1H) 7.24-7.38 (m, 2H) 7.57-7.71 (m, 2H) 7.98 (d, J=5.48 Hz, 1H) 8.20 (s, 1H) 8.76 (d, J=5.87 Hz, 1H). LCMS (m/z) (M+H)=461.4, Rt=0.66 min.

Example 140: 2-(2-cyanopropan-2-yl)-N-(4-methyl-3-(1-methyl-5-morpholino-6-oxo-1,6-dihydropyridin-3-yl)phenyl)isonicotinamide

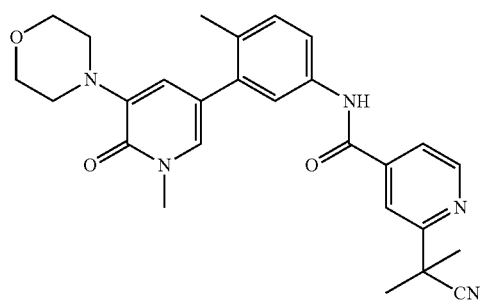 [SMILES: Cc1ccc(NC(=O)c2ccnc(C(C)(C)C#N)c2)cc1-c1cc(N2CCOCC2)c(=O)n(C)c1]

1H NMR (400 MHz, <cd3od>) δ ppm 1.81 (s, 6H) 2.31 (s, 3H) 3.10-3.23 (m, 4H) 3.64 (s, 3H) 3.82-3.95 (m, 4H) 7.01 (d, J=1.96 Hz, 1H) 7.30 (d, J=8.22 Hz, 1H) 7.40 (d, J=1.96 Hz, 1H) 7.58 (dd, J=8.22, 2.35 Hz, 1H) 7.63 (d, J=1.96 Hz, 1H) 7.80 (dd, J=5.09, 1.17 Hz, 1H) 8.06 (s, 1H) 8.76 (d, J=5.09 Hz, 1H). LCMS (m/z) (M+H)=472.2, Rt=0.73 min.

Example 141: 2-(2-cyanopropan-2-yl)-N-(1',2-dimethyl-5'-morpholino-6'-oxo-1',6'-dihydro-[3,3'-bipyridin]-5-yl)isonicotinamide

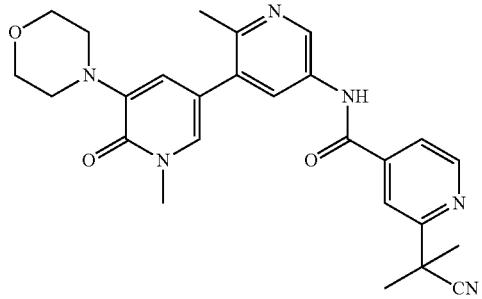 [SMILES: Cc1ncc(NC(=O)c2ccnc(C(C)(C)C#N)c2)cc1-c1cc(N2CCOCC2)c(=O)n(C)c1]

1H NMR (400 MHz, <cd3od>) δ ppm 1.78-1.86 (m, 6H) 2.70 (s, 3H) 3.16 (br. s., 4H) 3.65 (s, 3H) 3.85 (br. s., 4H) 6.90-6.99 (m, 1H) 7.49-7.56 (m, 1H) 7.82-7.89 (m, 1H) 8.09-8.16 (m, 1H) 8.38-8.45 (m, 1H) 8.78-8.85 (m, 1H) 9.20-9.26 (m, 1H). LCMS (m/z) (M+H)=473.2, Rt=0.54 min.

Example 142: N-(3-(1-(2-hydroxyethyl)-5-morpholino-6-oxo-1,6-dihydropyridin-3-yl)-4-methylphenyl)-3-(trifluoromethyl)benzamide

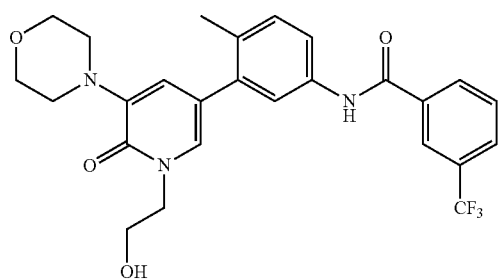 [SMILES: Cc1ccc(NC(=O)c2cccc(C(F)(F)F)c2)cc1-c1cc(N2CCOCC2)c(=O)n(CCO)c1]

¹H NMR (400 MHz, <cd3od>) δ ppm 2.31 (s, 3H) 3.13 (d, J=3.91 Hz, 4H) 3.80-3.95 (m, 6H) 4.17 (t, J=5.28 Hz, 2H) 6.93 (d, J=1.96 Hz, 1H) 7.26-7.33 (m, 2H) 7.54-7.63 (m, 2H) 7.72 (t, J=7.83 Hz, 1H) 7.89 (d, J=7.83 Hz, 1H) 8.20 (d, J=8.22 Hz, 1H) 8.25 (s, 1H). LCMS (m/z) (M+H)=502.2, Rt=0.78 min.

Example 143: 2-(2-cyanopropan-2-yl)-N-(3-(1-(2-hydroxyethyl)-5-morpholino-6-oxo-1,6-dihydropyridin-3-yl)-4-methylphenyl)isonicotinamide

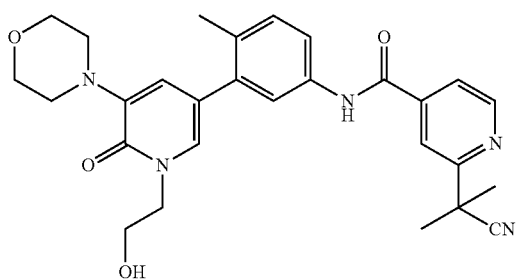 [SMILES: Cc1ccc(NC(=O)c2ccnc(C(C)(C)C#N)c2)cc1-c1cc(N2CCOCC2)c(=O)n(CCO)c1]

¹H NMR (400 MHz, <cd3od>) δ ppm 1.80 (s, 6H) 2.32 (s, 3H) 2.97-3.18 (m, 4H) 3.74-3.94 (m, 7H) 4.17 (t, J=5.28 Hz, 2H) 6.98 (d, J=2.35 Hz, 1H) 7.24-7.42 (m, 2H) 7.54-7.65 (m, 2H) 7.80 (dd, J=5.09, 1.17 Hz, 1H) 8.06 (s, 1H) 8.75 (d, J=5.09 Hz, 1H). LCMS (m/z) (M+H)=502.2, Rt=0.71 min.

Example 144: N-(1'-(2-hydroxyethyl)-2-methyl-5'-morpholino-6'-oxo-1',6'-dihydro-[3,3'-bipyridin]-5-yl)-3-(trifluoromethyl)benzamide

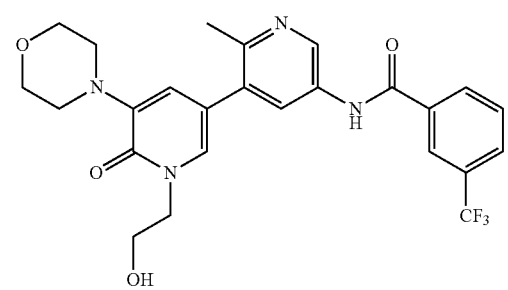 [SMILES: Cc1ncc(NC(=O)c2cccc(C(F)(F)F)c2)cc1-c1cc(N2CCOCC2)c(=O)n(CCO)c1]

¹H NMR (400 MHz, <cd3od>) δ ppm 2.72 (s, 3H) 3.07-3.20 (m, 4H) 3.80-3.99 (m, 6H) 4.19 (t, J=5.09 Hz, 2H) 6.98 (d, J=2.35 Hz, 1H) 7.50 (d, J=2.35 Hz, 1H) 7.78 (t, J=7.83 Hz, 1H) 7.96 (d, J=7.83 Hz, 1H) 8.28 (d, J=7.83 Hz, 1H) 8.34 (s, 1H) 8.47 (d, J=2.35 Hz, 1H) 9.30 (d, J=2.35 Hz, 1H). LCMS (m/z) (M+H)=503.2, Rt=0.63 min.

Example 145: N-(6'-(2-hydroxyethoxy)-2-methyl-5'-morpholino-[3,3'-bipyridin]-5-yl)-3-(trifluoromethyl)benzamide

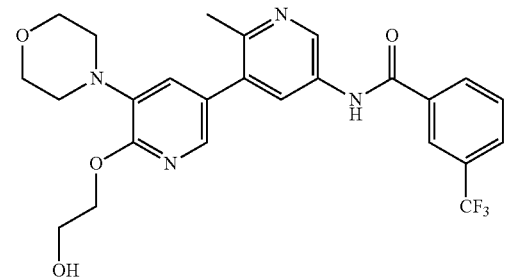 [SMILES: Cc1ncc(NC(=O)c2cccc(C(F)(F)F)c2)cc1-c1cnc(OCCO)c(N2CCOCC2)c1]

¹H NMR (400 MHz, <cd3od>) δ ppm 2.67 (s, 3H) 3.12-3.22 (m, 4H) 3.80-3.89 (m, 4H) 3.91-3.99 (m, 2H) 4.47-4.58 (m, 2H) 7.32 (d, J=1.96 Hz, 1H) 7.68-7.82 (m, 1H) 7.85 (d, J=1.96 Hz, 1H) 7.96 (d, J=7.83 Hz, 1H) 8.28 (d, J=7.83 Hz, 1H) 8.34 (s, 1H) 8.42 (d, J=1.96 Hz, 1H) 9.30 (d, J=2.35 Hz, 1H). LCMS (m/z) (M+H)=503.2, Rt=0.67 min.

Example 146: N-(4-methyl-3-(5-morpholino-6-oxo-1,6-dihydropyridin-3-yl)phenyl)-3-(trifluoromethyl)benzamide

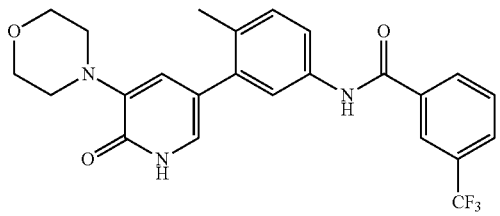 [SMILES: Cc1ccc(NC(=O)c2cccc(C(F)(F)F)c2)cc1-c1c[nH]c(=O)c(N2CCOCC2)c1]

¹H NMR (400 MHz, <cd3od>) δ ppm 2.20 (s, 3H) 2.98-3.12 (m, 4H) 3.67-3.84 (m, 4H) 6.89 (d, J=1.96 Hz, 1H) 6.99 (d, J=1.96 Hz, 1H) 7.20 (d, J=8.22 Hz, 1H) 7.45-7.54 (m, 2H) 7.59-7.67 (m, 1H) 7.79 (d, J=7.83 Hz, 1H) 8.10 (d, J=7.83 Hz, 1H) 8.16 (s, 1H). LCMS (m/z) (M+H)=458.3, Rt=0.82 min.

Example 147: N-(3-(1-(cyanomethyl)-5-morpholino-6-oxo-1,6-dihydropyridin-3-yl)-4-methylphenyl)-3-(trifluoromethyl)benzamide

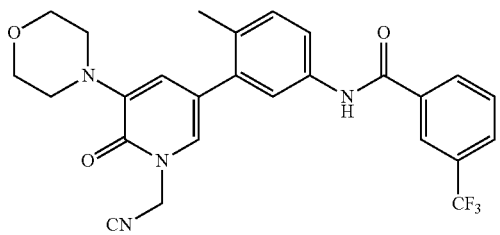

¹H NMR (400 MHz, <cd3od>) δ ppm 2.31 (s, 3H) 3.11-3.22 (m, 4H) 3.80-3.89 (m, 4H) 5.05 (s, 2H) 6.93 (d, J=1.96 Hz, 1H) 7.30 (d, J=8.22 Hz, 1H) 7.39 (d, J=1.96 Hz, 1H) 7.59 (dd, J=8.22, 1.96 Hz, 1H) 7.64 (d, J=1.96 Hz, 1H) 7.69-7.76 (m, 1H) 7.89 (d, J=7.83 Hz, 1H) 8.20 (d, J=7.83 Hz, 1H) 8.25 (s, 1H). LCMS (m/z) (M+H)=497.3, Rt=0.95 min.

Example 148: (R)—N-(3-(1-(1-cyanoethyl)-5-morpholino-6-oxo-1,6-dihydropyridin-3-yl)-4-methylphenyl)-3-(trifluoromethyl)benzamide

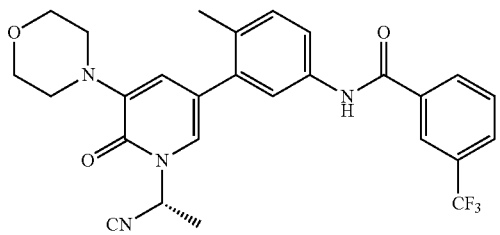

¹H NMR (400 MHz, <dmso>) δ ppm 1.72 (d, J=7.04 Hz, 6H) 2.25 (s, 6H) 3.11 (br. s., 8H) 3.71 (br. s., 8H) 5.87 (q, J=7.04 Hz, 2H) 6.73 (d, J=1.17 Hz, 2H) 7.28 (d, J=8.22 Hz, 2H) 7.43 (d, J=1.57 Hz, 2H) 7.63 (s, 2H) 7.71 (d, J=8.22 Hz, 2H) 7.77 (t, J=7.83 Hz, 2H) 7.95 (d, J=7.43 Hz, 2H) 8.21-8.32 (m, 5H) 10.45 (s, 1H). LCMS (m/z) (M+H)=511.2, Rt=1.00 min.

Example 149: (S)—N-(3-(1-(1-cyanoethyl)-5-morpholino-6-oxo-1,6-dihydropyridin-3-yl)-4-methylphenyl)-3-(trifluoromethyl)benzamide

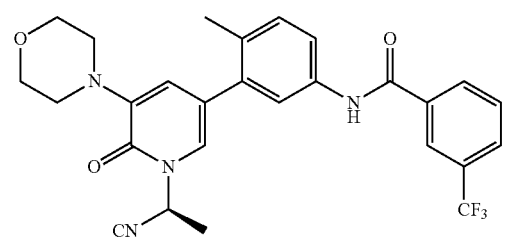

¹H NMR (400 MHz, <dmso>) δ ppm 1.80 (d, J=7.43 Hz, 3H) 2.33 (s, 3H) 3.20 (br. s., 4H) 3.78 (d, J=4.30 Hz, 4H) 5.95 (q, J=7.04 Hz, 1H) 6.81 (d, J=1.56 Hz, 1H) 7.36 (d, J=8.22 Hz, 1H) 7.51 (d, J=1.57 Hz, 1H) 7.71 (d, J=1.96 Hz, 1H) 7.79 (dd, J=8.22, 1.96 Hz, 1H) 7.83-7.90 (m, 1H) 8.04 (d, J=7.83 Hz, 1H) 8.28-8.44 (m, 2H) 10.53 (s, 1H). LCMS (m/z) (M+H)=511.3, Rt=1.01 min.

Example 150: N-(4-methyl-3-(1-(2-(methylsulfonyl)ethyl)-5-morpholino-6-oxo-1,6-dihydropyridin-3-yl)phenyl)-3-(trifluoromethyl)benzamide

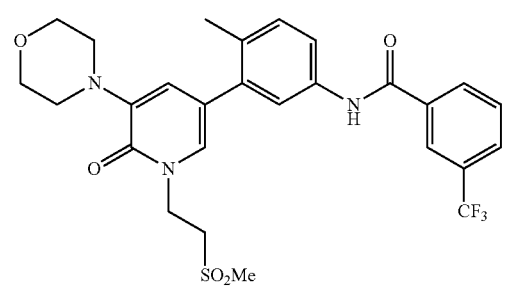 [SMILES: Cc1ccc(NC(=O)c2cccc(C(F)(F)F)c2)cc1-c1cc(N2CCOCC2)c(=O)n(CCS(C)(=O)=O)c1]

¹H NMR (400 MHz, <cd3od>) δ ppm 2.31 (s, 3H) 3.02 (s, 3H) 3.14-3.24 (m, 4H) 3.67 (t, J=6.46 Hz, 2H) 3.83-3.90 (m, 4H) 4.50 (t, J=6.46 Hz, 2H) 6.99 (d, J=1.96 Hz, 1H) 7.29 (d, J=8.22 Hz, 1H) 7.42 (d, J=1.96 Hz, 1H) 7.57 (dd, J=8.22, 1.96 Hz, 1H) 7.61 (s, 1H) 7.69-7.76 (m, 1H) 7.89 (d, J=7.43 Hz, 1H) 8.20 (d, J=7.83 Hz, 1H) 8.25 (s, 1H). LCMS (m/z) (M+H)=564.3, Rt=0.90 min.

Example 151: N-(2-methyl-1'-(2-(methylsulfonyl)
ethyl)-5'-morpholino-6'-oxo-1',6'-dihydro-[3,3'-bi-
pyridin]-5-yl)-3-(trifluoromethyl)benzamide

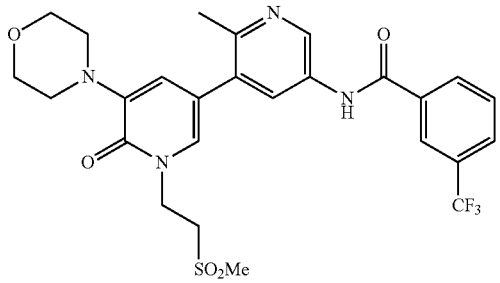 [SMILES: Cc1ncc(NC(=O)c2cccc(C(F)(F)F)c2)cc1-c1cc(N2CCOCC2)c(=O)n(CCS(C)(=O)=O)c1]

$^1$H NMR (400 MHz, <cd3od>) δ ppm 2.71 (s, 3H) 3.04 (s, 3H) 3.12-3.22 (m, 4H) 3.70 (t, J=6.06 Hz, 2H) 3.80-3.95 (m, 4H) 4.53 (t, J=6.06 Hz, 2H) 6.94 (d, J=1.96 Hz, 1H) 7.56 (d, J=1.96 Hz, 1H) 7.78 (t, J=8.02 Hz, 1H) 7.96 (d, J=7.43 Hz, 1H) 8.27 (d, J=7.43 Hz, 1H) 8.33 (s, 1H) 8.44 (d, J=2.35 Hz, 1H) 9.28 (d, J=2.35 Hz, 1H). LCMS (m/z) (M+H)= 565.2, Rt=0.68 min.

Example 152: (S)—N-(3-(6-(1-cyanoethoxy)-5-
morpholinopyridin-3-yl)-4-methylphenyl)-3-(trifluo-
romethyl)benzamide

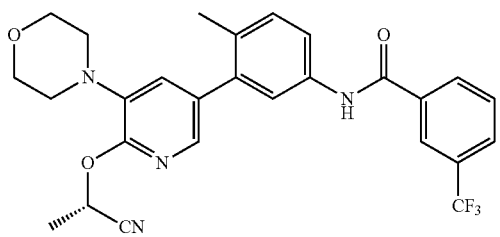 [SMILES: Cc1ccc(NC(=O)c2cccc(C(F)(F)F)c2)cc1-c1cnc(O[C@@H](C)C#N)c(N2CCOCC2)c1]

$^1$H NMR (400 MHz, <dmso>) δ ppm 1.73 (d, J=7.04 Hz, 3H) 2.22 (s, 3H) 3.06 (d, J=5.09 Hz, 4H) 3.74 (t, J=4.50 Hz, 4H) 5.78 (q, J=6.91 Hz, 1H) 7.26 (d, J=1.57 Hz, 1H) 7.30 (d, J=8.22 Hz, 1H) 7.65 (d, J=1.57 Hz, 1H) 7.70-7.82 (m, 3H) 7.95 (d, J=7.83 Hz, 1H) 8.22-8.30 (m, 2H) 10.44 (s, 1H). LCMS (m/z) (M+H)=511.5, Rt=1.13 min.

Example 153: (R)—N-(3-(6-(1-cyanoethoxy)-5-
morpholinopyridin-3-yl)-4-methylphenyl)-3-(trifluo-
romethyl)benzamide

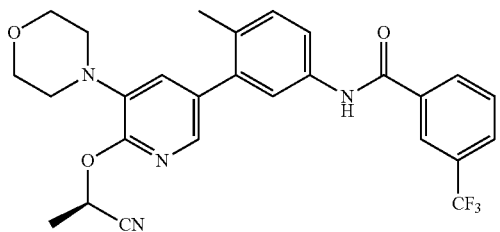 [SMILES: Cc1ccc(NC(=O)c2cccc(C(F)(F)F)c2)cc1-c1cnc(O[C@H](C)C#N)c(N2CCOCC2)c1]

$^1$H NMR (400 MHz, <dmso>) δ ppm 1.73 (d, J=7.04 Hz, 3H) 2.22 (s, 3H) 3.06 (d, J=5.09 Hz, 4H) 3.74 (t, J=4.50 Hz, 4H) 5.78 (q, J=6.65 Hz, 1H) 7.26 (d, J=1.57 Hz, 1H) 7.30 (d, J=8.22 Hz, 1H) 7.65 (d, J=1.96 Hz, 1H) 7.69-7.83 (m, 3H) 7.95 (d, J=7.83 Hz, 1H) 8.19-8.32 (m, 2H) 10.44 (s, 1H). LCMS (m/z) (M+H)=511.2, Rt=1.00 min.

Example 154: 4-methyl-3-(1-(2-(methylsulfonyl)
ethyl)-5-morpholino-6-oxo-1,6-dihydropyridin-3-
yl)-N-(3-(trifluoromethyl)phenyl)benzamide

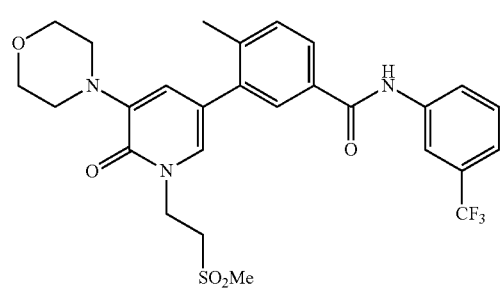 [SMILES: Cc1ccc(C(=O)Nc2cccc(C(F)(F)F)c2)cc1-c1cc(N2CCOCC2)c(=O)n(CCS(C)(=O)=O)c1]

$^1$H NMR (400 MHz, <cd3od>) δ ppm 2.40 (s, 3H) 3.03 (s, 3H) 3.10-3.22 (m, 4H) 3.68 (t, J=6.46 Hz, 2H) 3.81-3.92 (m, 4H) 4.51 (t, J=6.46 Hz, 2H) 7.00 (d, J=1.96 Hz, 1H) 7.36-7.48 (m, 2H) 7.54 (t, J=8.02 Hz, 1H) 7.81-7.88 (m, 2H) 7.93 (d, J=8.22 Hz, 1H) 8.15 (s, 1H). LCMS (m/z) (M+H)= 564.3, Rt=0.93 min.

Example 155: N-(3-(1-ethyl-5-morpholino-6-oxo-1,
6-dihydropyridin-3-yl)-4-methylphenyl)-3-(trifluo-
romethyl)benzamide

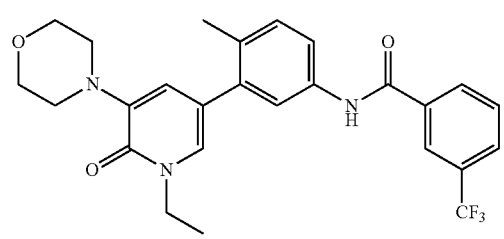 [SMILES: CCn1cc(-c2cc(NC(=O)c3cccc(C(F)(F)F)c3)ccc2C)cc(N2CCOCC2)c1=O]

$^1$H NMR (400 MHz, <cd3od>) δ ppm 1.38 (t, J=7.04 Hz, 3H) 2.31 (s, 3H) 3.11-3.21 (m, 4H) 3.82-3.91 (m, 4H) 4.11 (q, J=7.30 Hz, 2H) 6.96 (d, J=1.96 Hz, 1H) 7.29 (d, J=8.22 Hz, 1H) 7.38 (d, J=1.96 Hz, 1H) 7.58 (d, J=8.22 Hz, 1H) 7.62 (s, 1H) 7.69-7.76 (m, 1H) 7.89 (d, J=7.83 Hz, 1H) 8.20 (d, J=7.83 Hz, 1H) 8.25 (s, 1H). LCMS (m/z) (M+H)=486.2, Rt=0.95 min.

Example 156: N-(3-(6-ethoxy-5-morpholinopyridin-
3-yl)-4-methylphenyl)-3-(trifluoromethyl)benzamide

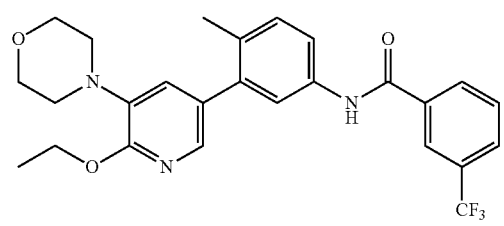 [SMILES: CCOc1ncc(-c2cc(NC(=O)c3cccc(C(F)(F)F)c3)ccc2C)cc1N1CCOCC1]

¹H NMR (400 MHz, <cd3od>) δ ppm 1.45 (t, J=7.04 Hz, 3H) 2.27 (s, 3H) 3.12-3.23 (m, 4H) 3.81-3.96 (m, 4H) 4.47 (q, J=7.04 Hz, 2H) 7.24-7.33 (m, 2H) 7.57-7.64 (m, 2H) 7.69-7.75 (m, 1H) 7.76 (d, J=1.96 Hz, 1H) 7.88 (d, J=7.83 Hz, 1H) 8.20 (d, J=7.83 Hz, 1H) 8.25 (s, 1H). LCMS (m/z) (M+H)=486.3, Rt=1.09 min.

Example 157: N-(1'-ethyl-2-methyl-5'-morpholino-6'-oxo-1',6'-dihydro-[3,3'-bipyridin]-5-yl)-3-(trifluoromethyl)benzamide

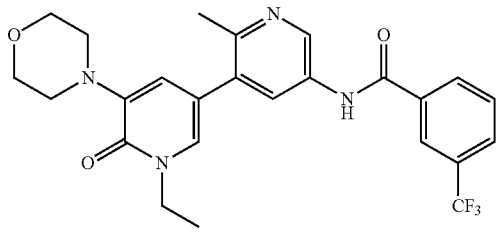 [SMILES: CCn1cc(-c2cc(NC(=O)c3cccc(C(F)(F)F)c3)cnc2C)cc(N2CCOCC2)c1=O]

1H NMR (400 MHz, <cd3od>) δ ppm 1.39 (t, J=7.24 Hz, 3H) 2.72 (s, 3H) 3.07-3.21 (m, 4H) 3.76-3.89 (m, 4H) 4.13 (q, J=7.30 Hz, 2H) 6.95 (d, J=1.96 Hz, 1H) 7.55 (d, J=2.35 Hz, 1H) 7.74-7.83 (m, 1H) 7.97 (d, J=7.83 Hz, 1H) 8.28 (d, J=7.83 Hz, 1H) 8.34 (s, 1H) 8.46 (d, J=2.35 Hz, 1H) 9.30 (d, J=2.35 Hz, 1H). LCMS (m/z) (M+H)=487.2, Rt=0.70 min.

Example 158: N-(3-(1-ethyl-5-morpholino-6-oxo-1,6-dihydropyridin-3-yl)-4-methylphenyl)-2-(trifluoromethyl)isonicotinamide

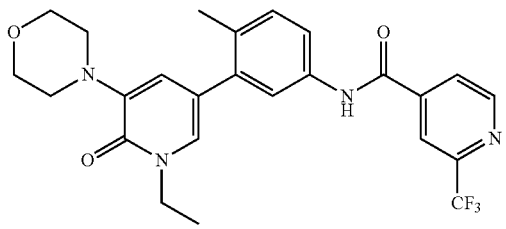 [SMILES: CCn1cc(-c2cc(NC(=O)c3ccnc(C(F)(F)F)c3)ccc2C)cc(N2CCOCC2)c1=O]

1H NMR (400 MHz, <cd3od>) δ ppm 1.29 (t, J=7.24 Hz, 3H) 2.22 (s, 3H) 3.03-3.13 (m, 4H) 3.71-3.82 (m, 4H) 4.03 (q, J=7.04 Hz, 2H) 6.93 (d, J=1.96 Hz, 1H) 7.22 (d, J=8.22 Hz, 1H) 7.32 (d, J=1.96 Hz, 1H) 7.51 (dd, J=8.22, 2.35 Hz, 1H) 7.56 (d, J=2.35 Hz, 1H) 8.02 (d, J=5.09 Hz, 1H) 8.20 (s, 1H) 8.81 (d, J=4.69 Hz, 1H). LCMS (m/z) (M+H)=487.2, Rt=0.89 min.

Example 159: N-(3-(6-ethoxy-5-morpholinopyridin-3-yl)-4-methylphenyl)-2-(trifluoromethyl)isonicotinamide

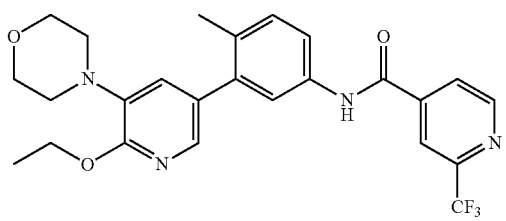 [SMILES: CCOc1ncc(-c2cc(NC(=O)c3ccnc(C(F)(F)F)c3)ccc2C)cc1N1CCOCC1]

1H NMR (400 MHz, <cd3od>) δ ppm 1.45 (t, J=7.04 Hz, 3H) 2.27 (s, 3H) 3.01-3.22 (m, 4H) 3.75-3.99 (m, 4H) 4.47 (q, J=7.04 Hz, 2H) 7.25 (d, J=1.96 Hz, 1H) 7.32 (d, J=8.22 Hz, 1H) 7.50-7.67 (m, 2H) 7.74 (d, J=1.96 Hz, 1H) 8.12 (d, J=5.09 Hz, 1H) 8.29 (s, 1H) 8.90 (d, J=5.09 Hz, 1H). LCMS (m/z) (M+H)=487.2, Rt=1.03 min.

Example 160: 2-(2-cyanopropan-2-yl)-N-(3-(1-ethyl-5-morpholino-6-oxo-1,6-dihydropyridin-3-yl)-4-methylphenyl)isonicotinamide

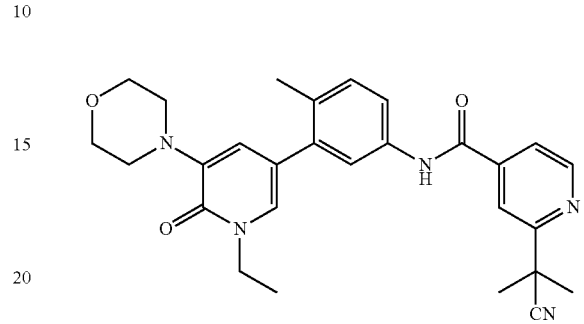

¹H NMR (400 MHz, <cd3od>) δ ppm 1.38 (t, J=7.04 Hz, 3H) 1.81 (s, 6H) 2.31 (s, 3H) 3.20 (d, J=3.91 Hz, 4H) 3.80-3.94 (m, 4H) 4.12 (q, J=7.04 Hz, 2H) 7.02 (d, J=1.96 Hz, 1H) 7.31 (d, J=8.61 Hz, 1H) 7.41 (d, J=1.96 Hz, 1H) 7.59 (d, J=8.22 Hz, 1H) 7.63 (s, 1H) 7.81 (d, J=4.70 Hz, 1H) 8.06 (s, 1H) 8.76 (d, J=5.09 Hz, 1H). LCMS (m/z) (M+H)= 486.3, Rt=0.79 min.

Example 161: 2-(2-cyanopropan-2-yl)-N-(3-(6-ethoxy-5-morpholinopyridin-3-yl)-4-methylphenyl)isonicotinamide

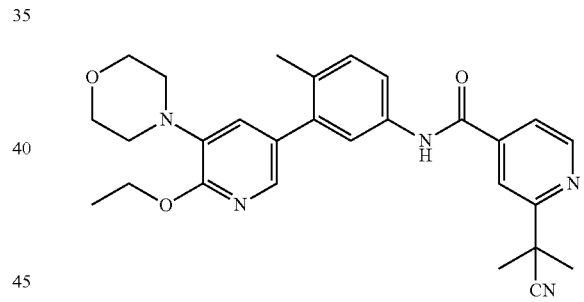

¹H NMR (400 MHz, <cd3od>) δ ppm 1.46 (t, J=7.04 Hz, 3H) 1.81 (s, 6H) 2.27 (s, 3H) 3.12-3.25 (m, 4H) 3.75-3.94 (m, 4H) 4.49 (q, J=7.04 Hz, 2H) 7.24-7.36 (m, 2H) 7.47-7.67 (m, 2H) 7.75-7.90 (m, 2H) 8.06 (s, 1H) 8.75 (d, J=5.09 Hz, 1H). LCMS (m/z) (M+H)=486.3, Rt=0.93 min.

Example 162: N-(4-methyl-3-(1-methyl-6-morpholino-2-oxo-1,2-dihydropyridin-4-yl)phenyl)-3-(trifluoromethyl)benzamide

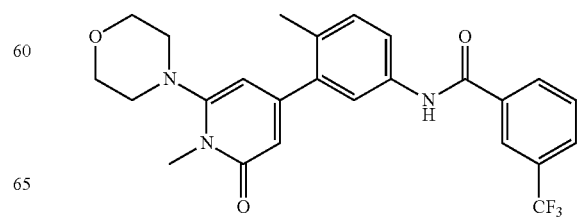

¹H NMR (400 MHz, <cd3od>) δ ppm 2.30 (s, 3H) 3.05 (d, J=3.91 Hz, 4H) 3.66 (s, 3H) 3.82-3.91 (m, 4H) 6.13 (d, J=0.78 Hz, 1H) 6.31 (s, 1H) 7.31 (d, J=9.00 Hz, 1H) 7.61-7.67 (m, 2H) 7.72 (t, J=7.83 Hz, 1H) 7.89 (d, J=7.83 Hz, 1H) 8.20 (d, J=7.83 Hz, 1H) 8.25 (s, 1H). LCMS (m/z) (M+H)=472.3, Rt=0.96 min.

Example 163: N-(1',2-dimethyl-6'-morpholino-2'-oxo-1',2'-dihydro-[3,4'-bipyridin]-5-yl)-3-trifluoromethyl)benzamide

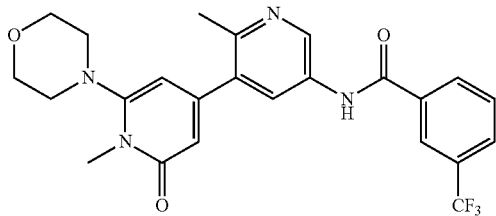 [SMILES: Cc1ncc(NC(=O)c2cccc(C(F)(F)F)c2)cc1-c1cc(N2CCOCC2)n(C)c(=O)c1]

¹H NMR (400 MHz, <cd3od>) δ ppm 2.64 (s, 3H) 2.99-3.11 (m, 4H) 3.65 (s, 3H) 3.80-3.96 (m, 4H) 6.12 (d, J=1.57 Hz, 1H) 6.35 (d, J=1.56 Hz, 1H) 7.73-7.81 (m, 1H) 7.95 (d, J=7.83 Hz, 1H) 8.26 (d, J=7.83 Hz, 1H) 8.33 (s, 1H) 8.36 (d, J=2.35 Hz, 1H) 9.21 (d, J=2.35 Hz, 1H). LCMS (m/z) (M+H)=473.2, Rt=0.69 min.

Example 164: N-(4-methyl-3-(1-methyl-5-morpholino-6-oxo-1,6-dihydropyridazin-3-yl)phenyl)-3-(trifluoromethyl)benzamide

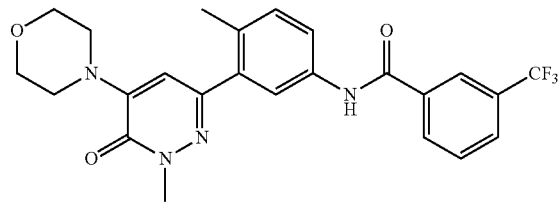 [SMILES: Cc1ccc(NC(=O)c2cccc(C(F)(F)F)c2)cc1-c1cc(N2CCOCC2)c(=O)n(C)n1]

1H NMR (400 MHz, <dmso>) δ ppm 2.29 (s, 3H) 3.37-3.51 (m, 4H) 3.67 (s, 3H) 3.68-3.77 (m, 5H) 6.59 (s, 1H) 7.28 (d, J=8.22 Hz, 1H) 7.69-7.83 (m, 3H) 7.95 (d, J=7.83 Hz, 1H) 8.21-8.27 (m, 1H) 8.29 (s, 1H) 10.47 (s, 1H). LCMS (m/z) (M+H)=473.1, Rt=0.94 min.

Example 165: 4-methyl-3-(1-methyl-5-morpholino-6-oxo-1,6-dihydropyridazin-3-yl)-N-(3-(trifluoromethyl)phenyl)benzamide

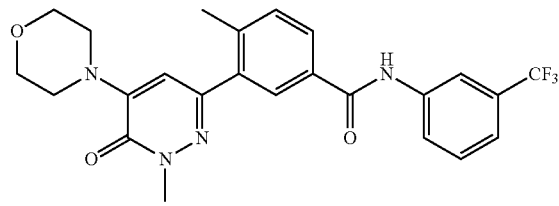 [SMILES: Cc1ccc(C(=O)Nc2cccc(C(F)(F)F)c2)cc1-c1cc(N2CCOCC2)c(=O)n(C)n1]

1H NMR (400 MHz, <dmso>) δ ppm 2.34 (s, 3H) 3.26 (br. s., 12H) 3.43 (br. s., 4H) 3.64 (br. s., 7H) 6.62 (s, 1H) 7.32-7.46 (m, 3H) 7.48-7.59 (m, 2H) 7.89 (d, J=8.22 Hz, 1H) 7.92 (s, 1H) 8.00 (d, J=7.83 Hz, 1H) 8.18 (s, 1H) 10.46 (s, 1H). LCMS (m/z) (M+H)=473.1, Rt=1.00 min.

Example 166: N-(6-methyl-5-(1-methyl-5-morpholino-6-oxo-1,6-dihydropyridazin-3-yl)pyridin-3-yl)-3-(trifluoromethyl)benzamide

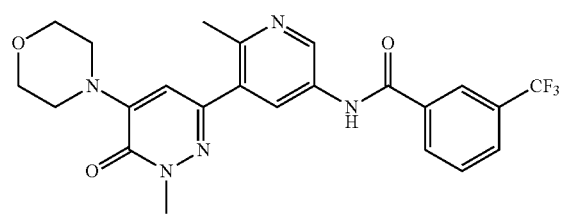 [SMILES: Cc1ncc(NC(=O)c2cccc(C(F)(F)F)c2)cc1-c1cc(N2CCOCC2)c(=O)n(C)n1]

1H NMR (400 MHz, <dmso>) δ ppm 2.56 (s, 3H) 3.40-3.54 (m, 4H) 3.62-3.77 (m, 8H) 6.72 (s, 1H) 7.75-7.87 (m, 1H) 8.00 (d, J=7.83 Hz, 1H) 8.25-8.31 (m, 2H) 8.33 (s, 1H) 8.99 (d, J=2.35 Hz, 1H) 10.84 (s, 1H). LCMS (m/z) (M+H)=474.3, Rt=0.72 min.

Example 167: 2-(2-cyanopropan-2-yl)-N-(6-methyl-5-(1-methyl-5-morpholino-6-oxo-1,6-dihydropyridazin-3-yl)pyridin-3-yl)isonicotinamide

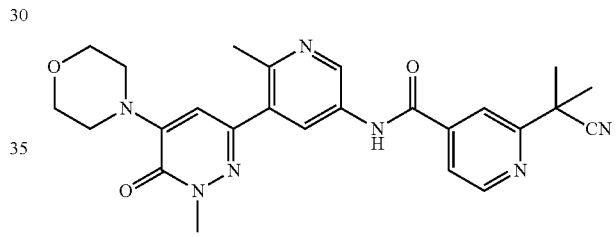

1H NMR (400 MHz, <dmso>) δ ppm 1.76 (s, 6H) 2.54 (s, 3H) 3.39-3.53 (m, 4H) 3.65-3.75 (m, 7H) 6.71 (s, 1H) 7.81-7.92 (m, 1H) 8.04 (s, 1H) 8.22 (d, J=2.35 Hz, 1H) 8.83 (d, J=5.09 Hz, 1H) 8.94 (d, J=1.96 Hz, 1H) 10.90 (s, 1H). LCMS (m/z) (M+H)=474.2, Rt=0.68 min.

Example 168: 2-(2-cyanopropan-2-yl)-N-(6-methyl-5-(1-methyl-5-morpholino-6-oxo-1,6-dihydropyridazin-3-yl)pyridin-3-yl)isonicotinamide

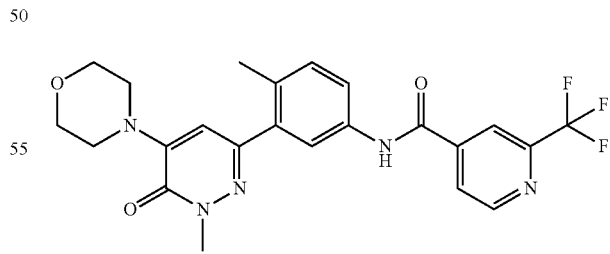

1H NMR (400 MHz, <dmso>) δ ppm 2.29 (s, 3H) 3.43-3.52 (m, 8H) 3.67 (s, 3H) 3.68-3.76 (m, 4H) 6.59 (s, 1H) 7.31 (d, J=8.22 Hz, 1H) 7.69-7.79 (m, 2H) 8.18 (d, J=4.30 Hz, 1H) 8.36 (s, 1H) 8.98 (d, J=5.09 Hz, 1H) 10.69 (s, 1H). LCMS (m/z) (M+H)=474.2, Rt=0.94 min.

The compounds listed below were prepared using methods similar to those described in Method 1 using the appropriate starting materials and purified via preparative HPLC to yield the corresponding TFA salt upon lyophilization.

Example 169: N-(3-(4-ethyl-6-morpholino-5-oxo-4, 5-dihydropyrazin-2-yl)-4-methylphenyl)-3-(trifluoromethyl)benzamide

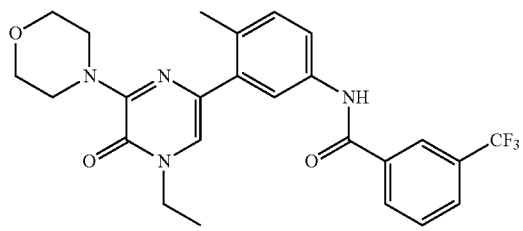 [SMILES: CCn1cc(-c2cc(NC(=O)c3cccc(C(F)(F)F)c3)ccc2C)nc(N2CCOCC2)c1=O]

Method 1 was followed using N-(4-methyl-3-(6-morpholino-5-oxo-4,5-dihydropyrazin-2-yl)phenyl)-3-(trifluoromethyl)benzamide (1.0 equiv.), iodoethane (1.2 equiv.) and potassium carbonate (2.0 equiv.) at room temperature. $^1$H NMR (400 MHz, <cd3od>) δ ppm 1.38 (t, J=7.24 Hz, 3H) 2.39 (s, 3H) 3.80 (s, 8H) 4.02 (q, J=7.30 Hz, 2H) 7.02-7.31 (m, 2H) 7.57 (dd, J=8.22, 1.96 Hz, 1H) 7.65-7.81 (m, 2H) 7.89 (d, J=7.83 Hz, 1H) 8.13-8.38 (m, 1H). LCMS (m/z) (M+H)=487.4, Rt=1.02 min.

Example 170: N-(3-(4-(2,2-difluoroethyl)-6-morpholino-5-oxo-4,5-dihydropyrazin-2-yl)-4-methylphenyl)-3-(trifluoromethyl)benzamide

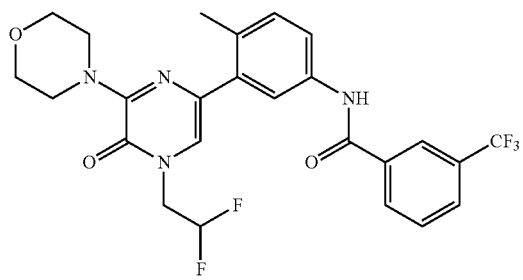 [SMILES: Cc1ccc(NC(=O)c2cccc(C(F)(F)F)c2)cc1-c1cn(CC(F)F)c(=O)c(N2CCOCC2)n1]

Method 1 was followed using N-(4-methyl-3-(6-morpholino-5-oxo-4,5-dihydropyrazin-2-yl)phenyl)-3-(trifluoromethyl)benzamide (1.0 equiv.), 1,1-difluoro-2-iodoethane (1.2 equiv.) and potassium carbonate (2.0 equiv.) at 60° C. $^1$H NMR (400 MHz, <cd3od>) δ ppm 2.39 (s, 3H) 3.81 (d, J=5.09 Hz, 8H) 4.38 (td, J=14.09, 3.91 Hz, 2H) 6.02-6.44 (m, 1H) 7.14 (s, 1H) 7.26 (d, J=8.22 Hz, 1H) 7.59 (dd, J=8.22, 1.96 Hz, 1H) 7.67-7.79 (m, 2H) 7.89 (d, J=7.83 Hz, 1H) 8.16-8.34 (m, 1H). LCMS (m/z) (M+H)=523.3, Rt=1.05 min.

Synthesis of 5-(5-amino-2-methylphenyl)-1-methyl-3-morpholinopyridin-2(1H)-one

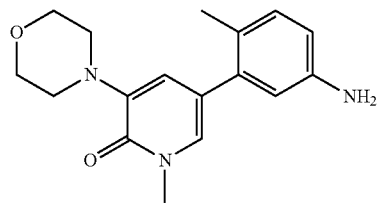 [SMILES: Cc1ccc(N)cc1-c1cc(N2CCOCC2)c(=O)n(C)c1]

To a solution of 5-bromo-1-methyl-3-morpholinopyridin-2(1H)-one (1.0 equiv.) and 4-methyl-3-(4,4,5,5-tetramethyl-1,3,2-dioxaborolan-2-yl)aniline (1.2 equiv.) in DME and 2M sodium carbonate (3:1, 0.14 M) was added PdCl$_2$(dppf)-DCM adduct (0.1 equiv.) in a microwave vial equipped with a stir bar. The reaction was heated to 120° C. for 15 min in the microwave. The solution was partitioned between water and ethyl acetate, the organic phase was dried with sodium sulfate, filtered and concentrated. The crude material was purified via silica gel column chromatography eluting with 100% ethyl acetate followed by 10% methanol in ethyl acetate. The pure fractions were concentrated and dried under vacuo to afford 5-(5-amino-2-methylphenyl)-1-methyl-3-morpholinopyridin-2(1H)-one in 31% yield. LCMS (m/z) (M+H)=300.2, Rt=0.41 min.

Synthesis of 5'-amino-1,2'-dimethyl-5-morpholino-[3,3'-bipyridin]-6(1H)-one

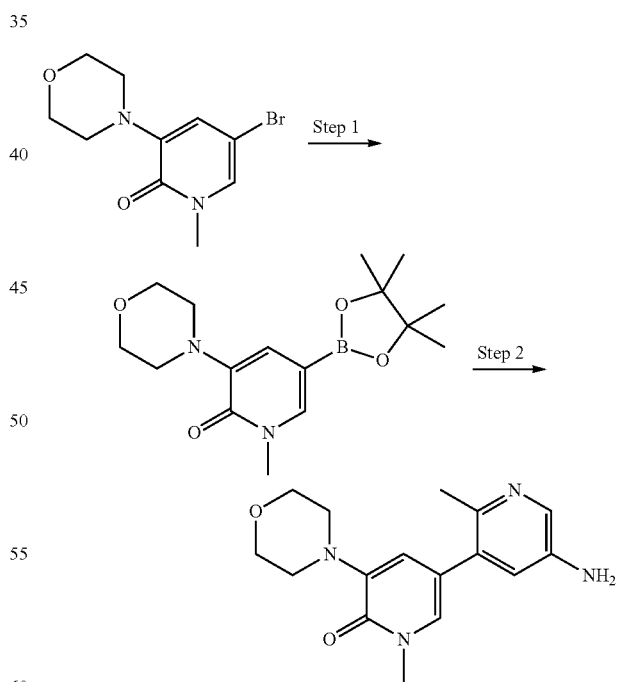

Step 1:
To a 0.18 M solution of 5-bromo-1-methyl-3-morpholinopyridin-2(1H)-one (1.00 equiv.) in 1,4-dioxane was added bis(pinacolato)diboron (1.50 equiv.), potassium acetate (2.00 equiv.), and PdCl$_2$(dppf).CH$_2$Cl$_2$ adduct (0.10 equiv.). The reaction was irradiated at 120° C. for 20 min. The reaction was diluted with DCM (20 mL) and filtered. The filtrate was concentrated to give 5'-amino-1,2'-dimethyl-5-morpholino-[3,3'-bipyridin]-6(1H)-one as a mixture with the corresponding boronic acid as a dark brown tacky solid in quantitative yield. LCMS (m/z) (M+H)=321.0, Rt=0.65 min.

Step 2:

To a 0.18 M solution of 5'-amino-1,2'-dimethyl-5-morpholino-[3,3'-bipyridin]-6(1H)-one (1.00 equiv.) in DME and 5-bromo-6-methylpyridin-3-amine (1.00 equiv.) was added PdCl₂(dppf).CH₂Cl₂ adduct (0.10 equiv.) and 2M aqueous sodium carbonate (3.00 equiv.). The reaction mixture was irradiated at 125° C. for 20 min. LC-MS showed primarily conversion to P. The cooled reaction mixture was diluted with 2:1 DCM:MeOH and filtered. The filtrate was concentrated and purified by flash chromatography over silica gel (ethyl acetate with a 0-15% methanol gradient) to give 5'-amino-1,2'-dimethyl-5-morpholino-[3,3'-bipyridin]-6(1H)-one as a brown solid. LCMS (m/z) (M+H)=301.0, Rt=0.33 min.

Synthesis of 6-(5-amino-2-methylphenyl)-2-methyl-4-morpholinopyridazin-3(2H)-one

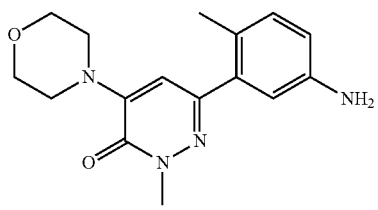 [SMILES: Cc1ccc(N)cc1-c1cc(N2CCOCC2)c(=O)n(C)n1]

To a solution of 6-chloro-2-methyl-4-morpholinopyridazin-3(2H)-one (1.0 equiv.) and 4-methyl-3-(4,4,5,5-tetramethyl-1,3,2-dioxaborolan-2-yl)aniline (1.1 equiv.) in DME and water (2:1, 0.2 M) was added PdCl₂(dppf).CH₂Cl₂ adduct (0.5 equiv.) and sodium carbonate (6.6 equiv.). The solution was heated in the microwave for 40 min at 120° C. Upon cooling to room temperature, the solution was diluted with ethyl acetate and water, the aqueous layer was extracted with ethyl acetate two more times, the organics were combined, dried over magnesium sulfate, filtered and concentrated to yield a brown solid. Isolated 6-(5-amino-2-methylphenyl)-2-methyl-4-morpholinopyridazin-3(2H)-one as the desired product. LCMS (m/z) (M+H)=301.1, Rt=0.49 min.

Method 3:

To a solution of the amine (1.0 equiv.) and the corresponding carboxylic acid (1.0-1.2 equiv.) in DMF (0.1 M) was added EDC (1.0-1.2 equiv.) and HOAt (1.0-1.2 equiv.) and the reaction was stirred at room temperature for 6-24 hours. Upon completion, the solution was filtered through a HPLC filter and purified via reverse phase preparative HPLC. Alternatively, the solution was partitioned between water and ethyl acetate, the organic phase was dried over sodium sulfate or magnesium sulfate, filtered and concentrated to yield a crude material that was further purified via reverse phase preparative HPLC. Upon lyophilization of the pure fractions, the desired product was isolated as the TFA salt.

Example 171: Synthesis of 3-(difluoromethyl)-N-(4-methyl-3-(1-methyl-5-morpholino-6-oxo-1,6-dihydropyridin-3-yl)phenyl)benzamide

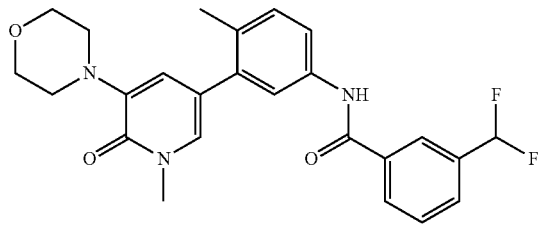 [SMILES: Cc1ccc(NC(=O)c2cccc(C(F)F)c2)cc1-c1cc(N2CCOCC2)c(=O)n(C)c1]

To a solution of 5-(5-amino-2-methylphenyl)-1-methyl-3-morpholinopyridin-2(1H)-one (1.0 equiv.) in DMF (0.07 M) was added 3-(difluoromethyl)benzoic acid (1.2 equiv.), EDC-HCl (1.2 equiv.) and HOAt (1.2 equiv.). The reaction was stirred at room temperature for 6 hours. Upon completion, the solution was filtered through a HPLC filter and purified via reverse phase preparative HPLC. Upon lyophilization of the pure fractions, 3-(difluoromethyl)-N-(4-methyl-3-(1-methyl-5-morpholino-6-oxo-1,6-dihydropyridin-3-yl)phenyl)benzamide was isolated as the TFA salt in 45% yield. LCMS (m/z) (M+H)=454.2, Rt=0.79 min. ¹H NMR (400 MHz, <cd3od>) δ ppm 2.30 (s, 3H) 3.08-3.22 (m, 4H) 3.64 (s, 3H) 3.81-3.94 (m, 4H) 6.66-7.05 (m, 2H) 7.29 (d, J=8.61 Hz, 1H) 7.40 (d, J=2.35 Hz, 1H) 7.56 (dd, J=8.41, 2.15 Hz, 1H) 7.60-7.68 (m, 2H) 7.76 (d, J=7.43 Hz, 1H) 8.05-8.15 (m, 1H).

The compounds listed below were prepared using methods similar to those described for the preparation of Example 171 (Method 3) using the appropriate starting materials.

Example 172: 3-(2-cyanopropan-2-yl)-N-(4-methyl-3-(1-methyl-5-morpholino-6-oxo-1,6-dihydropyridin-3-yl)phenyl)benzamide

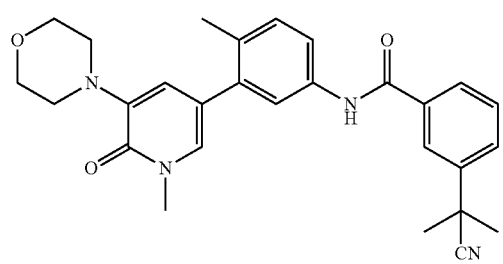 [SMILES: Cc1ccc(NC(=O)c2cccc(C(C)(C)C#N)c2)cc1-c1cc(N2CCOCC2)c(=O)n(C)c1]

¹H NMR (400 MHz, <cd3od>) δ ppm 1.78 (s, 6H) 2.30 (s, 3H) 3.08-3.25 (m, 4H) 3.64 (s, 3H) 3.82-3.95 (m, 4H) 7.03 (d, J=1.96 Hz, 1H) 7.29 (d, J=8.22 Hz, 1H) 7.41 (d, J=1.96 Hz, 1H) 7.51-7.66 (m, 3H) 7.76 (d, J=9.00 Hz, 1H) 7.90 (d, J=7.83 Hz, 1H) 8.08 (s, 1H). LCMS (m/z) (M+H)= 471.3, Rt=0.80 min.

Example 173: 3-((dimethylamino)methyl)-N-(4-methyl-3-(1-methyl-5-morpholino-6-oxo-1,6-dihydropyridin-3-yl)phenyl)-5-(trifluoromethyl)benzamide

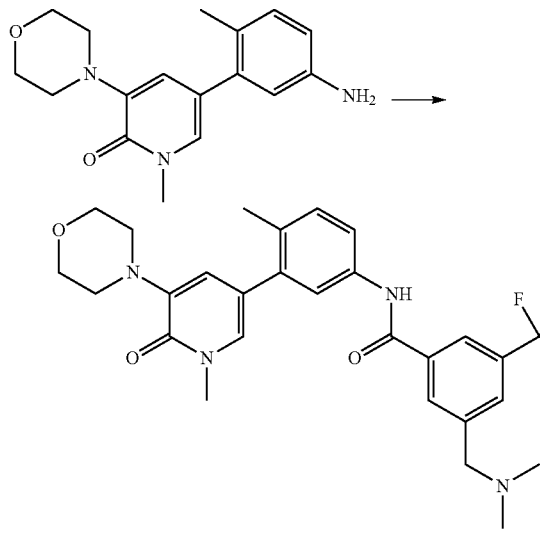

To a solution of 3-((dimethylamino)methyl)-5-(trifluoromethyl)benzoic acid (1.1 equiv.), N1-((ethylimino)methylene)-N3,N3-dimethylpropane-1,3-diamine hydrochloride (1.1 equiv.), 3H-[1,2,3]triazolo[4,5-b]pyridin-3-ol hydrate (1.1 equiv.) in DMF (0.3 M) was added 5-(5-amino-2-methylphenyl)-1-methyl-3-morpholinopyridin-2(1H)-one (1.0 equiv.) and the reaction was stirred overnight at rt. Diluted with 0.4 M aqueous sodium carbonate and extracted with ethyl acetate. The combined organics were dried over sodium sulfate, filtered and concentrated with silica gel to give the crude product. The material was purified by flash chromatography over silica gel (heptanes with 50-100% 90:10:1.5 ethyl acetate:methanol:triethylamine gradient) to give 3-((dimethylamino)methyl)-N-(4-methyl-3-(1-methyl-5-morpholino-6-oxo-1,6-dihydropyridin-3-yl)phenyl)-5-(trifluoromethyl)benzamide as a pale yellow-green solid in 46% yield. $^1$H NMR (400 MHz, <cd3od>) δ ppm 2.31 (s, 3H) 2.92 (s, 6H) 3.07-3.20 (m, 4H) 3.63 (s, 3H) 3.79-3.91 (m, 4H) 4.51 (s, 2H) 6.92 (d, J=1.96 Hz, 1H) 7.22-7.40 (m, 2H) 7.53-7.72 (m, 2H) 8.10 (s, 1H) 8.30-8.46 (m, 1H). LCMS (m/z) (M+H)=529.4, Rt=0.65 min.

Example 174: 3-(4-ethylpiperazin-1-yl)-N-(4-methyl-3-(1-methyl-5-morpholino-6-oxo-1,6-dihydropyridin-3-yl)phenyl)-5-(trifluoromethyl)benzamide

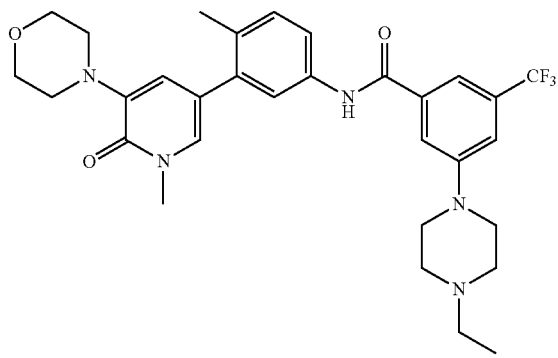 [SMILES: CCN1CCN(c2cc(C(=O)Nc3ccc(C)c(-c4cc(N5CCOCC5)c(=O)n(C)c4)c3)cc(C(F)(F)F)c2)CC1]

$^1$H NMR (400 MHz, <cd3od>) δ ppm 1.41 (t, J=7.24 Hz, 3H) 2.30 (s, 3H) 3.14 (d, J=4.30 Hz, 5H) 3.21 (d, J=18.00 Hz, 4H) 3.63 (s, 3H) 3.70 (br. s., 2H) 3.81-3.91 (m, 4H) 4.09 (d, J=12.13 Hz, 2H) 6.91 (d, J=1.96 Hz, 1H) 7.29 (d, J=7.83 Hz, 1H) 7.33 (d, J=1.96 Hz, 1H) 7.50 (s, 1H) 7.54-7.62 (m, 2H) 7.79 (d, J=4.70 Hz, 2H). LCMS (m/z) (M+H)=584.4, Rt=0.70 min.

Example 175: 5-(dimethylamino)-N-(4-methyl-3-(1-methyl-5-morpholino-6-oxo-1,6-dihydropyridin-3-yl)phenyl)nicotinamide

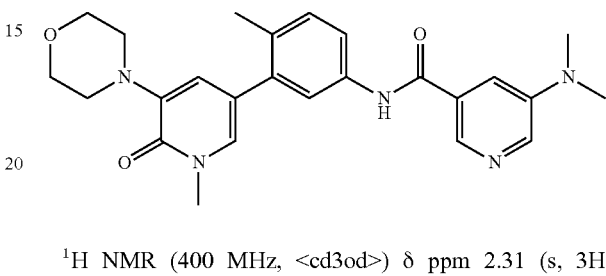

$^1$H NMR (400 MHz, <cd3od>) δ ppm 2.31 (s, 3H) 3.01-3.16 (m, 4H) 3.20 (s, 6H) 3.63 (s, 3H) 3.78-3.92 (m, 4H) 6.91 (d, J=2.35 Hz, 1H) 7.23-7.37 (m, 2H) 7.54-7.75 (m, 2H) 8.14-8.30 (m, 2H) 8.45 (s, 1H). LCMS (m/z) (M+H)=448.3, Rt=0.57 min.

Example 176: Synthesis of N-(4-methyl-3-(1-methyl-5-morpholino-6-oxo-1,6-dihydropyridin-3-yl)phenyl)-3-(methylsulfonyl)-5-(trifluoromethyl)benzamide

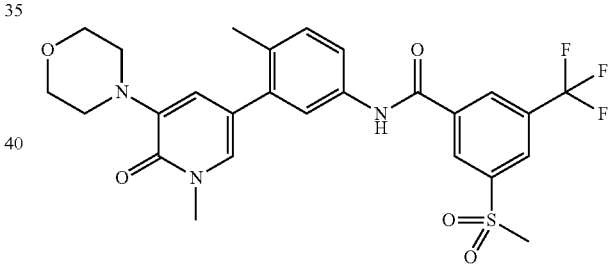

$^1$H NMR (400 MHz, <cd3od>) δ ppm 2.32 (s, 3H) 3.06-3.19 (m, 4H) 3.27 (s, 4H) 3.64 (s, 3H) 3.77-3.93 (m, 4H) 6.92 (d, J=1.96 Hz, 1H) 7.23-7.39 (m, 2H) 7.53-7.71 (m, 2H) 8.45 (s, 1H) 8.60 (s, 1H) 8.78 (s, 1H). LCMS (m/z) (M+H)=550.1, Rt=0.83.

Example 177: Synthesis of 3-(1,1-difluoroethyl)-N-(4-methyl-3-(1-methyl-5-morpholino-6-oxo-1,6-dihydropyridin-3-yl)phenyl)benzamide

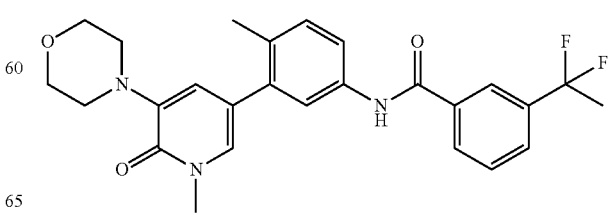

1H NMR (400 MHz, <cd3od>) δ ppm 1.98 (t, J=18.39 Hz, 3H) 2.31 (s, 3H) 3.13-3.23 (m, 4H) 3.65 (s, 3H) 3.82-3.93 (m, 4H) 7.01 (d, J=1.96 Hz, 1H) 7.29 (d, J=8.22 Hz, 1 H) 7.40 (d, J=1.96 Hz, 1H) 7.53-7.67 (m, 3H) 7.76 (d, J=7.83 Hz, 1H) 8.03 (d, J=7.83 Hz, 1H) 8.11 (s, 1H). LCMS (m/z) (M+H)=468.1, Rt=0.85.

Example 178: 2-(1,1-difluoroethyl)-N-(4-methyl-3-(1-methyl-5-morpholino-6-oxo-1,6-dihydropyridin-3-yl)phenyl)isonicotinamide

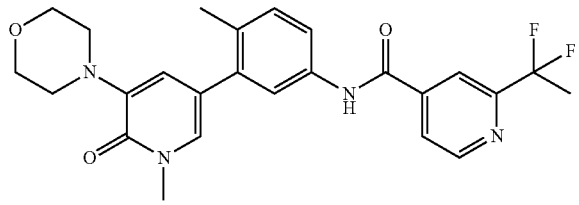

1H NMR (400 MHz, <cd3od>) δ ppm 2.04 (t, J=18.78 Hz, 3H) 2.31 (s, 3H) 3.10-3.23 (m, 4H) 3.65 (s, 3H) 3.81-3.93 (m, 4H) 7.00 (d, J=1.96 Hz, 1H) 7.31 (d, J=8.22 Hz, 1H) 7.39 (d, J=1.96 Hz, 1H) 7.55-7.68 (m, 2H) 7.96 (d, J=4.30 Hz, 1H) 8.17 (s, 1H) 8.81 (d, J=5.09 Hz, 1H). LCMS (m/z) (M+H)=469.1, Rt=0.78.

Example 179: N-(4-methyl-3-(1-methyl-5-morpholino-6-oxo-1,6-dihydropyridin-3-yl)phenyl)-2-(trifluoromethyl)isonicotinamide

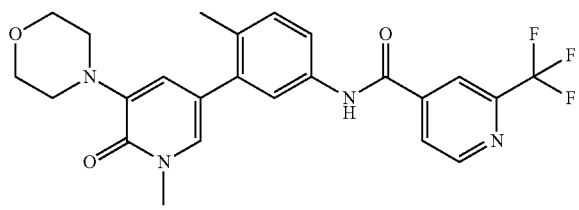 [SMILES: Cc1ccc(NC(=O)c2cccc(C(C)(F)F)c2)cc1-c1cc(N2CCOCC2)c(=O)n(C)c1]

1H NMR (400 MHz, <cd3od>) δ ppm 2.31 (s, 3H) 3.10-3.22 (m, 4H) 3.65 (s, 3H) 3.80-3.93 (m, 4H) 6.98 (d, J=1.96 Hz, 1H) 7.31 (d, J=8.22 Hz, 1H) 7.38 (d, J=2.35 Hz, 1H) 7.60 (dd, J=8.22, 2.35 Hz, 1H) 7.65 (d, J=1.96 Hz, 1H) 8.12 (d, J=5.09 Hz, 1H) 8.30 (s, 1H) 8.91 (d, J=5.09 Hz, 1H). LCMS (m/z) (M+H)=473.1, Rt=0.83.

Example 181: N-(1',2-dimethyl-5'-morpholino-6'-oxo-1',6'-dihydro-[3,3'-bipyridin]-5-yl)-4-methoxy-3-(trifluoromethyl)benzamide

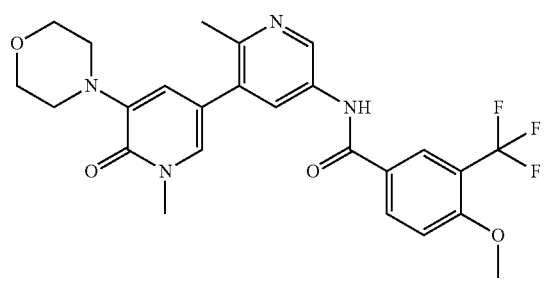 [SMILES: COc1ccc(C(=O)Nc2cnc(C)c(-c3cc(N4CCOCC4)c(=O)n(C)c3)c2)cc1C(F)(F)F]

1H NMR (400 MHz, <cd3od>) δ ppm 2.69 (s, 3H) 3.10-3.21 (m, 4H) 3.65 (s, 3H) 3.79-3.91 (m, 4H) 4.02 (s, 3H) 6.95 (d, J=1.96 Hz, 1H) 7.37 (d, J=8.61 Hz, 1H) 7.52 (d, J=1.96 Hz, 1H) 8.22-8.34 (m, 2H) 8.42 (d, J=2.35 Hz, 1H) 9.24 (d, J=2.35 Hz, 1H). LCMS (m/z) (M+H)=503.1, Rt=0.67 min.

Example 182: N-(1',2-dimethyl-5'-morpholino-6'-oxo-1',6'-dihydro-[3,3'-bipyridin]-5-yl)-4-fluoro-3-methoxybenzamide

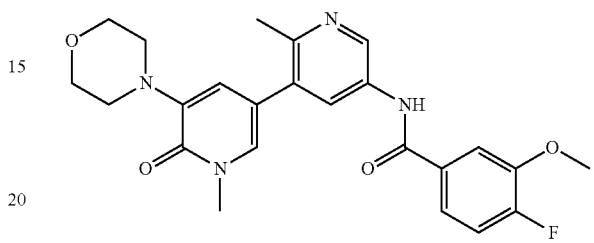

1H NMR (400 MHz, <cd3od>) δ ppm 2.70 (s, 3H) 3.12-3.20 (m, 4H) 3.65 (s, 3H) 3.80-3.89 (m, 4H) 3.97 (s, 3H) 6.95 (d, J=2.35 Hz, 1H) 7.27 (dd, J=10.96, 8.61 Hz, 1H) 7.53 (d, J=2.35 Hz, 1H) 7.62 (ddd, J=8.41, 4.11, 1.96 Hz, 1H) 7.75 (dd, J=8.22, 1.96 Hz, 1H) 8.43 (d, J=2.35 Hz, 1H) 9.25 (d, J=2.35 Hz, 1H). LCMS (m/z) (M+H)=453.0, Rt=0.58 min.

Example 184: N-(4-methyl-3-(1-methyl-5-morpholino-6-oxo-1,6-dihydropyridin-3-yl)phenyl)-2-(methylsulfonyl)isonicotinamide

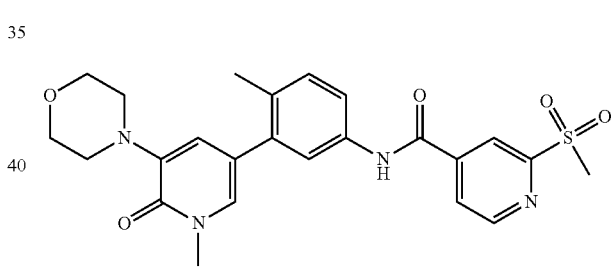

1H NMR (400 MHz, <dmso>) δ ppm 2.27 (s, 3H) 3.11 (br. s., 4H) 3.35 (s, 5H) 3.50 (s, 5H) 3.72 (br. s., 4H) 6.70 (s, 1H) 7.30 (d, J=8.22 Hz, 1H) 7.41 (s, 1H) 7.64 (s, 1H) 7.69 (d, J=8.22 Hz, 1H) 8.22 (d, J=4.69 Hz, 1H) 8.53 (s, 1H) 9.00 (d, J=5.09 Hz, 1H) 10.76 (s, 1H). LCMS (m/z) (M+H)=483.3, Rt=0.65.

Example 185: N-(4-methyl-3-(1-methyl-5-morpholino-6-oxo-1,6-dihydropyridin-3-yl)phenyl)-3-(methylsulfonyl)benzamide

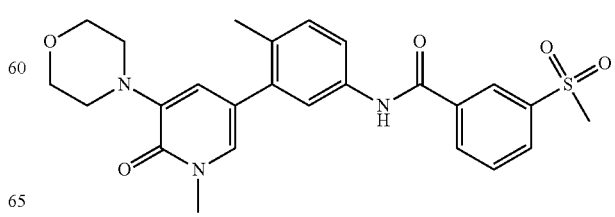

1H NMR (400 MHz, <dmso>) δ ppm 2.27 (s, 3H) 3.11 (br. s., 4H) 3.29 (s, 3H) 3.50 (s, 4H) 3.68-3.77 (m, 5H) 6.71 (d, J=1.96 Hz, 1H) 7.28 (d, J=8.22 Hz, 1H) 7.41 (d, J=1.96 Hz, 1H) 7.63 (d, J=1.96 Hz, 1H) 7.69 (dd, J=8.22, 1.96 Hz, 1H) 7.83 (t, J=7.83 Hz, 1H) 8.14 (d, J=7.83 Hz, 1H) 8.29 (d, J=8.22 Hz, 1H) 8.48 (s, 1H) 10.49 (s, 1H). LCMS (m/z) (M+H)=482.3, Rt=0.68.

Example 189: 2-(difluoromethyl)-N-(4-methyl-3-(1-methyl-5-morpholino-6-oxo-1,6-dihydropyridazin-3-yl)phenyl)isonicotinamide

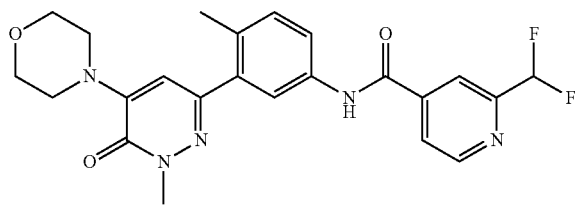 [SMILES: Cc1ccc(NC(=O)c2ccnc(C(F)F)c2)cc1-c1cc(N2CCOCC2)c(=O)n(C)n1]

1H NMR (400 MHz, <dmso>) δ ppm 2.31 (br. s., 1H) 3.42-3.49 (m, 5H) 3.67 (s, 3H) 3.68-3.74 (m, 4H) 6.59 (s, 1H) 7.07 (s, 1H) 7.30 (d, J=8.22 Hz, 1H) 7.74 (s, 2H) 8.05 (d, J=5.09 Hz, 1H) 8.17 (s, 1H) 8.89 (d, J=5.09 Hz, 1H) 10.65 (s, 1H), LCMS (m/z) (M+H)=456.0, Rt=0.76 min.

Example 190: 3-(difluoromethyl)-N-(4-methyl-3-(1-methyl-5-morpholino-6-oxo-1,6-dihydropyridazin-3-yl)phenyl)benzamide

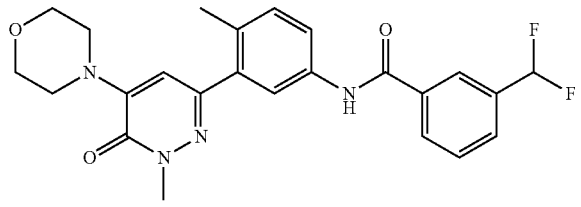

1H NMR (400 MHz, <dmso>) δ ppm 2.23-2.33 (m, 3H) 3.37-3.52 (m, 4H) 3.61-3.77 (m, 7H) 6.59 (s, 1H) 7.23-7.32 (m, 1H) 7.60-7.71 (m, 1H) 7.71-7.80 (m, 3H) 8.07-8.18 (m, 2H) 10.41 (s, 1H), LCMS (m/z) (M+H)=455.0, Rt=0.87 min.

Example 191: 2-(2-cyanopropan-2-yl)-N-(4-methyl-3-(1-methyl-5-morpholino-6-oxo-1,6-dihydropyridazin-3-yl)phenyl)isonicotinamide

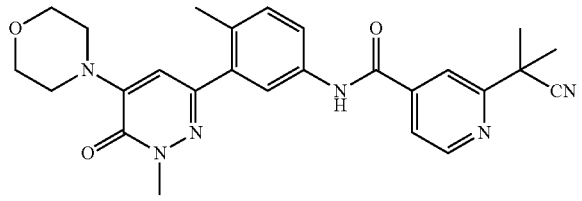 [SMILES: Cc1ccc(NC(=O)c2ccnc(C(C)(C)C#N)c2)cc1-c1cc(N2CCOCC2)c(=O)n(C)n1]

1H NMR (400 MHz, <dmso>) δ ppm 1.75 (s, 6H) 2.29 (s, 3H) 3.36-3.51 (m, 4H) 3.57-3.76 (m, 7H) 6.59 (s, 1H) 7.30 (d, J=8.22 Hz, 1H) 7.65-7.78 (m, 2H) 7.85 (d, J=3.91 Hz, 1H) 7.94-8.06 (m, 1H) 8.79 (d, J=5.09 Hz, 1H) 10.56 (s, 1H), LCMS (m/z) (M+H)=473.4, Rt=0.84 min.

Example 192: Synthesis of 4-(difluoromethyl)-3-(1-methyl-5-morpholino-6-oxo-1,6-dihydropyridin-3-yl)-N-(3-(trifluoromethyl)phenyl)benzamide

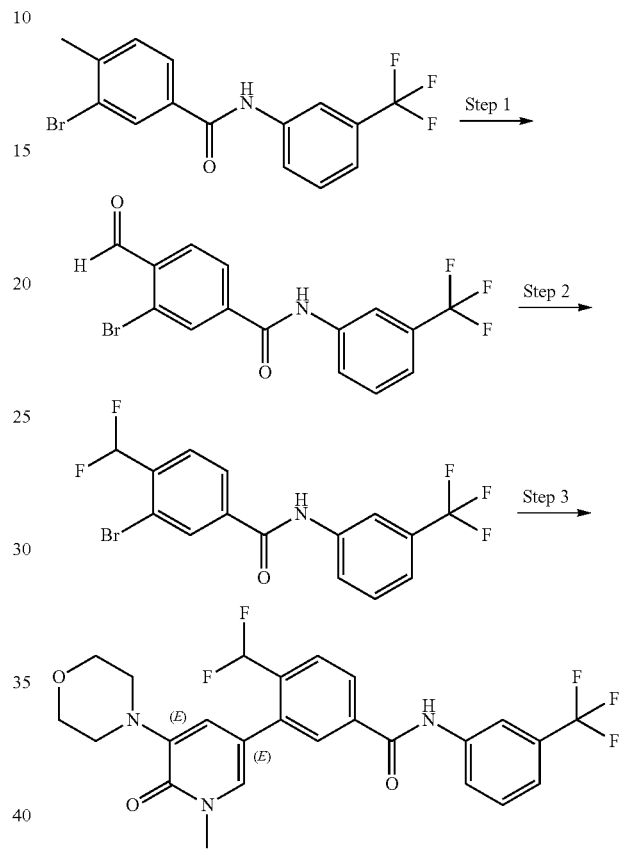

Step 1:

MnO$_2$ (8.0 equiv.) was added into a solution of 3-bromo-4-(hydroxymethyl)-N-(3-(trifluoromethyl)phenyl)benzamide (1.0 equiv.) in DCM (0.14 M). The suspension was stirred at rt for 1 hr. The mixture was filtered over celite and concentrated to yield 3-bromo-4-formyl-N-(3-(trifluoromethyl)phenyl)benzamide in 100% yield. LC/MS (m/z)= 373.9 (MH$^+$), R$_t$=0.0.94 min.

Step 2:

To a cooled solution of 3-bromo-4-formyl-N-(3-(trifluoromethyl)phenyl)benzamide (1.0 equiv.) in dry CH$_2$Cl$_2$ (0.18 M), (diethylamino)sulfur trifluoride (3.5 equiv.) was added under vigorous stirring. The resulting reaction mixture was stirred at 0° C. for 2 hrs. Quenched the reaction with sat NaHCO$_3$ and extracted with DCM. The organic layer was washed with Brine, filtered over Na$_2$SO$_4$ and concentrated to yield 3-bromo-4-(difluoromethyl)-N-(3-(trifluoromethyl)phenyl)benzamide in 47% yield. LC/MS (m/z)=393.9 (MH$^+$), R$_t$=1.11 min.

Step 3:

Method 2 was followed using 1-methyl-3-morpholino-5-(4,4,5,5-tetramethyl-1,3,2-dioxaborolan-2-yl)pyridin-2 (1H)-one and 3-bromo-4-(difluoromethyl)-N-(3-(trifluoromethyl)phenyl)benzamide to give 4-(difluoromethyl)-3-

(1-methyl-5-morpholino-6-oxo-1,6-dihydropyridin-3-yl)-N-(3-(trifluoromethyl)phenyl)benzamid in 8% yield. LC/MS (m/z)=508.1 (MH+), Rt=0.98 min. ¹H NMR (400 MHz, <cd3od>) δ ppm 3.12-3.21 (m, 4H), 3.64 (s, 3H), 3.80-3.90 (m, 4H), 6.96 (d, J=1.96 Hz, 2H), 7.41 (d, J=1.96 Hz, 2H), 7.52-7.62 (m, 1H), 7.84-7.92 (m, 1H), 7.97 (br. s., 2H), 8.05-8.12 (m, 1H), 8.14-8.20 (m, 1H).

Example 193: Synthesis of methyl(2-(2'-methyl-5-morpholino-6-oxo-5'-(3-(trifluoromethyl)benzamido)-[3,3'-bipyridin]-1(6H)-yl)ethyl)carbamate

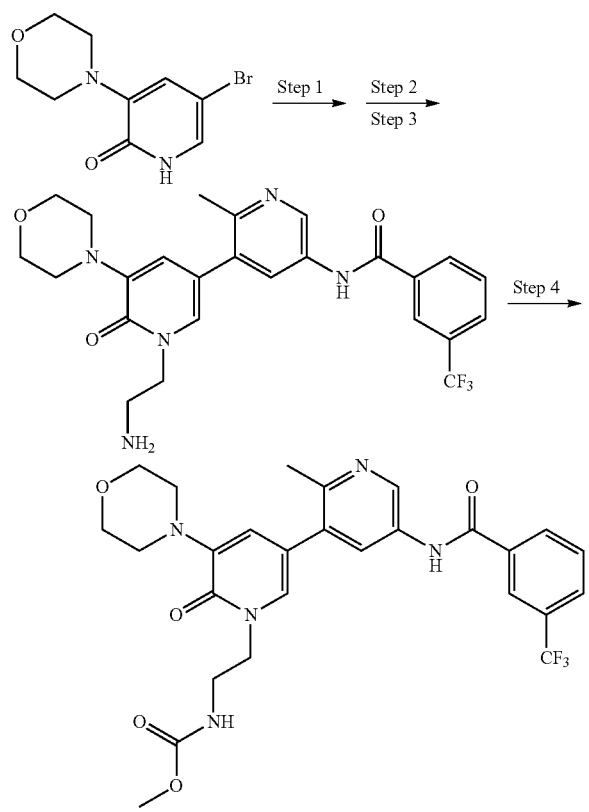

Step 1:
A 0.3 M solution of 5-bromo-3-morpholinopyridin-2(1H)-one (1.00 equiv.) in DMF was treated with sodium hydride (1.20 equiv.). The mixture was stirred for 15 min at ambient temperature. Tert-butyl(2-bromoethyl)carbamate (1.20 equiv.) was added. The mixture was stirred at 60° C. for 3 hr. The cooled reaction mixture was diluted with water and extracted with ethyl acetate. The combined organics were washed with saturated aqueous sodium bicarbonate, dried over sodium sulfate, filtered, and concentrated to give tert-butyl(2-(5-bromo-3-morpholino-2-oxopyridin-1(2H)-yl)ethyl)carbamate. LCMS (m/z) (M+H)=402.1/404.1, Rt=0.78 min.

Step 2:
Tert-butyl(2-(2'-methyl-5-morpholino-6-oxo-5'-(3-(trifluoromethyl)benzamido)-[3,3'-bipyridin]-1(6H)-yl)ethyl)carbamate was prepared using methods similar to those described for the preparation of Example 192 using the appropriate starting materials. LCMS (m/z) (M+H)=602.2, Rt=0.78 min.

Step 3:
A 0.1 M solution of tert-butyl(2-(2'-methyl-5-morpholino-6-oxo-5'-(3-(trifluoromethyl)benzamido)-[3,3'-bipyridin]-1(6H)-yl)ethyl)carbamate (1.00 equiv.) in 1:1 DCM:TFA was stirred for 15 min at ambient temperature. The reaction mixture was concentrated. The residue was basified with aqueous sodium carbonate and extracted with DCM. The combined extracts were dried over sodium sulfate, filtered, and concentrated to give crude N-(1'-(2-aminoethyl)-2-methyl-5'-morpholino-6'-oxo-1',6'-dihydro-[3,3'-bipyridin]-5-yl)-3-(trifluoromethyl)benzamide which was used without further purification. LCMS (m/z) (M+H)=502.2, Rt=0.58 min.

Step 4:
To a 0.2 M solution of N-(1'-(2-aminoethyl)-2-methyl-5'-morpholino-6'-oxo-1',6'-dihydro-[3,3'-bipyridin]-5-yl)-3-(trifluoromethyl)benzamide (1.0 equiv.) in DCM was added and triethylamine (3.00 equiv.) and methyl chloroformate (1.10 equiv.). The reaction was stirred at ambient temperature for 20 min. The reaction was quenched by the addition of water and concentrated. The crude material was purified via preparative reverse phase HPLC. Upon lyophilization of the pure fractions, methyl(2-(2'-methyl-5-morpholino-6-oxo-5'-(3-(trifluoromethyl)benzamido)-[3,3'-bipyridin]-1(6H)-yl)ethyl)carbamate was isolated as the TFA salt in 7% yield. ¹H NMR (400 MHz (400 MHz, <cd3od>) δ ppm 2.69 (s, 3H) 3.10-3.21 (m, 5H) 3.47-3.62 (m, 5H) 3.80-3.90 (m, 4H) 4.10-4.20 (m, 2H) 6.93 (d, J=2.05 Hz, 1H) 7.41 (d, J=2.10 Hz, 1H) 7.73-7.83 (m, 1H) 7.96 (dd, J=7.87, 0.68 Hz, 1H) 8.27 (d, J=7.87 Hz, 1H) 8.33 (s, 1H) 8.43 (d, J=2.20 Hz, 1H) 9.18 (d, J=2.15 Hz, 1H). LCMS (m/z) (M+H)=560.3, Rt=0.68 min.

The compound listed below was prepared using methods similar to those described for the preparation of Example 193 using the appropriate starting materials.

Example 194: Methyl(2-(5-(2-methyl-5-(3-(trifluoromethyl)benzamido)phenyl)-3-morpholino-2-oxopyridin-1(2H)-yl)ethyl)carbamate

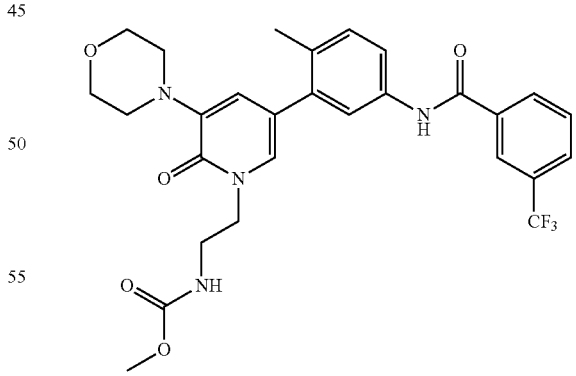

¹H NMR (400 MHz, <cd3od>) δ ppm 2.30 (s, 3H) 3.16 (br. s., 4H) 3.48-3.55 (m, 2H) 3.56 (s, 3H) 3.81-3.91 (m, 4H) 4.08-4.19 (m, 2H) 6.97 (d, J=1.57 Hz, 1H) 7.24 (d, J=1.56 Hz, 1H) 7.29 (d, J=8.22 Hz, 1H) 7.55 (d, J=8.22 Hz, 1H) 7.62 (s, 1H) 7.69-7.78 (m, 1H) 7.89 (d, J=7.83 Hz, 1H) 8.20 (d, J=7.83 Hz, 1H) 8.25 (s, 1H). LCMS (m/z) (M+H)=559.3, Rt=0.89 min.

Synthesis of 5-bromo-1-ethyl-3-(trifluoromethyl)pyridin-2(1H)-one

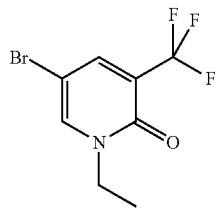

In a round bottom flask equipped with a stir bar and purged with nitrogen was added 5-bromo-3-(trifluoromethyl)pyridin-2-ol (1.0 equiv.), potassium carbonate (2.0 equiv.) and DMF (0.2 M). The mixture was stirred at room temperature and iodoethane (1.2 equiv.) was added via syringe. The mixture was warmed to 35° C. for 4 hours at which time LCMS indicated full conversion. The reaction was worked up by partitioning between water and ethyl acetate, the aqueous phase was extracted 3 more times with ethyl acetate, the organics were combined, washed with brine, dried with sodium sulfate, filtered and concentrated to yield 5-bromo-1-ethyl-3-(trifluoromethyl)pyridin-2(1H)-one (67%). $^1$H NMR (400 MHz, <cdcl3>) δ ppm 1.32-1.50 (m, 3H) 4.04 (q, J=7.17 Hz, 2H) 7.63 (br. s., 1H) 7.78 (br. s., 1H). LCMS (m/z) (M+H)=269.1/271.1, Rt=0.72 min

Example 196: N-(3-(4-methoxy-6-morpholinopyridin-2-yl)-4-methylphenyl)-3-(trifluoromethyl)benzamide Step 1:
A mixture of 2,6-dichloro-4-nitropyridine (1.0 equiv.), potassium carbonate (3 equiv.) and methanol (20 equiv.) were heated to 70° C. for 25 min in the microwave. The reaction mixture was diluted with methanol and was decanted from remaining solids. After concentration, the mixture was partitioned between water and EtOAc. The organic phase was washed with brine and dried over sodium sulfate. The solution was concentrated and dried under vacuo to give 2,6-dichloro-4-methoxypyridine in 88% yield. LCMS (m/z) (M+H)=177.9/179.9, Rt=0.72 min.

Step 2:
A mixture of 2,6-dichloro-4-methoxypyridine (1.0 equiv.) and morpholine (20 equiv.) were heated to 130° C. for 40 min in the microwave. The reaction mixture was centrifuged and the soluble portion was removed from solids. Water was added to the soluble portion which resulted in precipitation of product. This mixture was centrifuged and the soluble portion was discarded. The remaining solids were partitioned between water and EtOAc. The organic phase was washed with brine and dried over sodium sulfate. The solution was concentrated and dried under vacuo to give 4-(6-chloro-4-methoxypyridin-2-yl)morpholine in 43% yield. LCMS (m/z) (M+H)=229.1, Rt=0.76 min.

Step 3:
A mixture of 4-(6-chloro-4-methoxypyridin-2-yl)morpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over magnesium sulfate. After concentration, the crude material was purified via preparative reverse phase HPLC. Upon lyophilization of the pure fractions, N-(3-(4-methoxy-6-morpholinopyridin-2-yl)-4-methylphenyl)-3-(trifluoromethyl)benzamide was isolated as the TFA salt in 34% yield. LCMS (m/z) (M+H)=472.4, Rt=0.81 min.

Example 197: N-(4-methyl-3-(6-morpholino-4-oxo-1,4-dihydropyridin-2-yl)phenyl)-3-(trifluoromethyl)benzamide

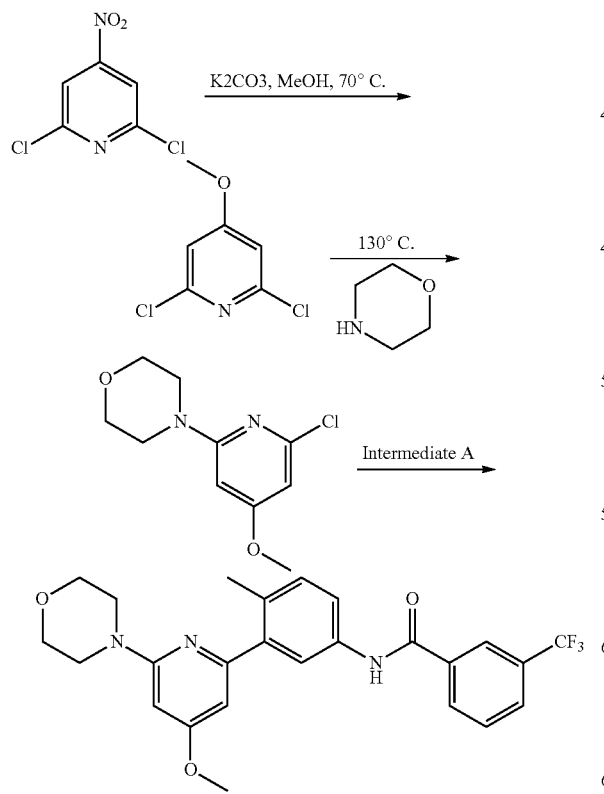

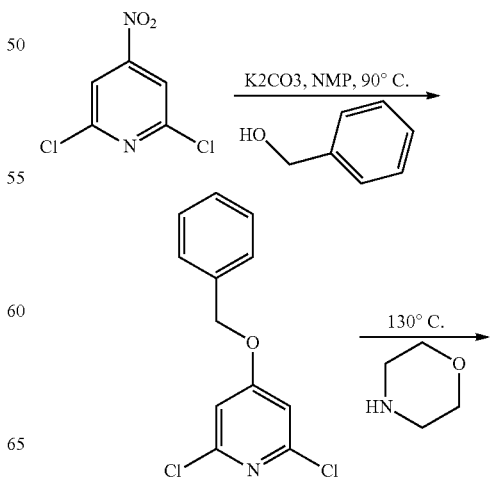

-continued

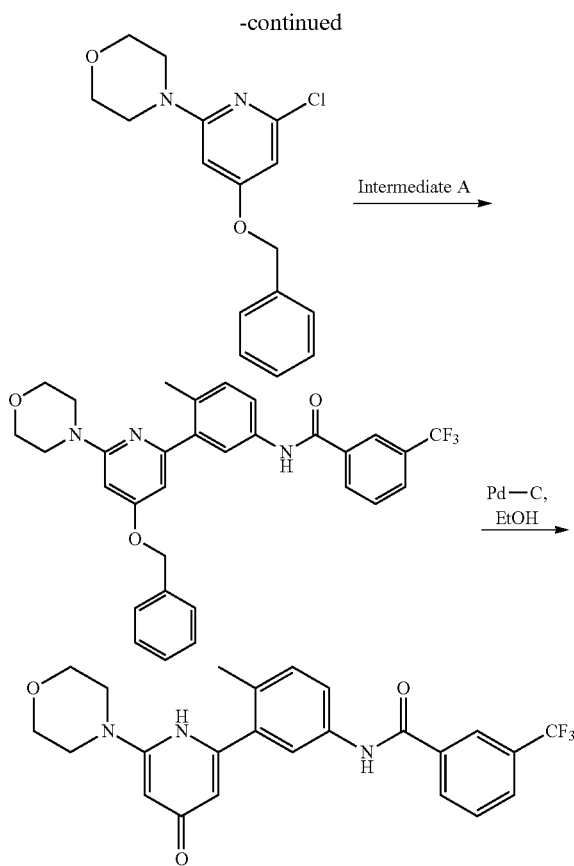

Step 1:
A mixture of 2,6-dichloro-4-nitropyridine (1.0 equiv.), potassium carbonate (2 equiv.) and benzyl alcohol (2.4 equiv.) in NMP (4 M) were heated to 90° C. for 2 h in the microwave. The mixture was partitioned between water and EtOAc. The organic phase was washed with brine and dried over sodium sulfate. The solution was concentrated and dried under vacuo to give crude 4-(benzyloxy)-2,6-dichloropyridine and was used in the next step without further purification. LCMS (m/z) (M+H)=254.0/256.0, Rt=1.05 min.

Step 2:
A mixture of 4-(benzyloxy)-2,6-dichloropyridine (1.0 equiv.) and morpholine (1.2 equiv.) in NMP (2 M) were heated to 130° C. for 1 h in the microwave. The reaction mixture was partitioned between water and EtOAc. The organic phase was washed with brine and dried over sodium sulfate. The solution was concentrated and dried under vacuo to give crude 4-(4-(benzyloxy)-6-chloropyridin-2-yl) morpholine and was used in the next step without further purification. LCMS (m/z) (M+H)=305.0, Rt=1.10 min.

Step 3:
A mixture of 4-(4-(benzyloxy)-6-chloropyridin-2-yl)morpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over magnesium sulfate. The solution was concentrated and dried under vacuo to give crude N-(3-(4-(benzyloxy)-6-morpholinopyridin-2-yl)-4-methylphenyl)-3-(trifluoromethyl)benzamide and was used in the next step without further purification. LCMS (m/z) (M+H)=548.2, Rt=0.99 min.

Step 4:
To N-(3-(4-(benzyloxy)-6-morpholinopyridin-2-yl)-4-methylphenyl)-3-(trifluoromethyl)benzamide (1.0 equiv.) in EtOH flushed with nitrogen was added Pd—C (0.2 equiv.). This mixture was then exposed to an atmosphere of hydrogen. After stirring for 4 h, the hydrogen atmosphere was replaced with nitrogen and the mixture was filtered over celite. After concentration, the crude material was purified via preparative reverse phase HPLC. Upon lyophilization of the pure fractions, N-(4-methyl-3-(6-morpholino-4-oxo-1,4-dihydropyridin-2-yl)phenyl)-3-(trifluoromethyl)benzamide was isolated as the TFA salt in 10% yield over four steps. $^1$H NMR (400 MHz, <dmso>) δ ppm 2.26 (s, 3H) 3.69 (br. s., 4H) 6.20-6.50 (m, 1H) 7.30 (br. s., 1H) 7.61-7.85 (m, 3H) 7.96 (d, J=7.83 Hz, 1H) 8.17-8.37 (m, 2H) 10.50 (br. s., 1H). LCMS (m/z) (M+H)=458.1, Rt=0.78 min.

Example 198: N-(4-methyl-3-(2-morpholinothiazol-5-yl)phenyl)-3-(trifluoromethyl)benzamide

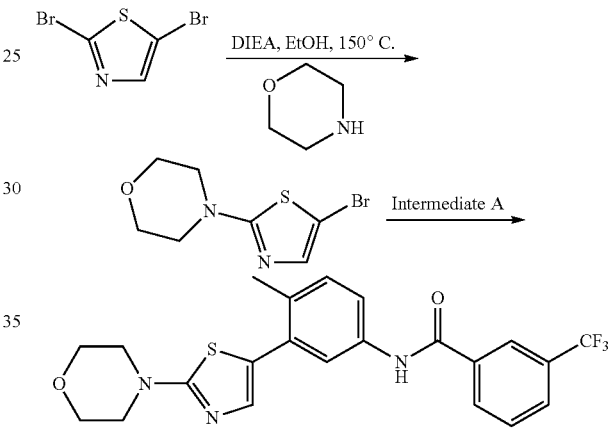

Step 1:
A solution of 2,5-dibromothiazole (1.0 equiv.), morpholine (1.5 equiv.) and triethylamine (4 equiv.) were heated to 150° C. for 2 h in the microwave. After concentration, the mixture was partitioned between water and EtOAc. The organic phase was washed with brine and dried over sodium sulfate. The solution was concentrated and dried under vacuo to give crude N-(4-methyl-3-(2-morpholinothiazol-5-yl)phenyl)-3-(trifluoromethyl)benzamide and was used in the next step without further purification. LCMS (m/z) (M+H)=448.2, Rt=0.83 min.

Step 2:
A mixture of 4-(5-bromothiazol-2-yl)morpholine (1.0 equiv.), N-(4-methyl-3-(4,4,5,5-tetramethyl-1,3,2-dioxaborolan-2-yl)phenyl)-3-(trifluoromethyl)benzamide (1.2 equiv.), sodium carbonate (2 M, 8 equiv.) and PdCl$_2$(dppf) (0.5 equiv.) in DME (0.1 M) were heated to 108° C. for 13 min in the microwave. After removing the DME soluble portion and concentrating, the resulting solid was partitioned between EtOAc and water. The organic phase was washed with brine and then dried over magnesium sulfate. After concentration, the crude material was purified via preparative reverse phase HPLC. Upon lyophilization of the pure fractions, N-(4-methyl-3-(2-morpholinothiazol-5-yl)phenyl)-3-(trifluoromethyl)benzamide was isolated as the TFA salt in 15% yield. $^1$H NMR (400 MHz, <dmso>) δ ppm 2.36 (s, 3H) 3.40-3.43 (m, 4H) 3.70-3.74 (m, 4H) 7.22-7.33 (m, 2H) 7.63 (dd, J=8.22, 1.96 Hz, 1H) 7.72-7.84 (m, 2H) 7.95

(d, J=7.43 Hz, 1H) 8.19-8.33 (m, 2H) 10.45 (s, 1H). LCMS (m/z) (M+H)=448.2, Rt=0.83 min.

Example 199: N-(4-methyl-3-(2-morpholinothiazol-4-yl)phenyl)-3-(trifluoromethyl)benzamide

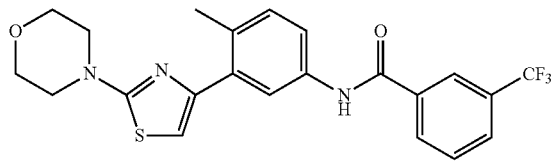 [SMILES: Cc1ccc(NC(=O)c2cccc(C(F)(F)F)c2)cc1-c1csc(N2CCOCC2)n1]

Starting with 2,4-dibromothiazole, the product was synthesized using the same procedure as for N-(4-methyl-3-(2-morpholinothiazol-5-yl)phenyl)-3-(trifluoromethyl)benzamide $^1$H NMR (400 MHz, <dmso>) δ ppm 2.39 (s, 3H) 3.68-3.77 (m, 4H) 6.94 (s, 1H) 7.17-7.27 (m, 1H) 7.68 (dd, J=8.41, 2.15 Hz, 1H) 7.77 (t, J=7.83 Hz, 1H) 7.89-8.00 (m, 2H) 8.19-8.34 (m, 2H) 10.43 (s, 1H). LCMS (m/z) (M+H)=448.2, Rt=0.85 min.

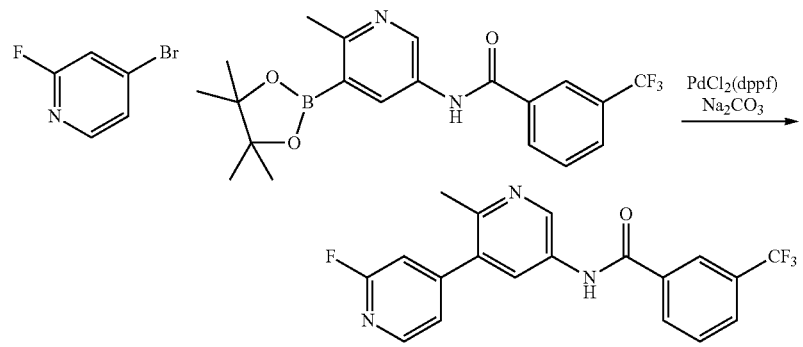

Synthesis of N-(2'-fluoro-2-methyl-[3,4'-bipyridin]-5-yl)-3-(trifluoromethyl)benzamide To a solution of 4-bromo-2-fluoropyridine (1.0 equiv.) and N-(6-methyl-5-(4,4,5,5-tetramethyl-1,3,2-dioxaborolan-2-yl)pyridin-3-yl)-3-(trifluoromethyl)benzamide (1.0 equiv.) in DME and 2M sodium carbonate (3:1, 0.08 M) was added PdCl$_2$(dppf)-DCM adduct (0.1 equiv.) in a microwave vial equipped with a stir bar. The reaction was heated to 110° C. for 15 min in the microwave. The reaction was quenched with water and extracted with ethyl acetate. The combined organic phase was dried with sodium sulfate, filtered and concentrated. The crude material N-(4-methyl-3-(2-morpholinopyridin-4-yl)phenyl)-3-(trifluoromethyl)benzamide was isolated as a solid and used in the subsequent step without purification. LCMS (m/z) (M+H)=376.0, Rt=0.71 min.

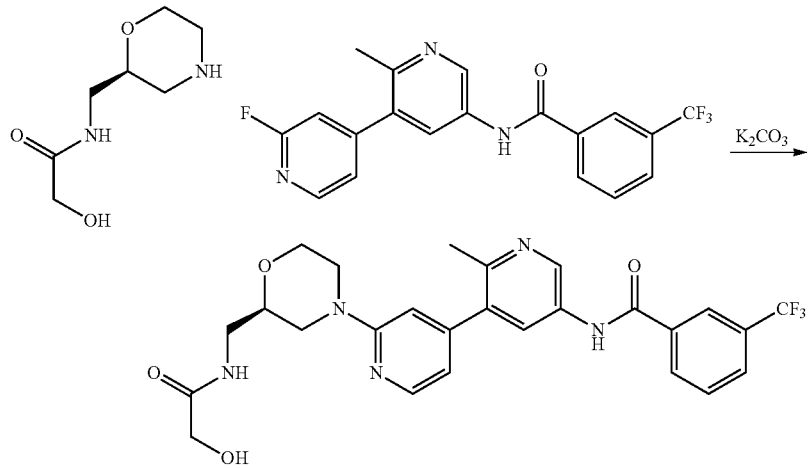

Example 215: 2-(difluoromethyl)-N-(4-methyl-3-(1-methyl-5-morpholino-6-oxo-1,6-dihydropyridin-3-yl)phenyl)isonicotinamide

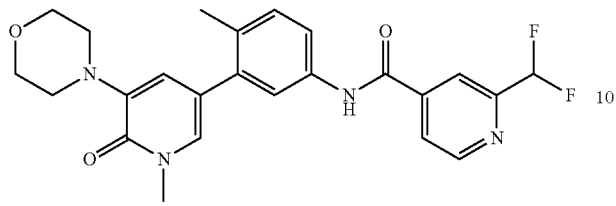

1H NMR (400 MHz, <cd3od>) δ ppm 2.31 (s, 3H) 3.17-3.22 (m, 4H) 3.65 (s, 3H) 3.85-3.91 (m, 4H) 6.67-6.98 (m, 1H) 7.02 (d, J=1.96 Hz, 1H) 7.31 (d, J=8.22 Hz, 1H) 7.40 (d, J=1.96 Hz, 1H) 7.59 (dd, J=8.41, 2.15 Hz, 1H) 7.65 (d, J=1.96 Hz, 1H) 8.01 (d, J=5.09 Hz, 1H) 8.17 (s, 1H) 8.83 (d, J=5.09 Hz, 1H). LCMS (m/z) (M+H)=455.1, Rt=0.75 min.

Example 222: Synthesis of N-(6'-cyano-2-methyl-5'-morpholino-[3,3'-bipyridin]-5-yl)-3-(trifluoromethyl)benzamide

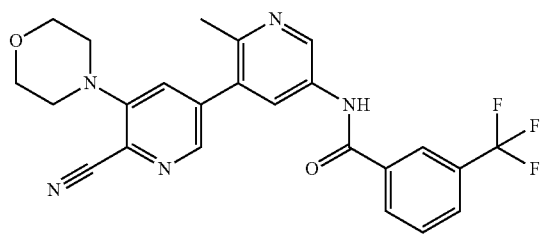

To a solution of 5'-amino-2'-methyl-5-morpholino-[3,3'-bipyridine]-6-carbonitrile (1.0 equiv.) and N-(6-methyl-5-(4,4,5,5-tetramethyl-1,3,2-dioxaborolan-2-yl)pyridin-3-yl)-3-(trifluoromethyl)benzamide (1.2 equiv.) in DME (0.1 M) and 2 M sodium carbonate (3 equiv.) was added PdCl$_2$(dppf)-DCM adduct (0.1 equiv.) in a microwave vial equipped with a stir bar. The reaction was heated to 120° C. for 10 min in the microwave. The organic phase was dried with sodium sulfate, filtered and concentrated. The crude material was purified via preparative reverse phase HPLC. Upon lyophilization of the pure fractions, N-(6'-cyano-2-methyl-5'-morpholino-[3,3'-bipyridin]-5-yl)-3-(trifluoromethyl)benzamide was isolated as the TFA salt in 23% yield. $^1$H NMR (400 MHz, <cd3od>) δ ppm 2.62 (s, 3H) 3.36-3.43 (m, 4H) 3.87-3.98 (m, 4H) 7.75 (d, J=1.57 Hz, 1H) 7.80 (t, J=7.83 Hz, 1H) 7.97 (d, J=7.43 Hz, 1H) 8.28 (d, J=7.83 Hz, 1H) 8.35 (s, 1H) 8.38 (d, J=1.57 Hz, 1H) 8.42 (d, J=1.96 Hz, 1H) 9.20 (d, J=2.35 Hz, 1H). LCMS (m/z) (M+H)=468.1, Rt=0.74 min.

The compounds listed below were prepared using methods similar to those described for the preparation of Example 222 using the corresponding bromides and boronic esters.

Example 223: 2-(2-cyanopropan-2-yl)-N-(3-(6-(difluoromethoxy)-5-morpholinopyridin-3-yl)-4-methylphenyl)isonicotinamide

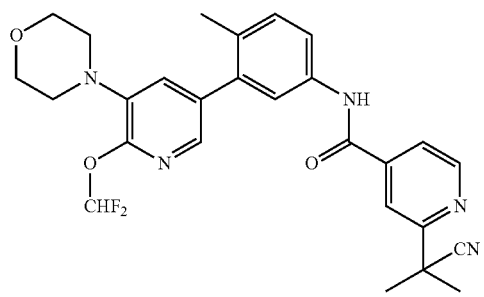 [SMILES: Cc1ccc(NC(=O)c2ccnc(C(C)(C)C#N)c2)cc1-c1cnc(OC(F)F)c(N2CCOCC2)c1]

$^1$H NMR (400 MHz, <dmso>) δ ppm 1.74 (s, 6H) 2.12-2.27 (m, 3H) 2.99-3.15 (m, 3H) 3.63-3.84 (m, 3H) 7.29-7.34 (m, 1H) 7.36-7.39 (m, 1H) 7.61-7.64 (m, 1H) 7.68-7.72 (m, 1H) 7.78-7.81 (m, 1H) 7.82-7.86 (m, 1H) 7.93-8.00 (m, 1H) 8.69-8.87 (m, 1H) 10.47-10.60 (m, 1H), LCMS (m/z) (M+H)=508.3, Rt=1.08 min.

Example 224: N-(6'-(difluoromethoxy)-2-methyl-5'-morpholino-[3,3'-bipyridin]-5-yl)-3-(trifluoromethyl)benzamide

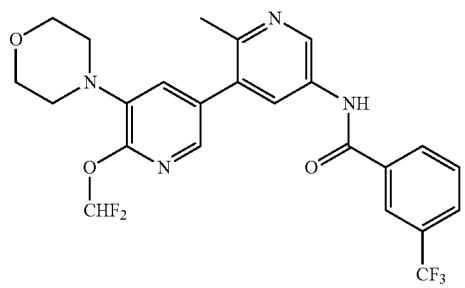 [SMILES: Cc1ncc(NC(=O)c2cccc(C(F)(F)F)c2)cc1-c1cnc(OC(F)F)c(N2CCOCC2)c1]

$^1$H NMR (400 MHz, <dmso>) δ ppm 2.97-3.11 (m, 4H) 3.69-3.72 (m, 4H) 7.43-7.49 (m, 1H) 7.69-7.81 (m, 2H) 7.83-7.87 (m, 1H) 7.89-7.99 (m, 1H) 8.10-8.17 (m, 1H) 8.21-8.30 (m, 2H) 8.87-8.95 (m, 1H) 10.73-10.86 (m, 1H) LCMS (m/z) (M+H)=509.2, Rt=0.86 min.

Example 225: 2-(2-cyanopropan-2-yl)-N-(6'-(difluoromethoxy)-2-methyl-5'-morpholino-[3,3'-bipyridin]-5-yl)isonicotinamide

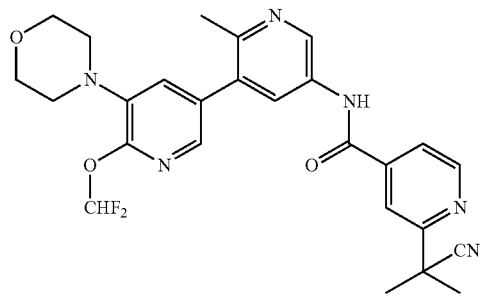

1H NMR (400 MHz, <dmso>) ™ppm 1.74 (s, 6H) 2.12-2.27 (m, 3H) 2.99-3.15 (m, 3H) 3.63-3.84 (m, 3H) 7.29-7.34 (m, 1H) 7.36-7.39 (m, 1H) 7.61-7.64 (m, 1H) 7.68-7.72 (m, 1H) 7.78-7.81 (m, 1H) 7.82-7.86 (m, 1H) 7.93-8.00 (m, 1H) 8.69-8.87 (m, 1H) 10.47-10.60 (m, 1H), LCMS (m/z) (M+H)=508.3, Rt=1.04 min.

Example 226: N-(3-(6-(difluoromethoxy)-5-morpholinopyridin-3-yl)-4-methylphenyl)-2-(2-hydroxypropan-2-yl)isonicotinamide

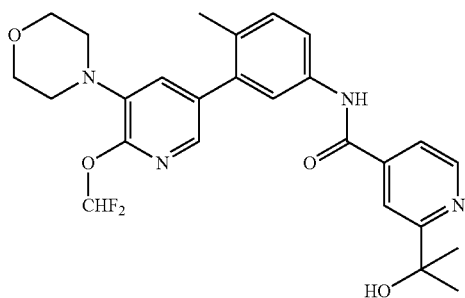 [SMILES: Cc1ccc(NC(=O)c2ccnc(C(C)(C)O)c2)cc1-c1cnc(OC(F)F)c(N2CCOCC2)c1]

LCMS (m/z) (M+H)=499.2, Rt=0.79 min.

Example 227: N-(6'-(2,2-difluoroethoxy)-2-methyl-5'-morpholino-[3,3'-bipyridin]-5-yl)-3-(trifluoromethyl)benzamide

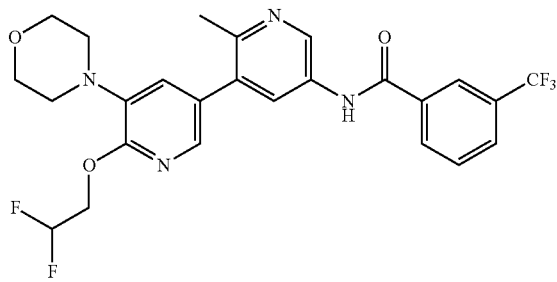 [SMILES: Cc1ncc(NC(=O)c2cccc(C(F)(F)F)c2)cc1-c1cnc(OCC(F)F)c(N2CCOCC2)c1]

¹H NMR (400 MHz, <cd3od>) δ ppm 2.69 (s, 3H) 3.05-3.20 (m, 4H) 3.76-3.96 (m, 4H) 4.67 (td, J=14.18, 3.72 Hz, 2H) 6.02-6.59 (m, 1H) 7.36 (d, J=1.96 Hz, 1H) 7.69-7.84 (m, 1H) 7.97 (d, J=7.83 Hz, 2H) 8.23-8.38 (m, 2H) 8.47 (d, J=2.35 Hz, 1H) 9.37 (d, J=2.35 Hz, 1H).

LCMS (m/z) (M+H)=523.1, Rt=0.82 min.

Example 228: 2-(2-cyanopropan-2-yl)-N-(6'-(2,2-difluoroethoxy)-2-methyl-5'-morpholino-[3,3'-bipyridin]-5-yl)isonicotinamide

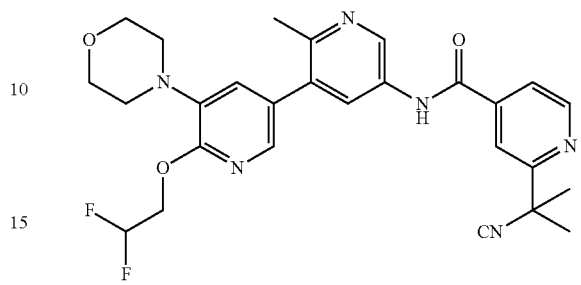

¹H NMR (400 MHz, <cd3od>) δ ppm 1.81 (s, 6H) 2.67 (s, 3H) 2.98-3.24 (m, 4H) 3.71-4.16 (m, 4H) 4.67 (td, J=14.18, 3.72 Hz, 2H) 6.03-6.57 (m, 1H) 7.36 (d, J=1.96 Hz, 1H) 7.80-7.92 (m, 2H) 8.13 (s, 1H) 8.42 (d, J=2.35 Hz, 1H) 8.82 (d, J=5.09 Hz, 1H) 9.30 (d, J=1.96 Hz, 1H). LCMS (m/z) (M+H)=523.2, Rt=0.72 min.

Example 229: Synthesis of N-(3-(6-ethoxy-5-morpholinopyridin-3-yl)-4-methylphenyl)-3-(methylsulfonyl)benzamide

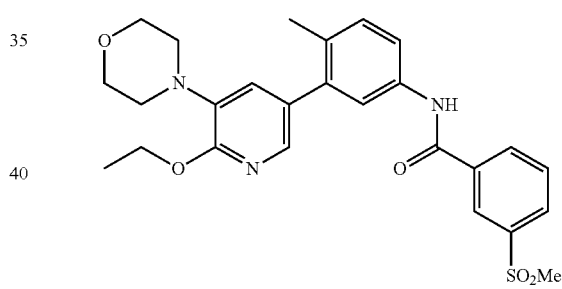

To a solution of 3-(6-ethoxy-5-morpholinopyridin-3-yl)-4-methylaniline (1.0 equiv) and 3-(methylsulfonyl)benzoic acid (1.1 equiv.) in DMA (0.1 M) at 25° C. were added HOAT (1.3 equiv.), i-Pr₂NEt (3 equiv.), and EDC (1.3 equiv) and the mixture was stirred for 20 h at 25° C. The mixture was quenched with a small amount of water, diluted with DMSO, filtered, and purified via preparative reverse phase HPLC. Upon lyophilization of the pure fractions, N-(3-(6-ethoxy-5-morpholinopyridin-3-yl)-4-methylphenyl)-3-(methylsulfonyl)benzamide was isolated as the TFA salt in 63% yield. ¹H NMR (400 MHz, <dmso>) δ ppm 1.35 (t, J=7.04 Hz, 3H) 2.21 (s, 3H) 3.05 (br. s., 4H) 3.27 (s, 3H) 3.66-3.82 (m, 4H) 4.38 (q, J=7.04 Hz, 2H) 7.12 (d, J=1.57 Hz, 1H) 7.29 (d, J=8.61 Hz, 1H) 7.62 (d, J=1.57 Hz, 1H) 7.68-7.74 (m, 2H) 7.81 (t, J=7.83 Hz, 1H) 8.12 (d, J=7.83 Hz, 1H) 8.27 (d, J=7.83 Hz, 1H) 8.46 (s, 1H) 10.48 (s, 1H). LCMS (m/z) (M+H)=496.1, Rt=0.88 min.

The compounds listed below were prepared using methods similar to those described for the preparation of Example 229 using the corresponding amines and acids:

Example 230: N-(3-(6-ethoxy-5-morpholinopyridin-3-yl)-4-methylphenyl)-3-(1,3,4-oxadiazol-2-yl)benzamide

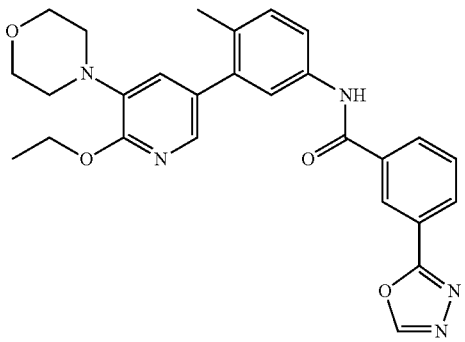 [SMILES: CCOc1ncc(-c2cc(NC(=O)c3cccc(-c4nnco4)c3)ccc2C)cc1N1CCOCC1]

¹H NMR (400 MHz, <dmso>) δ ppm 1.35 (t, J=6.85 Hz, 3H) 2.22 (s, 3H) 2.99-3.12 (m, 4H) 3.63-3.80 (m, 4H) 4.38 (q, J=6.78 Hz, 2H) 7.13 (d, J=1.57 Hz, 1H) 7.28 (d, J=8.22 Hz, 1H) 7.65 (d, J=1.57 Hz, 1H) 7.70-7.81 (m, 3H) 8.21 (t, J=7.43 Hz, 2H) 8.59 (s, 1H) 9.41 (s, 1H) 10.47 (s, 1H). LCMS (m/z) (M+H)=486.1, Rt=0.89 min.

Example 231: 3-(difluoromethyl)-N-(3-(6-ethoxy-5-morpholinopyridin-3-yl)-4-methylphenyl)benzamide

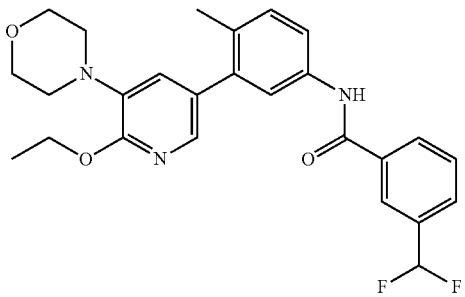 [SMILES: CCOc1ncc(-c2cc(NC(=O)c3cccc(C(F)F)c3)ccc2C)cc1N1CCOCC1]

¹H NMR (400 MHz, <dmso>) δ ppm 1.35 (t, J=7.04 Hz, 3H) 2.21 (s, 3H) 3.05 (br. s., 4H) 3.69-3.79 (m, 4H) 4.38 (q, J=7.04 Hz, 2H) 6.97-7.25 (m, 2H) 7.27 (d, J=7.83 Hz, 1H) 7.60-7.73 (m, 4H) 7.75-7.81 (m, 1H) 8.09-8.16 (m, 2H) 10.36 (s, 1H). LCMS (m/z) (M+H)=468.1, Rt=1.02 min.

Example 232: N-(3-(6-ethoxy-5-morpholinopyridin-3-yl)-4-methylphenyl)-2-(methylsulfonyl)isonicotinamide

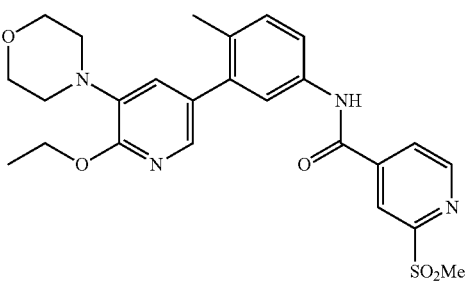 [SMILES: CCOc1ncc(-c2cc(NC(=O)c3ccnc(S(C)(=O)=O)c3)ccc2C)cc1N1CCOCC1]

¹H NMR (400 MHz, <dmso>) δ ppm 1.35 (t, J=7.04 Hz, 3H) 2.22 (s, 3H) 3.05 (br. s., 4H) 3.33 (s, 3H) 3.67-3.79 (m, 4H) 4.38 (q, J=7.04 Hz, 2H) 7.12 (d, J=1.57 Hz, 1H) 7.31 (d, J=8.22 Hz, 1H) 7.63 (d, J=1.96 Hz, 1H) 7.68-7.75 (m, 2H) 8.17-8.24 (m, 1H) 8.52 (s, 1H) 8.98 (d, J=5.09 Hz, 1H) 10.75 (s, 1H). LCMS (m/z) (M+H)=497.1, Rt=0.87 min.

Example 233: 2-(1,1-difluoroethyl)-N-(3-(6-ethoxy-5-morpholinopyridin-3-yl)-4-methylphenyl)isonicotinamide

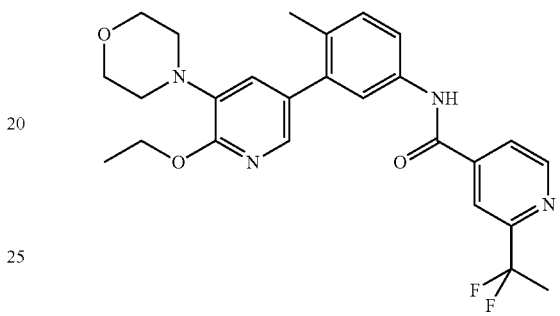

¹H NMR (400 MHz, <dmso>) δ ppm 1.35 (t, J=7.04 Hz, 3H) 2.03 (t, J=19.17 Hz, 3H) 2.22 (s, 3H) 3.05 (br. s., 4H) 3.64-3.80 (m, 4H) 4.38 (q, J=6.91 Hz, 2H) 7.12 (d, J=1.57 Hz, 1H) 7.30 (d, J=8.22 Hz, 1H) 7.62 (d, J=1.96 Hz, 1H) 7.68-7.74 (m, 2H) 8.01 (d, J=4.70 Hz, 1H) 8.16 (s, 1H) 8.86 (d, J=5.09 Hz, 1H) 10.60 (s, 1H). LCMS (m/z) (M+H)= 483.1, Rt=1.00 min.

Example 234: N-(3-(6-ethoxy-5-morpholinopyridin-3-yl)-4-methylphenyl)-1-ethyl-6-oxo-5-(trifluoromethyl)-1,6-dihydropyridine-3-carboxamide

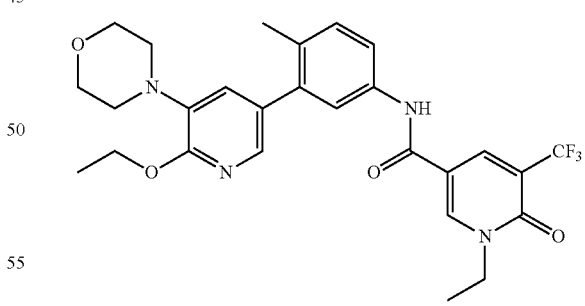

¹H NMR (400 MHz, <dmso>) δ ppm 1.29 (t, J=7.04 Hz, 3H) 1.35 (t, J=6.85 Hz, 3H) 2.20 (s, 3H) 3.04 (br. s., 4H) 3.72 (d, J=3.91 Hz, 4H) 4.06 (q, J=6.91 Hz, 2H) 4.38 (q, J=6.91 Hz, 2H) 7.11 (d, J=1.57 Hz, 1H) 7.27 (d, J=8.22 Hz, 1H) 7.52 (d, J=1.57 Hz, 1H) 7.63 (dd, J=8.22, 1.96 Hz, 1H) 7.70 (d, J=1.57 Hz, 1H) 8.45 (d, J=1.96 Hz, 1H) 8.79 (d, J=2.35 Hz, 1H) 10.12 (s, 1H). LCMS (m/z) (M+H)=531.1, Rt=0.99 min.

Example 235: 3-(6-ethoxy-5-morpholinopyridin-3-yl)-4-methyl-N-(3-trifluoromethyl)phenyl)benzamide

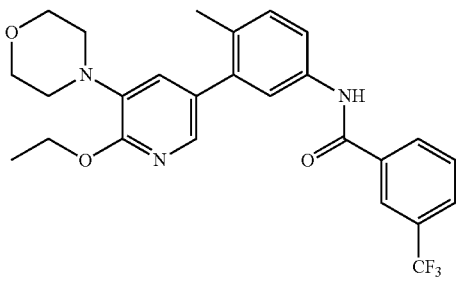 [SMILES: CCOc1ncc(-c2cc(NC(=O)c3cccc(C(F)(F)F)c3)ccc2C)cc1N1CCOCC1]

¹H NMR (400 MHz, <dmso>) δ ppm 1.35 (t, J=7.04 Hz, 3H) 2.32 (s, 3H) 3.07 (d, J=3.91 Hz, 4H) 3.68-3.77 (m, 4H) 4.39 (q, J=7.04 Hz, 2H) 7.18 (d, J=1.57 Hz, 1H) 7.45 (dd, J=15.85, 8.02 Hz, 2H) 7.58 (t, J=8.02 Hz, 1H) 7.78 (d, J=1.57 Hz, 1H) 7.85-7.92 (m, 2H) 8.05 (d, J=8.22 Hz, 1H) 8.22 (s, 1H) 10.45 (s, 1H). LCMS (m/z) (M+H)=486.1, Rt=1.13 min.

Example 236: 3-(6-ethoxy-5-morpholinopyridin-3-yl)-N-(3-(2-hydroxypropan-2-yl)phenyl)-4-methylbenzamide

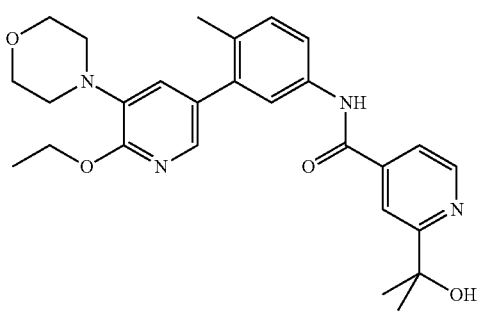 [SMILES: CCOc1ncc(-c2cc(NC(=O)c3ccnc(C(C)(C)O)c3)ccc2C)cc1N1CCOCC1]

¹H NMR (400 MHz, <dmso>) δ ppm 1.35 (t, J=7.04 Hz, 3H) 1.41 (s, 6H) 2.31 (s, 3H) 3.06 (br. s., 4H) 3.69-3.77 (m, 4H) 4.39 (q, J=7.04 Hz, 2H) 7.13-7.20 (m, 2H) 7.21-7.27 (m, 1H) 7.44 (d, J=8.22 Hz, 1H) 7.67 (d, J=8.22 Hz, 1H) 7.78 (d, J=1.57 Hz, 1H) 7.80 (s, 1H) 7.84-7.90 (m, 2H) 10.11 (s, 1H). LCMS (m/z) (M+H)=476.2, Rt=0.91 min.

Example 237: 2-(difluoromethyl)-N-(3-(6-ethoxy-5-morpholinopyridin-3-yl)-4-methylphenyl)isonicotinamide

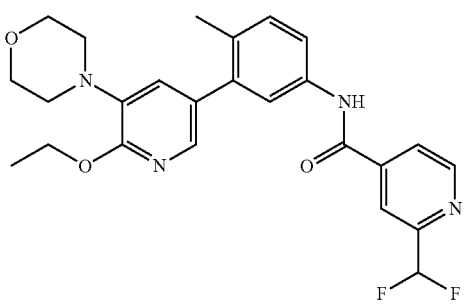 [SMILES: CCOc1ncc(-c2cc(NC(=O)c3ccnc(C(F)F)c3)ccc2C)cc1N1CCOCC1]

¹H NMR (400 MHz, <dmso>) δ ppm 1.35 (t, J=7.04 Hz, 3H) 2.21 (s, 3H) 3.05 (br. s., 4H) 3.68-3.79 (m, 4H) 4.38 (q, J=7.04 Hz, 2H) 6.88-7.22 (m, 2H) 7.30 (d, J=8.22 Hz, 1H) 7.62 (d, J=1.96 Hz, 1H) 7.67-7.75 (m, 2H) 8.04 (d, J=4.70 Hz, 1H) 8.16 (s, 1H) 8.88 (d, J=5.09 Hz, 1H) 10.61 (s, 1H). LCMS (m/z) (M+H)=469.1, Rt=0.95 min.

Example 238: 3-(6-ethoxy-5-morpholinopyridin-3-yl)-4-methyl-N-(3-(methylsulfonyl)phenyl)benzamide

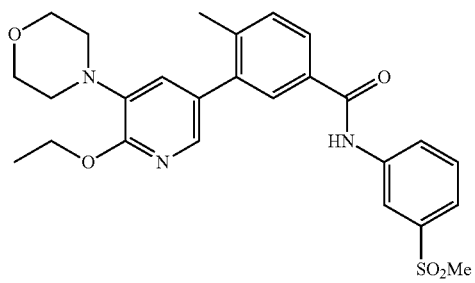 [SMILES: CCOc1ncc(-c2cc(C(=O)Nc3cccc(S(C)(=O)=O)c3)ccc2C)cc1N1CCOCC1]

¹H NMR (400 MHz, <dmso>) δ ppm 1.35 (t, J=7.04 Hz, 3H) 2.32 (s, 3H) 3.06 (br. s., 4H) 3.19 (s, 3H) 3.69-3.78 (m, 4H) 4.39 (q, J=7.04 Hz, 2H) 7.19 (d, J=1.96 Hz, 1H) 7.47 (d, J=8.61 Hz, 1H) 7.58-7.66 (m, 2H) 7.78 (d, J=1.96 Hz, 1H) 7.87-7.93 (m, 2H) 8.12 (dt, J=5.97, 2.69 Hz, 1H) 8.39 (s, 1H) 10.52 (s, 1H). LCMS (m/z) (M+H)=496.1, Rt=0.90 min.

Example 239: 2-(2-cyanopropan-2-yl)-N-(6'-ethoxy-2-methyl-5'-morpholino-[3,3'-bipyridin]-5-yl)isonicotinamide

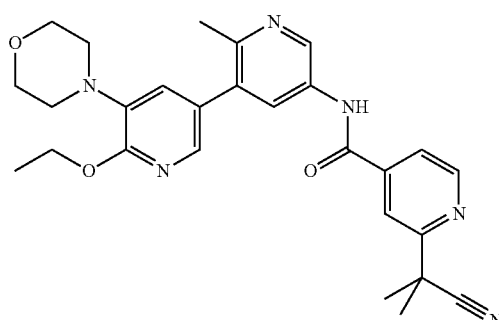

¹H NMR (400 MHz, <dmso>) δ ppm 1.36 (t, J=7.04 Hz, 3H) 1.75 (s, 6H) 2.49 (s, 3H) 2.99-3.12 (m, 4H) 3.66-3.78 (m, 4H) 4.39 (q, J=7.04 Hz, 2H) 7.23 (d, J=1.57 Hz, 1H) 7.80 (d, J=1.96 Hz, 1H) 7.86-7.92 (m, 1H) 8.02 (s, 1H) 8.14 (s, 1H) 8.83 (d, J=5.09 Hz, 1H) 8.93 (s, 1H) 10.90 (s, 1H). LCMS (m/z) (M+H)=487.1, Rt=0.70 min.

Example 240: N-(6'-ethoxy-2-methyl-5'-morpholino-[3,3'-bipyridin]-5-yl)-2-(2-hydroxypropan-2-yl)isonicotinamide

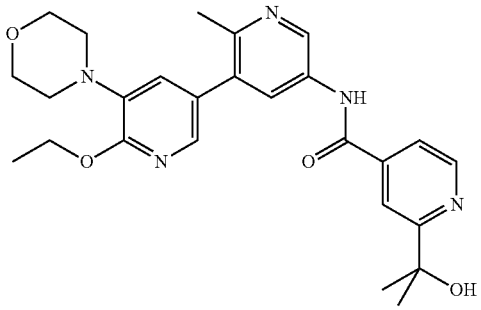 [SMILES: CCOc1ncc(-c2cc(NC(=O)c3ccnc(C(C)(C)O)c3)cnc2C)cc1N1CCOCC1]

¹H NMR (400 MHz, <dmso>) δ ppm 1.36 (t, J=7.04 Hz, 3H) 1.48 (s, 6H) 2.53 (s, 3H) 3.07 (br. s., 4H) 3.63-3.82 (m, 4H) 4.40 (q, J=7.04 Hz, 2H) 7.26 (d, J=1.57 Hz, 1H) 7.75 (dd, J=5.09, 1.17 Hz, 1H) 7.83 (d, J=1.57 Hz, 1H) 8.20 (s, 1H) 8.28 (s, 1H) 8.72 (d, J=5.09 Hz, 1H) 9.04 (s, 1H) 11.00 (s, 1H). LCMS (m/z) (M+H)=478.1, Rt=0.55 min.

Example 241: N-(6'-ethoxy-2-methyl-5'-morpholino-[3,3'-bipyridin]-5-yl)-1-ethyl-6-oxo-5-(trifluoromethyl)-1,6-dihydropyridine-3-carboxamide

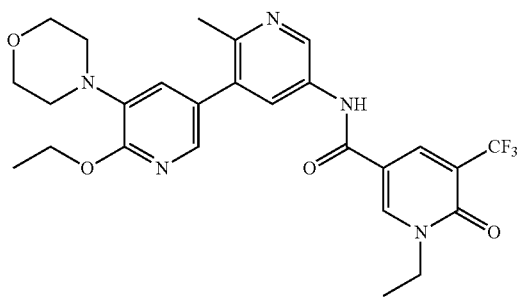 [SMILES: CCOc1ncc(-c2cc(NC(=O)c3cc(C(F)(F)F)c(=O)n(CC)c3)cnc2C)cc1N1CCOCC1]

¹H NMR (400 MHz, <dmso>) δ ppm 1.29 (t, J=7.04 Hz, 3H) 1.35 (t, J=7.04 Hz, 3H) 2.48 (s, 3H) 3.06 (br. s., 4H) 3.65-3.80 (m, 4H) 4.08 (q, J=7.17 Hz, 2H) 4.39 (q, J=7.04 Hz, 2H) 7.22 (d, J=1.96 Hz, 1H) 7.79 (d, J=1.57 Hz, 1H) 8.05 (s, 1H) 8.48 (d, J=1.96 Hz, 1H) 8.78-8.91 (m, 2H) 10.47 (s, 1H). LCMS (m/z) (M+H)=532.2, Rt=0.72 min.

Example 242: N-(6'-ethoxy-2-methyl-5'-morpholino-[3,3'-bipyridin]-5-yl)-3-(methylsulfonyl)benzamide

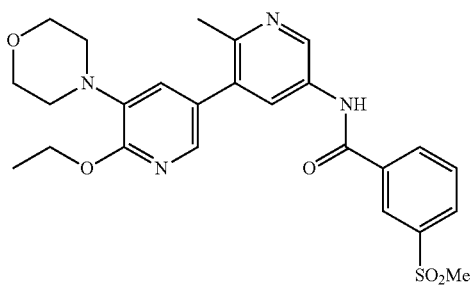 [SMILES: CCOc1ncc(-c2cc(NC(=O)c3cccc(S(C)(=O)=O)c3)cnc2C)cc1N1CCOCC1]

¹H NMR (400 MHz, <dmso>) δ ppm 1.36 (t, J=7.04 Hz, 3H) 2.52 (s, 3H) 3.07 (br. s., 4H) 3.29 (s, 3H) 3.63-3.81 (m, 4H) 4.40 (q, J=7.04 Hz, 2H) 7.25 (d, J=1.57 Hz, 1H) 7.82 (d, J=1.96 Hz, 1H) 7.86 (t, J=7.83 Hz, 1H) 8.18 (d, J=7.83 Hz, 1H) 8.23 (s, 1H) 8.31 (d, J=7.83 Hz, 1H) 8.52 (s, 1H) 9.01 (d, J=1.57 Hz, 1H) 10.95 (s, 1H). LCMS (m/z) (M+H)=497.1, Rt=0.64 min.

Example 243: N-(6'-ethoxy-2-methyl-5'-morpholino-[3,3'-bipyridin]-5-yl)-2-(methylsulfonyl)isonicotinamide

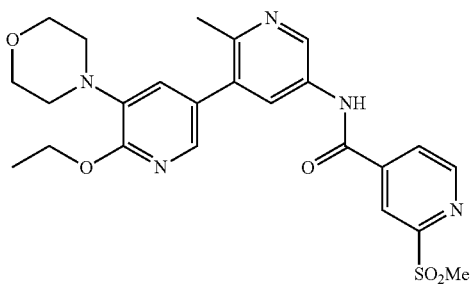 [SMILES: CCOc1ncc(-c2cc(NC(=O)c3ccnc(S(C)(=O)=O)c3)cnc2C)cc1N1CCOCC1]

¹H NMR (400 MHz, <dmso>) δ ppm 1.36 (t, J=7.04 Hz, 3H) 2.48 (br. s., 3H) 3.00-3.11 (m, 4H) 3.35 (s, 3H) 3.68-3.78 (m, 4H) 4.40 (q, J=7.04 Hz, 2H) 7.23 (d, J=1.96 Hz, 1H) 7.81 (d, J=1.96 Hz, 1H) 8.16 (s, 1H) 8.20-8.26 (m, 1H) 8.56 (s, 1H) 8.95 (s, 1H) 9.03 (d, J=5.09 Hz, 1H) 11.12 (s, 1H). LCMS (m/z) (M+H)=498.1, Rt=0.60 min.

Example 244: N-(6'-ethoxy-2-methyl-5'-morpholino-[3,3'-bipyridin]-5-yl)-3-(1,3,4-oxadiazol-2-yl)benzamide

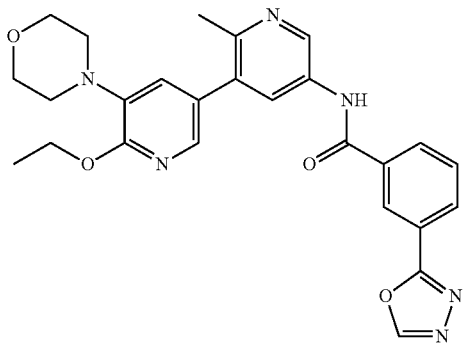 [SMILES: CCOc1ncc(-c2cc(NC(=O)c3cccc(-c4nnco4)c3)cnc2C)cc1N1CCOCC1]

¹H NMR (400 MHz, <dmso>) δ ppm 1.36 (t, J=7.04 Hz, 3H) 2.52 (s, 3H) 3.07 (br. s., 4H) 3.68-3.79 (m, 4H) 4.40 (q, J=6.91 Hz, 2H) 7.26 (d, J=1.96 Hz, 1H) 7.78-7.85 (m, 2H) 8.21-8.30 (m, 3H) 8.65 (s, 1H) 9.03 (s, 1H) 9.43 (s, 1H) 10.93 (s, 1H). LCMS (m/z) (M+H)=487.1, Rt=0.65 min.

Example 245: 5-cyclopropyl-N-(6'-ethoxy-2-methyl-5'-morpholino-[3,3'-bipyridin]-5-yl)isoxazole-3-carboxamide

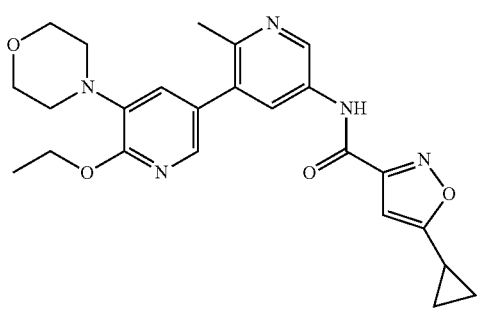 [SMILES: CCOc1ncc(-c2cc(NC(=O)c3cc(C4CC4)on3)cnc2C)cc1N1CCOCC1]

¹H NMR (400 MHz, <dmso>) δ ppm 0.91 (dd, J=4.89, 2.15 Hz, 2H) 1.07 (dd, J=8.41, 2.54 Hz, 2H) 1.30 (t, J=7.04 Hz, 3H) 2.12-2.22 (m, 1H) 2.41 (br. s., 3H) 3.01 (br. s., 4H) 3.63-3.74 (m, 4H) 4.34 (q, J=7.04 Hz, 2H) 6.59 (s, 1H) 7.16 (d, J=1.96 Hz, 1H) 7.73 (d, J=1.96 Hz, 1H) 8.10 (br. s., 1H) 8.87 (d, J=1.57 Hz, 1H) 10.93 (s, 1H). LCMS (m/z) (M+H)=450.1, Rt=0.73 min.

Example 246: N-(6'-ethoxy-2-methyl-5'-morpholino-[3,3'-bipyridin]-5-yl)-2-(trifluoromethyl)isonicotinamide

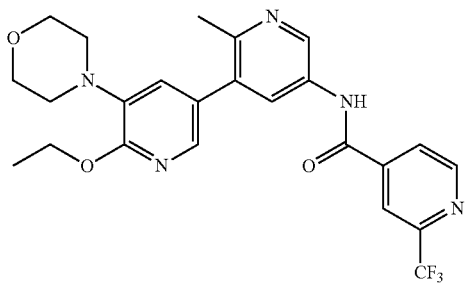 [SMILES: CCOc1ncc(-c2cc(NC(=O)c3ccnc(C(F)(F)F)c3)cnc2C)cc1N1CCOCC1]

¹H NMR (400 MHz, <dmso>) δ ppm 1.35 (t, J=7.04 Hz, 3H) 2.46 (br. s., 3H) 3.01-3.13 (m, 4H) 3.51-3.83 (m, 4H) 4.39 (q, J=7.04 Hz, 2H) 7.21 (d, J=1.96 Hz, 1H) 7.79 (d, J=1.96 Hz, 1H) 8.08 (s, 1H) 8.20 (d, J=5.09 Hz, 1H) 8.38 (s, 1H) 8.89 (d, J=1.96 Hz, 1H) 9.01 (d, J=4.70 Hz, 1H) 10.94 (s, 1H). LCMS (m/z) (M+H)=488.1, Rt=0.74 min.

Example 247: 2-(difluoromethyl)-N-(6'-ethoxy-2-methyl-5'-morpholino-[3,3'-bipyridin]-5-yl)isonicotinamide

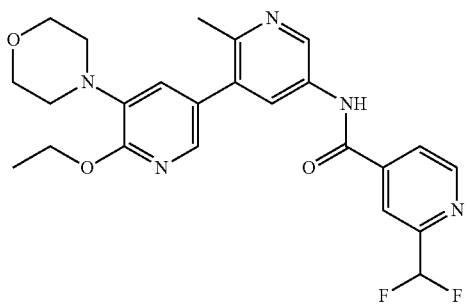 [SMILES: CCOc1ncc(-c2cc(NC(=O)c3ccnc(C(F)F)c3)cnc2C)cc1N1CCOCC1]

¹H NMR (400 MHz, <dmso>) δ ppm 1.36 (t, J=7.04 Hz, 3H) 2.49 (s, 3H) 3.06 (br. s., 4H) 3.62-3.80 (m, 4H) 4.40 (q, J=7.04 Hz, 2H) 6.90-7.28 (m, 2H) 7.81 (d, J=1.96 Hz, 1H) 8.07 (d, J=4.70 Hz, 1H) 8.14-8.27 (m, 2H) 8.93 (d, J=5.09 Hz, 1H) 8.95 (d, J=1.57 Hz, 1H) 10.99 (s, 1H). LCMS (m/z) (M+H)=470.1, Rt=0.67 min.

Example 248: N-(6'-ethoxy-2-methyl-5'-morpholino-[3,3'-bipyridin]-5-yl)-3-(trifluoromethyl)benzamide

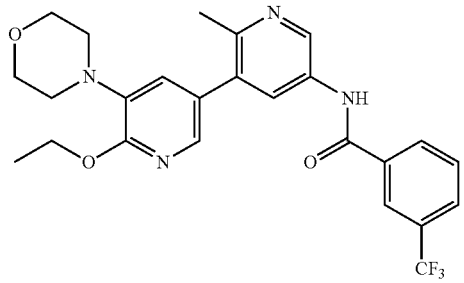 [SMILES: CCOc1ncc(-c2cc(NC(=O)c3cccc(C(F)(F)F)c3)cnc2C)cc1N1CCOCC1]

¹H NMR (400 MHz, <dmso>) δ ppm 1.36 (t, J=6.85 Hz, 3H) 2.50 (br. s., 3H) 3.07 (br. s., 4H) 3.62-3.81 (m, 4H) 4.40 (q, J=7.04 Hz, 2H) 7.24 (d, J=1.96 Hz, 1H) 7.77-7.87 (m, 2H) 8.01 (d, J=7.83 Hz, 1H) 8.20 (s, 1H) 8.28 (d, J=7.83 Hz, 1H) 8.33 (s, 1H) 8.99 (d, J=1.57 Hz, 1H) 10.85 (s, 1H). LCMS (m/z) (M+H)=487.2, Rt=0.81 min.

Example 249: N-(6'-cyano-2-methyl-5'-morpholino-[3,3'-bipyridin]-5-yl)-3-((dimethylamino)methyl)-5-(trifluoromethyl)benzamide

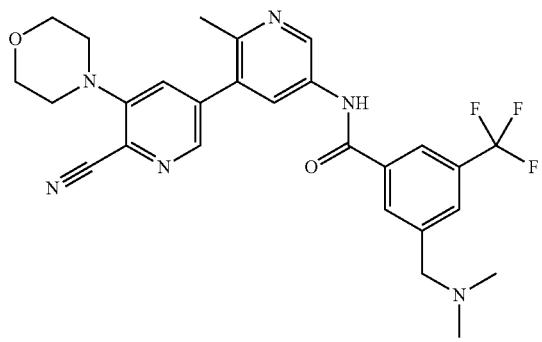 [SMILES: Cc1ncc(NC(=O)c2cc(CN(C)C)cc(C(F)(F)F)c2)cc1-c1cnc(C#N)c(N2CCOCC2)c1]

¹H NMR (400 MHz, <cd3od>) δ ppm 2.56 (s, 3H) 2.95 (s, 6H) 3.35-3.40 (m, 4H) 3.88-3.96 (m, 4H) 4.54 (s, 2H) 7.73 (d, J=1.57 Hz, 1H) 8.16 (s, 1H) 8.30 (d, J=2.35 Hz, 1H) 8.35 (d, J=1.57 Hz, 1H) 8.44 (s, 1H) 8.51 (s, 1H) 9.02 (d, J=2.35 Hz, 1H). LCMS (m/z) (M+H)=525.1, Rt=0.60 min.

Example 250: N-(6'-cyano-2-methyl-5'-morpholino-[3,3'-bipyridin]-5-yl)-2-(1,1-difluoroethyl)isonicotinamide

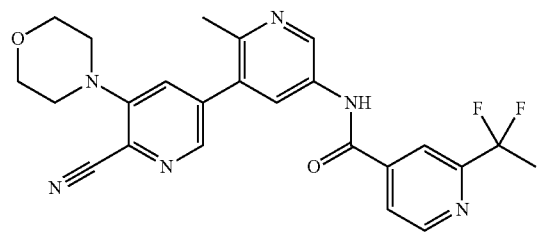 [SMILES: Cc1ncc(NC(=O)c2ccnc(C(C)(F)F)c2)cc1-c1cnc(C#N)c(N2CCOCC2)c1]

¹H NMR (400 MHz, <cd3od>) δ ppm 2.09 (t, J=18.78 Hz, 3H) 2.54 (s, 3H) 3.28-3.41 (m, 4H) 3.89-4.01 (m, 4H) 7.33 (d, J=1.57 Hz, 1H) 7.86 (d, J=4.70 Hz, 1H) 8.07 (s, 1H) 8.22 (s, 1H) 8.30-8.36 (m, 2H) 8.69 (d, J=2.35 Hz, 1H) 8.88 (d, J=5.09 Hz, 1H). LCMS (m/z) (M+H)=468.1, Rt=0.74 min.

Example 251: N-(6'-cyano-2-methyl-5'-morpholino-[3,3'-bipyridin]-5-yl)-2-isopropylisonicotinamide

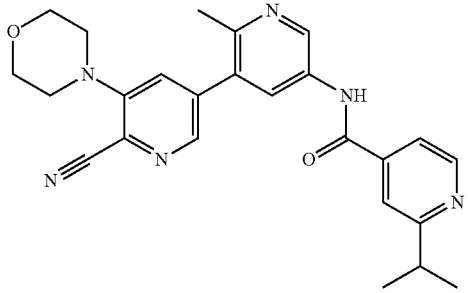 [SMILES: Cc1ncc(NC(=O)c2ccnc(C(C)C)c2)cc1-c1cnc(C#N)c(N2CCOCC2)c1]

¹H NMR (400 MHz, <cd3od>) δ ppm 1.43 (d, J=7.04 Hz, 6H) 2.61 (s, 3H) 3.25-3.30 (m, 1H) 3.35-3.41 (m, 4H) 3.88-3.96 (m, 4H) 7.74 (d, J=1.57 Hz, 1H) 7.97 (dd, J=5.48, 1.57 Hz, 1H) 8.09 (s, 1H) 8.36 (d, J=1.57 Hz, 1H) 8.39 (d, J=2.35 Hz, 1H) 8.78 (d, J=5.48 Hz, 1H) 9.13 (d, J=2.35 Hz, 1H). LCMS (m/z) (M+H)=443.2, Rt=0.55 min.

Example 252: N-(6'-ethoxy-2-methyl-5'-morpholino-[3,3'-bipyridin]-5-yl)-2-isopropylisonicotinamide

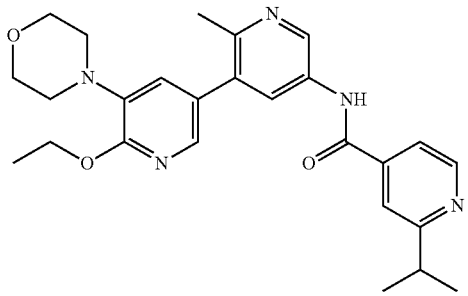 [SMILES: CCOc1ncc(-c2cc(NC(=O)c3ccnc(C(C)C)c3)cnc2C)cc1N1CCOCC1]

¹H NMR (400 MHz, <dmso>) δ ppm 1.29 (d, J=7.04 Hz, 6H) 1.36 (t, J=7.04 Hz, 3H) 2.54 (s, 3H) 3.07 (br. s., 4H) 3.16 (dt, J=13.69, 6.85 Hz, 1H) 3.66-3.79 (m, 4H) 4.40 (q, J=7.04 Hz, 2H) 7.26 (d, J=1.96 Hz, 1H) 7.75 (dd, J=5.28, 1.37 Hz, 1H) 7.80-7.88 (m, 2H) 8.29 (d, J=1.57 Hz, 1H) 8.75 (d, J=5.48 Hz, 1H) 9.05 (d, J=1.57 Hz, 1H) 11.00 (s, 1H). LCMS (m/z) (M+H)=462.1, Rt=0.58 min.

Example 253: N-(6'-ethoxy-2-methyl-5'-morpholino-[3,3'-bipyridin]-5-yl)-2-(2-fluoropropan-2-yl)isonicotinamide

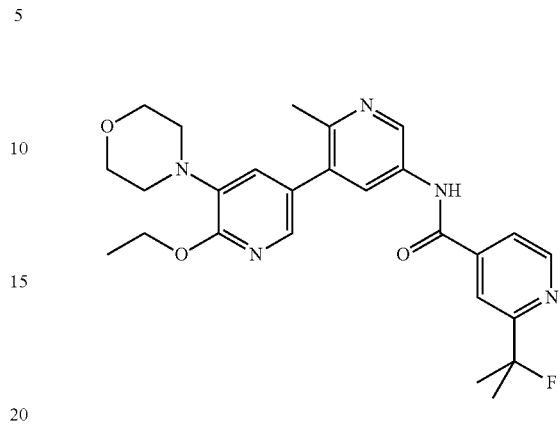

Step 1:

To a solution of 4-(5-bromo-2-ethoxypyridin-3-yl)morpholine (1.0 equiv.) and 6-methyl-5-(4,4,5,5-tetramethyl-1,3,2-dioxaborolan-2-yl)pyridin-3-amine (1.7 equiv.) in DME (0.3 M) and sodium carbonate (2M aqueous solution, 3.0 equiv.) was added $PdCl_2$(dppf)-DCM adduct (0.02 equiv.) and the solution was heated at 100° C. for 2 hours. The cooled mixture was poured into ice-water and extracted with ethyl acetate (3×). The combined organics were washed with brine, dried over $MgSO_4$, filtered and concentrated. The mixture was adsorbed onto Celite and purified by silica gel chromatography (ISCO, 0-70% ethyl acetate in heptanes). The pure fractions were concentrated to give 6'-ethoxy-2-methyl-5'-morpholino-[3,3'-bipyridin]-5-amine as a pale yellow solid in 78% yield. ¹H NMR (400 MHz, <cdcl3>) δ ppm 1.47 (t, J=7.04 Hz, 3H) 3.08-3.19 (m, 4H) 3.49 (s, 3H) 3.64 (br. s., 2H) 3.84-3.96 (m, 4H) 4.48 (q, J=7.04 Hz, 2H) 6.86 (d, J=2.35 Hz, 1H) 7.01 (d, J=1.96 Hz, 1H) 7.73 (d, J=1.96 Hz, 1H) 8.03 (d, J=2.35 Hz, 1H). LCMS (m/z) (M+H)=315.1, Rt=0.50 min.

Step 2:

To a solution of 2-(2-fluoropropan-2-yl)isonicotinic acid (1.3 equiv.), 6'-ethoxy-2-methyl-5'-morpholino-[3,3'-bipyridin]-5-amine (1.0 equiv.) and N-ethyl-N-isopropylpropan-2-amine (2.5 equiv.) in DCM (0.12 M) was added 2,4,6-tripropyl-1,3,5,2,4,6-trioxatriphosphinane 2,4,6-trioxide (1.3 quiv.) and the mixture was stirred at rt over the weekend. The reaction was diluted with DCM and washed with sat. sodium bicarbonate, the organic phase was concentrated to dryness and purified via silica gel chromatography (ISCO, 0-8% methanol in ethyl acetate) to give N-(6'-ethoxy-2-methyl-5'-morpholino-[3,3'-bipyridin]-5-yl)-2-(2-fluoropropan-2-yl)isonicotinamide. ¹H NMR (400 MHz, <cdcl3>) δ ppm 1.48 (t, J=7.04 Hz, 3H) 1.71-1.77 (m, 6H) 2.51 (s, 3H) 3.09-3.21 (m, 4H) 3.85-3.96 (m, 4H) 4.49 (q, J=7.04 Hz, 2H) 7.05 (d, J=1.96 Hz, 1H) 7.69 (dd, J=5.09, 1.57 Hz, 1H) 7.78 (d, J=1.96 Hz, 1H) 7.94 (s, 1H) 8.13 (d, J=2.35 Hz, 1H) 8.23 (s, 1H) 8.64 (d, J=2.35 Hz, 1H) 8.73 (d, J=4.70 Hz, 1H). LCMS (m/z) (M+H)=480.3, Rt=0.68 min.

Example 254: 2-cyclopropyl-N-(6'-ethoxy-2-methyl-5'-morpholino-[3,3'-bipyridin]-5-yl)isonicotinamide

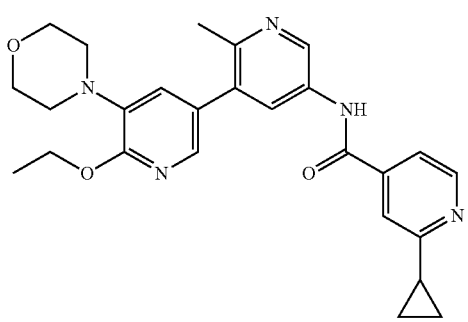 [SMILES: CCOc1ncc(-c2cc(NC(=O)c3ccnc(C4CC4)c3)cnc2C)cc1N1CCOCC1]

$^1$H NMR (400 MHz, <cd3od>) δ ppm 1.10-1.19 (m, 2H) 1.23 (dt, J=7.92, 3.08 Hz, 2H) 1.45 (t, J=7.04 Hz, 3H) 2.23-2.34 (m, 1H) 2.70 (s, 3H) 3.07-3.19 (m, 4H) 3.82-3.91 (m, 4H) 4.50 (d, J=7.04 Hz, 2H) 7.31 (d, J=1.96 Hz, 1H) 7.81 (dd, J=5.48, 1.57 Hz, 1H) 7.86 (d, J=1.96 Hz, 2H) 8.46 (d, J=2.35 Hz, 1H) 8.65 (d, J=5.48 Hz, 1H) 9.35 (d, J=2.35 Hz, 1H). LCMS (m/z) (M+H)=460.1, Rt=0.57 min.

Example 255: N-(6'-ethoxy-2-methyl-5'-morpholino-[3,3'-bipyridin]-5-yl)-2-(oxetan-3-yl)isonicotinamide

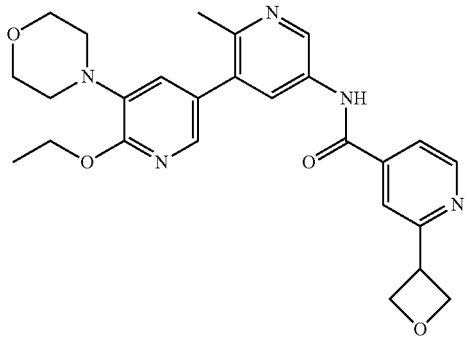 [SMILES: CCOc1ncc(-c2cc(NC(=O)c3ccnc(C4COC4)c3)cnc2C)cc1N1CCOCC1]

$^1$H NMR (400 MHz, <cd3od>) δ ppm 1.45 (t, J=7.04 Hz, 3H) 2.71 (s, 3H) 3.10-3.21 (m, 4H) 3.82-3.89 (m, 4H) 4.50 (q, J=7.04 Hz, 2H) 4.53-4.62 (m, 1H) 4.97 (t, J=6.26 Hz, 2H) 5.11 (dd, J=8.61, 5.87 Hz, 2H) 7.31 (d, J=1.96 Hz, 2H) 7.82-7.89 (m, 3H) 7.95 (s, 1H) 8.48 (d, J=1.96 Hz, 1H) 8.83 (d, J=5.09 Hz, 1H) 9.38 (d, J=2.35 Hz, 1H). LCMS (m/z) (M+H)=476.3, Rt=0.59 min.

Example 256: 3-(6-ethoxy-5-morpholinopyridin-3-yl)-N-(2-fluoro-5-(prop-1-en-2-yl)phenyl)-4-methylbenzamide

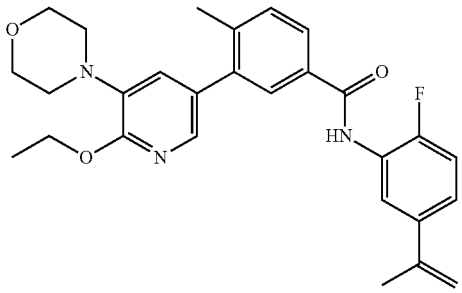 [SMILES: C=C(C)c1ccc(F)c(NC(=O)c2ccc(C)c(-c3cnc(OCC)c(N4CCOCC4)c3)c2)c1]

$^1$H NMR (400 MHz, <cd3od>) δ ppm 1.45 (t, J=7.04 Hz, 3H) 2.15 (s, 3H) 2.36 (s, 3H) 3.13-3.19 (m, 4H) 3.82-3.90 (m, 4H) 4.47 (d, J=7.04 Hz, 2H) 5.08-5.12 (m, 1H) 5.34-5.39 (m, 1H) 7.11-7.20 (m, 1H) 7.24-7.29 (m, 1H) 7.34-7.41 (m, 1H) 7.43-7.49 (m, 1H) 7.75-7.80 (m, 1H) 7.80-7.91 (m, 1H). LCMS (m/z) (M+H)=476.3, Rt=1.12 min.

Example 257: N-(6'-ethoxy-2-methyl-5'-morpholino-[3,3'-bipyridin]-5-yl)-3-(4-ethylpiperazin-1-yl)-5-(trifluoromethyl)benzamide

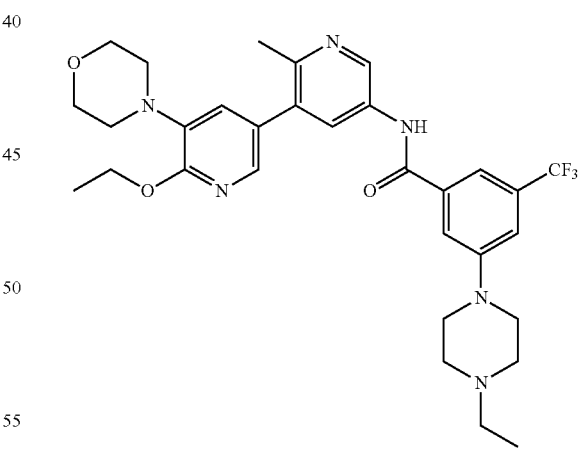

$^1$H NMR (400 MHz, <cd3od>) δ ppm 1.43 (dt, J=16.04, 7.24 Hz, 6H) 2.67 (s, 3H) 3.12-3.19 (m, 4H) 3.20-3.28 (m, 2H) 3.72 (br. s., 1H) 3.82-3.90 (m, 4H) 4.10 (br. s., 1H) 4.50 (q, J=7.04 Hz, 2H) 7.30 (d, J=2.35 Hz, 1H) 7.56 (s, 1H) 7.82-7.88 (m, 2H) 7.89 (s, 1H) 8.44 (d, J=2.35 Hz, 1H) 9.29 (d, J=2.35 Hz, 1H). LCMS (m/z) (M+H)=599.4, Rt=0.67 min.

Example 258: 3-((dimethylamino)methyl)-N-(6'-ethoxy-2-methyl-5'-morpholino-[3,3'-bipyridin]-5-yl)-5-(trifluoromethyl)benzamide

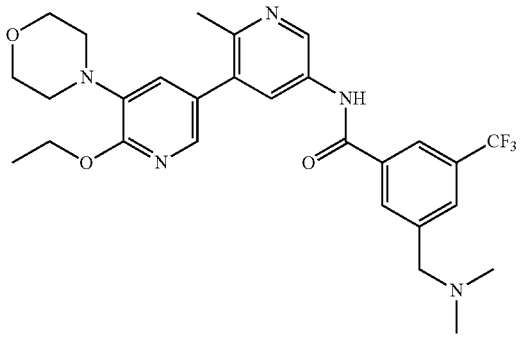 [SMILES: CCOc1ncc(-c2cc(NC(=O)c3cc(CN(C)C)cc(C(F)(F)F)c3)cnc2C)cc1N1CCOCC1]

¹H NMR (400 MHz, <cd3od>) δ ppm 1.46 (t, J=7.04 Hz, 3H) 2.68 (s, 3H) 2.93 (s, 6H) 3.11-3.23 (m, 4H) 3.81-3.91 (m, 4H) 4.47-4.56 (m, 4H) 7.30 (d, J=2.35 Hz, 1H) 7.85 (d, J=1.96 Hz, 1H) 8.16 (s, 1H) 8.45-8.50 (m, 2H) 8.51 (s, 1H) 9.32 (d, J=2.35 Hz, 1H). LCMS (m/z) (M+H)=544.3, Rt=0.62 min.

Example 259: N-(6'-ethoxy-2-methyl-5'-morpholino-[3,3'-bipyridin]-5-yl)-6-(trifluoromethyl)pyridazine-4-carboxamide

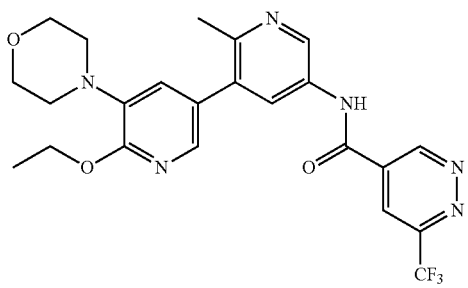

¹H NMR (400 MHz, <cd3od>) δ ppm 1.45 (t, J=7.04 Hz, 3H) 2.64 (s, 3H) 3.08-3.21 (m, 4H) 3.80-3.95 (m, 4H) 4.50 (q, J=7.04 Hz, 2H) 7.29 (d, J=1.96 Hz, 1H) 7.83 (d, J=1.96 Hz, 1H) 8.33 (d, J=2.35 Hz, 1H) 8.63 (d, J=1.96 Hz, 1H) 9.17 (d, J=2.35 Hz, 1H) 9.92 (d, J=1.96 Hz, 1H). LCMS (m/z) (M+H)=489.2, Rt=0.69 min.

Example 260: N-(2-chloro-6'-methoxy-5'-morpholino-[3,3'-bipyridin]-5-yl)-2-(1-cyanocyclopropyl)isonicotinamide

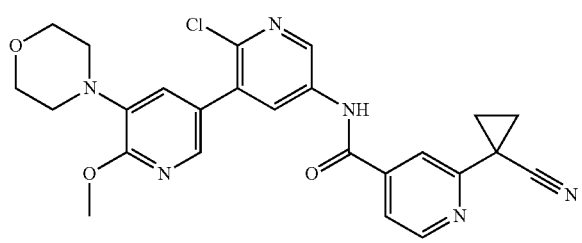 [SMILES: COc1ncc(-c2cc(NC(=O)c3ccnc(C4(C#N)CC4)c3)cnc2Cl)cc1N1CCOCC1]

¹H NMR (400 MHz, <cd3od>) δ ppm 1.78-1.93 (m, 4H) 3.13-3.25 (m, 4H) 3.82-3.95 (m, 4H) 4.06 (s, 3H) 7.43 (d, J=2.35 Hz, 1H) 7.77 (dd, J=5.09, 1.17 Hz, 1H) 7.94 (d, J=1.96 Hz, 1H) 8.13 (s, 1H) 8.32 (d, J=2.74 Hz, 1H) 8.69 (d, J=5.09 Hz, 1H) 8.80 (d, J=2.35 Hz, 1H). LCMS (m/z) (M+H)=491.1, Rt=0.86 min.

Example 261: N-(2-chloro-6'-methoxy-5'-morpholino-[3,3'-bipyridin]-5-yl)-2-(1,1-difluoroethyl)isonicotinamide

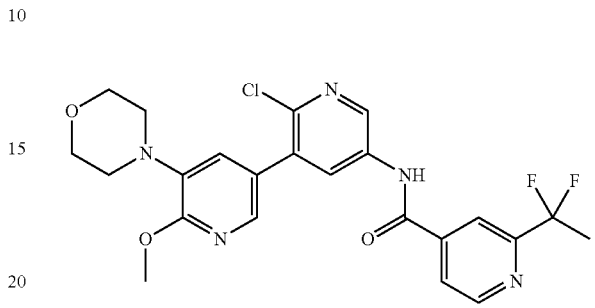

¹H NMR (400 MHz, <cd3od>) δ ppm 2.05 (t, J=18.78 Hz, 3H) 3.11-3.25 (m, 4H) 3.83-3.94 (m, 4H) 4.06 (s, 3H) 7.42 (d, J=1.96 Hz, 1H) 7.93 (d, J=1.96 Hz, 1H) 8.01 (d, J=4.69 Hz, 1H) 8.24 (s, 1H) 8.32 (d, J=2.35 Hz, 1H) 8.81 (d, J=2.35 Hz, 1H) 8.85 (d, J=5.09 Hz, 1H). LCMS (m/z) (M+H)=490.1, Rt=0.89 min.

Example 262: N-(2-chloro-6'-methoxy-5'-morpholino-[3,3'-bipyridin]-5-yl)-2-(2-fluoropropan-2-yl)isonicotinamide

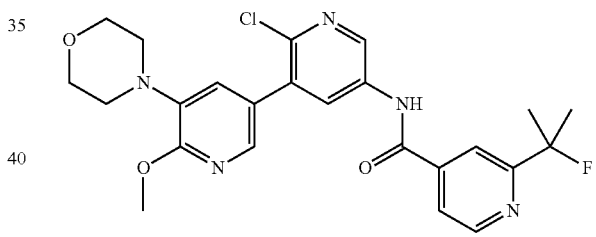

¹H NMR (400 MHz, <cd3od>) δ ppm 1.68-1.83 (m, 6H) 3.10-3.22 (m, 4H) 3.81-3.93 (m, 4H) 4.06 (s, 3H) 7.43 (d, J=2.35 Hz, 1H) 7.85 (dd, J=5.09, 1.57 Hz, 1H) 7.93 (d, J=1.96 Hz, 1H) 8.14 (s, 1H) 8.32 (d, J=2.74 Hz, 1H) 8.75 (d, J=5.09 Hz, 1H) 8.80 (d, J=2.74 Hz, 1H). LCMS (m/z) (M+H)=486.1, Rt=0.88 min.

Example 263: N-(2-chloro-6'-methoxy-5'-morpholino-[3,3'-bipyridin]-5-yl)-6-(trifluoromethyl)pyridazine-4-carboxamide

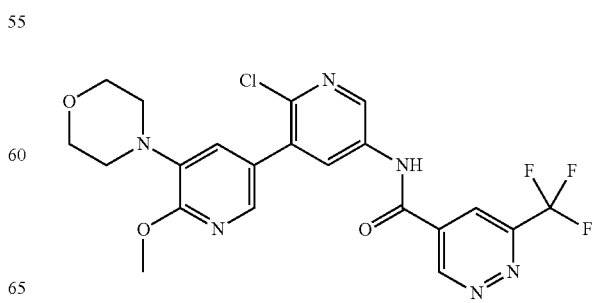

¹H NMR (400 MHz, <cd3od>) δ ppm 3.11-3.20 (m, 4H) 3.82-3.93 (m, 4H) 4.06 (s, 3H) 7.41 (d, J=1.96 Hz, 1H) 7.91 (d, J=1.96 Hz, 1H) 8.33 (d, J=2.35 Hz, 1H) 8.64 (d, J=1.96 Hz, 1H) 8.82 (d, J=2.74 Hz, 1H) 9.92 (d, J=1.96 Hz, 1H). LCMS (m/z) (M+H)=495.1, Rt=0.84 min.

Example 264: N-(2-chloro-6'-methoxy-5'-morpholino-[3,3'-bipyridin]-5-yl)-2-(2-cyanopropan-2-yl)isonicotinamide

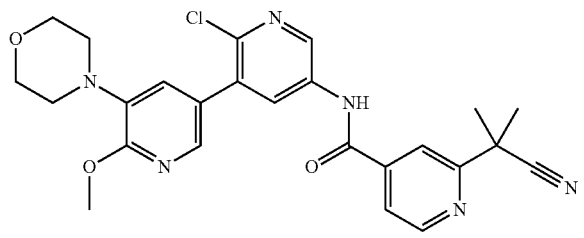 [SMILES: COc1ncc(-c2cc(NC(=O)c3ccnc(C(C)(C)C#N)c3)cnc2Cl)cc1N1CCOCC1]

¹H NMR (400 MHz, <cd3od>) δ ppm 1.84 (s, 6H) 3.11-3.21 (m, 4H) 3.82-3.93 (m, 4H) 4.06 (s, 3H) 7.40 (d, J=1.96 Hz, 1H) 7.87 (dd, J=4.89, 1.37 Hz, 1H) 7.92 (d, J=1.96 Hz, 1H) 8.12 (s, 1H) 8.32 (d, J=2.74 Hz, 1H) 8.77-8.84 (m, 2H). LCMS (m/z) (M+H)=493.1, Rt=0.86 min.

Example 265: 2-(2-cyanopropan-2-yl)-N-(6'-(dimethylamino)-2-methyl-5'-morpholino-[3,3'-bipyridin]-5-yl)isonicotinamide

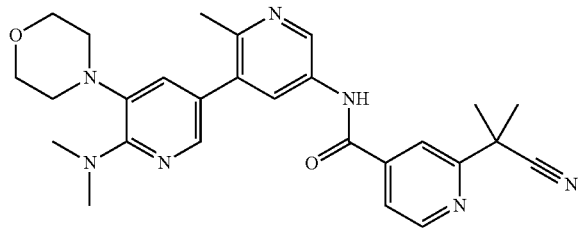 [SMILES: Cc1ncc(NC(=O)c2ccnc(C(C)(C)C#N)c2)cc1-c1cnc(N(C)C)c(N2CCOCC2)c1]

¹H NMR (400 MHz, <cd3od>) δ ppm 1.83 (s, 6H) 2.65 (s, 3H) 3.02-3.12 (m, 4H) 3.33 (s, 6H) 3.87-3.96 (m, 4H) 7.65 (d, J=1.96 Hz, 1H) 7.85-7.92 (m, 2H) 8.13 (s, 1H) 8.47 (d, J=2.35 Hz, 1H) 8.82 (d, J=5.09 Hz, 1H) 9.13 (d, J=2.35 Hz, 1H). LCMS (m/z) (M+H)=486.2, Rt=0.54 min.

Example 266: 2-(1-cyanocyclopropyl)-N-(6'-(dimethylamino)-2-methyl-5'-morpholino-[3,3'-bipyridin]-5-yl)isonicotinamide

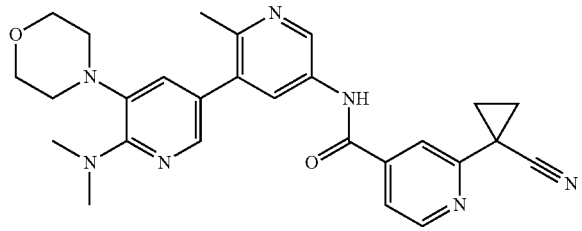 [SMILES: Cc1ncc(NC(=O)c2ccnc(C3(C#N)CC3)c2)cc1-c1cnc(N(C)C)c(N2CCOCC2)c1]

¹H NMR (400 MHz, <cd3od>) δ ppm 1.77-1.92 (m, 4H) 2.65 (s, 3H) 3.02-3.11 (m, 4H) 3.33 (s, 6H) 3.86-3.96 (m, 4H) 7.65 (d, J=1.96 Hz, 1H) 7.77 (dd, J=5.09, 1.57 Hz, 1H) 7.89 (d, J=1.56 Hz, 1H) 8.14 (s, 1H) 8.48 (d, J=2.35 Hz, 1H) 8.69 (d, J=4.70 Hz, 1H) 9.15 (d, J=2.35 Hz, 1H). LCMS (m/z) (M+H)=484.2, Rt=0.54 min.

Example 267: 2-(1,1-difluoroethyl)-N-(6'-(dimethylamino)-2-methyl-5-morpholino-[3,3'-bipyridin]-5-yl)isonicotinamide

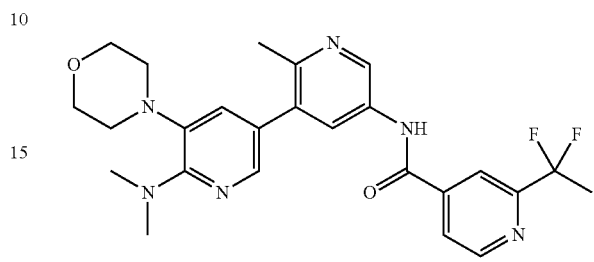

¹H NMR (400 MHz, <cd3od>) δ ppm 2.05 (t, J=18.78 Hz, 3H) 2.66 (s, 3H) 3.02-3.11 (m, 4H) 3.34 (s, 6H) 3.87-3.96 (m, 4H) 7.66 (d, J=1.96 Hz, 1H) 7.89 (d, J=1.96 Hz, 1H) 8.02 (d, J=3.91 Hz, 1H) 8.24 (s, 1H) 8.50 (d, J=2.35 Hz, 1H) 8.86 (d, J=5.09 Hz, 1H) 9.17 (d, J=2.35 Hz, 1H). LCMS (m/z) (M+H)=483.2, Rt=0.55 min.

Example 268: N-(6'-(dimethylamino)-2-methyl-5-morpholino-[3,3'-bipyridin]-5-yl)-2-(2-fluoropropan-2-yl)isonicotinamide

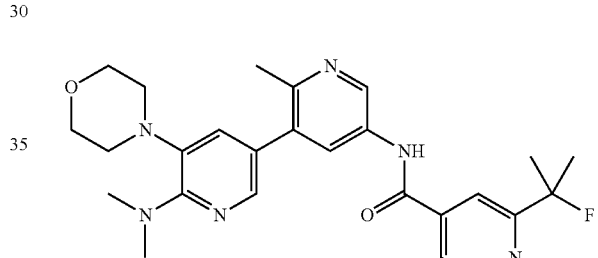

¹H NMR (400 MHz, <cd3od>) δ ppm 1.69-1.83 (m, 6H) 2.65 (s, 3H) 3.03-3.13 (m, 4H) 3.32 (s, 6H) 3.88-3.98 (m, 4H) 7.63 (d, J=1.96 Hz, 1H) 7.83 (dd, J=5.09, 1.96 Hz, 1H) 7.89 (d, J=1.56 Hz, 1H) 8.13 (s, 1H) 8.47 (d, J=2.35 Hz, 1H) 8.76 (d, J=5.09 Hz, 1H) 9.14 (d, J=1.96 Hz, 1H). LCMS (m/z) (M+H)=479.3, Rt=0.55 min.

Example 269: N-(6'-(dimethylamino)-2-methyl-5'-morpholino-[3,3'-bipyridin]-5-yl)-3-((dimethylamino)methyl)-5-(trifluoromethyl)benzamide

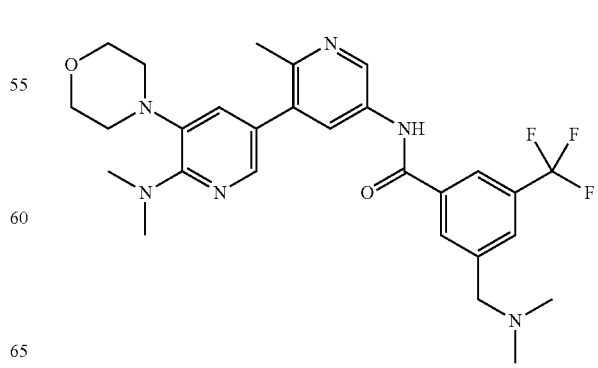

¹H NMR (400 MHz, <cd3od>) δ ppm 2.64 (s, 3H) 2.94 (s, 6H) 3.05-3.12 (m, 4H) 3.31 (s, 6H) 3.88-3.96 (m, 4H) 4.54 (s, 2H) 7.61 (d, J=1.96 Hz, 1H) 7.89 (d, J=1.57 Hz, 1H) 8.17 (s, 1H) 8.44 (d, J=2.35 Hz, 1H) 8.49 (d, J=9.39 Hz, 2H) 9.14 (d, J=2.35 Hz, 1H). LCMS (m/z) (M+H)=543.3, Rt=0.49 min.

Example 270: N-(6'-(dimethylamino)-2-methyl-5'-morpholino-[3,3'-bipyridin]-5-yl)-6-(trifluoromethyl)pyridazine-4-carboxamide

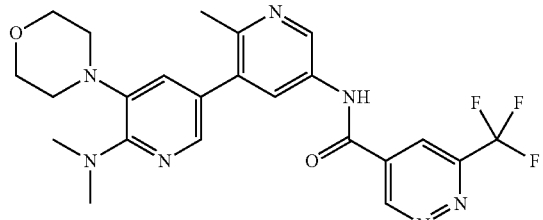

¹H NMR (400 MHz, <cd3od>) δ ppm 2.61 (s, 3H) 3.05-3.13 (m, 4H) 3.33 (s, 6H) 3.88-3.97 (m, 4H) 7.64 (d, J=1.96 Hz, 1H) 7.85 (d, J=1.96 Hz, 1H) 8.38 (d, J=2.35 Hz, 1H) 8.63 (d, J=1.96 Hz, 1H) 8.99 (d, J=2.35 Hz, 1H) 9.92 (d, J=1.57 Hz, 1H). LCMS (m/z) (M+H)=488.1, Rt=0.52 min.

Example 271: 6-cyclopropyl-N-(6'-(dimethylamino)-2-methyl-5'-morpholino-[3,3'-bipyridin]-5-yl)pyridazine-4-carboxamide

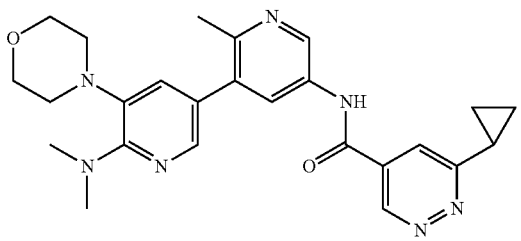 [SMILES: Cc1ncc(NC(=O)c2cnnc(C3CC3)c2)cc1-c1cnc(N(C)C)c(N2CCOCC2)c1]

¹H NMR (400 MHz, <cd3od>) δ ppm 1.18-1.37 (m, 4H) 2.36-2.46 (m, 1H) 2.63 (s, 3H) 3.03-3.13 (m, 4H) 3.33 (br. s., 6H) 3.85-3.98 (m, 4H) 7.64 (d, J=1.96 Hz, 1H) 7.87 (d, J=1.96 Hz, 1H) 7.98 (d, J=1.96 Hz, 1H) 8.42 (d, J=2.35 Hz, 1H) 9.05 (d, J=2.35 Hz, 1H) 9.42 (d, J=1.96 Hz, 1H). LCMS (m/z) (M+H)=460.2, Rt=0.47 min.

Example 272: 2-(2-cyanopropan-2-yl)-N-(2-methyl-5'-morpholino-6'-((tetrahydro-2H-pyran-4-yl)oxy)-[3,3'-bipyridin]-5-yl)isonicotinamide

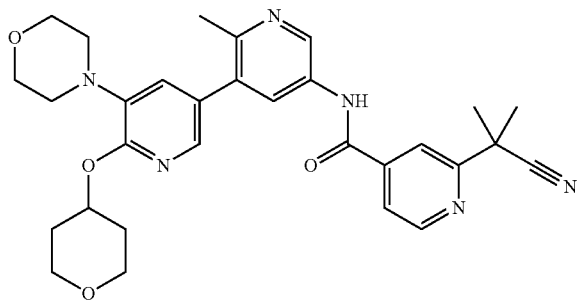 [SMILES: Cc1ncc(NC(=O)c2ccnc(C(C)(C)C#N)c2)cc1-c1cnc(OC2CCOCC2)c(N2CCOCC2)c1]

¹H NMR (400 MHz, <cd3od>) δ ppm 1.81-1.93 (m, 8H) 2.08-2.23 (m, 2H) 2.71 (s, 3H) 3.16-3.25 (m, 4H) 3.69 (ddd, J=11.54, 8.22, 3.33 Hz, 2H) 3.82-3.93 (m, 4H) 3.94-4.04 (m, 2H) 5.46 (tt, J=7.92, 3.81 Hz, 1H) 7.34 (d, J=1.96 Hz, 1H) 7.84-7.93 (m, 2H) 8.15 (s, 1H) 8.47 (d, J=2.35 Hz, 1H) 8.84 (d, J=5.09 Hz, 1H) 9.36 (d, J=2.35 Hz, 1H). LCMS (m/z) (M+H)=543.3, Rt=0.68 min.

Example 273: 2-(2-fluoropropan-2-yl)-N-(2-methyl-5'-morpholino-6'-((tetrahydro-2H-pyran-4-yl)oxy)-[3,3'-bipyridin]-5-yl)isonicotinamide

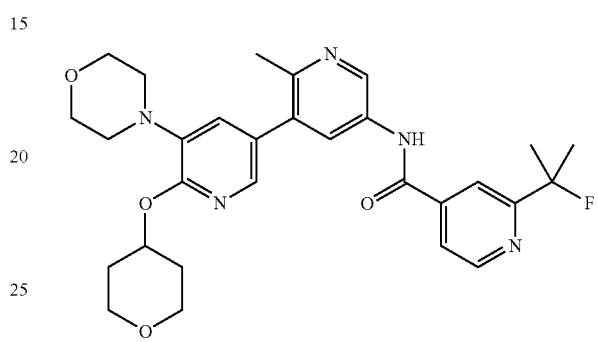

¹H NMR (400 MHz, <cd3od>) δ ppm 1.67-1.80 (m, 6H) 1.86 (dtd, J=12.72, 8.31, 8.31, 3.91 Hz, 2H) 2.09-2.23 (m, 2H) 2.72 (s, 3H) 3.15-3.24 (m, 4H) 3.69 (ddd, J=11.64, 8.31, 3.13 Hz, 2H) 3.81-3.93 (m, 4H) 3.94-4.06 (m, 2H) 5.46 (dt, J=7.83, 3.91 Hz, 1H) 7.34 (d, J=1.96 Hz, 1H) 7.85 (dd, J=5.09, 1.57 Hz, 1H) 7.88 (d, J=1.96 Hz, 1H) 8.15 (s, 1H) 8.50 (d, J=2.35 Hz, 1H) 8.77 (d, J=5.09 Hz, 1H) 9.38 (d, J=2.35 Hz, 1H). LCMS (m/z) (M+H)=536.3, Rt=0.69 min.

Example 274: N-(4-methyl-3-(5-morpholino-6-((tetrahydro-2H-pyran-4-yl)oxy)pyridin-3-yl)phenyl)-2-(methylsulfonyl)isonicotinamide

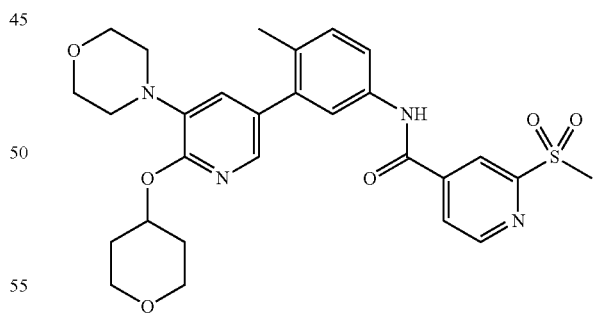

¹H NMR (400 MHz, <cd3od>) δ ppm 1.77-1.94 (m, 2H) 2.08-2.21 (m, 2H) 2.29 (s, 3H) 3.16-3.23 (m, 4H) 3.31 (s, 3H) 3.69 (ddd, J=11.64, 8.31, 3.13 Hz, 2H) 3.82-3.94 (m, 4H) 3.94-4.07 (m, 2H) 5.41 (tt, J=7.97, 3.96 Hz, 1H) 7.27 (d, J=1.57 Hz, 1H) 7.34 (d, J=8.22 Hz, 1H) 7.60-7.69 (m, 2H) 7.76 (d, J=1.96 Hz, 1H) 8.17 (dd, J=5.09, 1.57 Hz, 1H) 8.56 (s, 1H) 8.94 (d, J=5.09 Hz, 1H). LCMS (m/z) (M+H)=553.2, Rt=0.83 min.

Example 275: N-(4-methyl-3-(5-morpholino-6-((tetrahydro-2H-pyran-4-yl)oxy)pyridin-3-yl)phenyl)-6-(trifluoromethyl)pyridazine-4-carboxamide

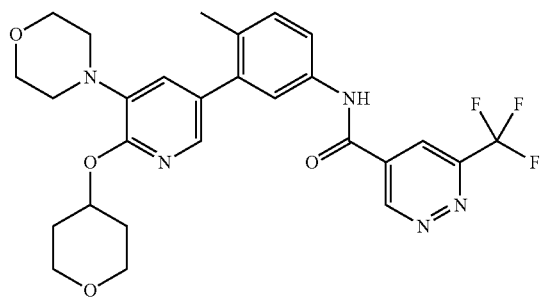 [SMILES: Cc1ccc(NC(=O)c2cnnc(C(F)(F)F)c2)cc1-c1cnc(OC2CCOCC2)c(N2CCOCC2)c1]

¹H NMR (400 MHz, <cd3od>) δ ppm 1.86 (dtd, J=12.67, 8.34, 8.34, 3.91 Hz, 2H) 2.07-2.22 (m, 2H) 2.29 (s, 3H) 3.14-3.25 (m, 4H) 3.68 (ddd, J=11.44, 8.31, 3.33 Hz, 2H) 3.82-3.94 (m, 4H) 3.95-4.06 (m, 2H) 5.41 (dt, J=7.92, 4.06 Hz, 1H) 7.27 (d, J=1.96 Hz, 1H) 7.34 (d, J=8.22 Hz, 1H) 7.61-7.72 (m, 2H) 7.76 (d, J=1.96 Hz, 1H) 8.59 (d, J=1.96 Hz, 1H) 9.88 (d, J=1.96 Hz, 1H). LCMS (m/z) (M+H)= 544.3, Rt=0.93 min.

Example 276: 6-cyclopropyl-N-(4-methyl-3-(5-morpholino-6-((tetrahydro-2H-pyran-4-yl)oxy)pyridin-3-yl)phenyl)pyridazine-4-carboxamide

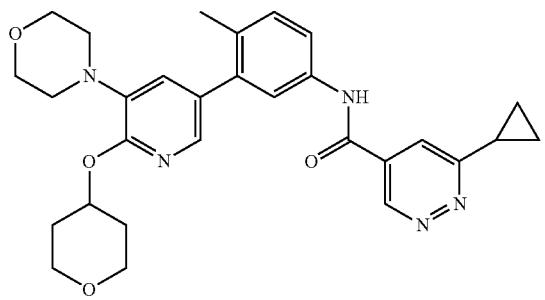 [SMILES: Cc1ccc(NC(=O)c2cnnc(C3CC3)c2)cc1-c1cnc(OC2CCOCC2)c(N2CCOCC2)c1]

¹H NMR (400 MHz, <cd3od>) δ ppm 1.18-1.39 (m, 4H) 1.85 (dtd, J=12.81, 8.46, 8.46, 3.91 Hz, 2H) 2.06-2.19 (m, 2H) 2.28 (s, 3H) 2.35-2.50 (m, 1H) 3.14-3.22 (m, 4H) 3.68 (ddd, J=11.44, 8.31, 3.33 Hz, 2H) 3.81-3.92 (m, 4H) 3.93-4.04 (m, 2H) 5.40 (tt, J=7.92, 3.81 Hz, 1H) 7.25 (d, J=1.96 Hz, 1H) 7.33 (d, J=8.22 Hz, 1H) 7.57-7.69 (m, 2H) 7.74 (d, J=1.96 Hz, 1H) 8.05 (d, J=1.96 Hz, 1H) 9.44 (d, J=1.96 Hz, 1H). LCMS (m/z) (M+H)=516.2, Rt=0.84 min.

Example 277: 2-(2-hydroxypropan-2-yl)-N-(4-methyl-3-(5-morpholino-6-((tetrahydro-2H-pyran-4-yl)oxy)pyridin-3-yl)phenyl)isonicotinamide

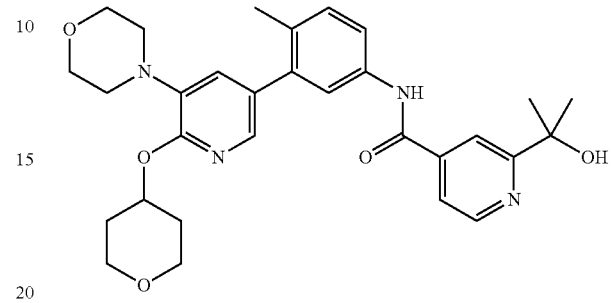

¹H NMR (400 MHz, <cd3od>) δ ppm 1.69 (s, 6H) 1.85 (dtd, J=12.77, 8.39, 8.39, 3.72 Hz, 2H) 2.07-2.21 (m, 2H) 2.30 (s, 3H) 3.09-3.21 (m, 4H) 3.69 (ddd, J=11.64, 8.31, 3.13 Hz, 2H) 3.81-3.93 (m, 4H) 3.94-4.06 (m, 2H) 5.41 (tt, J=7.92, 3.81 Hz, 1H) 7.23 (d, J=1.96 Hz, 1H) 7.35 (d, J=8.22 Hz, 1H) 7.63 (d, J=2.35 Hz, 1H) 7.67 (dd, J=8.22, 2.35 Hz, 1H) 7.74 (d, J=1.96 Hz, 1H) 8.10 (dd, J=5.48, 1.56 Hz, 1H) 8.40 (s, 1H) 8.77 (d, J=5.48 Hz, 1H). LCMS (m/z) (M+H)=533.3, Rt=0.73 min.

Example 278: N-(5'-(3-oxa-8-azabicyclo[3.2.1]octan-8-yl)-2-methyl-6'-((tetrahydro-2H-pyran-4-yl)oxy)-[3,3'-bipyridin]-5-yl)-2-(trifluoromethyl)isonicotinamide

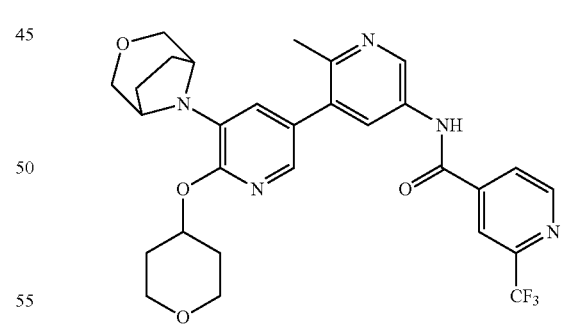

¹H NMR (400 MHz, <cd3od>) δ ppm 1.79-1.92 (m, 2H) 1.95-2.10 (m, 4H) 2.10-2.20 (m, 2H) 2.68 (s, 3H) 3.59-3.72 (m, 4H) 3.89-4.01 (m, 4H) 4.21 (br. s., 2H) 5.43 (dt, J=7.83, 3.91 Hz, 1H) 7.24 (d, J=1.96 Hz, 1H) 7.73 (d, J=2.35 Hz, 1H) 8.18 (d, J=5.09 Hz, 1H) 8.36 (s, 1H) 8.40 (d, J=2.35 Hz, 1H) 8.97 (d, J=5.09 Hz, 1H) 9.27 (d, J=2.35 Hz, 1H). LCMS (m/z) (M+H)=570.2, Rt=0.75 min.

Example 279: N-(5'-(3-oxa-8-azabicyclo[3.2.1]oc-tan-8-yl)-2-methyl-6'-((tetrahydro-2H-pyran-4-yl)oxy)-[3,3'-bipyridin]-5-yl)-2-(2-fluoropropan-2-yl)isonicotinamide

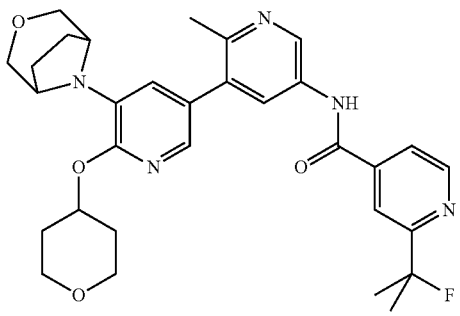 [SMILES: Cc1ncc(NC(=O)c2ccnc(C(C)(C)F)c2)cc1-c1cnc(OC2CCOCC2)c(N2C3CCC2COC3)c1]

¹H NMR (400 MHz, <cd3od>) δ ppm 1.71 (s, 3H) 1.77 (s, 3H) 1.84 (dtd, J=12.67, 8.34, 8.34, 3.91 Hz, 2H) 1.95-2.10 (m, 4H) 2.10-2.21 (m, 2H) 2.71 (s, 3H) 3.60-3.74 (m, 4H) 3.88-4.03 (m, 4H) 4.22 (br. s., 2H) 5.43 (dt, J=7.83, 3.91 Hz, 1H) 7.25 (d, J=1.96 Hz, 1H) 7.75 (d, J=1.96 Hz, 1H) 7.84 (dd, J=5.09, 1.57 Hz, 1H) 8.14 (s, 1H) 8.49 (d, J=2.35 Hz, 1H) 8.76 (d, J=5.09 Hz, 1H) 9.38 (d, J=2.35 Hz, 1H). LCMS (m/z) (M+H)=562.2, Rt=0.74 min.

Example 280: N-(3-(6-ethoxy-5-morpholinopyridin-3-yl)-4-methylphenyl)-6-(trifluoromethyl)pyridazine-4-carboxamide

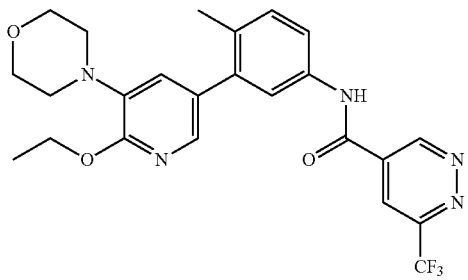 [SMILES: CCOc1ncc(-c2cc(NC(=O)c3cnnc(C(F)(F)F)c3)ccc2C)cc1N1CCOCC1]

¹H NMR (400 MHz, <cd3od>) δ ppm 1.46 (t, J=7.04 Hz, 3H) 2.28 (s, 3H) 3.14-3.21 (m, 4H) 3.83-3.91 (m, 4H) 4.47 (q, J=7.04 Hz, 2H) 7.26 (d, J=1.96 Hz, 1H) 7.33 (d, J=8.22 Hz, 1H) 7.63-7.71 (m, 2H) 7.75 (d, J=1.96 Hz, 1H) 8.58 (d, J=1.96 Hz, 1H) 9.87 (d, J=1.57 Hz, 1H). LCMS (m/z) (M+H)=488.1, Rt=0.94 min.

Example 281: N-(6'-methoxy-2-methyl-5'-morpholino-[3,3'-bipyridin]-5-yl)-2-(2-fluoropropan-2-yl)isonicotinamide

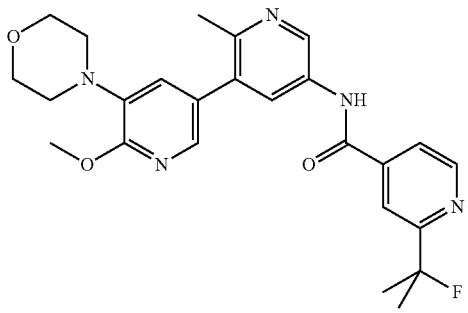 [SMILES: COc1ncc(-c2cc(NC(=O)c3ccnc(C(C)(C)F)c3)cnc2C)cc1N1CCOCC1]

¹H NMR (400 MHz, <cd3od>) δ ppm 1.71 (s, 3H) 1.77 (s, 3H) 2.71 (s, 3H) 3.09-3.19 (m, 4H) 3.83-3.90 (m, 4H) 4.06 (s, 3H) 7.32 (d, J=1.96 Hz, 1H) 7.84 (dd, J=5.09, 1.57 Hz, 1H) 7.90 (d, J=1.96 Hz, 1H) 8.15 (s, 1H) 8.50 (d, J=2.35 Hz, 1H) 8.76 (d, J=5.09 Hz, 1H) 9.40 (d, J=2.35 Hz, 1H). LCMS (m/z) (M+H)=466.3, Rt=0.64 min.

Example 282: N-(5'-(3-oxa-8-azabicyclo[3.2.1]oc-tan-8-yl)-6'-ethoxy-2-methyl-[3,3'-bipyridin]-5-yl)-6-(trifluoromethyl)pyridazine-4-carboxamide

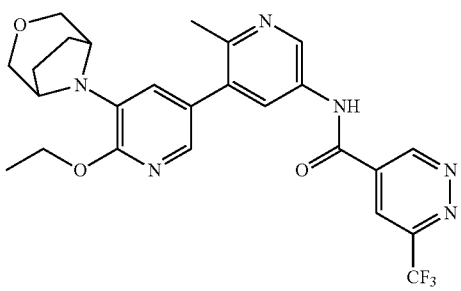 [SMILES: CCOc1ncc(-c2cc(NC(=O)c3cnnc(C(F)(F)F)c3)cnc2C)cc1N1C2CCC1COC2]

¹H NMR (400 MHz, <cd3od>) δ ppm 1.45 (t, J=7.04 Hz, 3H) 1.96-2.13 (m, 4H) 2.69 (s, 3H) 3.61 (d, J=10.17 Hz, 2H) 3.91 (d, J=10.56 Hz, 2H) 4.22 (br. s., 2H) 4.48 (q, J=7.04 Hz, 2H) 7.22 (d, J=1.96 Hz, 1H) 7.73 (d, J=1.96 Hz, 1H) 8.41 (d, J=2.35 Hz, 1H) 8.63 (d, J=1.96 Hz, 1H) 9.29 (d, J=2.35 Hz, 1H) 9.92 (d, J=1.57 Hz, 1H). LCMS (m/z) (M+H)=515.1, Rt=0.72 min.

Example 283: 2-(1-cyanocyclopropyl)-N-(6'-methoxy-2-methyl-5'-morpholino-[3,3'-bipyridin]-5-yl)isonicotinamide

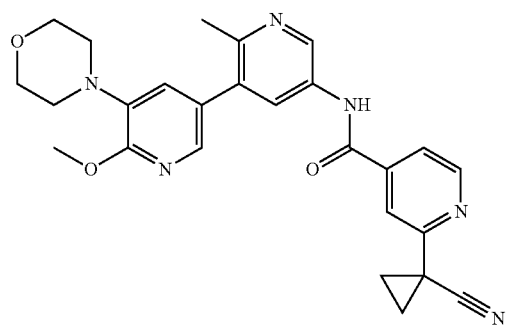 [SMILES: COc1ncc(-c2cc(NC(=O)c3ccnc(C4(C#N)CC4)c3)cnc2C)cc1N1CCOCC1]

¹H NMR (400 MHz, <cd3od>) δ ppm 1.85 (dt, J=12.52, 2.93 Hz, 4H) 2.69 (s, 3H) 3.11-3.19 (m, 4H) 3.81-3.91 (m, 4H) 4.05 (s, 3H) 7.32 (d, J=1.96 Hz, 1H) 7.78 (dd, J=5.09, 1.57 Hz, 1H) 7.89 (d, J=1.96 Hz, 1H) 8.16 (s, 1H) 8.44 (d, J=2.35 Hz, 1H) 8.70 (d, J=5.09 Hz, 1H) 9.33 (d, J=2.35 Hz, 1H). LCMS (m/z) (M+H)=471.3, Rt=0.65 min.

Example 284: 6-(2-cyanopropan-2-yl)-N-(3-(6-ethoxy-5-morpholinopyridin-3-yl)-4-methylphenyl)pyridazine-4-carboxamide

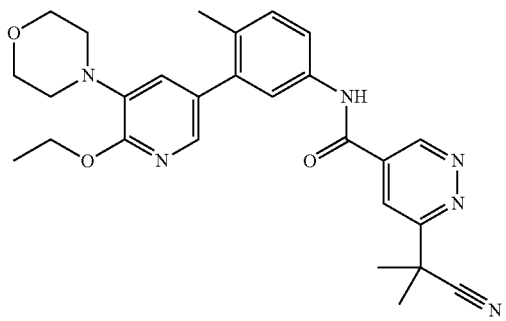 [SMILES: CCOc1ncc(-c2cc(NC(=O)c3cnnc(C(C)(C)C#N)c3)ccc2C)cc1N1CCOCC1]

¹H NMR (500 MHz, <cd3od>) δ ppm 1.49 (t, J=6.94 Hz, 3H) 1.94 (s, 6H) 2.31 (s, 3H) 3.18-3.25 (m, 4H) 3.85-3.93 (m, 4H) 4.51 (d, J=7.25 Hz, 2H) 7.33 (s, 2H) 7.67 (s, 2H) 7.80 (s, 1H) 8.38 (d, J=1.89 Hz, 1H) 9.64 (s, 1H). LCMS (m/z) (M+H)=487.2, Rt=0.88 min.

Example 285: (R)—N-(6'-ethoxy-2-methyl-5'-(3-methylmorpholino)-[3,3'-bipyridin]-5-yl)-6-trifluoromethyl)pyridazine-4-carboxamide

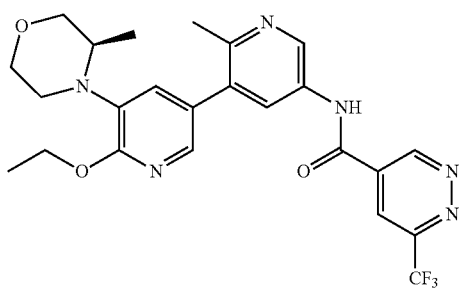 [SMILES: CCOc1ncc(-c2cc(NC(=O)c3cnnc(C(F)(F)F)c3)cnc2C)cc1N1CCOC[C@H]1C]

¹H NMR (500 MHz, <cd3od>) δ ppm 1.01 (d, J=6.31 Hz, 3H) 1.42-1.51 (m, 3H) 2.69 (s, 3H) 2.84-2.95 (m, 1H) 3.37-3.63 (m, 2H) 3.78-3.96 (m, 4H) 4.40-4.61 (m, 2H) 7.39-7.45 (m, 1H) 7.90-7.97 (m, 1H) 8.36-8.43 (m, 1H) 8.63-8.68 (m, 1H) 9.23-9.29 (m, 1H) 9.91-9.98 (m, 1H). LCMS (m/z) (M+H)=503.1, Rt=0.69 min.

Example 286: (S)—N-(6'-ethoxy-2-methyl-5'-(3-methylmorpholino)-[3,3'-bipyridin]-5-yl)-6-(trifluoromethyl)pyridazine-4-carboxamide

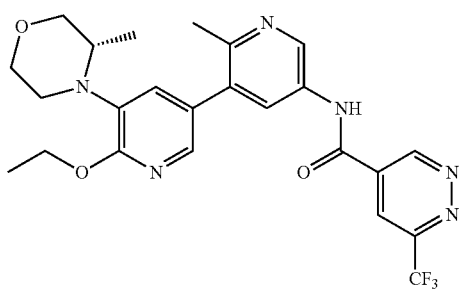 [SMILES: CCOc1ncc(-c2cc(NC(=O)c3cnnc(C(F)(F)F)c3)cnc2C)cc1N1CCOC[C@@H]1C]

¹H NMR (400 MHz, <cd3od>) δ ppm 0.98 (d, J=6.65 Hz, 3H) 1.45 (t, J=7.04 Hz, 3H) 2.66 (s, 3H) 2.88 (ddd, J=11.93, 6.06, 3.13 Hz, 1H) 3.34-3.39 (m, 1H) 3.54 (dd, J=11.15, 5.28 Hz, 1H) 3.75-3.95 (m, 4H) 4.41-4.60 (m, 2H) 7.40 (d, J=2.35 Hz, 1H) 7.91 (d, J=1.96 Hz, 1H) 8.36 (d, J=2.35 Hz, 1H) 8.63 (d, J=1.96 Hz, 1H) 9.21 (d, J=2.35 Hz, 1H) 9.92 (d, J=1.96 Hz, 1H). LCMS (m/z) (M+H)=503.1, Rt=0.69 min.

Example 287: 6-(2-cyanopropan-2-yl)-N-(6'-ethoxy-2-methyl-5'-morpholino-[3,3'-bipyridin]-5-yl)pyridazine-4-carboxamide

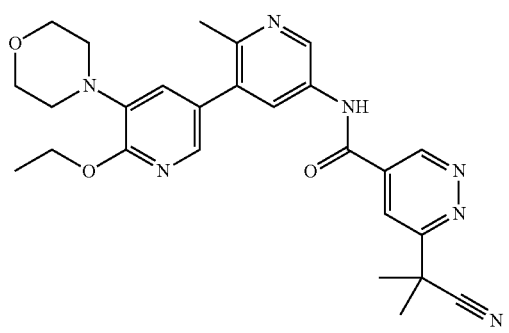 [SMILES: CCOc1ncc(-c2cc(NC(=O)c3cnnc(C(C)(C)C#N)c3)cnc2C)cc1N1CCOCC1]

¹H NMR (400 MHz, <cd3od>) δ ppm 1.45 (t, J=7.04 Hz, 3H) 1.92 (s, 6H) 2.70 (s, 3H) 3.11-3.19 (m, 4H) 3.81-3.90 (m, 4H) 4.50 (d, J=7.04 Hz, 2H) 7.30 (d, J=2.35 Hz, 1H) 7.86 (d, J=1.96 Hz, 1H) 8.43 (dd, J=9.19, 2.15 Hz, 2H) 9.32 (d, J=2.35 Hz, 1H) 9.66 (d, J=1.96 Hz, 1H). LCMS (m/z) (M+H)=488.1, Rt=0.64 min.

Example 288: N-(6'-chloro-2-methyl-5-morpholino-[3,3'-bipyridin]-5-yl)-2-(1-cyanocyclopropyl)isonicotinamide

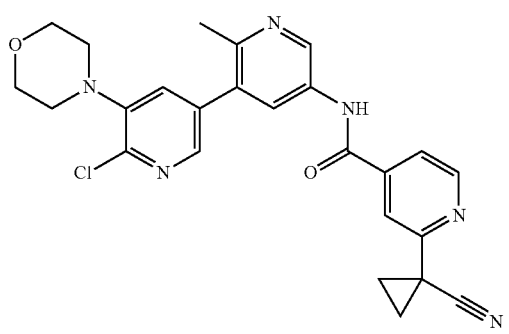 [SMILES: Cc1ncc(NC(=O)c2ccnc(C3(C#N)CC3)c2)cc1-c1cnc(Cl)c(N2CCOCC2)c1]

¹H NMR (400 MHz, <cd3od>) δ ppm 1.78-1.91 (m, 4H) 2.63 (s, 3H) 3.15-3.22 (m, 4H) 3.85-3.94 (m, 4H) 7.66 (d, J=1.96 Hz, 1H) 7.77 (dd, J=5.09, 1.57 Hz, 1H) 8.15 (d, J=1.96 Hz, 2H) 8.39 (d, J=2.35 Hz, 1H) 8.70 (d, J=5.09 Hz, 1H) 9.21 (d, J=2.35 Hz, 1H). LCMS (m/z) (M+H)=475.1, Rt=0.66 min.

Example 289: N-(6'-chloro-2-methyl-5'-morpholino-[3,3-bipyridin]-5-yl)-2-(2-cyanopropan-2-yl)isonicotinamide

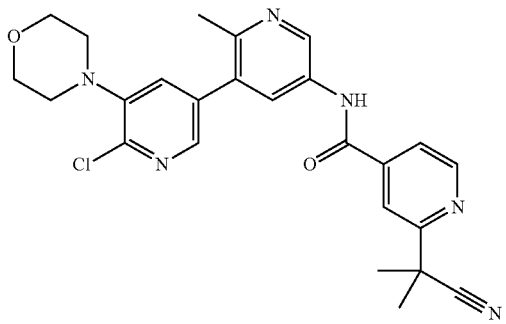 [SMILES: Cc1ncc(NC(=O)c2ccnc(C(C)(C)C#N)c2)cc1-c1cnc(Cl)c(N2CCOCC2)c1]

¹H NMR (400 MHz, <cd3od>) δ ppm 1.82 (s, 6H) 2.63 (s, 3H) 3.15-3.22 (m, 4H) 3.84-3.93 (m, 4H) 7.66 (d, J=1.96 Hz, 1H) 7.87 (dd, J=4.89, 1.37 Hz, 1H) 8.13 (s, 1H) 8.15 (d, J=1.96 Hz, 1H) 8.39 (d, J=2.35 Hz, 1H) 8.82 (d, J=5.09 Hz, 1H) 9.21 (d, J=2.35 Hz, 1H). LCMS (m/z) (M+H)=477.1, Rt=0.66 min.

Example 290: N-(6'-chloro-2-methyl-5'-morpholino-[3,3-bipyridin]-5-yl)-2-(2-fluoropropan-2-yl)isonicotinamide

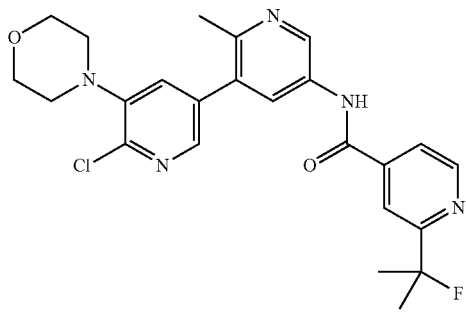 [SMILES: Cc1ncc(NC(=O)c2ccnc(C(C)(C)F)c2)cc1-c1cnc(Cl)c(N2CCOCC2)c1]

¹H NMR (400 MHz, <cd3od>) δ ppm 1.71 (s, 3H) 1.77 (s, 3H) 2.64 (s, 3H) 3.14-3.21 (m, 4H) 3.81-3.93 (m, 4H) 7.67 (d, J=1.96 Hz, 1H) 7.83 (dd, J=5.09, 1.96 Hz, 1H) 8.13 (s, 1H) 8.15 (d, J=1.96 Hz, 1H) 8.43 (d, J=2.35 Hz, 1H) 8.75 (d, J=5.09 Hz, 1H) 9.26 (d, J=2.35 Hz, 1H). LCMS (m/z) (M+H)=470.1, Rt=0.69 min.

Example 291: N-(6'-chloro-2-methyl-5'-morpholino-[3,3'-bipyridin]-5-yl)-2-(trifluoromethyl)isonicotinamide

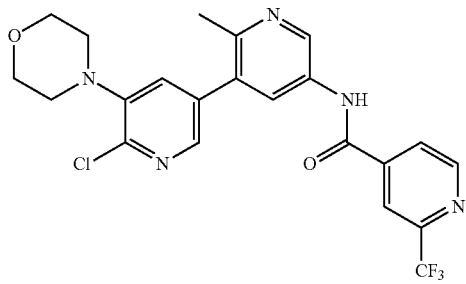 [SMILES: Cc1ncc(NC(=O)c2ccnc(C(F)(F)F)c2)cc1-c1cnc(Cl)c(N2CCOCC2)c1]

¹H NMR (400 MHz, <cd3od>) δ ppm 2.63 (s, 3H) 3.14-3.22 (m, 4H) 3.85-3.93 (m, 4H) 7.66 (d, J=2.35 Hz, 1H) 8.14 (d, J=2.35 Hz, 1H) 8.17 (d, J=3.91 Hz, 1H) 8.36 (s, 1H) 8.39 (d, J=2.35 Hz, 1H) 8.96 (d, J=4.70 Hz, 1H) 9.21 (d, J=2.35 Hz, 1H). LCMS (m/z) (M+H)=478.1, Rt=0.70 min.

Example 292: N-(6'-chloro-2-methyl-5'-morpholino-[3,3'-bipyridin]-5-yl)-6-(trifluoromethyl)pyridazine-4-carboxamide

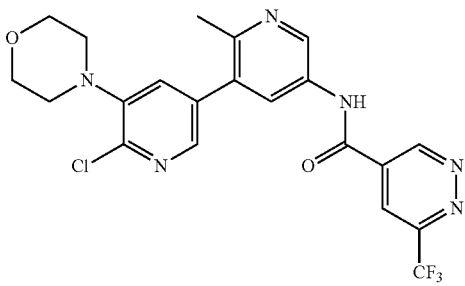

¹H NMR (400 MHz, <cd3od>) δ ppm 2.60 (s, 3H) 3.14-3.21 (m, 4H) 3.84-3.95 (m, 4H) 7.65 (d, J=1.96 Hz, 1H) 8.13 (d, J=2.35 Hz, 1H) 8.34 (d, J=2.35 Hz, 1H) 8.62 (d, J=1.96 Hz, 1H) 9.13 (d, J=2.35 Hz, 1H) 9.91 (d, J=1.96 Hz, 1H). LCMS (m/z) (M+H)=479.1, Rt=0.65 min.

Example 293: N-(6'-chloro-2-methyl-5'-morpholino-[3,3'-bipyridin]-5-yl)-6-(2-cyanopropan-2-yl)pyridazine-4-carboxamide

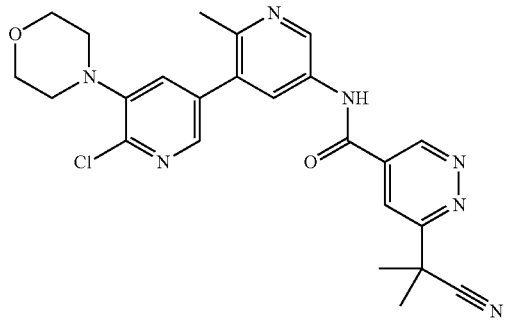

¹H NMR (400 MHz, <cd3od>) δ ppm 1.93 (s, 6H) 2.63 (s, 3H) 3.15-3.22 (m, 4H) 3.83-3.94 (m, 4H) 7.66 (d, J=1.96 Hz, 1H) 8.15 (d, J=2.35 Hz, 1H) 8.39 (d, J=2.35 Hz, 1H) 8.41 (d, J=1.96 Hz, 1H) 9.21 (d, J=2.35 Hz, 1H) 9.66 (d, J=1.96 Hz, 1H). LCMS (m/z) (M+H)=478.3, Rt=0.62 min.

Example 294: 2-(2-fluoropropan-2-yl)-N-(2-methyl-5'-morpholino-[3,3'-bipyridin]-5-yl)isonicotinamide

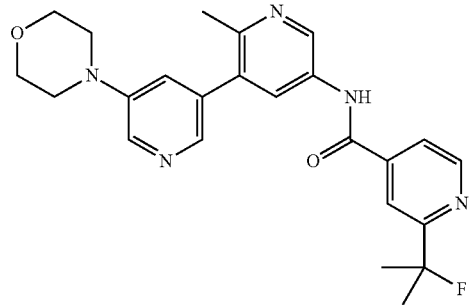 [SMILES: Cc1ncc(NC(=O)c2ccnc(C(C)(C)F)c2)cc1-c1cncc(N2CCOCC2)c1]

¹H NMR (400 MHz, <cd3od>) δ ppm 1.71 (s, 3H) 1.77 (s, 3H) 2.59 (s, 3H) 3.44-3.50 (m, 4H) 3.85-3.93 (m, 4H) 7.82 (dd, J=5.09, 1.57 Hz, 1H) 8.04 (d, J=0.78 Hz, 1H) 8.12

(s, 1H) 8.28 (d, J=0.78 Hz, 1H) 8.48 (t, J=2.35 Hz, 2H) 8.75 (d, J=5.09 Hz, 1H) 9.07 (d, J=2.35 Hz, 1H). LCMS (m/z) (M+H)=436.4, Rt=0.52 min.

Example 295: N-(2-methyl-5'-morpholino-[3,3'-bipyridin]-5-yl)-2-trifluoromethyl)isonicotinamide

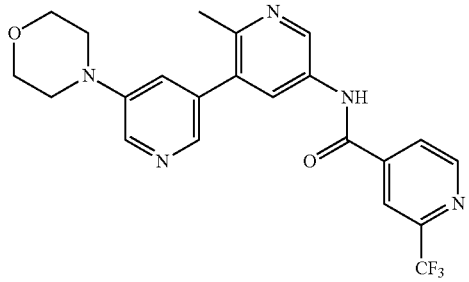 [SMILES: Cc1ncc(NC(=O)c2ccnc(C(F)(F)F)c2)cc1-c1cncc(N2CCOCC2)c1]

$^1$H NMR (400 MHz, <cd3od>) δ ppm 2.56 (s, 3H) 3.42-3.47 (m, 4H) 3.84-3.94 (m, 4H) 8.01 (s, 1H) 8.16 (d, J=3.91 Hz, 1H) 8.26 (d, J=0.78 Hz, 1H) 8.34 (s, 1H) 8.42 (d, J=2.35 Hz, 1H) 8.46 (d, J=2.74 Hz, 1H) 8.92-9.00 (m, 2H). LCMS (m/z) (M+H)=444.3, Rt=0.52 min.

Example 296: 6-(2-cyanopropan-2-yl)-N-(2-methyl-5'-morpholino-[3,3'-bipyridin]-5-yl)pyridazine-4-carboxamide

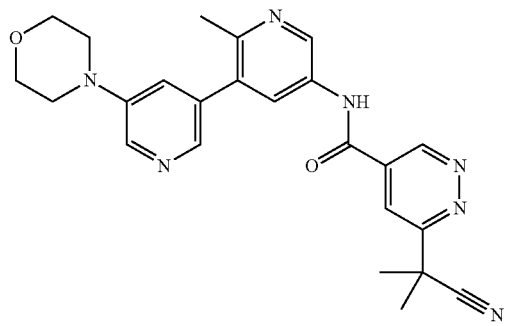

$^1$H NMR (400 MHz, <cd3od>) δ ppm 1.92 (s, 6H) 2.55 (s, 3H) 3.42-3.48 (m, 4H) 3.82-3.93 (m, 4H) 8.02 (s, 1H) 8.25 (d, J=1.17 Hz, 1H) 8.40 (t, J=1.96 Hz, 2H) 8.46 (d, J=2.74 Hz, 1H) 8.93 (d, J=2.35 Hz, 1H) 9.65 (d, J=1.96 Hz, 1H). LCMS (m/z) (M+H)=444.1, Rt=0.45 min.

Example 297: 2-(2-cyanopropan-2-yl)-N-(2-methyl-5'-morpholino-[3,3'-bipyridin]-5-yl)isonicotinamide

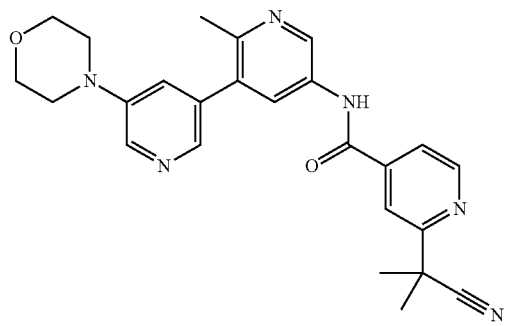 [SMILES: Cc1ncc(NC(=O)c2ccnc(C(C)(C)C#N)c2)cc1-c1cncc(N2CCOCC2)c1]

$^1$H NMR (400 MHz, <cd3od>) δ ppm 1.82 (s, 6H) 2.57 (s, 3H) 3.42-3.51 (m, 4H) 3.83-3.92 (m, 4H) 7.85 (dd, J=4.89, 1.37 Hz, 1H) 8.02 (d, J=0.78 Hz, 1H) 8.12 (s, 1H) 8.26 (d, J=1.17 Hz, 1H) 8.43 (d, J=2.35 Hz, 1H) 8.47 (d, J=2.74 Hz, 1H) 8.81 (d, J=4.70 Hz, 1H) 8.99 (d, J=2.35 Hz, 1H). LCMS (m/z) (M+H)=443.4, Rt=0.50 min.

Example 298: N-(6'-fluoro-2-methyl-5'-morpholino-[3,3'-bipyridin]-5-yl)-2-(2-fluoropropan-2-yl)isonicotinamide

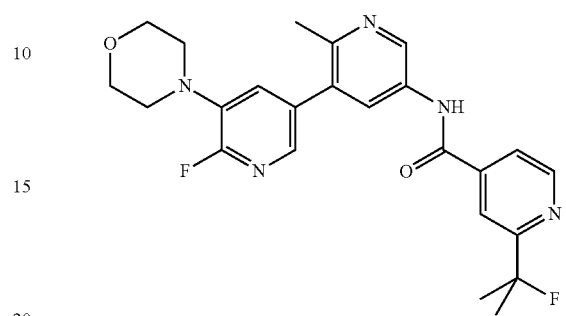

$^1$H NMR (400 MHz, <cd3od>) δ ppm 1.71 (s, 3H) 1.77 (s, 3H) 2.65 (s, 3H) 3.16-3.24 (m, 4H) 3.82-3.91 (m, 4H) 7.57 (dd, J=9.78, 1.96 Hz, 1H) 7.79-7.87 (m, 2H) 8.13 (s, 1H) 8.44 (d, J=1.96 Hz, 1H) 8.76 (d, J=5.09 Hz, 1H) 9.29 (d, J=2.35 Hz, 1H). LCMS (m/z) (M+H)=454.1, Rt=0.69 min.

Example 299: 2-(2-fluoropropan-2-yl)-N-(6'-(2-hydroxyethoxy)-2-methyl-5'-morpholino-[3,3'-bipyridin]-5-yl)isonicotinamide

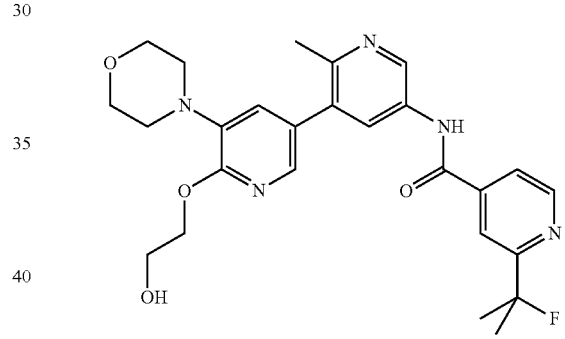

$^1$H NMR (400 MHz, <cd3od>) δ ppm 1.71 (s, 3H) 1.77 (s, 3H) 2.67-2.73 (m, 3H) 3.16-3.22 (m, 4H) 3.85-3.91 (m, 4H) 3.93-3.99 (m, 2H) 4.50-4.57 (m, 2H) 7.33 (d, J=1.96 Hz, 1H) 7.81-7.88 (m, 2H) 8.14 (s, 1H) 8.46 (d, J=1.96 Hz, 1H) 8.76 (d, J=5.09 Hz, 1H) 9.34 (d, J=2.35 Hz, 1H). LCMS (m/z) (M+H)=496.1, Rt=0.61 min.

Example 300: 2-(2-cyanopropan-2-yl)-N-(6'-(2-hydroxyethoxy)-2-methyl-5'-morpholino-[3,3'-bipyridin]-5-yl)isonicotinamide

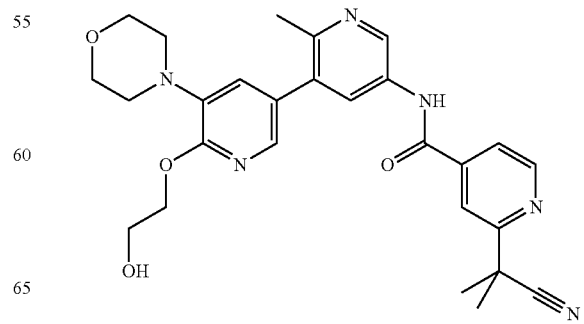

$^1$H NMR (400 MHz, <cd3od>) δ ppm 1.76-1.86 (m, 6H) 2.66-2.71 (m, 3H) 3.16-3.23 (m, 4H) 3.83-3.89 (m, 4H) 3.91-3.97 (m, 2H) 4.51-4.56 (m, 2H) 7.32 (d, J=2.35 Hz, 1H) 7.84-7.88 (m, 2H) 8.11-8.15 (m, 1H) 8.42 (d, J=2.35 Hz, 1H) 8.82 (d, J=5.09 Hz, 1H) 9.31 (d, J=2.35 Hz, 1H). LCMS (m/z) (M+H)=503.4, Rt=0.60 min.

Example 301: N-(6'-(2-hydroxyethoxy)-2-methyl-5'-morpholino-[3,3'-bipyridin]-5-yl)-4-(trifluoromethyl)picolinamide

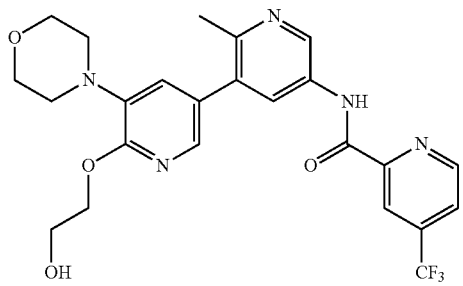 [SMILES: Cc1ncc(NC(=O)c2cc(C(F)(F)F)ccn2)cc1-c1cnc(OCCO)c(N2CCOCC2)c1]

$^1$H NMR (400 MHz, <cd3od>) δ ppm 2.67-2.72 (m, 3H) 3.16-3.23 (m, 4H) 3.84-3.90 (m, 4H) 3.92-3.98 (m, 2H) 4.49-4.57 (m, 2H) 7.34 (d, J=1.96 Hz, 1H) 7.88 (d, J=1.96 Hz, 1H) 7.99 (d, J=4.30 Hz, 1H) 8.50 (s, 1H) 8.67 (d, J=2.35 Hz, 1H) 9.02 (d, J=5.09 Hz, 1H) 9.43 (d, J=2.35 Hz, 1H). LCMS (m/z) (M+H)=504.3, Rt=0.67 min.

Example 302: 6-(1-cyanocyclopropyl)-N-(4-methyl-3-(5-morpholino-6-((tetrahydro-2H-pyran-4-yl)oxy)pyridin-3-yl)phenyl)pyridazine-4-carboxamide

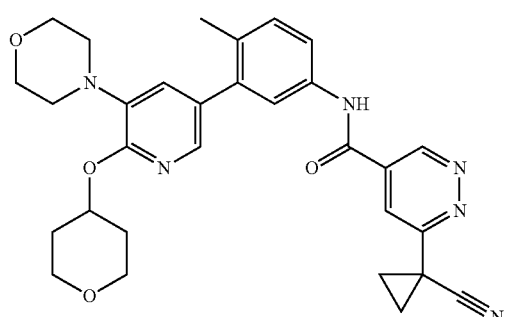

$^1$H NMR (400 MHz, <dmso>) δ ppm 1.63-1.74 (m, 2H) 1.90-1.95 (m, 2H) 2.01 (d, J=3.13 Hz, 4H) 2.22 (s, 3H) 3.06 (br. s., 4H) 3.54 (ddd, J=11.35, 8.41, 2.93 Hz, 2H) 3.68-3.76 (m, 4H) 3.78-3.86 (m, 2H) 5.31 (dt, J=7.92, 4.06 Hz, 1H) 7.12 (d, J=1.96 Hz, 1H) 7.31 (d, J=8.61 Hz, 1H) 7.59 (d, J=1.96 Hz, 1H) 7.66 (dd, J=8.22, 2.35 Hz, 1H) 7.70 (d, J=1.96 Hz, 1H) 8.00 (d, J=1.96 Hz, 1H) 9.53 (d, J=1.96 Hz, 1H) 10.70 (s, 1H). LCMS (m/z) (M+H)=541.2, Rt=0.85 min.

Example 303: (R)-6-(2-cyanopropan-2-yl)-N-(6'-ethoxy-2-methyl-5'-(3-methylmorpholino)-[3,3'-bipyridin]-5-yl)pyridazine-4-carboxamide

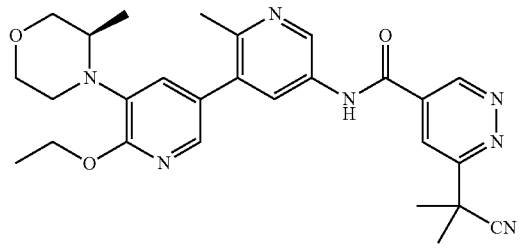 [SMILES: CCOc1ncc(-c2cc(NC(=O)c3cnnc(C(C)(C)C#N)c3)cnc2C)cc1N1CCOC[C@H]1C]

$^1$H NMR (500 MHz, <cd3od>) δ ppm 1.01 (d, J=6.31 Hz, 3H) 1.48 (t, J=6.94 Hz, 3H) 1.95 (s, 6H) 2.72 (s, 3H) 2.86-2.95 (m, 1H) 3.42-3.44 (m, 1H) 3.53-3.62 (m, 1H) 3.91 (br. s., 4H) 4.42-4.61 (m, 2H) 7.45 (d, J=2.21 Hz, 1H) 7.95 (d, J=1.89 Hz, 1H) 8.46 (dd, J=7.09, 2.36 Hz, 2H) 9.34 (d, J=2.21 Hz, 1H) 9.70 (d, J=1.89 Hz, 1H). LCMS (m/z) (M+H)=502.2, Rt=0.65 min.

Example 304: N-(3-(6-ethoxy-5-morpholinopyridin-3-yl)-4-methylphenyl)-6-(2-fluoropropan-2-yl)pyridazine-4-carboxamide

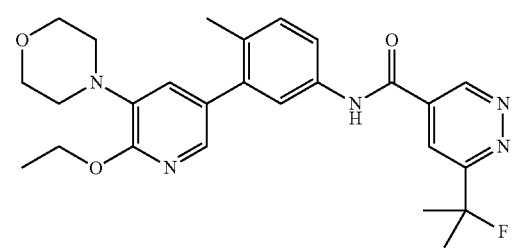 [SMILES: CCOc1ncc(-c2cc(NC(=O)c3cnnc(C(C)(C)F)c3)ccc2C)cc1N1CCOCC1]

$^1$H NMR (400 MHz, <cd3od>) δ ppm 1.45 (t, J=7.04 Hz, 3H) 1.78-1.91 (m, 6H) 2.27 (s, 3H) 3.11-3.23 (m, 4H) 3.81-3.93 (m, 4H) 4.47 (d, J=7.04 Hz, 2H) 7.28 (d, J=1.96 Hz, 2H) 7.64 (s, 2H) 7.76 (d, J=1.96 Hz, 1H) 8.34 (d, J=1.57 Hz, 1H) 9.56 (d, J=2.35 Hz, 1H). LCMS (m/z) (M+H)=480.2, Rt=0.92 min.

Example 305: N-(6'-ethoxy-2-methyl-5'-morpholino-[3,3'-bipyridin]-5-yl)-6-(2-fluoropropan-2-yl)pyridazine-4-carboxamide

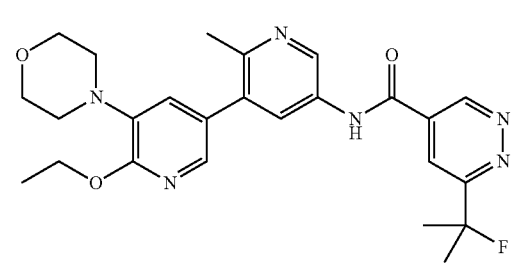 [SMILES: CCOc1ncc(-c2cc(NC(=O)c3cnnc(C(C)(C)F)c3)cnc2C)cc1N1CCOCC1]

$^1$H NMR (400 MHz, <cd3od>) δ ppm 1.45 (t, J=7.04 Hz, 3H) 1.79-1.93 (m, 6H) 2.70 (s, 3H) 3.08-3.21 (m, 4H)

3.80-3.94 (m, 4H) 4.50 (d, J=7.04 Hz, 2H) 7.30 (d, J=1.96 Hz, 1H) 7.86 (d, J=1.96 Hz, 1H) 8.41 (d, J=1.96 Hz, 1H) 8.45 (d, J=2.35 Hz, 1H) 9.33 (d, J=1.96 Hz, 1H) 9.61 (d, J=1.96 Hz, 1H). LCMS (m/z) (M+H)=481.2, Rt=0.66 min.

Example 306: Synthesis of 3-(6-ethoxy-5-morpholinopyridin-3-yl)-4-methyl-N-(2-(trifluoromethyl)pyridin-4-yl)benzamide

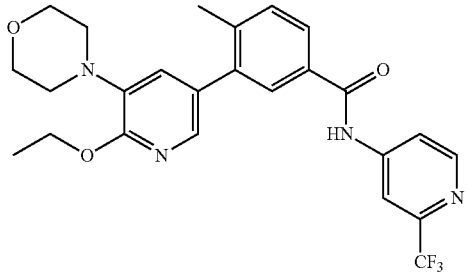 [SMILES: CCOc1ncc(-c2cc(C(=O)Nc3ccnc(C(F)(F)F)c3)ccc2C)cc1N1CCOCC1]

To a solution of 3-(6-ethoxy-5-morpholinopyridin-3-yl)-4-methylbenzoic acid (1.0 equiv.) in DCM (0.1 M) at 0° C. was added 1-chloro-N,N,2-trimethyl-1-propenylamine (1.2 equiv.) and the mixture was allowed to stir at for 1 h. The mixture was subsequently added to a solution of 4-amino-2-(trifluoromethyl)pyridine (1.3 equiv.) and Et$_3$N (3 equiv.) in DCM (0.1 M) and the reaction was allowed to warm to 25° C. and stirred for 1 h. The mixture was concentrated, taken up in DMSO, filtered, and purified via preparative reverse phase HPLC. Upon lyophilization of the pure fractions, 3-(6-ethoxy-5-morpholinopyridin-3-yl)-4-methyl-N-(2-(trifluoromethyl)pyridin-4-yl)benzamide was isolated as the TFA salt in 52% yield. $^1$H NMR (400 MHz, <dmso>) δ ppm 1.35 (t, J=7.04 Hz, 3H) 2.27-2.35 (m, 3H) 3.06 (br. s., 4H) 3.72 (d, J=4.30 Hz, 4H) 4.39 (d, J=7.04 Hz, 2H) 7.18 (d, J=1.96 Hz, 1H) 7.50 (d, J=8.61 Hz, 1H) 7.78 (d, J=1.96 Hz, 1H) 7.87-7.96 (m, 2H) 8.06 (d, J=3.91 Hz, 1H) 8.28 (d, J=1.57 Hz, 1H) 8.65 (d, J=5.48 Hz, 1H) 10.81 (s, 1H). LCMS (m/z) (M+H)=487.1, Rt=1.09 min.

Example 307: Synthesis of N-(6'-(dimethylamino)-2-methyl-5'-morpholino-[3,3'-bipyridin]-5-yl)-3-(trifluoromethyl)benzamide

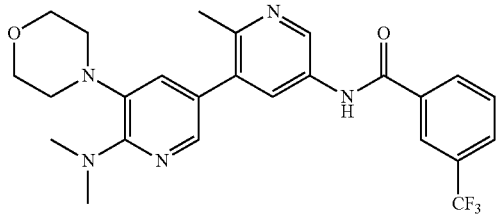 [SMILES: Cc1ncc(NC(=O)c2cccc(C(F)(F)F)c2)cc1-c1cnc(N(C)C)c(N2CCOCC2)c1]

To a solution of N-(6'-fluoro-2-methyl-5'-morpholino-[3,3'-bipyridin]-5-yl)-3-(trifluoromethyl)benzamide (1.0 equiv.) in DMF (0.25 M) was added a 5.6M solution of dimethylamine in ethanol (5.0 equiv.). The mixture was stirred at 90° C. overnight. The cooled mixture was diluted with DMSO, filtered, and purified via preparative reverse phase HPLC. Upon lyophilization of the pure fractions N-(6'-(dimethylamino)-2-methyl-5'-morpholino-[3,3'-bipyridin]-5-yl)-3-(trifluoromethyl)benzamide was isolated as the TFA salt, a light yellow solid, in 28% yield. $^1$H NMR (400 MHz, <cd3od>) δ ppm 2.65 (s, 3H) 3.04-3.12 (m, 4H) 3.30 (s, 6H) 3.87-3.96 (m, 4H) 7.61 (d, J=1.96 Hz, 1H) 7.74-7.83 (m, 1H) 7.90 (d, J=1.56 Hz, 1H) 7.97 (d, J=7.83 Hz, 1H) 8.28 (d, J=8.22 Hz, 1H) 8.34 (s, 1H) 8.46 (d, J=2.35 Hz, 1H) 9.13 (d, J=1.96 Hz, 1H); LCMS (m/z) (M+H)= 486.3, Rt=0.60 min.

The compounds listed below were prepared using methods similar to those described for the preparation of Example 307 using the appropriate starting materials.

Example 308: N-(6'-(dimethylamino)-2-methyl-5'-morpholino-[3,3'-bipyridin]-5-yl)-2-isopropylisonicotinamide

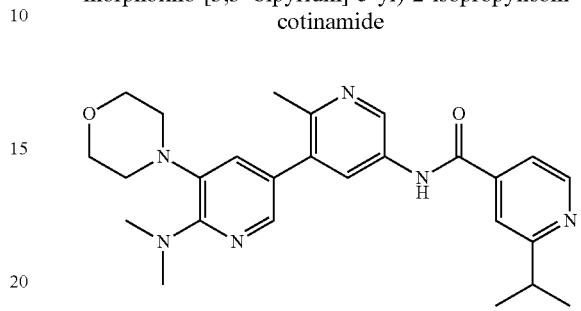

$^1$H NMR (400 MHz, <cd3od>) δ ppm 1.42 (d, J=7.04 Hz, 6H) 2.65 (s, 3H) 3.02-3.11 (m, 4H) 3.33 (s, 6H) 3.86-3.97 (m, 4H) 7.65 (d, J=1.96 Hz, 1H) 7.88 (d, J=1.96 Hz, 1H) 7.97 (dd, J=5.48, 1.57 Hz, 1H) 8.08 (s, 1H) 8.47 (d, J=1.96 Hz, 1H) 8.77 (d, J=5.48 Hz, 1H) 9.12 (d, J=2.35 Hz, 1H). LCMS (m/z) (M+H)=461.2, Rt=0.45 min.

Example 309: Synthesis of N-(2-methyl-5'-(3-oxomorpholino)-6'-((tetrahydro-2H-pyran-4-yl)oxy)-[3,3'-bipyridin]-5-yl)-3-(trifluoromethyl)benzamide

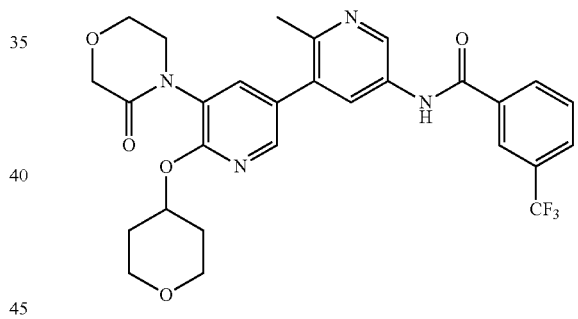

To a solution of N-(2-methyl-5'-morpholino-6'-((tetrahydro-2H-pyran-4-yl)oxy)-[3,3'-bipyridin]-5-yl)-3-(trifluoromethyl)benzamide (1.0 equiv.) in DCM (0.1 M) was added benzyltriethylammonium chloride (6.1 equiv.) and potassium permanganate (6.0 equiv.). The mixture was stirred at 45° C. for 2 hr. The cooled reaction mixture was diluted with water and treated with sodium bisulfite (18 equiv.). The mixture was stirred for 15 min at ambient temperature. Additional water was added, and the mixture was extracted with DCM. The organic layer was washed with saturated aqueous sodium bicarbonate, dried over sodium sulfate, filtered, and concentrated. The crude material was purified by preparative reverse phase HPLC. Upon lyophilization of the pure fractions, N-(2-methyl-5'-(3-oxomorpholino)-6'-((tetrahydro-2H-pyran-4-yl)oxy)-[3,3'-bipyridin]-5-yl)-3-(trifluoromethyl)benzamide was isolated as the TFA salt, a white solid, in 27% yield. $^1$H NMR (400 MHz, <cd3od>) δ ppm 1.80-1.94 (m, 2H) 2.13 (ddd, J=9.59, 6.46, 3.13 Hz, 2H) 2.69 (s, 3H) 3.69 (ddd, J=11.54, 7.83, 3.33 Hz, 2H) 3.79 (t, J=5.09 Hz, 2H) 3.97 (ddd, J=11.25, 6.95, 3.72 Hz, 2H) 4.06-4.16 (m, 2H) 4.36 (s, 2H) 5.48 (tt, J=7.58, 3.77 Hz, 1H) 7.76-7.84 (m, 1H) 7.92 (d, J=2.35 Hz, 1H) 7.98 (d, J=7.83

Hz, 1H) 8.26-8.33 (m, 2H) 8.36 (s, 1H) 8.45 (d, J=2.35 Hz, 1H) 9.28 (d, J=2.35 Hz, 1H); LCMS (m/z) (M+H)=557.2, Rt=0.75 min.

Example 310: Synthesis of (S)—N-(2-methyl-5'-morpholino-6'-((tetrahydrofuran-3-yl)oxy)-[3,3'-bipyridin]-5-yl)-3-(trifluoromethyl)benzamide

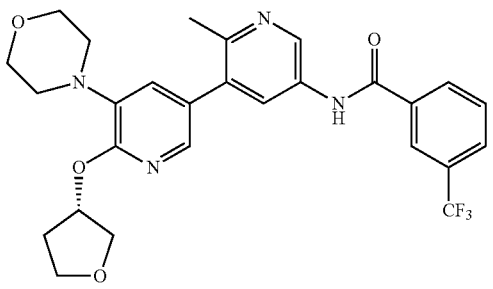 [SMILES: Cc1ncc(NC(=O)c2cccc(C(F)(F)F)c2)cc1-c1cnc(O[C@H]2CCOC2)c(N2CCOCC2)c1]

To a solution of (S)-(+)-3-hydroxytetrahydrofuran (5 equiv.) in dioxane (0.1 M) at 25° C. was added NaH (5.2 equiv.), and the mixture was stirred for 15 min. N-(6'-fluoro-2-methyl-5'-morpholino-[3,3'-bipyridin]-5-yl)-3-(trifluoromethyl)benzamide (1.0 equiv.) was then added, and the reaction was heated to 105° C. and stirred for 1 h. The reaction was cooled to room temperature, quenched with a few drops of water, and concentrated. The crude material was purified by preparative reverse phase HPLC. Upon lyophilization of the pure fractions, (S)—N-(2-methyl-5'-morpholino-6'-((tetrahydrofuran-3-yl)oxy)-[3,3'-bipyridin]-5-yl)-3-(trifluoromethyl)benzamide was isolated as the TFA salt, a pale yellow solid, in 44% yield. $^1$H NMR (400 MHz, <dmso>) δ ppm 2.05-2.13 (m, 1H) 2.22-2.29 (m, 1H) 2.52 (s, 3H) 3.08 (br. s., 4H) 3.71-3.78 (m, 4H) 3.78-3.91 (m, 3H) 3.96 (dd, J=10.37, 4.50 Hz, 1H) 5.61 (dd, J=5.87, 4.70 Hz, 1H) 7.28 (d, J=1.57 Hz, 1H) 7.78-7.90 (m, 2H) 8.02 (d, J=7.83 Hz, 1H) 8.22 (s, 1H) 8.30 (d, J=7.83 Hz, 1H) 8.34 (s, 1H) 8.99 (d, J=1.96 Hz, 1H) 10.85 (s, 1H). LCMS (m/z) (M+H)=529.2, Rt=0.77 min. The compounds listed below were prepared using methods similar to those described for the preparation of Example 310 using the appropriate starting materials Differences in the workup and/or purification protocols are noted where applicable.

Example 311: (R)—N-(2-methyl-5'-morpholino-6'-((tetrahydrofuran-3-yl)oxy)-[3,3'-bipyridin]-5-yl)-3-(trifluoromethyl)benzamide

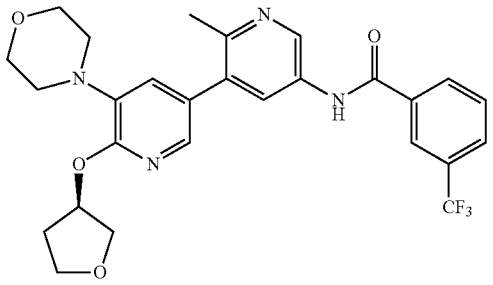 [SMILES: Cc1ncc(NC(=O)c2cccc(C(F)(F)F)c2)cc1-c1cnc(O[C@@H]2CCOC2)c(N2CCOCC2)c1]

$^1$H NMR (400 MHz, <dmso>) δ ppm 2.09 (d, J=6.65 Hz, 1H) 2.22-2.31 (m, 1H) 2.53 (s, 3H) 3.08 (br. s., 4H) 3.67-3.77 (m, 4H) 3.78-3.91 (m, 3H) 3.96 (dd, J=10.17, 4.70 Hz, 1H) 5.55-5.67 (m, 1H) 7.28 (d, J=1.56 Hz, 1H) 7.84 (s, 2H) 8.03 (d, J=7.83 Hz, 1H) 8.23 (s, 1H) 8.30 (d, J=8.22 Hz, 1H) 8.34 (s, 1H) 9.00 (s, 1H) 10.88 (s, 1H). LCMS (m/z) (M+H)=529.2, Rt=0.76 min.

Example 312: N-(6'-(2-methoxyethoxy)-2-methyl-5'-morpholino-[3,3'-bipyridin]-5-yl)-3-(trifluoromethyl)benzamide

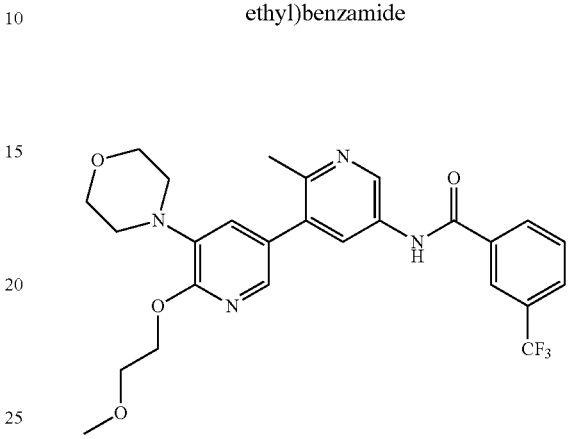

$^1$H NMR (400 MHz, <dmso>) δ ppm 2.49 (s, 3H) 3.05-3.12 (m, 4H) 3.31 (s, 3H) 3.67-3.77 (m, 6H) 4.42-4.49 (m, 2H) 7.25 (d, J=1.56 Hz, 1H) 7.77-7.86 (m, 2H) 8.01 (d, J=7.83 Hz, 1H) 8.19 (s, 1H) 8.28 (d, J=7.83 Hz, 1H) 8.32 (s, 1H) 8.97 (d, J=1.96 Hz, 1H) 10.83 (s, 1H). LCMS (m/z) (M+H)=517.2, Rt=0.72 min.

Example 313: 2-isopropyl-N-(2-methyl-5'-morpholino-6'-((tetrahydro-2H-pyran-4-yl)oxy)-[3,3'-bipyridin]-5-yl)isonicotinamide

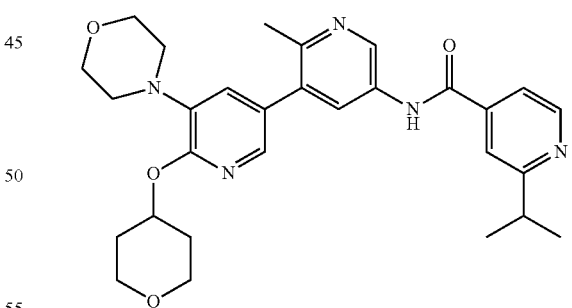

$^1$H NMR (400 MHz, <cd3od>) δ ppm 1.39 (d, J=7.04 Hz, 6H) 1.84 (dtd, J=12.77, 8.29, 8.29, 3.91 Hz, 2H) 2.08-2.18 (m, 2H) 2.69 (s, 3H) 3.15-3.19 (m, 4H) 3.21-3.27 (m, 1H) 3.67 (ddd, J=11.35, 8.22, 3.13 Hz, 2H) 3.83-3.90 (m, 4H) 3.93-4.01 (m, 2H) 5.44 (tt, J=7.83, 3.91 Hz, 1H) 7.31 (d, J=1.96 Hz, 1H) 7.85 (d, J=1.96 Hz, 1H) 7.89 (dd, J=5.28, 1.37 Hz, 1H) 8.00 (s, 1H) 8.44 (d, J=2.35 Hz, 1H) 8.74 (d, J=5.48 Hz, 1H) 9.31 (d, J=1.96 Hz, 1H). LCMS (m/z) (M+H)=518.3, Rt=0.57 min.

Example 314: N-(2-methyl-5'-morpholino-6'-((tetrahydro-2H-pyran-4-yl)oxy)-[3,3'-bipyridin]-5-yl)-2-(trifluoromethyl)isonicotinamide

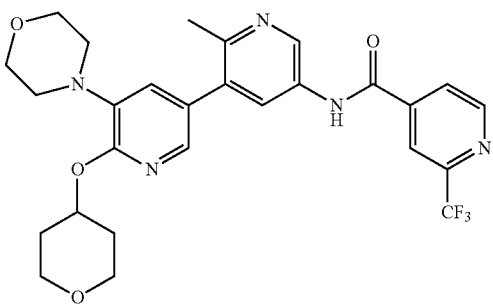 [SMILES: Cc1ncc(NC(=O)c2ccnc(C(F)(F)F)c2)cc1-c1cnc(OC2CCOCC2)c(N2CCOCC2)c1]

$^1$H NMR (400 MHz, <cd3od>) δ ppm 1.85 (td, J=8.51, 4.11 Hz, 2H) 2.08-2.19 (m, 2H) 2.67 (s, 3H) 3.13-3.18 (m, 4H) 3.67 (ddd, J=11.64, 8.31, 3.13 Hz, 2H) 3.82-3.90 (m, 4H) 3.93-4.01 (m, 2H) 5.44 (tt, J=7.83, 3.91 Hz, 1H) 7.31 (d, J=1.96 Hz, 1H) 7.85 (d, J=1.96 Hz, 1H) 8.18 (d, J=4.30 Hz, 1H) 8.36 (s, 1H) 8.41 (d, J=2.35 Hz, 1H) 8.97 (d, J=5.09 Hz, 1H) 9.28 (d, J=1.96 Hz, 1H). LCMS (m/z) (M+H)=544.3, Rt=0.69 min.

Example 315: N-(2-methyl-5'-morpholino-6'-(oxetan-3-yloxy)-[3,3'-bipyridin]-5-yl)-3-trifluoromethyl)benzamide

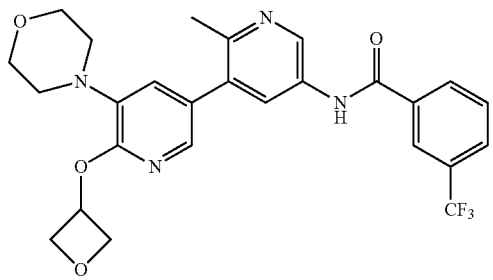 [SMILES: Cc1ncc(NC(=O)c2cccc(C(F)(F)F)c2)cc1-c1cnc(OC2COC2)c(N2CCOCC2)c1]

The reaction mixture was quenched with water and extracted three times with ethyl acetate. The combined organics were dried over magnesium sulfate, filtered, and concentrated. The crude residue was purified via flash chromatography over silica gel eluting with heptane and 0-100% ethyl acetate gradient. Pure product fractions were concentrated, re-dissolved in acetonitrile/water, and lyophilized. Isolated N-(2-methyl-5'-morpholino-6'-(oxetan-3-yloxy)-[3,3'-bipyridin]-5-yl)-3-(trifluoromethyl)benzamide as a white solid in 44% yield. $^1$H NMR (400 MHz, <dmso>) δ ppm 2.43 (s, 3H) 3.13 (br. s., 4H) 3.70-3.83 (m, 4H) 4.62 (dd, J=7.04, 5.48 Hz, 2H) 4.93 (t, J=6.85 Hz, 2H) 5.63 (quin, J=5.67 Hz, 1H) 7.28 (d, J=1.96 Hz, 1H) 7.74 (d, J=1.56 Hz, 1H) 7.81 (t, J=7.83 Hz, 1H) 8.00 (d, J=7.83 Hz, 1H) 8.04 (d, J=2.35 Hz, 1H) 8.28 (d, J=7.83 Hz, 1H) 8.32 (s, 1H) 8.84 (d, J=2.35 Hz, 1H) 10.65 (s, 1H). LCMS (m/z) (M+H)=515.1, Rt=0.72 min.

Examples 316 and 317: N-(6'-(((1r,4r)-4-hydroxycyclohexyl)oxy)-2-methyl-5'-morpholino-[3,3'-bipyridin]-5-yl)-3-(trifluoromethyl)benzamide and N-(6'-(((1s,4s)-4-hydroxycyclohexyl)oxy)-2-methyl-5'-morpholino-[3,3'-bipyridin]-5-yl)-3-(trifluoromethyl)benzamide

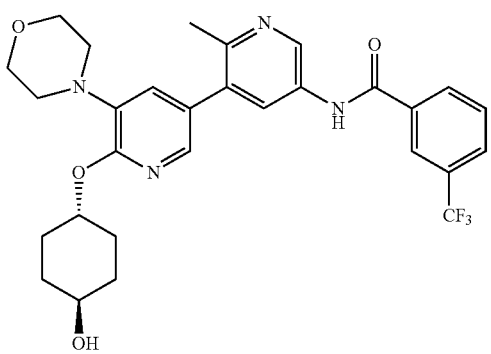

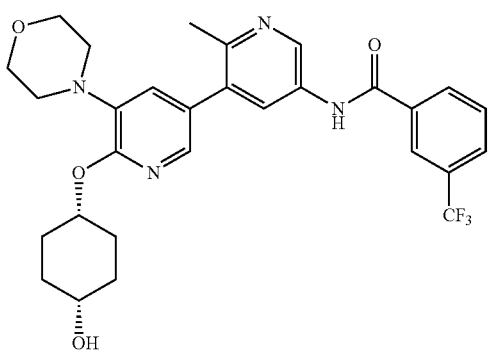

After initial purification by preparative reverse phase HPLC, a second purification of the diastereomeric mixture was performed via chiral HPLC (SFC, methanol, OJ column). Isolated N-(6'-(((1r,4r)-4-hydroxycyclohexyl)oxy)-2-methyl-5'-morpholino-[3,3'-bipyridin]-5-yl)-3-(trifluoromethyl)benzamide and N-(6'-(((1s,4s)-4-hydroxycyclohexyl)oxy)-2-methyl-5'-morpholino-[3,3'-bipyridin]-5-yl)-3-(trifluoromethyl)benzamide as white solids. The stereochemical identity of the two peaks was not determined. Peak 1 (11% yield, Rt=1.91 min)$^1$H NMR (400 MHz, <cdcl3>) δ ppm 1.70-1.91 (m, 6H) 2.08-2.19 (m, 2H) 2.53 (s, 3H) 3.12-3.22 (m, 4H) 3.83-3.93 (m, 5H) 5.32 (br. s., 1H) 7.04 (d, J=1.96 Hz, 1H) 7.61-7.71 (m, 1H) 7.76 (d, J=1.96 Hz, 1H) 7.85 (d, J=7.83 Hz, 1H) 7.92 (br. s., 1H) 8.09 (d, J=7.83 Hz, 1H) 8.15 (s, 2H) 8.62 (d, J=2.35 Hz, 1H). LCMS (m/z) (M+H)=557.2, Rt=0.75. Peak 2 (4% yield, Rt=5.19 min)$^1$H NMR (400 MHz, <cdcl3>) δ ppm 1.59-1.72 (m, 4H) 2.06 (d, J=6.26 Hz, 2H) 2.23-2.32 (m, 2H) 2.53 (s, 3H) 3.14 (br. s., 4H) 3.80-3.93 (m, 5H) 5.15-5.25 (m, 1H) 7.04 (s, 1H) 7.68 (t, J=7.63 Hz, 1H) 7.77 (s, 1H) 7.82-7.90 (m, 2H) 8.09 (d, J=7.43 Hz, 1H) 8.12-8.19 (m, 2H) 8.61 (d, J=1.96 Hz, 1H). LCMS (m/z) (M+H)=557.2, Rt=0.75 min.

Examples 318 and 319: rac-N-(6'-(((1,3-cis)-3-hydroxycyclopentyl)oxy)-2-methyl-5'-morpholino-[3,3'-bipyridin]-5-yl)-3-(trifluoromethyl)benzamide and rac-N-(6'-(((1,3-trans)-3-hydroxycyclopentyl)oxy)-2-methyl-5'-morpholino-[3,3'-bipyridin]-5-yl)-3-trifluoromethyl)benzamide

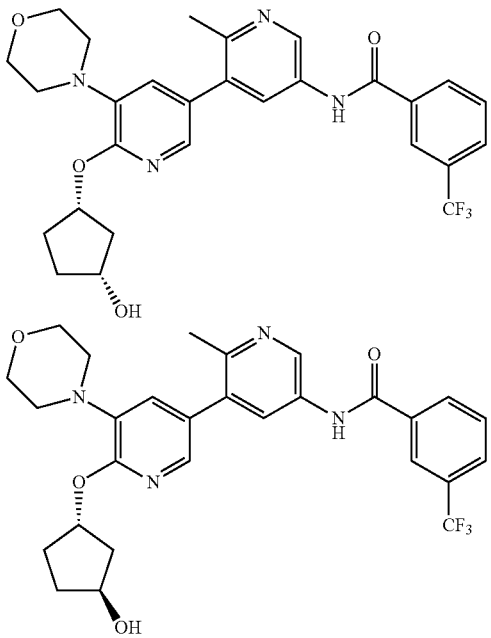

After initial purification by preparative reverse phase HPLC, a second purification of the diastereomeric mixture was performed via chiral HPLC (SFC, ethanol, OJ column). Isolated rac-N-(6'-(((1,3-cis)-3-hydroxycyclopentyl)oxy)-2-methyl-5'-morpholino-[3,3'-bipyridin]-5-yl)-3-(trifluoromethyl)benzamide (Peak 1, Rt=2.28 min) in 6% yield and rac-N-(6'-(((1,3-trans)-3-hydroxycyclopentyl)oxy)-2-methyl-5'-morpholino-[3,3'-bipyridin]-5-yl)-3-(trifluoromethyl)benzamide (Peak 2, Rt=5.35 min) in 4% yield as white solids. rac-N-(6'-(((1,3-cis)-3-hydroxycyclopentyl)oxy)-2-methyl-5'-morpholino-[3,3'-bipyridin]-5-yl)-3-(trifluoromethyl)benzamide $^1$H NMR (400 MHz, <cdcl3>) δ ppm 1.90-2.08 (m, 4H) 2.09-2.28 (m, 2H) 2.53 (s, 3H) 2.97-3.08 (m, 2H) 3.10-3.24 (m, 2H) 3.79-3.95 (m, 4H) 4.40 (br. s., 1H) 5.69 (br. s., 1H) 7.11 (d, J=1.57 Hz, 1H) 7.64-7.71 (m, 1H) 7.81-7.89 (m, 3H) 8.09 (d, J=7.83 Hz, 1H) 8.14 (d, J=2.74 Hz, 2H) 8.62 (d, J=2.35 Hz, 1H). LCMS (m/z) (M+H)=543.1, Rt=0.72 min. rac-N-(6'-(((1,3-trans)-3-hydroxycyclopentyl)oxy)-2-methyl-5'-morpholino-[3,3'-bipyridin]-5-yl)-3-(trifluoromethyl)benzamide $^1$H NMR (400 MHz, <cdcl3>) δ ppm 1.67-1.80 (m, 1H) 1.87-1.99 (m, 1H) 2.06-2.16 (m, 1H) 2.19 (t, J=4.89 Hz, 2H) 2.31-2.44 (m, 1H) 2.52 (s, 3H) 3.12 (d, J=2.74 Hz, 4H) 3.88 (t, J=4.30 Hz, 4H) 4.58 (d, J=4.30 Hz, 1H) 5.68 (br. s., 1H) 7.04 (s, 1H) 7.63-7.72 (m, 1H) 7.79 (s, 1H) 7.83-7.91 (m, 2H) 8.09 (d, J=7.83 Hz, 1H) 8.14 (d, J=6.26 Hz, 2H) 8.61 (d, J=2.35 Hz, 1H). LCMS (m/z) (M+H)=543.1, Rt=0.73 min.

Example 320: N-(6'-((3-hydroxycyclohexyl)oxy)-2-methyl-5'-morpholino-[3,3'-bipyridin]-5-yl)-3-(trifluoromethyl)benzamide

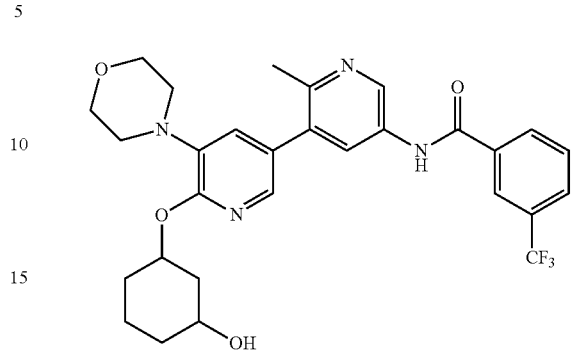

After initial purification by preparative reverse phase HPLC, a second purification of the diastereomeric mixture was performed via chiral HPLC (SFC, isopropanol, OD column). One of the four enantiomerically pure possible stereoisomers was isolated in pure form (Rt=10.29 min); the absolute or relative configuration of this compound was not determined. Isolated N-(6'-((3-hydroxycyclohexyl)oxy)-2-methyl-5'-morpholino-[3,3'-bipyridin]-5-yl)-3-(trifluoromethyl)benzamide as a white solid in 31% yield. $^1$H NMR (400 MHz, <cdcl3>) δ ppm 1.47-1.56 (m, 3H) 1.69-1.89 (m, 3H) 1.90-2.07 (m, 2H) 2.24 (d, J=12.91 Hz, 1H) 2.52 (s, 3H) 3.07 (br. s., 2H) 3.14-3.22 (m, 2H) 3.89 (t, J=4.11 Hz, 5H) 5.38 (dt, J=7.24, 3.81 Hz, 1H) 7.09 (d, J=1.96 Hz, 1H) 7.64-7.71 (m, 1H) 7.79 (d, J=1.96 Hz, 1H) 7.83-7.91 (m, 2H) 8.06-8.17 (m, 3H) 8.62 (d, J=2.35 Hz, 1H). LCMS (m/z) (M+H)=557.1, Rt=0.76 min.

Example 321: N-(2-methyl-6'-((1-methylazetidin-3-yl)oxy)-5'-morpholino-[3,3'-bipyridin]-5-yl)-3-(trifluoromethyl)benzamide

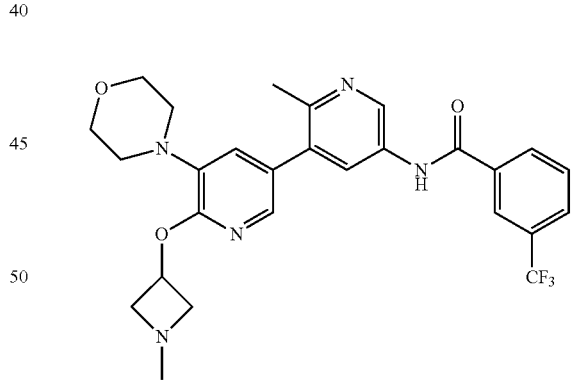

After purification by preparative reverse phase HPLC, pure product fractions were stirred with saturated aqueous sodium carbonate for 15 min. The mixture was extracted three times with ethyl acetate; the combined organics were washed with brine, dried over magnesium sulfate, and concentrated. The residue was taken up in acetonitrile/water and lyophilized. Isolated N-(2-methyl-6'-((1-methylazetidin-3-yl)oxy)-5'-morpholino-[3,3'-bipyridin]-5-yl)-3-(trifluoromethyl)benzamide as a white solid in 23% yield. $^1$H NMR (400 MHz, <cd3od>) δ ppm 2.48 (s, 3H) 2.50-2.56 (m, 5H) 3.13-3.21 (m, 4H) 3.40-3.48 (m, 2H) 3.83-3.90 (m, 4H) 3.98 (dd, J=8.80, 7.24 Hz, 2H) 5.34 (t, J=5.67 Hz, 1H)

7.28 (d, J=1.96 Hz, 1H) 7.70-7.81 (m, 2H) 7.92 (d, J=7.83 Hz, 1H) 8.11 (d, J=2.35 Hz, 1H) 8.24 (d, J=7.83 Hz, 2H) 8.30 (s, 2H) 8.81 (d, J=2.35 Hz, 1H). LCMS (m/z) (M+H)= 528.1, Rt=0.61 min.

Example 322: N-(6'-(2-oxaspiro[3.3]heptan-6-yloxy)-2-methyl-5'-morpholino-[3,3'-bipyridin]-5-yl)-3-(trifluoromethyl)benzamide

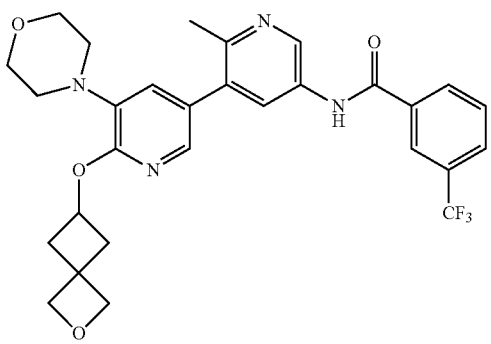 [SMILES: Cc1ncc(NC(=O)c2cccc(C(F)(F)F)c2)cc1-c1cnc(OC2CC3(COC3)C2)c(N2CCOCC2)c1]

The crude residue was purified by preparative neutral reverse phase HPLC (acetonitrile/3.75 mM aqueous ammonium acetate eluent). Upon lyophilization of the pure fractions, N-(6'-(2-oxaspiro[3.3]heptan-6-yloxy)-2-methyl-5'-morpholino-[3,3'-bipyridin]-5-yl)-3-(trifluoromethyl)benzamide was isolated as the free base, a white solid, in 53% yield.

$^1$H NMR (400 MHz, <cd3od>) δ ppm 2.32-2.42 (m, 2H) 2.48 (s, 3H) 2.88 (ddd, J=10.37, 7.04, 2.93 Hz, 2H) 3.09-3.17 (m, 4H) 3.79-3.89 (m, 4H) 4.71 (s, 2H) 4.79 (s, 2H) 5.16 (quin, J=6.95 Hz, 1H) 7.25 (d, J=1.96 Hz, 1H) 7.72-7.79 (m, 2H) 7.92 (d, J=7.43 Hz, 1H) 8.10 (d, J=2.35 Hz, 1H) 8.24 (d, J=7.83 Hz, 1H) 8.30 (s, 1H) 8.81 (d, J=2.35 Hz, 1H). LCMS (m/z) (M+H)=555.2, Rt=0.78 min.

Example 323: Synthesis of 2-isopropyl-N-(6'-methoxy-2-methyl-5'-morpholino-[3,3'-bipyridin]-5-yl)isonicotinamide

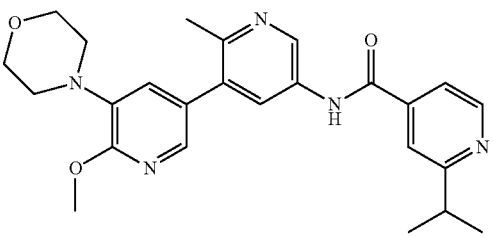 [SMILES: COc1ncc(-c2cc(NC(=O)c3ccnc(C(C)C)c3)cnc2C)cc1N1CCOCC1]

To a solution of NaOMe (5 equiv.) in dioxane (0.1 M) at 25° C. was added N-(6'-fluoro-2-methyl-5'-morpholino-[3,3'-bipyridin]-5-yl)-2-isopropylisonicotinamide (1.0 equiv.), and the reaction was heated to 105° C. and stirred for 1 h. The reaction was cooled to room temperature, quenched with a few drops of water, and concentrated. The crude material was purified by preparative reverse phase HPLC. Upon lyophilization of the pure fractions, 2-isopropyl-N-(6'-methoxy-2-methyl-5'-morpholino-[3,3'-bipyridin]-5-yl)isonicotinamide was isolated as the TFA salt, a pale yellow solid, in 52% yield. $^1$H NMR (400 MHz, <cd3od>) δ ppm 1.40 (d, J=6.65 Hz, 6H) 2.69 (s, 3H) 3.10-3.18 (m, 4H) 3.22-3.29 (m, 1H) 3.80-3.90 (m, 4H) 4.06 (s, 3H) 7.32 (d, J=1.96 Hz, 1H) 7.89 (d, J=1.57 Hz, 1H) 7.91 (dd, J=5.48, 1.57 Hz, 1H) 8.02 (s, 1H) 8.45 (d, J=1.96 Hz, 1H) 8.75 (d, J=5.48 Hz, 1H) 9.33 (d, J=2.35 Hz, 1H). LCMS (m/z) (M+H)=448.3, Rt=0.52 min.

The compounds listed below were prepared using methods similar to those described for the preparation of Example 323 using the appropriate starting materials Differences in the workup and/or purification protocols are noted where applicable.

Example 324: N-(6'-methoxy-2-methyl-5'-morpholino-[3,3'-bipyridin]-5-yl)-2-(trifluoromethyl)isonicotinamide

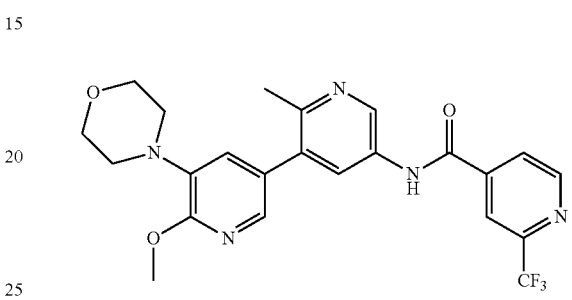

$^1$H NMR (400 MHz, <cd3od>) δ ppm 2.69 (s, 3H) 3.05-3.18 (m, 4H) 3.79-3.90 (m, 4H) 4.05 (s, 3H) 7.31 (d, J=1.96 Hz, 1H) 7.88 (d, J=1.96 Hz, 1H) 8.18 (d, J=4.30 Hz, 1H) 8.36 (s, 1H) 8.44 (d, J=2.35 Hz, 1H) 8.97 (d, J=5.09 Hz, 1H) 9.33 (d, J=1.96 Hz, 1H). LCMS (m/z) (M+H)=474.2, Rt=0.66 min.

Example 325: Synthesis of N-(6'-(azetidin-3-yloxy)-2-methyl-5'-morpholino-[3,3'-bipyridin]-5-yl)-3-(trifluoromethyl)benzamide

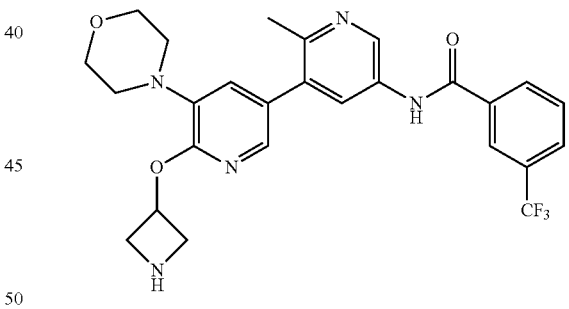

To a solution of 1-N-Boc-3-hydroxyazetidine (6 equiv.) in dioxane (0.1 M) at 25° C. was added NaH (5.2 equiv.), and the mixture was stirred for 15 min. N-(6'-fluoro-2-methyl-5'-morpholino-[3,3'-bipyridin]-5-yl)-3-(trifluoromethyl)benzamide (1.0 equiv.) was then added, and the reaction was heated to 105° C. and stirred for 4 h. The reaction was cooled to room temperature, poured onto water, and extracted three times with ethyl acetate. The combined organics were dried over magnesium sulfate, filtered, and concentrated. The crude residue was taken up in DCM/TFA (5:1, 0.05 M), stirred at 25° C. overnight, and then concentrated. The crude material was purified by preparative reverse phase HPLC. Upon lyophilization of the pure fractions, N-(6'-(azetidin-3-yloxy)-2-methyl-5'-morpholino-[3,3'-bipyridin]-5-yl)-3-(trifluoromethyl)benzamide was isolated as the TFA salt, a pale yellow solid, in 61% yield. $^1$H NMR (400 MHz, <cd3od>) δ ppm 2.56 (s, 3H) 3.35-3.46 (m, 4H) 3.66-3.74

(m, 2H) 3.87 (dt, J=5.58, 3.47 Hz, 4H) 4.87-4.93 (m, 1H) 5.27 (dd, J=12.52, 9.78 Hz, 1H) 5.75-5.88 (m, 1H) 7.73-7.80 (m, 1H) 7.86 (s, 1H) 7.94 (d, J=7.83 Hz, 1H) 8.22-8.27 (m, 2H) 8.30 (s, 1H) 8.45 (d, J=2.35 Hz, 1H) 8.85 (d, J=2.35 Hz, 1H). LCMS (m/z) (M+H)=514.3, Rt=0.53 min.

Example 326: N-(6'-(2-cyanopropan-2-yl)-2-methyl-5'-morpholino-[3,3'-bipyridin]-5-yl)-3-(trifluoromethyl)benzamide

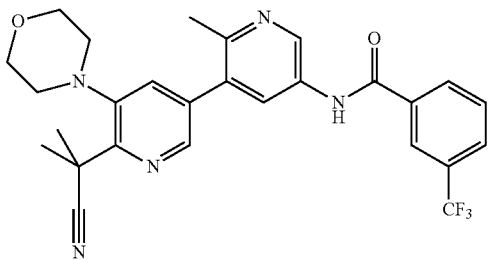 [SMILES: Cc1ncc(NC(=O)c2cccc(C(F)(F)F)c2)cc1-c1cnc(C(C)(C)C#N)c(N2CCOCC2)c1]

To a solution of isobutyronitrile (5 equiv.) in dioxane (0.1 M) at 25° C. was added KHMDS (0.5 M in toluene, 5.2 equiv.) and the mixture was stirred for 15 min. N-(6'-fluoro-2-methyl-5'-morpholino-[3,3'-bipyridin]-5-yl)-3-(trifluoromethyl)benzamide (1.0 equiv.) was then added, and the reaction was stirred for 30 min. The reaction was cooled to room temperature, quenched with a few drops of water, and concentrated. The crude material was purified by preparative reverse phase HPLC. Upon lyophilization of the pure fractions, N-(6'-(2-cyanopropan-2-yl)-2-methyl-5'-morpholino-[3,3'-bipyridin]-5-yl)-3-(trifluoromethyl)benzamide was isolated as the TFA salt, a white solid, in 49% yield. ¹H NMR (400 MHz, <cd3od>) δ ppm 1.86 (s, 6H) 2.65 (s, 3H) 2.92-3.12 (m, 4H) 3.92 (t, J=4.50 Hz, 4H) 7.75-7.82 (m, 1H) 7.96 (d, J=7.83 Hz, 1H) 8.17 (d, J=1.96 Hz, 1H) 8.28 (d, J=7.83 Hz, 1H) 8.35 (s, 1H) 8.44 (d, J=2.35 Hz, 1H) 8.57 (d, J=1.96 Hz, 1H) 9.29 (d, J=2.35 Hz, 1H). LCMS (m/z) (M+H)=510.1, Rt=0.82 min.

Example 327: N-(2-methyl-6'-((methylsulfonyl)methyl)-5'-morpholino-[3,3'-bipyridin]-5-yl)-3-(trifluoromethyl)benzamide

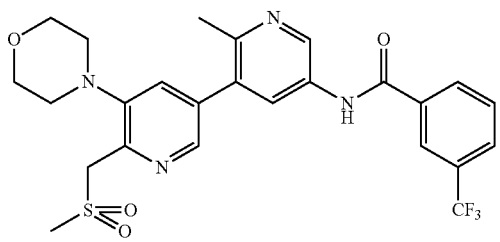 [SMILES: Cc1ncc(NC(=O)c2cccc(C(F)(F)F)c2)cc1-c1cnc(CS(C)(=O)=O)c(N2CCOCC2)c1]

To a solution of N-(6'-fluoro-2-methyl-5'-morpholino-[3,3'-bipyridin]-5-yl)-3-(trifluoromethyl)benzamide (1.0 equiv.) in THF (0.26 M) at 25° C. was added NaHMDS (1 M in THF, 5.1 equiv.) followed by methyl sulfone (5 equiv.). The reaction was heated to 80° C. and stirred for 2 h. The reaction was cooled to room temperature, poured onto brine and extracted three times with ethyl acetate. The combined organics were dried over magnesium sulfate, filtered, and concentrated. The crude residue was purified by preparative neutral reverse phase HPLC (acetonitrile/3.75 mM aqueous ammonium acetate eluent). Upon lyophilization of the pure fractions, N-(2-methyl-6'-((methylsulfonyl)methyl)-5'-morpholino-[3,3'-bipyridin]-5-yl)-3-(trifluoromethyl)benzamide was isolated as the free base in 60% yield. ¹H NMR (500 MHz, <cd3od>) δ ppm 2.54 (s, 3H) 3.02-3.08 (m, 4H) 3.24 (s, 3H) 3.88-3.93 (m, 4H) 4.84-4.87 (m, 2H) 7.78 (t, J=7.72 Hz, 1H) 7.89 (d, J=1.89 Hz, 1H) 7.95 (d, J=7.88 Hz, 1H) 8.22 (d, J=2.21 Hz, 1H) 8.27 (d, J=8.20 Hz, 1H) 8.33 (s, 1H) 8.49 (d, J=1.89 Hz, 1H) 8.90 (d, J=2.21 Hz, 1H). LCMS (m/z) (M+H)=535.2, Rt=0.67 min.

Example 328: Synthesis of N-methyl-N-(2-methyl-5'-morpholino-6'-((tetrahydro-2H-pyran-4-yl)oxy)-[3,3'-bipyridin]-5-yl)-3-(trifluoromethyl)benzamide

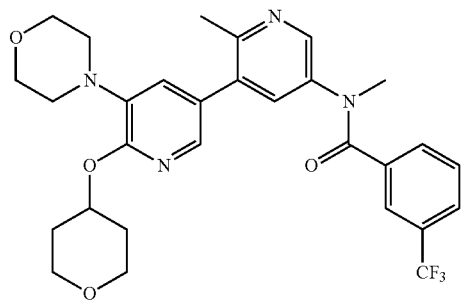 [SMILES: Cc1ncc(N(C)C(=O)c2cccc(C(F)(F)F)c2)cc1-c1cnc(OC2CCOCC2)c(N2CCOCC2)c1]

To a solution of N-(2-methyl-5'-morpholino-6'-((tetrahydro-2H-pyran-4-yl)oxy)-[3,3'-bipyridin]-5-yl)-3-(trifluoromethyl)benzamide (1.0 equiv.) in THF/DMF (5:1; 0.05 M) was added sodium hydride (1.5 equiv.) and methyl iodide (1.5 equiv.) and the reaction was heated to 60° C. and stirred for 3 h. The reaction mixture was partitioned between water and ethyl acetate, and the organic phase was dried with sodium sulfate, filtered and concentrated. The crude material was purified via preparative reverse phase HPLC. Upon lyophilization of the pure fractions, N-methyl-N-(2-methyl-5'-morpholino-6'-((tetrahydro-2H-pyran-4-yl)oxy)-[3,3'-bipyridin]-5-yl)-3-(trifluoromethyl)benzamide was isolated as the TFA salt in 2% yield. LCMS (m/z) (M+H)=557.2, Rt=0.81 min.

The compounds listed below were prepared using methods similar to those described for the preparation of Example 328 using the appropriate starting materials.

Example 329: N-ethyl-N-(2-methyl-5'-morpholino-6'-((tetrahydro-2H-pyran-4-yl)oxy)-[3,3'-bipyridin]-5-yl)-3-(trifluoromethyl)benzamide

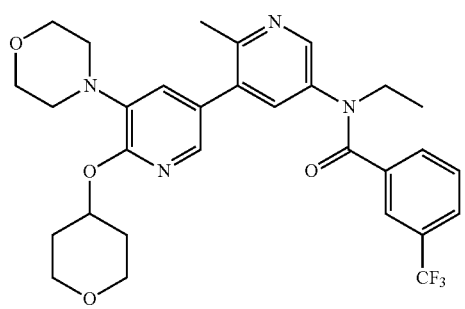 [SMILES: CCN(C(=O)c1cccc(C(F)(F)F)c1)c1cnc(C)c(-c2cnc(OC3CCOCC3)c(N3CCOCC3)c2)c1]

¹H NMR (400 MHz, <dmso>) δ ppm 1.07 (s, 3H) 1.54-1.71 (m, 2H) 1.92-2.05 (m, 2H) 2.30 (s, 3H) 2.99 (br. s., 4H) 3.48-3.53 (m, 3H) 3.69 (br. s., 7H) 5.15-5.32 (m, 1H) 6.83-6.93 (m, 1H) 7.39-7.50 (m, 1H) 7.51-7.74 (m, 4H) 8.07-8.21 (m, 1H). LCMS (m/z) (M+H)=571.2, Rt=0.84 min.

Example 330: N-(2-methyl-5'-morpholino-6'-((tetrahydro-2H-pyran-4-yl)oxy)-[3,3'-bipyridin]-5-yl)-N-propyl-3-(trifluoromethyl)benzamide

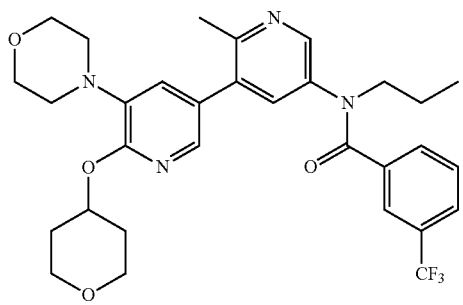 [SMILES: CCCN(C(=O)c1cccc(C(F)(F)F)c1)c1cnc(C)c(-c2cnc(OC3CCOCC3)c(N3CCOCC3)c2)c1]

¹H NMR (400 MHz, <dmso>) δ ppm 0.74-0.85 (m, 2H) 1.00-1.18 (m, 2H) 1.38-1.55 (m, 1H) 1.59-1.72 (m, 2H) 1.87-2.03 (m, 2H) 2.32 (s, 3H) 2.99 (br. s., 4H) 3.49 (br. s., 2H) 3.69 (d, J=3.91 Hz, 7H) 5.16-5.42 (m, 1H) 6.82-7.04 (m, 1H) 7.40-7.74 (m, 6H) 8.05-8.38 (m, 1H). LCMS (m/z) (M+H)=585.3, Rt=0.9 min.

The compounds listed below were prepared using methods similar to those described for the preparation of Example 117 using the appropriate starting materials.

Example 331: N-(3-(1-ethyl-5-morpholino-6-oxo-1,6-dihydropyridin-3-yl)-4-methylphenyl)-3-(trifluoromethyl)benzamide

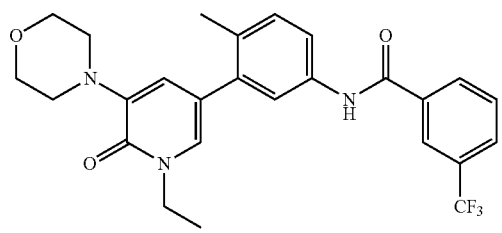 [SMILES: CCn1cc(-c2cc(NC(=O)c3cccc(C(F)(F)F)c3)ccc2C)cc(N2CCOCC2)c1=O]

¹H NMR (400 MHz, <cd3od>) δ ppm 1.38 (t, J=7.04 Hz, 3H) 2.31 (s, 3H) 3.11-3.21 (m, 4H) 3.82-3.91 (m, 4H) 4.11 (q, J=7.30 Hz, 2H) 6.96 (d, J=1.96 Hz, 1H) 7.29 (d, J=8.22 Hz, 1H) 7.38 (d, J=1.96 Hz, 1H) 7.58 (d, J=8.22 Hz, 1H) 7.62 (s, 1H) 7.69-7.76 (m, 1H) 7.89 (d, J=7.83 Hz, 1H) 8.20 (d, J=7.83 Hz, 1H) 8.25 (s, 1H), LCMS (m/z) (M+H)=486.2, Rt=0.95 min.

Example 332: 2-(2-cyanopropan-2-yl)-N-(1'-ethyl-2-methyl-5'-morpholino-6'-oxo-1',6'-dihydro-[3,3'-bipyridin]-5-yl)isonicotinamide

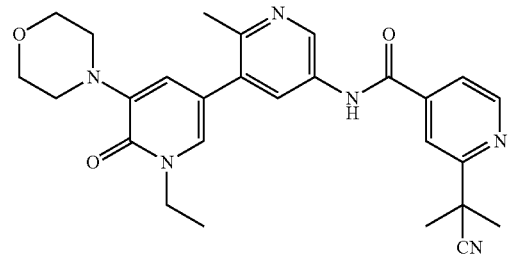 [SMILES: CCn1cc(-c2cc(NC(=O)c3ccnc(C(C)(C)C#N)c3)cnc2C)cc(N2CCOCC2)c1=O]

¹H NMR (400 MHz, <cd3od>) δ ppm 1.39 (t, J=7.24 Hz, 3H) 1.82 (s, 6H) 2.70 (s, 3H) 3.16 (br. s., 4H) 3.66-3.91 (m, 4H) 4.13 (q, J=7.30 Hz, 2H) 6.94 (d, J=1.96 Hz, 1H) 7.54 (d, J=1.96 Hz, 1H) 7.86 (d, J=5.09 Hz, 1H) 8.13 (s, 1H) 8.41 (d, J=1.96 Hz, 1H) 8.82 (d, J=5.09 Hz, 1H) 9.22 (d, J=1.96 Hz, 1H), LCMS (m/z) (M+H)=487.3, Rt=0.56 min.

Example 333: N-(1'-(2-cyanoethyl)-2-methyl-5'-morpholino-6'-oxo-1',6'-dihydro-[3,3'-bipyridin]-5-yl)-3-(trifluoromethyl)benzamide

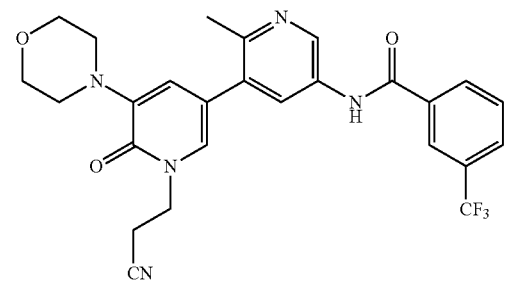 [SMILES: Cc1ncc(NC(=O)c2cccc(C(F)(F)F)c2)cc1-c1cc(N2CCOCC2)c(=O)n(CCC#N)c1]

¹H NMR (500 MHz, DMSO-d₆) δ ppm 2.55 (s, 3H) 3.05 (t, J=6.46 Hz, 2H) 3.14 (br. s., 4H) 3.74 (t, J=4.41 Hz, 4H) 4.24 (t, J=6.46 Hz, 2H) 6.83 (d, J=1.58 Hz, 1H) 7.60 (d, J=1.58 Hz, 1H) 7.84 (t, J=7.88 Hz, 1H) 8.03 (d, J=7.88 Hz, 1H) 8.18 (br. s., 1H) 8.30 (d, J=7.88 Hz, 1H) 8.35 (s, 1H) 8.93 (s, 1H) 10.83 (br. s., 1H), LCMS (m/z) (M+H)=512.3, Rt=0.66 min.

Example 334: N-(3-(1-(2-cyanoethyl)-5-morpholino-6-oxo-1,6-dihydropyridin-3-yl)-4-methylphenyl)-2-(1,1-difluoroethyl)isonicotinamide

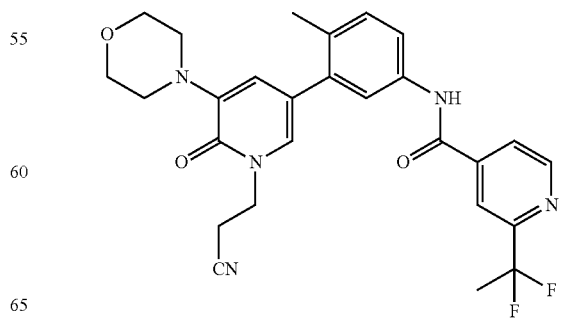

¹H NMR (400 MHz, <dmso>) δ ppm 2.03 (t, J=19.17 Hz, 3H) 2.25 (s, 3H) 3.00 (t, J=6.46 Hz, 2H) 3.10 (br. s., 4H) 3.60-3.69 (m, 4H) 4.20 (t, J=6.46 Hz, 2H) 6.71 (s, 1H) 7.28 (d, J=8.61 Hz, 1H) 7.43 (d, J=1.57 Hz, 1H) 7.62 (d, J=1.96 Hz, 1H) 7.67 (d, J=8.22 Hz, 1H) 8.01 (d, J=4.70 Hz, 1H) 8.16 (s, 1H) 8.86 (d, J=4.70 Hz, 1H) 10.61 (s, 1H), LCMS (m/z) (M+H)=508.2, Rt=0.78 min.

Example 335: N-(3-(1-(2-cyanoethyl)-5-morpholino-6-oxo-1,6-dihydropyridin-3-yl)-4-methylphenyl)-2-(2-cyanopropan-2-yl)isonicotinamide

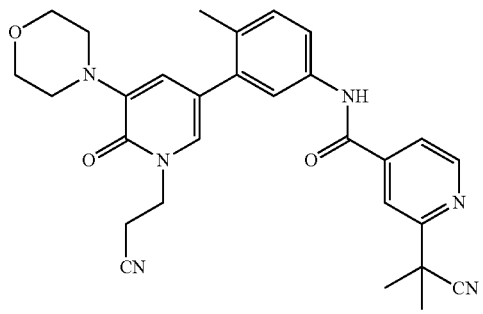 [SMILES: Cc1ccc(NC(=O)c2ccnc(C(C)(C)C#N)c2)cc1-c1cc(N2CCOCC2)c(=O)n(CCC#N)c1]

¹H NMR (400 MHz, <dmso>) δ ppm 1.75 (s, 6H) 2.26 (s, 3H) 3.00 (t, J=6.26 Hz, 2H) 3.10 (br. s., 4H) 3.70 (d, J=4.30 Hz, 4H) 4.20 (t, J=6.46 Hz, 2H) 6.71 (d, J=1.57 Hz, 1H) 7.28 (d, J=8.22 Hz, 1H) 7.43 (d, J=1.96 Hz, 1H) 7.61 (s, 1H) 7.65 (d, J=8.61 Hz, 1H) 7.84 (d, J=5.09 Hz, 1H) 7.99 (s, 1H) 8.79 (d, J=5.09 Hz, 1H) 10.53 (s, 1H), LCMS (m/z) (M+H)=511.3, Rt=0.76 min.

Example 336: N-(3-(1-(2-cyanoethyl)-5-morpholino-6-oxo-1,6-dihydropyridin-3-yl)-4-methylphenyl)-3-(difluoromethyl)benzamide

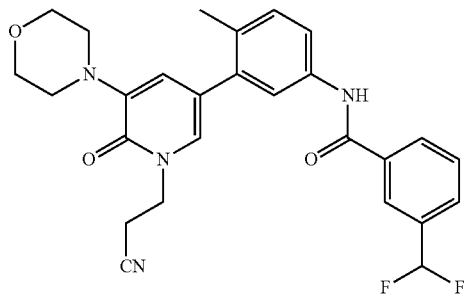 [SMILES: Cc1ccc(NC(=O)c2cccc(C(F)F)c2)cc1-c1cc(N2CCOCC2)c(=O)n(CCC#N)c1]

¹H NMR (400 MHz, <dmso>) δ ppm 2.25 (s, 3H) 3.00 (t, J=6.26 Hz, 2H) 3.11 (br. s., 4H) 3.70 (d, J=4.30 Hz, 4H) 4.20 (t, J=6.46 Hz, 2H) 6.72 (d, J=1.96 Hz, 2H) 6.91-7.30 (m, 2H) 7.43 (d, J=1.96 Hz, 1H) 7.60-7.69 (m, 3H) 7.77 (d, J=7.43 Hz, 1H) 8.06-8.18 (m, 2H) 10.37 (s, 1H), LCMS (m/z) (M+H)=493.3, Rt=0.80 min.

Example 337: N-(4-methyl-3-(1-((3-methyloxetan-3-yl)methyl)-5-morpholino-6-oxo-1,6-dihydropyridin-3-yl)phenyl)-3-(trifluoromethyl)benzamide

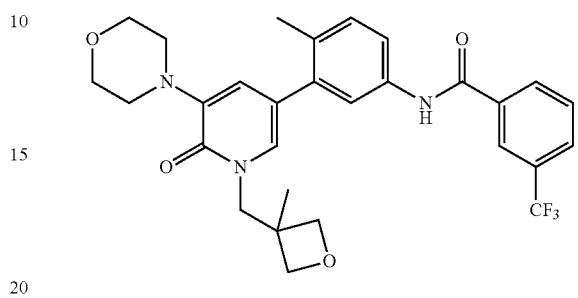

¹H NMR (400 MHz, <dmso>) δ ppm 1.04 (s, 3H) 2.25 (s, 3H) 3.01-3.20 (m, 4H) 3.43 (br. s., 2H) 3.74 (t, J=4.30 Hz, 4H) 4.34 (d, J=13.69 Hz, 1H) 4.44-4.58 (m, 2H) 4.65 (d, J=10.56 Hz, 1H) 7.37 (d, J=8.22 Hz, 1H) 7.68 (dd, J=8.22, 1.96 Hz, 1H) 7.75-7.86 (m, 2H) 7.97 (d, J=7.83 Hz, 1H) 8.07 (s, 1H) 8.21-8.32 (m, 2H) 10.55 (s, 1H), LCMS (m/z) (M+H)=542.4, Rt=0.80 min.

Example 338: 2-(2-cyanopropan-2-yl)-N-(4-methyl-3-(1-((3-methyloxetan-3-yl)methyl)-5-morpholino-6-oxo-1,6-dihydropyridin-3-yl)phenyl)isonicotinamide

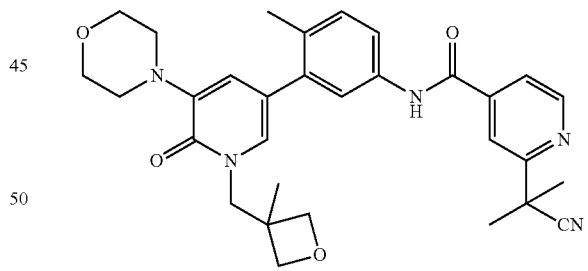

¹H NMR (400 MHz, <dmso>) δ ppm 0.95 (s, 3H) 1.72 (s, 6H) 2.40 (s, 3H) 2.76-3.01 (m, 4H) 3.64 (br. s., 5H) 4.30 (d, J=13.69 Hz, 1H) 4.39-4.52 (m, 2H) 4.61 (d, J=10.56 Hz, 1H) 7.24-7.49 (m, 3H) 7.63-7.78 (m, 2H) 7.92 (s, 1H) 8.19 (s, 1H) 8.76 (d, J=4.70 Hz, 1H) 10.42 (s, 1H), LCMS (m/z) (M+H)=542.4, Rt=0.66 min.

The compounds listed below were prepared using methods similar to those described for the preparation of Example 171 using the appropriate starting materials.

Example 339: 4-methoxy-N-(4-methyl-3-(1-methyl-5-morpholino-6-oxo-1,6-dihydropyridin-3-yl)phenyl)-3-(trifluoromethyl)benzamide

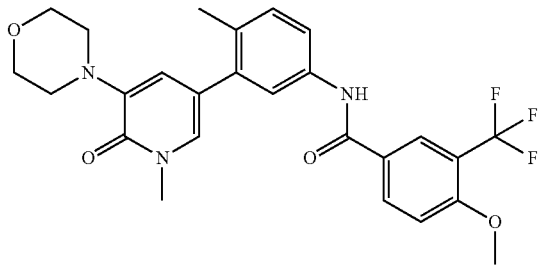 [SMILES: COc1ccc(C(=O)Nc2ccc(C)c(-c3cc(N4CCOCC4)c(=O)n(C)c3)c2)cc1C(F)(F)F]

$^1$H NMR (400 MHz, <cd3od>) δ ppm 2.32 (s, 3H) 3.13-3.25 (m, 4H) 3.66 (s, 3H) 3.84-3.94 (m, 4H) 4.02 (s, 3H) 7.02 (d, J=1.96 Hz, 1H) 7.31 (dd, J=15.65, 8.22 Hz, 2H) 7.40 (d, J=1.96 Hz, 1H) 7.55 (dd, J=8.22, 1.96 Hz, 1H) 7.61 (d, J=1.96 Hz, 1H) 8.17-8.27 (m, 2H). LCMS (m/z) (M+H)=502.2, Rt=0.87 min.

Example 340: N-(4-methyl-3-(1-methyl-5-morpholino-6-oxo-1,6-dihydropyridin-3-yl)phenyl)-3-(trifluoromethoxy)benzamide

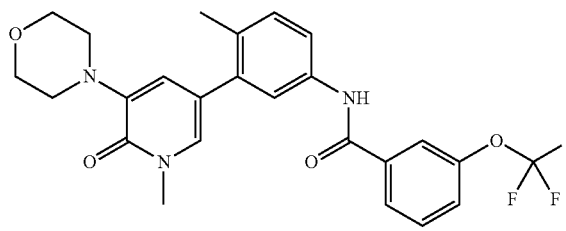

$^1$H NMR (400 MHz, <cd3od>) δ ppm 2.32 (s, 3H) 3.15-3.22 (m, 4H) 3.66 (s, 3H) 3.84-3.93 (m, 4H) 6.99 (d, J=1.96 Hz, 1H) 7.31 (d, J=8.22 Hz, 1H) 7.39 (d, J=1.96 Hz, 1H) 7.53 (d, J=8.22 Hz, 1H) 7.58 (dd, J=8.02, 2.15 Hz, 1H) 7.61-7.68 (m, 2H) 7.87 (s, 1H) 7.97 (d, J=7.83 Hz, 1H). LCMS (m/z) (M+H)=488.3, Rt=0.93 min.

Example 341: 2-(1,1-difluoropropyl)-N-(4-methyl-3-(1-methyl-5-morpholino-6-oxo-1,6-dihydropyridin-3-yl)phenyl)isonicotinamide

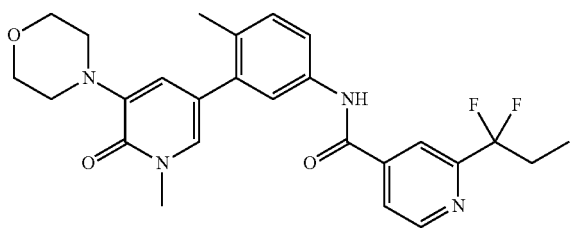 [SMILES: CCC(F)(F)c1cc(C(=O)Nc2ccc(C)c(-c3cc(N4CCOCC4)c(=O)n(C)c3)c2)ccn1]

$^1$H NMR (400 MHz, <cdcl3>) δ ppm 1.03 (t, J=7.43 Hz, 3H) 2.29 (s, 3H) 2.32-2.49 (m, 2H) 3.17 (d, J=3.91 Hz, 4H) 3.60 (s, 3H) 3.80-3.94 (m, 4H) 6.64 (s, 1H) 6.99 (d, J=1.56 Hz, 1H) 7.29 (d, J=8.61 Hz, 1H) 7.49-7.62 (m, 2H) 7.86 (d, J=4.30 Hz, 1H) 8.06 (s, 1H) 8.24 (s, 1H) 8.85 (d, J=5.09 Hz, 1H). LCMS (m/z) (M+H)=483.2, Rt=0.85 min.

Example 344: 3-ethoxy-4-fluoro-N-(4-methyl-3-(1-methyl-5-morpholino-6-oxo-1,6-dihydropyridin-3-yl)phenyl)benzamide

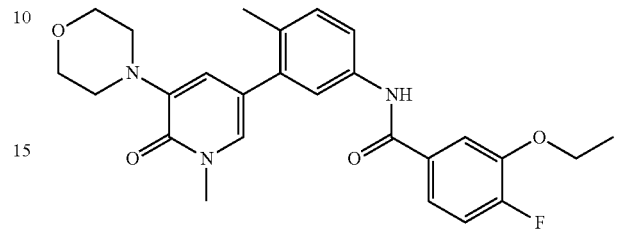

$^1$H NMR (400 MHz, <cd3od>) δ ppm 1.46 (t, J=7.04 Hz, 3H) 2.31 (s, 3H) 3.17-3.27 (m, 4H) 3.66 (s, 3H) 3.84-3.96 (m, 4H) 4.21 (q, J=7.04 Hz, 2H) 7.06 (d, J=2.35 Hz, 1H) 7.23 (dd, J=10.76, 8.41 Hz, 1H) 7.29 (d, J=8.22 Hz, 1H) 7.42 (d, J=2.35 Hz, 1H) 7.50-7.58 (m, 2H) 7.61 (d, J=1.96 Hz, 1H) 7.67 (dd, J=8.22, 1.96 Hz, 1H). LCMS (m/z) (M+H)=466.1, Rt=0.87 min.

Example 345: 3-isopropoxy-N-(4-methyl-3-(1-methyl-5-morpholino-6-oxo-1,6-dihydropyridin-3-yl)phenyl)benzamide

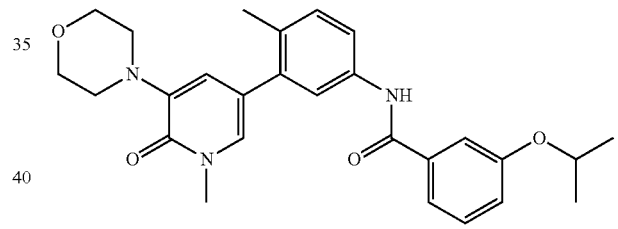

$^1$H NMR (400 MHz, <cd3od>) δ ppm 1.36 (d, J=5.87 Hz, 6H) 2.32 (s, 3H) 3.15-3.26 (m, 4H) 3.66 (s, 3H) 3.84-3.96 (m, 4H) 4.70 (dt, J=12.13, 6.06 Hz, 1H) 7.02 (d, J=2.35 Hz, 1H) 7.13 (dd, J=8.22, 1.57 Hz, 1H) 7.29 (d, J=8.22 Hz, 1H) 7.38-7.44 (m, 2H) 7.45-7.52 (m, 2H) 7.56 (dd, J=8.22, 2.35 Hz, 1H) 7.61 (d, J=1.96 Hz, 1H). LCMS (m/z) (M+H)=462.2, Rt=0.89 min.

Example 346: 2-chloro-3-(1-cyanocyclopropyl)-N-(4-methyl-3-(1-methyl-5-morpholino-6-oxo-1,6-dihydropyridin-3-yl)phenyl)benzamide

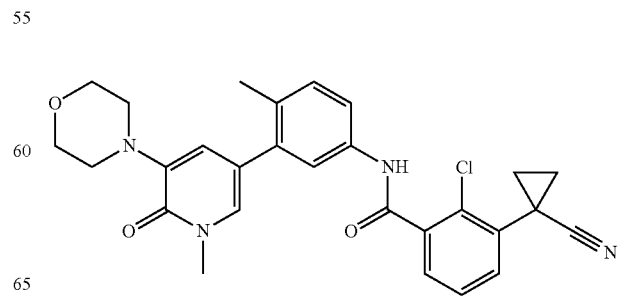

¹H NMR (400 MHz, <cd3od>) δ ppm 1.45-1.53 (m, 2H) 1.77-1.85 (m, 2H) 2.32 (s, 3H) 3.16-3.26 (m, 4H) 3.66 (s, 3H) 3.84-3.96 (m, 4H) 7.03 (d, J=2.35 Hz, 1H) 7.30 (d, J=8.61 Hz, 1H) 7.41 (d, J=2.35 Hz, 1H) 7.45-7.52 (m, 1H) 7.52-7.60 (m, 1H) 7.60-7.66 (m, 1H). LCMS (m/z) (M+H)= 503.1, Rt=0.80 min.

Example 347: N-(4-methyl-3-(1-methyl-5-morpholino-6-oxo-1,6-dihydropyridin-3-yl)phenyl)benzamide

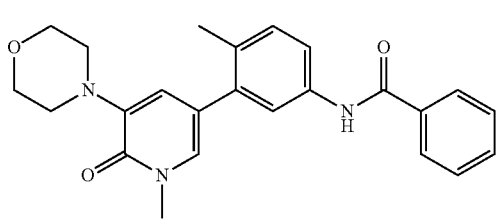 [SMILES: Cc1ccc(NC(=O)c2ccccc2)cc1-c1cc(N2CCOCC2)c(=O)n(C)c1]

¹H NMR (400 MHz, <cd3od>) δ ppm 2.30 (s, 3H) 2.99-3.20 (m, 4H) 3.64 (s, 3H) 3.78-3.94 (m, 4H) 6.99 (d, J=1.96 Hz, 1H) 7.27 (d, J=8.22 Hz, 1H) 7.38 (d, J=1.96 Hz, 1H) 7.47-7.63 (m, 3H) 7.92 (d, J=7.04 Hz, 1H), LCMS (m/z) (M+H)=404.1, Rt=0.75 min.

Example 348: 2-isopropyl-N-(4-methyl-3-(1-methyl-5-morpholino-6-oxo-1,6-dihydropyridin-3-yl)phenyl)isonicotinamide

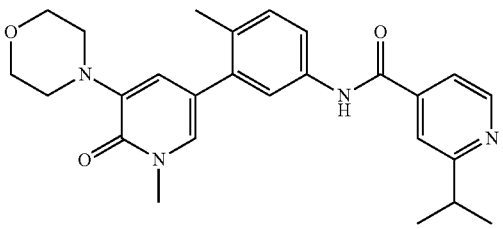 [SMILES: Cc1ccc(NC(=O)c2ccnc(C(C)C)c2)cc1-c1cc(N2CCOCC2)c(=O)n(C)c1]

¹H NMR (400 MHz, <cd3od>) δ ppm 1.45 (d, J=7.04 Hz, 6H) 2.31 (s, 3H) 3.03-3.19 (m, 4H) 3.32-3.44 (m, 1H) 3.63 (s, 3H) 3.76-3.96 (m, 4H) 6.93 (d, J=1.96 Hz, 1H) 7.28-7.41 (m, 2H) 7.58-7.70 (m, 2H) 8.12 (dd, J=5.67, 1.37 Hz, 1H) 8.23 (s, 1H) 8.79 (d, J=5.87 Hz, 1H), LCMS (m/z) (M+H)= 447.1, Rt=0.60 min.

Example 349: N-(4-methyl-3-(1-methyl-5-morpholino-6-oxo-1,6-dihydropyridin-3-yl)phenyl)-3-(1,3,4-oxadiazol-2-yl)benzamide

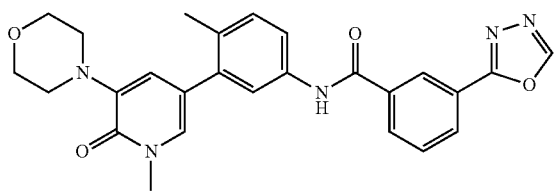 [SMILES: Cc1ccc(NC(=O)c2cccc(-c3nnco3)c2)cc1-c1cc(N2CCOCC2)c(=O)n(C)c1]

¹H NMR (400 MHz, <cd3od>) δ ppm 2.31 (s, 3H) 3.17 (br. s., 4H) 3.64 (s, 3H) 3.80-3.93 (m, 4H) 6.99 (d, J=1.96 Hz, 1H) 7.30 (d, J=8.22 Hz, 1H) 7.39 (d, J=1.96 Hz, 1H) 7.54-7.66 (m, 2H) 7.75 (t, J=7.83 Hz, 1H) 8.17 (d, J=8.22 Hz, 1H) 8.29 (d, J=7.83 Hz, 1H) 8.64 (s, 1H) 9.07 (s, 1H), LCMS (m/z) (M+H)=472.3, Rt=0.69 min.

Example 350: 2-(2-hydroxypropan-2-yl)-N-(4-methyl-3-(1-methyl-5-morpholino-6-oxo-1,6-dihydropyridin-3-yl)phenyl)isonicotinamide

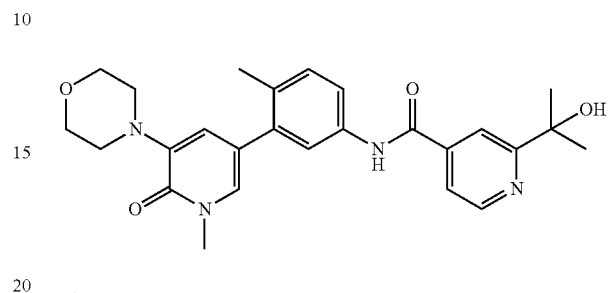

¹H NMR (400 MHz, METHANOL-d₄) δ ppm 1.67 (s, 6H) 2.31 (s, 3H) 3.05-3.19 (m, 4H) 3.63 (s, 3H) 3.79-3.92 (m, 4H) 6.93 (d, J=1.57 Hz, 1H) 7.26-7.40 (m, 2H) 7.53-7.73 (m, 2H) 8.10 (d, J=5.87 Hz, 1H) 8.40 (s, 1H) 8.76 (d, J=5.48 Hz, 1H), LCMS (m/z) (M+H)=463.3, Rt=0.55 min.

Example 351: N-(4-methyl-3-(1-methyl-5-morpholino-6-oxo-1,6-dihydropyridin-3-yl)-phenyl)-3-(2-(methylsulfonyl)propan-2-yl)benzamide

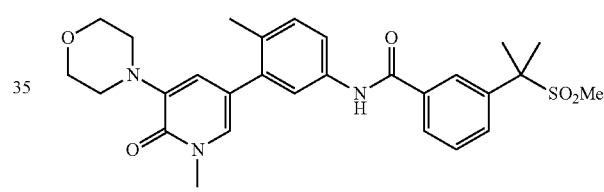

¹H NMR (400 MHz, <dmso>) δ ppm 1.80 (s, 6H) 2.24 (s, 3H) 2.72 (s, 3H) 3.09 (br. s., 4H) 3.48 (s, 3H) 3.66-3.77 (m, 4H) 6.69 (d, J=1.96 Hz, 1H) 7.25 (d, J=8.22 Hz, 1H) 7.38 (d, J=1.96 Hz, 1H) 7.56 (t, J=7.83 Hz, 1H) 7.60-7.68 (m, 2H) 7.81 (d, J=8.22 Hz, 1H) 7.96 (d, J=7.43 Hz, 1H) 8.10 (s, 1H) 10.25 (s, 1H), LCMS (m/z) (M+H)=524, Rt=0.70 min.

Example 352: N-(4-methyl-3-(1-methyl-5-morpholino-6-oxo-1,6-dihydropyridin-3-yl)phenyl)-3-(oxetan-3-yl)benzamide

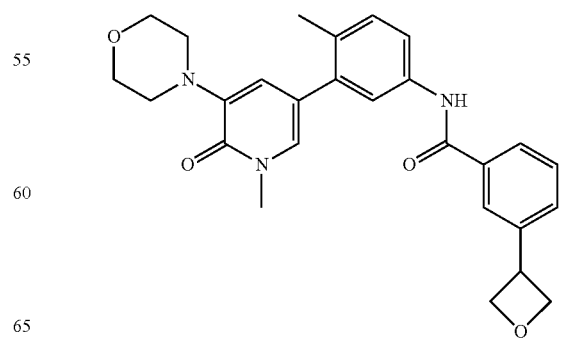

¹H NMR (400 MHz, <dmso>) δ ppm 2.24 (s, 3H) 3.09 (br. s., 4H) 3.48 (br. s., 3H) 3.69 (d, J=4.30 Hz, 4H) 4.33 (t, J=7.63 Hz, 1H) 4.67 (t, J=6.26 Hz, 2H) 4.96 (dd, J=8.22, 5.87 Hz, 2H) 6.69 (d, J=1.96 Hz, 1H) 7.24 (d, J=8.22 Hz, 1H) 7.38 (d, J=1.96 Hz, 1H) 7.46-7.54 (m, 1H) 7.57-7.71 (m, 3H) 7.83 (d, J=7.43 Hz, 1H) 7.96 (s, 1H) 10.21 (s, 1H), LCMS (m/z) (M+H)=460.2, Rt=0.70 min.

Example 353: 2-ethyl-N-(4-methyl-3-(1-methyl-5-morpholino-6-oxo-1,6-dihydropyridin-3-yl)phenyl)isonicotinamide

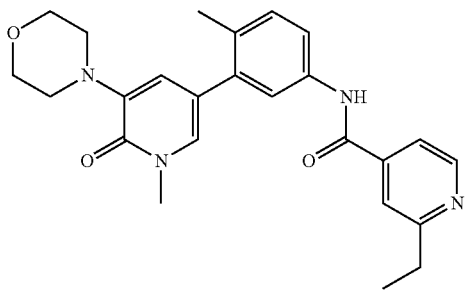 [SMILES: CCc1cc(C(=O)Nc2ccc(C)c(-c3cc(N4CCOCC4)c(=O)n(C)c3)c2)ccn1]

¹H NMR (400 MHz, <dmso>) δ ppm 1.28 (t, J=7.63 Hz, 3H) 2.25 (s, 3H) 2.90 (q, J=7.70 Hz, 2H) 3.09 (br. s., 4H) 3.48 (s, 3H) 3.64-3.88 (m, 4H) 6.69 (d, J=1.96 Hz, 1H) 7.27 (d, J=8.22 Hz, 1H) 7.39 (d, J=1.96 Hz, 1H) 7.58-7.69 (m, 2H) 7.80 (d, J=4.70 Hz, 1H) 7.87 (s, 1H) 8.73 (d, J=5.09 Hz, 1H) 10.51 (s, 1H), LCMS (m/z) (M+H)=433.1, Rt=0.59 min.

Example 354: 2-cyclopropyl-N-(4-methyl-3-(1-methyl-5-morpholino-6-oxo-1,6-dihydropyridin-3-yl)phenyl)isonicotinamide

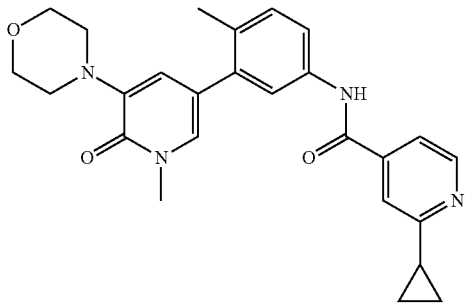 [SMILES: Cc1ccc(NC(=O)c2ccnc(C3CC3)c2)cc1-c1cc(N2CCOCC2)c(=O)n(C)c1]

¹H NMR (400 MHz, <cd3od>) δ ppm 1.08-1.23 (m, 2H) 1.31 (dd, J=8.02, 2.93 Hz, 2H) 2.30 (s, 4H) 3.02-3.18 (m, 4H) 3.63 (s, 3H) 3.78-3.92 (m, 4H) 6.91 (d, J=1.96 Hz, 1H) 7.24-7.42 (m, 2H) 7.53-7.69 (m, 2H) 7.81-8.04 (m, 2H) 8.64 (d, J=5.48 Hz, 1H), LCMS (m/z) (M+H)=445.1, Rt=0.60 min.

Example 355: 2-(2-fluoropropan-2-yl)-N-(4-methyl-3-(1-methyl-5-morpholino-6-oxo-1,6-dihydropyridin-3-yl)phenyl)isonicotinamide

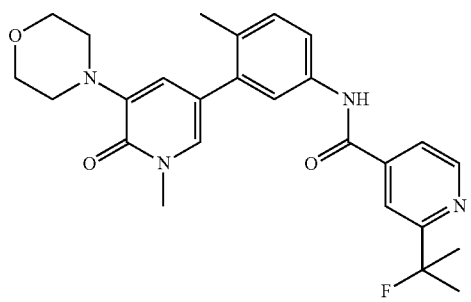 [SMILES: Cc1ccc(NC(=O)c2ccnc(C(C)(C)F)c2)cc1-c1cc(N2CCOCC2)c(=O)n(C)c1]

¹H NMR (400 MHz, <cd3od>) δ ppm 1.71 (s, 3H) 1.76 (s, 3H) 2.31 (s, 3H) 3.11-3.22 (m, 4H) 3.64 (s, 3H) 3.83-3.99 (m, 4H) 7.03 (d, J=1.96 Hz, 1H) 7.30 (d, J=8.22 Hz, 1H) 7.41 (d, J=1.96 Hz, 1H) 7.58 (dd, J=8.22, 2.35 Hz, 1H) 7.64 (d, J=1.96 Hz, 1H) 7.80 (dd, J=5.09, 1.57 Hz, 1H) 8.08 (s, 1H) 8.71 (d, J=5.09 Hz, 1H), LCMS (m/z) (M+H)=465.0, Rt=0.79 min.

Example 356: N-(4-methyl-3-(1-methyl-5-morpholino-6-oxo-1,6-dihydropyridin-3-yl)phenyl)-2-(oxetan-3-yl)isonicotinamide

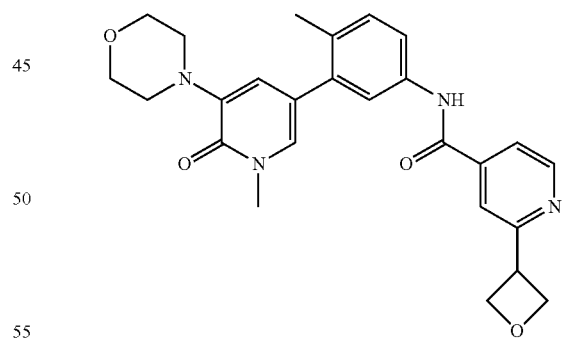

¹H NMR (400 MHz, <cd3od>) δ ppm 2.30 (s, 3H) 2.98-3.20 (m, 4H) 3.64 (s, 3H) 3.79-3.95 (m, 4H) 4.45-4.65 (m, 1H) 4.96 (t, J=6.26 Hz, 2H) 5.11 (dd, J=8.61, 5.87 Hz, 2H) 6.97 (d, J=2.35 Hz, 1H) 7.30 (d, J=8.22 Hz, 1H) 7.37 (d, J=1.96 Hz, 1H) 7.53-7.67 (m, 2H) 7.86 (dd, J=5.28, 1.37 Hz, 1H) 7.99 (s, 1H) 8.78 (d, J=5.48 Hz, 1H), LCMS (m/z) (M+H)=461.0, Rt=0.61 min.

Example 357: 2-(1-cyanocyclopropyl)-N-(4-methyl-3-(1-methyl-5-morpholino-6-oxo-1,6-dihydropyridin-3-yl)phenyl)isonicotinamide

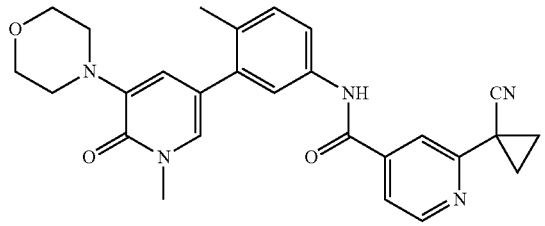 [SMILES: Cc1ccc(NC(=O)c2ccnc(C3(C#N)CC3)c2)cc1-c1cc(N2CCOCC2)c(=O)n(C)c1]

¹H NMR (400 MHz, <cd3od>) δ ppm 1.74-1.89 (m, 4H) 2.30 (s, 3H) 3.05-3.20 (m, 4H) 3.64 (s, 3H) 3.80-3.93 (m, 4H) 6.93 (d, J=1.96 Hz, 1H) 7.26-7.43 (m, 2H) 7.52-7.63 (m, 2H) 7.67-7.80 (m, 1H) 8.07 (s, 1H) 8.64 (d, J=5.09 Hz, 1H), LCMS (m/z) (M+H)=470.0, Rt=0.77 min.

Example 358: 2-(difluoromethyl)-N-(4-methyl-3-(1-methyl-5-morpholino-6-oxo-1,6-dihydropyridin-3-yl)phenyl)isonicotinamide

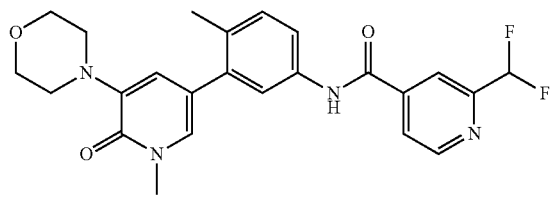 [SMILES: Cc1ccc(NC(=O)c2ccnc(C(F)F)c2)cc1-c1cc(N2CCOCC2)c(=O)n(C)c1]

1H NMR (400 MHz, <cd3od>) δ ppm 2.31 (s, 3H) 3.17-3.22 (m, 4H) 3.65 (s, 3H) 3.85-3.91 (m, 4H) 6.67-6.98 (m, 1H) 7.02 (d, J=1.96 Hz, 1H) 7.31 (d, J=8.22 Hz, 1H) 7.40 (d, J=1.96 Hz, 1H) 7.59 (dd, J=8.41, 2.15 Hz, 1H) 7.65 (d, J=1.96 Hz, 1H) 8.01 (d, J=5.09 Hz, 1H) 8.17 (s, 1H) 8.83 (d, J=5.09 Hz, 1H). LCMS (m/z) (M+H)=455.1, Rt=0.75 min.

Example 359: 3-(cyanomethyl)-N-(4-methyl-3-(1-methyl-5-morpholino-6-oxo-1,6-dihydropyridin-3-yl)phenyl)benzamide

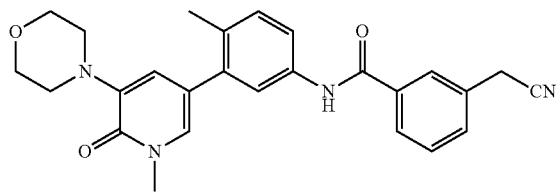 [SMILES: Cc1ccc(NC(=O)c2cccc(CC#N)c2)cc1-c1cc(N2CCOCC2)c(=O)n(C)c1]

1H NMR (400 MHz, <dmso>) δ ppm 2.24 (s, 3H) 3.09 (br. s., 4H) 3.43-3.52 (m, 3H) 3.62-3.75 (m, 4H) 3.86 (s, 1H) 4.09-4.18 (m, 3H) 6.69 (d, J=1.96 Hz, 1H) 7.20-7.28 (m, 1H) 7.39 (d, J=1.96 Hz, 1H) 7.48-7.58 (m, 2H) 7.59-7.71 (m, 2H) 7.86-7.92 (m, 2H) 10.27 (s, 1H). LCMS (m/z) (M+H)= 443.3, Rt=0.71 min.

Example 360: 6-(2-cyanopropan-2-yl)-N-(4-methyl-3-(1-methyl-5-morpholino-6-oxo-1,6-dihydropyridin-3-yl)phenyl)pyridazine-4-carboxamide

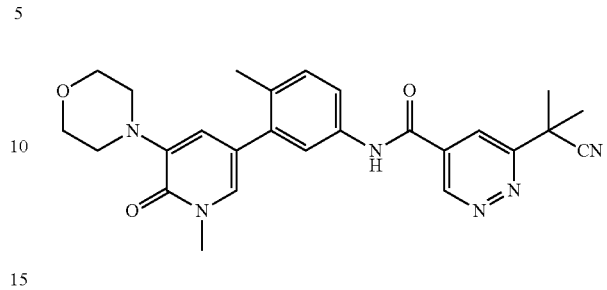

1H NMR (400 MHz, <dmso>) δ ppm 1.84 (s, 6H) 2.26 (s, 3H) 3.09 (br. s., 4H) 3.48 (s, 3H) 3.66-3.72 (m, 5H) 6.68 (d, J=1.57 Hz, 1H) 7.30 (d, J=8.22 Hz, 1H) 7.39 (d, J=1.96 Hz, 1H) 7.60 (d, J=1.96 Hz, 1H) 7.64 (dd, J=8.22, 1.96 Hz, 1H) 8.28 (d, J=1.56 Hz, 1H) 9.63 (d, J=1.96 Hz, 1H) 10.71 (s, 1H). LCMS (m/z) (M+H)=473.1, Rt=0.67 min.

Example 361: N-(4-methyl-3-(1-methyl-5-morpholino-6-oxo-1,6-dihydropyridin-3-yl)phenyl)-6-(trifluoromethyl)pyridazine-4-carboxamide

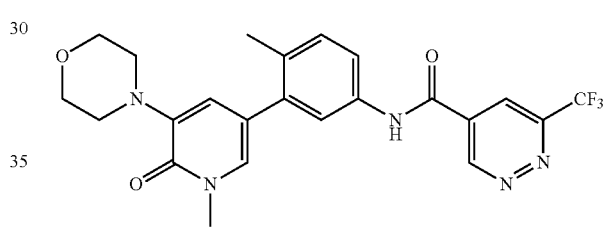

¹H NMR (400 MHz, <cd3od>) δ ppm 2.31 (s, 3H) 3.08-3.22 (m, 4H) 3.64 (s, 3H) 3.80-3.93 (m, 4H) 7.01 (d, J=1.96 Hz, 1H) 7.32 (d, J=8.22 Hz, 1H) 7.40 (d, J=2.35 Hz, 1H) 7.55-7.70 (m, 2H) 8.57 (d, J=1.96 Hz, 1H) 9.86 (d, J=1.57 Hz, 1H). LCMS (m/z) (M+H)=474.1, Rt=0.76 min.

Example 362: 6-cyclopropyl-N-(4-methyl-3-(1-methyl-5-morpholino-6-oxo-1,6-dihydropyridin-3-yl)phenyl)pyridazine-4-carboxamide

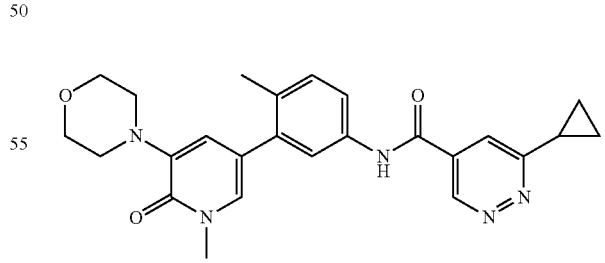

¹H NMR (400 MHz, <cd3od>) δ ppm 1.15-1.34 (m, 4H) 2.30 (s, 3H) 2.33-2.45 (m, 1H) 3.11-3.19 (m, 4H) 3.64 (s, 3H) 3.82-3.89 (m, 4H) 6.95 (d, J=1.96 Hz, 1H) 7.30 (d, J=8.22 Hz, 1H) 7.36 (d, J=1.96 Hz, 1H) 7.55-7.65 (m, 2H) 7.96 (d, J=1.96 Hz, 1H) 9.39 (d, J=1.96 Hz, 1H). LCMS (m/z) (M+H)=446.2, Rt=0.68 min.

Example 363: 6-(2-fluoropropan-2-yl)-N-(4-methyl-3-(1-methyl-5-morpholino-6-oxo-1,6-dihydropyridin-3-yl)phenyl)pyridazine-4-carboxamide

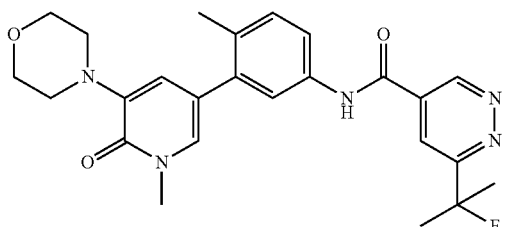

$^1$H NMR (400 MHz, <cd3od>) δ ppm 1.77-1.92 (m, 6H) 2.31 (s, 3H) 3.13-3.23 (m, 4H) 3.64 (s, 3H) 3.81-3.95 (m, 4H) 7.02 (d, J=1.96 Hz, 1H) 7.31 (d, J=8.22 Hz, 1H) 7.40 (d, J=2.35 Hz, 1H) 7.60 (dd, J=8.22, 2.35 Hz, 1H) 7.66 (d, J=1.96 Hz, 1H) 8.33 (d, J=1.57 Hz, 1H) 9.56 (d, J=1.96 Hz, 1H). LCMS (m/z) (M+H)=466.2, Rt=0.74 min.

Example 364: N-(4-methyl-3-(1-methyl-5-morpholino-6-oxo-1,6-dihydropyridin-3-yl)phenyl)-4-(trifluoromethyl)picolinamide

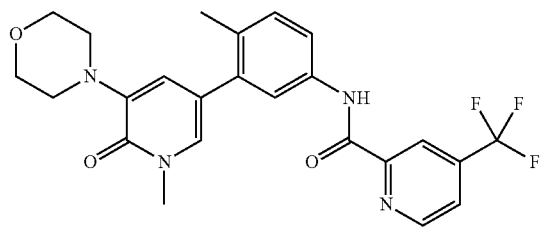 [SMILES: Cc1ccc(NC(=O)c2cc(C(F)(F)F)ccn2)cc1-c1cc(N2CCOCC2)c(=O)n(C)c1]

$^1$H NMR (400 MHz, <cd3od>) δ ppm 2.33 (s, 3H) 3.16-3.26 (m, 4H) 3.67 (s, 3H) 3.84-3.96 (m, 4H) 7.02 (d, J=2.35 Hz, 1H) 7.33 (d, J=8.22 Hz, 1H) 7.42 (d, J=1.96 Hz, 1H) 7.67-7.78 (m, 2H) 7.94 (d, J=3.91 Hz, 1H) 8.45 (s, 1H) 8.98 (d, J=5.09 Hz, 1H). LCMS (m/z) (M+H)=473.1, Rt=0.89 min.

Example 365: 1-ethyl-3-methyl-N-(4-methyl-3-(1-methyl-5-morpholino-6-oxo-1,6-dihydropyridin-3-yl)phenyl)-1H-pyrazole-4-carboxamide

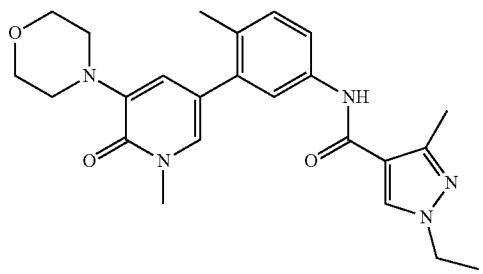 [SMILES: CCn1cc(C(=O)Nc2ccc(C)c(-c3cc(N4CCOCC4)c(=O)n(C)c3)c2)c(C)n1]

$^1$H NMR (500 MHz, DMSO-$d_6$) δ ppm 1.38 (t, J=7.25 Hz, 3H) 2.23 (s, 3H) 2.34 (s, 3H) 3.11 (br. s., 4H) 3.49 (s, 3H) 3.72 (t, J=4.41 Hz, 4H) 4.09 (q, J=7.25 Hz, 2H) 6.70 (d, J=1.89 Hz, 1H) 7.20 (d, J=8.20 Hz, 1H) 7.39 (d, J=2.21 Hz, 1H) 7.51-7.61 (m, 2H) 8.33 (s, 1H) 9.61 (s, 1H). LCMS (m/z) (M+H)=436.1, Rt=0.67 min.

Example 366: 1,3-dimethyl-N-(4-methyl-3-(1-methyl-5-morpholino-6-oxo-1,6-dihydropyridin-3-yl)phenyl)-1H-pyrazole-4-carboxamide

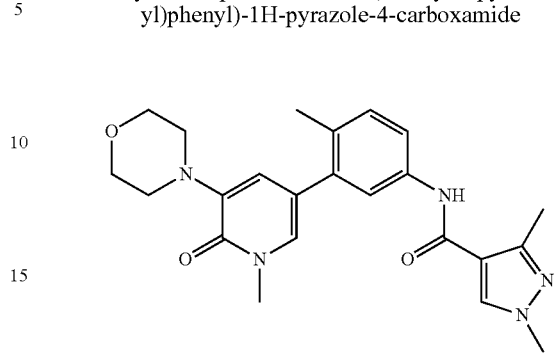

$^1$H NMR (500 MHz, DMSO-$d_6$) δ ppm 2.22 (s, 3H) 2.33 (s, 3H) 3.10 (m, 4H) 3.49 (s, 3H) 3.72 (t, J=4.41 Hz, 4H) 3.81 (s, 3H) 6.70 (d, J=2.21 Hz, 1H) 7.14-7.26 (m, 1H) 7.39 (d, J=1.89 Hz, 1H) 7.56 (dd, J=4.41, 2.21 Hz, 2H) 8.27 (s, 1H) 9.62 (s, 1H). LCMS (m/z) (M+H)=422.1, Rt=0.62 min.

Example 367: 1-isopropyl-3-methyl-N-(4-methyl-3-(1-methyl-5-morpholino-6-oxo-1,6-dihydropyridin-3-yl)phenyl)-1H-pyrazole-4-carboxamide

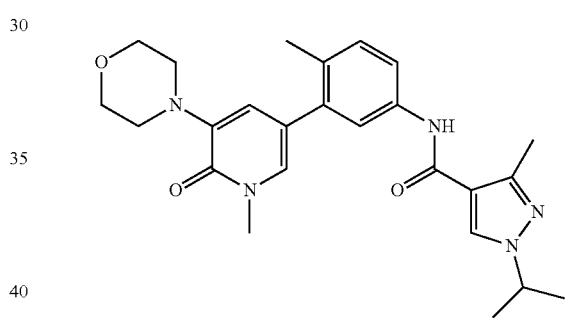

$^1$H NMR (500 MHz, DMSO-$d_6$) δ ppm 1.42 (d, J=6.62 Hz, 6H) 2.23 (s, 3H) 2.35 (s, 3H) 3.10 (br. s., 4H) 3.49 (s, 3H) 3.72 (t, J=4.41 Hz, 4H) 4.43 (spt, J=6.62 Hz, 1H) 6.70 (d, J=2.21 Hz, 1H) 7.20 (d, J=8.20 Hz, 1H) 7.39 (d, J=2.21 Hz, 1H) 7.49-7.65 (m, 2H) 8.38 (s, 1H) 9.59 (s, 1H). LCMS (m/z) (M+H)=450.1, Rt=0.72 min.

Example 368: 3-cyclopropyl-1-methyl-N-(4-methyl-3-(1-methyl-5-morpholino-6-oxo-1,6-dihydropyridin-3-yl)phenyl)-1H-pyrazole-5-carboxamide

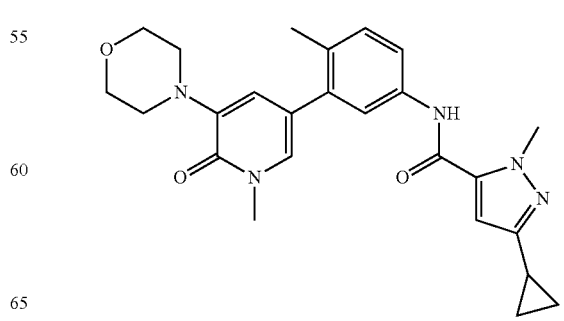

¹H NMR (500 MHz, DMSO-d$_6$) δ ppm 1.42 (d, J=6.62 Hz, 6H) 2.23 (s, 3H) 2.35 (s, 3H) 3.10 (br. s., 4H) 3.49 (s, 3H) 3.72 (t, J=4.41 Hz, 4H) 4.43 (spt, J=6.62 Hz, 1H) 6.70 (d, J=2.21 Hz, 1H) 7.20 (d, J=8.20 Hz, 1H) 7.39 (d, J=2.21 Hz, 1H) 7.49-7.65 (m, 2H) 8.38 (s, 1H) 9.59 (s, 1H). LCMS (m/z) (M+H)=448.1, Rt=0.78 min.

Example 369: 1-methyl-N-(4-methyl-3-(1-methyl-5-morpholino-6-oxo-1,6-dihydropyridin-3-yl)phenyl)-3-(trifluoromethyl)-1H-pyrazole-5-carboxamide

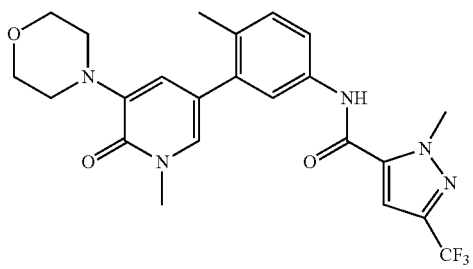 [SMILES: Cc1ccc(NC(=O)c2cc(C(F)(F)F)nn2C)cc1-c1cc(N2CCOCC2)c(=O)n(C)c1]

¹H NMR (500 MHz, DMSO-d$_6$) δ ppm 2.26 (s, 3H) 3.11 (br. s., 4H) 3.50 (s, 3H) 3.72 (t, J=4.41 Hz, 4H) 4.16 (s, 3H) 6.70 (d, J=1.89 Hz, 1H) 7.28 (d, J=8.20 Hz, 1H) 7.41 (d, J=1.89 Hz, 1H) 7.51 (s, 1H) 7.57-7.63 (m, 2H) 10.38 (s, 1H). LCMS (m/z) (M+H)=476.1, Rt=0.86 min.

Example 371: 5-isopropyl-N-(4-methyl-3-(1-methyl-5-morpholino-6-oxo-1,6-dihydropyridin-3-yl)phenyl)isoxazole-3-carboxamide

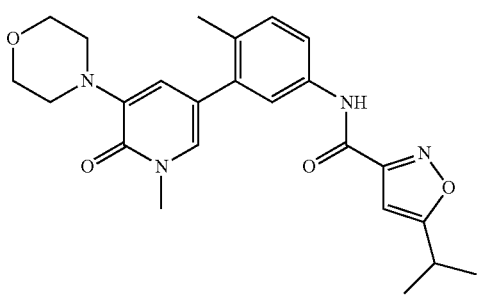 [SMILES: Cc1ccc(NC(=O)c2cc(C(C)C)on2)cc1-c1cc(N2CCOCC2)c(=O)n(C)c1]

¹H NMR (500 MHz, DMSO-d$_6$) δ ppm 1.29 (d, J=6.94 Hz, 6H) 2.25 (s, 3H) 3.10 (br. s., 4H) 3.13-3.22 (m, 1H) 3.49 (s, 3H) 3.68-3.74 (m, 4H) 6.61-6.77 (m, 2H) 7.25 (d, J=8.20 Hz, 1H) 7.40 (d, J=2.21 Hz, 1H) 7.58-7.74 (m, 2H) 10.59 (s, 1H). LCMS (m/z) (M+H)=437.1, Rt=0.87 min.

Example 372: 5-cyclopropyl-N-(4-methyl-3-(1-methyl-5-morpholino-6-oxo-1,6-dihydropyridin-3-yl)phenyl)isoxazole-3-carboxamide

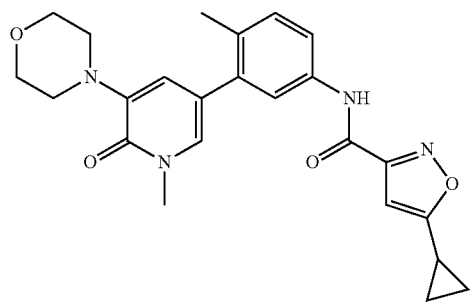 [SMILES: Cc1ccc(NC(=O)c2cc(C3CC3)on2)cc1-c1cc(N2CCOCC2)c(=O)n(C)c1]

¹H NMR (500 MHz, DMSO-d$_6$) δ ppm 0.92-0.99 (m, 2H) 1.09-1.16 (m, 2H) 2.19-2.24 (m, 1H) 2.25 (s, 3H) 3.10 (br. s., 4H) 3.49 (s, 3H) 3.71 (t, J=4.26 Hz, 4H) 6.61 (s, 1H) 6.70 (d, J=1.89 Hz, 1H) 7.25 (d, J=8.83 Hz, 1H) 7.40 (d, J=1.89 Hz, 1H) 7.56-7.75 (m, 2H) 10.56 (s, 1H). LCMS (m/z) (M+H)=435.1, Rt=0.82 min.

Example 373: N-(1',2-dimethyl-5'-morpholino-6'-oxo-1',6'-dihydro-[3,3'-bipyridin]-5-yl)-1-ethyl-3-methyl-1H-pyrazole-4-carboxamide

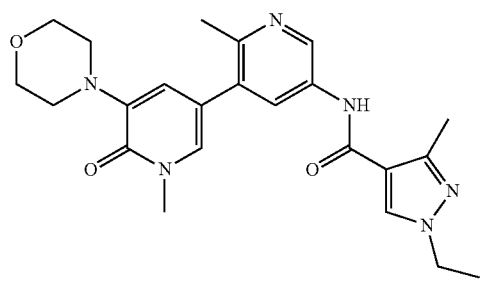 [SMILES: CCn1cc(C(=O)Nc2cnc(C)c(-c3cc(N4CCOCC4)c(=O)n(C)c3)c2)c(C)n1]

LCMS (m/z) (M+H)=437.1, Rt=0.48 min.

Example 374: N-(1',2-dimethyl-5'-morpholino-6'-oxo-1',6'-dihydro-[3,3'-bipyridin]-5-yl)-1,3-dimethyl-1H-pyrazole-4-carboxamide

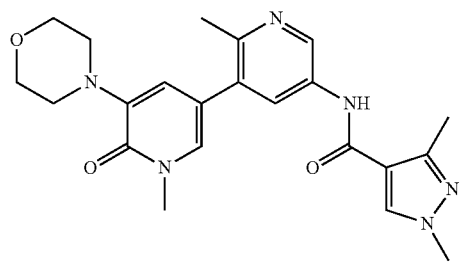 [SMILES: Cc1nn(C)cc1C(=O)Nc1cnc(C)c(-c2cc(N3CCOCC3)c(=O)n(C)c2)c1]

LCMS (m/z) (M+H)=423.1, Rt=0.44 min.

Example 375: N-(1',2-dimethyl-5'-morpholino-6'-oxo-1',6'-dihydro-[3,3'-bipyridin]-5-yl)-1-isopropyl-3-methyl-1H-pyrazole-4-carboxamide

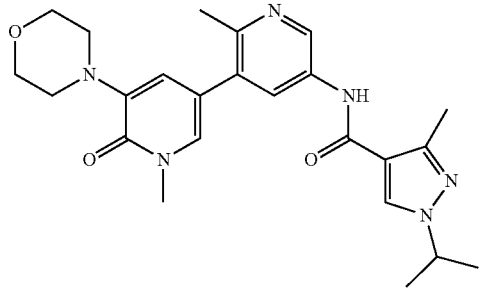 [SMILES: Cc1nn(C(C)C)cc1C(=O)Nc1cnc(C)c(-c2cc(N3CCOCC3)c(=O)n(C)c2)c1]

LCMS (m/z) (M+H)=451.1, Rt=0.52 min.

Example 376: N-(1',2-dimethyl-5'-morpholino-6'-oxo-1',6'-dihydro-[3,3'-bipyridin]-5-yl)-1,3-dimethyl-1H-pyrazole-5-carboxamide

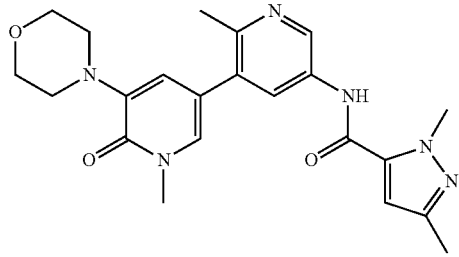 [SMILES: Cc1cc(C(=O)Nc2cnc(C)c(-c3cc(N4CCOCC4)c(=O)n(C)c3)c2)n(C)n1]

LCMS (m/z) (M+H)=423.1, Rt=0.47 min.

Example 377: 3-cyclopropyl-N-(1',2-dimethyl-5'-morpholino-6'-oxo-1',6'-dihydro-[3,3'-bipyridin]-5-yl)-1-methyl-1H-pyrazole-5-carboxamide

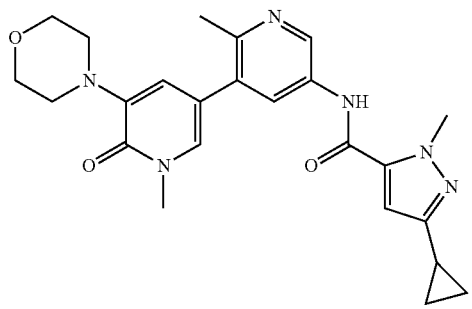 [SMILES: Cc1ncc(NC(=O)c2cc(C3CC3)nn2C)cc1-c1cc(N2CCOCC2)c(=O)n(C)c1]

LCMS (m/z) (M+H)=449.1, Rt=0.54 min.

Example 379: N-(1',2-dimethyl-5'-morpholino-6'-oxo-1',6'-dihydro-[3,3'-bipyridin]-5-yl)-5-isopropylisoxazole-3-carboxamide

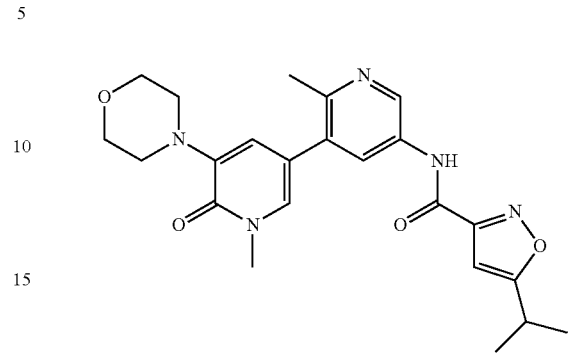

LCMS (m/z) (M+H)=438.1, Rt=0.59 min.

Example 380: 5-cyclopropyl-N-(1',2-dimethyl-5'-morpholino-6'-oxo-1',6'-dihydro-[3,3'-bipyridin]-5-yl)isoxazole-3-carboxamide

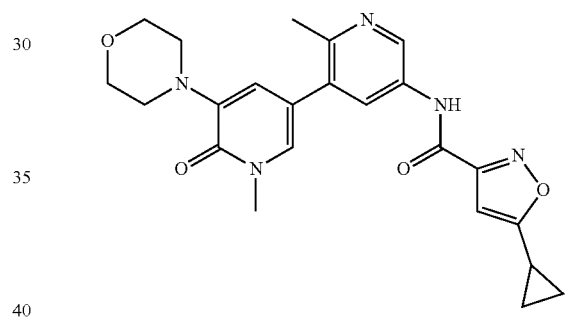

LCMS (m/z) (M+H)=436.1, Rt=0.55 min.

Example 381: 1,3-dimethyl-N-(4-methyl-3-(1-methyl-5-morpholino-6-oxo-1,6-dihydropyridin-3-yl)phenyl)-1H-pyrazole-5-carboxamide

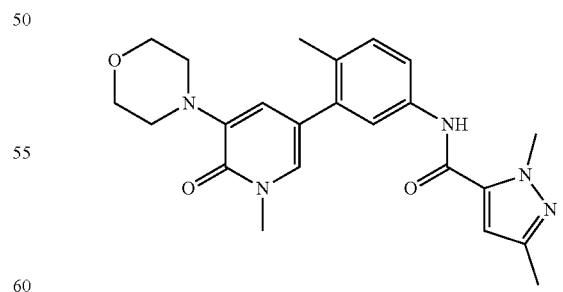

$^1$H NMR (500 MHz, DMSO-d$_6$) δ ppm 2.08-2.31 (m, 6H) 3.11 (br. s., 4H) 3.50 (s, 3H) 3.72 (t, J=4.41 Hz, 4H) 3.99 (s, 3H) 6.69 (d, J=1.89 Hz, 1H) 6.82 (s, 1H) 7.25 (d, J=8.51 Hz, 1H) 7.40 (d, J=1.89 Hz, 1H) 7.52-7.70 (m, 3H) 10.09 (s, 1H). LCMS (m/z) (M+H)=422.1, Rt=0.69 min.

Example 382: N-(1',2-dimethyl-5'-morpholino-6'-oxo-1',6'-dihydro-[3,3'-bipyridin]-5-yl)-1-methyl-3-(trifluoromethyl)-1H-pyrazole-5-carboxamide

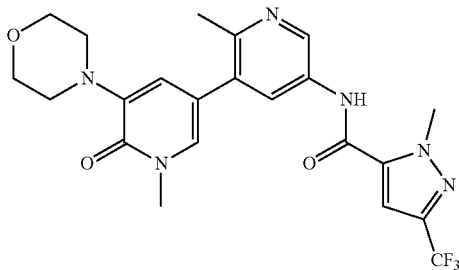 [SMILES: Cc1ncc(NC(=O)c2cc(C(F)(F)F)nn2C)cc1-c1cc(N2CCOCC2)c(=O)n(C)c1]

LCMS (m/z) (M+H)=477.1, Rt=0.60 min.

Example 383: N-(1',2-dimethyl-5'-morpholino-6'-oxo-1',6'-dihydro-[3,3'-bipyridin]-5-yl)-2,5-dimethyloxazole-4-carboxamide

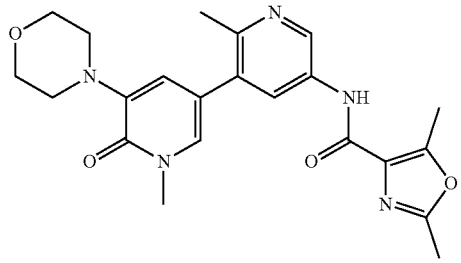 [SMILES: Cc1nc(C(=O)Nc2cnc(C)c(-c3cc(N4CCOCC4)c(=O)n(C)c3)c2)c(C)o1]

LCMS (m/z) (M+H)=424.1, Rt=0.51 min.

Example 384: N-(1',2-dimethyl-5'-morpholino-6'-oxo-1',6'-dihydro-[3,3'-bipyridin]-5-yl)-2,5-dimethyloxazole-4-carboxamide

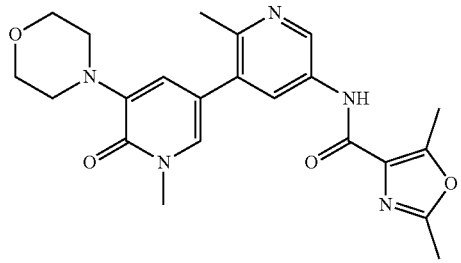 [SMILES: Cc1nc(C(=O)Nc2cnc(C)c(-c3cc(N4CCOCC4)c(=O)n(C)c3)c2)c(C)o1]

LCMS (m/z) (M+H)=424.1, Rt=0.51 min.

Example 385: racemic trans-1,3-dimethyl-N-(4-methyl-3-(1-methyl-5-morpholino-6-oxo-1,6-dihydropyridin-3-yl)phenyl)-1H-pyrazole-5-carboxamide

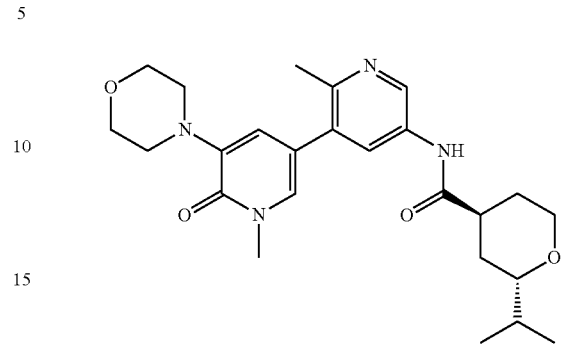

$^1$H NMR (400 MHz, CDCl$_3$) δ ppm 0.93 (dd, J=16.82, 6.65 Hz, 6H) 1.57-2.08 (m, 7H) 2.50 (s, 3H) 2.81-2.95 (m, 1H) 3.11-3.29 (m, 4H) 3.42 (ddd, J=9.88, 7.14, 2.15 Hz, 1H) 3.60 (s, 3H) 3.71-4.01 (m, 7H) 6.60 (d, J=1.96 Hz, 1H) 7.00 (d, J=2.35 Hz, 1H) 7.57 (br. s., 1H) 8.23 (br. s., 1H) 8.38 (d, J=2.35 Hz, 1H). LCMS (m/z) (M+H)=455.1, Rt=0.52 min.

Example 386: racemic cis-1,3-dimethyl-N-(4-methyl-3-(1-methyl-5-morpholino-6-oxo-1,6-dihydropyridin-3-yl)phenyl)-1H-pyrazole-5-carboxamide

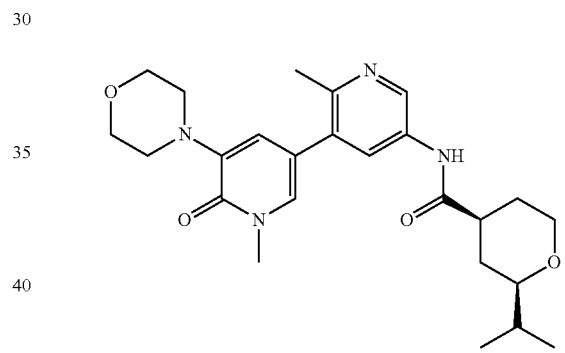

$^1$H NMR (400 MHz, CDCl$_3$) δ ppm 0.94 (dd, J=12.52, 6.65 Hz, 6H) 1.42-2.01 (m, 8H) 2.43-2.62 (m, 4H) 3.06 (dd, J=9.98, 6.06 Hz, 1H) 3.20 (d, J=4.30 Hz, 4H) 3.40-3.53 (m, 1H) 3.60 (s, 3H) 3.80-3.99 (m, 4H) 4.03-4.24 (m, 1H) 6.61 (d, J=1.57 Hz, 1H) 7.00 (d, J=1.57 Hz, 1H) 8.22 (br. s., 1H) 8.40 (s, 1H). LCMS (m/z) (M+H)=455.1, Rt=0.52 min.

Example 387: (R)—N-(1',2-dimethyl-5'-morpholino-6'-oxo-1',6'-dihydro-[3,3'-bipyridin]-5-yl)-2-(tetrahydrofuran-2-yl)acetamide

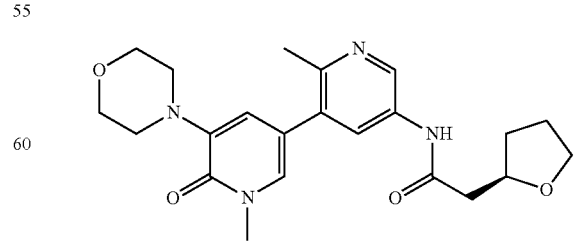

$^1$H NMR (400 MHz, CDCl$_3$) δ ppm 1.50-1.83 (m, 7H) 1.90-2.05 (m, 2H) 2.08-2.22 (m, 1H) 2.49 (s, 2H) 2.55-2.63 (m, 1H) 2.63-2.71 (m, 1H) 3.15-3.27 (m, 4H) 3.60 (s, 3H)

3.84-3.94 (m, 5H) 3.96-4.08 (m, 1H) 4.15-4.32 (m, 1H) 6.61 (d, J=1.96 Hz, 1H) 6.99 (d, J=1.96 Hz, 1H) 8.12 (d, J=1.57 Hz, 1H) 8.41 (d, J=2.35 Hz, 1H) 8.78 (br. s., 1H). LCMS (m/z) (M+H)=413.1, Rt=0.43 min.

Example 388: (S)—N-(1',2-dimethyl-5'-morpholino-6'-oxo-1',6'-dihydro-[3,3'-bipyridin]-5-yl)-2-(tetrahydrofuran-2-yl)acetamide

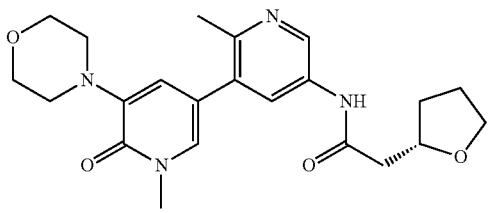 [SMILES: Cc1ncc(NC(=O)C[C@@H]2CCCO2)cc1-c1cc(N2CCOCC2)c(=O)n(C)c1]

$^1$H NMR (400 MHz, CDCl$_3$) δ ppm 1.50-1.83 (m, 7H) 1.90-2.05 (m, 2H) 2.08-2.22 (m, 1H) 2.49 (s, 2H) 2.55-2.63 (m, 1H) 2.63-2.71 (m, 1H) 3.15-3.27 (m, 4H) 3.60 (s, 3H) 3.84-3.94 (m, 5H) 3.96-4.08 (m, 1H) 4.15-4.32 (m, 1H) 6.61 (d, J=1.96 Hz, 1H) 6.99 (d, J=1.96 Hz, 1H) 8.12 (d, J=1.57 Hz, 1H) 8.41 (d, J=2.35 Hz, 1H) 8.78 (br. s., 1H). LCMS (m/z) (M+H)=413.1, Rt=0.43 min.

Example 389: 3-(2-cyanopropan-2-yl)-N-(1',2-dimethyl-5'-morpholino-6'-oxo-1',6'-dihydro-[3,3'-bipyridin]-5-yl)benzamide

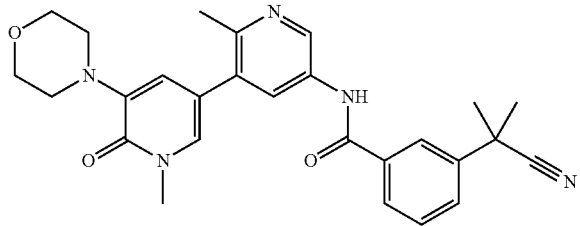 [SMILES: Cc1ncc(NC(=O)c2cccc(C(C)(C)C#N)c2)cc1-c1cc(N2CCOCC2)c(=O)n(C)c1]

$^1$H NMR (400 MHz, <cd3od>) δ ppm 1.82 (s, 6H) 2.69 (s, 3H) 3.15-3.22 (m, 4H) 3.67 (s, 3H) 3.83-3.93 (m, 4H) 6.98 (d, J=1.96 Hz, 1H) 7.53 (d, J=1.96 Hz, 1H) 7.65 (t, J=7.83 Hz, 1H) 7.85 (d, J=7.83 Hz, 1H) 7.99 (d, J=7.83 Hz, 1H) 8.18 (s, 1H) 8.39 (d, J=1.96 Hz, 1H) 9.19 (s, 1H). LCMS (m/z) (M+H)=472.1, Rt=0.60 min.

Example 390: N-(1',2-dimethyl-5'-morpholino-6'-oxo-1',6'-dihydro-[3,3'-bipyridin]-5-yl)-2-(trifluoromethyl)isonicotinamide

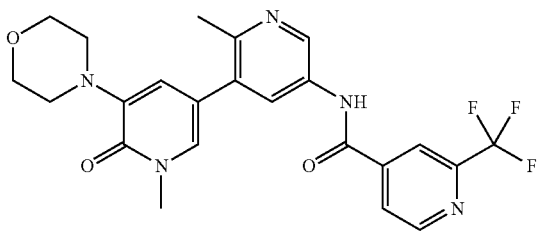 [SMILES: Cc1ncc(NC(=O)c2ccnc(C(F)(F)F)c2)cc1-c1cc(N2CCOCC2)c(=O)n(C)c1]

$^1$H NMR (400 MHz, <cd3od>) δ ppm 2.72 (s, 3H) 3.14-3.22 (m, 4H) 3.67 (s, 3H) 3.83-3.91 (m, 4H) 6.97 (d, J=2.30 Hz, 1H) 7.54 (d, J=2.25 Hz, 1H) 8.19 (dd, J=5.01, 1.54 Hz, 1H) 8.37 (s, 1H) 8.43 (d, J=2.35 Hz, 1H) 8.99 (d, J=5.14 Hz, 1H) 9.23 (d, J=2.35 Hz, 1H). LCMS (m/z) (M+H)=474.0, Rt=0.56 min.

Example 391: 2-(1,1-difluoroethyl)-N-(1',2-dimethyl-5'-morpholino-6'-oxo-1',6'-dihydro-[3,3'-bipyridin]-5-yl)isonicotinamide

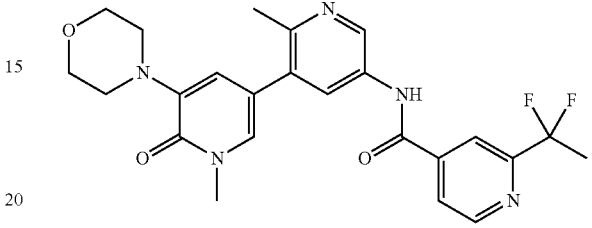

$^1$H NMR (400 MHz, <cd3od>) δ ppm 2.07 (t, J=18.73 Hz, 3H) 2.69 (s, 3H) 3.14-3.22 (m, 4H) 3.67 (s, 3H) 3.83-3.92 (m, 4H) 6.97 (d, J=2.25 Hz, 1H) 7.53 (d, J=2.20 Hz, 1H) 8.03 (d, J=5.09 Hz, 1H) 8.26 (d, J=0.73 Hz, 1H) 8.39 (d, J=2.35 Hz, 1H) 8.88 (d, J=5.09 Hz, 1H) 9.17 (d, J=2.30 Hz, 1H). LCMS (m/z) (M+H)=470.1, Rt=0.55 min.

Example 392: 2-(difluoromethyl)-N-(1',2-dimethyl-5'-morpholino-6'-oxo-1',6'-dihydro-[3,3'-bipyridin]-5-yl)isonicotinamide

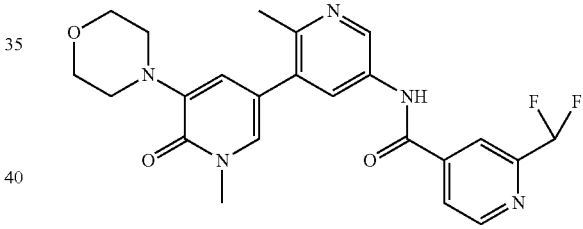

$^1$H NMR (400 MHz, <cd3od>) δ ppm 2.71 (s, 3H) 3.16-3.22 (m, 4H) 3.67 (s, 3H) 3.84-3.92 (m, 4H) 6.70-7.03 (m, 2H) 7.54 (d, J=2.30 Hz, 1H) 8.08 (d, J=5.14 Hz, 1H) 8.26 (s, 1H) 8.42 (d, J=2.40 Hz, 1H) 8.91 (d, J=4.99 Hz, 1H) 9.22 (d, J=2.30 Hz, 1H). LCMS (m/z) (M+H)=456.0, Rt=0.50 min.

Example 393: 3-(1,1-difluoroethyl)-N-(1',2-dimethyl-5'-morpholino-6'-oxo-1',6'-dihydro-[3,3'-bipyridin]-5-yl)benzamide

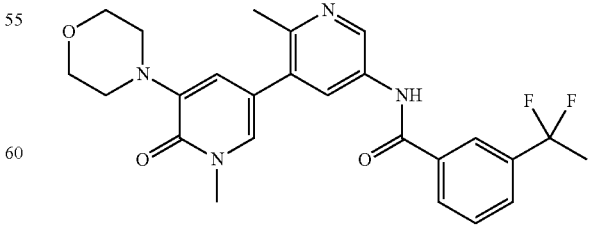

$^1$H NMR (400 MHz, <cd3od>) δ ppm 2.01 (t, J=18.39 Hz, 3H) 2.73 (s, 3H) 3.12-3.25 (m, 4H) 3.67 (s, 3H) 3.81-3.95 (m, 4H) 6.98 (d, J=1.96 Hz, 1H) 7.56 (d, J=1.96 Hz, 1H) 7.64-7.74 (m, 1H) 7.84 (d, J=7.83 Hz, 1H) 8.13 (d, J=7.83

Hz, 1H) 8.22 (s, 1H) 8.48 (d, J=2.35 Hz, 1H) 9.32 (d, J=1.96 Hz, 1H). LCMS (m/z) (M+H)=469.1, Rt=0.62 min.

Example 394: 3-(difluoromethyl)-N-(1',2-dimethyl-5'-morpholino-6'-oxo-1',6'-dihydro-[3,3'-bipyridin]-5-yl)benzamide

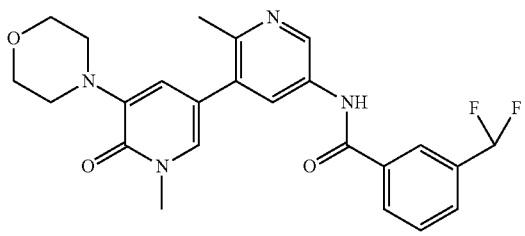 [SMILES: Cc1ncc(NC(=O)c2cccc(C(F)F)c2)cc1-c1cc(N2CCOCC2)c(=O)n(C)c1]

¹H NMR (400 MHz, <cd3od>) δ ppm 2.73 (s, 3H) 3.15-3.23 (m, 4H) 3.67 (s, 3H) 3.83-3.93 (m, 4H) 6.74-7.09 (m, 2H) 7.55 (d, J=2.30 Hz, 1H) 7.67-7.76 (m, 1H) 7.85 (d, J=7.58 Hz, 1H) 8.17 (d, J=7.82 Hz, 1H) 8.23 (s, 1H) 8.47 (d, J=2.35 Hz, 1H) 9.30 (d, J=2.35 Hz, 1H). LCMS (m/z) (M+H)=455.0, Rt=0.57 min.

Example 395: N-(1',2-dimethyl-5'-morpholino-6'-oxo-1',6'-dihydro-[3,3'-bipyridin]-5-yl)-3-ethoxy-4-fluorobenzamide

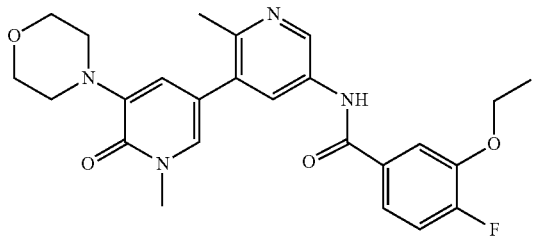 [SMILES: CCOc1cc(C(=O)Nc2cnc(C)c(-c3cc(N4CCOCC4)c(=O)n(C)c3)c2)ccc1F]

¹H NMR (400 MHz, <cd3od>) δ ppm 1.48 (t, J=7.04 Hz, 3H) 2.68 (s, 3H) 3.13-3.23 (m, 4H) 3.67 (s, 3H) 3.82-3.93 (m, 4H) 4.23 (q, J=7.04 Hz, 2H) 6.97 (d, J=1.96 Hz, 1H) 7.28 (dd, J=10.76, 8.41 Hz, 1H) 7.52 (d, J=2.35 Hz, 1H) 7.62 (ddd, J=8.22, 4.11, 2.15 Hz, 1H) 7.74 (dd, J=8.02, 1.76 Hz, 1H) 8.36 (d, J=2.35 Hz, 1H) 9.15 (s, 1H). LCMS (m/z) (M+H)=467.3, Rt=0.61 min.

Example 396: N-(1',2-dimethyl-5'-morpholino-6'-oxo-1',6'-dihydro-[3,3'-bipyridin]-5-yl)-4-fluoro-3-isopropoxybenzamide

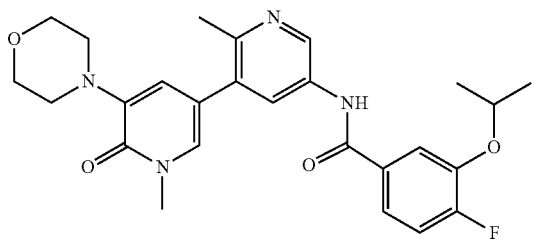 [SMILES: Cc1ncc(NC(=O)c2ccc(F)c(OC(C)C)c2)cc1-c1cc(N2CCOCC2)c(=O)n(C)c1]

¹H NMR (400 MHz, <cd3od>) δ ppm 1.40 (d, J=5.87 Hz, 6H) 2.70 (s, 3H) 3.12-3.24 (m, 4H) 3.67 (s, 3H) 3.82-3.94 (m, 4H) 4.74 (dt, J=12.13, 6.06 Hz, 1H) 6.97 (d, J=1.96 Hz, 1H) 7.29 (dd, J=10.56, 8.61 Hz, 1H) 7.54 (d, J=1.96 Hz, 1H) 7.64 (ddd, J=8.41, 4.11, 2.35 Hz, 1H) 7.76 (dd, J=7.83, 1.96 Hz, 1H) 8.41 (d, J=1.96 Hz, 1H) 9.22 (d, J=2.35 Hz, 1H). LCMS (m/z) (M+H)=481.2, Rt=0.66 min.

Example 397: N-(1',2-dimethyl-5'-morpholino-6'-oxo-1',6'-dihydro-[3,3'-bipyridin]-5-yl)-3-ethoxybenzamide

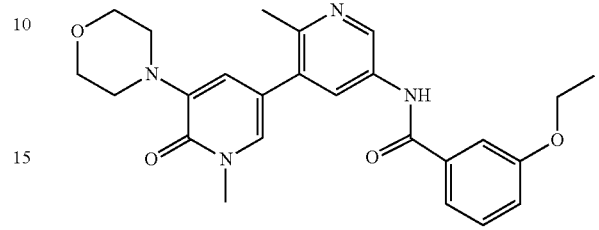

¹H NMR (400 MHz, <cd3od>) δ ppm 1.44 (t, J=6.85 Hz, 3H) 2.70 (s, 3H) 3.14-3.23 (m, 4H) 3.67 (s, 3H) 3.83-3.93 (m, 4H) 4.15 (q, J=6.78 Hz, 2H) 6.97 (d, J=1.96 Hz, 1H) 7.21 (dd, J=8.02, 2.15 Hz, 1H) 7.47 (t, J=8.02 Hz, 1H) 7.51-7.62 (m, 3H) 8.41 (d, J=1.96 Hz, 1H) 9.23 (d, J=1.96 Hz, 1H). LCMS (m/z) (M+H)=449.3, Rt=0.59 min.

Example 398: N-(1',2-dimethyl-5'-morpholino-6'-oxo-1',6'-dihydro-[3,3'-bipyridin]-5-yl)-3-isopropoxybenzamide

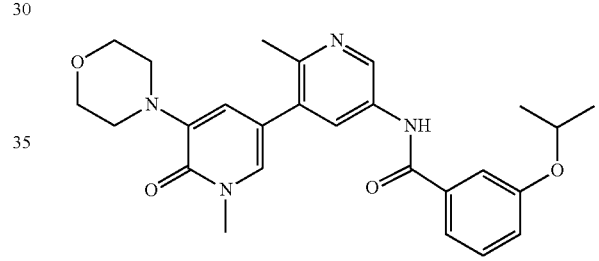

¹H NMR (400 MHz, <cd3od>) δ ppm 1.37 (d, J=5.87 Hz, 6H) 2.70 (s, 3H) 3.15-3.24 (m, 4H) 3.67 (s, 3H) 3.81-3.94 (m, 4H) 4.72 (quin, J=6.16 Hz, 1H) 6.97 (d, J=1.96 Hz, 1H) 7.20 (dd, J=8.02, 2.15 Hz, 1H) 7.47 (t, J=8.02 Hz, 1H) 7.50-7.60 (m, 3H) 8.42 (d, J=1.96 Hz, 1H) 9.23 (d, J=1.96 Hz, 1H). LCMS (m/z) (M+H)=463.3, Rt=0.63 min.

Example 399: 2-(tert-butyl)-N-(1',2-dimethyl-5'-morpholino-6'-oxo-1',6'-dihydro-[3,3'-bipyridin]-5-yl)isonicotinamide

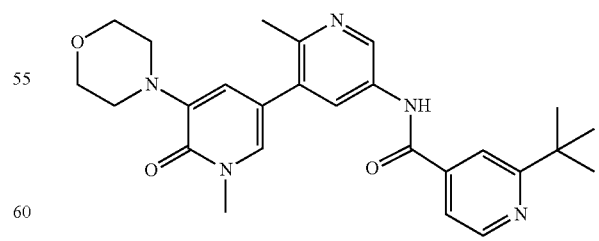

¹H NMR (400 MHz, <cd3od>) δ ppm 1.47 (s, 9H) 2.73 (s, 3H) 3.15-3.24 (m, 4H) 3.67 (s, 3H) 3.82-3.93 (m, 4H) 6.97 (d, J=1.96 Hz, 1H) 7.55 (d, J=2.35 Hz, 1H) 7.78-7.87 (m, 1H) 8.07 (s, 1H) 8.46 (d, J=1.96 Hz, 1H) 8.76 (d, J=5.09 Hz, 1H) 9.27 (d, J=2.35 Hz, 1H). LCMS (m/z) (M+H)=462.3, Rt=0.47 min.

Example 400: N-(1',2-dimethyl-5'-morpholino-6'-oxo-1',6'-dihydro-[3,3'-bipyridin]-5-yl)-2-isopropylisonicotinamide

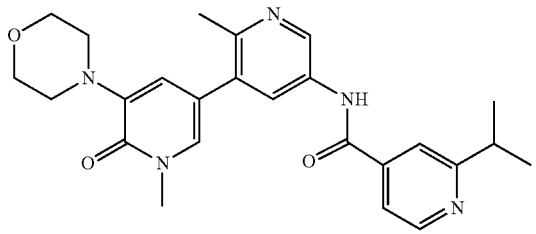 [SMILES: Cc1ncc(NC(=O)c2ccnc(C(C)C)c2)cc1-c1cc(N2CCOCC2)c(=O)n(C)c1]

$^1$H NMR (400 MHz, <cd3od>) δ ppm 1.42 (d, J=6.65 Hz, 6H) 2.72 (s, 3H) 3.15-3.22 (m, 4H) 3.23-3.30 (m, 1H) 3.67 (s, 3H) 3.82-3.93 (m, 4H) 6.97 (d, J=1.96 Hz, 1H) 7.54 (d, J=1.96 Hz, 1H) 7.91 (dd, J=5.28, 1.37 Hz, 1H) 8.02 (s, 1H) 8.45 (d, J=2.35 Hz, 1H) 8.76 (d, J=5.48 Hz, 1H) 9.26 (d, J=1.96 Hz, 1H). LCMS (m/z) (M+H)=448.3, Rt=0.44 min.

Example 401: N-(1',2-dimethyl-5'-morpholino-6'-oxo-1',6'-dihydro-[3,3'-bipyridin]-5-yl)-3-((dimethylamino)methyl)-5-(trifluoromethyl)benzamide

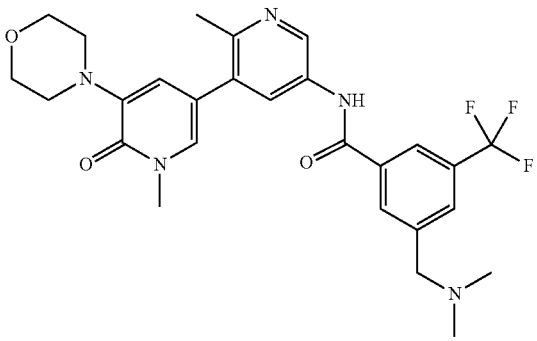 [SMILES: Cc1ncc(NC(=O)c2cc(CN(C)C)cc(C(F)(F)F)c2)cc1-c1cc(N2CCOCC2)c(=O)n(C)c1]

$^1$H NMR (400 MHz, <cd3od>) δ ppm 2.70 (s, 3H) 2.94 (s, 6H) 3.15-3.23 (m, 4H) 3.67 (s, 3H) 3.83-3.93 (m, 4H) 4.55 (s, 2H) 6.96 (d, J=2.35 Hz, 1H) 7.53 (d, J=1.96 Hz, 1H) 8.17 (s, 1H) 8.45 (d, J=1.96 Hz, 1H) 8.50 (d, J=6.65 Hz, 2H) 9.21 (d, J=2.35 Hz, 1H). LCMS (m/z) (M+H)=540.3, Rt=0.50 min.

Example 402: N-(1',2-dimethyl-5'-morpholino-6'-oxo-1',6'-dihydro-[3,3'-bipyridin]-5-yl)-3-(4-ethylpiperazin-1-yl)-5-(trifluoromethyl)benzamide

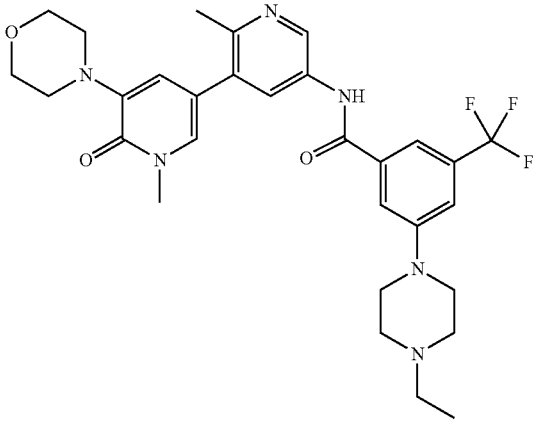 [SMILES: CCN1CCN(c2cc(C(=O)Nc3cnc(C)c(-c4cc(N5CCOCC5)c(=O)n(C)c4)c3)cc(C(F)(F)F)c2)CC1]

$^1$H NMR (400 MHz, <cd3od>) δ ppm 1.43 (t, J=7.24 Hz, 3H) 2.67 (s, 3H) 3.11-3.20 (m, 4H) 3.21-3.29 (m, 2H) 3.67 (s, 3H) 3.73 (br. s., 1H) 3.83-3.94 (m, 4H) 4.11 (br. s., 1H) 6.96 (d, J=2.35 Hz, 1H) 7.51 (d, J=1.96 Hz, 1H) 7.58 (s, 1H) 7.88 (d, J=8.61 Hz, 2H) 8.36 (d, J=1.96 Hz, 1H) 9.12 (d, J=1.96 Hz, 1H). LCMS (m/z) (M+H)=585.2, Rt=0.55 min.

Example 403: 2-chloro-3-(1-cyanocyclopropyl)-N-(1',2-dimethyl-5'-morpholino-6'-oxo-1',6'-dihydro-[3,3'-bipyridin]-5-yl)benzamide

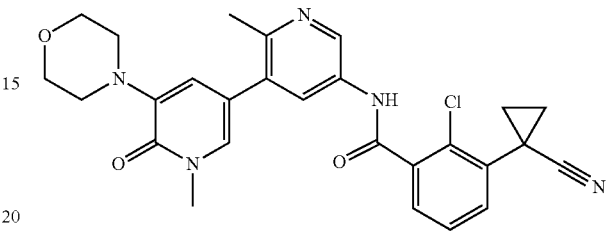

$^1$H NMR (400 MHz, <cd3od>) δ ppm 1.45-1.53 (m, 2H) 1.78-1.88 (m, 2H) 2.70 (s, 3H) 3.11-3.23 (m, 4H) 3.66 (s, 3H) 3.81-3.92 (m, 4H) 6.96 (d, J=1.96 Hz, 1H) 7.48-7.58 (m, 2H) 7.65 (dd, J=7.83, 1.57 Hz, 1H) 7.70 (dd, J=7.63, 1.37 Hz, 1H) 8.28 (d, J=2.35 Hz, 1H) 9.19 (d, J=1.96 Hz, 1H). LCMS (m/z) (M+H)=504.2, Rt=0.59 min.

The following compounds were prepared using methods similar to those described in Method 7 and Example 171 using the appropriate starting materials.

Example 404: N-(2-chloro-1'-methyl-5'-morpholino-6'-oxo-1',6'-dihydro-[3,3'-bipyridin]-5-yl)-2-(trifluoromethyl)isonicotinamide

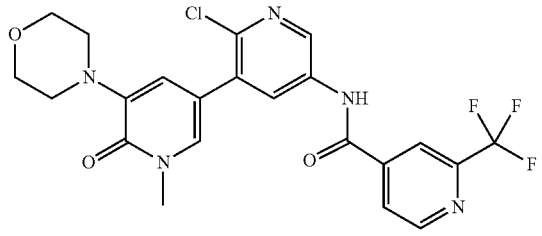 [SMILES: Cn1cc(-c2cc(NC(=O)c3ccnc(C(F)(F)F)c3)cnc2Cl)cc(N2CCOCC2)c1=O]

$^1$H NMR (400 MHz, <cd3od>) δ ppm 3.14-3.24 (m, 4H) 3.67 (s, 3H) 3.82-3.93 (m, 4H) 7.10 (d, J=1.96 Hz, 1H) 7.59 (d, J=2.35 Hz, 1H) 8.17 (d, J=4.70 Hz, 1H) 8.30-8.39 (m, 2H) 8.75 (d, J=2.74 Hz, 1H) 8.96 (d, J=4.70 Hz, 1H). LCMS (m/z) (M+H)=494.0, Rt=0.74 min.

Example 405: N-(2-chloro-1'-methyl-5'-morpholino-6'-oxo-1',6'-dihydro-[3,3-bipyridin]-5-yl)-2-(1,1-difluoroethyl)isonicotinamide

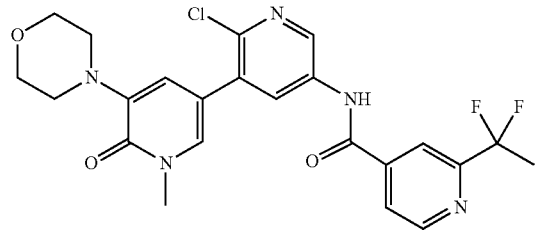 [SMILES: Cn1cc(-c2cc(NC(=O)c3ccnc(C(C)(F)F)c3)cnc2Cl)cc(N2CCOCC2)c1=O]

$^1$H NMR (400 MHz, <cd3od>) δ ppm 2.06 (t, J=18.78 Hz, 3H) 3.12-3.26 (m, 4H) 3.67 (s, 3H) 3.82-3.95 (m, 4H) 7.10 (d, J=2.35 Hz, 1H) 7.59 (d, J=1.96 Hz, 1H) 8.01 (d, J=5.09

Hz, 1H) 8.23 (s, 1H) 8.35 (d, J=2.35 Hz, 1H) 8.75 (d, J=2.74 Hz, 1H) 8.85 (d, J=5.09 Hz, 1H). LCMS (m/z) (M+H)=490.1, Rt=0.72 min.

Example 406: N-(2-chloro-1'-methyl-5'-morpholino-6'-oxo-1',6'-dihydro-[3,3'-bipyridin]-5-yl)-3-(difluoromethyl)benzamide

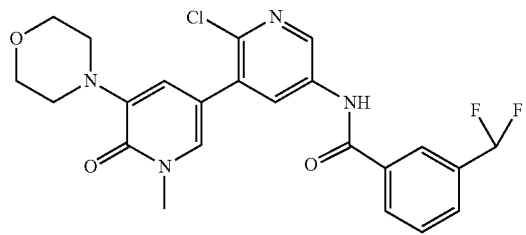 [SMILES: Cn1cc(-c2cc(NC(=O)c3cccc(C(F)F)c3)cnc2Cl)cc(N2CCOCC2)c1=O]

$^1$H NMR (400 MHz, <cd3od>) δ ppm 3.14-3.24 (m, 4H) 3.67 (s, 3H) 3.85-3.94 (m, 4H) 6.73-7.06 (m, 1H) 7.10 (d, J=1.96 Hz, 1H) 7.59 (d, J=1.96 Hz, 1H) 7.65-7.74 (m, 1H) 7.82 (d, J=7.43 Hz, 1H) 8.14 (d, J=7.43 Hz, 1H) 8.19 (s, 1H) 8.34 (d, J=2.35 Hz, 1H) 8.74 (d, J=2.35 Hz, 1H). LCMS (m/z) (M+H)=475.0, Rt=0.75 min.

Example 407: N-(2-chloro-1'-methyl-5'-morpholino-6'-oxo-1',6'-dihydro-[3,3-bipyridin]-5-yl)-3-(trifluoromethyl)benzamide

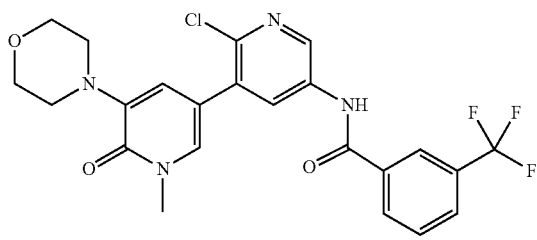 [SMILES: Cn1cc(-c2cc(NC(=O)c3cccc(C(F)(F)F)c3)cnc2Cl)cc(N2CCOCC2)c1=O]

$^1$H NMR (400 MHz, <cd3od>) δ ppm 3.15-3.24 (m, 4H) 3.67 (s, 3H) 3.85-3.93 (m, 4H) 7.11 (d, J=1.96 Hz, 1H) 7.59 (d, J=2.35 Hz, 1H) 7.73-7.83 (m, 1H) 7.95 (d, J=7.83 Hz, 1H) 8.26 (d, J=7.83 Hz, 1H) 8.32 (s, 1H) 8.35 (d, J=2.74 Hz, 1H) 8.75 (d, J=2.74 Hz, 1H). LCMS (m/z) (M+H)=493.0, Rt=0.84 min.

Example 408: N-(2-chloro-1'-methyl-5'-morpholino-6'-oxo-1',6'-dihydro-[3,3-bipyridin]-5-yl)-4-methoxy-3-(trifluoromethyl)benzamide

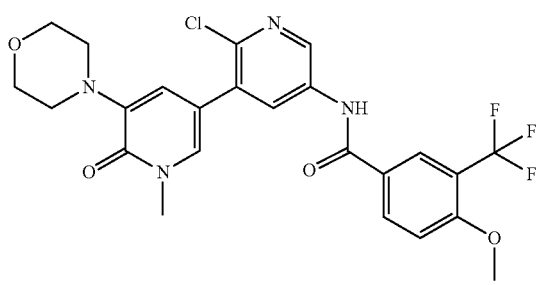 [SMILES: COc1ccc(C(=O)Nc2cnc(Cl)c(-c3cc(N4CCOCC4)c(=O)n(C)c3)c2)cc1C(F)(F)F]

$^1$H NMR (400 MHz, <cd3od>) δ ppm 3.12-3.24 (m, 4H) 3.67 (s, 3H) 3.84-3.93 (m, 4H) 4.03 (s, 3H) 7.10 (d, J=1.96 Hz, 1H) 7.37 (d, J=8.61 Hz, 1H) 7.59 (d, J=1.96 Hz, 1H) 8.21-8.37 (m, 3H) 8.72 (d, J=2.74 Hz, 1H). LCMS (m/z) (M+H)=523.2, Rt=0.83 min.

Example 409: N-(4-chloro-3-(1-methyl-5-morpholino-6-oxo-1,6-dihydropyridin-3-yl)phenyl)-3-(trifluoromethyl)benzamide

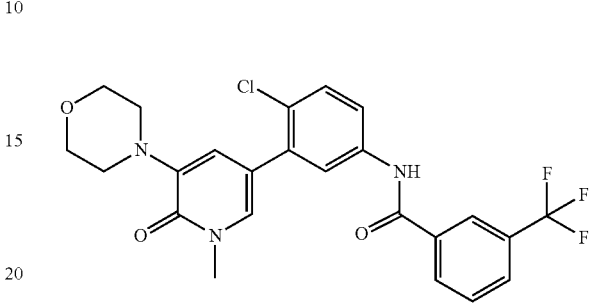

$^1$H NMR (400 MHz, <cd3od>) δ ppm 3.14-3.23 (m, 4H) 3.67 (s, 3H) 3.84-3.93 (m, 4H) 7.10 (d, J=1.96 Hz, 1H) 7.48-7.56 (m, 2H) 7.68-7.80 (m, 2H) 7.86 (d, J=2.74 Hz, 1H) 7.92 (d, J=7.83 Hz, 1H) 8.23 (d, J=7.83 Hz, 1H) 8.28 (s, 1H). LCMS (m/z) (M+H)=492.2, Rt=0.90 min.

Example 410: N-(4-chloro-3-(1-methyl-5-morpholino-6-oxo-1,6-dihydropyridin-3-yl)phenyl)-3-(trifluoromethyl)benzamide

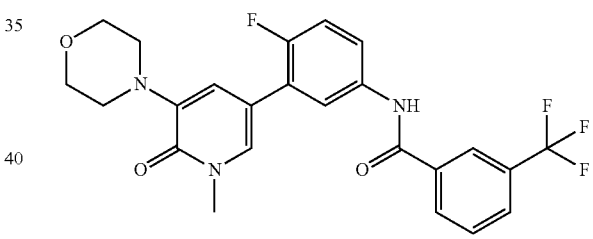

$^1$H NMR (400 MHz, <cd3od>) δ ppm 3.17-3.25 (m, 4H) 3.68 (s, 3H) 3.86-3.93 (m, 4H) 7.19 (s, 1H) 7.20-7.29 (m, 1H) 7.64-7.72 (m, 2H) 7.72-7.81 (m, 1H) 7.85-7.96 (m, 2H) 8.24 (d, J=7.83 Hz, 1H) 8.30 (s, 1H). LCMS (m/z) (M+H)=476.3, Rt=0.86 min.

Example 411: N-(4-cyano-3-(1-methyl-5-morpholino-6-oxo-1,6-dihydropyridin-3-yl)phenyl)-3-(trifluoromethyl)benzamide

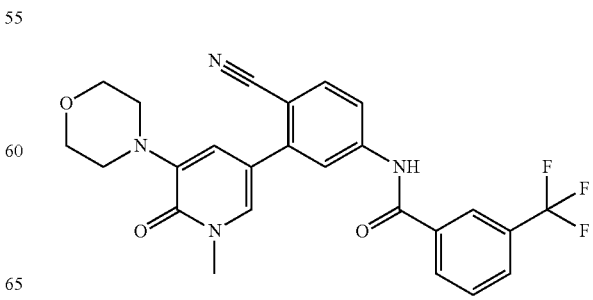

¹H NMR (400 MHz, <cd3od>) δ ppm 3.18-3.23 (m, 4H) 3.68 (s, 3H) 3.85-3.92 (m, 4H) 7.22 (d, J=1.96 Hz, 1H) 7.68 (dd, J=8.22, 1.57 Hz, 1H) 7.77-7.83 (m, 1H) 7.83-7.89 (m, 2H) 7.93 (d, J=1.57 Hz, 1H) 7.98 (d, J=7.83 Hz, 1H) 8.26-8.33 (m, 2H) 8.36 (s, 1H). LCMS (m/z) (M+H)=483.3, Rt=0.86 min.

Example 412: N-(4-chloro-3-(1-methyl-5-morpholino-6-oxo-1,6-dihydropyridin-3-yl)phenyl)-3-(difluoromethyl)benzamide

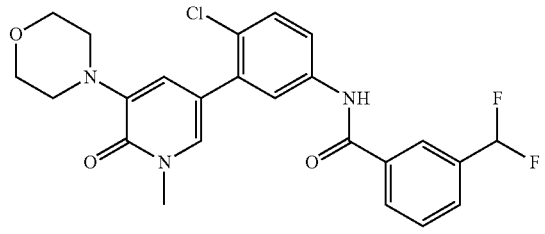 [SMILES: Cn1cc(-c2cc(NC(=O)c3cccc(C(F)F)c3)ccc2Cl)cc(N2CCOCC2)c1=O]

¹H NMR (400 MHz, <cd3od>) δ ppm 3.12-3.24 (m, 4H) 3.67 (s, 3H) 3.85-3.93 (m, 4H) 6.73-7.05 (m, 1H) 7.08 (d, J=2.35 Hz, 1H) 7.52 (dd, J=5.28, 3.33 Hz, 2H) 7.63-7.75 (m, 2H) 7.80 (d, J=7.83 Hz, 1H) 7.85 (d, J=2.35 Hz, 1H) 8.11 (d, J=7.83 Hz, 1H) 8.15 (s, 1H). LCMS (m/z) (M+H)=474.0, Rt=0.88 min.

Example 413: N-(4-chloro-3-(1-methyl-5-morpholino-6-oxo-1,6-dihydropyridin-3-yl)phenyl)-2-(trifluoromethyl)isonicotinamide

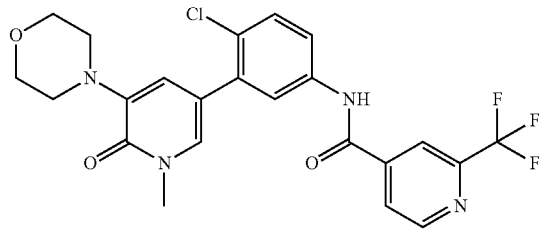

¹H NMR (400 MHz, <cd3od>) δ ppm 3.15-3.25 (m, 4H) 3.67 (s, 3H) 3.82-3.95 (m, 4H) 7.10 (d, J=1.96 Hz, 1H) 7.48-7.59 (m, 2H) 7.74 (dd, J=8.80, 2.54 Hz, 1H) 7.87 (d, J=2.35 Hz, 1H) 8.14 (d, J=4.70 Hz, 1H) 8.32 (s, 1H) 8.94 (d, J=5.09 Hz, 1H). LCMS (m/z) (M+H)=493.1, Rt=0.87 min.

Example 414: N-(4-chloro-3-(1-methyl-5-morpholino-6-oxo-1,6-dihydropyridin-3-yl)phenyl)-2-(1,1-difluoroethyl)isonicotinamide

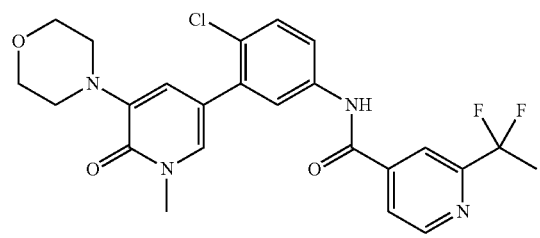 [SMILES: Cn1cc(-c2cc(NC(=O)c3ccnc(C(C)(F)F)c3)ccc2Cl)cc(N2CCOCC2)c1=O]

¹H NMR (400 MHz, <cd3od>) δ ppm 2.05 (t, J=18.78 Hz, 3H) 3.16-3.25 (m, 4H) 3.67 (s, 3H) 3.83-3.94 (m, 4H) 7.12 (d, J=2.35 Hz, 1H) 7.48-7.58 (m, 2H) 7.74 (dd, J=8.80, 2.54 Hz, 1H) 7.87 (d, J=2.74 Hz, 1H) 7.98 (d, J=4.70 Hz, 1H) 8.20 (s, 1H) 8.83 (d, J=5.09 Hz, 1H). LCMS (m/z) (M+H)=489.2, Rt=0.81 min.

Example 415: N-(4-cyano-3-(1-methyl-5-morpholino-6-oxo-1,6-dihydropyridin-3-yl)phenyl)-2-(trifluoromethyl)isonicotinamide

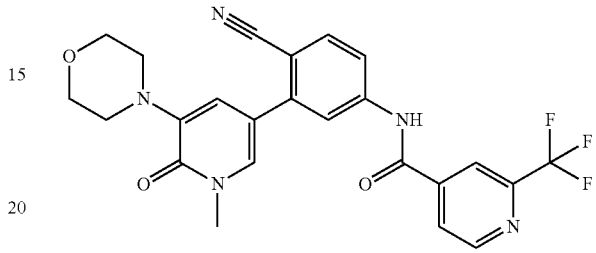

¹H NMR (400 MHz, <cd3od>) δ ppm 3.18-3.26 (m, 4H) 3.68 (s, 3H) 3.84-3.94 (m, 4H) 7.24 (d, J=1.96 Hz, 1H) 7.70 (dd, J=8.22, 1.57 Hz, 1H) 7.82-7.91 (m, 2H) 7.95 (d, J=1.57 Hz, 1H) 8.20 (d, J=4.30 Hz, 1H) 8.37 (s, 1H) 8.99 (d, J=5.09 Hz, 1H). LCMS (m/z) (M+H)=484.2, Rt=0.72 min.

Example 416: N-(4-cyano-3-(1-methyl-5-morpholino-6-oxo-1,6-dihydropyridin-3-yl)phenyl)-2-(1,1-difluoroethyl)isonicotinamide

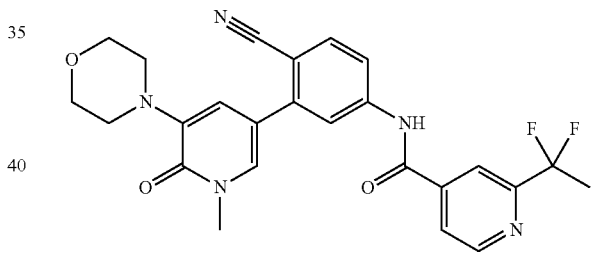

¹H NMR (400 MHz, <cd3od>) δ ppm 2.07 (t, J=18.78 Hz, 3H) 3.18-3.28 (m, 4H) 3.68 (s, 3H) 3.83-3.96 (m, 4H) 7.27 (d, J=1.96 Hz, 1H) 7.69 (dd, J=8.22, 1.57 Hz, 1H) 7.87 (dd, J=5.09, 3.13 Hz, 2H) 7.94 (d, J=1.17 Hz, 1H) 8.04 (d, J=4.70 Hz, 1H) 8.27 (s, 1H) 8.88 (d, J=4.70 Hz, 1H). LCMS (m/z) (M+H)=484.2, Rt=0.72 min.

Example 417: 3-(difluoromethyl)-N-(4-fluoro-3-(1-methyl-5-morpholino-6-oxo-1,6-dihydropyridin-3-yl)phenyl)benzamide

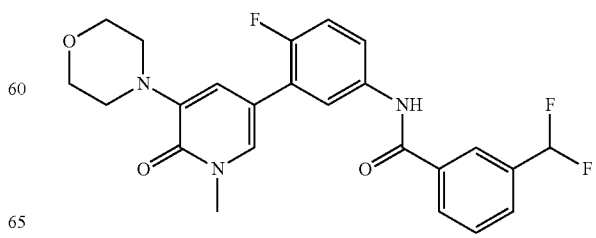

¹H NMR (400 MHz, <cd3od>) δ ppm 3.18-3.27 (m, 4H) 3.68 (s, 3H) 3.86-3.95 (m, 4H) 6.73-7.07 (m, 1H) 7.18-7.29 (m, 2H) 7.62-7.73 (m, 3H) 7.79 (d, J=7.83 Hz, 1H) 7.89 (dd, J=7.04, 2.74 Hz, 1H) 8.12 (d, J=7.83 Hz, 1H) 8.16 (s, 1H). LCMS (m/z) (M+H)=458.2, Rt=0.79 min.

Example 418: N-(4-cyano-3-(1-methyl-5-morpholino-6-oxo-1,6-dihydropyridin-3-yl)phenyl)-2-(trifluoromethyl)isonicotinamide

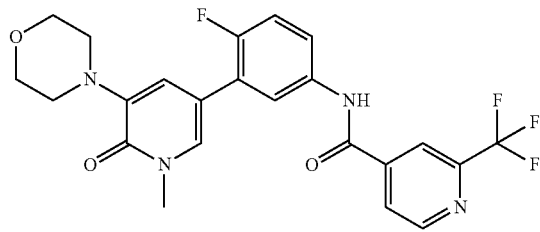 [SMILES: Cn1cc(-c2cc(NC(=O)c3ccnc(C(F)(F)F)c3)ccc2F)cc(N2CCOCC2)c1=O]

¹H NMR (400 MHz, <cd3od>) δ ppm 3.19-3.26 (m, 4H) 3.68 (s, 3H) 3.86-3.95 (m, 4H) 7.17-7.32 (m, 2H) 7.63-7.74 (m, 2H) 7.92 (dd, J=6.85, 2.54 Hz, 1H) 8.15 (d, J=4.70 Hz, 1H) 8.33 (s, 1H) 8.94 (d, J=5.09 Hz, 1H). LCMS (m/z) (M+H)=477.2, Rt=0.78 min.

Example 419: N-(4-cyano-3-(1-methyl-5-morpholino-6-oxo-1,6-dihydropyridin-3-yl)phenyl)-2-(trifluoromethyl)isonicotinamide

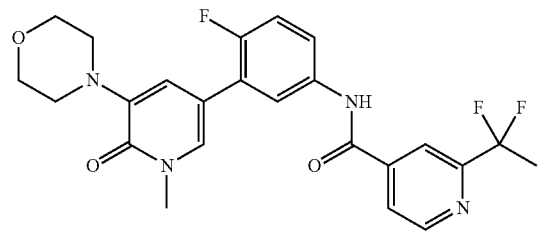 [SMILES: Cn1cc(-c2cc(NC(=O)c3ccnc(C(C)(F)F)c3)ccc2F)cc(N2CCOCC2)c1=O]

¹H NMR (400 MHz, <cd3od>) δ ppm 2.06 (t, J=18.59 Hz, 3H) 3.19-3.27 (m, 4H) 3.68 (s, 3H) 3.86-3.97 (m, 4H) 7.17-7.31 (m, 2H) 7.63-7.75 (m, 2H) 7.91 (dd, J=7.04, 2.35 Hz, 1H) 7.99 (d, J=4.70 Hz, 1H) 8.21 (s, 1H) 8.84 (d, J=5.09 Hz, 1H). LCMS (m/z) (M+H)=473.2, Rt=0.76 min.

Example 420: N-(4-cyano-3-(1-methyl-5-morpholino-6-oxo-1,6-dihydropyridin-3-yl)phenyl)-3-(difluoromethyl)benzamide

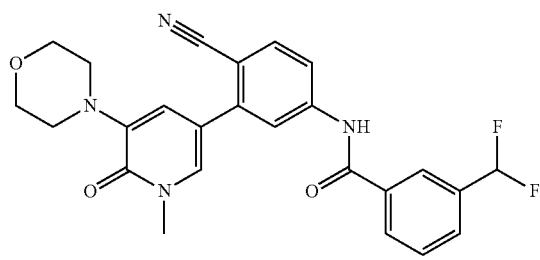 [SMILES: Cn1cc(-c2cc(NC(=O)c3cccc(C(F)F)c3)ccc2C#N)cc(N2CCOCC2)c1=O]

¹H NMR (400 MHz, <cd3od>) δ ppm 3.18-3.24 (m, 4H) 3.68 (s, 3H) 3.85-3.91 (m, 4H) 6.76-7.10 (m, 1H) 7.22 (d, J=2.35 Hz, 1H) 7.64-7.69 (m, 1H) 7.69-7.77 (m, 1H) 7.80-7.89 (m, 3H) 7.93 (d, J=1.57 Hz, 1H) 8.19 (d, J=7.83 Hz, 1H) 8.23 (s, 1H). LCMS (m/z) (M+H)=465.3, Rt=0.78 min.

Example 421: N-(4-chloro-3-(1-methyl-5-morpholino-6-oxo-1,6-dihydropyridin-3-yl)phenyl)-2-isopropylisonicotinamide

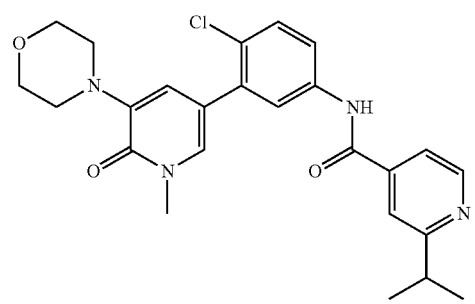 [SMILES: CC(C)c1cc(C(=O)Nc2ccc(Cl)c(-c3cc(N4CCOCC4)c(=O)n(C)c3)c2)ccn1]

¹H NMR (400 MHz, <cd3od>) δ ppm 1.44 (d, J=7.04 Hz, 6H) 3.12-3.21 (m, 4H) 3.66 (s, 3H) 3.83-3.93 (m, 4H) 7.04 (d, J=1.96 Hz, 1H) 7.50 (d, J=1.96 Hz, 1H) 7.55 (d, J=8.61 Hz, 1H) 7.71-7.78 (m, 1H) 7.86 (d, J=2.35 Hz, 1H) 8.00 (d, J=5.48 Hz, 1H) 8.11 (s, 1H) 8.77 (d, J=5.87 Hz, 1H). LCMS (m/z) (M+H)=467.1, Rt=0.67 min.

Example 422: N-(2-chloro-1'-methyl-5'-morpholino-6'-oxo-1',6'-dihydro-[3,3'-bipyridin]-5-yl)-2-isopropylisonicotinamide

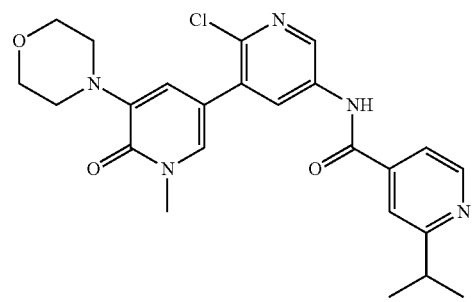 [SMILES: CC(C)c1cc(C(=O)Nc2cnc(Cl)c(-c3cc(N4CCOCC4)c(=O)n(C)c3)c2)ccn1]

¹H NMR (400 MHz, <cd3od>) δ ppm 1.45 (d, J=7.04 Hz, 6H) 3.14-3.22 (m, 4H) 3.67 (s, 3H) 3.84-3.92 (m, 4H) 7.07 (d, J=2.35 Hz, 1H) 7.57 (d, J=2.35 Hz, 1H) 8.05 (dd, J=5.48, 1.17 Hz, 1H) 8.16 (s, 1H) 8.34 (d, J=2.74 Hz, 1H) 8.76 (d, J=2.74 Hz, 1H) 8.80 (d, J=5.48 Hz, 1H). LCMS (m/z) (M+H)=468.1, Rt=0.59 min.

The compounds listed below were prepared using methods similar to those described for the preparation of Example 171 using the appropriate starting materials.

Example 423: 2-chloro-1'-methyl-5'-morpholino-6'-oxo-N-(3-(trifluoromethyl)phenyl)-1',6'-dihydro-[3,3'-bipyridine]-5-carboxamide

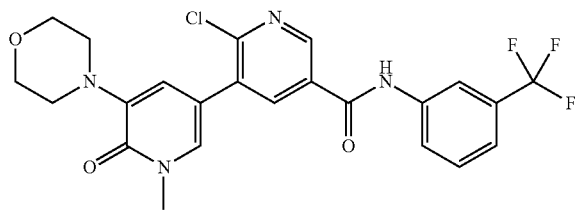 [SMILES: Cn1cc(-c2cc(C(=O)Nc3cccc(C(F)(F)F)c3)cnc2Cl)cc(N2CCOCC2)c1=O]

$^1$H NMR (400 MHz, <cd3od>) δ ppm 3.16-3.24 (m, 4H) 3.67 (s, 3H) 3.85-3.92 (m, 4H) 7.14 (d, J=1.96 Hz, 1H) 7.48 (d, J=7.83 Hz, 1H) 7.55-7.65 (m, 2H) 7.97 (d, J=7.83 Hz, 1H) 8.18 (s, 1H) 8.39 (d, J=2.35 Hz, 1H) 8.93 (d, J=2.35 Hz, 1H). LCMS (m/z) (M+H)=493.2, Rt=0.86 min.

Example 424: 2-chloro-N-(3-(2-hydroxypropan-2-yl)phenyl)-t-methyl-5'-morpholino-6'-oxo-1',6'-dihydro-[3,3'-bipyridine]-5-carboxamide

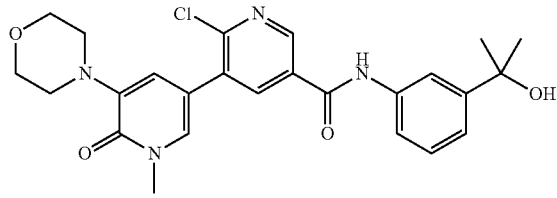 [SMILES: Cn1cc(-c2cc(C(=O)Nc3cccc(C(C)(C)O)c3)cnc2Cl)cc(N2CCOCC2)c1=O]

$^1$H NMR (400 MHz, <cd3od>) δ ppm 1.57 (s, 6H) 3.14-3.24 (m, 4H) 3.67 (s, 3H) 3.84-3.92 (m, 4H) 7.13 (d, J=1.96 Hz, 1H) 7.31-7.39 (m, 2H) 7.58-7.66 (m, 2H) 7.82 (s, 1H) 8.37 (d, J=2.35 Hz, 1H) 8.91 (d, J=1.96 Hz, 1H). LCMS (m/z) (M+H)=483.2, Rt=0.67 min.

Example 425: 4-chloro-3-(1-methyl-5-morpholino-6-oxo-1,6-dihydropyridin-3-yl)-N-(3-(trifluoromethyl)phenyl)benzamide

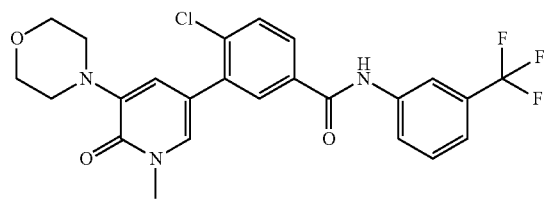 [SMILES: Cn1cc(-c2cc(C(=O)Nc3cccc(C(F)(F)F)c3)ccc2Cl)cc(N2CCOCC2)c1=O]

$^1$H NMR (400 MHz, <cd3od>) δ ppm 3.16-3.25 (m, 4H) 3.67 (s, 3H) 3.84-3.94 (m, 4H) 7.15 (d, J=2.35 Hz, 1H) 7.46 (d, J=7.83 Hz, 1H) 7.52-7.62 (m, 2H) 7.69 (d, J=8.61 Hz, 1H) 7.91-7.99 (m, 2H) 8.01 (d, J=2.35 Hz, 1H) 8.17 (s, 1H). LCMS (m/z) (M+H)=492.2, Rt=0.92 min.

Example 426: 4-chloro-N-(3-(difluoromethyl)phenyl)-3-(1-methyl-5-morpholino-6-oxo-1,6-dihydropyridin-3-yl)benzamide

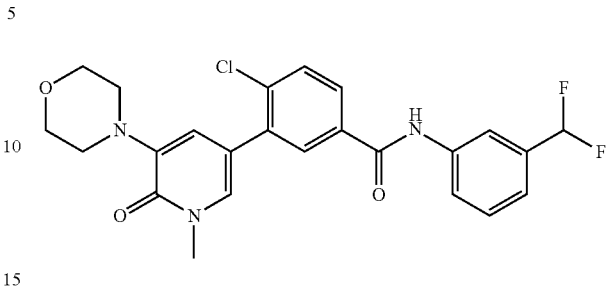

$^1$H NMR (400 MHz, <cd3od>) δ ppm 3.16-3.25 (m, 4H) 3.67 (s, 3H) 3.84-3.95 (m, 4H) 6.60-6.97 (m, 1H) 7.13 (d, J=2.35 Hz, 1H) 7.35 (d, J=7.83 Hz, 1H) 7.51 (t, J=7.83 Hz, 1H) 7.57 (d, J=1.96 Hz, 1H) 7.69 (d, J=8.22 Hz, 1H) 7.85 (d, J=8.22 Hz, 1H) 7.94 (dd, J=8.22, 1.96 Hz, 1H) 7.97-8.07 (m, 2H). LCMS (m/z) (M+H)=474.2, Rt=0.84 min.

Example 427: 4-chloro-N-(3-(2-cyanopropan-2-yl)phenyl)-3-(1-methyl-5-morpholino-6-oxo-1,6-dihydropyridin-3-yl)benzamide

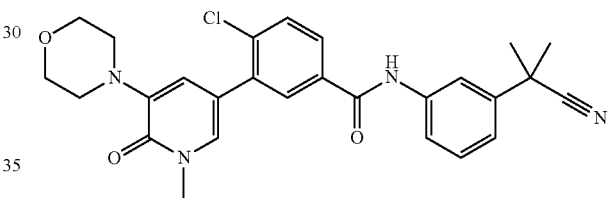

$^1$H NMR (400 MHz, <cd3od>) δ ppm 1.77 (s, 6H) 3.15-3.22 (m, 4H) 3.67 (s, 3H) 3.83-3.93 (m, 4H) 7.10 (d, J=2.35 Hz, 1H) 7.35 (d, J=8.22 Hz, 1H) 7.45 (t, J=8.02 Hz, 1H) 7.56 (d, J=2.35 Hz, 1H) 7.66-7.75 (m, 2H) 7.91-7.98 (m, 2H) 8.01 (d, J=2.35 Hz, 1H). LCMS (m/z) (M+H)=491.3, Rt=0.85 min.

Example 428: 4-methyl-N-(3-(4-methyl-1H-imidazol-1-yl)-5-(trifluoromethyl)phenyl)-3-(1-methyl-5-morpholino-6-oxo-1,6-dihydropyridin-3-yl)benzamide

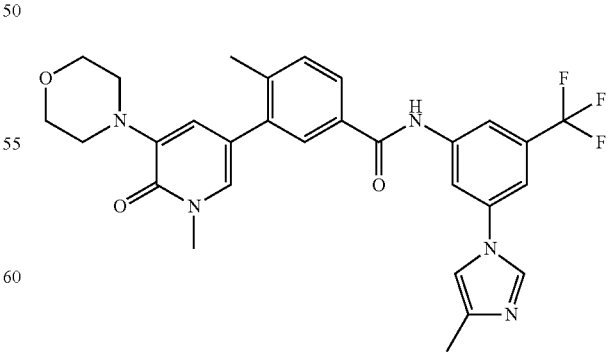

$^1$H NMR (400 MHz, <cd3od>) δ ppm 2.43 (s, 3H) 2.48 (s, 3H) 3.10-3.22 (m, 4H) 3.67 (s, 3H) 3.82-3.94 (m, 4H) 6.95 (d, J=1.96 Hz, 1H) 7.40 (d, J=1.96 Hz, 1H) 7.50 (d, J=7.83 Hz, 1H) 7.79-7.99 (m, 4H) 8.16 (s, 1H) 8.61 (s, 1H) 9.44 (s, 1H). LCMS (m/z) (M+H)=552.3, Rt=0.69 min.

Example 429: 4-methyl-3-(1-methyl-5-morpholino-6-oxo-1,6-dihydropyridin-3-yl)-N-phenylbenzamide

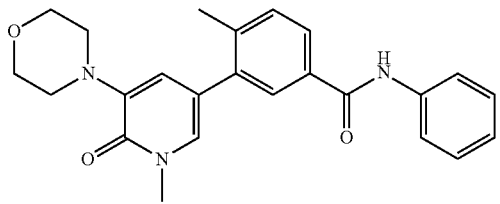 [SMILES: Cc1ccc(C(=O)Nc2ccccc2)cc1-c1cc(N2CCOCC2)c(=O)n(C)c1]

¹H NMR (400 MHz, <cd3od>) δ ppm 2.39 (s, 3H) 3.09-3.24 (m, 4H) 3.65 (s, 3H) 3.81-4.07 (m, 4H) 7.03 (d, J=1.96 Hz, 1H) 7.11-7.19 (m, 1H) 7.35 (t, J=7.83 Hz, 2H) 7.41-7.46 (m, 2H) 7.67 (d, J=7.83 Hz, 2H) 7.81 (s, 1H) 7.84 (dd, J=7.83, 1.96 Hz, 1H), LCMS (m/z) (M+H)=404.1, Rt=0.77 min.

Example 430: N-(3-(difluoromethyl)phenyl)-4-methyl-3-(1-methyl-5-morpholino-6-oxo-1,6-dihydropyridin-3-yl)benzamide

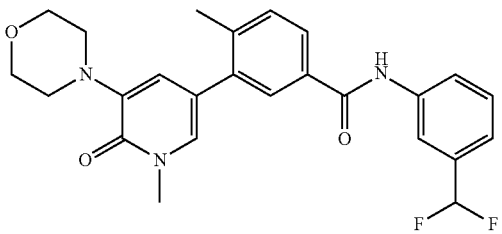 [SMILES: Cc1ccc(C(=O)Nc2cccc(C(F)F)c2)cc1-c1cc(N2CCOCC2)c(=O)n(C)c1]

¹H NMR (400 MHz, <cd3od>) δ ppm 2.40 (s, 3H) 3.07-3.23 (m, 4H) 3.65 (s, 3H) 3.80-3.92 (m, 4H) 6.51-6.95 (m, 1H) 7.02 (d, J=1.96 Hz, 1H) 7.31 (d, J=7.83 Hz, 1H) 7.38-7.62 (m, 3H) 7.74-7.89 (m, 3H) 7.97 (s, 1H), LCMS (m/z) (M+H)=454.1, Rt=0.85 min.

Example 431: N-(3-(2-cyanopropan-2-yl)phenyl)-4-methyl-3-(1-methyl-5-morpholino-6-oxo-1,6-dihydropyridin-3-yl)benzamide

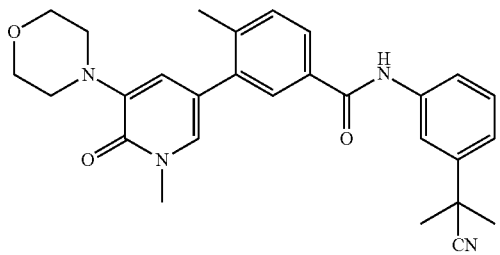 [SMILES: Cc1ccc(C(=O)Nc2cccc(C(C)(C)C#N)c2)cc1-c1cc(N2CCOCC2)c(=O)n(C)c1]

¹H NMR (400 MHz, <cd3od>) δ ppm 1.74 (s, 6H) 2.40 (s, 3H) 3.09-3.23 (m, 4H) 3.65 (s, 3H) 3.82-3.94 (m, 4H) 7.03 (d, J=1.96 Hz, 1H) 7.31 (d, J=7.83 Hz, 1H) 7.38-7.51 (m, 3H) 7.68 (d, J=8.22 Hz, 1H) 7.80-7.89 (m, 2H) 7.93 (s, 1H), LCMS (m/z) (M+H)=471.2, Rt=0.85 min.

Example 432: 4-methyl-3-(1-methyl-5-morpholino-6-oxo-1,6-dihydropyridin-3-yl)-N-(pyridin-2-yl)benzamide

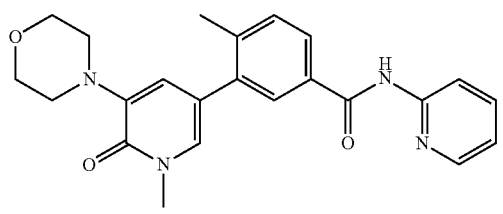 [SMILES: Cc1ccc(C(=O)Nc2ccccn2)cc1-c1cc(N2CCOCC2)c(=O)n(C)c1]

¹H NMR (400 MHz, <cd3od>) δ ppm 2.42 (s, 3H) 3.01-3.20 (m, 4H) 3.64 (s, 3H) 3.80-3.91 (m, 4H) 6.94 (d, J=1.96 Hz, 1H) 7.39 (d, J=2.35 Hz, 1H) 7.44-7.63 (m, 2H) 7.83-8.00 (m, 3H) 8.15-8.31 (m, 1H) 8.42 (d, J=5.48 Hz, 1H), LCMS (m/z) (M+H)=405.1, Rt=0.56 min.

Example 433: 4-methyl-3-(1-methyl-5-morpholino-6-oxo-1,6-dihydropyridin-3-yl)-N-(pyridin-3-yl)benzamide

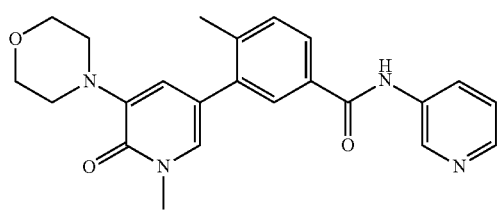 [SMILES: Cc1ccc(C(=O)Nc2cccnc2)cc1-c1cc(N2CCOCC2)c(=O)n(C)c1]

¹H NMR (400 MHz, <cd3od>) δ ppm 2.41 (s, 3H) 3.07-3.18 (m, 4H) 3.64 (s, 3H) 3.81-3.92 (m, 4H) 6.92 (d, J=1.96 Hz, 1H) 7.38 (d, J=1.96 Hz, 1H) 7.48 (d, J=7.83 Hz, 1H) 7.84-8.01 (m, 3H) 8.52 (d, J=5.09 Hz, 1H) 8.61 (d, J=8.22 Hz, 1H) 9.42 (d, J=2.35 Hz, 1H), LCMS (m/z) (M+H)=405.1, Rt=0.51 min.

Example 434: 4-methyl-3-(1-methyl-5-morpholino-6-oxo-1,6-dihydropyridin-3-yl)-N-(4-(trifluoromethyl)pyridin-2-yl)benzamide

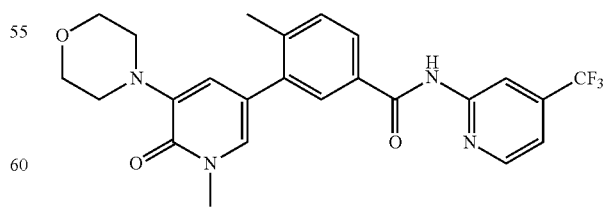

¹H NMR (400 MHz, <cd3od>) δ ppm 2.41 (s, 3H) 3.00-3.22 (m, 4H) 3.65 (s, 3H) 3.82-3.98 (m, 4H) 7.01 (d, J=1.56 Hz, 1H) 7.35-7.54 (m, 3H) 7.79-7.99 (m, 2H) 8.48-8.65 (m, 2H), LCMS (m/z) (M+H)=473.2, Rt=0.86 min.

Example 435: N-(3-ethylphenyl)-4-methyl-3-(1-methyl-5-morpholino-6-oxo-1,6-dihydropyridin-3-yl)benzamide

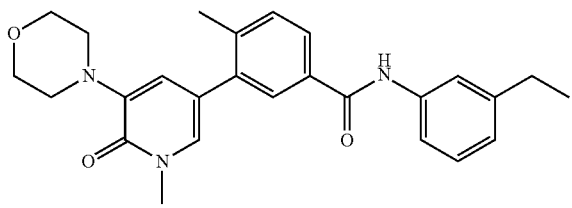 [SMILES: CCc1cccc(NC(=O)c2ccc(C)c(-c3cc(N4CCOCC4)c(=O)n(C)c3)c2)c1]

¹H NMR (400 MHz, <cd3od>) δ ppm 1.25 (t, J=7.43 Hz, 3H) 2.39 (s, 3H) 2.66 (q, J=7.56 Hz, 2H) 3.08-3.23 (m, 4H) 3.65 (s, 3H) 3.80-3.98 (m, 4H) 6.85-7.09 (m, 2H) 7.26 (t, J=7.83 Hz, 1H) 7.35-7.58 (m, 4H) 7.75-7.98 (m, 2H), LCMS (m/z) (M+H)=432.3, Rt=0.87 min.

Example 436: N-(3-isopropylphenyl)-4-methyl-3-(1-methyl-5-morpholino-6-oxo-1,6-dihydropyridin-3-yl)benzamide

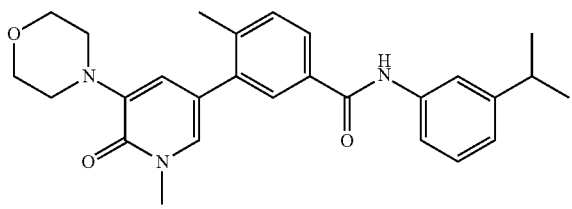 [SMILES: Cc1ccc(C(=O)Nc2cccc(C(C)C)c2)cc1-c1cc(N2CCOCC2)c(=O)n(C)c1]

1H NMR (400 MHz, <cd3od>) δ ppm 1.26 (d, J=7.04 Hz, 7H) 2.39 (s, 3H) 2.90 (dt, J=13.69, 6.85 Hz, 1H) 3.13-3.25 (m, 4H) 3.65 (s, 3H) 3.81-4.01 (m, 4H) 7.03 (d, J=7.43 Hz, 1H) 7.09 (d, J=1.57 Hz, 1H) 7.26 (t, J=7.83 Hz, 1H) 7.38-7.52 (m, 3H) 7.56 (s, 1H) 7.78-7.91 (m, 1H), LCMS (m/z) (M+H)=446.3, Rt=0.92 min.

Example 437: N-(3-(1,3,4-oxadiazol-2-yl)phenyl)-4-methyl-3-(1-methyl-5-morpholino-6-oxo-1,6-dihydropyridin-3-yl)benzamide

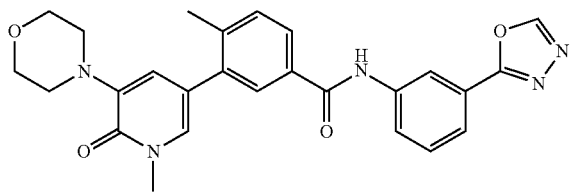 [SMILES: Cc1ccc(C(=O)Nc2cccc(-c3nnco3)c2)cc1-c1cc(N2CCOCC2)c(=O)n(C)c1]

¹H NMR (400 MHz, <cd3od>) δ ppm 2.40 (s, 3H) 3.17 (br. s., 4H) 3.65 (s, 3H) 3.78-3.99 (m, 4H) 6.99 (d, J=1.96 Hz, 1H) 7.41 (d, J=1.96 Hz, 1H) 7.46 (d, J=7.83 Hz, 1H) 7.58 (t, J=8.02 Hz, 1H) 7.82-7.90 (m, 3H) 7.96 (d, J=7.83 Hz, 1H) 8.52 (s, 1H) 9.03 (s, 1H), LCMS (m/z) (M+H)=472.2, Rt=0.69 min.

Example 438: 4-methyl-N-(3-(5-methyl-1,2,4-oxadiazol-3-yl)phenyl)-3-(1-methyl-5-morpholino-6-oxo-1,6-dihydropyridin-3-yl)benzamide

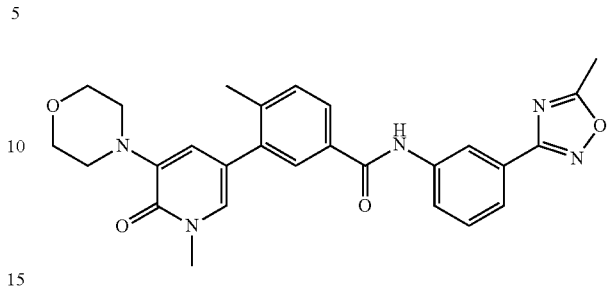

¹H NMR (400 MHz, <cd3od>) δ ppm 2.41 (s, 3H) 2.66 (s, 3H) 3.25 (br. s., 4H) 3.66 (s, 3H) 3.83-3.99 (m, 4H) 7.12 (s, 1H) 7.49 (dt, J=16.34, 8.07 Hz, 3H) 7.77-7.96 (m, 4H) 8.42 (s, 1H), LCMS (m/z) (M+H)=486.3, Rt=0.80 min.

Example 439: N-(3-(2-hydroxypropan-2-yl)phenyl)-4-methyl-3-(1-methyl-5-morpholino-6-oxo-1,6-dihydropyridin-3-yl)benzamide

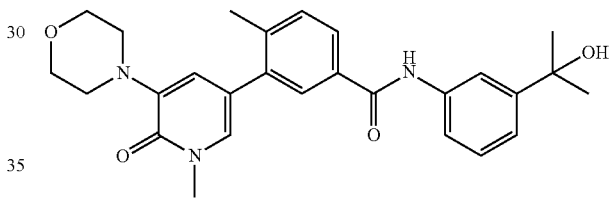

¹H NMR (400 MHz, <cd3od>) δ ppm 1.54 (s, 6H) 2.39 (s, 3H) 3.16 (br. s., 4H) 3.64 (s, 3H) 3.79-4.13 (m, 4H) 6.98 (d, J=1.57 Hz, 1H) 7.18-7.34 (m, 2H) 7.35-7.50 (m, 2H) 7.58 (d, J=7.04 Hz, 1H) 7.75-7.94 (m, 1H), LCMS (m/z) (M+H)=462.3, Rt=0.70 min.

Example 440: N-(3-methoxyphenyl)-4-methyl-3-(1-methyl-5-morpholino-6-oxo-1,6-dihydropyridin-3-yl)benzamide

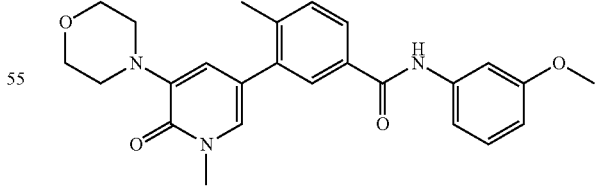

¹H NMR (400 MHz, <cd3od>) δ ppm 2.41 (s, 3H) 3.16-3.22 (m, 4H) 3.67 (s, 3H) 3.83 (s, 3H) 3.85-3.91 (m, 4H) 6.74 (dt, J=7.14, 2.10 Hz, 1H) 7.01 (d, J=1.96 Hz, 1H) 7.20-7.31 (m, 2H) 7.39-7.44 (m, 2H) 7.46 (d, J=7.83 Hz, 1H) 7.82 (s, 1H) 7.86 (dd, J=8.02, 1.76 Hz, 1H). LCMS (m/z) (M+H)=434.3, Rt=0.80 min.

Example 441: 4-methyl-3-(1-methyl-5-morpholino-6-oxo-1,6-dihydropyridin-3-yl)-N-(3-(trifluoromethoxy)phenyl)benzamide

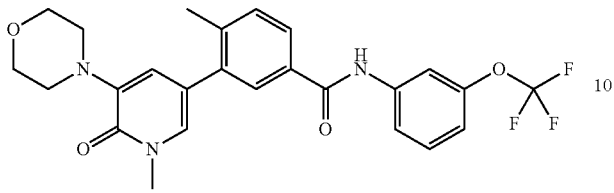

$^1$H NMR (400 MHz, <cd3od>) δ ppm 2.42 (s, 3H) 3.17-3.23 (m, 4H) 3.67 (s, 3H) 3.85-3.93 (m, 4H) 7.00-7.09 (m, 2H) 7.41-7.50 (m, 3H) 7.67 (d, J=9.39 Hz, 1H) 7.82-7.90 (m, 3H). LCMS (m/z) (M+H)=488.4, Rt=0.96 min.

Example 442: N-(5-methoxypyridin-3-yl)-4-methyl-3-(1-methyl-5-morpholino-6-oxo-1,6-dihydropyridin-3-yl)benzamide

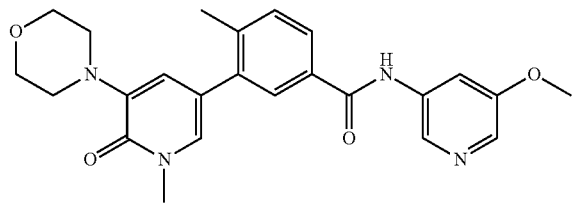 [SMILES: COc1cncc(NC(=O)c2ccc(C)c(-c3cc(N4CCOCC4)c(=O)n(C)c3)c2)c1]

$^1$H NMR (400 MHz, <cd3od>) δ ppm 2.43 (s, 3H) 3.13-3.19 (m, 4H) 3.66 (s, 3H) 3.85-3.91 (m, 4H) 4.01 (s, 3H) 6.95 (d, J=1.96 Hz, 1H) 7.40 (d, J=1.96 Hz, 1H) 7.50 (d, J=7.83 Hz, 1H) 7.89 (s, 1H) 7.90-7.96 (m, 1H) 8.21 (d, J=16.04 Hz, 2H) 8.88 (s, 1H). LCMS (m/z) (M+H)=435.3, Rt=0.57 min.

Synthesis of 1',2-dimethyl-5'-morpholino-6'-oxo-1',6'-dihydro-[3,3'-bipyridine]-5-carboxylic acid

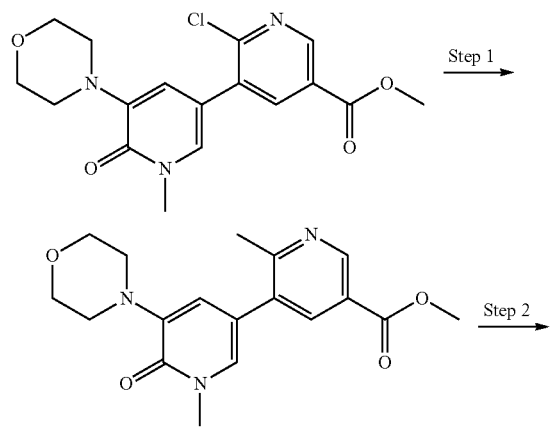

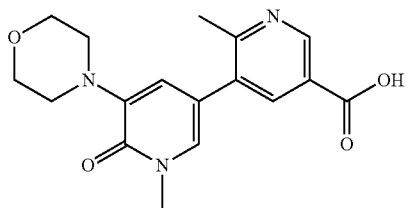

Step 1:

To a 0.15M solution of methyl 2-chloro-1-methyl-5'-morpholino-6'-oxo-1',6'-dihydro-[3,3-bipyridine]-5-carboxylate (1.00 equiv.) in DME was added trimethylboroxine (2.00 equiv.), PdCl2(dppf).CH2Cl2 adduct (0.10 equiv.), and 2M aqueous sodium carbonate (3.00 equiv.). The reaction mixture was irradiated at 130° C. for 15 min in the microwave. The cooled reaction mixture was diluted with 2:1 DCM:MeOH and filtered. The filtrate was concentrated and purified by flash chromatography over silica gel (heptanes with 50-100% 10:1 ethyl acetate:methanol gradient) to give methyl 1',2-dimethyl-5'-morpholino-6'-oxo-1',6'-dihydro-[3,3'-bipyridine]-5-carboxylate (17.0% yield) as a yellow film. LCMS (m/z) (M+H)=344.1, Rt=0.43 min.

Step 2:

To a 0.10M solution of methyl 1',2-dimethyl-5'-morpholino-6'-oxo-1',6'-dihydro-[3,3'-bipyridine]-5-carboxylate (1.00 equiv.) in THF was added 2.0M aqueous lithium hydroxide (3.00 equiv.). The mixture was stirred at ambient temperature for 1.5 hr. The reaction mixture was acidified to pH 3 with aqueous HCl and concentrated to give crude 1',2-dimethyl-5'-morpholino-6'-oxo-1',6'-dihydro-[3,3'-bipyridine]-5-carboxylic acid as a yellow solid (assumed 100% yield). LCMS (m/z) (M+H)=330.0, Rt=0.32 min.

The compounds listed below were prepared using methods similar to those described for the preparation of Example 171 using the appropriate starting materials.

Example 443: 1',2-dimethyl-5'-morpholino-6'-oxo-N-(3-(trifluoromethyl)phenyl)-1',6'-dihydro-[3,3'-bipyridine]-5-carboxamide

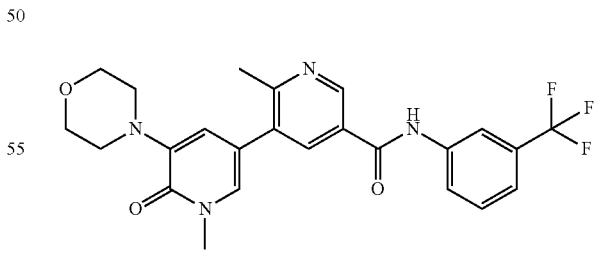

$^1$H NMR (400 MHz, <cd3od>) δ ppm 2.74 (s, 3H) 3.13-3.26 (m, 4H) 3.67 (s, 3H) 3.83-3.94 (m, 4H) 7.01 (d, J=1.96 Hz, 1H) 7.49 (d, J=7.83 Hz, 1H) 7.54 (d, J=2.35 Hz, 1H) 7.60 (t, J=8.02 Hz, 1H) 7.98 (d, J=8.22 Hz, 1H) 8.19 (s, 1H) 8.55 (d, J=1.96 Hz, 1H) 9.11 (d, J=1.96 Hz, 1H). LCMS (m/z) (M+H)=473.2, Rt=0.69 min.

Example 444: N-(3-(2-cyanopropan-2-yl)phenyl)-1',2-dimethyl-5'-morpholino-6'-oxo-1',6'-dihydro-[3,3'-bipyridine]-5-carboxamide

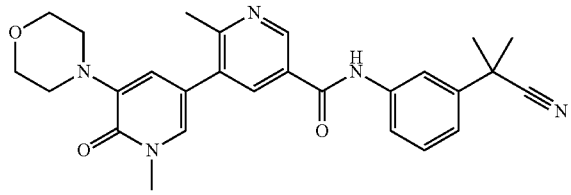 [SMILES: Cc1ncc(C(=O)Nc2cccc(C(C)(C)C#N)c2)cc1-c1cc(N2CCOCC2)c(=O)n(C)c1]

$^1$H NMR (400 MHz, <cd3od>) δ ppm 1.76 (s, 6H) 2.77 (s, 3H) 3.12-3.25 (m, 4H) 3.67 (s, 3H) 3.80-3.94 (m, 4H) 7.01 (d, J=2.35 Hz, 1H) 7.36 (d, J=8.22 Hz, 1H) 7.46 (t, J=7.83 Hz, 1H) 7.55 (d, J=1.96 Hz, 1H) 7.75 (d, J=8.22 Hz, 1H) 7.98 (s, 1H) 8.64 (d, J=1.96 Hz, 1H) 9.13 (d, J=1.57 Hz, 1H). LCMS (m/z) (M+H)=472.3, Rt=0.63 min.

Example 445: N-(3-(difluoromethyl)phenyl)-1',2-dimethyl-5'-morpholino-6'-oxo-1',6'-dihydro-[3,3'-bipyridine]-5-carboxamide

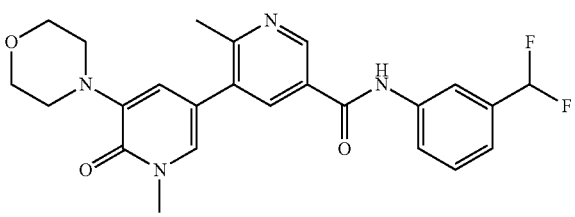 [SMILES: Cc1ncc(C(=O)Nc2cccc(C(F)F)c2)cc1-c1cc(N2CCOCC2)c(=O)n(C)c1]

$^1$H NMR (400 MHz, <cd3od>) δ ppm 2.73 (s, 3H) 3.15-3.24 (m, 4H) 3.67 (s, 3H) 3.83-3.94 (m, 4H) 6.63-6.97 (m, 1H) 7.01 (d, J=1.96 Hz, 1H) 7.37 (d, J=7.83 Hz, 1H) 7.48-7.60 (m, 2H) 7.87 (d, J=8.22 Hz, 1H) 8.02 (s, 1H) 8.51 (d, J=1.96 Hz, 1H) 9.09 (d, J=2.35 Hz, 1H). LCMS (m/z) (M+H)=455.2, Rt=0.60 min.

Example 446: N-(3-(2-hydroxypropan-2-yl)phenyl)-1',2-dimethyl-5'-morpholino-6'-oxo-1',6'-dihydro-[3,3'-bipyridine]-5-carboxamide

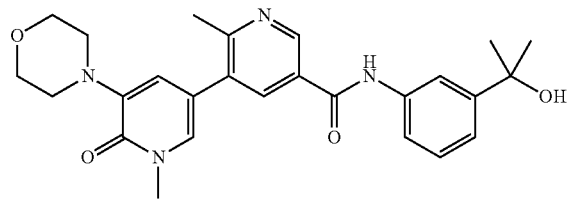 [SMILES: Cc1ncc(C(=O)Nc2cccc(C(C)(C)O)c2)cc1-c1cc(N2CCOCC2)c(=O)n(C)c1]

$^1$H NMR (400 MHz, <cd3od>) δ ppm 1.56 (s, 6H) 2.77 (s, 3H) 3.11-3.25 (m, 4H) 3.67 (s, 3H) 3.80-3.94 (m, 4H) 7.02 (d, J=1.96 Hz, 1H) 7.29-7.41 (m, 2H) 7.56 (d, J=1.96 Hz, 1H) 7.64 (d, J=7.04 Hz, 1H) 7.83 (s, 1H) 8.67 (d, J=1.57 Hz, 1H) 9.13 (d, J=1.96 Hz, 1H). LCMS (m/z) (M+H)=463.3, Rt=0.52 min.

Example 451: N-(4-methyl-3-(1-methyl-6-oxo-5-(3-oxomorpholino)-1,6-dihydropyridin-3-yl)phenyl)-3-(trifluoromethyl)benzamide

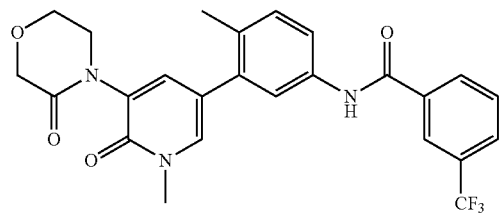 [SMILES: Cc1ccc(NC(=O)c2cccc(C(F)(F)F)c2)cc1-c1cc(N2CCOCC2=O)c(=O)n(C)c1]

To a 0.1M solution of N-(4-methyl-3-(1-methyl-5-morpholino-6-oxo-1,6-dihydropyridin-3-yl)phenyl)-3-(trifluoromethyl)benzamide (1.00 equiv.) in DCM was added benzyltriethylammonium chloride (4.10 equiv.) and potassium permanganate (4.00 equiv.). The mixture was stirred at 45° C. for 7 hr. The cooled reaction mixture was diluted with water and treated with sodium bisulfite (12.0 equiv.). The mixture was stirred for 15 min at ambient temperature. Additional water was added, and the mixture was extracted with DCM. The organic layer was washed with saturated aqueous sodium bicarbonate, dried over sodium sulfate, filtered, and concentrated. The crude material was purified by reverse-phase HPLC and lyophilized to give N-(4-methyl-3-(1-methyl-6-oxo-5-(3-oxomorpholino)-1,6-dihydropyridin-3-yl)phenyl)-3-(trifluoromethyl)benzamide as its TFA salt, a white solid, in 11.0% yield.

$^1$H NMR (400 MHz, <cd3od>) δ ppm 2.35 (s, 3H) 3.67-3.80 (m, 5H) 4.02-4.12 (m, 2H) 4.31 (s, 2H) 7.33 (d, J=8.22 Hz, 1H) 7.58-7.68 (m, 2H) 7.71-7.78 (m, 2H) 7.80 (d, J=2.35 Hz, 1H) 7.91 (d, J=7.83 Hz, 1H) 8.22 (d, J=7.83 Hz, 1H) 8.28 (s, 1H); LCMS (m/z) (M+H)=486.1, Rt=0.86 min.

Example 452: 2-(dimethylamino)-N-(4-methyl-3-(1-methyl-5-morpholino-6-oxo-1,6-dihydropyridin-3-yl)phenyl)isonicotinamide

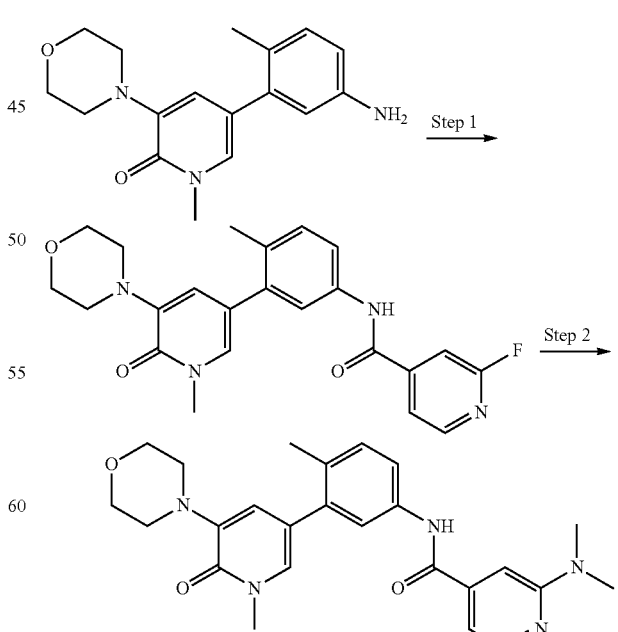

Step 1:

To a solution of 5-(5-amino-2-methylphenyl)-1-methyl-3-morpholinopyridin-2(1H)-one (1.0 equiv.) in DMF (0.09M) was added 2-fluoroisonicotinic acid (1.2 equiv), EDC (1.2 equiv.) and HOAt (1.2 equiv.). The solution was stirred at room temperature overnight. Worked up by partitioning between water and ethyl acetate, the organic phase was dried with sodium sulfate, filtered and concentrated. The crude material was used for the next step without further purification. LCMS (m/z) (M+H)=423, Rt=0.74 min.

Step 2:

To a solution of 2-fluoro-N-(4-methyl-3-(1-methyl-5-morpholino-6-oxo-1,6-dihydropyridin-3-yl)phenyl)isonicotinamide (1.0 equiv.) in DMSO was added dimethyl amine (1.5 equiv., HCl salt) and DIEA (2.0 equiv.) and the reaction was heated to 140 C for 3 hours. The solution was then filtered through a HPLC filter and purified via reverse phase prep-HPLC. The pure fractions were lyophilized to yield 2-(dimethylamino)-N-(4-methyl-3-(1-methyl-5-morpholino-6-oxo-1,6-dihydropyridin-3-yl)phenyl)isonicotinamide as the TFA salt. 1H NMR (400 MHz, <cd3od>) δ ppm 2.31 (s, 3H) 3.13 (d, J=3.52 Hz, 4H) 3.34 (s, 6H) 3.63 (s, 3H) 3.78-3.91 (m, 4H) 6.89 (d, J=1.96 Hz, 1H) 7.19-7.39 (m, 3H) 7.53-7.74 (m, 3H) 8.04 (d, J=6.65 Hz, 1H), LCMS (m/z) (M+H)=449.2, Rt=0.60 min.

The compounds listed below were prepared using methods similar to those described for the preparation of Example 452 using the appropriate starting materials.

Example 453: 2-(ethyl(methyl)amino)-N-(4-methyl-3-(1-methyl-5-morpholino-6-oxo-1,6-dihydropyridin-3-yl)phenyl)isonicotinamide

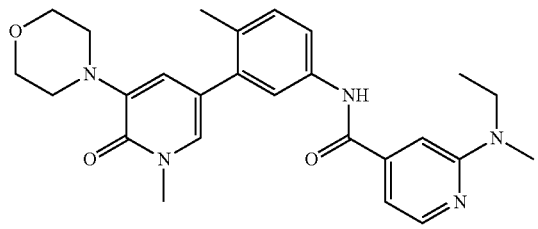 [SMILES: CCN(C)c1cc(C(=O)Nc2ccc(C)c(-c3cc(N4CCOCC4)c(=O)n(C)c3)c2)ccn1]

1H NMR (400 MHz, <cd3od>) δ ppm 1.31 (t, J=7.24 Hz, 3H) 2.31 (s, 3H) 3.03-3.18 (m, 4H) 3.75 (q, J=7.04 Hz, 2H) 3.81-3.91 (m, 4H) 6.89 (d, J=1.96 Hz, 1H) 7.20-7.38 (m, 3H) 7.54-7.70 (m, 3H) 8.02 (d, J=6.26 Hz, 1H), LCMS (m/z) (M+H)=462.2, Rt=0.61 min.

Example 454: 2-(azetidin-1-yl)-N-(4-methyl-3-(1-methyl-5-morpholino-6-oxo-1,6-dihydropyridin-3-yl)phenyl)isonicotinamide

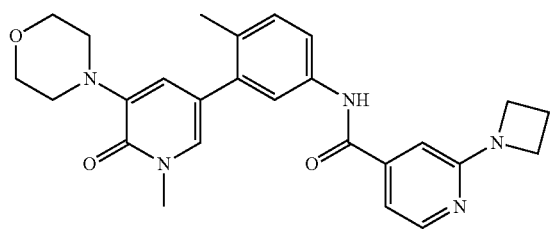 [SMILES: Cc1ccc(NC(=O)c2ccnc(N3CCC3)c2)cc1-c1cc(N2CCOCC2)c(=O)n(C)c1]

1H NMR (400 MHz, <cd3od>) δ ppm 2.30 (s, 3H) 2.61 (quin, J=7.73 Hz, 2H) 3.03-3.16 (m, 4H) 3.63 (s, 3H) 3.79-4.05 (m, 4H) 4.39 (t, J=7.63 Hz, 4H) 6.89 (d, J=2.35 Hz, 1H) 7.18-7.37 (m, 4H) 7.53-7.67 (m, 2H) 7.98 (d, J=6.65 Hz, 1H), LCMS (m/z) (M+H)=460.2, Rt=0.60 min.

Example 455: 2-((2-methoxyethyl)(methyl)amino)-N-(4-methyl-3-(1-methyl-5-morpholino-6-oxo-1,6-dihydropyridin-3-yl)phenyl)isonicotinamide

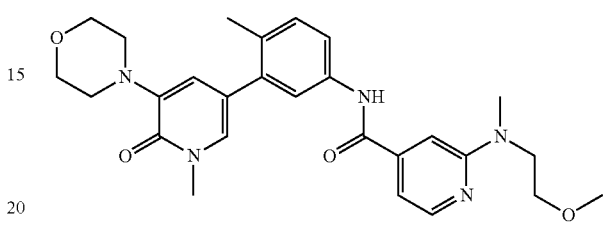

¹H NMR (500 MHz, METHANOL-d₄) δ ppm 2.34 (s, 3H) 3.16 (br. s., 4H) 3.37 (s, 3H) 3.39 (s, 3H) 3.66 (s, 3H) 3.74 (t, J=4.89 Hz, 2H) 3.82-3.90 (m, 4H) 3.94 (t, J=5.04 Hz, 2H) 6.93 (d, J=1.89 Hz, 1H) 7.29-7.39 (m, 3H) 7.59-7.65 (m, 2H) 7.73 (s, 1H) 8.05 (d, J=6.31 Hz, 1H), LCMS (m/z) (M+H)=492.2, Rt=0.64 min.

Example 456: 2-(2-hydroxyethyl)(methyl)amino)-N-(4-methyl-3-(1-methyl-5-morpholino-6-oxo-1,6-dihydropyridin-3-yl)phenyl)isonicotinamide

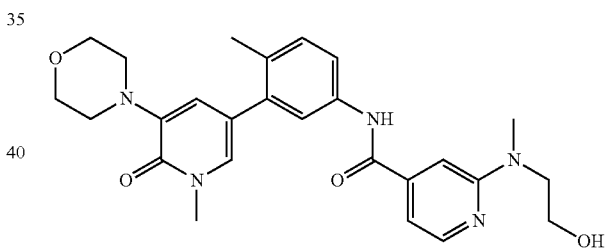

¹H NMR (500 MHz, METHANOL-d₄) δ ppm 2.33 (s, 3H) 3.04-3.18 (m, 4H) 3.38 (s, 3H) 3.66 (s, 3H) 3.84-3.97 (m, 8H) 6.94 (d, J=2.21 Hz, 1H) 7.29-7.35 (m, 2H) 7.37 (d, J=2.21 Hz, 1H) 7.59-7.67 (m, 2H) 7.77 (s, 1H) 8.05 (d, J=6.62 Hz, 1H), LCMS (m/z) (M+H)=478.2, Rt=0.60 min.

Example 457: 2-(methyl(2-(methylamino)ethyl)amino)-N-(4-methyl-3-(1-methyl-5-morpholino-6-oxo-1,6-dihydropyridin-3-yl)phenyl)isonicotinamide

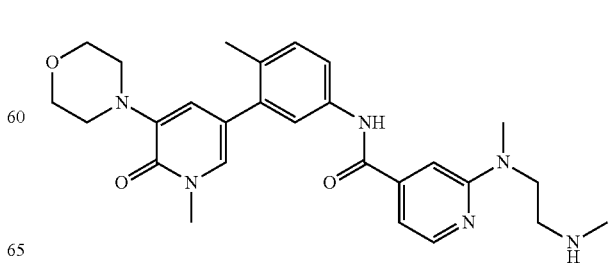

¹H NMR (500 MHz, METHANOL-d₄) δ ppm 2.33 (s, 3H) 2.77 (s, 3H) 3.17 (br. s., 4H) 3.21 (s, 3H) 3.66 (s, 3H) 3.78-3.92 (m, 4H) 3.98 (t, J=5.67 Hz, 2H) 6.97 (d, J=2.21 Hz, 1H) 7.20 (d, J=5.36 Hz, 1H) 7.26 (s, 1H) 7.32 (d, J=8.20 Hz, 1H) 7.38 (d, J=1.89 Hz, 1H) 7.57-7.65 (m, 2H) 8.29 (d, J=5.36 Hz, 1H), LCMS (m/z) (M+H)=491.3, Rt=0.60 min.

Example 460: 4-(1,2-dihydroxyethyl)-N-(4-methyl-3-(1-methyl-5-morpholino-6-oxo-1,6-dihydropyridin-3-yl)phenyl)-3-(trifluoromethyl)benzamide in a microwave vial equipped with a stir bar. The reaction was heated to 120° C. for 30 min in the microwave. The reaction was quenched with water and extracted with ethyl acetate. The aqueous phase was acidified with conc. HCl, and extracted with ethyl acetate. The organic phase was dried with magnesium sulfate, filtered and concentrated to give 3-(trifluoromethyl)-4-vinylbenzoic acid as a white solid in 18% yield. LCMS (m/z) (M+H)=217.1, Rt=0.85 min.

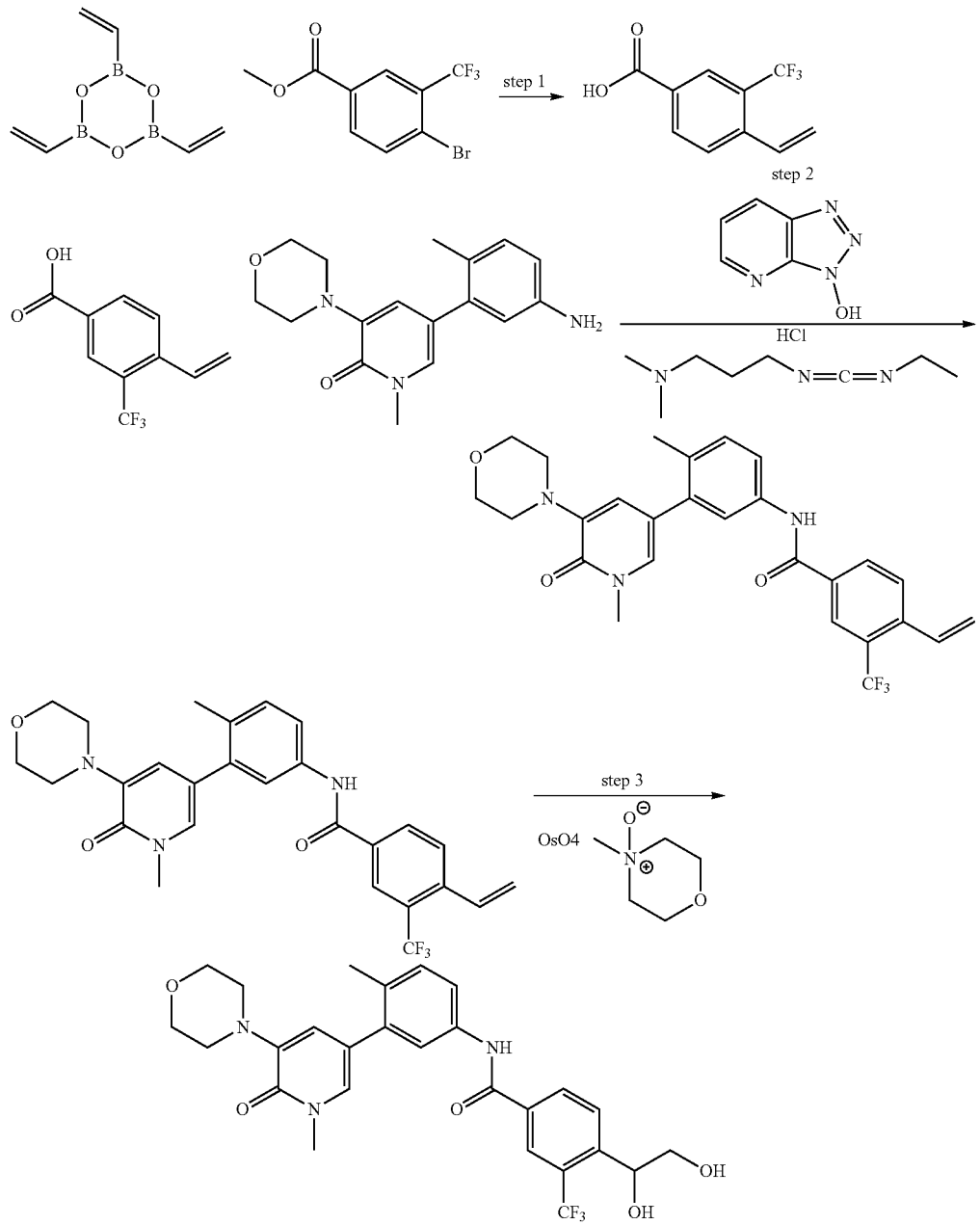

Step 1:
To a solution of methyl 4-bromo-3-(trifluoromethyl)benzoate (1.0 equiv.) and 2,4,6-trivinyl-1,3,5,2,4,6-trioxatriborinane (2.0 equiv.) in DME and 2M sodium carbonate (3:1, 0.18 M) was added PdCl₂(dppf)-DCM adduct (0.05 equiv.)

Step 2:
5-(5-amino-2-methylphenyl)-1-methyl-3-morpholinopyridin-2(1H)-one (1.0 equiv.), 3H-[1,2,3]triazolo[4,5-b]pyridin-3-ol (1.0 equiv.), N1-((ethylimino)methylene)-N3,N3-dimethylpropane-1,3-diamine hydrochloride (1.0 equiv.), and 3-(trifluoromethyl)-4-vinylbenzoic acid (1.0 equiv.) were dissolved in DMF (0.095 M) at RT. The reaction was monitored by LCMS. After about 3 hr, the reaction mixture was purified via preparative reverse phase HPLC to give N-(4-methyl-3-(1-methyl-5-morpholino-6-oxo-1,6-dihydropyridin-3-yl)phenyl)-3-(trifluoromethyl)-4-vinylbenzamide in 64% yield. LCMS (m/z) (M+H)=498.2, Rt=0.99 min.

Step 3:

N-(4-methyl-3-(1-methyl-5-morpholino-6-oxo-1,6-dihydropyridin-3-yl)phenyl)-3-(trifluoromethyl)-4-vinylbenzamide (1.0 equiv.), 4-methylmorpholine 4-oxide (1.5 equiv.), and 2.5 wt % osmium(VIII) oxide in t-butanol (0.1 equiv.) were dissolved in 1:1 THF and water (0.03 M) at RT. The reaction was monitored by LCMS. After about 4 hr, the reaction mixture was purified via preparative reverse phase HPLC to give 4-(1,2-dihydroxyethyl)-N-(4-methyl-3-(1-methyl-5-morpholino-6-oxo-1,6-dihydropyridin-3-yl)phenyl)-3-(trifluoromethyl)benzamide in 39% yield. 1H NMR (400 MHz, <cdcl3>) δ ppm 2.29 (s, 3H) 2.61 (br. s., 2H) 3.20 (br. s., 6H) 3.52 (dd, J=11.15, 8.02 Hz, 1H) 3.62 (s, 3H) 3.73 (dd, J=11.35, 2.35 Hz, 1H) 3.80-3.99 (m, 4H) 5.20 (d, J=7.04 Hz, 1H) 6.71 (s, 1H) 7.07 (s, 1H) 7.24 (d, J=8.22 Hz, 1H) 7.41-7.51 (m, 3H) 7.60 (d, J=8.22 Hz, 1H) 7.75 (s, 1H) 7.96 (d, J=7.83 Hz, 1H) 8.22 (d, J=8.22 Hz, 1H) 8.31 (s, 1H) 9.90 (br. s., 1H). LCMS (m/z) (M+H)=532.1, Rt=0.71 min.

Example 461: 4-(1,2-dihydroxyethyl)-N-(4-methyl-3-(1-methyl-5-morpholino-6-oxo-1,6-dihydropyridin-3-yl)phenyl)-3-(trifluoromethyl)benzamide Step 1:

5-(5-amino-2-methylphenyl)-1-methyl-3-morpholinopyridin-2(1H)-one (1.0 equiv.), 3H-[1,2,3]triazolo[4,5-b]pyridin-3-ol (1.0 equiv.), N1-((ethylimino)methylene)-N3,N3-dimethylpropane-1,3-diamine hydrochloride (1.0 equiv.), and 4-(bromomethyl)-3-(trifluoromethyl)benzoic acid (1.0 equiv.) were dissolved in DMF (0.114 M) at RT. The reaction was monitored by LCMS. After about 5 hr, the reaction mixture was purified via preparative reverse phase HPLC to give 4-(chloromethyl)-N-(4-methyl-3-(1-methyl-5-morpholino-6-oxo-1,6-dihydropyridin-3-yl)phenyl)-3-(trifluoromethyl)benzamide in 46% yield. LCMS (m/z) (M+H)=520.2, Rt=0.97 min.

Step 2:

4-(chloromethyl)-N-(4-methyl-3-(1-methyl-5-morpholino-6-oxo-1,6-dihydropyridin-3-yl)phenyl)-3-(trifluoromethyl)benzamide (1.0 equiv.) was dissovled in 7 M ammonia in methanol (0.046 M). After being heated at 50° C. until no further progress by LCMS, the reaction mixture was concentrated and purified via preparative reverse phase HPLC to give 4-(aminomethyl)-N-(4-methyl-3-(1-methyl-5-morpholino-6-oxo-1,6-dihydropyridin-3-yl)phenyl)-3-(trifluoromethyl)benzamide in 47% yield. LCMS (m/z) (M+H)=501.3, Rt=0.62 min.

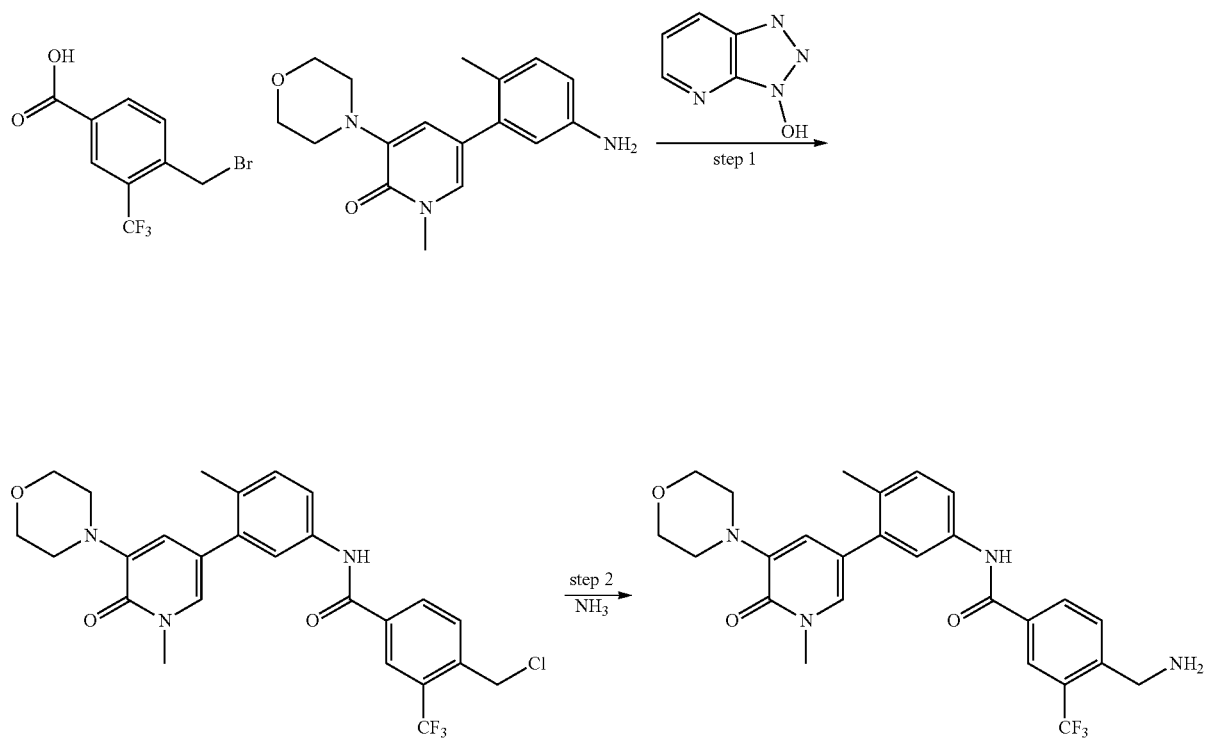

Example 462: 4-(hydroxymethyl)-N-(4-methyl-3-(1-methyl-5-morpholino-6-oxo-1,6-dihydropyridin-3-yl)phenyl)-3-(trifluoromethyl)benzamide and Example 463: 4-(2-aminoethyl)-N-(4-methyl-3-(1-methyl-5-morpholino-6-oxo-1,6-dihydropyridin-3-yl)phenyl)-3-(trifluoromethyl)benzamide

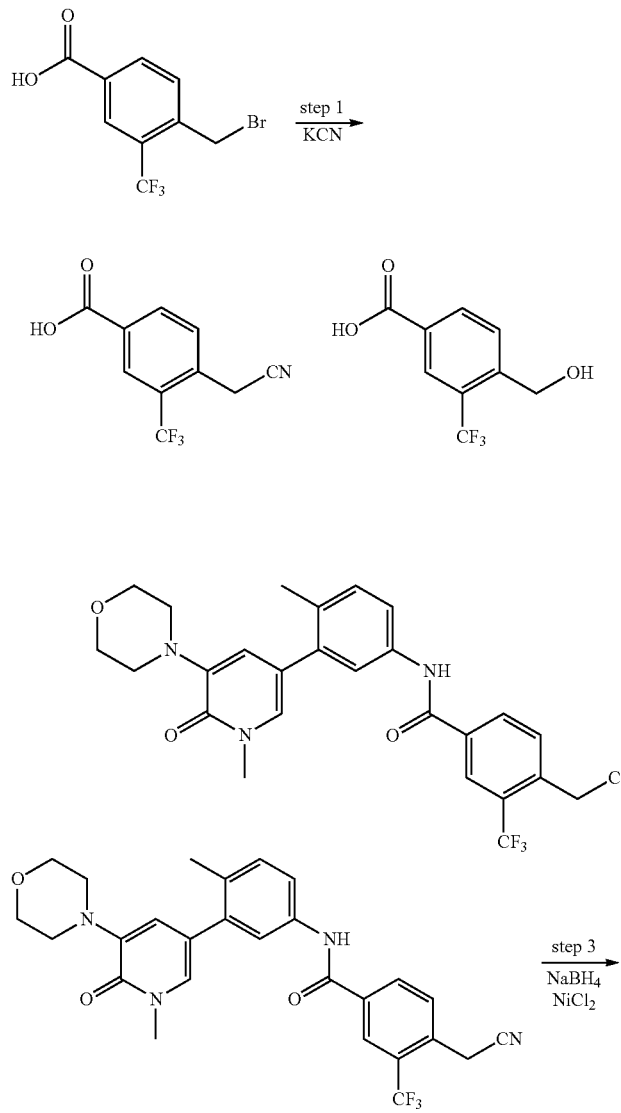

droxymethyl)-N-(4-methyl-3-(1-methyl-5-morpholino-6-oxo-1,6-dihydropyridin-3-yl)phenyl)-3-(trifluoromethyl)benzamide and 4-(cyanomethyl)-N-(4-methyl-3-(1-methyl-5-morpholino-6-oxo-1,6-dihydropyridin-3-yl)phenyl)-3-(trifluoromethyl)benzamide in 2.8% yield and 8.5% yield respectively over two steps. For 4-(hydroxymethyl)-N-(4-methyl-3-(1-methyl-5-morpholino-6-oxo-1,6-dihydropyri- Step 1:

4-(bromomethyl)-3-(trifluoromethyl)benzoic acid (1.0 equiv.) and potassium cyanide (0.9 equiv.) in DMSO (0.177 M) were stirred at RT. The reaction was monitored by LCMS until no further progression. The crude reaction mixture was used directly for next step.

Step 2:

The crude mixture from previous step and 5-(5-amino-2-methylphenyl)-1-methyl-3-morpholinopyridin-2(1H)-one (1 equiv.), 3H-[1,2,3]triazolo[4,5-b]pyridin-3-ol (1.0 equiv.), and N1-((ethylimino)methylene)-N3,N3-dimethylpropane-1,3-diamine hydrochloride (1.0 equiv.) were mixed in DMF (0.233 M). After 3 hr, the reaction mixture was purified via preparative reverse phase HPLC to give 4-(hydin-3-yl)phenyl)-3-(trifluoromethyl)benzamide, LCMS (m/z) (M+H)=502.1, Rt=0.79 min. For 4-(cyanomethyl)-N-(4-methyl-3-(1-methyl-5-morpholino-6-oxo-1,6-dihydropyridin-3-yl)phenyl)-3-(trifluoromethyl)benzamide, LCMS (m/z) (M+H)=511.2, Rt=0.86 min.

Step 3:

To a solution of 4-(cyanomethyl)-N-(4-methyl-3-(1-methyl-5-morpholino-6-oxo-1,6-dihydropyridin-3-yl)phenyl)-3-(trifluoromethyl)benzamide (1 equiv.) in ethanol (0.02 M), nickel chloride (4 equiv.) and sodium borohydride (20 equiv.) were added at RT. After 2 hr, the reaction mixture was quenched with diethyltriamine, partitioned between saturated sodium bicarbonate solution and ethyl acetate. The organic phase was dried over magnesium sulfate, filtered and concentrated. The residue was purified via preparative reverse phase HPLC to give 4-(2-aminoethyl)-N-(4-methyl-3-(1-methyl-5-morpholino-6-oxo-1,6-dihydropyridin-3-yl)phenyl)-3-(trifluoromethyl)benzamide in 47% yield. LCMS (m/z) (M+H)=515.1, Rt=0.66 min.

Synthesis of 3-(6-oxa-3-azabicyclo[3.1.1]heptan-3-yl)-5-bromo-1-methylpyridin-2(1H)-one

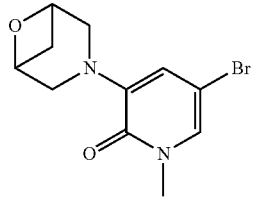 [SMILES: Cn1cc(Br)cc(N2CC3CC(C2)O3)c1=O]

To a solution of 3,5-dibromo-1-methylpyridin-2(1H)-one (1.0 equiv.) in dioxane (0.190 M) in a microwave vial, were added 6-oxa-3-azabicyclo[3.1.1]heptane TsOH (1.0 equiv.), xantphos (0.1 equiv.), cesium carbonate (3.0 equiv.) and Pd2(dba)3 (0.05 equiv.). The reaction vessel was degassed by a stream of argon for 15 min and the reaction vessel was sealed and stirred at 80° C. in a regular sand bath for 16 hr. LCMS showed an estimated 45% conversion. The reaction temperature was increased at 100° C. for 6 hr. The reaction mixture was cooled to room temperature and extracted with ethyl acetate. The organic phase was washed with brine, dried over sodium sulfate, filtered and concentrated The solvent was removed under vacuum and the crude material was purified via flash chromatography over silica gel eluting with DCM and 0-10% MeOH gradient. Isolated 3-(6-oxa-3-azabicyclo[3.1.1]heptan-3-yl)-5-bromo-1-methylpyridin-2(1H)-one in 39% yield. LCMS (m/z) (M+H)=286.9, Rt=0.64 min.

Example 464: N-(3-(5-(6-oxa-3-azabicyclo[3.1.1]heptan-3-yl)-1-methyl-6-oxo-1,6-dihydropyridin-3-yl)-4-methylphenyl)-3-(trifluoromethyl)benzamide

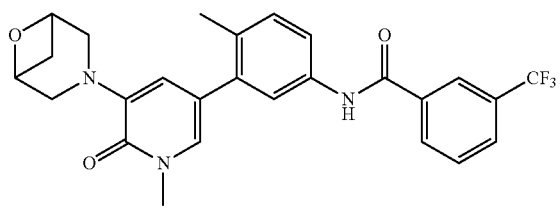 [SMILES: Cc1ccc(NC(=O)c2cccc(C(F)(F)F)c2)cc1-c1cc(N2CC3CC(C2)O3)c(=O)n(C)c1]

1H NMR (400 MHz, <dmso>) δ ppm 1.06-1.29 (m, 1H) 2.04-2.11 (m, 1H) 2.22 (s, 3H) 2.90-3.01 (m, 1H) 3.43 (s, 3H) 4.04 (d, J=12.13 Hz, 2H) 4.50 (d, J=5.87 Hz, 2H) 6.43-6.63 (m, 1H) 7.12-7.27 (m, 2H) 7.51-7.66 (m, 2H) 7.72 (t, J=7.83 Hz, 1H) 7.90 (d, J=7.43 Hz, 1H) 8.13-8.30 (m, 2H) 10.38 (s, 1H). LCMS (m/z) (M+H)=484.2, Rt=0.98 min.

Example 465: N-(3-(5-(6-oxa-3-azabicyclo[3.1.1]heptan-3-yl)-1-methyl-6-oxo-1,6-dihydropyridin-3-yl)-4-methylphenyl)-2-(2-cyanopropan-2-yl)isonicotinamide

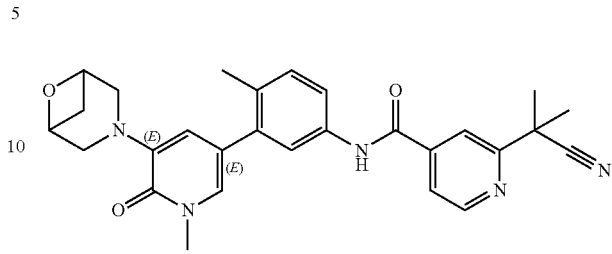

1H NMR (400 MHz, <dmso>) δ ppm 1.14-1.27 (m, 4H) 1.75 (s, 6H) 2.12 (d, J=8.22 Hz, 1H) 2.27 (s, 3H) 3.01 (q, J=6.65 Hz, 1H) 3.48 (s, 3H) 4.08 (d, J=12.13 Hz, 2H) 4.54 (d, J=6.26 Hz, 2H) 6.55-6.61 (m, 1H) 7.20-7.31 (m, 2H) 7.62-7.68 (m, 2H) 7.85 (d, J=5.09 Hz, 1H) 7.93-8.06 (m, 1H) 8.79 (d, J=5.09 Hz, 1H) 10.42-10.61 (m, 1H) LCMS (m/z) (M+H)=484, Rt=0.79 min.

Example 466: N-(4-methyl-3-(1-methyl-5-morpholino-6-oxo-1,6-dihydropyridin-3-yl)phenyl)-4-((methylamino)methyl)-3-(trifluoromethyl)benzamide

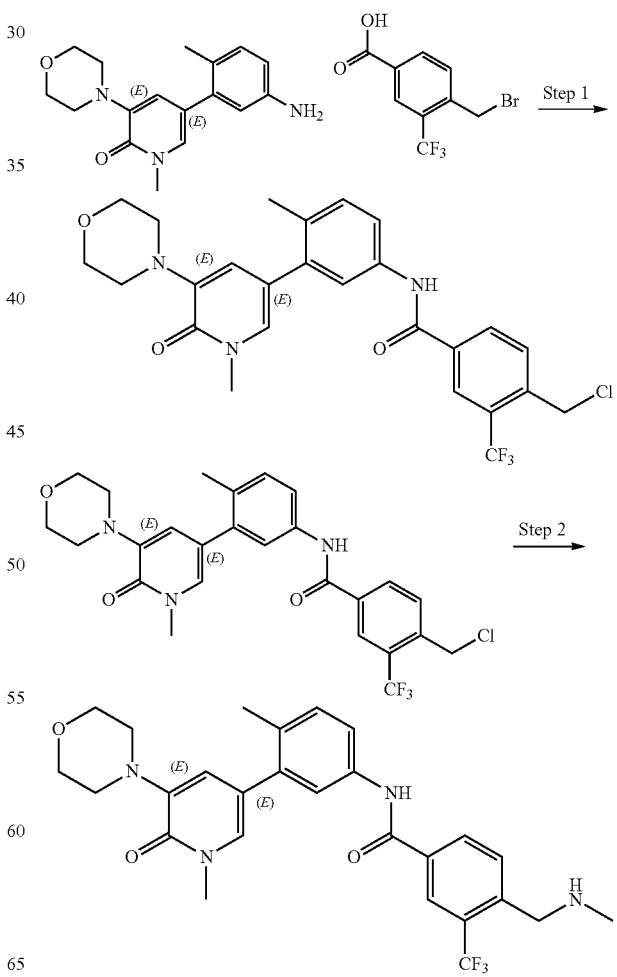

Step 1:

Aza-HOBt (1.0 equiv.) was added to a solution of 5-(5-amino-2-methylphenyl)-1-methyl-3-morpholinopyridin-2(1H)-one (1.0 equiv.), 4-(bromomethyl)-3-(trifluoromethyl)benzoic acid (1.5 equiv.) and EDC.HCl (1.0 equiv.) in DMF (0.11 M) and the reaction mix was stirred at RT for 5 hr. The crude was partitioned in H₂O/EtOAc. The organic layer was isolated, dried over Na₂SO₄, filtered and concentrated. Crude was purified silicagel column to give the desired 4-(chloromethyl)-N-(4-methyl-3-(1-methyl-5-morpholino-6-oxo-1,6-dihydropyridin-3-yl)phenyl)-3-(trifluoromethyl)benzamide in 46% yield. LCMS (m/z) (M+H)=520, Rt=0.97 min.

Step 2:

A mixture of 4-(chloromethyl)-N-(4-methyl-3-(1-methyl-5-morpholino-6-oxo-1,6-dihydropyridin-3-yl)phenyl)-3-(trifluoromethyl)benzamide (1.0 equiv.) and MeNH₂ 2 M in THF (70 equiv.) was stirred at RT overnight. LCMS showed desired product MH+=515 at LC=0.64 mins. The solvent was removed under vacuum and the residue was purified by HPLC to give N-(4-methyl-3-(1-methyl-5-morpholino-6-oxo-1,6-dihydropyridin-3-yl)phenyl)-4-((methylamino)methyl)-3-(trifluoromethyl)benzamide as the TFA salt in 46% yield. 1H NMR (400 MHz, <dmso>) δ ppm 2.20 (s, 3H) 2.66 (t, J=4.89 Hz, 3H) 3.04 (br. s., 4H) 3.43 (s, 4H) 3.65 (d, J=4.30 Hz, 4H) 4.33 (br. s., 2H) 6.62 (d, J=1.96 Hz, 1H) 7.22 (d, J=8.22 Hz, 1H) 7.33 (d, J=1.96 Hz, 1H) 7.56 (d, J=1.96 Hz, 1H) 7.62 (d, J=8.61 Hz, 1H) 7.82 (d, J=8.61 Hz, 1H) 8.19-8.39 (m, 2H) 8.95 (br. s., 2H) 10.32-10.51 (m, 1H). LCMS (m/z) (M+H)=515, Rt=0.64 min.

Example 467: N-(4-(aminomethyl)-3-(trifluoromethyl)phenyl)-4-methyl-3-(1-methyl-5-morpholino-6-oxo-1,6-dihydropyridin-3-yl)benzamide

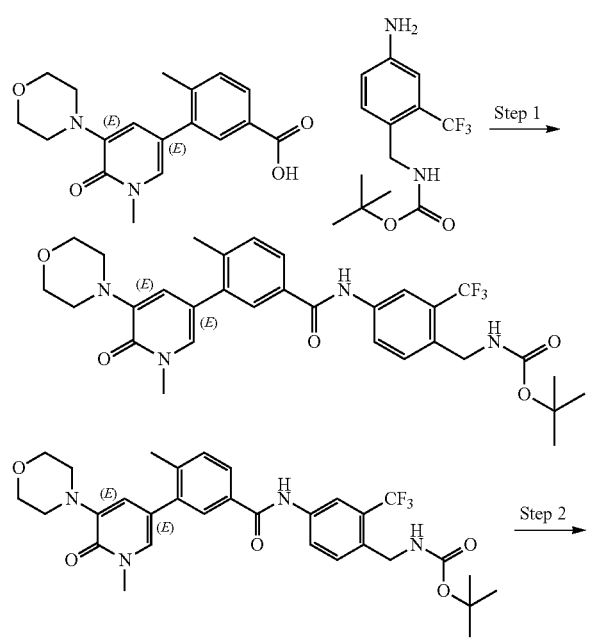

-continued

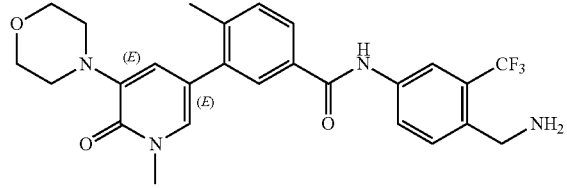

Step 1:

HATU (1.1 equiv.) was added to a solution of 4-methyl-3-(1-methyl-5-morpholino-6-oxo-1,6-dihydropyridin-3-yl)benzoic acid (1.0 and DIEA (2.0 equiv.) in DMF (Volume: 1 mL) at 0° C., and the mixture was stirred for 30 min. Tert-butyl 4-amino-2-(trifluoromethyl)benzylcarbamate (1.0) was added and the reaction mix was left stirring overnight at RT. Reaction mix was treated with water and extracted twice with EtOAc. The combined organics were concentrated to dryness. The crude was purified on silicagel column using 0 to 70% EtOAc in heptane to give tert-butyl 4-(4-methyl-3-(1-methyl-5-morpholino-6-oxo-1,6-dihydropyridin-3-yl)benzamido)-2-(trifluoromethyl)benzylcarbamate in 20% yield. LCMS (m/z) (M+H)=601, Rt=1.0 min.

Step 2:

To a solution of tert-butyl 4-(4-methyl-3-(1-methyl-5-morpholino-6-oxo-1,6-dihydropyridin-3-yl)benzamido)-2-(trifluoromethyl)benzylcarbamate (1.0 equiv.) in DCM (0.01 M) was added TFA (15 equiv.) and the reaction mix was stirred at RT for 1 h. The solvent was removed under vacuum and the residue was purified by HPLC to give N-(4-(aminomethyl)-3-(trifluoromethyl)phenyl)-4-methyl-3-(1-methyl-5-morpholino-6-oxo-1,6-dihydropyridin-3-yl)benzamide as the TFA salt in 51% yield. 1H NMR (400 MHz, <dmso>) δ ppm 2.35 (s, 3H) 3.10 (br. s., 4H) 3.70 (d, J=4.30 Hz, 4H) 4.14 (d, J=5.48 Hz, 2H) 6.58-6.82 (m, 1H) 7.35-7.54 (m, 2H) 7.66 (d, J=8.61 Hz, 1H) 7.78-7.98 (m, 2H) 8.18 (d, J=8.61 Hz, 1H) 8.25 (br. s., 4H) 10.53 (s, 1H). LCMS (m/z) (M+H)=501, Rt=0.63 min.

Example 468 and Example 469: Synthesis of N-(4-methyl-3-(1-methyl-5-morpholino-6-oxo-1,6-dihydropyridin-3-yl)phenyl)-3-((methylamino)methyl)-5-(trifluoromethyl)benzamide AND 3-(hydroxymethyl)-N-(4-methyl-3-(1-methyl-5-morpholino-6-oxo-1,6-dihydropyridin-3-yl)phenyl)-5-(trifluoromethyl)benzamide

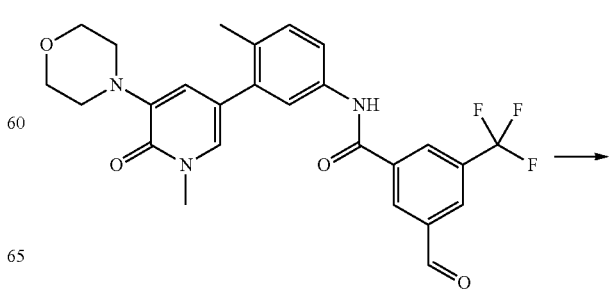

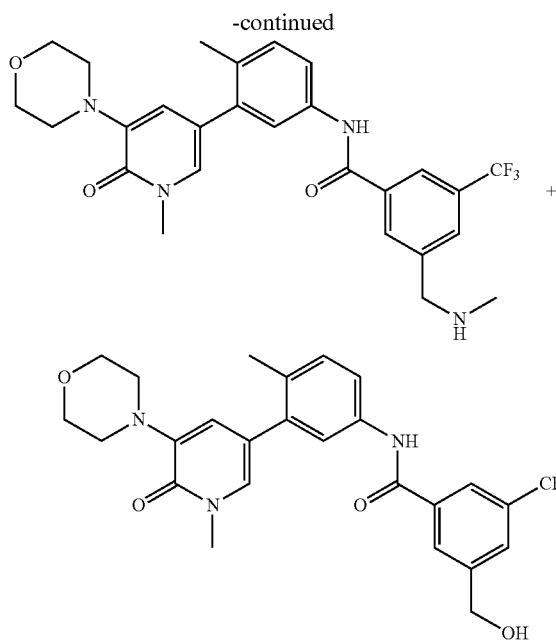

To a 0.08 M solution of 3-formyl-N-(4-methyl-3-(1-methyl-5-morpholino-6-oxo-1,6-dihydropyridin-3-yl)phenyl)-5-(trifluoromethyl)benzamide (1.00 equiv.), prepared using methods similar to those described for the preparation of Example 171 using the appropriate starting materials) in ethanol was added methylamine, 33 wt % in ethanol (5.00 equiv.). The mixture was stirred overnight at ambient temperature. The reaction mixture was degassed by bubbling argon through the solution for 5 min. Degussa type 10% palladium on carbon (23.86 mg, 0.022 mmol) was added. The reaction vessel was purged and flushed twice with hydrogen from a balloon. The reaction was stirred under a hydrogen atmosphere for 2.5 hr and then filtered. The filtrate was concentrated and purified by reverse phase HPLC and lyophilized to give N-(4-methyl-3-(1-methyl-5-morpholino-6-oxo-1,6-dihydropyridin-3-yl)phenyl)-3-((methylamino)methyl)-5-(trifluoromethyl)benzamide (17.4% yield) and 3-(hydroxymethyl)-N-(4-methyl-3-(1-methyl-5-morpholino-6-oxo-1,6-dihydropyridin-3-yl)phenyl)-5-(trifluoromethyl)benzamide (8.5% yield) as their TFA salts.

N-(4-methyl-3-(1-methyl-5-morpholino-6-oxo-1,6-dihydropyridin-3-yl)phenyl)-3-((methylamino)methyl)-5-(trifluoromethyl)benzamide: $^1$H NMR (400 MHz, <cd3od>) δ ppm 2.33 (s, 3H) 2.81 (s, 3H) 3.10-3.21 (m, 4H) 3.65 (s, 3H) 3.82-3.94 (m, 4H) 4.40 (s, 2H) 6.94 (d, J=1.96 Hz, 1H) 7.32 (d, J=8.22 Hz, 1H) 7.36 (d, J=1.96 Hz, 1H) 7.57-7.66 (m, 2H) 8.08 (s, 1H) 8.34 (s, 1H) 8.41 (s, 1H). LCMS (m/z) (M+H)=515.2, Rt=0.67 min.

3-(hydroxymethyl)-N-(4-methyl-3-(1-methyl-5-morpholino-6-oxo-1,6-dihydropyridin-3-yl)phenyl)-5-(trifluoromethyl)benzamide: $^1$H NMR (400 MHz, <cd3od>) δ ppm 2.33 (s, 3H) 3.16-3.24 (m, 4H) 3.66 (s, 3H) 3.84-3.95 (m, 4H) 4.79 (s, 2H) 7.01 (d, J=1.96 Hz, 1H) 7.31 (d, J=8.22 Hz, 1H) 7.41 (d, J=1.96 Hz, 1H) 7.59 (dd, J=8.02, 2.15 Hz, 1H) 7.64 (d, J=1.96 Hz, 1H) 7.91 (s, 1H) 8.16 (s, 1H) 8.19 (s, 1H). LCMS (m/z) (M+H)=502.1, Rt=0.79 min.

Example 470: Synthesis of 3-(aminomethyl)-N-(4-methyl-3-(1-methyl-5-morpholino-6-oxo-1,6-dihydropyridin-3-yl)phenyl)-5-(trifluoromethyl)benzamide

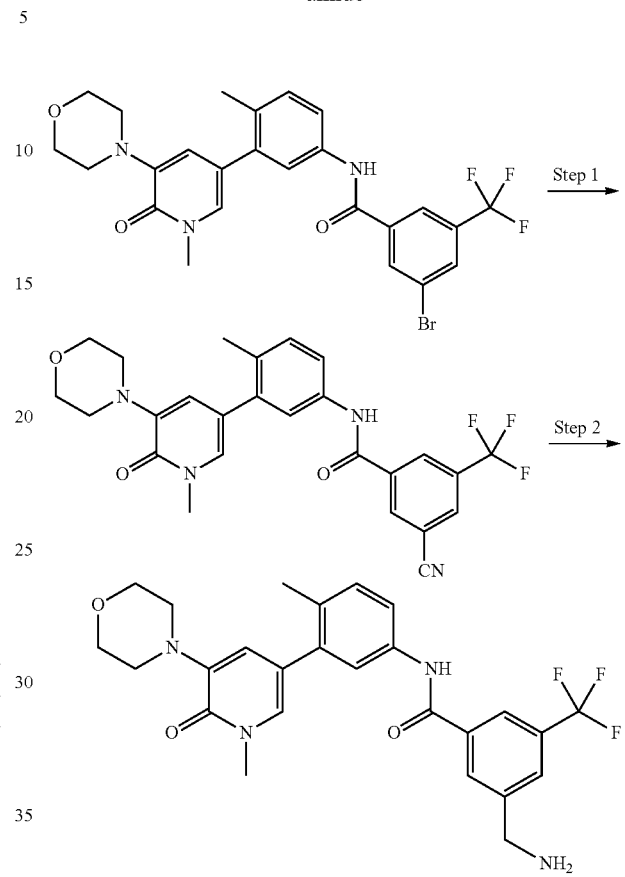

Step 1:
To a 0.15M solution of 3-bromo-N-(4-methyl-3-(1-methyl-5-morpholino-6-oxo-1,6-dihydropyridin-3-yl)phenyl)-5-(trifluoromethyl)benzamide (1.00 equiv., prepared using methods similar to those described for the preparation of Example 171 using the appropriate starting materials) in DMF was added zinc cyanide (4.00 equiv.) and tetrakis(triphenylphosphine)palladium (0.100 equiv.). The reaction mixture was irradiated at 130° C. for 15 min in the microwave. The cooled reaction mixture was filtered. The filtrate was concentrated and purified by flash chromatography over silica gel (95:5 ethyl acetate:methanol) to give 3-cyano-N-(4-methyl-3-(1-methyl-5-morpholino-6-oxo-1,6-dihydropyridin-3-yl)phenyl)-5-(trifluoromethyl)benzamide (99.0% yield) as a yellow solid. LCMS (m/z) (M+H)=497.2, Rt=0.89 min.

Step 2:
To a degassed 0.05M solution of 3-cyano-N-(4-methyl-3-(1-methyl-5-morpholino-6-oxo-1,6-dihydropyridin-3-yl)phenyl)-5-(trifluoromethyl)benzamide (1.00 equiv.) in methanol was added a methanol slurry of washed Raney-Ni. The mixture was hydrogenated under 60 psi of hydrogen overnight. The degassed reaction mixture was filtered. The filtrate was concentrated to dryness. The residue was purified by reverse phase HPLC and lyophilized to give 3-(aminomethyl)-N-(4-methyl-3-(1-methyl-5-morpholino-6-oxo-1,6-dihydropyridin-3-yl)phenyl)-5-(trifluoromethyl)benzamide as its TFA salt (8.8% yield), a white solid.

¹H NMR (400 MHz, <cd3od>) δ ppm 2.33 (s, 3H) 3.16 (d, J=4.70 Hz, 4H) 3.66 (s, 3H) 3.83-3.92 (m, 4H) 4.34 (s, 2H) 6.93 (d, J=1.96 Hz, 1H) 7.32 (d, J=8.22 Hz, 1H) 7.36 (d, J=1.96 Hz, 1H) 7.56-7.66 (m, 2H) 8.06 (s, 1H) 8.33 (s, 1H) 8.38 (s, 1H). LCMS (m/z) (M+H)=501.1, Rt=0.69 min.

The compounds listed below were prepared using methods similar to those described for the preparation of Example 171 using the appropriate starting materials.

Example 471: 2-(1,1-difluoroethyl)-N-(4-methyl-3-(1-methyl-6-morpholino-2-oxo-1,2-dihydropyridin-4-yl)phenyl)isonicotinamide Synthesis of 4-(5-amino-2-methylphenyl)-1-methyl-6-morpholinopyridin-2(1H)-one

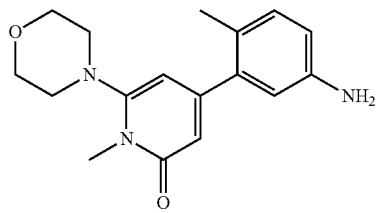 [SMILES: Cc1ccc(N)cc1-c1cc(N2CCOCC2)n(C)c(=O)c1]

To a 0.2M solution of 4-bromo-1-methyl-6-morpholinopyridin-2(1H)-one (1.00 equiv.) in DME was added 4-methyl-3-(4,4,5,5-tetramethyl-1,3,2-dioxaborolan-2-yl)aniline (1.00 equiv.), PdCl2(dppf).CH2Cl2 adduct (0.50 equiv.), and 2M aqueous sodium carbonate (8.00 equiv.). The reaction mixture was irradiated at 110° C. for 20 min in the microwave. The cooled reaction mixture was diluted with water and extracted with ethyl acetate. The combined organics were dried over magnesium sulfate, filtered, concentrated, and purified by flash chromatography over silica gel (heptanes with 50-100% ethyl acetate gradient) to give 4-(5-amino-2-methylphenyl)-1-methyl-6-morpholinopyridin-2(1H)-one (43.8% yield) as a brown oil. LCMS (m/z) (M+H)=300.1, Rt=0.44 min.

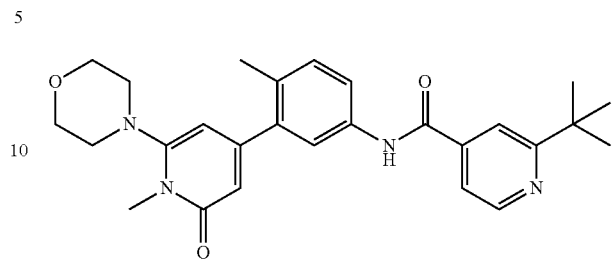

1H NMR (400 MHz, <dmso>) δ ppm 1.91-2.12 (m, 3H) 2.24 (s, 3H) 2.93 (br. s., 4H) 3.45 (s, 3H) 3.73 (br. s., 4H) 5.80 (s, 1H) 6.05 (s, 1H) 7.29 (d, J=8.22 Hz, 1H) 7.65 (s, 1H) 7.72 (d, J=8.22 Hz, 1H) 8.01 (d, J=4.70 Hz, 1H) 8.16 (s, 1H) 8.86 (d, J=5.09 Hz, 1H) 10.63 (s, 1H). LCMS (m/z) (M+H)=469.2, Rt=0.80 min.

Example 472: 2-(tert-butyl)-N-(4-methyl-3-(1-methyl-6-morpholino-2-oxo-1,2-dihydropyridin-4-yl)phenyl)isonicotinamide

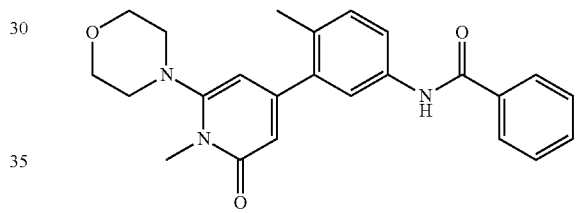

1H NMR (400 MHz, <dmso>) δ ppm 1.29-1.38 (m, 9H) 2.16-2.27 (m, 3H) 2.93 (br. s., 4H) 3.45 (s, 3H) 3.73 (t, J=4.11 Hz, 4H) 5.74-5.86 (m, 1H) 6.05 (d, J=1.17 Hz, 1H) 7.29 (d, J=8.22 Hz, 1H) 7.63 (d, J=1.57 Hz, 1H) 7.70 (d, J=5.87 Hz, 2H) 7.87 (s, 1H) 8.71 (d, J=5.09 Hz, 1H) 10.47 (s, 1H). LCMS (m/z) (M+H)=461.2, Rt=0.67 min.

Example 473: N-(4-methyl-3-(1-methyl-6-morpholino-2-oxo-1,2-dihydropyridin-4-yl)phenyl)benzamide

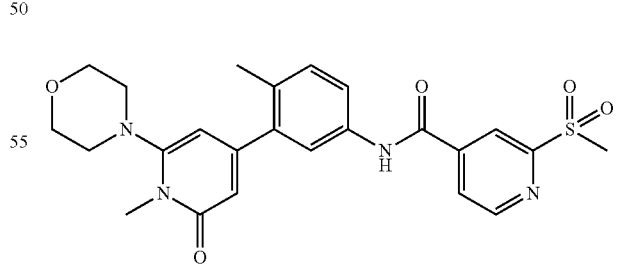

1H NMR (400 MHz, <dmso>) δ ppm 2.23 (s, 3H) 2.94 (br. s., 4H) 3.45 (s, 3H) 3.73 (br. s., 4H) 5.80 (s, 1H) 6.05 (s, 1H) 7.25 (d, J=8.61 Hz, 1H) 7.45-7.54 (m, 2H) 7.54-7.61 (m, 1H) 7.66 (s, 1H) 7.72 (d, J=8.22 Hz, 1H) 7.93 (d, J=7.83 Hz, 2H) 10.23 (s, 1H). LCMS (m/z) (M+H)=404.2, Rt=0.77 min.

Example 474: N-(4-methyl-3-(1-methyl-6-morpholino-2-oxo-1,2-dihydropyridin-4-yl)phenyl)-2-(methylsulfonyl)isonicotinamide 1H NMR (400 MHz, <dmso>) δ ppm 2.25 (s, 3H) 2.94 (br. s., 4H) 3.27-3.36 (m, 3H) 3.40-3.50 (m, 3H) 3.62-3.79 (m, 4H) 5.81 (s, 1H) 6.05 (s, 1H) 7.30 (d, J=8.22 Hz, 1H) 7.66 (s, 1H) 7.72 (d, J=8.61 Hz, 1H) 8.20 (d, J=4.70 Hz, 1H) 8.51 (s, 1H) 8.98 (d, J=4.70 Hz, 1H) 10.57-10.91 (m, 1H). LCMS (m/z) (M+H)=483.1, Rt=0.68 min.

Example 475: 2-(1,1-difluoropropyl)-N-(4-methyl-3-(1-methyl-6-morpholino-2-oxo-1,2-dihydropyridin-4-yl)phenyl)isonicotinamide

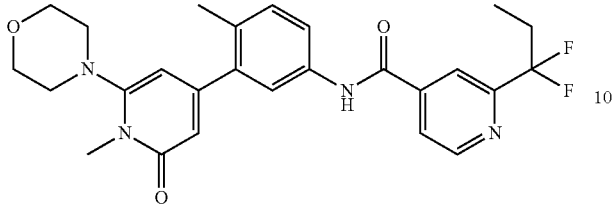

¹H NMR (400 MHz, <dmso>) δ ppm 0.94 (t, J=7.24 Hz, 3H) 2.26 (s, 3H) 2.28-2.46 (m, 2H) 2.95 (br. s., 4H) 3.46 (s., 3H) 3.64-3.81 (m, 4H) 5.82 (s, 1H) 6.07 (s, 1H) 7.31 (d, J=8.22 Hz, 1H) 7.67 (s, 1H) 7.73 (d, J=8.22 Hz, 1H) 8.02 (d, J=5.09 Hz, 1H) 8.16 (s, 1H) 8.89 (d, J=4.70 Hz, 1H) 10.56-10.72 (m, 1H). LCMS (m/z) (M+H)=483.2, Rt=0.89 min.

Example 476: 2-ethyl-N-(4-methyl-3-(1-methyl-6-morpholino-2-oxo-1,2-dihydropyridin-4-yl)phenyl)isonicotinamide

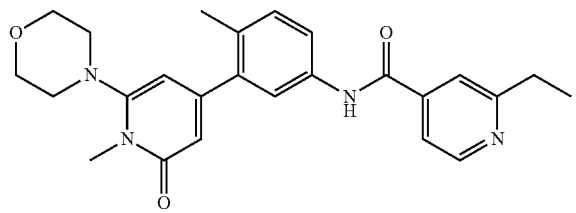 [SMILES: CCc1cc(C(=O)Nc2ccc(C)c(-c3cc(N4CCOCC4)n(C)c(=O)c3)c2)ccn1]

¹H NMR (400 MHz, <dmso>) δ ppm 1.21-1.32 (m, 3H) 2.24 (s, 3H) 2.82-3.00 (m, 6H) 3.46 (s., 3H) 3.73 (d, J=3.91 Hz, 4H) 5.80 (d, J=1.17 Hz, 1H) 6.05 (d, J=1.17 Hz, 1H) 7.29 (d, J=8.22 Hz, 1H) 7.64 (d, J=1.96 Hz, 1H) 7.70 (dd, J=8.22, 1.96 Hz, 1H) 7.78 (br. s., 1H) 7.85 (br. s., 1H) 8.67-8.78 (m, 1H) 10.53 (br. s., 1H). LCMS (m/z) (M+H)=433.1, Rt=0.62 min.

Example 477: 2-cyclopropyl-N-(4-methyl-3-(1-methyl-6-morpholino-2-oxo-1,2-dihydropyridin-4-yl)phenyl)isonicotinamide

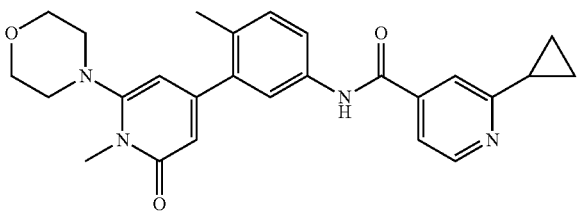 [SMILES: Cc1ccc(NC(=O)c2ccnc(C3CC3)c2)cc1-c1cc(N2CCOCC2)n(C)c(=O)c1]

¹H (400 MHz, <cd3od>) δ ppm 1.29-1.41 (m, 2H) 1.53-1.68 (m, 2H) 2.32 (s, 3H) 2.45-2.58 (m, 1H) 3.09 (br. s., 4H) 3.68 (s, 3H) 3.95-4.04 (m, 4H) 6.20 (s, 1H) 6.36 (s, 1H) 7.43 (d, J=7.83 Hz, 1H) 7.48-7.57 (m, 2H) 7.96 (s, 1H) 8.08-8.17 (m, 1H) 8.75 (d, J=6.26 Hz, 1H). LCMS (m/z) (M+H)=445.1, Rt=0.63 min.

Example 478: N-(4-methyl-3-(1-methyl-6-morpholino-2-oxo-1,2-dihydropyridin-4-yl)phenyl)-2-(oxetan-3-yl)isonicotinamide

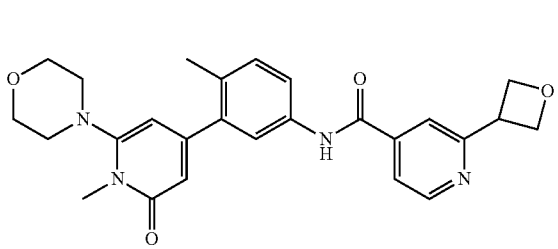 [SMILES: Cc1ccc(NC(=O)c2ccnc(C3COC3)c2)cc1-c1cc(N2CCOCC2)n(C)c(=O)c1]

¹H NMR (400 MHz, <cd3od>) δ ppm 2.06 (s, 2H) 2.29 (s, 2H) 3.06 (br. s., 4H) 3.63 (s, 3H) 3.91 (br. s., 4H) 4.56 (m, 1H) 6.14 (s, 1H) 6.32 (s, 1H) 7.39 (d, J=9.00 Hz, 1H) 7.56 (br. s., 2H) 7.76 (d, J=5.48 Hz, 1H) 7.83 (s, 1H) 8.74 (d, J=5.09 Hz, 1H). LCMS (m/z) (M+H)=461.0, Rt=0.59 min.

Example 479: 2-(2-fluoropropan-2-yl)-N-(4-methyl-3-(1-methyl-6-morpholino-2-oxo-1,2-dihydropyridin-4-yl)phenyl)isonicotinamide

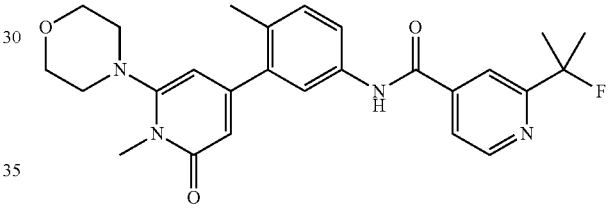

¹H NMR (400 MHz, <cd3od>) δ ppm 1.85-1.97 (m, 6H) 2.38 (s, 3H) 3.17 (br. s., 4H) 3.73 (s, 3H) 4.02 (br. s., 4H) 6.35 (s, 1H) 6.46 (s, 1H) 7.48-7.54 (m, 1H) 7.58 (s, 1H) 7.58-7.64 (m, 1H) 8.05 (br. s., 1H) 8.25 (s, 1H) 8.85 (d, J=5.48 Hz, 1H). LCMS (m/z) (M+H)=465.1, Rt=0.80 min.

Example 480: 2-(1-cyanocyclopropyl)-N-(4-methyl-3-(1-methyl-6-morpholino-2-oxo-1,2-dihydropyridin-4-yl)phenyl)isonicotinamide

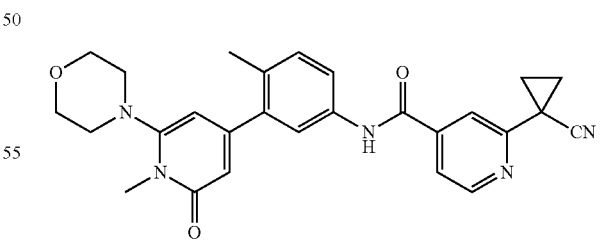

¹H NMR (400 MHz, <dmso>) δ ppm 1.70-1.78 (m, 2H) 1.83-1.92 (m, 2H) 2.24 (s, 3H) 2.93 (br. s., 4H) 3.45 (s, 3H) 3.73 (br. s., 4H) 5.80 (d, J=1.57 Hz, 1H) 6.05 (d, J=1.17 Hz, 1H) 7.29 (d, J=8.61 Hz, 1H) 7.63 (d, J=1.96 Hz, 1H) 7.70 (dd, J=8.22, 1.96 Hz, 1H) 7.77 (dd, J=4.89, 0.98 Hz, 1H) 7.90 (s, 1H) 8.69 (d, J=5.09 Hz, 1H) 10.56 (s, 1H). LCMS (m/z) (M+H)=470.1, Rt=0.77 min.

Example 481: 1-ethyl-N-(4-methyl-3-(1-methyl-6-morpholino-2-oxo-1,2-dihydropyridin-4-yl)phenyl)-6-oxo-5-(trifluoromethyl)-1,6-dihydropyridine-3-carboxamide

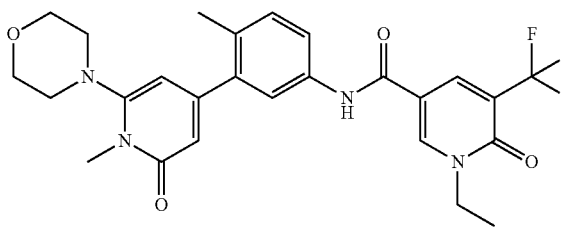

$^1$H NMR (400 MHz, <dmso>) δ ppm 1.29 (t, J=7.04 Hz, 3H) 2.23 (s, 3H) 2.93 (br. s., 4H) 3.45 (s, 3H) 3.73 (t, J=3.91 Hz, 4H) 4.06 (q, J=7.04 Hz, 2H) 5.79 (d, J=1.17 Hz, 1H) 6.04 (d, J=1.17 Hz, 1H) 7.27 (d, J=8.22 Hz, 1H) 7.54 (d, J=1.96 Hz, 1H) 7.64 (dd, J=8.22, 1.96 Hz, 1H) 8.45 (d, J=1.96 Hz, 1H) 8.79 (d, J=2.35 Hz, 1H) 10.14 (s, 1H). LCMS (m/z) (M+H)=517.2, Rt=0.79 min.

Example 482: 2-isopropyl-N-(4-methyl-3-(1-methyl-6-morpholino-2-oxo-1,2-dihydropyridin-4-yl)phenyl)isonicotinamide

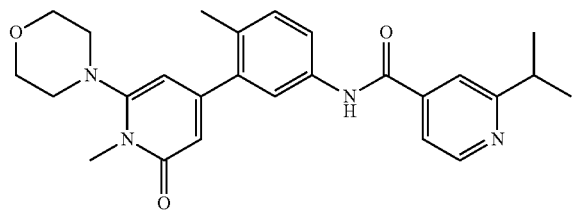 [SMILES: Cc1ccc(NC(=O)c2ccnc(C(C)C)c2)cc1-c1cc(N2CCOCC2)n(C)c(=O)c1]

$^1$H NMR (400 MHz, <dmso>) δ ppm 1.28 (d, J=7.04 Hz, 6H) 2.24 (s, 3H) 2.93 (br. s., 4H) 3.15 (spt, J=6.85 Hz, 1H) 3.45 (s, 3H) 3.73 (t, J=3.91 Hz, 4H) 5.80 (d, J=1.17 Hz, 1H) 6.05 (s, 1H) 7.29 (d, J=8.61 Hz, 1H) 7.63 (d, J=1.57 Hz, 1H) 7.67-7.75 (m, 2H) 7.80 (s, 1H) 8.71 (d, J=5.09 Hz, 1H) 10.41-10.56 (m, 1H). LCMS (m/z) (M+H)=447.2, Rt=0.63 min.

Example 483: 2-(2-hydroxypropan-2-yl)-N-(4-methyl-3-(1-methyl-6-morpholino-2-oxo-1,2-dihydropyridin-4-yl)phenyl)isonicotinamide

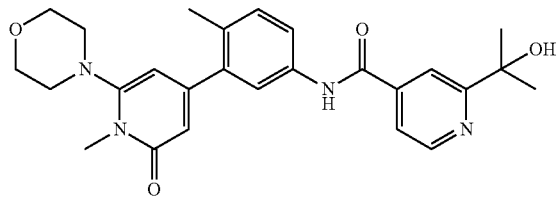 [SMILES: Cc1ccc(NC(=O)c2ccnc(C(C)(C)O)c2)cc1-c1cc(N2CCOCC2)n(C)c(=O)c1]

$^1$H NMR (400 MHz, <dmso>) δ ppm 1.48 (s, 6H) 2.24 (s, 3H) 2.93 (br. s., 4H) 3.45 (s, 3H) 3.73 (t, J=3.91 Hz, 4H) 5.80 (d, J=1.57 Hz, 1H) 6.00-6.10 (m, 1H) 7.20-7.37 (m, 1H) 7.64 (d, J=1.96 Hz, 1H) 7.68-7.79 (m, 2H) 8.16 (s, 1H) 8.68 (d, J=5.48 Hz, 1H) 10.54 (s, 1H). LCMS (m/z) (M+H)=463.2, Rt=0.59 min.

Example 484: 3-(difluoromethyl)-N-(4-methyl-3-(1-methyl-6-morpholino-2-oxo-1,2-dihydropyridin-4-yl)phenyl)benzamide

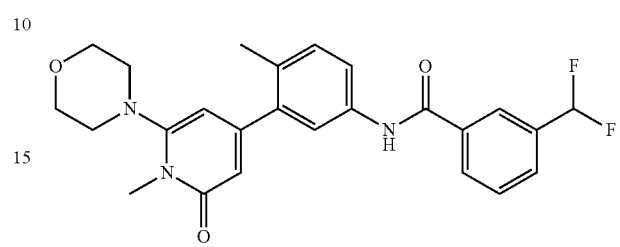

$^1$H NMR (400 MHz, <dmso>) δ ppm 2.24 (s, 3H) 2.94 (br. s., 4H) 3.45 (s, 3H) 3.71-3.78 (m, 4H) 5.80 (d, J=1.17 Hz, 1H) 6.05 (d, J=1.17 Hz, 1H) 6.96-7.31 (m, 2H) 7.63-7.75 (m, 3H) 7.77 (d, J=7.43 Hz, 1H) 8.07-8.16 (m, 2H) 10.35-10.42 (m, 1H). LCMS (m/z) (M+H)=454.2, Rt=0.82 min.

Example 485: N-(4-methyl-3-(1-methyl-6-morpholino-2-oxo-1,2-dihydropyridin-4-yl)phenyl)-2-(trifluoromethyl)isonicotinamide

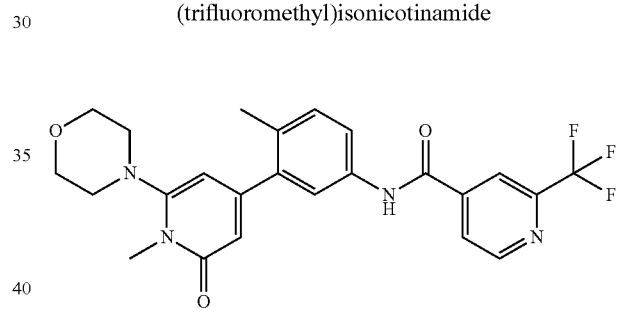

$^1$H NMR (400 MHz, <dmso>) δ ppm 2.25 (s, 3H) 2.93 (br. s., 4H) 3.45 (s, 3H) 3.74 (d, J=3.91 Hz, 4H) 5.80 (s, 1H) 6.05 (s, 1H) 7.30 (d, J=8.22 Hz, 1H) 7.65 (s, 1H) 7.71 (dd, J=8.22, 1.96 Hz, 1H) 8.17 (d, J=5.09 Hz, 1H) 8.34 (s, 1H) 8.97 (d, J=4.69 Hz, 1H) 10.67 (s, 1H). LCMS (m/z) (M+H)=473.3, Rt=0.82 min.

Example 486: 2-(difluoromethyl)-N-(4-methyl-3-(1-methyl-6-morpholino-2-oxo-1,2-dihydropyridin-4-yl)phenyl)isonicotinamide

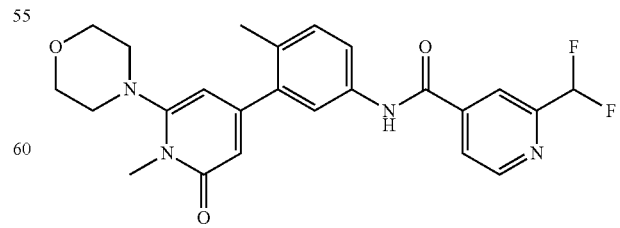

$^1$H NMR (400 MHz, <dmso>) δ ppm 2.25 (s, 3H) 2.94 (br. s., 4H) 3.45 (s, 3H) 3.73 (d, J=3.91 Hz, 4H) 5.70-5.88 (m, 1H) 6.05 (d, J=1.17 Hz, 1H) 6.83-7.23 (m, 1H) 7.25-7.37

(m, 1H) 7.57-7.67 (m, 1H) 7.72 (dd, J=8.22, 1.96 Hz, 1H) 8.04 (d, J=5.09 Hz, 1H) 8.16 (s, 1H) 8.89 (d, J=5.09 Hz, 1H) 10.63 (s, 1H). LCMS (m/z) (M+H)=455.2, Rt=0.74 min.

Example 487: 2-(2-cyanopropan-2-yl)-N-(4-methyl-3-(1-methyl-6-morpholino-2-oxo-1,2-dihydropyridin-4-yl)phenyl)isonicotinamide

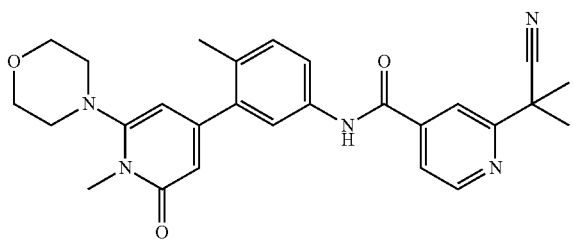 [SMILES: Cc1ccc(NC(=O)c2ccnc(C(C)(C)C#N)c2)cc1-c1cc(N2CCOCC2)n(C)c(=O)c1]

¹H NMR (400 MHz, <dmso>) δ ppm 1.75 (s, 6H) 2.24 (s, 3H) 2.93 (br. s., 4H) 3.45 (s, 3H) 3.73 (br. s., 4H) 5.80 (s, 1H) 6.05 (s, 1H) 7.30 (d, J=8.22 Hz, 1H) 7.63 (s, 1H) 7.70 (dd, J=8.41, 1.76 Hz, 1H) 7.84 (d, J=4.70 Hz, 1H) 7.98 (s, 1H) 8.79 (d, J=4.70 Hz, 1H) 10.54 (s, 1H). LCMS (m/z) (M+H)=472.3, Rt=0.77 min.

Example 488: N-(4-methyl-3-(1-methyl-6-morpholino-2-oxo-1,2-dihydropyridin-4-yl)phenyl)-3-(methylsulfonyl)benzamide

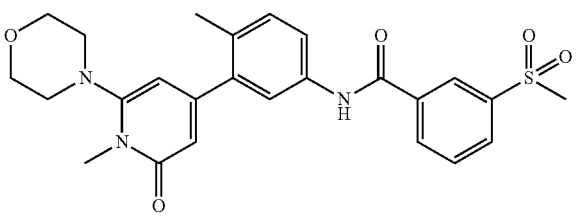 [SMILES: Cc1ccc(NC(=O)c2cccc(S(C)(=O)=O)c2)cc1-c1cc(N2CCOCC2)n(C)c(=O)c1]

¹H NMR (400 MHz, <dmso>) δ ppm 2.24 (s, 3H) 2.94 (br. s., 4H) 3.21-3.34 (m, 3H) 3.39-3.48 (m, 3H) 3.8 (br. s., 4H) 5.74-5.88 (m, 1H) 5.98-6.12 (m, 1H) 7.19-7.34 (m, 1H) 7.65 (d, J=1.56 Hz, 1H) 7.68-7.75 (m, 1H) 7.76-7.87 (m, 1H) 8.08-8.17 (m, 1H) 8.22-8.32 (m, 1H) 8.39-8.53 (m, 1H) 10.51 (s, 1H). LCMS (m/z) (M+H)=482.3, Rt=0.70 min.

Example 489: 6-(2-cyanopropan-2-yl)-N-(4-methyl-3-(1-methyl-6-morpholino-2-oxo-1,2-dihydropyridin-4-yl)phenyl)pyridazine-4-carboxamide

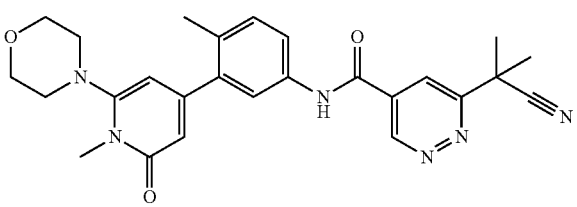 [SMILES: Cc1ccc(NC(=O)c2cnnc(C(C)(C)C#N)c2)cc1-c1cc(N2CCOCC2)n(C)c(=O)c1]

¹H NMR (400 MHz, <dmso>) δ ppm 1.83 (s, 6H) 2.25 (s, 3H) 2.93 (br. s., 4H) 3.45 (s, 3H) 3.73 (d, J=4.30 Hz, 4H) 5.80 (d, J=1.57 Hz, 1H) 6.05 (s, 1H) 7.32 (d, J=8.61 Hz, 1H) 7.62 (d, J=1.96 Hz, 1H) 7.69 (dd, J=8.22, 1.96 Hz, 1H) 8.28 (d, J=1.96 Hz, 1H) 9.62 (d, J=1.57 Hz, 1H) 10.74 (s, 1H). LCMS (m/z) (M+H)=473.2, Rt=0.74 min.

Example 490: 3-(4-ethylpiperazin-1-yl)-N-(4-methyl-3-(1-methyl-6-morpholino-2-oxo-1,2-dihydropyridin-4-yl)phenyl)-5-(trifluoromethyl)benzamide

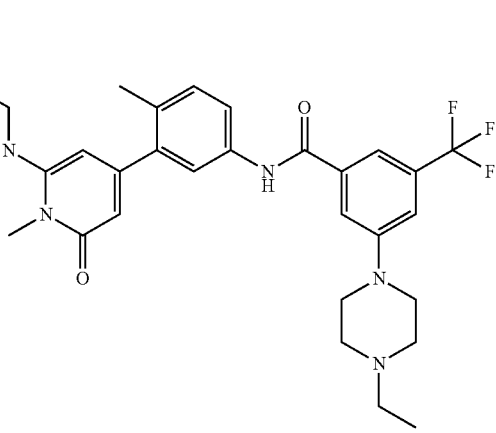

¹H NMR (400 MHz, <dmso>) δ ppm 1.25 (t, J=7.24 Hz, 3H) 2.24 (s, 3H) 2.93 (br. s., 4H) 3.06-3.15 (m, 4H) 3.18-3.24 (m, 2H) 3.45 (s, 3H) 3.59 (d, J=7.43 Hz, 2H) 3.73 (t, J=4.11 Hz, 4H) 4.10 (d, J=9.78 Hz, 2H) 5.80 (d, J=1.56 Hz, 1H) 6.04 (d, J=1.17 Hz, 1H) 7.19-7.35 (m, 1H) 7.50 (s, 1H) 7.61 (d, J=1.96 Hz, 1H) 7.65-7.80 (m, 3H) 9.42 (br. s., 1H) 10.36 (s, 1H). LCMS (m/z) (M+H)=584.3, Rt=0.77 min.

Example 491: 3-fluoro-N-(4-methyl-3-(1-methyl-6-morpholino-2-oxo-1,2-dihydropyridin-4-yl)phenyl)-5-morpholinobenzamide

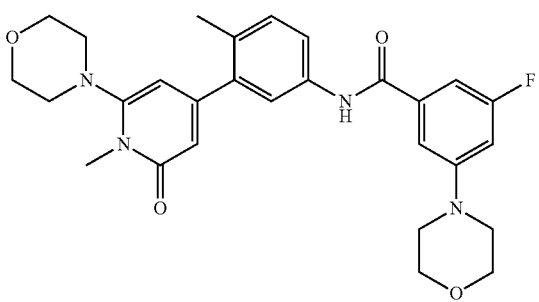 [SMILES: Cc1ccc(NC(=O)c2cc(F)cc(N3CCOCC3)c2)cc1-c1cc(N2CCOCC2)n(C)c(=O)c1]

¹H NMR (400 MHz, <dmso>) δ ppm 2.23 (s, 3H) 2.93 (br. s., 4H) 3.17-3.24 (m, 4H) 3.45 (s, 3H) 3.71-3.75 (m, 8H) 5.79 (d, J=1.56 Hz, 1H) 6.04 (d, J=1.57 Hz, 1H) 6.90-7.01 (m, 1H) 7.11 (d, J=8.61 Hz, 1H) 7.20-7.34 (m, 2H) 7.61 (d, J=2.35 Hz, 1H) 7.69 (dd, J=8.22, 2.35 Hz, 1H) 10.17 (s, 1H). LCMS (m/z) (M+H)=507.1, Rt=0.86 min.

Example 492: N-(4-methyl-3-(1-methyl-6-morpholino-2-oxo-1,2-dihydropyridin-4-yl)phenyl)-3-(oxetan-3-yl)benzamide

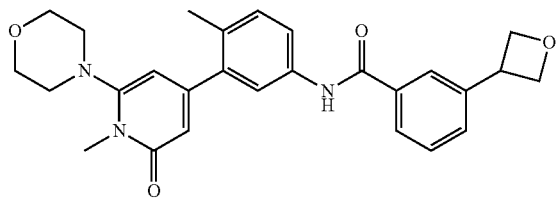 [SMILES: Cc1ccc(NC(=O)c2cccc(C3COC3)c2)cc1-c1cc(N2CCOCC2)n(C)c(=O)c1]

LCMS (m/z) (M+H)=460.2, Rt=0.78 min.

Example 493: N-(4-methyl-3-(1-methyl-6-morpholino-2-oxo-1,2-dihydropyridin-4-yl)phenyl)-3-(1,3,4-oxadiazol-2-yl)benzamide

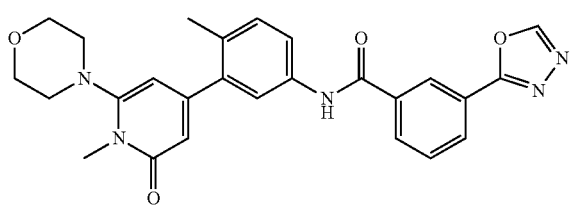 [SMILES: Cc1ccc(NC(=O)c2cccc(-c3nnco3)c2)cc1-c1cc(N2CCOCC2)n(C)c(=O)c1]

$^1$H NMR (400 MHz, <dmso>) δ ppm 2.25 (s, 3H) 2.94 (br. s., 4H) 3.45 (s, 3H) 3.72-3.75 (m, 4H) 5.81 (d, J=1.57 Hz, 1H) 6.06 (d, J=1.57 Hz, 1H) 7.17-7.36 (m, 1H) 7.58-7.87 (m, 3H) 8.16-8.28 (m, 2H) 8.59 (s, 1H) 9.40 (s, 1H) 10.50 (s, 1H). LCMS (m/z) (M+H)=472.1, Rt=0.75 min.

Example 494: N-(4-methyl-3-(1-methyl-6-morpholino-2-oxo-1,2-dihydropyridin-4-yl)phenyl)-3-(2-(methylsulfonyl)propan-2-yl)benzamide

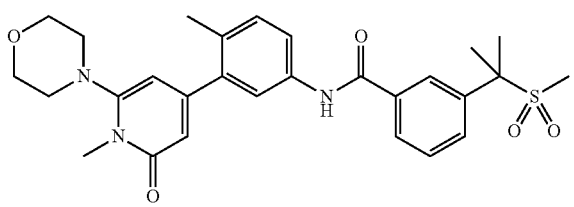 [SMILES: Cc1ccc(NC(=O)c2cccc(C(C)(C)S(C)(=O)=O)c2)cc1-c1cc(N2CCOCC2)n(C)c(=O)c1]

$^1$H NMR (400 MHz, <dmso>) δ ppm 1.80 (s, 6H) 2.24 (s, 3H) 2.72 (s, 3H) 2.93 (br. s., 4H) 3.45 (s, 3H) 3.73 (t, J=4.11 Hz, 4H) 5.80 (d, J=1.57 Hz, 1H) 6.05 (d, J=1.57 Hz, 1H) 7.27 (d, J=8.61 Hz, 1H) 7.56 (t, J=7.83 Hz, 1H) 7.63 (d, J=1.96 Hz, 1H) 7.70 (dd, J=8.22, 1.96 Hz, 1H) 7.81 (d, J=8.22 Hz, 1H) 7.96 (d, J=7.83 Hz, 1H) 8.10 (s, 1H) 10.28 (s, 1H). LCMS (m/z) (M+H)=524.1, Rt=0.77 min.

Example 495: N-(4-methyl-3-(1-methyl-6-morpholino-2-oxo-1,2-dihydropyridin-4-yl)phenyl)-6-(trifluoromethyl)pyridazine-4-carboxamide

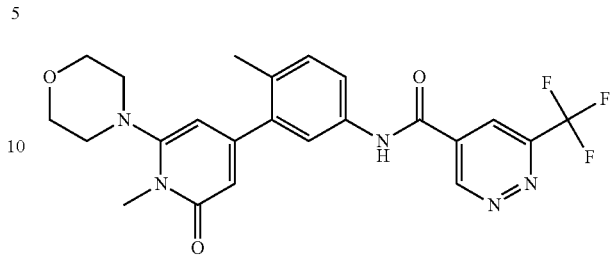

$^1$H NMR (500 MHz, <dmso>) δ ppm 2.27 (s, 3H), 2.94 (s, 4H), 3.46 (s, 3H), 3.74 (d, J=4.7 Hz, 4H), 5.81 (d, J=1.7 Hz, 1H), 6.06 (d, J=1.7 Hz, 1H), 7.34 (d, J=8.4 Hz, 1H), 7.65 (d, J=2.3 Hz, 1H), 7.72 (dd, J=8.3, 2.3 Hz, 1H), 8.67 (d, J=2.0 Hz, 1H), 9.91 (d, J=2.0 Hz, 1H), 10.86 (s, 1H). LCMS (m/z) (M+H)=474.0, Rt=0.80 min.

Example 496: 6-cyclopropyl-N-(4-methyl-3-(1-methyl-6-morpholino-2-oxo-1,2-dihydropyridin-4-yl)phenyl)pyridazine-4-carboxamide

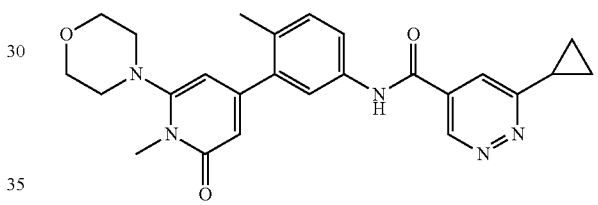

$^1$H NMR (400 MHz, <dmso>) δ ppm 1.07-1.23 (m, 4H) 2.24 (s, 3H) 2.32-2.40 (m, 1H) 2.93 (br. s., 4H) 3.45 (s, 3H) 3.73 (br. s., 4H) 5.79 (d, J=1.57 Hz, 1H) 6.04 (d, J=1.57 Hz, 1H) 7.30 (d, J=8.22 Hz, 1H) 7.62 (d, J=1.96 Hz, 1H) 7.68 (dd, J=8.22, 2.35 Hz, 1H) 7.87 (d, J=1.96 Hz, 1H) 9.36 (d, J=1.96 Hz, 1H) 10.61 (s, 1H). LCMS (m/z) (M+H)=446.2, Rt=0.70 min.

Example 497: 3-((dimethylamino)methyl)-N-(4-methyl-3-(1-methyl-6-morpholino-2-oxo-1,2-dihydropyridin-4-yl)phenyl)-5-(trifluoromethyl)benzamide

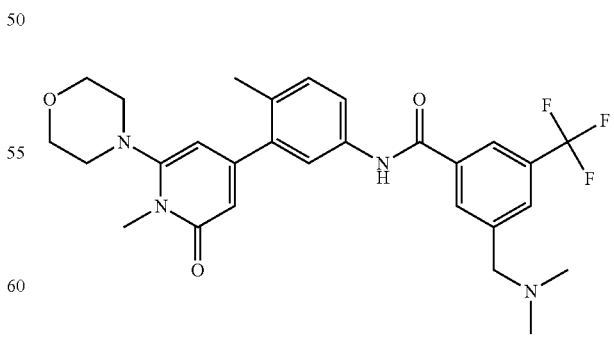

$^1$H NMR (400 MHz, <dmso>) δ ppm 2.25 (s, 3H) 2.77 (br. s., 6H) 2.93 (br. s., 4H) 3.45 (s, 3H) 3.70-3.76 (m, 4H) 4.43-4.49 (m, 2H) 5.80 (d, J=1.57 Hz, 1H) 6.05 (d, J=1.57 Hz, 1H) 7.30 (d, J=8.22 Hz, 1H) 7.62 (d, J=1.96 Hz, 1H)

7.71 (dd, J=8.22, 1.96 Hz, 1H) 8.12 (s, 1H) 8.35 (s, 1H) 8.43 (s, 1H) 10.53 (s, 1H). LCMS (m/z) (M+H)=529.3, Rt=0.68 min.

The compounds listed below were prepared using methods similar to those described in the preparation of Example 171 using the appropriate starting materials.

Example 498: N-(1',2-dimethyl-6'-morpholino-2'-oxo-1',2'-dihydro-[3,4'-bipyridin]-5-yl)-3-(trifluoromethyl)benzamide Synthesis of 5-amino-1',2-dimethyl-6'-morpholino-[3,4'-bipyridin]-2'(1'H)-one

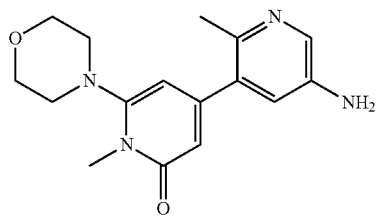 [SMILES: Cc1ncc(N)cc1-c1cc(N2CCOCC2)n(C)c(=O)c1]

Following the preparation of the precursor in Example 471, using the appropriate starting materials gave 5-amino-1',2-dimethyl-6'-morpholino-[3,4'-bipyridin]-2'(1'H)-one (60% yield) as a light brown residue. LCMS (m/z) (M+H)= 301.1, Rt=0.35 min.

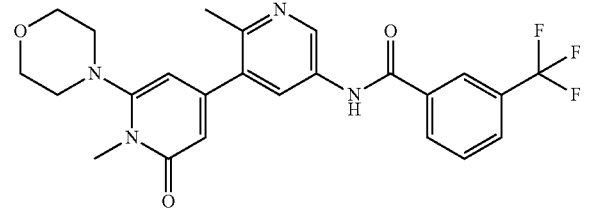 [SMILES: Cc1ncc(NC(=O)c2cccc(C(F)(F)F)c2)cc1-c1cc(N2CCOCC2)n(C)c(=O)c1]

$^1$H NMR (400 MHz, <dmso>) δ ppm 2.44 (s, 3H) 2.95 (br. s., 4H) 3.45 (s, 3H) 3.73 (t, J=4.11 Hz, 4H) 5.87 (d, J=1.56 Hz, 1H) 6.13 (d, J=1.56 Hz, 1H) 7.79 (t, J=7.63 Hz, 1H) 7.98 (d, J=7.83 Hz, 1H) 8.03 (d, J=2.35 Hz, 1H) 8.26 (d, J=7.83 Hz, 1H) 8.30 (s, 1H) 8.85 (d, J=2.35 Hz, 1H) 10.66 (s, 1H). LCMS (m/z) (M+H)=473.0, Rt=0.67 min.

Example 499: 2-(2-cyanopropan-2-yl)-N-(1',2-dimethyl-6'-morpholino-6'-oxo-1',2'-dihydro-[3,4'-bipyridin]-5-yl)isonicotinamide

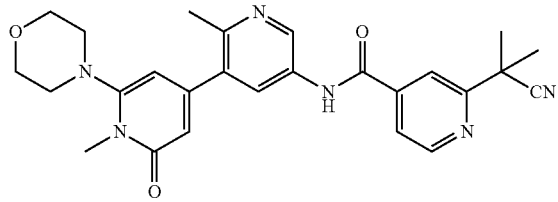 [SMILES: Cc1ncc(NC(=O)c2ccnc(C(C)(C)C#N)c2)cc1-c1cc(N2CCOCC2)n(C)c(=O)c1]

$^1$H NMR (400 MHz, <dmso>) δ ppm 1.77 (s, 6H) 2.96 (br. s., 4H) 3.47 (s, 3H) 3.75 (br. s., 4H) 5.91 (s, 1H) 6.17 (s, 1H) 7.89 (d, J=4.70 Hz, 1H) 8.04 (s, 1H) 8.12 (s, 1.57 Hz, 1H) 8.84 (d, J=5.09 Hz, 1H) 8.93 (d, J=1.57 Hz, 1H) 10.90 (s, 1H). LCMS (m/z) (M+H)=473.2, Rt=0.54 min.

Example 500: N-(1',2-dimethyl-6'-morpholino-2'-oxo-1',2'-dihydro-[3,4'-bipyridin]-5-yl)-2-trifluoromethyl)isonicotinamide

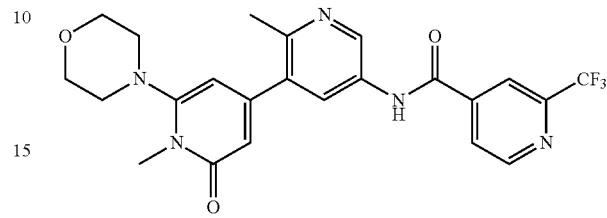

$^1$H NMR (400 MHz, <dmso>) δ ppm 2.95 (br. s., 4H) 3.46 (s, 3H) 3.74 (t, J=4.11 Hz, 4H) 5.89 (d, J=1.17 Hz, 1H) 6.16 (d, J=1.17 Hz, 1H) 8.13 (d, J=2.35 Hz, 1H) 8.20 (d, J=4.70 Hz, 1H) 8.37 (s, 1H) 8.93 (d, J=2.35 Hz, 1H) 9.01 (d, J=5.09 Hz, 1H) 11.01 (s, 1H). LCMS (m/z) (M+H)=474.1, Rt=0.57 min.

Example 501: N-(1',2-dimethyl-6'-morpholino-2'-oxo-1',2'-dihydro-[3,4'-bipyridin]-5-yl)-2-(2-hydroxypropan-2-yl)isonicotinamide

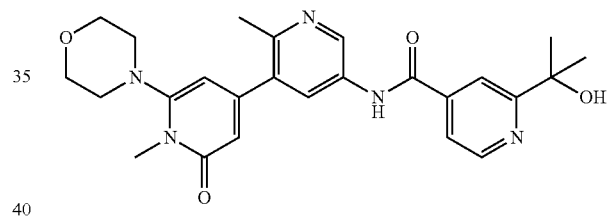

$^1$H NMR (400 MHz, <dmso>) δ ppm 1.46 (s., 6H) 2.52 (s, 3H) 2.95 (br. s., 4H) 3.38-3.50 (m, 3H) 3.67-3.80 (m, 4H) 5.91 (s, 1H) 6.10-6.25 (m, 1H) 7.66-7.83 (m, 1H) 8.14-8.25 (m, 2H) 8.65-8.77 (m, 1H) 9.00 (d, J=1.96 Hz, 1H) 10.97 (s, 1H). LCMS (m/z) (M+H)=464.1, Rt=0.33 min.

Example 502: N-(1',2-dimethyl-6'-morpholino-2'-oxo-1',2'-dihydro-[3,4'-bipyridin]-5-yl)-1-ethyl-6-oxo-5-(trifluoromethyl)-1,6-dihydropyridine-3-carboxamide

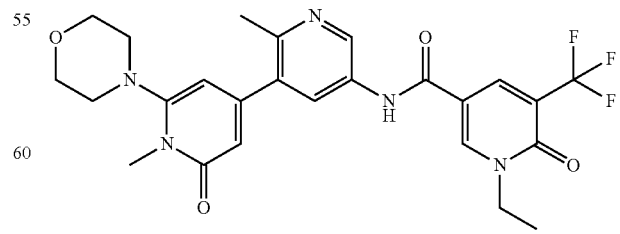

$^1$H NMR (400 MHz, <dmso>) δ ppm 1.31 (t, J=7.24 Hz, 3H) 2.96 (br. s., 4H) 3.48 (s, 3H) 3.76 (t, J=4.11 Hz, 4H) 4.09 (quin, J=7.53 Hz, 2H) 5.91 (s, 1H) 6.18 (s, 1H) 8.15 (d, J=1.96 Hz, 1H) 8.49 (d, J=1.57 Hz, 1H) 8.79 (d, J=1.96 Hz, 1H) 8.85 (s, 1H) 10.56 (br. s., 1H). LCMS (m/z) (M+H)= 518.1, Rt=0.58 min.

Example 503: N-(1',2-dimethyl-6'-morpholino-2'-oxo-1',2'-dihydro-[3,4'-bipyridin]-5-yl)benzamide

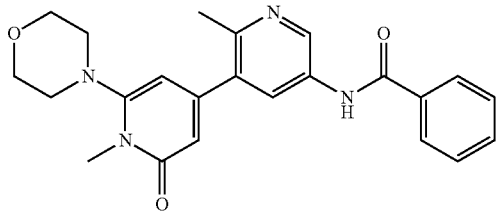 [SMILES: Cc1ncc(NC(=O)c2ccccc2)cc1-c1cc(N2CCOCC2)n(C)c(=O)c1]

¹H NMR (400 MHz, <dmso>) δ ppm 2.45 (br. s., 3H) 2.90 (br. s., 4H) 3.35-3.47 (m, 3H) 3.69 (t, J=4.11 Hz, 4H) 5.86 (d, J=1.17 Hz, 1H) 6.12 (d, J=1.17 Hz, 1H) 7.44-7.54 (m, 2H) 7.54-7.63 (m, 1H) 7.93 (d, J=7.04 Hz, 2H) 8.10-8.20 (m, 1H) 8.95 (d, J=1.96 Hz, 1H) 10.59 (s, 1H). LCMS (m/z) (M+H)=405.0, Rt=0.53 min.

Example 504: N-(1',2-dimethyl-6'-morpholino-2'-oxo-1',2'-dihydro-[3,4'-bipyridin]-5-yl)-2-(methylsulfonyl)isonicotinamide

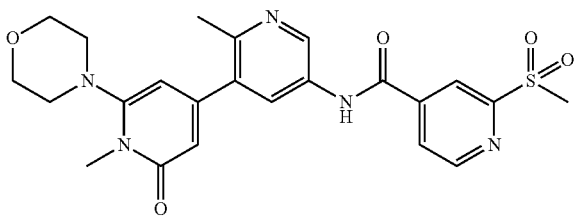 [SMILES: Cc1ncc(NC(=O)c2ccnc(S(C)(=O)=O)c2)cc1-c1cc(N2CCOCC2)n(C)c(=O)c1]

¹H NMR (400 MHz, <dmso>) δ ppm 2.44 (br. s., 3H) 2.90 (br. s., 4H) 3.23-3.33 (m, 3H) 3.41 (s, 3H) 3.69 (br. s., 4H) 5.85 (s, 1H) 6.11 (s, 1H) 8.09 (s, 1H) 8.17 (d, J=5.09 Hz, 1H) 8.50 (s, 1H) 8.89 (s, 1H) 8.97 (d, J=4.70 Hz, 1H) 11.06 (s, 1H). LCMS (m/z) (M+H)=484.0, Rt=0.46 min.

Example 505: N-(1',2-dimethyl-6'-morpholino-2'-oxo-1',2'-dihydro-[3,4'-bipyridin]-5-yl)-2-isopropylisonicotinamide

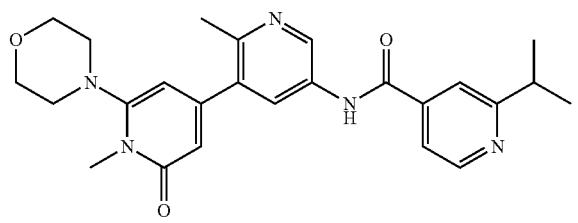 [SMILES: Cc1ncc(NC(=O)c2ccnc(C(C)C)c2)cc1-c1cc(N2CCOCC2)n(C)c(=O)c1]

¹H NMR (400 MHz, <dmso>) δ ppm 1.29 (d, J=6.65 Hz, 6H) 2.52 (s, 3H) 2.95 (br. s., 4H) 3.16 (spt, J=6.72 Hz, 1H) 3.46 (s, 3H) 3.74 (br. s., 4H) 5.91 (s, 1H) 6.18 (s, 1H) 7.77

(d, J=5.09 Hz, 1H) 7.84 (s, 1H) 8.21 (s, 1H) 8.75 (d, J=5.09 Hz, 1H) 9.00 (s, 1H) 10.95 (s, 1H). LCMS (m/z) (M+H)= 448.1, Rt=0.45 min.

Example 506: 3-(difluoromethyl)-N-(1',2-dimethyl-6'-morpholino-2'-oxo-1',2'-dihydro-[3,4'-bipyridin]-5-yl)benzamide

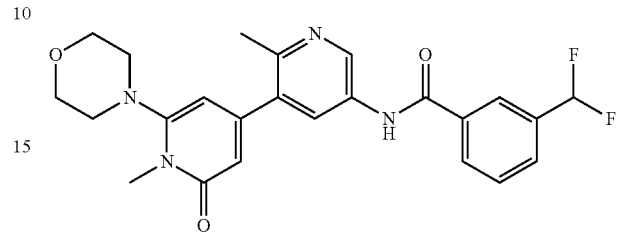

¹H NMR (400 MHz, <dmso>) δ ppm 2.49 (br. s., 3H) 2.95 (br. s., 4H) 3.46 (s, 3H) 3.72-3.76 (m, 4H) 5.90 (d, J=1.17 Hz, 1H) 6.11-6.21 (m, 1H) 6.95-7.33 (m, 1H) 7.67-7.76 (m, 1H) 7.82 (d, J=7.83 Hz, 1H) 8.10-8.22 (m, 3H) 8.97 (d, J=1.96 Hz, 1H) 10.45-10.96 (m, 1H). LCMS (m/z) (M+H)= 455.2, Rt=0.57 min.

Example 507: 2-(tert-butyl)-N-(1',2-dimethyl-6'-morpholino-2'-oxo-1',2'-dihydro-[3,4'-bipyridin]-5-yl)isonicotinamide

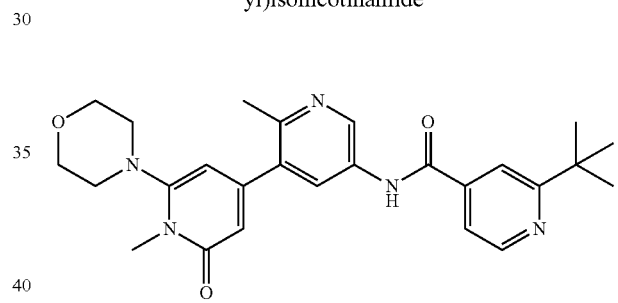

¹H NMR (400 MHz, <dmso>) ᵀᴹppm 1.36 (s, 9H) 2.50 (br. s., 3H) 2.95 (br. s., 4H) 3.46 (s, 3H) 3.74 (t, J=4.11 Hz, 4H) 5.90 (d, J=1.17 Hz, 1H) 6.17 (d, J=1.17 Hz, 1H) 7.70 (dd, J=5.09, 1.17 Hz, 1H) 7.88 (s, 1H) 8.15 (d, J=1.57 Hz, 1H) 8.68-8.80 (m, 1H) 8.96 (d, J=1.96 Hz, 1H) 10.82 (s, 1H). LCMS (m/z) (M+H)=462.3, Rt=0.48 min.

Example 508: 2-(difluoromethyl)-N-(1',2-dimethyl-6'-morpholino-2'-oxo-1',2'-dihydro-[3,4'-bipyridin]-5-yl)isonicotinamide

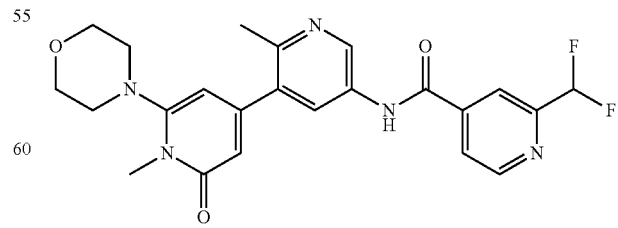

¹H NMR (400 MHz, <dmso>) δ ppm 2.48 (s, 3H) 2.95 (br. s., 4H) 3.46 (s, 3H) 3.74 (br. s., 4H) 5.89 (d, J=1.17 Hz, 1H) 6.16 (d, J=1.56 Hz, 1H) 6.90-7.27 (m, 1H) 8.06 (d, J=5.09 Hz, 1H) 8.12 (d, J=1.96 Hz, 1H) 8.19 (s, 1H) 8.87-8.99 (m, 2H) 10.95 (s, 1H). LCMS (m/z) (M+H)=456.3, Rt=0.50 min.

Example 509: N-(1',2-dimethyl-6'-morpholino-2'-oxo-1',2'-dihydro-[3,4'-bipyridin]-5-yl)-3-(methylsulfonyl)benzamide

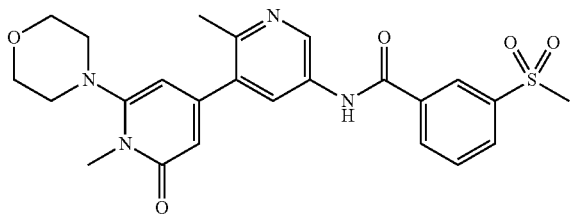 [SMILES: Cc1ncc(NC(=O)c2cccc(S(C)(=O)=O)c2)cc1-c1cc(N2CCOCC2)n(C)c(=O)c1]

$^1$H NMR (400 MHz, <dmso>) δ ppm 2.48 (s, 3H) 2.91 (br. s., 4H) 3.24 (s, 3H) 3.41 (s, 3H) 3.66-3.72 (m, 4H) 5.85 (d, J=1.57 Hz, 1H) 6.12 (d, J=1.57 Hz, 1H) 7.80 (t, J=7.83 Hz, 1H) 8.06-8.16 (m, 2H) 8.26 (d, J=7.83 Hz, 1H) 8.46 (s, 1H) 8.91 (d, J=2.35 Hz, 1H) 10.81 (s, 1H). LCMS (m/z) (M+H)=483.3, Rt=0.47 min.

Example 510: 2-(1,1-difluoroethyl)-N-(1',2-dimethyl-6'-morpholino-2'-oxo-1',2'-dihydro-[3,4'-bipyridin]-5-yl)isonicotinamide

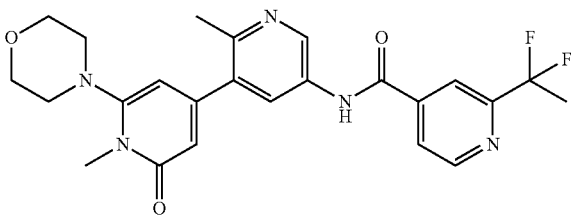 [SMILES: Cc1ncc(NC(=O)c2ccnc(C(C)(F)F)c2)cc1-c1cc(N2CCOCC2)n(C)c(=O)c1]

LCMS (m/z) (M+H)=470.4, Rt=0.55 min.

Example 511: 2-cyclopropyl-N-(1',2-dimethyl-6'-morpholino-2'-oxo-1',2'-dihydro-[3,4'-bipyridin]-5-yl)isonicotinamide

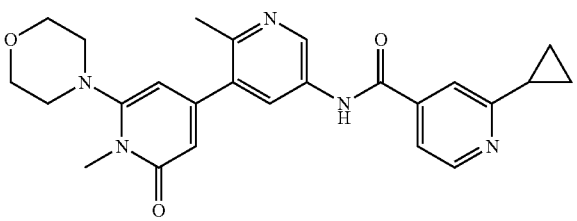 [SMILES: Cc1ncc(NC(=O)c2ccnc(C3CC3)c2)cc1-c1cc(N2CCOCC2)n(C)c(=O)c1]

$^1$H NMR (400 MHz, <dmso>) δ ppm 0.88-1.10 (m, 4H) 2.15-2.27 (m, 1H) 2.49 (s, 3H) 2.95 (br. s., 4H) 3.46 (s, 3H) 3.71-3.76 (m, 4H) 5.89 (d, J=1.57 Hz, 1H) 6.15 (d, J=1.56 Hz, 1H) 7.60 (dd, J=5.09, 1.17 Hz, 1H) 7.76 (s, 1H) 8.12 (d, J=1.96 Hz, 1H) 8.60 (d, J=5.09 Hz, 1H) 8.93 (d, J=2.35 Hz, 1H) 10.77 (s, 1H). LCMS (m/z) (M+H)=446.2, Rt=0.48 min.

Example 512: N-(1',2-dimethyl-6'-morpholino-2'-oxo-1',2'-dihydro-[3,4'-bipyridin]-5-yl)-3-(2-(methylsulfonyl)propan-2-yl)benzamide

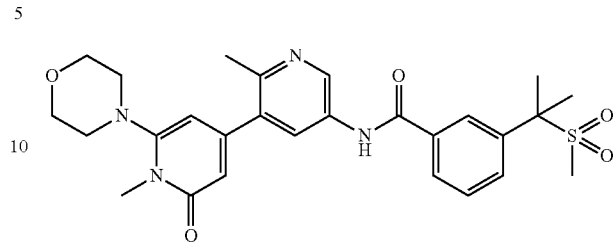

$^1$H NMR (400 MHz, <dmso>) δ ppm 1.81 (s, 6H) 2.49 (s, 3H) 2.73 (s, 3H) 2.89-3.00 (m, 4H) 3.46 (s, 3H) 3.73 (d, J=4.30 Hz, 4H) 5.90 (d, J=1.57 Hz, 1H) 6.16 (d, J=1.17 Hz, 1H) 7.60 (s, 1H) 7.85 (d, J=8.61 Hz, 1H) 8.01 (d, J=7.83 Hz, 1H) 8.08-8.18 (m, 2H) 8.94 (d, J=1.96 Hz, 1H) 10.60 (s, 1H). LCMS (m/z) (M+H)=525.1, Rt=0.56 min.

The compounds listed below were prepared using methods similar to those described in the preparation of Example 171 using the appropriate starting materials.

Synthesis of 5-amino-2-chloro-1-methyl-6'-morpholino-[3,4'-bipyridin]-2'(1'H)-one Following the preparation in Example 471 using the appropriate starting materials gave crude 5-amino-2-chloro-1-methyl-6'-morpholino-[3,4'-bipyridin]-2'(1'H)-one (assumed 100% yield) which was used without further purification.

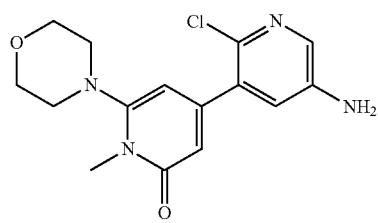 [SMILES: Cn1c(N2CCOCC2)cc(-c2cc(N)cnc2Cl)cc1=O]

LCMS (m/z) (M+H)=321.0, Rt=0.49 min.

Example 513: N-(2-chloro-1'-methyl-6'-morpholino-2'-oxo-1',2'-dihydro-[3,4'-bipyridin]-5-yl)-2-(1,1-difluoroethyl)isonicotinamide

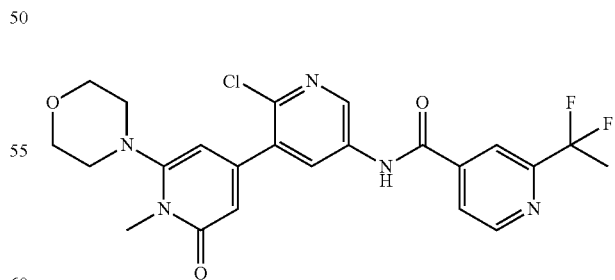

$^1$H NMR (400 MHz, <dmso>) δ ppm 2.04 (t, J=19.17 Hz, 3H) 2.95 (br. s., 4H) 3.46 (s, 3H) 3.71-3.76 (m, 4H) 5.95 (d, J=1.57 Hz, 1H) 6.22 (d, J=1.17 Hz, 1H) 8.03 (d, J=5.09 Hz, 1H) 8.20 (s, 1H) 8.26 (d, J=2.35 Hz, 1H) 8.84 (d, J=2.35 Hz, 1H) 8.91 (d, J=5.09 Hz, 1H) 11.03 (s, 1H). LCMS (m/z) (M+H)=490.2, Rt=0.76 min.

321

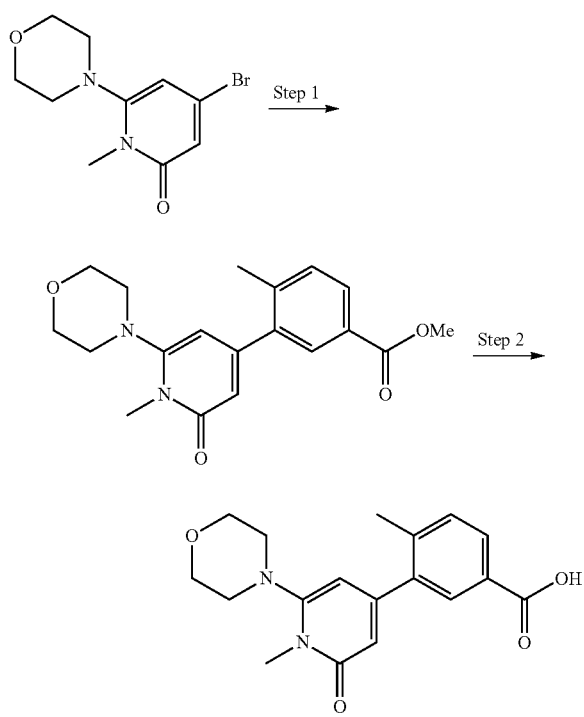

Step 1: Synthesis of methyl 4-methyl-3-(1-methyl-6-morpholino-2-oxo-1,2-dihydropyridin-4-yl)benzoate

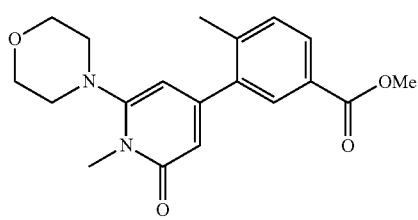 [SMILES: COC(=O)c1ccc(C)c(-c2cc(N3CCOCC3)n(C)c(=O)c2)c1]

To a 0.20M solution of 4-bromo-1-methyl-6-morpholinopyridin-2(1H)-one (1.00 equiv.) in DME was added methyl 4-methyl-3-(4,4,5,5-tetramethyl-1,3,2-dioxaborolan-2-yl)benzoate (1.10 equiv.), PdCl2(dppf).CH2Cl2 adduct (0.50 equiv.), and 2M aqueous sodium carbonate (8.00 equiv.). The reaction mixture was irradiated at 110° C. for 15 min in the microwave. The cooled reaction mixture was diluted with water and extracted with ethyl acetate. The combined extracts were dried over magnesium sulfate, filtered, concentrated to give crude methyl 4-methyl-3-(1-methyl-6-morpholino-2-oxo-1,2-dihydropyridin-4-yl)benzoate (80.0% yield) as a brown oil. LCMS (m/z) (M+H)=343.2, Rt=0.72 min.

322

Step 2: Synthesis of 4-methyl-3-(1-methyl-6-morpholino-2-oxo-1,2-dihydropyridin-4-yl)benzoic acid

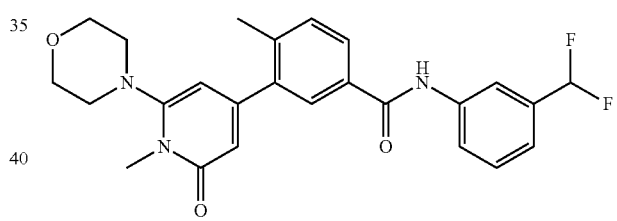

To a 0.20M solution of methyl 4-methyl-3-(1-methyl-6-morpholino-2-oxo-1,2-dihydropyridin-4-yl)benzoate (1.00 equiv.) in 1:1 THF:water was added lithium hydroxide (2.00 equiv.). The mixture was stirred at ambient temperature for 20 hr. The reaction mixture was acidified with aqueous HCl and extracted with ethyl acetate. The combined extracts were dried over magnesium sulfate, filtered, and concentrated to give crude 4-methyl-3-(1-methyl-6-morpholino-2-oxo-1,2-dihydropyridin-4-yl)benzoic acid as an off-white solid (63% yield). LCMS (m/z) (M+H)=329.1, Rt=0.56 min.

The compounds listed below were prepared using methods similar to those described for the preparation of Example 171 using the appropriate starting materials.

Example 514: N-(3-(difluoromethyl)phenyl)-4-methyl-3-(1-methyl-6-morpholino-2-oxo-1,2-dihydropyridin-4-yl)benzamide

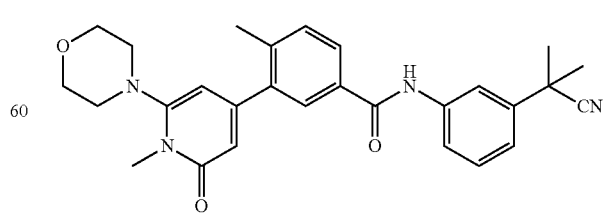

$^1$H NMR (400 MHz, <dmso>) δ ppm 2.27-2.39 (m, 3H) 2.95 (br. s., 4H) 3.46 (s, 3H) 3.63-3.85 (m, 4H) 5.87 (d, J=1.17 Hz, 1H) 6.15 (d, J=1.17 Hz, 1H) 6.80-7.20 (m, 1H) 7.27 (d, J=7.83 Hz, 1H) 7.41-7.52 (m, 2H) 7.85 (s, 1H) 7.90 (d, J=7.83 Hz, 2H) 8.04 (s, 1H) 10.38 (s, 1H). LCMS (m/z) (M+H)=454.2, Rt=0.83 min.

Example 515: N-(3-(2-cyanopropan-2-yl)phenyl)-4-methyl-3-(1-methyl-6-morpholino-2-oxo-1,2-dihydropyridin-4-yl)benzamide $^1$H NMR (400 MHz, <dmso>) δ ppm 1.60-1.71 (m, 6H) 2.34 (s, 3H) 2.95 (br. s., 4H) 3.46 (s, 3H) 3.73 (t, J=3.91 Hz, 4H) 5.87 (d, J=1.17 Hz, 1H) 6.15 (s, 1H) 7.22 (d, J=7.83 Hz, 1H) 7.39 (t, J=7.83 Hz, 1H) 7.45 (d, J=8.22 Hz, 1H) 7.80 (d, J=8.22 Hz, 1H) 7.85 (s, 1H) 7.87-7.98 (m, 2H) 10.30 (s, 1H). LCMS (m/z) (M+H)=471.3, Rt=0.85 min.

Example 516: N-(3-(2-hydroxypropan-2-yl)phenyl)-4-methyl-3-(1-methyl-6-morpholino-2-oxo-1,2-dihydropyridin-4-yl)benzamide

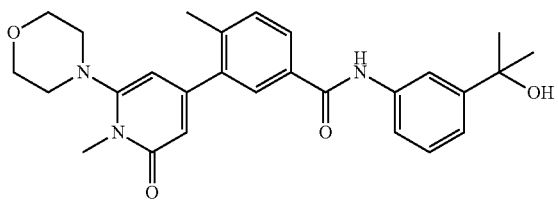 [SMILES: Cc1ccc(C(=O)Nc2cccc(C(C)(C)O)c2)cc1-c1cc(N2CCOCC2)n(C)c(=O)c1]

¹H NMR (400 MHz, <dmso>) δ ppm 1.43 (s, 6H) 2.36 (s, 3H) 2.96 (br. s., 4H) 3.48 (s, 3H) 3.75 (d, J=3.91 Hz, 4H) 5.88 (d, J=1.56 Hz, 1H) 6.17 (d, J=1.17 Hz, 1H) 7.14-7.22 (m, 1H) 7.23-7.30 (m, 1H) 7.45 (d, J=8.22 Hz, 1H) 7.69 (d, J=8.22 Hz, 1H) 7.78-7.88 (m, 2H) 7.88-7.96 (m, 1H) 10.16 (s, 1H). LCMS (m/z) (M+H)=462.3, Rt=0.74 min.

Example 517: 4-methyl-3-(1-methyl-6-morpholino-2-oxo-1,2-dihydropyridin-4-yl)-N-(3-(trifluoromethyl)phenyl)benzamide

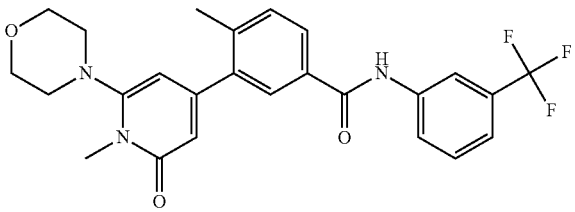 [SMILES: Cc1ccc(C(=O)Nc2cccc(C(F)(F)F)c2)cc1-c1cc(N2CCOCC2)n(C)c(=O)c1]

¹H NMR (400 MHz, <dmso>) δ ppm 2.35 (s, 3H) 2.95 (br. s., 4H) 3.46 (s, 3H) 3.73 (d, J=4.30 Hz, 4H) 5.86 (d, J=1.57 Hz, 1H) 6.15 (d, J=1.57 Hz, 1H) 7.38-7.51 (m, 2H) 7.58 (t, J=8.02 Hz, 1H) 7.86 (d, J=1.17 Hz, 1H) 7.91 (dd, J=7.83, 1.57 Hz, 1H) 8.04 (d, J=8.22 Hz, 1H) 8.21 (s, 1H) 10.48 (s, 1H). LCMS (m/z) (M+H)=472.1, Rt=0.91 min.

Example 518: 4-methyl-3-(1-methyl-6-morpholino-2-oxo-1,2-dihydropyridin-4-yl)-N-phenylbenzamide

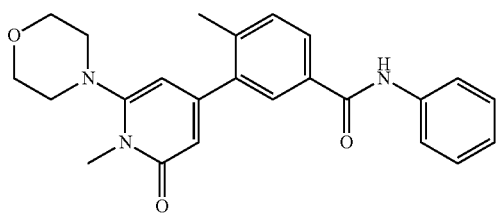 [SMILES: Cc1ccc(C(=O)Nc2ccccc2)cc1-c1cc(N2CCOCC2)n(C)c(=O)c1]

¹H NMR (400 MHz, <dmso>) δ ppm 2.34 (s, 3H) 2.95 (br. s., 4H) 3.46 (s, 3H) 3.73 (br. s., 4H) 5.86 (d, J=1.56 Hz, 1H) 6.15 (d, J=1.56 Hz, 1H) 7.03-7.13 (m, 1H) 7.33 (t, J=8.02 Hz, 2H) 7.44 (d, J=7.83 Hz, 1H) 7.74 (d, J=7.83 Hz, 2H) 7.83 (d, J=1.17 Hz, 1H) 7.88 (dd, J=7.83, 1.57 Hz, 1H) 10.18 (s, 1H). LCMS (m/z) (M+H)=404.1, Rt=0.77 min.

Synthesis of 4-(5-amino-2-methylphenyl)-1-ethyl-6-morpholinopyridin-2(1H)-one

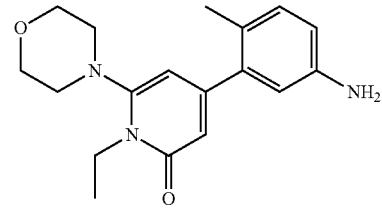 [SMILES: CCn1c(N2CCOCC2)cc(-c2cc(N)ccc2C)cc1=O]

Following the preparation of 4-(5-amino-2-methylphenyl)-1-methyl-6-morpholinopyridin-2(1H)-one using the appropriate starting materials gave 4-(5-amino-2-methylphenyl)-1-ethyl-6-morpholinopyridin-2(1H)-one (37.7% yield) as a white solid. LCMS (m/z) (M+H)=314.2, Rt=0.51 min.

The compounds listed below were prepared using methods similar to those described in the preparation of Example 171 using the appropriate starting materials.

Example 519: 2-(1,1-difluoroethyl)-N-(3-(1-ethyl-6-morpholino-2-oxo-1,2-dihydropyridin-4-yl)-4-methylphenyl)isonicotinamide

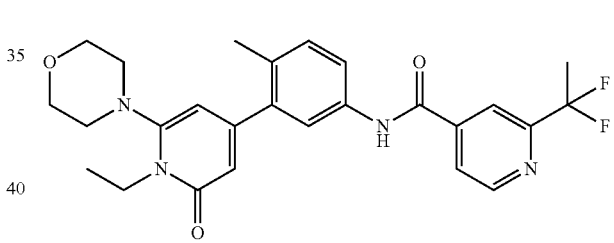

¹H NMR (400 MHz, <dmso>) δ ppm 1.22 (t, J=6.85 Hz, 3H) 2.03 (t, J=19.17 Hz, 3H) 2.25 (s, 3H) 2.91 (d, J=4.30 Hz, 4H) 3.72 (br. s., 4H) 4.08 (q, J=6.65 Hz, 2H) 5.95 (d, J=1.17 Hz, 1H) 6.09 (s, 1H) 7.30 (d, J=8.61 Hz, 1H) 7.66 (d, J=1.96 Hz, 1H) 7.71 (d, J=8.22 Hz, 1H) 8.01 (d, J=5.09 Hz, 1H) 8.16 (s, 1H) 8.81-8.89 (m, 1H) 10.57-10.66 (m, 1H). LCMS (m/z) (M+H)=483.0, Rt=0.88 min.

Example 520: 2-(1,1-difluoropropyl)-N-(3-(1-ethyl-6-morpholino-2-oxo-1,2-dihydropyridin-4-yl)-4-methylphenyl)isonicotinamide

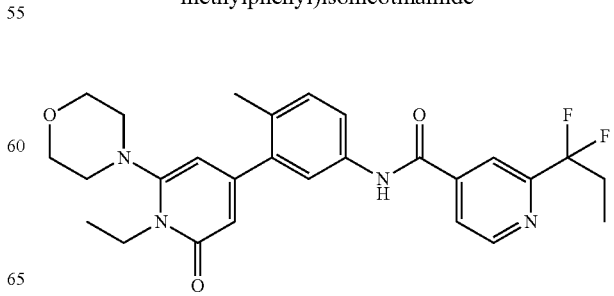

¹H NMR (400 MHz, <dmso>) δ ppm 0.93 (t, J=7.63 Hz, 3H) 1.22 (t, J=6.85 Hz, 3H) 2.25 (s, 3H) 2.30-2.41 (m, 2H) 2.91 (t, J=4.11 Hz, 4H) 3.72 (br. s., 4H) 4.08 (q, J=7.04 Hz, 2H) 5.95 (d, J=1.57 Hz, 1H) 6.10 (d, J=1.56 Hz, 1H) 7.30 (d, J=8.61 Hz, 1H) 7.65 (d, J=1.96 Hz, 1H) 7.71 (dd, J=8.41, 2.15 Hz, 1H) 8.00 (d, J=4.30 Hz, 1H) 8.14 (s, 1H) 8.87 (d, J=5.09 Hz, 1H) 10.62 (s, 1H). LCMS (m/z) (M+H)=497.3, Rt=0.91 min.

Example 521: N-(3-(1-ethyl-6-morpholino-2-oxo-1,2-dihydropyridin-4-yl)-4-methylphenyl)-2-(2-fluoropropan-2-yl)isonicotinamide

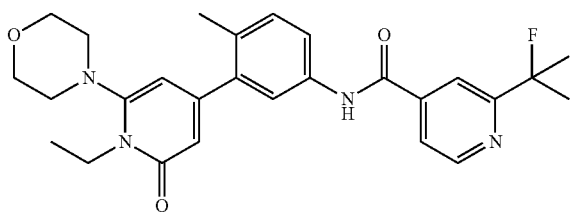 [SMILES: CCn1c(N2CCOCC2)cc(-c2cc(NC(=O)c3ccnc(C(C)(C)F)c3)ccc2C)cc1=O]

¹H NMR (400 MHz, <dmso>) δ ppm 1.22 (t, J=6.85 Hz, 3H) 1.66 (s, 3H) 1.72 (s, 3H) 2.25 (s, 3H) 2.91 (t, J=4.11 Hz, 4H) 3.72 (br. s., 4H) 4.08 (d, J=7.04 Hz, 2H) 5.95 (d, J=1.57 Hz, 1H) 6.10 (d, J=1.57 Hz, 1H) 7.29 (d, J=8.22 Hz, 1H) 7.65 (d, J=1.96 Hz, 1H) 7.71 (dd, J=8.22, 1.96 Hz, 1H) 7.80 (dd, J=4.89, 1.37 Hz, 1H) 8.00 (s, 1H) 8.74 (d, J=5.09 Hz, 1H) 10.54 (s, 1H). LCMS (m/z) (M+H)=479.2, Rt=0.85 min.

Example 522: N-(3-(1-ethyl-6-morpholino-2-oxo-1,2-dihydropyridin-4-yl)-4-methylphenyl)-2-isopropylisonicotinamide

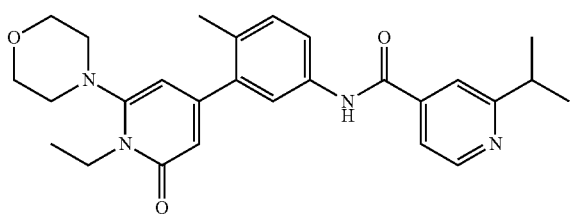 [SMILES: CCn1c(N2CCOCC2)cc(-c2cc(NC(=O)c3ccnc(C(C)C)c3)ccc2C)cc1=O]

¹H NMR (400 MHz, <dmso>) δ ppm 1.19-1.28 (m, 9H) 2.25 (s, 3H) 2.85-2.95 (m, 4H) 3.11 (dt, J=13.69, 6.85 Hz, 1H) 3.72 (br. s., 4H) 4.08 (d, J=6.65 Hz, 2H) 5.94 (d, J=1.57 Hz, 1H) 6.09 (d, J=1.57 Hz, 1H) 7.28 (d, J=8.22 Hz, 1H) 7.58-7.79 (m, 4H) 8.67 (d, J=5.09 Hz, 1H) 10.43 (s, 1H). LCMS (m/z) (M+H)=461.2, Rt=0.68 min.

The compounds listed below were prepared using methods similar to those described in the preparation of Example 162 using the appropriate starting materials.

Synthesis of (R)-4-bromo-1-methyl-6-(3-methylmorpholino)pyridin-2(1H)-one

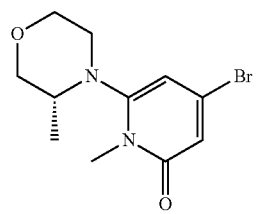 [SMILES: C[C@@H]1COCCN1c1cc(Br)cc(=O)n1C]

Following the preparation of 4-bromo-1-methyl-6-morpholinopyridin-2(1H)-one using the appropriate starting materials gave (R)-4-bromo-1-methyl-6-(3-methylmorpholino)pyridin-2(1H)-one (assumed quantitative yield) as a brown residue. LCMS (m/z) (M+H)=286.8/288.8, Rt=0.63 min.

Example 523: (R)-2-(1,1-difluoroethyl)-N-(4-methyl-3-(1-methyl-6-(3-methylmorpholino)-2-oxo-1,2-dihydropyridin-4-yl)phenyl)isonicotinamide

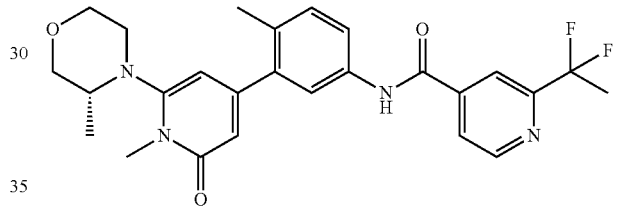

¹H NMR (400 MHz, <dmso>) δ ppm 0.87 (d, J=5.87 Hz, 3H) 2.00 (t, J=19.17 Hz, 3H) 2.21 (s, 3H) 2.56-2.64 (m, 1H) 3.08 (br. s., 1H) 3.21 (br. s., 1H) 3.26-3.35 (m, 1H) 3.44 (s, 3H) 3.58-3.72 (m, 2H) 3.77 (dd, J=10.96, 2.74 Hz, 1H) 5.94 (br. s., 1H) 6.07 (s, 1H) 7.27 (d, J=8.22 Hz, 1H) 7.61 (d, J=1.96 Hz, 1H) 7.66-7.75 (m, 1H) 7.98 (d, J=4.70 Hz, 1H) 8.13 (s, 1H) 8.83 (d, J=5.09 Hz, 1H) 10.60 (s, 1H). LCMS (m/z) (M+H)=483.1, Rt=0.86 min.

Example 524: (R)-2-(1,1-difluoroethyl)-N-(1',2-dimethyl-6'-(3-methylmorpholino)-2'-oxo-1',2'-dihydro-[3,4'-bipyridin]-5-yl)isonicotinamide

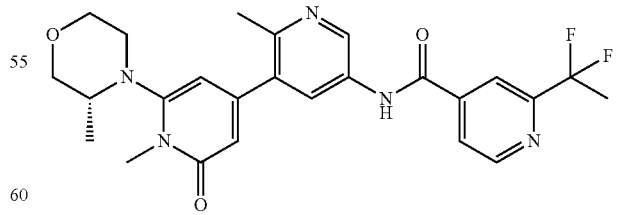

¹H (400 MHz, <dmso>) δ ppm 0.93 (d, J=6.26 Hz, 3H) 2.06 (t, J=19.17 Hz, 3H) 2.67 (dt, J=11.35, 5.67 Hz, 1H) 3.16 (d, J=10.96 Hz, 1H) 3.23-3.32 (m, 1H) 3.36 (d, J=5.87 Hz, 1H) 3.50 (s, 3H) 3.74 (br. s., 2H) 3.82 (dd, J=10.76, 2.54 Hz, 1H) 6.08 (br. s., 1H) 6.21 (s, 1H) 8.05 (d, J=4.30 Hz, 1H)

8.11 (d, J=2.35 Hz, 1H) 8.21 (s, 1H) 8.91 (d, J=5.09 Hz, 1H) 8.94 (d, J=2.35 Hz, 1H) 10.94 (s, 1H). LCMS (m/z) (M+H)= 484.1, Rt=0.62 min.

Synthesis of (S)-4-bromo-1-methyl-6-(3-methylmorpholino)pyridin-2(1H)-one

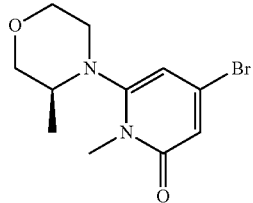 [SMILES: C[C@H]1COCCN1c1cc(Br)cc(=O)n1C]

Following the preparation of 4-bromo-1-methyl-6-morpholinopyridin-2(1H)-one using the appropriate starting materials gave (S)-4-bromo-1-methyl-6-(3-methylmorpholino)pyridin-2(1H)-one (assumed quantitative yield) as a brown residue. LCMS (m/z) (M+H)=286.8/288.8, Rt=0.63 min.

The compounds listed below were prepared using methods similar to those described in the preparation of Example 162 using the appropriate starting materials.

Example 525: (S)-2-(1,1-difluoroethyl)-N-(4-methyl-3-(1-methyl-6-(3-methylmorpholino)-2-oxo-1,2-dihydropyridin-4-yl)phenyl)isonicotinamide

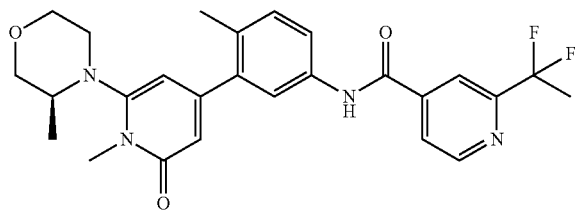 [SMILES: Cc1ccc(NC(=O)c2ccnc(C(C)(F)F)c2)cc1-c1cc(N2CCOC[C@@H]2C)n(C)c(=O)c1]

$^1$H NMR (400 MHz, <dmso>) δ ppm 0.92 (d, J=5.87 Hz, 3H) 2.05 (t, J=19.17 Hz, 3H) 2.26 (s, 3H) 2.61-2.70 (m, 1H) 3.13 (br. s., 1H) 3.26 (br. s., 1H) 3.36 (br. s., 1H) 3.49 (s, 3H) 3.74 (br. s., 2H) 3.82 (dd, J=10.96, 2.74 Hz, 1H) 5.99 (br. s., 1H) 6.12 (s, 1H) 7.32 (d, J=8.22 Hz, 1H) 7.66 (d, J=1.96 Hz, 1H) 7.75 (dd, J=8.22, 1.96 Hz, 1H) 8.03 (d, J=4.70 Hz, 1H) 8.18 (s, 1H) 8.88 (d, J=5.09 Hz, 1H) 10.65 (s, 1H). LCMS (m/z) (M+H)=483.2, Rt=0.86 min.

Example 526: (S)-2-(1,1-difluoroethyl)-N-(1',2-dimethyl-6'-(3-methylmorpholino)-2'-oxo-1',2'-dihydro-[3,4'-bipyridin]-5-yl)isonicotinamide

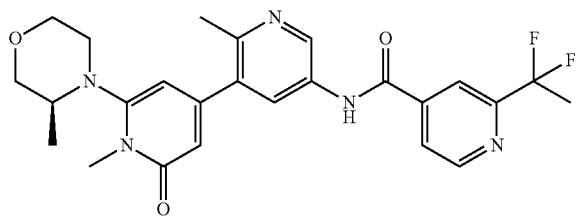 [SMILES: Cc1ncc(NC(=O)c2ccnc(C(C)(F)F)c2)cc1-c1cc(N2CCOC[C@@H]2C)n(C)c(=O)c1]

$^1$H NMR (400 MHz, <dmso>) δ ppm 0.93 (d, J=5.87 Hz, 3H) 2.06 (t, J=19.17 Hz, 3H) 2.61-2.71 (m, 1H) 3.16 (d, J=10.96 Hz, 1H) 3.28 (br. s., 1H) 3.33-3.41 (m, 1H) 3.50 (s, 3H) 3.74 (br. s., 2H) 3.82 (dd, J=11.15, 2.54 Hz, 1H) 6.09 (br. s., 1H) 6.23 (s, 1H) 8.05 (d, J=4.30 Hz, 1H) 8.16 (d, J=1.96 Hz, 1H) 8.22 (s, 1H) 8.92 (d, J=4.70 Hz, 1H) 8.98 (d, J=2.35 Hz, 1H) 10.99

Synthesis of 6-(3-oxa-8-azabicyclo[3.2.1]octan-8-yl)-4-bromo-1-methylpyridin-2(1H)-one

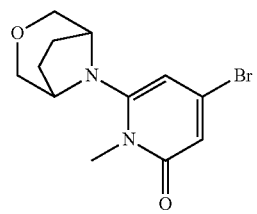 [SMILES: Cn1c(N2C3CCC2COC3)cc(Br)cc1=O]

Following the preparation of 4-bromo-1-methyl-6-morpholinopyridin-2(1H)-one using the appropriate starting materials gave (S)-4-bromo-1-methyl-6-(3-methylmorpholino)pyridin-2(1H)-one (36% yield). LCMS (m/z) (M+H)=299.0/301.0, Rt=0.59 min.

The compounds listed below were prepared using methods similar to those described in the preparation of Example 162 using the appropriate starting materials.

Example 527: N-(3-(6-(3-oxa-8-azabicyclo[3.2.1]octan-8-yl)-1-methyl-2-oxo-1,2-dihydropyridin-4-yl)-4-methylphenyl)-2-(1,1-difluoroethyl)isonicotinamide

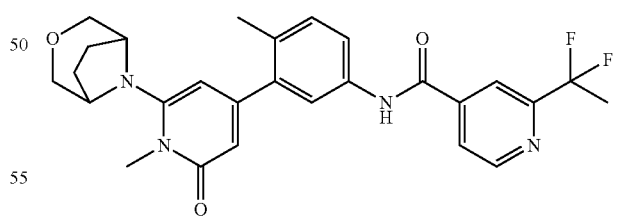

$^1$H NMR (400 MHz, <dmso>) δ ppm 1.90 (s, 4H) 2.03 (t, J=19.17 Hz, 3H) 2.23 (s, 3H) 3.52 (s, 3H) 3.58 (d, J=10.17 Hz, 2H) 3.75-3.85 (m, 4H) 5.64 (d, J=1.17 Hz, 1H) 5.93 (s, 1H) 7.28 (d, J=8.22 Hz, 1H) 7.63 (d, J=1.96 Hz, 1H) 7.71 (dd, J=8.22, 1.96 Hz, 1H) 8.00 (d, J=4.70 Hz, 1H) 8.15 (s, 1H) 8.86 (d, J=5.09 Hz, 1H) 10.61 (s, 1H). LCMS (m/z) (M+H)=495.3, Rt=0.86 min.

Synthesis of 5-amino-6'-(3-oxa-8-azabicyclo[3.2.1]
octan-8-yl)-2-chloro-1'-methyl-[3,4'-bipyridin]-2'
(1'H)-one

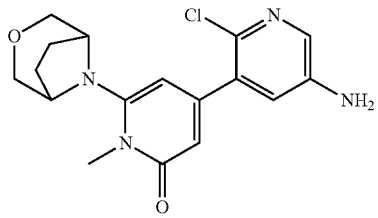 [SMILES: Cn1c(N2C3CCC2COC3)cc(-c2cc(N)cnc2Cl)cc1=O]

Following the preparation in Example 527, using the appropriate starting materials gave 5-amino-6'-(3-oxa-8-azabicyclo[3.2.1]octan-8-yl)-2-chloro-1'-methyl-[3,4'-bipyridin]-2'(1'H)-one (assumed 100% yield) as a light brown residue. LCMS (m/z) (M+H)=347.1, Rt=0.53 min.

The compounds listed below were prepared using methods similar to those described in the preparation of Example 171 using the appropriate starting materials.

Example 528: N-(6'-(3-oxa-8-azabicyclo[3.2.1]octan-8-yl)-2-chloro-1'-methyl-2'-oxo-1',2'-dihydro-[3,4'-bipyridin]-5-yl)-2-(1,1-difluoroethyl)isonicotinamide

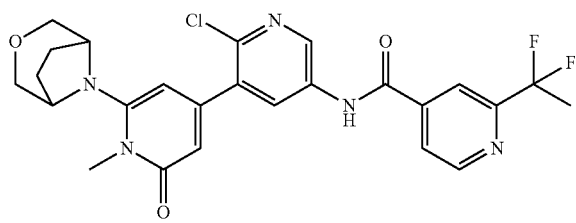 [SMILES: Cn1c(N2C3CCC2COC3)cc(-c2cc(NC(=O)c3ccnc(C(C)(F)F)c3)cnc2Cl)cc1=O]

¹H NMR (500 MHz, <dmso>) δ ppm 1.90 (s, 3H), 2.03 (t, J=19.1 Hz, 3H), 3.30-3.60 (m, 8H), 3.74-3.83 (m, 2H), 5.83 (s, 1H), 6.08 (s, 1H), 8.01 (d, J=5.0 Hz, 1H), 8.17 (s, 1H), 8.21 (d, J=2.6 Hz, 1H), 8.82 (d, J=2.5 Hz, 1H), 8.88 (d, J=5.0 Hz, 1H). LCMS (m/z) (M+H)=516.3, Rt=0.81 min.

The compounds listed below were prepared using methods similar to those described in the preparation of Example 171 using the appropriate starting materials.

Synthesis of 4-bromo-6-(2-(hydroxymethyl)morpholino)-1-methylpyridin-2(1H)-one

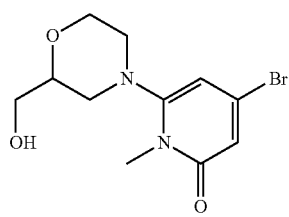 [SMILES: Cn1c(N2CCOC(CO)C2)cc(Br)cc1=O]

To a solution of 4-bromo-6-chloro-1-methylpyridin-2 (1H)-one (1.0 equiv.) and morpholin-2-ylmethanol (1.5 equiv.) was added potassium carbonate (6.0 equiv.) and the mixture was heated to 115° C. for 18 h. The reaction mixture was partitioned between EtOAc and water, and was then extracted five times with EtOAc. The combined organics were dried over sodium sulfate and then purified by normal phase chromatography. Product eluted with 25% MeOH in DCM. 4-bromo-6-(2-(hydroxymethyl)morpholino)-1-methylpyridin-2(1H)-one was used in the next step without further purification. LCMS (m/z) (M+H)=273.0, Rt=0.23 min.

Example 529: (R)-2-(1,1-difluoroethyl)-N-(6'-(2-(hydroxymethyl)morpholino)-1',2-dimethyl-2'-oxo-1',2'-dihydro-[3,4'-bipyridin]-5-yl)isonicotinamide

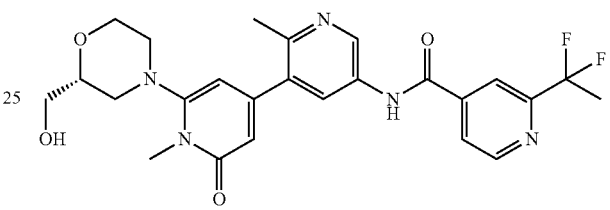

¹H NMR (400 MHz, <dmso>) δ ppm 1.96-2.11 (m, 3H) 2.44 (s, 3H) 2.53 (m, 2H) 2.63-2.68 (m, 1H) 2.75 (d, J=2.35 Hz, 1H) 3.10 (d, J=11.74 Hz, 1H) 3.16 (d, J=11.74 Hz, 1H) 3.45 (s, 3H) 3.56-3.74 (m, 2H) 3.88 (d, J=10.96 Hz, 1H) 5.86 (d, J=1.57 Hz, 1H) 6.13 (d, J=1.17 Hz, 1H) 8.02 (d, J=2.35 Hz, 2H) 8.19 (s, 1H) 8.79-8.93 (m, 2H) 10.83 (s, 1H). LCMS (m/z) (M+H)=500.2, Rt=0.52 min.

Example 530: (S)-2-(1,1-difluoroethyl)-N-(6'-(2-(hydroxymethyl)morpholino)-1',2-dimethyl-2-oxo-1',2'-dihydro-[3,4'-bipyridin]-5-yl)isonicotinamide

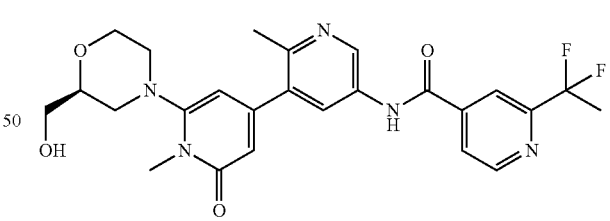

¹H NMR (400 MHz, <dmso>) δ ppm 2.04 (t, J=19.17 Hz, 3H) 2.31 (d, J=1.96 Hz, 1H) 2.44 (s, 3H) 2.53-2.59 (m, 1H) 2.62-2.66 (m, 1H) 2.69-2.81 (m, 1H) 3.07-3.18 (m, 2H) 3.45 (s, 3H) 3.61 (d, J=7.83 Hz, 1H) 3.69 (d, J=1.96 Hz, 1H) 3.88 (d, J=10.96 Hz, 1H) 5.86 (d, J=1.57 Hz, 1H) 6.13 (d, J=1.57 Hz, 1H) 8.03 (d, J=2.35 Hz, 2H) 8.19 (s, 1H) 8.79-8.93 (m, 2H) 10.84 (s, 1H). LCMS (m/z) (M+H)=500.2, Rt=0.52 min.

The compounds listed below were prepared using methods similar to those described for the preparation of Example 118 using the appropriate starting materials.

Example 531: 2-(2-cyanopropan-2-yl)-N-(4-methyl-3-(6-morpholinopyrazin-2-yl)phenyl)isonicotinamide

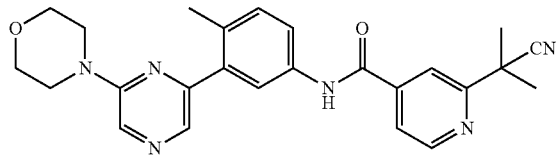 [SMILES: Cc1ccc(NC(=O)c2ccnc(C(C)(C)C#N)c2)cc1-c1cncc(N2CCOCC2)n1]

¹H NMR (400 MHz, <cd3od>) δ ppm 1.81 (s, 6H) 2.41 (s, 3H) 3.60-3.71 (m, 4H) 3.78-3.87 (m, 4H) 7.34 (d, J=8.22 Hz, 1H) 7.70 (dd, J=8.22, 2.35 Hz, 1H) 7.78-7.90 (m, 2H) 8.01 (s, 1H) 8.07 (s, 1H) 8.18 (s, 1H) 8.76 (d, J=5.09 Hz, 1H). LCMS (m/z) (M+H)=443.2, Rt=0.94 min.

Example 532: 2-(2-cyanopropan-2-yl)-N-(6-methyl-5-(6-morpholinopyrazin-2-yl)pyridin-3-yl)isonicotinamide

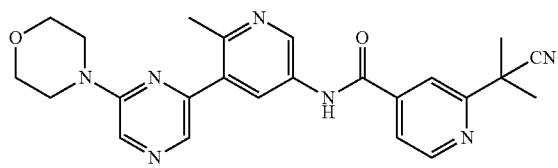 [SMILES: Cc1ncc(NC(=O)c2ccnc(C(C)(C)C#N)c2)cc1-c1cncc(N2CCOCC2)n1]

¹H NMR (400 MHz, <cd3od>) δ ppm 1.82 (s, 6H) 2.81 (s, 3H) 3.63-3.72 (m, 4H) 3.78-3.90 (m, 4H) 7.87 (dd, J=5.09, 1.57 Hz, 1H) 8.09-8.20 (m, 2H) 8.35 (s, 1H) 8.66 (d, J=2.35 Hz, 1H) 8.82 (d, J=5.09 Hz, 1H) 9.31 (d, J=2.35 Hz, 1H). LCMS (m/z) (M+H)=444.1, Rt=0.61 min.

Example 533: 2-(1,1-difluoroethyl)-N-(6-methyl-5-(6-morpholinopyrazin-2-yl)pyridin-3-yl)isonicotinamide

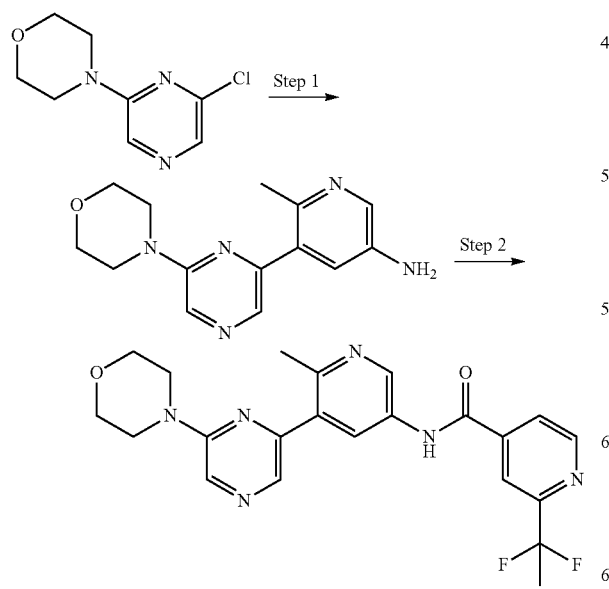

Step 1:

To a solution of 4-(6-chloropyrazin-2-yl)morpholine (1.0 equiv.) in DME (0.2M) was added 6-methyl-5-(4,4,5,5-tetramethyl-1,3,2-dioxaborolan-2-yl)pyridin-3-amine (1.1 equiv.) and PdCl2(dppf).CH2Cl2 adduct (0.1 equiv.), followed by 2M sodium carbonate solution (3.0 equiv.). The reaction was heated to 120° C. in a microwave vial for 10 min. Partitioned between water and ethyl acetate, the aqueous phase was extracted with ethyl acetate three times, the organics were combined, dried with sodium sulfate, filtered and concentrated. The crude material was purified via silica gel column chromatography eluting with 0-100% ethyl acetate in heptanes, then 10% methanol in ethyl acetate. The pure fractions were concentrated to yield 6-methyl-5-(6-morpholinopyrazin-2-yl)pyridin-3-amine in 74% yield. LCMS (m/z) (M+H)=272.0, Rt=0.41 min.

Step 2:

To a solution of 6-methyl-5-(6-morpholinopyrazin-2-yl)pyridin-3-amine in DMF (0.1M) was added EDC (1.2 equiv.), HOAt (1.2 equiv.) and 2-(1,1-difluoroethyl)isonicotinic acid (1.2 equiv.) and the reaction was stirred at rt for 3 hours. Upon completion, filtered through a HPLC filter and purified via reverse phase prep-HPLC. The pure fractions were lyophilized to yield 2-(1,1-difluoroethyl)-N-(6-methyl-5-(6-morpholinopyrazin-2-yl)pyridin-3-yl)isonicotinamide as the TFA salt in 39% yield. ¹H NMR (400 MHz, <cd3od>) δ ppm 2.05 (t, J=18.78 Hz, 3H) 2.84 (s, 3H) 3.64-3.74 (m, 4H) 3.79-3.91 (m, 4H) 8.03 (d, J=4.70 Hz, 1H) 8.17 (s, 1H) 8.26 (s, 1H) 8.37 (s, 1H) 8.73 (d, J=2.35 Hz, 1H) 8.87 (d, J=5.09 Hz, 1H) 9.39 (d, J=2.35 Hz, 1H). LCMS (m/z) (M+H)=441.2, Rt=0.63 min.

The compounds listed below were prepared using methods similar to those described for the preparation of Example 533 using the appropriate starting materials.

Example 534: 2-(2-fluoropropan-2-yl)-N-(6-methyl-5-(6-morpholinopyrazin-2-yl)pyridin-3-yl)isonicotinamide

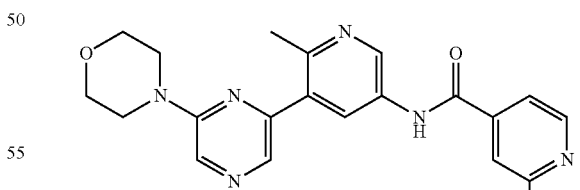

¹H NMR (400 MHz, <cd3od>) δ ppm 1.66-1.82 (m, 6H) 2.84 (s, 3H) 3.61-3.73 (m, 4H) 3.78-3.87 (m, 4H) 7.84 (dd, J=4.89, 1.76 Hz, 1H) 8.11-8.21 (m, 2H) 8.36 (s, 1H) 8.73 (d, J=2.35 Hz, 1H) 8.76 (d, J=5.09 Hz, 1H) 9.38 (d, J=2.35 Hz, 1H). LCMS (m/z) (M+H)=437.2, Rt=0.63 min.

Example 535: 2-(difluoromethyl)-N-(6-methyl-5-(6-morpholinopyrazin-2-yl)pyridin-3-yl)isonicotinamide

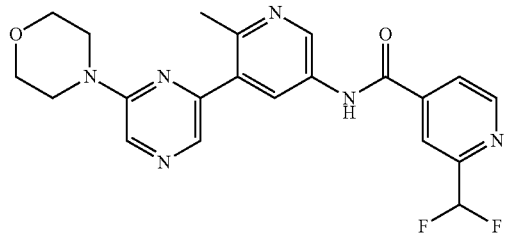 [SMILES: Cc1ncc(NC(=O)c2ccnc(C(F)F)c2)cc1-c1cncc(N2CCOCC2)n1]

1H NMR (400 MHz, <cd3od>) δ ppm 2.85 (s, 3H) 3.61-3.73 (m, 4H) 3.78-3.89 (m, 4H) 6.64-7.08 (m, 1H) 8.08 (d, J=5.09 Hz, 1H) 8.17 (s, 1H) 8.26 (s, 1H) 8.37 (s, 1H) 8.74 (d, J=2.35 Hz, 1H) 8.89 (d, J=4.70 Hz, 1H) 9.39 (d, J=2.35 Hz, 1H). LCMS (m/z) (M+H)=427.1, Rt=0.58 min.

Example 536: N-(6-methyl-5-(6-morpholinopyrazin-2-yl)pyridin-3-yl)-2-(trifluoromethyl)isonicotinamide

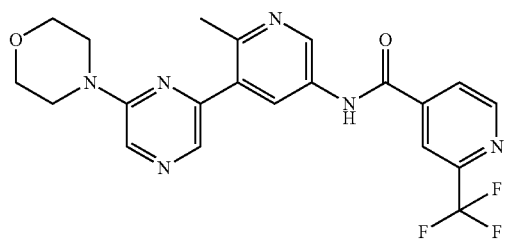 [SMILES: Cc1ncc(NC(=O)c2ccnc(C(F)(F)F)c2)cc1-c1cncc(N2CCOCC2)n1]

1H NMR (400 MHz, <cd3od>) δ ppm 2.69 (s, 3H) 3.59-3.72 (m, 4H) 3.78-3.89 (m, 4H) 8.10 (s, 1H) 8.16 (d, J=5.09 Hz, 1H) 8.29 (s, 1H) 8.35 (s, 1H) 8.47 (d, J=2.35 Hz, 1H) 8.95 (d, J=5.09 Hz, 1H) 9.06 (s, 1H). LCMS (m/z) (M+H)=445.1, Rt=0.65 min.

Example 537: 2-(1,1-difluoropropyl)-N-(6-methyl-5-(6-morpholinopyrazin-2-yl)pyridin-3-yl)isonicotinamide

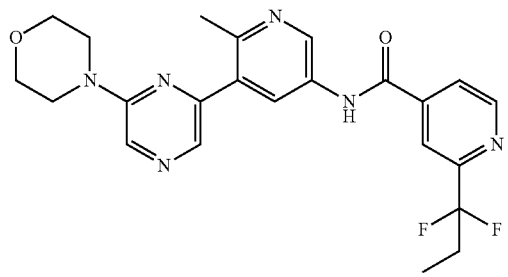 [SMILES: CCC(F)(F)c1cc(C(=O)Nc2cnc(C)c(-c3cncc(N4CCOCC4)n3)c2)ccn1]

1H NMR (400 MHz, <cd3od>) δ ppm 1.01 (t, J=7.43 Hz, 3H) 2.39 (td, J=16.63, 7.43 Hz, 2H) 2.81 (s, 3H) 3.59-3.73 (m, 4H) 3.78-3.89 (m, 4H) 8.03 (d, J=3.91 Hz, 1H) 8.15 (s, 1H) 8.35 (s, 2H) 8.68 (d, J=2.35 Hz, 1H) 8.87 (d, J=5.09 Hz, 1H) 9.31 (d, J=2.35 Hz, 1H). LCMS (m/z) (M+H)=455.2, Rt=0.68 min.

Example 538: N-(3-(5-ethoxy-6-morpholinopyrazin-2-yl)-4-methylphenyl)-3-(trifluoromethyl)benzamide

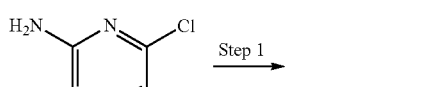

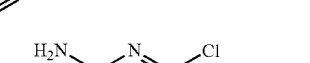

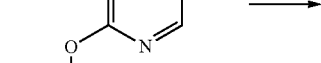

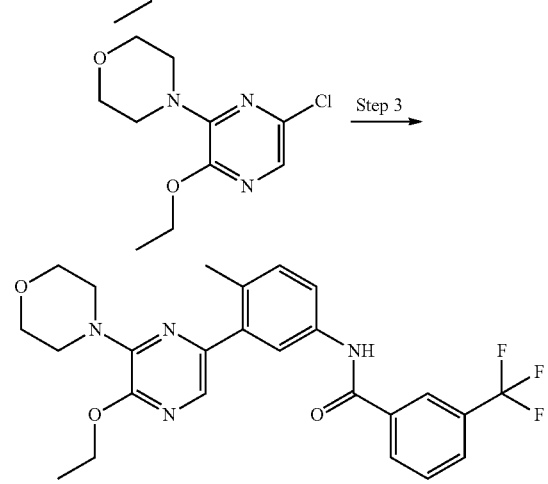

Step 1: Synthesis of 6-chloro-3-ethoxypyrazin-2-amine

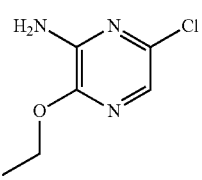

To a 0.5M solution of 3-bromo-6-chloropyrazin-2-amine (1.00 equiv.) in ethanol was added sodium ethoxide, 21 wt % in ethanol (3.00 equiv.). The mixture was stirred at 85° C. for 1.5 hr. The cooled reaction mixture was diluted with DCM and washed with saturated aqueous sodium bicarbonate. The organic phase was dried over sodium sulfate, filtered, and concentrated to give 6-chloro-3-ethoxypyrazin-2-amine as a peach solid in 82.0% yield. LCMS (m/z) (M+H)=174.0, Rt=0.65 min.

Step 2: Synthesis of 4-(6-chloro-3-ethoxypyrazin-2-yl)morpholine

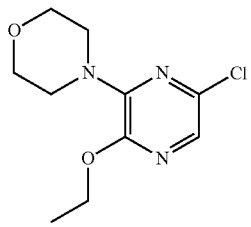 [SMILES: CCOc1ncc(Cl)nc1N1CCOCC1]

6-Chloro-3-ethoxypyrazin-2-amine (1.00 equiv.) was added to a 0.6M solution of NaH, 60% dispersion (3.00 equiv.) in DMF at ambient temperature. The mixture was stirred for 20 min at ambient temperature. Bis(2-bromoethyl) ether (1.50 equiv.) was added. The mixture was heated to 80° C. and stirred for 1 hr. The cooled reaction mixture was poured into water and stirred for 1 hr. The mixture was filtered. The filter cake was rinsed with water and air-dried to give 4-(6-chloro-3-ethoxypyrazin-2-yl)morpholine as a yellow solid in 43.4% yield. LCMS (m/z) (M+H)=244.0, Rt=0.93 min.

The compounds listed below were prepared using methods similar to those described for the preparation of Example 118 using the appropriate starting materials.

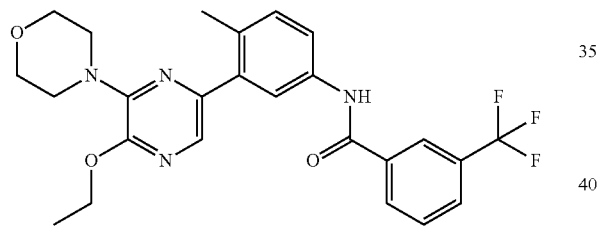

$^1$H NMR (400 MHz, <cd3od>) δ ppm 1.46 (t, J=7.04 Hz, 3H) 2.39 (s, 3H) 3.54-3.66 (m, 4H) 3.79-3.87 (m, 4H) 4.48 (q, J=7.04 Hz, 2H) 7.30 (d, J=8.61 Hz, 1H) 7.65 (dd, J=8.22, 2.35 Hz, 1H) 7.70-7.77 (m, 2H) 7.78 (d, J=1.96 Hz, 1H) 7.90 (d, J=7.83 Hz, 1H) 8.22 (d, J=7.83 Hz, 1H) 8.27 (s, 1H); LCMS (m/z) (M+H)=487.1, Rt=1.13 min.

Example 539: N-(5-(5-ethoxy-6-morpholinopyrazin-2-yl)-6-methylpyridin-3-yl)-3-(trifluoromethyl)benzamide

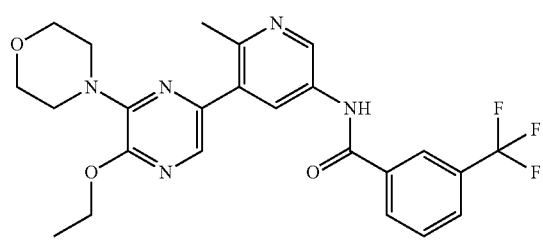 [SMILES: CCOc1ncc(-c2cc(NC(=O)c3cccc(C(F)(F)F)c3)cnc2C)nc1N1CCOCC1]

$^1$H NMR (400 MHz, <cd3od>) δ ppm 1.48 (t, J=7.04 Hz, 3H) 2.83 (s, 3H) 3.61-3.70 (m, 4H) 3.81-3.87 (m, 4H) 4.54 (q, J=7.04 Hz, 2H) 7.80 (t, J=8.02 Hz, 1H) 7.92 (s, 1H) 7.98 (d, J=8.22 Hz, 1H) 8.30 (d, J=8.22 Hz, 1H) 8.36 (s, 1H) 8.66 (d, J=1.96 Hz, 1H) 9.29 (d, J=2.35 Hz, 1H); LCMS (m/z) (M+H)=488.1, Rt=0.85 min.

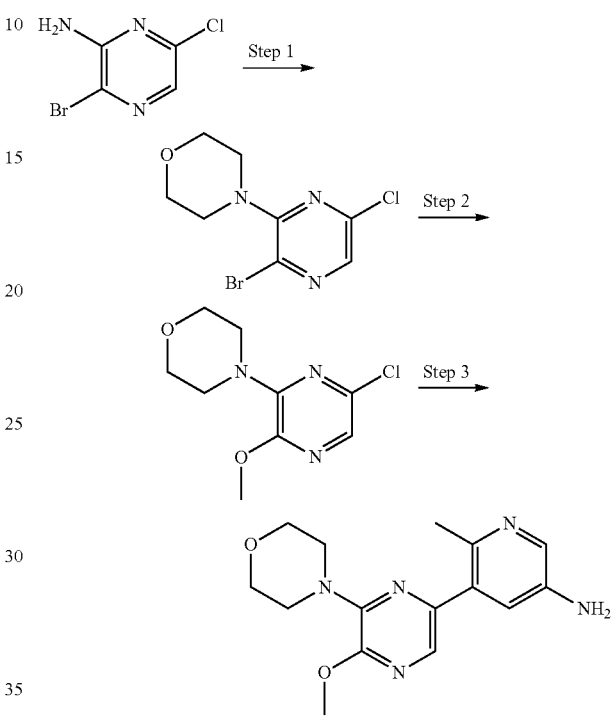

Step 1: Synthesis of 4-(3-bromo-6-chloropyrazin-2-yl)morpholine

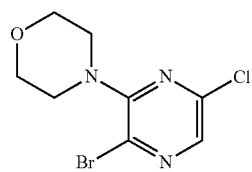 [SMILES: Clc1cnc(Br)c(N2CCOCC2)n1]

6-Chloro-3-ethoxypyrazin-2-amine (1.00 equiv.) was added to a 0.6M solution of NaH, 60% dispersion (3.00 equiv.) in DMF at ambient temperature. The mixture was stirred for 20 min at ambient temperature. Bis(2-bromoethyl) ether (1.50 equiv.) was added. The mixture was heated to 60° C. and stirred for 45 min. The cooled reaction mixture was poured into water and extracted with ethyl acetate. The combined organic layers were dried over sodium sulfate, filtered and concentrated to give crude 4-(3-bromo-6-chloropyrazin-2-yl)morpholine as a tan oil in 100% yield. LCMS (m/z) (M+H)=277.8/279.8, Rt=0.82 min.

Step 2: Synthesis of 4-(6-chloro-3-methoxypyrazin-2-yl)morpholine

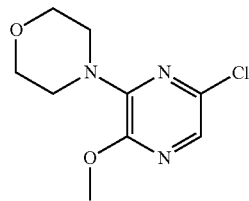

To a 0.3M solution of 4-(3-bromo-6-chloropyrazin-2-yl)morpholine (1.00 equiv.) in methanol was added sodium methoxide (3.00 equiv.). The mixture was stirred at 60° C. for 1 hr. The cooled reaction mixture was concentrated to about half of its original volume and poured into 4 volumes of water. The resulting precipitate was collected by vacuum filtration and air-dried to give 4-(6-chloro-3-methoxypyrazin-2-yl)morpholine as a yellow solid in 76.0% yield. LCMS (m/z) (M+H)=230.0, Rt=0.80 min

Step 3: Synthesis of 5-(5-methoxy-6-morpholinopyrazin-2-yl)-6-methylpyridin-3-amine

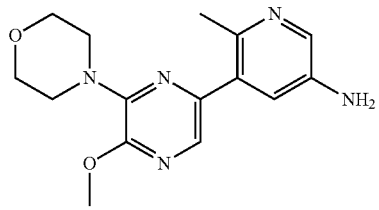 [SMILES: COc1ncc(-c2cc(N)cnc2C)nc1N1CCOCC1]

To a 0.15M solution of 4-(6-chloro-3-methoxypyrazin-2-yl)morpholine (1.00 equiv.) in DME was added 6-methyl-5-(4,4,5,5-tetramethyl-1,3,2-dioxaborolan-2-yl)pyridin-3-amine (1.00 equiv.), PdCl2(dppf).CH2Cl2 adduct (0.10 equiv.), and 2M aqueous sodium carbonate (3.00 equiv.). The reaction mixture was irradiated at 130° C. for 15 min in the microwave. The cooled reaction mixture was diluted with 2:1 DCM:MeOH and filtered. The filtrate was concentrated and purified by flash chromatography over silica gel (ethyl acetate with 5% methanol) to give 5-(5-methoxy-6-morpholinopyrazin-2-yl)-6-methylpyridin-3-amine (44.7% yield) as a tan solid. LCMS (m/z) (M+H)=302.0, Rt=0.51 min.

The compounds listed below were prepared using methods similar to those described for the preparation of Example 539 using the appropriate starting materials.

Example 540: 2-(2-cyanopropan-2-yl)-N-(5-(5-methoxy-6-morpholinopyrazin-2-yl)-6-methylpyridin-3-yl)isonicotinamide

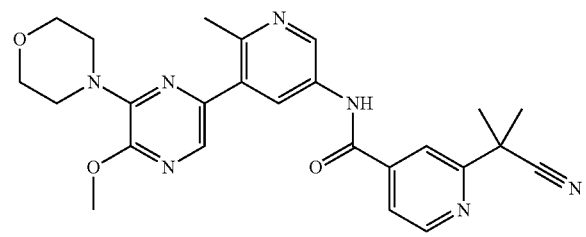 [SMILES: COc1ncc(-c2cc(NC(=O)c3ccnc(C(C)(C)C#N)c3)cnc2C)nc1N1CCOCC1]

$^1$H NMR (400 MHz, <cd3od>) δ ppm 1.84 (s, 6H) 2.86 (s, 3H) 3.60-3.70 (m, 4H) 3.78-3.89 (m, 4H) 4.08 (s, 3H) 7.90 (dd, J=5.09, 1.57 Hz, 1H) 7.95 (s, 1H) 8.16 (s, 1H) 8.70 (d, J=2.35 Hz, 1H) 8.84 (d, J=4.70 Hz, 1H) 9.33 (d, J=2.35 Hz, 1H); LCMS (m/z) (M+H)=474.2, Rt=0.69 min.

Example 541: 2-(1-cyanocyclopropyl)-N-(5-(5-methoxy-6-morpholinopyrazin-2-yl)-6-methylpyridin-3-yl)isonicotinamide

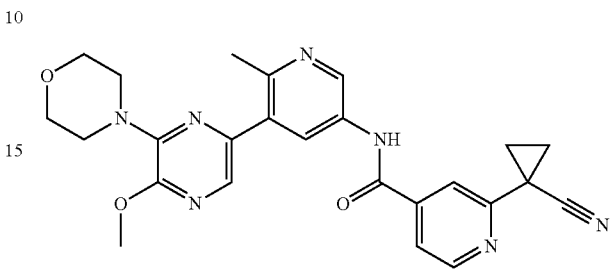

$^1$H NMR (400 MHz, <cd3od>) δ ppm 1.79-1.93 (m, 4H) 2.85 (s, 3H) 3.60-3.68 (m, 4H) 3.78-3.89 (m, 4H) 4.08 (s, 3H) 7.79 (dd, J=4.89, 1.37 Hz, 1H) 7.95 (s, 1H) 8.18 (s, 1H) 8.68 (d, J=2.35 Hz, 1H) 8.72 (d, J=4.70 Hz, 1H) 9.30 (d, J=2.35 Hz, 1H); LCMS (m/z) (M+H)=472.2, Rt=0.69 min.

Example 542: 2-(1,1-difluoroethyl)-N-(5-(5-methoxy-6-morpholinopyrazin-2-yl)-6-methylpyridin-3-yl)isonicotinamide

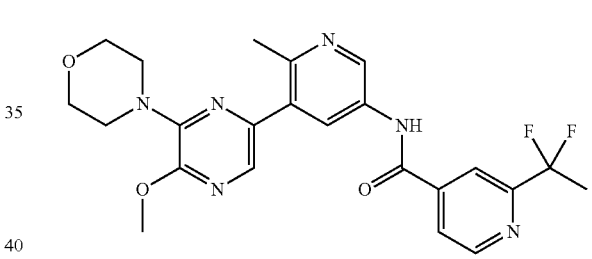

$^1$H NMR (400 MHz, <cd3od>) δ ppm 2.07 (t, J=18.78 Hz, 3H) 2.81 (s, 3H) 3.61-3.69 (m, 4H) 3.80-3.89 (m, 4H) 4.08 (s, 3H) 7.92 (s, 1H) 8.04 (d, J=3.52 Hz, 1H) 8.27 (s, 1H) 8.63 (d, J=1.96 Hz, 1H) 8.88 (d, J=5.09 Hz, 1H) 9.23 (d, J=1.96 Hz, 1H); LCMS (m/z) (M+H)=471.2, Rt=0.71 min.

Example 543: 3-((dimethylamino)methyl)-N-(5-(5-methoxy-6-morpholinopyrazin-2-yl)-6-methylpyridin-3-yl)-5-(trifluoromethyl)benzamide

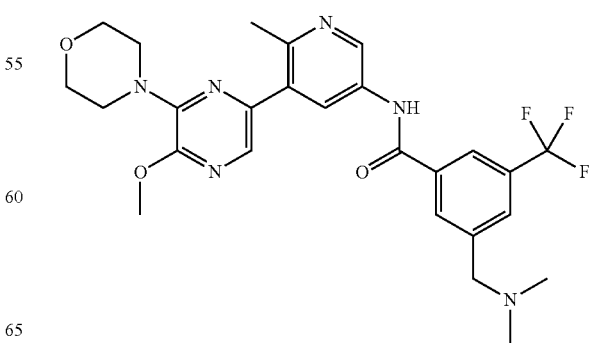

¹H NMR (400 MHz, <cd3od>) δ ppm 2.71 (s, 3H) 2.95 (s, 6H) 3.60-3.67 (m, 4H) 3.80-3.89 (m, 4H) 4.07 (s, 3H) 4.54 (s, 2H) 7.87 (s, 1H) 8.16 (s, 1H) 8.43 (s, 1H) 8.46 (s, 1H) 8.53 (s, 1H) 9.02 (s, 1H); LCMS (m/z) (M+H)=495.1, Rt=0.84 min.

Example 544: 2-(2-fluoropropan-2-yl)-N-(5-(5-methoxy-6-morpholinopyrazin-2-yl)-6-methylpyridin-3-yl)isonicotinamide

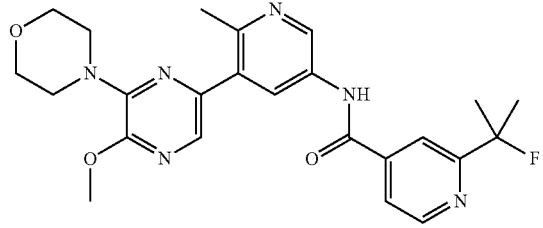 [SMILES: COc1ncc(-c2cc(NC(=O)c3ccnc(C(C)(C)F)c3)cnc2C)nc1N1CCOCC1]

¹H NMR (400 MHz, <cd3od>) δ ppm 1.69-1.82 (m, 6H) 2.86 (s, 3H) 3.61-3.69 (m, 4H) 3.81-3.88 (m, 4H) 4.09 (s, 3H) 7.86 (dd, J=5.09, 1.57 Hz, 1H) 7.95 (s, 1H) 8.16 (s, 1H) 8.72 (d, J=2.35 Hz, 1H) 8.78 (d, J=5.09 Hz, 1H) 9.35 (d, J=2.35 Hz, 1H); LCMS (m/z) (M+H)=467.2, Rt=0.71 min.

Synthesis of 5-(5-ethoxy-6-morpholinopyrazin-2-yl)-6-methylpyridin-3-amine

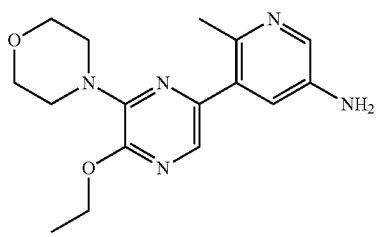 [SMILES: CCOc1ncc(-c2cc(N)cnc2C)nc1N1CCOCC1]

Following the preparation in Example 539 using the appropriate starting materials gave 5-(5-ethoxy-6-morpholinopyrazin-2-yl)-6-methylpyridin-3-amine (68.3% yield) as a tan solid. LCMS (m/z) (M+H)=316.1, Rt=0.59 min.

The compounds listed below were prepared using methods similar to those described for the preparation of Example 539 using the appropriate starting materials.

Example 540: 2-(2-cyanopropan-2-yl)-N-(5-(5-ethoxy-6-morpholinopyrazin-2-yl)-6-methylpyridin-3-yl)isonicotinamide

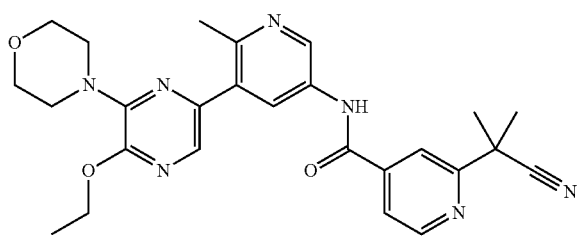 [SMILES: CCOc1ncc(-c2cc(NC(=O)c3ccnc(C(C)(C)C#N)c3)cnc2C)nc1N1CCOCC1]

¹H NMR (400 MHz, <cd3od>) δ ppm 1.48 (t, J=7.04 Hz, 3H) 1.84 (s, 6H) 2.83 (s, 3H) 3.61-3.72 (m, 4H) 3.80-3.91 (m, 4H) 4.54 (q, J=7.04 Hz, 2H) 7.86-7.93 (m, 2H) 8.15 (s, 1H) 8.64 (d, J=2.35 Hz, 1H) 8.84 (d, J=5.09 Hz, 1H) 9.26 (d, J=2.35 Hz, 1H); LCMS (m/z) (M+H)=488.2, Rt=0.74 min.

Example 541: N-(5-(5-ethoxy-6-morpholinopyrazin-2-yl)-6-methylpyridin-3-yl)-2-(trifluoromethyl)isonicotinamide

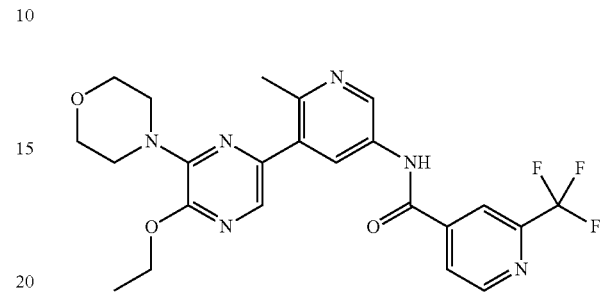

¹H NMR (400 MHz, <cd3od>) δ ppm 1.48 (t, J=7.04 Hz, 3H) 2.83 (s, 3H) 3.60-3.72 (m, 4H) 3.78-3.91 (m, 4H) 4.54 (q, J=7.04 Hz, 2H) 7.91 (s, 1H) 8.20 (d, J=3.91 Hz, 1H) 8.38 (s, 1H) 8.66 (d, J=2.35 Hz, 1H) 8.98 (d, J=5.09 Hz, 1H) 9.27 (d, J=2.35 Hz, 1H); LCMS (m/z) (M+H)=489.1, Rt=0.78 min.

Example 542: 2-(1,1-difluoroethyl)-N-(5-(5-ethoxy-6-morpholinopyrazin-2-yl)-6-methylpyridin-3-yl)isonicotinamide

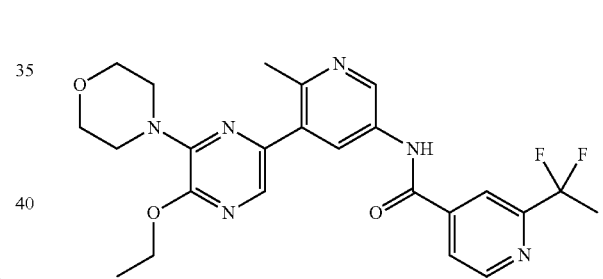

¹H NMR (400 MHz, <cd3od>) δ ppm 1.48 (t, J=7.04 Hz, 3H) 2.07 (t, J=18.78 Hz, 3H) 2.84 (s, 3H) 3.58-3.72 (m, 4H) 3.78-3.91 (m, 4H) 4.54 (q, J=7.04 Hz, 2H) 7.92 (s, 1H) 8.04 (d, J=4.30 Hz, 1H) 8.27 (s, 1H) 8.68 (d, J=1.96 Hz, 1H) 8.88 (d, J=5.09 Hz, 1H) 9.29 (d, J=2.35 Hz, 1H); LCMS (m/z) (M+H)=485.1, Rt=0.76 min.

Example 543: N-(5-(5-ethoxy-6-morpholinopyrazin-2-yl)-6-methylpyridin-3-yl)-2-(2-fluoropropan-2-yl)isonicotinamide

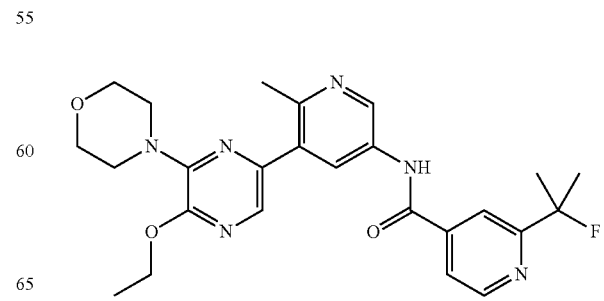

¹H NMR (400 MHz, <cd3od>) δ ppm 1.48 (t, J=7.04 Hz, 3H) 1.76 (m, J=1.00 Hz, 6H) 2.85 (s, 3H) 3.58-3.73 (m, 4H) 3.79-3.91 (m, 4H) 4.54 (q, J=7.04 Hz, 2H) 7.85 (dd, J=5.09, 1.57 Hz, 1H) 7.93 (s, 1H) 8.16 (s, 1H) 8.72 (d, J=2.35 Hz, 1H) 8.77 (d, J=5.09 Hz, 1H) 9.33 (d, J=2.35 Hz, 1H); LCMS (m/z) (M+H)=481.1, Rt=0.77 min.

Example 544: N-(5-(5-ethoxy-6-morpholinopyrazin-2-yl)-6-methylpyridin-3-yl)-4-(trifluoromethyl)picolinamide

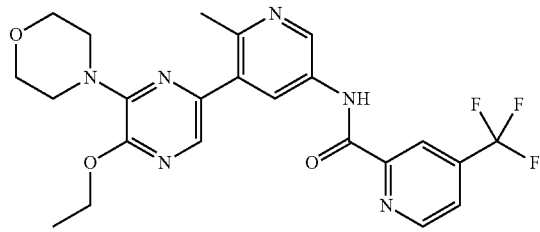 [SMILES: CCOc1ncc(-c2cc(NC(=O)c3cc(C(F)(F)F)ccn3)cnc2C)nc1N1CCOCC1]

¹H NMR (400 MHz, <cd3od>) δ ppm 1.49 (t, J=7.04 Hz, 3H) 2.85 (s, 3H) 3.60-3.73 (m, 4H) 3.77-3.92 (m, 4H) 4.54 (q, J=7.04 Hz, 2H) 7.94 (s, 1H) 8.01 (d, J=4.30 Hz, 1H) 8.51 (s, 1H) 8.89 (d, J=2.35 Hz, 1H) 9.04 (d, J=4.70 Hz, 1H) 9.39 (d, J=2.35 Hz, 1H); LCMS (m/z) (M+H)=489.2, Rt=0.83 min.

Example 545: 3-((dimethylamino)methyl)-N-(5-(5-ethoxy-6-morpholinopyrazin-2-yl)-6-methylpyridin-3-yl)-5-(trifluoromethyl)benzamide

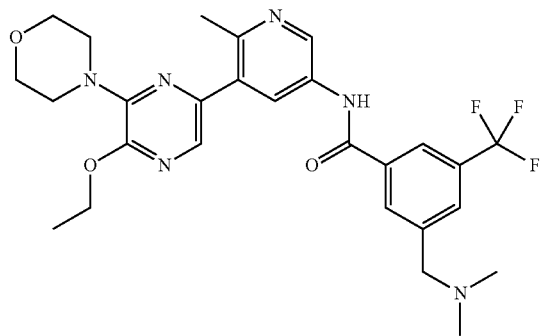 [SMILES: CCOc1ncc(-c2cc(NC(=O)c3cc(CN(C)C)cc(C(F)(F)F)c3)cnc2C)nc1N1CCOCC1]

¹H NMR (400 MHz, <cd3od>) δ ppm 1.48 (t, J=7.04 Hz, 3H) 2.77 (s, 3H) 2.95 (s, 6H) 3.60-3.70 (m, 4H) 3.79-3.91 (m, 4H) 4.48-4.60 (m, 4H) 7.88 (s, 1H) 8.17 (s, 1H) 8.46 (s, 1H) 8.54 (s, 1H) 8.57 (d, J=2.35 Hz, 1H) 9.15 (d, J=1.96 Hz, 1H); LCMS (m/z) (M+H)=545.3, Rt=0.67 min.

Synthesis of 3-(5-methoxy-6-morpholinopyrazin-2-yl)-4-methylaniline

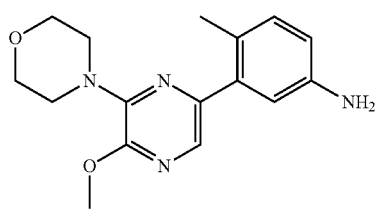 [SMILES: COc1ncc(-c2cc(N)ccc2C)nc1N1CCOCC1]

Following the preparation in Example 539 using the appropriate starting materials gave 3-(5-methoxy-6-morpholinopyrazin-2-yl)-4-methylaniline (88.0% yield) as a tan solid. LCMS (m/z) (M+H)=301.0, Rt=0.57 min.

Example 546: N-(3-(5-methoxy-6-morpholinopyrazin-2-yl)-4-methylphenyl)-2-(methylsulfonyl)isonicotinamide

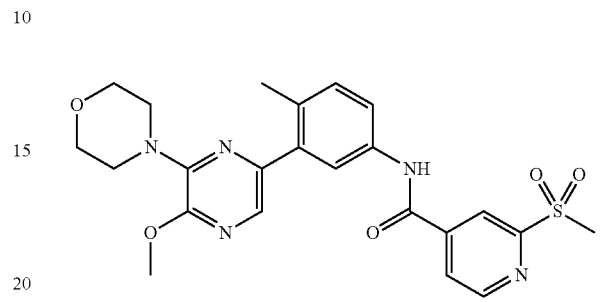

¹H NMR (400 MHz, <cd3od>) ™ ¹H NMR (400 MHz, <cd3od>) δ ppm 2.39 (s, 3H) 3.30 (s, 3H) 3.51-3.67 (m, 4H) 3.77-3.90 (m, 4H) 4.03 (s, 3H) 7.30 (d, J=8.22 Hz, 1H) 7.68 (dd, J=8.22, 2.35 Hz, 1H) 7.74 (s, 1H) 7.80 (d, J=2.35 Hz, 1H) 8.16 (dd, J=4.89, 1.37 Hz, 1H) 8.56 (s, 1H) 8.93 (d, J=5.09 Hz, 1H); LCMS (m/z) (M+H)=484.0, Rt=0.85 min.

Example 547: N-(3-(6-methoxy-5-morpholinopyridazin-3-yl)-4-methylphenyl)-2-(trifluoromethyl)isonicotinamide

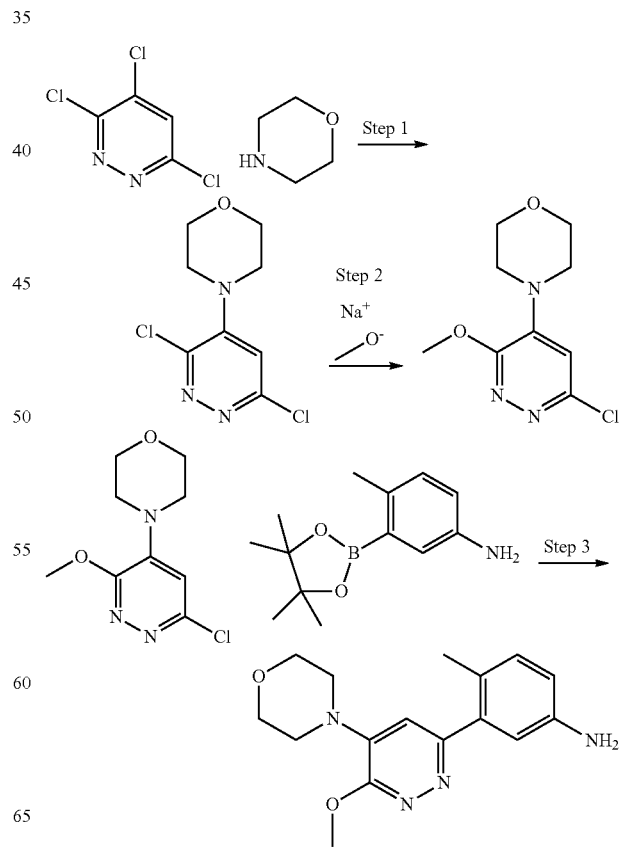

-continued

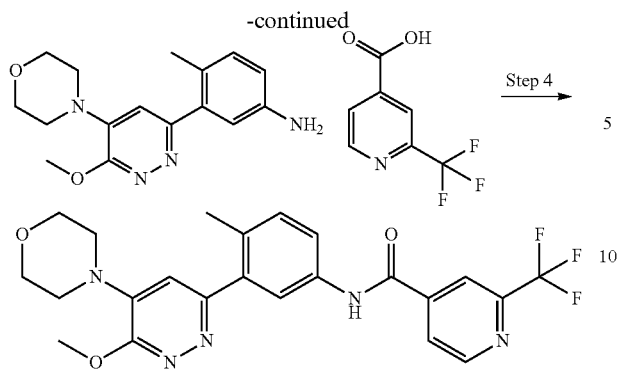

Step 1:
To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:
Sodium methoxide (2.0 equiv.) was added portion wise to a flask containing 4-(3,6-dichloropyridazin-4-yl)morpholine (1.0 equiv.) in MeOH (0.43 M) and the reaction mix was stirred overnight at RT. The solvent was removed under vacuum and the crude was partitioned in brine/EtOAc. The organic phase was isolated and the aqueous layer was extracted once more with EtOAc. The combined organics were concentrated to dryness and the residue was dissolved in DCM, and adsorbed in silica gel. The solid was loaded into a cartridge and purified on a silica gel column using 0 to 60% EtOAc in heptane. The desired 4-(6-chloro-3-methoxypyridazin-4-yl)morpholine was obtained in 71% yield. LCMS (m/z) (M+H)=230, Rt=0.44 min.

Step 3:
To a solution of 4-(6-chloro-3-methoxypyridazin-4-yl)morpholine (1.0 equiv.) and 4-methyl-3-(4,4,5,5-tetramethyl-1,3,2-dioxaborolan-2-yl)aniline (1.0 equiv.) in DME (0.12 M) was added $Na_2CO_3$ (3.0 equiv.) and the system was flushed with nitrogen. $PdCl_2(dppf) \cdot CH_2Cl_2$ adduct (0.05 equiv.) was added to the reaction mix and the system was flushed once again with nitrogen. The reaction mix was heated in a bath at 110° C., overnight. The crude was partitioned in $H_2O$/EtOAc. The organic layer was isolated, dried over $Na_2SO_4$, filtered and concentrated. Crude was purified using a reverse phase system of 0 to 40% acetonitrile in water. The fractions containing the product were concentrated until a small volume of solvent was left and extracted three times with EtOAc. The combined organics were dried over $Na_2SO_4$, filtered and concentrated to give 3-(6-methoxy-5-morpholinopyridazin-3-yl)-4-methylaniline in 78% yield.

LCMS (m/z) (M+H)=301, Rt=0.38 min.

Step 4:
DIEA (3.0 equiv.) was added to a solution of 3-(6-methoxy-5-morpholinopyridazin-3-yl)-4-methylaniline (1.0 equiv.), 2-(trifluoromethyl)isonicotinic acid (1.0 equiv.) and HATU (1.0 equiv.) in DMF (0.07 M), and the mixture was left stirring at RT overnight. The reaction mix was treated with water and extracted three times with EtOAc. The combined organics were concentrated to dryness and the crude purified by HPLC giving N-(3-(6-methoxy-5-morpholinopyridazin-3-yl)-4-methylphenyl)-2-(trifluoromethyl)isonicotinamide as the TFA salt in 33% yield. 1H NMR (400 MHz, <dmso>) δ ppm 2.27 (s, 3H) 3.74 (br. s., 8H) 4.07 (s, 3H) 7.28 (br. s., 1H) 7.44 (d, J=8.61 Hz, 1H) 7.80 (dd, J=8.22, 1.96 Hz, 1H) 7.92 (s, 1H) 8.18 (d, J=5.09 Hz, 1H) 8.35 (s, 1H) 8.99 (d, J=5.09 Hz, 1H) 10.84 (s, 1H). LCMS (m/z) (M+H)=474, Rt=0.70 min.

Example 548: 2-(1,1-difluoroethyl)-N-(3-(6-methoxy-5-morpholinopyridazin-3-yl)-4-methylphenyl)isonicotinamide

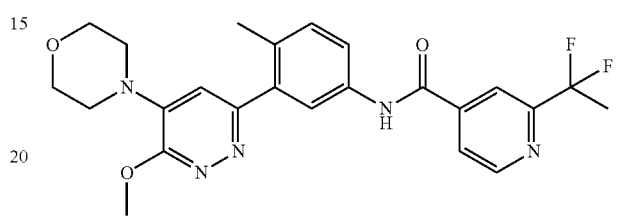

1H NMR (400 MHz, <dmso>) δ ppm 1.95-2.11 (m, 3H) 2.26 (s, 3H) 3.74 (br. s., 8H) 4.07 (s, 3H) 7.29 (br. s., 1H) 7.43 (d, J=8.22 Hz, 1H) 7.81 (dd, J=8.61, 1.96 Hz, 1H) 7.93 (s, 1H) 8.01 (d, J=4.70 Hz, 1H) 8.16 (s, 1H) 8.88 (d, J=5.09 Hz, 1H) 10.79 (s, 1H). LCMS (m/z) (M+H)=470, Rt=0.69 min.

Example 549: 2-(1,1-difluoropropyl)-N-(3-(6-methoxy-5-morpholinopyridazin-3-yl)-4-methylphenyl)isonicotinamide

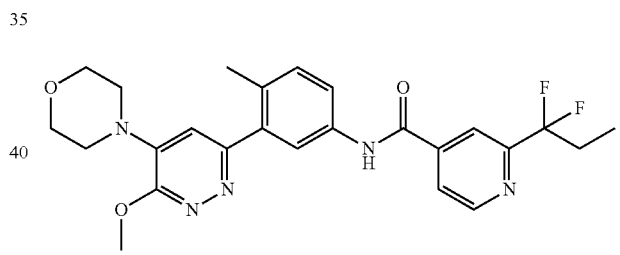

1H NMR (400 MHz, <dmso>) δ 0.93 (t, J=7.43 Hz, 4H) 1.21 (s, 2H) 2.27 (s, 4H) 2.79 (d, J=10.96 Hz, 1H) 3.73 (br. s., 5H) 4.07 (s, 4H) 7.41 (d, J=8.61 Hz, 1H) 7.79 (d, J=10.17 Hz, 1H) 7.89 (br. s., 1H) 8.01 (d, J=5.09 Hz, 1H) 8.15 (s, 1H) 8.89 (d, J=5.09 Hz, 1H) 10.75 (br. s., 1H). LCMS (m/z) (M+H)=484, Rt=0.74 min.

Example 550: 2-cyclopropyl-N-(3-(6-methoxy-5-morpholinopyridazin-3-yl)-4-methylphenyl)isonicotinamide

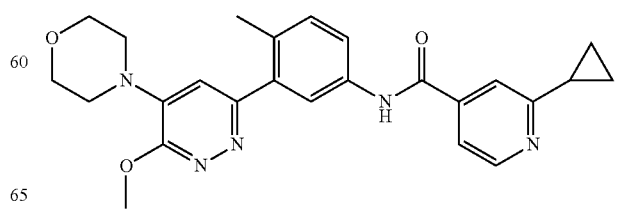

1H NMR (400 MHz, <dmso>) δ ppm 0.87-1.11 (m, 4H) 2.15-2.24 (m, 1H) 2.26 (s, 3H) 3.74 (d, J=4.70 Hz, 8H) 4.00-4.11 (m, 4H) 7.34 (s, 1H) 7.43 (d, J=8.61 Hz, 1H) 7.55 (dd, J=5.09, 1.57 Hz, 1H) 7.72 (s, 1H) 7.79 (dd, J=8.41, 2.15 Hz, 1H) 7.96 (d, J=1.56 Hz, 1H) 8.58 (d, J=5.09 Hz, 1H) 10.62 (s, 1H). LCMS (m/z) (M+H)=446, Rt=0.52 min.

Example 551: N-(3-(6-methoxy-5-morpholinopyridazin-3-yl)-4-methylphenyl)-6-(trifluoromethyl)pyridazine-4-carboxamide

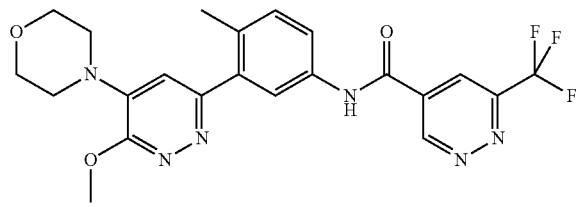 [SMILES: COc1nnc(-c2cc(NC(=O)c3cnnc(C(F)(F)F)c3)ccc2C)cc1N1CCOCC1]

1H NMR (400 MHz, <dmso>) δ ppm 2.27 (s, 3H) 3.73 (br. s., 7H) 4.07 (s, 3H) 7.28 (br. s., 1H) 7.46 (d, J=8.22 Hz, 1H) 7.79 (dd, J=8.22, 1.96 Hz, 1H) 7.91 (s, 1H) 8.66 (d, J=1.96 Hz, 1H) 9.91 (d, J=1.96 Hz, 1H) 11.00 (s, 1H). LCMS (m/z) (M+H)=475, Rt=0.76 min.

Example 552: 2-(2-fluoropropan-2-yl)-N-(3-(6-methoxy-5-morpholinopyridazin-3-yl)-4-methylphenyl)isonicotinamide

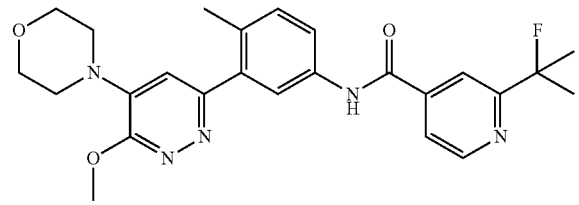 [SMILES: COc1nnc(-c2cc(NC(=O)c3ccnc(C(C)(C)F)c3)ccc2C)cc1N1CCOCC1]

1H NMR (400 MHz, <dmso>) δ ppm 1.66 (s, 3H) 1.72 (s, 3H) 2.26 (s, 3H) 3.70-3.90 (m, 8H) 4.01-4.12 (m, 3H) 7.33 (br. s., 1H) 7.43 (d, J=8.22 Hz, 1H) 7.76-7.85 (m, 2H) 7.94 (s, 1H) 8.00 (s, 1H) 8.76 (d, J=5.09 Hz, 1H) 10.73 (s, 1H). LCMS (m/z) (M+H)=466, Rt=0.68 min.

Example 553: N-(3-(6-methoxy-5-morpholinopyridazin-3-yl)-4-methylphenyl)-3-(methylsulfonyl)benzamide

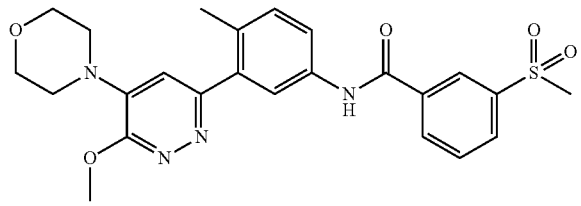 [SMILES: COc1nnc(-c2cc(NC(=O)c3cccc(S(C)(=O)=O)c3)ccc2C)cc1N1CCOCC1]

1H NMR (400 MHz, <dmso>) δ ppm 2.26 (s, 3H) 3.28 (s, 3H) 3.74 (br. s., 7H) 4.07 (s, 3H) 7.30 (br. s., 1H) 7.42 (d, J=8.61 Hz, 1H) 7.78-7.86 (m, 2H) 7.93 (s, 1H) 8.15 (d, J=7.83 Hz, 1H) 8.27 (d, J=7.83 Hz, 1H) 8.46 (s, 1H) 10.68 (s, 1H). LCMS (m/z) (M+H)=483, Rt=0.60 min.

Example 554: N-(3-(6-methoxy-5-morpholinopyridazin-3-yl)-4-methylphenyl)-6-(trifluoromethyl)pyridazine-4-carboxamide

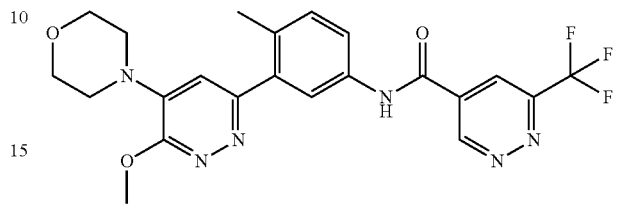

1H NMR (400 MHz, <dmso>) δ ppm 2.27 (s, 3H) 3.73 (br. s., 7H) 4.07 (s, 3H) 7.28 (br. s., 1H) 7.46 (d, J=8.22 Hz, 1H) 7.79 (dd, J=8.22, 1.96 Hz, 1H) 7.91 (s, 1H) 8.66 (d, J=1.96 Hz, 1H) 9.91 (d, J=1.96 Hz, 1H) 11.00 (s, 1H). LCMS (m/z) (M+H)=475, Rt=0.76 min.

Example 555: 2-(2-fluoropropan-2-yl)-N-(3-(6-methoxy-5-morpholinopyridazin-3-yl)-4-methylphenyl)isonicotinamide

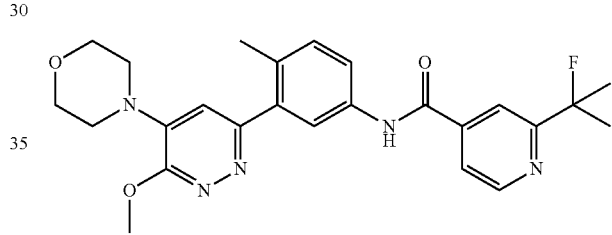

1H NMR (400 MHz, <dmso>) δ ppm 1.66 (s, 3H) 1.72 (s, 3H) 2.26 (s, 3H) 3.70-3.90 (m, 8H) 4.01-4.12 (m, 3H) 7.33 (br. s., 1H) 7.43 (d, J=8.22 Hz, 1H) 7.76-7.85 (m, 2H) 7.94 (s, 1H) 8.00 (s, 1H) 8.76 (d, J=5.09 Hz, 1H) 10.73 (s, 1H). LCMS (m/z) (M+H)=466, Rt=0.68 min.

Example 556: 2-(2-hydroxypropan-2-yl)-N-(3-(6-methoxy-5-morpholinopyridazin-3-yl)-4-methylphenyl)isonicotinamide

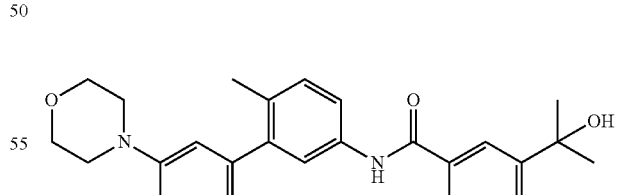

1H NMR (400 MHz, <dmso>) δ ppm 1.42-1.52 (m, 7H) 2.26 (s, 3H) 4.03-4.12 (m, 4H) 7.36 (s, 1H) 7.44 (d, J=8.61 Hz, 1H) 7.69 (dd, J=5.09, 1.57 Hz, 1H) 7.81 (dd, J=8.41, 2.15 Hz, 1H) 7.96 (d, J=1.96 Hz, 1H) 8.12 (s, 1H) 8.68 (d, J=5.09 Hz, 1H) 10.71 (s, 1H). LCMS (m/z) (M+H)=464, Rt=0.50 min.

Example 557: 6-(2-cyanopropan-2-yl)-N-(3-(6-methoxy-5-morpholinopyridazin-3-yl)-4-methylphenyl)pyridazine-4-carboxamide

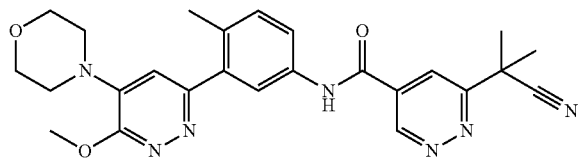 [SMILES: COc1nnc(-c2cc(NC(=O)c3cnnc(C(C)(C)C#N)c3)ccc2C)cc1N1CCOCC1]

1H NMR (400 MHz, <dmso>) δ ppm 1.84 (s, 12H) 2.27 (s, 8H) 2.31 (br. s., 1H) 3.73 (br. s., 15H) 4.04-4.10 (m, 8H) 7.26 (br. s., 1H) 7.45 (d, J=8.22 Hz, 1H) 7.78 (dd, J=8.61, 1.96 Hz, 1H) 7.88 (br. s., 1H) 8.28 (d, J=1.96 Hz, 1H) 9.63 (d, J=1.96 Hz, 1H) 10.90 (br. s., 1H). LCMS (m/z) (M+H)= 474, Rt=0.61 min.

Example 558: 2-(2-cyanopropan-2-yl)-N-(3-(6-methoxy-5-morpholinopyridazin-3-yl)-4-methylphenyl)isonicotinamide

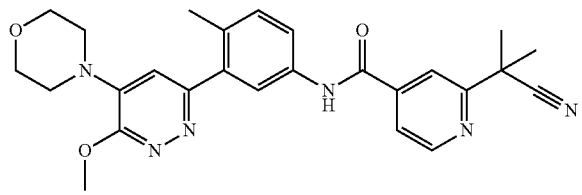 [SMILES: COc1nnc(-c2cc(NC(=O)c3ccnc(C(C)(C)C#N)c3)ccc2C)cc1N1CCOCC1]

1H NMR (400 MHz, <dmso>) δ ppm 1.75 (s, 6H) 2.18-2.32 (m, 3H) 3.62-3.88 (m, 7H) 3.99-4.15 (m, 3H) 7.30 (br. s., 1H) 7.43 (d, J=8.61 Hz, 1H) 7.79 (dd, J=8.22, 1.96 Hz, 1H) 7.84 (dd, J=4.89, 1.37 Hz, 1H) 7.90 (s, 1H) 7.98 (s, 1H) 8.81 (d, J=5.09 Hz, 1H) 10.72 (s, 1H). LCMS (m/z) (M+H)=473, Rt=0.66 min.

Example 559: N-(3-(6-ethoxy-5-morpholinopyridazin-3-yl)-4-methylphenyl)-3-(methylsulfonyl)benzamide

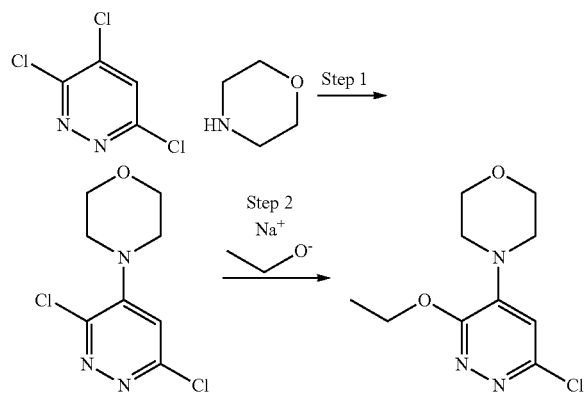

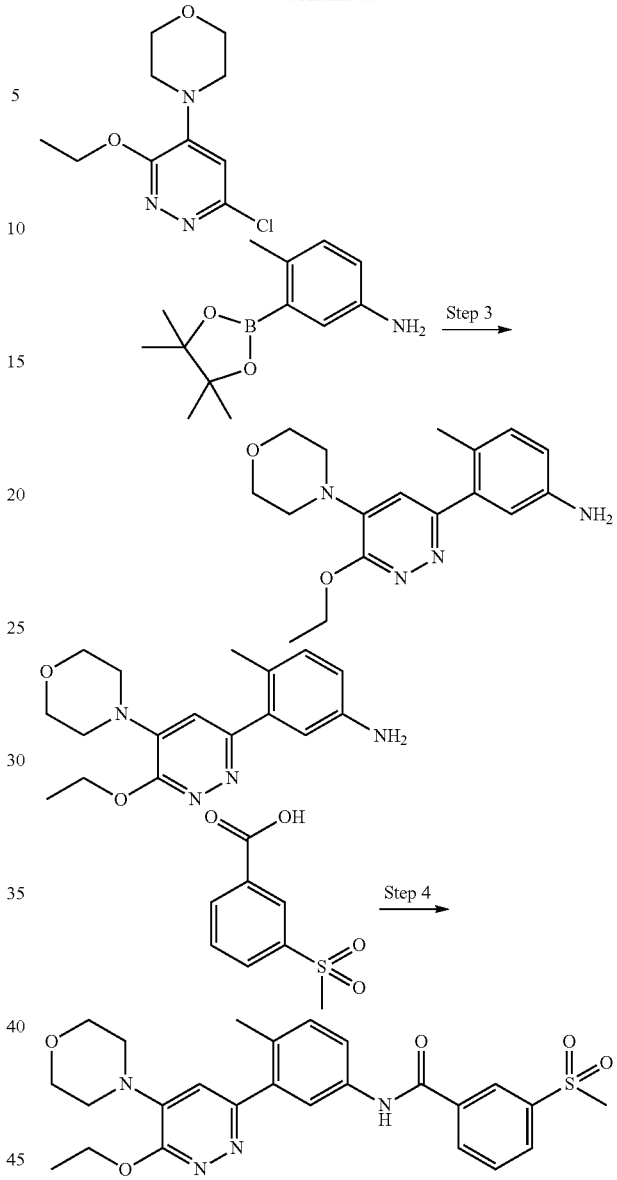

Step 1:
To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:
To a flask containing 4-(3,6-dichloropyridazin-4-yl)morpholine (1.0 equiv.) in EtOH (0.23 M) was added sodium ethoxide 21% in ethanol (1.4 equiv.) and the reaction mix was stirred o.n. at RT. The solvent was removed under vacuum and the crude was partitioned in brine/EtOAc. The organic phase was concentrated to dryness and the residue was dissolved in DCM, and adsorbed in silica gel. The solid was loaded into a cartridge and purified on a silica gel column. using 0 to 40% EtOAc in heptane. The desired 4-(6-chloro-3-ethoxypyridazin-4-yl)morpholine was obtained in 48% yield. LCMS (m/z) (M+H)=246, Rt=0.36 min.

Step 3:

To a solution of 4-(6-chloro-3-ethoxypyridazin-4-yl)morpholine (1.0 equiv.) and 4-methyl-3-(4,4,5,5-tetramethyl-1,3,2-dioxaborolan-2-yl)aniline (1.0 equiv.) in DME (0.11 M) was added $Na_2CO_3$ (2M, 3.0 equiv.) and the system was flushed with nitrogen. $PdCl_2(dppf).CH_2Cl_2$ adduct (0.05 equiv.) was added to the reaction mix and the system was flushed once again with nitrogen. The reaction flask was heated in a bath at 110° C. overnight. The reaction mix was partitioned in $H_2O$/EtOAc. The organic layer was isolated, dried over $Na_2SO_4$, filtered and concentrated. Crude was purified using a reverse phase system of 0 to 40% acetonitrile in water. The fractions containing the product were concentrated until a small volume of solvent was left and extracted three times with EtOAc. The combined organics were dried over $Na_2SO_4$, filtered and concentrated to give 3-(6-ethoxy-5-morpholinopyridazin-3-yl)-4-methylaniline in 62% yield. LCMS (m/z) (M+H)=315, Rt=0.44 min.

Step 4:

DIEA (3.0 equiv.) was added to a solution of 3-(6-ethoxy-5-morpholinopyridazin-3-yl)-4-methylaniline (1.0 equiv.), 3-(methylsulfonyl)benzoic acid (1.0 equiv.) and HATU (1.0 equiv.) in DMF (0.07 M), and the mixture was left stirring at RT overnight. The reaction mix was treated with water and extracted three times with EtOAc. The combined organics were concentrated to dryness and the crude purified by HPLC giving N-(3-(6-ethoxy-5-morpholinopyridazin-3-yl)-4-methylphenyl)-3-(methylsulfonyl)benzamide as the TFA salt in 53% yield. 1H NMR (400 MHz, <dmso>) δ ppm 1.43 (d, J=3.52 Hz, 3H) 2.26 (br. s., 4H) 3.63-3.91 (m, 8H) 4.36-4.57 (m, 2H) 7.33 (br. s., 1H) 7.43 (d, J=6.26 Hz, 1H) 7.75-7.87 (m, 2H) 7.94 (br. s., 1H) 8.14 (d, J=6.65 Hz, 1H) 8.27 (d, J=6.65 Hz, 1H) 8.46 (br. s., 1H) 10.69 (br. s., 1H). LCMS (m/z) (M+H)=497, Rt=0.66 min.

Example 560: 2-(1,1-difluoropropyl)-N-(3-(6-ethoxy-5-morpholinopyridazin-3-yl)-4-methylphenyl)isonicotinamide

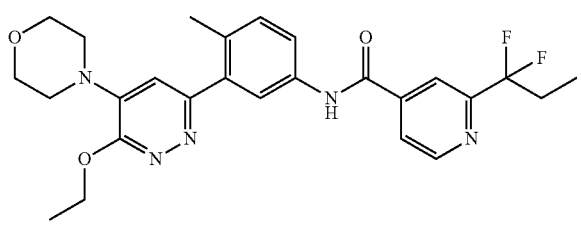 [SMILES: CCOc1nnc(-c2cc(NC(=O)c3ccnc(C(F)(F)CC)c3)ccc2C)cc1N1CCOCC1]

1H NMR (400 MHz, <dmso>) δ ppm 0.82-0.99 (m, 3H) 1.34-1.51 (m, 3H) 2.26 (s, 3H) 2.29-2.43 (m, 2H) 3.71-3.77 (m, 4H) 3.81 (br. s., 3H) 4.48 (q, J=7.04 Hz, 2H) 7.32 (br. s., 1H) 7.44 (d, J=8.22 Hz, 1H) 7.81 (dd, J=8.22, 1.96 Hz, 1H) 7.93 (s, 1H) 8.01 (d, J=4.30 Hz, 1H) 8.14 (s, 1H) 8.89 (d, J=5.09 Hz, 1H) 10.80 (s, 1H). LCMS (m/z) (M+H)=498, Rt=0.78 min.

Example 561: Synthesis of 3-(difluoromethyl)-N-(3-(6-ethoxy-5-morpholinopyridazin-3-yl)-4-methylphenyl)benzamide

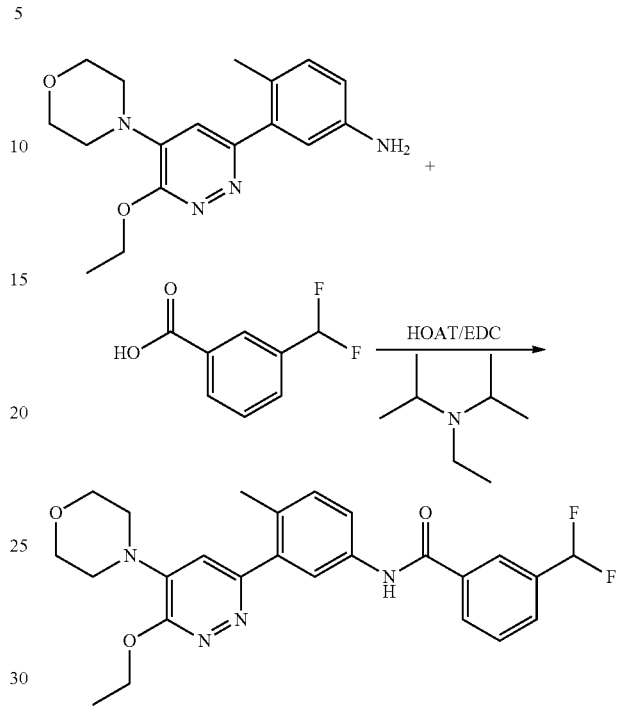

5-(6-Ethoxy-5-morpholinopyridazin-3-yl)-6-methylpyridin-3-amine (1.0 equiv.), N1-((ethylimino)methylene)-N3,N3-dimethylpropane-1,3-diamine hydrochloride (1.1 equiv.), and 4-(bromomethyl)-3-(trifluoromethyl)benzoic acid (1.1 equiv.) were dissolved in DMF (0.106 M) at RT. Hunig's base (2.2 equiv.) was subsequently added to mixture. The reaction was monitored by LCMS. After about 1 hr, the reaction mixture was purified via preparative reverse phase HPLC to give 3-(difluoromethyl)-N-(3-(6-ethoxy-5-morpholinopyridazin-3-yl)-4-methylphenyl)benzamidein 47% yield. 1H NMR (400 MHz, <dmso>) δ ppm 1.43 (s, 1H) 2.26 (s, 1H) 3.74 (br. s., 2H) 4.48 (d, J=7.04 Hz, 1H) 6.94-7.33 (m, 2H) 7.40 (d, J=8.61 Hz, 1H) 7.62-7.74 (m, 1H) 7.79 (d, J=8.22 Hz, 2H) 7.94 (br. s., 1H) 8.07-8.20 (m, 2H) 10.55 (br. s., 1H). LCMS (m/z) (M+H)=469.2, Rt=0.78 min.

Example 562: Synthesis of 2-(difluoromethyl)-N-(3-(6-ethoxy-5-morpholinopyridazin-3-yl)-4-methylphenyl)isonicotinamide

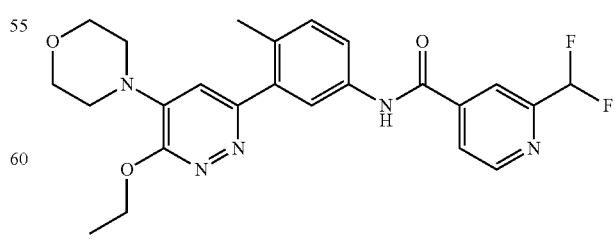

1H NMR (400 MHz, <dmso>) δ ppm 1.43 (t, J=7.04 Hz, 1H) 2.26 (s, 1H) 3.74 (br. s., 3H) 4.48 (q, J=7.04 Hz, 1H) 6.94 (s, 1H) 7.07 (s, 2H) 7.21 (s, 1H) 7.29 (br. s., 1H) 7.43

(d, J=8.22 Hz, 1H) 7.80 (dd, J=8.41, 2.15 Hz, 1H) 7.93 (s, 1H) 8.04 (d, J=5.09 Hz, 1H) 8.16 (s, 1H) 8.90 (d, J=5.09 Hz, 1H) 10.80 (s, 1H). LCMS (m/z) (M+H)=470.2, Rt=0.70 min.

Example 563: Synthesis of 2-cyclopropyl-N-(3-(6-ethoxy-5-morpholinopyridazin-3-yl)-4-methylphenyl)isonicotinamide

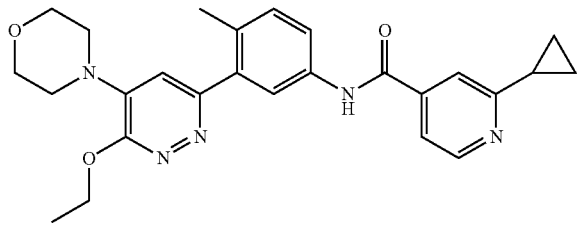 [SMILES: CCOc1nnc(-c2cc(NC(=O)c3ccnc(C4CC4)c3)ccc2C)cc1N1CCOCC1]

1H NMR (400 MHz, <dmso>) δ ppm 0.92-1.08 (m, 1H) 1.43 (t, J=7.04 Hz, 1H) 2.15-2.28 (m, 1H) 3.74 (br. s., 1H) 4.48 (q, J=6.78 Hz, 1H) 7.41 (d, J=8.22 Hz, 1H) 7.55 (dd, J=5.09, 1.57 Hz, 1H) 7.66-7.83 (m, 2H) 7.93 (br. s., 1H) 8.57 (d, J=5.09 Hz, 1H) 10.58 (br. s., 1H). LCMS (m/z) (M+H)=460.2, Rt=0.60 min.

Example 564: Synthesis of N-(3-(6-ethoxy-5-morpholinopyridazin-3-yl)-4-methylphenyl)-2-(2-fluoropropan-2-yl)isonicotinamide

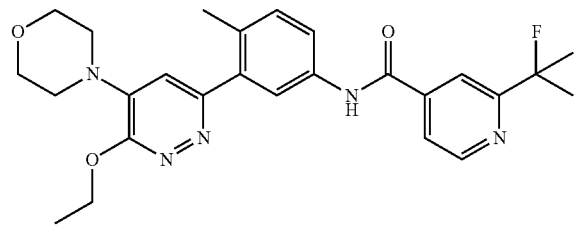 [SMILES: CCOc1nnc(-c2cc(NC(=O)c3ccnc(C(C)(C)F)c3)ccc2C)cc1N1CCOCC1]

1H NMR (400 MHz, <dmso>) δ ppm 1.43 (t, J=7.04 Hz, 1H) 1.59-1.76 (m, 2H) 2.26 (s, 1H) 3.68-3.89 (m, 3H) 4.48 (q, J=7.04 Hz, 1H) 7.29-7.37 (m, 1H) 7.43 (d, J=8.61 Hz, 1H) 7.76-7.84 (m, 2H) 7.94 (s, 1H) 8.00 (s, 1H) 8.63-8.88 (m, 1H) 10.58-10.79 (m, 1H). LCMS (m/z) (M+H)=480.2, Rt=0.75 min.

Example 565: Synthesis of 2-(1,1-difluoroethyl)-N-(3-(6-ethoxy-5-morpholinopyridazin-3-yl)-4-methylphenyl)isonicotinamide

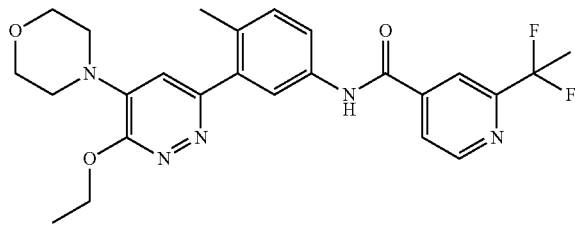 [SMILES: CCOc1nnc(-c2cc(NC(=O)c3ccnc(C(C)(F)F)c3)ccc2C)cc1N1CCOCC1]

1H NMR (400 MHz, <dmso>) δ ppm 1.43 (t, J=7.04 Hz, 1H) 2.04 (t, J=19.17 Hz, 1H) 2.26 (s, 1H) 3.74 (d, J=2.35 Hz, 2H) 4.48 (d, J=7.04 Hz, 1H) 7.19-7.35 (m, 1H) 7.42 (d, J=8.22 Hz, 2H) 7.80 (dd, J=8.22, 1.96 Hz, 2H) 7.91 (br. s., 2H) 8.01 (d, J=4.70 Hz, 2H) 8.17 (s, 2H) 8.80-9.01 (m, 2H) 10.65-10.87 (m, 2H). LCMS (m/z) (M+H)=484.2, Rt=0.76 min.

Example 566: Synthesis of N-(3-(6-ethoxy-5-morpholinopyridazin-3-yl)-4-methylphenyl)-2-(trifluoromethyl)isonicotinamide

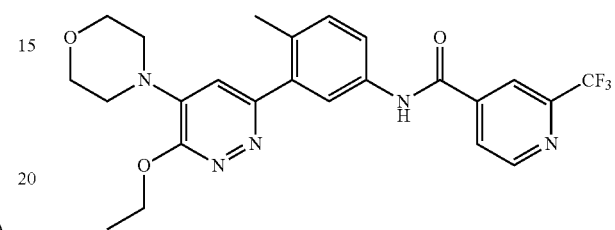

1H NMR (400 MHz, <dmso>) δ ppm 1.38 (t, J=7.04 Hz, 4H) 2.22 (s, 4H) 3.69 (br. s., 10H) 4.43 (q, J=6.91 Hz, 3H) 7.23 (br. s., 1H) 7.39 (d, J=8.22 Hz, 1H) 7.75 (dd, J=8.22, 1.96 Hz, 1H) 7.87 (br. s., 1H) 8.13 (d, J=4.30 Hz, 1H) 8.30 (s, 1H) 8.94 (d, J=5.09 Hz, 1H) 10.78 (s, 1H). LCMS (m/z) (M+H)=480.2, Rt=0.75 min.

Example 567: Synthesis of 6-(2-cyanopropan-2-yl)-N-(3-(6-ethoxy-5-morpholinopyridazin-3-yl)-4-methylphenyl)pyridazine-4-carboxamide

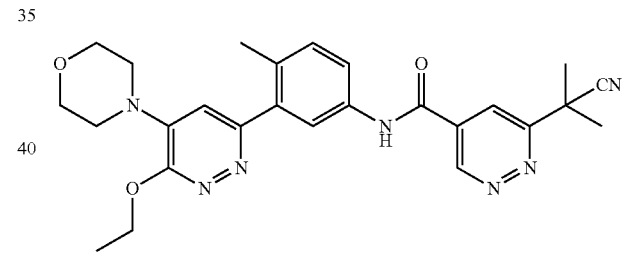

1H NMR (400 MHz, <dmso>) δ ppm 1.42 (s, 1H) 1.84 (s, 2H) 2.27 (s, 1H) 3.73 (br. s., 1H) 4.49 (d, J=7.04 Hz, 1H) 7.43 (d, J=8.22 Hz, 1H) 7.68-7.95 (m, 2H) 8.28 (d, J=1.96 Hz, 1H) 9.63 (d, J=1.57 Hz, 1H) 10.78-10.95 (m, 1H). LCMS (m/z) (M+H)=488.2, Rt=0.68 min.

Example 568: Synthesis of 2-(1-cyanocyclopropyl)-N-(3-(6-ethoxy-5-morpholinopyridazin-3-yl)-4-methylphenyl)isonicotinamide

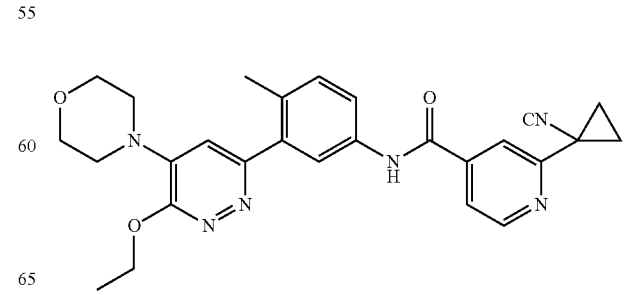

1H NMR (400 MHz, <dmso>) δ ppm 1.43 (t, J=7.04 Hz, 1H) 1.69-1.79 (m, 1H) 1.83-1.93 (m, 1H) 2.26 (s, 1H) 3.74 (d, J=2.35 Hz, 2H) 4.48 (q, J=7.04 Hz, 1H) 7.41 (d, J=8.22 Hz, 1H) 7.69-8.02 (m, 5H) 8.70 (d, J=5.09 Hz, 1H) 10.71 (br. s., 1H). LCMS (m/z) (M+H)=485.2, Rt=0.74 min.

Example 569: Synthesis of N-(3-(6-ethoxy-5-morpholinopyridazin-3-yl)-4-methylphenyl)-2-(2-hydroxypropan-2-yl)isonicotinamide

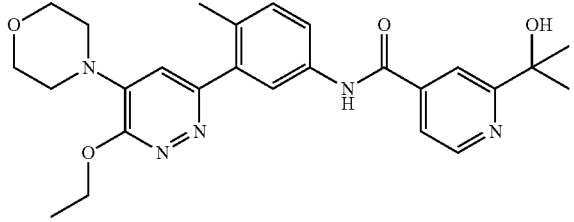 [SMILES: CCOc1nnc(-c2cc(NC(=O)c3ccnc(C(C)(C)O)c3)ccc2C)cc1N1CCOCC1]

1H NMR (400 MHz, <dmso>) δ ppm 1.37-1.55 (m, 12H) 2.26 (s, 4H) 3.71-3.78 (m, 9H) 3.86 (br. s., 7H) 4.47 (d, J=7.04 Hz, 3H) 7.36 (s, 1H) 7.44 (d, J=8.22 Hz, 1H) 7.68 (dd, J=5.09, 1.57 Hz, 1H) 7.81 (dd, J=8.41, 2.15 Hz, 1H) 7.96 (d, J=1.96 Hz, 1H) 8.12 (s, 1H) 8.68 (d, J=5.09 Hz, 1H) 10.55-10.85 (m, 1H). LCMS (m/z) (M+H)=478.1, Rt=0.56 min.

Example 570: Synthesis of N-(3-(6-ethoxy-5-morpholinopyridazin-3-yl)-4-methylphenyl)-6-(trifluoromethyl)pyridazine-4-carboxamide

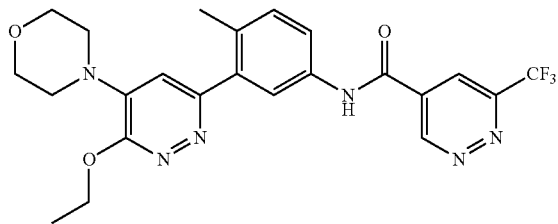 [SMILES: CCOc1nnc(-c2cc(NC(=O)c3cnnc(C(F)(F)F)c3)ccc2C)cc1N1CCOCC1]

1H NMR (400 MHz, <dmso>) δ ppm 1.43 (t, J=7.04 Hz, 5H) 2.27 (s, 5H) 3.74 (br. s., 10H) 4.38-4.63 (m, 3H) 7.25 (br. s., 1H) 7.45 (d, J=8.22 Hz, 1H) 7.78 (dd, J=8.41, 2.15 Hz, 1H) 7.86-7.94 (m, 1H) 8.55-8.78 (m, 2H) 9.90 (d, J=1.57 Hz, 2H) 10.99 (s, 2H). LCMS (m/z) (M+H)=489.1, Rt=0.71 min.

Example 571: Synthesis of (S)—N-(5-(6-ethoxy-5-(3-methylmorpholino)pyridazin-3-yl)-6-methylpyridin-3-yl)-3-(trifluoromethyl)benzamide

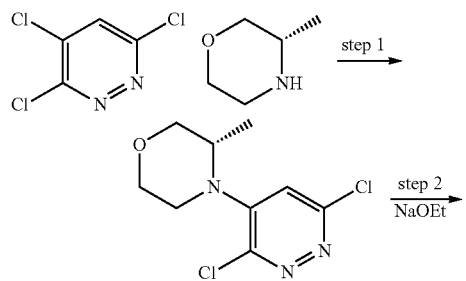

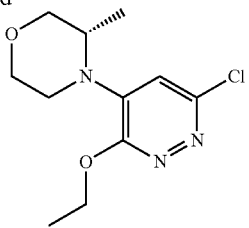

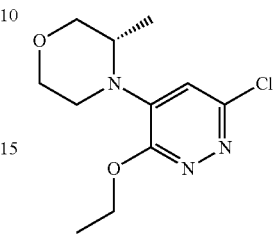

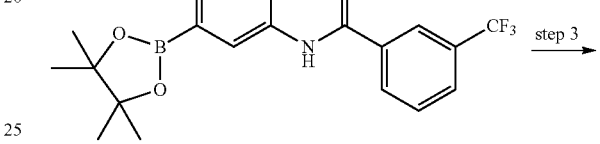

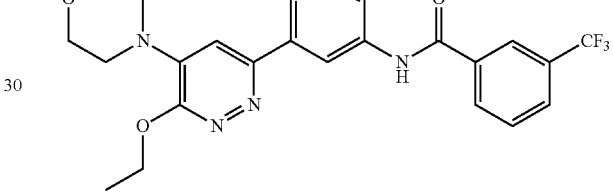

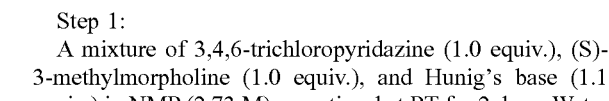

Step 1:
A mixture of 3,4,6-trichloropyridazine (1.0 equiv.), (S)-3-methylmorpholine (1.0 equiv.), and Hunig's base (1.1 equiv.) in NMP (2.73 M) was stirred at RT for 2 days. Water was added to the reaction mixture. The solid that precipitated was collected by filtration and dried in air to give (S)-4-(3,6-dichloropyridazin-4-yl)-3-methylmorpholine as white solid in 62% yield. LC/MS (m/z)=247.9 (MH$^+$), R$_f$=0.63 min.

Step 2:
A mixture of (S)-4-(3,6-dichloropyridazin-4-yl)-3-methylmorpholine (1.0 equiv.) and 21 wt % sodium ethoxide in ethanol (2.0 equiv.) in 1.5:1 ethanol and water was stirred overnight at RT. The resulting mixture was partitioned between EtOAc and water. The organic phase was washed with brine and then dried over magnesium sulfate. After concentration, the crude material was purified via preparative reverse phase HPLC.

Upon lyophilization of the pure fractions, (S)-4-(6-chloro-3-ethoxypyridazin-4-yl)-3-methylmorpholine was isolated as the TFA salt in 55% yield. LC/MS (m/z)=258.0 (MH$^+$), R$_f$=0.59 min.

Step 3:
A mixture of (S)-4-(6-chloro-3-ethoxypyridazin-4-yl)-3-methylmorpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.), Na$_2$CO$_3$ (2 M, 3 equiv.) and PdCl$_2$(dppf) (0.05 equiv.) in DME (0.203 M) were heated at 120° C. for 15 min in the microwave. The resulting mixture was partitioned between EtOAc and water. The organic phase was washed with brine and then dried over magnesium sulfate. After concentration, the crude material was purified via preparative reverse phase HPLC. Upon lyophilization of the pure fractions, (S)—N-(5-(6-ethoxy-5-(3-methylmorpholino)pyridazin-3-yl)-6-methylpyridin-3-yl)-3-(trifluoromethyl)benzamide was isolated as the TFA salt in 32% yield. 1H NMR (400 MHz, <dmso>) δ ppm 1.31 (d, J=6.65 Hz, 5H) 1.43 (t, J=6.85 Hz, 5H) 3.69 (d, J=1.57 Hz, 4H) 3.91 (d, J=9.78 Hz, 2H) 4.36-4.64 (m, 3H) 7.34 (br. s., 1H) 7.81 (t, J=7.83 Hz, 1H) 8.01 (d, J=7.83 Hz, 1H) 8.24-8.39 (m, 3H) 8.95 (d, J=2.35 Hz, 1H) 10.84 (s, 1H). LCMS (m/z) (M+H)=502.2, Rt=0.78 min.

Example 572: Synthesis of (S)-2-(2-cyanopropan-2-yl)-N-(3-(6-ethoxy-5-(3-methylmorpholino)pyridazin-3-yl)-4-methylphenyl)isonicotinamide material was purified via preparative reverse phase HPLC. Upon lyophilization of the pure fractions, (S)-2-(2-cyanopropan-2-yl)-N-(3-(6-ethoxy-5-(3-methylmorpholino)pyridazin-3-yl)-4-methylphenyl)isonicotinamide was isolated as the TFA salt in 11% yield. 1H NMR (400 MHz, <dmso>) δ ppm 1.32 (br. s., 2H) 1.43 (t, J=6.85 Hz, 3H) 1.75 (s, 6H) 2.05 (s, 2H) 2.26 (s, 3H) 3.50-3.63 (m, 2H) 3.68 (s, 2H) 3.89 (br. s., 1H) 4.41-4.54 (m, 2H) 7.43 (d, J=8.61 Hz, 1H) 7.76-7.93 (m, 3H) 7.98 (s, 1H) 8.81 (d, J=5.09 Hz, 1H) 10.71 (br. s., 1H). LCMS (m/z) (M+H)=501.2, Rt=0.78 min.

Example 573: 2-(2-cyanopropan-2-yl)-N-(3-(6-ethoxy-5-morpholinopyridazin-3-yl)-4-methylphenyl)isonicotinamide

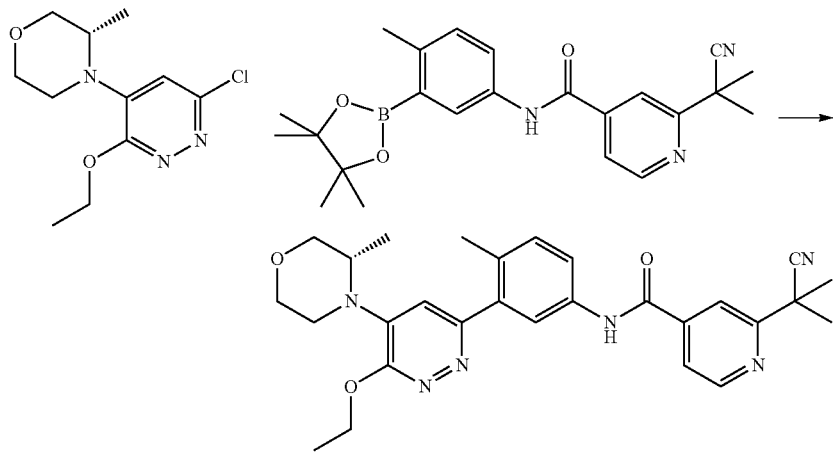

A mixture of (S)-4-(6-chloro-3-ethoxypyridazin-4-yl)-3-methylmorpholine (1.0 equiv.), 2-(2-cyanopropan-2-yl)-N-(4-methyl-3-(4,4,5,5-tetramethyl-1,3,2-dioxaborolan-2-yl)phenyl)isonicotinamide (1.0 equiv.), Na2CO3 (2 M, 3 equiv.) and PdCl$_2$(dppf) (0.05 equiv.) in DME (0.058 M) were heated at 120° C. for 15 min in the microwave. The resulting mixture was partitioned between EtOAc and water. The organic phase was washed with brine and then dried over magnesium sulfate. After concentration, the crude

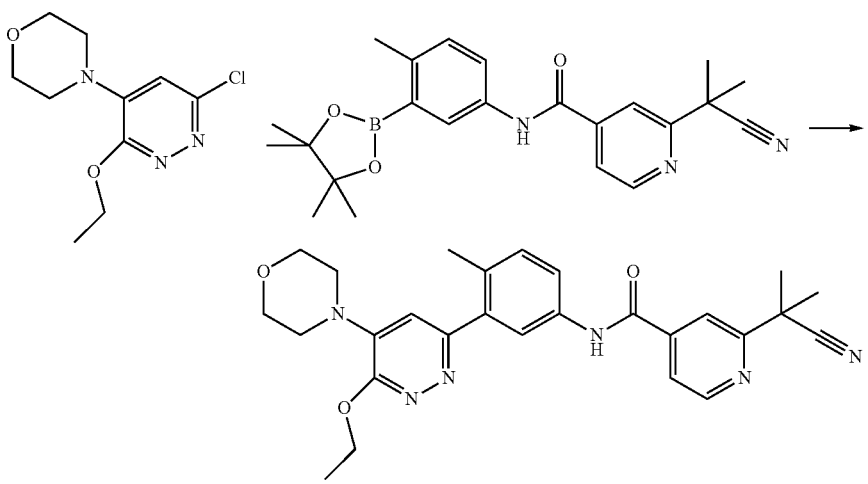

PdCl$_2$(dppf).CH$_2$Cl$_2$ adduct (0.1 equiv.) was added to a solution of 4-(6-chloro-3-ethoxypyridazin-4-yl)morpholine (1.0 equiv.), 2-(2-cyanopropan-2-yl)-N-(4-methyl-3-(4,4,5,5-tetramethyl-1,3,2-dioxaborolan-2-yl)phenyl)isonicotinamide (1.0 equiv.) and Na$_2$CO$_3$ 2 M solution (3.0 equiv.) in DME (0.04 M) and the system was flushed with nitrogen. The vial was sealed and placed in the microwave for 20 minutes at 120° C. The solvent was removed under vacuum and the residue was partitioned in EtOAC/H2O. The organic layer was isolated and the aqueous layer was back extracted twice with EtOAc. The combined organics were dried over Na$_2$SO$_4$, filtered and concentrated. The crude was purified by HPLC to give 2-(2-cyanopropan-2-yl)-N-(3-(6-ethoxy-5-morpholinopyridazin-3-yl)-4-methylphenyl)isonicotinamide in 25% yield. 1H NMR (400 MHz, <dmso>) δ ppm 1.32-1.49 (m, 3H) 1.68-1.80 (m, 7H) 2.27 (s, 3H) 3.65-3.78 (m, 5H) 4.52 (q, J=7.04 Hz, 2H) 6.94 (br. s., 1H) 7.32 (d, J=8.22 Hz, 1H) 7.69-7.79 (m, 2H) 7.85 (dd, J=5.09, 1.17 Hz, 1H) 8.00 (s, 1H) 8.79 (d, J=5.09 Hz, 1H) 10.57 (s, 1H). LCMS (m/z) (M+H)=487, Rt=0.73 min.

Example 574: Synthesis of N-(3-(6-ethoxy-5-morpholinopyridazin-3-yl)-4-methylphenyl)-4-((methylamino)methyl)-3-(trifluoromethyl)benzamide

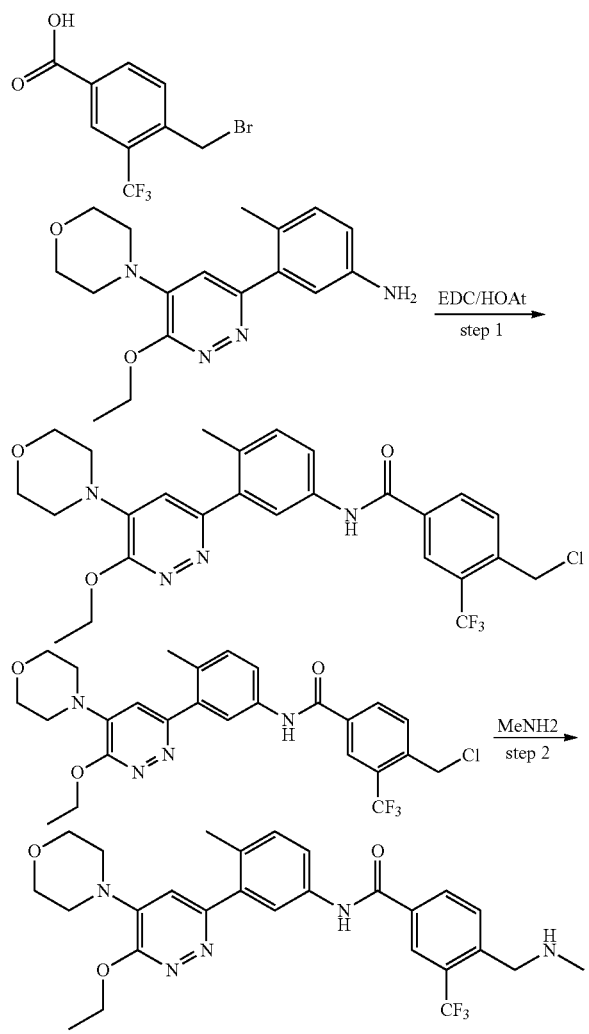

Step 1:
3-(6-ethoxy-5-morpholinopyridazin-3-yl)-4-methylaniline (1.0 equiv.), N1-((ethylimino)methylene)-N3,N3-dimethylpropane-1,3-diamine hydrochloride (1.1 equiv.), 3H-[1,2,3]triazolo[4,5-b]pyridin-3-ol (1.1 equiv.) and 4-(bromomethyl)-3-(trifluoromethyl)benzoic acid (1.1 equiv.) were dissolved in DMF (0.181 M) at RT. The reaction was monitored by LCMS. After about 1 hr, the reaction mixture was purified via preparative reverse phase HPLC to give 4-(chloromethyl)-N-(3-(6-ethoxy-5-morpholinopyridazin-3-yl)-4-methylphenyl)-3-(trifluoromethyl)benzamide in 68% yield. LCMS (m/z) (M+H)=535.1, Rt=1.02 min.

Step 2:
4-(chloromethyl)-N-(3-(6-ethoxy-5-morpholinopyridazin-3-yl)-4-methylphenyl)-3-(trifluoromethyl)benzamide (1.0 equiv.) was dissolved in 2M ammonia in methanol (0.028 M). After stirring at RT overnight, the reaction mixture was concentrated and purified via preparative reverse phase HPLC to give N-(3-(6-ethoxy-5-morpholinopyridazin-3-yl)-4-methylphenyl)-4-((methylamino)methyl)-3-(trifluoromethyl)benzamide in 58% yield. 1H NMR (400 MHz, <dmso>) δ ppm 1.42 (t, J=7.04 Hz, 6H) 2.26 (s, 6H) 2.36 (d, J=6.26 Hz, 2H) 2.71 (br. s., 6H) 3.74 (br. s., 7H) 4.38 (br. s., 4H) 4.44-4.59 (m, 4H) 7.16 (br. s., 1H) 7.39 (d, J=8.22 Hz, 1H) 7.79 (dd, J=8.22, 1.96 Hz, 2H) 7.83-7.94 (m, 1H) 8.35 (br. s., 1H) 8.94-9.22 (m, 3H) 10.50-10.74 (m, 1H). LCMS (m/z) (M+H)=530.1, Rt=0.62 min.

Example 575: N-(3-(6-ethoxy-5-morpholinopyridazin-3-yl)-4-methylphenyl)-4-((ethylamino)methyl)-3-(trifluoromethyl)benzamide

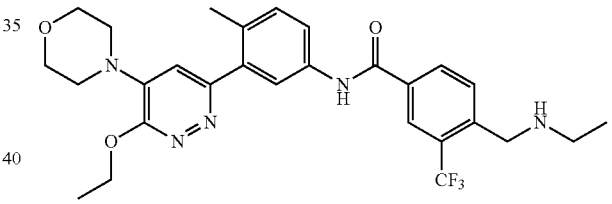

1H NMR (400 MHz, <dmso>) δ ppm 1.11 (t, J=7.43 Hz, 2H) 1.25 (t, J=7.24 Hz, 10H) 1.43 (t, J=7.04 Hz, 8H) 2.26 (s, 8H) 2.36 (d, J=6.26 Hz, 1H) 2.74-2.90 (m, 1H) 3.13 (dd, J=11.93, 6.46 Hz, 1H) 3.74 (br. s., 2H) 4.38 (br. s., 1H) 4.49 (d, J=7.04 Hz, 1H) 7.12-7.29 (m, 2H) 7.40 (d, J=8.22 Hz, 3H) 7.80 (dd, J=8.22, 1.96 Hz, 3H) 7.85-7.98 (m, 6H) 8.35 (d, J=3.91 Hz, 6H) 8.86-9.12 (m, 5H) 10.66 (br. s., 2H). LCMS (m/z) (M+H)=544.1, Rt=0.64 min.

Example 576: 4-((dimethylamino)methyl)-N-(3-(6-ethoxy-5-morpholinopyridazin-3-yl)-4-methylphenyl)-3-(trifluoromethyl)benzamide

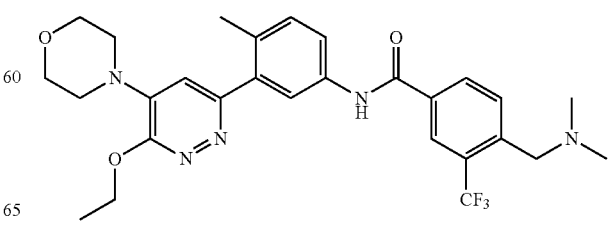

1H NMR (400 MHz, <dmso>) δ ppm 1.38 (t, J=6.85 Hz, 1H) 2.22 (s, 1H) 2.46-2.55 (m, 1H) 2.77 (br. s., 1H) 3.69 (br. s., 1H) 4.35-4.60 (m, 1H) 7.34 (d, J=8.22 Hz, 1H) 7.74 (dd, J=8.41, 1.76 Hz, 1H) 7.78-7.88 (m, 2H) 7.95 (d, J=8.61 Hz, 2H) 8.33 (br. s., 4H) 10.48-10.74 (m, 2H). LCMS (m/z) (M+H)=544.1, Rt=0.63 min.

Example 577: N-(4-methyl-3-(5-morpholino-6-((tetrahydro-2H-pyran-4-yl)oxy)pyridazin-3-yl)phenyl)-6-(trifluoromethyl)pyridazine-4-carboxamide

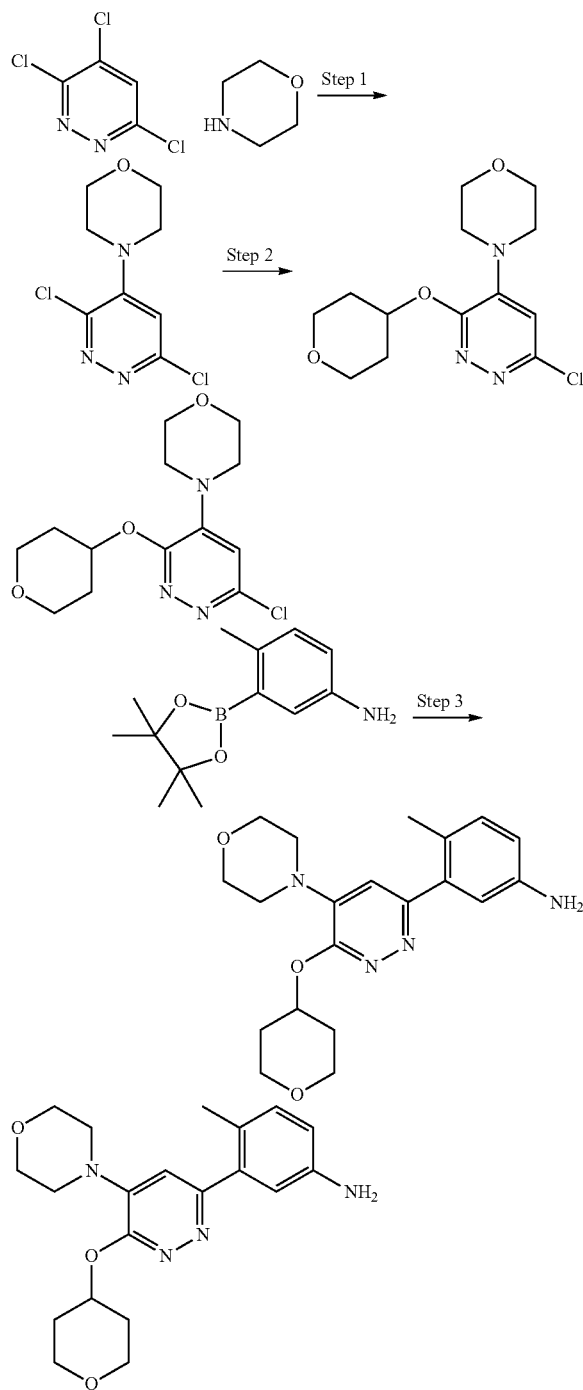

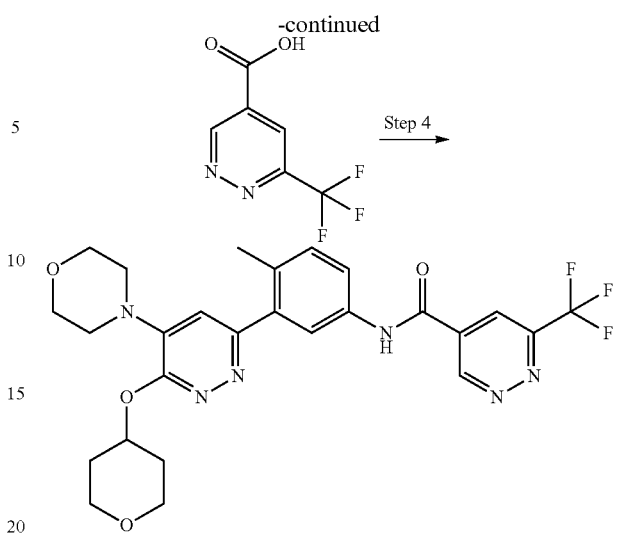

Step 1:
To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:
NaH (2.0 equiv.) was added to a solution of tetrahydro-2H-pyran-4-ol (1.7 equiv.) and 4-(3,6-dichloropyridazin-4-yl)morpholine (1.0 equiv.) in THF (0.3 M) at 0° C. and the reaction mix was left stirring overnight at RT. The reaction mix was quench with water and extracted three times with EtOAc. The combined organics were washed with brine and dried over Na$_2$SO4. The crude was dissolved in DCM, and adsorbed in silica gel. The solid was loaded into a cartridge and purified on a silica gel column using 0 to 40% EtOAc in heptane. The desired 4-(6-chloro-3-((tetrahydro-2H-pyran-4-yl)oxy)pyridazin-4-yl)morpholine was obtained in 75% yield. LCMS (m/z) (M+H)=300, Rt=0.54 min.

Step 3:
To a solution of 4-(6-chloro-3-((tetrahydro-2H-pyran-4-yl)oxy)pyridazin-4-yl)morpholine (1.0 equiv.) and 4-methyl-3-(4,4,5,5-tetramethyl-1,3,2-dioxaborolan-2-yl)aniline (1.0 equiv.) in DME (0.11 M) was added Na$_2$CO$_3$ (2M, 3.0 equiv.) and the system was flushed with nitrogen. PdCl$_2$(dppf).CH$_2$Cl$_2$ adduct (0.05 equiv.) was added to the reaction mix and the system was flushed once again with nitrogen. The reaction mix was heated in a bath for 4 hr at 120° C. The crude was partitioned in H$_2$O/EtOAc. The organic layer was isolated, dried over Na$_2$SO$_4$, filtered and concentrated. Crude was purified silica gel column using DCM to 5% MeOH in DCM to give 4-methyl-3-(5-morpholino-6-((tetrahydro-2H-pyran-4-yl)oxy)pyridazin-3-yl)aniline in 77% yield. LCMS (m/z) (M+H)=371, Rt=0.43 min.

Step 4:
DIEA (3.0 equiv.) was added to a solution of 4-methyl-3-(5-morpholino-6-((tetrahydro-2H-pyran-4-yl)oxy)pyridazin-3-yl)aniline (1.0 equiv.), 6-(trifluoromethyl)pyridazine-4-carboxylic acid (1.0 equiv.) and HATU (1.0 equiv.) in DMF (0.05 M), and the mixture was left stirring at RT overnight. The reaction mix was treated with water and extracted three times with EtOAc. The combined organics were dried over Na$_2$SO$_4$, filtered and concentrated. The crude was purified by HPLC giving N-(4-methyl-3-(5-morpholino-6-((tetrahydro-2H-pyran-4-yl)oxy)pyridazin-3-yl)phenyl)-6-(trifluoromethyl)pyridazine-4-carboxamide as the TFA salt in 55% yield. 1H NMR (400 MHz, <dmso>) δ ppm 1.71-1.91 (m, 2H) 2.00-2.17 (m, 2H) 2.21-2.33 (m, 3H) 3.67-3.90 (m, 10H) 5.25-5.44 (m, 1H) 7.29 (br. s., 1H) 7.46 (d, J=8.61 Hz, 1H) 7.77 (dd, J=8.22, 1.96 Hz, 1H) 7.92 (s, 1H) 8.66 (d, J=1.96 Hz, 1H) 9.90 (d, J=1.56 Hz, 1H) 11.01 (s, 1H). LCMS (m/z) (M+H)=545, Rt=0.69 min.

Example 578: 2-(2-fluoropropan-2-yl)-N-(4-methyl-3-(5-morpholino-6-((tetrahydro-2H-pyran-4-yl)oxy)pyridazin-3-yl)phenyl)isonicotinamide

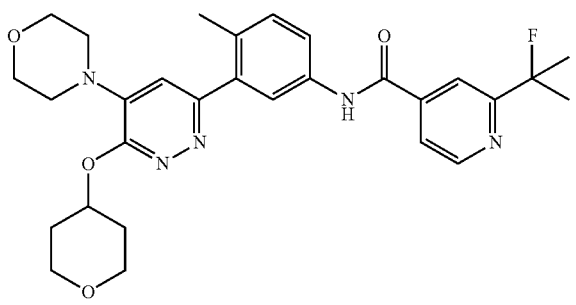 [SMILES: Cc1ccc(NC(=O)c2ccnc(C(C)(C)F)c2)cc1-c1cc(N2CCOCC2)c(OC2CCOCC2)nn1]

1H NMR (400 MHz, <dmso>) δ ppm 1.61-1.74 (m, 6H) 1.76-1.90 (m, 2H) 2.02-2.17 (m, 2H) 2.21-2.31 (m, 3H) 7.34 (br. s., 1H) 7.43 (d, J=8.22 Hz, 1H) 7.75-7.84 (m, 2H) 7.95 (s, 1H) 8.00 (s, 1H) 8.76 (d, J=5.09 Hz, 1H) 10.73 (s, 1H). LCMS (m/z) (M+H)=536, Rt=0.70 min.

Example 579: 2-(1,1-difluoroethyl)-N-(4-methyl-3-(5-morpholino-6-((tetrahydro-2H-pyran-4-yl)oxy)pyridazin-3-yl)phenyl)isonicotinamide

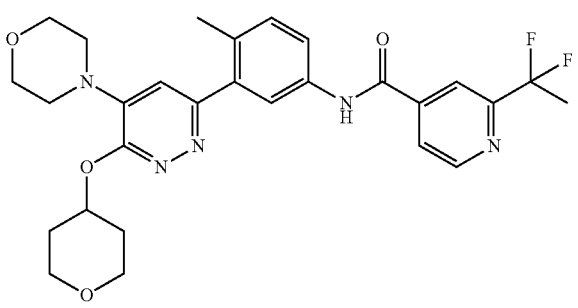 [SMILES: Cc1ccc(NC(=O)c2ccnc(C(C)(F)F)c2)cc1-c1cc(N2CCOCC2)c(OC2CCOCC2)nn1]

1H NMR (400 MHz, <dmso>) δ ppm 1.68-1.83 (m, 3H) 1.94 (s, 1H) 1.97-2.11 (m, 4H) 2.22 (s, 3H) 5.19-5.38 (m, 1H) 7.28 (br. s., 1H) 7.39 (d, J=8.22 Hz, 1H) 7.74 (dd, J=8.22, 1.96 Hz, 1H) 7.90 (s, 1H) 7.96 (d, J=4.70 Hz, 1H) 8.11 (s, 1H) 8.83 (d, J=5.09 Hz, 1H) 10.75 (s, 1H). LCMS (m/z) (M+H)=540, Rt=0.71 min.

Example 580: N-(4-methyl-3-(5-morpholino-6-((tetrahydro-2H-pyran-4-yl)oxy)pyridazin-3-yl)phenyl)-4-(trifluoromethyl)picolinamide

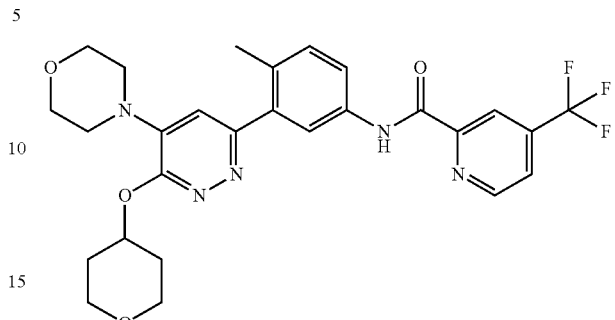

1H NMR (400 MHz, <dmso>) δ ppm 1.77 (d, J=8.61 Hz, 3H) 2.03 (br. s., 3H) 2.23 (s, 4H) 3.53 (t, J=8.22 Hz, 3H) 5.31 (br. s., 1H) 7.26 (br. s., 1H) 7.37 (d, J=8.22 Hz, 1H) 7.91 (d, J=7.83 Hz, 1H) 8.04 (br. s., 2H) 8.27 (s, 1H) 8.98 (d, J=4.70 Hz, 1H) 10.91 (br. s., 1H). LCMS (m/z) (M+H)=544, Rt=0.80 min.

Example 581: 2-(2-hydroxypropan-2-yl)-N-(4-methyl-3-(5-morpholino-6-((tetrahydro-2H-pyran-4-yl)oxy)pyridazin-3-yl)phenyl)isonicotinamide

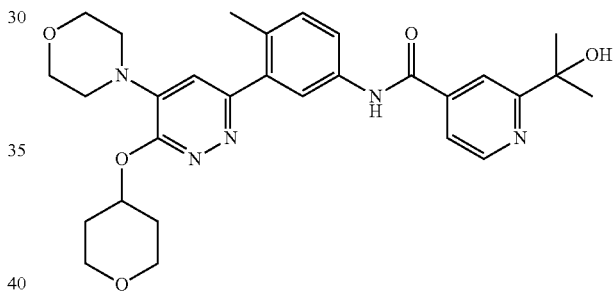

1H NMR (400 MHz, <dmso>) δ ppm 1.41-1.50 (m, 7H) 1.75-1.91 (m, 2H) 2.02-2.14 (m, 2H) 2.26 (s, 3H) 3.58 (ddd, J=11.35, 7.83, 3.13 Hz, 2H) 5.33 (dt, J=7.43, 3.72 Hz, 1H) 7.37 (s, 1H) 7.43 (d, J=8.22 Hz, 1H) 7.68 (dd, J=5.09, 1.57 Hz, 1H) 7.79 (dd, J=8.22, 1.96 Hz, 1H) 7.97 (d, J=1.57 Hz, 1H) 8.12 (s, 1H) 8.68 (d, J=5.09 Hz, 1H) 10.70 (s, 1H). LCMS (m/z) (M+H)=534, Rt=0.55 min.

Example 582: N-(4-methyl-3-(5-morpholino-6-((tetrahydro-2H-pyran-4-yl)oxy)pyridazin-3-yl)phenyl)-2-(methylsulfonyl)isonicotinamide

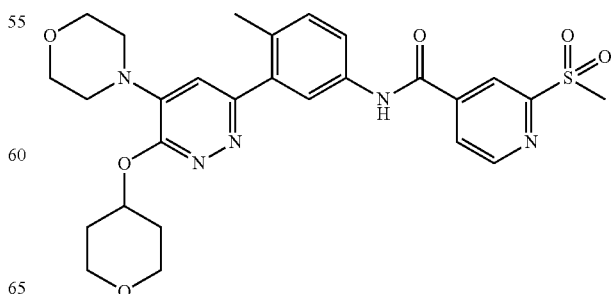

1H NMR (400 MHz, <dmso>) δ ppm 1.74-1.89 (m, 2H) 2.10 (dt, J=6.65, 3.33 Hz, 2H) 2.27 (s, 3H) 3.34 (s, 4H) 3.72-3.88 (m, 10H) 5.35 (br. s., 1H) 7.31 (br. s., 1H) 7.44 (d, J=8.22 Hz, 1H) 7.80 (dd, J=8.41, 2.15 Hz, 1H) 7.94 (s, 1H) 8.20 (dd, J=4.89, 1.37 Hz, 1H) 8.51 (s, 1H) 9.00 (d, J=4.70 Hz, 1H) 10.93 (s, 1H). LCMS (m/z) (M+H)=554, Rt=0.61 min.

Example 583: 6-(2-cyanopropan-2-yl)-N-(4-methyl-3-(5-morpholino-6-((tetrahydro-2H-pyran-4-yl)oxy)pyridazin-3-yl)phenyl)pyridazine-4-carboxamide

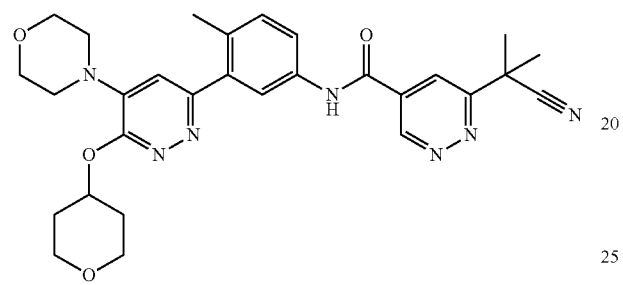

1H NMR (400 MHz, <dmso>) δ ppm 1.67-1.92 (m, 9H) 1.97-2.15 (m, 2H) 2.18-2.35 (m, 4H) 3.65-3.90 (m, 7H) 5.38 (br. s., 1H) 7.43 (d, J=8.22 Hz, 1H) 7.76 (dd, J=8.22, 1.96 Hz, 1H) 7.88 (br. s., 1H) 8.28 (d, J=1.96 Hz, 1H) 9.63 (d, J=1.96 Hz, 1H) 10.88 (br. s., 1H). LCMS (m/z) (M+H)=544, Rt=0.65 min.

Example 584: 2-(2-cyanopropan-2-yl)-N-(4-methyl-3-(5-morpholino-6-((tetrahydro-2H-pyran-4-yl)oxy)pyridazin-3-yl)phenyl)isonicotinamide

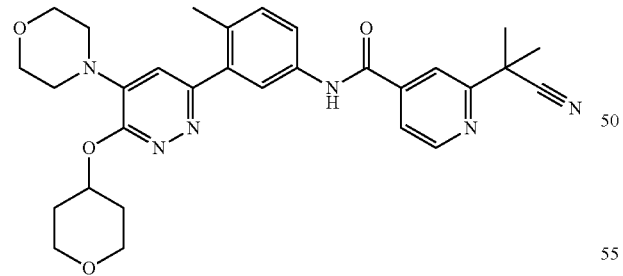

1H NMR (400 MHz, <dmso>) δ ppm 1.21 (s, 1H) 1.66-1.83 (m, 9H) 1.97 (s, 2H) 2.04-2.15 (m, 2H) 2.27 (s, 3H) 3.52-3.62 (m, 2H) 3.67-3.77 (m, 4H) 3.79-3.87 (m, 2H) 4.01 (q, J=7.04 Hz, 1H) 5.41-5.58 (m, 1H) 6.95 (br. s., 1H) 7.32 (d, J=8.61 Hz, 1H) 7.69-7.79 (m, 2H) 7.85 (d, J=5.09 Hz, 1H) 7.99 (s, 1H) 8.79 (d, J=5.09 Hz, 1H) 10.56 (s, 1H). LCMS (m/z) (M+H)=543, Rt=0.71 min.

Example 585: N-(3-(6-(2-hydroxyethoxy)-5-morpholinopyridazin-3-yl)-4-methylphenyl)-2-(trifluoromethyl)isonicotinamide

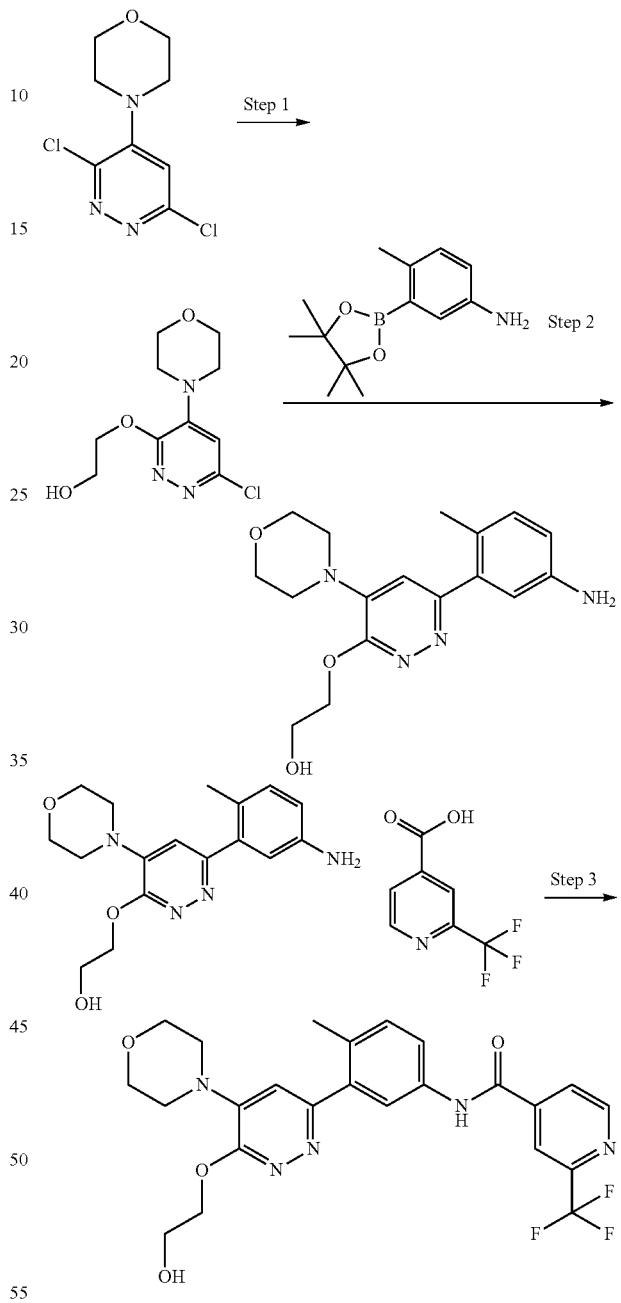

Step 1:
To a solution of 4-(3,6-dichloropyridazin-4-yl)morpholine (1.0 equiv.) and ethane-1,2-diol (3.0 equiv.) in THF (0.14M) was added sodium hydride (60% oil dispersion, 3.0 equiv.) under nitrogen and the reaction was heated to 60° C. for 4 hours. Upon completion, cooled to room temperature and quenched by the addition of water. Extracted with ethyl acetate three times, the organics were combined, dried with Na$_2$SO$_4$, filtered and concentrated. The crude material was triturated in DCM and the precipitate was filtered. Isolated 2-((6-chloro-4-morpholinopyridazin-3-yl)oxy)ethanol as the desired product in 51% yield as a white solid. LCMS (m/z) (M+H)=260.0, Rt=0.39 min.

Step 2:

To a solution 2-((6-chloro-4-morpholinopyridazin-3-yl)oxy)ethanol (1.0 equiv.) in DME (0.2 M) was added 4-methyl-3-(4,4,5,5-tetramethyl-1,3,2-dioxaborolan-2-yl) aniline (1.2 equiv.) and PdCl₂(dppf).CH₂Cl₂ adduct (0.10 equiv.), and 2M Na₂CO₃ (3.00 equiv.). The reaction was heated in the microwave at 120° C. for 20 min. Partitioned between water and ethyl acetate, the aqueous phase was extracted 3 times with ethyl acetate, the organics were combined, dried with sodium sulfate, filtered and concentrated. The crude material was purified via silica gel chromatography eluting with 0-100% ethyl acetate in heptanes followed by 10% methanol in EtOAc. The pure fractions were concentrated under vacuum to yield 2-((6-(5-amino-2-methylphenyl)-4-morpholinopyridazin-3-yl)oxy)ethanol in 39% yield. LCMS (m/z) (M+H)=331.0, Rt=0.35 min.

Step 3:

To a solution of 2-((6-(5-amino-2-methylphenyl)-4-morpholinopyridazin-3-yl)oxy)ethanol (1.0 equiv.) in DMF (0.06 M) was added 2-(trifluoromethyl)isonicotinic acid (1.0 equiv.) and EDC (1.0 equiv.) and HOAt (1.0 equiv.). The solution was stirred at room temperature overnight. Filtered through a HPLC filter and purified via reverse phase prep-HPLC. The pure fractions were lyophilized for several days to yield N-(3-(6-(2-hydroxyethoxy)-5-morpholinopyridazin-3-yl)-4-methylphenyl)-2-(trifluoromethyl)isonicotinamide in 21% yield. 1H NMR (400 MHz, <cd3od>) δ ppm 2.35 (s, 3H) 3.81-3.90 (m, 4H) 3.94-4.08 (m, 6H) 4.51-4.63 (m, 2H) 7.31 (s, 1H) 7.48 (d, J=8.61 Hz, 1H) 7.72 (dd, J=8.41, 2.15 Hz, 1H) 8.05 (d, J=2.35 Hz, 1H) 8.12 (d, J=3.91 Hz, 1H) 8.29 (s, 1H) 8.92 (d, J=5.09 Hz, 1H). LCMS (m/z) (M+H)=504.1, Rt=0.64 min.

Example 586: N-(3-(6-(2-hydroxyethoxy)-5-morpholinopyridazin-3-yl)-4-methylphenyl)-4-(trifluoromethyl)picolinamide

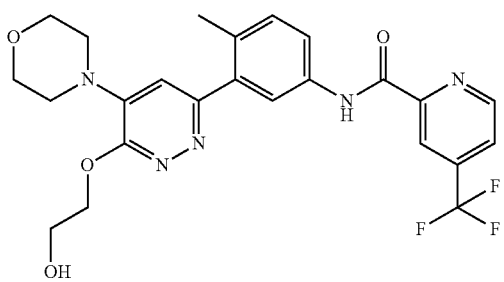 [SMILES: Cc1ccc(NC(=O)c2cc(C(F)(F)F)ccn2)cc1-c1cc(N2CCOCC2)c(OCCO)nn1]

1H NMR (400 MHz, <cd3od>) δ ppm 2.35 (s, 3H) 3.78-3.90 (m, 4H) 3.95-4.08 (m, 6H) 4.49-4.61 (m, 2H) 7.32 (s, 1H) 7.48 (d, J=8.61 Hz, 1H) 7.87 (dd, J=8.22, 2.35 Hz, 1H) 7.94 (d, J=4.30 Hz, 1H) 8.09 (d, J=2.35 Hz, 1H) 8.43 (s, 1H) 8.97 (d, J=5.09 Hz, 1H). LCMS (m/z) (M+H)=504.2, Rt=0.70 min.

Example 587: 2-(1,1-difluoroethyl)-N-(3-(6-(2-hydroxyethoxy)-5-morpholinopyridazin-3-yl)-4-methylphenyl)isonicotinamide

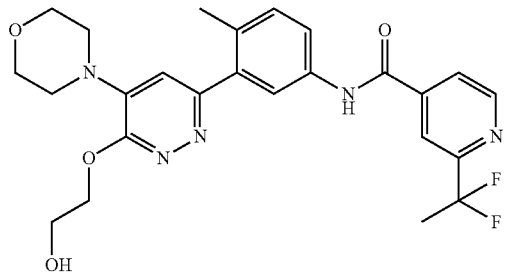 [SMILES: Cc1ccc(NC(=O)c2ccnc(C(C)(F)F)c2)cc1-c1cc(N2CCOCC2)c(OCCO)nn1]

1H NMR (400 MHz, <cd3od>) δ ppm 2.03 (t, J=18.78 Hz, 3H) 2.35 (s, 3H) 3.77-3.90 (m, 4H) 3.94-4.06 (m, 6H) 4.48-4.62 (m, 2H) 7.30 (s, 1H) 7.47 (d, J=8.61 Hz, 1H) 7.71 (dd, J=8.22, 1.96 Hz, 1H) 7.96 (d, J=4.70 Hz, 1H) 8.04 (d, J=2.35 Hz, 1H) 8.17 (s, 1H) 8.82 (d, J=5.09 Hz, 1H). LCMS (m/z) (M+H)=500.1, Rt=0.63 min.

Example 588: 2-(2-fluoropropan-2-yl)-N-(3-(6-(2-hydroxyethoxy)-5-morpholinopyridazin-3-yl)-4-methylphenyl)isonicotinamide

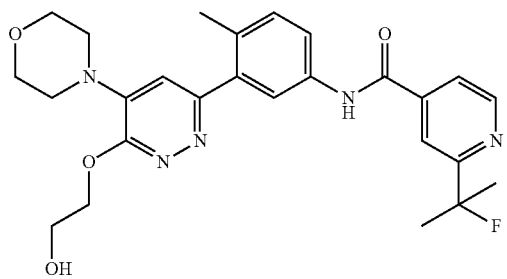 [SMILES: Cc1ccc(NC(=O)c2ccnc(C(C)(C)F)c2)cc1-c1cc(N2CCOCC2)c(OCCO)nn1]

1H NMR (400 MHz, <cd3od>) δ ppm 1.62-1.83 (m, 6H) 2.35 (s, 3H) 3.80-3.90 (m, 4H) 3.95-4.07 (m, 6H) 4.49-4.65 (m, 2H) 7.31 (s, 1H) 7.47 (d, J=8.22 Hz, 1H) 7.62-7.79 (m, 2H) 7.97-8.10 (m, 2H) 8.71 (d, J=5.09 Hz, 1H). LCMS (m/z) (M+H)=496.2, Rt=0.62 min.

Example 589: 2-(1,1-difluoropropyl)-N-(3-(6-(2-hydroxyethoxy)-5-morpholinopyridazin-3-yl)-4-methylphenyl)isonicotinamide

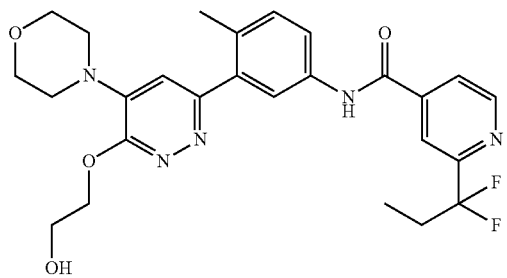 [SMILES: CCC(F)(F)c1cc(C(=O)Nc2ccc(C)c(-c3cc(N4CCOCC4)c(OCCO)nn3)c2)ccn1]

1H NMR (400 MHz, <cd3od>) δ ppm 1.00 (t, J=7.43 Hz, 3H) 2.25-2.50 (m, 5H) 3.82-3.91 (m, 4H) 3.95-4.05 (m, 5H) 4.52-4.65 (m, 2H) 7.30 (s, 1H) 7.47 (d, J=8.22 Hz, 1H) 7.72 (dd, J=8.61, 2.35 Hz, 1H) 7.96 (d, J=3.91 Hz, 1H) 8.04 (d, J=1.96 Hz, 1H) 8.15 (s, 1H) 8.83 (d, J=5.09 Hz, 1H). LCMS (m/z) (M+H)=514.2, Rt=0.67 min.

Example 590: N-(3-(6-(2-hydroxyethoxy)-5-morpholinopyridazin-3-yl)-4-methylphenyl)-3-(trifluoromethyl)benzamide

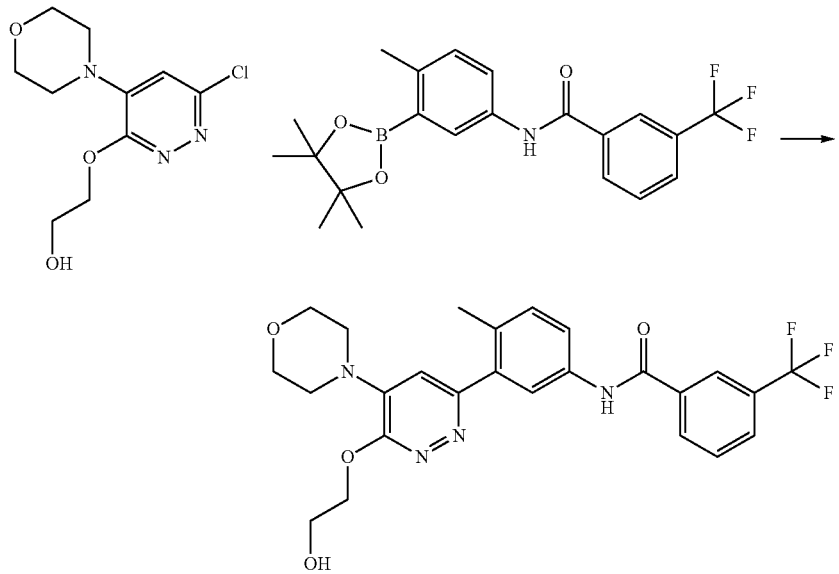

1H NMR (400 MHz, <cd3od>) δ ppm 2.25 (s, 3H) 3.71-3.82 (m, 4H) 3.84-3.96 (m, 6H) 4.42-4.53 (m, 2H) 7.22 (s, 1H) 7.37 (d, J=8.22 Hz, 1H) 7.57-7.71 (m, 2H) 7.82 (d, J=7.83 Hz, 1H) 7.93 (d, J=1.96 Hz, 1H) 8.11 (d, J=8.22 Hz, 1H) 8.16 (s, 1H). LCMS (m/z) (M+H)=503.1, Rt=0.72 min.

Example 591: 2-(2-cyanopropan-2-yl)-N-(3-(6-(2-hydroxyethoxy)-5-morpholinopyridazin-3-yl)-4-methylphenyl)isonicotinamide

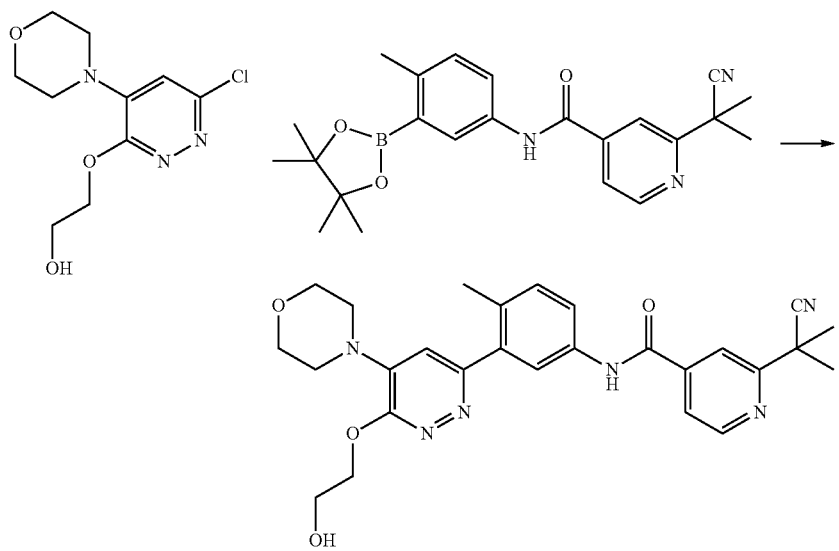

To a solution of 2-((6-chloro-4-morpholinopyridazin-3-yl)oxy)ethanol (1.0 equiv.) in DME (0.06 M) was added 2-(2-cyanopropan-2-yl)-N-(4-methyl-3-(4,4,5,5-tetramethyl-1,3,2-dioxaborolan-2-yl)phenyl)isonicotinamide (1.2 equiv.), followed by PdCl$_2$(dppf).CH$_2$Cl$_2$ adduct (0.1 equiv.) and 2M Na$_2$CO$_3$ (3.0 equiv.). The reaction was heated to 120° C. for 10 min the microwave. The layers were separated; the organic phase was concentrated to dryness and purified via reverse phase HPLC. The pure fractions were lyophilized for several days to yield 2-(2-cyanopropan-2-yl)-N-(3-(6-(2-hydroxyethoxy)-5-morpholinopyridazin-3-yl)-4-methylphenyl)isonicotinamide as the TFA salt in 29% yield. 1H NMR (400 MHz, <cd3od>) δ ppm 1.81 (s, 6H) 2.35 (s, 3H) 3.76-3.90 (m, 4H) 3.93-4.08 (m, 6H) 4.51-4.65 (m, 2H) 7.31 (s, 1H) 7.47 (d, J=8.61 Hz, 1H) 7.71 (dd, J=8.22, 2.35 Hz, 1H) 7.81 (dd, J=5.09, 1.57 Hz, 1H) 8.00-8.13 (m, 2H) 8.77 (d, J=5.09 Hz, 1H). LCMS (m/z) (M+H)=503.1, Rt=0.61 min.

Example 592: 2-(1,1-difluoroethyl)-N-(3-(6-isopropoxy-5-morpholinopyridazin-3-yl)-4-methylphenyl)isonicotinamide

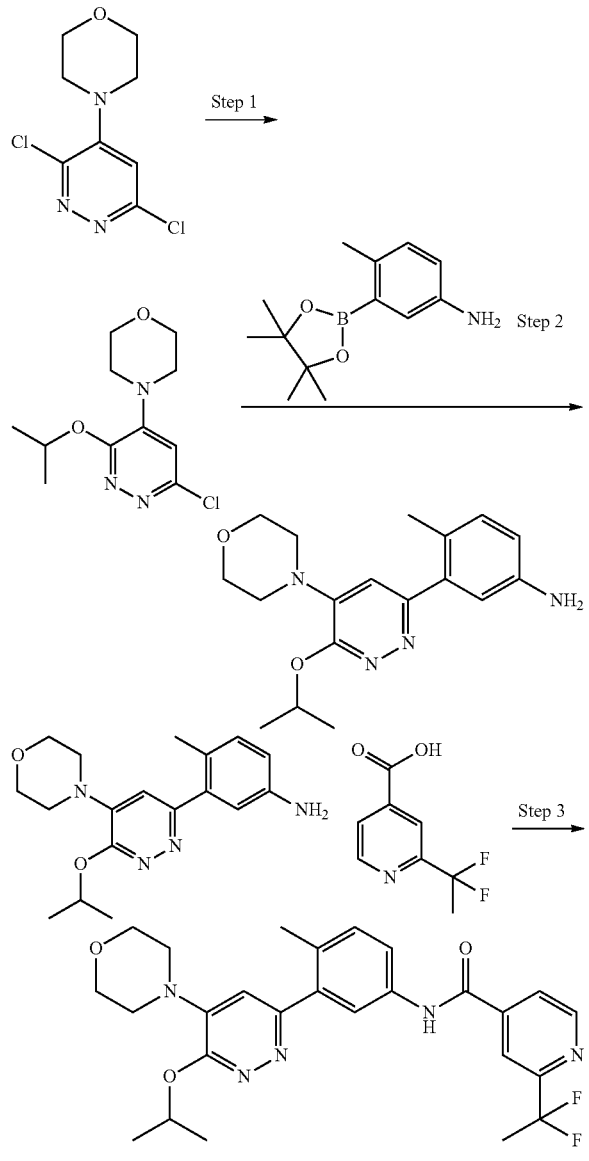

Synthetic conditions similar to Example 585.
Step 1:
4-(6-chloro-3-isopropoxypyridazin-4-yl)morpholine. LCMS (m/z) (M+H)=258.2, 259.7, Rt=0.59 min.
Step 2:
3-(6-isopropoxy-5-morpholinopyridazin-3-yl)-4-methylaniline. LCMS (m/z) (M+H)=329.3, Rt=0.50 min.
Step 3:
2-(1,1-difluoroethyl)-N-(3-(6-isopropoxy-5-morpholinopyridazin-3-yl)-4-methylphenyl)isonicotinamide. ¹H NMR (400 MHz, <dmso>) δ ppm 1.42 (d, J=6.26 Hz, 6H) 2.03 (t, J=19.17 Hz, 3H) 2.27 (s, 3H) 3.74 (br. s., 8H) 5.23-5.40 (m, 1H) 7.28 (br. s., 1H) 7.42 (d, J=8.61 Hz, 1H) 7.79 (dd, J=8.41, 2.15 Hz, 1H) 7.93 (s, 1H) 8.01 (d, J=4.70 Hz, 1H) 8.16 (s, 1H) 8.88 (d, J=5.09 Hz, 1H) 10.79 (s, 1H). LCMS (m/z) (M+H)=498.2, Rt=0.76 min.

Example 593: 2-(difluoromethyl)-N-(3-(6-isopropoxy-5-morpholinopyridazin-3-yl)-4-methylphenyl)isonicotinamide

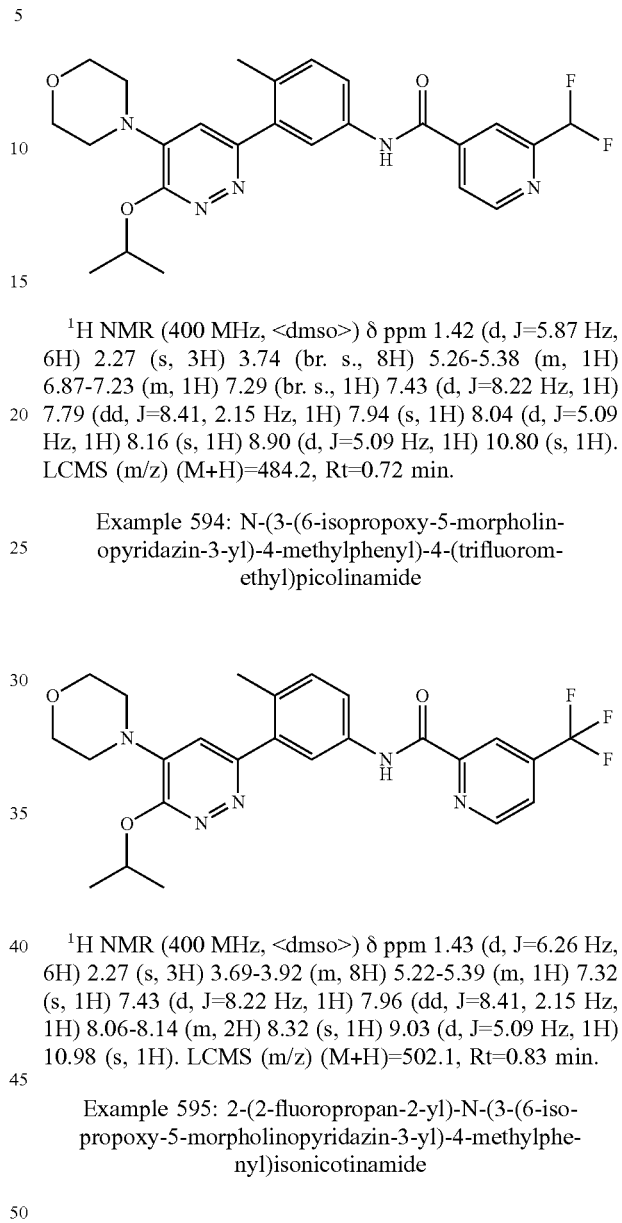

¹H NMR (400 MHz, <dmso>) δ ppm 1.42 (d, J=5.87 Hz, 6H) 2.27 (s, 3H) 3.74 (br. s., 8H) 5.26-5.38 (m, 1H) 6.87-7.23 (m, 1H) 7.29 (br. s., 1H) 7.43 (d, J=8.22 Hz, 1H) 7.79 (dd, J=8.41, 2.15 Hz, 1H) 7.94 (s, 1H) 8.04 (d, J=5.09 Hz, 1H) 8.16 (s, 1H) 8.90 (d, J=5.09 Hz, 1H) 10.80 (s, 1H). LCMS (m/z) (M+H)=484.2, Rt=0.72 min.

Example 594: N-(3-(6-isopropoxy-5-morpholinopyridazin-3-yl)-4-methylphenyl)-4-(trifluoromethyl)picolinamide

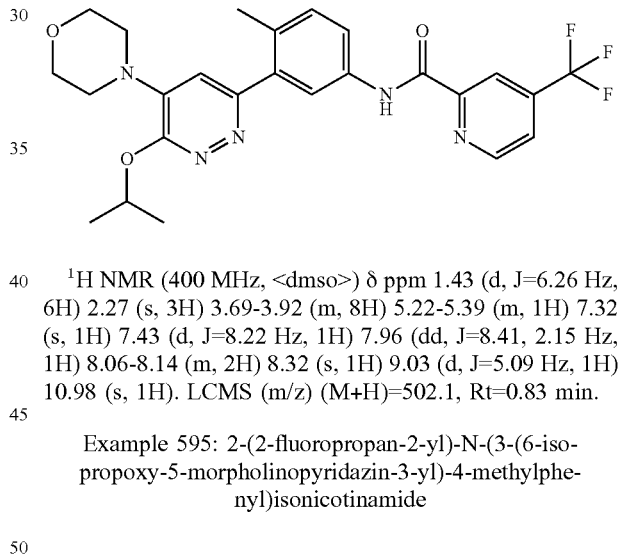

¹H NMR (400 MHz, <dmso>) δ ppm 1.43 (d, J=6.26 Hz, 6H) 2.27 (s, 3H) 3.69-3.92 (m, 8H) 5.22-5.39 (m, 1H) 7.32 (s, 1H) 7.43 (d, J=8.22 Hz, 1H) 7.96 (dd, J=8.41, 2.15 Hz, 1H) 8.06-8.14 (m, 2H) 8.32 (s, 1H) 9.03 (d, J=5.09 Hz, 1H) 10.98 (s, 1H). LCMS (m/z) (M+H)=502.1, Rt=0.83 min.

Example 595: 2-(2-fluoropropan-2-yl)-N-(3-(6-isopropoxy-5-morpholinopyridazin-3-yl)-4-methylphenyl)isonicotinamide

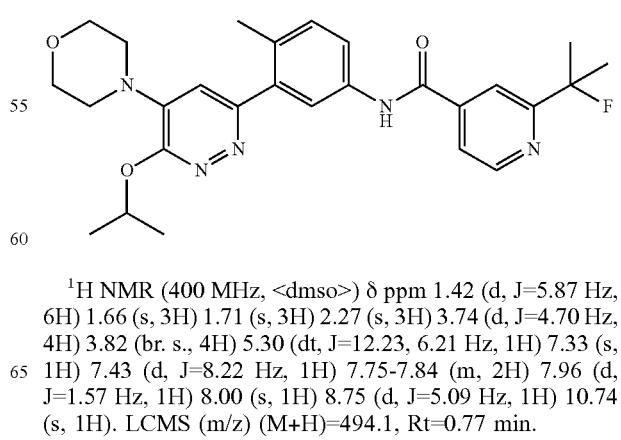

¹H NMR (400 MHz, <dmso>) δ ppm 1.42 (d, J=5.87 Hz, 6H) 1.66 (s, 3H) 1.71 (s, 3H) 2.27 (s, 3H) 3.74 (d, J=4.70 Hz, 4H) 3.82 (br. s., 4H) 5.30 (dt, J=12.23, 6.21 Hz, 1H) 7.33 (s, 1H) 7.43 (d, J=8.22 Hz, 1H) 7.75-7.84 (m, 2H) 7.96 (d, J=1.57 Hz, 1H) 8.00 (s, 1H) 8.75 (d, J=5.09 Hz, 1H) 10.74 (s, 1H). LCMS (m/z) (M+H)=494.1, Rt=0.77 min.

Example 596: 2-(2-cyanopropan-2-yl)-N-(3-(6-isopropoxy-5-morpholinopyridazin-3-yl)-4-methylphenyl)isonicotinamide

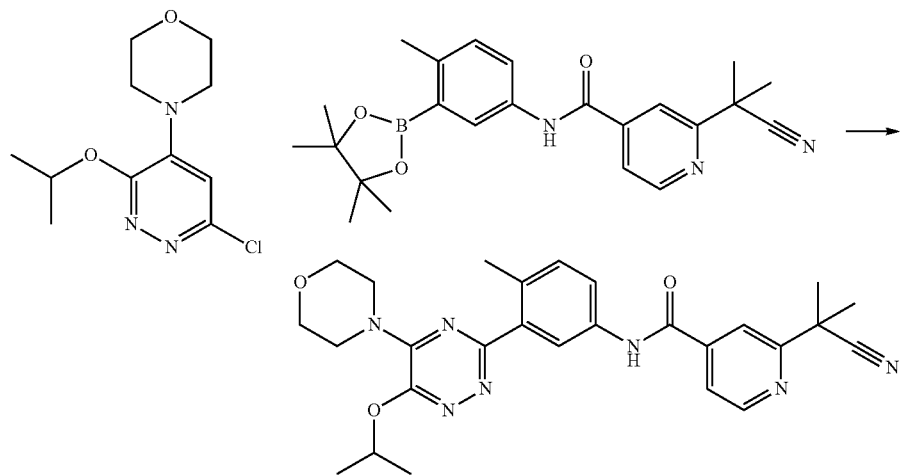

It was prepared following similar procedure as LXH202. 1H NMR (400 MHz, <dmso>) δ ppm 1.42 (d, J=6.26 Hz, 6H) 1.70-1.82 (m, 6H) 2.27 (s, 3H) 3.74 (br. s., 8H) 5.25-5.39 (m, 1H) 7.29 (br. s., 1H) 7.43 (d, J=8.22 Hz, 1H) 7.78 (dd, J=8.22, 1.96 Hz, 1H) 7.84 (dd, J=5.09, 1.17 Hz, 1H) 7.91 (s, 1H) 7.98 (s, 1H) 8.81 (d, J=5.09 Hz, 1H) 10.71 (s, 1H). LCMS (m/z) (M+H)=501.2, Rt=0.75 min.

Example 597: 2-(1,1-difluoroethyl)-N-(3-(6-(2-methoxyethoxy)-5-morpholinopyridazin-3-yl)-4-methylphenyl)isonicotinamide

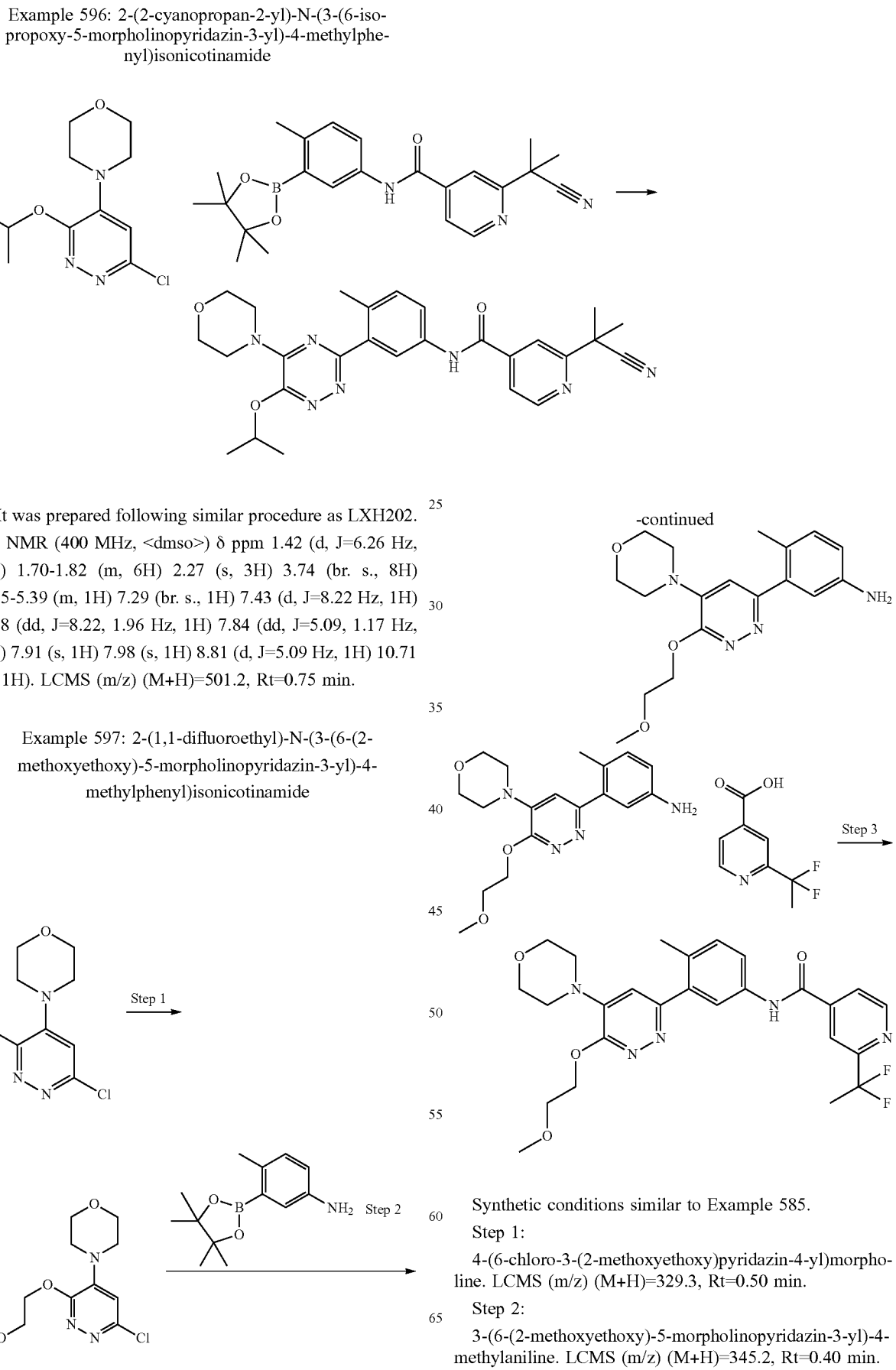

Synthetic conditions similar to Example 585.

Step 1:
4-(6-chloro-3-(2-methoxyethoxy)pyridazin-4-yl)morpholine. LCMS (m/z) (M+H)=329.3, Rt=0.50 min.

Step 2:
3-(6-(2-methoxyethoxy)-5-morpholinopyridazin-3-yl)-4-methylaniline. LCMS (m/z) (M+H)=345.2, Rt=0.40 min.

Step 3:
2-(1,1-difluoroethyl)-N-(3-(6-(2-methoxyethoxy)-5-morpholinopyridazin-3-yl)-4-methylphenyl)isonicotinamide.
¹H NMR (400 MHz, <dmso>) δ ppm 1.94-2.13 (m, 3H) 2.26 (s, 3H) 3.32 (s, 3H) 3.68-3.82 (m, 10H) 4.49-4.57 (m, 2H) 7.27 (br. s., 1H) 7.42 (d, J=8.61 Hz, 1H) 7.80 (dd, J=8.41, 2.15 Hz, 1H) 7.89-7.94 (m, 1H) 8.01 (d, J=4.70 Hz, 1H) 8.16 (s, 1H) 8.88 (d, J=4.70 Hz, 1H) 10.78 (s, 1H). LCMS (m/z) (M+H)=514.2, Rt=0.68 min.

Example 598: 2-(difluoromethyl)-N-(3-(6-(2-methoxyethoxy)-5-morpholinopyridazin-3-yl)-4-methylphenyl)isonicotinamide

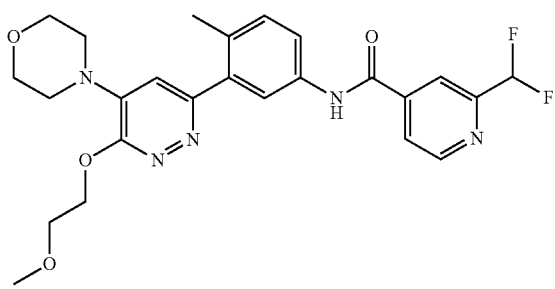 [SMILES: COCCOc1nnc(-c2cc(NC(=O)c3ccnc(C(F)F)c3)ccc2C)cc1N1CCOCC1]

¹H NMR (400 MHz, <dmso>) δ ppm 2.26 (s, 3H) 3.32 (s, 4H) 3.70-3.80 (m, 10H) 4.53 (br. s., 2H) 6.89-7.32 (m, 2H) 7.42 (d, J=8.61 Hz, 1H) 7.79 (dd, J=8.61, 1.96 Hz, 1H) 7.91 (br. s., 1H) 8.04 (d, J=5.09 Hz, 1H) 8.16 (s, 1H) 8.90 (d, J=4.70 Hz, 1H) 10.78 (br. s., 1H). LCMS (m/z) (M+H)= 500.2, Rt=0.64 min.

Example 599: N-(3-(6-(2-methoxyethoxy)-5-morpholinopyridazin-3-yl)-4-methylphenyl)-4-(trifluoromethyl)picolinamide

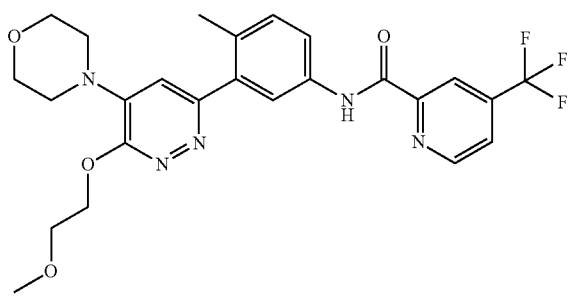 [SMILES: COCCOc1nnc(-c2cc(NC(=O)c3cc(C(F)(F)F)ccn3)ccc2C)cc1N1CCOCC1]

¹H NMR (400 MHz, <dmso>) δ ppm 2.27 (s, 3H) 3.33 (s, 3H) 3.67-3.82 (m, 10H) 4.49-4.58 (m, 2H) 7.28 (br. s., 1H) 7.41 (d, J=8.22 Hz, 1H) 7.96 (dd, J=8.22, 1.96 Hz, 1H) 8.03-8.14 (m, 2H) 8.32 (s, 1H) 9.03 (d, J=4.70 Hz, 1H) 10.95 (s, 1H). LCMS (m/z) (M+H)=518.1, Rt=0.76 min.

Example 600: 2-(2-fluoropropan-2-yl)-N-(3-(6-(2-methoxyethoxy)-5-morpholinopyridazin-3-yl)-4-methylphenyl)isonicotinamide

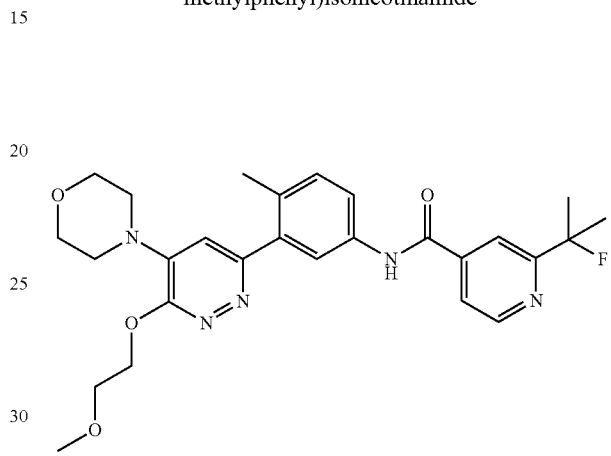

¹H NMR (400 MHz, <dmso>) δ ppm 1.66 (s, 3H) 1.71 (s, 3H) 2.26 (s, 3H) 3.32 (s, 3H) 3.70-3.82 (m, 10H) 4.52 (dd, J=5.09, 3.52 Hz, 2H) 7.31 (br. s., 1H) 7.42 (d, J=8.22 Hz, 1H) 7.75-7.84 (m, 2H) 7.93 (d, J=1.57 Hz, 1H) 8.00 (s, 1H) 8.75 (d, J=5.09 Hz, 1H) 10.72 (s, 1H). LCMS (m/z) (M+H)= 510.1, Rt=0.68 min.

Example 601: 2-(2-cyanopropan-2-yl)-N-(3-(6-(2-methoxyethoxy)-5-morpholinopyridazin-3-yl)-4-methylphenyl)isonicotinamide

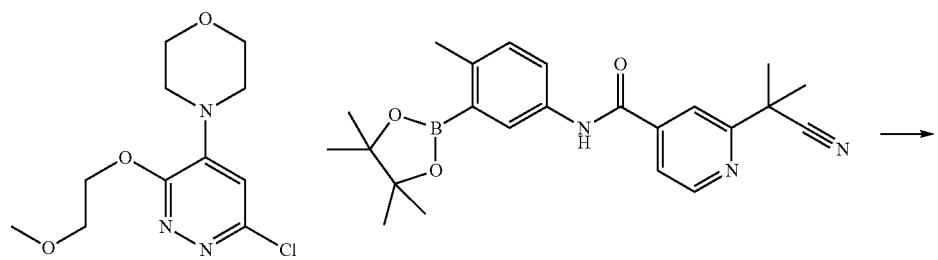

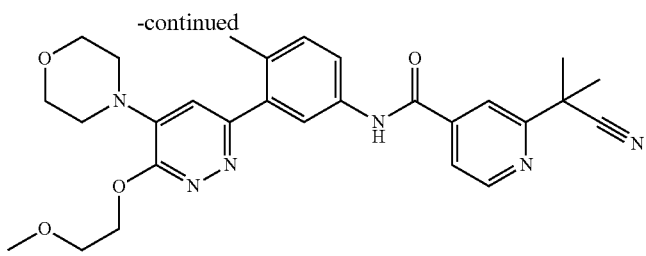

It was prepared following similar procedure as LXH202. 1H NMR (400 MHz, <dmso>) δ ppm 1.75 (s, 6H) 2.26 (s, 3H) 3.32 (s, 3H) 3.68-3.84 (m, 10H) 4.53 (dd, J=5.28, 3.33 Hz, 2H) 7.29 (br. s., 1H) 7.43 (d, J=8.22 Hz, 1H) 7.79 (dd, J=8.22, 1.96 Hz, 1H) 7.84 (dd, J=5.09, 1.17 Hz, 1H) 7.89 (s, 1H) 7.98 (s, 1H) 8.81 (d, J=5.09 Hz, 1H) 10.71 (s, 1H). LCMS (m/z) (M+H)=517.3, Rt=0.67 min.

Example 602: N-(4-methyl-3-(6-(methylsulfonyl)-5-morpholinopyridazin-3-yl)phenyl)-3-(trifluoromethyl)benzamide minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:

To a flask containing 4-(3,6-dichloropyridazin-4-yl)morpholine (1.0 equiv.) in DMF (0.14 M) was added sodium thiomethoxide (1.5 equiv.) and the reaction mix was stirred at RT overnight. The solvent was removed under vacuum and the crude was suspended in large volume of water. The

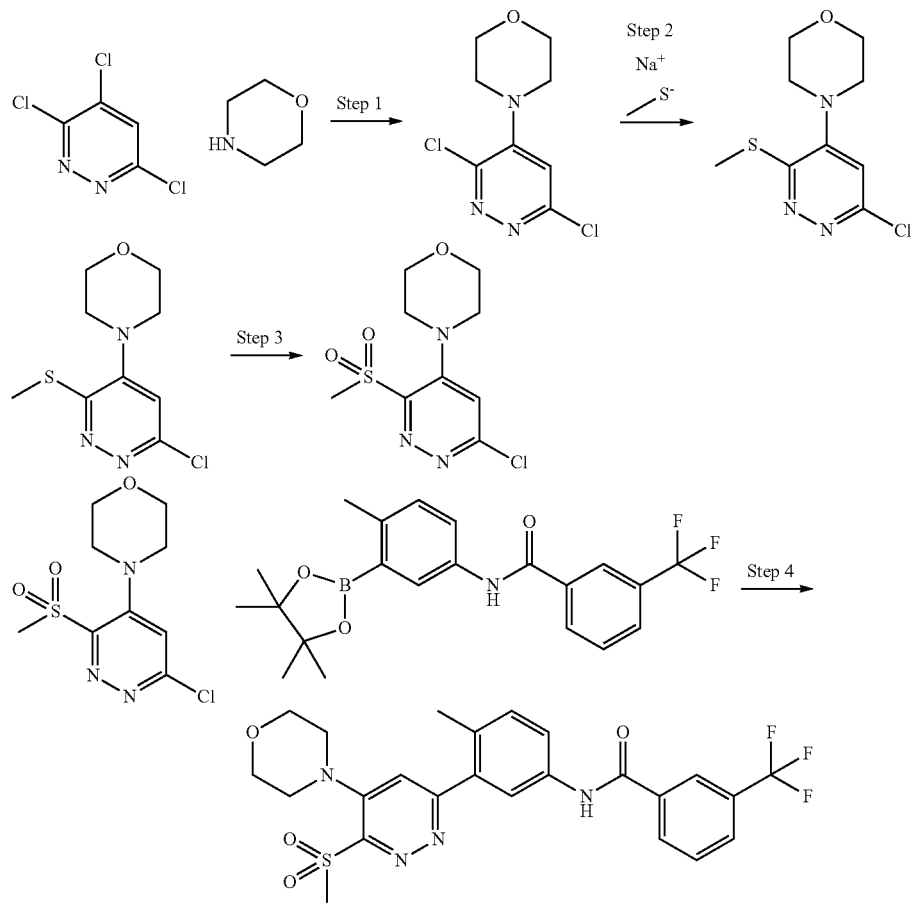

Step 1:

To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few solids that were removed by filtration were dissolved in DCM. The small aqueous layer was removed and the organic layer was dried over MgSO₄, filtered and concentrated. The crude 4-(6-chloro-3-(methylthio)pyridazin-4-yl)morpholine was used as is in the next step. Yield was assumed to be quantitative.

Step 3:

A solution of Oxone (2.2 equiv.) in water (0.043M) was added to a solution of 4-(6-chloro-3-(methylthio)pyridazin-4-yl)morpholine (1.0 equiv.) in THF (0.043 M) at 0° C. and the reaction mix was left to reach RT overnight. The reaction mix was poured into water and extracted three times with EtOAc. The combined organics were dried over Na₂SO₄, filtered and concentrated. The residue was dissolved in DCM, and adsorbed in silica gel. The solid was loaded into a cartridge and purified on a silica gel column using 0 to 60% EtOAc in heptane. The desired 4-(6-chloro-3-(methylsulfonyl)pyridazin-4-yl)morpholine was obtained in 63% yield. LCMS (m/z) (M+H)=278, Rt=0.48 min.

Step 4:

To a solution of 4-(6-chloro-3-(methylsulfonyl)pyridazin-4-yl)morpholine (1.0 equiv.) and 4-methyl-3-(4,4,5,5-tetramethyl-1,3,2-dioxaborolan-2-yl)aniline (1.0 equiv.) in DME (0.11 M) was added Na₂CO₃ (2M, 3.0 equiv.) and the system was flushed with nitrogen. PdCl₂(dppf).CH₂Cl₂ adduct (0.1 equiv.) was added to the reaction mix and the system was flushed once again with nitrogen. The reaction vial was heated in a microwave reactor at 120° C. for 20 minutes. The reaction mix was partitioned in H₂O/EtOAc. The organic layer was isolated, dried over Na2SO4, filtered and concentrated. Crude was purified by HPLC to give N-(4-methyl-3-(6-(methylsulfonyl)-5-morpholinopyridazin-3-yl)phenyl)-3-(trifluoromethyl)benzamide in 24% yield. 1H NMR (400 MHz, <dmso>) δ ppm 2.22-2.37 (m, 3H) 3.68-3.79 (m, 7H) 7.34-7.40 (m, 1H) 7.41 (s, 1H) 7.73-7.83 (m, 2H) 7.90 (d, J=2.35 Hz, 1H) 7.96 (d, J=7.83 Hz, 1H) 8.25 (d, J=7.83 Hz, 1H) 8.29 (s, 1H) 10.43-10.66 (m, 1H). LCMS (m/z) (M+H)=521, Rt=0.89 min.

Example 603: 2-(1,1-difluoroethyl)-N-(5-(6-methoxy-5-morpholinopyridazin-3-yl)-6-methylpyridin-3-yl)isonicotinamide

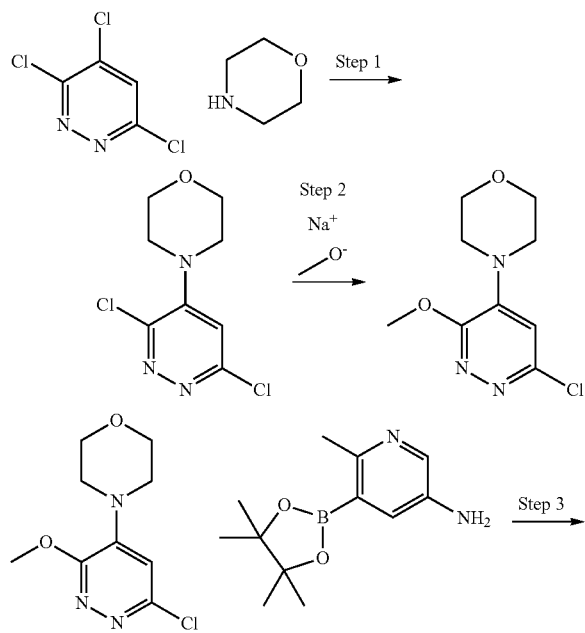

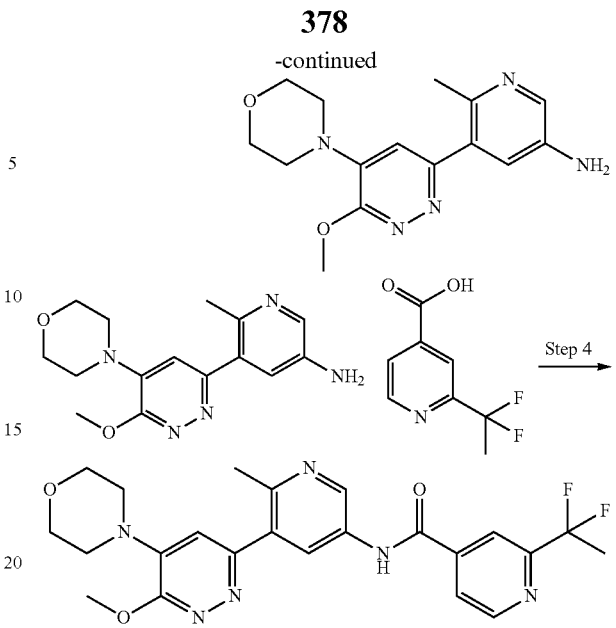

Step 1:

To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:

Sodium methoxide (2.0 equiv.) was added portion wise to a flask containing 4-(3,6-dichloropyridazin-4-yl)morpholine (1.0 equiv.) in MeOH (0.43 M) and the reaction mix was stirred overnight at RT. The solvent was removed under vacuum and the crude was partitioned in brine/EtOAc. The organic phase was isolated and the aqueous layer was extracted once more with EtOAc. The combined organics were concentrated to dryness and the residue was dissolved in DCM, and adsorbed in silica gel. The solid was loaded into a cartridge and purified on a silica gel column. using 0 to 60% EtOAc in heptane. The desired 4-(6-chloro-3-methoxypyridazin-4-yl)morpholine was obtained in 71% yield. LCMS (m/z) (M+H)=230, Rt=0.44 min.

Step 3:

To a solution of 4-(6-chloro-3-methoxypyridazin-4-yl)morpholine (1.0 equiv.) and 6-methyl-5-(4,4,5,5-tetramethyl-1,3,2-dioxaborolan-2-yl)pyridin-3-amine (1.0 equiv.) in DME (0.08 M) was added Na₂CO₃ (2M, 3.0 equiv.) and the system was flushed with nitrogen. PdCl₂(dppf).CH₂Cl₂ adduct (0.1 equiv.) was added to the reaction mix and the system was flushed once again with nitrogen. The reaction vial was capped and heated in a bath for 4 hr at 120° C. The crude was partitioned in H₂O/EtOAc. The organic layer was isolated, dried over Na2SO4, filtered and concentrated. Crude was purified silica gel column using DCM to 5% MeOH in DCM to give 5-(6-methoxy-5-morpholinopyridazin-3-yl)-6-methylpyridin-3-amine in 54% yield. LCMS (m/z) (M+H)=317, Rt=0.38 min.

Step 4:

DIEA (3.0 equiv.) was added to a solution of 5-(6-methoxy-5-morpholinopyridazin-3-yl)-6-methylpyridin-3-amine (1.0 equiv.), 2-(1,1-difluoroethyl)isonicotinic acid (1.0 equiv.) and HATU (1.0 equiv.) in DMF (0.07 M), and the mixture was left stirring at RT overnight. The reaction mix was treated with water and the precipitate was filtered. The solid was purified by HPLC giving 2-(1,1-difluoroethyl)-N-(5-(6-methoxy-5-morpholinopyridazin-3-yl)-6-methylpyridin-3-yl)isonicotinamide as the TFA salt in 30% yield. 1H NMR (400 MHz, <dmso>) δ ppm 2.04 (t, J=19.17 Hz, 3H) 3.74 (s, 8H) 4.08 (s, 3H) 7.38 (s, 1H) 8.04 (d, J=4.70 Hz, 1H) 8.20 (s, 1H) 8.35 (d, J=1.96 Hz, 1H) 8.83-9.01 (m, 2H) 10.91-11.13 (m, 1H). LCMS (m/z) (M+H)=471, Rt=0.59 min.

Example 604: 3-(difluoromethyl)-N-(5-(6-methoxy-5-morpholinopyridazin-3-yl)-6-methylpyridin-3-yl)benzamide

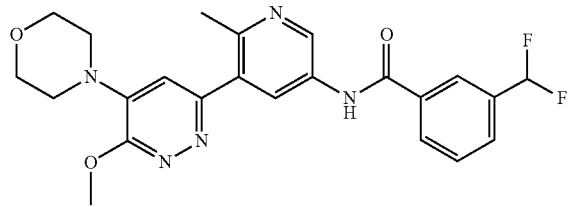 [SMILES: COc1nnc(-c2cc(NC(=O)c3cccc(C(F)F)c3)cnc2C)cc1N1CCOCC1]

1H NMR (400 MHz, <dmso>) δ ppm 4.07 (s, 12H) 6.97-7.31 (m, 1H) 7.01 (s, 1H) 7.15 (s, 2H) 7.29 (s, 1H) 7.35 (s, 1H) 7.67-7.75 (m, 1H) 7.82 (d, J=7.83 Hz, 1H) 8.09-8.21 (m, 2H) 8.37 (d, J=2.35 Hz, 1H) 8.95 (d, J=2.35 Hz, 1H) 10.80 (s, 1H). LCMS (m/z) (M+H)=456, Rt=0.61 min.

Example 605: N-(5-(6-methoxy-5-morpholinopyridazin-3-yl)-6-methylpyridin-3-yl)-2-(trifluoromethyl)isonicotinamide

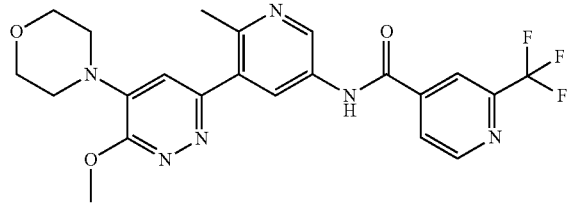 [SMILES: COc1nnc(-c2cc(NC(=O)c3ccnc(C(F)(F)F)c3)cnc2C)cc1N1CCOCC1]

1H NMR (400 MHz, <dmso>) δ ppm 3.69 (br. s., 7H) 4.03 (s, 3H) 7.31 (br. s., 1H) 8.16 (d, J=4.70 Hz, 1H) 8.29 (d, J=1.96 Hz, 1H) 8.33 (s, 1H) 8.89 (d, J=2.35 Hz, 1H) 8.97 (d, J=4.70 Hz, 1H) 11.01 (s, 1H). LCMS (m/z) (M+H)=475, Rt=0.61 min.

Example 606: 2-cyclopropyl-N-(5-(6-methoxy-5-morpholinopyridazin-3-yl)-6-methylpyridin-3-yl)isonicotinamide

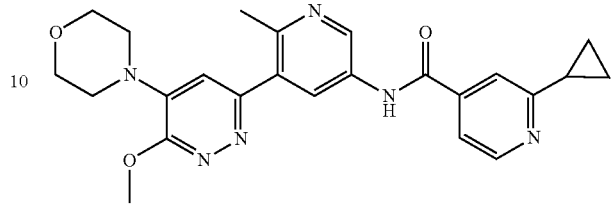

1H NMR (400 MHz, <dmso>) δ ppm 0.87-1.05 (m, 5H) 2.11-2.27 (m, 1H) 3.66-3.86 (m, 8H) 3.98-4.14 (m, 3H) 7.39 (s, 1H) 7.58 (dd, J=5.09, 1.17 Hz, 1H) 7.75 (s, 1H) 8.36 (d, J=2.35 Hz, 1H) 8.59 (d, J=5.09 Hz, 1H) 8.93 (d, J=2.35 Hz, 1H) 10.88 (s, 1H). LCMS (m/z) (M+H)=447, Rt=0.45 min.

Example 607: 2-(1,1-difluoropropyl)-N-(5-(6-methoxy-5-morpholinopyridazin-3-yl)-6-methylpyridin-3-yl)isonicotinamide

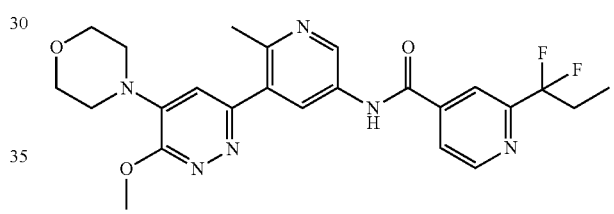

1H NMR (400 MHz, <dmso>) δ ppm 0.93 (t, J=7.43 Hz, 2H) 2.26-2.43 (m, 2H) 3.74 (s, 7H) 3.65-3.82 (m, 1H) 3.87-4.36 (m, 8H) 7.38 (s, 1H) 8.03 (d, J=4.30 Hz, 1H) 8.18 (s, 1H) 8.35 (d, J=2.35 Hz, 1H) 8.83-9.02 (m, 1H) 11.03 (s, 1H). LCMS (m/z) (M+H)=485, Rt=0.65 min.

Example 608: 2-(2-fluoropropan-2-yl)-N-(5-(6-methoxy-5-morpholinopyridazin-3-yl)-6-methylpyridin-3-yl)isonicotinamide

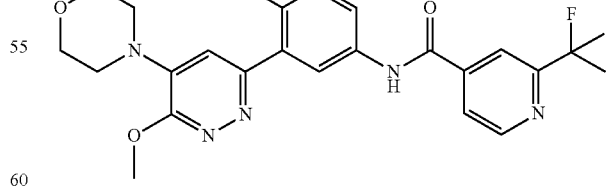

1H NMR (400 MHz, <dmso>) δ ppm 1.56-1.83 (m, 6H) 3.62-3.78 (m, 4H) 3.99-4.15 (m, 3H) 6.97-7.11 (m, 1H) 7.83 (dd, J=5.09, 1.57 Hz, 1H) 8.05 (s, 1H) 8.19 (d, J=2.35 Hz, 1H) 8.76 (d, J=5.09 Hz, 1H) 8.88 (d, J=2.35 Hz, 1H) 10.78 (s, 1H). LCMS (m/z) (M+H)=543, Rt=0.71 min.

Example 609: N-(5-(6-ethoxy-5-morpholinopyridazin-3-yl)-6-methylpyridin-3-yl)-3-(trifluoromethyl)benzamide

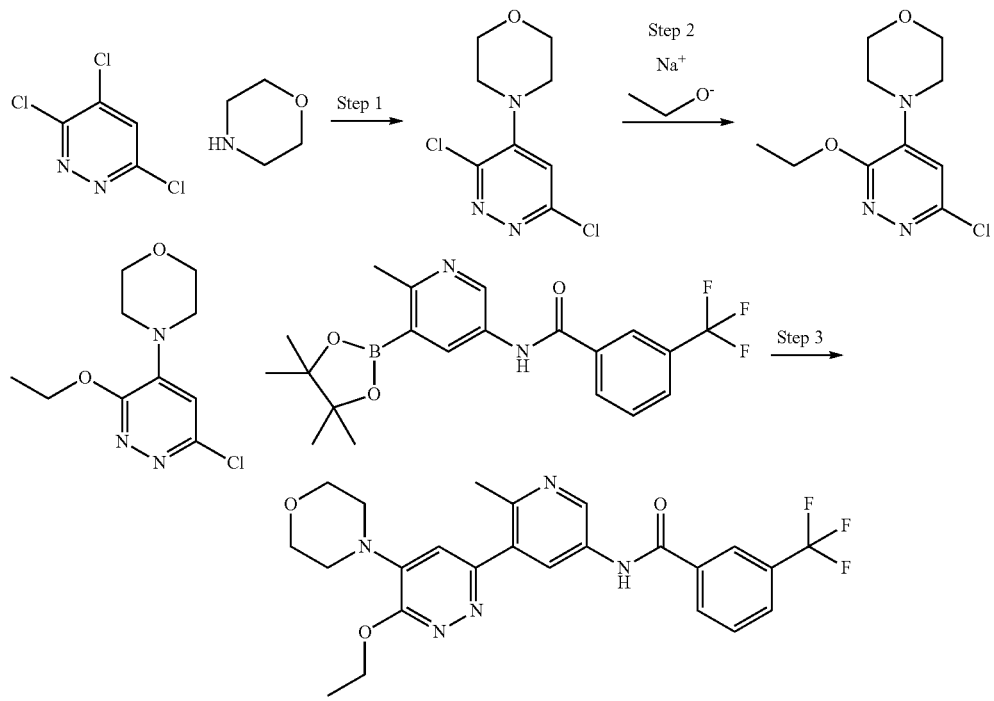

Step 1:

To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:

To a flask containing 4-(3,6-dichloropyridazin-4-yl)morpholine (1.0 equiv.) in EtOH (0.23 M) was added sodium ethoxide 21% in ethanol (1.4 equiv.) and the reaction mix was stirred overnight at RT. The solvent was removed under vacuum and the crude was partitioned in brine/EtOAc. The organic phase was concentrated to dryness and the residue was dissolved in DCM, and adsorbed in silica gel. The solid was loaded into a cartridge and purified on a silica gel column using 0 to 40% EtOAc in heptane. The desired 4-(6-chloro-3-ethoxypyridazin-4-yl)morpholine was obtained in 48% yield. LCMS (m/z) (M+H)=246, Rt=0.36 min.

Step 3:

PdCl$_2$(dppf).CH$_2$Cl$_2$ adduct (0.1) was added to a solution of 4-(6-chloro-3-ethoxypyridazin-4-yl)morpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.) and Na$_2$CO$_3$ 2 M solution (3.0 equiv.) in DME (0.07 M) and the system was flushed with nitrogen. The vial was sealed and placed in the microwave reactor for 20 minutes at 120° C. The solvent was removed under vacuum and the residue was partitioned in EtOAC/H$_2$O. The organic layer was isolated and the aqueous layer was back extracted twice with EtOAc. The combined organics were dried over Na$_2$SO$_4$, filtered and concentrated. The crude was purified by HPLC giving N-(5-(6-ethoxy-5-morpholinopyridazin-3-yl)-6-methylpyridin-3-yl)-3-(trifluoromethyl)benzamide as the TFA salt in 33% yield. 1H NMR (400 MHz, <dmso>) δ ppm 1.43 (t, J=7.04 Hz, 3H) 3.74 (br. s., 8H) 4.50 (q, J=7.04 Hz, 2H) 7.36 (s, 1H) 7.81 (t, J=7.83 Hz, 1H) 8.01 (d, J=7.83 Hz, 1H) 8.28 (d, J=7.83 Hz, 1H) 8.32 (s, 1H) 8.36 (d, J=2.35 Hz, 1H) 8.80-9.07 (m, 1H) 10.71-10.95 (m, 1H). LCMS (m/z) (M+H)=488, Rt=0.75 min.

Example 610: N-(5-(6-ethoxy-5-morpholinopyridazin-3-yl)-6-methylpyridin-3-yl)-2-(2-fluoropropan-2-yl)isonicotinamide

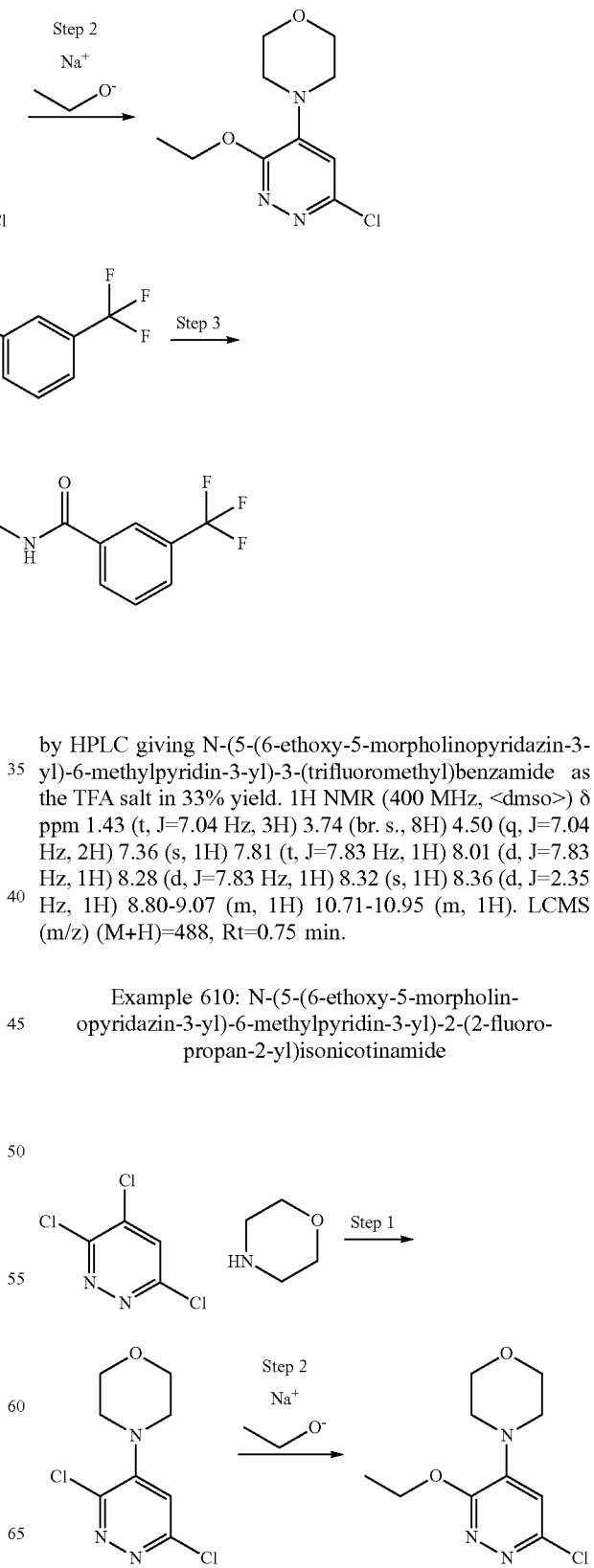

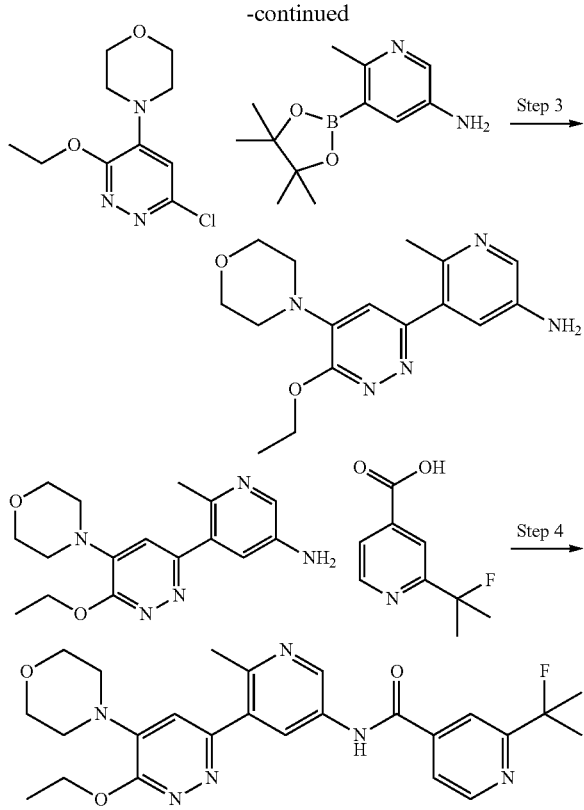

Step 1:

To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:

To a flask containing 4-(3,6-dichloropyridazin-4-yl)morpholine (1.0 equiv.) in EtOH (0.23 M) was added sodium ethoxide 21% in ethanol (1.4 equiv.) and the reaction mix was stirred overnight at RT. The solvent was removed under vacuum and the crude was partitioned in brine/EtOAc. The organic phase was concentrated to dryness and the residue was dissolved in DCM, and adsorbed in silica gel. The solid was loaded into a cartridge and purified on a silica gel column using 0 to 40% EtOAc in heptane. The desired 4-(6-chloro-3-ethoxypyridazin-4-yl)morpholine was obtained in 48% yield. LCMS (m/z) (M+H)=246, Rt=0.36 min.

Step 3:

To a solution of 4-(6-chloro-3-ethoxypyridazin-4-yl)morpholine (1.0 equiv.) and 6-methyl-5-(4,4,5,5-tetramethyl-1,3,2-dioxaborolan-2-yl)pyridin-3-amine (1.0 equiv.) in DME (0.08 M) was added $Na_2CO_3$ (2M, 3.0 equiv.) and the system was flushed with nitrogen. $PdCl_2(dppf) \cdot CH_2Cl_2$ adduct (0.1 equiv.) was added to the reaction mix and the system was flushed once again with nitrogen. The reaction vial was capped and heated in a bath for 4 hr at 120° C. The crude was partitioned in $H_2O$/EtOAc. The organic layer was isolated, dried over $Na_2SO_4$, filtered and concentrated. Crude was purified silica gel column using DCM to 5% MeOH in DCM to give 5-(6-ethoxy-5-morpholino-1,6-dihydropyridazin-3-yl)-6-methylpyridin-3-amine in 54% yield. LCMS (m/z) (M+H)=317, Rt=0.38 min.

Step 4:

DIEA (3.0 equiv.) was added to a solution of 5-(6-ethoxy-5-morpholinopyridazin-3-yl)-6-methylpyridin-3-amine (1.0 equiv.), 2-(2-fluoropropan-2-yl)isonicotinic acid (1.0 equiv.) and HATU (1.0 equiv.) in DMF (0.07 M), and the mixture was left stirring at RT overnight. The reaction mix was treated with water and the precipitate was filtered. The solid was purified by HPLC giving N-(5-(6-ethoxy-5-morpholinopyridazin-3-yl)-6-methylpyridin-3-yl)-2-(2-fluoropropan-2-yl)isonicotinamide as the TFA salt in 50% yield. 1H NMR (400 MHz, <dmso>) δ ppm 1.36-1.52 (m, 3H) 1.60-1.82 (m, 7H) 4.50 (q, J=6.91 Hz, 2H) 7.39 (s, 1H) 7.83 (dd, J=5.09, 1.57 Hz, 1H) 8.04 (s, 1H) 8.36 (d, J=2.35 Hz, 1H) 8.78 (d, J=5.09 Hz, 1H) 8.96 (d, J=2.35 Hz, 1H) 10.97 (s, 1H). LCMS (m/z) (M+H)=481, Rt=0.65 min.

Example 611: N-(5-(6-ethoxy-5-morpholinopyridazin-3-yl)-6-methylpyridin-3-yl)-4-(trifluoromethyl)picolinamide

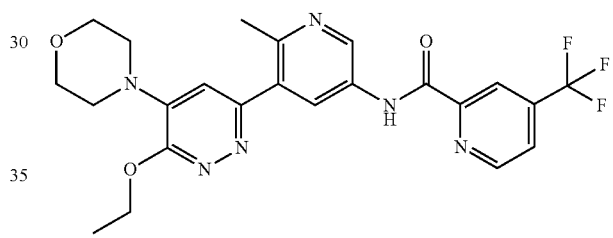

1H NMR (400 MHz, <dmso>) δ ppm 1.28-1.54 (m, 3H) 3.76 (br. s., 9H) 4.50 (q, J=7.04 Hz, 2H) 7.27-7.49 (m, 1H) 8.13 (d, J=4.30 Hz, 1H) 8.34 (s, 1H) 8.50 (d, J=1.96 Hz, 1H) 8.95-9.20 (m, 2H) 11.29 (s, 1H). LCMS (m/z) (M+H)=489, Rt=0.75 min.

Example 612: 2-cyclopropyl-N-(5-(6-ethoxy-5-morpholinopyridazin-3-yl)-6-methylpyridin-3-yl)isonicotinamide

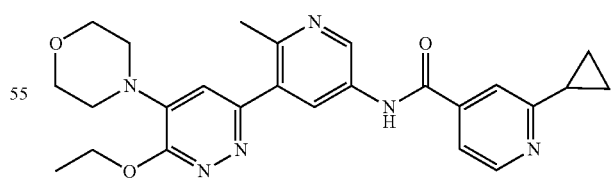

1H NMR (400 MHz, <dmso>) δ ppm 0.88-1.11 (m, 5H) 1.29-1.53 (m, 4H) 2.05-2.08 (m, 1H) 2.15-2.28 (m, 1H) 2.71 (s, 1H) 2.87 (s, 1H) 3.64-3.81 (m, 9H) 4.37-4.63 (m, 2H) 7.33 (br. s., 1H) 7.58 (dd, J=5.09, 1.57 Hz, 1H) 7.75 (s, 1H) 7.93 (s, 1H) 8.34 (d, J=1.96 Hz, 1H) 8.60 (d, J=5.09 Hz, 1H) 8.82-9.03 (m, 1H) 10.73-10.91 (m, 1H). LCMS (m/z) (M+H)=461, Rt=0.57 min.

Example 613: 2-(2-cyanopropan-2-yl)-N-(5-(6-ethoxy-5-morpholinopyridazin-3-yl)-6-methylpyridin-3-yl)isonicotinamide

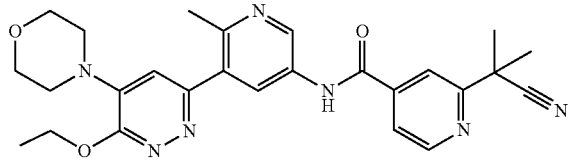 [SMILES: CCOc1nnc(-c2cc(NC(=O)c3ccnc(C(C)(C)C#N)c3)cnc2C)cc1N1CCOCC1]

1H NMR (400 MHz, <dmso>) δ ppm 1.43 (t, J=6.85 Hz, 3H) 1.71-1.84 (m, 7H) 4.50 (q, J=6.91 Hz, 2H) 7.35 (s, 1H) 7.88 (dd, J=5.09, 1.17 Hz, 1H) 8.02 (s, 1H) 8.32 (d, J=1.96 Hz, 1H) 8.77-8.88 (m, 1H) 8.93 (d, J=2.35 Hz, 1H) 10.95 (s, 1H). LCMS (m/z) (M+H)=488, Rt=0.68 min.

Example 614: N-(5-(6-ethoxy-5-morpholinopyridazin-3-yl)-6-methylpyridin-3-yl)-6-(trifluoromethyl)pyridazine-4-carboxamide

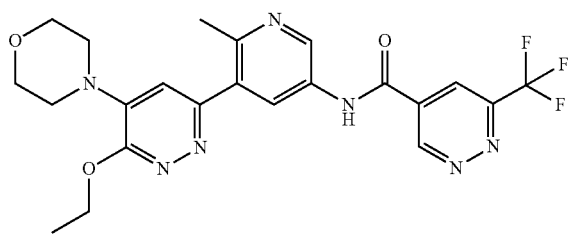 [SMILES: CCOc1nnc(-c2cc(NC(=O)c3cnnc(C(F)(F)F)c3)cnc2C)cc1N1CCOCC1]

1H NMR (400 MHz, <dmso>) δ ppm 1.43 (t, J=6.85 Hz, 3H) 4.50 (q, J=7.04 Hz, 2H) 7.36 (s, 1H) 8.32 (d, J=2.35 Hz, 1H) 8.69 (d, J=1.96 Hz, 1H) 8.92 (d, J=2.35 Hz, 1H) 9.93 (d, J=1.96 Hz, 1H) 11.24 (s, 1H). LCMS (m/z) (M+H)=490, Rt=0.61 min.

Example 615: N-(5-(6-ethoxy-5-morpholinopyridazin-3-yl)-6-methylpyridin-3-yl)-2-(methylsulfonyl)isonicotinamide

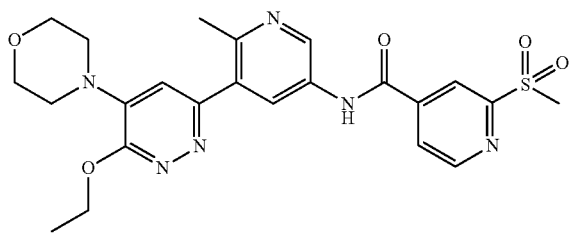 [SMILES: CCOc1nnc(-c2cc(NC(=O)c3ccnc(S(C)(=O)=O)c3)cnc2C)cc1N1CCOCC1]

1H NMR (400 MHz, <dmso>) δ ppm 1.38 (t, J=6.85 Hz, 3H) 2.01 (s, 2H) 3.30 (s, 3H) 4.45 (q, J=7.04 Hz, 2H) 7.30 (br. s., 1H) 8.18 (dd, J=4.70, 1.56 Hz, 1H) 8.29 (d, J=2.35 Hz, 1H) 8.50 (s, 1H) 8.90 (d, J=2.35 Hz, 1H) 8.98 (d, J=4.70 Hz, 1H) 10.96-11.22 (m, 1H). LCMS (m/z) (M+H)=499, Rt=0.53 min.

Example 616: N-(5-(6-ethoxy-5-morpholinopyridazin-3-yl)-6-methylpyridin-3-yl)-2-(trifluoromethyl)isonicotinamide

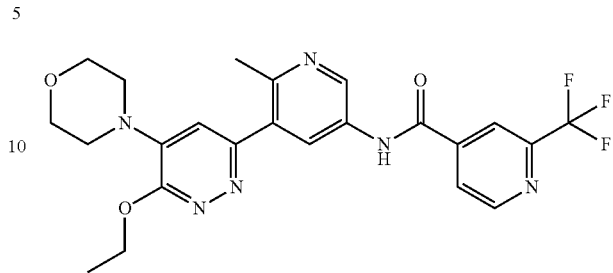

1H NMR (400 MHz, <dmso>) δ ppm 1.43 (t, J=7.04 Hz, 4H) 3.43-3.83 (m, 16H) 4.51 (q, J=7.04 Hz, 3H) 7.28 (br. s., 1H) 8.20 (d, J=5.09 Hz, 1H) 8.30 (s, 1H) 8.38 (s, 1H) 8.92 (d, J=2.35 Hz, 1H) 9.01 (d, J=5.09 Hz, 1H) 11.02 (s, 1H). LCMS (m/z) (M+H)=489, Rt=0.66 min.

Example 617: 2-(1,1-difluoropropyl)-N-(5-(6-ethoxy-5-morpholinopyridazin-3-yl)-6-methylpyridin-3-yl)isonicotinamide

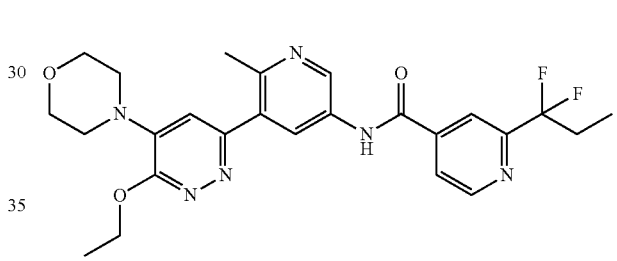

1H NMR (400 MHz, <dmso>) δ ppm 0.85-0.98 (m, 3H) 1.43 (t, J=7.04 Hz, 3H) 2.25-2.41 (m, 2H) 3.75 (s, 7H) 4.50 (q, J=7.04 Hz, 2H) 7.37 (s, 1H) 8.03 (d, J=4.70 Hz, 1H) 8.18 (s, 1H) 8.34 (d, J=2.35 Hz, 1H) 8.87-9.00 (m, 2H) 11.02 (s, 1H). LCMS (m/z) (M+H)=499, Rt=0.69 min.

Example 618: N-(5-(6-ethoxy-5-morpholinopyridazin-3-yl)-6-methylpyridin-3-yl)-3-(methylsulfonyl)benzamide

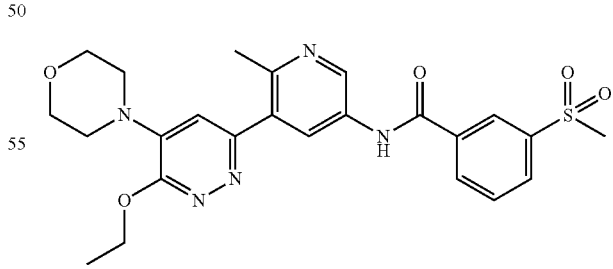

1H NMR (400 MHz, <dmso>) δ ppm 1.36-1.50 (m, 3H) 2.52 (s, 1H) 3.19-3.34 (m, 4H) 4.37-4.59 (m, 2H) 7.39 (s, 1H) 7.85 (t, J=7.83 Hz, 1H) 8.18 (d, J=7.83 Hz, 1H) 8.30 (d, J=7.83 Hz, 1H) 8.37 (d, J=2.35 Hz, 1H) 8.50 (s, 1H) 8.96 (d, J=2.35 Hz, 1H) 10.93 (s, 1H). LCMS (m/z) (M+H)=498, Rt=0.56 min.

Example 619: 3-(difluoromethyl)-N-(5-(6-ethoxy-5-morpholinopyridazin-3-yl)-6-methylpyridin-3-yl)benzamide

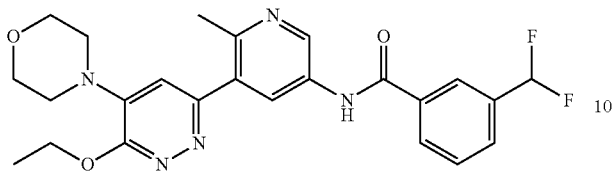

1H NMR (400 MHz, <dmso>) δ ppm 1.36 (t, J=7.04 Hz, 3H) 2.01 (s, 1H) 3.68 (br. s., 4H) 4.49 (q, J=6.91 Hz, 2H) 6.92-7.26 (m, 2H) 7.54-7.83 (m, 2H) 8.01-8.21 (m, 3H) 8.83 (d, J=1.96 Hz, 1H) 10.43-10.68 (m, 1H). LCMS (m/z) (M+H)=460, Rt=0.68 min.

Example 620: 2-(1,1-difluoroethyl)-N-(5-(6-ethoxy-5-morpholinopyridazin-3-yl)-6-methylpyridin-3-yl)isonicotinamide

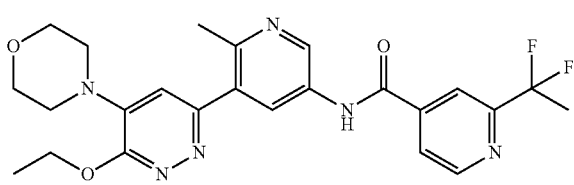 [SMILES: CCOc1nnc(-c2cc(NC(=O)c3ccnc(C(C)(F)F)c3)cnc2C)cc1N1CCOCC1]

1H NMR (400 MHz, <dmso>) δ ppm 1.41 (t, J=7.04 Hz, 3H) 1.96-2.12 (m, 4H) 3.65-3.79 (m, 4H) 4.54 (q, J=7.04 Hz, 2H) 6.89-7.17 (m, 1H) 8.04 (d, J=4.30 Hz, 1H) 8.15-8.25 (m, 2H) 8.75-8.99 (m, 2H) 10.72-10.94 (m, 1H). LCMS (m/z) (M+H)=485, Rt=0.65 min.

Example 621: N-(5-(6-ethoxy-5-morpholinopyridazin-3-yl)-6-methylpyridin-3-yl)-2-isopropylisonicotinamide

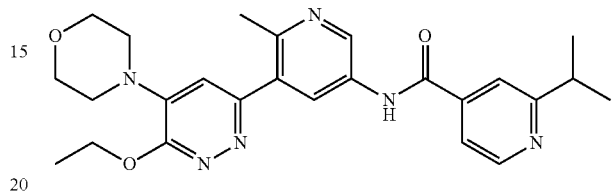

1H NMR (400 MHz, <dmso>) δ ppm 1.17-1.32 (m, 9H) 1.35-1.46 (m, 3H) 2.05 (s, 1H) 3.01-3.18 (m, 1H) 3.66-3.77 (m, 4H) 4.54 (q, J=7.04 Hz, 2H) 7.04 (s, 1H) 7.68 (dd, J=5.09, 1.57 Hz, 1H) 7.75 (s, 1H) 8.18 (d, J=2.35 Hz, 1H) 8.65-8.74 (m, 1H) 8.88 (d, J=2.35 Hz, 1H) 10.65 (s, 1H). LCMS (m/z) (M+H)=463, Rt=0.51 min.

Example 622: Synthesis of (R)—N-(5-(6-ethoxy-5-(3-methylmorpholino)pyridazin-3-yl)-6-methylpyridin-3-yl)-3-(trifluoromethyl)benzamide

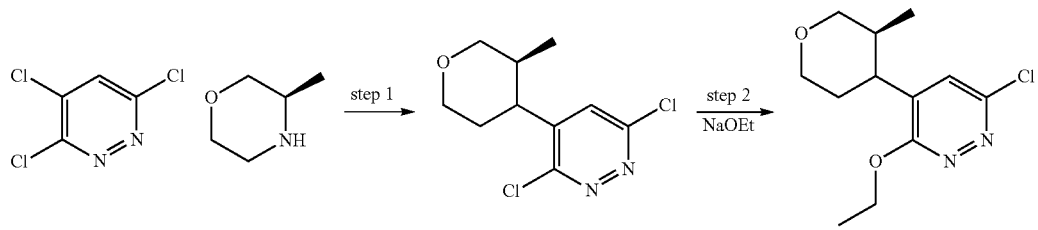

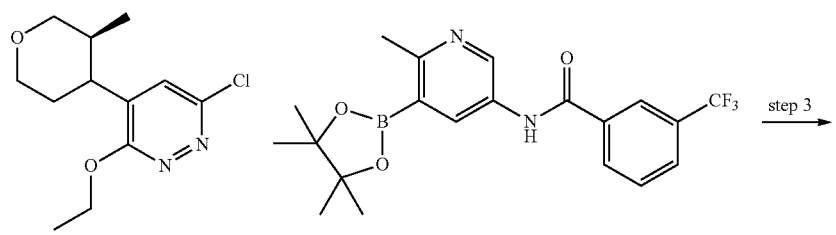

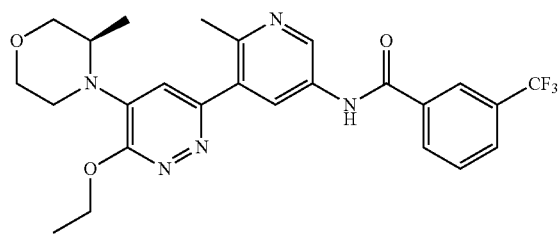

Step 1:

A mixture of 3,4,6-trichloropyridazine (1.0 equiv.), (R)-3-methylmorpholine (1.0 equiv.), and Hunig's base (1.1 equiv.) in NMP (2.73 M) was stirred at RT for 2 days. Water was added to the reaction mixture. The resulting precipitate was collected by filtration and dried in air to give (R)-4-(3,6-dichloropyridazin-4-yl)-3-methylmorpholine as white solid in 66% yield. LC/MS (m/z)=247.9 (MH+), Rt=0.63 min.

Step 2:

A mixture of (R)-4-(3,6-dichloropyridazin-4-yl)-3-methylmorpholine (1.0 equiv.) and 21 wt % sodium ethoxide in ethanol (2.0 equiv.) in 1.5:1 ethanol and water was stirred overnight at RT. The resulting mixture was partitioned between EtOAc and water. The organic phase was washed with brine and then dried over magnesium sulfate. After concentration, the crude material was purified via preparative reverse phase HPLC. Upon lyophilization of the pure fractions, (R)-4-(6-chloro-3-ethoxypyridazin-4-yl)-3-methylmorpholine was isolated as the TFA salt in 41% yield. LC/MS (m/z)=258.0 (MH+), Rt=0.59 min.

Step 3:

A mixture of (R)-4-(6-chloro-3-ethoxypyridazin-4-yl)-3-methylmorpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.), Na$_2$CO$_3$ (2 M, 3 equiv.) and PdCl$_2$(dppf) (0.05 equiv.) in DME (0.203 M) were heated at 120° C. for 15 min in the microwave. The resulting mixture was partitioned between EtOAc and water. The organic phase was washed with brine and then dried over magnesium sulfate. After concentration, the crude material was purified via preparative reverse phase HPLC. Upon lyophilization of the pure fractions, (R)—N-(5-(6-ethoxy-5-(3-methylmorpholino)pyridazin-3-yl)-6-methylpyridin-3-yl)-3-(trifluoromethyl)benzamide was isolated as the TFA salt in 20% yield. 1H NMR (400 MHz, <dmso>) δ ppm 1.30 (d, J=6.26 Hz, 2H) 1.43 (t, J=7.04 Hz, 2H) 2.05 (s, 2H) 3.52-3.62 (m, 3H) 3.69 (s, 2H) 3.91 (d, J=9.78 Hz, 1H) 4.49 (dd, J=7.04, 1.96 Hz, 4H) 7.33 (br. s., 1H) 7.76-7.86 (m, 1H) 8.00 (d, J=7.83 Hz, 1H) 8.23-8.38 (m, 3H) 8.95 (d, J=2.35 Hz, 1H) 10.84 (s, 1H). LCMS (m/z) (M+H)=502.2, Rt=0.84 min.

Example 623: Synthesis of (R)-2-(2-cyanopropan-2-yl)-N-(5-(6-ethoxy-5-(3-methylmorpholino)pyridazin-3-yl)-6-methylpyridin-3-yl)isonicotinamide

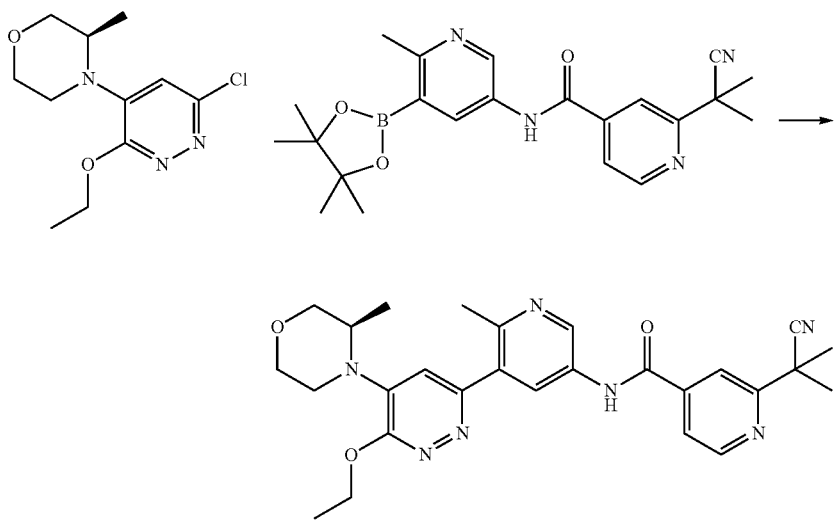 [SMILES: CCOc1nnc(Cl)cc1N1CCOC[C@H]1C ; Cc1ncc(NC(=O)c2ccnc(C(C)(C)C#N)c2)cc1B1OC(C)(C)C(C)(C)O1 ; CCOc1nnc(-c2cc(NC(=O)c3ccnc(C(C)(C)C#N)c3)cnc2C)cc1N1CCOC[C@H]1C]

A mixture of (R)-4-(6-chloro-3-ethoxypyridazin-4-yl)-3-methylmorpholine (1.0 equiv.), 2-(2-cyanopropan-2-yl)-N-(6-methyl-5-(4,4,5,5-tetramethyl-1,3,2-dioxaborolan-2-yl)pyridin-3-yl)isonicotinamide (1.0 equiv.), Na$_2$CO$_3$ (2 M, 3 equiv.) and PdCl$_2$(dppf) (0.05 equiv.) in DME (0.203 M) were heated at 120° C. for 30 min in the microwave. The resulting mixture was partitioned between EtOAc and water. The organic phase was washed with brine and then dried over magnesium sulfate. After concentration, the crude material was purified via preparative reverse phase HPLC. Upon lyophilization of the pure fractions, (R)-2-(2-cyanopropan-2-yl)-N-(5-(6-ethoxy-5-(3-methylmorpholino)pyridazin-3-yl)-6-methylpyridin-3-yl)isonicotinamide was isolated as the TFA salt in 20% yield. 1H NMR (400 MHz, <dmso>) d ppm 1.30 (d, J=5.87 Hz, 2H) 1.43 (t, J=7.04 Hz, 2H) 1.75 (s, 5H) 2.05 (s, 2H) 3.54-3.63 (m, 4H) 3.69 (s, 2H) 3.91 (d, J=9.78 Hz, 1H) 4.49 (dd, J=7.04, 1.96 Hz, 4H) 7.25-7.40 (m, 1H) 7.88 (dd, J=5.09, 1.17 Hz, 1H) 8.02 (s, 1H) 8.31 (d, J=1.96 Hz, 1H) 8.72-9.04 (m, 2H) 10.86-11.02 (m, 1H) LCMS (m/z) (M+H)=502.4, Rt=0.66 min.

Example 624: Synthesis of (R)-2-(2-cyanopropan-2-yl)-N-(3-(6-ethoxy-5-(3-methylmorpholino)pyridazin-3-yl)-4-methylphenyl)isonicotinamide

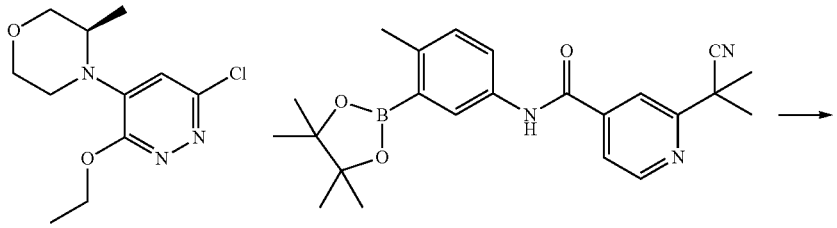

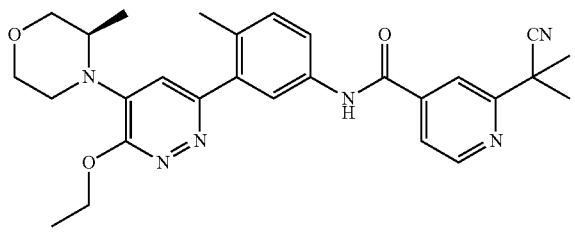

A mixture of (R)-4-(6-chloro-3-ethoxypyridazin-4-yl)-3-methylmorpholine (1.0 equiv.), 2-(2-cyanopropan-2-yl)-N-(4-methyl-3-(4,4,5,5-tetramethyl-1,3,2-dioxaborolan-2-yl)phenyl)isonicotinamide (1.0 equiv.), Na$_2$CO$_3$ (2 M, 3 equiv.) and PdCl$_2$(dppf) (0.05 equiv.) in DME (0.058 M) were heated at 120° C. for 15 min in the microwave. The resulting mixture was partitioned between EtOAc and water. The organic phase was washed with brine and then dried over magnesium sulfate. After concentration, the crude material was purified via preparative reverse phase HPLC. Upon lyophilization of the pure fractions, (R)-2-(2-cyanopropan-2-yl)-N-(3-(6-ethoxy-5-(3-methylmorpholino)pyridazin-3-yl)-4-methylphenyl)isonicotinamide was isolated as the TFA salt in 13% yield. 1H NMR (400 MHz, <dmso>) δ ppm 1.31 (br. s., 3H) 1.43 (t, J=6.85 Hz, 4H) 1.75 (s, 8H) 2.05 (s, 2H) 2.26 (s, 3H) 3.50-3.63 (m, 3H) 3.68 (s, 2H) 3.83-4.02 (m, 1H) 4.38-4.56 (m, 2H) 7.42 (d, J=8.22 Hz, 1H) 7.76-7.92 (m, 3H) 7.99 (s, 1H) 8.81 (d, J=4.70 Hz, 1H) 10.55-10.83 (m, 1H). LCMS (m/z) (M+H)=501.2, Rt=0.76 min.

Example 625: Synthesis of N-(5-(5-(2-(1H-imidazol-2-yl)morpholino)-6-ethoxypyridazin-3-yl)-6-methylpyridin-3-yl)-3-(trifluoromethyl)benzamide

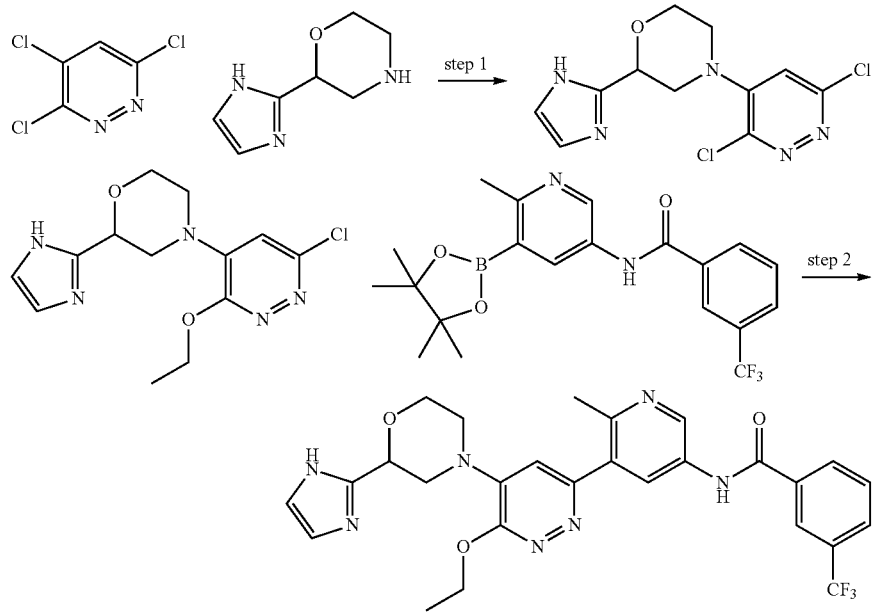

Step 1:

A mixture of 3,4,6-trichloropyridazine (1.0 equiv.), 2-(1H-imidazol-2-yl)morpholine (1.0 equiv.), and Hunig's base (3.0 equiv.) in NMP (0.182 M) was stirred at RT for 1 hr. A few drops of water were added to result in a solution, which was purified via preparative reverse phase HPLC. Upon lyophilization of the pure fractions, 4-(3,6-dichloropyridazin-4-yl)-2-(1H-imidazol-2-yl)morpholine was isolated as the TFA salt in 50% yield. LC/MS (m/z)=299.9 (MH$^+$), Rt=0.37 min.

J=7.04 Hz, 10H) 4.56 (dd, J=7.04, 3.52 Hz, 2H) 5.13 (dd, J=9.98, 2.54 Hz, 1H) 7.28 (s, 1H) 7.68 (s, 2H) 7.75-7.87 (m, 1H) 8.00 (d, J=7.83 Hz, 1H) 8.22-8.34 (m, 3H) 8.90 (d, J=2.35 Hz, 1H) 10.80 (s, 1H). LCMS (m/z) (M+H)=554.2, Rt=0.61 min.

Example 626: Synthesis of N-(5-(6-ethoxy-5-morpholinopyridazin-3-yl)-6-methylpyridin-3-yl)-4-((methylamino)methyl)-3-(trifluoromethyl)benzamide

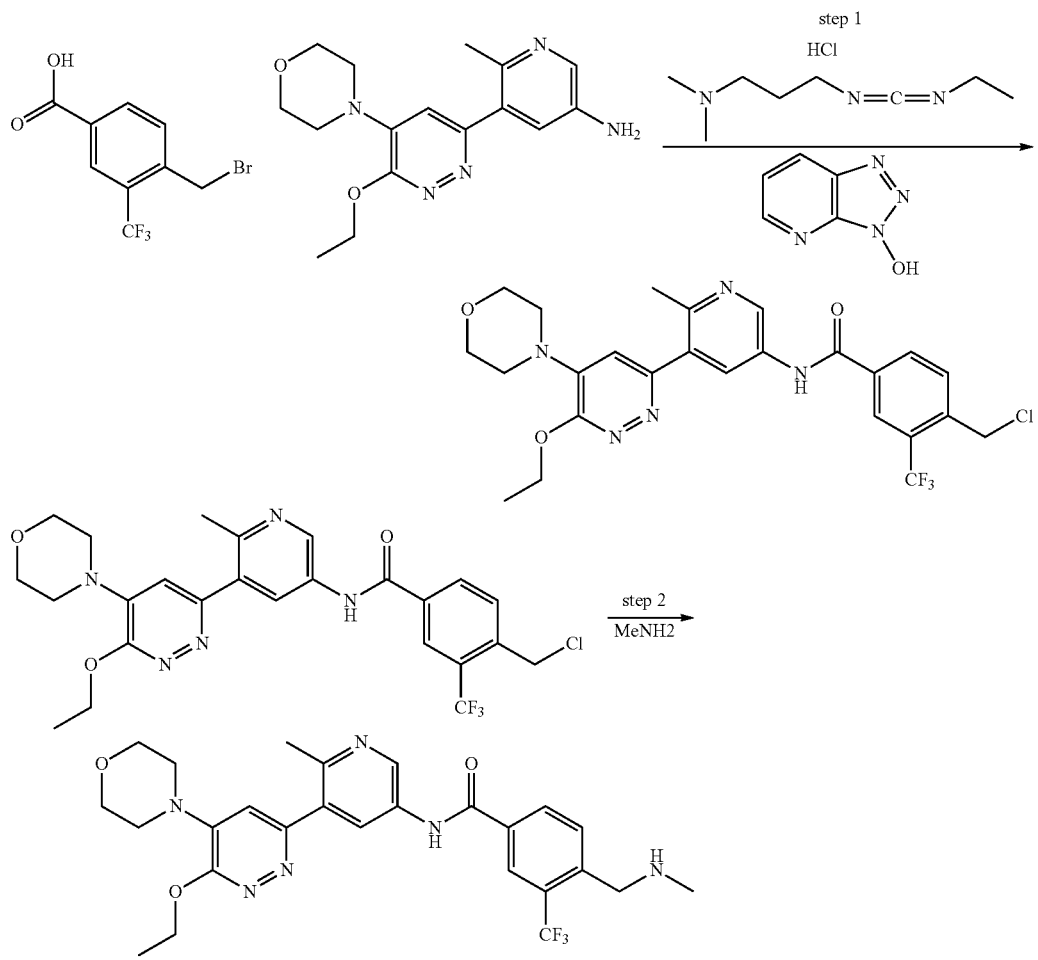

Step 2:

A mixture of 4-(6-chloro-3-ethoxypyridazin-4-yl)-2-(1H-imidazol-2-yl)morpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.), Na$_2$CO$_3$ (2 M, 3 equiv.) and PdCl$_2$(dppf) (0.05 equiv.) in DME (0.203 M) were heated at 120° C. for 30 min in the microwave. The resulting mixture was partitioned between EtOAc and water. The organic phase was washed with brine and then dried over magnesium sulfate. After concentration, the crude material was purified via preparative reverse phase HPLC. Upon lyophilization of the pure fractions, N-(5-(5-(2-(1H-imidazol-2-yl)morpholino)-6-ethoxypyridazin-3-yl)-6-methylpyridin-3-yl)-3-(trifluoromethyl)benzamide was isolated as the TFA salt in 9.3% yield. 1H NMR (400 MHz, <dmso>) δ ppm 1.16 (t, J=7.24 Hz, 16H) 1.43 (t, J=7.04 Hz, 3H) 1.97 (s, 9H) 2.76 (s, 1H) 3.12-3.48 (m, 4H) 4.01 (q, Step 1:

5-(6-ethoxy-5-morpholinopyridazin-3-yl)-6-methylpyridin-3-amine (1.0 equiv.), N1-((ethylimino)methylene)-N3,N3-dimethylpropane-1,3-diamine hydrochloride (1.0 equiv.), and 4-(bromomethyl)-3-(trifluoromethyl)benzoic acid (1.0 equiv.) were dissolved in DMF (0.106 M) at RT. The reaction was monitored by LCMS. After about 1 hr, the reaction mixture was purified via preparative reverse phase HPLC to give 4-(chloromethyl)-N-(5-(6-ethoxy-5-morpholinopyridazin-3-yl)-6-methylpyridin-3-yl)-3-(trifluoromethyl)benzamide in 62% yield. LCMS (m/z) (M+H)= 536.1, Rt=0.80 min.

Step 2:

4-(chloromethyl)-N-(5-(6-ethoxy-5-morpholinopyridazin-3-yl)-6-methylpyridin-3-yl)-3-(trifluoromethyl)benzamide (1.0 equiv.) was dissolved in 2M ammonia in methanol (0.08 M). After stirring at RT overnight, the reaction mixture was concentrated and purified via preparative reverse phase HPLC to give N-(5-(6-ethoxy-5-morpholinopyridazin-3-yl)-6-methylpyridin-3-yl)-4-((methylamino)methyl)-3-(trifluoromethyl)benzamide in 24% yield. 1H NMR (400 MHz, <dmso>) δ ppm 1.34-1.50 (m, 7H) 2.29 (s, 7H) 3.62-3.78 (m, 9H) 3.86 (s, 4H) 4.46-4.62 (m, 5H) 7.04 (s, 2H) 7.87-8.01 (m, 2H) 8.16-8.33 (m, 6H) 8.85-8.92 (m, 2H) 10.44-10.97 (m, 1H). LCMS (m/z) (M+H)=531.2, Rt=0.54 min.

Example 627: Synthesis of N-(5-(6-ethoxy-5-morpholinopyridazin-3-yl)-6-methylpyridin-3-yl)-4-(hydroxymethyl)-3-(trifluoromethyl)benzamide

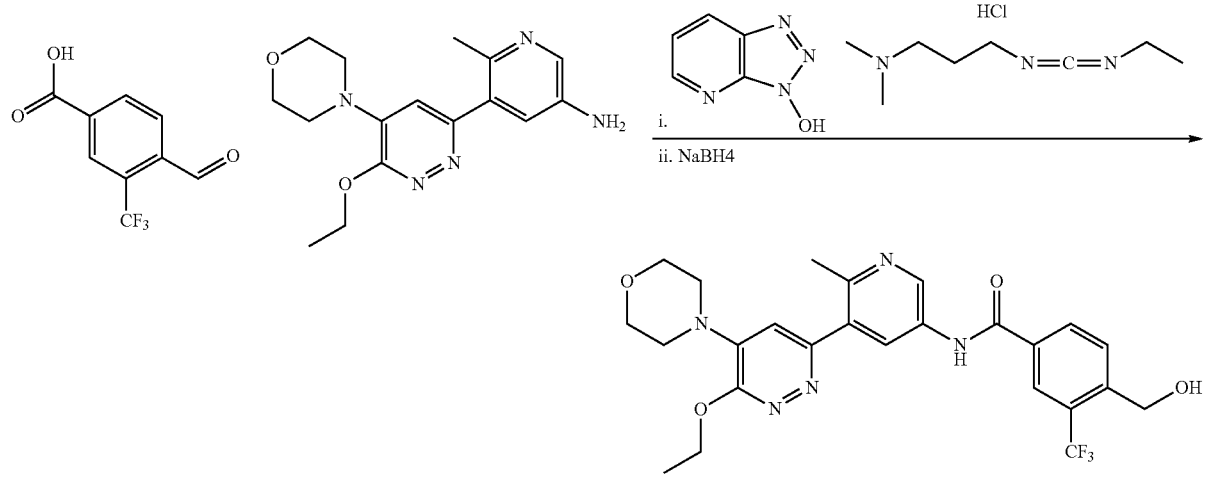

5-(6-ethoxy-5-morpholinopyridazin-3-yl)-6-methylpyridin-3-amine (1.0 equiv.), N1-((ethylimino)methylene)-N3,N3-dimethylpropane-1,3-diamine hydrochloride (1.0 equiv.), and 4-formyl-3-(trifluoromethyl)benzoic acid (1.0 equiv.) were dissolved in DMF (0.02 M) at RT. The reaction was monitored by LCMS. After about 1 hr, the reaction mixture was purified via preparative reverse phase HPLC to give N-(5-(6-ethoxy-5-morpholinopyridazin-3-yl)-6-methylpyridin-3-yl)-4-formyl-3-(trifluoromethyl)benzamide. LCMS (m/z) (M+H)=516.2, Rt=0.72 min. The product was subsequently dissolved in MeOH and treated with excess sodium borohydride at RT. The reaction mixture was purified via preparative reverse phase HPLC when bubbling ceased to give N-(5-(6-ethoxy-5-morpholinopyridazin-3-yl)-6-methylpyridin-3-yl)-4-(hydroxymethyl)-3-(trifluoromethyl)benzamide in 13% yield over two steps. 1H NMR (400 MHz, <dmso>) δ ppm 1.43 (s, 3H) 2.05 (s, 8H) 3.74 (br. s., 9H) 4.44-4.59 (m, 2H) 4.69-4.81 (m, 2H) 7.34 (s, 1H) 7.97 (d, J=8.22 Hz, 1H) 8.23-8.40 (m, 3H) 8.95 (d, J=2.35 Hz, 1H) 10.63-10.94 (m, 1H). LCMS (m/z) (M+H)=518.1, Rt=0.65 min.

Example 628: 2-(1,1-difluoroethyl)-N-(6-methyl-5-(5-morpholino-6-((tetrahydro-2H-pyran-4-yl)oxy)pyridazin-3-yl)pyridin-3-yl)isonicotinamide

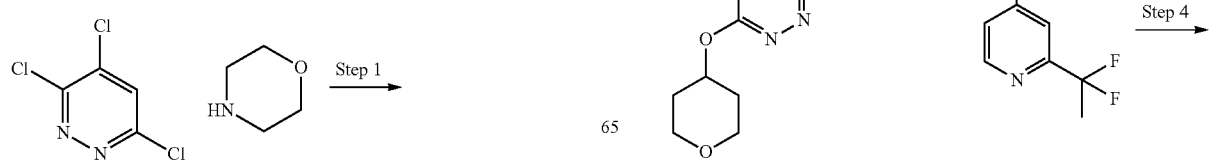

-continued

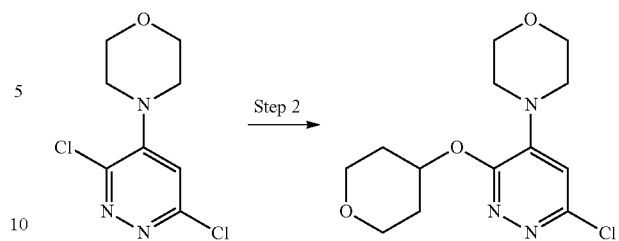

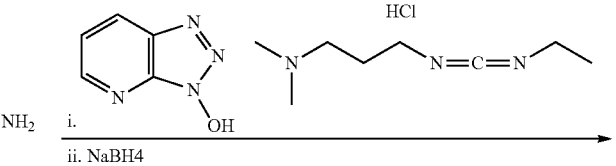

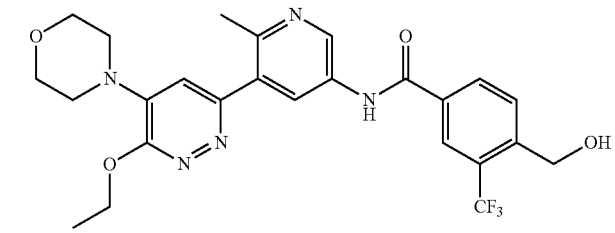

-continued

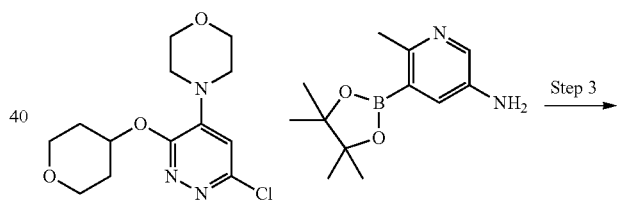

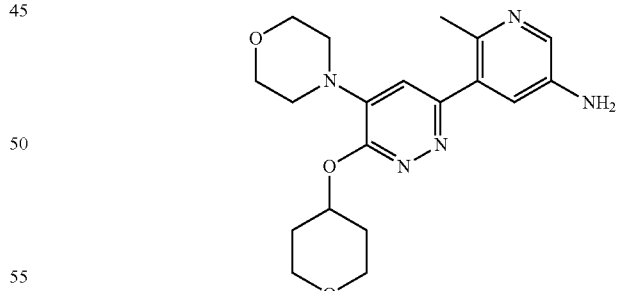

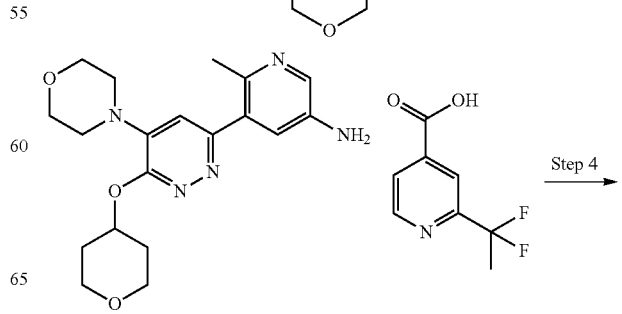

-continued

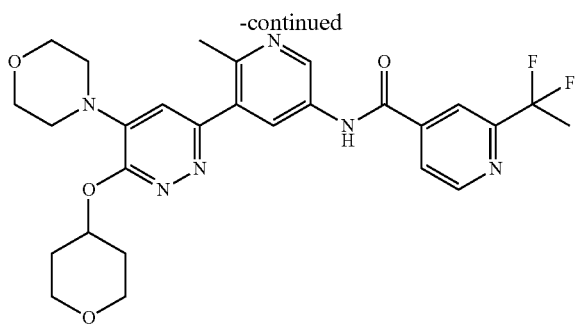

Step 1:
To a flask containing 3,4,6-trichloropyridazine (1.0 equiv.) in EtOH (1.3 M) was added morpholine (2.3 equiv.) and the reaction mix was stirred at RT for 60 min. A precipitate appeared which was removed by filtration. The solid recovered was suspended in water and stirred for few minutes to remove salts. After filtration the solid was dried under vacuum giving 4-(3,6-dichloropyridazin-4-yl)morpholine in 86% yield which was used as is in the next step. LCMS (m/z) (M+H)=234/236, Rt=0.57 min.

Step 2:
NaH (2.0 equiv.) was added to a solution of tetrahydro-2H-pyran-4-ol (1.7 equiv.) and 4-(3,6-dichloropyridazin-4-yl)morpholine (1.0 equiv.) in THF (0.3 M) at 0° C. and the reaction mix was left stirring overnight at RT. The reaction mix was quench with water and extracted three times with EtOAc. The combined organics were washed with brine and dried over Na$_2$SO$_4$. The crude was dissolved in DCM, and adsorbed in silica gel. The solid was loaded into a cartridge and purified on a silica gel column using 0 to 40% EtOAc in heptane. The desired 4-(6-chloro-3-((tetrahydro-2H-pyran-4-yl)oxy)pyridazin-4-yl)morpholine was obtained in 75% yield. LCMS (m/z) (M+H)=300, Rt=0.54 min.

Step 3:
To a solution of 4-(6-chloro-3-((tetrahydro-2H-pyran-4-yl)oxy)pyridazin-4-yl)morpholine (1.0 equiv.) and 6-methyl-5-(4,4,5,5-tetramethyl-1,3,2-dioxaborolan-2-yl)pyridin-3-amine (1.0 equiv.) in DME (0.11 M) was added Na$_2$CO$_3$ (2M, 3.0 equiv.) and the system was flushed with nitrogen. PdCl$_2$(dppf).CH$_2$Cl$_2$ adduct (0.05 equiv.) was added to the reaction mix and the system was flushed once again with nitrogen. The reaction mix was heated in a bath for 4 hr at 120° C. The crude was partitioned in H$_2$O/EtOAc. The organic layer was isolated, dried over Na$_2$SO$_4$, filtered and concentrated. Crude was purified silica gel column using DCM to 5% MeOH in DCM to give 6-methyl-5-(5-morpholino-6-((tetrahydro-2H-pyran-4-yl)oxy)pyridazin-3-yl)pyridin-3-amine in 40% yield. LCMS (m/z) (M+H)=372, Rt=0.37 min.

Step 4:
DIEA (3.0 equiv.) was added to a solution of 6-methyl-5-(5-morpholino-6-((tetrahydro-2H-pyran-4-yl)oxy)pyridazin-3-yl)pyridin-3-amine (1.0 equiv.), 2-(1,1-difluoroethyl)isonicotinic acid (1.0 equiv.) and HATU (1.0 equiv.) in DMF (0.05 M), and the mixture was left stirring at RT overnight. The reaction mix was treated with water and extracted three times with EtOAc. The combined organics were dried over Na$_2$SO$_4$, filtered and concentrated. The crude was purified by HPLC 2-(1,1-difluoroethyl)-N-(6-methyl-5-(5-morpholino-6-((tetrahydro-2H-pyran-4-yl)oxy)pyridazin-3-yl)pyridin-3-yl)isonicotinamide as the TFA salt in 39% yield. 1H NMR (400 MHz, <dmso>) δ ppm 1.70-1.86 (m, 2H) 2.04 (t, J=19.17 Hz, 5H) 5.40 (br. s., 1H) 7.32 (br. s., 1H) 8.04 (d, J=4.70 Hz, 1H) 8.20 (s, 1H) 8.33 (d, J=1.96 Hz, 1H) 8.79-8.97 (m, 2H) 10.90-11.07 (m, 1H). LCMS (m/z) (M+H)=541, Rt=0.63 min.

Example 629: N-(6-methyl-5-(5-morpholino-6-((tetrahydro-2H-pyran-4-yl)oxy)pyridazin-3-yl)pyridin-3-yl)-4-(trifluoromethyl)picolinamide

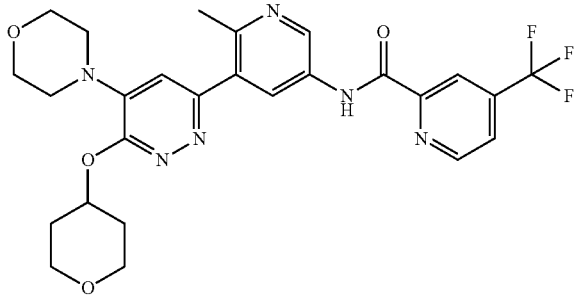 [SMILES: Cc1ncc(NC(=O)c2cc(C(F)(F)F)ccn2)cc1-c1cc(N2CCOCC2)c(OC2CCOCC2)nn1]

1H NMR (400 MHz, <dmso>) δ ppm 1.75 (dtd, J=12.57, 8.29, 8.29, 3.72 Hz, 2H) 1.98-2.12 (m, 2H) 3.68-3.82 (m, 8H) 5.37 (dt, J=7.53, 3.86 Hz, 1H) 7.25 (s, 1H) 8.07 (d, J=4.70 Hz, 1H) 8.30 (s, 1H) 8.41 (d, J=1.96 Hz, 1H) 8.92-9.12 (m, 2H) 11.06-11.31 (m, 1H). LCMS (m/z) (M+H)= 545, Rt=0.69 min.

Example 630: 2-(2-fluoropropan-2-yl)-N-(6-methyl-5-(5-morpholino-6-((tetrahydro-2H-pyran-4-yl)oxy)pyridazin-3-yl)pyridin-3-yl)isonicotinamide

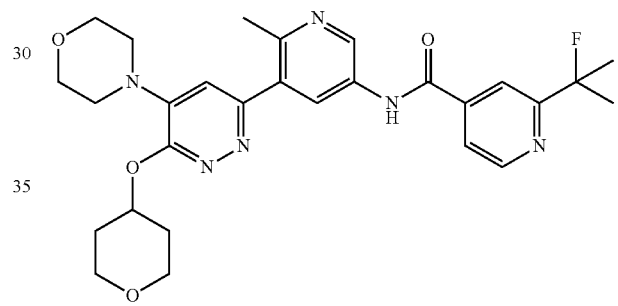

1H NMR (400 MHz, <dmso>) δ ppm 1.70-1.89 (m, 9H) 1.97-2.18 (m, 2H) 5.41 (br. s., 1H) 7.17-7.41 (m, 1H) 8.17-8.38 (m, 2H) 8.90 (d, J=2.35 Hz, 1H) 9.65 (d, J=1.96 Hz, 1H) 11.11 (s, 1H). LCMS (m/z) (M+H)=537, Rt=0.63 min.

Example 631: N-(6-methyl-5-(5-morpholino-6-((tetrahydro-2H-pyran-4-yl)oxy)pyridazin-3-yl)pyridin-3-yl)-6-(trifluoromethyl)pyridazine-4-carboxamide

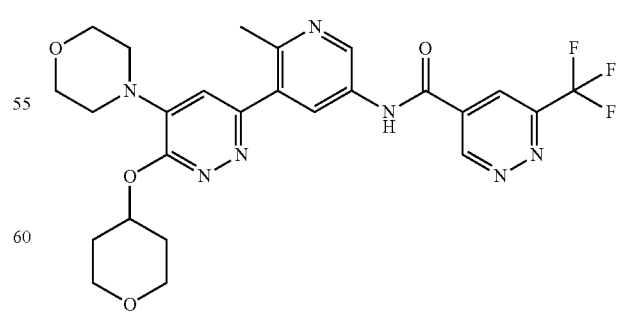

1H NMR (400 MHz, <cd3od>) δ ppm 1.71-1.88 (m, 2H) 2.01-2.18 (m, 2H) 3.60 (ddd, J=11.44, 8.12, 3.13 Hz, 3H) 3.55-3.64 (m, 1H) 5.41 (dt, J=7.53, 3.86 Hz, 1H) 7.39 (s, 1H) 8.35 (d, J=1.96 Hz, 1H) 8.71 (d, J=1.57 Hz, 1H) 8.93 (d, J=2.35 Hz, 1H) 9.94 (d, J=1.57 Hz, 1H) 11.14-11.39 (m, 1H). LCMS (m/z) (M+H)=546, Rt=0.60 min.

Example 632: N-(6-methyl-5-(5-morpholino-6-((tetrahydro-2H-pyran-4-yl)oxy)pyridazin-3-yl)pyridin-3-yl)-2-(methylsulfonyl)isonicotinamide

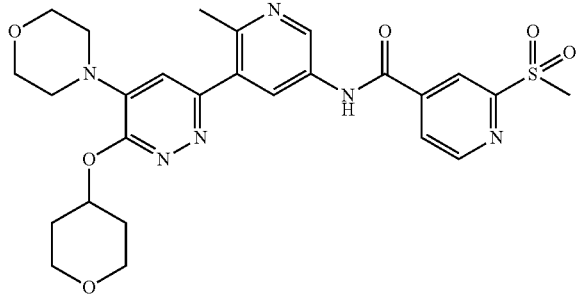 [SMILES: Cc1ncc(NC(=O)c2ccnc(S(C)(=O)=O)c2)cc1-c1cc(N2CCOCC2)c(OC2CCOCC2)nn1]

1H NMR (400 MHz, <dmso>) δ ppm 1.67-1.83 (m, 2H) 1.98-2.12 (m, 2H) 3.30 (s, 3H) 5.29-5.42 (m, 1H) 7.29 (br. s., 1H) 8.18 (dd, J=4.89, 1.37 Hz, 1H) 8.29 (d, J=1.96 Hz, 1H) 8.50 (s, 1H) 8.89 (d, J=2.35 Hz, 1H) 8.98 (d, J=4.70 Hz, 1H) 11.09 (s, 1H). LCMS (m/z) (M+H)=555, Rt=0.52 min.

Example 633: 2-(2-cyanopropan-2-yl)-N-(6-methyl-5-(5-morpholino-6-((tetrahydro-2H-pyran-4-yl)oxy)pyridazin-3-yl)pyridin-3-yl)isonicotinamide

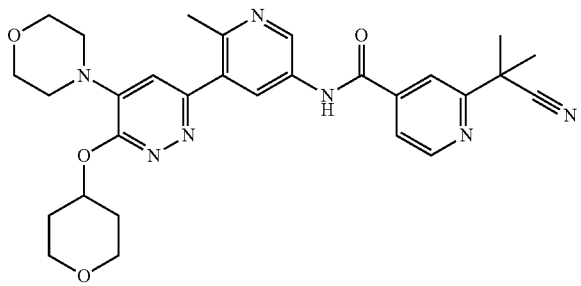 [SMILES: Cc1ncc(NC(=O)c2ccnc(C(C)(C)C#N)c2)cc1-c1cc(N2CCOCC2)c(OC2CCOCC2)nn1]

LCMS (m/z) (M+H)=544, Rt=0.62 min.

Example 634: 2-(2-hydroxypropan-2-yl)-N-(6-methyl-5-(5-morpholino-6-((tetrahydro-2H-pyran-4-yl)oxy)pyridazin-3-yl)pyridin-3-yl)isonicotinamide

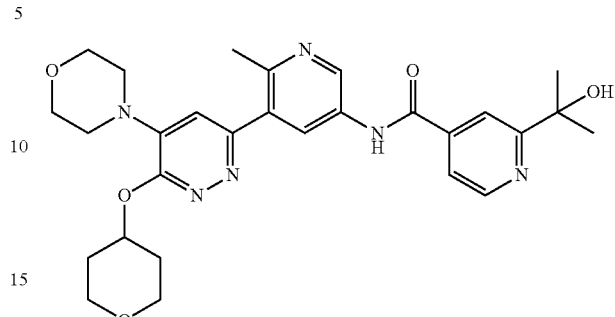

1H NMR (400 MHz, <dmso>) δ ppm 1.47 (s, 6H) 1.67-1.91 (m, 2H) 2.01-2.18 (m, 2H) 3.47-3.67 (m, 2H) 4.39 (br. s., 1H) 5.23-5.45 (m, 1H) 7.41 (s, 1H) 7.73 (dd, J=4.89, 1.37 Hz, 1H) 8.17 (s, 1H) 8.39 (d, J=2.35 Hz, 1H) 8.71 (d, J=5.09 Hz, 1H) 8.95 (d, J=2.35 Hz, 1H) 10.96 (s, 1H). LCMS (m/z) (M+H)=535, Rt=0.48 min.

Example 635: 6-(2-cyanopropan-2-yl)-N-(6-methyl-5-(5-morpholino-6-((tetrahydro-2H-pyran-4-yl)oxy)pyridazin-3-yl)pyridin-3-yl)pyridazine-4-carboxamide

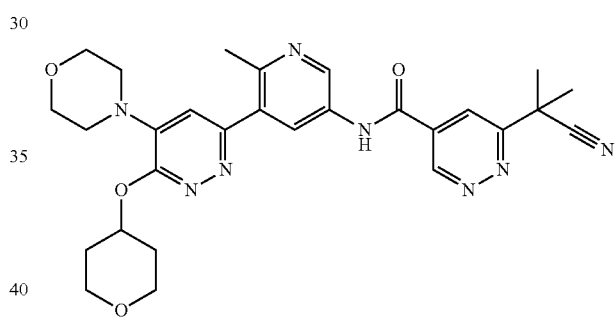

1H NMR (400 MHz, <cd3od>) δ ppm 1.74-1.89 (m, 10H) 2.06-2.17 (m, 2H) 3.60 (ddd, J=11.35, 8.22, 3.13 Hz, 7H) 3.73-3.80 (m, 5H) 3.80-3.89 (m, 2H) 5.45 (br. s., 1H) 7.26 (br. s., 1H) 8.28 (s, 1H) 8.33 (d, J=1.96 Hz, 1H) 8.91 (d, J=2.35 Hz, 1H) 9.67 (d, J=1.96 Hz, 1H) 11.00-11.20 (m, 1H). LCMS (m/z) (M+H)=555, Rt=0.49 min.

Example 636: Synthesis of N-(6-methyl-5-(5-morpholino-6-((tetrahydro-2H-pyran-4-yl)oxy)pyridazin-3-yl)pyridin-3-yl)-3-(trifluoromethyl)benzamide

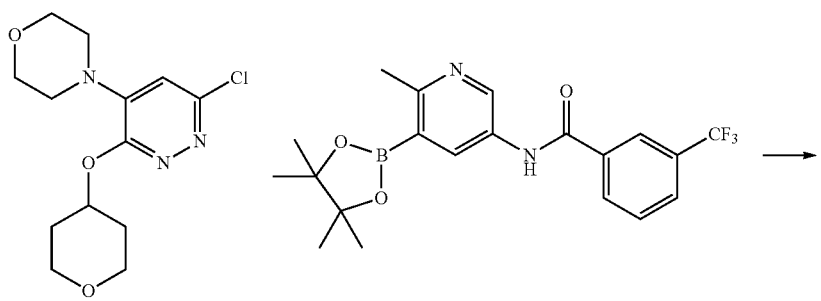

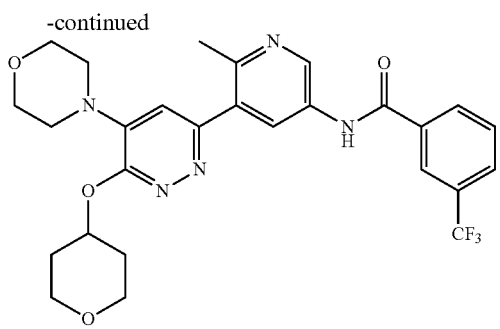

A mixture of 4-(6-chloro-3-((tetrahydro-2H-pyran-4-yl)oxy)pyridazin-4-yl)morpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.), Na$_2$CO$_3$ (2 M, 3 equiv.) and PdCl$_2$(dppf) (0.05 equiv.) in THF (0.214 M) were heated at 130° C. for 30 min in the microwave. The resulting mixture was partitioned between EtOAc and water. The organic phase was washed with brine and then dried over magnesium sulfate. After concentration, the crude material was purified via preparative reverse phase HPLC. Upon lyophilization of the pure fractions, N-(6-methyl-5-(5-morpholino-6-((tetrahydro-2H-pyran-4-yl)oxy)pyridazin-3-yl)pyridin-3-yl)-3-(trifluoromethyl)benzamide was isolated as the TFA salt in 12% yield. 1H NMR (400 MHz, <dmso>) δ ppm 1.70-1.90 (m, 2H) 2.00-2.20 (m, 2H) 3.33-4.18 (m, 60H) 5.29-5.46 (m, 1H) 7.37 (s, 1H) 7.76-7.87 (m, 1H) 8.01 (d, J=7.83 Hz, 1H) 8.23-8.42 (m, 3H) 8.94 (d, J=2.35 Hz, 1H) 10.87 (s, 1H). LCMS (m/z) (M+H)=544.2, Rt=0.76 min.

Example 637: N-(4-methyl-3-(1-methyl-5-morpholino-6-oxo-1,6-dihydropyridazin-3-yl)phenyl)-3-(2-(methylsulfonyl)propan-2-yl)benzamide

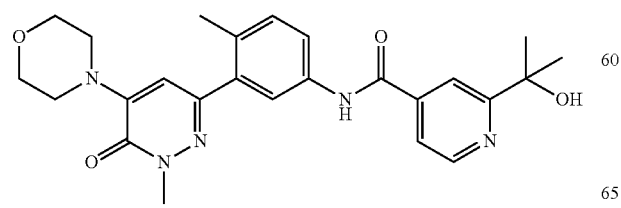

$^1$H NMR (400 MHz, <dmso>) δ ppm 1.80 (s, 6H) 2.28 (s, 3H) 2.68-2.77 (m, 3H) 3.44-3.47 (m, 4H) 3.63-3.75 (m, 7H) 6.59 (s, 1H) 7.27 (d, J=8.61 Hz, 1H) 7.56 (t, J=7.83 Hz, 1H) 7.67-7.77 (m, 2H) 7.82 (d, J=8.22 Hz, 1H) 7.98 (d, J=7.83 Hz, 1H) 8.07-8.17 (m, 1H) 10.30 (s, 1H). LCMS (m/z) (M+H)=525.3, Rt=0.78 min.

Example 638: 2-(2-hydroxypropan-2-yl)-N-(4-methyl-3-(1-methyl-5-morpholino-6-oxo-1,6-dihydropyridazin-3-yl)phenyl)isonicotinamide $^1$H NMR (400 MHz, <dmso>) δ ppm 1.47 (s, 6H) 2.25-2.34 (m, 3H) 3.43-3.48 (m, 4H) 3.67 (s, 3H) 3.70 (d, J=3.91 Hz, 4H) 6.59 (s, 1H) 7.28 (d, J=9.00 Hz, 1H) 7.65-7.81 (m, 3H) 8.15 (s, 1H) 8.67 (d, J=5.09 Hz, 1H) 10.54 (s, 1H). LCMS (m/z) (M+H)=464.2, Rt=0.66 min.

Example 639: N-(4-methyl-3-(1-methyl-5-morpholino-6-oxo-1,6-dihydropyridazin-3-yl)phenyl)-3-(1,3,4-oxadiazol-2-yl)benzamide $^1$H NMR (400 MHz, <dmso>) δ ppm 2.26-2.31 (m, 3H) 3.41-3.52 (m, 4H) 3.63-3.76 (m, 7H) 6.60 (s, 1H) 7.28 (d, J=9.00 Hz, 1H) 7.69-7.83 (m, 3H) 8.21 (t, J=6.85 Hz, 2H) 8.60 (s, 1H) 9.41 (s, 1H) 10.52 (s, 1H). LCMS (m/z) (M+H)=473.3, Rt=0.77 min.

Example 640: 2-(2-cyanopropan-2-yl)-N-(4-methyl-3-(1-methyl-5-morpholino-6-oxo-1,6-dihydropyridazin-3-yl)phenyl)isonicotinamide

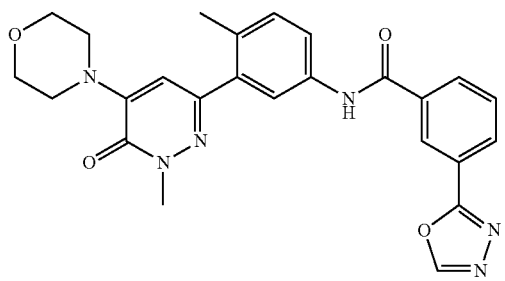 [SMILES: Cc1ccc(NC(=O)c2cccc(-c3nnco3)c2)cc1-c1cc(N2CCOCC2)c(=O)n(C)n1]

$^1$H NMR (400 MHz, <dmso>) δ ppm 1.75 (s, 6H) 2.29 (s, 3H) 3.40-3.52 (m, 4H) 3.62-3.76 (m, 7H) 6.59 (s, 1H) 7.30 (d, J=8.22 Hz, 1H) 7.67-7.77 (m, 2H) 7.81-7.91 (m, 1H) 8.00 (s, 1H) 8.79 (d, J=5.09 Hz, 1H) 10.56 (s, 1H). LCMS (m/z) (M+H)=473.2, Rt=0.81 min.

Example 641: 1-ethyl-N-(4-methyl-3-(1-methyl-5-morpholino-6-oxo-1,6-dihydropyridazin-3-yl)phenyl)-6-oxo-5-(trifluoromethyl)-1,6-dihydropyridine-3-carboxamide

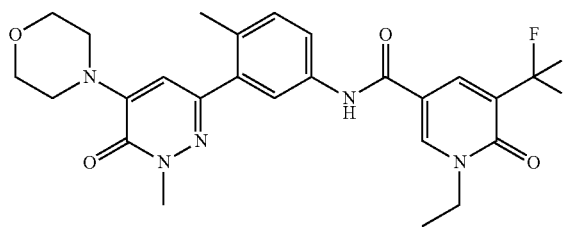

$^1$H NMR (400 MHz, <dmso>) δ ppm 1.29 (t, J=7.04 Hz, 3H) 2.28 (s, 3H) 3.43-3.47 (m, 4H) 3.65-3.72 (m, 7H) 4.06 (q, J=7.30 Hz, 2H) 6.58 (s, 1H) 7.27 (d, J=8.61 Hz, 1H) 7.63 (d, J=2.35 Hz, 1H) 7.69 (dd, J=8.22, 2.35 Hz, 1H) 8.46 (d, J=1.96 Hz, 1H) 8.80 (d, J=2.35 Hz, 1H) 10.16 (s, 1H). LCMS (m/z) (M+H)=518.1, Rt=0.87 min.

Example 642: 2-ethyl-N-(4-methyl-3-(1-methyl-5-morpholino-6-oxo-1,6-dihydropyridazin-3-yl)phenyl)isonicotinamide

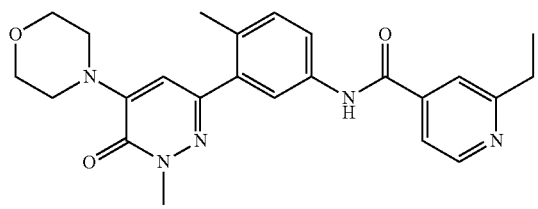 [SMILES: CCc1cc(C(=O)Nc2ccc(C)c(-c3cc(N4CCOCC4)c(=O)n(C)n3)c2)ccn1]

$^1$H NMR (400 MHz, <dmso>) δ ppm 1.27 (t, J=7.63 Hz, 3H) 2.29 (s, 3H) 2.86 (d, J=7.83 Hz, 2H) 3.44-3.47 (m, 4H) 3.67 (s, 3H) 3.68-3.71 (m, 6H) 6.55-6.63 (m, 1H) 7.23-7.35 (m, 1H) 7.68-7.76 (m, 3H) 7.80 (s, 1H) 8.69 (d, J=5.09 Hz, 1H) 10.49 (s, 1H). LCMS (m/z) (M+H)=434.2, Rt=0.61 min.

Example 643: 2-(1,1-difluoropropyl)-N-(4-methyl-3-(1-methyl-5-morpholino-6-oxo-1,6-dihydropyridazin-3-yl)phenyl)isonicotinamide

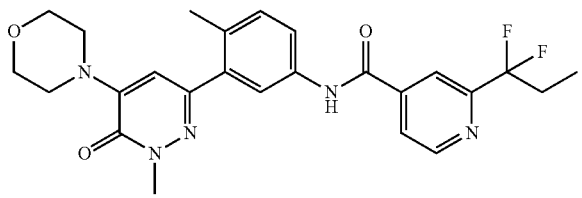 [SMILES: CCC(F)(F)c1cc(C(=O)Nc2ccc(C)c(-c3cc(N4CCOCC4)c(=O)n(C)n3)c2)ccn1]

$^1$H NMR (400 MHz, <dmso>) δ ppm 0.93 (t, J=7.43 Hz, 3H) 2.24-2.42 (m, 5H) 3.43-3.51 (m, 4H) 3.62-3.77 (m, 7H) 6.59 (s, 1H) 7.30 (d, J=8.22 Hz, 1H) 7.67-7.83 (m, 2H) 8.01 (d, J=4.30 Hz, 1H) 8.15 (s, 1H) 8.87 (d, J=5.09 Hz, 1H) 10.64 (s, 1H). LCMS (m/z) (M+H)=484.1, Rt=0.93 min.

Example 644: 6-cyclopropyl-N-(4-methyl-3-(1-methyl-5-morpholino-6-oxo-1,6-dihydropyridazin-3-yl)-phenyl)pyridazine-4-carboxamide

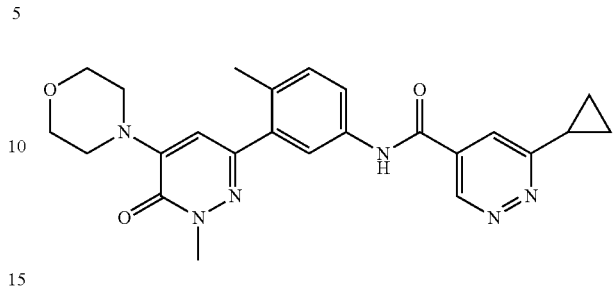

$^1$H NMR (400 MHz, <dmso>) δ ppm 1.10-1.18 (m, 4H) 2.29 (s, 3H) 2.32-2.39 (m, 1H) 3.46 (d, J=4.70 Hz, 4H) 3.67 (s, 7H) 6.58 (s, 1H) 7.19-7.37 (m, 1H) 7.63-7.79 (m, 2H) 7.88 (d, J=1.96 Hz, 1H) 9.37 (d, J=1.96 Hz, 1H) 10.57-10.67 (m, 1H). LCMS (m/z) (M+H)=447.2, Rt=0.71 min.

Example 645: 2-(2-cyanopropan-2-yl)-N-(6-methyl-5-(1-methyl-5-morpholino-6-oxo-1,6-dihydropyridazin-3-yl)pyridin-3-yl)isonicotinamide

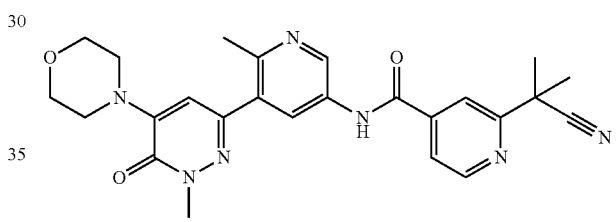

$^1$H NMR (400 MHz, <dmso>) δ ppm 1.76 (s, 6H) 2.54 (s, 3H) 3.39-3.53 (m, 4H) 3.65-3.75 (m, 7H) 6.71 (s, 1H) 7.81-7.92 (m, 1H) 8.04 (s, 1H) 8.22 (d, J=2.35 Hz, 1H) 8.83 (d, J=5.09 Hz, 1H) 8.94 (d, J=1.96 Hz, 1H) 10.90 (s, 1H). LCMS (m/z) (M+H)=474.2, Rt=0.67 min.

Example 646: 6-(2-cyanopropan-2-yl)-N-(4-methyl-3-(1-methyl-5-morpholino-6-oxo-1,6-dihydropyridazin-3-yl)phenyl)pyridazine-4-carboxamide

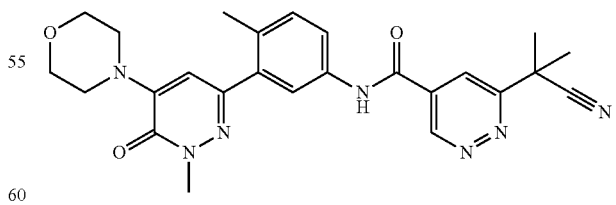

$^1$H NMR (400 MHz, <dmso>) δ ppm 1.76-1.88 (s, 6H) 2.30 (s, 3H) 3.41-3.48 (m, 4H) 3.67 (s, 3H) 3.68-3.73 (m, 5H) 6.59 (s, 1H) 7.32 (d, J=8.61 Hz, 1H) 7.66-7.78 (m, 2H) 8.29 (d, J=1.57 Hz, 1H) 9.63 (d, J=1.57 Hz, 1H) 10.76 (s, 1H). LCMS (m/z) (M+H)=474.1, Rt=0.81 min.

Example 647: N-(4-methyl-3-(1-methyl-5-morpholino-6-oxo-1,6-dihydropyridazin-3-yl)phenyl)-6-(trifluoromethyl)pyridazine-4-carboxamide

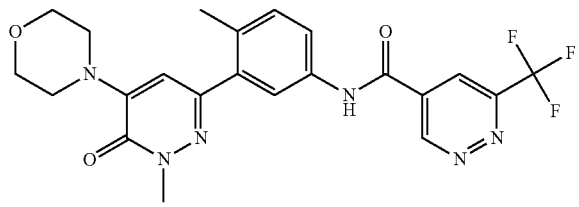 [SMILES: Cc1ccc(NC(=O)c2cnnc(C(F)(F)F)c2)cc1-c1cc(N2CCOCC2)c(=O)n(C)n1]

¹H NMR (400 MHz, <dmso>) δ ppm 2.30 (s, 3H) 3.46 (d, J=3.13 Hz, 4H) 3.67 (s, 3H) 3.69 (d, J=3.52 Hz, 4H) 6.56-6.61 (m, 1H) 7.27-7.35 (m, 1H) 7.56-7.66 (m, 2H) 7.70-7.78 (m, 1H) 8.68 (d, J=1.56 Hz, 1H) 9.91 (d, J=1.57 Hz, 1H) 10.88 (s, 1H). LCMS (m/z) (M+H)=475.0, Rt=0.80 min.

Example 648: N-(4-methyl-3-(1-methyl-5-morpholino-6-oxo-1,6-dihydropyridazin-3-yl)phenyl)-2-(oxetan-3-yl)isonicotinamide

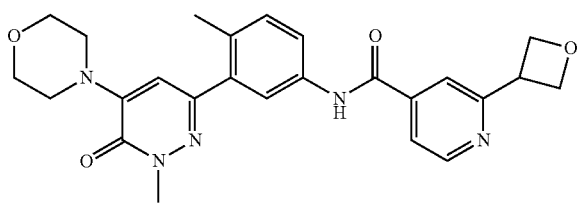 [SMILES: Cc1ccc(NC(=O)c2ccnc(C3COC3)c2)cc1-c1cc(N2CCOCC2)c(=O)n(C)n1]

¹H NMR (400 MHz, <dmso>) δ ppm 2.28 (s, 3H) 3.43-3.49 (m, 4H) 3.67 (s, 3H) 3.68-3.73 (m, 4H) 4.49 (q, J=7.73 Hz, 1H) 4.82 (t, J=6.26 Hz, 2H) 4.92 (dd, J=8.41, 5.67 Hz, 2H) 6.58 (s, 1H) 7.28 (d, J=9.00 Hz, 1H) 7.65-7.77 (m, 3H) 7.80 (s, 1H) 8.78 (d, J=5.09 Hz, 1H) 10.49 (s, 1H). LCMS (m/z) (M+H)=462.1, Rt=0.66 min.

Example 649: 3-(4-ethylpiperazin-1-yl)-N-(4-methyl-3-(1-methyl-5-morpholino-6-oxo-1,6-dihydropyridazin-3-yl)phenyl)-5-(trifluoromethyl)benzamide

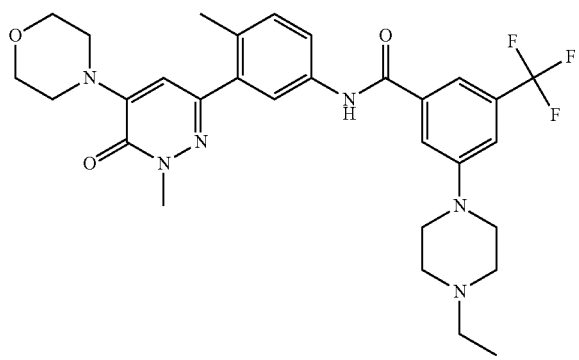 [SMILES: CCN1CCN(c2cc(C(=O)Nc3ccc(C)c(-c4cc(N5CCOCC5)c(=O)n(C)n4)c3)cc(C(F)(F)F)c2)CC1]

¹H NMR (400 MHz, <dmso>) δ ppm 1.25 (t, J=7.43 Hz, 3H) 2.29 (s, 3H) 3.11 (d, J=8.22 Hz, 4H) 3.20 (d, J=6.26 Hz, 2H) 3.42-3.48 (m, 4H) 3.60 (d, J=5.87 Hz, 2H) 3.67 (s, 3H) 3.68-3.74 (m, 4H) 4.10 (d, J=8.61 Hz, 2H) 6.58 (s, 1H) 7.28 (d, J=8.22 Hz, 1H) 7.50 (s, 1H) 7.70 (d, J=1.96 Hz, 1H) 7.74 (m, 3H) 10.39 (s, 1H). LCMS (m/z) (M+H)=585.2, Rt=0.75 min.

Example 650: 2-(difluoromethyl)-N-(4-methyl-3-(1-methyl-5-morpholino-6-oxo-1,6-dihydropyridazin-3-yl)phenyl)isonicotinamide

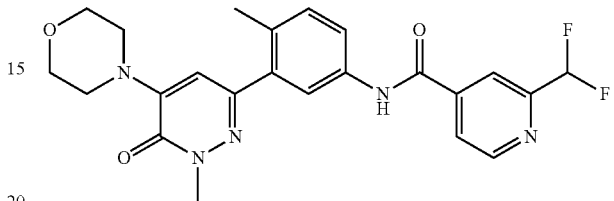

¹H NMR (400 MHz, <dmso>) δ ppm 2.29 (s, 3H) 2.31 (m, 1H) 3.42-3.49 (m, 4H) 3.67 (s, 3H) 3.68-3.74 (m, 4H) 6.59 (s, 1H) 7.30 (d, J=8.22 Hz, 1H) 7.76 (m, 2H) 8.05 (d, J=5.09 Hz, 1H) 8.17 (s, 1H) 8.89 (d, J=5.09 Hz, 1H) 10.65 (s, 1H). LCMS (m/z) (M+H)=456.0, Rt=0.74 min.

Example 651: N-(6-methyl-5-(1-methyl-5-morpholino-6-oxo-1,6-dihydropyridazin-3-yl)pyridin-3-yl)-3-(trifluoromethyl)benzamide

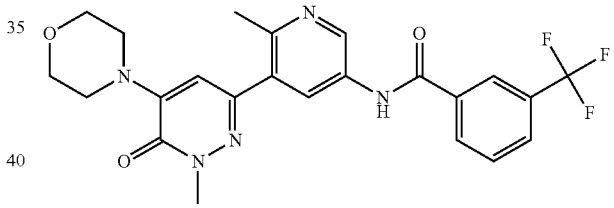

¹H NMR (400 MHz, <dmso>) δ ppm 2.56 (s, 3H) 3.40-3.54 (m, 4H) 3.62-3.77 (m, 7H) 6.72 (s, 1H) 7.75-7.87 (m, 1H) 8.00 (d, J=7.83 Hz, 1H) 8.25-8.31 (m, 2H) 8.33 (s, 1H) 8.99 (d, J=2.35 Hz, 1H) 10.84 (s, 1H). LCMS (m/z) (M+H)=474.3, Rt=0.71 min.

Example 652: 3-(cyanomethyl)-N-(4-methyl-3-(1-methyl-5-morpholino-6-oxo-1,6-dihydropyridazin-3-yl)phenyl)benzamide

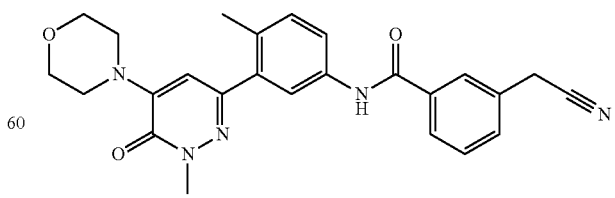

¹H NMR (400 MHz, <dmso>) δ ppm 2.28 (s, 3H) 3.43-3.49 (m, 4H) 3.67 (s, 3H) 3.68-3.75 (m, 4H) 4.13 (s, 2H) 6.58 (s, 1H) 7.26 (d, J=9.00 Hz, 1H) 7.52-7.58 (m, 2H)

7.70-7.78 (m, 2H) 7.85-7.95 (m, 2H) 10.32 (s, 1H). LCMS (m/z) (M+H)=444.3, Rt=0.76 min.

Example 653: 4-methyl-3-(1-methyl-5-morpholino-6-oxo-1,6-dihydropyridazin-3-yl)-N-(3-(trifluoromethyl)phenyl)benzamide

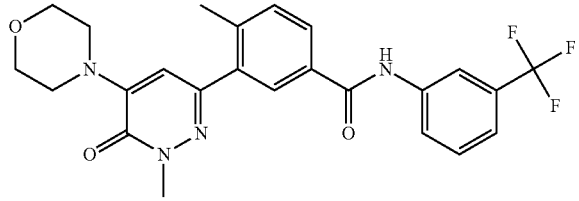 [SMILES: Cc1ccc(C(=O)Nc2cccc(C(F)(F)F)c2)cc1-c1cc(N2CCOCC2)c(=O)n(C)n1]

¹H NMR (400 MHz, <dmso>) δ ppm 2.34 (s, 3H) 3.43 (br. s., 4H) 3.64 (m 7H) 6.62 (s, 1H) 7.32-7.46 (m, 2H) 7.48-7.59 (m, 1H) 7.89 (d, J=8.22 Hz, 1H) 7.92 (s, 1H) 8.00 (d, J=7.83 Hz, 1H) 8.18 (s, 1H) 10.46 (s, 1H). LCMS (m/z) (M+H)=473.2, Rt=0.99 min.

Example 654: 2-(2-fluoropropan-2-yl)-N-(4-methyl-3-(1-methyl-5-morpholino-6-oxo-1,6-dihydropyridazin-3-yl)phenyl)isonicotinamide

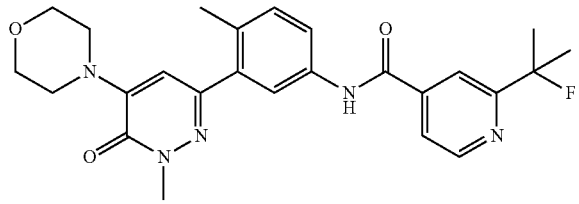 [SMILES: Cc1ccc(NC(=O)c2ccnc(C(C)(C)F)c2)cc1-c1cc(N2CCOCC2)c(=O)n(C)n1]

¹H NMR (400 MHz, <dmso>) δ ppm 1.66 (s, 3H) 1.72 (s, 3H) 2.29 (s, 3H) 3.39-3.49 (m, 4H) 3.67 (s, 3H) 3.68-3.72 (m, 4H) 6.59 (s, 1H) 7.29 (d, J=7.83 Hz, 1H) 7.68-7.78 (m, 2H) 7.81 (dd, J=5.09, 1.57 Hz, 1H) 8.01 (s, 1H) 8.74 (d, J=4.70 Hz, 1H) 10.57 (s, 1H). LCMS (m/z) (M+H)=466.1, Rt=0.86 min.

Example 655: 3-(difluoromethyl)-N-(4-methyl-3-(1-methyl-5-morpholino-6-oxo-1,6-dihydropyridazin-3-yl)phenyl)benzamide

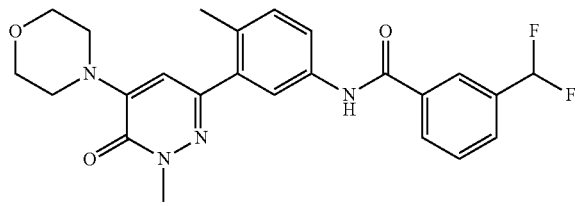 [SMILES: Cc1ccc(NC(=O)c2cccc(C(F)F)c2)cc1-c1cc(N2CCOCC2)c(=O)n(C)n1]

¹H NMR (400 MHz, <dmso>) δ ppm 2.23-2.33 (m, 3H) 3.37-3.52 (m, 4H) 3.61-3.77 (m, 7H) 6.59 (s, 1H) 6.95-7.32 (m, 2H) 7.60-7.71 (m, 1H) 7.71-7.80 (m, 2H) 8.07-8.18 (m, 2H) 10.41 (s, 1H). LCMS (m/z) (M+H)=455.0, Rt=0.86 min.

Example 656: 2-cyclopropyl-N-(4-methyl-3-(1-methyl-5-morpholino-6-oxo-1,6-dihydropyridazin-3-yl)phenyl)isonicotinamide

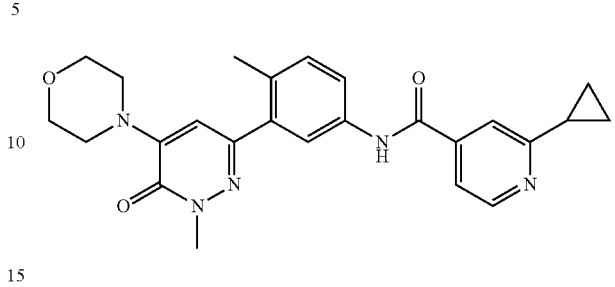

¹H NMR (400 MHz, <dmso>) δ ppm 0.91-1.07 (m, 4H) 2.20 (m, 1H) 2.28 (s, 3H) 3.36-3.51 (m, 4H) 3.68-3.73 (m, 7H) 6.58 (s, 1H) 7.25-7.30 (m, 1H) 7.47-7.55 (m, 1H) 7.59 (dd, J=5.09, 1.57 Hz, 1H) 7.68-7.79 (m, 2H) 8.57 (d, J=5.09 Hz, 1H) 10.46 (s, 1H). LCMS (m/z) (M+H)=466.0, Rt=0.67 min.

Example 657: 2-(1,1-difluoroethyl)-N-(4-methyl-3-(1-methyl-5-morpholino-6-oxo-1,6-dihydropyridazin-3-yl)phenyl)isonicotinamide

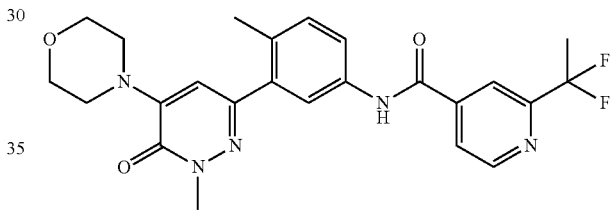

¹H NMR (400 MHz, <dmso>) δ ppm 2.03 (t, J=19.17 Hz, 3H) 2.29 (s, 3H) 3.40-3.48 (m, 4H) 3.67 (s, 3H) 3.68-3.72 (m, 4H) 6.59 (s, 1H) 7.29 (d, J=8.22 Hz, 1H) 7.70-7.78 (m, 2H) 8.02 (d, J=4.70 Hz, 1H) 8.18 (s, 1H) 8.86 (d, J=4.70 Hz, 1H) 10.65 (s, 1H). LCMS (m/z) (M+H)=470.1, Rt=0.87 min.

Example 658: N-(4-methyl-3-(1-methyl-5-morpholino-6-oxo-1,6-dihydropyridazin-3-yl)phenyl)-2-(trifluoromethyl)isonicotinamide

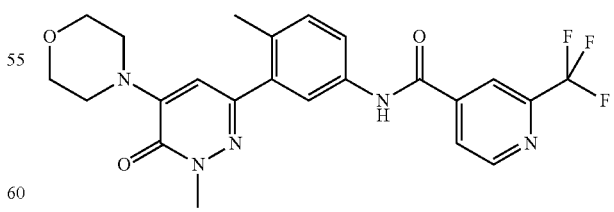

¹H NMR (400 MHz, <dmso>) δ ppm 2.29 (s, 3H) 3.43-3.52 (m, 4H) 3.67 (s, 3H) 3.68-3.76 (m, 4H) 6.59 (s, 1H) 7.31 (d, J=8.22 Hz, 1H) 7.69-7.79 (m, 2H) 8.18 (d, J=4.30 Hz, 1H) 8.36 (s, 1H) 8.98 (d, J=5.09 Hz, 1H) 10.69 (s, 1H). LCMS (m/z) (M+H)=474.2, Rt=0.93 min.

Example 659: 2-(1-cyanocyclopropyl)-N-(4-methyl-3-(1-methyl-5-morpholino-6-oxo-1,6-dihydro-pyridazin-3-yl)phenyl)isonicotinamide

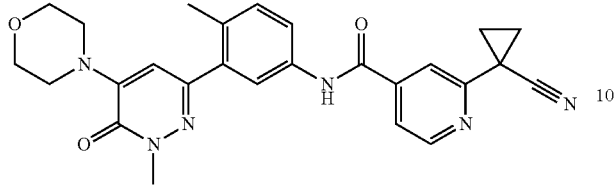

$^1$H NMR (400 MHz, <dmso>) δ ppm 1.69-1.77 (m, 2H) 1.84-1.90 (m, 2H) 2.29 (s, 3H) 3.38-3.50 (m, 4H) 3.67 (s, 3H) 3.68-3.72 (m, 4H) 6.59 (s, 1H) 7.29 (d, J=9.00 Hz, 1H) 7.67-7.76 (m, 2H) 7.78 (dd, J=5.09, 1.17 Hz, 1H) 7.92 (s, 1H) 8.69 (d, J=5.09 Hz, 1H) 10.58 (s, 1H). LCMS (m/z) (M+H)=471.1, Rt=0.84 min.

Example 660: 2-isopropyl-N-(4-methyl-3-(1-methyl-5-morpholino-6-oxo-1,6-dihydropyridazin-3-yl)phenyl)isonicotinamide

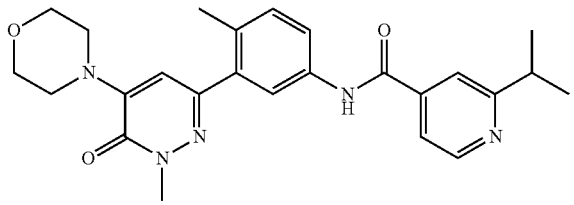 [SMILES: Cc1ccc(NC(=O)c2ccnc(C(C)C)c2)cc1-c1cc(N2CCOCC2)c(=O)n(C)n1]

$^1$H NMR (400 MHz, <D2O>) δ ppm 1.24-1.38 (m, 6H) 2.16 (s, 3H) 3.23-3.32 (m, 4H) 3.33 (m, 1H) 3.65 (s, 3H) 3.72-3.80 (m, 4H) 6.67 (s, 1H) 7.29 (d, J=8.22 Hz, 1H) 7.39-7.49 (m, 2H) 8.07 (dd, J=6.06, 1.37 Hz, 1H) 8.19 (s, 1H) 8.66 (d, J=6.26 Hz, 1H). LCMS (m/z) (M+H)=448.1, Rt=0.65 min.

Example 661: 3-((dimethylamino)methyl)-N-(4-methyl-3-(1-methyl-5-morpholino-6-oxo-1,6-dihydropyridazin-3-yl)phenyl)-5-(trifluoromethyl)benzamide

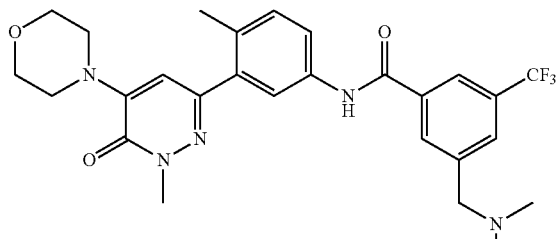

$^1$H NMR (400 MHz, <dmso>) δ ppm 2.29 (s, 3H) 2.77 (d, J=3.13 Hz, 6H) 3.43-3.47 (m, 4H) 3.64-3.76 (m, 7H) 4.46 (d, J=3.91 Hz, 2H) 6.59 (s, 1H) 7.30 (d, J=8.22 Hz, 1H) 7.70 (d, J=1.96 Hz, 1H) 7.75 (dd, J=8.22, 1.96 Hz, 1H) 8.12 (s, 1H) 8.36 (s, 1H) 8.45 (s, 1H) 10.54 (s, 1H). LCMS (m/z) (M+H)=530.3, Rt=0.69 min.

(S)-6-chloro-2-methyl-4-(3-methylmorpholino)pyridazin-3(2H)-one

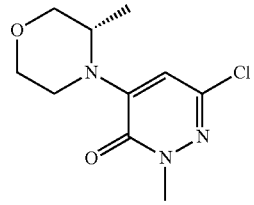 [SMILES: C[C@H]1COCCN1c1cc(Cl)nn(C)c1=O]

A mixture of 4-bromo-6-chloro-2-methylpyridazin-3(2H)-one (1.0 equiv.), (S)-3-methylmorpholine (1 eq) and potassium carbonate (6 eq) in NMP (0.15 M) was heated in an oil bath at 115° C. for 18 h. The reaction mixture was partitioned between EtOAc and water. The organics were washed with brine and dried over sodium sulfate. After concentration, the resulting (S)-6-chloro-2-methyl-4-(3-methylmorpholino)pyridazin-3(2H)-one was used in the next step without further purification. LCMS (m/z) (M+H)= 244.0, Rt=0.63 min.

Example 662: (S)-2-(2-fluoropropan-2-yl)-N-(4-methyl-3-(1-methyl-5-(3-methylmorpholino)-6-oxo-1,6-dihydropyridazin-3-yl)phenyl)isonicotinamide

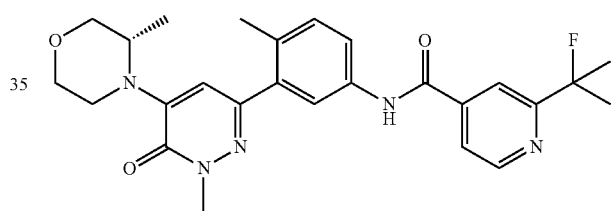

$^1$H NMR (400 MHz, <dmso>) δ ppm 1.09 (d, J=6.65 Hz, 3H) 1.66 (s, 3H) 1.69-1.76 (m, 3H) 2.28 (s, 3H) 3.22 (d, J=3.13 Hz, 1H) 3.44-3.72 (m, 9H) 6.51 (s, 1H) 7.28 (d, J=8.22 Hz, 1H) 7.67-7.78 (m, 2H) 7.81 (dd, J=4.89, 1.37 Hz, 1H) 8.01 (s, 1H) 8.73 (d, J=5.09 Hz, 1H) 10.56 (s, 1H). LCMS (m/z) (M+H)=480.2, Rt=0.86 min.

Example 663: (S)-2-(2-cyanopropan-2-yl)-N-(4-methyl-3-(1-methyl-5-(3-methylmorpholino)-6-oxo-1,6-dihydropyridazin-3-yl)phenyl)isonicotinamide

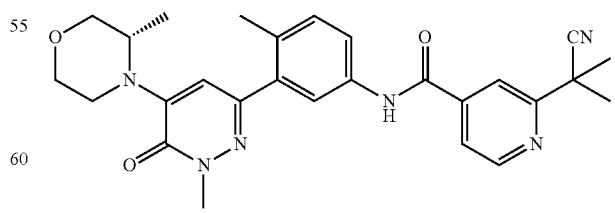

$^1$H NMR (400 MHz, <dmso>) δ ppm 1.09 (d, J=6.65 Hz, 3H) 1.75 (s, 6H) 2.28 (s, 3H) 3.17-3.28 (m, 1H) 3.47-3.63 (m, 4H) 3.66 (m, 3H) 3.68-3.72 (m, 1H) 3.85 (d, J=10.56 Hz, 2H) 6.51 (s, 1H) 7.29 (d, J=8.22 Hz, 1H) 7.70 (d, J=1.96 Hz, 1H) 7.74 (dd, J=8.22, 1.96 Hz, 1H) 7.85 (dd, J=5.09, 1.17 Hz, 1H) 8.00 (s, 1H) 8.79 (d, J=5.09 Hz, 1H) 10.55 (s, 1H). LCMS (m/z) (M+H)=487.2, Rt=0.85 min.

Example 664: (S)-2-(1,1-difluoroethyl)-N-(4-methyl-3-(1-methyl-5-(3-methylmorpholino)-6-oxo-1,6-dihydropyridazin-3-yl)phenyl)isonicotinamide

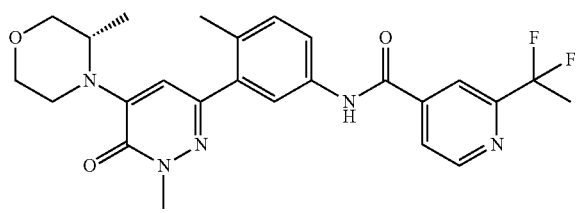 [SMILES: Cc1ccc(NC(=O)c2ccnc(C(C)(F)F)c2)cc1-c1cc(N2CCOC[C@@H]2C)c(=O)n(C)n1]

$^1$H NMR (400 MHz, <dmso>) δ ppm 1.22 (d, J=6.65 Hz, 3H) 2.16 (t, J=19.17 Hz, 3H) 2.37-2.44 (m, 3H) 3.30-3.40 (m, 1H) 3.64-3.86 (m, 8H) 3.98 (d, J=12.13 Hz, 1H) 6.64 (s, 1H) 7.36-7.48 (m, 1H) 7.79-7.94 (m, 2H) 8.15 (d, J=4.70 Hz, 1H) 8.30 (s, 1H) 8.99 (d, J=5.09 Hz, 1H) 10.77 (s, 1H). LCMS (m/z) (M+H)=484.2, Rt=0.87 min.

6-chloro-4-(2,2-dimethylmorpholino)-2-methyl-pyridazin-3(2H)-one

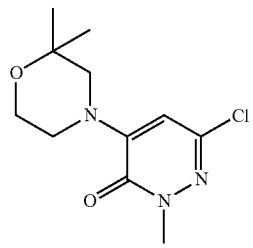 [SMILES: Cn1nc(Cl)cc(N2CCOC(C)(C)C2)c1=O]

6-Chloro-4-(2,2-dimethylmorpholino)-2-methyl-pyridazin-3(2H)-one was synthesized using the same method as (S)-6-chloro-2-methyl-4-(3-methylmorpholino)pyridazin-3(2H)-one. LCMS (m/z) (M+H)=258.0, Rt=0.69 min.

Example 665: N-(3-(5-(2,2-dimethylmorpholino)-1-methyl-6-oxo-1,6-dihydropyridazin-3-yl)-4-methyl-phenyl)-2-(2-fluoropropan-2-yl)isonicotinamide

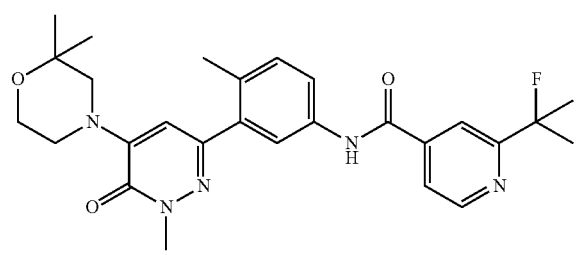 [SMILES: Cc1ccc(NC(=O)c2ccnc(C(C)(C)F)c2)cc1-c1cc(N2CCOC(C)(C)C2)c(=O)n(C)n1]

$^1$H NMR (400 MHz, <dmso>) δ ppm 1.18 (s, 6H) 1.66 (s, 3H) 1.69-1.76 (m, 3H) 2.28 (s, 3H) 3.33-3.41 (m, 4H) 3.66 (s, 3H) 3.70-3.76 (m, 2H) 6.57 (s, 1H) 7.24-7.32 (m, 1H) 7.71 (d, J=1.96 Hz, 1H) 7.73 (s, 1H) 7.81 (dd, J=4.89, 1.37 Hz, 1H) 8.01 (s, 1H) 8.74 (d, J=5.09 Hz, 1H) 10.56 (s, 1H). LCMS (m/z) (M+H)=494.3, Rt=0.90 min.

Example 666: 2-(2-cyanopropan-2-yl)-N-(3-(5-(2,2-dimethylmorpholino)-1-methyl-6-oxo-1,6-dihydro-pyridazin-3-yl)-4-methylphenyl)isonicotinamide

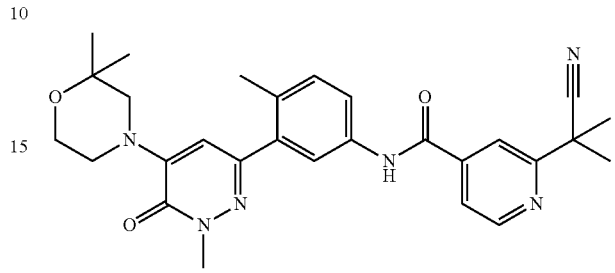

$^1$H NMR (400 MHz, <dmso>) δ ppm 1.18 (s, 6H) 1.75 (s, 6H) 2.28 (s, 3H) 3.38-3.40 (m, 4H) 3.66 (s, 3H) 3.69-3.76 (m, 2H) 6.57 (s, 1H) 7.26-7.33 (m, 1H) 7.69 (d, J=1.96 Hz, 1H) 7.73 (dd, J=8.22, 1.96 Hz, 1H) 7.85 (dd, J=5.09, 1.17 Hz, 1H) 7.99 (s, 1H) 8.79 (d, J=4.70 Hz, 1H) 10.55 (s, 1H). LCMS (m/z) (M+H)=501.2, Rt=0.89 min.

Example 667: 2-(1,1-difluoroethyl)-N-(3-(5-(2,2-dimethylmorpholino)-1-methyl-6-oxo-1,6-dihydro-pyridazin-3-yl)-4-methylphenyl)isonicotinamide

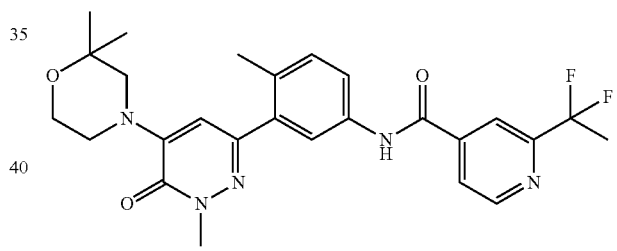

$^1$H NMR (400 MHz, <dmso>) δ ppm 1.18 (s, 6H) 2.03 (s, 3H) 2.28 (s, 3H) 3.37-3.40 (m, 4H) 3.66 (s, 3H) 3.69-3.76 (m, 2H) 6.57 (s, 1H) 7.29 (d, J=8.22 Hz, 1H) 7.72 (d, J=1.96 Hz, 1H) 7.75 (dd, J=8.22, 1.96 Hz, 1H) 8.02 (d, J=4.70 Hz, 1H) 8.17 (s, 1H) 8.86 (d, J=4.70 Hz, 1H) 10.64 (s, 1H). LCMS (m/z) (M+H)=498.3, Rt=0.89 min.

4-(3-oxa-8-azabicyclo[3.2.1]octan-8-yl)-6-chloro-2-methylpyridazin-3(2H)-one

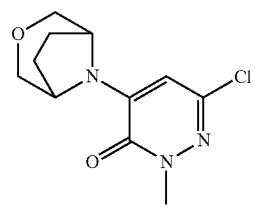 [SMILES: Cn1nc(Cl)cc(N2C3CCC2COC3)c1=O]

4-(3-oxa-8-azabicyclo[3.2.1]octan-8-yl)-6-chloro-2-methylpyridazin-3(2H)-one was synthesized using the same method as (S)-6-chloro-2-methyl-4-(3-methylmorpholino)pyridazin-3(2H)-one. LCMS (m/z) (M+H)=255.0, Rt=0.63 min.

Example 668: N-(3-(5-(3-oxa-8-azabicyclo[3.2.1]octan-8-yl)-1-methyl-6-oxo-1,6-dihydropyridazin-3-yl)-4-methylphenyl)-2-(2-fluoropropan-2-yl)isonicotinamide

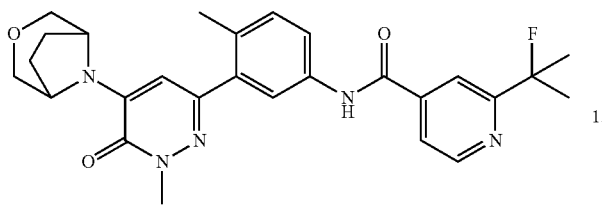

¹H NMR (400 MHz, <dmso>) δ ppm 1.66 (s, 3H) 1.71 (s, 3H) 1.85-1.97 (m, 4H) 2.29 (s, 3H) 3.48-3.51 (m, 4H) 3.60-3.63 (m, 2H) 3.65 (s, 3H) 6.57 (s, 1H) 7.27 (d, J=8.61 Hz, 1H) 7.70-7.77 (m, 2H) 7.80 (dd, J=5.09, 1.17 Hz, 1H) 8.01 (s, 1H) 8.73 (d, J=5.09 Hz, 1H) 10.55 (s, 1H). LCMS (m/z) (M+H)=492.1, Rt=0.87 min.

Example 669: N-(3-(5-(3-oxa-8-azabicyclo[3.2.1]octan-8-yl)-1-methyl-6-oxo-1,6-dihydropyridazin-3-yl)-4-methylphenyl)-2-(2-cyanopropan-2-yl)isonicotinamide

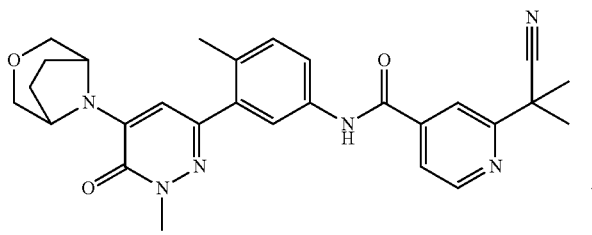

¹H NMR (400 MHz, <dmso>) δ ppm 1.75 (s, 6H) 1.85-1.98 (m, 4H) 2.26-2.31 (m, 3H) 3.48-3.54 (m, 4H) 3.58-3.63 (m, 2H) 3.65 (s, 3H) 6.57 (s, 1H) 7.28 (d, J=8.61 Hz, 1H) 7.69 (d, J=1.96 Hz, 1H) 7.74 (dd, J=8.22, 1.96 Hz, 1H) 7.85 (dd, J=5.09, 1.17 Hz, 1H) 7.99 (s, 1H) 8.78 (d, J=5.09 Hz, 1H) 10.54 (s, 1H). LCMS (m/z) (M+H)=499.1, Rt=0.86 min.

Example 670: N-(3-(5-(3-oxa-8-azabicyclo[3.2.1]octan-8-yl)-1-methyl-6-oxo-1,6-dihydropyridazin-3-yl)-4-methylphenyl)-2-(1,1-difluoroethyl)isonicotinamide

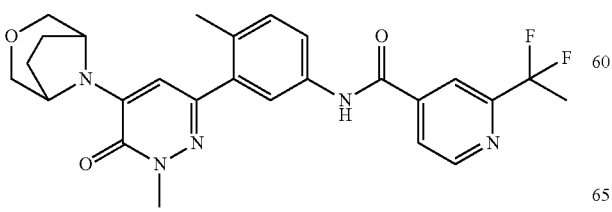

¹H NMR (400 MHz, <dmso>) δ ppm 1.95-2.10 (m, 4H) 2.10-2.23 (m, 3H) 2.43 (s, 3H) 3.58 (d, J=10.96 Hz, 4H) 3.70-3.84 (m, 5H) 6.70 (s, 1H) 7.42 (d, J=8.22 Hz, 1H) 7.79-7.94 (m, 2H) 8.15 (d, J=4.70 Hz, 1H) 8.31 (s, 1H) 9.00 (d, J=5.09 Hz, 1H) 10.77 (s, 1H). LCMS (m/z) (M+H)=496.2, Rt=0.88 min.

6-chloro-4-(3,3-dimethylmorpholino)-2-methylpyridazin-3(2H)-one

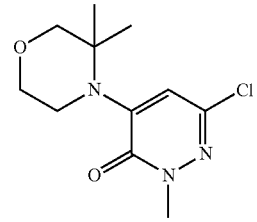 [SMILES: Cn1nc(Cl)cc(N2CCOCC2(C)C)c1=O]

6-chloro-4-(3,3-dimethylmorpholino)-2-methylpyridazin-3(2H)-one was synthesized using the same method as (S)-6-chloro-2-methyl-4-(3-methylmorpholino)pyridazin-3(2H)-one. LCMS (m/z) (M+H)=258.0, Rt=0.67 min.

Example 671: 2-(2-cyanopropan-2-yl)-N-(3-(5-(3,3-dimethylmorpholino)-1-methyl-6-oxo-1,6-dihydropyridazin-3-yl)-4-methylphenyl)isonicotinamide

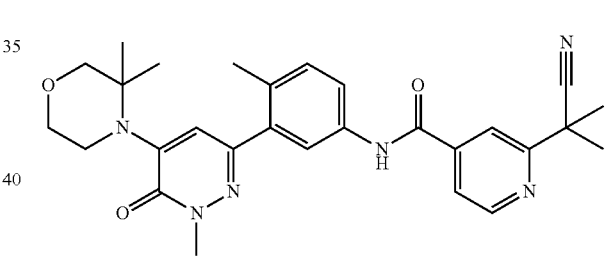

¹H NMR (400 MHz, <dmso>) δ ppm 1.39 (s, 6H) 1.88 (s, 6H) 2.44 (s, 3H) 3.49 (br. s., 4H) 3.80 (s, 3H) 3.84 (t, J=4.50 Hz, 2H) 6.92 (s, 1H) 7.44 (d, J=9.00 Hz, 1H) 7.82-7.90 (m, 2H) 7.98 (dd, J=5.09, 1.17 Hz, 1H) 8.12 (s, 1H) 8.92 (d, J=5.09 Hz, 1H) 10.71 (s, 1H). LCMS (m/z) (M+H)=501.2, Rt=0.88 min.

Synthesis of (R)-6-chloro-2-methyl-4-(3-methylmorpholino)pyridazin-3(2H)-one

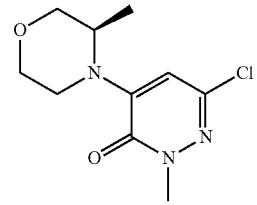 [SMILES: C[C@@H]1COCCN1c1cc(Cl)nn(C)c1=O]

To a solution of 4-bromo-6-chloro-2-methylpyridazin-3(2H)-one (1.0 equiv.) in DMF (0.2 M) was added Huenig's Base (1.0 equiv.) and (R)-3-methylmorpholine (1.0 equiv.) at room temperature. The reaction was heated to 130° C. for 5 hours. Cooled to room temperature, partitioned between water and ethyl acetate, the organic phase was dried with sodium sulfate, filtered and concentrated. The crude material was used for the next step without further purification. LCMS (m/z) (M+H)=244.0, Rt=0.63 min.

Example 672: (R)-2-(2-cyanopropan-2-yl)-N-(4-methyl-3-(1-methyl-5-(3-methylmorpholino)-6-oxo-1,6-dihydropyridazin-3-yl)phenyl)isonicotinamide

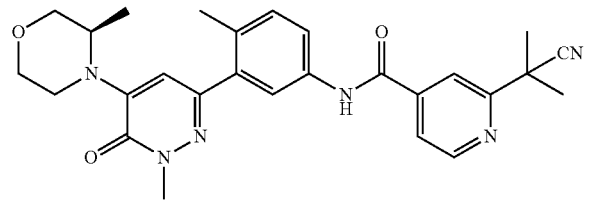 [SMILES: Cc1ccc(NC(=O)c2ccnc(C(C)(C)C#N)c2)cc1-c1cc(N2CCOC[C@H]2C)c(=O)n(C)n1]

¹H NMR (400 MHz, <cd3od>) δ ppm 1.21 (d, J=7.04 Hz, 3H) 1.81 (s, 6H) 2.35 (s, 3H) 3.34-3.55 (m, 2H) 3.63-3.76 (m, 2H) 3.79 (s, 3H) 3.87 (dd, J=11.35, 2.74 Hz, 1H) 3.94 (d, J=10.56 Hz, 1H) 6.62 (s, 1H) 7.31 (d, J=8.22 Hz, 1H) 7.66 (dd, J=8.22, 2.35 Hz, 1H) 7.76 (d, J=2.35 Hz, 1H) 7.81 (dd, J=4.89, 1.37 Hz, 1H) 8.06 (s, 1H) 8.76 (d, J=5.09 Hz, 1H). LCMS (m/z) (M+H)=487.2, Rt=0.85 min.

Example 673: (R)-2-(2-fluoropropan-2-yl)-N-(4-methyl-3-(1-methyl-5-(3-methylmorpholino)-6-oxo-1,6-dihydropyridazin-3-yl)phenyl)isonicotinamide

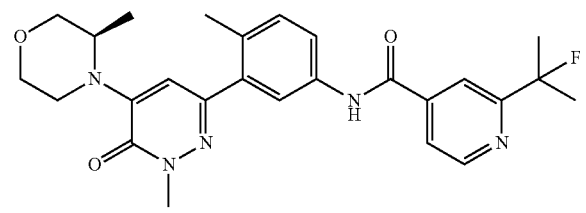 [SMILES: Cc1ccc(NC(=O)c2ccnc(C(C)(C)F)c2)cc1-c1cc(N2CCOC[C@H]2C)c(=O)n(C)n1]

¹H NMR (400 MHz, <cd3od>) δ ppm 1.21 (d, J=7.04 Hz, 3H) 1.65-1.79 (m, 6H) 2.35 (s, 3H) 3.36-3.50 (m, 1H) 3.64-3.76 (m, 2H) 3.79 (s, 3H) 3.87 (dd, J=11.54, 2.93 Hz, 1H) 3.94 (d, J=13.69 Hz, 1H) 6.62 (s, 1H) 7.31 (d, J=8.22 Hz, 1H) 7.66 (dd, J=8.22, 2.35 Hz, 1H) 7.73-7.85 (m, 2H) 8.06 (s, 1H) 8.70 (d, J=5.09 Hz, 1H). LCMS (m/z) (M+H)=480.2, Rt=0.86 min.

Example 674: (R)-2-(1,1-difluoroethyl)-N-(4-methyl-3-(1-methyl-5-(3-methylmorpholino)-6-oxo-1,6-dihydropyridazin-3-yl)phenyl)isonicotinamide

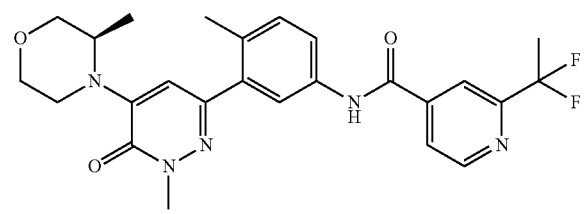 [SMILES: Cc1ccc(NC(=O)c2ccnc(C(C)(F)F)c2)cc1-c1cc(N2CCOC[C@H]2C)c(=O)n(C)n1]

¹H NMR (400 MHz, <cd3od>) δ ppm 1.21 (d, J=6.65 Hz, 3H) 2.03 (t, J=18.59 Hz, 3H) 2.35 (s, 3H) 3.40 (dd, J=11.74, 3.52 Hz, 1H) 3.47 (br. s., 1H) 3.62-3.76 (m, 2H) 3.79 (s, 3H) 3.87 (dd, J=11.35, 3.13 Hz, 1H) 3.94 (d, J=10.96 Hz, 1H) 6.62 (s, 1H) 7.31 (d, J=8.22 Hz, 1H) 7.67 (dd, J=8.22, 1.96 Hz, 1H) 7.77 (d, J=2.35 Hz, 1H) 7.96 (d, J=4.30 Hz, 1H) 8.17 (s, 1H) 8.80 (d, J=5.09 Hz, 1H). LCMS (m/z) (M+H)=484.2, Rt=0.88 min.

Synthesis of 6-(5-amino-2-methylphenyl)-2-methyl-4-(tetrahydro-2H-pyran-4-yl)pyridazin-3(2H)-one

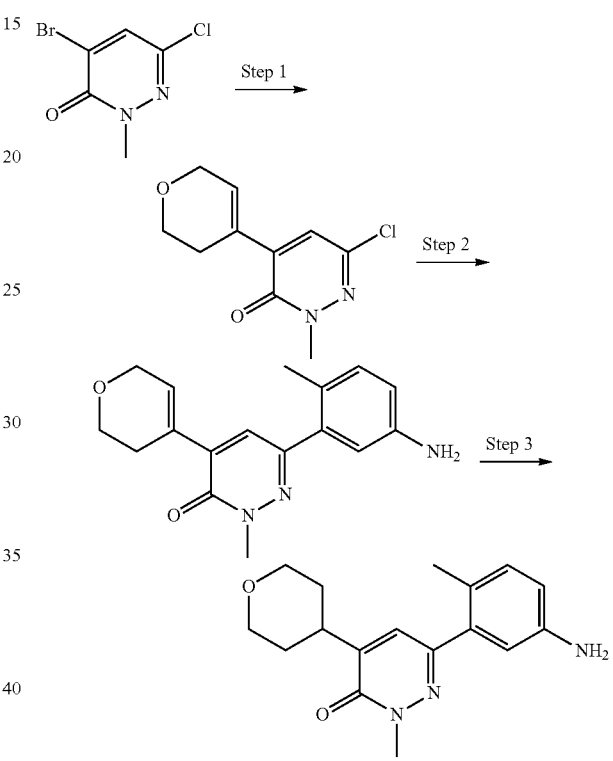

Step 1:

To a solution of 4-bromo-6-chloro-2-methylpyridazin-3(2H)-one (1.0 equiv.) in DME (0.2 M) was added 2-(3,6-dihydro-2H-pyran-4-yl)-4,4,5,5-tetramethyl-1,3,2-dioxaborolane (1.0 equiv.) and PdCl₂(dppf).CH₂Cl₂ adduct (0.1 equiv.), followed by 2M Na₂CO₃ (3.0 equiv.). The reaction was heated to 80° C. for 30 min at which time LC/MS indicated completion. The solution was partitioned between water and ethyl acetate, the organic phase was dried with sodium sulfate, filtered and concentrated to give 6-chloro-4-(3,6-dihydro-2H-pyran-4-yl)-2-methylpyridazin-3(2H)-one. The crude material was used for the next step without further purification. LCMS (m/z) (M+H)=227.0, Rt=0.61 min.

Step 2:

To a solution of 6-chloro-4-(3,6-dihydro-2H-pyran-4-yl)-2-methylpyridazin-3(2H)-one (1.0 equiv.) in DME (0.15 M) was added 4-methyl-3-(4,4,5,5-tetramethyl-1,3,2-dioxaborolan-2-yl)aniline (1.0 equiv.) and PdCl₂(dppf).CH₂Cl₂ adduct (0.1 equiv.), followed by 2M Na₂CO₃ (3.0 equiv.). The solution was heated to 100° C. for 3 hours. Cooled to room temperature, partitioned between water and ethyl acetate, the organic phase was washed with water, dried with sodium sulfate, filtered and concentrated under vacuo. The crude material was purified via silica gel column chromatography eluting with 0-100% ethyl acetate in heptanes. The pure fractions were concentrated under vacuo to yield 6-(5-amino-2-methylphenyl)-4-(3,6-dihydro-2H-pyran-4-yl)-2-methylpyridazin-3(2H)-one as the desired product in 56% yield. LCMS (m/z) (M+H)=298.0, Rt=0.49 min.

Step 3:

To a degassed solution of 6-(5-amino-2-methylphenyl)-4-(3,6-dihydro-2H-pyran-4-yl)-2-methylpyridazin-3(2H)-one (1.0 equiv.) in ethanol (0.06 M) was added Pd/C (0.1 equiv.) and the reaction was stirred under a hydrogen balloon. After 2 hours, the reaction was filtered and concentrated to dryness under vacuo. Obtained 6-(5-amino-2-methylphenyl)-2-methyl-4-(tetrahydro-2H-pyran-4-yl)pyridazin-3(2H)-one as the desired product in 78% yield. LCMS (m/z) (M+H)=300.1, Rt=0.46 min.

Example 675: 2-(2-cyanopropan-2-yl)-N-(4-methyl-3-(1-methyl-6-oxo-5-(tetrahydro-2H-pyran-4-yl)-1,6-dihydropyridazin-3-yl)phenyl)isonicotinamide

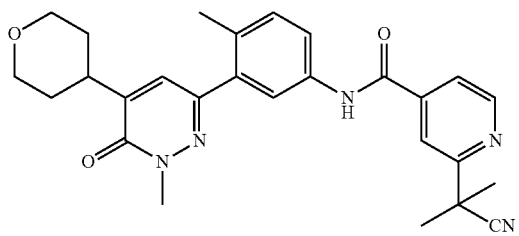 [SMILES: Cc1ccc(NC(=O)c2ccnc(C(C)(C)C#N)c2)cc1-c1cc(C2CCOCC2)c(=O)n(C)n1]

¹H NMR (400 MHz, <cd3od>) δ ppm 1.64-1.76 (m, 2H) 1.81 (s, 6H) 1.83-1.91 (m, 2H) 2.37 (s, 3H) 3.10-3.22 (m, 1H) 3.59 (td, J=11.74, 1.96 Hz, 2H) 3.85 (s, 3H) 4.05 (dd, J=11.15, 3.72 Hz, 2H) 7.33 (d, J=8.22 Hz, 1H) 7.42 (s, 1H) 7.69 (dd, J=8.41, 2.15 Hz, 1H) 7.76-7.83 (m, 2H) 8.07 (s, 1H) 8.76 (d, J=4.70 Hz, 1H). LCMS (m/z) (M+H)=472.2, Rt=0.84 min.

Example 676: 2-(2-fluoropropan-2-yl)-N-(4-methyl-3-(1-methyl-6-oxo-5-(tetrahydro-2H-pyran-4-yl)-1,6-dihydropyridazin-3-yl)phenyl)isonicotinamide

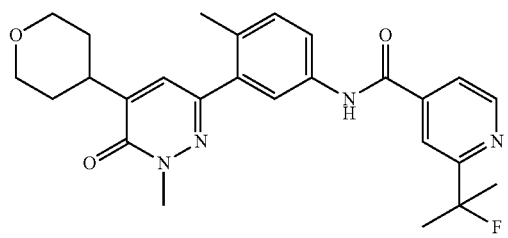 [SMILES: Cc1ccc(NC(=O)c2ccnc(C(C)(C)F)c2)cc1-c1cc(C2CCOCC2)c(=O)n(C)n1]

¹H NMR (400 MHz, <cd3od>) δ ppm 1.61-1.80 (m, 8H) 1.87 (d, J=11.74 Hz, 2H) 2.37 (s, 3H) 3.08-3.23 (m, 1H) 3.53-3.65 (m, 2H) 3.85 (s, 3H) 4.05 (dd, J=11.35, 3.91 Hz, 2H) 7.33 (d, J=8.61 Hz, 1H) 7.42 (s, 1H) 7.70 (dd, J=8.41, 2.15 Hz, 1H) 7.77-7.86 (m, 2H) 8.10 (s, 1H) 8.71 (d, J=5.09 Hz, 1H). LCMS (m/z) (M+H)=465.2, Rt=0.85 min.

Synthesis of 6-(5-amino-2-methylpyridin-3-yl)-2-methyl-4-morpholinopyridazin-3(2H)-one

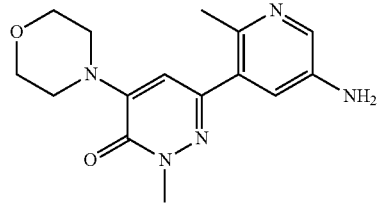 [SMILES: Cc1ncc(N)cc1-c1cc(N2CCOCC2)c(=O)n(C)n1]

To a solution of 6-chloro-2-methyl-4-morpholinopyridazin-3(2H)-one (1.0 equiv.) in DME (0.26 M) was added 6-methyl-5-(4,4,5,5-tetramethyl-1,3,2-dioxaborolan-2-yl)pyridin-3-amine (1.0 equiv.), PdCl₂(dppf).CH₂Cl₂ adduct (0.5 equiv.) and 2M Na₂CO₃ (7.0 equiv.). The solution was heated to 120° C. for 2 hours, at which point LC/MS indicated the reaction was complete. Diluted with ethyl acetate and water, the aqueous layer was separated and extracted with ethyl acetate two more times. The organic layers were combined, dried over magnesium sulfate, and concentrated invacuo to yield a brown oil. The residue was further purified via flash column chromatography eluting with 100% heptanes to 50% ethyl acetate and heptanes to 80% ethyl acetate and heptanes. The pure fractions were concentrated to yield 6-(5-amino-2-methylpyridin-3-yl)-2-methyl-4-morpholinopyridazin-3(2H)-one as a brown residue in 99% yield. LCMS (m/z) (M+H)=302.0, Rt=0.38 min.

Example 677: 2-(2-fluoropropan-2-yl)-N-(6-methyl-5-(1-methyl-5-morpholino-6-oxo-1,6-dihydropyridazin-3-yl)pyridin-3-yl)isonicotinamide

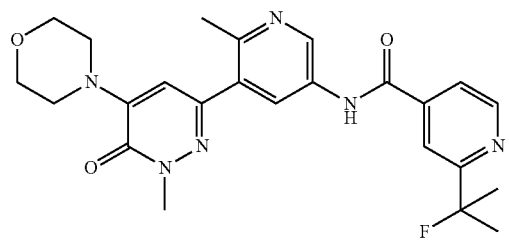 [SMILES: Cc1ncc(NC(=O)c2ccnc(C(C)(C)F)c2)cc1-c1cc(N2CCOCC2)c(=O)n(C)n1]

¹H NMR (400 MHz, <cd3od>) δ ppm 1.53-1.89 (m, 6H) 2.73 (s, 3H) 3.41-3.61 (m, 4H) 3.71-3.93 (m, 7H) 6.77 (s, 1H) 7.82 (dd, J=5.09, 1.57 Hz, 1H) 8.12 (s, 1H) 8.55 (d, J=2.35 Hz, 1H) 8.74 (d, J=5.09 Hz, 1H) 9.19 (d, J=2.35 Hz, 1H). LCMS (m/z) (M+H)=467.2, Rt=0.61 min.

Example 678: 2-(1,1-difluoroethyl)-N-(6-methyl-5-(1-methyl-5-morpholino-6-oxo-1,6-dihydropyridazin-3-yl)pyridin-3-yl)isonicotinamide

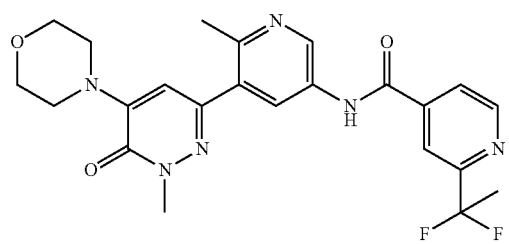 [SMILES: Cc1ncc(NC(=O)c2ccnc(C(C)(F)F)c2)cc1-c1cc(N2CCOCC2)c(=O)n(C)n1]

¹H NMR (400 MHz, <cd3od>) δ ppm 1.94 (t, J=18.59 Hz, 3H) 2.48 (s, 3H) 3.36-3.46 (m, 4H) 3.67-3.82 (m, 7H) 6.64 (s, 1H) 7.90 (d, J=4.30 Hz, 1H) 8.12 (s, 1H) 8.19 (d, J=2.35 Hz, 1H) 8.68-8.78 (m, 1H). LCMS (m/z) (M+H)=471.2, Rt=0.61 min.

Example 679: 2-(1,1-difluoropropyl)-N-(6-methyl-5-(1-methyl-5-morpholino-6-oxo-1,6-dihydro-pyridazin-3-yl)pyridin-3-yl)isonicotinamide

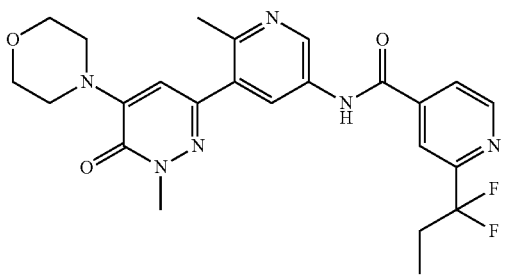 [SMILES: CCC(F)(F)c1cc(C(=O)Nc2cnc(C)c(-c3cc(N4CCOCC4)c(=O)n(C)n3)c2)ccn1]

¹H NMR (400 MHz, <cd3od>) δ ppm 1.01 (t, J=7.43 Hz, 3H) 2.22-2.53 (m, 2H) 2.73 (s, 3H) 3.44-3.61 (m, 4H) 3.76-3.98 (m, 7H) 6.76 (s, 1H) 8.01 (d, J=3.91 Hz, 1H) 8.22 (s, 1H) 8.53 (d, J=2.35 Hz, 1H) 8.86 (d, J=5.09 Hz, 1H) 9.17 (d, J=2.35 Hz, 1H). LCMS (m/z) (M+H)=485.2, Rt=0.64 min.

Example 680: 2-(difluoromethyl)-N-(6-methyl-5-(1-methyl-5-morpholino-6-oxo-1,6-dihydropyridazin-3-yl)pyridin-3-yl)isonicotinamide

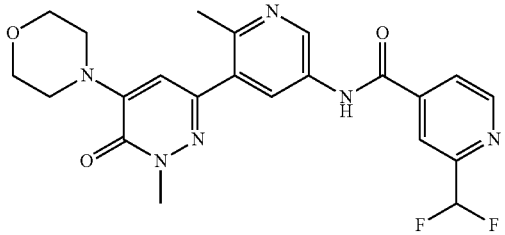 [SMILES: Cc1ncc(NC(=O)c2ccnc(C(F)F)c2)cc1-c1cc(N2CCOCC2)c(=O)n(C)n1]

¹H NMR (400 MHz, <cd3od>) δ ppm 2.73 (s, 3H) 3.42-3.62 (m, 4H) 3.74-3.92 (m, 7H) 6.65-7.05 (m, 2H) 8.06 (d, J=5.09 Hz, 1H) 8.23 (s, 1H) 8.53 (d, J=2.35 Hz, 1H) 8.88 (d, J=5.09 Hz, 1H) 9.18 (d, J=2.35 Hz, 1H). LCMS (m/z) (M+H)=457.1, Rt=0.56 min.

Example 681: 3-(difluoromethyl)-N-(6-methyl-5-(1-methyl-5-morpholino-6-oxo-1,6-dihydropyridazin-3-yl)pyridin-3-yl)benzamide

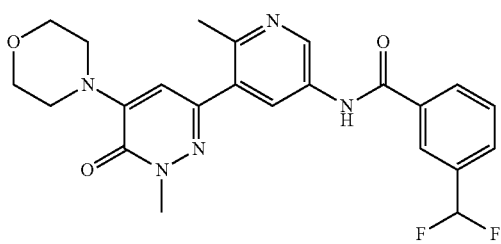 [SMILES: Cc1ncc(NC(=O)c2cccc(C(F)F)c2)cc1-c1cc(N2CCOCC2)c(=O)n(C)n1]

¹H NMR (400 MHz, <cd3od>) δ ppm 2.74 (s, 3H) 3.46-3.61 (m, 4H) 3.76-3.88 (m, 7H) 6.66-7.11 (m, 2H) 7.58-7.76 (m, 1H) 7.82 (d, J=7.83 Hz, 1H) 8.08-8.27 (m, 2H) 8.56 (d, J=2.35 Hz, 1H) 9.21 (d, J=2.35 Hz, 1H). LCMS (m/z) (M+H)=456.2, Rt=0.64 min.

Example 682: 2-cyclopropyl-N-(6-methyl-5-(1-methyl-5-morpholino-6-oxo-1,6-dihydropyridazin-3-yl)pyridin-3-yl)isonicotinamide

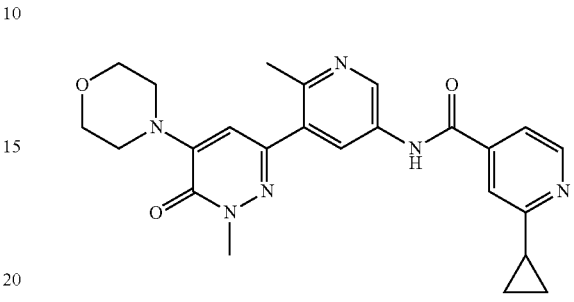

¹H NMR (400 MHz, <cd3od>) δ ppm 1.02-1.37 (m, 4H) 2.08-2.38 (m, 1H) 2.74 (s, 3H) 3.49-3.61 (m, 4H) 3.75-3.95 (m, 7H) 6.77 (s, 1H) 7.71-7.94 (m, 2H) 8.47-8.73 (m, 2H) 9.20 (d, J=2.35 Hz, 1H). LCMS (m/z) (M+H)=447.2, Rt=0.48 min.

Example 683: 2-(1-cyanocyclopropyl)-N-(6-methyl-5-(1-methyl-5-morpholino-6-oxo-1,6-dihydro-pyridazin-3-yl)pyridin-3-yl)isonicotinamide

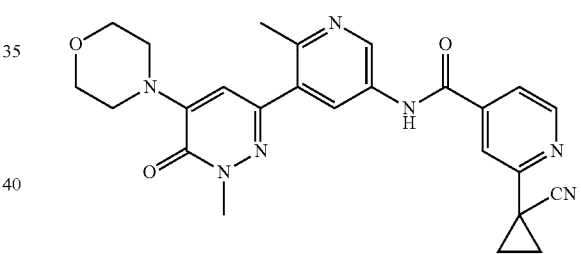

¹H NMR (400 MHz, <cd3od>) δ ppm 1.71-1.98 (m, 4H) 2.57 (s, 3H) 3.43-3.62 (m, 4H) 3.74-3.96 (m, 8H) 6.73 (s, 1H) 7.74 (d, J=5.09 Hz, 1H) 8.10 (s, 1H) 8.27 (d, J=2.35 Hz, 1H) 8.66 (d, J=5.09 Hz, 1H) 8.83 (d, J=2.35 Hz, 1H). LCMS (m/z) (M+H)=472.2, Rt=0.60 min.

Synthesis of 4-(5-amino-2-methylpyridin-3-yl)-2-morpholinobenzonitrile

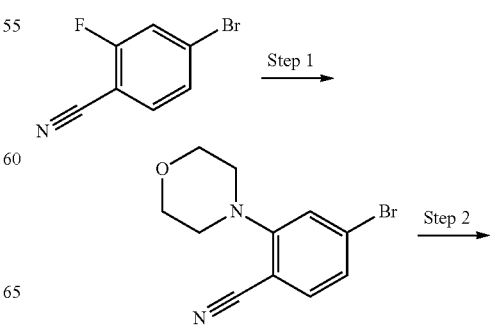

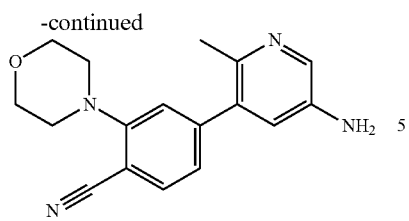

Step 1:

A 0.5M solution of 4-bromo-2-fluorobenzonitrile (1.00 equiv.) in acetonitrile was treated with morpholine (1.10 equiv.), and DIEA (2.00 equiv.). The mixture was stirred at 90° C. for 4 hr. The cooled reaction mixture was diluted with four volumes of water. The precipitate was collected by vacuum filtration and air-dried to give 4-bromo-2-morpholinobenzonitrile as a peach solid in 82% yield. LCMS (m/z) (M+H)=266.9/268.9, Rt=0.90 min.

Step 2:

To a 0.15M solution of 4-bromo-2-morpholinobenzonitrile (1.00 equiv.) in DME was added 6-methyl-5-(4,4,5,5-tetramethyl-1,3,2-dioxaborolan-2-yl)pyridin-3-amine (1.40 equiv.), PdCl2(dppf).CH2Cl2 adduct (0.10 equiv.), and 2M aqueous sodium carbonate (3.00 equiv.). The reaction mixture was irradiated at 120° C. for 10 min in the microwave. The cooled reaction mixture was diluted with 2:1 DCM:MeOH and filtered. The filtrate was concentrated and purified by flash chromatography over silica gel (ethyl acetate with 0-15% methanol gradient) to give 4-(5-amino-2-methylpyridin-3-yl)-2-morpholinobenzonitrile in 87.0% yield as a tan solid. LCMS (m/z) (M+H)=295.1, Rt=0.52 min.

The compounds listed below were prepared using methods similar to those described for the preparation of Example 171 using the appropriate starting materials.

Example 684: N-(5-(4-cyano-3-morpholinophenyl)-6-methylpyridin-3-yl)-3-trifluoromethyl)benzamide

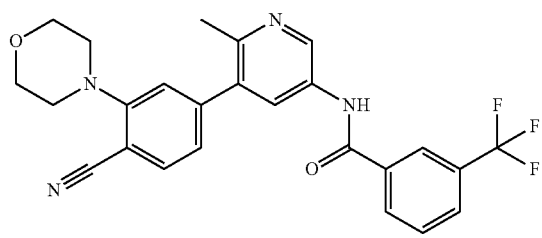 [SMILES: Cc1ncc(NC(=O)c2cccc(C(F)(F)F)c2)cc1-c1ccc(C#N)c(N2CCOCC2)c1]

$^1$H NMR (400 MHz, <cd3od>) δ ppm 2.62 (s, 3H) 3.30 (d, J=4.60 Hz, 4H) 3.88-3.94 (m, 4H) 7.19-7.27 (m, 2H) 7.76-7.86 (m, 2H) 7.97 (d, J=7.87 Hz, 1H) 8.29 (d, J=7.82 Hz, 1H) 8.35 (s, 1H) 8.40 (d, J=2.40 Hz, 1H) 9.23 (d, J=2.40 Hz, 1H). LCMS (m/z) (M+H)=467.1, Rt=0.77 min.

Example 685: N-(5-(4-cyano-3-morpholinophenyl)-6-methylpyridin-3-yl)-3-((dimethylamino)methyl)-5-(trifluoromethyl)benzamide

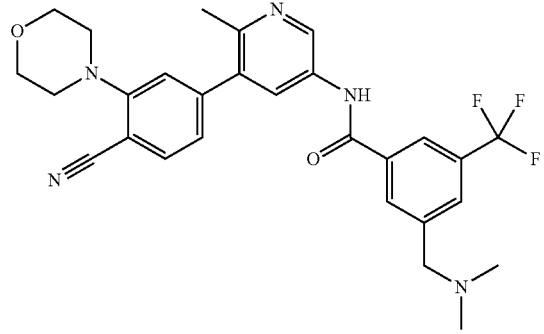 [SMILES: Cc1ncc(NC(=O)c2cc(CN(C)C)cc(C(F)(F)F)c2)cc1-c1ccc(C#N)c(N2CCOCC2)c1]

$^1$H NMR (400 MHz, <cd3od>) δ ppm 2.57 (s, 3H) 2.95 (s, 6H) 3.26-3.31 (m, 4H) 3.84-3.97 (m, 4H) 4.54 (s, 2H) 7.16-7.25 (m, 2H) 7.81 (d, J=7.83 Hz, 1H) 8.16 (s, 1H) 8.31 (d, J=2.35 Hz, 1H) 8.45 (s, 1H) 8.51 (s, 1H) 9.08 (d, J=2.35 Hz, 1H). LCMS (m/z) (M+H)=524.2, Rt=0.63 min.

Example 686: N-(5-(4-cyano-3-morpholinophenyl)-6-methylpyridin-3-yl)-2-isopropylisonicotinamide

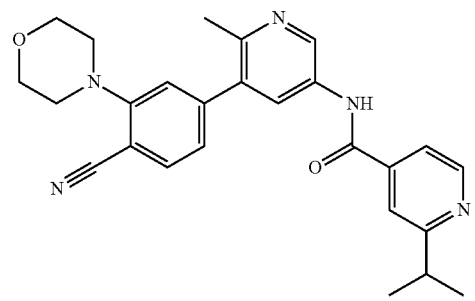 [SMILES: Cc1ncc(NC(=O)c2ccnc(C(C)C)c2)cc1-c1ccc(C#N)c(N2CCOCC2)c1]

$^1$H NMR (400 MHz, <cd3od>) δ ppm 1.42 (d, J=6.65 Hz, 6H) 2.63 (s, 3H) 3.23-3.31 (m, 5H) 3.86-3.96 (m, 4H) 7.22 (d, J=8.22 Hz, 1H) 7.25 (s, 1H) 7.83 (d, J=7.83 Hz, 1H) 7.92 (dd, J=5.28, 1.37 Hz, 1H) 8.03 (s, 1H) 8.40 (d, J=2.35 Hz, 1H) 8.76 (d, J=5.09 Hz, 1H) 9.23 (d, J=1.96 Hz, 1H). LCMS (m/z) (M+H)=442.2, Rt=0.59 min.

Example 687: N-(6-methyl-5-(4-(methylsulfonyl)-3-morpholinophenyl)pyridin-3-yl)-3-(trifluoromethyl)benzamide

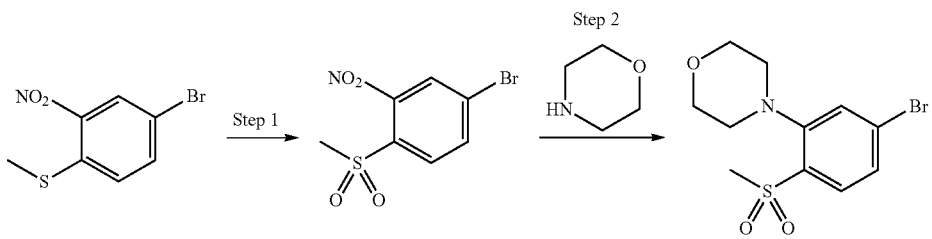

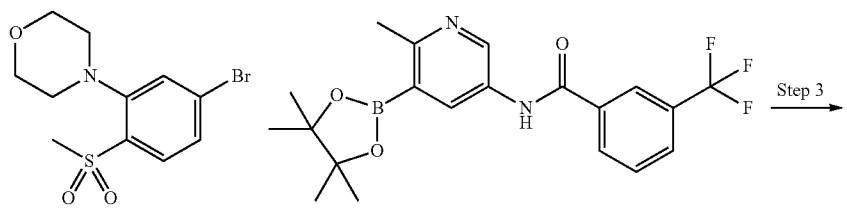

Step 3 →

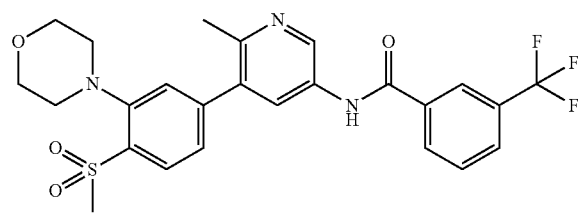

Step 1:

A solution of (4-bromo-2-nitrophenyl)(methyl)sulfane (1.0 equiv.) and mCPBA (3.0 equiv.) in DCM (0.13 M) was stirred at RT overnight. The reaction mix was partitioned between 1N NaOH solution and EtOAc. The organic layer was isolated, washed twice with 1N NaOH solution, dried over MgSO$_4$, filtered and concentrated. The crude 4-bromo-1-(methylsulfonyl)-2-nitrobenzene will be used as is in the next step.

Step 2:

Morpholine (3.0 equiv.) was added to a solution of 4-bromo-1-(methylsulfonyl)-2-nitrobenzene (1.0 equiv.) in DME (Volume: 15 mL) and the reaction mix was stirred at RT overnight. The crude was partitioned in H$_2$O/EtOAc. The organic layer was isolated, dried over Na$_2$SO$_4$, filtered and concentrated and purified on silicagel column using heptane to 100% EtOAc in heptane giving 4-(5-bromo-2-(methylsulfonyl)phenyl)morpholine in 8.7% yield. LCMS (m/z) (M+H)=321, Rt=0.75 min.

Step 3:

PdCl$_2$(dppf).CH$_2$Cl$_2$ adduct (0.1 equiv.) was added to a solution of 4-(5-bromo-2-(methylsulfonyl)phenyl)morpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.) and 2M Na$_2$CO$_3$ solution (3.0 equiv.) in DME (0.08) and the system was flushed with nitrogen. The vial was sealed and the mixture was irradiated at 120° C. for 20 min in the microwave. The solvent was removed under vacuum and the residue was partitioned in EtOAC/H$_2$O. The organic layer was isolated and the aqueous layer was back extracted twice with EtOAc. The combined organics were dried over Na$_2$SO$_4$, filtered and concentrated. The residue was taken in DMSO and purified by HPLC to give N-(6-methyl-5-(4-(methylsulfonyl)-3-morpholinophenyl)pyridin-3-yl)-3-(trifluoromethyl)benzamide as the TFA salt in 22% yield. LCMS (m/z) (M+H)=520, Rt=0.76 min.

Example 691: N-(3-(4-(3-oxa-8-azabicyclo[3.2.1]octan-8-yl)-1-methyl-6-oxo-1,6-dihydropyridin-2-yl)-4-methylphenyl)-2-(1,1-difluoroethyl)isonicotinamide

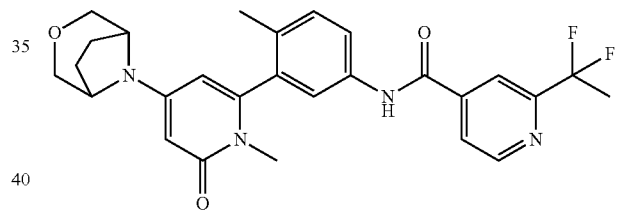

$^1$H NMR (400 MHz, <dmso>) δ ppm 1.92 (br. s., 4H) 2.03 (s, 3H) 2.12 (s, 3H) 2.99 (s, 3H) 3.42 (d, J=10.96 Hz, 2H) 3.59-3.63 (m, 2H) 4.23 (br. s., 2H) 5.62 (d, J=2.35 Hz, 1H) 6.00 (d, J=1.96 Hz, 1H) 7.36 (d, J=8.22 Hz, 1H) 7.68 (d, J=1.56 Hz, 1H) 7.79 (dd, J=8.22, 1.96 Hz, 1H) 8.01 (d, J=5.09 Hz, 1H) 8.16 (s, 1H) 8.87 (d, J=4.70 Hz, 1H) 10.70 (s, 1H). LCMS (m/z) (M+H)=495.3, Rt=0.79 min.

Synthesis of 4-(3-oxa-8-azabicyclo[3.2.1]octan-8-yl)-6-chloro-1-methylpyridin-2(1H)-one

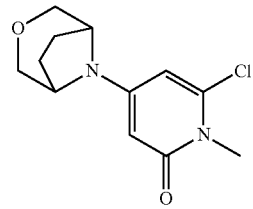 [SMILES: Cn1c(Cl)cc(N2C3CCC2COC3)cc1=O]

A solution of 4-bromo-6-chloro-1-methylpyridin-2(1H)-one (1.0 equiv.), 3-oxa-8-azabicyclo[3.2.1]octane (1.3 equiv.) and DIEA (2.5 equiv.) in DMF (2.8 M) was heated to 110° C. for 18 h. The reaction mixture was partitioned between EtOAc and water, washed with brine and dried over Na₂SO₄. After concentration the crude product was purified by normal phase chromatography to give 4-(3-oxa-8-azabicyclo[3.2.1]octan-8-yl)-6-chloro-1-methylpyridin-2(1H)-one in 14% yield. LCMS (m/z) (M+H)=255.1, Rt=0.52 min.

Example 694: Synthesis of N-(3-(2-(ethylamino)-6-morpholinopyrimidin-4-yl)-4-methylphenyl)-2-(trifluoromethyl)isonicotinamide

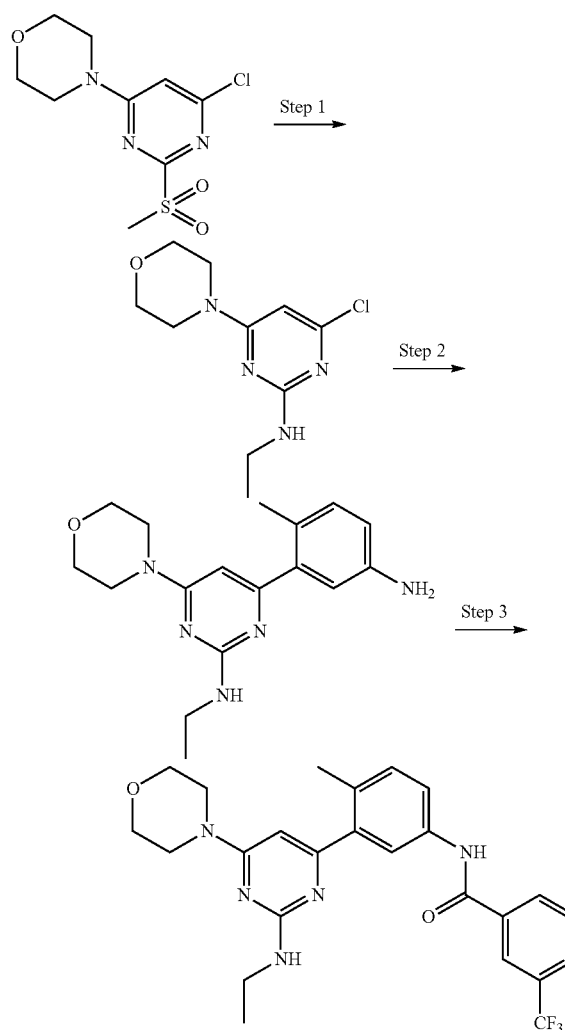

Step 1:

To a solution of 4-(6-chloro-2-(methylsulfonyl)pyrimidin-4-yl)morpholine (1.0 equiv.) in THF (0.14 M) was added 2M ethylamine solution in THF (2.0 equiv.) at room temperature. The reaction was stirred at ambient temperature for 16 h. The reaction was partitioned between water and ethyl acetate and the separated organic phase was dried with sodium sulfate, filtered and concentrated under vacuo to yield 4-chloro-N-ethyl-6-morpholinopyrimidin-2-amine in quantitative yield. LCMS (m/z) (M+H)=243/245, Rt=0.5 min.

Step 2:

To a solution of 4-chloro-N-ethyl-6-morpholinopyrimidin-2-amine (1.0 equiv.) in DME (0.6 M) was added 4-methyl-3-(4,4,5,5-tetramethyl-1,3,2-dioxaborolan-2-yl)aniline (1. equiv.), PdCl2(dppf)-DCM adduct (0.1 equiv.) and 2M aqueous sodium carbonate (3.00 equiv.), and the reaction was heated to 120° C. for 20 min in the microwave. LC/MS showed incomplete reaction, allowed to heat in the oil bath at 100° C. for 3 hours. At this time, the reaction was complete. Cooled to room temperature, partitioned between water and ethyl acetate, the organic phase was dried with sodium sulfate, filtered and concentrated. The crude material was purified via silica gel column chromatography eluting with 0-100% ethyl acetate in heptanes. The pure fractions were concentrated under vacuo to yield 4-(5-amino-2-methylphenyl)-N-ethyl-6-morpholinopyrimidin-2-amine as the desired product in 84% yield. LCMS (m/z) (M+H)=314.2, Rt=0.48 min.

Step 3:

To a solution of 2-(trifluoromethyl)isonicotinic acid (1. equiv.) in DMF (0.04 M) was added EDC (1 eq) and HOBT (1 eq) followed by 4-(5-amino-2-methylphenyl)-N-ethyl-6-morpholinopyrimidin-2-amine (1.0 equiv.) and the reaction mixture was stirred at ambient temperature for 16 h. The reaction mixture was partitioned between water and ethyl acetate, and the separated organic layer was dried with sodium sulfate, filtered and concentrated. The concentrated crude was dissolved in DMSO, filtered through a HPLC filter and purified via auto-preparative reverse phase HPLC. The pure fractions were lyophilized to yield N-(3-(2-(ethylamino)-6-morpholinopyrimidin-4-yl)-4-methylphenyl)-2-(trifluoromethyl)isonicotinamide.

1H NMR (400 MHz, <demos>) δ ppm 1.16 (s, 3H) 2.30 (s, 3H) 3.69 (br. s., 8H) 6.50-6.62 (m, 1H) 7.36-7.46 (m, 1H) 7.62-7.72 (m, 1H) 7.74-7.82 (m, 1H) 7.84-7.93 (m, 1H) 8.11-8.22 (m, 1H) 8.32-8.43 (m, 1H) 8.90-9.04 (m, 1H) 10.82-10.90 (m, 1H) LCMS (m/z) (M+H)=487.3, Rt=0.7 min.

Example 695: N-(3-(2-(ethylamino)-6-morpholinopyrimidin-4-yl)-4-methylphenyl)benzamide

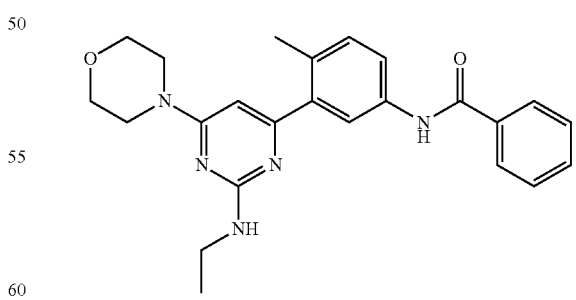

1H NMR (400 MHz, <dmso>) δ ppm 1.16 (s, 3H) 2.29 (s, 3H) 3.35-3.46 (m, 4H) 3.57-3.79 (m, 5H) 3.86-4.01 (m, 1H) 6.51-6.65 (m, 1H) 7.29-7.40 (m, 1H) 7.48-7.64 (m, 3H) 7.73-7.82 (m, 1H) 7.90-8.00 (m, 3H) 10.32-10.44 (m, 1H) LCMS (m/z) (M+H)=418.2, Rt=0.72 min.

Example 696: 2-(tert-butyl)-N-(3-(2-(ethylamino)-6-morpholinopyrimidin-4-yl)-4-methylphenyl)isonicotinamide

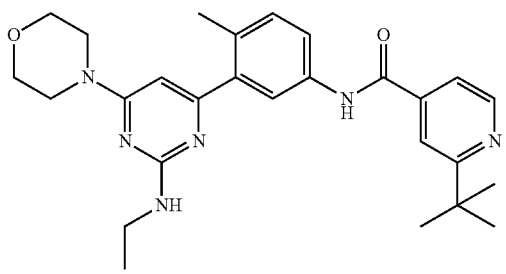 [SMILES: CCNc1nc(-c2cc(NC(=O)c3ccnc(C(C)(C)C)c3)ccc2C)cc(N2CCOCC2)n1]

1H NMR (400 MHz, <dmso>) δ ppm 1.12-1.20 (m, 3H) 1.35 (s, 9H) 2.23-2.33 (m, 3H) 3.27-3.45 (m, 2H) 3.72-3.80 (m, 5H) 3.81-4.06 (m, 3H) 6.49-6.65 (m, 1H) 7.35-7.45 (m, 1H) 7.60-7.69 (m, 1H) 7.76-7.91 (m, 3H) 8.65-8.78 (m, 1H) 10.57-10.66 (m, 1H), LCMS (m/z) (M+H)=475.4, Rt=0.64 min.

Example 697: 2-(1,1-difluoroethyl)-N-(3-(2-(ethylamino)-6-morpholinopyrimidin-4-yl)-4-methylphenyl)isonicotinamide

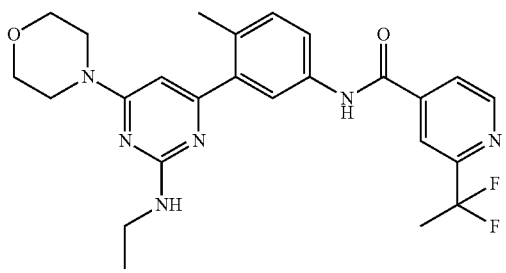 [SMILES: CCNc1nc(-c2cc(NC(=O)c3ccnc(C(C)(F)F)c3)ccc2C)cc(N2CCOCC2)n1]

1H NMR (400 MHz, <dmso>) δ ppm 1.16 (s, 3H) 2.04 (s, 3H) 2.30 (s, 3H) 3.63-4.04 (m, 8H) 6.47-6.62 (m, 1H) 7.34-7.48 (m, 1H) 7.54-7.65 (m, 1H) 7.72-7.84 (m, 1H) 7.86-7.91 (m, 1H) 7.98-8.05 (m, 1H) 8.13-8.24 (m, 1H) 8.82-8.92 (m, 1H) 10.73-10.85 (m, 1H), LCMS (m/z) (M+H)=483.3, Rt=0.75 min.

Example 698: 3-(difluoromethyl)-N-(3-(2-(ethylamino)-6-morpholinopyrimidin-4-yl)-4-methylphenyl)benzamide

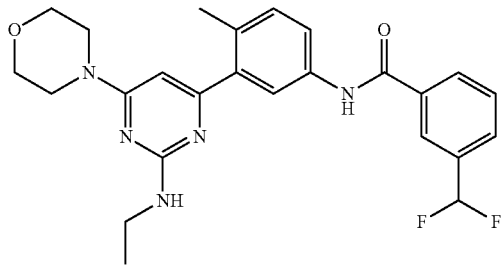 [SMILES: CCNc1nc(-c2cc(NC(=O)c3cccc(C(F)F)c3)ccc2C)cc(N2CCOCC2)n1]

1H NMR (400 MHz, <dmso>) δ ppm 1.03-1.23 (m, 3H) 2.29 (s, 3H) 3.64-3.97 (m, 7H) 6.96-7.02 (m, 1H) 7.10-7.17 (m, 1H) 7.23-7.30 (m, 1H) 7.34-7.43 (m, 1H) 7.64-7.73 (m, 1H) 7.75-7.81 (m, 2H) 7.87-7.96 (m, 1H) 8.06-8.21 (m, 2H) 10.48-10.63 (m, 1H), LCMS (m/z) (M+H)=468.3, Rt=0.77 min.

Example 699: N-(3-(2-(ethylamino)-6-morpholinopyrimidin-4-yl)-4-methylphenyl)-3-(1,3,4-oxadiazol-2-yl)benzamide

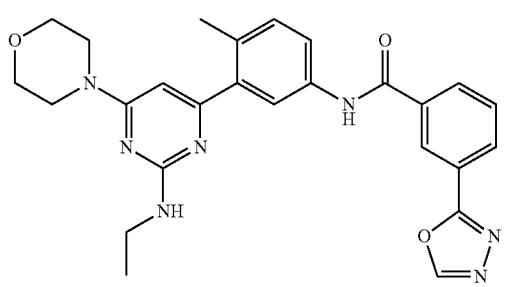 [SMILES: CCNc1nc(-c2cc(NC(=O)c3cccc(-c4nnco4)c3)ccc2C)cc(N2CCOCC2)n1]

1H NMR (400 MHz, <dmso>) δ ppm 1.16 (t, J=7.04 Hz, 3H) 2.30 (s, 3H) 3.41-3.48 (m, 1H) 3.49-3.57 (m, 1H) 3.59-3.78 (m, 5H) 3.80-4.03 (m, 1H) 6.53-6.64 (m, 1H) 7.33-7.44 (m, 1H) 7.73-7.85 (m, 2H) 7.89-7.99 (m, 1H) 8.15-8.27 (m, 2H) 8.56-8.64 (m, 1H) 9.36-9.47 (m, 1H) 10.58-10.71 (m, 1H), LCMS (m/z) (M+H)=486.3, Rt=0.69 min.

Example 700: N-(3-(2-(ethylamino)-6-morpholinopyrimidin-4-yl)-4-methylphenyl)-2-isopropylisonicotinamide

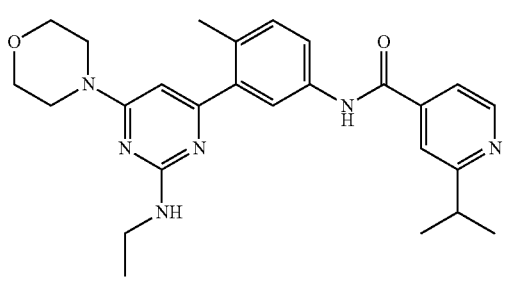 [SMILES: CCNc1nc(-c2cc(NC(=O)c3ccnc(C(C)C)c3)ccc2C)cc(N2CCOCC2)n1]

1H NMR (400 MHz, <dmso>) δ ppm 1.10-1.19 (m, 3H) 1.27 (d, J=7.04 Hz, 6H) 2.29 (s, 3H) 3.04-3.17 (m, 1H) 3.67-3.78 (m, 7H) 3.85-3.97 (m, 2H) 6.54-6.61 (m, 1H) 7.33-7.47 (m, 1H) 7.62-7.80 (m, 3H) 7.86-7.95 (m, 1H) 8.65-8.72 (m, 1H) 10.55-10.64 (m, 1H), LCMS (m/z) (M+H)=461.4, Rt=0.58 min.

Example 701: 3-(1,1-difluoroethyl)-N-(3-(2-(ethylamino)-6-morpholinopyrimidin-4-yl)-4-methylphenyl)benzamide

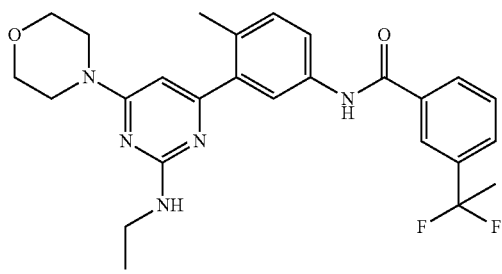 [SMILES: CCNc1nc(-c2cc(NC(=O)c3cccc(C(C)(F)F)c3)ccc2C)cc(N2CCOCC2)n1]

1H NMR (400 MHz, <dmso>) δ ppm 1.03-1.29 (m, 3H) 1.97 (s, 3H) 2.24 (s, 3H) 3.55-3.72 (m, 6H) 3.79-3.94 (m, 1H) 6.48-6.57 (m, 1H) 7.28-7.41 (m, 1H) 7.57-7.67 (m, 1H) 7.69-7.78 (m, 2H) 7.80-7.91 (m, 1H) 7.97-8.13 (m, 2H) 10.46-10.51 (m, 1H), LCMS (m/z) (M+H)=482.4, Rt=0.82 min.

Example 702: N-(3-(2-(ethylamino)-6-morpholinopyrimidin-4-yl)-4-methylphenyl)-2-(methylsulfonyl)isonicotinamide

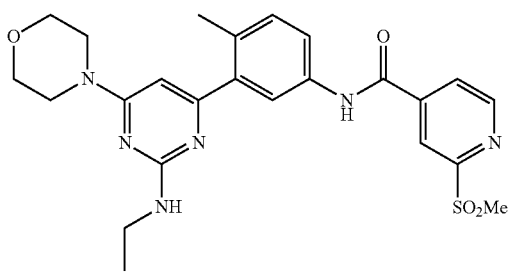 [SMILES: CCNc1nc(-c2cc(NC(=O)c3ccnc(S(C)(=O)=O)c3)ccc2C)cc(N2CCOCC2)n1]

1H NMR (400 MHz, <dmso>) v ppm 1.15 (s, 3H) 2.30 (s, 4H) 3.62-3.75 (m, 5H) 3.85-3.99 (m, 1H) 6.50-6.61 (m, 1H) 7.37-7.47 (m, 1H) 7.74-7.93 (m, 2H) 8.11-8.25 (m, 1H) 8.46-8.56 (m, 1H) 8.92-9.05 (m, 1H) 10.88-10.97 (m, 1H), LCMS (m/z) (M+H)=497.3, Rt=0.6 min.

Example 703: 1-ethyl-N-(3-(2-(ethylamino)-6-morpholinopyrimidin-4-yl)-4-methylphenyl)-6-oxo-5-(trifluoromethyl)-1,6-dihydropyridine-3-carboxamide

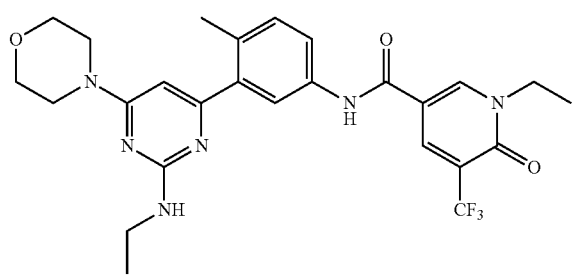 [SMILES: CCNc1nc(-c2cc(NC(=O)c3cc(C(F)(F)F)c(=O)n(CC)c3)ccc2C)cc(N2CCOCC2)n1]

1H NMR (400 MHz, <dmso>) δ ppm 1.04-1.21 (m, 3H) 1.29 (s, 3H) 2.28 (s, 3H) 3.39-3.44 (m, 2H) 3.61-3.80 (m, 5H) 3.85-3.98 (m, 1H) 4.02-4.15 (m, 2H) 6.50-6.65 (m, 1H) 7.35-7.47 (m, 1H) 7.67-7.84 (m, 2H) 8.41-8.50 (m, 1H) 8.74-8.87 (m, 1H) 10.21-10.35 (m, 1H), LCMS (m/z) (M+H)=531.3, Rt=0.74 min.

Example 704: N-(3-(2-(ethylamino)-6-morpholinopyrimidin-4-yl)-4-methylphenyl)-3-(methylsulfonyl)benzamide

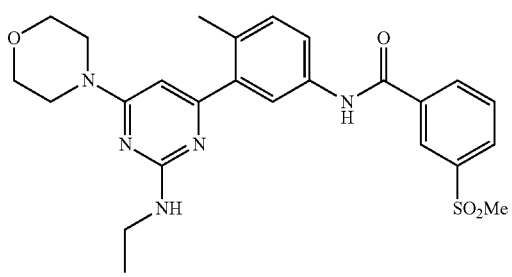 [SMILES: CCNc1nc(-c2cc(NC(=O)c3cccc(S(C)(=O)=O)c3)ccc2C)cc(N2CCOCC2)n1]

1H NMR (400 MHz, <dmso>) δ ppm 1.00-1.17 (m, 3H) 2.23-2.35 (m, 4H) 3.27-3.27 (m, 5H) 3.47-3.56 (m, 4H) 3.59-3.69 (m, 4H) 6.00-6.10 (m, 1H) 7.17-7.27 (m, 1H) 7.66-7.74 (m, 2H) 7.77-7.85 (m, 1H) 8.07-8.16 (m, 1H) 8.24-8.32 (m, 1H) 8.43-8.52 (m, 1H) 10.42-10.51 (m, 1H), LCMS (m/z) (M+H)=474.3, Rt=0.89 min.

Example 705: N-(3-(2-(ethylamino)-6-morpholinopyrimidin-4-yl)-4-methylphenyl)-2-(2-hydroxypropan-2-yl)isonicotinamide

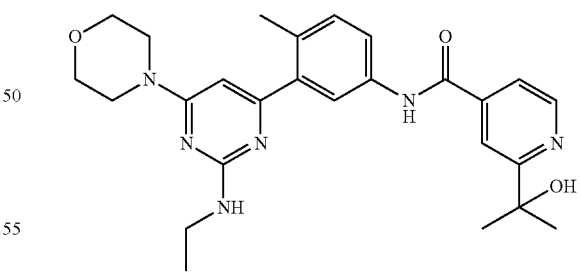

1H NMR (500 MHz, DMSO-d6) δ ppm 1.19 (t, J=7.09 Hz, 3H) 1.49 (s, 6H) 2.32 (s, 4H) 3.43 (br. s., 3H) 3.73-3.79 (m, 5H) 3.95 (br. s., 3H) 6.62 (s, 1H) 6.64-6.65 (m, 1H) 7.43 (d, J=8.51 Hz, 1H) 7.71 (dd, J=5.04, 1.26 Hz, 1H) 7.78-7.86 (m, 1H) 7.93 (s, 1H) 8.15 (s, 1H) 8.71 (d, J=5.04 Hz, 1H) 10.72 (s, 1H), LCMS (m/z) (M+H)=477.3, Rt=0.55 min.

Example 706: 2-(1,1-difluoropropyl)-N-(3-(2-(ethylamino)-6-morpholinopyrimidin-4-yl)-4-methylphenyl)isonicotinamide

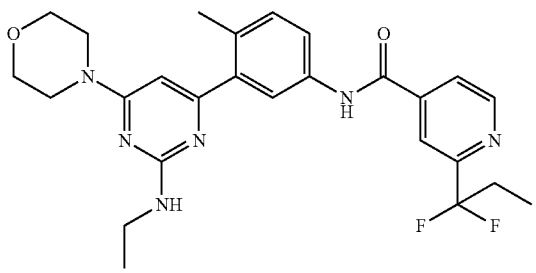 [SMILES: CCNc1nc(-c2cc(NC(=O)c3ccnc(C(F)(F)CC)c3)ccc2C)cc(N2CCOCC2)n1]

1H NMR (400 MHz, <dmso>) δ ppm 0.93 (t, J=7.43 Hz, 3H) 1.16 (t, J=7.04 Hz, 3H) 2.26-2.43 (m, 5H) 3.69 (br. s., 9H) 3.83-4.07 (m, 1H) 6.46-6.65 (m, 1H) 7.32-7.46 (m, 1H) 7.71-7.85 (m, 1H) 7.85-7.93 (m, 1H) 7.97-8.06 (m, 1H) 8.15 (s, 1H) 8.79-8.96 (m, 1H) 10.71-10.83 (m, 1H), LCMS (m/z) (M+H)=497.3, Rt=0.85 min.

Example 707: N-(3-(2-(ethylamino)-6-morpholinopyrimidin-4-yl)-4-methylphenyl)-2-(oxetan-3-yl)isonicotinamide

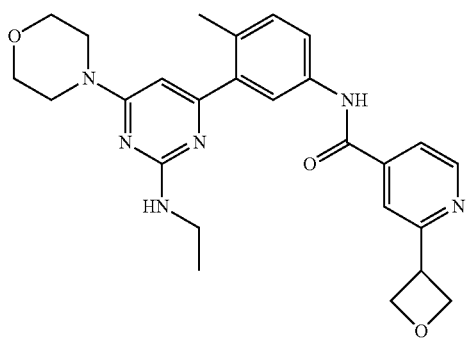 [SMILES: CCNc1nc(-c2cc(NC(=O)c3ccnc(C4COC4)c3)ccc2C)cc(N2CCOCC2)n1]

1H NMR (400 MHz, <dmso>) δ ppm 1.08-1.23 (m, 3H) 2.24-2.35 (m, 3H) 3.64-3.78 (m, 7H) 3.86-3.98 (m, 1H) 4.43-4.55 (m, 1H) 4.77-4.84 (m, 1H) 4.89-4.94 (m, 1H) 6.52-6.61 (m, 1H) 7.34-7.48 (m, 1H) 7.65-7.81 (m, 3H) 7.86-7.94 (m, 1H) 8.76-8.86 (m, 1H) 10.59-10.67 (m, 1H), LCMS (m/z) (M+H)=475.2, Rt=0.61 min.

Example 708: 2-(1-cyanocyclopropyl)-N-(3-(2-(ethylamino)-6-morpholinopyrimidin-4-yl)-4-methylphenyl)isonicotinamide

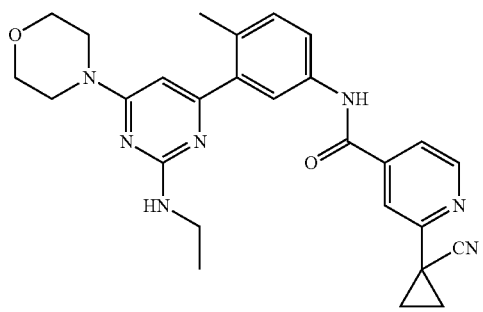 [SMILES: CCNc1nc(-c2cc(NC(=O)c3ccnc(C4(C#N)CC4)c3)ccc2C)cc(N2CCOCC2)n1]

1H NMR (400 MHz, <dmso>) δ ppm 1.08-1.21 (m, 3H) 1.68-1.80 (m, 2H) 1.84-1.95 (m, 2H) 2.30 (s, 3H) 3.62-3.79 (m, 5H) 3.92 (br. s., 1H) 6.51-6.61 (m, 1H) 7.32-7.47 (m, 1H) 7.72-7.80 (m, 2H) 7.86-7.96 (m, 2H) 8.66-8.77 (m, 1H) 10.71-10.77 (m, 1H), LCMS (m/z) (M+H)=484.2, Rt=0.76 min.

Example 709: 6-(2-cyanopropan-2-yl)-N-(3-(2-(ethylamino)-6-morpholinopyrimidin-4-yl)-4-methylphenyl)pyridazine-4-carboxamide

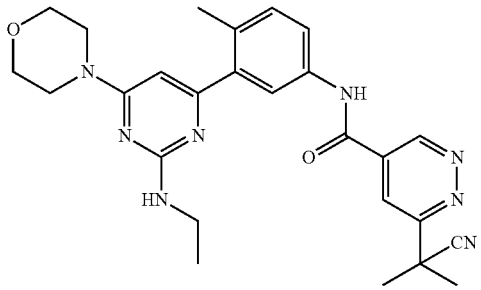 [SMILES: CCNc1nc(-c2cc(NC(=O)c3cnnc(C(C)(C)C#N)c3)ccc2C)cc(N2CCOCC2)n1]

1H NMR (400 MHz, <dmso>) δ ppm 1.08-1.22 (m, 3H) 1.84 (s, 6H) 2.27-2.34 (m, 3H) 3.41-3.52 (m, 2H) 3.60-3.79 (m, 6H) 3.83-4.00 (m, 1H) 6.51-6.62 (m, 1H) 7.36-7.48 (m, 1H) 7.72-7.87 (m, 2H) 8.25-8.32 (m, 1H) 9.55-9.68 (m, 1H) 10.86-10.95 (m, 1H), LCMS (m/z) (M+H)=487.3, Rt=0.7 min.

Example 710: 3-(2-(ethylamino)-6-morpholinopyrimidin-4-yl)-4-methyl-N-(3-(trifluoromethyl)phenyl)benzamide

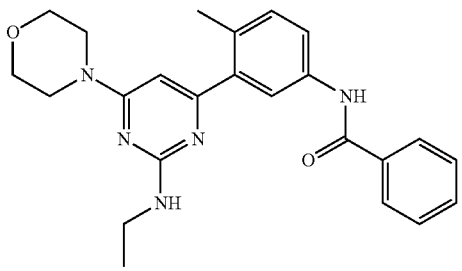 [SMILES: CCNc1nc(-c2cc(NC(=O)c3ccccc3)ccc2C)cc(N2CCOCC2)n1]

1H NMR (400 MHz, <dmso>) δ ppm 1.05-1.22 (m, 3H) 2.40 (s, 3H) 3.39-3.44 (m, 4H) 3.64-3.94 (m, 6H) 6.54-6.69 (m, 1H) 7.40-7.49 (m, 1H) 7.54-7.69 (m, 2H) 7.96-8.12 (m, 3H) 8.19-8.25 (m, 1H) 10.51-10.59 (m, 1H), LCMS (m/z) (M+H)=486.3, Rt=0.85 min.

Example 711: (R)-2-(2-cyanopropan-2-yl)-N-(3-(2-(ethylamino)-6-(3-methylmorpholino)pyrimidin-4-yl)-4-methylphenyl)isonicotinamide

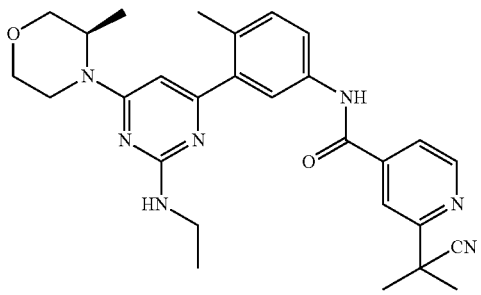 [SMILES: CCNc1nc(-c2cc(NC(=O)c3ccnc(C(C)(C)C#N)c3)ccc2C)cc(N2CCOC[C@H]2C)n1]

1H NMR (400 MHz, <dmso>) δ ppm 1.16 (s, 3H) 1.23-1.32 (m, 3H) 1.75 (s, 6H) 2.30 (s, 3H) 3.46-3.55 (m, 8H) 6.48-6.58 (m, 1H) 7.37-7.44 (m, 1H) 7.73-7.90 (m, 3H)

7.95-8.02 (m, 1H) 8.74-8.86 (m, 1H) 10.69-10.77 (m, 1H), LCMS (m/z) (M+H)=500.3, Rt=0.78 min.

Example 712: (R)—N-(3-(2-(ethylamino)-6-(3-methylmorpholino)pyrimidin-4-yl)-4-methylphenyl)-2-(2-hydroxypropan-2-yl)isonicotinamide

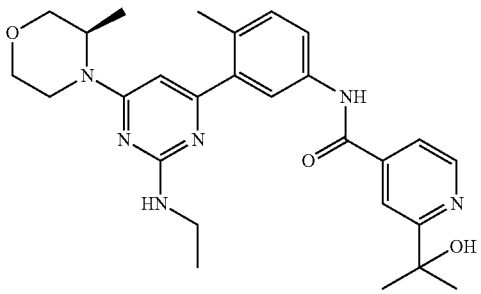 [SMILES: CCNc1nc(-c2cc(NC(=O)c3ccnc(C(C)(C)O)c3)ccc2C)cc(N2CCOC[C@H]2C)n1]

1H NMR (400 MHz, <dmso>) δ ppm 1.16 (s, 6H) 1.46 (s, 6H) 2.29 (s, 3H) 3.54-3.78 (m, 2H) 3.83-4.04 (m, 1H) 6.51-6.60 (m, 1H) 7.31-7.47 (m, 1H) 7.59-7.70 (m, 1H) 7.75-7.83 (m, 1H) 7.86-7.94 (m, 1H) 8.06-8.16 (m, 1H) 8.60-8.73 (m, 1H) 10.61-10.73 (m, 1H), LCMS (m/z) (M+H)=491.3, Rt=0.62 min.

Example 713: (S)—N-(3-(2-(ethylamino)-6-(3-methylmorpholino)pyrimidin-4-yl)-4-methylphenyl)-2-(2-hydroxypropan-2-yl)isonicotinamide

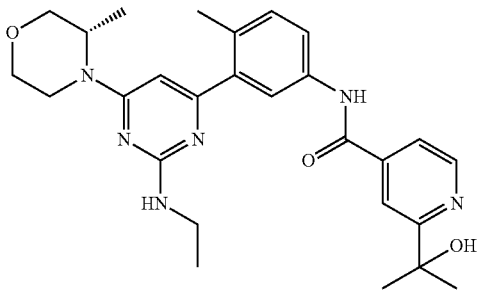 [SMILES: CCNc1nc(-c2cc(NC(=O)c3ccnc(C(C)(C)O)c3)ccc2C)cc(N2CCOC[C@@H]2C)n1]

1H NMR (400 MHz, <dmso>) δ ppm 1.10-1.20 (m, 3H) 1.23-1.31 (m, 3H) 2.21-2.36 (m, 3H) 3.55-4.40 (m, 8H) 6.47-6.62 (m, 1H) 7.35-7.44 (m, 1H) 7.63-7.71 (m, 1H) 7.75-7.81 (m, 1H) 7.86-7.94 (m, 1H) 8.06-8.16 (m, 1H) 8.62-8.72 (m, 1H) 10.60-10.74 (m, 1H), LCMS (m/z) (M+H)=491.3, Rt=0.62 min.

Example 714: (S)-2-(2-cyanopropan-2-yl)-N-(3-(2-(ethylamino)-6-(3-methylmorpholino)pyrimidin-4-yl)-4-methylphenyl)isonicotinamide

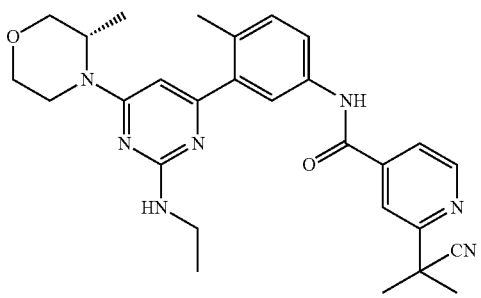 [SMILES: CCNc1nc(-c2cc(NC(=O)c3ccnc(C(C)(C)C#N)c3)ccc2C)cc(N2CCOC[C@@H]2C)n1]

1H NMR (400 MHz, <dmso>) δ ppm 1.10-1.19 (m, 3H) 1.21-1.32 (m, 3H) 1.75 (s, 6H) 2.23-2.34 (m, 3H) 3.45-3.49 (m, 7H) 6.46-6.61 (m, 1H) 7.36-7.48 (m, 1H) 7.75-7.91 (m, 3H) 7.95-8.03 (m, 1H) 8.75-8.86 (m, 1H) 10.69-10.75 (m, 1H), LCMS (m/z) (M+H)=500.3, Rt=0.79 min.

Example 716: N-(5-(2-(ethylamino)-6-morpholinopyrimidin-4-yl)-6-methylpyridin-3-yl)-3-(trifluoromethyl)benzamide

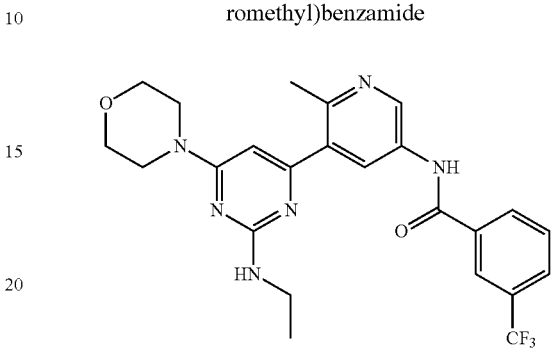

To a solution of 4-chloro-N-ethyl-6-morpholinopyrimidin-2-amine (1.0 equiv.) in DME was added N-(6-methyl-5-(4,4,5,5-tetramethyl-1,3,2-dioxaborolan-2-yl)pyridin-3-yl)-3-(trifluoromethyl)benzamide (Intermediate B, 1.3 equiv.), followed by PdCl2(dppf).CH2Cl2 adduct (0.10 equiv.), and 2M aqueous sodium carbonate (3.00 equiv.). The reaction was heated in the microwave for 10 min at 120° C. LC/MS showed completion of the reaction. The organic phase was concentrated to dryness, dissolved in DMSO, filtered through a HPLC filter and purified via auto-preparative reverse phase HPLC. The pure fractions were lyophilized to yield N-(5-(2-(ethylamino)-6-morpholinopyrimidin-4-yl)-6-methylpyridin-3-yl)-3-(trifluoromethyl)benzamide in 43% yield. 1H NMR (400 MHz, <dmso>) δ ppm 1.06-1.24 (m, 3H) 3.29-3.47 (m, 2H) 3.64-3.76 (m, 11H) 6.62-6.75 (m, 1H) 7.63-7.86 (m, 1H) 7.96-8.04 (m, 1H) 8.23-8.40 (m, 3H) 8.85-8.98 (m, 1H) 10.78-10.91 (m, 1H), LCMS (m/z) (M+H)=487.1, Rt=0.73 min.

Example 717: 2-(2-cyanopropan-2-yl)-N-(3-(2-(ethylamino)-6-morpholinopyrimidin-4-yl)-4-methylphenyl)isonicotinamide

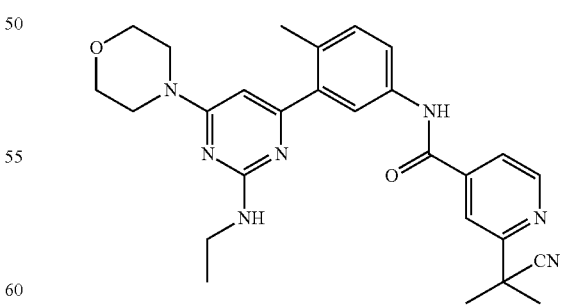

1H NMR (400 MHz, <dmso>) δ ppm 1.01-1.24 (m, 3H) 1.75 (s, 5H) 2.29 (s, 3H) 3.27-3.45 (m, 2H) 3.64-4.07 (m, 9H) 6.45-6.58 (m, 1H) 7.28-7.47 (m, 1H) 7.70-7.93 (m, 3H) 7.93-8.11 (m, 1H) 8.74-8.84 (m, 1H) 10.65-10.81 (m, 1H), LCMS (m/z) (M+H)=486.3, Rt=0.7 min.

Example 718: 2-(2-cyanopropan-2-yl)-N-(5-(2-(ethylamino)-6-morpholinopyrimidin-4-yl)-6-methylpyridin-3-yl)isonicotinamide

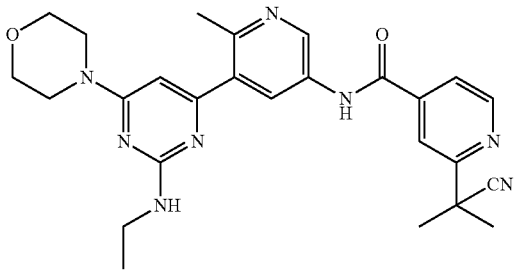 [SMILES: CCNc1nc(-c2cc(NC(=O)c3ccnc(C(C)(C)C#N)c3)cnc2C)cc(N2CCOCC2)n1]

1H NMR (400 MHz, <dmso>) δ ppm 1.01-1.16 (m, 3H) 1.75 (s, 7H) 2.51 (br. s., 3H) 3.50-3.69 (m, 9H) 6.08-6.20 (m, 1H) 7.82-7.91 (m, 1H) 7.98-8.05 (m, 1H) 8.07-8.18 (m, 1H) 8.74-8.88 (m, 2H) 10.64-10.79 (m, 1H), LCMS (m/z) (M+H)=487.2, Rt=0.65 min.

Example 719: Synthesis of N-(3-(2-(ethylamino)-6-morpholinopyrimidin-4-yl)-4-methylphenyl)-2-(trifluoromethyl)isonicotinamide

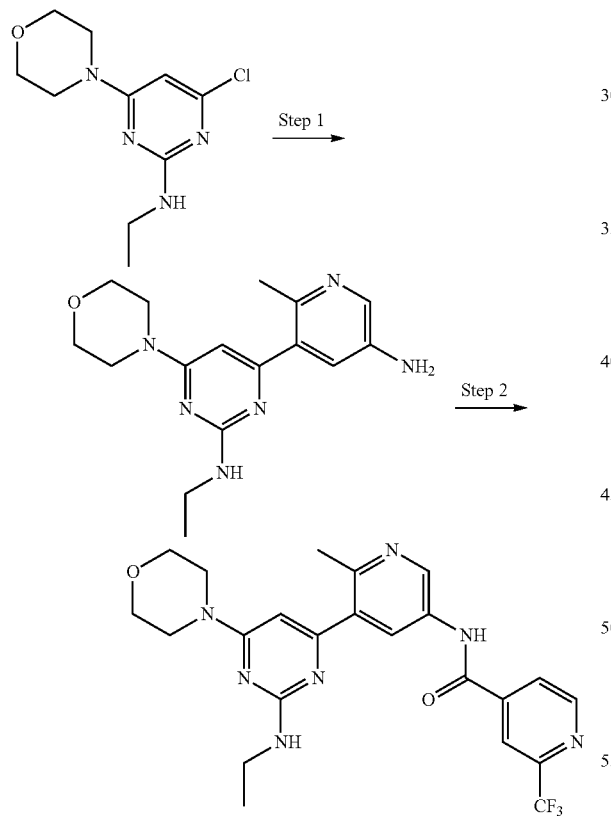

Step 1:
To a solution of 4-chloro-N-ethyl-6-morpholinopyrimidin-2-amine (1.0 equiv.) in DME (0.1 M) was added 6-methyl-5-(4,4,5,5-tetramethyl-1,3,2-dioxaborolan-2-yl) pyridin-3-amine (1.1 equiv.), PdCl2(dppf)-DCM adduct (0.05 equiv.) and 2M aqueous sodium carbonate (3.00 equiv.), and the reaction mixture was purged with nitrogen and was heated to 100° C. for 2 h. Cooled to room temperature, partitioned between water and ethyl acetate and the organic phase was dried with sodium sulfate, filtered and concentrated to yield 4-(5-amino-2-methylpyridin-3-yl)-N-ethyl-6-morpholinopyrimidin-2-amine as the desired product in 79% yield. LCMS (m/z) (M+H)=315.1, Rt=0.4 min.

Step 2:
To a solution of 2-(trifluoromethyl)isonicotinic acid (1. equiv.) in DMF (0.04 M) was added EDC (1 eq) and HOAT (1 eq) followed by 4-(5-amino-2-methylpyridin-3-yl)-N-ethyl-6-morpholinopyrimidin-2-amine (1.0 equiv.) and the reaction mixture was stirred at ambient temperature for 16 h. The reaction mixture was partitioned between water and ethyl acetate, and the separated organic layer was dried sodium sulfate, filtered and concentrated. The concentrated crude was dissolved in DMSO, filtered through a HPLC filter and purified via auto-preparative reverse phase HPLC. The pure fractions were lyophilized to yield N-(3-(2-(ethylamino)-6-morpholinopyrimidin-4-yl)-4-methylphenyl)-2-(trifluoromethyl)isonicotinamide.

1H NMR (400 MHz, <demos>) δ ppm 1.18 (t, J=7.24 Hz, 1H) 2.50 (br. s., 12H) 3.29-3.55 (m, 1H) 3.71 (br. s., 10H) 3.78 (br. s., 13H) 6.68 (br. s., 1H) 8.22 (d, J=4.70 Hz, 1H) 8.30 (br. s., 1H) 8.39 (s, 1H) 8.93 (d, J=1.96 Hz, 1H) 9.04 (d, J=5.09 Hz, 1H) 11.07 (s, 1H) LCMS (m/z) (M+H)= 488.8, Rt=0.62 min.

Example 720: 1-ethyl-N-(5-(2-(ethylamino)-6-morpholinopyrimidin-4-yl)-6-methylpyridin-3-yl)-6-oxo-5-(trifluoromethyl)-1,6-dihydropyridine-3-carboxamide

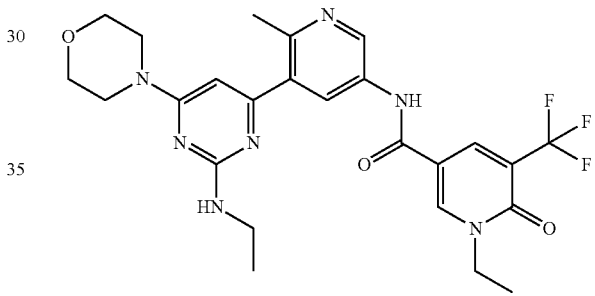

1H NMR (400 MHz, DMSO-d6) δ ppm 0.92-1.43 (m, 13H) 3.28-3.51 (m, 3H) 4.07 (s, 5H) 6.54-6.73 (m, 1H) 8.02-8.29 (m, 2H) 8.47 (d, J=1.96 Hz, 1H) 8.68-8.94 (m, 3H) 10.46-10.63 (m, 1H), LCMS (m/z) (M+H)=532.3, Rt=0.61 min.

Example 721: 2-(difluoromethyl)-N-(5-(2-(ethylamino)-6-morpholinopyrimidin-4-yl)-6-methylpyridin-3-yl)isonicotinamide

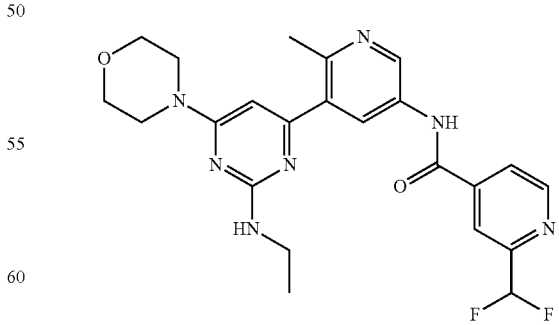

1H NMR (400 MHz, <dmso>) δ ppm 1.18 (t, J=7.04 Hz, 5H) 3.71 (br. s., 8H) 6.42-6.46 (m, 1H) 6.65-7.28 (m, 3H) 8.06-8.07 (m, 1H) 8.08 (d, J=4.70 Hz, 1H) 8.21 (s, 1H) 8.31 (s, 1H) 8.93-8.97 (m, 3H) 11.04 (s, 1H), LCMS (m/z) (M+H)=470.4, Rt=0.46 min.

Example 722: 3-(difluoromethyl)-N-(5-(2-(ethylamino)-6-morpholinopyrimidin-4-yl)-6-methylpyridin-3-yl)benzamide

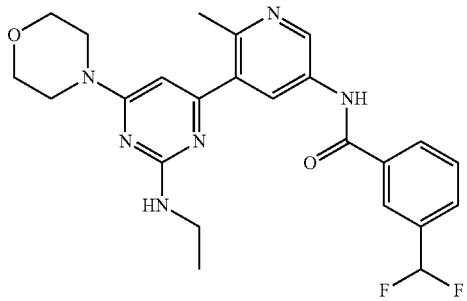 [SMILES: CCNc1nc(-c2cc(NC(=O)c3cccc(C(F)F)c3)cnc2C)cc(N2CCOCC2)n1]

1H NMR (400 MHz, <dmso>) δ ppm 1.18 (t, J=7.04 Hz, 1H) 3.20 (s, 1H) 3.42 (br. s., 1H) 3.71 (br. s., 3H) 3.88 (br. s., 13H) 4.14 (br. s., 19H) 6.69 (s, 3H) 7.03 (s, 1H) 7.17 (s, 2H) 7.31 (s, 1H) 7.71-7.76 (m, 5H) 7.84 (d, J=7.83 Hz, 4H) 8.14-8.21 (m, 8H) 8.33 (d, J=1.57 Hz, 3H) 8.94 (d, J=2.35 Hz, 3H) 10.80 (s, 3H), LCMS (m/z) (M+H)=469.3, Rt=0.62 min.

Example 723: N-(5-(2-(ethylamino)-6-morpholinopyrimidin-4-yl)-6-methylpyridin-3-yl)-2-(2-hydroxypropan-2-yl)isonicotinamide

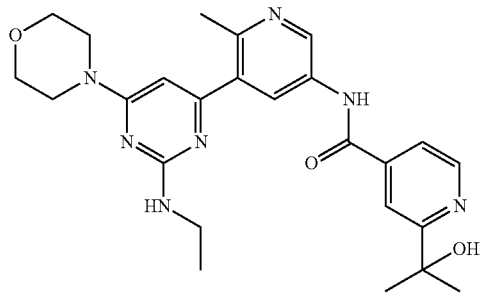 [SMILES: CCNc1nc(-c2cc(NC(=O)c3ccnc(C(C)(C)O)c3)cnc2C)cc(N2CCOCC2)n1]

1H NMR (400 MHz, DMSO-d6) δ ppm 1.18 (t, J=7.04 Hz, 1H) 1.49 (s, 2H) 2.54 (s, 1H) 3.42 (br. s., 2H) 6.69 (s, 1H) 7.73 (dd, J=4.89, 1.37 Hz, 1H) 7.72-7.74 (m, 2H) 7.72-7.74 (m, 2H) 8.18 (s, 1H) 8.31 (d, J=1.96 Hz, 1H) 8.72 (d, J=5.09 Hz, 1H) 8.94 (d, J=2.35 Hz, 1H) 10.92 (s, 1H), LCMS (m/z) (M+H)=478.8, Rt=0.47 min.

Example 724: 2-(tert-butyl)-N-(5-(2-(ethylamino)-6-morpholinopyrimidin-4-yl)-6-methylpyridin-3-yl)isonicotinamide

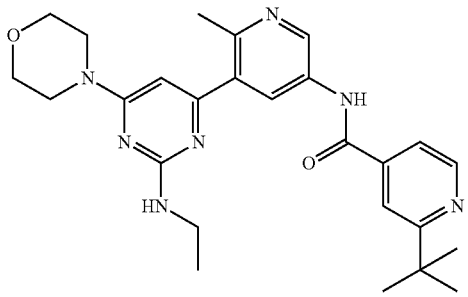 [SMILES: CCNc1nc(-c2cc(NC(=O)c3ccnc(C(C)(C)C)c3)cnc2C)cc(N2CCOCC2)n1]

1H NMR (400 MHz, <dmso>) δ ppm 1.18 (t, J=7.04 Hz, 1H) 1.38 (s, 3H) 3.21 (d, J=7.04 Hz, 1H) 3.35 (s, 1H) 3.52 (br. s., 1H) 3.59-3.64 (m, 1H) 3.71 (br. s., 2H) 6.69 (s, 4H) 7.69-7.73 (m, 5H) 7.69-7.74 (m, 5H) 7.89 (s, 6H) 8.29 (d, J=1.96 Hz, 5H) 8.75 (d, J=4.70 Hz, 6H) 8.94 (d, J=2.35 Hz, 5H) 10.87 (s, 5H), LCMS (m/z) (M+H)=476.4, Rt=0.55 min.

Example 725: 2-(1,1-difluoroethyl)-N-(5-(2-(ethylamino)-6-morpholinopyrimidin-4-yl)-6-methylpyridin-3-yl)isonicotinamide

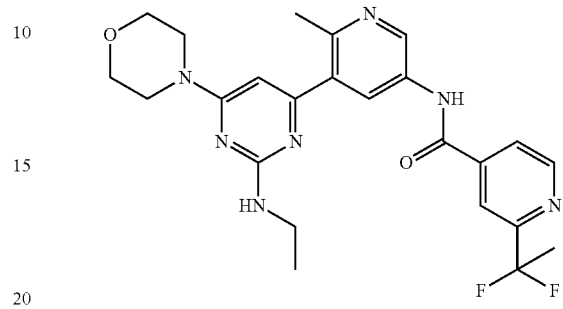

1H NMR (400 MHz, <dmso>) δ ppm 1.18 (t, J=7.04 Hz, 1H) 2.06 (t, J=19.17 Hz, 1H) 2.34-2.69 (m, 3H) 2.48-2.50 (m, 11H) 2.53-2.54 (m, 1H) 3.42 (br. s., 3H) 6.68 (s, 2H) 8.05 (d, J=4.70 Hz, 2H) 8.18-8.35 (m, 4H) 8.89-8.97 (m, 4H) 11.04 (s, 2H), LCMS (m/z) (M+H)=488.8, Rt=0.62 min.

Example 726: 3-(2-cyanopropan-2-yl)-N-(5-(2-(ethylamino)-6-morpholinopyrimidin-4-yl)-6-methylpyridin-3-yl)benzamide

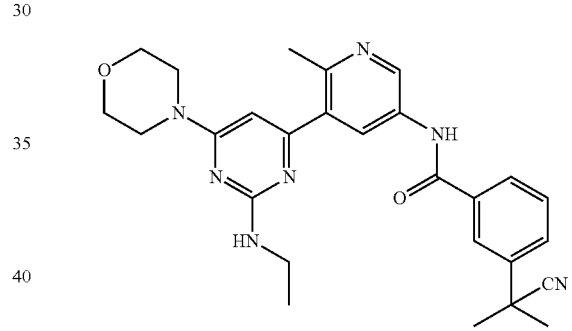

1H NMR (400 MHz, <dmso>) δ ppm 1.18 (t, J=7.24 Hz, 1H) 1.76 (s, 12H) 3.42 (br. s., 1H) 6.68 (br. s., 1H) 7.60-7.68 (m, 1H) 7.80 (d, J=7.83 Hz, 1H) 7.98 (d, J=7.83 Hz, 1H) 8.08 (s, 1H) 8.31 (s, 1H) 8.94 (d, J=2.35 Hz, 1H) 10.71 (s, 2H), LCMS (m/z) (M+H)=486.5, Rt=0.65 min.

Example 727: 6-cyclopropyl-N-(5-(2-(ethylamino)-6-morpholinopyrimidin-4-yl)-6-methylpyridin-3-yl)pyridazine-4-carboxamide

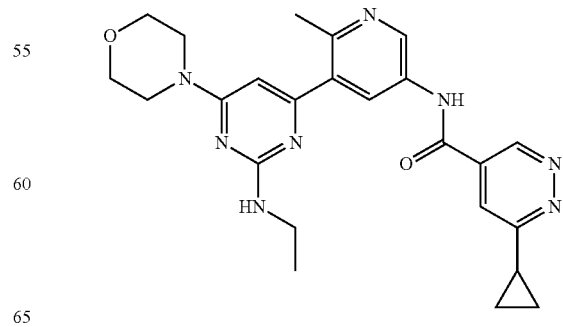

1H NMR (400 MHz, <dmso>) δ ppm 1.02-1.19 (m, 7H) 2.27-2.37 (m, 1H) 3.32-3.39 (m, 1H) 3.67-3.74 (m, 6H)

6.52-6.66 (m, 1H) 7.80-7.94 (m, 1H) 8.15-8.26 (m, 1H) 8.79-8.88 (m, 1H) 9.30-9.41 (m, 1H) 10.92-11.01 (m, 1H), LCMS (m/z) (M+H)=461.2, Rt=0.56 min.

Example 728: 2-(1-cyanocyclopropyl)-N-(5-(2-(ethylamino)-6-morpholinopyrimidin-4-yl)-6-methylpyridin-3-yl)isonicotinamide

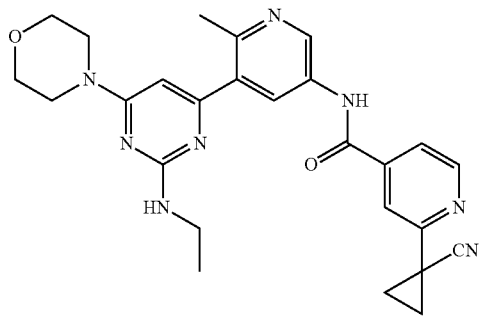 [SMILES: CCNc1nc(-c2cc(NC(=O)c3ccnc(C4(C#N)CC4)c3)cnc2C)cc(N2CCOCC2)n1]

1H NMR (400 MHz, <dmso>) δ ppm 1.03-1.14 (m, 3H) 1.51-1.59 (m, 3H) 1.70-1.78 (m, 2H) 1.80-1.94 (m, 2H) 3.51-3.57 (m, 3H) 3.60-3.70 (m, 3H) 6.07-6.22 (m, 1H) 7.76-7.85 (m, 1H) 7.92-7.96 (m, 1H) 8.07-8.14 (m, 1H) 8.63-8.72 (m, 1H) 8.79-8.85 (m, 1H), LCMS (m/z) (M+H)= 485.3, Rt=0.65 min.

Example 729: N-(5-(2-(ethylamino)-6-morpholinopyrimidin-4-yl)-6-methylpyridin-3-yl)-2-(oxetan-3-yl)isonicotinamide

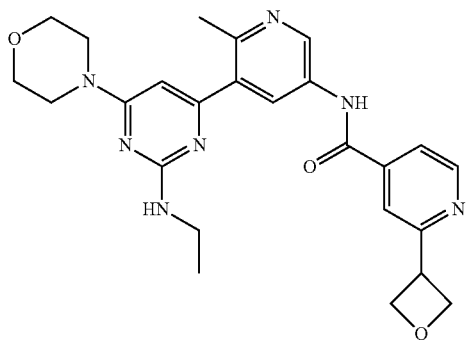 [SMILES: CCNc1nc(-c2cc(NC(=O)c3ccnc(C4COC4)c3)cnc2C)cc(N2CCOCC2)n1]

1H NMR (400 MHz, <dmso>) δ ppm 1.02-1.21 (m, 3H) 3.34-3.44 (m, 2H) 3.79-3.94 (m, 8H) 4.41-4.60 (m, 1H) 4.76-4.88 (m, 2H) 4.88-4.94 (m, 1H) 6.57-6.71 (m, 1H) 7.68-7.88 (m, 2H) 8.21-8.35 (m, 1H) 8.76-8.99 (m, 2H) 10.76-10.92 (m, 1H), LCMS (m/z) (M+H)=476.2, Rt=0.51 min.

Example 730: 6-(2-cyanopropan-2-yl)-N-(5-(2-(ethylamino)-6-morpholinopyrimidin-4-yl)-6-methylpyridin-3-yl)pyridazine-4-carboxamide

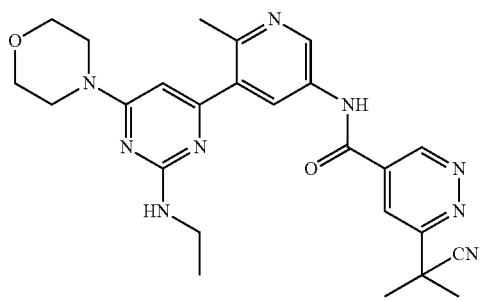 [SMILES: CCNc1nc(-c2cc(NC(=O)c3cnnc(C(C)(C)C#N)c3)cnc2C)cc(N2CCOCC2)n1]

1H NMR (400 MHz, <dmso>) δ ppm 1.10-1.21 (m, 3H) 1.85 (s, 6H) 3.39-3.40 (m, 9H) 3.69 (br. s., 4H) 8.20-8.43 (m, 2H) 8.84-8.93 (m, 1H) 9.60-9.70 (m, 1H) 11.04-11.16 (m, 1H), LCMS (m/z) (M+H)=488.2, Rt=0.59 min.

Example 731: Synthesis of 3-(2-(ethylamino)-6-morpholinopyrimidin-4-yl)-4-methyl-N-phenylbenzamide

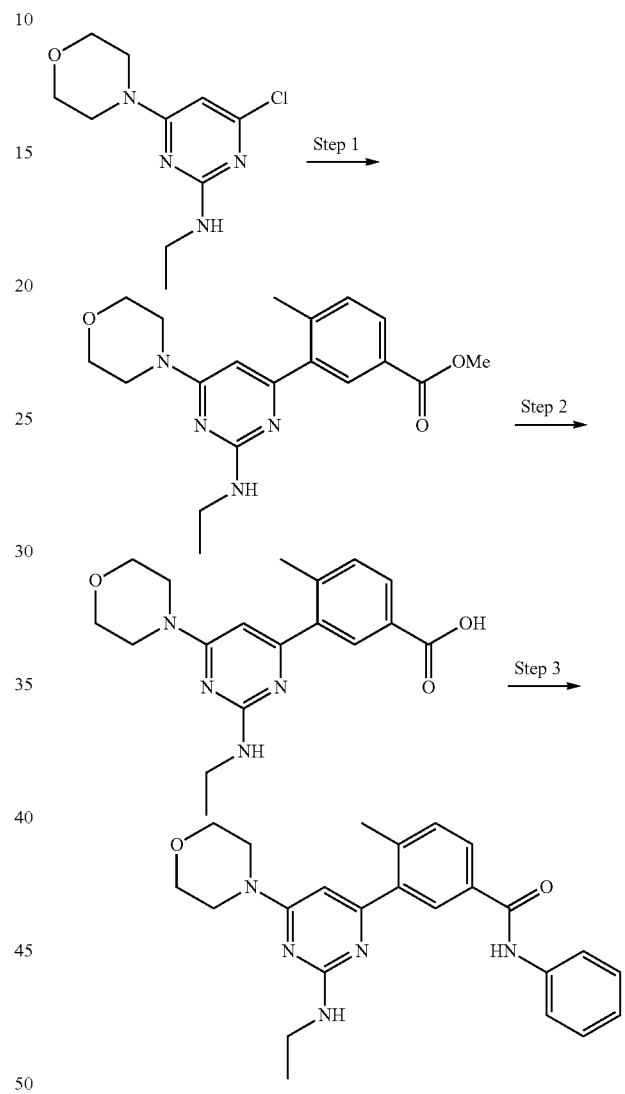

Step 1:
To a solution of 4-chloro-N-ethyl-6-morpholinopyrimidin-2-amine (1.0 equiv.) in DME (0.6 M) was added methyl 4-methyl-3-(4,4,5,5-tetramethyl-1,3,2-dioxaborolan-2-yl)benzoate (1. equiv.), PdCl2(dppf)-DCM adduct (0.1 equiv.) and 2M aqueous sodium carbonate (3.00 equiv.), and the reaction was heated in the oil bath at 100° C. for 4 hours. At this time, the reaction was complete. Cooled to room temperature, partitioned between water and ethyl acetate and the organic phase was dried with sodium sulfate, filtered and concentrated. The crude material was purified via silica gel column chromatography eluting with 0-100% ethyl acetate in heptanes. The pure fractions were concentrated under vacuo to yield methyl 3-(2-(ethylamino)-6-morpholinopyrimidin-4-yl)-4-methylbenzoate as the desired product in 75% yield. LCMS (m/z) (M+H)=357.1, Rt=0.65 min.

Step 2:

To a solution of methyl 3-(2-(ethylamino)-6-morpholinopyrimidin-4-yl)-4-methylbenzoate (1. equiv.) in THF (0.15 M) was added 2M lithium hydroxide solution and the mixture was stirred at RT for 16 h. 40% of starting material still remained when checked by LC/MS. The reaction mixture was heated 70° C. for 3 h. The reaction mixture was acidified with 1N HCl to pH=2 and was extracted with ethyl acetate. The separated organic layer was dried with sodium sulfate and concentrated to give 3-(2-(ethylamino)-6-morpholinopyrimidin-4-yl)-4-methylbenzoic acid in 65% yield. LCMS (m/z) (M+H)=343.4, Rt=0.56 min.

Step 3:

To a solution of 3-(2-(ethylamino)-6-morpholinopyrimidin-4-yl)-4-methylbenzoic acid (1. equiv.) in DMF (0.01 M) was added EDC (1 eq) and HOBT (1 eq) followed by aniline (1.0 equiv.) and the reaction mixture was stirred at ambient temperature for 16 h. The reaction mixture was partitioned between water and ethyl acetate, and the separated organic layer was dried sodium sulfate, filtered and concentrated. The concentrated crude was dissolved in DMSO, filtered through a HPLC filter and purified via auto-preparative reverse phase HPLC. The pure fractions were lyophilized to yield 3-(2-(ethylamino)-6-morpholinopyrimidin-4-yl)-4-methyl-N-phenylbenzamide.

1H NMR (400 MHz, <dmso>) δ ppm 0.94-1.35 (m, 3H) 2.38-2.41 (m, 3H) 3.31-3.47 (m, 3H) 3.62-3.81 (m, 10H) 6.54-6.68 (m, 1H) 6.96-7.18 (m, 1H) 7.27-7.43 (m, 2H) 7.49-7.59 (m, 1H) 7.69-7.82 (m, 2H) 7.98-8.16 (m, 2H) 10.20-10.31 (m, 1H) LCMS (m/z) (M+H)=418.3, Rt=0.7 min.

Example 732: N-(3-(2-cyanopropan-2-yl)phenyl)-3-(2-(ethylamino)-6-morpholinopyrimidin-4-yl)-4-methylbenzamide

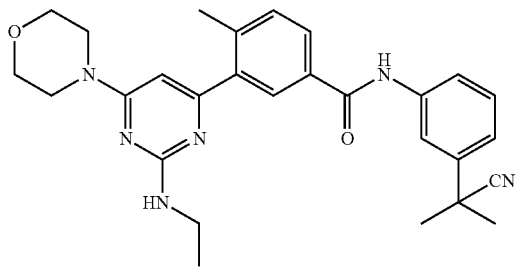 [SMILES: CCNc1nc(-c2cc(C(=O)Nc3cccc(C(C)(C)C#N)c3)ccc2C)cc(N2CCOCC2)n1]

1H NMR (400 MHz, <dmso>) δ ppm 1.02-1.22 (m, 3H) 1.68 (s, 6H) 2.34-2.42 (m, 3H) 3.52-3.59 (m, 3H) 3.67-3.78 (m, 5H) 3.84-4.02 (m, 1H) 6.59-6.69 (m, 1H) 7.18-7.30 (m, 1H) 7.33-7.46 (m, 1H) 7.52-7.62 (m, 1H) 7.79-7.87 (m, 1H) 7.91-7.98 (m, 1H) 8.00-8.15 (m, 2H) 10.33-10.44 (m, 1H), LCMS (m/z) (M+H)=485.4, Rt=0.78 min.

Example 733: N-(3-(difluoromethyl)phenyl)-3-(2-(ethylamino)-6-morpholinopyrimidin-4-yl)-4-methylbenzamide

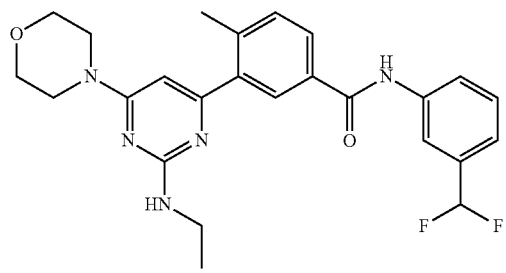 [SMILES: CCNc1nc(-c2cc(C(=O)Nc3cccc(C(F)F)c3)ccc2C)cc(N2CCOCC2)n1]

1H NMR (400 MHz, <dmso>) δ ppm 1.16 (s, 3H) 2.40 (s, 3H) 3.38-3.44 (m, 2H) 3.69 (br. s., 6H) 3.85-4.02 (m, 2H) 6.56-6.70 (m, 1H) 6.86-6.93 (m, 1H) 7.00-7.06 (m, 1H) 7.12-7.22 (m, 1H) 7.26-7.36 (m, 1H) 7.42-7.63 (m, 2H) 7.83-7.97 (m, 1H) 8.01-8.11 (m, 3H) 10.41-10.50 (m, 1H), LCMS (m/z) (M+H)=468.3, Rt=0.76 min.

Synthesis of 2-((4-chloro-6-morpholinopyrimidin-2-yl)amino)ethanol

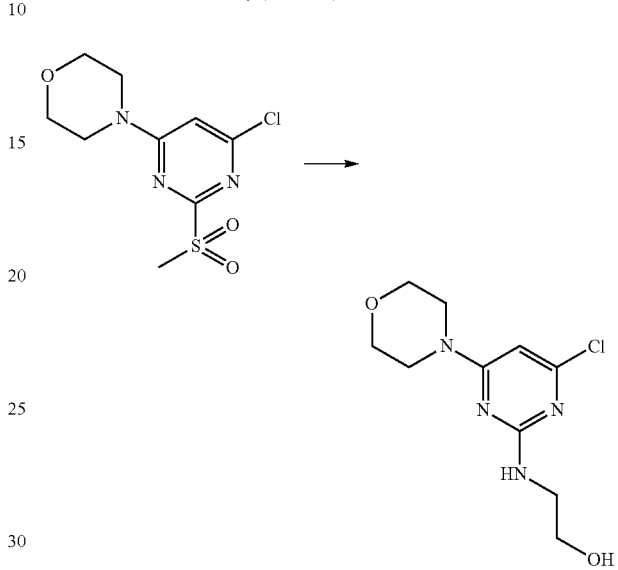

To a solution of 4-(6-chloro-2-(methylsulfonyl)pyrimidin-4-yl) morpholine (1.0 equiv.) in 1:1 THF: DMF (0.17M) was added ethanolamine (2.0 equiv.) and DIEA (2 eq) at room temperature. The reaction was stirred at ambient temperature for 16 h. The reaction was partitioned between water and ethyl acetate and the separated organic phase was dried with sodium sulfate, filtered and concentrated under vacuo to yield 2-((4-chloro-6-morpholinopyrimidin-2-yl)amino)ethanol in 87% yield. LCMS (m/z) (M+H)=259.1/261, Rt=0.39 min.

Example 734: 2-(2-cyanopropan-2-yl)-N-(3-(2-((2-hydroxyethyl)amino)-6-morpholinopyrimidin-4-yl)-4-methylphenyl)isonicotinamide

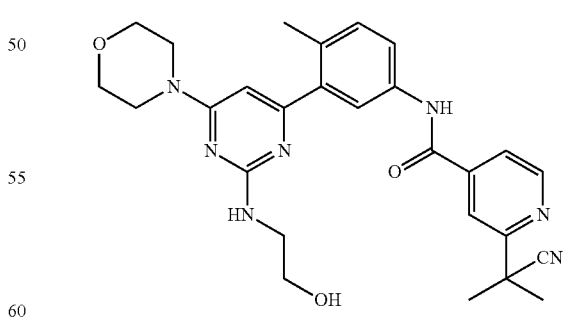

1H NMR (400 MHz, <dmso>) δ ppm 1.73 (s, 6H) 2.38 (s, 3H) 3.40 (br. s., 2H) 3.46-3.54 (m, 2H) 3.56-3.65 (m, 4H) 3.67-3.78 (m, 4H) 6.61-6.69 (m, 1H) 7.22-7.35 (m, 1H) 7.42-7.49 (m, 2H) 7.57-7.67 (m, 1H) 7.67-7.75 (m, 1H) 7.87-7.95 (m, 1H) 8.73-8.83 (m, 1H), LCMS (m/z) (M+H)= 502.4, Rt=0.64 min.

Example 735: N-(5-(2-((2-hydroxyethyl)amino)-6-morpholinopyrimidin-4-yl)-6-methylpyridin-3-yl)-3-(trifluoromethyl)benzamide

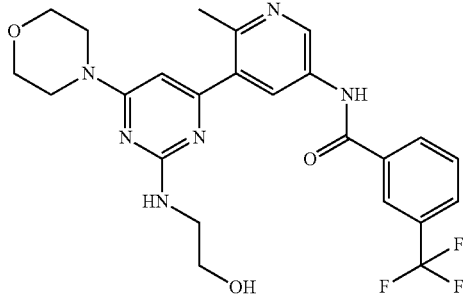 [SMILES: Cc1ncc(NC(=O)c2cccc(C(F)(F)F)c2)cc1-c1cc(N2CCOCC2)nc(NCCO)n1]

1H NMR (400 MHz, <dmso>) δ ppm 2.45-2.46 (m, 3H) 3.37-3.47 (m, 2H) 3.49-3.54 (m, 2H) 3.58-3.69 (m, 8H) 6.58-6.67 (m, 1H) 7.69-7.83 (m, 1H) 7.91-8.00 (m, 1H) 8.17-8.33 (m, 3H) 8.83-8.93 (m, 1H) 10.71-10.85 (m, 1H), LCMS (m/z) (M+H)=503.3, Rt=0.65 min.

Example 736: 2-(2-cyanopropan-2-yl)-N-(5-(2-((2-hydroxyethyl)amino)-6-morpholinopyrimidin-4-yl)-6-methylpyridin-3-yl)isonicotinamide

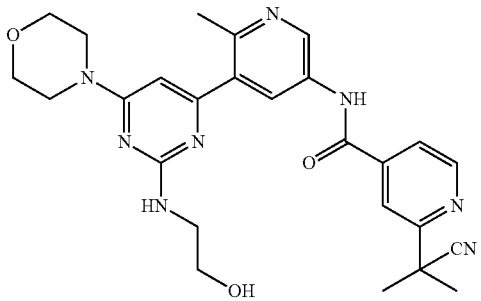 [SMILES: Cc1ncc(NC(=O)c2ccnc(C(C)(C)C#N)c2)cc1-c1cc(N2CCOCC2)nc(NCCO)n1]

1H NMR (400 MHz, <dmso>) δ ppm 1.76 (s, 6H) 3.56 (d, J=5.09 Hz, 8H) 6.63-6.74 (m, 1H) 7.79-7.92 (m, 1H) 7.97-8.08 (m, 1H) 8.22-8.41 (m, 1H) 8.83-8.99 (m, 2H) 10.88-11.01 (m, 1H), LCMS (m/z) (M+H)=503.3, Rt=0.55 min.

Example 737: 6-(2-cyanopropan-2-yl)-N-(3-(2-((2-hydroxyethyl)amino)-6-morpholinopyrimidin-4-yl)-4-methylphenyl)pyridazine-4-carboxamide

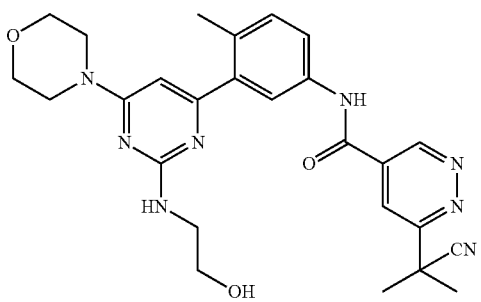 [SMILES: Cc1ccc(NC(=O)c2cnnc(C(C)(C)C#N)c2)cc1-c1cc(N2CCOCC2)nc(NCCO)n1]

LCMS (m/z) (M+H)=503.2, Rt=0.61 min.

Synthesis of (S)-1-((4-chloro-6-morpholinopyrimidin-2-yl)amino) propan-2-ol

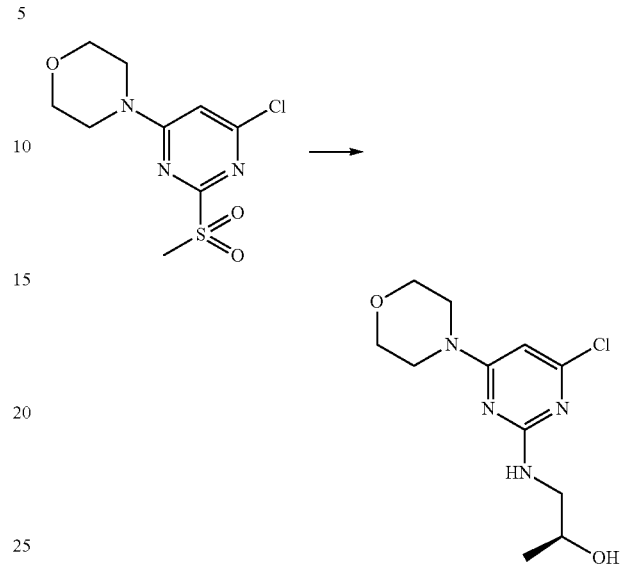

To a solution of 4-(6-chloro-2-(methylsulfonyl)pyrimidin-4-yl) morpholine (1.0 equiv.) in DMF (0.18 M) was added (S)-1-aminopropan-2-ol (2.0 equiv.) and DIEA (2 eq) at room temperature. The reaction was stirred at ambient temperature for 16 h. The reaction was partitioned between water and ethyl acetate and the separated organic phase was dried with sodium sulfate, filtered and concentrated under vacuo to yield of (S)-1-((4-chloro-6-morpholinopyrimidin-2-yl)amino)propan-2-ol I in quantitative yield. LCMS (m/z) (M+H)=273/274.9, Rt=0.44 min.

Example 738: (S)-2-(2-cyanopropan-2-yl)-N-(5-(2-((2-hydroxypropyl)amino)-6-morpholinopyrimidin-4-yl)-6-methylpyridin-3-yl)isonicotinamide

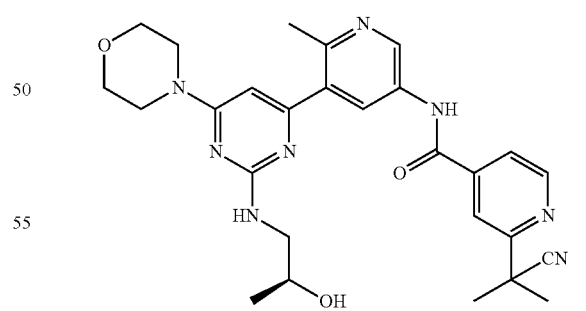

1H NMR (400 MHz, <dmso>) δ ppm 1.00-1.11 (m, 3H) 1.71 (s, 7H) 2.45-2.49 (m, 3H) 3.15-3.25 (m, 1H) 3.30-3.43 (m, 1H) 3.60-3.68 (m, 5H) 3.74-3.84 (m, 4H) 6.58-6.67 (m, 1H) 7.53-7.63 (m, 1H) 7.79-7.87 (m, 1H) 7.93-8.00 (m, 1H) 8.19-8.28 (m, 1H) 8.74-8.81 (m, 1H) 8.84-8.89 (m, 1H) 10.88-10.99 (m, 1H), LCMS (m/z) (M+H)=517.3, Rt=0.58 min.

Example 739: (S)-2-(2-cyanopropan-2-yl)-N-(3-(2-((2-hydroxypropyl)amino)-6-morpholinopyrimidin-4-yl)-4-methylphenyl)isonicotinamide

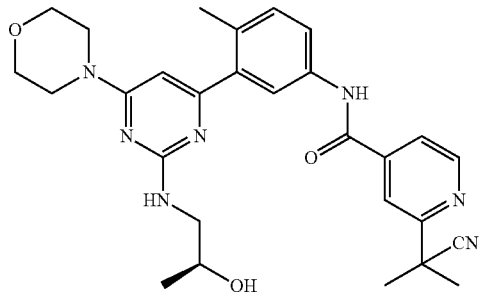 [SMILES: Cc1ccc(NC(=O)c2ccnc(C(C)(C)C#N)c2)cc1-c1cc(N2CCOCC2)nc(NC[C@H](C)O)n1]

1H NMR (400 MHz, <dmso>) δ ppm 0.99-1.11 (m, 3H) 1.70 (s, 6H) 2.22-2.31 (m, 3H) 3.13-3.25 (m, 1H) 3.57-3.93 (m, 10H) 6.49-6.57 (m, 1H) 7.32-7.42 (m, 2H) 7.69-7.88 (m, 3H) 7.93-7.99 (m, 1H) 8.73-8.80 (m, 1H) 10.67-10.73 (m, 1H), LCMS (m/z) (M+H)=516.2, Rt=0.68 min.

Example 740: (S)—N-(5-(2-((2-hydroxypropyl)amino)-6-morpholinopyrimidin-4-yl)-6-methylpyridin-3-yl)-3-(trifluoromethyl)benzamide

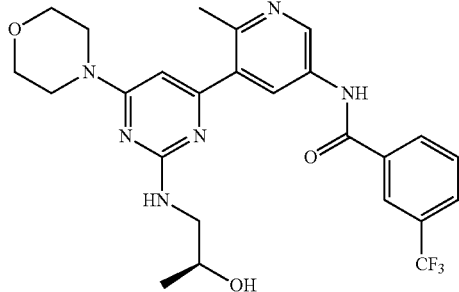 [SMILES: Cc1ncc(NC(=O)c2cccc(C(F)(F)F)c2)cc1-c1cc(N2CCOCC2)nc(NC[C@H](C)O)n1]

1H NMR (400 MHz, <dmso>) δ ppm 1.04-1.15 (m, 3H) 2.50-2.52 (m, 3H) 3.19-3.30 (m, 1H) 3.69 (br. s., 6H) 3.75-3.93 (m, 4H) 6.65-6.71 (m, 1H) 7.43-7.59 (m, 1H) 7.75-7.86 (m, 1H) 7.95-8.06 (m, 1H) 8.21-8.38 (m, 3H) 8.89-8.95 (m, 1H) 10.79-10.89 (m, 1H), LCMS (m/z) (M+H)=517.2, Rt=0.67 min.

Synthesis of (R)-1-((4-chloro-6-morpholinopyrimidin-2-yl)amino) propan-2-ol

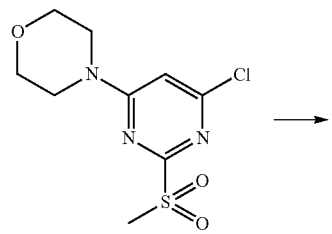

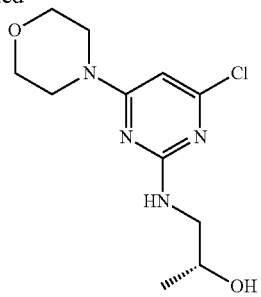

To a solution of 4-(6-chloro-2-(methylsulfonyl)pyrimidin-4-yl) morpholine (1.0 equiv.) in DMF (0.18 M) was added (R)-1-aminopropan-2-ol (2.0 equiv.) and DIEA (2 eq) at room temperature. The reaction was stirred at ambient temperature for 16 h. The reaction mixture was partitioned between water and ethyl acetate and the separated organic phase was dried with sodium sulfate, filtered and concentrated under vacuo to yield of (R)-1-((4-chloro-6-morpholinopyrimidin-2-yl)amino)propan-2-ol I in quantitative yield. LCMS (m/z) (M+H)=273/274.9, Rt=0.43 min.

Example 741: (R)-2-(2-cyanopropan-2-yl)-N-(3-(2-((2-hydroxypropyl)amino)-6-morpholinopyrimidin-4-yl)-4-methylphenyl)isonicotinamide

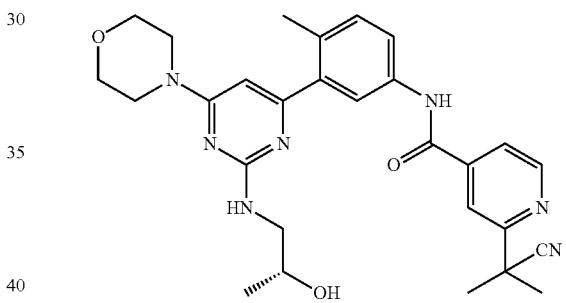

1H NMR (400 MHz, <dmso>) δ ppm 1.03-1.11 (m, 3H) 1.75 (s, 6H) 2.26-2.35 (m, 3H) 3.17-3.30 (m, 1H) 3.35-3.47 (m, 1H) 3.68-3.82 (m, 9H) 6.55-6.65 (m, 1H) 7.37-7.48 (m, 2H) 7.73-7.93 (m, 3H) 7.96-8.03 (m, 1H) 8.75-8.86 (m, 1H) 10.70-10.78 (m, 1H), LCMS (m/z) (M+H)=516.2, Rt=0.68 min.

Example 742: (R)-2-(2-cyanopropan-2-yl)-N-(5-(2-((2-hydroxypropyl)amino)-6-morpholinopyrimidin-4-yl)-6-methylpyridin-3-yl)isonicotinamide

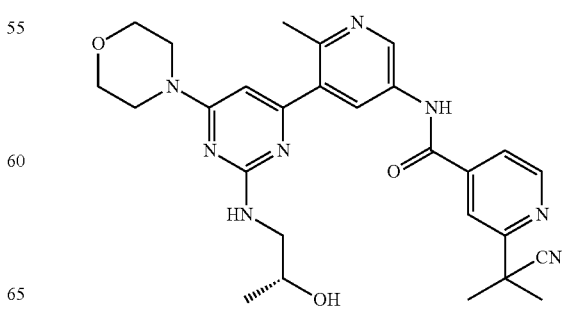

1H NMR (400 MHz, <dmso>) δ ppm 1.00-1.11 (m, 3H) 1.71 (s, 6H) 2.46-2.47 (m, 3H) 3.13-3.25 (m, 1H) 3.73-3.89 (m, 9H) 6.56-6.69 (m, 1H) 7.76-7.89 (m, 1H) 7.94-8.02 (m, 1H) 8.19-8.30 (m, 1H) 8.76-8.90 (m, 2H) 10.82-10.94 (m, 1H), LCMS (m/z) (M+H)=517.2, Rt=0.57 min.

Example 743: (R)—N-(5-(2-((2-hydroxypropyl)amino)-6-morpholinopyrimidin-4-yl)-6-methylpyridin-3-yl)-3-(trifluoromethyl)benzamide

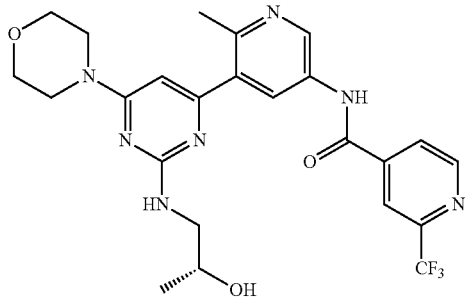 [SMILES: Cc1ncc(NC(=O)c2ccnc(C(F)(F)F)c2)cc1-c1cc(N2CCOCC2)nc(NC[C@@H](C)O)n1]

1H NMR (400 MHz, <dmso>) δ ppm 1.02-1.17 (m, 3H) 2.50-2.51 (m, 3H) 3.18-3.31 (m, 1H) 3.65-3.86 (m, 9H) 6.64-6.73 (m, 1H) 7.76-7.86 (m, 1H) 7.97-8.04 (m, 1H) 8.23-8.36 (m, 3H) 8.87-8.95 (m, 1H) 10.80-10.88 (m, 1H), LCMS (m/z) (M+H)=517.2, Rt=0.66 min.

Synthesis of (S)-2-((4-chloro-6-morpholinopyrimidin-2-yl)amino) propan-1-ol

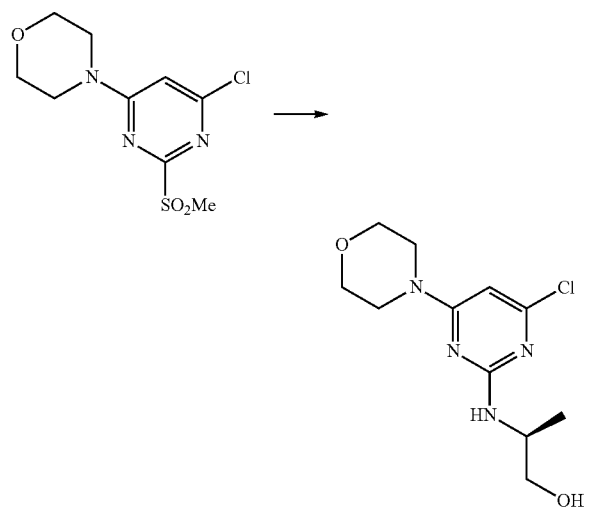

To a solution of 4-(6-chloro-2-(methylsulfonyl)pyrimidin-4-yl) morpholine (1.0 equiv.) in DMF (0.18 M) was added (S)-2-aminopropan-1-ol (2.0 equiv.) and DIEA (2 eq) at room temperature. The reaction was stirred at ambient temperature for 16 h. As starting material remained when checked by LCMS more (S)-2-aminopropan-1-ol (4.0 equiv.) and DIEA (4 eq) was added and the stirred the mixture for 5 h. The reaction mixture was partitioned between water and ethyl acetate and the separated organic phase was dried with sodium sulfate, filtered and concentrated under vacuo. The concentrated crude was purified via silica gel chromatography and eluted with 0 to 100% ethyl acetate in heptanes to yield to yield (S)-2-((4-chloro-6-morpholinopyrimidin-2-yl)amino)propan-1-ol in 88% yield. LCMS (m/z) (M+H)=273/274.8, Rt=0.48 min.

Example 744: (S)-2-(2-cyanopropan-2-yl)-N-(5-(2-((1-hydroxypropan-2-yl)amino)-6-morpholinopyrimidin-4-yl)-6-methylpyridin-3-yl)isonicotinamide

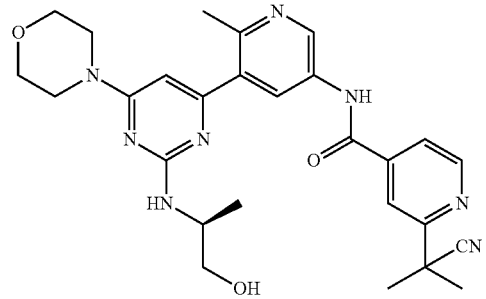 [SMILES: Cc1ncc(NC(=O)c2ccnc(C(C)(C)C#N)c2)cc1-c1cc(N2CCOCC2)nc(N[C@@H](C)CO)n1]

1H NMR (400 MHz, <dmso>) δ ppm 1.09-1.29 (m, 3H) 1.76 (s, 6H) 2.51 (s, 3H) 3.70 (br. s., 12H) 6.64-6.74 (m, 1H) 7.84-7.92 (m, 1H) 8.02 (s, 1H) 8.26-8.36 (m, 1H) 8.79-8.93 (m, 2H) 10.89-11.00 (m, 1H), LCMS (m/z) (M+H)=517.2, Rt=0.6 min.

Example 745: (S)—N-(5-(2-((1-hydroxypropan-2-yl)amino)-6-morpholinopyrimidin-4-yl)-6-methylpyridin-3-yl)-3-(trifluoromethyl)benzamide

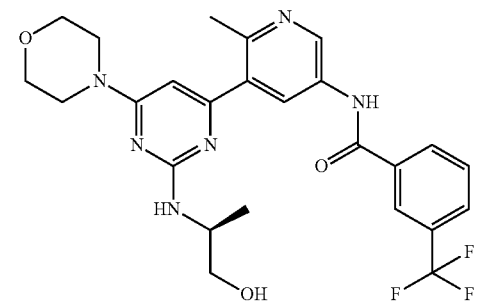 [SMILES: Cc1ncc(NC(=O)c2cccc(C(F)(F)F)c2)cc1-c1cc(N2CCOCC2)nc(N[C@@H](C)CO)n1]

1H NMR (400 MHz, <dmso>) δ ppm 1.04-1.18 (m, 3H) 2.45-2.48 (m, 3H) 3.28-3.53 (m, 10H) 3.99-4.05 (m, 1H) 6.56-6.68 (m, 1H) 7.32-7.44 (m, 1H) 7.68-7.84 (m, 1H) 7.93-8.01 (m, 1H) 8.18-8.35 (m, 3H) 8.81-8.91 (m, 1H) 10.74-10.83 (m, 1H), LCMS (m/z) (M+H)=517.2, Rt=0.7 min.

Example 746: (S)-2-(2-cyanopropan-2-yl)-N-(3-(2-((1-hydroxypropan-2-4 amino)-6-morpholinopyrimidin-4-yl)-4-methylphenyl)isonicotinamide

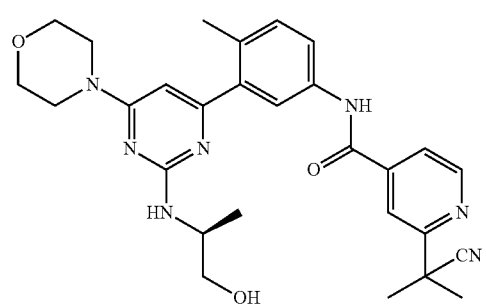 [SMILES: Cc1ccc(NC(=O)c2ccnc(C(C)(C)C#N)c2)cc1-c1cc(N2CCOCC2)nc(N[C@@H](C)CO)n1]

1H NMR (400 MHz, <dmso>) δ ppm 1.08-1.26 (m, 3H) 1.75 (s, 6H) 2.32 (s, 3H) 3.61-3.82 (m, 6H) 3.82-4.22 (m, 3H) 6.47-6.68 (m, 1H) 7.26-7.49 (m, 1H) 7.70-8.10 (m, 4H) 8.76-8.86 (m, 1H) 10.68-10.77 (m, 1H), LCMS (m/z) (M+H)=516.3, Rt=0.72 min.

Synthesis of (R)-2-((4-chloro-6-morpholinopyrimidin-2-yl)amino) propan-1-ol

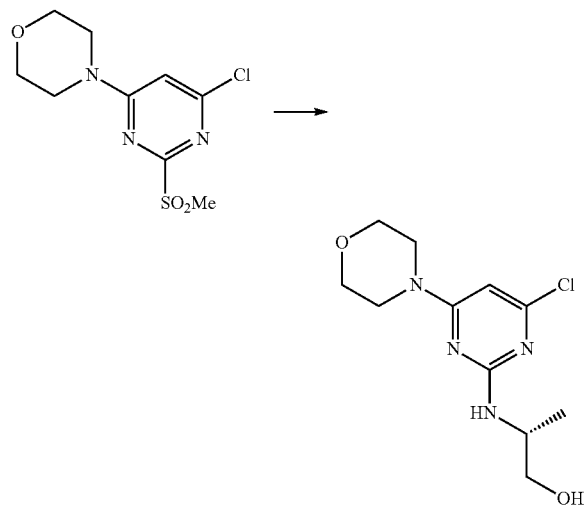

To a solution of 4-(6-chloro-2-(methylsulfonyl)pyrimidin-4-yl) morpholine (1.0 equiv.) in DMF (0.18 M) was added (R)-2-aminopropan-1-ol (2.0 equiv.) and DIEA (2 eq) and the reaction was stirred at ambient temperature for 16 h. As the reaction was incomplete by LCMS to it was added (R)-2-aminopropan-1-ol (4.0 equiv.) and DIEA (4 eq) and the stirred the mixture for 5 h. The reaction mixture was partitioned between water and ethyl acetate and the separated organic phase was dried with sodium sulfate, filtered and concentrated under vacuo. The concentrated crude was purified via silica gel chromatography and eluted with 0 to 100% ethyl acetate in heptanes to yield to yield (R)-2-((4-chloro-6-morpholinopyrimidin-2-yl)amino)propan-1-ol in 92% yield. LCMS (m/z) (M+H)=273/274.8, Rt=0.48 min.

Example 747: (R)-2-(2-cyanopropan-2-yl)-N-(5-(2-((1-hydroxypropan-2-yl)amino)-6-morpholinopyrimidin-4-yl)-6-methylpyridin-3-yl)isonicotinamide

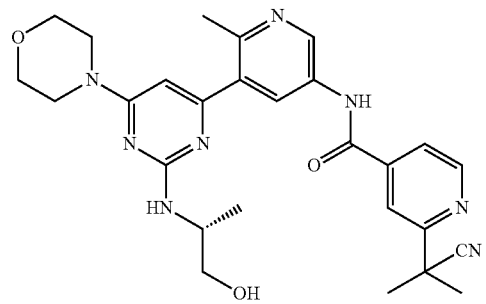 [SMILES: Cc1ncc(NC(=O)c2ccnc(C(C)(C)C#N)c2)cc1-c1cc(N2CCOCC2)nc(N[C@H](C)CO)n1]

1H NMR (400 MHz, <dmso>) δ ppm 1.11-1.27 (m, 3H) 1.76 (s, 6H) 2.51-2.52 (m, 2H) 3.70 (br. s., 8H) 6.60-6.75 (m, 1H) 7.81-7.92 (m, 1H) 7.97-8.07 (m, 1H) 8.22-8.35 (m, 1H) 8.78-8.95 (m, 2H) 10.88-10.99 (m, 1H)), LCMS (m/z) (M+H)=517.3, Rt=0.64 min.

Example 748: (R)—N-(5-(2-((1-hydroxypropan-2-yl)amino)-6-morpholinopyrimidin-4-yl)-6-methylpyridin-3-yl)-3-(trifluoromethyl)benzamide

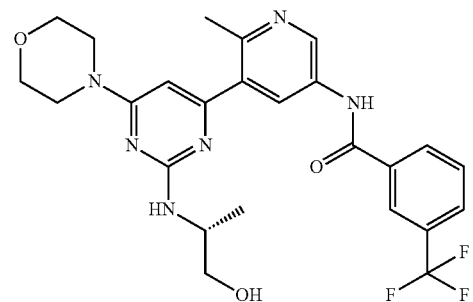 [SMILES: Cc1ncc(NC(=O)c2cccc(C(F)(F)F)c2)cc1-c1cc(N2CCOCC2)nc(N[C@H](C)CO)n1]

1H NMR (400 MHz, <dmso>) δ ppm 1.09-1.28 (m, 3H) 2.50-2.55 (m, 3H) 3.42-3.48 (m, 2H) 3.69 (d, J=4.30 Hz, 8H) 4.01-4.16 (m, 1H) 6.62-6.75 (m, 1H) 7.41-7.58 (m, 1H) 7.77-7.87 (m, 1H) 7.92-8.05 (m, 1H) 8.23-8.37 (m, 3H) 8.86-8.98 (m, 1H) 10.78-10.89 (m, 1H), LCMS (m/z) (M+H)=517.2, Rt=0.7 min.

Example 749: (R)-2-(2-cyanopropan-2-yl)-N-(3-(2-((1-hydroxypropan-2-yl)amino)-6-morpholinopyrimidin-4-yl)-4-methylphenyl)isonicotinamide

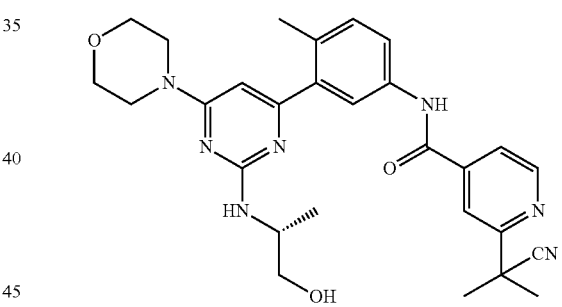

1H NMR (400 MHz, <dmso>) δ ppm 1.09-1.24 (m, 3H) 1.75 (s, 6H) 2.32 (s, 3H) 3.44-3.51 (m, 3H) 3.61-3.78 (m, 5H) 3.82-4.24 (m, 2H) 6.53-6.65 (m, 1H) 7.35-7.45 (m, 1H) 7.64-7.93 (m, 3H) 7.97-8.05 (m, 1H) 8.72-8.87 (m, 1H) 10.67-10.76 (m, 1H), LCMS (m/z) (M+H)=516.3, Rt=0.7 min.

Synthesis of 2-((4-chloro-6-morpholinopyrimidin-2-yl)amino)-2-methylpropan-1-ol

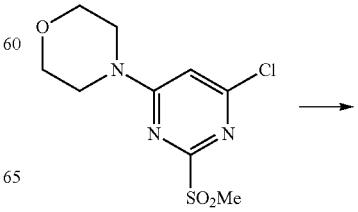

451

-continued

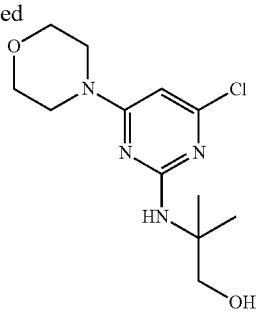

To a solution of 4-(6-chloro-2-(methylsulfonyl)pyrimidin-4-yl) morpholine (1.0 equiv.) in DMF (0.18 M) was added 2-amino-2-methylpropan-1-ol (2.0 equiv.) and DIEA (2 eq) at room temperature. The reaction was stirred at ambient temperature for 16 h. The reaction mixture was partitioned between water and ethyl acetate and the separated organic phase was dried with sodium sulfate, filtered and concentrated under vacuo. The concentrated crude was purified via silica gel chromatography and eluted with 0 to 100% ethyl acetate in heptanes to yield to yield (R)-2-((4-chloro-6-morpholinopyrimidin-2-yl)amino)propan-1-ol. LCMS (m/z) (M+H)=287.1, Rt=0.5 min.

Example 750: 2-(2-cyanopropan-2-yl)-N-(5-(2-((1-hydroxy-2-methylpropan-2-yl)amino)-6-morpholinopyrimidin-4-yl)-6-methylpyridin-3-yl)isonicotinamide

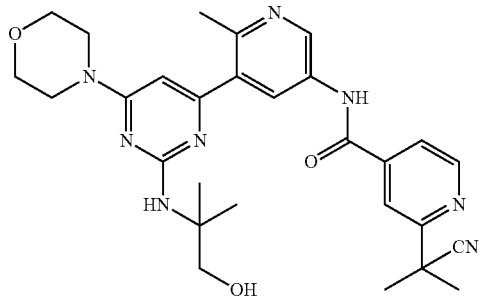 [SMILES: Cc1ncc(NC(=O)c2ccnc(C(C)(C)C#N)c2)cc1-c1cc(N2CCOCC2)nc(NC(C)(C)CO)n1]

1H NMR (400 MHz, <dmso>) δ ppm 1.36 (s, 5H) 1.76 (s, 6H) 2.53 (s, 3H) 3.43-3.52 (m, 2H) 3.66-3.79 (m, 9H) 6.65-6.75 (m, 1H) 7.12-7.23 (m, 1H) 7.83-7.91 (m, 1H) 7.98-8.04 (m, 1H) 8.29-8.37 (m, 1H) 8.80-8.94 (m, 2H) 10.93-11.01 (m, 1H), LCMS (m/z) (M+H)=531.2, Rt=0.62 min.

Example 751: 2-(2-cyanopropan-2-yl)-N-(3-(2-((1-hydroxy-2-methylpropan-2-yl)amino)-6-morpholinopyrimidin-4-yl)-4-methylphenyl)isonicotinamide

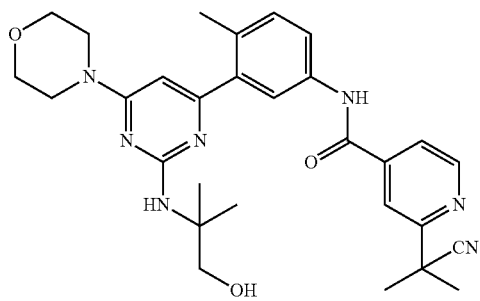 [SMILES: Cc1ccc(NC(=O)c2ccnc(C(C)(C)C#N)c2)cc1-c1cc(N2CCOCC2)nc(NC(C)(C)CO)n1]

LCMS (m/z) (M+H)=530.4, Rt=0.74 min.

452

Example 752: N-(5-(2-((1-hydroxy-2-methylpropan-2-yl)amino)-6-morpholinopyrimidin-4-yl)-6-methylpyridin-3-yl)-3-(trifluoromethyl)benzamide

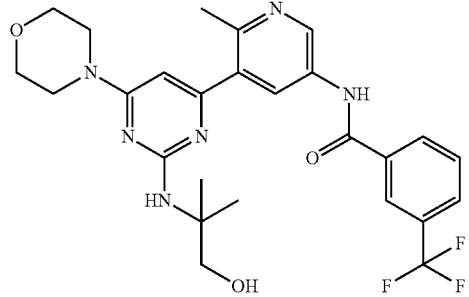 [SMILES: Cc1ncc(NC(=O)c2cccc(C(F)(F)F)c2)cc1-c1cc(N2CCOCC2)nc(NC(C)(C)CO)n1]

¹H NMR (400 MHz, <dmso>) δ ppm 1.37 (s, 6H) 2.53 (s, 3H) 3.66-3.95 (m, 8H) 6.64-6.76 (m, 1H) 7.02-7.15 (m, 1H) 7.75-7.88 (m, 1H) 7.95-8.06 (m, 1H) 8.22-8.44 (m, 3H) 8.84-8.94 (m, 1H) 10.73-10.89 (m, 1H), LCMS (m/z) (M+H)=531.3, Rt=0.7 min.

Example 753: 2-(2-cyanopropan-2-yl)-N-(5-(2-((4-(hydroxymethyl)tetrahydro-2H-pyran-4-yl)amino)-6-morpholinopyrimidin-4-yl)-6-methylpyridin-3-yl)isonicotinamide

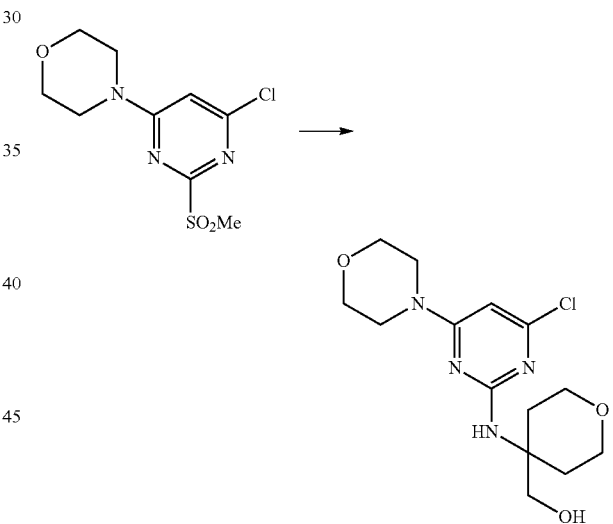

Synthesis of (4-((4-chloro-6-morpholinopyrimidin-2-yl)amino)tetrahydro-2H-pyran-4-yl)methanol To a solution of 4-(6-chloro-2-(methylsulfonyl)pyrimidin-4-yl)morpholine (1.0 equiv.) in DMF (0.18 M) was added 2-amino-2-methylpropan-1-ol (2.0 equiv.) and DIEA (2 eq) and the reaction mixture was heated to 100° C. for 48 h. The reaction mixture was partitioned between water and ethyl acetate and the separated organic phase was dried with sodium sulfate, filtered and concentrated under vacuo. The concentrated crude was purified via silica gel chromatography and eluted with 0 to 100% ethyl acetate in heptanes to yield (4-((4-chloro-6-morpholinopyrimidin-2-yl)amino)tetrahydro-2H-pyran-4-yl)methanol. LCMS (m/z) (M+H)= 329, Rt=0.47 min.

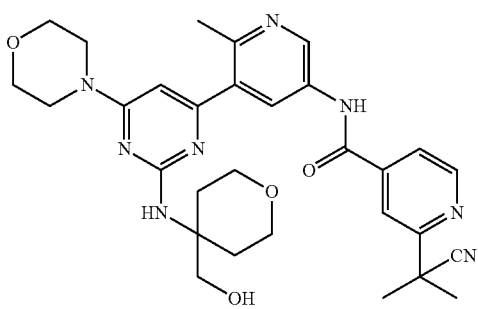 [SMILES: Cc1ncc(NC(=O)c2ccnc(C(C)(C)C#N)c2)cc1-c1cc(N2CCOCC2)nc(NC2(CO)CCOCC2)n1]

1H NMR (400 MHz, <dmso>) δ ppm 1.57-1.68 (m, 2H) 1.71 (s, 6H) 1.96-2.13 (m, 2H) 2.47-2.56 (m, 3H) 3.67-3.86 (m, 8H) 6.63-6.72 (m, 1H) 6.99-7.11 (m, 1H) 7.78-7.87 (m, 1H) 7.94-8.02 (m, 1H) 8.25-8.37 (m, 1H) 8.75-8.89 (m, 2H) 10.86-10.95 (m, 1H), LCMS (m/z) (M+H)=573.4.3, Rt=0.58 min.

Example 754: 2-(2-cyanopropan-2-yl)-N-(3-(2-((4-(hydroxymethyl)tetrahydro-2H-pyran-4-yl)amino)-6-morpholinopyrimidin-4-yl)-4-methylphenyl)isonicotinamide

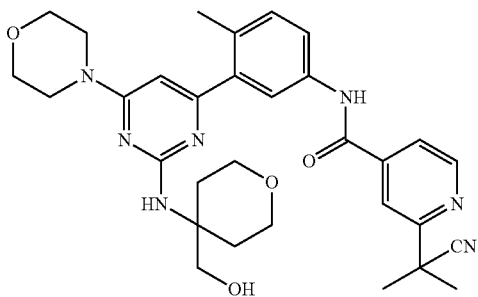 [SMILES: Cc1ccc(NC(=O)c2ccnc(C(C)(C)C#N)c2)cc1-c1cc(N2CCOCC2)nc(NC2(CO)CCOCC2)n1]

LCMS (m/z) (M+H)=572.3, Rt=0.68 min.

Synthesis of 4-(5-amino-2-methylphenyl)-N,N-dimethyl-6-morpholinopyrimidin-2-amine

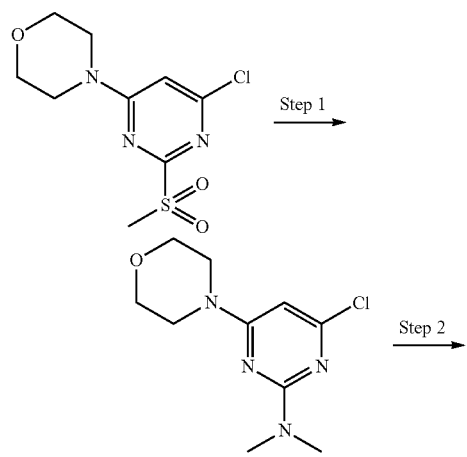

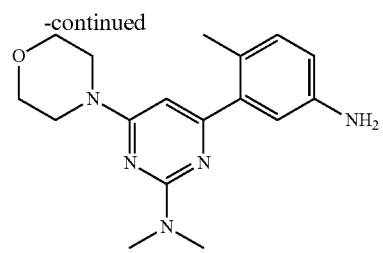

Step 1:

To a solution of 4-(6-chloro-2-(methylsulfonyl)pyrimidin-4-yl)morpholine (1.0 equiv.) in 1,4-dioxane (0.18 M) was added dimethylamine solution in ethanol (2.0 equiv.) at room temperature. The reaction was stirred for 30 min, at which point two products were observed with the desired one as the major product. The reaction was concentrated to dryness under vacuo and the crude was purified via silica gel column chromatography eluting with 0-100% ethyl acetate in heptanes to yield 4-chloro-N,N-dimethyl-6-morpholinopyrimidin-2-amine as a white solid in 57% yield. LCMS (m/z) (M+H)=243.2, Rt=0.60 min.

Step 2:

To a solution of 4-chloro-N,N-dimethyl-6-morpholinopyrimidin-2-amine (1.0 equiv.) in DME (0.14 M) was added 4-methyl-3-(4,4,5,5-tetramethyl-1,3,2-dioxaborolan-2-yl)aniline (1.3 equiv.), PdCl2(dppf)-DCM adduct (0.1 equiv.) and 2M aqueous sodium carbonate (3.00 equiv.), and the reaction was heated to 120° C. for 35 min in the microwave. LC/MS showed incomplete reaction, allowed to heat in the oil bath at 100° C. for 3 hours. At this time, the reaction was complete. Cooled to room temperature, partitioned between water and ethyl acetate, the organic phase was dried with sodium sulfate, filtered and concentrated. The crude material was purified via silica gel column chromatography eluting with 0-100% ethyl acetate in heptanes. The pure fractions were concentrated under vacuo to yield 4-(5-amino-2-methylphenyl)-N,N-dimethyl-6-morpholinopyrimidin-2-amine as the desired product in 76% yield. LCMS (m/z) (M+H)=314, Rt=0.41 min.

Example 755: 2-(2-cyanopropan-2-yl)-N-(3-(2-(dimethylamino)-6-morpholinopyrimidin-4-yl)-4-methylphenyl)isonicotinamide

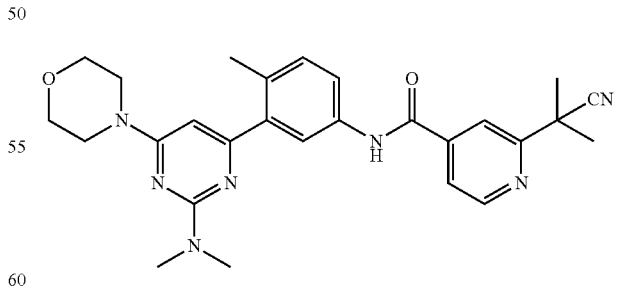

1H NMR (400 MHz, <cd3od>) δ ppm 1.81 (s, 6H) 2.37 (s, 3H) 3.25 (s, 6H) 3.78 (br. s., 5H) 4.03 (br. s., 1H) 6.52 (s, 1H) 7.42 (d, J=8.61 Hz, 1H) 7.65 (dd, J=8.22, 1.96 Hz, 1H) 7.81 (dd, J=5.09, 1.17 Hz, 1H) 7.95 (d, J=1.96 Hz, 1H) 8.07 (s, 1H) 8.77 (d, J=5.09 Hz, 1H), LCMS (m/z) (M+H)=486.2, Rt=0.73 min.

Example 756: 2-(1,1-difluoroethyl)-N-(3-(2-(dimethylamino)-6-morpholinopyrimidin-4-yl)-4-methylphenyl)isonicotinamide

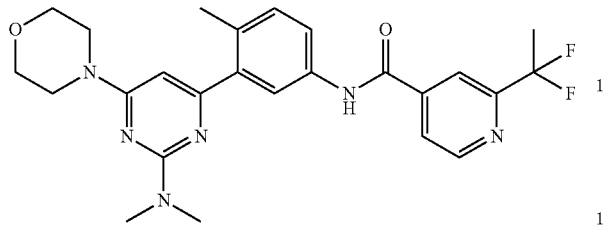

1H NMR (400 MHz, <cd3od>) δ ppm 2.03 (t, J=18.59 Hz, 3H) 2.37 (s, 3H) 3.25 (s, 6H) 3.78 (br. s., 5H) 6.52 (s, 1H) 7.42 (d, J=8.22 Hz, 1H) 7.66 (dd, J=8.22, 2.35 Hz, 1H) 7.96 (d, J=2.35 Hz, 2H) 8.17 (s, 1H) 8.82 (d, J=5.09 Hz, 1H), LCMS (m/z) (M+H)=483.2, Rt=0.76 min.

Example 757: N-(3-(2-(dimethylamino)-6-morpholinopyrimidin-4-yl)-4-methylphenyl)-2-isopropylisonicotinamide

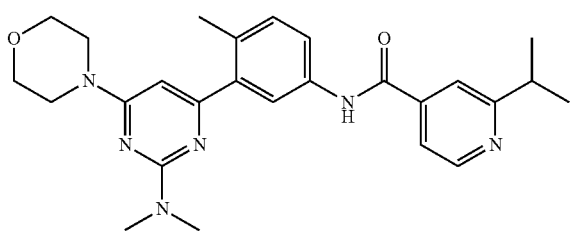 [SMILES: Cc1ccc(NC(=O)c2ccnc(C(C)C)c2)cc1-c1cc(N2CCOCC2)nc(N(C)C)n1]

¹H NMR (400 MHz, <dmso>) δ ppm 1.11 (t, J=7.24 Hz, 1H) 1.22 (d, J=7.04 Hz, 6H) 2.23 (s, 3H) 2.84-3.25 (m, 7H) 3.63 (br. s., 3H) 7.31 (br. s., 1H) 7.55-8.04 (m, 3H) 8.63 (d, J=5.09 Hz, 1H), LCMS (m/z) (M+H)=461.1, Rt=0.54 min.

Example 758: N-(3-(2-(dimethylamino)-6-morpholinopyrimidin-4-yl)-4-methylphenyl)-2-(trifluoromethyl)isonicotinamide

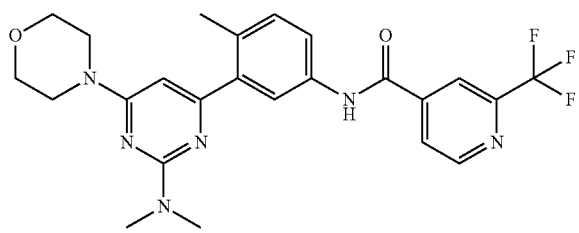 [SMILES: Cc1ccc(NC(=O)c2ccnc(C(F)(F)F)c2)cc1-c1cc(N2CCOCC2)nc(N(C)C)n1]

1H NMR (400 MHz, <cd3od>) δ ppm 2.37 (s, 3H) 3.25 (s, 6H) 3.78 (br. s., 5H) 6.52 (s, 1H) 7.42 (d, J=8.22 Hz, 1H) 7.67 (dd, J=8.41, 2.15 Hz, 1H) 7.96 (d, J=1.96 Hz, 1H) 8.12 (d, J=4.70 Hz, 1H) 8.29 (s, 1H) 8.92 (d, J=5.09 Hz, 1H), LCMS (m/z) (M+H)=487.1, Rt=0.76 min.

Example 759: N-(3-(2-(dimethylamino)-6-morpholinopyrimidin-4-yl)-4-methylphenyl)-2-(methylsulfonyl)isonicotinamide

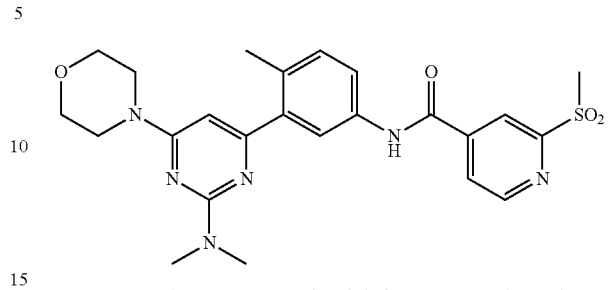

1H NMR (400 MHz, <cd3od>) δ ppm 2.37 (s, 3H) 3.25 (s, 7H) 3.78 (br. s., 7H) 6.52 (s, 1H) 7.42 (d, J=8.61 Hz, 1H) 7.68 (dd, J=8.22, 2.35 Hz, 1H) 7.96 (d, J=1.96 Hz, 1H) 8.10-8.22 (m, 1H) 8.54 (s, 1H) 8.94 (d, J=5.09 Hz, 1H), LCMS (m/z) (M+H)=497.1, Rt=0.63 min.

Example 760: N-(5-(2-(dimethylamino)-6-morpholinopyrimidin-4-yl)-6-methylpyridin-3-yl)-3-(trifluoromethyl)benzamide

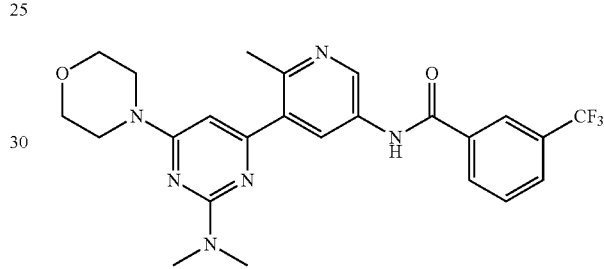

To a solution of 4-chloro-N,N-dimethyl-6-morpholinopyrimidin-2-amine (1.0 equiv.) in DME was added N-(6-methyl-5-(4,4,5,5-tetramethyl-1,3,2-dioxaborolan-2-yl)pyridin-3-yl)-3-(trifluoromethyl)benzamide (Intermediate B, 1.3 equiv.), followed by PdCl2(dppf).CH2Cl2 adduct (0.10 equiv.), and 2M aqueous sodium carbonate (3.00 equiv.). The reaction was heated in the microwave for 10 min at 120° C. LC/MS showed completion of the reaction. The organic phase was concentrated to dryness, dissolved in DMSO, filtered through a HPLC filter and purified via auto-preparative reverse phase HPLC. The pure fractions were lyophilized to yield N-(5-(2-(dimethylamino)-6-morpholinopyrimidin-4-yl)-6-methylpyridin-3-yl)-3-(trifluoromethyl)benzamide as a fluffy solid in 19% yield. 1H NMR (400 MHz, <cd3od>) δ ppm 2.57 (s, 3H) 3.26 (s, 6H) 3.80 (d, J=4.70 Hz, 4H) 6.61 (s, 1H) 7.70-7.80 (m, 1H) 7.94 (d, J=7.83 Hz, 1H) 8.24 (d, J=7.43 Hz, 1H) 8.30 (s, 1H) 8.46 (d, J=2.35 Hz, 1H) 8.84 (d, J=2.35 Hz, 1H), LCMS (m/z) (M+H)=487.2, Rt=0.66 min.

Synthesis of 4-(6-chloro-2-ethoxypyrimidin-4-yl)morpholine

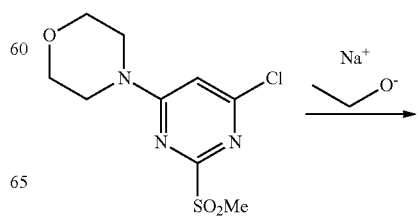

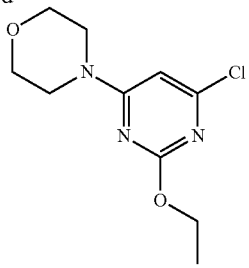

To a solution of 4-(6-chloro-2-(methylsulfonyl)pyrimidin-4-yl)morpholine (1.0 equiv.) was added 21% sodium ethoxide in ethanol (2 equiv.) and the mixture was stirred at ambient temperature for 16 h. The reaction was partitioned between water and ethyl acetate the separated organic phase was dried with sodium sulfate, filtered and concentrated under vacuo. The concentrated crude was purified via silica gel chromatography and eluted with 0 to 100% ethyl acetate in heptanes to 4-(6-chloro-2-ethoxypyrimidin-4-yl) morpholine in 87% yield. LCMS (m/z) (M+H)=244/245.9, Rt=0.71 min.

Example 761: 2-(1,1-difluoroethyl)-N-(3-(2-ethoxy-6-morpholinopyrimidin-4-yl)-4-methylphenyl)isonicotinamide

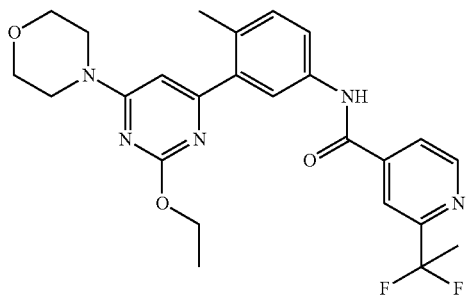 [SMILES: CCOc1nc(-c2cc(NC(=O)c3ccnc(C(C)(F)F)c3)ccc2C)cc(N2CCOCC2)n1]

1H NMR (400 MHz, <dmso>) δ ppm 1.27 (t, J=7.04 Hz, 3H) 1.99 (t, J=19.17 Hz, 3H) 2.26 (s, 3H) 3.63 (br. s., 8H) 4.33 (d, J=4.30 Hz, 2H) 6.54-6.68 (m, 1H) 7.22-7.30 (m, 1H) 7.64-7.82 (m, 2H) 7.88-8.02 (m, 1H) 8.08-8.19 (m, 1H) 8.75-8.88 (m, 1H) 10.55-10.73 (m, 1H), LCMS (m/z) (M+H)=484.2, Rt=0.74 min.

Example 762: N-(3-(2-ethoxy-6-morpholinopyrimidin-4-yl)-4-methylphenyl)-2-(trifluoromethyl)isonicotinamide

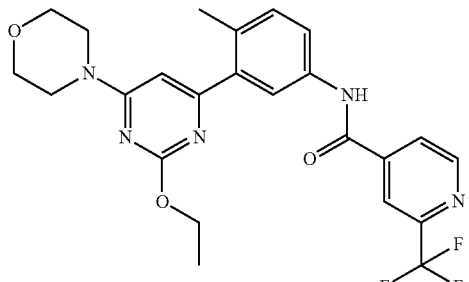

1H NMR (400 MHz, <dmso>) δ ppm 1.27 (t, J=7.04 Hz, 3H) 2.26 (s, 3H) 3.63 (br. s., 8H) 4.32 (d, J=4.30 Hz, 2H) 6.55-6.74 (m, 1H) 7.19-7.40 (m, 1H) 7.66-7.83 (m, 2H) 8.03-8.20 (m, 1H) 8.25-8.38 (m, 1H) 8.88-9.01 (m, 1H) 10.58-10.81 (m, 1H), LCMS (m/z) (M+H)=488.2, Rt=0.76 min.

Example 763: N-(3-(2-ethoxy-6-morpholinopyrimidin-4-yl)-4-methylphenyl)-2-isopropylisonicotinamide

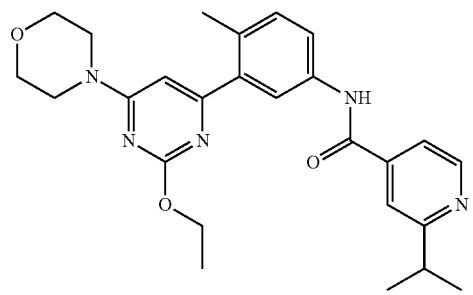 [SMILES: CCOc1nc(-c2cc(NC(=O)c3ccnc(C(C)C)c3)ccc2C)cc(N2CCOCC2)n1]

1H NMR (400 MHz, <dmso>) δ ppm 1.27 (t, J=7.04 Hz, 3H) 1.99 (t, J=19.17 Hz, 3H) 2.26 (s, 3H) 3.63 (br. s., 8H) 4.33 (d, J=4.30 Hz, 2H) 6.54-6.68 (m, 1H) 7.22-7.30 (m, 1H) 7.64-7.82 (m, 2H) 7.88-8.02 (m, 1H) 8.08-8.19 (m, 1H) 8.75-8.88 (m, 1H) 10.55-10.73 (m, 1H), LCMS (m/z) (M+H)=484.2, Rt=0.74 min.

Example 764: 2-(2-cyanopropan-2-yl)-N-(3-(2-ethoxy-6-morpholinopyrimidin-4-yl)-4-methylphenyl)isonicotinamide

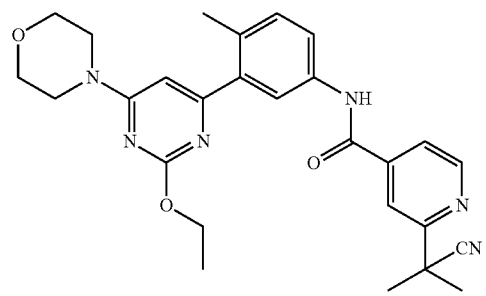 [SMILES: CCOc1nc(-c2cc(NC(=O)c3ccnc(C(C)(C)C#N)c3)ccc2C)cc(N2CCOCC2)n1]

1H NMR (400 MHz, <dmso>) δ ppm 1.33 (s, 3H) 1.75 (s, 6H) 2.31 (s, 3H) 3.69 (d, J=2.74 Hz, 9H) 4.36-4.50 (m, 2H) 6.63-6.78 (m, 1H) 7.27-7.39 (m, 1H) 7.70-7.88 (m, 3H) 7.95-8.05 (m, 1H) 8.76-8.81 (m, 1H) 10.59-10.71 (m, 1H), LCMS (m/z) (M+H)=487.2, Rt=0.74 min.

Synthesis of 1-(4-chloro-6-morpholinopyrimidin-2-yl)azetidin-3-ol

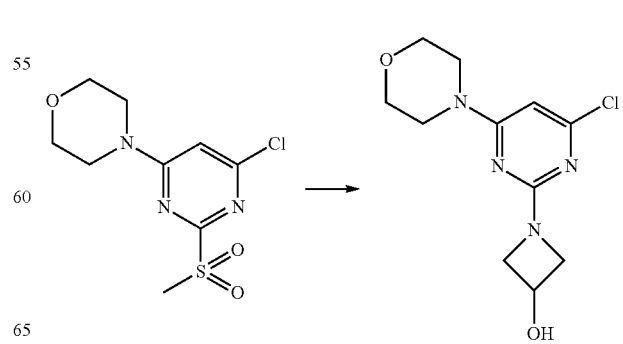

To a solution of 4-(6-chloro-2-(methylsulfonyl)pyrimidin-4-yl) morpholine (1.0 equiv.) in THF (0.01 M) was added azetidine-3-ol (2.0 equiv.) and DIEA (2 eq) at room temperature. The reaction was stirred at ambient temperature for 16 h. The reaction mixture showed 50% starting material being present by LC/MS. To the mixture was added 5 ml of DMF and another portion of azetidine-3-ol (2.0 equiv.) and DIEA (2 eq) and the mixture was stirred at ambient temperature for 4 h. The reaction was partitioned between water and ethyl acetate the separated organic phase was dried with sodium sulfate, filtered and concentrated under vacuo to yield 1-(4-chloro-6-morpholinopyrimidin-2-yl)azetidin-3-ol in quantitative yield. LCMS (m/z) (M+H)= 271/273, Rt=0.43 min.

Example 765: N-(3-(2-(3-hydroxyazetidin-1-yl)-6-morpholinopyrimidin-4-yl)-4-methylphenyl)-3-(trifluoromethyl)benzamide

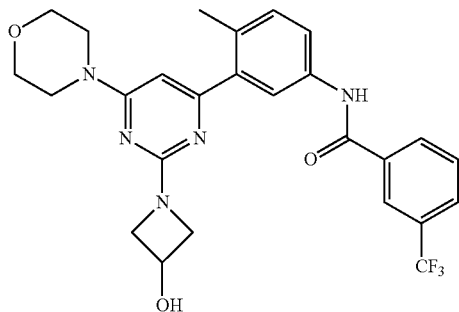 [SMILES: Cc1ccc(NC(=O)c2cccc(C(F)(F)F)c2)cc1-c1cc(N2CCOCC2)nc(N2CC(O)C2)n1]

1H NMR (400 MHz, <dmso>) δ ppm 2.22 (s, 3H) 3.62 (br. s., 6H) 3.78-3.96 (m, 3H) 4.25-4.39 (m, 1H) 4.48-4.59 (m, 1H) 6.44-6.69 (m, 1H) 7.28-7.42 (m, 1H) 7.65-7.83 (m, 3H) 7.88-7.98 (m, 1H) 8.16-8.34 (m, 2H) 10.45-10.61 (m, 1H) 12.20-12.34 (m, 1H), LCMS (m/z) (M+H)=514.2, Rt=0.79 min.

Example 766: 3-(2-(3-hydroxyazetidin-1-yl)-6-morpholinopyrimidin-4-yl)-4-methyl-N-(3-(trifluoromethyl)phenyl)benzamide

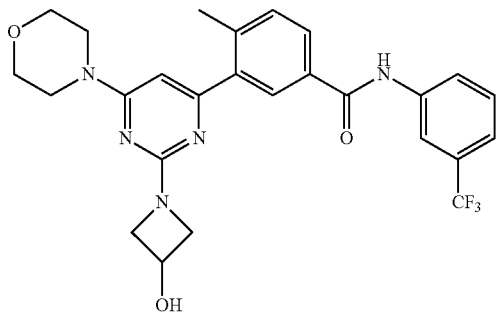 [SMILES: Cc1ccc(C(=O)Nc2cccc(C(F)(F)F)c2)cc1-c1cc(N2CCOCC2)nc(N2CC(O)C2)n1]

1H NMR (400 MHz, <dmso>) δ ppm 2.27-2.37 (m, 3H) 3.54-3.70 (m, 6H) 3.75-3.95 (m, 3H) 4.23-4.40 (m, 1H) 4.44-4.58 (m, 1H) 7.34-7.43 (m, 1H) 7.47-7.62 (m, 2H) 7.86-8.08 (m, 3H) 8.14-8.21 (m, 1H) 10.44-10.53 (m, 1H), LCMS (m/z) (M+H)=514.2, Rt=0.81 min.

Example 767: 2-(2-cyanopropan-2-yl)-N-(5-(2-(3-hydroxyazetidin-1-yl)-6-morpholinopyrimidin-4-yl)-6-methylpyridin-3-yl)isonicotinamide

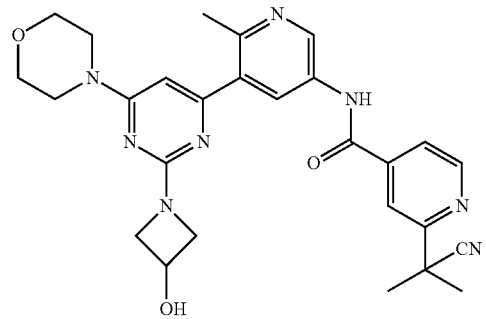 [SMILES: Cc1ncc(NC(=O)c2ccnc(C(C)(C)C#N)c2)cc1-c1cc(N2CCOCC2)nc(N2CC(O)C2)n1]

LCMS (m/z) (M+H)=515.4, Rt=0.56 min.

Example 768: N-(5-(2-(3-hydroxyazetidin-1-yl)-6-morpholinopyrimidin-4-yl)-6-methylpyridin-3-yl)-3-(trifluoromethyl)benzamide

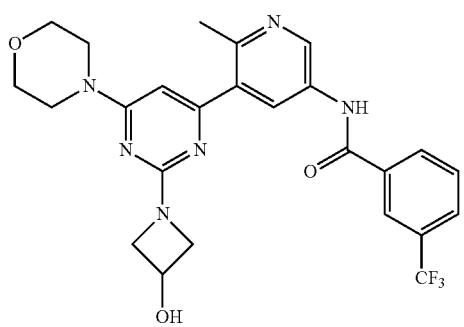 [SMILES: Cc1ncc(NC(=O)c2cccc(C(F)(F)F)c2)cc1-c1cc(N2CCOCC2)nc(N2CC(O)C2)n1]

1H NMR (400 MHz, <dmso>) δ ppm 2.27-2.37 (m, 3H) 3.54-3.70 (m, 6H) 3.75-3.95 (m, 3H) 4.23-4.40 (m, 1H) 4.44-4.58 (m, 1H) 7.34-7.43 (m, 1H) 7.47-7.62 (m, 2H) 7.86-8.08 (m, 3H) 8.14-8.21 (m, 1H) 10.44-10.53 (m, 1H), LCMS (m/z) (M+H)=515.3, Rt=0.65 min.

Example 769: N-(5-(2-(3-hydroxyazetidin-1-yl)-6-morpholinopyrimidin-4-yl)-6-methylpyridin-3-yl)-3-(trifluoromethyl)benzamide

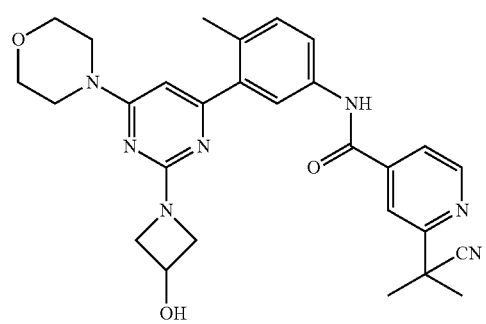 [SMILES: Cc1ccc(NC(=O)c2ccnc(C(C)(C)C#N)c2)cc1-c1cc(N2CCOCC2)nc(N2CC(O)C2)n1]

1H NMR (400 MHz, <dmso>) δ ppm 1.73 (s, 6H) 2.38 (s, 3H) 3.41-3.67 (m, 4H) 3.71-4.09 (m, 3H) 4.13-4.35 (m, 1H) 4.42-4.59 (m, 1H) 6.53-6.69 (m, 1H) 7.34-7.52 (m, 2H) 7.64-7.73 (m, 1H) 7.84-7.90 (m, 1H) 8.73-8.85 (m, 1H), LCMS (m/z) (M+H)=514.3, Rt=0.65 min.

Example 770: 3-(difluoromethyl)-N-(5-(2-(3-hydroxyazetidin-1-yl)-6-morpholinopyrimidin-4-yl)-6-methylpyridin-3-yl)benzamide

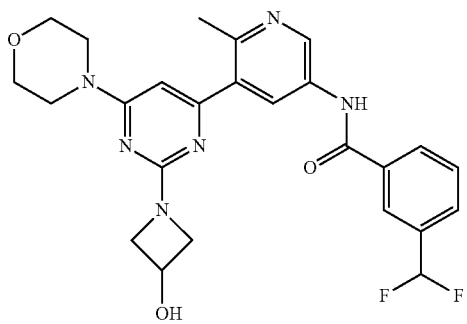 [SMILES: Cc1ncc(NC(=O)c2cccc(C(F)F)c2)cc1-c1cc(N2CCOCC2)nc(N2CC(O)C2)n1]

1H NMR (400 MHz, <dmso>) δ ppm 3.60-3.74 (m, 4H) 3.84-3.99 (m, 2H) 4.27-4.43 (m, 2H) 4.49-4.69 (m, 1H) 7.12-7.17 (m, 1H) 7.63-7.79 (m, 1H) 7.77-7.90 (m, 1H) 8.09-8.20 (m, 2H) 8.24-8.33 (m, 1H) 8.88-8.95 (m, 1H) 10.70-10.83 (m, 1H), LCMS (m/z) (M+H)=497.3, Rt=0.57 min.

Example 771: N-(3-(2-(3-hydroxyazetidin-1-yl)-6-morpholinopyrimidin-4-yl)-4-methylphenyl)-2-isopropylisonicotinamide

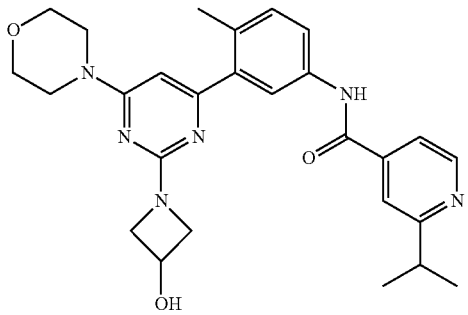 [SMILES: Cc1ccc(NC(=O)c2ccnc(C(C)C)c2)cc1-c1cc(N2CCOCC2)nc(N2CC(O)C2)n1]

1H NMR (400 MHz, <dmso>) δ ppm 1.22 (d, J=7.04 Hz, 6H) 2.22 (s, 3H) 2.97-3.14 (m, 1H) 3.56-3.73 (m, 5H) 3.78-3.91 (m, 3H) 4.22-4.40 (m, 2H) 4.45-4.58 (m, 1H) 6.46-6.60 (m, 1H) 7.29-7.39 (m, 1H) 7.60-7.63 (m, 1H) 7.66-7.69 (m, 1H) 7.70-7.86 (m, 2H) 8.59-8.67 (m, 1H) 10.49-10.58 (m, 1H), LCMS (m/z) (M+H)=489.2, Rt=0.61 min.

Example 772: 2-(1,1-difluoroethyl)-N-(3-(2-(3-hydroxyazetidin-1-yl)-6-morpholinopyrimidin-4-yl)-4-methylphenyl)isonicotinamide

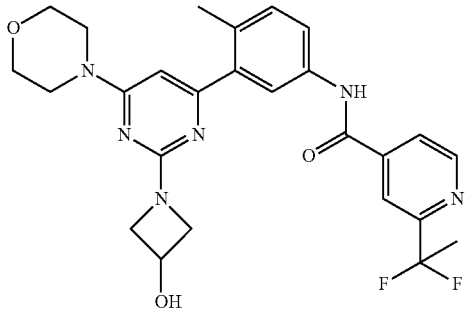 [SMILES: Cc1ccc(NC(=O)c2ccnc(C(C)(F)F)c2)cc1-c1cc(N2CCOCC2)nc(N2CC(O)C2)n1]

1H NMR (400 MHz, <dmso>) $^{TM}$δ ppm 2.04 (s, 3H) 2.27 (s, 3H) 3.65-3.70 (m, 6H) 3.82-3.96 (m, 4H) 4.30-4.43 (m, 2H) 4.50-4.68 (m, 1H) 6.50-6.60 (m, 1H) 7.33-7.47 (m, 1H) 7.77-7.92 (m, 2H) 7.96-8.08 (m, 1H) 8.14-8.22 (m, 1H) 8.79-8.94 (m, 1H) 10.70-10.84 (m, 1H), LCMS (m/z) (M+H)=511.2, Rt=0.65 min.

Example 773: N-(3-(2-(3-hydroxyazetidin-1-yl)-6-morpholinopyrimidin-4-yl)-4-methylphenyl)-2-(trifluoromethyl)isonicotinamide

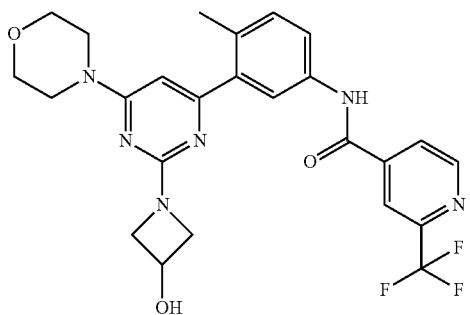 [SMILES: Cc1ccc(NC(=O)c2ccnc(C(F)(F)F)c2)cc1-c1cc(N2CCOCC2)nc(N2CC(O)C2)n1]

1H NMR (400 MHz, <dmso>) δ ppm 2.28 (s, 3H) 3.56-3.77 (m, 6H) 3.80-3.98 (m, 3H) 4.31-4.43 (m, 2H) 4.49-4.68 (m, 1H) 6.52-6.69 (m, 1H) 7.33-7.47 (m, 1H) 7.76-7.91 (m, 2H) 8.12-8.22 (m, 1H) 8.32-8.40 (m, 1H) 8.93-9.07 (m, 1H) 10.72-10.92 (m, 1H), LCMS (m/z) (M+H)=515.3, Rt=0.67 min.

Example 774: N-(5-(2-(4-ethylpiperazin-1-yl)-6-morpholinopyrimidin-4-yl)-6-methylpyridin-3-yl)-3-(trifluoromethyl)benzamide

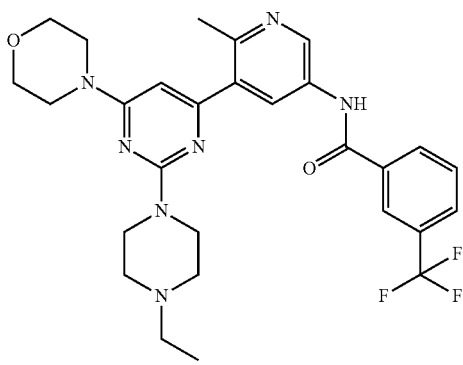 [SMILES: CCN1CCN(c2nc(-c3cc(NC(=O)c4cccc(C(F)(F)F)c4)cnc3C)cc(N3CCOCC3)n2)CC1]

1H NMR (400 MHz, <dmso>) δ ppm 1.24 (t, J=7.24 Hz, 1H) 2.38-2.67 (m, 6H) 3.19 (d, J=11.74 Hz, 1H) 3.54 (d, J=11.35 Hz, 1H) 3.63-3.70 (m, 4H) 3.77 (br. s., 6H) 4.74 (d, J=14.09 Hz, 1H) 6.42 (s, 1H) 7.80-7.85 (m, 2H) 8.01 (d, J=7.43 Hz, 2H) 8.27 (d, J=2.35 Hz, 1H) 8.28 (br. s., 1H) 8.31 (s, 1H) 8.33 (s, 2H) 8.91 (d, J=2.35 Hz, 1H) 10.79 (s, 1H), LCMS (m/z) (M+H)=556.3, Rt=0.63 min.

Example 775: N-(6-methyl-5-(6-morpholino-2-(piperazin-1-yl)pyrimidin-4-yl)pyridin-3-yl)-3-(trifluoromethyl)benzamide

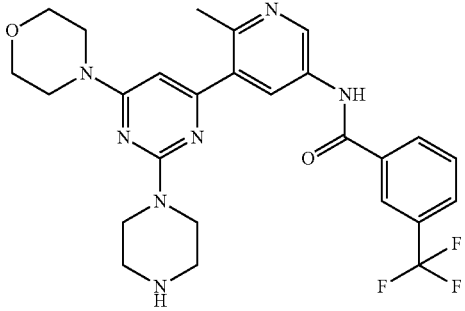 [SMILES: Cc1ncc(NC(=O)c2cccc(C(F)(F)F)c2)cc1-c1cc(N2CCOCC2)nc(N2CCNCC2)n1]

1H NMR (400 MHz, <dmso>) δ ppm 2.55 (s, 1H) 3.17 (br. s., 1H) 3.29 (s, 1H) 3.66 (br. s., 5H) 3.92 (br. s., 4H) 6.40 (s, 1H) 7.79-7.85 (m, 1H) 8.01 (d, J=7.83 Hz, 1H) 8.23 (d, J=2.35 Hz, 1H) 8.28 (s, 1H) 8.30 (s, 1H) 8.33 (s, 2H) 8.88 (d, J=2.35 Hz, 1H) 10.74 (s, 1H), LCMS (m/z) (M+H)= 528.2, Rt=0.61 min.

Synthesis of tert-butyl 3-((4-chloro-6-morpholinopyrimidin-2-yl)oxy) azetidine-1-carboxylate

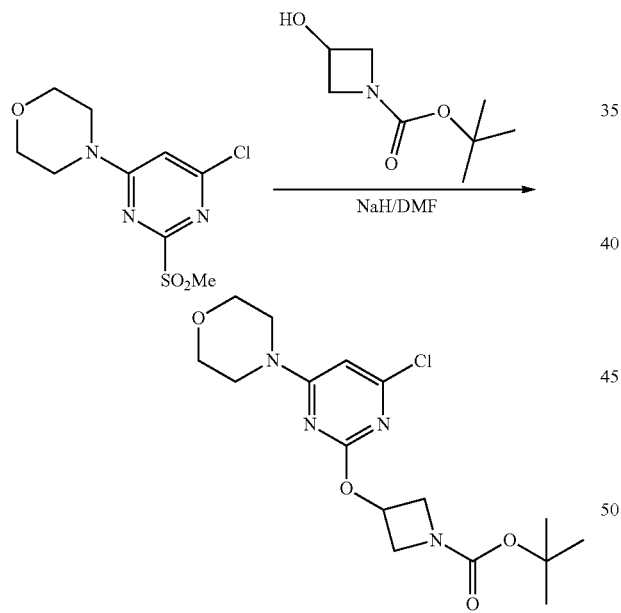

To N-BOC-3-azetidinol (1.2 eq) in DMF (0.36M) in a flame dried flask was added 60% sodium hydride (1.2 eq) followed by 4-(6-chloro-2-(methylsulfonyl)pyrimidin-4-yl)morpholine (1.0 equiv.) and the reaction was stirred at ambient temperature for 16 h. The reaction was partitioned between water and ethyl acetate the separated organic phase was dried with sodium sulfate, filtered and concentrated under vacuo. The concentrated crude was purified via silica gel chromatography and eluted with 0 to 100% ethyl acetate in heptanes to yield tert-butyl 3-((4-chloro-6-morpholinopyrimidin-2-yl)oxy)azetidine-1-carboxylate in 84% yield. LCMS (m/z) (M+H)=371.2, Rt=0.85 min.

Example 776: N-(5-(2-(azetidin-3-yloxy)-6-morpholinopyrimidin-4-yl)-6-methylpyridin-3-yl)-3-(trifluoromethyl)benzamide

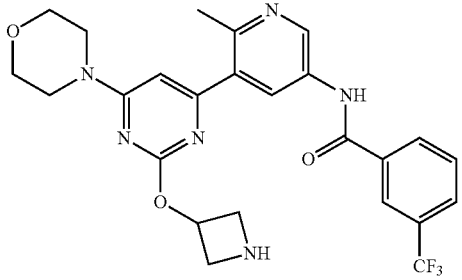 [SMILES: Cc1ncc(NC(=O)c2cccc(C(F)(F)F)c2)cc1-c1cc(N2CCOCC2)nc(OC2CNC2)n1]

To a solution of tert-butyl 3-((4-chloro-6-morpholinopyrimidin-2-yl)oxy)azetidine-1-carboxylate (1.0 equiv.) in DME was added N-(6-methyl-5-(4,4,5,5-tetramethyl-1,3,2-dioxaborolan-2-yl)pyridin-3-yl)-3-(trifluoromethyl)benzamide (Intermediate B, 1.0 equiv.), followed by PdCl2(dppf).CH2Cl2 adduct (0.10 equiv.), and 2M aqueous sodium carbonate (3.00 equiv.). The reaction mixture was heated in the microwave for 20 min at 120° C. LC/MS showed completion of the reaction. The reaction was partitioned between water and ethyl acetate and the separated organic phase was dried with sodium sulfate, filtered and concentrated under vacuo. It was purified via silica gel chromatography and eluted with 0 to 100% ethyl acetate in heptanes to yield tert-butyl 3-((4-(2-methyl-5-(3-(trifluoromethyl)benzamido)pyridin-3-yl)-6-morpholinopyrimidin-2-yl)oxy)azetidine-1-carboxylate in 60% yield. To it was added 30% TFA in DCM and stirred for 1 h. The concentrated crude was dissolved in DMSO, filtered through a HPLC filter and purified via auto-preparative reverse phase HPLC. The pure fractions were lyophilized to give N-(5-(2-(azetidin-3-yloxy)-6-morpholinopyrimidin-4-yl)-6-methylpyridin-3-yl)-3-(trifluoromethyl)benzamide.

1H NMR (400 MHz, <demos>) δ ppm 3.29-3.51 (m, 2H) 3.60-3.78 (m, 4H) 3.82-4.10 (m, 5H) 4.14-4.27 (m, 1H) 4.32-4.43 (m, 1H) 4.58-4.66 (m, 1H) 4.78 (d, J=10.17 Hz, 1H) 5.31-5.51 (m, 1H) 7.15-7.25 (m, 1H) 7.74-7.89 (m, 1H) 7.98-8.07 (m, 1H) 8.24-8.34 (m, 4H) 8.43-8.53 (m, 1H) 8.83-8.90 (m, 1H) 10.92-11.01 (m, 1H), LCMS (m/z) (M+H)=515.4, Rt=0.57 min.

Example 777: N-(3-(2-(azetidin-3-yloxy)-6-morpholinopyrimidin-4-yl)-4-methylphenyl)-2-(2-cyanopropan-2-yl)isonicotinamide

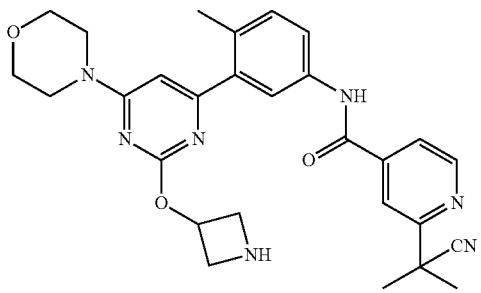 [SMILES: Cc1ccc(NC(=O)c2ccnc(C(C)(C)C#N)c2)cc1-c1cc(N2CCOCC2)nc(OC2CNC2)n1]

1H NMR (400 MHz, <dmso>) δ ppm 1.75 (s, 6H) 2.27-2.36 (m, 3H) 3.66-3.69 (m, 8H) 4.01-4.14 (m, 2H) 4.29-4.40 (m, 2H) 5.25-5.38 (m, 1H) 6.60-6.69 (m, 1H) 7.25-7.33 (m, 1H) 7.62-7.73 (m, 1H) 7.79-7.88 (m, 2H) 7.95-8.01 (m, 1H) 8.75-8.84 (m, 1H) 10.56-10.61 (m, 1H), LCMS (m/z) (M+H)=515.4, Rt=0.58 min.

Example 778: N-(3-(2-(azetidin-3-yloxy)-6-morpholinopyrimidin-4-yl)-4-methylphenyl)-2-isopropylisonicotinamide

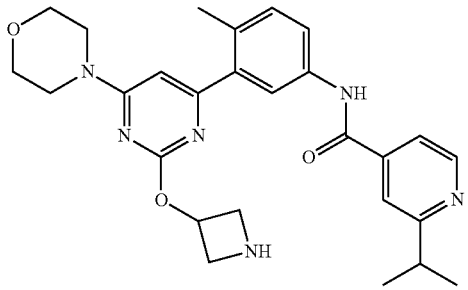 [SMILES: Cc1ccc(NC(=O)c2ccnc(C(C)C)c2)cc1-c1cc(N2CCOCC2)nc(OC2CNC2)n1]

LCMS (m/z) (M+H)=489.3, Rt=0.49 min.

Example 779: N-(3-(2-(azetidin-3-yloxy)-6-morpholinopyrimidin-4-yl)-4-methylphenyl)-2-(1,1-difluoroethyl)isonicotinamide

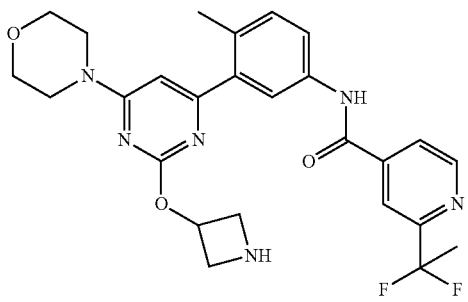 [SMILES: Cc1ccc(NC(=O)c2ccnc(C(C)(F)F)c2)cc1-c1cc(N2CCOCC2)nc(OC2CNC2)n1]

1H NMR (400 MHz, <dmso>) δ ppm 1.96-2.10 (m, 3H) 2.32 (s, 3H) 3.64 (d, J=5.48 Hz, 6H) 3.98-4.12 (m, 2H) 4.27-4.43 (m, 3H) 5.27-5.40 (m, 1H) 6.59-6.70 (m, 1H) 7.22-7.37 (m, 1H) 7.64-7.75 (m, 1H) 7.79-7.92 (m, 1H) 7.95-8.07 (m, 1H) 8.12-8.20 (m, 1H) 8.66-8.77 (m, 1H) 8.83-8.90 (m, 1H) 8.93-9.07 (m, 1H) 10.61-10.75 (m, 1H), LCMS (m/z) (M+H)=511.3, Rt=0.61 min.

Example 780: N-(3-(2-(azetidin-3-yloxy)-6-morpholinopyrimidin-4-yl)-4-methylphenyl)-2-(trifluoromethyl)isonicotinamide

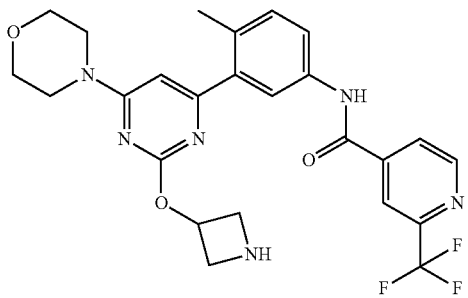 [SMILES: Cc1ccc(NC(=O)c2ccnc(C(F)(F)F)c2)cc1-c1cc(N2CCOCC2)nc(OC2CNC2)n1]

1H NMR (400 MHz, <dmso>) δ ppm 2.32 (s, 3H) 3.95-4.25 (m, 8H) 4.26-4.44 (m, 3H) 5.25-5.41 (m, 1H) 6.59-6.70 (m, 1H) 7.26-7.36 (m, 1H) 7.64-7.74 (m, 1H) 7.80-7.91 (m, 1H) 8.14-8.23 (m, 1H) 8.31-8.38 (m, 1H) 8.57-8.78 (m, 1H) 8.92-9.06 (m, 2H) 10.67-10.78 (m, 1H), LCMS (m/z) (M+H)=515.2, Rt=0.62 min.

Synthesis (S)-3-(4-chloro-6-morpholinopyrimidin-2-yl)-4-methyloxazolidin-2-one

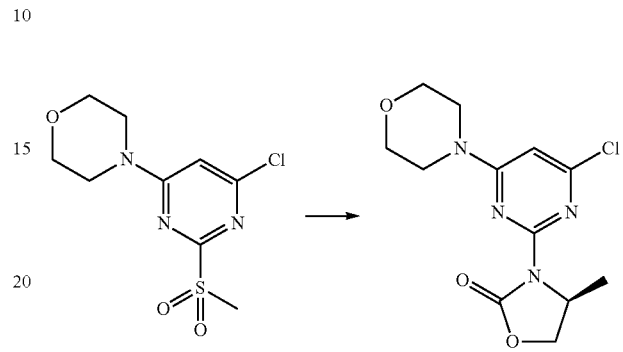

To a solution of (S)-4-methyloxazolidin-2-one (2 equiv.) in THF (0.27M) was added sodium hydride (2.1 equiv.) portion wise. The reaction mixture was stirred at RT for 10 min. To the reaction mixture was added 4-(6-chloro-2-(methylsulfonyl)pyrimidin-4-yl) morpholine (1 equiv.) and was stirred at RT 4 h. The reaction was partitioned between water and ethyl acetate the separated organic phase was dried with sodium sulfate, filtered and concentrated under vacuo to give (S)-3-(4-chloro-6-morpholinopyrimidin-2-yl)-4-methyloxazolidin-2-one. LCMS (m/z) (M+H)=299.2, Rt=0.59 min.

Example 781: (S)—N-(6-methyl-5-(2-(4-methyl-2-oxooxazolidin-3-yl)-6-morpholinopyrimidin-4-yl)pyridin-3-yl)-3-(trifluoromethyl)benzamide

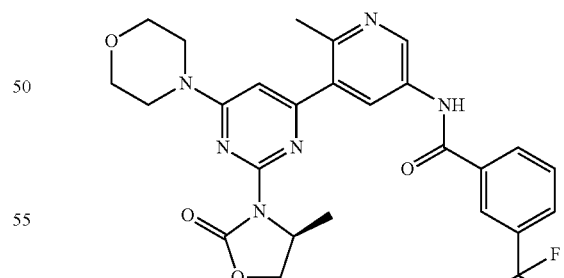

1H NMR (400 MHz, DMSO-d6) δ ppm 1.39 (d, J=5.87 Hz, 4H) 2.51-2.67 (m, 5H) 3.86-4.07 (m, 3H) 4.55-4.79 (m, 2H) 6.82 (s, 1H) 7.53-7.64 (m, 1H) 7.68-8.40 (m, 5H) 8.91-9.06 (m, 1H) 10.75-10.91 (m, 1H), LCMS (m/z) (M+H)=543.3, Rt=0.69 min.

Example 782: (S)-2-(2-cyanopropan-2-yl)-N-(4-methyl-3-(2-(4-methyl-2-oxooxazolidin-3-yl)-6-morpholinopyrimidin-4-yl)phenyl)isonicotinamide

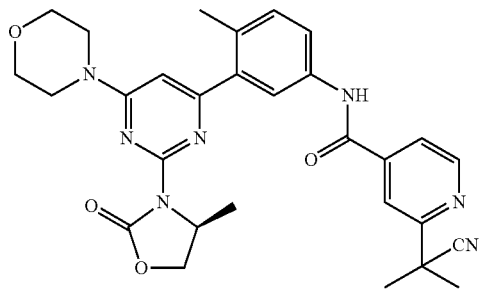 [SMILES: Cc1ccc(NC(=O)c2ccnc(C(C)(C)C#N)c2)cc1-c1cc(N2CCOCC2)nc(N2C(=O)OC[C@@H]2C)n1]

1H NMR (400 MHz, DMSO-d6) δ ppm 0.99-1.51 (m, 3H) 1.75 (s, 6H) 4.28-4.84 (m, 2H) 6.25-6.95 (m, 1H) 7.16-8.12 (m, 7H) 8.64-8.89 (m, 1H) 10.51-10.65 (m, 1H), LCMS (m/z) (M+H)=542.2, Rt=0.7 min.

Example 783: (S)—N-(4-methyl-3-(2-(4-methyl-2-oxooxazolidin-3-yl)-6-morpholinopyrimidin-4-yl)phenyl)-3-(trifluoromethyl)benzamide

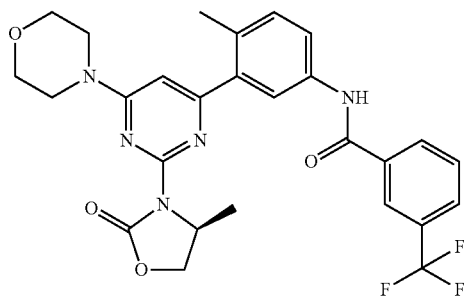 [SMILES: Cc1ccc(NC(=O)c2cccc(C(F)(F)F)c2)cc1-c1cc(N2CCOCC2)nc(N2C(=O)OC[C@@H]2C)n1]

1H NMR (400 MHz, DMSO-d6) δ ppm 1.33 (d, J=6.26 Hz, 3H) 3.63 (br. s., 8H) 7.18-8.30 (m, 7H) 10.34-10.57 (m, 1H), LCMS (m/z) (M+H)=542.1, Rt=0.86 min.

Example 784: (S)-2-(2-cyanopropan-2-yl)-N-(6-methyl-5-(2-(4-methyl-2-oxooxazolidin-3-yl)-6-morpholinopyrimidin-4-yl)pyridin-3-yl)isonicotinamide

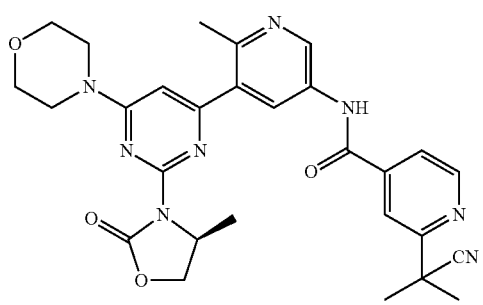 [SMILES: Cc1ncc(NC(=O)c2ccnc(C(C)(C)C#N)c2)cc1-c1cc(N2CCOCC2)nc(N2C(=O)OC[C@@H]2C)n1]

1H NMR (400 MHz, DMSO-d6) δ ppm 1.37 (d, J=5.87 Hz, 4H) 1.54-1.86 (m, 9H) 4.26-4.81 (m, 4H) 6.55-6.85 (m, 2H) 7.51 (br. s., 21H) 8.65-9.00 (m, 2H) 10.72-11.01 (m, 1H), LCMS (m/z) (M+H)=543.3, Rt=0.6 min.

Example 785: (S)-2-(difluoromethyl)-N-(4-methyl-3-(2-(4-methyl-2-oxooxazolidin-3-yl)-6-morpholinopyrimidin-4-yl)phenyl)isonicotinamide

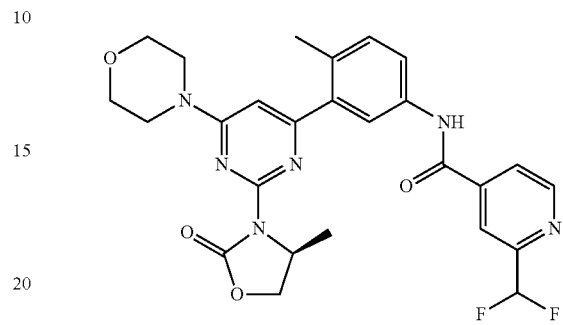

LCMS (m/z) (M+H)=525.2, Rt=0.71 min.

Synthesis of tert-butyl 3-((4-chloro-6-morpholinopyrimidin-2-yl)amino)azetidine-1-carboxylate

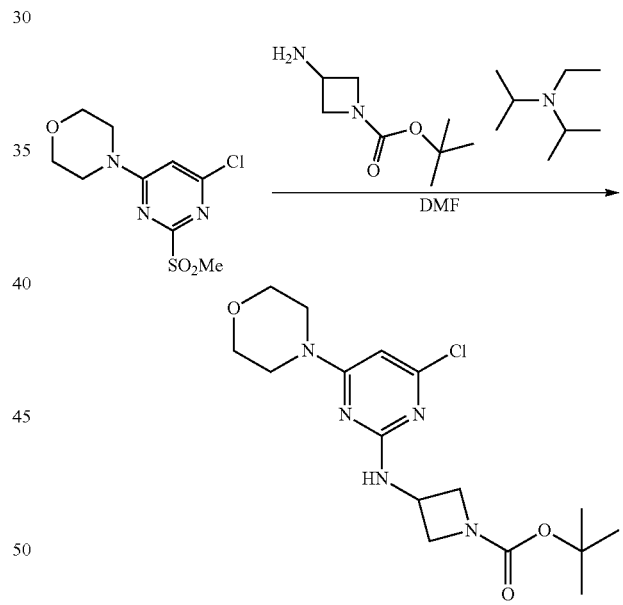

To a solution of 4-(6-chloro-2-(methylsulfonyl)pyrimidin-4-yl) morpholine (1.0 equiv.) in DMF (0.36M) was added tert-butyl 3-aminoazetidine-1-carboxylate (2.0 equiv.) and DIEA (2 eq) at room temperature. The reaction was stirred at ambient temperature for 16 h. The reaction was partitioned between water and ethyl acetate and the separated organic phase was dried with sodium sulfate, filtered and concentrated under vacuo. The concentrated crude was purified via silica gel chromatography and eluted with 0 to 100% ethyl acetate in heptanes to yield tert-butyl 3-((4-chloro-6-morpholinopyrimidin-2-yl)amino)azetidine-1-carboxylate in 76% yield. LCMS (m/z) (M+H)=371.2, Rt=0.85 min.

Example 786: N-(3-(2-(azetidin-3-ylamino)-6-morpholinopyrimidin-4-yl)-4-methylphenyl)-2-(2-cyanopropan-2-yl)isonicotinamide

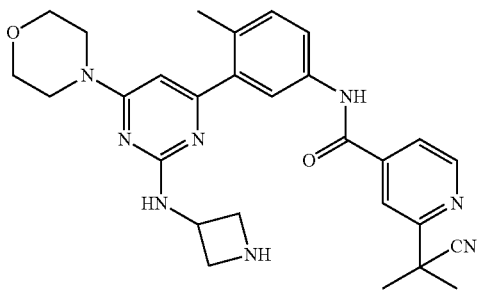 [SMILES: Cc1ccc(NC(=O)c2ccnc(C(C)(C)C#N)c2)cc1-c1cc(N2CCOCC2)nc(NC2CNC2)n1]

1H NMR (400 MHz, <dmso>) δ ppm 1.75 (s, 6H) 2.25-2.34 (m, 3H) 3.61-3.73 (m, 6H) 3.90-4.04 (m, 1H) 4.12-4.23 (m, 1H) 4.73-4.94 (m, 1H) 7.67-7.73 (m, 1H) 7.80-7.87 (m, 2H) 7.94-8.05 (m, 1H) 8.52-8.64 (m, 1H) 8.74-8.84 (m, 1H), LCMS (m/z) (M+H)=513.3, Rt=0.64 min.

Example 787: N-(5-(2-(azetidin-3-ylamino)-6-morpholinopyrimidin-4-yl)-6-methylpyridin-3-yl)-3-(trifluoromethyl)benzamide

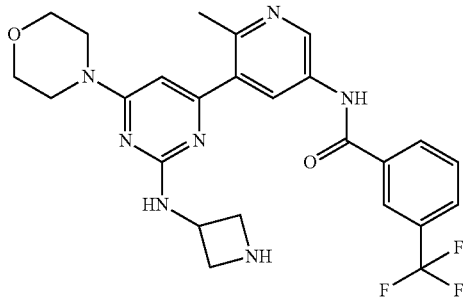 [SMILES: Cc1ncc(NC(=O)c2cccc(C(F)(F)F)c2)cc1-c1cc(N2CCOCC2)nc(NC2CNC2)n1]

LCMS (m/z) (M+H)=514.3, Rt=0.63 min.

Synthesis of 2-(4-chloro-6-morpholinopyrimidin-2-yl)propan-2-ol

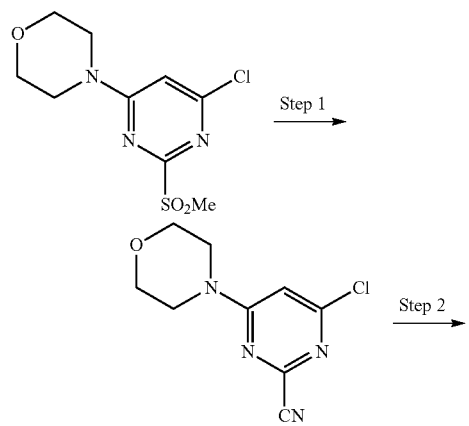

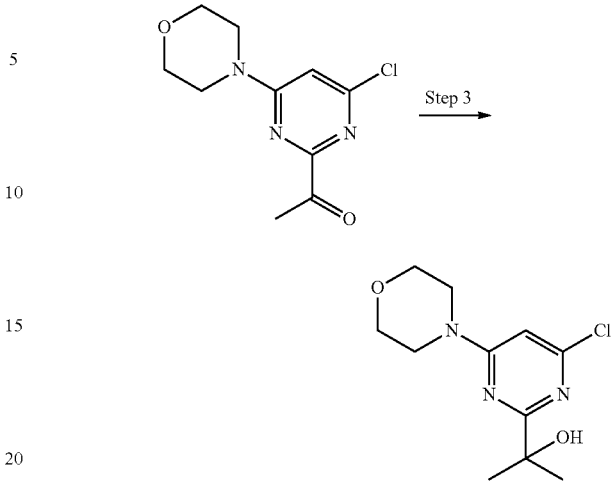

Step 1:

To a solution of sodium cyanide (1.2 equiv.) in 1:1 DMSO: water (0.12M) and triethylenediamine (0.5 equiv.) was added 4-(6-chloro-2-(methylsulfonyl)pyrimidin-4-yl)morpholine (1 equiv.) and the mixture was stirred at RT for 16 h. As starting material remained by LC/MS to it was added sodium cyanide (4 eq) and as the reaction mixture remained a suspension to it was added water 1:1 water: DMSO until the reaction mixture went in to a solution. It was then let stir at RT over 16 h. The reaction was partitioned between water and ethyl acetate the separated organic phase was dried with sodium sulfate, filtered and concentrated under vacuo. The concentrated crude was purified via silica gel chromatography and eluted with 0 to 100% ethyl acetate in heptanes to yield 4-chloro-6-morpholinopyrimidine-2-carbonitrile in 20% yield. LCMS (m/z) (M+H)= 243.1, Rt=0.39 min.

Step 2:

To a solution of 4-chloro-6-morpholinopyrimidine-2-carbonitrile (1.0 equiv.) in THF (0.024M) at −78° C. was added 3M methyl magnesium bromide in THF and the reaction mixture was stirred at that temperature for 20 min. The reaction was then brought to ambient temperature and quenched with saturated ammonium chloride and then partitioned between water and ethyl acetate. The separated organic phase was dried with sodium sulfate, filtered and concentrated under vacuo to give 1-(4-chloro-6-morpholinopyrimidin-2-yl)ethanone 87% yield. LCMS (m/z) (M+H)= 242.1/244, Rt=0.59 min.

Step 3:

To a solution of 1-(4-chloro-6-morpholinopyrimidin-2-yl)ethanone (1 equiv.) at −78° C. in THF (0.33M) was added 3M methyl magnesium bromide (5 equiv.). The reaction mixture was stirred at −78° C. for 20 mins. The reaction was then brought to ambient temperature and quenched with saturated ammonium chloride and then partitioned between water and ethyl acetate. The concentrated crude was purified by silica gel chromatography and eluted with 0 to 100% ethyl acetate in heptanes to yield 2-(4-chloro-6-morpholinopyrimidin-2-yl)propan-2-ol in 22% yield.

471

Example 788: N-(5-(2-(2-hydroxypropan-2-yl)-6-morpholinopyrimidin-4-yl)-6-methylpyridin-3-yl)-3-(trifluoromethyl)benzamide

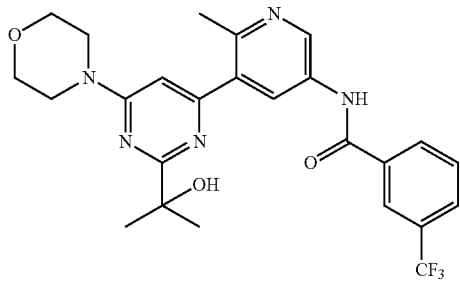 [SMILES: Cc1ncc(NC(=O)c2cccc(C(F)(F)F)c2)cc1-c1cc(N2CCOCC2)nc(C(C)(C)O)n1]

1H NMR (400 MHz, <dmso>) δ ppm 1.44 (s, 6H) 3.56-3.87 (m, 7H) 7.00 (br. s., 1H) 7.70-7.82 (m, 1H) 7.91-8.02 (m, 1H) 8.17-8.35 (m, 3H) 8.82-8.88 (m, 1H) 10.68-10.76 (m, 1H), LCMS (m/z) (M+H)=502.3, Rt=0.69 min.

Example 789: 2-(2-cyanopropan-2-yl)-N-(3-(2-(2-hydroxypropan-2-yl)-6-morpholinopyrimidin-4-yl)-4-methylphenyl)isonicotinamide

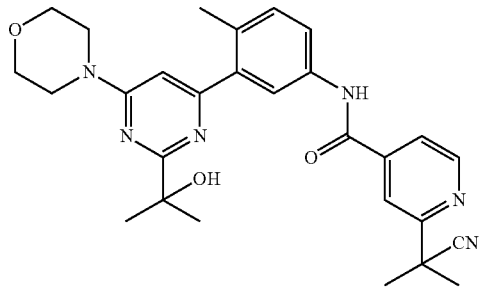 [SMILES: Cc1ccc(NC(=O)c2ccnc(C(C)(C)C#N)c2)cc1-c1cc(N2CCOCC2)nc(C(C)(C)O)n1]

LCMS (m/z) (M+H)=501.1, Rt=0.68 min.

Example 790: Synthesis of 2-(2-fluoropropan-2-yl)-N-(6-methyl-5-(7-morpholinopyrazolo[1,5-a]pyrimidin-5-yl)pyridin-3-yl)isonicotinamide

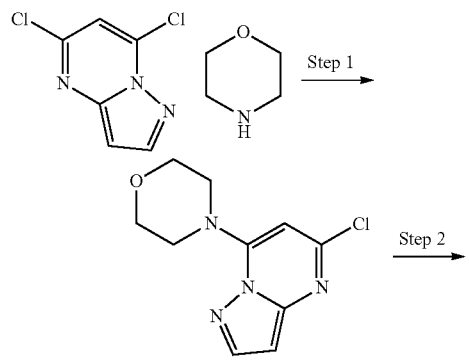

472

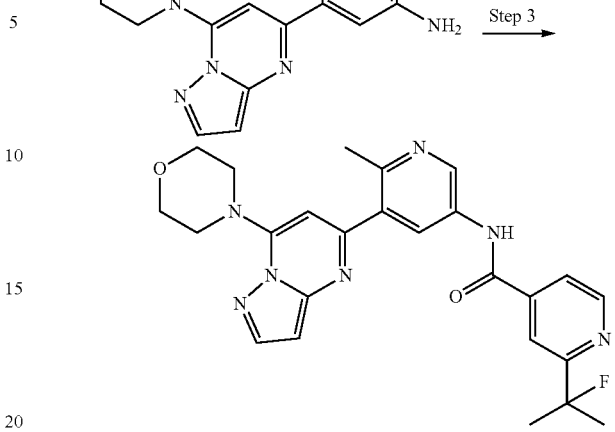

Step 1:

To 5,7-dichloropyrazolo(1,5-a)pyrimidine (1.0 eq) in Ethanol (Volume: 15 mL) was added morpholine (1.0 eq) and the mixture was heated to 120° C. for 20 mins in the microwave. 50% conversion to the product was observed by LCMS. To the reaction mixture was added morpholine (1 eq) and it was reheated in the microwave for 10 mins at 120° C. The crude reaction mixture was partitioned between ethyl acetate and water. The separated organic layer was dried with sodium sulfate and concentrated. The concentrated crude was purified via silica gel column chromatography eluting with 0-100% ethyl acetate in heptanes. The pure fractions were concentrated under vacuo to 4-(5-chloropyrazolo[1,5-a]pyrimidin-7-yl)morpholine as the desired product in 90% yield. LCMS (m/z) (M+H)=239/240.8, Rt=0.63 min.

1H NMR (400 MHz, <dmso>) δ ppm 3.72-3.87 (m, 8H) 6.35-6.44 (m, 1H) 6.48-6.57 (m, 1H) 8.09-8.22 (m, 1H), LCMS (m/z) (M+H)=239/240.8, Rt=0.63 min.

Step 2:

To a solution of 4-(5-chloropyrazolo[1,5-a]pyrimidin-7-yl)morpholine (1.0 equiv.) and 6-methyl-5-(4,4,5,5-tetramethyl-1,3,2-dioxaborolan-2-yl)pyridin-3-amine (1.2 equiv.) in DME (0.3 M) was added sodium carbonate (2.0 equiv, 2 M aqueous solution) and the mixture was degassed for 10 mins before adding PdCl$_2$(dppf)-DCM adduct (0.05 equiv.) and the mixture was heated in an oil bath for 3 hours at 120° C. Methanol was added and the mixture and partitioned between ethyl acetate and water. The organic layer was dried with sodium sulfate, filtered, concentrated and purified by silica gel chromatography (ISCO, 0-20% methanol in DCM). The pure fractions were concentrated to give 6-methyl-5-(7-morpholinopyrazolo[1,5-a]pyrimidin-5-yl)pyridin-3-amine in 78% yield. LCMS (m/z) (M+H)=311.1, Rt=0.42 min.

Step 3:

To a solution of 2-(2-fluoropropan-2-yl)isonicotinic acid (1.0 equiv.) in DMF (0.18 M) was added N1-((ethylimino)methylene)-N3,N3-dimethylpropane-1,3-diamine hydrochloride (1.0 equiv.), 1H-benzo[d][1,2,3]triazol-1-ol hydrate (1.0 equiv.) and 6-methyl-5-(7-morpholinopyrazolo[1,5-a]pyrimidin-5-yl)pyridin-3-amine (1.0 equiv.) and the mixture was stirred at rt overnight. The solution was partitioned between ethyl acetate and water. The organic phase was washed 3× with water and brine solution, dried over sodium sulfate, filtered and concentrated. The crude material was purified via silica gel chromatography (ISCO, 0-100% ethyl acetate in heptanes, then 0-20% methanol in DCM) and again via reverse phase prep-HPLC (acetonitrile, TFA/water). The pure fractions were neutralized with solid sodium bicarbonate and extracted with ethyl acetate. The organic phase was dried with sodium sulfate, filtered and concentrated to give 2-(2-fluoropropan-2-yl)-N-(6-methyl-5-(7-morpholinopyrazolo[1,5-a]pyrimidin-5-yl)pyridin-3-yl)isonicotinamide as a white solid in 46% yield. $^1$H NMR (400 MHz, <dmso>) δ ppm 1.60-1.76 (m, 6H) 2.58-2.65 (m, 3H) 3.82 (s, 8H) 6.55-6.69 (m, 2H) 7.79-7.89 (m, 1H) 8.02-8.10 (m, 1H) 8.17-8.24 (m, 1H) 8.33-8.42 (m, 1H) 8.70-8.85 (m, 1H) 8.94-9.05 (m, 1H) 10.88-10.97 (m, 1H), LCMS (m/z) (M+H)=476.2, Rt=0.64 min.

Example 791: 2-(2-cyanopropan-2-yl)-N-(6-methyl-5-(7-morpholinopyrazolo[1,5-a]pyrimidin-5-yl)pyridin-3-yl)isonicotinamide

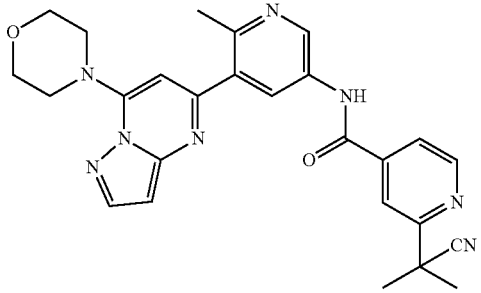 [SMILES: Cc1ncc(NC(=O)c2ccnc(C(C)(C)C#N)c2)cc1-c1cc(N2CCOCC2)n2nccc2n1]

1H NMR (400 MHz, <dmso>) δ ppm 1.76 (s, 6H) 2.60-2.71 (m, 3H) 3.72-3.93 (m, 8H) 6.58-6.71 (m, 2H) 7.85-7.95 (m, 1H) 8.03-8.08 (m, 1H) 8.18-8.25 (m, 1H) 8.42-8.48 (m, 1H) 8.78-8.87 (m, 1H) 9.00-9.13 (m, 1H) 10.97-11.08 (m, 1H), LCMS (m/z) (M+H)=483.2, Rt=0.64 min.

Example 792: 2(2-cyanopropan-2-yl)-N-(4-methyl-3 (7-morpholinopyrazolo[1,5-a]pyrimidin-5-yl)phenyl)isonicotinamide

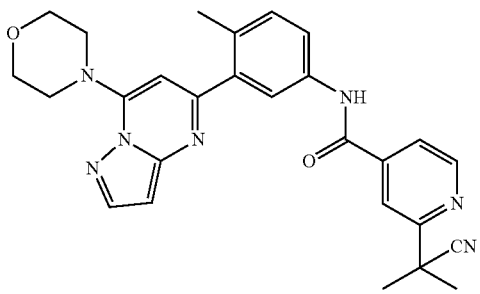

LCMS (m/z) (M+H)=482.2, Rt=0.7 min.

Example 793: N-(6-methyl-5-(7-morpholinopyrazolo[1,5-a]pyrimidin-5-yl)pyridin-3-yl)-3-trifluoromethyl)benzamide

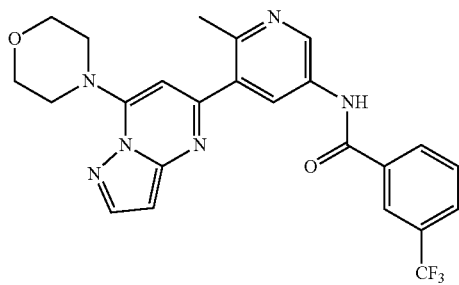 [SMILES: Cc1ncc(NC(=O)c2cccc(C(F)(F)F)c2)cc1-c1cc(N2CCOCC2)n2nccc2n1]

1H NMR (400 MHz, <dmso>) δ ppm 2.58-2.70 (m, 3H) 3.79-3.84 (m, 8H) 6.56-6.68 (m, 2H) 7.76-7.85 (m, 1H) 7.93-8.06 (m, 1H) 8.13-8.23 (m, 1H) 8.26-8.37 (m, 2H) 8.39-8.46 (m, 1H) 8.98-9.09 (m, 1H) 10.80-10.91 (m, 1H), LCMS (m/z) (M+H)=483.4, Rt=0.74 min.

Example 794: 2-(2-hydroxypropan-2-yl)-N-(4-methyl-3-(7-morpholinopyrazolo[1,5-a]pyrimidin-5-yl)phenyl)isonicotinamide

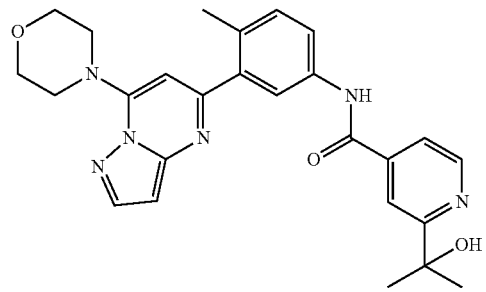 [SMILES: Cc1ccc(NC(=O)c2ccnc(C(C)(C)O)c2)cc1-c1cc(N2CCOCC2)n2nccc2n1]

LCMS (m/z) (M+H)=473.2, Rt=0.54 min.

Example 795: 6-(2-cyanopropan-2-yl)-N-(4-methyl-3-(7-morpholinopyrazolo[1,5-a]pyrimidin-5-yl)phenyl)pyridazine-4-carboxamide

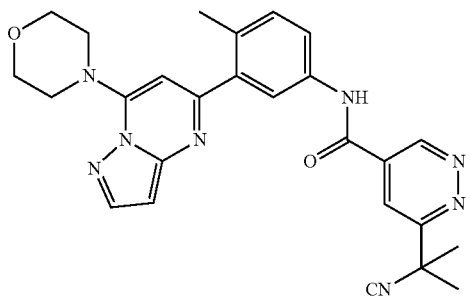

1H NMR (400 MHz, <dmso>) δ ppm 1.84 (s, 6H) 2.35-2.42 (m, 3H) 3.74-3.89 (m, 8H) 6.44-6.52 (m, 1H) 6.57-6.66 (m, 1H) 7.30-7.42 (m, 1H) 7.75-7.91 (m, 2H) 8.16-8.23 (m, 1H) 8.26-8.34 (m, 1H) 9.55-9.69 (m, 1H) 10.77-10.83 (m, 1H), LCMS (m/z) (M+H)=483.2, Rt=0.65 min.

Example 796: 2-(1-cyanocyclopropyl)-N-(4-methyl-3-(7-morpholinopyrazolo[1,5-a]pyrimidin-5-yl)phenyl)isonicotinamide

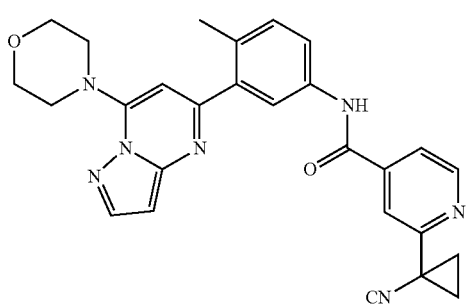

1H NMR (400 MHz, <dmso>) δ ppm 1.73-1.78 (m, 2H) 1.84-1.88 (m, 2H) 2.34-2.40 (m, 3H) 3.74-3.92 (m, 8H)

6.42-6.50 (m, 1H) 6.55-6.64 (m, 1H) 7.27-7.40 (m, 1H) 7.73-7.82 (m, 2H) 7.84-7.97 (m, 2H) 8.12-8.22 (m, 1H) 8.62-8.75 (m, 1H) 10.58-10.66 (m, 1H)), LCMS (m/z) (M+H)=480.1, Rt=0.7 min.

Example 797: 2-(2-hydroxypropan-2-yl)-N-(6-methyl-5-(7-morpholinopyrazolo[1,5-a]pyrimidin-5-yl)pyridin-3-yl)isonicotinamide

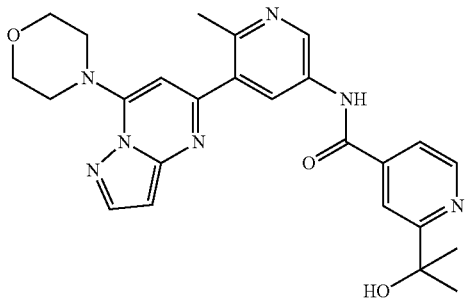 [SMILES: Cc1ncc(NC(=O)c2ccnc(C(C)(C)O)c2)cc1-c1cc(N2CCOCC2)n2nccc2n1]

1H NMR (400 MHz, <dmso>) δ ppm 1.49 (s, 6H) 2.59-2.73 (m, 3H) 3.66-3.91 (m, 9H) 6.53-6.69 (m, 2H) 7.71-7.81 (m, 1H) 8.16-8.27 (m, 2H) 8.44-8.57 (m, 1H) 8.68-8.79 (m, 1H) 9.04-9.14 (m, 1H) 10.99-11.08 (m, 1H), LCMS (m/z) (M+H)=474.1, Rt=0.5 min.

Example 798: N-(6-methyl-5-(7-morpholinopyrazolo[1,5-a]pyrimidin-5-yl)pyridin-3-yl)-2-(trifluoromethyl)isonicotinamide

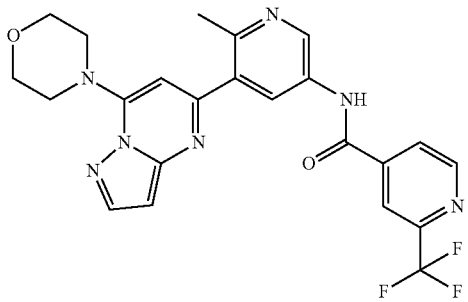 [SMILES: Cc1ncc(NC(=O)c2ccnc(C(F)(F)F)c2)cc1-c1cc(N2CCOCC2)n2nccc2n1]

1H NMR (400 MHz, <dmso>) δ ppm 2.52-2.62 (m, 3H) 3.69-3.83 (m, 7H) 6.43-6.63 (m, 2H) 8.12-8.22 (m, 2H) 8.28-8.41 (m, 2H) 8.88-9.01 (m, 2H) 10.90-11.01 (m, 1H), LCMS (m/z) (M+H)=484.2, Rt=0.66 min.

Example 799: 2-(1,1-difluoroethyl)-N-(6-methyl-5-(7-morpholinopyrazolo[1,5-a]pyrimidin-5-yl)pyridin-3-yl)isonicotinamide

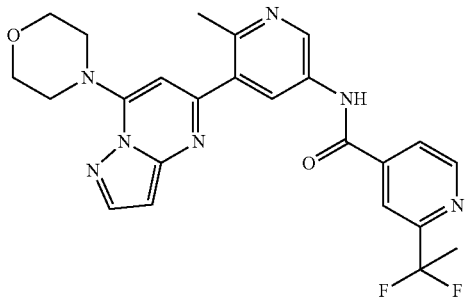 [SMILES: Cc1ncc(NC(=O)c2ccnc(C(C)(F)F)c2)cc1-c1cc(N2CCOCC2)n2nccc2n1]

1H NMR (400 MHz, <dmso>) δ ppm 1.91-2.12 (m, 3H) 2.55-2.65 (m, 4H) 3.82 (s, 8H) 6.57-6.59 (m, 1H) 6.62-6.64 (m, 1H) 8.00-8.10 (m, 1H) 8.17-8.27 (m, 2H) 8.29-8.38 (m, 1H) 8.84-9.01 (m, 2H) 10.88-10.97 (m, 1H), LCMS (m/z) (M+H)=480.2, Rt=0.65 min.

Example 800: 2-(1,1-difluoropropyl)-N-(6-methyl-5-(7-morpholinopyrazolo[1,5-a]pyrimidin-5-yl)pyridin-3-yl)isonicotinamide

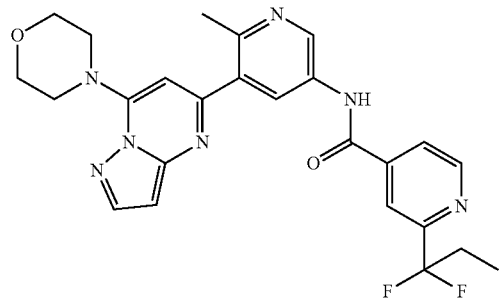 [SMILES: CCC(F)(F)c1cc(C(=O)Nc2cnc(C)c(-c3cc(N4CCOCC4)n4nccc4n3)c2)ccn1]

1H NMR (400 MHz, <dmso>) δ ppm 0.85-1.02 (m, 3H) 2.54-2.62 (m, 4H) 3.82 (s, 8H) 6.55-6.59 (m, 1H) 6.61-6.66 (m, 1H) 7.98-8.10 (m, 1H) 8.15-8.26 (m, 2H) 8.29-8.37 (m, 1H) 8.85-9.02 (m, 2H) 10.86-10.98 (m, 1H)), LCMS (m/z) (M+H)=494.1, Rt=0.69 min.

Example 801: N-(6-methyl-5-(7-morpholinopyrazolo[1,5-a]pyrimidin-5-yl)pyridin-3-yl)-6-(trifluoromethyl)pyridazine-4-carboxamide

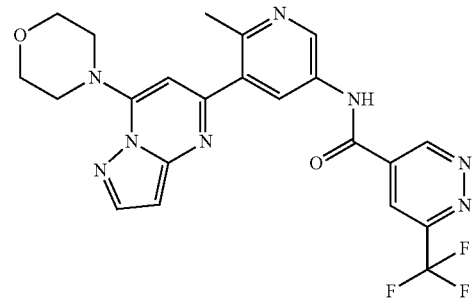 [SMILES: Cc1ncc(NC(=O)c2cnnc(C(F)(F)F)c2)cc1-c1cc(N2CCOCC2)n2nccc2n1]

1H NMR (400 MHz, <dmso>) δ ppm 2.56 (s, 3H) 3.77 (s, 8H) 6.48-6.64 (m, 2H) 8.08-8.20 (m, 1H) 8.22-8.34 (m, 1H) 8.63-8.75 (m, 1H) 8.82-8.95 (m, 1H) 9.83-9.97 (m, 1H) 11.00-11.19 (m, 1H), LCMS (m/z) (M+H)=485.1, Rt=0.61 min.

Example 802: 2-(1-cyanocyclopropyl)-N-(6-methyl-5-(7-morpholinopyrazolo[1,5-a]pyrimidin-5-yl)pyridin-3-yl)isonicotinamide

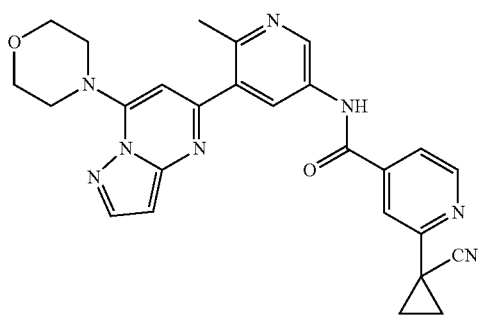 [SMILES: Cc1ncc(NC(=O)c2ccnc(C3(C#N)CC3)c2)cc1-c1cc(N2CCOCC2)n2nccc2n1]

1H NMR (400 MHz, <dmso>) δ ppm 1.71-1.80 (m, 2H) 1.83-1.94 (m, 2H) 2.57-2.62 (m, 3H) 3.82 (s, 8H) 6.53-6.68

(m, 2H) 7.79-7.84 (m, 1H) 7.94-7.99 (m, 1H) 8.17-8.25 (m, 1H) 8.32-8.38 (m, 1H) 8.68-8.77 (m, 1H) 8.92-9.01 (m, 1H) 10.85-10.94 (m, 1H), LCMS (m/z) (M+H)=481.1, Rt=0.61 min.

Example 803: 2-(difluoromethyl)-N-(6-methyl-5-(7-morpholinopyrazolo[1,5-a]pyrimidin-5-yl)pyridin-3-yl)isonicotinamide

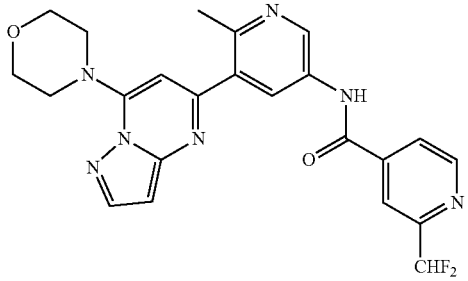 [SMILES: Cc1ncc(NC(=O)c2ccnc(C(F)F)c2)cc1-c1cc(N2CCOCC2)n2nccc2n1]

1H NMR (400 MHz, <dmso>) δ ppm 2.53-2.62 (m, 3H) 3.69-3.86 (m, 8H) 6.52-6.65 (m, 2H) 7.00-7.08 (m, 1H) 8.00-8.07 (m, 1H) 8.14-8.20 (m, 2H) 8.30-8.39 (m, 1H) 8.83-8.90 (m, 1H) 8.95-9.03 (m, 1H) 10.93-11.01 (m, 1H), LCMS (m/z) (M+H)=466.1, Rt=0.6 min.

Example 804: 3-(difluoromethyl)-N-(6-methyl-5-(7-morpholinopyrazolo[1,5-a]pyrimidin-5-yl)pyridin-3-yl)benzamide

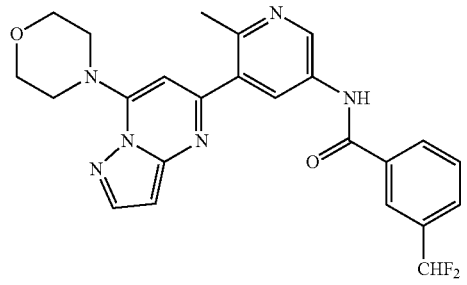 [SMILES: Cc1ncc(NC(=O)c2cccc(C(F)F)c2)cc1-c1cc(N2CCOCC2)n2nccc2n1]

1H NMR (400 MHz, <dmso>) δ ppm 2.56-2.63 (m, 4H) 3.82 (s, 8H) 6.53-6.67 (m, 2H) 7.64-7.73 (m, 1H) 7.77-7.84 (m, 1H) 8.11-8.25 (m, 3H) 8.33-8.47 (m, 1H) 8.94-9.04 (m, 1H) 10.69-10.77 (m, 1H) LCMS (m/z) (M+H)=465.1, Rt=0.67 min.

Example 805: 2-(difluoromethyl)-N-(4-methyl-3-(7-morpholinopyrazolo[1,5-a]pyrimidin-5-yl)phenyl)isonicotinamide

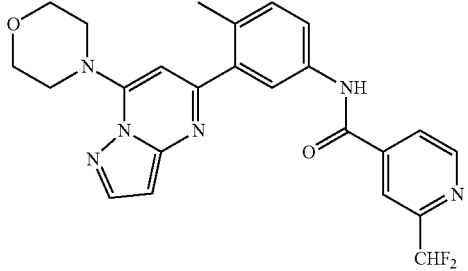 [SMILES: Cc1ccc(NC(=O)c2ccnc(C(F)F)c2)cc1-c1cc(N2CCOCC2)n2nccc2n1]

1H NMR (400 MHz, <dmso>) δ ppm 2.30-2.34 (m, 2H) 3.26-3.30 (m, 4H) 3.70-3.86 (m, 8H) 6.37-6.46 (m, 1H) 6.50-6.60 (m, 1H) 7.25-7.34 (m, 1H) 7.70-7.89 (m, 2H) 8.06-8.21 (m, 2H) 8.42-8.52 (m, 1H) 8.87-8.99 (m, 1H) 10.74-10.83 (m, 1H), LCMS (m/z) (M+H)=465.3, Rt=0.68 min.

Example 806: N-(4-methyl-3-(7-morpholinopyrazolo[1,5-a]pyrimidin-5-yl)phenyl)-2-methylsulfonyl)isonicotinamide

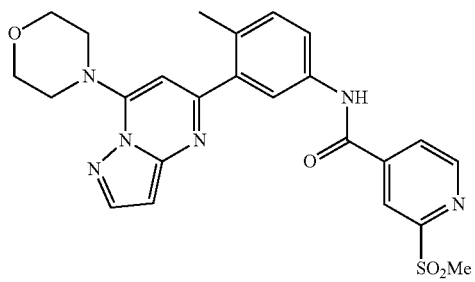 [SMILES: Cc1ccc(NC(=O)c2ccnc(S(C)(=O)=O)c2)cc1-c1cc(N2CCOCC2)n2nccc2n1]

1H NMR (400 MHz, <dmso>) δ ppm 2.37 (s, 3H) 3.81 (s, 9H) 6.42-6.51 (m, 1H) 6.55-6.63 (m, 1H) 6.87-6.96 (m, 1H) 7.00-7.09 (m, 1H) 7.15-7.23 (m, 1H) 7.29-7.36 (m, 1H) 7.77-7.84 (m, 1H) 7.87-7.95 (m, 1H) 8.03-8.09 (m, 1H) 8.14-8.22 (m, 2H) 8.85-8.93 (m, 1H) 10.64-10.73 (m, 1H), LCMS (m/z) (M+H)=493.2, Rt=0.59 min.

Example 807: N-(6-methyl-5-(7-morpholinopyrazolo[1,5-a]pyrimidin-5-yl)pyridin-3-yl)-2-(methylsulfonyl)isonicotinamide

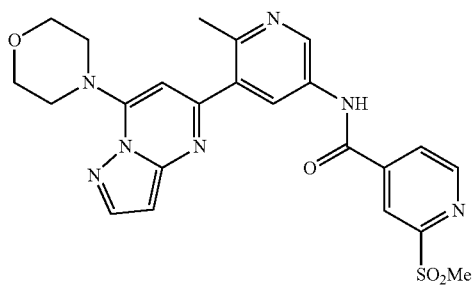 [SMILES: Cc1ncc(NC(=O)c2ccnc(S(C)(=O)=O)c2)cc1-c1cc(N2CCOCC2)n2nccc2n1]

1H NMR (400 MHz, <dmso>) δ ppm 2.61 (s, 3H) 3.27-3.41 (m, 3H) 3.78-3.89 (m, 8H) 6.51-6.70 (m, 2H) 8.14-8.25 (m, 2H) 8.34-8.38 (m, 1H) 8.56-8.61 (m, 1H) 8.94-9.07 (m, 2H) 11.06-11.11 (m, 1H), LCMS (m/z) (M+H)=494.1, Rt=0.53 min.

Example 808: 6-(2-cyanopropan-2-yl)-N-(6-methyl-5-(7-morpholinopyrazolo[1,5-a]pyrimidin-5-yl)pyridin-3-yl)pyridazine-4-carboxamide

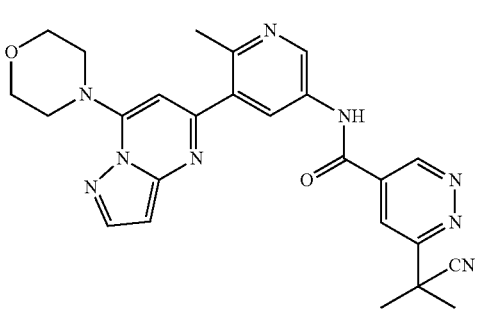 [SMILES: Cc1ncc(NC(=O)c2cnnc(C(C)(C)C#N)c2)cc1-c1cc(N2CCOCC2)n2nccc2n1]

1H NMR (400 MHz, <dmso>) δ ppm 1.84 (s, 6H) 2.58-2.63 (m, 3H) 3.82 (s, 8H) 6.52-6.70 (m, 2H) 8.15-8.24 (m, 1H) 8.31-8.37 (m, 2H) 8.92-8.97 (m, 1H) 9.62-9.71 (m, 1H) 11.02-11.09 (m, 1H), LCMS (m/z) (M+H)=484.2, Rt=0.58 min.

Example 810: N-(6-methyl-5-(7-morpholinopyrazolo[1,5-a]pyrimidin-5-yl)pyridin-3-yl)-4-(trifluoromethyl)picolinamide

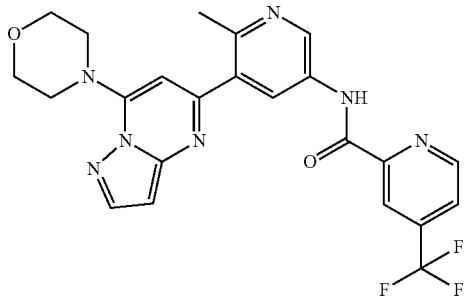 [SMILES: Cc1ncc(NC(=O)c2cc(C(F)(F)F)ccn2)cc1-c1cc(N2CCOCC2)n2nccc2n1]

1H NMR (400 MHz, <dmso>) δ ppm 2.56-2.61 (m, 3H) 3.82 (s, 8H) 6.51-6.70 (m, 2H) 8.07-8.13 (m, 1H) 8.18-8.24 (m, 1H) 8.32-8.40 (m, 1H) 8.50-8.56 (m, 1H) 8.99-9.15 (m, 2H) 11.15-11.22 (m, 1H), LCMS (m/z) (M+H)=484.1, Rt=0.7 min.

Example 811: (R)—N-(4-methyl-3-(4-(3-methylmorpholino)-1H-imidazo[4,5-c]pyridin-6-yl)phenyl)-3-(trifluoromethyl)benzamide Step 1:
A solution of 2-bromo-N-methyl-5-nitro-4-pyridinamine (1.0 equiv.) in conc. HCl (0.29 M) in a 500 ml RB was heated to 90° C. Tin(II) chloride dihydrate (5 equiv.) was added portion wise and the resulting mixture was stirred at 90° C. for 90 min. and allowed to cool to RT. The acidic solution was cooled to RT and concentrated until about ¼ of liquid was left. The mixture was poured in an ice bath and made basic (pH~10) by cautious addition of 50% aqueous NaOH while stirring. The suspension was extracted with EtOAc and the combined organic extracts were dried over $Na_2SO_4$. The solvent was evaporated to give 6-bromo-2-chloropyridine-3,4-diamine in 89% yield as a low melting brown solid. Product was used without further purification. LCMS (m/z) (M+H)=222/224/226, Rt=0.44 min.

Step 2:
Acetic anhydride (9.0 equiv.) was added to a solution of 6-bromo-2-chloropyridine-3,4-diamine (1.0 equiv.) in triethyl orthoformate (6.0 equiv.), and the resulting mixture was heated at 60° C. for about 2 min and slowly increased to 90° C. and maintained at this temperature for 6 hr, then allowed to cool to room temperature. The reaction mixture was concentrated to dryness, then dissolved in aqueous NaOH (10 M, 14.0 equiv.) and stirred at 55° C. for 30 minutes. After cooling, the mixture was acidified using glacial acetic acid until pH 6. The suspension was stirred in

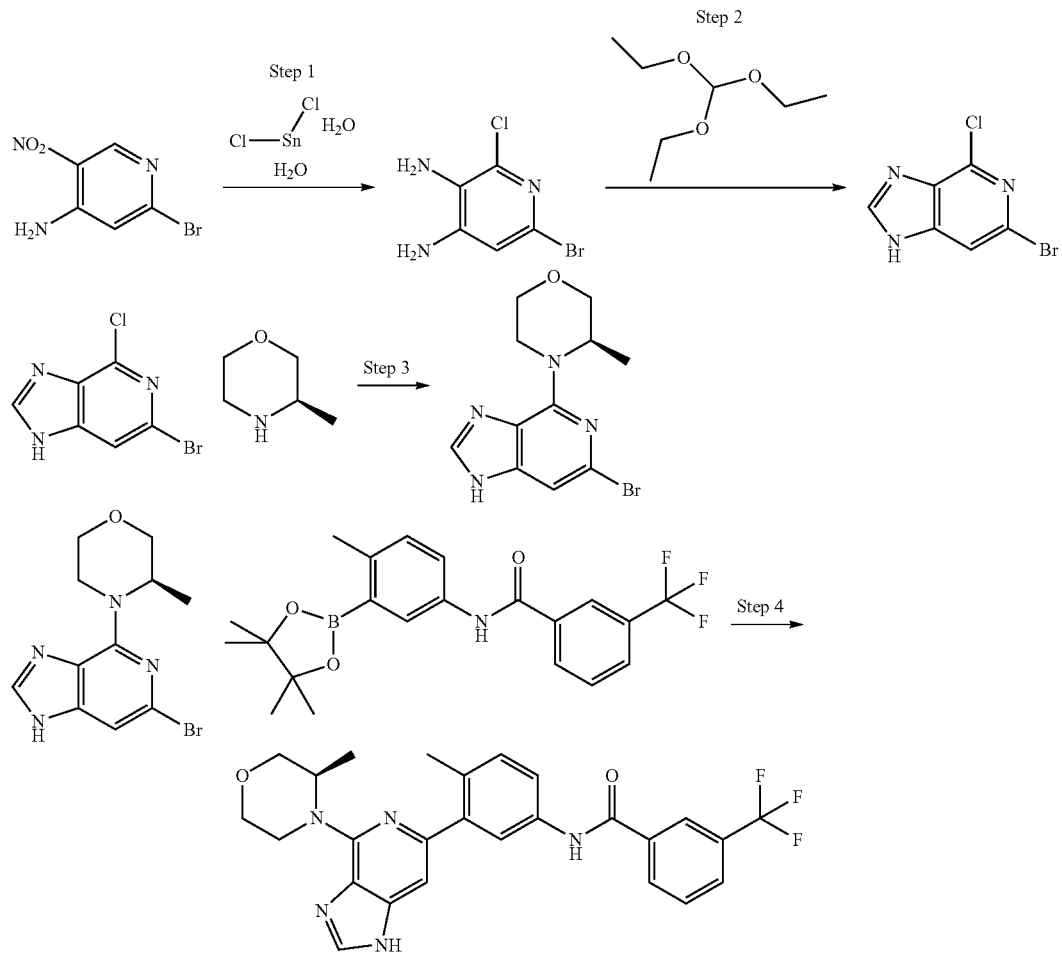

an ice bath for 1 hr, then filtered off and washed with small amounts of water The precipitate was dissolved in a 1:2 THF: ether solution. The solution was dried over sodium sulfate, filtered and concentrated, giving 6-bromo-4-chloro-1H-imidazo[4,5-c]pyridine (4.7 g, 20.22 mmol, 100% yield) as a brown solid. LCMS (m/z) (M+H)=231.9/233.9/235.9, Rt=0.48 min.

Step 3:

6-bromo-4-chloro-1H-imidazo[4,5-c]pyridine (1.0 equiv.), (R)-3-methylmorpholine (5.0 equiv.), TEA (2.0 equiv.) in NMP (1.4 M) were mixed in a 20 mL vessel, sealed and heated at 140° C. for 72 hours. The reaction vessel was left to reach RT and the mixture was partitioned between EtOAc and water. The aqueous layer was extracted three times with EtOAc. The combined organics were washed with brine dried over sodium sulfate, filtered and concentrated. The residue was purified via flash chromatography over silica gel eluting with heptane and 0-70% EtOAc gradient. (R)-4-(6-bromo-1H-imidazo[4,5-c]pyridin-4-yl)-3-methylmorpholine was isolated as a light yellow solid in 58% yield. LCMS (m/z) (M+H)=297/299, Rt=0.65 min.

Step 4:

To a solution of (R)-4-(6-bromo-1H-imidazo[4,5-c]pyridin-4-yl)-3-methylmorpholine (1.0 equiv.) and N-(4-methyl-3-(4,4,5,5-tetramethyl-1,3,2-dioxaborolan-2-yl)phenyl)-3-(trifluoromethyl)benzamide (1.0 equiv.) in DME (0.1 M) was added $Na_2CO_3$ (3.0 equiv.) and the system was flushed with nitrogen for 5 minutes. $PdCl_2(dppf).CH_2Cl_2$ adduct (0.1 equiv.) was added and the system was flushed once again. The vial was capped and place in a microwave reactor for 20 minutes at 120° C. The reaction mix was partitioned in EtOAc/$H_2O$. The organic layer was isolated, dried over $Na_2SO_4$, filtered and concentrated. The crude was purified by HPLC. (R)—N-(4-methyl-3-(4-(3-methylmorpholino)-1H-imidazo[4,5-c]pyridin-6-yl)phenyl)-3-(trifluoromethyl)benzamide was obtained in 12% yield. 1H NMR (400 MHz, <dmso>) δ ppm 1.17 (br. s., 1H) 2.26 (br. s., 3H) 2.60 (d, J=1.57 Hz, 1H) 3.51 (br. s., 1H) 3.68 (br. s., 2H) 3.90 (d, J=9.39 Hz, 1H) 5.37 (br. s., 1H) 6.88 (br. s., 1H) 7.21 (br. s., 1H) 7.57-7.83 (m, 2H) 7.91 (d, J=7.83 Hz, 1H) 8.14-8.29 (m, 2H) 10.28-10.47 (m, 1H). LCMS (m/z) (M+H)=496 at Rt=0.77 mins.

Example 812: N-(4-methyl-3-(4-morpholino-1H-imidazo[4,5-c]pyridin-6-yl)phenyl)-3-(trifluoromethyl)benzamide

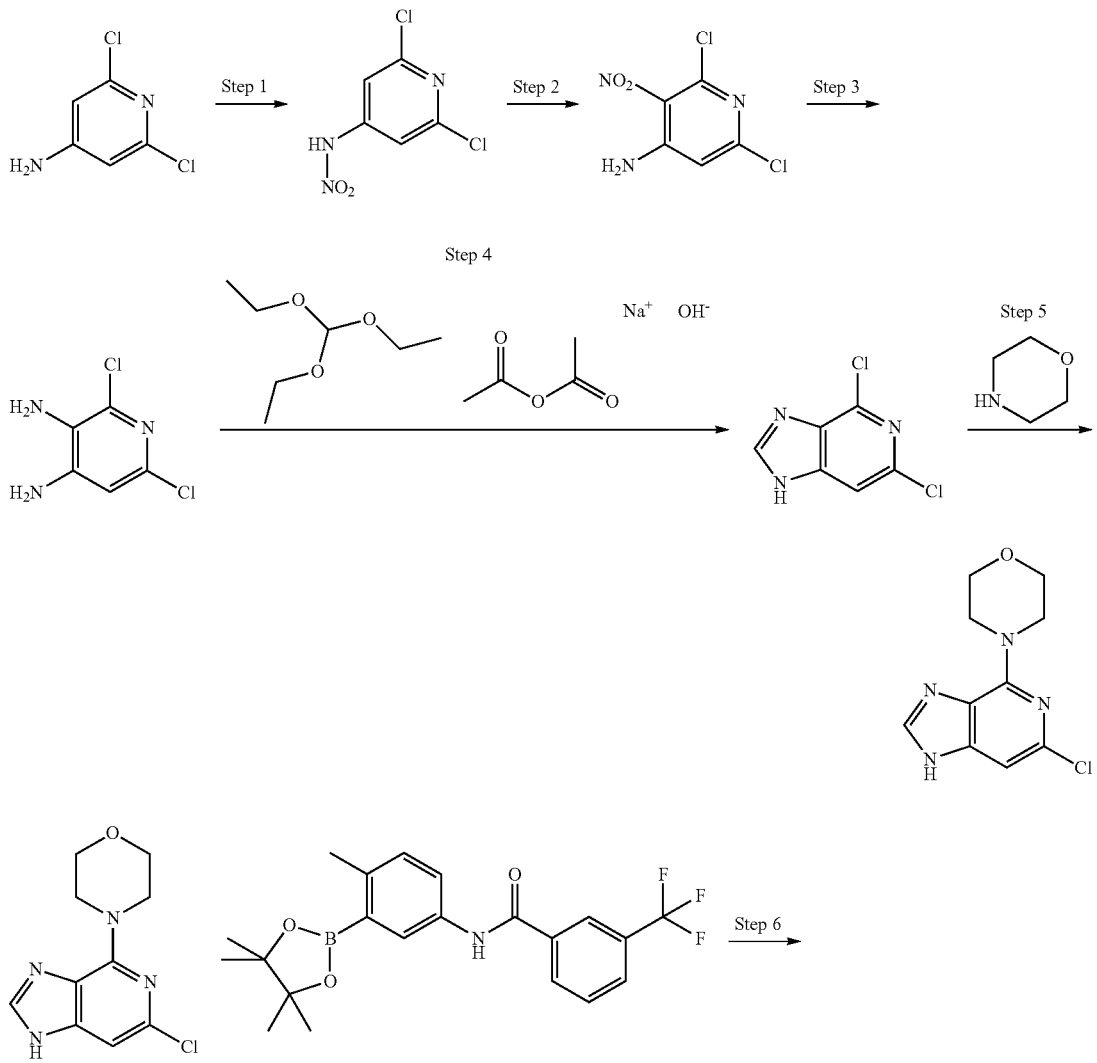

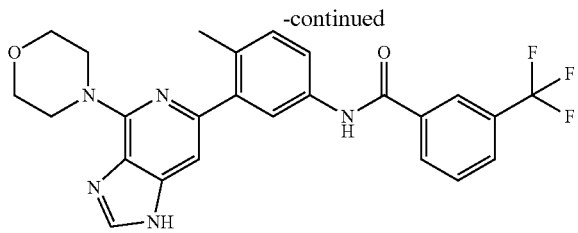

Step 1:

Sulfuric acid (3:1 ratio to nitric acid) was cooled to 0° C. and 2,6-dichloropyridin-4-amine (1.0 equiv.) was added portion wise so that the rate of addition did not increase the internal temperature above 10° C. The mixture was cooled to −5° C. and 90% nitric acid fuming (0.746 M final concentration) was added over a period of 30 minutes ensuring that the internal temperature remained at 0° C. The reaction was continued for 2 hr at 0° C. The reaction mixture was poured on ice water and stirred at 0° C. for 30 minutes, then filtered. The filter cake was suspended in water and stirred for 15 minutes, then filtered, and dried by azeotroping with toluene. N-(2,6-dichloropyridin-4-yl)nitramide was obtained in 94% yield and used as is in the next step. LCMS (m/z) (M+H)=207.9/209.9, Rt=0.70 min.

Step 2:

N-(2,6-dichloropyridin-4-yl)nitramide (1.0 equiv.) was added portion wise to a flask containing sulfuric acid (1 M) making sure that the temperature did not rise above 40° C. The reaction was then heated at 100° C. for 1 h. The resulting mixture was red clear. The reaction mixture was poured on ice water and the pH was adjusted to 9.5 by addition of 10N sodium hydroxide solution and then stirred for 10 minutes at RT. The precipitate was collected by filtration, suspended in water, stirred for 15 minutes and filtered. The water was removed by azeotroping with toluene. The desired 2,6-dichloro-3-nitropyridin-4-amine was isolated in 90% yield and used as is in the next step. LCMS (m/z) (M+H)=207.9/209.9, Rt=0.68 min.

Step 3:

Raney Nickel (1.0 equiv.) was washed with water (3 times) and methanol (3 times) and was then transferred as slurry into a flask containing 2,6-dichloro-3-nitropyridin-4-amine (1.0 equiv.) in MeOH (0.155 M) under nitrogen. The reaction mix was then hydrogenated overnight under atmospheric pressure. The system was purged with nitrogen and the reaction mixture was filtered over a celite pad. The filtrate was concentrated to give 2,6-dichloropyridine-3,4-diamine as a brown solid in 96% yield which was used as is in next step. LCMS (m/z) (M+H)=179.8, Rt=0.31 min.

Step 4:

2,6-dichloropyridine-3,4-diamine (1.0 equiv.) in triethyl orthoformate (6.0 equiv.) and acetic anhydride (9.0 equiv.) in a round bottom flask was fitted a condenser and the mixture was warmed to 60° C. and then the temperature was increased to 90° C. and the mixture was stirred at that temperature for 5 hr. LCMS showed acetylated product LCMS (m/z) (M+H)=229.8/231.7 Rt=0.64 mins. The reaction mixture was concentrated and then dissolved in 10% NaOH (1.0 equiv.) and warmed at 60° C. for 30 mins when complete conversion to the desired product was observed. The reaction mix was cooled to room temperature, treated with acetic acid until pH=6 and the mixture cooled to 0° C. for 20 mins. The brown solid that formed was filtered and then azeotroped with toluene to give 4,6-dichloro-1H-imidazo[4,5-c]pyridine in quantitative yield. Product was used as is in the next step. LCMS (m/z) (M+H)=187.9/189.8 Rt=0.45 min.

Step 5:

4,6-dichloro-1H-imidazo[4,5-c]pyridine (1.0 equiv.) and morpholine (2.0 equiv.) in ethanol (0.7 M) were stirred at 120° C. in a sealed tube overnight. Some starting material was still present, therefore 2 equivalents of morpholine were added and the reaction left for 6 hr until reaction completion. The cooled reaction mixture was concentrated to dryness. Crude 4-(6-chloro-1H-imidazo[4,5-c]pyridin-4-yl)morpholine was used as is in the next step. LCMS (m/z) (M+H)=239.2 Rt=0.51 min.

Step 6:

To a solution of 4-(6-chloro-1H-imidazo[4,5-c]pyridin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (1.0 equiv) in DME (0.1 M) was added 2M $Na_2CO_3$ (3.0 equiv.) and the system was flushed with nitrogen for 5 minutes. $PdCl_2(dppf) \cdot CH_2Cl_2$ adduct (0.1 equiv.) was added and the system was flushed once again. The vial was capped and place in a microwave reactor for 20 minutes at 120° C. The reaction mix was partitioned in $EtOAc/H_2O$. The organic layer was isolated, dried over $Na_2SO_4$, filtered and concentrated. The crude was purified by HPLC giving N-(4-methyl-3-(4-morpholino-1H-imidazo[4,5-c]pyridin-6-yl)phenyl)-3-(trifluoromethyl)benzamide as the TFA salt in 16% yield. 1H NMR (400 MHz, <dmso>) δ ppm 2.29 (s, 3H) 4.15 (br. s., 3H) 7.08 (br. s., 1H) 7.33 (br. s., 1H) 7.68-7.82 (m, 2H) 7.86 (br. s., 1H) 7.96 (d, J=7.83 Hz, 1H) 8.16-8.38 (m, 2H) 10.52 (br. s., 1H). LCMS (m/z) (M+H)=482 at Rt=0.76 mins.

Example 813: N-(4-methyl-3-(4-morpholino-1H-imidazo[4,5-c]pyridin-6-yl)phenyl)-3-(methylsulfonyl)benzamide

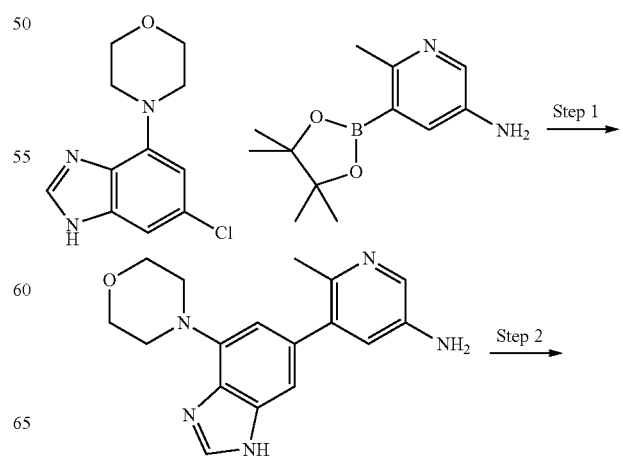

-continued

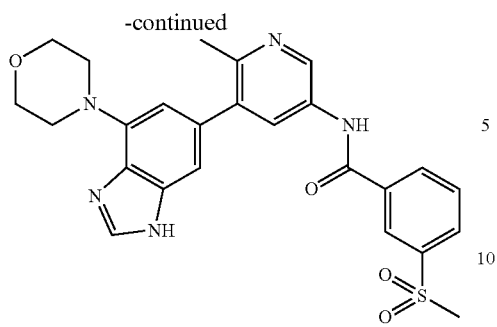

Step 1:
To a solution of 4-(6-chloro-1H-imidazo[4,5-c]pyridin-4-yl)morpholine (1.0 equiv's), 4-methyl-3-(4,4,5,5-tetramethyl-1,3,2-dioxaborolan-2-yl)aniline (1.2 equiv's), in DME (12 mL) and 2M aqueous $Na_2CO_3$ (6.00 mL) was added $PdCl_2$(dppf).CH2Cl2 adduct (0.05 equiv's). The resulting mixture was then degassed by bubbling Ar through for 15 mins. The stirred mixture was then heated to 95° C. After 6 h, additional $PdCl_2$(dppf).$CH_2Cl_2$ adduct (0.1 equiv's) was added and continued refluxing for 22 h. The mixture was then allowed to cool to RT, then filtered through Celite rinsing well with EtOAc. The solvent was evaporated under reduced pressure, and the residue then partitioned between EtOAc and 1M NaOH. The organics were separated, then washed with 1M NaOH (×2), sat. brine (×4) then dried, (Na2SO4), filtered and evaporated under reduced. The residue was purified by silica gel chromatography eluting with 0-12% MeOH/CH2Cl2 increasing to 17% MeOH/CH2Cl2 to give 4-methyl-3-(4-morpholino-1H-imidazo[4,5-c]pyridin-6-yl)aniline in 40% yield as a tan solid. LCMS (m/z) (M+H)=310.1, Rt=0.37 min.

Step 2:
To a solution of 6-methyl-5-(4-morpholino-1H-imidazo[4,5-c]pyridin-6-yl)pyridin-3-amine (1.0 equiv's), 3-(methylsulfonyl)benzoic acid (1.0 equiv's) and 1-hydroxy-7-azabenzatriazole (HOAT) (1.3 equiv's) in DMA (0.7 mL) was added Et3N (1.3 equiv's). After 5 mins, EDC.HCl (1.3 equiv's) was added. After 5 d the homogeneous reaction mixture was diluted with DMSO and water then filtering through 0.45 micron filter and the solution purified by reverse phase prep HPLC. The pure fractions were collected and lyophilized to give N-(4-methyl-3-(4-morpholino-1H-imidazo[4,5-c]pyridin-6-yl)phenyl)-3-(methylsulfonyl)benzamide in 26% yield as the TFA salt. 1H NMR (500 MHz, <dmso>) δ ppm 2.30 (br. s., 5H) 3.30 (s, 5H) 3.80 (br. s., 6H) 4.17 (br. s., 3H) 7.35 (br. s., 1H) 7.67-7.97 (m, 3H) 8.15 (d, J=7.57 Hz, 1H) 8.30 (d, J=7.88 Hz, 1H) 8.49 (s, 1H). LCMS (m/z) (M+H)=492.0 at Rt=0.58 mins.

Example 814: 1-ethyl-3-methyl-N-(4-methyl-3-(4-morpholino-1H-imidazo[4,5-c]pyridin-6-yl)phenyl)-1H-pyrazole-4-carboxamide

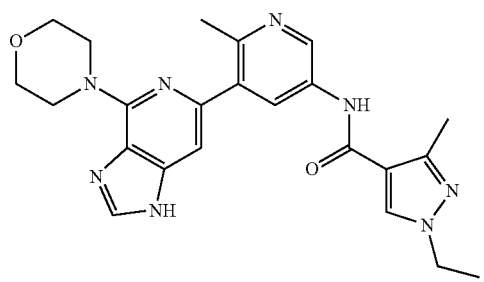 [SMILES: CCn1cc(C(=O)Nc2cnc(C)c(-c3cc4[nH]cnc4c(N4CCOCC4)n3)c2)c(C)n1]

This compound was prepared following the same procedures described for Example 813. 1H NMR (500 MHz, <dmso>) δ ppm 1.39 (t, J=7.25 Hz, 3H) 2.26 (s, 3H) 2.35 (s, 3H) 3.80 (br. s., 4H) 4.10 (q, J=7.25 Hz, 2H) 4.18 (br. s., 4H) 7.10 (br. s., 1H) 7.28 (br. s., 1H) 7.66 (d, J=7.57 Hz, 1H) 7.83 (br. s., 1H) 8.36 (s, 1H) 9.75 (br. s., 1H). LCMS (m/z) (M+H)=446.2, Rt=0.57 mins.

Example 815: 1,3-dimethyl-N-(4-methyl-3-(4-morpholino-1H-imidazo[4,5-c]pyridin-6-yl)phenyl)-1H-pyrazole-4-carboxamide

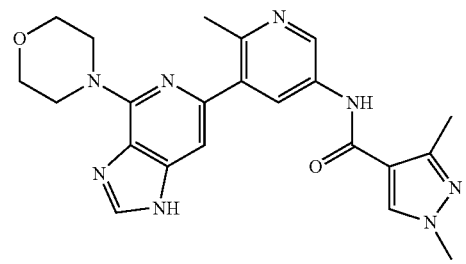 [SMILES: Cc1nn(C)cc1C(=O)Nc1cnc(C)c(-c2cc3[nH]cnc3c(N3CCOCC3)n2)c1]

This compound was prepared following the same procedures described for Example 813. LCMS (m/z) (M+H)=432.2, Rt=0.53 mins.

Example 816: 1-isopropyl-3-methyl-N-(4-methyl-3-(4-morpholino-1H-imidazo[4,5-c]pyridin-6-yl)phenyl)-1H-pyrazole-4-carboxamide

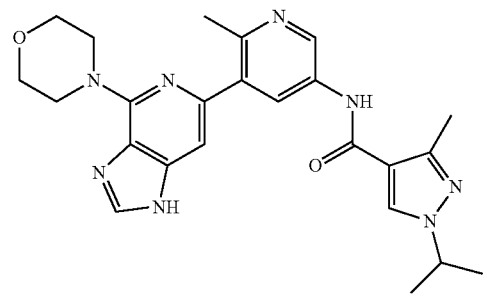 [SMILES: Cc1nn(C(C)C)cc1C(=O)Nc1cnc(C)c(-c2cc3[nH]cnc3c(N3CCOCC3)n2)c1]

This compound was prepared following the same procedures described for Example 813. LCMS (m/z) (M+H)=460.2, Rt=0.61 mins.

Example 817: 1,3-dimethyl-N-(4-methyl-3-(4-morpholino-1H-imidazo[4,5-c]pyridin-6-yl)phenyl)-1H-pyrazole-5-carboxamide

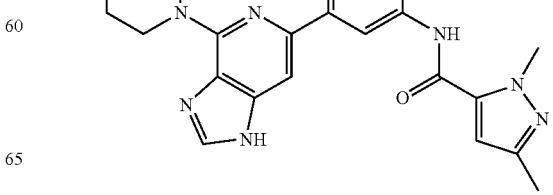

This compound was prepared following the same procedures described for Example 813. LCMS (m/z) (M+H)= 432.2, Rt=0.57 mins.

Example 818: 3-cyclopropyl-1-methyl-N-(4-methyl-3-(4-morpholino-1H-imidazo[4,5-c]pyridin-6-yl)phenyl)-1H-pyrazole-5-carboxamide

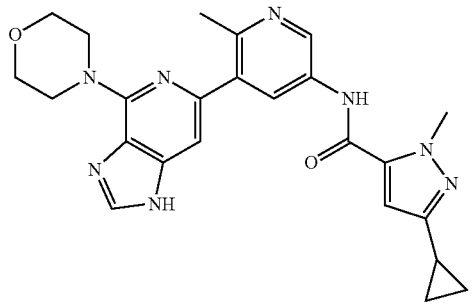 [SMILES: Cc1ncc(NC(=O)c2cc(C3CC3)nn2C)cc1-c1cc2[nH]cnc2c(N2CCOCC2)n1]

This compound was prepared following the same procedures described for Example 813. LCMS (m/z) (M+H)= 458.2, Rt=0.64 mins.

Example 820: 5-cyclopropyl-N-(4-methyl-3-(4-morpholino-1H-imidazo[4,5-c]pyridin-6-yl)phenyl)isoxazole-3-carboxamide

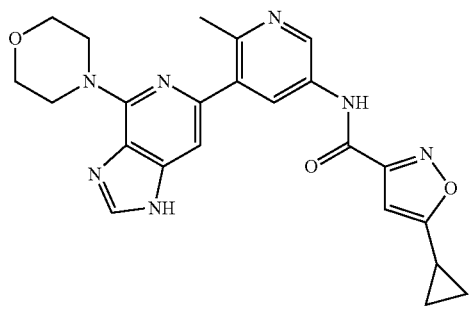 [SMILES: Cc1ncc(NC(=O)c2cc(C3CC3)on2)cc1-c1cc2[nH]cnc2c(N2CCOCC2)n1]

This compound was prepared following the same procedures described for Example 813. LCMS (m/z) (M+H)= 445.1, Rt=0.68 mins.

Example 821: N-(4-methyl-3-(4-morpholino-1H-imidazo[4,5-c]pyridin-6-yl)phenyl)-2-methylsulfonyl)isonicotinamide

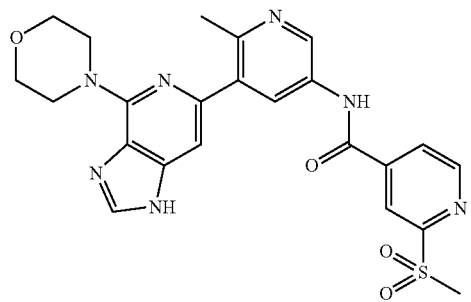 [SMILES: Cc1ncc(NC(=O)c2ccnc(S(C)(=O)=O)c2)cc1-c1cc2[nH]cnc2c(N2CCOCC2)n1]

This compound was prepared following the same procedures described for Example 813. LCMS (m/z) (M+H)= 493.1, Rt=0.55 mins.

Example 822: N-(4-methyl-3-(4-morpholino-1H-imidazo[4,5-c]pyridin-6-yl)phenyl)-3-(1,3,4-oxadiazol-2-yl)benzamide

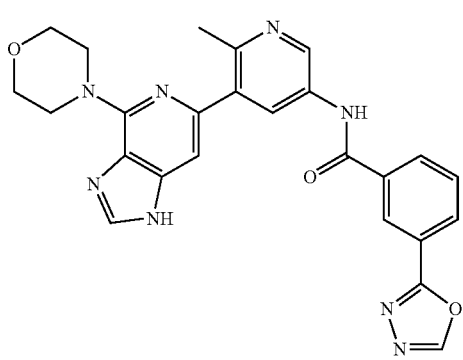 [SMILES: Cc1ncc(NC(=O)c2cccc(-c3nnco3)c2)cc1-c1cc2[nH]cnc2c(N2CCOCC2)n1]

This compound was prepared following the same procedures described for Example 813. LCMS (m/z) (M+H)= 482.1, Rt=0.60 mins.

Example 823: 2(2-hydroxypropan-2-yl)-N-(4-methyl-3-(4-morpholino-1H-imidazo[4,5-c]pyridin-6-yl)phenyl)isonicotinamide

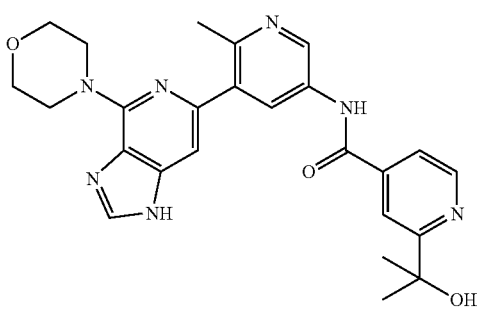 [SMILES: Cc1ncc(NC(=O)c2ccnc(C(C)(C)O)c2)cc1-c1cc2[nH]cnc2c(N2CCOCC2)n1]

This compound was prepared following the same procedures described for Example 813. LCMS (m/z) (M+H)= 473.3, Rt=0.51 mins.

Example 824: N-(4-methyl-3-(8-morpholinoimidazo[1,2-a]pyrazin-6-yl)phenyl)-3-trifluoromethyl)benzamide

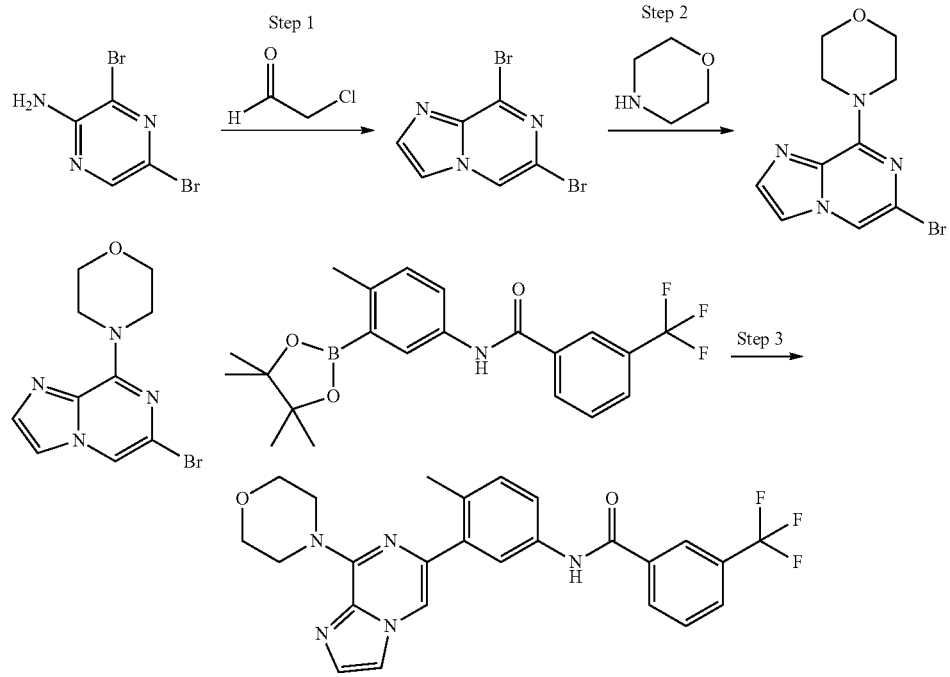

Step 1:

To 3,5-dibromopyrazin-2-amine (1.0 equiv.) in DMF (0.4 M) was added chloroacetaldehyde 50% in water (10.0 equiv.) and the mixture was heated to 100° C. for 16 hr. The reaction mixture was concentrated to a slurry and the crude 6,8-dibromoimidazo[1,2-a]pyrazine was used as such in the next step. Yield is assumed to be quantitative. LCMS (m/z) (M+H)=275.9/277.9/279.9 at Rt=0.51 mins.

Step 2:

6,8-Dibromoimidazo[1,2-a]pyrazine (1.0 equiv.) and morpholine (10.0 equiv.) were stirred in a sealed tube at 60° C. for 4 hr. The crude was transferred to a round bottom flask and concentrated to dryness. The reaction mixture was purified via flash chromatography over silica gel eluting with heptane and 0-80% EtOAc gradient. 4-(6-Bromoimidazo[1,2-a]pyrazin-8-yl)morpholine was isolated in 67% yield. LCMS (m/z) (M+H)=285 at Rt=0.69 mins.

Step 3:

To a solution of 4-(6-bromoimidazo[1,2-a]pyrazin-8-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M $Na_2CO_3$ (3.0 equiv.) and the system was flushed with nitrogen for 5 minutes. $PdCl_2(dppf).CH_2Cl_2$ adduct (0.1 equiv.) was added and the system was flushed once again. The vial was capped and place in a microwave reactor for 20 minutes at 120° C. The reaction mix was partitioned in EtOAc/$H_2O$. The organic layer was isolated, dried over $Na_2SO_4$, filtered and concentrated. The crude was purified by HPLC giving N-(4-methyl-3-(8-morpholinoimidazo[1,2-a]pyrazin-6-yl)phenyl)-3-(trifluoromethyl)benzamide as the TFA salt in 32% yield. 1H NMR (400 MHz, <dmso>) δ ppm 2.35 (s, 3H) 4.14-4.26 (m, 4H) 7.27 (d, J=8.22 Hz, 1H) 7.60 (d, J=0.78 Hz, 1H) 7.70 (dd, J=8.41, 2.15 Hz, 1H) 7.78 (t, J=7.83 Hz, 1H) 7.87 (d, J=2.35 Hz, 1H) 7.92-8.02 (m, 2H) 8.10 (s, 1H) 8.21-8.33 (m, 2H) 10.40-10.54 (m, 1H). LCMS (m/z) (M+H)=482 at Rt=0.88 mins.

Example 825: (R)—N-(4-methyl-3-(8-(3-methylmorpholino)imidazo[1,2-a]pyrazin-6-yl)phenyl)-3-(trifluoromethyl)benzamide

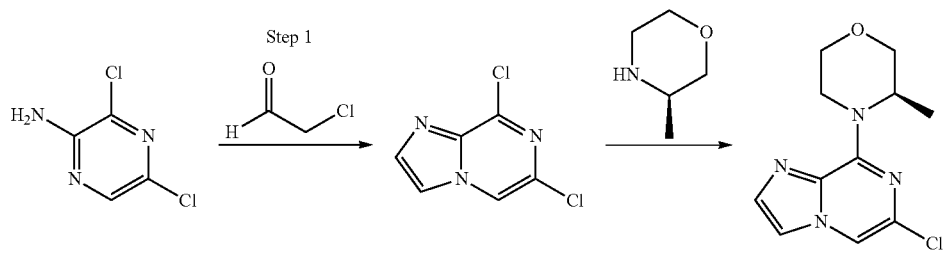

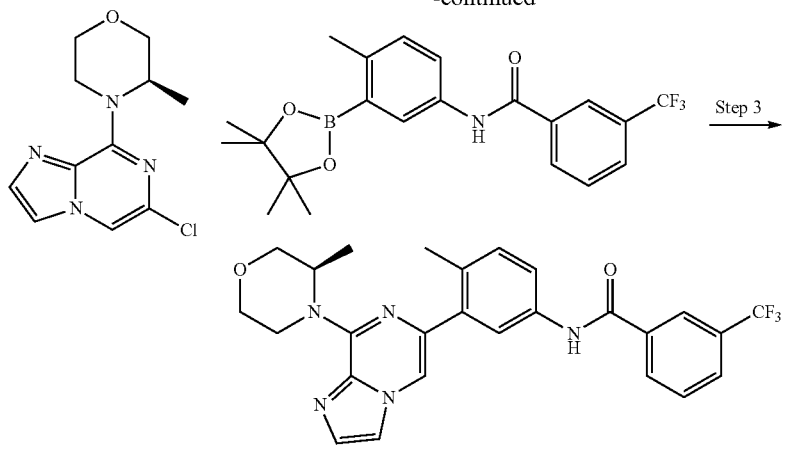

Step 1:

To 3,5-dichloropyrazin-2-amine (1.0 equiv.) in DMF (1.0 M) was added chloroacetaldehyde 50% in water (10.0 equiv.) and the mixture was heated to 100° C. for 16 hr. The reaction mixture was concentrated to a slurry and the crude 6,8-dibromoimidazo[1,2-a]pyrazine was used as such in the next step. Yield is assumed to be quantitative. LCMS (m/z) (M+H)=188/190/192 at Rt=0.46 mins.

Step 2:

6,8-Dichloroimidazo[1,2-a]pyrazine (1.0 equiv.) and (R)-3-methylmorpholine (3.0 equiv.) were stirred in a sealed tube at 50° C. for 3 hr. Some product was observed, additional 2 equiv of (R)-3-methylmorpholine were added, the temperature increased to 65° C. and the reaction was left overnight. The crude was transferred to a round bottom flask and concentrated to dryness. The reaction mixture was purified via flash chromatography over silica gel eluting with heptane and 0-30% EtOAc gradient. (R)-4-(6-chloroimidazo[1,2-a]pyrazin-8-yl)-3-methylmorpholine was isolated in 97% yield. LCMS (m/z) (M+H)=253/255 at Rt=0.77 mins.

Step 3:

To a solution of (R)-4-(6-chloroimidazo[1,2-a]pyrazin-8-yl)-3-methylmorpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 15 minutes at 120° C. Some starting material was still present. Additional 0.3 equiv. of N-(4-methyl-3-(4,4,5,5-tetramethyl-1,3,2-dioxaborolan-2-yl)phenyl)-3-(trifluoromethyl)benzamide and 0.1 equiv of the palladium catalyst were added and the system was flushed with nitrogen. The vial was capped and placed in the microwave reactor for 15 minutes at 120° C. The reaction mix was partitioned in EtOAc/H$_2$O. The organic layer was isolated, dried over Na$_2$SO$_4$, filtered and concentrated. The crude was purified by HPLC giving (R)—N-(4-methyl-3-(8-(3-methylmorpholino)imidazo[1,2-a]pyrazin-6-yl)phenyl)-3-(trifluoromethyl)benzamide as the TFA salt in 8% yield. 1H NMR (400 MHz, <dmso>) δ ppm 1.12-1.33 (m, 3H) 2.30 (s, 3H) 3.21-3.38 (m, 1H) 3.50 (td, J=11.74, 2.35 Hz, 2H) 4.97 (br. s., 1H) 5.51 (br. s., 1H) 7.18-7.33 (m, 1H) 7.54 (s, 1H) 7.65 (dd, J=8.22, 1.96 Hz, 1H) 7.73 (t, J=7.83 Hz, 1H) 7.81 (d, J=2.35 Hz, 1H) 7.87-7.96 (m, 2H) 8.02 (s, 1H) 8.12-8.31 (m, 2H) 10.41 (s, 1H). LCMS (m/z) (M+H)=496 at Rt=0.88 mins.

Example 826: N-(4-methyl-3-(5-morpholino-2-oxo-2,3-dihydrobenzo[d]oxazol-7-yl)phenyl)-3-(trifluoromethyl)benzamide and Example 827: N-(4-methyl-3-(7-morpholino-2-oxo-2,3-dihydrobenzo[d]oxazol-5-yl)phenyl)-3-(trifluoromethyl)benzamide

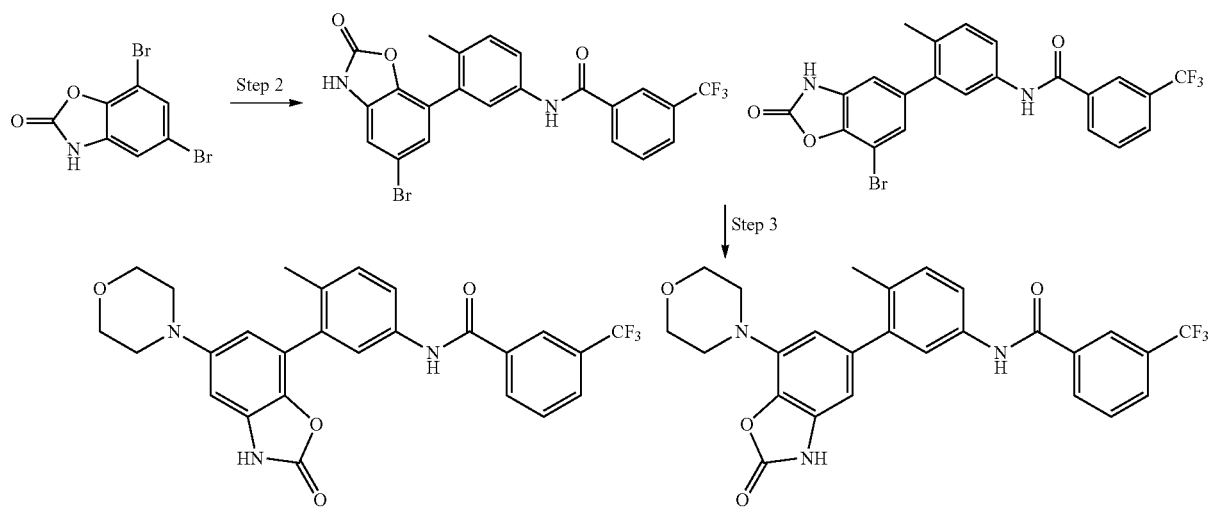

Step 1:

3,5-dibromo-2-hydroxybenzoic acid (1.0 equiv.), triethylamine (1.0 equiv.) and diphenyl phosphoryl azide (1.0 equiv.) were suspended in toluene (1.7 M) and the reaction mix was heated at 110° C. for 20 hr. The reaction mix was cooled to RT, quenched with brine and extracted with EtOAc. The isolated organic was washed twice with saturated solution of sodium bicarbonate, dried over MgSO4, filtered and concentrated. The crude material was purified via flash chromatography over silica gel eluting with heptane and 0-40% EtOAc gradient. Isolated 5,7-dibromobenzo[d]oxazol-2(3H)-one in 63% yield as a white solid. LCMS (m/z) (M+H)=490./492.9/494.9, Rt=0.80 min.

Step 2:

To a solution of 5,7-dibromobenzo[d]oxazol-2(3H)-one (1.0 equiv.) and N-(4-methyl-3-(4,4,5,5-tetramethyl-1,3,2-dioxaborolan-2-yl)phenyl)-3-(trifluoromethyl)benzamide (1.0 equiv.) in DME (0.68 M) was added Na$_2$CO$_3$ (3.0 equiv.) and the system was flushed with nitrogen. PdCl$_2$(dppf).CH$_2$Cl$_2$ adduct (0.1 equiv.) was added to the reaction mix and the system was flushed with nitrogen once again. The vial was capped and microwaved for 20 minutes at 120° C. The crude was partitioned in H2O/EtOAc and the organic layer was isolated, dried over Na$_2$SO$_4$, filtered and concentrated. The crude material was purified via flash chromatography over silica gel eluting with heptane and 0-50% EtOAc gradient. The reaction gave an almost 1:1 ratio of the two possible products (N-(3-(5-bromo-2-oxo-2,3-dihydrobenzo[d]oxazol-7-yl)-4-methylphenyl)-3-(trifluoromethyl)benzamide and N-(3-(7-bromo-2-oxo-2,3-dihydrobenzo[d]oxazol-5-yl)-4-methylphenyl)-3-(trifluoromethyl)benzamide) which were taken together into the next step. LCMS (m/z) (M+H)=493.1 at Rt=1.07 and 1.08.

Step 3:

A mixture of N-(3-(5-bromo-2-oxo-2,3-dihydrobenzo[d]oxazol-7-yl)-4-methylphenyl)-3-(trifluoromethyl)benzamide and N-(3-(7-bromo-2-oxo-2,3-dihydrobenzo[d]oxazol-5-yl)-4-methylphenyl)-3-(trifluoromethyl)benzamide (1.0 equiv.), morpholine (4.0 equiv.), RuPhos precatalyst (0.1 equiv.), 2-dicyclehexylphosphino-2",6"-diisopropoxybiphenyl (0.1 equiv.) were dissolved in THF (0.055) and the system was purged with nitrogen. HMDS (7.0 equiv.) was added to the mix and the reaction vessel was sealed and heated at 70° C. overnight. The reaction mixture was cooled to room temperature, diluted with a saturated solution of NH4Cl and extracted three times with EtOAc. The combined organics were dried over MgSO4, filtered and concentrated. The crude material was purified via preparative reverse phase HPLC. Upon lyophilization of the pure fractions, N-(4-methyl-3-(5-morpholino-2-oxo-2,3-dihydrobenzo[d]oxazol-7-yl)phenyl)-3-(trifluoromethyl)benzamide and N-(4-methyl-3-(7-morpholino-2-oxo-2,3-dihydrobenzo[d]oxazol-5-yl)phenyl)-3-(trifluoromethyl)benzamide were isolated as the TFA salt in 9 and 8% yield respectively. LCMS (m/z) (M+H)=498 at Rt=0.84 and LCMS (m/z) (M+H)=498 at Rt=0.93. Structure assignment is tentative; no HNMR data available at this time.

Example 828: N-(4-methyl-3-(5-morpholinoimidazo[1,2-c]pyrimidin-7-yl)phenyl)-3-(trifluoromethyl)benzamid

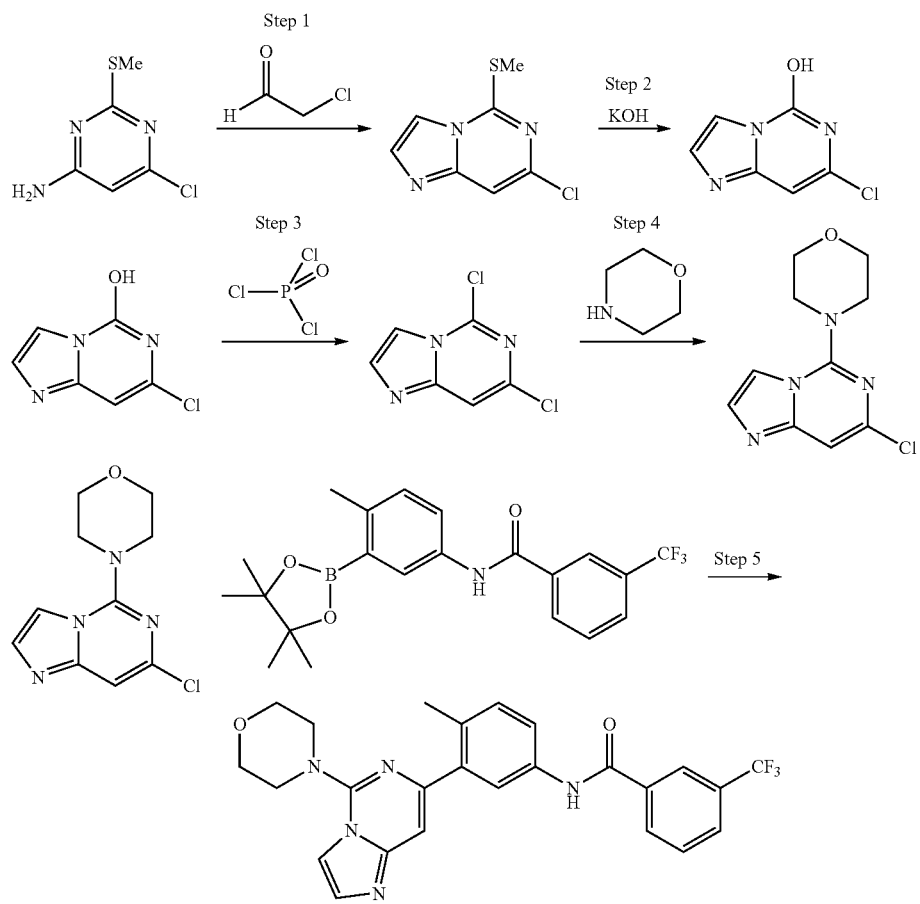

Step 1:

To 6-chloro-2-(methylthio)pyrimidin-4-amine (1.0 equiv.) in EtOH (0.7 M)) was added chloroacetaldehyde 50% in water (10.0 equiv.) and the mixture was refluxed for 3 h. LCMS showed product (m/z) (M+H)=200 at Rt=0.41 mins and small amounts of starting material. Reaction was left for additional 40 minutes. The reaction mixture was cooled to RT and concentrated. The residue was dissolved in DCM, washed with saturated solution of sodium bicarbonate, brine, dried over sodium sulfate, filtered and concentrated. The crude material was purified via flash chromatography over silica gel eluting with DCM and 0-4% MeOH gradient. The desired 7-chloro-5-(methylthio)imidazo[1,2-c]pyrimidine was isolated in quantitative yield. LCMS (m/z) (M+H)=201.9 at Rt=0.40 mins.

Step 2:

7-chloro-5-(methylthio)imidazo[1,2-c]pyrimidine (1.0 equiv.) in MeOH (1.13M) and 2N potassium hydroxide solution (3.5 equiv.) was refluxed for 2 h. The reaction mixture was concentrated and the residue was dissolved in DCM and small amounts of MeOH, loaded onto celite, concentrated and transferred to a cartridge. The crude material was purified via flash chromatography over silica gel eluting with DCM and 0-13% MeOH gradient. Isolated 7-chloroimidazo[1,2-c]pyrimidin-5-ol in 75%. LCMS (m/z) (M+H)=170 at Rt=0.23 mins.

Step 3:

To a flask containing 7-chloroimidazo[1,2-c]pyrimidin-5-ol (1.0 equiv.) was added $POCl_3$ (13.0 equiv.) and the reaction mix was refluxed overnight. The reaction mixture was concentrated, loaded on celite and purified via flash chromatography over silica gel eluting with DCM and 0-10% MeOH gradient. Isolated 5,7-dichloroimidazo[1,2-c]pyrimidine in 56% yield. LCMS (m/z) (M+H)=188/190 at Rt=0.49 mins.

Step 4:

To a flask containing 5,7-dichloroimidazo[1,2-c]pyrimidine (1.0 equiv.) in a 3:1 mixture of DCM and MeOH (0.7 M) at 0° C. was added morpholine (4.0 equiv.) and the reaction mix was brought to RT. After 3 h there was little starting material left. Reaction mix was stirred for 1 h more to ensure completion. The reaction mixture was concentrated and purified via flash chromatography over silica gel eluting with DCM and 0-5% MeOH gradient. Isolated 4-(7-chloroimidazo[1,2-c]pyrimidin-5-yl)morpholine in 27% yield. LCMS (m/z) (M+H)=238.9 at Rt=0.41 mins.

Step 5:

To a solution of 4-(7-chloroimidazo[1,2-c]pyrimidin-5-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. $PdCl_2$(dppf).$CH_2Cl_2$ adduct (0.1 equiv.) was added and the system was flushed once again. The vial was capped and place in a microwave reactor for 15 minutes at 120° C. Some starting material was still present. Additional 0.1 equiv. of the palladium catalyst were added and the system was flushed with nitrogen. The vial was capped and placed in the microwave reactor for 15 minutes at 120° C. The reaction mix was partitioned in EtOAc/$H_2O$. The organic layer was isolated, dried over $Na_2SO_4$, filtered and concentrated. The crude was purified by HPLC giving N-(4-methyl-3-(5-morpholinoimidazo[1,2-c]pyrimidin-7-yl)phenyl)-3-(trifluoromethyl)benzamide as the TFA salt in 20% yield. 1H NMR (400 MHz, <dmso>) δ ppm 2.41 (s, 3H) 2.52 (s, 1H) 3.54 (br. s., 4H) 3.82 (d, J=4.30 Hz, 4H) 7.33 (s, 1H) 7.49 (s, 1H) 7.71-7.83 (m, 2H) 7.97 (d, J=7.83 Hz, 1H) 8.03-8.10 (m, 2H) 8.17 (s, 1H) 8.23-8.35 (m, 2H) 10.56 (s, 1H). LCMS (m/z) (M+H)=482 at Rt=0.78 mins.

Example 829: N-(4-methyl-3-(4-morpholinothieno [3,2-d]pyrimidin-2-yl)phenyl)-3-(trifluoromethyl) benzamide

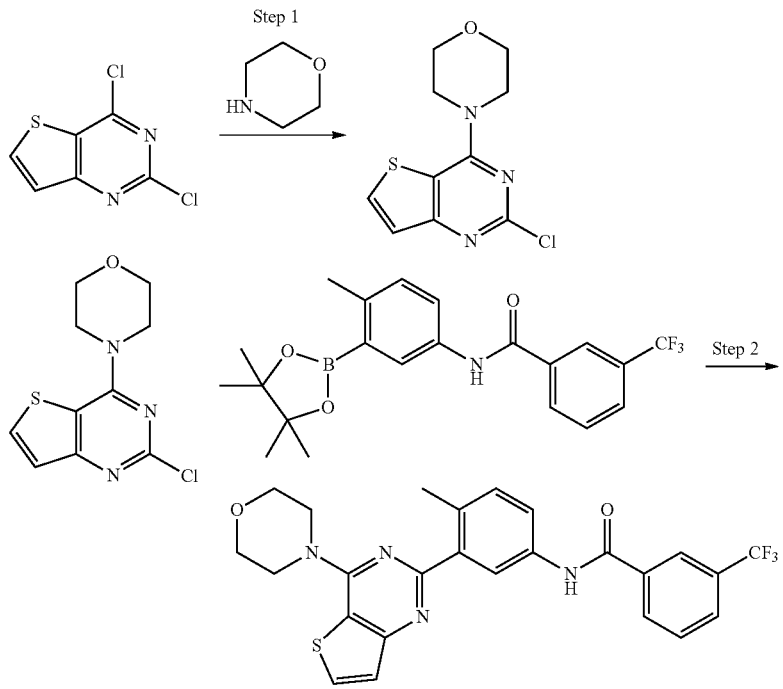

Step 1:

2,4-Dichlorothieno[3,2-d]pyrimidine (1.0 equiv.) and morpholine (2.2 equiv.) were stirred in a sealed tube at RT for 2 hr. The reaction mixture was concentrated and the residue was purified via flash chromatography over silica gel eluting with heptane and 0-100% EtOAc gradient. The desired 4-(2-chlorothieno[3,2-d]pyrimidin-4-yl)morpholine was isolated in 90% yield. LCMS (m/z) (M+H)=256 at Rt=0.68 mins.

Step 2:

To a solution of 4-(2-chlorothieno[3,2-d]pyrimidin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. $PdCl_2(dppf) \cdot CH_2Cl_2$ adduct (0.1 equiv.) was added and the system was flushed once again. The vial was capped and place in a microwave reactor for 20 minutes at 120° C. Some starting material was still present. The vial was placed in the microwave reactor for additional 20 minutes at 120° C. The reaction mix was partitioned in $EtOAc/H_2O$. The organic layer was isolated, dried over $Na_2SO_4$, filtered and concentrated. The crude was purified by HPLC giving N-(4-methyl-3-(4-morpholinothieno[3,2-d]pyrimidin-2-yl)phenyl)-3-(trifluoromethyl)benzamide as the TFA salt in 14% yield. 1H NMR (400 MHz, <dmso>) δ ppm 3.67-3.71 (m, 1H) 3.75 (t, J=4.70 Hz, 4H) 3.82-3.88 (m, 1H) 3.97 (d, J=4.30 Hz, 4H) 7.29 (d, J=8.61 Hz, 1H) 7.47 (d, J=5.48 Hz, 1H) 7.68-7.82 (m, 2H) 7.91 (d, J=7.83 Hz, 1H) 8.12 (d, J=1.96 Hz, 1H) 8.19-8.29 (m, 2H) 8.33 (d, J=5.09 Hz, 1H) 10.51 (s, 1H). LCMS (m/z) (M+H)=499 at Rt=0.83 mins.

Example 830: N-(4-methyl-3-(4-morpholino-5H-pyrrolo[3,2-d]pyrimidin-2-yl)phenyl)-3-(trifluoromethyl)benzamide Step 1:

To a solution of 2,4-dichloro-5H-pyrrolo[3,2-d]pyrimidine (1.0 equiv.) in THF (0.53 M) was added morpholine (1.2 equiv.) followed by DIEA (2.0 equiv.) and the reaction mixture was stirred at RT for overnight. The reaction mixture was concentrated and the crude was partitioned in $EtOAc/NaHCO_3$. The organic layer was isolated, washed with brine, dried over $Na_2SO_4$, filtered and concentrated. The desired 4-(2-chloro-5H-pyrrolo[3,2-d]pyrimidin-4-yl)morpholine was used as is in the next step. LCMS (m/z) (M+H)=239 at Rt=0.56 mins.

Step 2:

To a solution of 4-(2-chloro-5H-pyrrolo[3,2-d]pyrimidin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. $PdCl_2(dppf) \cdot CH_2Cl_2$ adduct (0.1 equiv.) was added and the system was flushed once again. The vial was capped and place in a microwave reactor for 20 minutes at 120° C. The reaction mix was partitioned in $EtOAc/H_2O$. The organic layer was isolated, dried over $Na_2SO_4$, filtered and concentrated. The crude was purified by HPLC giving N-(4-methyl-3-(4-morpholino-5H-pyrrolo[3,2-d]pyrimidin-2-yl)phenyl)-3-(trifluoromethyl)benzamide as the TFA salt in 20% yield. 1H NMR (400 MHz, <dmso>) δ ppm 2.38 (s, 3H) 3.80 (t, J=4.50 Hz, 4H) 4.04 (br. s., 4H) 6.60 (br. s., 1H) 7.42 (d, J=7.83 Hz, 1H) 7.74-7.87 (m, 2H) 7.87-8.01 (m, 2H) 8.11 (d, J=1.96 Hz, 1H) 8.21-8.32 (m, 2H) 10.64 (br. s., 1H). LCMS (m/z) (M+H)=482 at Rt=0.81 mins.

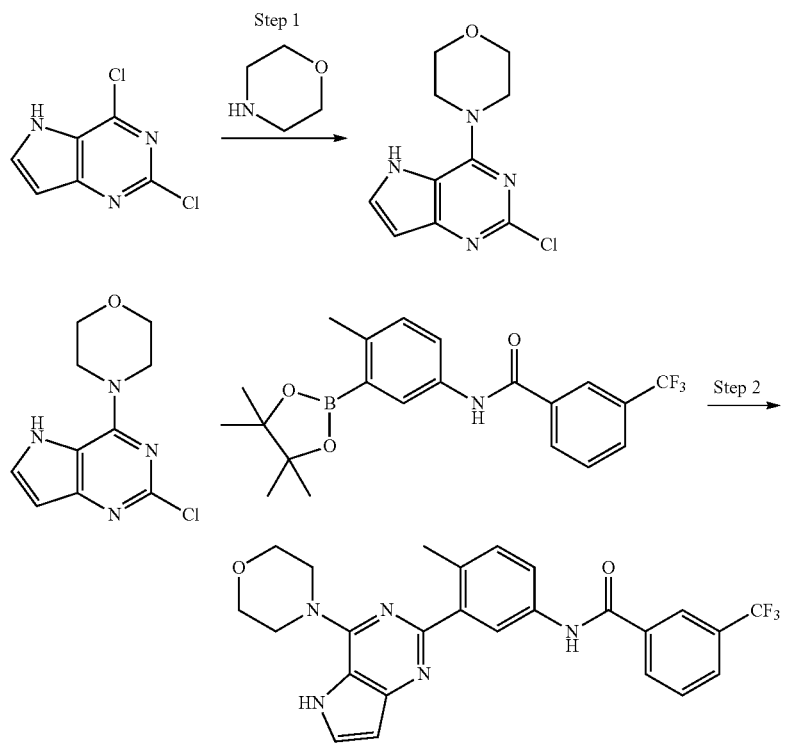

Example 831: N-(4-methyl-3-(8-morpholinoimidazo[1,2-b]pyridazin-6-yl)phenyl)-3-(trifluoromethyl)benzamide

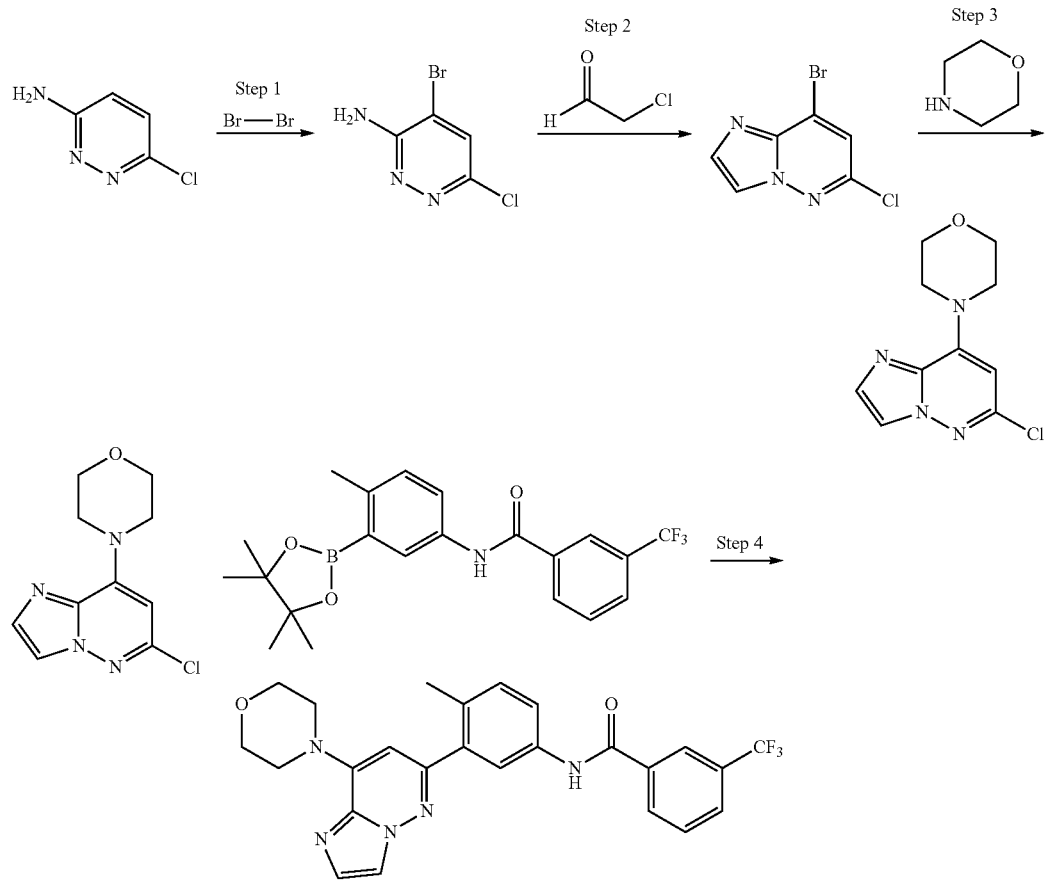

Step 1:

To 6-chloropyridazin-3-amine (1.0 equiv.) and NaHCO3 (1.84 equiv.) in MeOH (2.3 M) at 0° C. was added bromine (1.1 equiv.) drop wise and the mixture was left stirring for 3 hr at RT. The reaction mixture was quenched by addition of water and concentrated until the solid precipitated. The mixture was then cooled in an ice water bath, filtered and dried to afford the desired 4-bromo-6-chloropyridazin-3-amine as a brown solid in 86% yield. LCMS (m/z) (M+H)=207.9/209.9/211.9 at Rt=0.50 mins.

Step 2:

To 4-bromo-6-chloropyridazin-3-amine (1.0 equiv.) in EtOH (0.48 M) was added chloroacetaldehyde 50% in water (10.0 equiv.) and the mixture was heated to 100° C. for 16 h. The reaction mixture was concentrated to a brown slurry and the desired 8-bromo-6-chloroimidazo[1,2-b]pyridazine was used as such in the next step. Yield was assumed to be quantitative. LCMS (m/z) (M+H)=231.9/233.9/235.9 at Rt=0.55 mins.

Step 3:

To a flask containing 8-bromo-6-chloroimidazo[1,2-b]pyridazine (1.0 equiv.) in EtOH (0.650 M) was added morpholine (10.0 equiv.) and the reaction mix was stirred at RT for 3 hr when the reaction was complete. The solvent was removed under vacuum and the crude 4-(6-chloroimidazo[1,2-b]pyridazin-8-yl)morpholine was used as is in the next step. Yield was assumed to be quantitative. LCMS (m/z) (M+H)=239.1 at Rt=0.68 mins.

Step 4:

To a solution of 4-(6-chloroimidazo[1,2-b]pyridazin-8-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 15 minutes at 120° C. Some unreacted starting material was still present, additional 0.3 equivalents of N-(4-methyl-3-(4,4,5,5-tetramethyl-1,3,2-dioxaborolan-2-yl)phenyl)-3-(trifluoromethyl)benzamide were added and the vial was placed in the microwave reactor for 15 minutes at 130° C. The reaction mix was partitioned in EtOAc/H$_2$O. The organic layer was isolated, dried over Na$_2$SO$_4$, filtered and concentrated. The crude was purified by HPLC giving N-(4-methyl-3-(8-morpholinoimidazo[1,2-b]pyridazin-6-yl)phenyl)-3-(trifluoromethyl)benzamide as the TFA salt in 20% yield. 1H NMR (400 MHz, <dmso>) δ ppm 0.96-1.10 (m, 5H) 2.25-2.35 (m, 3H) 3.42 (q, J=7.04 Hz, 4H) 3.71-3.80 (m, 5H) 6.31-6.41 (m, 1H) 7.26-7.37 (m, 1H) 7.55-7.65 (m, 1H) 7.71-7.86 (m, 3H) 7.90-8.00 (m, 1H) 8.06-8.13 (m, 1H) 8.20-8.34 (m, 2H) 10.44-10.55 (m, 1H). LCMS (m/z) (M+H)=482 at Rt=0.89 mins.

Example 832: Synthesis of N-(5-(8-(2-(1H-imidazol-2-yl)morpholino)imidazo[1,2-b]pyridazin-6-yl)-6-methylpyridin-3-yl)-3-(trifluoromethyl)benzamide

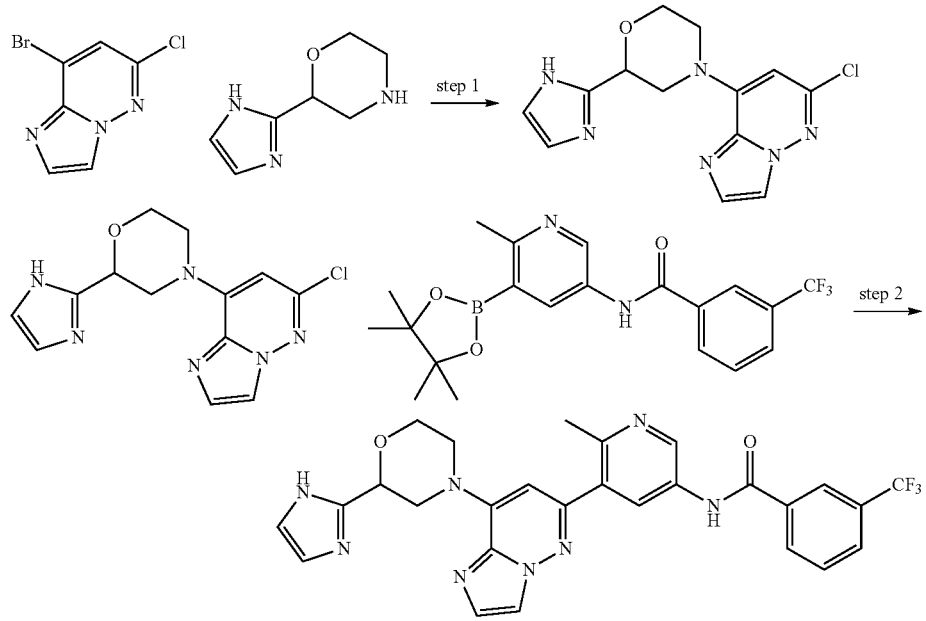

Step 1:

A solution of 8-bromo-6-chloroimidazo[1,2-b]pyridazine (1.0 equiv.), 2-(1H-imidazol-2-yl)morpholine bis-hydrochloride salt (1.0 equiv.) and triethylamine (3.0 equiv.) in NMP (0.143 M) was heated at 60° C. for 1 hr. The mixture was purified via preparative reverse phase HPLC. Upon lyophilization of the pure fractions, 4-(6-chloroimidazo[1,2-b]pyridazin-8-yl)-2-(1H-imidazol-2-yl)morpholine was isolated as the TFA salt in 14% yield. LCMS (m/z) (M+H)= 304.9, Rt=0.50 min.

Step 2:

A mixture of 4-(6-chloroimidazo[1,2-b]pyridazin-8-yl)-2-(1H-imidazol-2-yl)morpholine (1.0 equiv.), N-(6-methyl-5-(4,4,5,5-tetramethyl-1,3,2-dioxaborolan-2-yl)pyridin-3-yl)-3-(trifluoromethyl)benzamide (1.0 equiv.), sodium carbonate (2 M, 3 equiv.) and PdCl$_2$(dppf) (0.5 equiv.) in DME (0.08 M) were heated to 120° C. for 30 min in the microwave. After cooling to RT, the organic phase purified via preparative reverse phase HPLC. Upon lyophilization of the pure fractions, N-(5-(8-(2-(1H-imidazol-2-yl)morpholino)imidazo[1,2-b]pyridazin-6-yl)-6-methylpyridin-3-yl)-3-(trifluoromethyl)benzamide was isolated as the TFA salt in 3.1% yield. LCMS (m/z) (M+H)=549.2, Rt=0.67 min. 1H NMR (400 MHz, <cd3od>) δ ppm 3.12-3.21 (m, 4H), 3.64 (s, 3H), 3.80-3.90 (m, 4H), 6.96 (d, J=1.96 Hz, 2H), 7.41 (d, J=1.96 Hz, 2H), 7.52-7.62 (m, 1H), 7.84-7.92 (m, 1H), 7.97 (br. s., 2H), 8.05-8.12 (m, 1H), 8.14-8.20 (m, 1H).

Example 833: N-(4-methyl-3-(4-morpholinopyrido[2,3-d]pyrimidin-2-yl)phenyl)-3-(trifluoromethyl)benzamide

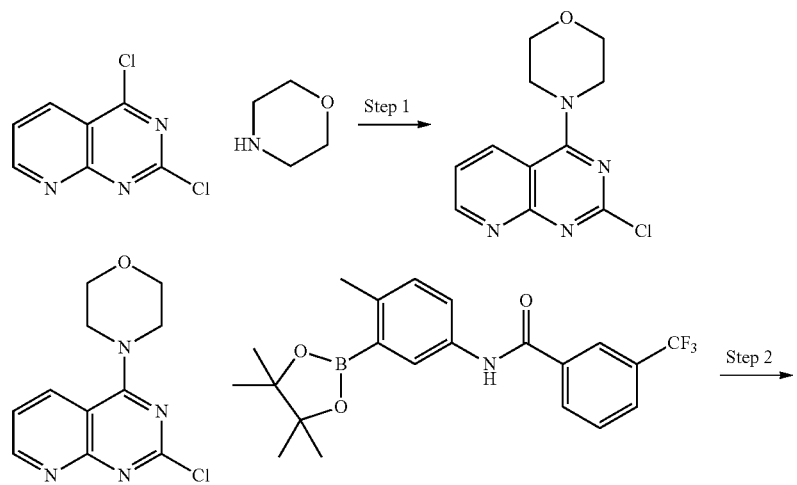

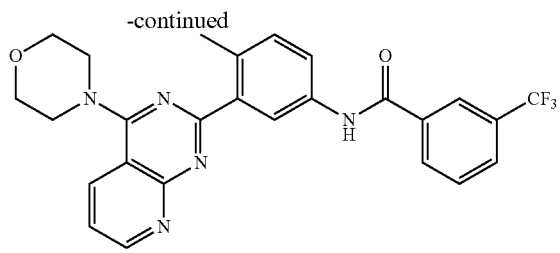

Step 1:

To a flask containing 2,4-dichloropyrido[2,3-d]pyrimidine (1.0 equiv.) in THF (0.42 M) was added morpholine (1.2 equiv.) and DIEA (2.0 equiv.) and the reaction mix was stirred at RT for 1 hr. The solvent was removed under vacuum and the residue was partitioned in EtOAC/NaHCO$_3$. The organic layer was isolated, washed with brine, dried over Na$_2$SO$_4$, filtered and concentrated. The crude 4-(2-chloropyrido[2,3-d]pyrimidin-4-yl)morpholine was used as is in the next step. Yield was assumed to be quantitative. LCMS (m/z) (M+H)=251 at Rt=0.58 mins.

Step 2:

To a solution of 4-(2-chloropyrido[2,3-d]pyrimidin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by HPLC giving N-(4-methyl-3-(4-morpholinopyrido[2,3-d]pyrimidin-2-yl)phenyl)-3-(trifluoromethyl)benzamide as the TFA salt in 40% yield. 1H NMR (400 MHz, <dmso>) δ ppm 2.40-2.47 (m, 9H) 2.47 (s, 1H) 3.68-3.83 (m, 1H) 3.76 (t, J=4.50 Hz, 1H) 4.04 (br. s., 1H) 7.34 (d, J=8.22 Hz, 1H) 7.62 (dd, J=8.22, 4.30 Hz, 1H) 7.70-7.77 (m, 1H) 7.80 (dd, J=8.22, 1.96 Hz, 1H) 7.92 (d, J=7.43 Hz, 1H) 8.12-8.32 (m, 1H) 8.61 (d, J=8.22 Hz, 1H) 8.93-9.05 (m, 1H) 10.58 (s, 1H). LCMS (m/z) (M+H)=494 at Rt=0.78 mins.

Example 834: N-(4-methyl-3-(4-morpholino-5,6,7,8-tetrahydropyrido[3,4-d]pyrimidin-2-yl)phenyl)-3-(trifluoromethyl)benzamide

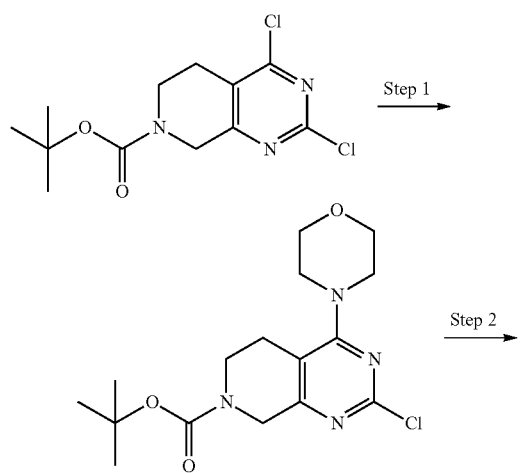

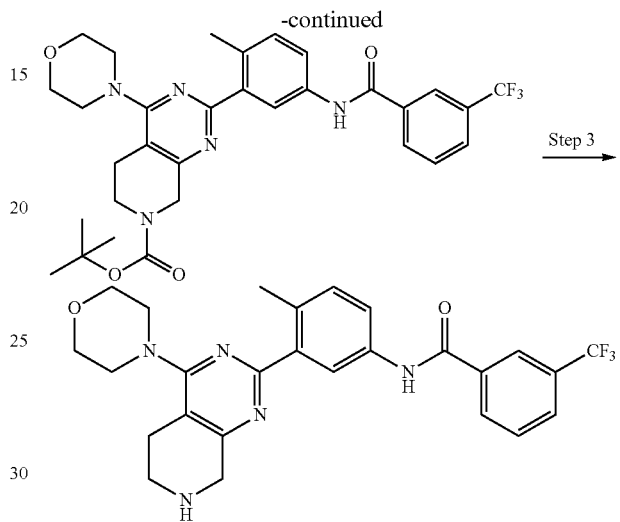

Step 1.

To a flask containing tert-butyl 2,4-dichloro-5,6-dihydropyrido[3,4-d]pyrimidine-7(8H)-carboxylate (1.0 equiv.) in THF (0.55 M) was added morpholine (1.2 equiv.) and DIEA (2.0 equiv.) and the reaction mix was stirred at RT for 2 h. LCMS showed one major product. The reaction mixture was concentrated and the mixture used as is in the next step. LCMS (m/z) (M+H)=355 at Rt=0.82 mins.

Step 2.

To a solution of the crude tert-butyl 2-chloro-4-morpholino-5,6-dihydropyrido[3,4-d]pyrimidine-7(8H)-carboxylate (1.0 equiv.) and N-(4-methyl-3-(4,4,5,5-tetramethyl-1,3,2-dioxaborolan-2-yl)phenyl)-3-(trifluoromethyl)benzamide (1.0 equiv.) in DME (0.14 M) was added 2M Na$_2$CO$_3$ solution (3.0 equiv.) and the system was flushed with nitrogen. PdCl$_2$(dppf).CH$_2$Cl$_2$ adduct (0.1 equiv.) was added to the reaction mix and the system was flushed once again with nitrogen. The reaction vial was capped and microwaved for 20 minutes at 120° C. The crude was partitioned in H2O/EtOAc. The organic layer was isolated, dried over Na$_2$SO$_4$, filtered and concentrated. Crude was purified on a silica gel column using heptane to 50% EtOAc in heptane. Isolated tert-butyl 2-(2-methyl-5-(3-(trifluoromethyl)benzamido)phenyl)-4-morpholino-5,6-dihydropyrido[3,4-d]pyrimidine-7(8H)-carboxylate in 27% yield. LCMS (m/z) [M+H]+=598 at Rt=0.89 min.

Step 3.

To a solution of tert-butyl 2-(2-methyl-5-(3-(trifluoromethyl)benzamido)phenyl)-4-morpholino-5,6-dihydropyrido[3,4-d]pyrimidine-7(8H)-carboxylate (1.0 equiv.) in DCM (0.04 M) was added TFA (15 equiv.) and the reaction mix was stirred at RT for 1 h. The solvent was removed under vacuum and the residue was taken in DMSO and purified on the prep. Isolated N-(4-methyl-3-(4-morpholino-5,6,7,8-tetrahydropyrido[3,4-d]pyrimidin-2-yl)phenyl)-3-(trifluoromethyl)benzamide as the TFA salt in 68% yield. 1H NMR (400 MHz, <dmso>) δ ppm 2.75-3.01 (m, 2H) 3.22 (s, 1H) 3.73 (d, J=4.30 Hz, 4H) 4.08-4.37 (m, 2H) 5.74 (s, 1H) 7.28 (d, J=8.22 Hz, 1H) 7.67-7.83 (m, 2H) 7.96 (d, J=7.83 Hz, 1H) 8.11-8.40 (m, 3H) 9.17 (br. s., 2H) 10.34-10.65 (m, 1H). LCMS (m/z) (M+H)=498 at Rt=0.57 mins.

Example 835: N-(4-methyl-3-(4-morpholino-5,6,7,8-tetrahydropyrido[4,3-d]pyrimidin-2-yl)phenyl)-3-(trifluoromethyl)benzamide

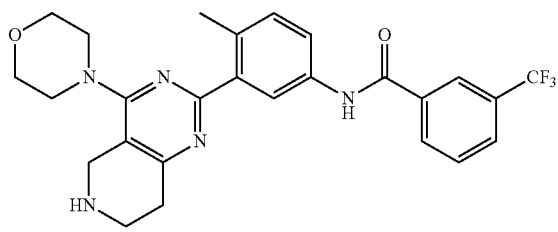 [SMILES: Cc1ccc(NC(=O)c2cccc(C(F)(F)F)c2)cc1-c1nc2c(c(N3CCOCC3)n1)CNCC2]

This compound was prepared following the same procedure reported for compound Example 834. 1H NMR (400 MHz, <dmso>) δ ppm 3.02 (t, J=6.26 Hz, 2H) 3.35 (d, J=4.30 Hz, 5H) 3.67 (d, J=4.30 Hz, 5H) 4.07-4.26 (m, 2H) 7.08-7.37 (m, 1H) 7.61-7.79 (m, 2H) 7.91 (d, J=7.83 Hz, 1H) 8.06-8.33 (m, 3H) 8.80-9.08 (m, 2H) 10.47 (s, 1H). LCMS (m/z) (M+H)=498 at Rt=0.68 mins.

Example 836: N-(4-methyl-3-(4-morpholino-6,7-dihydro-5H-pyrrolo[3,4-d]pyrimidin-2-yl)phenyl)-3-(trifluoromethyl)benzamide

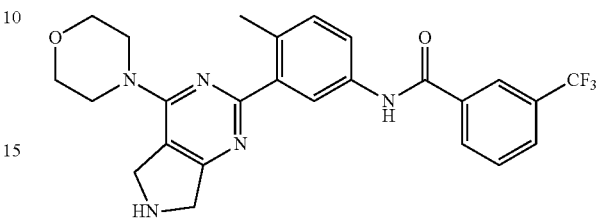

This compound was prepared following the same procedure reported for compound Example 834. 1H NMR (400 MHz, <dmso>) δ ppm 2.37-2.61 (m, 11H) 3.68 (br. s., 5H) 4.39 (br. s., 1H) 4.75 (br. s., 1H) 7.28 (d, J=8.22 Hz, 1H) 7.69-7.82 (m, 1H) 7.96 (d, J=7.83 Hz, 1H) 8.12-8.36 (m, 1H) 9.59 (br. s., 1H) 10.51 (s, 1H). LCMS (m/z) (M+H)=484 at Rt=0.72 mins.

Example 837: N-(4-methyl-3-(1-methyl-7-morpholino-1H-pyrazolo[4,3-d]pyrimidin-5-yl)phenyl)-3-(trifluoromethyl)benzamide

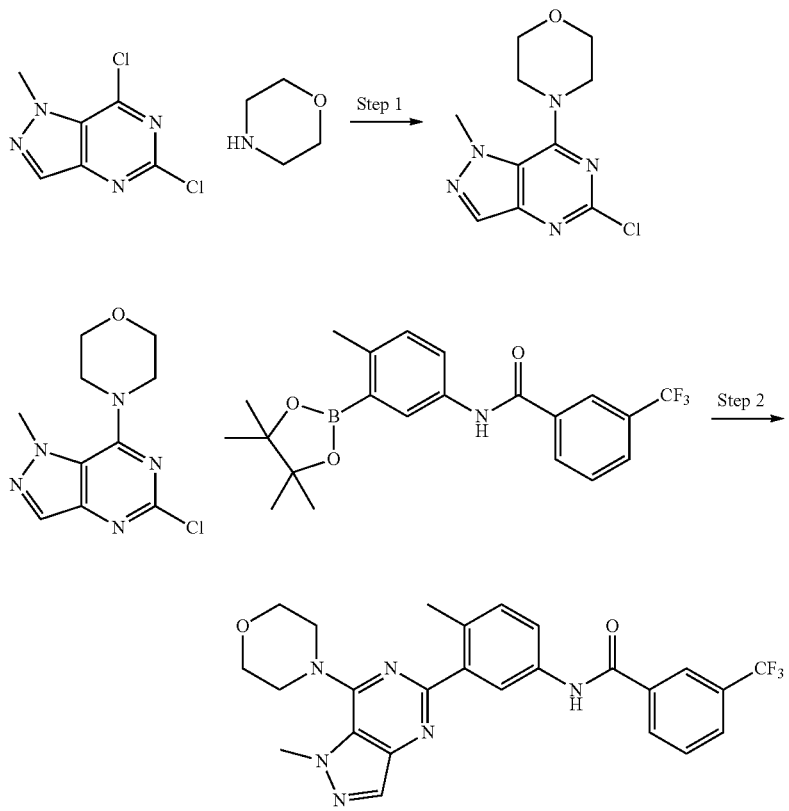

Step 1:

To a flask containing 5,7-dichloro-1-methyl-3a,7a-dihydro-1H-pyrazolo[4,3-d]pyrimidine (1.0 equiv.) in EtOH (0.25 M) was added morpholine (10.0 equiv.) and the reaction mix was stirred at RT for 45 min. The solvent was removed under vacuum and the crude 4-(5-chloro-1-methyl-1H-pyrazolo[4,3-d]pyrimidin-7-yl)morpholine was used as is in the next step. Yield was assumed to be quantitative. LCMS (m/z) (M+H)=254 at Rt=0.56 mins.

Step 2:

To a solution of 4-(5-chloro-1-methyl-1H-pyrazolo[4,3-d]pyrimidin-7-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by HPLC giving N-(4-methyl-3-(1-methyl-7-morpholino-1H-pyrazolo[4,3-d]pyrimidin-5-yl)phenyl)-3-(trifluoromethyl)benzamide was the TFA salt in 20% yield. 1H NMR (400 MHz, <dmso>) δ ppm 3.72-3.88 (m, 5H) 4.09-4.25 (m, 3H) 7.14-7.41 (m, 1H) 7.70-7.84 (m, 2H) 7.89-8.03 (m, 1H) 8.15-8.38 (m, 4H) 10.51 (s, 1H). LCMS (m/z) (M+H)=497 at Rt=0.82 mins.

Example 838: N-(4-methyl-3-(4-morpholinofuro[3,2-d]pyrimidin-2-yl)phenyl)-3-(trifluoromethyl)benzamide Step 1:

To a flask containing 2,4-dichlorofuro[3,2-d]pyrimidine (1.0 equiv.) in EtOH (0.79 M) was added morpholine (10.0 equiv.) and the reaction mix was stirred at RT for 2 hr. The solvent was removed under vacuum and the crude 2-chloro-4-morpholinofuro[3,2-d]pyrimidine was used as is in the next step. Yield was assumed to be quantitative. LCMS (m/z) (M+H)=240/242 at Rt=0.59 mins.

Step 2:

To a solution of 2-chloro-4-morpholinofuro[3,2-d]pyrimidine (1.0 equiv.) and N-(4-methyl-3-(4,4,5,5-tetramethyl-1,3,2-dioxaborolan-2-yl)phenyl)-3-(trifluoromethyl)benzamide (1.0 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by HPLC giving N-(4-methyl-3-(4-morpholinofuro[3,2-d]pyrimidin-2-yl)phenyl)-3-(trifluoromethyl)benzamide as the TFA salt in 40% yield. 1H NMR (400 MHz, <dmso>) δ ppm 2.45 (s, 3H) 3.76 (t, J=4.50 Hz, 4H) 3.98 (d, J=4.30 Hz, 4H) 7.07 (d, J=1.96 Hz, 1H) 7.28 (d, J=8.22 Hz, 1H) 7.66-7.85 (m, 2H) 7.95 (d, J=7.43 Hz, 1H) 8.12 (d, J=1.96 Hz, 1H) 8.21-8.39 (m, 3H) 10.50 (s, 1H). LCMS (m/z) (M+H)=483 at Rt=0.81 mins.

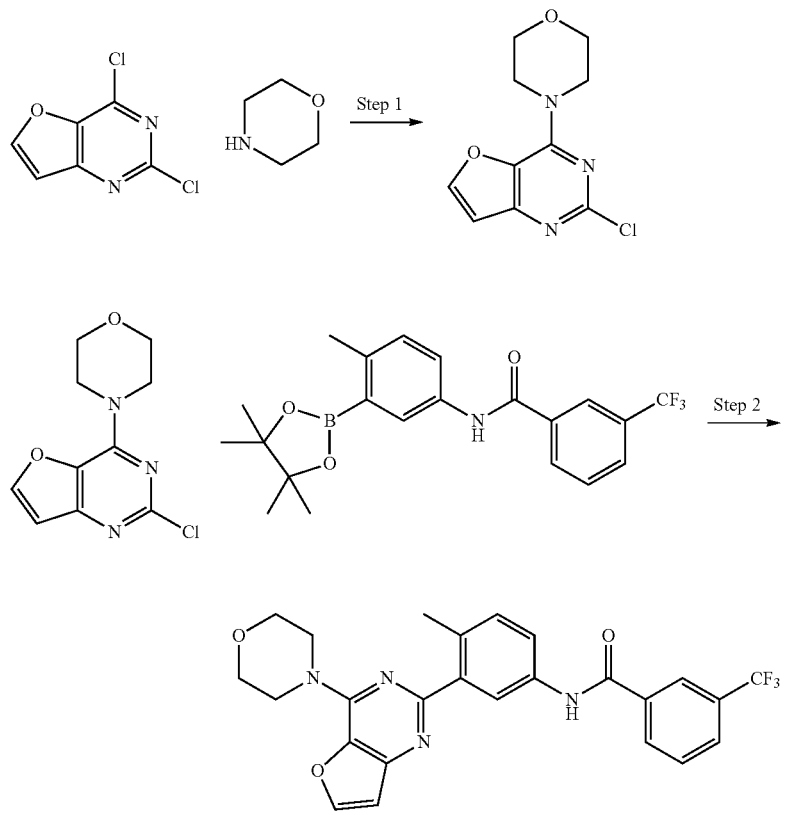

Example 839: N-(4-methyl-3-(7-morpholinothiazolo[5,4-d]pyrimidin-5-yl)phenyl)-3-(trifluoromethyl)benzamide

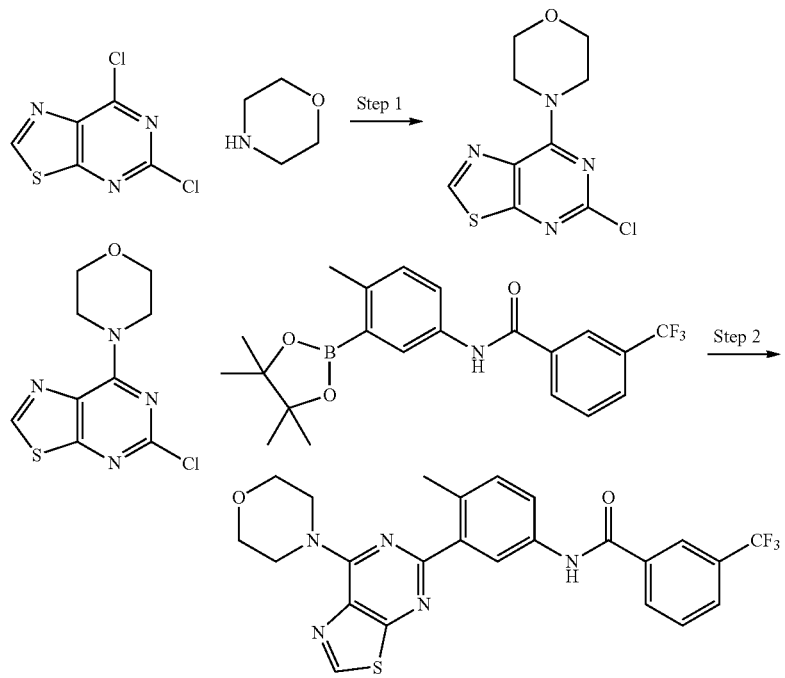

Step 1:
To a flask containing 5,7-dichlorothiazolo[5,4-d]pyrimidine (1.0 equiv.) in EtOH (0.73 M) was added morpholine (10.0 equiv.) and the reaction mix was stirred at RT for 2 hr. The solvent was removed under vacuum and the crude 4-(5-chlorothiazolo[5,4-d]pyrimidin-7-yl)morpholine was used as is in the next step. Yield was assumed to be quantitative. LCMS (m/z) (M+H)=257/259 at Rt=0.70 mins.

Step 2:
To a solution of 4-(5-chlorothiazolo[5,4-d]pyrimidin-7-yl)morpholine (1.0 equiv.) and N-(4-methyl-3-(4,4,5,5-tetramethyl-1,3,2-dioxaborolan-2-yl)phenyl)-3-(trifluoromethyl)benzamide (1.0 equiv) in DME (0.1 M) was added 2M $Na_2CO_3$ (3.0 equiv.) and the system was flushed with nitrogen for 5 minutes. $PdCl_2(dppf) \cdot CH_2Cl_2$ adduct (0.1 equiv.) was added and the system was flushed once again. The vial was capped and place in a microwave reactor for 20 minutes at 125° C. The reaction mix was partitioned in $EtOAc/H_2O$. The organic layer was isolated, dried over $Na_2SO_4$, filtered and concentrated. The crude was purified by HPLC giving N-(4-methyl-3-(7-morpholinothiazolo[5,4-d]pyrimidin-5-yl)phenyl)-3-(trifluoromethyl)benzamide as the TFA salt in 40% yield. 1H NMR (400 MHz, <dmso>) δ ppm 1.73 (s, 1H) 2.52 (s, 1H) 3.76 (t, J=4.50 Hz, 4H) 4.33 (br. s., 3H) 7.29 (d, J=8.22 Hz, 1H) 7.77 (t, J=7.83 Hz, 1H) 7.84 (dd, J=8.22, 1.96 Hz, 1H) 7.95 (d, J=7.83 Hz, 1H) 8.20 (d, J=1.96 Hz, 1H) 8.24-8.35 (m, 2H) 9.26 (s, 1H) 10.52 (s, 1H). LCMS (m/z) (M+H)=500 at Rt=1.02 mins.

Example 840: N-(4-methyl-3-(1-methyl-4-morpholino-1H-pyrazolo[3,4-d]pyrimidin-6-yl)phenyl)-3-(trifluoromethyl)benzamide

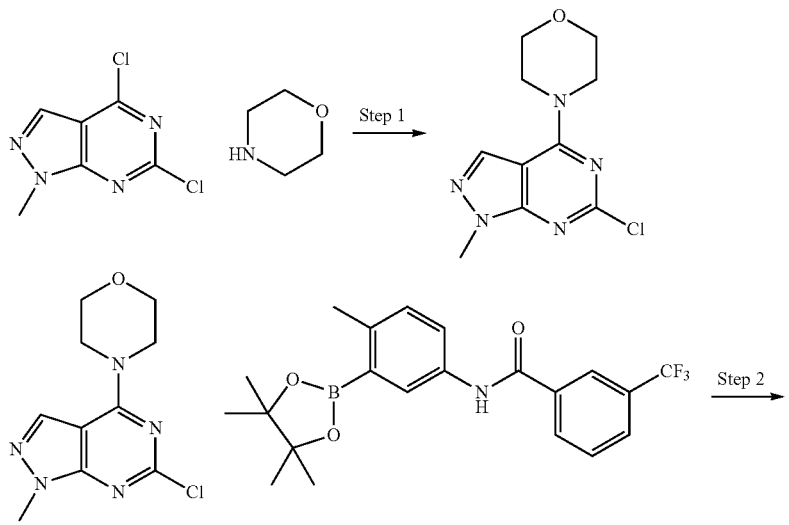

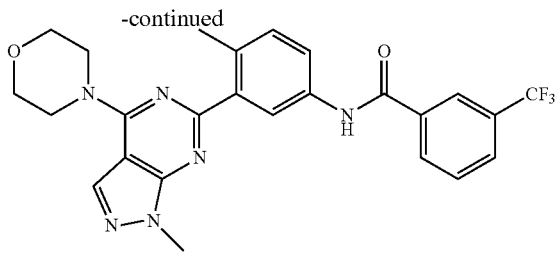

Step 1:

To a flask containing 4,6-dichloro-1-methyl-1H-pyrazolo[3,4-d]pyrimidine (1.0 equiv.) in EtOH (0.70 M) was added morpholine (10.0 equiv.) and the reaction mix was stirred at RT for 2 hr. The solvent was removed under vacuum and the crude 4-(6-chloro-1-methyl-1H-pyrazolo[3,4-d]pyrimidin-4-yl)morpholine was used as is in the next step. Yield was assumed to be quantitative. LCMS (m/z) (M+H)=254/256 at Rt=0.60 mins.

Step 2:

To a solution of 4-(6-chloro-1-methyl-1H-pyrazolo[3,4-d]pyrimidin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (1.0 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 15 minutes at 125° C. The reaction mix was partitioned in EtOAc/H$_2$O. The organic layer was isolated, dried over Na$_2$SO$_4$, filtered and concentrated. The crude was purified by HPLC giving N-(4-methyl-3-(1-methyl-4-morpholino-1H-pyrazolo[3,4-d]pyrimidin-6-yl)phenyl)-3-(trifluoromethyl)benzamide as the TFA salt in 40% yield. 1H NMR (400 MHz, <dmso>) δ ppm 1.73 (s, 1H) 3.72-3.78 (m, 8H) 7.27 (d, J=8.22 Hz, 2H) 7.70-7.85 (m, 3H) 7.95 (d, J=7.83 Hz, 1H) 8.16 (d, J=1.96 Hz, 1H) 8.23-8.36 (m, 5H) 10.50 (s, 2H). LCMS (m/z) (M+H)=497 at Rt=0.93 mins.

Example 841: 2-(2-hydroxypropan-2-yl)-N-(4-methyl-3-(8 morpholinoimidazo[1,2-b]pyridazin-6-yl)phenyl)isonicotinamide

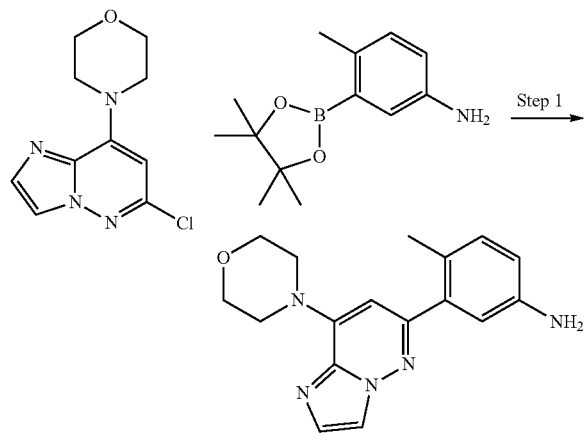

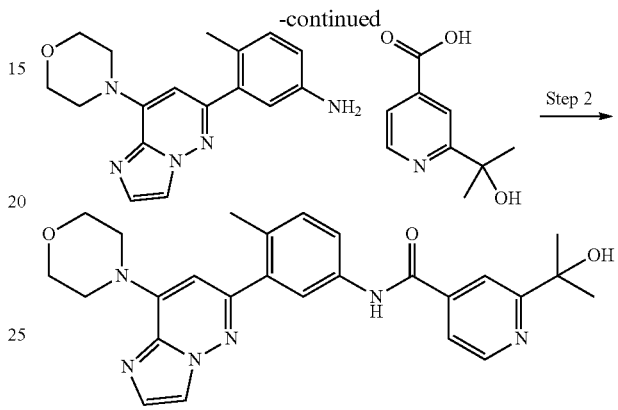

Step 1:

A round bottom flask containing a solution of 4-(6-chloroimidazo[1,2-b]pyridazin-8-yl)morpholine (1.0 equiv.) and 4-methyl-3-(4,4,5,5-tetramethyl-1,3,2-dioxaborolan-2-yl)aniline (1.0 equiv) and 2M Na$_2$CO$_3$ (3.0 equiv.) in DME (1.3M) was flushed with nitrogen for 5 minutes. PdCl$_2$(dppf).CH$_2$Cl$_2$ adduct (0.07 equiv.) was added to the solution and the system was flushed again for 10 more minutes. The reaction mix was refluxed at 120° C. overnight under an inert atmosphere. The reaction mix was cooled to RT, diluted with water and extracted with EtOAc. The combined organics were dried over MgSO4, filtered and concentrated. The crude was purified on a neutral reverse phase column using 40% acetonitrile/water giving 4-methyl-3-(8-morpholinoimidazo[1,2-b]pyridazin-6-yl)aniline in 60% yield. 1H NMR (400 MHz, <dmso>) δ ppm 2.01-2.19 (m, 3H) 3.65-3.80 (m, 4H) 3.89-4.04 (m, 4H) 4.96 (s, 2H) 6.24 (s, 1H) 6.55 (dd, J=8.22, 2.35 Hz, 1H) 6.61 (d, J=2.35 Hz, 1H) 6.93 (d, J=7.83 Hz, 1H) 7.54 (d, J=0.78 Hz, 1H) 8.03 (d, J=0.78 Hz, 1H). LCMS (m/z) (M+H)=310 at Rt=0.42 mins.

Step 2:

To a round bottom flask containing a solution of 4-methyl-3-(8-morpholinoimidazo[1,2-b]pyridazin-6-yl)aniline (1.0 equiv.) and 2-(2-hydroxypropan-2-yl)isonicotinic acid (1.1 equiv) in DMF (3.9 M) was added HATU (1.1 equiv.) and DIEA (3.0 equiv.) and the reaction mix was left stirring overnight at RT. The reaction mix was diluted with water and was extracted three times with EtOAc/H$_2$O. The combined organics were dried over MgSO4, filtered and concentrated. purified on a neutral reverse phase column using 40% acetonitrile/water giving 2-(2-hydroxypropan-2-yl)-N-(4-methyl-3-(8-morpholinoimidazo[1,2-b]pyridazin-6-yl)phenyl)isonicotinamide in 64% yield. 1H NMR (400 MHz, <dmso>) δ ppm 1.39-1.54 (m, 6H) 2.30 (s, 3H) 3.30 (s, 6H) 3.69-3.84 (m, 4H) 3.93-4.10 (m, 4H) 5.34 (s, 1H) 6.34 (s, 1H) 7.32 (d, J=8.61 Hz, 1H) 7.58 (d, J=1.17 Hz, 1H) 7.69 (dd, J=5.09, 1.57 Hz, 1H) 7.75-7.86 (m, 2H) 8.08 (d, J=0.78

Hz, 1H) 8.12 (s, 1H) 8.66 (d, J=4.70 Hz, 1H) 10.40-10.66 (m, 1H). LCMS (m/z) (M+H)=473 at Rt=0.58 mins.

Example 842: 2-isopropyl-N-(4-methyl-3-(8-morpholinoimidazo[1,2-b]pyridazin-6-yl)phenyl)isonicotinamide

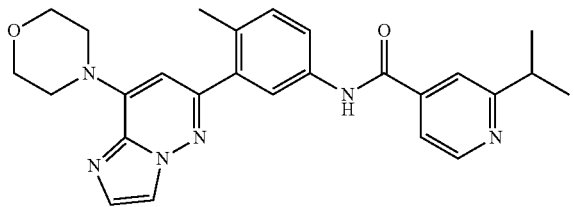 [SMILES: Cc1ccc(NC(=O)c2ccnc(C(C)C)c2)cc1-c1cc(N2CCOCC2)c2nccn2n1]

This compound was prepared following the same procedure reported for Example 841. 1H NMR (400 MHz, <dmso>) δ ppm 1.28 (d, J=6.65 Hz, 6H) 2.30 (s, 3H) 3.15 (spt, J=6.91 Hz, 1H) 3.70-3.80 (m, 5H) 6.36 (s, 1H) 7.33 (d, J=8.22 Hz, 1H) 7.60 (s, 1H) 7.71-7.86 (m, 4H) 7.99-8.17 (m, 1H) 8.55-8.86 (m, 1H) 10.53 (s, 1H). LCMS (m/z) (M+H)=457.3 at Rt=0.59 mins.

Example 843: 2-(1,1-difluoroethyl)-N-(4-methyl-3-(8-morpholinoimidazo[1,2-b]pyridazin-6-yl)phenyl)isonicotinamide

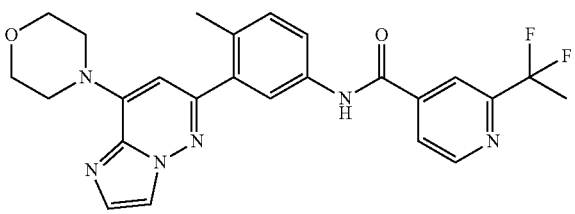 [SMILES: Cc1ccc(NC(=O)c2ccnc(C(C)(F)F)c2)cc1-c1cc(N2CCOCC2)c2nccn2n1]

This compound was prepared following the same procedure reported for Example 841. 1H NMR (400 MHz, <dmso>) δ ppm 2.03 (t, J=19.17 Hz, 3H) 2.31 (s, 3H) 3.76 (d, J=4.30 Hz, 5H) 3.99 (d, J=4.70 Hz, 8H) 6.36 (s, 1H) 7.34 (d, J=8.22 Hz, 1H) 7.60 (s, 1H) 7.75-7.85 (m, 2H) 8.02 (d, J=4.70 Hz, 1H) 8.10 (s, 1H) 8.18 (s, 1H) 8.73-9.01 (m, 1H) 10.55-10.80 (m, 1H). LCMS (m/z) (M+H)=479.3 at Rt=0.74 mins.

Example 844: 2-(2-cyanopropan-2-yl)-N-(4-methyl-3-(8-morpholinoimidazo[1,2-b]pyridazin-6-yl)phenyl)isonicotinamide

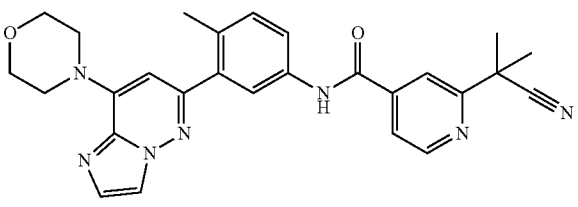 [SMILES: Cc1ccc(NC(=O)c2ccnc(C(C)(C)C#N)c2)cc1-c1cc(N2CCOCC2)c2nccn2n1]

This compound was prepared following the same procedure reported for compound Example 841. 1H NMR (400 MHz, <dmso>) δ ppm 1.67-1.75 (m, 6H) 2.26 (s, 4H) 3.66-3.76 (m, 4H) 3.95 (d, J=4.30 Hz, 4H) 6.30 (s, 1H) 7.29 (d, J=8.61 Hz, 1H) 7.54 (s, 1H) 7.70-7.76 (m, 2H) 7.80 (d, J=4.70 Hz, 1H) 7.95 (s, 1H) 8.04 (s, 1H) 8.74 (d, J=5.09 Hz, 1H) 10.53 (s, 1H). LCMS (m/z) (M+H)=482 at Rt=0.74 mins.

Example 845: 2-(tert-butyl)-N-(4-methyl-3-(8-morpholinoimidazo[1,2-b]pyridazin-6-yl)phenyl)isonicotinamide

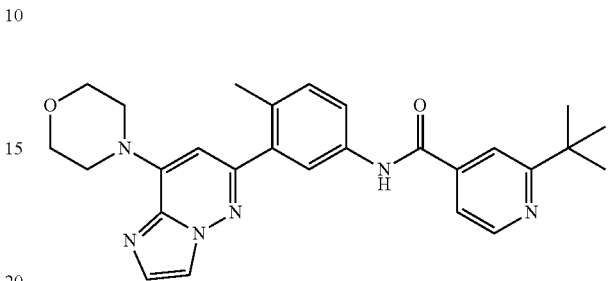

This compound was prepared following the same procedure reported for Example 841. 1H NMR (400 MHz, <dmso>) δ ppm 1.31 (s, 9H) 2.25 (s, 3H) 3.58-3.77 (m, 5H) 6.32 (s, 1H) 7.28 (d, J=8.22 Hz, 1H) 7.57 (s, 1H) 7.65 (d, J=3.91 Hz, 1H) 7.70-7.78 (m, 2H) 7.83 (s, 1H) 8.05 (s, 1H) 8.66 (d, J=5.09 Hz, 1H) 10.46 (s, 1H). LCMS (m/z) (M+H)=471 at Rt=0.63 mins.

Example 846: 3-(2-cyanopropan-2-yl)-N-(4-methyl-3-(8-morpholinoimidazo[1,2-b]pyridazin-6-yl)phenyl)benzamide

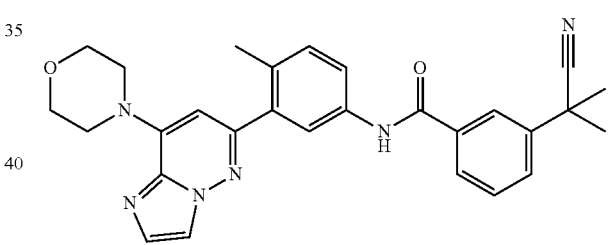

This compound was prepared following the same procedure reported for Example 841. 1H NMR (400 MHz, <dmso>) δ ppm 1.69-1.78 (m, 6H) 2.30 (s, 3H) 3.71-3.81 (m, 4H) 3.94-4.01 (m, 5H) 6.38 (s, 1H) 7.31 (d, J=7.83 Hz, 1H) 7.54-7.63 (m, 2H) 7.73 (d, J=8.22 Hz, 1H) 7.76-7.83 (m, 2H) 7.93 (d, J=7.83 Hz, 1H) 8.04 (s, 1H) 8.11 (s, 1H) 10.34 (s, 1H). LCMS (m/z) (M+H)=481 at Rt=0.78 mins.

Example 847: 3-(difluoromethyl)-N-(4-methyl-3-(8-morpholinoimidazo[1,2-b]pyridazin-6-yl)phenyl)benzamide

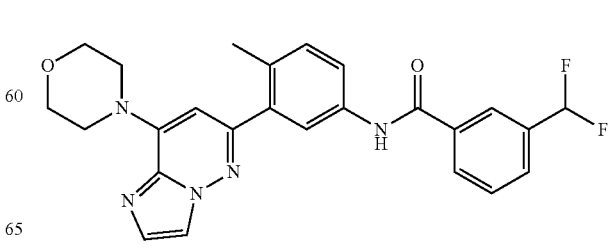

This compound was prepared following the same procedure reported for Example 841. 1H NMR (400 MHz, <dmso>) δ ppm 2.30 (s, 3H) 3.95-4.04 (m, 5H) 6.38 (s, 1H) 6.99 (s, 1H) 6.96-7.28 (m, 1H) 7.13 (s, 1H) 7.27 (s, 1H) 7.31 (d, J=8.61 Hz, 1H) 7.61 (s, 1H) 7.64-7.71 (m, 1H) 7.74-7.86 (m, 3H) 8.01-8.23 (m, 3H) 10.35-10.55 (m, 1H). LCMS (m/z) (M+H)=464 at Rt=0.77 mins.

Example 848: N-(6-methyl-5-(8-morpholinoimidazo[1,2-a]pyridin-6-yl)pyridin-3-yl)-3-(trifluoromethyl)benzamide

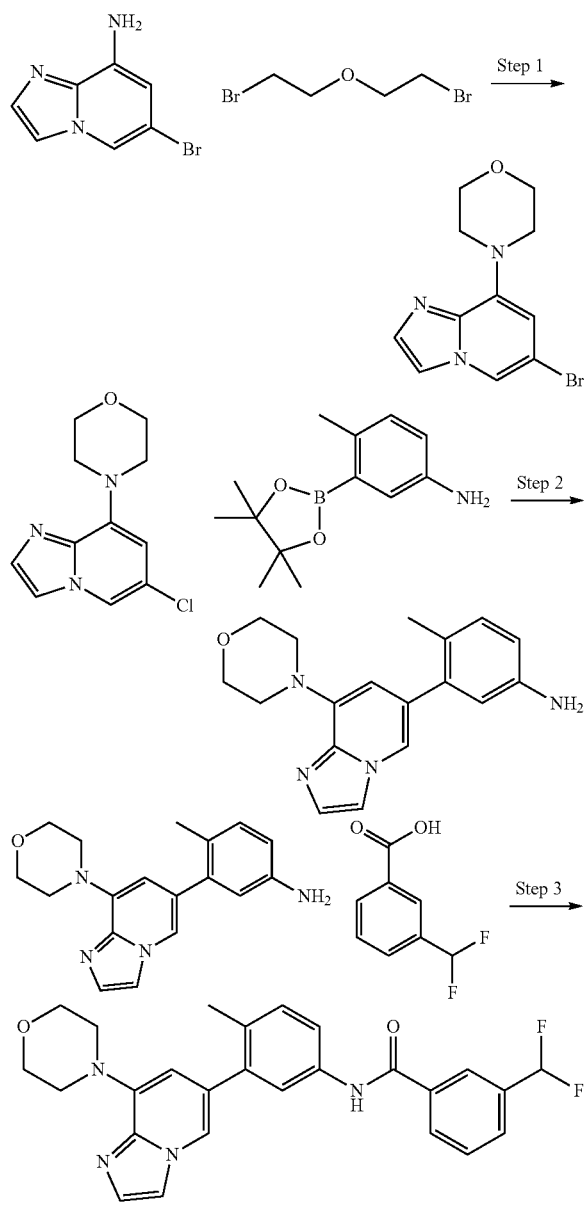

Step 1:
NaH (3.0 equiv.) was added to a solution of 6-bromoimidazo[1,2-a]pyridin-8-amine (1.0 equiv.) in DMF (2.4 M) at 0° C. The mix was left to reach RT and stirred for 15 min. 1-Bromo-2-(2-bromoethoxy)ethane (1.5 equiv) was added to it and the reaction mixture was warmed to 80° C. overnight. The reaction mix was cooled in an ice bath and quenched by dropwise addition of water. A solid precipitated which was filtered and the aqueous layer was back extracted twice with EtOAc. The combined organics were dried over MgSO4, filtered and concentrated. The precipitate and the extraction product were combined to give the desired 4-(6-bromoimidazo[1,2-a]pyridin-8-yl)morpholine in 56% yield which was used as is in the next step. LCMS (m/z) (M+H)=284 at Rt=0.38 mins.

Step 2:
To a solution of 4-(6-bromoimidazo[1,2-a]pyridin-8-yl)morpholine (1.0 equiv.) and 4-methyl-3-(4,4,5,5-tetramethyl-1,3,2-dioxaborolan-2-yl)aniline (1.0 equiv) in DME (0.07 M) was added 2M Na2CO3 (3.0 equiv.) and the system was flushed with nitrogen for 5 minutes. PdCl2(dppf).CH2Cl2 adduct (0.1 equiv.) was added to the solution and the system was flushed once again. The vial was capped and place in a microwave reactor for 20 minutes at 120° C. Some boronate ester was still present therefore additional 0.5 equiv. of 4-(6-bromoimidazo[1,2-a]pyridin-8-yl)morpholine were added and the vial was placed in the microwave reactor for additional 20 min at 120° C. The reaction mix was partitioned in EtOAc/H2O. The organic layer was isolated, dried over Na2SO4, filtered and concentrated. The crude was purified on a silica gel column using heptane to 100% EtOAc in heptane. 4-Methyl-3-(8-morpholinoimidazo[1,2-a]pyridin-6-yl)aniline was obtained in 61% yield. LCMS (m/z) (M+H)=309 at Rt=0.37 mins.

Step 3:
HATU (1.1 equiv.) was added to a solution of 4-methyl-3-(8-morpholinoimidazo[1,2-a]pyridin-6-yl)aniline (1.0 equiv.), 3-(difluoromethyl)benzoic acid (1.0 equiv) and DIEA (2.0 equiv.) in DMF (0.1 M) and the reaction mix was left stirring overnight at RT. The reaction was treated with water and the precipitate was removed by filtration. The solid was dissolved in DCM and purified on a silica gel column using heptane to 85% EtOAc in heptane. 3-(difluoromethyl)-N-(4-methyl-3-(8-morpholinoimidazo[1,2-a]pyridin-6-yl)phenyl)benzamide was obtained in 76% yield. 1H NMR (400 MHz, <dmso>) δ ppm 2.26 (s, 3H) 2.67 (s, 1H) 3.54 (d, J=4.30 Hz, 4H) 3.75-3.84 (m, 4H) 6.38 (s, 1H) 6.98-7.27 (m, 1H) 7.30 (d, J=9.00 Hz, 1H) 7.50 (s, 1H) 7.64-7.80 (m, 4H) 7.89 (s, 1H) 8.06-8.23 (m, 3H) 10.26-10.51 (m, 1H). LCMS (m/z) (M+H)=463.2 at Rt=0.76 mins.

Example 849: N-(4-methyl-3-(8-morpholinoimidazo[1,2-a]pyridin-6-yl)phenyl)-2-(trifluoromethyl)isonicotinamide This compound was prepared following the same procedure described for Example 848. The crude was purified by HPLC and the product isolated as the TFA salt in 71% yield. 1H NMR (400 MHz, <dmso>) δ ppm 2.22 (s, 3H) 3.20 (br. s., 4H) 3.74-3.84 (m, 4H) 6.97-7.15 (m, 1H) 7.33 (d, J=8.22 Hz, 1H) 7.66 (dd, J=8.22, 1.96 Hz, 1H) 7.77 (d, J=1.96 Hz, 1H) 8.00 (br. s., 1H) 8.06-8.22 (m, 2H) 8.30 (s, 1H) 8.45 (br.

s., 1H) 8.93 (d, J=5.09 Hz, 1H) 10.70 (s, 1H). LCMS (m/z) (M+H)=482.2 at Rt=0.74 mins.

Example 850: 2-(difluoromethyl)-N-(4-methyl-3-(8-morpholinoimidazo[1,2-a]pyridin-6-yl)phenyl)isonicotinamide

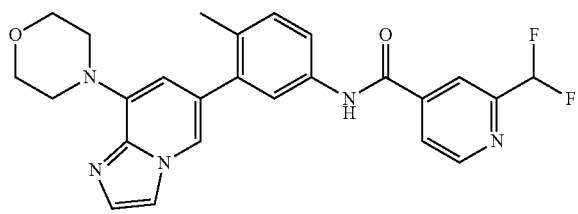 [SMILES: Cc1ccc(NC(=O)c2ccnc(C(F)F)c2)cc1-c1cc(N2CCOCC2)c2nccn2c1]

This compound was prepared following the same procedure described for Example 848. 1H NMR (400 MHz, <dmso>) δ ppm 2.26 (s, 3H) 3.54 (d, J=4.30 Hz, 4H) 3.71-3.85 (m, 4H) 6.37 (s, 1H) 6.88-7.23 (m, 1H) 7.32 (d, J=9.00 Hz, 1H) 7.50 (s, 1H) 7.69-7.75 (m, 2H) 7.90 (s, 1H) 8.04 (d, J=4.70 Hz, 1H) 8.16 (d, J=2.35 Hz, 2H) 8.89 (d, J=4.70 Hz, 1H) 10.64 (s, 1H). LCMS (m/z) (M+H)=464.4 at Rt=0.68 mins.

Example 851: N-(4-methyl-3-(8-morpholinoimidazo[1,2-a]pyridin-6-yl)phenyl)-2-methylsulfonyl)isonicotinamide

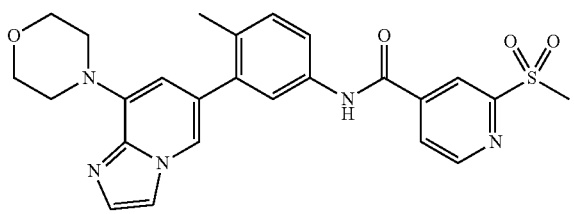 [SMILES: Cc1ccc(NC(=O)c2ccnc(S(C)(=O)=O)c2)cc1-c1cc(N2CCOCC2)c2nccn2c1]

This compound was prepared following the same procedure described for Example 848. The crude was purified by HPLC and the product isolated as the TFA salt in 37% yield. 1H NMR (400 MHz, <dmso>) δ ppm 2.27 (s, 3H) 3.24 (br. s., 4H) 3.30-3.37 (m, 4H) 3.79-3.90 (m, 4H) 7.04-7.23 (m, 1H) 7.39 (d, J=8.22 Hz, 1H) 7.72 (dd, J=8.22, 1.96 Hz, 1H) 7.83 (d, J=1.56 Hz, 1H) 8.08 (br. s., 1H) 8.17-8.29 (m, 2H) 8.51 (s, 2H) 8.99 (d, J=4.70 Hz, 1H) 10.84 (s, 1H). LCMS (m/z) (M+H)=492.2 at Rt=0.61 mins.

Example 852: N-(4-methyl-3-(8-morpholinoimidazo[1,2-a]pyridin-6-yl)phenyl)-6-trifluoromethyl)pyridazine-4-carboxamide

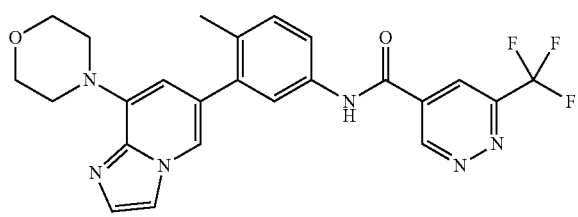 [SMILES: Cc1ccc(NC(=O)c2cnnc(C(F)(F)F)c2)cc1-c1cc(N2CCOCC2)c2nccn2c1]

This compound was prepared following the same procedure described for Example 848. The crude was purified by HPLC and the product isolated as the TFA salt in 36% yield. 1H NMR (400 MHz, <dmso>) δ ppm 2.27 (s, 6H) 3.26 (br. s., 8H) 3.78-3.90 (m, 7H) 7.08 (d, J=7.83 Hz, 1H) 7.41 (d, J=8.22 Hz, 1H) 7.70 (dd, J=8.22, 2.35 Hz, 1H) 7.81 (d, J=1.57 Hz, 1H) 8.05 (br. s., 1H) 8.23 (br. s., 1H) 8.49 (br. s., 1H) 8.66 (d, J=1.57 Hz, 1H) 9.90 (d, J=1.56 Hz, 1H) 10.92 (s, 1H). LCMS (m/z) (M+H)=483.2 at Rt=0.69 mins.

Example 853: N-(4-methyl-3-(8-morpholinoimidazo[1,2-a]pyridin-6-yl)phenyl)-4-((methylamino)methyl)-3-(trifluoromethyl)benzamide

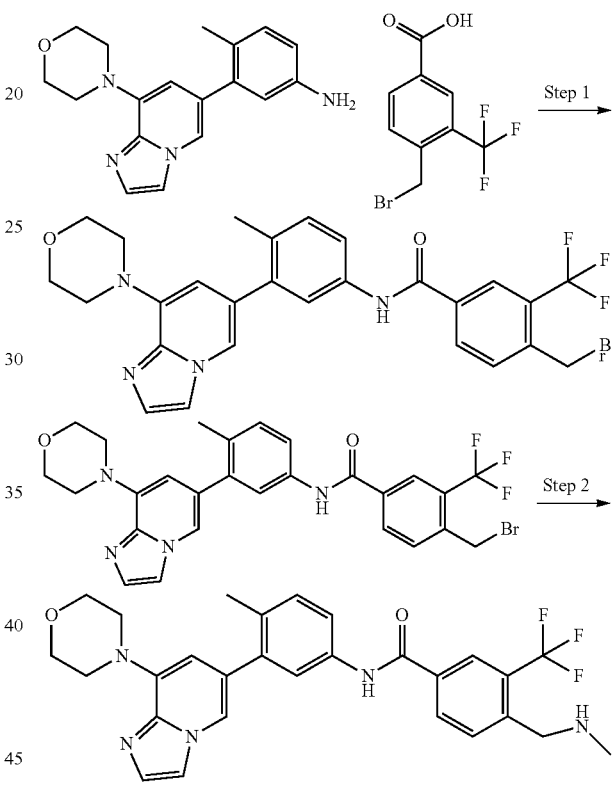

Step 1:
1-Hydroxy-7-azabenzotriazole (1.0 equiv.) was added to a solution of 4-methyl-3-(8-morpholinoimidazo[1,2-a]pyridin-6-yl)aniline (1.0 equiv.), 4-(bromomethyl)-3-(trifluoromethyl)benzoic acid (1.0 equiv) and EDC.HCl (1.0 equiv.) in DMF (0.1 M) and the reaction mix was left stirring overnight at RT. The reaction was treated with water and the precipitate was removed by filtration. The solid was dried and used as is in the next step.

Step 2:
Methylamine 2M in THF (70 equiv.) was added to a solution 4-(bromomethyl)-N-(4-methyl-3-(8-morpholinoimidazo[1,2-a]pyridin-6-yl)phenyl)-3-(trifluoromethyl)benzamide (1.0 equiv.) and the vial was sealed and heated to 70° C. overnight. The reaction mix was concentrated to dryness and the crude was purified by HPLC to give the desired N-(4-methyl-3-(8-morpholinoimidazo[1,2-a]pyridin-6-yl)phenyl)-4-((methylamino)methyl)-3-(trifluoromethyl)benzamide as the TFA salt in 53% yield. 1H NMR (400 MHz, <dmso>) δ ppm 2.26 (s, 3H) 2.71 (br. s., 3H)

3.30 (br. s., 4H) 3.79-3.87 (m, 4H) 4.38 (br. s., 2H) 7.36 (d, J=8.61 Hz, 1H) 7.72 (dd, J=8.22, 1.96 Hz, 1H) 7.79 (s, 1H) 7.88 (d, J=8.61 Hz, 1H) 7.96 (br. s., 1H) 8.17 (br. s., 1H) 8.29-8.38 (m, 2H) 8.43 (br. s., 1H) 9.08 (br. s., 2H) 10.59 (s, 1H) LCMS (m/z) (M+H)=524 at Rt=0.59 mins.

Example 854: 3-(difluoromethyl)-N-(4-methyl-3-(4-morpholino-5,5-dioxido-6,7-dihydrothieno[3,2-d]pyrimidin-2-yl)phenyl)benzamide

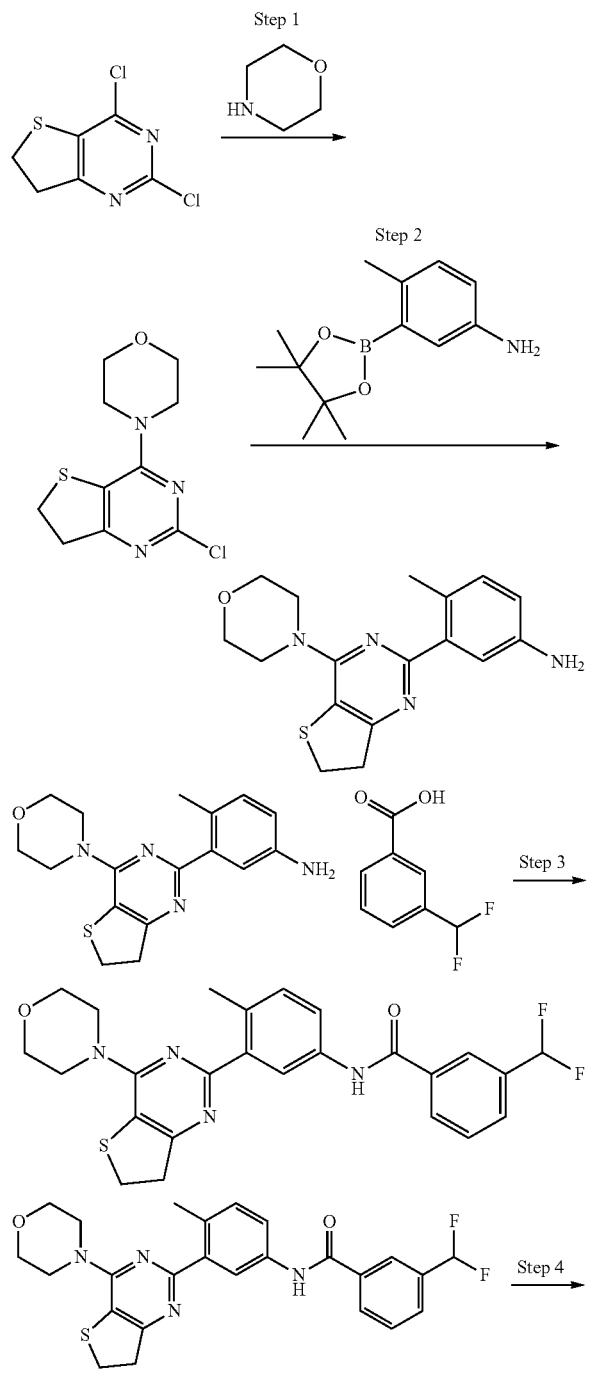

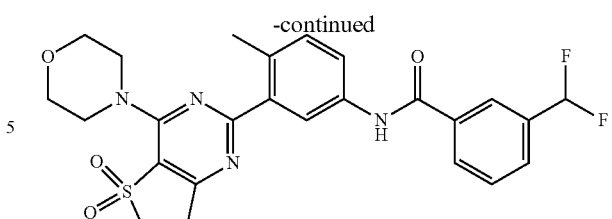

Step 1:

To a flask containing 2,4-dichloro-6,7-dihydrothieno[3,2-d]pyrimidine (1.0 equiv.) in EtOH (0.48 M) was added morpholine (10.0 equiv.) and the reaction mix was stirred at RT for 30 min. The solvent was removed under vacuum and the crude 4-(2-chloro-6,7-dihydrothieno[3,2-d]pyrimidin-4-yl)morpholine was used as is in the next step. Yield was assumed to be quantitative. LCMS (m/z) (M+H)=254/258 at Rt=0.68 mins.

Step 2:

A round bottom flask containing a solution of 4-(2-chloro-6,7-dihydrothieno[3,2-d]pyrimidin-4-yl)morpholine (1.0 equiv.) and 4-methyl-3-(4,4,5,5-tetramethyl-1,3,2-dioxaborolan-2-yl)aniline (1.0 equiv) and 2M $Na_2CO_3$ (3.0 equiv.) in DME (1.3M) was flushed with nitrogen for 5 minutes. $PdCl_2(dppf).CH_2Cl_2$ adduct (0.07 equiv.) was added to the solution and the system was flushed again for 10 more minutes. The reaction mix was refluxed at 120° C. overnight under an inert atmosphere. The reaction mix was cooled to RT, diluted with water and extracted with EtOAc. The combined organics were dried over MgSO4, filtered and concentrated. The crude was purified on a silica gel column using heptane to 100% EtOAc in heptane giving 4-methyl-3-(4-morpholino-6,7-dihydrothieno[3,2-d]pyrimidin-2-yl)aniline in 41% yield. LCMS (m/z) (M+H)=329 at Rt=0.44 mins.

Step 3:

HATU (1.1 equiv.) was added to a solution of 4-methyl-3-(4-morpholino-6,7-dihydrothieno[3,2-d]pyrimidin-2-yl)aniline (1.0 equiv.), 3-(difluoromethyl)benzoic acid (1.0 equiv.) and DIEA (2.0) in DMF (0.17 M), and the mixture was left stirring at RT overnight. The reaction flask was cooled in an ice bath and water was added dropwise to it. A precipitate formed that was removed by filtration and an additional amount of product was obtained by extracting the filtrate with EtOAc and concentrating it to dryness. The solid and extraction were purified on a silica gel column using heptane to 60% Heptane EtOAc.). LCMS (m/z) (M+H)=483 at Rt=0.81 mins.

Step 4:

mCPBA (2.2 equiv.) was added portion wise to a solution of 3-(difluoromethyl)-N-(4-methyl-3-(4-morpholino-6,7-dihydrothieno[3,2-d]pyrimidin-2-yl)phenyl)benzamide (1.0 equiv.) in DCM (0.03 M) at 0° C. and the reaction mix was left stirring overnight at RT. The reaction mix was diluted with DCM and washed three times with 0.5 M aqueous $Na_2CO_3$. It was dried over $Na_2SO_4$, filtered and concentrated to give the crude product as a white solid. Crude was purified on silica gel column using heptane to 80% EtOAc in heptane giving 3-(difluoromethyl)-N-(4-methyl-3-(4-morpholino-5,5-dioxido-6,7-dihydrothieno[3,2-d]pyrimidin-2-yl)phenyl)benzamide in 45% yield. 1H NMR (400 MHz, <dmso>) δ ppm 3.32 (t, J=7.24 Hz, 2H) 3.56-3.74 (m, 6H) 3.82-3.98 (m, 4H) 6.93-7.23 (m, 1H) 7.24 (d, J=8.22 Hz, 1H) 7.58-7.67 (m, 1H) 7.73 (d, J=7.43 Hz, 1H) 7.79 (dd, J=8.22, 1.96 Hz, 1H) 8.04-8.14 (m, 2H) 8.17 (d, J=1.96 Hz, 1H) 10.29-10.53 (m, 1H). LCMS (m/z) (M+H)=515 at Rt=0.89 mins.

Example 855: 2-(2-cyanopropan-2-yl)-N-(4-methyl-3-(4-morpholino-5,5-dioxido-6,7-dihydrothieno[3,2-d]pyrimidin-2-yl)phenyl)isonicotinamide

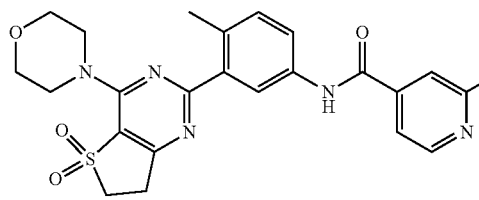

This compound was prepared following the same procedure described for Example 855. 1H NMR (400 MHz, <dmso>) δ ppm 1.60-1.91 (m, 6H) 3.36 (t, J=7.24 Hz, 2H) 3.57-3.81 (m, 6H) 3.87-4.06 (m, 4H) 7.22-7.42 (m, 1H) 7.80-7.90 (m, 2H) 8.01 (s, 1H) 8.09-8.30 (m, 1H) 8.68-8.90 (m, 1H) 10.51-10.73 (m, 1H). LCMS (m/z) (M+H)=533 at Rt=0.81 mins.

Example 856: 2-(difluoromethyl)-N-(4-methyl-3-(4-morpholino-5,5-dioxido-6,7-dihydrothieno[3,2-d]pyrimidin-2-yl)phenyl)isonicotinamide

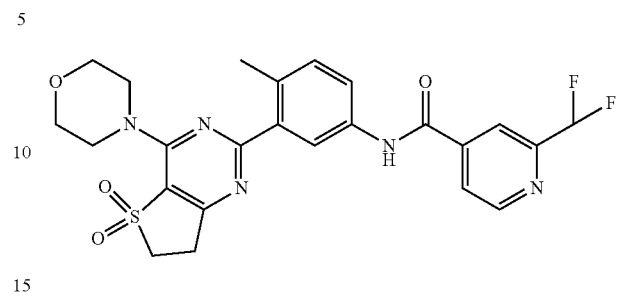

This compound was prepared following the same procedure described for Example 855. 1H NMR (400 MHz, <dmso>) δ ppm 3.60-3.73 (m, 7H) 3.91 (t, J=4.50 Hz, 4H) 6.84-7.17 (m, 1H) 7.27 (d, J=8.61 Hz, 1H) 7.80 (dd, J=8.41, 2.15 Hz, 1H) 8.01 (d, J=5.09 Hz, 1H) 8.13 (s, 1H) 8.17 (d, J=1.96 Hz, 1H) 8.84 (d, J=5.09 Hz, 1H) 10.56-10.77 (m, 1H). LCMS (m/z) (M+H)=516 at Rt=0.78 mins.

Example 857: N-(4-methyl-3-(4-morpholino-5,5-dioxido-6,7-dihydrothieno[3,2-d]pyrimidin-2-yl)phenyl)-3-(trifluoromethyl)benzamide

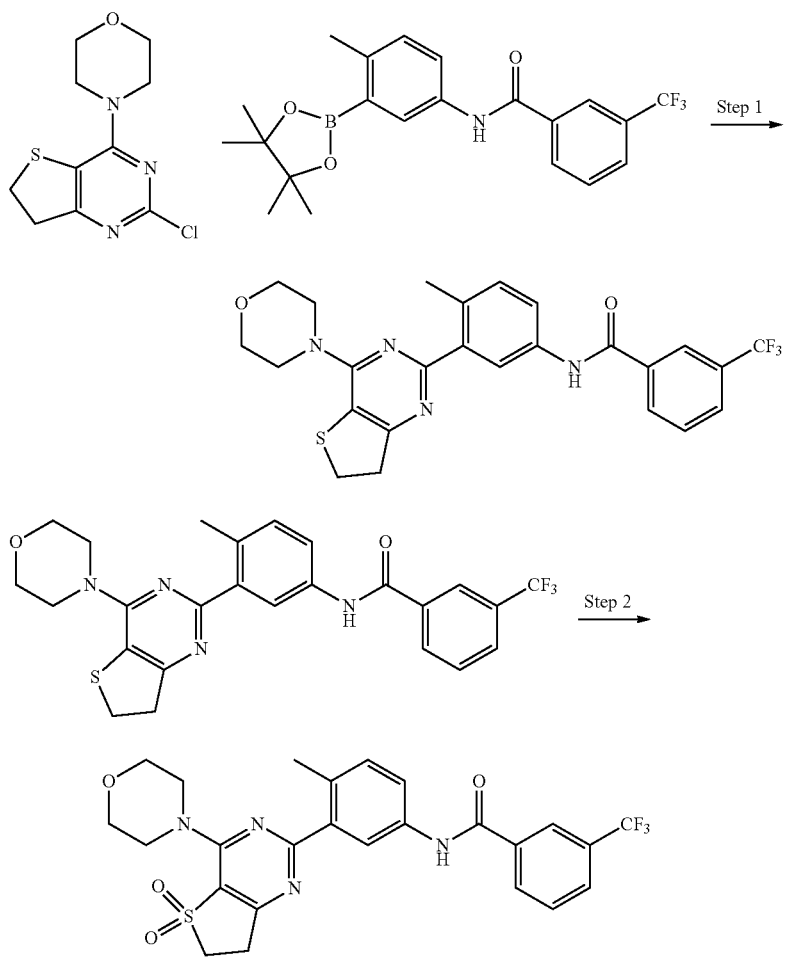

Step 1:
To a solution of 4-(2-chloro-6,7-dihydrothieno[3,2-d]pyrimidin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (0.9 equiv) in DME (0.1 M) was added 2M Na₂CO₃ (3.0 equiv.) and the system was flushed with nitrogen for 5 minutes. PdCl₂(dppf).CH₂Cl₂ adduct (0.1 equiv.) was added and the system was flushed once again. The vial was capped and place in a microwave reactor for 15 minutes at 120° C. Some starting boronic ester was present therefore, additional 0.5 quiv. of 4-(2-chloro-6,7-dihydrothieno[3,2-d]pyrimidin-4-yl)morpholine were added and the vial microwaved for 30 minutes at 100° C. The reaction mix was partitioned in EtOAc/H₂O. The organic layer was isolated, dried over Na₂SO₄, filtered and concentrated. The crude was purified on a silica gel column using heptane to 35% EtOAc in heptane giving N-(4-methyl-3-(5-morpholinoimidazo[1,2-c]pyrimidin-7-yl)phenyl)-3-(trifluoromethyl)benzamide in 39% yield. LCMS (m/z) (M+H)=501 at Rt=0.82 mins.

Step 2:
mCPBA (2.2 equiv.) was added portionwise to a solution of N-(4-methyl-3-(5-morpholinoimidazo[1,2-c]pyrimidin-7-yl)phenyl)-3-(trifluoromethyl)benzamide (1.0 equiv.) in DCM (0.02 M) at 0° C. and the reaction mix was left stirring overnight at RT. The reaction mix was diluted with DCM and washed three times with 0.5 M aqueous Na₂CO₃. It was dried over Na₂SO₄, filtered and concentrated to give the crude product as a white solid. Crude was purified on silica gel column using heptane to 50% EtOAc in heptane giving N-(4-methyl-3-(4-morpholino-5,5-dioxido-6,7-dihydrothieno[3,2-d]pyrimidin-2-yl)phenyl)-3-(trifluoromethyl)benzamide in 85% yield. 1H NMR (500 MHz, DMSO-d6) δ ppm 3.32 (s, 2H) 3.39 (t, J=7.25 Hz, 2H) 3.69-3.79 (m, 6H) 3.99 (t, J=4.57 Hz, 4H) 7.33 (d, J=8.20 Hz, 1H) 7.80 (t, J=7.72 Hz, 1H) 7.88 (dd, J=8.35, 2.05 Hz, 1H) 7.98 (d, J=7.57 Hz, 1H) 8.24 (d, J=1.89 Hz, 1H) 8.29 (d, J=7.88 Hz, 1H) 8.33 (s, 1H) 10.45-10.77 (m, 1H). LCMS (m/z) (M+H)=533 at Rt=0.90 mins.

Example 858: (R)-2-(2-cyanopropan-2-yl)-N-(4-methyl-3-(4-(3 methylmorpholino)-1H-imidazo[4,5-c]pyridin-6-yl)phenyl)isonicotinamide

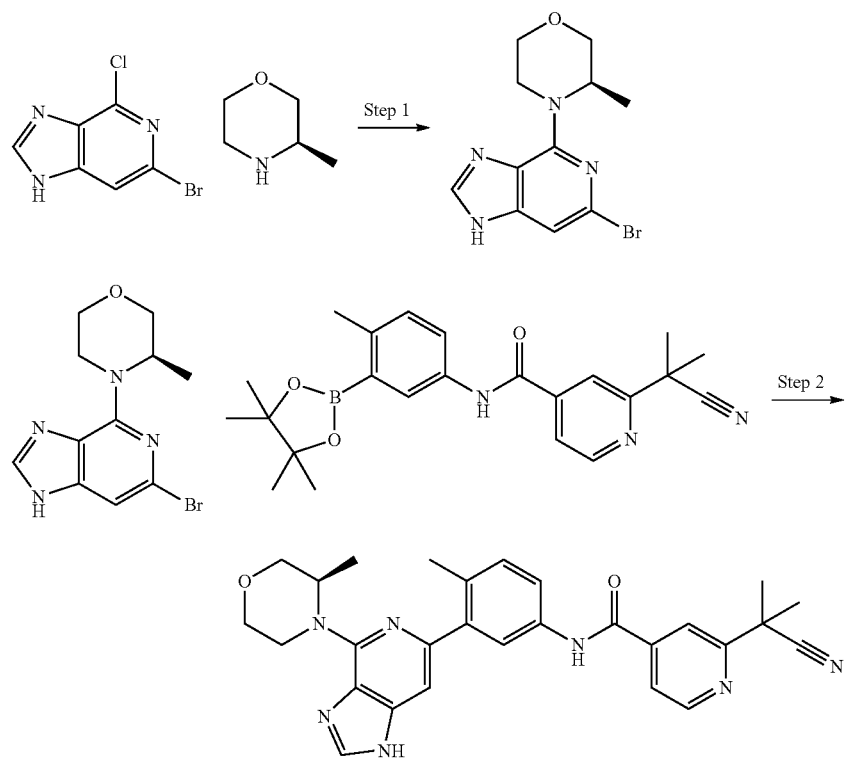

Step 2:
To a solution of (R)-4-(6-bromo-1H-imidazo[4,5-c]pyridin-4-yl)-3-methylmorpholine (1.0 equiv.) and 2-(2-cyanopropan-2-yl)-N-(4-methyl-3-(4,4,5,5-tetramethyl-1,3,2-dioxaborolan-2-yl)phenyl)isonicotinamide (1.0 equiv) in DME (0.1 M) was added 2M Na₂CO₃ (3.0 equiv.) and the system was flushed with nitrogen for 5 minutes. PdCl₂(dppf).CH₂Cl₂ adduct (0.1 equiv.) was added and the system was flushed once again. The vial was capped and place in a microwave reactor for 20 minutes at 120° C. The reaction mix was partitioned in EtOAc/H₂O. The organic layer was isolated, dried over Na₂SO₄, filtered and concentrated. The crude was purified by HPLC. (R)-2-(2-cyanopropan-2-yl)-N-(4-methyl-3-(4-(3-methylmorpholino)-1H-imidazo[4,5-c]pyridin-6-yl)phenyl)isonicotinamide was obtained in 24% yield. 1H NMR (400 MHz, <dmso>) δ ppm 1.11-1.48 (m, 3H) 1.75 (s, 6H) 2.29 (br. s., 3H) 2.65 (d, J=1.57 Hz, 1H) 3.74 (br. s., 2H) 3.96 (d, J=8.61 Hz, 1H) 5.41 (br. s., 1H) 7.32 (br. s., 1H) 7.72 (br. s., 1H) 7.79-7.89 (m, 2H) 7.95-8.04 (m, 1H) 8.80 (d, J=5.09 Hz, 1H) 10.44-10.69 (m, 1H). LCMS (m/z) (M+H)=496 at Rt=0.67 mins.

Example 859: 2-(2-cyanopropan-2-yl)-N-(4-methyl-3-(8-morpholinoimidazo[1,2-a]pyridin-6-yl)phenyl)isonicotinamide

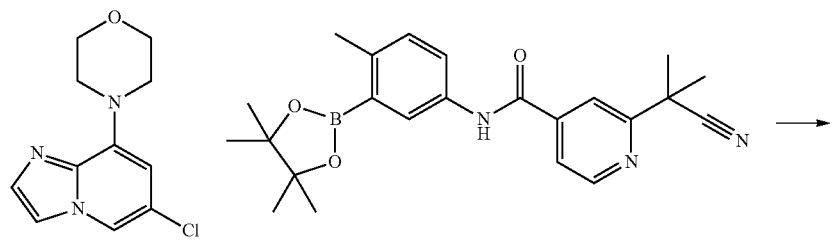

To a solution 4-(6-chloroimidazo[1,2-a]pyrazin-8-yl)morpholine (1.0 equiv.) and 2-(2-cyanopropan-2-yl)-N-(4-methyl-3-(4,4,5,5-tetramethyl-1,3,2-dioxaborolan-2-yl)phenyl)isonicotinamide (1.0 equiv) in DME (0.1 M) was added 2M Na$_2$CO$_3$ (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was extracted three times with EtOAc. The combined organic layers were dried over Na$_2$SO$_4$, filtered and concentrated. The crude was purified by HPLC giving 2-(2-cyanopropan-2-yl)-N-(4-methyl-3-(8-morpholinoimidazo[1,2-a]pyridin-6-yl)phenyl)isonicotinamide as the TFA salt in 27% yield. 1H NMR (400 MHz, <dmso>) δ ppm 1.68 (s, 6H) 2.40 (s, 3H) 2.52 (s, 1H) 2.99 (br. s., 4H) 7.20 (br. s., 1H) 7.31-7.40 (m, 2H) 7.42-7.48 (m, 1H) 7.68 (d, J=4.30 Hz, 1H) 7.86 (s, 1H) 8.07 (br. s., 1H) 8.27 (s, 1H) 8.63 (s, 1H) 8.72 (d, J=4.70 Hz, 1H) 10.36 (s, 1H). LCMS (m/z) (M+H)=481 at Rt=0.67 mins.

Example 860: 2-(2-cyanopropan-2-yl)-N-(4-methyl-3-(8-morpholinoimidazo[1,2-a]pyrazin-6-yl)phenyl)isonicotinamide

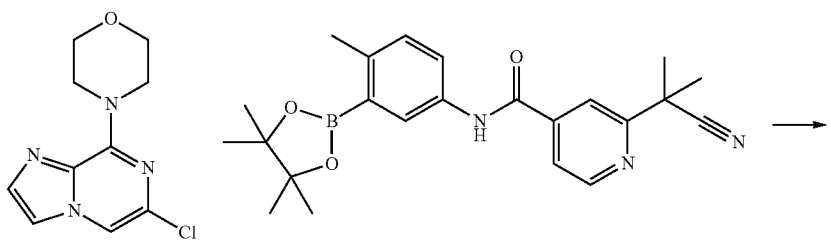

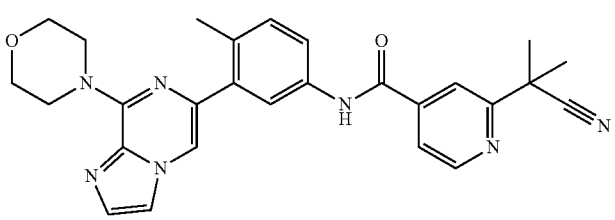

To a solution 4-(6-chloroimidazo[1,2-a]pyrazin-8-yl)morpholine (1.0 equiv.) and 2-(2-cyanopropan-2-yl)-N-(4-methyl-3-(4,4,5,5-tetramethyl-1,3,2-dioxaborolan-2-yl)phenyl)isonicotinamide (1.0 equiv) in DME (0.1 M) was added 2M Na$_2$CO$_3$ (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by HPLC giving 2-(2-cyanopropan-2-yl)-N-(4-methyl-3-(8-morpholinoimidazo[1,2-a]pyrazin-6-yl)phenyl)isonicotinamide as the TFA salt in 23% yield. 1H NMR (400 MHz, <dmso>) δ ppm 1.69-1.83 (m, 6H) 2.36 (s, 3H) 3.74 (t, J=4.50 Hz, 4H) 4.20 (br. s., 4H) 7.29 (d, J=8.61 Hz, 1H) 7.60 (s, 1H) 7.68 (dd, J=8.22, 1.96 Hz, 1H) 7.85 (d, J=2.35 Hz, 2H) 7.94-8.04 (m, 2H) 8.10 (s, 1H) 8.79 (d, J=4.70 Hz, 1H) 10.55 (s, 1H) 1H LCMS (m/z) (M+H)=482 at Rt=0.74 mins.

system was flushed with nitrogen for 5 minutes. PdCl$_2$(dppf).CH$_2$Cl$_2$ adduct (0.1 equiv.) was added and the system was flushed once again. The vial was capped and place in a microwave reactor for 15 minutes at 125° C. The reaction mix was partitioned in EtOAc/H$_2$O. The organic layer was isolated, dried over Na$_2$SO$_4$, filtered and concentrated. The crude was purified by HPLC giving 2-(2-cyanopropan-2-yl)-N-(4-methyl-3-(1-methyl-7-morpholino-1H-pyrazolo[4,3-d]pyrimidin-5-yl)phenyl)isonicotinamide as the TFA salt in 22% yield. 1H NMR (400 MHz, <dmso>) δ ppm 1.70-1.79 (m, 6H) 3.59 (br. s., 5H) 4.19 (s, 3H) 7.31 (d, J=8.22 Hz, 1H) 7.79 (dd, J=8.22, 1.96 Hz, 1H) 7.87 (d, J=4.30 Hz, 1H) 8.01 (s, 1H) 8.21 (d, J=1.96 Hz, 1H) 8.26 (s, 1H) 8.79 (d, J=5.09 Hz, 1H) 10.60 (s, 1H). LCMS (m/z) (M+H)=497 at Rt=0.71 mins.

Example 861: 2-(2-cyanopropan-2-yl)-N-(4-methyl-3-(1-methyl-7-morpholino-1H-pyrazolo[4,3-d]pyrimidin-5-yl)phenyl)isonicotinamide Example 862: 2-(2-cyanopropan-2-yl)-N-(4-methyl-3-(4-morpholinothieno[3,2-d]pyrimidin-2-yl)phenyl)isonicotinamide

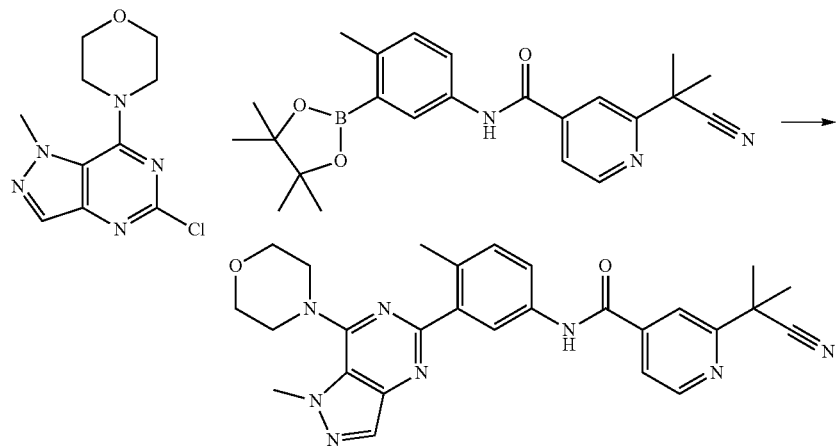

To a solution 4-(5-chloro-1-methyl-1H-pyrazolo[4,3-d]pyrimidin-7-yl)morpholine (1.0 equiv.) and 2-(2-cyanopropan-2-yl)-N-(4-methyl-3-(4,4,5,5-tetramethyl-1,3,2-dioxaborolan-2-yl)phenyl)isonicotinamide (1.0 equiv) in DME (0.1 M) was added 2M sodium carbonate (3.0 equiv.) and the

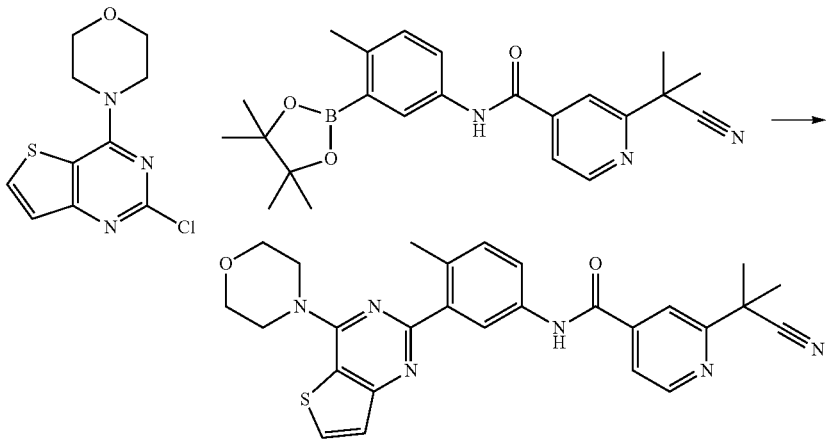

To a solution 4-(2-chlorothieno[3,2-d]pyrimidin-4-yl)morpholine (1.0 equiv.) and 2-(2-cyanopropan-2-yl)-N-(4-methyl-3-(4,4,5,5-tetramethyl-1,3,2-dioxaborolan-2-yl)phenyl)isonicotinamide (1.0 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by HPLC giving 2-(2-cyanopropan-2-yl)-N-(4-methyl-3-(4-morpholinothieno[3,2-d]pyrimidin-2-yl)phenyl)isonicotinamide as the TFA salt in 19% yield. 1H NMR (400 MHz, <dmso>) δ ppm 1.75 (s, 6H) 3.76-3.85 (m, 5H) 3.96-4.07 (m, 4H) 7.34 (d, J=8.61 Hz, 1H) 7.51 (d, J=5.48 Hz, 1H) 7.78-7.89 (m, 2H) 8.01 (s, 1H) 8.14 (d, J=1.96 Hz, 1H) 8.36 (d, J=5.09 Hz, 1H) 8.80 (d, J=5.09 Hz, 1H) 10.64 (s, 1H). LCMS (m/z) (M+H)=499 at Rt=0.72 mins.

Example 863: 2-(2-cyanopropan-2-yl)-N-(4-methyl-3-(4-morpholino-5H-pyrrolo[3,2-d]pyrimidin-2-yl)phenyl)isonicotinamide (4-methyl-3-(4,4,5,5-tetramethyl-1,3,2-dioxaborolan-2-yl)phenyl)isonicotinamide (1.0 equiv) in DME (0.1 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 125° C. The reaction mix was partitioned in EtOAc/H$_2$O. The organic layer was isolated, dried over Na$_2$SO$_4$, filtered and concentrated. The crude was purified by HPLC giving 2-(2-cyanopropan-2-yl)-N-(4-methyl-3-(4-morpholino-5H-pyrrolo[3,2-d]pyrimidin-2-yl)phenyl)isonicotinamide as the TFA salt in 45% yield. 1H NMR (400 MHz, <dmso>) δ ppm 1.75 (s, 6H) 2.34-2.43 (m, 3H) 3.81 (d, J=4.30 Hz, 4H) 4.04 (br. s., 4H) 6.61 (br. s., 1H) 7.44 (d, J=8.22 Hz, 1H) 7.78-7.88 (m, 2H) 7.89-7.97 (m, 1H) 8.00 (s, 1H) 8.08 (d, J=1.57 Hz, 1H) 8.81 (d, J=5.09 Hz, 1H) 10.74 (s, 1H). LCMS (m/z) (M+H)=482 at Rt=0.70 mins.

Example 864: tert-butyl 2-(5-(2-(2-cyanopropan-2-yl)isonicotinamido)-2-methylphenyl)-4-morpholino-7,8-dihydropyrido[4,3-d]pyrimidine-6(5H)-carboxylate

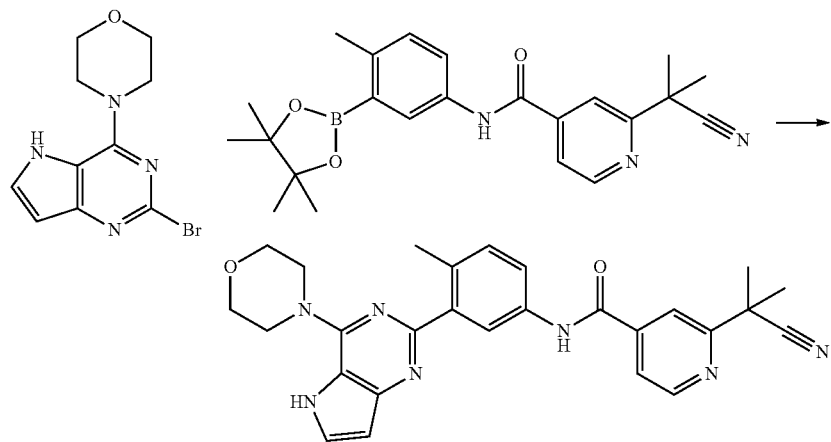

To a solution 4-(2-bromo-5H-pyrrolo[3,2-d]pyrimidin-4-yl)morpholine (1.0 equiv.) and 2-(2-cyanopropan-2-yl)-N-

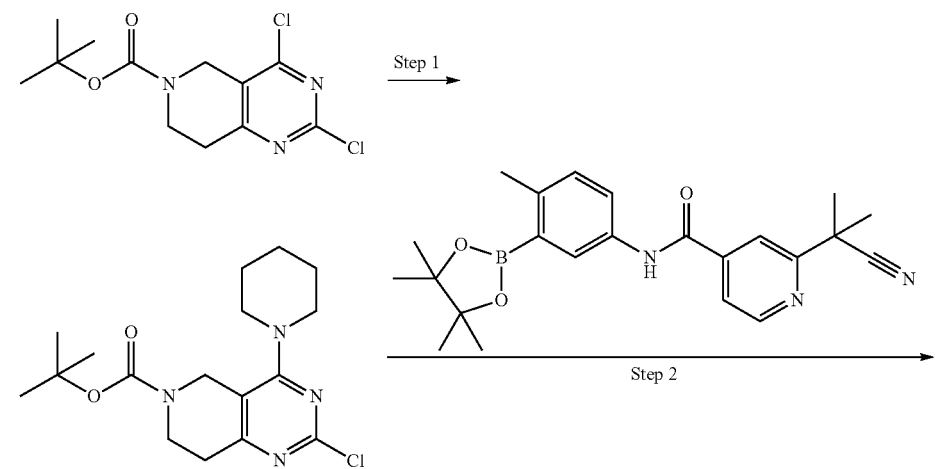

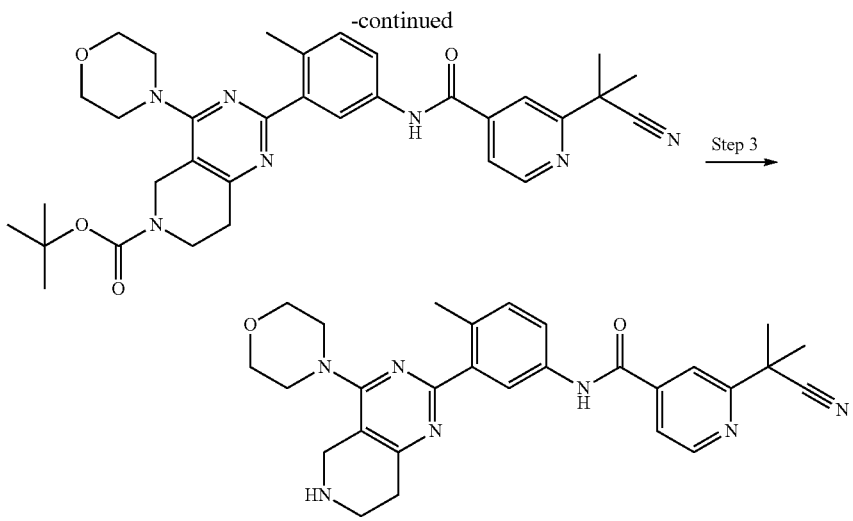

Step 2.

To a solution of tert-butyl 2-chloro-4-morpholino-7,8-dihydropyrido[4,3-d]pyrimidine-6(5H)-carboxylate (1.0 equiv.) and N-(4-methyl-3-(4,4,5,5-tetramethyl-1,3,2-dioxaborolan-2-yl)phenyl)-3-(trifluoromethyl)benzamide (1.0 equiv.) in DME (0.14 M) was added 2M $Na_2CO_3$ solution (3.0 equiv.) and the system was flushed with nitrogen. $PdCl_2(dppf).CH_2Cl_2$ adduct (0.1 equiv.) was added to the reaction mix and the system was flushed once again with nitrogen. The reaction vial was capped and microwaved for 20 minutes at 120° C. The crude was partitioned in $H_2O$/EtOAc. The organic layer was isolated, dried over $Na_2SO_4$, filtered and concentrated. Crude was purified on a silica gel column using heptane to 50% EtOAc in heptane. Isolated tert-butyl 2-(5-(2-(2-cyanopropan-2-yl)isonicotinamido)-2-methylphenyl)-4-morpholino-7,8-dihydropyrido[4,3-d]pyrimidine-6(5H)-carboxylate in 35% yield. LCMS (m/z) [M+H]+=598 at Rt=1.03 min.

Step 3.

To a solution of tert-butyl 2-(5-(2-(2-cyanopropan-2-yl)isonicotinamido)-2-methylphenyl)-4-morpholino-7,8-dihydropyrido[4,3-d]pyrimidine-6(5H)-carboxylate (1.0 equiv.) in DCM (0.04 M) was added TFA (15 equiv.) and the reaction mix was stirred at RT for 1 h. The solvent was removed under vacuum and the residue was taken in DMSO and purified on the prep. Isolated 2-(2-cyanopropan-2-yl)-N-(4-methyl-3-(4-morpholino-5,6,7,8-tetrahydropyrido[4,3-d]pyrimidin-2-yl)phenyl)isonicotinamide as the TFA salt in 75% yield. 1H NMR (400 MHz, <dmso>) δ ppm 1.75 (s, 6H) 2.37 (s, 3H) 3.03 (t, J=6.26 Hz, 2H) 3.40-3.53 (m, 7H) 3.71 (d, J=4.30 Hz, 5H) 4.24 (br. s., 3H) 7.39 (dd, J=8.22, 1.56 Hz, 1H) 7.81-7.91 (m, 1H) 7.99 (s, 1H) 8.27 (s, 1H) 8.48 (d, J=8.22 Hz, 1H) 8.88 (d, J=5.09 Hz, 1H) 9.08 (br. s., 2H) 13.31 (s, 1H). LCMS (m/z) (M+H)=498 at Rt=0.57 mins.

Example 865: 2-(2-cyanopropan-2-yl)-N-(4-methyl-3-(4-morpholino-5,6,7,8-tetrahydropyrido[3,4-d]pyrimidin-2-yl)phenyl)isonicotinamide

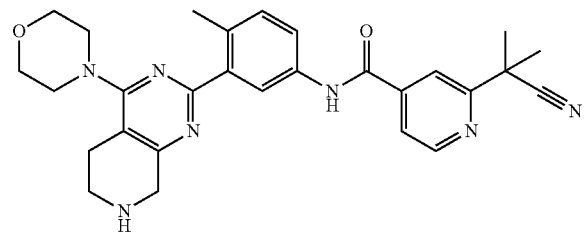 [SMILES: Cc1ccc(NC(=O)c2ccnc(C(C)(C)C#N)c2)cc1-c1nc2c(c(N3CCOCC3)n1)CCNC2]

This compound was prepared following the same synthetic procedure reported for Example 864. 1H NMR (400 MHz, <dmso>) δ ppm 1.63-1.85 (m, 6H) 2.37 (s, 3H) 2.79-2.91 (m, 2H) 3.50 (d, J=4.30 Hz, 5H) 3.70 (d, J=4.30 Hz, 4H) 4.24 (br. s., 2H) 5.74 (s, 1H) 7.38 (d, J=8.61 Hz, 1H) 7.89 (d, J=4.30 Hz, 1H) 7.98 (s, 1H) 8.27 (s, 1H) 8.47 (d, J=8.22 Hz, 1H) 8.86 (d, J=5.09 Hz, 1H) 9.16 (br. s., 2H) 13.07 (s, 1H). LCMS (m/z) (M+H)=498 at Rt=0.77 mins.

Example 866: 2-(2-cyanopropan-2-yl)-N-(4-methyl-3-(4-morpholino-6,7-dihydro-5H-pyrrolo[3,4-d]pyrimidin-2-yl)phenyl)isonicotinamide

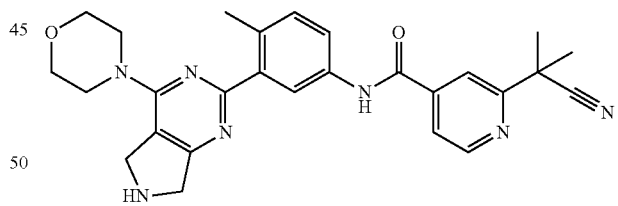

This compound was prepared following a similar synthetic procedure as reported for Example 864. H NMR (400 MHz, <dmso>) δ ppm 1.63-1.76 (m, 6H) 2.47 (s, 1H) 4.02 (br. s., 1H) 4.34 (br. s., 2H) 4.70 (br. s., 2H) 7.25 (d, J=8.22 Hz, 1H) 7.70 (dd, J=8.22, 1.96 Hz, 1H) 7.81 (d, J=4.30 Hz, 1H) 7.88-8.01 (m, 1H) 8.13 (d, J=1.96 Hz, 1H) 8.74 (d, J=5.09 Hz, 1H) 9.43-9.66 (m, 2H) 10.55 (s, 1H). LCMS (m/z) (M+H)=484 at Rt=0.64 mins.

Example 867: N-(6-methyl-5-(8-morpholinoimidazo[1,2-b]pyridazin-6-yl)pyridin-3-yl)-3-(trifluoromethyl)benzamide

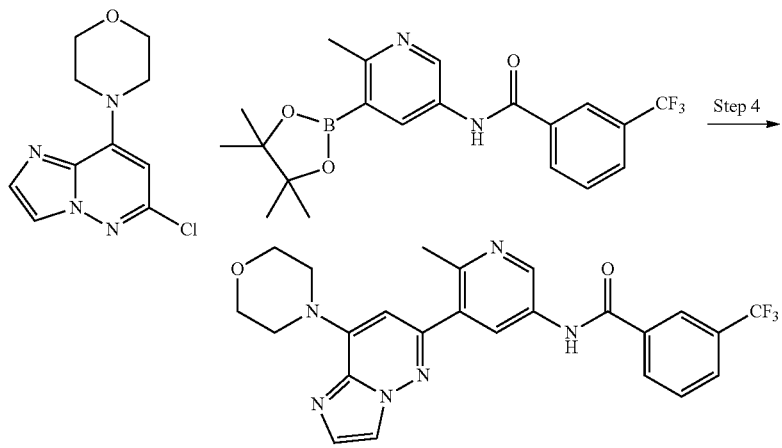

Step 4:

To a solution of 4-(6-chloroimidazo[1,2-b]pyridazin-8-yl)morpholine (1.0 equiv.) and N-(6-methyl-5-(4,4,5,5-tetramethyl-1,3,2-dioxaborolan-2-yl)pyridin-3-yl)-3-(trifluoromethyl)benzamide (0.9 equiv) in DME (0.1 M) was added 2M Na$_2$CO$_3$ (3.0 equiv.) and the system was flushed with nitrogen for 5 minutes. PdCl$_2$(dppf).CH$_2$Cl$_2$ adduct (0.1 equiv.) was added and the system was flushed once again. The reaction mix was partitioned in EtOAc/H$_2$O. The organic layer was isolated, dried over Na$_2$SO$_4$, filtered and concentrated. The crude was purified by HPLC giving N-(6-methyl-5-(8-morpholinoimidazo[1,2-b]pyridazin-6-yl)pyridin-3-yl)-3-(trifluoromethyl)benzamide as the TFA salt in 6% yield. 1H NMR (400 MHz, <dmso>) δ ppm 2.13-2.66 (m, 230H) 3.68-3.76 (m, 4H) 3.99 (d, J=4.70 Hz, 4H) 5.69 (s, 4H) 6.40 (s, 1H) 7.56 (s, 1H) 7.75 (t, J=7.83 Hz, 1H) 7.94 (d, J=7.83 Hz, 1H) 8.07 (s, 1H) 8.20 (d, J=2.35 Hz, 1H) 8.23 (d, J=7.83 Hz, 1H) 8.28 (s, 1H) 8.90 (d, J=2.35 Hz, 1 H) 10.68 (s, 1H). LCMS (m/z) (M+H)=483 at Rt=0.69 mins.

Example 868: N-(6-methyl-5-(8-morpholinoimidazo[1,2-b]pyridazin-6-yl)pyridin-3-yl)-4-(trifluoromethyl)picolinamide

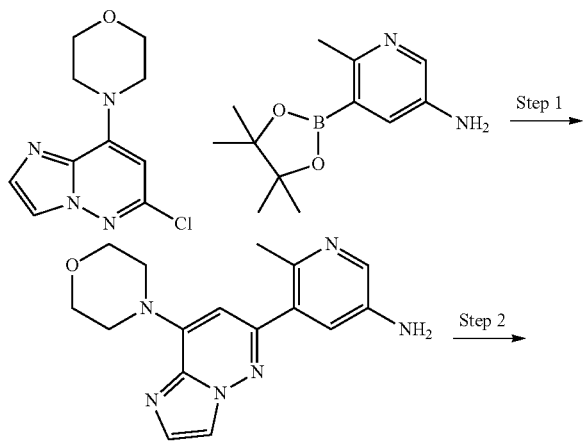

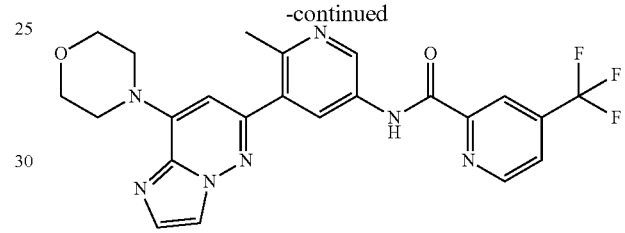

Step 1:

A round bottom flask containing a solution of 4-(6-chloroimidazo[1,2-b]pyridazin-8-yl)morpholine (1.0 equiv.) and 6-methyl-5-(4,4,5,5-tetramethyl-1,3,2-dioxaborolan-2-yl)pyridin-3-amine (1.0 equiv) and 2M Na$_2$CO$_3$ (3.0 equiv.) in DME (0.1 M) was flushed with nitrogen for 5 minutes. PdCl$_2$(dppf).CH$_2$Cl$_2$ adduct (0.07 equiv.) was added to the solution and the system was flushed again for 10 more minutes. The reaction mix was heated at 120° C. for 4 hr. under an inert atmosphere. The reaction mix was cooled to RT, diluted with water and extracted three times with EtOAc. The combined organics were dried over MgSO$_4$, filtered and concentrated. The crude was purified on a silica gel column using DCM to 5% MeOH in DCM giving 6-methyl-5-(8-morpholinoimidazo[1,2-b]pyridazin-6-yl)pyridin-3-amine in 35% yield. LCMS (m/z) (M+H)=311 at Rt=0.38 mins.

Step 2:

To a round bottom flask containing a solution of 6-methyl-5-(8-morpholinoimidazo[1,2-b]pyridazin-6-yl)pyridin-3-amine (1.0 equiv.) and 4-(trifluoromethyl)picolinic acid (1.0 equiv) in DMF (0.1 M) was added HATU (1.0 equiv.) and DIEA (3.0 equiv.) and the reaction mix was left stirring overnight at RT. The reaction mix was diluted with water and was extracted three times with EtOAc/H$_2$O. The combined organics were dried over MgSO4, filtered and concentrated. The crude was purified by HPLC giving N-(6-methyl-5-(8-morpholinoimidazo[1,2-b]pyridazin-6-yl)pyridin-3-yl)-4-(trifluoromethyl)picolinamide as the TFA salt in 21% yield. 1H NMR (400 MHz, <dmso>) δ ppm 2.54 (s, 4H) 3.74-3.81 (m, 5H) 4.04 (d, J=4.30 Hz, 4H) 6.46 (s, 1H) 7.61 (d, J=0.78 Hz, 1H) 8.08-8.16 (m, 2H) 8.36 (s, 1H) 8.45 (d, J=1.96 Hz, 1H) 8.98-9.15 (m, 2H) 11.20 (s, 1H). LCMS (m/z) (M+H)=484 at Rt=0.71 mins.

Example 869: 2-isopropyl-N-(6-methyl-5-(8-morpholinoimidazo[1,2-b]pyridazin-6-yl)pyridin-3-yl)isonicotinamide

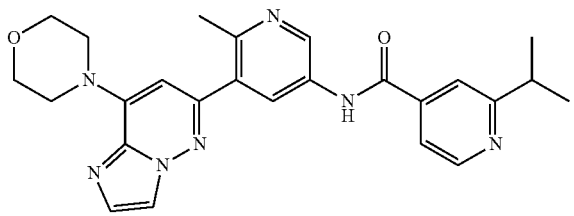 [SMILES: Cc1ncc(NC(=O)c2ccnc(C(C)C)c2)cc1-c1cc(N2CCOCC2)c2nccn2n1]

This compound was prepared following the same procedures described for Example 868. LCMS (m/z) (M+H)= 458.1 at Rt=0.52 mins.

Example 870: 2-(2-hydroxypropan-2-yl)-N-(6-methyl-5-(8-morpholinoimidazo[1,2-b]pyridazin-6-yl)pyridin-3-yl)isonicotinamide

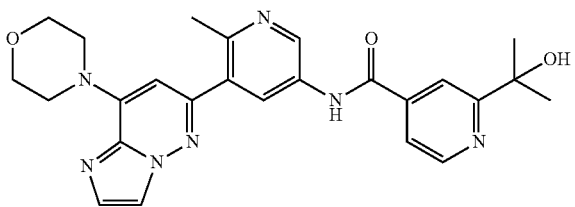

This compound was prepared following the same procedures described for Example 868. 1H NMR (400 MHz, <dmso>) δ ppm 1.43-1.52 (m, 7H) 2.52-2.57 (m, 4H) 3.74-3.80 (m, 6H) 4.04 (d, J=4.30 Hz, 4H) 6.47 (s, 1H) 7.62 (s, 1H) 7.74 (d, J=5.09 Hz, 1H) 8.13 (s, 1H) 8.18 (s, 1H) 8.30 (s, 1H) 8.70 (d, J=5.09 Hz, 1H) 8.98 (d, J=1.96 Hz, 1H) 10.87 (s, 1H). LCMS (m/z) (M+H)=474.2 at Rt=0.49 mins.

Example 871: 2-(1,1-difluoroethyl)-N-(6-methyl-5-(8-morpholinoimidazo[1,2-b]pyridazin-6-yl)pyridin-3-yl)isonicotinamide

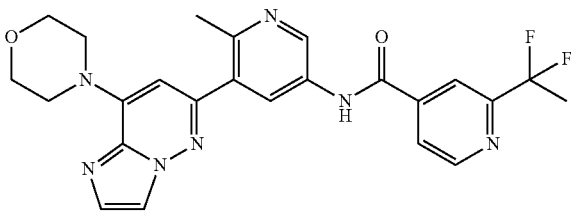 [SMILES: Cc1ncc(NC(=O)c2ccnc(C(C)(F)F)c2)cc1-c1cc(N2CCOCC2)c2nccn2n1]

This compound was prepared following the same procedures described for Example 868. The final compound was purified on silica gel prep plate obtaining 2-(1,1-difluoroethyl)-N-(6-methyl-5-(8-morpholinoimidazo[1,2-b]pyridazin-6-yl)pyridin-3-yl)isonicotinamide as the free base. 1H NMR (400 MHz, <dmso>) δ ppm 1.90-2.08 (m, 3H) 3.63-3.79 (m, 4H) 3.99 (d, J=4.30 Hz, 4H) 6.40 (s, 1H) 7.56 (s, 1H) 7.99 (d, J=5.09 Hz, 1H) 8.07 (s, 1H) 8.16 (s, 1H) 8.20 (d, J=1.96 Hz, 1H) 8.72-8.98 (m, 2H) 10.74-10.94 (m, 1H). LCMS (m/z) (M+H)=480.1 at Rt=0.64 mins.

Example 872: 3-(difluoromethyl)-N-(6-methyl-5-(8-morpholinoimidazo[1,2-b]pyridazin-6-yl)pyridin-3-yl)benzamide

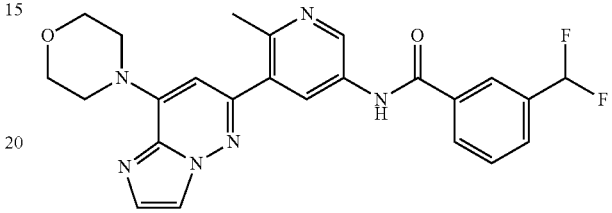

This compound was prepared following the same procedures described for Example 868. 1H NMR (400 MHz, <dmso>) δ ppm 3.72-3.82 (m, 4H) 4.04 (d, J=4.30 Hz, 4H) 6.46 (s, 1H) 6.97-7.32 (m, 1H) 7.61 (s, 1H) 7.67-7.74 (m, 1H) 7.81 (d, J=7.83 Hz, 1H) 8.09-8.21 (m, 3H) 8.28 (d, J=1.96 Hz, 1H) 8.97 (d, J=2.35 Hz, 1H) 10.70 (s, 1H). LCMS (m/z) (M+H)=465.1 at Rt=0.67 mins.

Example 873: 4-(1,2-dihydroxyethyl)-N-(6-methyl-5-(8-morpholinoimidazo[1,2-b]pyridazin-6-yl)pyridin-3-yl)-3-(trifluoromethyl)benzamide

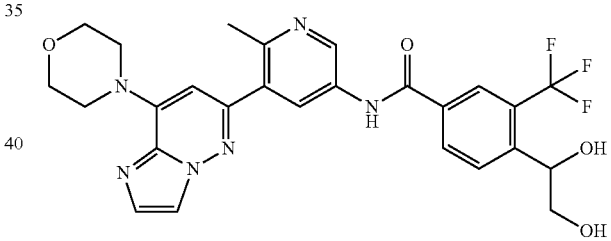

This compound was prepared following the same procedures described for Example 868. LCMS (m/z) (M+H)= 543.1 at Rt=0.57 mins.

Example 874: 3-(difluoromethyl)-N-(4-methyl-3-(8-morpholinoimidazo[1,2-b]pyridazin-6-yl)phenyl)benzamide

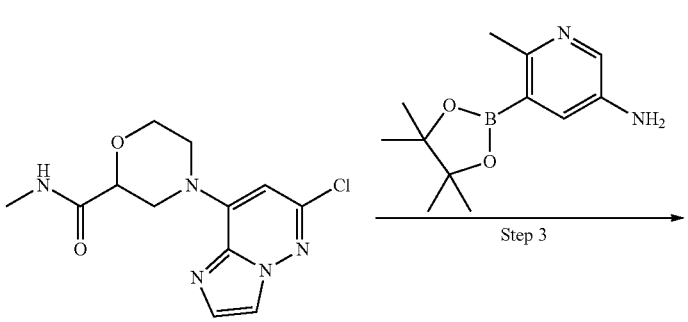

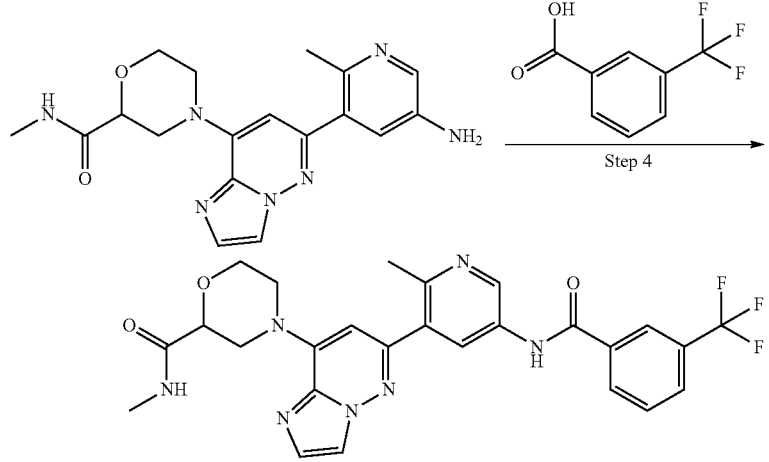

Step 1:
A mixture of 8-bromo-6-chloroimidazo[1,2-b]pyridazine (1.0 equiv.), R,S-2-carboxymorpholine hydrochloride (1.0 equiv.) and DIEA (3.0 equiv.) in DMF (0.57 M) was stirred at RT overnight. LCMS showed conversion to the desired product. The reaction mix was concentrated to dryness to give 4-(6-chloroimidazo[1,2-b]pyridazin-8-yl)morpholine-2-carboxylic acid as a brown syrup which was used as is in the next step. LCMS (m/z) (M+H)=282 at Rt=0.53 mins.

Step 2:
1-hydroxy-7-azabenzotriazole (1.0 equiv.) was added to a solution of 4-(6-chloroimidazo[1,2-b]pyridazin-8-yl)morpholine-2-carboxylic acid (1.0 equiv.), EDC.HCl (1.0 equiv.) methyl amine (2M THF, 1.2 equiv.) and DIEA (30. Equiv.) in DMF (0.14 M), and the mixture was left stirring at RT during the weekend. The reaction mix was treated with water and extracted three times with EtOAc. The combined organics were dried over Na$_2$SO$_4$, filtered and concentrated and the crude was purified on the HPLC. The desired 4-(6-chloroimidazo[1,2-b]pyridazin-8-yl)-N-methylmorpholine-2-carboxamide was isolated as the TFA salt in 60% yield. LCMS (m/z) (M+H)=296 at Rt=0.56 mins.

Step 3:
To a solution of 4-(6-chloroimidazo[1,2-b]pyridazin-8-yl)-N-methylmorpholine-2-carboxamide (1.0 equiv.) and 6-methyl-5-(4,4,5,5-tetramethyl-1,3,2-dioxaborolan-2-yl)pyridin-3-amine (1.0 equiv) in DME (0.04 M) was added 2M Na$_2$CO$_3$ (5.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was concentrated to dryness and the crude was purified by HPLC giving 4-(6-(5-amino-2-methylpyridin-3-yl)imidazo[1,2-b]pyridazin-8-yl)-N-methylmorpholine-2-carboxamide as the TFA salt in 32% yield. LCMS (m/z) (M+H)=368 at Rt=0.48 mins.

Step 4:
1-Hydroxy-7-azabenzotriazole was added to a solution of 4-(6-(5-amino-2-methylpyridin-3-yl)imidazo[1,2-b]pyridazin-8-yl)-N-methylmorpholine-2-carboxamide (1.0 equiv.) and 3-(trifluoromethyl)benzoic acid (1.1 equiv) and EDC.HCl (1.0 equiv.) in DMF (0.03 M) and the reaction mix was left stirring overnight at RT. The reaction was not complete, additional 0.3 equiv. of EDC.HCl and HOAt were added and the reaction was left stirring for additional 24 hr. The reaction mix was concentrated to dryness and the crude was purified by HPLC. N-methyl-4-(6-(2-methyl-5-(3-(trifluoromethyl)benzamido)pyridin-3-yl)imidazo[1,2-b]pyridazin-8-yl)morpholine-2-carboxamide was obtained as the TFA salt in 39% yield. 1H NMR (400 MHz, <dmso>) δ ppm 2.61 (d, J=4.70 Hz, 3H) 3.15 (dd, J=12.91, 10.56 Hz, 1H) 3.71-3.84 (m, 1H) 4.04 (d, J=11.35 Hz, 1H) 4.13 (dd, J=10.37, 2.54 Hz, 1H) 4.71 (d, J=12.13 Hz, 1H) 5.19 (br. s., 1H) 6.49 (s, 1H) 7.64 (s, 1H) 7.80 (t, J=7.83 Hz, 1H) 7.89 (d, J=4.70 Hz, 1H) 7.99 (d, J=7.83 Hz, 1H) 8.14 (s, 1H) 8.24-8.37 (m, 3H) 8.98 (d, J=1.96 Hz, 1H) 10.78 (s, 1H). LCMS (m/z) (M+H)=540 at Rt=0.72 mins.

Example 875: N-(6-methyl-5-(8-morpholinoimidazo[1,2-a]pyridin-6-yl)pyridin-3-yl)-4-((methylamino)methyl)-3-(trifluoromethyl)benzamide

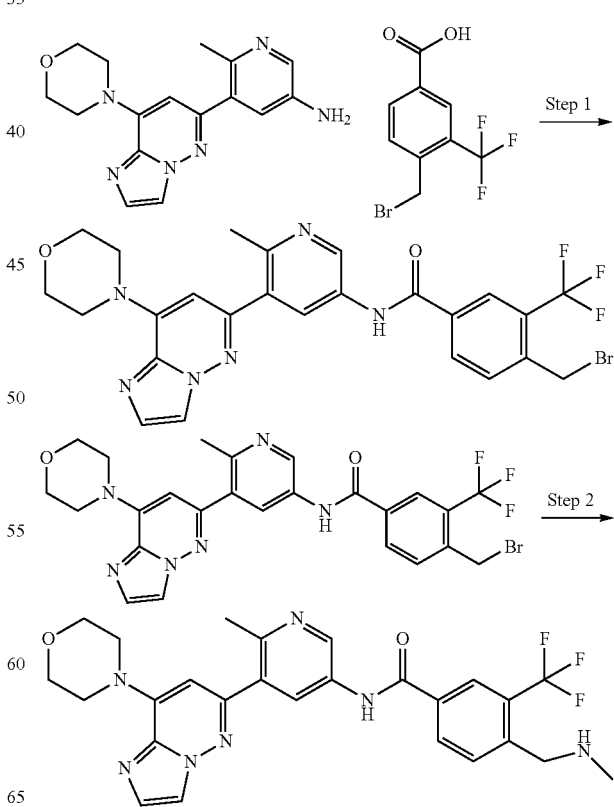

Step 1:

1-Hydroxy-7-azabenzotriazole (1.0 equiv.) was added to a solution of 6-methyl-5-(8-morpholinoimidazo[1,2-b]pyridazin-6-yl)pyridin-3-amine (1.0 equiv.), 4-(bromomethyl)-3-(trifluoromethyl)benzoic acid (1.0 equiv) and EDC.HCl (1.0 equiv.) in DMF (0.11 M) and the reaction mix was left stirring at RT for 2 hr. The reaction was treated with water and the precipitate was removed by filtration. The crude was purified on silica gel column using DCM to 10% MeOH in DCM. 4-(Bromomethyl)-N-(6-methyl-5-(8-morpholinoimidazo[1,2-a]pyridin-6-yl)pyridin-3-yl)-3-(trifluoromethyl)benzamide was isolated in 59% yield. LCMS (m/z) (M+H)=531 at Rt=0.78 mins.

Step 2:

Methylamine 2M in THF (60 equiv.) was added to a solution 4-(Bromomethyl)-N-(6-methyl-5-(8-morpholinoimidazo[1,2-a]pyridin-6-yl)pyridin-3-yl)-3-(trifluoromethyl)benzamide (1.0 equiv.) and the vial was sealed and heated to 70° C. overnight. The reaction mix was concentrated to dryness and the crude was purified by HPLC to give the desired N-(6-methyl-5-(8-morpholinoimidazo[1,2-b]pyridazin-6-yl)pyridin-3-yl)-4-((methylamino)methyl)-3-(trifluoromethyl)benzamide as the TFA salt in 63% yield. 1H NMR (400 MHz, <dmso>) δ ppm 2.52-2.57 (m, 4H) 2.71 (t, J=4.70 Hz, 3H) 3.72-3.80 (m, 5H) 4.39 (br. s., 2H) 6.46 (s, 1H) 7.62 (d, J=0.78 Hz, 1H) 7.90 (d, J=8.22 Hz, 1H) 8.12 (d, J=1.17 Hz, 1H) 8.27 (d, J=2.35 Hz, 1H) 8.35-8.43 (m, 2H) 8.97 (d, J=2.35 Hz, 1H) 9.07 (br. s., 2H) 10.83 (s, 1H). LCMS (m/z) (M+H)=526 at Rt=0.52 mins.

Example 876: N-(6-methyl-5-(8-morpholinoimidazo[1,2-a]pyridin-6-yl)pyridin-3-yl)-4-(trifluoromethyl)picolinamide in DME (0.1 M) was flushed with nitrogen for 5 minutes. PdCl₂(dppf).CH₂Cl₂ adduct (0.07 equiv.) was added to the solution and the system was flushed again for 10 more minutes. The reaction mix was heated at 120° C. for 4 hr. under an inert atmosphere. The reaction mix was cooled to RT, diluted with water and extracted three times with EtOAc. The combined organics were dried over MgSO₄, filtered and concentrated. The crude was purified on a silica gel column using DCM to 5% MeOH in DCM giving 6-methyl-5-(8-morpholinoimidazo[1,2-a]pyridin-6-yl)pyridin-3-amine in 27% yield. LCMS (m/z) (M+H)=310 at Rt=0.29 mins.

Step 2:

To a round bottom flask containing a solution of 6-methyl-5-(8-morpholinoimidazo[1,2-a]pyridin-6-yl)pyridin-3-amine (1.0 equiv.) and 4-(trifluoromethyl)picolinic acid (1.0 equiv) in DMF (0.07 M) was added HATU (1.1 equiv.) and DIEA (2.0 equiv.) and the reaction mix was left stirring overnight at RT. The reaction mix was diluted with water and was extracted three times with EtOAc/H₂O. The combined organics were dried over MgSO4, filtered and concentrated. The crude was purified by HPLC giving N-(6-methyl-5-(8-morpholinoimidazo[1,2-a]pyridin-6-yl)pyridin-3-yl)-4-(trifluoromethyl)picolinamide as the TFA salt in 38% yield. 1H NMR (400 MHz, <dmso>) δ ppm 3.76-3.89 (m, 21H) 7.97 (br. s., 1H) 8.12 (d, J=4.30 Hz, 1H) 8.19 (br. s., 1H) 8.31-8.40 (m, 3H) 8.53 (br. s., 1H) 8.95-9.14 (m, 2H) 11.19 (s, 1H). LCMS (m/z) (M+H)=483 at Rt=0.6 mins.

Example 877: 4-cyano-N-(6-methyl-5-(8-morpholinoimidazo[1,2-a]pyridin-6-yl)pyridin-3-yl)-3-(trifluoromethyl)benzamide

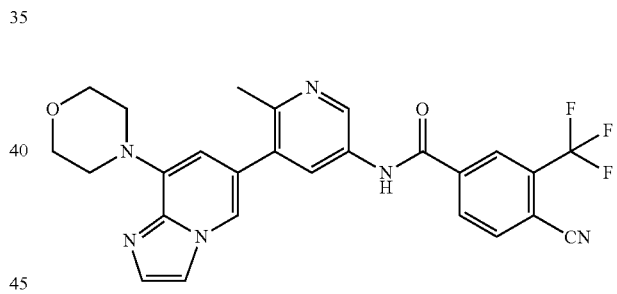

This compound was prepared following the same procedures described for Example 876. LCMS (m/z) (M+H)= 507.1 at Rt=0.59 mins.

Example 878: 2-(2-hydroxypropan-2-yl)-N-(6-methyl-5-(8-morpholinoimidazo[1,2-a]pyridin-6-yl)pyridin-3-yl)isonicotinamide

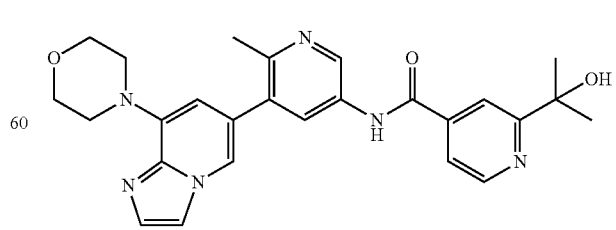

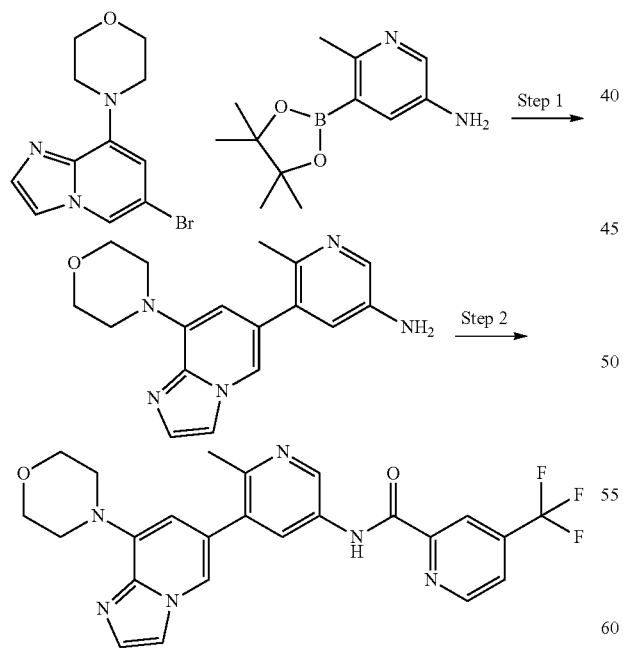

Step 1:

A round bottom flask containing a solution of 4-(6-bromoimidazo[1,2-a]pyridin-8-yl)morpholine (1.0 equiv.) and 6-methyl-5-(4,4,5,5-tetramethyl-1,3,2-dioxaborolan-2-yl)pyridin-3-amine (1.0 equiv) and 2M Na₂CO₃ (3.0 equiv.)

This compound was prepared following the same procedures described for Example 876. 1H NMR (400 MHz, <dmso>) δ ppm 1.47 (s, 6H) 3.28 (br. s., 5H) 3.83 (br. s., 4H) 7.71 (d, J=3.91 Hz, 1H) 8.05 (br. s., 1H) 8.16 (s, 1H) 8.20-8.28 (m, 2H) 8.57 (br. s., 1H) 8.70 (d, J=5.09 Hz, 1H) 8.89 (d, J=1.96 Hz, 1H) 10.84 (s, 1H). LCMS (m/z) (M+H)= 473.3 at Rt=0.39 mins.

Example 879: 2-(1,1-difluoroethyl)-N-(6-methyl-5-(8-morpholinoimidazo[1,2-a]pyridin-6-yl)pyridin-3-yl)isonicotinamide

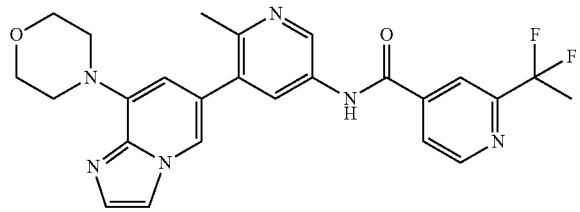 [SMILES: Cc1ncc(NC(=O)c2ccnc(C(C)(F)F)c2)cc1-c1cc(N2CCOCC2)c2nccn2c1]

This compound was prepared following the same procedures described for Example 876. 1H NMR (400 MHz, <dmso>) δ ppm 2.06 (t, J=19.17 Hz, 3H) 3.27 (br. s., 5H) 7.25 (br. s., 1H) 8.01-8.15 (m, 2H) 8.22 (s, 1H) 8.28 (s, 2H) 8.62 (s, 1H) 8.89-8.95 (m, 2H) 10.95-11.08 (m, 1H). LCMS (m/z) (M+H)=479.3 at Rt=0.52 mins.

Example 880: 3-(difluoromethyl)-N-(6-methyl-5-(8-morpholinoimidazo[1,2-a]pyridin-6-yl)pyridin-3-yl)benzamide

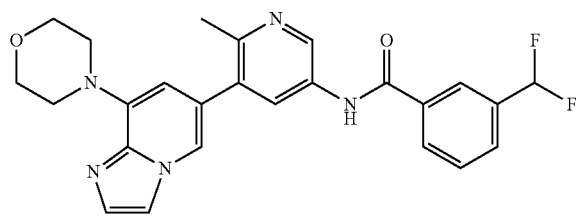 [SMILES: Cc1ncc(NC(=O)c2cccc(C(F)F)c2)cc1-c1cc(N2CCOCC2)c2nccn2c1]

This compound was prepared following the same procedures described for Example 876. 1H NMR (400 MHz, <dmso>) δ ppm 3.67-3.92 (m, 7H) 6.92-7.36 (m, 2H) 7.66-7.74 (m, 2H) 7.81 (d, J=7.83 Hz, 2H) 8.11-8.20 (m, 5H) 8.23 (s, 2H) 8.50 (br. s., 1H) 8.88 (d, J=1.96 Hz, 1H) 10.70 (s, 1H). LCMS (m/z) (M+H)=464.2 at Rt=0.53 mins.

Example 881: 2-(2-cyanopropan-2-yl)-N-(6-methyl-5-(8-morpholinoimidazo[1,2-a]pyridin-6-yl)pyridin-3-yl)isonicotinamide

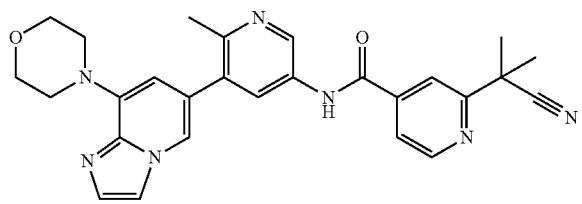 [SMILES: Cc1ncc(NC(=O)c2ccnc(C(C)(C)C#N)c2)cc1-c1cc(N2CCOCC2)c2nccn2c1]

This compound was prepared following the same procedures described for Example 876. 1H NMR (400 MHz, <dmso>) δ ppm 1.61-1.83 (m, 7H) 3.25 (br. s., 4H) 7.24 (br. s., 1H) 7.88 (d, J=3.91 Hz, 1H) 8.02 (s, 1H) 8.11 (br. s., 1H) 8.20-8.30 (m, 2H) 8.60 (s, 1H) 8.83 (d, J=4.70 Hz, 1H) 8.88 (d, J=1.96 Hz, 1H) 10.92 (s, 1H). LCMS (m/z) (M+H)= 482.4 at Rt=0.52 mins.

Example 882: 2-isopropyl-N-(6-methyl-5-(8-morpholinoimidazo[1,2-a]pyridin-6-yl)pyridin-3-yl)isonicotinamide

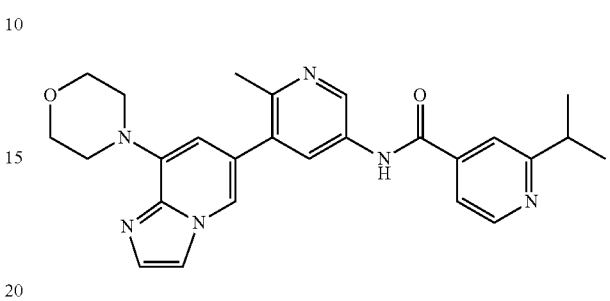

This compound was prepared following the same procedures described for Example 876. 1H NMR (400 MHz, <dmso>) δ ppm 1.25-1.34 (m, 7H) 2.52 (s, 7H) 3.05-3.18 (m, 1H) 3.20-3.35 (m, 4H) 7.07-7.26 (m, 1H) 7.70 (dd, J=5.09, 1.17 Hz, 1H) 7.76 (s, 1H) 8.06 (br. s., 1H) 8.24 (d, J=1.96 Hz, 2H) 8.57 (s, 1H) 8.71 (d, J=5.09 Hz, 1H) 8.88 (d, J=1.96 Hz, 1H) 10.64-10.91 (m, 1H). LCMS (m/z) (M+H)= 457.2 at Rt=0.42 mins.

Example 883: N-(6-methyl-5-(8-morpholinoimidazo[1,2-a]pyridin-6-yl)pyridin-3-yl)-3-(trifluoromethyl)benzamide

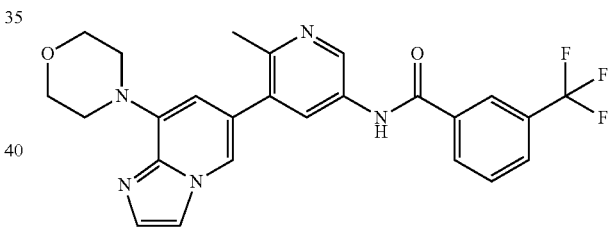

This compound was prepared following the same procedures described for Example 876. 1H NMR (400 MHz, <dmso>) δ ppm 3.25 (br. s., 4H) 3.83 (d, J=4.70 Hz, 3H) 3.84 (br. s., 1H) 7.23 (br. s., 1H) 7.75-7.86 (m, 1H) 8.00 (d, J=7.83 Hz, 1H) 8.10 (br. s., 1H) 8.23-8.35 (m, 4H) 8.51-8.68 (m, 1H) 8.91 (d, J=2.35 Hz, 1H) 10.83 (s, 1H). LCMS (m/z) (M+H)=482.3 at Rt=0.60 mins.

Example 884: N-(6-methyl-5-(8-morpholinoimidazo[1,2-a]pyridin-6-yl)pyridin-3-yl)-3-(trifluoromethyl)benzamide

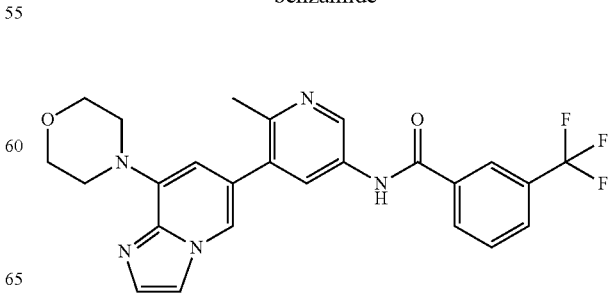

1H NMR (400 MHz, <dmso>) δ ppm 3.25 (br. s., 4H) 3.83 (d, J=4.70 Hz, 3H) 3.84 (br. s., 1H) 7.23 (br. s., 1H) 7.75-7.86 (m, 1H) 8.00 (d, J=7.83 Hz, 1H) 8.10 (br. s., 1H) 8.23-8.35 (m, 4H) 8.51-8.68 (m, 1H) 8.91 (d, J=2.35 Hz, 1H) 10.83 (s, 1H). LCMS (m/z) (M+H)=482.3 at Rt=0.60 mins.

Example 885: N-(6-methyl-5-(8-morpholinoimidazo[1,2-a]pyridin-6-yl)pyridin-3-yl)-4-((methylamino)methyl)-3-(trifluoromethyl)benzamide

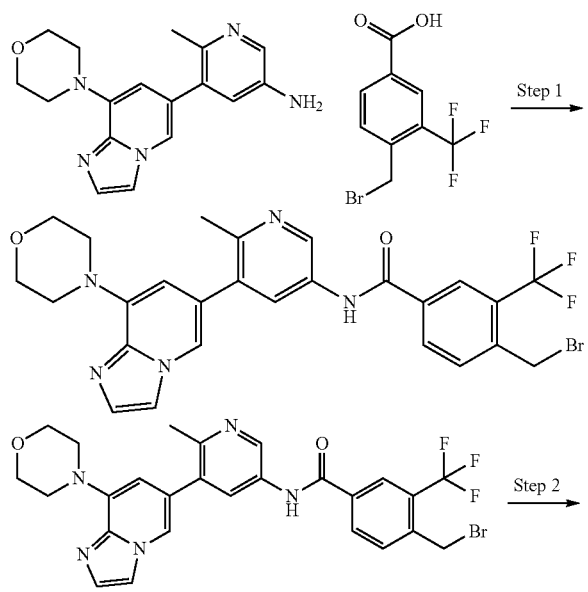

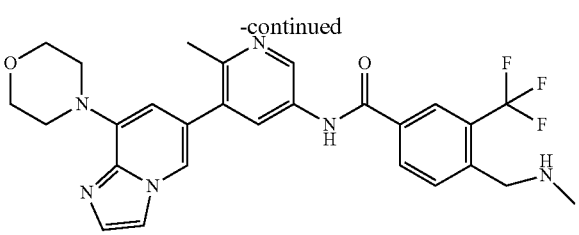

Step 1:
1-Hydroxy-7-azabenzotriazole (1.0 equiv.) was added to a solution of 4-methyl-3-(8-morpholinoimidazo[1,2-a]pyridin-6-yl)aniline (1.0 equiv.), 4-(bromomethyl)-3-(trifluoromethyl)benzoic acid (1.0 equiv) and EDC.HCl (1.0 equiv.) in DMF (0.1 M) and the reaction mix was left stirring at RT for 1 hr. The reaction was treated with water and the precipitate was removed by filtration. The solid 4-(bromomethyl)-N-(6-methyl-5-(8-morpholinoimidazo[1,2-a]pyridin-6-yl)pyridin-3-yl)-3-(trifluoromethyl)benzamide was dried and used as is in the next step. LCMS (m/z) (M+H)=530 at Rt=0.65 mins.

Step 2:
Methylamine 2M in THF (60 equiv.) was added to a solution 4-(bromomethyl)-N-(6-methyl-5-(8-morpholinoimidazo[1,2-a]pyridin-6-yl)pyridin-3-yl)-3-(trifluoromethyl)benzamide (1.0 equiv.) and the vial was sealed and heated to 70° C. overnight. The reaction mix was concentrated to dryness and the crude was purified by HPLC to give the desired N-(6-methyl-5-(8-morpholinoimidazo[1,2-a]pyridin-6-yl)pyridin-3-yl)-4-((methylamino)methyl)-3-(trifluoromethyl)benzamide as the TFA salt in 33% yield. LCMS (m/z) (M+H)=526 at Rt=0.56 mins.

Example 886: N-(6-methyl-5-(4-morpholino-6,6-dioxido-5,7-dihydrothieno[3,4-d]pyrimidin-2-yl)pyridin-3-yl)-3-(trifluoromethyl)benzamide

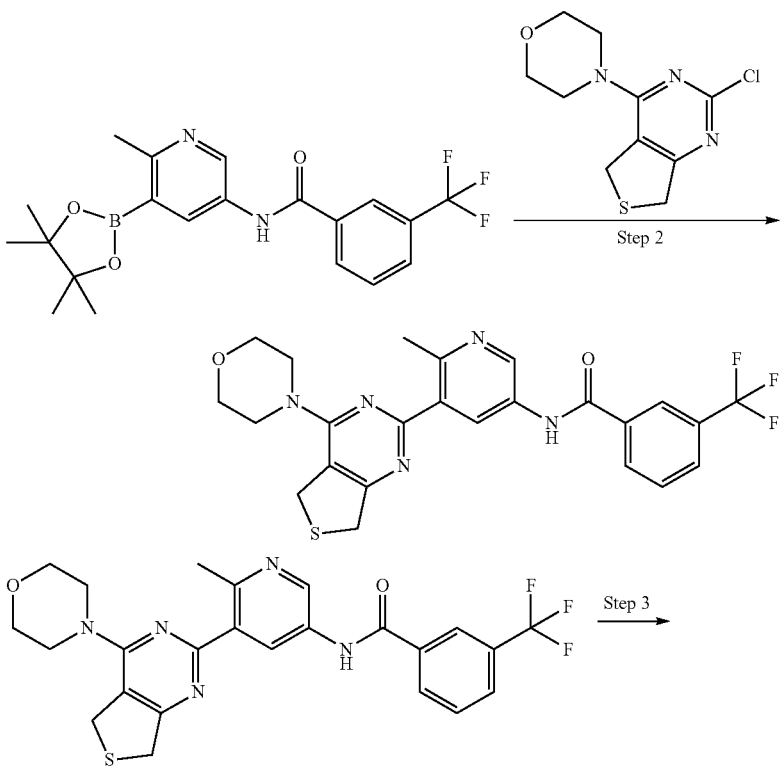

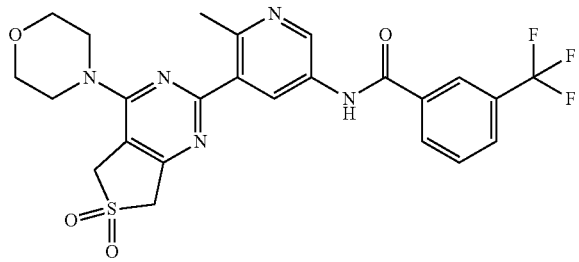

Step 1:

To a flask containing 2,4-dichloro-5,7-dihydrothieno[3,4-d]pyrimidine (1.0 equiv.) in EtOH (2.4 M) was added morpholine (10.0 equiv.) and the reaction mix was stirred at RT for 30 min. The solvent was removed under vacuum and the crude 4-(2-chloro-6,7-dihydrothieno[3,2-d]pyrimidin-4-yl)morpholine was used as is in the next step. Yield was assumed to be quantitative. LCMS (m/z) (M+H)=254/258 at Rt=0.68 mins.

Step 2:

To a solution of 4-(2-chloro-6,7-dihydrothieno[3,2-d]pyrimidin-4-yl)morpholine (1.0 equiv.) and N-(4-methyl-3-(4,4,5,5-tetramethyl-1,3,2-dioxaborolan-2-yl)phenyl)-3-(trifluoromethyl)benzamide (1.0 equiv) in DME (0.12 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by on a silica gel column using heptane to 90% EtOAc in heptane giving N-(6-methyl-5-(4-morpholino-5,7-dihydrothieno[3,4-d]pyrimidin-2-yl)pyridin-3-yl)-3-(trifluoromethyl)benzamide in 51% yield. LCMS (m/z) (M+H)= 502 at Rt=0.81 mins.

Step 3:

A solution of oxone (2.3 equiv.) in 3 ml of water was added portionwise to a solution of N-(6-methyl-5-(4-morpholino-5,7-dihydrothieno[3,4-d]pyrimidin-2-yl)pyridin-3-yl)-3-(trifluoromethyl)benzamide (1.0 equiv.) in THF (0.013 M) at 0° C. and the reaction mix was left stirring for 4 hr at the same temperature. The reaction mix was diluted with DCM and washed three times with 0.5 M aqueous Na$_2$CO$_3$. It was dried over Na$_2$SO$_4$, filtered and concentrated. The crude was purified by HPLC giving N-(6-methyl-5-(4-morpholino-6,6-dioxido-5,7-dihydrothieno[3,4-d]pyrimidin-2-yl)pyridin-3-yl)-3-(trifluoromethyl)benzamide as the TFA salt in 38% yield. 1H NMR (400 MHz, <dmso>) δ ppm 2.52 (s, 1H) 2.69-2.81 (m, 3H) 3.68 (d, J=4.30 Hz, 10H) 4.56 (s, 2H) 4.74 (s, 2H) 7.81 (t, J=7.83 Hz, 1H) 8.00 (d, J=7.83 Hz, 1H) 8.21-8.42 (m, 2H) 8.72 (d, J=1.96 Hz, 1H) 9.04 (d, J=1.96 Hz, 1H) 10.84 (s, 1H). LCMS (m/z) (M+H)=515 at Rt=0.89 mins.

Example 887: 2-methyl-3-(4-morpholino-6,6-dioxido-5,7-dihydrothieno[3,4-d]pyrimidin-2-yl)-5-(3-(trifluoromethyl)benzamido)pyridine 1-oxide

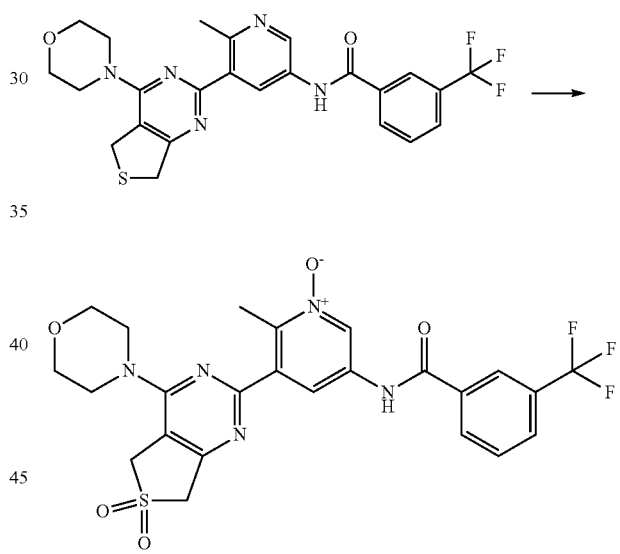

mCPBA (2.2 equiv was added portionwise to a solution of N-(6-methyl-5-(4-morpholino-5,7-dihydrothieno[3,4-d]pyrimidin-2-yl)pyridin-3-yl)-3-(trifluoromethyl)benzamide (1.0 equiv.) in DCM (0.024 M) at 0° C. and the reaction mix was left stirring overnight at RT. The reaction mix was diluted with DCM and washed three times with 0.5 M aqueous Na$_2$CO$_3$. It was dried over Na$_2$SO$_4$, filtered and concentrated. The crude was purified by HPLC giving 2-methyl-3-(4-morpholino-6,6-dioxido-5,7-dihydrothieno[3,4-d]pyrimidin-2-yl)-5-(3-(trifluoromethyl)benzamido)pyridine 1-oxide as the TFA salt in 19% yield. 1H NMR (400 MHz, <dmso>) δ ppm 2.54 (s, 2H) 3.53-3.79 (m, 6H) 3.81-4.27 (m, 6H) 4.56 (s, 2H) 4.75 (s, 1H) 7.75-7.85 (m, 1H) 7.96-8.05 (m, 1H) 8.20-8.37 (m, 1H) 8.98-9.11 (m, 1H) 10.79 (s, 1H). LCMS (m/z) (M+H)=550 at Rt=0.76 mins.

Example 888: 4-methyl-3-(8-morpholinoimidazo[1,2-b]pyridazin-6-yl)-N-(3-(trifluoromethyl)phenyl)benzamide

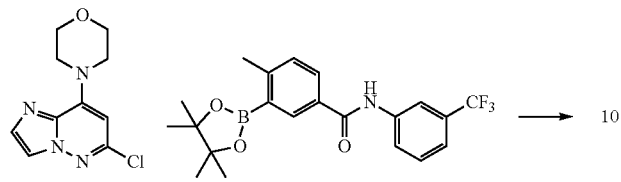

Step 2:

To a solution of 4-(6-chloroimidazo[1,2-b]pyridazin-8-yl)morpholine (1.0 equiv.) 4-methyl-3-(4,4,5,5-tetramethyl-1,3,2-dioxaborolan-2-yl)-N-(3-(trifluoromethyl)phenyl)benzamide (0.9 equiv) in DME (0.11 M) was added 2M sodium carbonate (3.0 equiv.) and the system was flushed with nitrogen for 5 minutes. PdCl$_2$(dppf).CH$_2$Cl$_2$ adduct (0.1 equiv.) was added and the system was flushed once again. The vial was capped and place in a microwave reactor for 20 minutes at 120° C. The reaction mix was partitioned in EtOAc/H$_2$O. The organic layer was isolated, dried over Na$_2$SO$_4$, filtered and concentrated. The crude was purified by HPLC giving 4-methyl-3-(8-morpholinoimidazo[1,2-b]pyridazin-6-yl)-N-(3-(trifluoromethyl)phenyl)benzamide in 40% yield. 1H NMR (400 MHz, <dmso>) δ ppm 2.35 (s, 3H) 3.66-3.76 (m, 4H) 3.99 (br. s., 4H) 6.36 (s, 1H) 7.39 (d, J=7.83 Hz, 1H) 7.46 (d, J=7.83 Hz, 1H) 7.50-7.57 (m, 2H) 7.89-7.96 (m, 1H) 7.97-8.03 (m, 2H) 8.05 (s, 1H) 8.18 (s, 1H) 10.46 (s, 1H). LCMS (m/z) (M+H)=482 at Rt=0.88 mins.

Example 889: 4-methyl-3-(4-morpholino-6,7-dihydro-5H-pyrrolo[3,4-d]pyrimidin-2-yl)-N-(3-(trifluoromethyl)phenyl)benzamide

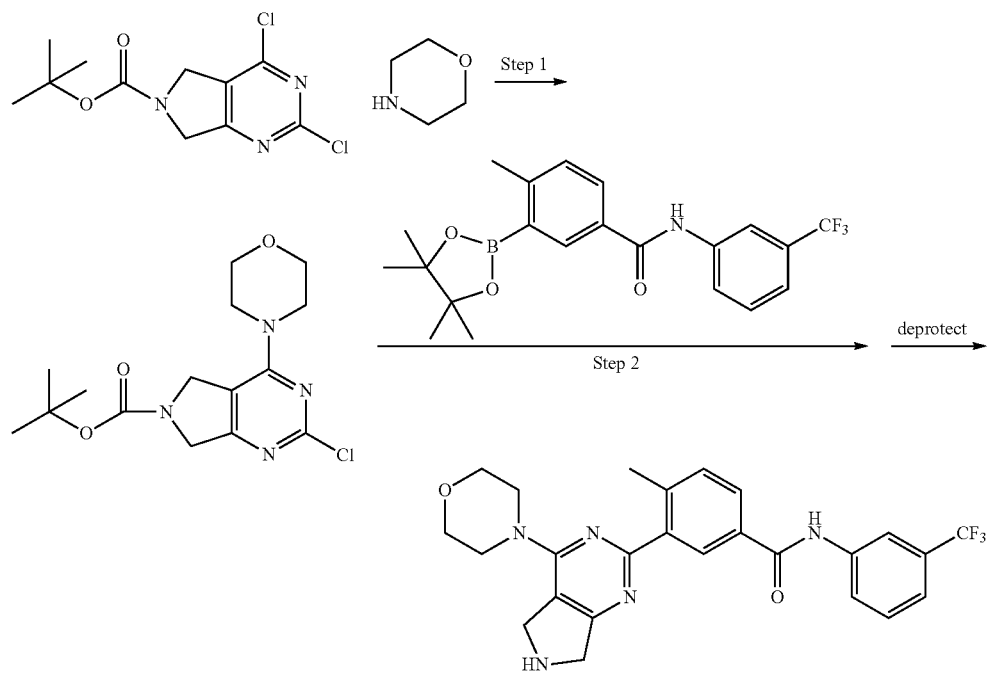

Step 1:

To a flask containing 2,4-dichloropyrido[2,3-d]pyrimidine (1 equiv.) in THF (0.46) was added morpholine (1.2 equiv.) and the reaction mix was stirred at RT for 1 h. The reaction mixture was concentrated to dryness and the crude tert-butyl 2-chloro-4-morpholino-5H-pyrrolo[3,4-d]pyrimidine-6(7H)-carboxylate was used as is in the next step. Yield is assumed to be quantitative. LCMS (m/z) [M+H]+=341 at Rt=0.91 min.

Step 2:

To a solution of tert-butyl 2-chloro-4-morpholino-5H-pyrrolo[3,4-d]pyrimidine-6(7H)-carboxylate (1.0 equiv.) and 4-methyl-3-(4,4,5,5-tetramethyl-1,3,2-dioxaborolan-2-yl)-N-(3-(trifluoromethyl)phenyl)benzamide (0.9 equiv.) in DME (0.44 M) was added 2M Na$_2$CO$_3$ solution (3.0 equiv.) and the system was flushed with nitrogen. PdCl$_2$(dppf).CH$_2$Cl$_2$ adduct (0.1 equiv.) was added to the reaction mix and the system was flushed once again with nitrogen. The reaction vial was capped and microwaved for 20 minutes at 120° C. The crude was partitioned in H2O/EtOAc. The organic layer was isolated, dried over Na$_2$SO$_4$, filtered and concentrated. The crude was purified on a silica gel column using heptane to 50% EtOAc in heptane. Isolated tert-butyl 2-(2-methyl-5-((3-(trifluoromethyl)phenyl)carbamoyl)phe- -continued

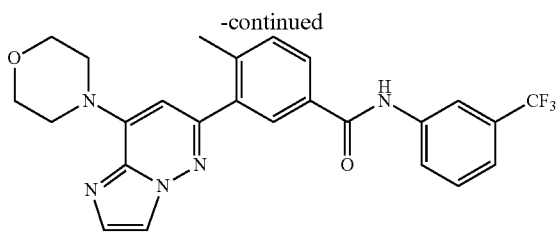

nyl)-4-morpholino-5H-pyrrolo[3,4-d]pyrimidine-6(7H)-carboxylate in 28% yield. LCMS (m/z) [M+H]+=584 at Rt=0.95 min.

Step 3.

To a solution of tert-butyl 2-(2-methyl-5-((3-(trifluoromethyl)phenyl)carbamoyl)phenyl)-4-morpholino-5H-pyrrolo[3,4-d]pyrimidine-6(7H)-carboxylate (1.0 equiv.) in DCM (0.07 M) was added TFA (10 equiv.) and the reaction mix was stirred at RT overnight. The solvent was removed under vacuum and the residue was taken in DMSO and purified on the prep. Isolated 4-methyl-3-(4-morpholino-6,7-dihydro-5H-pyrrolo[3,4-d]pyrimidin-2-yl)-N-(3-(trifluoromethyl)phenyl)benzamide as the TFA salt in 24% yield. 1H NMR (400 MHz, <dmso>) δ ppm 2.56 (s, 3H) 3.69 (br. s., 10H) 4.43 (br. s., 2H) 4.76 (br. s., 2H) 7.46 (dd, J=14.09, 7.83 Hz, 2H) 7.59 (t, J=8.02 Hz, 1H) 7.98 (dd, J=7.83, 1.57 Hz, 1H) 8.04 (d, J=8.22 Hz, 1H) 8.24 (s, 1H) 8.34 (d, J=1.17 Hz, 1H) 9.67 (br. s., 2H) 10.42-10.65 (m, 1H). LCMS (m/z) (M+H)= 484 at Rt=0.76 mins.

Example 899: 6-(1-cyanocyclopropyl)-N-(4-methyl-3-(1-methyl-6-morpholino-2-oxo-1,2-dihydropyridin-4-yl)phenyl)pyridazine-4-carboxamide

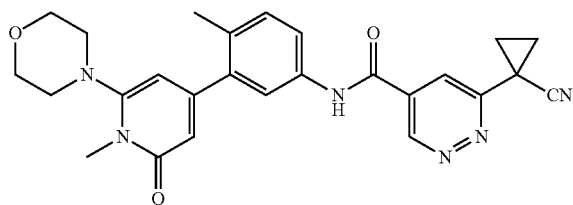 [SMILES: Cc1ccc(NC(=O)c2cnnc(C3(C#N)CC3)c2)cc1-c1cc(N2CCOCC2)n(C)c(=O)c1]

¹H NMR (400 MHz, <dmso>) δ ppm 1.83-1.92 (m, 2H) 1.94-2.03 (m, 2H) 2.20 (s, 3H) 2.88 (br. s., 4H) 3.40 (s, 3H) 3.69 (d, J=3.91 Hz, 4H) 5.75 (d, J=1.57 Hz, 1H) 6.00 (d, J=1.17 Hz, 1H) 7.26 (d, J=8.22 Hz, 1H) 7.56 (d, J=1.96 Hz, 1H) 7.63 (dd, J=8.22, 1.96 Hz, 1H) 7.96 (d, J=1.56 Hz, 1H) 9.49 (d, J=1.57 Hz, 1H) 10.67 (s, 1H). LCMS (m/z) (M+H)= 471.1, Rt=0.71 min.

Example 900: 4-(2-cyanopropan-2-yl)-N-(4-methyl-3-(1-methyl-6-morpholino-2-oxo-1,2-dihydropyridin-4-yl)phenyl)picolinamide

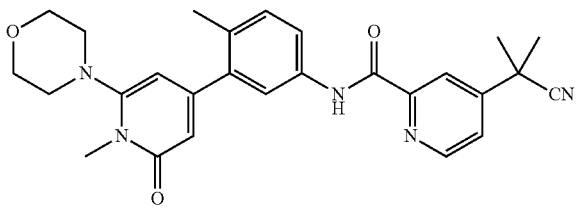 [SMILES: Cc1ccc(NC(=O)c2cc(C(C)(C)C#N)ccn2)cc1-c1cc(N2CCOCC2)n(C)c(=O)c1]

¹H NMR (400 MHz, <dmso>) δ ppm 1.67-1.78 (m, 6H) 2.25 (s, 3H) 2.94 (br. s., 4H) 3.45 (s, 3H) 3.70-3.76 (m, 4H) 5.82 (d, J=1.57 Hz, 1H) 6.02-6.13 (m, 1H) 7.27 (d, J=8.61 Hz, 1H) 7.75-7.89 (m, 3H) 8.24 (d, J=1.57 Hz, 1H) 8.77 (d, J=5.48 Hz, 1H) 10.69 (s, 1H). LCMS (m/z) (M+H)=472.2, Rt=0.84 min.

Example 901: N-(4-methyl-3-(1-methyl-6-morpholino-2-oxo-1,2-dihydropyridin-4-yl)phenyl)-5-(trifluoromethyl)nicotinamide

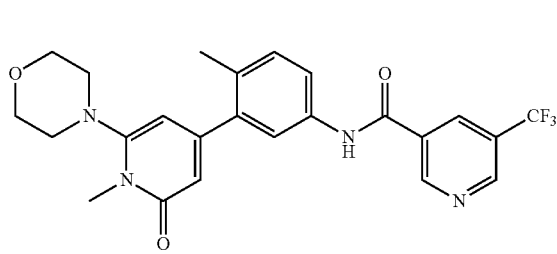 [SMILES: Cc1ccc(NC(=O)c2cncc(C(F)(F)F)c2)cc1-c1cc(N2CCOCC2)n(C)c(=O)c1]

¹H NMR (400 MHz, <dmso>) δ ppm 2.24 (s, 3H) 2.93 (br. s., 4H) 3.45 (s, 3H) 3.70-3.75 (m, 4H) 5.80 (d, J=1.57 Hz, 1H) 6.05 (d, J=1.57 Hz, 1H) 7.29 (d, J=8.22 Hz, 1H) 7.63 (d, J=1.96 Hz, 1H) 7.70 (dd, J=8.22, 2.35 Hz, 1H) 8.66 (s, 1H) 9.16 (d, J=0.78 Hz, 1H) 9.35 (d, J=1.57 Hz, 1H) 10.61 (s, 1H). LCMS (m/z) (M+H)=473.1, Rt=0.80 min.

Example 902: 6-(1-cyanocyclopropyl)-N-(4-methyl-3-(1-methyl-5-morpholino-6-oxo-1,6-dihydropyridin-3-yl)phenyl)pyridazine-4-carboxamide

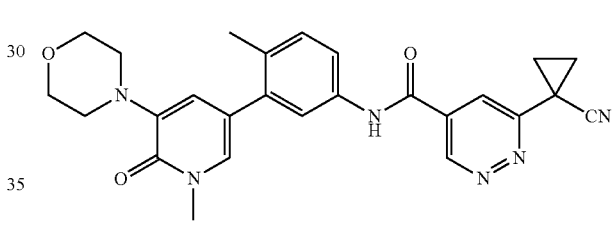

¹H NMR (400 MHz, <dmso>) δ ppm 1.87-1.97 (m, 2H) 1.97-2.06 (m, 2H) 2.25 (s, 3H) 3.08 (br. s., 4H) 3.48 (s, 3H) 3.65-3.77 (m, 4H) 6.68 (d, J=1.96 Hz, 1H) 7.29 (d, J=8.22 Hz, 1H) 7.38 (d, J=1.96 Hz, 1H) 7.59 (d, J=1.96 Hz, 1H) 7.63 (dd, J=8.22, 2.35 Hz, 1H) 8.01 (d, J=1.96 Hz, 1H) 9.54 (d, J=1.96 Hz, 1H) 10.68 (s, 1H). LCMS (m/z) (M+H)= 471.1, Rt=0.67 min.

Example 903: 4-(2-cyanopropan-2-yl)-N-(4-methyl-3-(1-methyl-5-morpholino-6-oxo-1,6-dihydropyridin-3-yl)phenyl)picolinamide

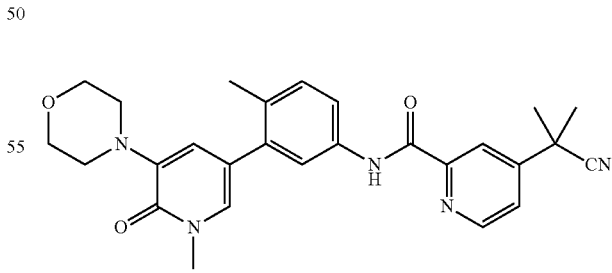

¹H NMR (400 MHz, <dmso>) δ ppm 1.74 (s, 6H) 2.25 (s, 3H) 3.10 (br. s., 4H) 3.48 (s, 3H) 3.67-3.73 (m, 4H) 6.71 (d, J=1.96 Hz, 1H) 7.25 (d, J=8.22 Hz, 1H) 7.40 (d, J=2.35 Hz, 1H) 7.73-7.86 (m, 3H) 8.24 (d, J=1.57 Hz, 1H) 8.77 (d, J=5.09 Hz, 1H) 10.63 (s, 1H). LCMS (m/z) (M+H)=472.1, Rt=0.82 min.

Example 904: N-(4-methyl-3-(1-methyl-5-morpholino-6-oxo-1,6-dihydropyridin-3-yl)phenyl)-5-(trifluoromethyl)nicotinamide

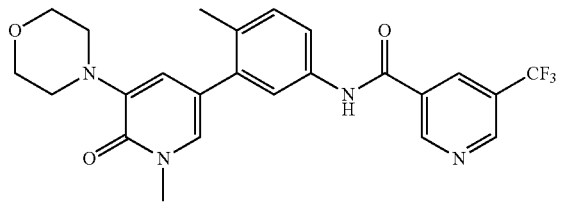

¹H NMR (400 MHz, <dmso>) δ ppm 2.25 (s, 3H) 3.09 (br. s., 4H) 3.48 (s, 3H) 3.66-3.73 (m, 4H) 6.69 (d, J=1.96 Hz, 1H) 7.27 (d, J=8.22 Hz, 1H) 7.39 (d, J=2.35 Hz, 1H) 7.61 (d, J=1.96 Hz, 1H) 7.66 (dd, J=8.22, 1.96 Hz, 1H) 8.66 (s, 1H) 9.16 (s, 1H) 9.35 (d, J=1.57 Hz, 1H) 10.57 (s, 1H). LCMS (m/z) (M+H)=473.0, Rt=0.77 min.

Example 905: 4-(1,1-difluoroethyl)-N-(4-methyl-3-(1-methyl-5-morpholino-6-oxo-1,6-dihydropyridin-3-yl)phenyl)picolinamide

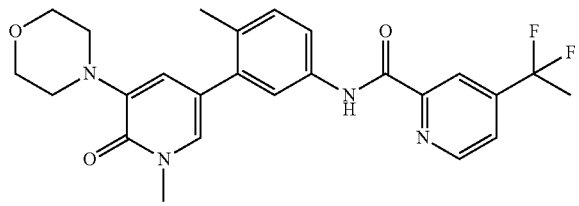 [SMILES: Cc1ccc(NC(=O)c2cc(C(C)(F)F)ccn2)cc1-c1cc(N2CCOCC2)c(=O)n(C)c1]

¹H NMR (400 MHz, <dmso>) δ ppm 2.03 (t, J=19.17 Hz, 3H) 2.26 (s, 3H) 3.10 (br. s., 4H) 3.48 (s, 3H) 3.63-3.76 (m, 4H) 6.72 (d, J=1.96 Hz, 1H) 7.26 (d, J=8.22 Hz, 1H) 7.40 (d, J=1.96 Hz, 1H) 7.77 (d, J=1.96 Hz, 1H) 7.81 (dd, J=8.22, 1.96 Hz, 1H) 7.83-7.87 (m, 1H) 8.22 (s, 1H) 8.88 (d, J=5.09 Hz, 1H) 10.67 (s, 1H). LCMS (m/z) (M+H)=469.1, Rt=0.85 min.

Example 906: 4-(2-hydroxypropan-2-yl)-N-(4-methyl-3-(1-methyl-5-morpholino-6-oxo-1,6-dihydropyridin-3-yl)phenyl)picolinamide

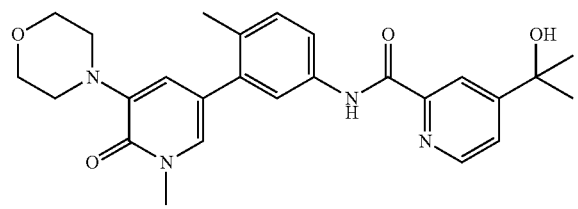 [SMILES: Cc1ccc(NC(=O)c2cc(C(C)(C)O)ccn2)cc1-c1cc(N2CCOCC2)c(=O)n(C)c1]

¹H NMR (400 MHz, <dmso>) δ ppm 1.45 (s, 6H) 2.25 (s, 3H) 3.10 (br. s., 4H) 3.48 (s, 3H) 3.66-3.74 (m, 4H) 6.72 (d, J=1.96 Hz, 1H) 7.24 (d, J=8.61 Hz, 1H) 7.40 (d, J=1.96 Hz, 1H) 7.70 (d, J=5.09, 1.57 Hz, 1H) 7.76 (d, J=1.96 Hz, 1H) 7.80 (dd, J=8.41, 2.15 Hz, 1H) 8.23 (d, J=1.17 Hz, 1H) 8.63 (d, J=5.09 Hz, 1H) 10.55 (s, 1H). LCMS (m/z) (M+H)= 463.1, Rt=0.71 min.

Example 907: 4-(2-fluoropropan-2-yl)-N-(4-methyl-3-(1-methyl-5-morpholino-6-oxo-1,6-dihydropyridin-3-yl)phenyl)picolinamide

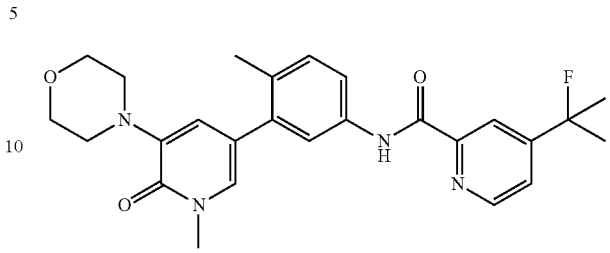

¹H NMR (400 MHz, <dmso>) δ ppm 1.66 (s, 3H) 1.72 (s, 3H) 2.26 (s, 3H) 3.10 (br. s., 4H) 3.48 (s, 3H) 3.67-3.74 (m, 4H) 6.72 (d, J=1.96 Hz, 1H) 7.25 (d, J=8.22 Hz, 1H) 7.40 (d, J=1.96 Hz, 1H) 7.68 (dd, J=5.09, 1.96 Hz, 1H) 7.76 (d, J=1.96 Hz, 1H) 7.80 (dd, J=8.22, 1.96 Hz, 1H) 8.13 (d, J=1.17 Hz, 1H) 8.72 (d, J=5.09 Hz, 1H) 10.60 (s, 1H). LCMS (m/z) (M+H)=465.1, Rt=0.87 min.

Example 908: 3-(2-aminopropan-2-yl)-N-(4-methyl-3-(1-methyl-5-morpholino-6-oxo-1,6-dihydropyridin-3-yl)phenyl)-5-(trifluoromethyl)benzamide

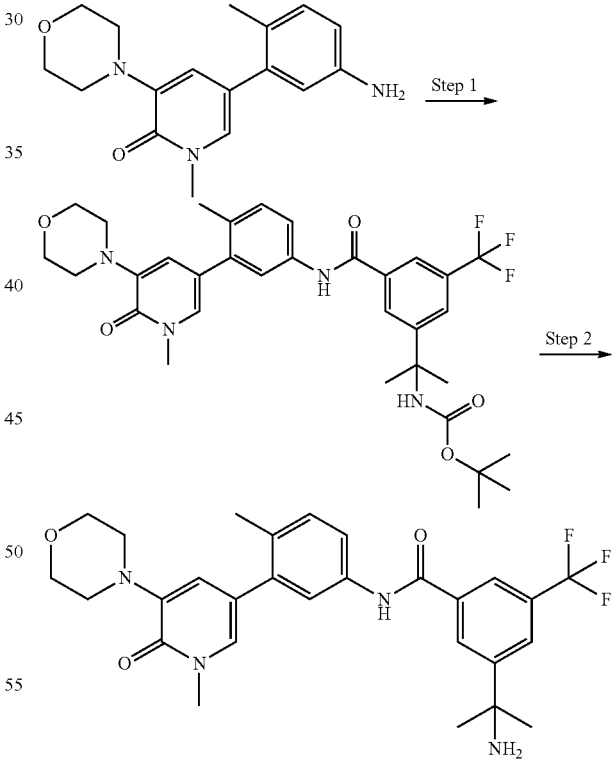

Step 1:

To a solution of 5-(5-amino-2-methylphenyl)-1-methyl-3-morpholinopyridin-2(1H)-one (1.0 equiv.) and 3-(2-((tert-butoxycarbonyl)amino)propan-2-yl)-5-(trifluoromethyl)benzoic acid (1.0 equiv.) in DMF (0.1 M) was added EDC (2.2 equiv.) and HOAt (2.2 equiv.) and the reaction was stirred at rt until completion. Purified via reverse phase HPLC and lyophilize to give tert-butyl(2-(3-((4-methyl-3-

(1-methyl-5-morpholino-6-oxo-1,6-dihydropyridin-3-yl)phenyl)carbamoyl)-5-(trifluoromethyl)phenyl)propan-2-yl)carbamate that was used for the next step. LCMS (m/z) (M+H)=629.3, Rt=1.00 min.

Step 2:

A solution of tert-butyl(2-(3-((4-methyl-3-(1-methyl-5-morpholino-6-oxo-1,6-dihydropyridin-3-yl)phenyl)carbamoyl)-5-(trifluoromethyl)phenyl)propan-2-yl)carbamate (1.0 equiv.) was dissolved in DCM and TFA (4:1) and the reaction was stirred at rt for 4 hours. Concentrated to dryness and dissolved in acetonitrile and water and lyophilized to give 3-(2-aminopropan-2-yl)-N-(4-methyl-3-(1-methyl-5-morpholino-6-oxo-1,6-dihydropyridin-3-yl)phenyl)-5-(trifluoromethyl)benzamide in 57% yield. $^1$H NMR (400 MHz, <dmso>) δ ppm 1.70 (s, 6H) 2.26 (s, 3H) 3.02-3.13 (m, 4H) 3.48 (s, 3H) 3.65-3.75 (m, 4H) 6.68 (d, J=2.35 Hz, 1H) 7.28 (d, J=8.61 Hz, 1H) 7.38 (d, J=2.35 Hz, 1H) 7.59 (d, J=2.35 Hz, 1H) 7.68 (dd, J=8.22, 2.35 Hz, 1H) 8.08 (s, 1H) 8.34 (s, 2H) 10.49 (s, 1H). LCMS (m/z) (M+H)=529.1, Rt=0.68 min.

Example 909: N-(4-methyl-3-(1-methyl-5-morpholino-6-oxo-1,6-dihydropyridazin-3-yl)phenyl)-5-(trifluoromethyl)nicotinamide

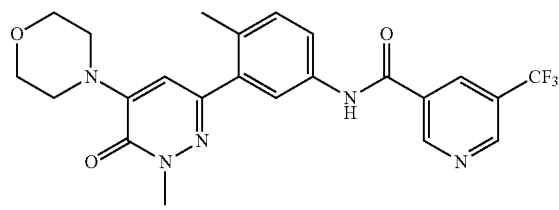 [SMILES: Cc1ccc(NC(=O)c2cncc(C(F)(F)F)c2)cc1-c1cc(N2CCOCC2)c(=O)n(C)n1]

$^1$H NMR (400 MHz, <dmso>) δ ppm 2.29 (s, 3H) 3.42-3.47 (m, 4H) 3.65-3.72 (m, 7H) 6.58 (s, 1H) 7.30 (d, J=8.22 Hz, 1H) 7.67-7.80 (m, 2H) 8.68 (s, 1H) 9.16 (d, J=0.78 Hz, 1H) 9.36 (d, J=1.57 Hz, 1H) 10.62 (s, 1H). LCMS (m/z) (M+H)=474.2, Rt=0.85 min.

Example 910: 4-(2-cyanopropan-2-yl)-N-(4-methyl-3-(1-methyl-5-morpholino-6-oxo-1,6-dihydropyridazin-3-yl)phenyl)picolinamide

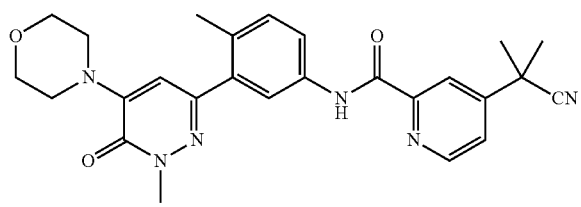 [SMILES: Cc1ccc(NC(=O)c2cc(C(C)(C)C#N)ccn2)cc1-c1cc(N2CCOCC2)c(=O)n(C)n1]

$^1$H NMR (400 MHz, <dmso>) δ ppm 1.74 (s, 6H) 2.30 (s, 3H) 3.41-3.50 (m, 4H) 3.67 (s, 3H) 3.68-3.72 (m, 4H) 6.60 (s, 1H) 7.24-7.31 (m, 1H) 7.82 (dd, J=5.09, 1.96 Hz, 1H) 7.86 (dd, J=8.22, 2.35 Hz, 1H) 7.92 (d, J=1.96 Hz, 1H) 8.25 (d, J=1.57 Hz, 1H) 8.77 (d, J=5.09 Hz, 1H) 10.68 (s, 1H). LCMS (m/z) (M+H)=473.3, Rt=0.92 min.

Synthesis of 5-(6-isopropoxy-5-morpholinopyridazin-3-yl)-6-methylpyridin-3-amine

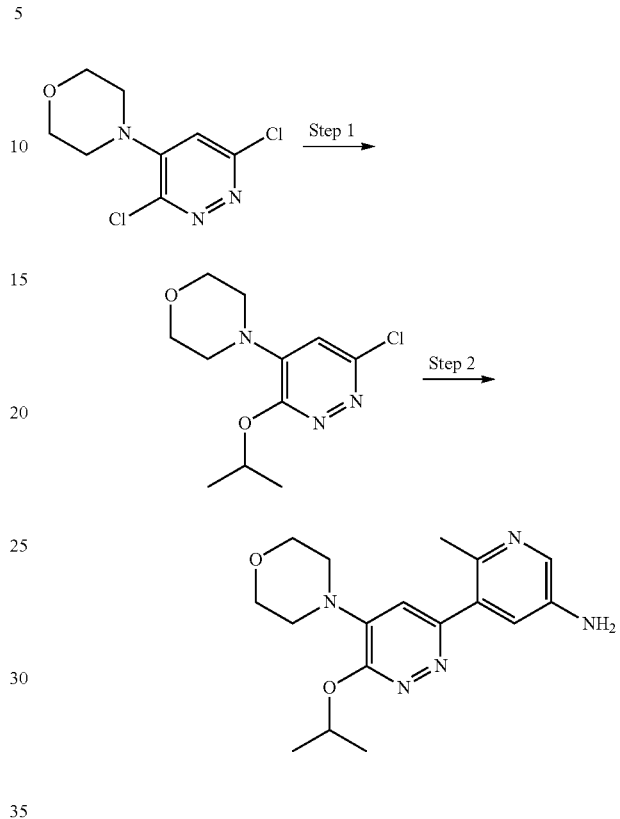

Step 1:

To a solution of 4-(3,6-dichloropyridazin-4-yl)morpholine (1.0 equiv.) and propan-2-ol (1.8 equiv.) in THF (0.3M) was added sodium hydride (2.0 equiv.) and the reaction was stirred at room temperature until completion. The mixture was quenched with water and extracted with ethyl acetate twice. The combined organics were washed with brine and dried over sodium sulfate. The crude material was purified via silica gel chromatography (ISCO, 10% methanol/DCM) to give 4-(6-chloro-3-isopropoxypyridazin-4-yl)morpholine in 72% yield as a white solid. LCMS (m/z) (M+H)=258.2/259.7, Rt=0.59 min.

Step 2:

To a solution of 4-(6-chloro-3-isopropoxypyridazin-4-yl)morpholine (1.1 equiv.) and 6-methyl-5-(4,4,5,5-tetramethyl-1,3,2-dioxaborolan-2-yl)pyridin-3-amine (1.0 equiv.) in DME (0.1 M) was added PdCl$_2$(dppf)-DCM adduct (0.5 equiv.) and sodium carbonate (8.0 equiv, 2M aqueous solution) and the mixture was heated to 110° C. for 15 min in the microwave. The reaction was concentrated to dryness and then partitioned between ethyl acetate and water. The organic layer was washed with brine and dried over sodium sulfate. The crude material was purified via silica gel chromatography (ISCO, 10% methanol/DCM) to give 5-(6-isopropoxy-5-morpholinopyridazin-3-yl)-6-methylpyridin-3-amine in 88% yield. LCMS (m/z) (M+H)=330.0, Rt=0.46 min.

Example 911: 2-(2-fluoropropan-2-yl)-N-(5-(6-isopropoxy-5-morpholinopyridazin-3-yl)-6-methylpyridin-3-yl)isonicotinamide

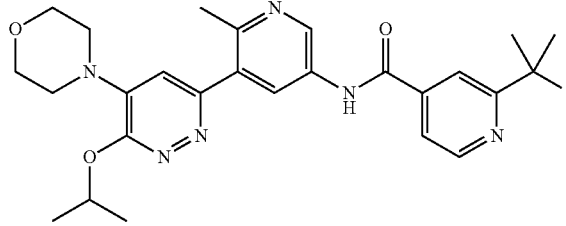

¹H NMR (400 MHz, <dmso>) δ ppm 1.42 (s, 3H) 1.43 (s, 3H) 1.66 (s, 3H) 1.72 (s, 3H) 3.74 (s, 7H) 5.28-5.43 (m, 1H) 7.37 (s, 1H) 7.83 (dd, J=4.89, 1.37 Hz, 1H) 8.04 (s, 1H) 8.36 (d, J=2.35 Hz, 1H) 8.78 (d, J=5.09 Hz, 1H) 8.94 (d, J=2.35 Hz, 1H) 10.95 (s, 1H). LCMS (m/z) (M+H)=495.3, Rt=0.70 min.

Example 912: 2-(1,1-difluoroethyl)-N-(5-(6-isopropoxy-5-morpholinopyridazin-3-yl)-6-methylpyridin-3-yl)isonicotinamide

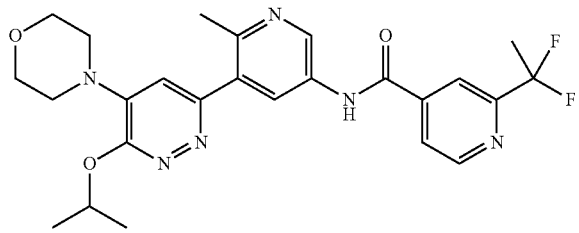 [SMILES: Cc1ncc(NC(=O)c2ccnc(C(C)(F)F)c2)cc1-c1cc(N2CCOCC2)c(OC(C)C)nn1]

¹H NMR (400 MHz, <dmso>) δ ppm 1.42 (d, J=6.26 Hz, 6H) 1.98-2.11 (m, 3H) 3.73 (br. s., 7H) 5.36 (spt, J=6.13 Hz, 1H) 7.34 (s, 1H) 8.03 (d, J=4.70 Hz, 1H) 8.19 (s, 1H) 8.35 (d, J=2.35 Hz, 1H) 8.90 (d, J=5.09 Hz, 1H) 8.93 (d, J=2.35 Hz, 1H) 11.02 (s, 1H). LCMS (m/z) (M+H)=499.3, Rt=0.69 min.

Example 913: 2-(difluoromethyl)-N-(5-(6-isopropoxy-5-morpholinopyridazin-3-yl)-6-methylpyridin-3-yl)isonicotinamide

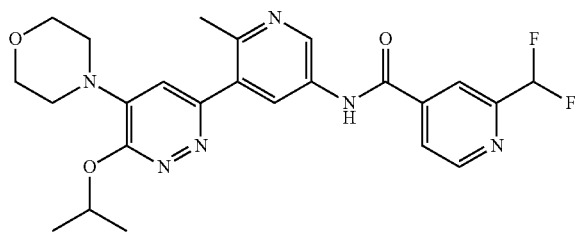 [SMILES: Cc1ncc(NC(=O)c2ccnc(C(F)F)c2)cc1-c1cc(N2CCOCC2)c(OC(C)C)nn1]

¹H NMR (400 MHz, <dmso>) δ ppm 1.42 (d, J=6.26 Hz, 6H) 3.74 (s, 7H) 5.27-5.42 (m, 1H) 6.86-7.25 (m, 1H) 7.36 (s, 1H) 8.07 (d, J=4.69 Hz, 1H) 8.19 (s, 1H) 8.36 (d, J=2.35 Hz, 1H) 8.87-8.98 (m, 2H) 11.04 (s, 1H). LCMS (m/z) (M+H)=485.3, Rt=0.66 min.

Synthesis of 5-(6-(2,2-difluoroethoxy)-5-morpholinopyridazin-3-yl)-6-methylpyridin-3-amine

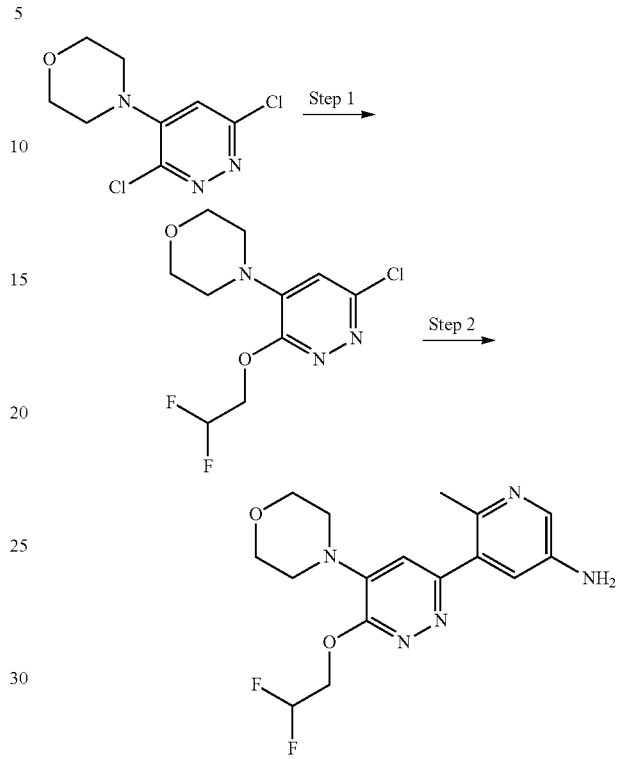

Step 1:

NaH (3.0 equiv.) was added slowly in portions to a solution of 2,2-difluoroethanol (3.0 equiv.) and 4-(3,6-dichloropyridazin-4-yl)morpholine (1.0 equiv.) in THF (0.15 M) under nitrogen. The solution was stirred at room temperature for 2 hours. Quenched by the addition of water and extracted 3 times with ethyl acetate. The organics were combined dried with sodium sulfate, filtered and concentrated. The crude material was purified via silica gel column chromatography eluting with ethyl acetate and heptanes (product elutes at about 50/50 ethyl acetate/heptanes). The pure fractions were concentrated to give 4-(6-chloro-3-(2,2-difluoroethoxy)pyridazin-4-yl)morpholine as a white solid in 65% yield. LCMS (m/z) (M+H)=279.9, Rt=0.59 min.

Step 2:

To a solution of 4-(6-chloro-3-(2,2-difluoroethoxy)pyridazin-4-yl)morpholine (1.0 equiv.) in DME and 2M Na₂CO₃ (3:1, 0.18 M) was added 6-methyl-5-(4,4,5,5-tetramethyl-1,3,2-dioxaborolan-2-yl)pyridin-3-amine (1.2 equiv.) and PdCl₂(dppf).CH₂Cl₂ adduct (0.1 equiv.). The reaction was heated to reflux for 3 hours, then cooled to room temperature. Partitioned between water and ethyl acetate, the organic phase was dried with sodium sulfate, filtered and concentrated. Purification via silica gel column chromatography eluting with 0-100 ethyl acetate in heptanes followed by 10% methanol in ethyl acetate give 5-(6-(2,2-difluoroethoxy)-5-morpholinopyridazin-3-yl)-6-methylpyridin-3-amine in 60% yield. LCMS (m/z) (M+H)=352, Rt=0.39 min.

Example 914: N-(5-(6-(2,2-difluoroethoxy)-5-morpholinopyridazin-3-yl)-6-methylpyridin-3-yl)-2-(1,1-difluoropropyl)isonicotinamide

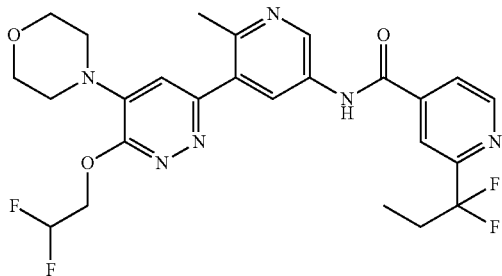 [SMILES: CCC(F)(F)c1cc(C(=O)Nc2cnc(C)c(-c3cc(N4CCOCC4)c(OCC(F)F)nn3)c2)ccn1]

¹H NMR (400 MHz, <cd3od>) δ ppm 1.01 (t, J=7.43 Hz, 3H) 2.20-2.47 (m, 2H) 2.56 (s, 3H) 3.89 (d, J=5.09 Hz, 8H) 4.77 (td, J=14.28, 3.13 Hz, 2H) 6.17-6.56 (m, 1H) 7.39 (s, 1H) 7.99 (d, J=3.91 Hz, 1H) 8.20 (s, 1H) 8.56 (d, J=2.74 Hz, 1H) 8.85 (d, J=5.09 Hz, 1H) 8.93 (d, J=2.35 Hz, 1H). LCMS (m/z) (M+H)=535.2, Rt=0.72 min.

Example 915: N-(5-(6-(2,2-difluoroethoxy)-5-morpholinopyridazin-3-yl)-6-methylpyridin-3-yl)-2-(1,1-difluoroethyl)isonicotinamide

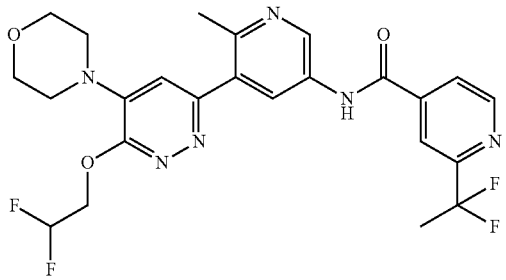

¹H NMR (400 MHz, <cd3od>) δ ppm 1.94 (t, J=18.78 Hz, 3H) 2.43 (s, 3H) 3.31-3.44 (m, 4H) 3.69-3.86 (m, 4H) 4.63-4.73 (m, 2H) 6.07-6.47 (m, 1H) 7.01 (s, 1H) 7.90 (d, J=4.70 Hz, 1H) 8.12 (s, 1H) 8.19 (d, J=2.35 Hz, 1H) 8.73 (d, J=4.70 Hz, 1H) 8.80 (d, J=2.35 Hz, 1H). LCMS (m/z) (M+H)=521.1, Rt=0.64 min.

Example 916: N-(5-(6-(2,2-difluoroethoxy)-5-morpholinopyridazin-3-yl)-6-methylpyridin-3-yl)-4-(trifluoromethyl)picolinamide

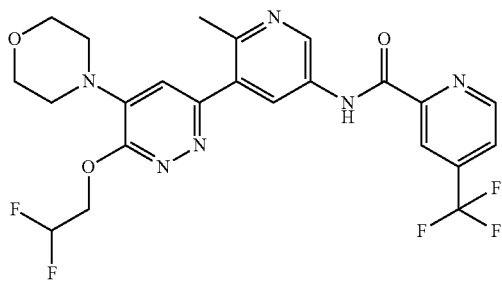 [SMILES: Cc1ncc(NC(=O)c2cc(C(F)(F)F)ccn2)cc1-c1cc(N2CCOCC2)c(OCC(F)F)nn1]

¹H NMR (400 MHz, <cd3od>) δ ppm 2.57 (s, 3H) 3.89 (d, J=4.30 Hz, 7H) 4.77 (td, J=14.28, 3.13 Hz, 2H) 6.13-6.59 (m, 1H) 7.40 (s, 1H) 7.97 (d, J=3.91 Hz, 1H) 8.45 (s, 1H) 8.63 (d, J=2.35 Hz, 1H) 9.00 (d, J=5.09 Hz, 1H) 9.11 (d, J=2.35 Hz, 1H). LCMS (m/z) (M+H)=525.1, Rt=0.73 min.

Example 917: N-(5-(6-(2,2-difluoroethoxy)-5-morpholinopyridazin-3-yl)-6-methylpyridin-3-yl)-5-(trifluoromethyl)nicotinamide

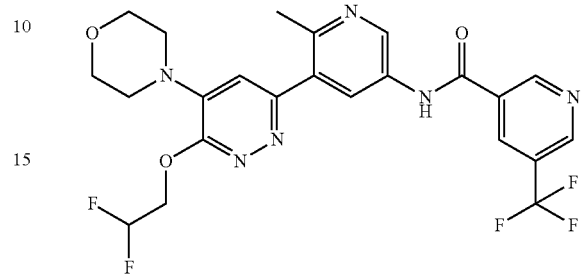

¹H NMR (400 MHz, <cd3od>) δ ppm 2.43 (s, 3H) 3.34-3.42 (m, 4H) 3.70-3.79 (m, 4H) 4.62-4.74 (m, 2H) 6.03-6.47 (m, 1H) 7.02 (s, 1H) 8.19 (d, J=2.35 Hz, 1H) 8.60 (s, 1H) 8.80 (d, J=2.35 Hz, 1H) 9.00 (s, 1H) 9.28 (d, J=1.57 Hz, 1H). LCMS (m/z) (M+H)=525.1, Rt=0.67 min.

Example 918: N-(5-(6-(2,2-difluoroethoxy)-5-morpholinopyridazin-3-yl)-6-methylpyridin-3-yl)-3-(trifluoromethyl)benzamide

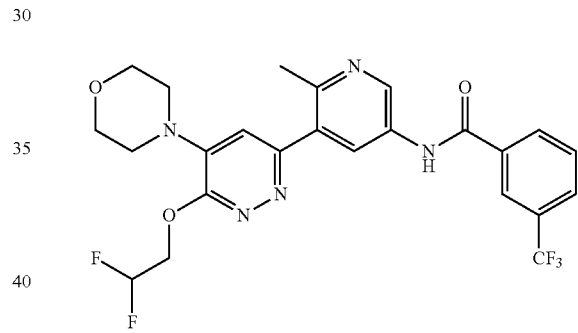

¹H NMR (400 MHz, <cd3od>) δ ppm 2.56 (s, 3H) 3.88 (s, 8H) 4.77 (td, J=14.28, 3.52 Hz, 2H) 6.16-6.69 (m, 1H) 7.38 (s, 1H) 7.72-7.81 (m, 1H) 7.94 (d, J=7.83 Hz, 1H) 8.17-8.35 (m, 2H) 8.55 (d, J=2.35 Hz, 1H) 8.93 (d, J=2.74 Hz, 1H). LCMS (m/z) (M+H)=524.1, Rt=0.72 min.

Synthesis of 6-methyl-5-(6-(methylsulfonyl)-5-morpholinopyridazin-3-yl)pyridin-3-amine

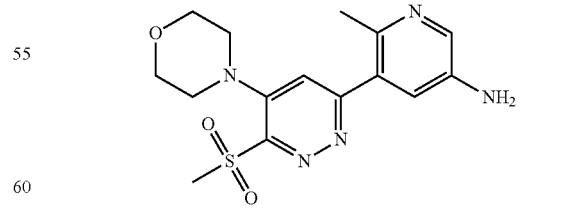

To a solution of 4-(6-chloro-3-(methylsulfonyl)pyridazin-4-yl)morpholine (1.0 equiv.) and 6-methyl-5-(4,4,5,5-tetramethyl-1,3,2-dioxaborolan-2-yl)pyridin-3-amine (1.0 equiv.) in DME (0.05 M) was added sodium carbonate (3.0 equiv., 2M) and purged with nitrogen. PdCl₂(dppf)-DCM adduct (0.06 equiv.) was added to the reaction and the system was flushed once again with nitrogen. The reaction was heated to 120° C. for 20 min in the microwave. The crude was partitioned between water and ethyl acetate, the organic layer was isolated, dried over sodium sulfate, filtered and concentrated. The crude material was purified via reverse phase chromatography (Grace system, 0-30% acetonitrile in water). Upon partial concentration, the precipitate was filtered off and dried under high vacuo to give 6-methyl-5-(6-(methylsulfonyl)-5-morpholinopyridazin-3-yl)pyridin-3-amine in 54% yield. LCMS (m/z) (M+H)=350.2, Rt=0.40 min.

Synthesis of 4-methyl-3-(6-(methylsulfonyl)-5-morpholinopyridazin-3-yl)aniline

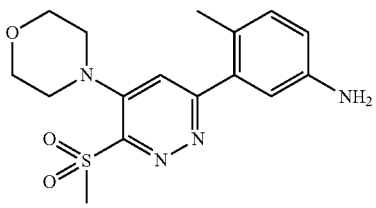 [SMILES: Cc1ccc(N)cc1-c1cc(N2CCOCC2)c(S(C)(=O)=O)nn1]

To a solution of 4-(6-chloro-3-(methylsulfonyl)pyridazin-4-yl)morpholine (1.0 equiv.) and 4-methyl-3-(4,4,5,5-tetramethyl-1,3,2-dioxaborolan-2-yl)aniline (1.0 equiv.) in DME (0.04 M) was added sodium carbonate (3.0 equiv., 2M) and purged with nitrogen. PdCl$_2$(dppf)-DCM adduct (0.06 equiv.) was added to the reaction and the system was flushed once again with nitrogen. The reaction was heated to 120° C. for 20 min in the microwave. The crude was partitioned between water and ethyl acetate, the organic layer was isolated, dried over sodium sulfate, filtered and concentrated. The crude material was purified via silica gel chromatography (5% methanol in DCM) to give 4-methyl-3-(6-(methylsulfonyl)-5-morpholinopyridazin-3-yl)aniline in 60% yield. LCMS (m/z) (M+H)=349.2, Rt=0.43 min.

Example 919: N-(6-methyl-5-(6-(methylsulfonyl)-5-morpholinopyridazin-3-yl)pyridin-3-yl)-3-(trifluoromethyl)benzamide

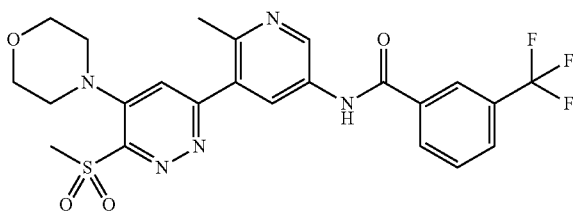 [SMILES: Cc1ncc(NC(=O)c2cc(C(F)(F)F)ccn2)cc1-c1cc(N2CCOCC2)c(S(C)(=O)=O)nn1]

To a solution of 6-methyl-5-(6-(methylsulfonyl)-5-morpholinopyridazin-3-yl)pyridin-3-amine (1.0 equiv.) in DMF was added DIEA (3.0 equiv.), 3-(trifluoromethyl)benzoic acid (1.0 equiv.) and HATU (1.0 equiv.) and the reaction was stirred at rt overnight. Partitioned between water and ethyl acetate, the organic layer was isolated and the aqueous layer was back-extracted with ethyl acetate. The combined organics were dried over sodium sulfate, filtered and concentrated. The crude material was dissolved in DMSO and purified via reverse phase HPLC. The pure fractions were lyophilized to give N-(6-methyl-5-(6-(methylsulfonyl)-5-morpholinopyridazin-3-yl)pyridin-3-yl)-3-(trifluoromethyl)benzamide in 35% yield. LCMS (m/z) (M+H)=522.1, Rt=0.68 min.

The compounds listed below were prepared using methods similar to those described for the preparation of Example 919 above using the appropriate starting materials.

Example 920: 2-(1,1-difluoroethyl)-N-(6-methyl-5-(6-(methylsulfonyl)-5-morpholinopyridazin-3-yl)pyridin-3-yl)isonicotinamide

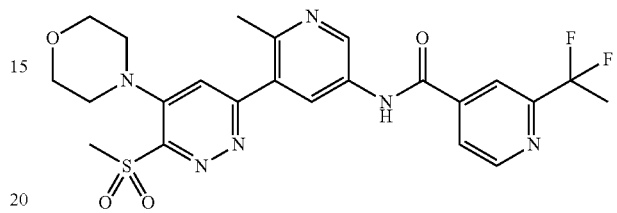

1H NMR (400 MHz, <dmso>) δ ppm 1.97-2.12 (m, 3H) 2.52-2.56 (m, 4H) 3.47-3.56 (m, 8H) 3.70-3.78 (m, 4H) 4.09 (br. s., 1H) 7.54 (s, 1H) 8.05 (d, J=4.70 Hz, 1H) 8.21 (s, 1H) 8.35 (d, J=2.35 Hz, 1H) 8.90 (d, J=5.09 Hz, 1H) 8.96 (d, J=2.35 Hz, 1H) 10.90-11.02 (m, 1H). LCMS (m/z) (M+H)=519.2, Rt=0.59 min.

Example 921: N-(6-methyl-5-(6-(methylsulfonyl)-5-morpholinopyridazin-3-yl)pyridin-3-yl)-2-(trifluoromethyl)isonicotinamide

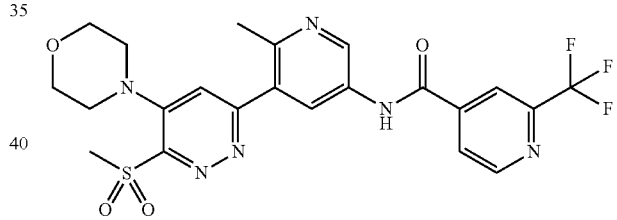

1H NMR (400 MHz, <dmso>) δ ppm 2.52-2.56 (m, 3H) 3.47-3.57 (m, 7H) 3.71-3.79 (m, 4H) 7.54 (s, 1H) 8.21 (d, J=4.69 Hz, 1H) 8.35 (d, J=2.35 Hz, 1H) 8.39 (s, 1H) 8.95 (d, J=2.35 Hz, 1H) 9.01 (d, J=4.70 Hz, 1H) 11.02 (s, 1H). LCMS (m/z) (M+H)=523.1, Rt=0.61 min.

Example 923: N-(6-methyl-5-(6-(methylsulfonyl)-5-morpholinopyridazin-3-yl)pyridin-3-yl)-4-(trifluoromethyl)picolinamide

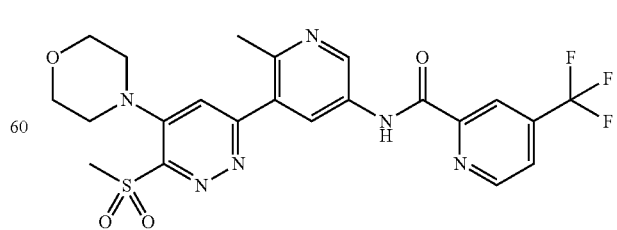

1H NMR (400 MHz, <dmso>) δ ppm 2.53 (s, 5H) 3.72-3.78 (m, 7H) 7.54 (s, 2H) 8.12 (d, J=4.69 Hz, 2H) 8.35

(s, 1H) 8.49 (d, J=2.35 Hz, 1H) 9.05 (d, J=4.70 Hz, 1H) 9.11 (d, J=2.35 Hz, 1H) 11.10-11.28 (m, 1H). LCMS (m/z) (M+H)=523.1, Rt=0.65 min.

Example 924: 2-(2-cyanopropan-2-yl)-N-(6-methyl-5-(6-(methylsulfonyl)-5-morpholinopyridazin-3-yl)pyridin-3-yl)isonicotinamide

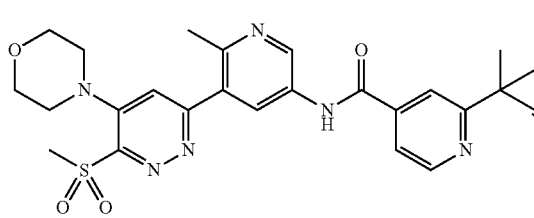

1H NMR (400 MHz, <dmso>) δ ppm 1.76 (s, 6H) 2.52-2.56 (m, 4H) 3.47-3.56 (m, 7H) 3.70-3.78 (m, 4H) 7.54 (s, 1H) 7.89 (dd, J=4.89, 1.37 Hz, 1H) 8.03 (s, 1H) 8.33 (d, J=1.96 Hz, 1H) 8.83 (d, J=5.09 Hz, 1H) 8.95 (d, J=2.35 Hz, 1H) 10.90 (s, 1H). LCMS (m/z) (M+H)=522.2, Rt=0.59 min.

Example 925: 2-(1,1-difluoropropyl)-N-(6-methyl-5-(6-(methylsulfonyl)-5-morpholinopyridazin-3-yl)pyridin-3-yl)isonicotinamide

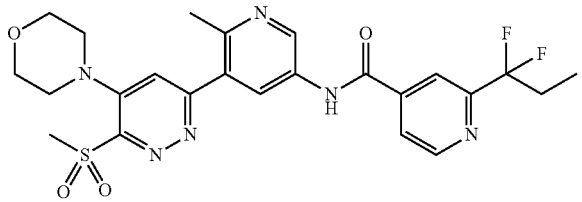 [SMILES: CCC(F)(F)c1cc(C(=O)Nc2cnc(C)c(-c3cc(N4CCOCC4)c(S(C)(=O)=O)nn3)c2)ccn1]

1H NMR (400 MHz, <dmso>) δ ppm 0.93 (t, J=7.63 Hz, 3H) 2.26-2.42 (m, 2H) 2.53 (s, 3H) 3.47-3.57 (m, 7H) 3.67-3.81 (m, 4H) 7.54 (s, 1H) 8.04 (d, J=3.91 Hz, 1H) 8.19 (s, 1H) 8.35 (d, J=2.35 Hz, 1H) 8.91 (d, J=4.70 Hz, 1H) 8.96 (d, J=2.35 Hz, 1H) 10.97 (s, 1H). LCMS (m/z) (M+H)= 533.1, Rt=0.64 min.

Example 926: 2-(1,1-difluoropropyl)-N-(4-methyl-3-(6-(methylsulfonyl)-5-morpholinopyridazin-3-yl)phenyl)isonicotinamide

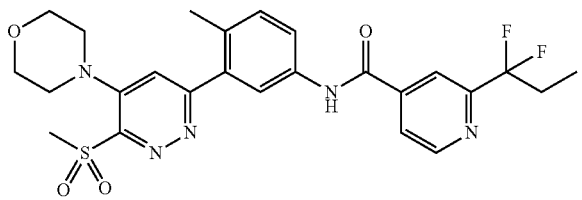 [SMILES: CCC(F)(F)c1cc(C(=O)Nc2ccc(C)c(-c3cc(N4CCOCC4)c(S(C)(=O)=O)nn3)c2)ccn1]

1H NMR (400 MHz, <dmso>) δ ppm 0.93 (t, J=7.43 Hz, 3H) 2.31 (s, 3H) 2.33-2.42 (m, 2H) 3.52 (s, 4H) 3.69-3.78 (m, 4H) 7.35-7.44 (m, 2H) 7.81 (dd, J=8.41, 2.15 Hz, 1H) 7.90 (d, J=2.35 Hz, 1H) 8.02 (d, J=4.30 Hz, 1H) 8.16 (s, 1H) 8.88 (d, J=5.09 Hz, 1H) 10.61-10.77 (m, 1H). LCMS (m/z) (M+H)=532.1, Rt=0.78 min.

Example 927: 2-(2-fluoropropan-2-yl)-N-(6-methyl-5-(6-(methylsulfonyl)-5-morpholinopyridazin-3-yl)pyridin-3-yl)isonicotinamide

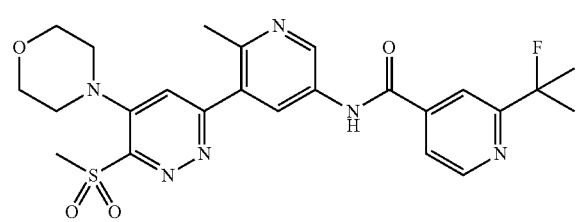 [SMILES: Cc1ncc(NC(=O)c2ccnc(C(C)(C)F)c2)cc1-c1cc(N2CCOCC2)c(S(C)(=O)=O)nn1]

1H NMR (400 MHz, <dmso>) δ ppm 1.67 (s, 3H) 1.72 (s, 3H) 3.74 (d, J=4.70 Hz, 4H) 7.53 (s, 1H) 7.84 (d, J=5.09 Hz, 1H) 8.05 (s, 1H) 8.33 (d, J=2.35 Hz, 1H) 8.77 (d, J=4.70 Hz, 1H) 8.94 (d, J=2.74 Hz, 1H) 10.87 (s, 1H). LCMS (m/z) (M+H)=515.2, Rt=0.59 min.

Example 928: 2-(2-fluoropropan-2-yl)-N-(4-methyl-3-(6-(methylsulfonyl)-5-morpholinopyridazin-3-yl)phenyl)isonicotinamide

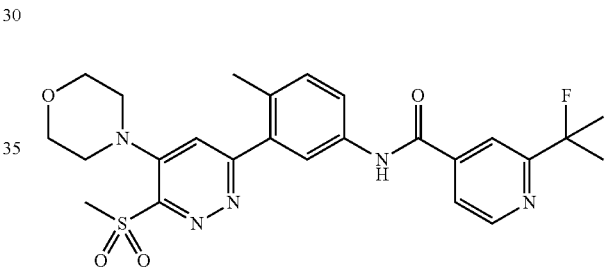

1H NMR (400 MHz, <dmso>) δ ppm 1.57-1.77 (m, 7H) 2.31 (s, 3H) 7.29-7.46 (m, 2H) 7.77-7.84 (m, 2H) 7.90 (d, J=1.96 Hz, 1H) 7.94-8.07 (m, 1H) 8.75 (d, J=5.09 Hz, 1H) 10.64 (s, 1H). LCMS (m/z) (M+H)=514.1, Rt=0.72 min.

Example 929: 2-(1,1-difluoroethyl)-N-(4-methyl-3-(6-(methylsulfonyl)-5-morpholinopyridazin-3-yl)phenyl)isonicotinamide

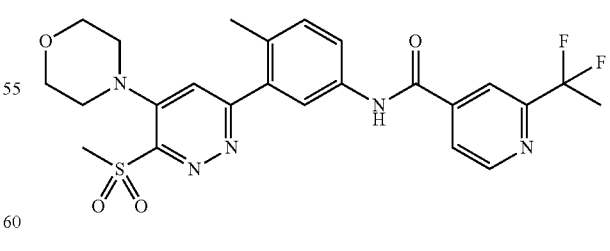

1H NMR (400 MHz, <dmso>) δ ppm 1.95-2.11 (m, 3H) 2.28-2.34 (m, 3H) 3.43-3.57 (m, 7H) 3.69-3.78 (m, 4H) 7.34-7.45 (m, 2H) 7.81 (dd, J=8.22, 1.96 Hz, 1H) 7.91 (d, J=2.35 Hz, 1H) 7.99-8.05 (m, 1H) 8.18 (s, 1H) 8.77-8.95 (m, 1H) 10.72 (s, 1H). LCMS (m/z) (M+H)=518.1, Rt=0.74 min.

Example 930: N-(4-methyl-3-(6-(methylsulfonyl)-5-morpholinopyridazin-3-yl)phenyl)-2-trifluoromethyl)isonicotinamide

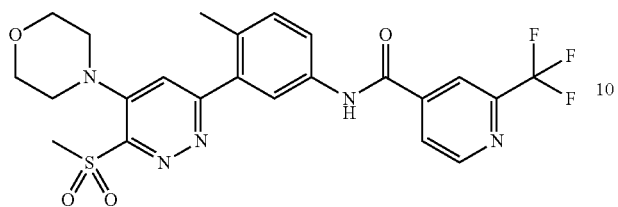

1H NMR (400 MHz, <dmso>) δ ppm 2.27-2.36 (m, 3H) 3.43-3.56 (m, 8H) 7.27-7.51 (m, 2H) 7.80 (dd, J=8.22, 2.35 Hz, 1H) 7.90 (d, J=1.96 Hz, 1H) 8.10-8.27 (m, 1H) 8.29-8.45 (m, 1H) 8.89-9.06 (m, 1H) 10.77 (s, 1H). LCMS (m/z) (M+H)=522.1, Rt=0.76 min.

Example 931: 2-(2-cyanopropan-2-yl)-N-(4-methyl-3-(6-(methylsulfonyl)-5-morpholinopyridazin-3-yl)phenyl)isonicotinamide

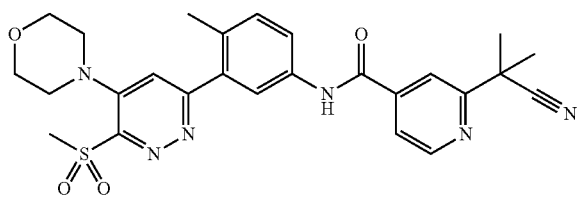 [SMILES: Cc1ccc(NC(=O)c2ccnc(C(C)(C)C#N)c2)cc1-c1cc(N2CCOCC2)c(S(C)(=O)=O)nn1]

1H NMR (400 MHz, <dmso>) δ ppm 1.66-1.83 (m, 8H) 2.32 (s, 4H) 3.49 (d, J=4.70 Hz, 5H) 3.72-3.78 (m, 6H) 7.36-7.45 (m, 2H) 7.79 (dd, J=8.22, 1.96 Hz, 1H) 7.83-7.91 (m, 2H) 7.94-8.06 (m, 1H) 8.70-8.87 (m, 1H) 10.57-10.71 (m, 1H). LCMS (m/z) (M+H)=521.1, Rt=0.72 min.

Example 932: 2-(2-hydroxypropan-2-yl)-N-(4-methyl-3-(6-(methylsulfonyl)-5-morpholinopyridazin-3-yl)phenyl)isonicotinamide

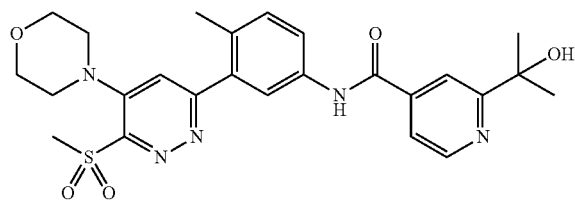 [SMILES: Cc1ccc(NC(=O)c2ccnc(C(C)(C)O)c2)cc1-c1cc(N2CCOCC2)c(S(C)(=O)=O)nn1]

1H NMR (400 MHz, <dmso>) δ ppm 1.48 (s, 6H) 2.27-2.34 (m, 3H) 3.42-3.57 (m, 7H) 3.69-3.80 (m, 4H) 7.34-7.44 (m, 2H) 7.73 (dd, J=4.89, 1.37 Hz, 1H) 7.80 (dd, J=8.22, 2.35 Hz, 1H) 7.90 (d, J=1.96 Hz, 1H) 8.16 (s, 1H) 8.68 (d, J=5.09 Hz, 1H) 10.62 (s, 1H). LCMS (m/z) (M+H)= 512.1, Rt=0.55 min.

Example 933: N-(4-methyl-3-(6-(methylsulfonyl)-5-morpholinopyridazin-3-yl)phenyl)-4-(trifluoromethyl)picolinamide

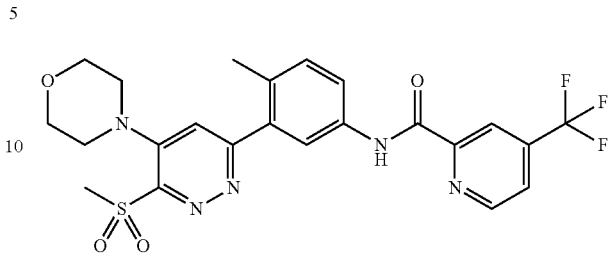

1H NMR (400 MHz, <dmso>) δ ppm 2.25-2.37 (m, 3H) 3.37-3.62 (m, 7H) 3.66-3.84 (m, 4H) 7.29-7.47 (m, 2H) 7.96 (dd, J=8.41, 2.15 Hz, 1H) 8.05 (d, J=2.35 Hz, 1H) 8.09 (d, J=3.91 Hz, 1H) 8.33 (s, 1H) 9.02 (d, J=4.70 Hz, 1H) 10.80-10.91 (m, 1H). LCMS (m/z) (M+H)=522.1, Rt=0.83 min.

Example 934: N-(5-(6-methoxy-5-morpholinopyridin-3-yl)-6-methylpyridazin-3-yl)-3-(trifluoromethyl)benzamide

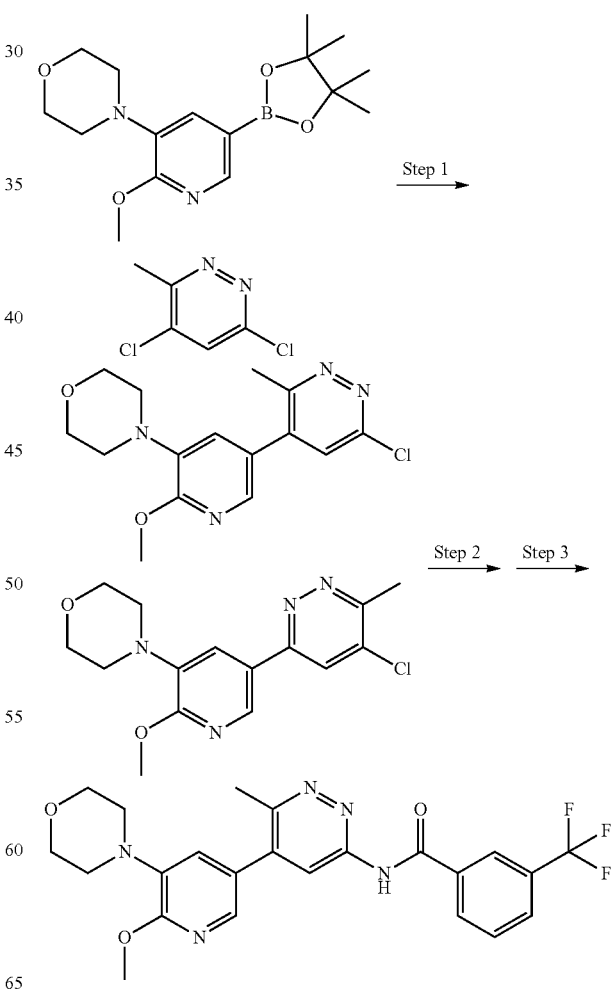

Step 1:

To a degassed mixture of 4-(2-methoxy-5-(4,4,5,5-tetramethyl-1,3,2-dioxaborolan-2-yl)pyridin-3-yl)morpholine (1.0 equiv.) and 4,6-dichloro-3-methylpyridazine (1.0 equiv.) in 4:1 1,4-dioxane:water (0.2 M) was added cesium carbonate (3.0 equiv.), Pd(OAc)$_2$ (0.1 equiv.) and tri-t-butylphosphine (1.0 M in toluene, 0.2 equiv.). The reaction mixture was stirred at 75° C. for 5 hr. LC-MS shows a mixture of isomeric products. The cooled reaction mixture was diluted with water and extracted with ethyl acetate (2×). The combined extracts were dried over sodium sulfate, filtered, concentrated, and purified by flash chromatography over silica gel (ISCO, ethyl acetate with 0-5% methanol gradient) to give 4-(5-(6-chloro-3-methylpyridazin-4-yl)-2-methoxypyridin-3-yl)morpholine in 68% yield as a light brown, crystalline solid. The minor isomer is also present (20%). LCMS (m/z) (M+H)=321.0, Rt=0.66 min.

Step 2:

To a solution of 4-(5-(6-chloro-3-methylpyridazin-4-yl)-2-methoxypyridin-3-yl)morpholine and 4-(5-(5-chloro-6-methylpyridazin-3-yl)-2-methoxypyridin-3-yl)morpholine (1.0 equiv.) in 1,4-dioxane (0.2 M) was added ammonium hydroxide (32 equiv.) and the mixture was stirred at 140° C. overnight. Upon overnight stirring, an additional 32 equiv. of ammonium hydroxide was added and the mixture was stirred at 175° C. for 3 days. The reaction was concentrated to dryness to give 5-(6-methoxy-5-morpholinopyridin-3-yl)-6-methylpyridazin-3-amine and 6-(6-methoxy-5-morpholinopyridin-3-yl)-3-methylpyridazin-4-amine as a mixture of isomers (1:1 ratio). LCMS (m/z) (M+H)=301.9, Rt=0.45 and 0.47 min.

Step 3:

To a solution of 5-(6-methoxy-5-morpholinopyridin-3-yl)-6-methylpyridazin-3-amine and 6-(6-methoxy-5-morpholinopyridin-3-yl)-3-methylpyridazin-4-amine (1.0 equiv, mixture of isomers) in DCM (0.1 M) was added DIEA (5.0 equiv.) and 3-(trifluoromethyl)benzoyl chloride (2.2 equiv.). The mixture was stirred at ambient temperature. LC-MS at 4 hr showed partial conversion to product. An additional 3.00 equiv of DIEA and 1.3 equiv of acyl chloride were added. The reaction was stirred for 7 days at ambient temperature. The reaction mixture was quenched with saturated aqueous sodium bicarbonate and extracted with DCM (2×). The combined extracts were dried over sodium sulfate, filtered, and concentrated. The crude product was purified by reverse phase HPLC and lyophilized to give N-(5-(6-methoxy-5-morpholinopyridin-3-yl)-6-methylpyridazin-3-yl)-3-(trifluoromethyl)benzamide in 28% yield as its TFA salt, a yellow solid. $^1$H NMR (400 MHz, <cd3od>) δ ppm 2.76 (s, 3H) 3.15-3.23 (m, 4H) 3.83-3.93 (m, 4H) 4.08 (s, 3H) 7.39 (d, J=2.35 Hz, 1H) 7.76-7.85 (m, 1H) 7.95-8.02 (m, 2H) 8.31 (d, J=8.22 Hz, 1H) 8.37 (s, 1H) 8.70 (s, 1H). LCMS (m/z) (M+H)=474.1, Rt=0.85 min.

Example 935: N-(6'-(2,2-difluoroethoxy)-2-methyl-5'-morpholino-[3,3'-bipyridin]-5-yl)-5-(trifluoromethyl)nicotinamide

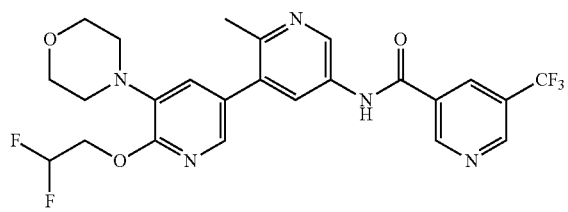 [SMILES: Cc1ncc(NC(=O)c2cncc(C(F)(F)F)c2)cc1-c1cnc(OCC(F)F)c(N2CCOCC2)c1]

$^1$H NMR (400 MHz, <dmso>) δ ppm 3.08 (d, J=3.91 Hz, 4H) 3.69-3.75 (m, 4H) 4.64 (td, J=15.16, 3.33 Hz, 2H) 6.21-6.64 (m, 1H) 7.32 (d, J=1.96 Hz, 1H) 7.83 (d, J=1.96 Hz, 1H) 8.17 (d, J=1.96 Hz, 1H) 8.70 (s, 1H) 8.91-9.01 (m, 1H) 9.21 (s, 1H) 9.39 (d, J=1.57 Hz, 1H) 11.00 (s, 1H). LCMS (m/z) (M+H)=524.3, Rt=0.74 min.

Example 936: 6-(1-cyanocyclopropyl)-N-(6'-(2,2-difluoroethoxy)-2-methyl-5'-morpholino-[3,3'-bipyridin]-5-yl)pyridazine-4-carboxamide

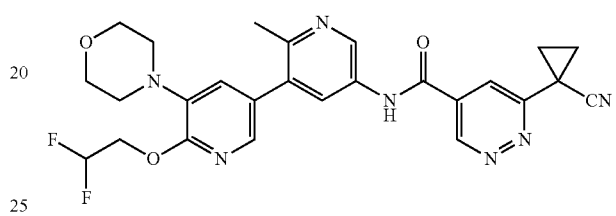

$^1$H NMR (400 MHz, <dmso>) δ ppm 1.87-1.96 (m, 2H) 2.00-2.08 (m, 2H) 3.07 (br. s., 4H) 3.70-3.75 (m, 4H) 4.64 (d, J=3.52 Hz, 2H) 6.26-6.63 (m, 1H) 7.29 (d, J=1.96 Hz, 1H) 7.81 (d, J=1.96 Hz, 1H) 8.06 (dd, J=4.50, 2.15 Hz, 2H) 8.87 (d, J=2.35 Hz, 1H) 9.56 (d, J=1.96 Hz, 1H) 11.03 (s, 1H). LCMS (m/z) (M+H)=522.1, Rt=0.68 min.

Example 937: N-(2-methyl-5'-morpholino-6'-((tetrahydro-2H-pyran-4-yl)oxy)-[3,3'-bipyridin]-5-yl)-3-(methylsulfonyl)benzamide

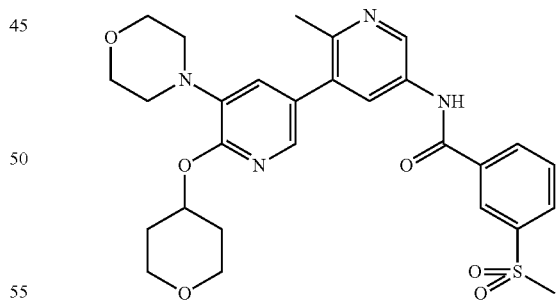

$^1$H NMR (400 MHz, <cd3od>) δ ppm 1.86 (dtd, J=12.67, 8.34, 8.34, 3.91 Hz, 2H) 2.08-2.22 (m, 2H) 2.71 (s, 3H) 3.15-3.26 (m, 7H) 3.69 (ddd, J=11.64, 8.31, 3.13 Hz, 2H) 3.82-3.93 (m, 4H) 3.94-4.06 (m, 2H) 5.46 (tt, J=7.92, 3.81 Hz, 1H) 7.34 (d, J=2.35 Hz, 1H) 7.82-7.92 (m, 2H) 8.25 (d, J=8.22 Hz, 1H) 8.36 (d, J=7.83 Hz, 1H) 8.48 (d, J=2.35 Hz, 1H) 8.61 (s, 1H) 9.36 (d, J=2.35 Hz, 1H). LCMS (m/z) (M+H)=553.1, Rt=0.61 min.

Example 938: 2-(1,1-difluoroethyl)-N-(2-methyl-5'-morpholino-6'-((tetrahydro-2H-pyran-4-yl)oxy)-[3,3'-bipyridin]-5-yl)isonicotinamide

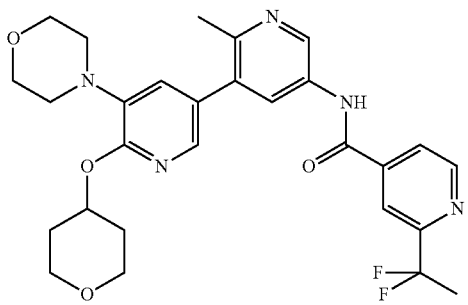 [SMILES: Cc1ncc(NC(=O)c2ccnc(C(C)(F)F)c2)cc1-c1cnc(OC2CCOCC2)c(N2CCOCC2)c1]

¹H NMR (400 MHz, <cd3od>) δ ppm 1.86 (dtd, J=12.67, 8.34, 8.34, 3.91 Hz, 2H) 2.07 (t, J=18.78 Hz, 3H) 2.12-2.22 (m, 2H) 2.71 (s, 3H) 3.16-3.23 (m, 4H) 3.69 (ddd, J=11.64, 8.31, 3.13 Hz, 2H) 3.83-3.93 (m, 4H) 3.94-4.07 (m, 2H) 5.46 (tt, J=7.83, 3.91 Hz, 1H) 7.33 (d, J=2.35 Hz, 1H) 7.87 (d, J=1.96 Hz, 1H) 8.04 (d, J=4.30 Hz, 1H) 8.27 (s, 1H) 8.46 (d, J=2.35 Hz, 1H) 8.88 (d, J=5.09 Hz, 1H) 9.34 (d, J=2.35 Hz, 1H). LCMS (m/z) (M+H)=540.1, Rt=0.69 min.

Example 939: 2-(2-hydroxypropan-2-yl)-N-(2-methyl-5'-morpholino-6'-((tetrahydro-2H-pyran-4-yl)oxy)-[3,3'-bipyridin]-5-yl)isonicotinamide

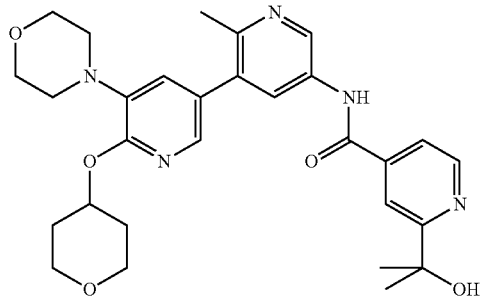 [SMILES: Cc1ncc(NC(=O)c2ccnc(C(C)(C)O)c2)cc1-c1cnc(OC2CCOCC2)c(N2CCOCC2)c1]

¹H NMR (400 MHz, <cd3od>) δ ppm 1.64 (s, 6H) 1.76-1.91 (m, 2H) 2.06-2.20 (m, 2H) 2.70 (s, 3H) 3.10-3.23 (m, 4H) 3.66 (ddd, J=11.64, 8.31, 3.13 Hz, 2H) 3.80-3.91 (m, 4H) 3.91-4.04 (m, 2H) 5.44 (tt, J=7.83, 3.91 Hz, 1H) 7.32 (d, J=1.96 Hz, 1H) 7.85 (d, J=2.35 Hz, 1H) 8.03 (dd, J=5.48, 1.57 Hz, 1H) 8.39 (s, 1H) 8.51 (d, J=2.35 Hz, 1H) 8.78 (d, J=5.48 Hz, 1H) 9.36 (d, J=2.35 Hz, 1H). LCMS (m/z) (M+H)=534.2, Rt=0.53 min.

Example 940: 2-(1-cyanocyclopropyl)-N-(2-methyl-5'-morpholino-6'-((tetrahydro-2H-pyran-4-yl)oxy)-[3,3'-bipyridin]-5-yl)isonicotinamide

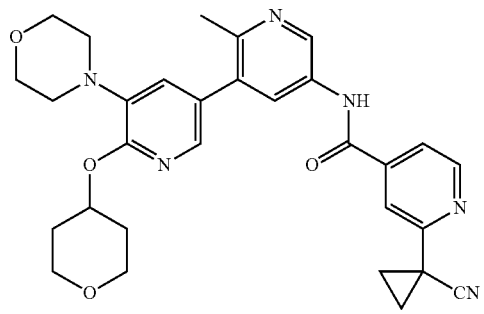 [SMILES: Cc1ncc(NC(=O)c2ccnc(C3(C#N)CC3)c2)cc1-c1cnc(OC2CCOCC2)c(N2CCOCC2)c1]

¹H NMR (400 MHz, <cd3od>) δ ppm 1.77-1.94 (m, 6H) 2.07-2.23 (m, 2H) 2.67 (s, 3H) 3.15-3.23 (m, 4H) 3.69 (ddd, J=11.64, 8.31, 3.13 Hz, 2H) 3.83-3.93 (m, 4H) 3.94-4.05 (m, 2H) 5.46 (dt, J=8.12, 3.96 Hz, 1H) 7.33 (d, J=1.96 Hz, 1H) 7.78 (dd, J=5.09, 1.57 Hz, 1H) 7.86 (d, J=2.35 Hz, 1H) 8.17 (s, 1H) 8.39 (d, J=2.35 Hz, 1H) 8.71 (d, J=5.09 Hz, 1H) 9.24 (d, J=1.96 Hz, 1H). LCMS (m/z) (M+H)=531.2, Rt=0.68 min.

Example 941: 2-cyclopropyl-N-(2-methyl-5'-morpholino-6'-((tetrahydro-2H-pyran-4-yl)oxy)-[3,3'-bipyridin]-5-yl)isonicotinamide

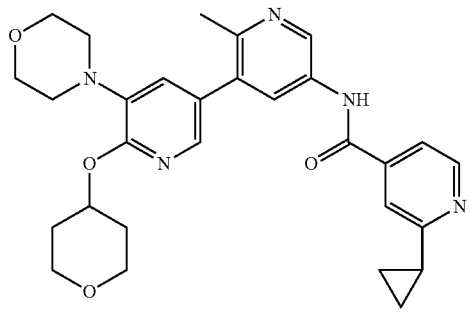 [SMILES: Cc1ncc(NC(=O)c2ccnc(C3CC3)c2)cc1-c1cnc(OC2CCOCC2)c(N2CCOCC2)c1]

¹H NMR (400 MHz, <cd3od>) δ ppm 1.07-1.18 (m, 2H) 1.22 (dt, J=8.02, 3.03 Hz, 2H) 1.86 (dtd, J=12.77, 8.29, 8.29, 3.91 Hz, 2H) 2.08-2.21 (m, 2H) 2.23-2.36 (m, 1H) 2.71 (s, 3H) 3.15-3.24 (m, 4H) 3.68 (ddd, J=11.54, 8.22, 3.33 Hz, 2H) 3.82-3.93 (m, 4H) 3.94-4.06 (m, 2H) 5.46 (tt, J=7.83, 3.91 Hz, 1H) 7.33 (d, J=1.96 Hz, 1H) 7.81 (dd, J=5.48, 1.57 Hz, 1H) 7.87 (d, J=2.35 Hz, 2H) 8.46 (d, J=2.35 Hz, 1H) 8.65 (d, J=5.48 Hz, 1H) 9.34 (d, J=2.35 Hz, 1H). LCMS (m/z) (M+H)=516.2, Rt=0.56 min.

Example 942: N-(2-methyl-5'-morpholino-6'-((tetrahydro-2H-pyran-4-yl)oxy)-[3,3'-bipyridin]-5-yl)-4-(trifluoromethyl)picolinamide

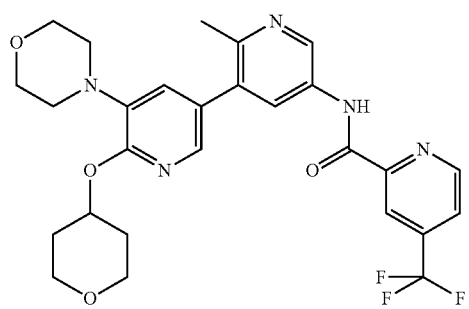 [SMILES: Cc1ncc(NC(=O)c2cc(C(F)(F)F)ccn2)cc1-c1cnc(OC2CCOCC2)c(N2CCOCC2)c1]

¹H NMR (400 MHz, <cd3od>) δ ppm 1.87 (dtd, J=12.67, 8.34, 8.34, 3.91 Hz, 2H) 2.10-2.22 (m, 2H) 2.71 (s, 3H) 3.16-3.24 (m, 4H) 3.69 (ddd, J=11.64, 8.31, 3.13 Hz, 2H) 3.84-3.94 (m, 4H) 3.94-4.06 (m, 2H) 5.47 (dt, J=8.12, 3.96 Hz, 1H) 7.35 (d, J=1.96 Hz, 1H) 7.89 (d, J=1.96 Hz, 1H) 8.01 (d, J=3.91 Hz, 1H) 8.51 (s, 1H) 8.69 (d, J=2.35 Hz, 1H) 9.03 (d, J=5.09 Hz, 1H) 9.44 (d, J=2.35 Hz, 1H). LCMS (m/z) (M+H)=544.2, Rt=0.75 min.

Example 943: 4-(2-cyanopropan-2-yl)-N-(2-methyl-5'-morpholino-6'-((tetrahydro-2H-pyran-4-yl)oxy)-[3,3'-bipyridin]-5-yl)picolinamide

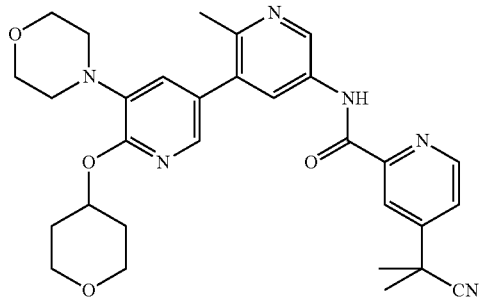 [SMILES: Cc1ncc(NC(=O)c2cc(C(C)(C)C#N)ccn2)cc1-c1cnc(OC2CCOCC2)c(N2CCOCC2)c1]

¹H NMR (400 MHz, <cd3od>) δ ppm 1.76-1.93 (m, 8H) 2.09-2.22 (m, 2H) 2.71 (s, 3H) 3.16-3.25 (m, 4H) 3.69 (ddd, J=11.64, 8.31, 3.13 Hz, 2H) 3.83-3.94 (m, 4H) 3.94-4.05 (m, 2H) 5.47 (dt, J=7.83, 3.91 Hz, 1H) 7.35 (d, J=1.96 Hz, 1H) 7.85 (dd, J=5.09, 1.96 Hz, 1H) 7.89 (d, J=2.35 Hz, 1H) 8.44 (d, J=1.57 Hz, 1H) 8.69 (d, J=2.35 Hz, 1H) 8.82 (d, J=5.09 Hz, 1H) 9.45 (d, J=2.35 Hz, 1H). LCMS (m/z) (M+H)= 543.3, Rt=0.70 min.

Example 944: 6-(1-cyanocyclopropyl)-N-(2-methyl-5'-morpholino-6'-((tetrahydro-2H-pyran-4-yl)oxy)-[3,3'-bipyridin]-5-yl)pyridazine-4-carboxamide

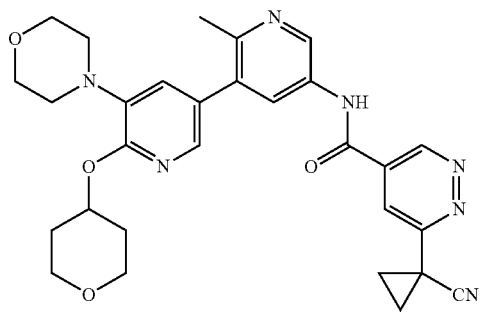 [SMILES: Cc1ncc(NC(=O)c2cnnc(C3(C#N)CC3)c2)cc1-c1cnc(OC2CCOCC2)c(N2CCOCC2)c1]

¹H NMR (400 MHz, <cd3od>) δ ppm 1.87 (dtd, J=12.77, 8.29, 8.29, 3.91 Hz, 2H) 1.99-2.11 (m, 4H) 2.11-2.21 (m, 2H) 2.64-2.69 (m, 3H) 3.16-3.22 (m, 4H) 3.69 (ddd, J=11.44, 8.31, 3.33 Hz, 2H) 3.83-3.93 (m, 4H) 3.94-4.05 (m, 2H) 5.46 (dt, J=7.83, 3.91 Hz, 1H) 7.32 (d, J=1.96 Hz, 1H) 7.85 (d, J=1.96 Hz, 1H) 8.36 (d, J=1.96 Hz, 2H) 9.20 (d, J=2.35 Hz, 1H) 9.59 (d, J=1.96 Hz, 1H). LCMS (m/z) (M+H)=542.2, Rt=0.61 min.

Synthesis of 3-(6-isopropoxy-5-morpholinopyridin-3-yl)-4-methylaniline

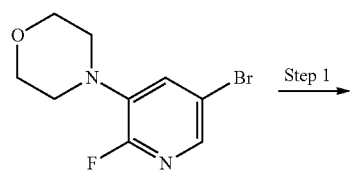

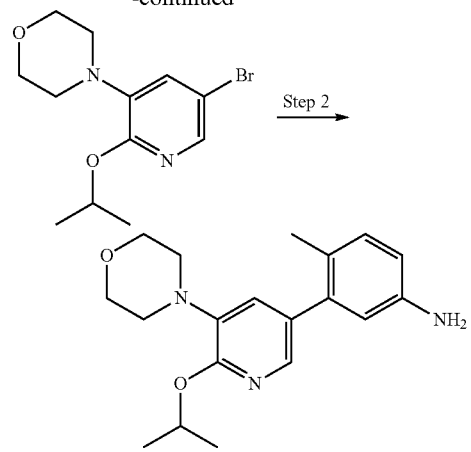

Step 1:
Sodium hydride (3.0 equiv.) was added to 2-propanol (0.4M) at rt and the mixture was stirred for 20 min at 90° C. The reaction was cooled to rt and 4-(5-bromo-2-fluoropyridin-3-yl)morpholine (1.0 equiv.) was added. The mixture was stirred at 90° C. for 1.5 hours. The cooled reaction was poured into water and extracted with ethyl acetate (2×). The combined extracts were dried over sodium sulfate, filtered and concentrated. The crude material was purified via silica gel chromatography (DCM with 0-10% methanol) to give 4-(5-bromo-2-isopropoxypyridin-3-yl)morpholine as a yellow green oil. LCMS (m/z) (M+H)=301/303.1, Rt=0.99 min.

Step 2:
To a degassed mixture of 4-(5-bromo-2-isopropoxypyridin-3-yl)morpholine (1.0 equiv.) and 4-methyl-3-(4,4,5,5-tetramethyl-1,3,2-dioxaborolan-2-yl)aniline (1.2 equiv.) and 2M aqueous sodium carbonate (3.0 equiv.) in DME (0.18 M) was added PdCl₂(dppf)-DCM adduct (0.1 equiv.) and the reaction mixture was heated in the microwave at 120° C. for 15 min. The cooled reaction mixture was diluted with water and extracted with ethyl acetate. The combined organics were dried over sodium sulfate, filtered and concentrated. The crude product was purified via silica gel flash chromatography (10-70% ethyl acetate/heptanes) to give 3-(6-isopropoxy-5-morpholinopyridin-3-yl)-4-methylaniline as a yellow oil in 37% yield. LCMS (m/z) (M+H)=328.0, Rt=0.65 min.

Synthesis of 6'-isopropoxy-2-methyl-5'-morpholino-[3,3'-bipyridin]-5-amine

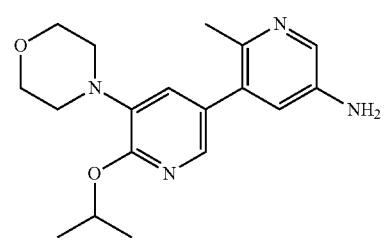 [SMILES: Cc1ncc(N)cc1-c1cnc(OC(C)C)c(N2CCOCC2)c1]

To a solution of 4-(5-bromo-2-isopropoxypyridin-3-yl)morpholine (1.0 equiv.) and 6-methyl-5-(4,4,5,5-tetramethyl-1,3,2-dioxaborolan-2-yl)pyridin-3-amine (1.2 equiv.)

in DME (0.18 M) was added PdCl$_2$(dppf)-DCM adduct (0.1 equiv.) and 2M aqueous sodium carbonate (3.0 equiv.) and the mixture was heated to 125° C. for 20 min the microwave followed by 130° C. for 15 min. The cooled reaction mixture was diluted with water and extracted with ethyl acetate. The combined organics were dried over sodium sulfate, filtered and concentrated. The crude product was purified via silica gel chromatography (ethyl acetate/5-15% methanol) to give 6'-isopropoxy-2-methyl-5'-morpholino-[3,3'-bipyridin]-5-amine as a purple oil in 54% yield. LCMS (m/z) (M+H)= 329.2, Rt=0.60 min.

Example 945: 2-(1,1-difluoroethyl)-N-(3-(6-isopropoxy-5-morpholinopyridin-3-yl)-4-methylphenyl)isonicotinamide

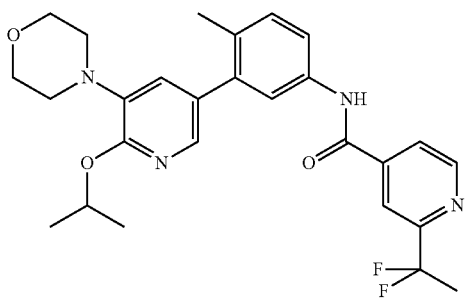 [SMILES: Cc1ccc(NC(=O)c2ccnc(C(C)(F)F)c2)cc1-c1cnc(OC(C)C)c(N2CCOCC2)c1]

$^1$H NMR (400 MHz, <cd3od>) δ ppm 1.43 (d, J=6.26 Hz, 6H) 2.05 (t, J=18.78 Hz, 3H) 2.29 (s, 3H) 3.15-3.24 (m, 4H) 3.83-3.95 (m, 4H) 5.42 (dt, J=12.23, 6.21 Hz, 1H) 7.29 (d, J=2.35 Hz, 1H) 7.33 (d, J=9.39 Hz, 1H) 7.61-7.67 (m, 2H) 7.79 (d, J=2.35 Hz, 1H) 7.95-8.00 (m, 1H) 8.19 (s, 1H) 8.81 (d, J=5.09 Hz, 1H). LCMS (m/z) (M+H)=497.1, Rt=1.06 min.

Example 946: 2-(2-fluoropropan-2-yl)-N-(3-(6-isopropoxy-5-morpholinopyridin-3-yl)-4-methylphenyl)isonicotinamide

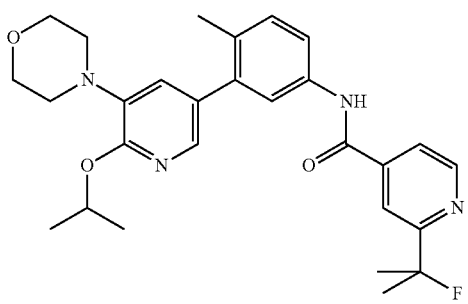 [SMILES: Cc1ccc(NC(=O)c2ccnc(C(C)(C)F)c2)cc1-c1cnc(OC(C)C)c(N2CCOCC2)c1]

$^1$H NMR (400 MHz, <cd3od>) δ ppm 1.43 (d, J=6.26 Hz, 6H) 1.69-1.81 (m, 6H) 2.29 (s, 3H) 3.17-3.26 (m, 4H) 3.84-3.94 (m, 4H) 5.42 (quin, J=6.16 Hz, 1H) 7.29-7.36 (m, 2H) 7.60-7.66 (m, 2H) 7.80 (d, J=2.35 Hz, 1H) 7.83 (dd, J=5.28, 1.76 Hz, 1H) 8.08-8.12 (m, 1H) 8.69-8.75 (m, 1H). LCMS (m/z) (M+H)=493.1, Rt=1.05 min.

Example 947: 2-(2-hydroxypropan-2-yl)-N-(3-(6-isopropoxy-5-morpholinopyridin-3-yl)-4-methylphenyl)isonicotinamide

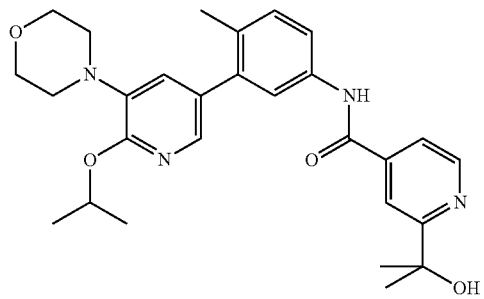 [SMILES: Cc1ccc(NC(=O)c2ccnc(C(C)(C)O)c2)cc1-c1cnc(OC(C)C)c(N2CCOCC2)c1]

$^1$H NMR (400 MHz, <cd3od>) δ ppm 1.42 (d, J=6.26 Hz, 6H) 1.70 (s, 6H) 2.30 (s, 3H) 3.09-3.21 (m, 4H) 3.81-3.93 (m, 4H) 5.41 (quin, J=6.16 Hz, 1H) 7.22 (d, J=1.96 Hz, 1H) 7.35 (d, J=8.22 Hz, 1H) 7.63 (d, J=2.35 Hz, 1H) 7.68 (dd, J=8.22, 2.35 Hz, 1H) 7.75 (d, J=1.96 Hz, 1H) 8.18 (dd, J=5.67, 1.76 Hz, 1H) 8.46 (dd, J=1.57, 0.78 Hz, 1H) 8.77-8.81 (m, 1H). LCMS (m/z) (M+H)=491.1, Rt=0.81 min.

Example 948: 4-(2-cyanopropan-2-yl)-N-(3-(6-isopropoxy-5-morpholinopyridin-3-yl)-4-methylphenyl)picolinamide

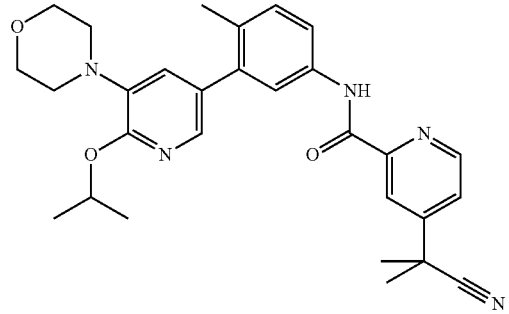 [SMILES: Cc1ccc(NC(=O)c2cc(C(C)(C)C#N)ccn2)cc1-c1cnc(OC(C)C)c(N2CCOCC2)c1]

$^1$H NMR (400 MHz, <cd3od>) δ ppm 1.44 (d, J=6.26 Hz, 6H) 1.81 (s, 6H) 2.29 (s, 3H) 3.21 (dd, J=5.48, 3.91 Hz, 4H) 3.83-3.94 (m, 4H) 5.43 (quin, J=6.16 Hz, 1H) 7.29-7.37 (m, 2H) 7.68-7.74 (m, 2H) 7.76-7.82 (m, 2H) 8.37 (dd, J=1.96, 0.78 Hz, 1H) 8.73-8.78 (m, 1H). LCMS (m/z) (M+H)= 500.1, Rt=1.11 min.

Example 949: 4-(2-hydroxypropan-2-yl)-N-(3-(6-isopropoxy-5-morpholinopyridin-3-yl)-4-methylphenyl)picolinamide

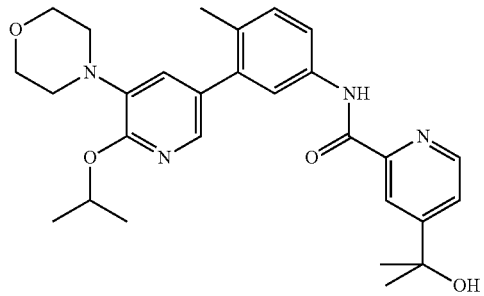 [SMILES: Cc1ccc(NC(=O)c2cc(C(C)(C)O)ccn2)cc1-c1cnc(OC(C)C)c(N2CCOCC2)c1]

$^1$H NMR (400 MHz, <cd3od>) δ ppm 1.44 (d, J=6.26 Hz, 6H) 1.58 (s, 6H) 2.29 (s, 3H) 3.22 (dd, J=5.48, 3.91 Hz, 4H)

3.86-3.95 (m, 4H) 5.43 (quin, J=6.16 Hz, 1H) 7.31-7.36 (m, 2H) 7.67-7.74 (m, 2H) 7.76 (dd, J=5.28, 1.76 Hz, 1H) 7.81 (d, J=2.35 Hz, 1H) 8.38 (dd, J=1.96, 0.78 Hz, 1H) 8.64-8.68 (m, 1H). LCMS (m/z) (M+H)=491.1, Rt=1.00 min.

Example 950: N-(3-(6-isopropoxy-5-morpholin-opyridin-3-yl)-4-methylphenyl)-2-(methylsulfonyl)isonicotinamide

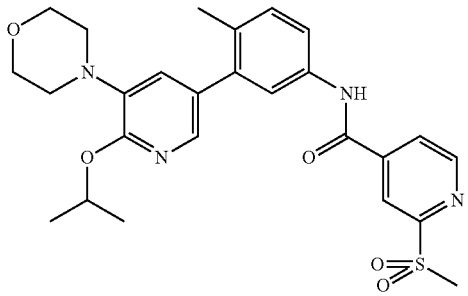 [SMILES: Cc1ccc(NC(=O)c2ccnc(S(C)(=O)=O)c2)cc1-c1cnc(OC(C)C)c(N2CCOCC2)c1]

$^1$H NMR (400 MHz, <cd3od>) δ ppm 1.43 (d, J=6.26 Hz, 6H) 2.30 (s, 3H) 3.16-3.24 (m, 4H) 3.83-3.94 (m, 4H) 5.43 (quin, J=6.16 Hz, 1H) 7.27 (d, J=1.96 Hz, 1H) 7.34 (d, J=7.83 Hz, 1H) 7.62-7.69 (m, 2H) 7.78 (d, J=1.96 Hz, 1H) 8.17 (dd, J=5.09, 1.57 Hz, 1H) 8.54-8.58 (m, 1H) 8.95 (dd, J=4.69, 0.78 Hz, 1H). LCMS (m/z) (M+H)=511.1, Rt=0.93 min.

Example 951: N-(3-(6-isopropoxy-5-morpholin-opyridin-3-yl)-4-methylphenyl)-5-(trifluoromethyl)nicotinamide

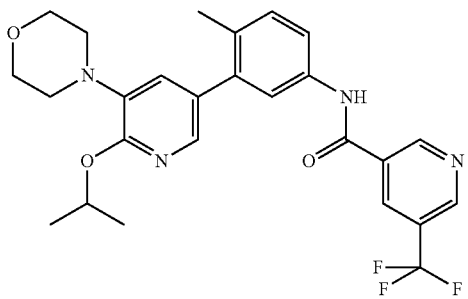 [SMILES: Cc1ccc(NC(=O)c2cncc(C(F)(F)F)c2)cc1-c1cnc(OC(C)C)c(N2CCOCC2)c1]

$^1$H NMR (400 MHz, <cd3od>) δ ppm 1.43 (d, J=6.26 Hz, 6H) 2.29 (s, 3H) 3.19 (dd, J=5.48, 3.91 Hz, 4H) 3.83-3.94 (m, 4H) 5.42 (dt, J=12.23, 6.21 Hz, 1H) 7.28 (d, J=1.96 Hz, 1H) 7.30-7.36 (m, 1H) 7.60-7.67 (m, 2H) 7.78 (d, J=1.96 Hz, 1H) 8.64-8.70 (m, 1H) 9.08 (d, J=1.17 Hz, 1H) 9.36 (d, J=1.96 Hz, 1H). LCMS (m/z) (M+H)=501.1, Rt=1.06 min.

Example 952: 2-(1,1-difluoroethyl)-N-(6'-isopropoxy-2-methyl-5'-morpholino-[3,3'-bipyridin]-5-yl)isonicotinamide

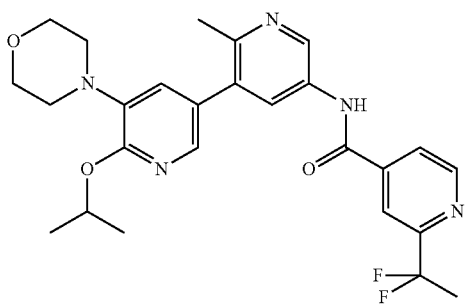 [SMILES: Cc1ncc(NC(=O)c2ccnc(C(C)(F)F)c2)cc1-c1cnc(OC(C)C)c(N2CCOCC2)c1]

$^1$H NMR (400 MHz, <cd3od>) δ ppm 1.43 (d, J=6.26 Hz, 6H) 2.06 (t, J=18.78 Hz, 3H) 2.72 (s, 3H) 3.12-3.21 (m, 4H) 3.82-3.92 (m, 4H) 5.47 (quin, J=6.16 Hz, 1H) 7.31 (d, J=1.96 Hz, 1H) 7.88 (d, J=2.35 Hz, 1H) 8.02-8.07 (m, 1H) 8.26-8.29 (m, 1H) 8.48 (d, J=2.35 Hz, 1H) 8.88 (dd, J=5.09, 0.78 Hz, 1H) 9.37 (d, J=2.35 Hz, 1H). LCMS (m/z) (M+H)=498.1, Rt=0.79 min.

Example 953: 2-(2-fluoropropan-2-yl)-N-(6'-isopropoxy-2-methyl-5'-morpholino-[3,3'-bipyridin]-5-yl)isonicotinamide

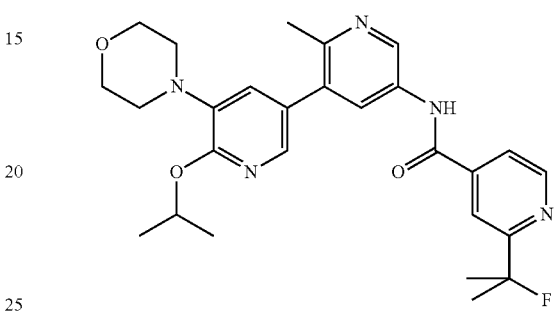

$^1$H NMR (400 MHz, <cd3od>) δ ppm 1.43 (d, J=6.26 Hz, 6H) 1.66-1.83 (m, 6H) 2.73 (s, 3H) 3.10-3.22 (m, 4H) 3.82-3.93 (m, 4H) 5.47 (quin, J=6.16 Hz, 1H) 7.31 (d, J=2.35 Hz, 1H) 7.85 (dd, J=5.09, 1.56 Hz, 1H) 7.88 (d, J=2.35 Hz, 1H) 8.14-8.18 (m, 1H) 8.50 (d, J=2.35 Hz, 1H) 8.75-8.80 (m, 1H) 9.39 (d, J=2.35 Hz, 1H). LCMS (m/z) (M+H)=494.1, Rt=0.79 min.

Example 954: 2-(2-cyanopropan-2-yl)-N-(6'-isopropoxy-2-methyl-5'-morpholino-[3,3'-bipyridin]-5-yl)isonicotinamide

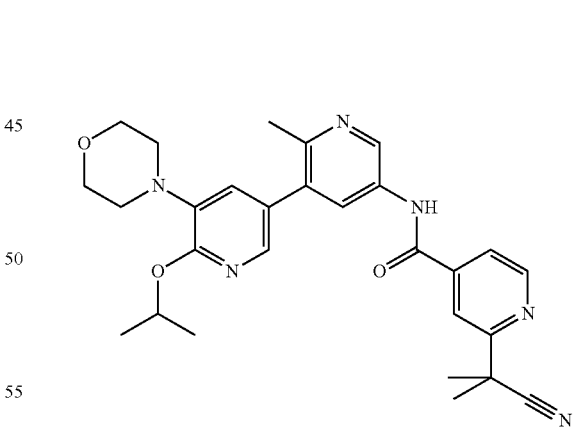

$^1$H NMR (400 MHz, <cd3od>) δ ppm 1.43 (d, J=5.87 Hz, 6H) 1.84 (s, 6H) 2.72 (s, 3H) 3.12-3.21 (m, 4H) 3.83-3.93 (m, 4H) 5.47 (quin, J=6.16 Hz, 1H) 7.31 (d, J=2.35 Hz, 1H) 7.86-7.92 (m, 2H) 8.14-8.18 (m, 1H) 8.47 (d, J=2.35 Hz, 1H) 8.84 (dd, J=5.09, 0.78 Hz, 1H) 9.38 (d, J=2.35 Hz, 1H). LCMS (m/z) (M+H)=501.1, Rt=0.77 min.

Example 955: 2-(2-hydroxypropan-2-yl)-N-(6'-iso-propoxy-2-methyl-5'-morpholino-[3,3'-bipyridin]-5-yl)isonicotinamide

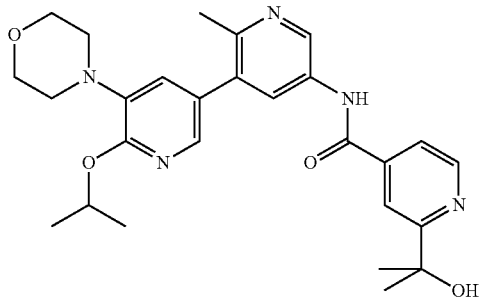 [SMILES: Cc1ncc(NC(=O)c2ccnc(C(C)(C)O)c2)cc1-c1cnc(OC(C)C)c(N2CCOCC2)c1]

¹H NMR (400 MHz, <cd3od>) δ ppm 1.43 (d, J=6.26 Hz, 6H) 1.64 (s, 6H) 2.71 (s, 3H) 3.13-3.20 (m, 4H) 3.84-3.92 (m, 4H) 5.47 (dt, J=12.23, 6.21 Hz, 1H) 7.30 (d, J=2.35 Hz, 1H) 7.87 (d, J=2.35 Hz, 1H) 7.91-7.95 (m, 1H) 8.34 (dd, J=1.76, 0.98 Hz, 1H) 8.48 (d, J=2.35 Hz, 1H) 8.77 (dd, J=5.28, 0.98 Hz, 1H) 9.36 (d, J=2.35 Hz, 1H). LCMS (m/z) (M+H)=492.1, Rt=0.62 min.

Example 956: 4-(1,1-difluoroethyl)-N-(6'-iso-propoxy-2-methyl-5-morpholino-[3,3'-bipyridin]-5-yl)picolinamide

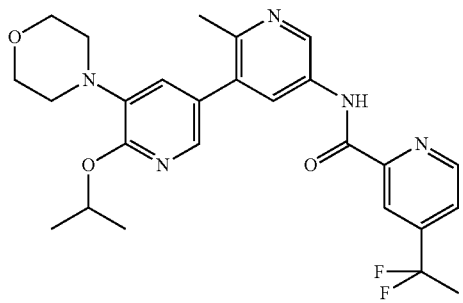 [SMILES: Cc1ncc(NC(=O)c2cc(C(C)(F)F)ccn2)cc1-c1cnc(OC(C)C)c(N2CCOCC2)c1]

¹H NMR (400 MHz, <cd3od>) δ ppm 1.43 (d, J=5.87 Hz, 6H) 2.02 (t, J=18.58 Hz, 3H) 2.72 (s, 3H) 3.14-3.22 (m, 4H) 3.81-3.93 (m, 4H) 5.48 (dt, J=12.23, 6.21 Hz, 1H) 7.32 (d, J=2.35 Hz, 1H) 7.81-7.86 (m, 1H) 7.89 (d, J=2.35 Hz, 1H) 8.38-8.41 (m, 1H) 8.70 (d, J=2.35 Hz, 1H) 8.88-8.92 (m, 1H) 9.46 (d, J=2.35 Hz, 1H). LCMS (m/z) (M+H)=498.1, Rt=0.85 min.

Example 957: 4-(2-fluoropropan-2-yl)-N-(6'-iso-propoxy-2-methyl-5'-morpholino-[3,3'-bipyridin]-5-yl)picolinamide

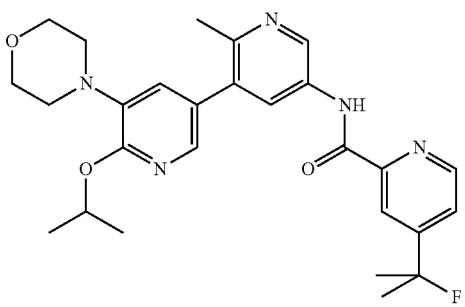 [SMILES: Cc1ncc(NC(=O)c2cc(C(C)(C)F)ccn2)cc1-c1cnc(OC(C)C)c(N2CCOCC2)c1]

¹H NMR (400 MHz, <cd3od>) δ ppm 1.43 (d, J=6.26 Hz, 6H) 1.67-1.81 (m, 6H) 2.72 (s, 3H) 3.15-3.23 (m, 4H) 3.83-3.93 (m, 4H) 5.48 (dt, J=12.23, 6.21 Hz, 1H) 7.32 (d, J=2.35 Hz, 1H) 7.71 (dd, J=5.28, 1.76 Hz, 1H) 7.89 (d, J=2.35 Hz, 1H) 8.28-8.32 (m, 1H) 8.70 (d, J=2.35 Hz, 1H) 8.76 (d, J=5.09 Hz, 1H) 9.46 (d, J=2.35 Hz, 1H). LCMS (m/z) (M+H)=494.1, Rt=0.87 min.

Example 958: 4-(2-cyanopropan-2-yl)-N-(6'-iso-propoxy-2-methyl-5'-morpholino-[3,3'-bipyridin]-5-yl)picolinamide

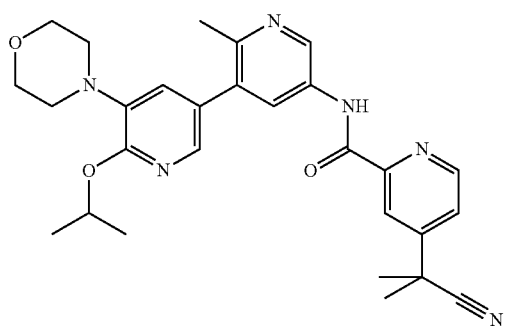 [SMILES: Cc1ncc(NC(=O)c2cc(C(C)(C)C#N)ccn2)cc1-c1cnc(OC(C)C)c(N2CCOCC2)c1]

¹H NMR (400 MHz, <cd3od>) δ ppm 1.43 (d, J=5.87 Hz, 6H) 1.83 (s, 6H) 2.72 (s, 3H) 3.15-3.23 (m, 4H) 3.80-3.92 (m, 4H) 5.42-5.54 (m, 1H) 7.32 (d, J=2.35 Hz, 1H) 7.85 (dd, J=5.09, 1.96 Hz, 1H) 7.89 (d, J=1.96 Hz, 1H) 8.44 (dd, J=1.96, 0.78 Hz, 1H) 8.70 (d, J=2.35 Hz, 1H) 8.79-8.84 (m, 1H) 9.47 (d, J=2.35 Hz, 1H). LCMS (m/z) (M+H)=501.1, Rt=0.82 min.

Example 959: 4-(2-hydroxypropan-2-yl)-N-(6'-iso-propoxy-2-methyl-5'-morpholino-[3,3'-bipyridin]-5-yl)picolinamide

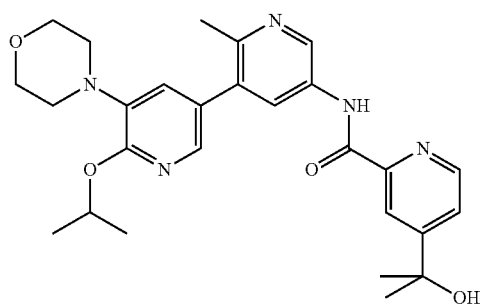 [SMILES: Cc1ncc(NC(=O)c2cc(C(C)(C)O)ccn2)cc1-c1cnc(OC(C)C)c(N2CCOCC2)c1]

¹H NMR (400 MHz, <cd3od>) δ ppm 1.44 (d, J=6.26 Hz, 6H) 1.59 (s, 6H) 2.71 (s, 3H) 3.15-3.21 (m, 4H) 3.83-3.92 (m, 4H) 5.48 (dt, J=12.23, 6.21 Hz, 1H) 7.32 (d, J=2.35 Hz, 1H) 7.77 (dd, J=5.09, 1.96 Hz, 1H) 7.89 (d, J=2.35 Hz, 1H) 8.41 (dd, J=1.96, 0.78 Hz, 1H) 8.67 (d, J=2.35 Hz, 1H) 8.70 (dd, J=5.09, 0.78 Hz, 1H) 9.45 (d, J=2.35 Hz, 1H). LCMS (m/z) (M+H)=492.1, Rt=0.74 min.

Example 960: N-(6'-isopropoxy-2-methyl-5'-morpholino-[3,3'-bipyridin]-5-yl)-5-(trifluoromethyl)nicotinamide

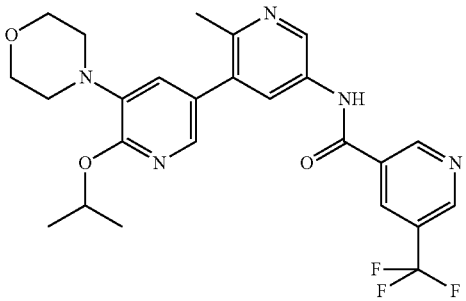 [SMILES: Cc1ncc(NC(=O)c2cncc(C(F)(F)F)c2)cc1-c1cnc(OC(C)C)c(N2CCOCC2)c1]

$^1$H NMR (400 MHz, <cd3od>) δ ppm 1.43 (d, J=6.26 Hz, 6H) 2.71 (s, 3H) 3.14-3.21 (m, 4H) 3.83-3.93 (m, 4H) 5.47 (quin, J=6.26 Hz, 1H) 7.31 (d, J=2.35 Hz, 1H) 7.87 (d, J=2.35 Hz, 1H) 8.44 (d, J=2.35 Hz, 1H) 8.73-8.77 (m, 1H) 9.14-9.18 (m, 1H) 9.33 (d, J=2.35 Hz, 1H) 9.43 (d, J=1.96 Hz, 1H). LCMS (m/z) (M+H)=502.1, Rt=0.79 min.

Example 961: 3-(6-ethoxy-5-morpholinopyridin-3-yl)-N-(5-fluoro-2-(trifluoromethyl)pyridin-4-yl)-4-methylbenzamide

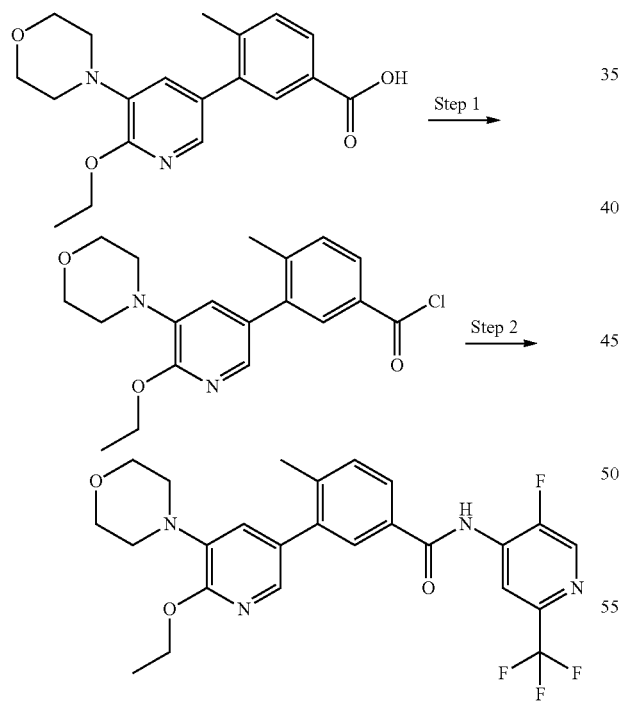

Step 1:
To a solution of 3-(6-ethoxy-5-morpholinopyridin-3-yl)-4-methylbenzoic acid (1.0 equiv.) in DCM (0.06 M) was added 1-chloro-N,N,2-trimethylprop-1-en-1-amine (2.0 equiv.) and the mixture was stirred at 0° C. for 1 hour. Upon concentration under vacuo, the crude residue was used for the next step without further purification.

Step 2:
5-fluoro-2-(trifluoromethyl)pyridin-4-amine (1.0 equiv.) was dissolved in 2-methyltetrahydrofuran (0.17 M) and NaHMDS (2.0 equiv.) was added and stirred for 1 h at rt. The crude solution from the above reaction was added to this mixture and stirred for 1 h at rt. The reaction was quenched by the addition of water, then partitioned between with ethyl acetate and the organic phase was concentrated to dryness. The residue was purified via silica gel chromatography followed by reverse phase HPLC to give 3-(6-ethoxy-5-morpholinopyridin-3-yl)-N-(5-fluoro-2-(trifluoromethyl)pyridin-4-yl)-4-methylbenzamide in 10% yield. $^1$H NMR (500 MHz, METHANOL-d$_4$) δ ppm 1.48 (t, J=6.94 Hz, 3H) 2.40 (s, 3H) 3.14-3.23 (m, 4H) 3.84-3.93 (m, 4H) 4.51 (d, J=6.94 Hz, 2H) 7.32 (d, J=1.89 Hz, 1H) 7.53 (s, 1H) 7.82 (d, J=2.21 Hz, 1H) 7.86 (d, J=2.21 Hz, 1H) 7.89-7.95 (m, 1H) 8.64 (d, J=2.21 Hz, 1H) 8.79 (d, J=5.99 Hz, 1H). LCMS (m/z) (M+H)=505.0, Rt=1.07 min.

Synthesis of 6'-(2,2-difluoroethoxy)-2-methyl-5'-morpholino-[3,3'-bipyridin]-5-amine

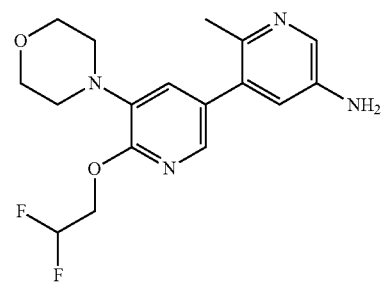 [SMILES: Cc1ncc(N)cc1-c1cnc(OCC(F)F)c(N2CCOCC2)c1]

To a degassed solution of 4-(5-bromo-2-(2,2-difluoroethoxy)pyridin-3-yl)morpholine (1.0 equiv.) in DME and 2M Na$_2$CO$_3$ (3:1, 0.1 M) was added 6-methyl-5-(4,4,5,5-tetramethyl-1,3,2-dioxaborolan-2-yl)pyridin-3-amine (1.1 equiv.) and PdCl$_2$(dppf)-DCM adduct (0.1 equiv.). The reaction was heated to 100° C. for 2 hours in an oil bath. LCMS indicated completion. Cooled to rt, partitioned between water and ethyl acetate, the organic phase was dried with sodium sulfate, filtered and concentrated. The crude material was purified via silica gel column chromatography (ISCO, eluting with 0-100% ethyl acetate in heptanes, followed by 10% methanol in ethyl acetate). The pure fractions were combined and concentrated under vacuo to give 6'-(2,2-difluoroethoxy)-2-methyl-5'-morpholino-[3,3'-bipyridin]-5-amine in 79% yield. LCMS (m/z) (M+H)=351, Rt=0.55 min.

Example 962: 6-(2-cyanopropan-2-yl)-N-(6'-(2,2-difluoroethoxy)-2-methyl-5'-morpholino-[3,3'-bipyridin]-5-yl)pyridazine-4-carboxamide

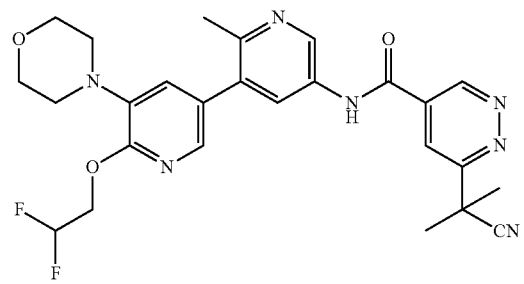 [SMILES: Cc1ncc(NC(=O)c2cnnc(C(C)(C)C#N)c2)cc1-c1cnc(OCC(F)F)c(N2CCOCC2)c1]

$^1$H NMR (400 MHz, <cd3od>) δ ppm 1.92 (s, 6H) 2.63 (s, 3H) 3.12-3.19 (m, 4H) 3.79-4.03 (m, 4H) 4.66 (td, J=14.18, 3.72 Hz, 2H) 6.04-6.57 (m, 1H) 7.34 (d, J=1.96 Hz, 1H) 7.85 (d, J=1.96 Hz, 1H) 8.28-8.48 (m, 2H) 9.16 (d, J=2.35 Hz, 1H) 9.66 (d, J=1.96 Hz, 1H). LCMS (m/z) (M+H)=524.1, Rt=0.66 min.

Synthesis of 6'-(2-oxaspiro[3.3]heptan-6-yloxy)-2-methyl-5'-morpholino-[3,3'-bipyridin]-5-amine

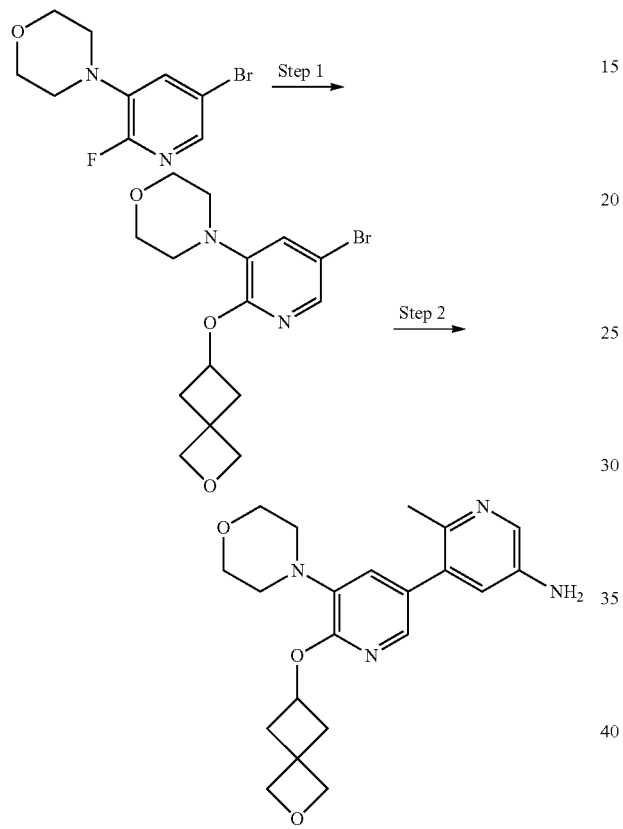

Step 1:
To a solution of 2-oxaspiro[3.3]heptan-6-ol (1.5 equiv.) in dioxane (0.13 M) at rt was added sodium hydride (1.5 equiv.) and the mixture was stirred for 15 min. 4-(5-bromo-2-fluoropyridin-3-yl)morpholine (1.0 equiv.) was then added, and the reaction was heated to 105° C. and stirred for 1.5 hours. Added another 1.5 equiv. of 2-oxaspiro[3.3] heptan-6-ol and sodium hydride and heated for 3 more hours. The mixture was carefully poured into water and extracted three times with ethyl acetate. The combined organics were washed with water, brine, dried over magnesium sulfate, filtered and concentrated. The crude residue was purified via Grace flash column chromatography over silica gel, eluting with heptanes and 0-50% ethyl acetate. The pure fractions were concentrated to give 4-(2-(2-oxaspiro[3.3]heptan-6-yloxy)-5-bromopyridin-3-yl)morpholine as a pale yellow oil in 72% yield. LCMS (m/z) (M+H)= 355.1/357.1, Rt=0.86 min.

Step 2:
A solution of 4-(2-(2-oxaspiro[3.3]heptan-6-yloxy)-5-bromopyridin-3-yl)morpholine (1.0 equiv.) and 6-methyl-5-(4,4,5,5-tetramethyl-1,3,2-dioxaborolan-2-yl)pyridin-3-amine (1.2 equiv.) in DME (0.1 M) and sodium carbonate (2M aqueous, 3.0 equiv.) was purged with argon for 5 min. PdCl$_2$(dppf)-DCM adduct (0.05 equiv.) was then added, and the mixture was purged with argon again, then heated to 100° C. for 1 hour. The mixture was poured onto water and extracted three times with ethyl acetate. The combined organics were washed with brine, dried over magnesium sulfate, filtered and concentrated. The crude residue was purified via Grace flash column chromatography over silica gel eluting with DCM and 0-15% methanol. Product fractions were concentrated to give 6'-(2-oxaspiro[3.3]heptan-6-yloxy)-2-methyl-5'-morpholino-[3,3'-bipyridin]-5-amine as a light brown foam in 86% yield. LCMS (m/z) (M+H)= 383.1, Rt=0.52 min.

Example 963: N-(6'-(2-oxaspiro[3.3]heptan-6-yloxy)-2-methyl-5'-morpholino-[3,3'-bipyridin]-5-yl)-2-(2-fluoropropan-2-yl)isonicotinamide

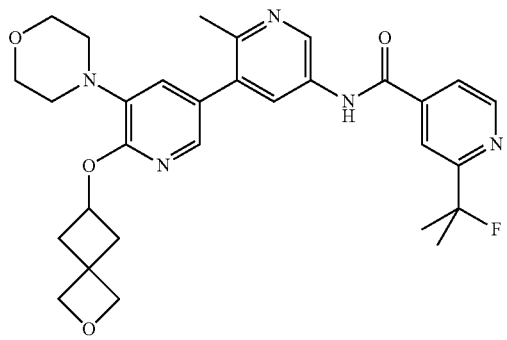 [SMILES: Cc1ncc(NC(=O)c2ccnc(C(C)(C)F)c2)cc1-c1cnc(OC2CC3(COC3)C2)c(N2CCOCC2)c1]

$^1$H NMR (400 MHz, <cd3od>) δ ppm 1.74 (d, J=1.00 Hz, 6H) 2.32-2.42 (m, 2H) 2.50 (s, 3H) 2.81-2.92 (m, 2H) 3.09-3.18 (m, 4H) 3.83-3.90 (m, 4H) 4.71 (s, 2H) 4.79 (s, 2H) 5.17 (t, J=7.04 Hz, 1H) 7.25 (d, J=2.35 Hz, 1H) 7.76 (d, J=2.35 Hz, 1H) 7.80 (dd, J=5.09, 1.57 Hz, 1H) 8.10 (s, 1H) 8.13 (d, J=2.35 Hz, 1H) 8.72 (d, J=5.09 Hz, 1H) 8.86 (d, J=2.35 Hz, 1H). LCMS (m/z) (M+H)=548.3, Rt=0.72 min.

Example 964: N-(6'-(2-oxaspiro[3.3]heptan-6-yloxy)-2-methyl-5'-morpholino-[3,3'-bipyridin]-5-yl)-2-(2-hydroxypropan-2-yl)isonicotinamide

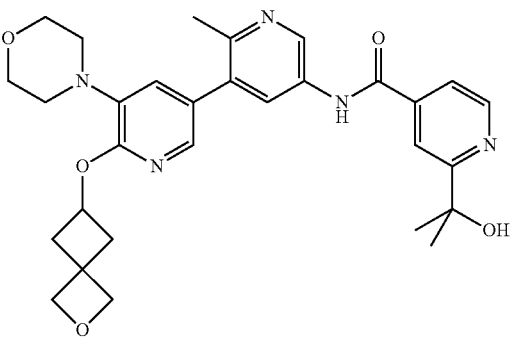 [SMILES: Cc1ncc(NC(=O)c2ccnc(C(C)(C)O)c2)cc1-c1cnc(OC2CC3(COC3)C2)c(N2CCOCC2)c1]

$^1$H NMR (400 MHz, <cd3od>) δ ppm 1.59 (s, 6H) 2.30-2.43 (m, 2H) 2.50 (s, 3H) 2.82-2.93 (m, 2H) 3.10-3.18 (m, 4H) 3.79-3.91 (m, 4H) 4.71 (s, 2H) 4.79 (s, 2H) 5.17 (quin, J=6.95 Hz, 1H) 7.25 (d, J=1.96 Hz, 1H) 7.74 (dd, J=5.28, 1.76 Hz, 1H) 7.76 (d, J=1.96 Hz, 1H) 8.13 (d, J=2.35 Hz, 1H) 8.19 (s, 1H) 8.69 (d, J=4.69 Hz, 1H) 8.87 (d, J=2.35 Hz, 1H). LCMS (m/z) (M+H)=546.3, Rt=0.57 min.

Example 965: N-(6'-(2-oxaspiro[3.3]heptan-6-yloxy)-2-methyl-5'-morpholino-[3,3'-bipyridin]-5-yl)-2-(difluoromethyl)isonicotinamide

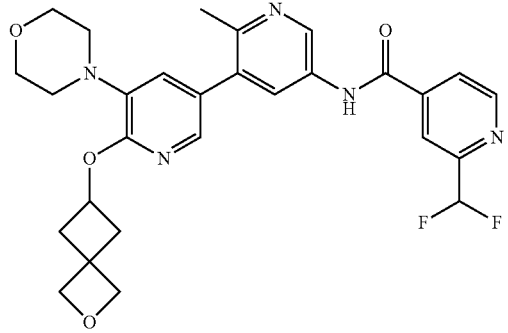 [SMILES: Cc1ncc(NC(=O)c2ccnc(C(F)F)c2)cc1-c1cnc(OC2CC3(COC3)C2)c(N2CCOCC2)c1]

¹H NMR (400 MHz, <cd3od>) δ ppm 2.28-2.41 (m, 2H) 2.49 (s, 3H) 2.81-2.94 (m, 2H) 3.07-3.16 (m, 4H) 3.75-3.92 (m, 4H) 4.71 (s, 2H) 4.79 (s, 2H) 5.17 (t, J=6.85 Hz, 1H) 6.83 (t, J=1.00 Hz, 1H) 7.25 (d, J=1.96 Hz, 1H) 7.76 (d, J=2.35 Hz, 1H) 8.04 (d, J=4.70 Hz, 1H) 8.12 (d, J=2.35 Hz, 1H) 8.22 (s, 1H) 8.80-8.90 (m, 2H). LCMS (m/z) (M+H)=538.3, Rt=0.67 min.

Example 966: N-(6'-(2-oxaspiro[3.3]heptan-6-yloxy)-2-methyl-5'-morpholino-[3,3'-bipyridin]-5-yl)-2-cyclopropylisonicotinamide

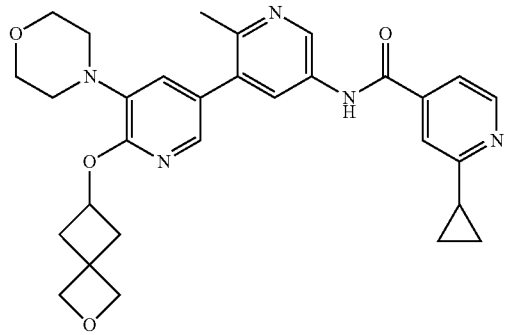 [SMILES: Cc1ncc(NC(=O)c2ccnc(C3CC3)c2)cc1-c1cnc(OC2CC3(COC3)C2)c(N2CCOCC2)c1]

¹H NMR (400 MHz, <cd3od>) δ ppm 1.02-1.14 (m, 4H) 2.16-2.26 (m, 1H) 2.33-2.41 (m, 2H) 2.49 (s, 3H) 2.88 (ddd, J=10.47, 7.14, 3.13 Hz, 2H) 3.09-3.16 (m, 4H) 3.81-3.90 (m, 4H) 4.71 (s, 2H) 4.79 (s, 2H) 5.16 (t, J=6.85 Hz, 1H) 7.24 (d, J=1.96 Hz, 1H) 7.61 (dd, J=5.09, 1.57 Hz, 1H) 7.71 (s, 1H) 7.75 (d, J=1.96 Hz, 1H) 8.11 (d, J=2.35 Hz, 1H) 8.55 (d, J=5.09 Hz, 1H) 8.84 (d, J=2.35 Hz, 1H). LCMS (m/z) (M+H)=528.3, Rt=0.59 min.

Example 967: N-(6'-(2-oxaspiro[3.3]heptan-6-yloxy)-2-methyl-5'-morpholino-[3,3'-bipyridin]-5-yl)-2-(2-cyanopropan-2-yl)isonicotinamide

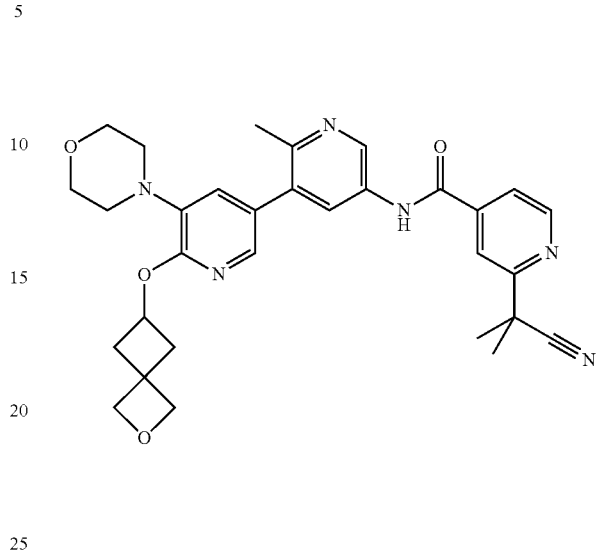

¹H NMR (400 MHz, <cd3od>) δ ppm 1.82 (s, 6H) 2.32-2.41 (m, 2H) 2.50 (s, 3H) 2.81-2.93 (m, 2H) 3.04-3.16 (m, 4H) 3.79-3.90 (m, 4H) 4.71 (s, 2H) 4.79 (s, 2H) 5.17 (quin, J=6.95 Hz, 1H) 7.25 (d, J=1.96 Hz, 1H) 7.76 (d, J=1.96 Hz, 1H) 7.85 (dd, J=4.89, 1.37 Hz, 1H) 8.10 (s, 1H) 8.13 (d, J=2.35 Hz, 1H) 8.79 (d, J=5.09 Hz, 1H) 8.86 (d, J=2.35 Hz, 1H). LCMS (m/z) (M+H)=555.3, Rt=0.70 min.

Example 968: N-(6'-(2-oxaspiro[3.3]heptan-6-yloxy)-2-methyl-5'-morpholino-[3,3'-bipyridin]-5-yl)-4-(2-fluoropropan-2-yl)picolinamide

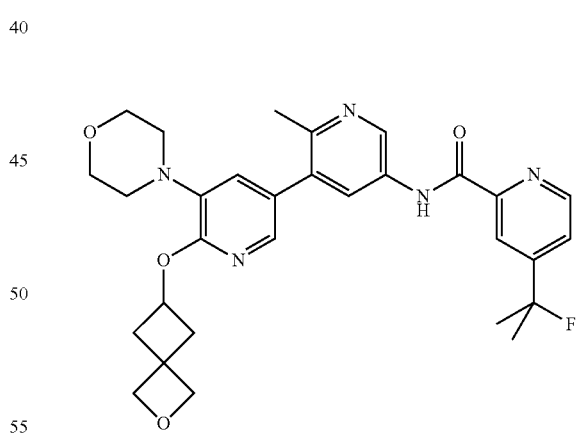

¹H NMR (400 MHz, <cd3od>) δ ppm 1.72 (d, J=1.00 Hz, 6H) 2.34-2.42 (m, 2H) 2.49 (s, 3H) 2.78-2.93 (m, 2H) 3.10-3.19 (m, 4H) 3.79-3.90 (m, 4H) 4.72 (s, 2H) 4.80 (s, 2H) 5.17 (t, J=6.85 Hz, 1H) 7.26 (d, J=1.96 Hz, 1H) 7.65 (dd, J=4.89, 1.76 Hz, 1H) 7.77 (d, J=1.96 Hz, 1H) 8.21 (d, J=2.35 Hz, 1H) 8.24 (d, J=1.17 Hz, 1H) 8.72 (d, J=5.09 Hz, 1H) 8.95 (d, J=2.35 Hz, 1H). LCMS (m/z) (M+H)=548.3, Rt=0.78 min.

Example 969: N-(6'-(2-oxaspiro[3.3]heptan-6-yloxy)-2-methyl-5'-morpholino-[3,3'-bipyridin]-5-yl)-4-(2-hydroxypropan-2-yl)picolinamide

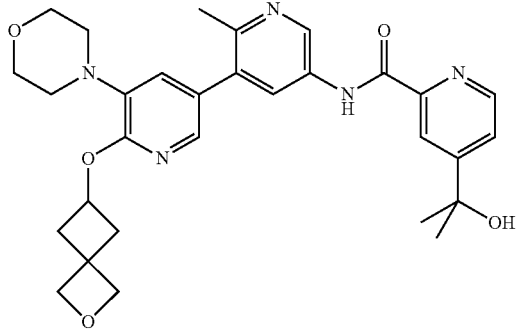 [SMILES: Cc1ncc(NC(=O)c2cc(C(C)(C)O)ccn2)cc1-c1cnc(OC2CC3(COC3)C2)c(N2CCOCC2)c1]

$^1$H NMR (400 MHz, <cd3od>) δ ppm 1.57 (s, 6H) 2.32-2.43 (m, 2H) 2.50 (s, 3H) 2.75-2.95 (m, 2H) 3.06-3.18 (m, 4H) 3.76-3.93 (m, 4H) 4.72 (s, 2H) 4.80 (s, 2H) 5.17 (t, J=6.85 Hz, 1H) 7.26 (d, J=1.96 Hz, 1H) 7.72 (dd, J=5.28, 1.76 Hz, 1H) 7.77 (d, J=1.96 Hz, 1H) 8.22 (d, J=2.35 Hz, 1H) 8.35 (d, J=1.17 Hz, 1H) 8.66 (d, J=5.09 Hz, 1H) 8.96 (d, J=2.35 Hz, 1H). LCMS (m/z) (M+H)=546.3, Rt=0.66 min.

Example 970: N-(6'-(2-oxaspiro[3.3]heptan-6-yloxy)-2-methyl-5'-morpholino-[3,3'-bipyridin]-5-yl)-4-(2-cyanopropan-2-yl)picolinamide

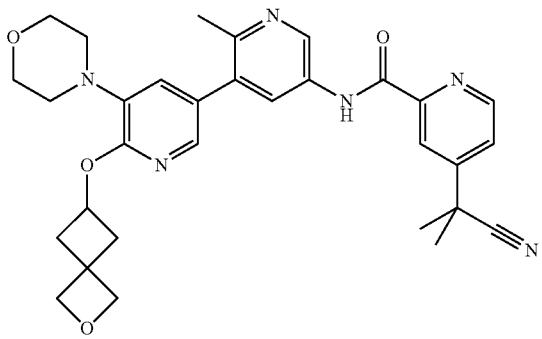 [SMILES: Cc1ncc(NC(=O)c2cc(C(C)(C)C#N)ccn2)cc1-c1cnc(OC2CC3(COC3)C2)c(N2CCOCC2)c1]

$^1$H NMR (400 MHz, <cd3od>) δ ppm 1.81 (s, 6H) 2.34-2.42 (m, 2H) 2.50 (s, 3H) 2.80-2.93 (m, 2H) 3.10-3.17 (m, 4H) 3.75-3.92 (m, 4H) 4.72 (s, 2H) 4.80 (s, 2H) 5.17 (quin, J=6.95 Hz, 1H) 7.26 (d, J=2.35 Hz, 1H) 7.77 (d, J=2.35 Hz, 1H) 7.80 (dd, J=5.09, 1.96 Hz, 1H) 8.23 (d, J=2.35 Hz, 1H) 8.38 (d, J=1.57 Hz, 1H) 8.77 (d, J=5.09 Hz, 1H) 8.97 (d, J=2.35 Hz, 1H). LCMS (m/z) (M+H)=555.3, Rt=0.74 min.

Example 971: 4-(2-fluoropropan-2-yl)-N-(6'-(2-hydroxyethoxy)-2-methyl-5-morpholino-[3,3'-bipyridin]-5-yl)picolinamide

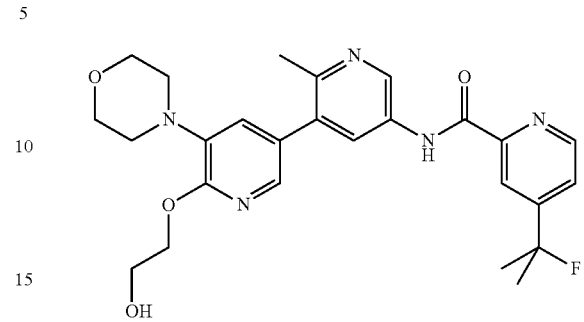

$^1$H NMR (400 MHz, <cd3od>) δ ppm 1.68-1.78 (m, 6H) 2.71 (s, 3H) 3.13-3.23 (m, 4H) 3.80-3.90 (m, 4H) 3.93-3.98 (m, 2H) 4.51-4.56 (m, 2H) 7.33-7.37 (m, 1H) 7.70 (dd, J=5.09, 1.57 Hz, 1H) 7.86-7.91 (m, 1H) 8.29 (d, J=1.17 Hz, 1H) 8.72 (d, J=2.35 Hz, 1 H) 8.75 (d, J=5.09 Hz, 1H) 9.48 (d, J=2.35 Hz, 1H). LCMS (m/z) (M+H)=496.1, Rt=0.55 min.

Example 972: N-(6'-(2-hydroxyethoxy)-2-methyl-5-morpholino-[3,3'-bipyridin]-5-yl)-4-(2-hydroxypropan-2-yl)picolinamide

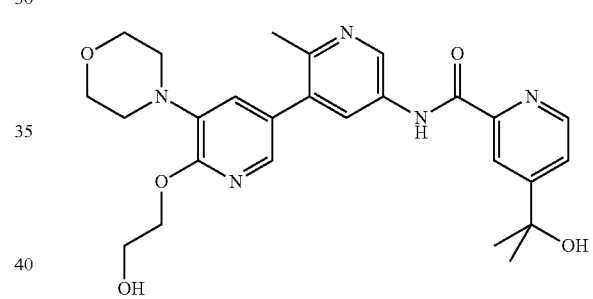

$^1$H NMR (400 MHz, <cd3od>) δ ppm 1.58 (s, 6H) 2.71 (s, 3H) 3.12-3.24 (m, 4H) 3.81-3.91 (m, 4H) 3.93-3.98 (m, 2H) 4.52-4.57 (m, 2H) 7.33-7.37 (m, 1H) 7.76 (dd, J=5.09, 1.57 Hz, 1H) 7.87-7.91 (m, 1H) 8.40 (d, J=1.17 Hz, 1H) 8.69 (d, J=5.09 Hz, 1H) 8.72 (d, J=1.96 Hz, 1H) 9.49 (d, J=2.35 Hz, 1H). LCMS (m/z) (M+H)=494.1, Rt=0.53 min.

Example 973: 4-(2-cyanopropan-2-yl)-N-(6'-(2-hydroxyethoxy)-2-methyl-5'-morpholino-[3,3'-bipyridin]-5-yl)picolinamide

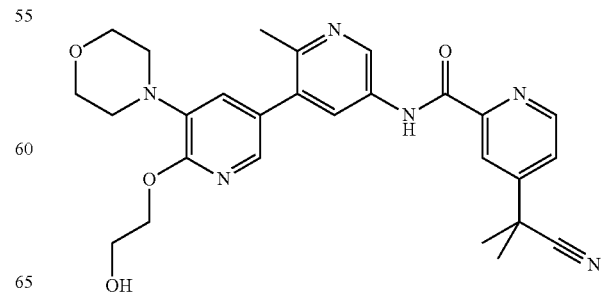

¹H NMR (400 MHz, <cd3od>) δ ppm 1.81 (s, 6H) 2.71 (s, 3H) 3.13-3.23 (m, 4H) 3.79-3.91 (m, 4H) 3.93-3.99 (m, 2H) 4.49-4.58 (m, 2H) 7.31-7.37 (m, 1H) 7.84 (dd, J=5.48, 1.96 Hz, 1H) 7.87-7.91 (m, 1H) 8.43 (d, J=1.57 Hz, 1H) 8.72 (d, J=2.35 Hz, 1H) 8.80 (d, J=5.09 Hz, 1H) 9.48 (d, J=2.35 Hz, 1H). LCMS (m/z) (M+H)=503.1, Rt=0.61 min.

Example 974: 4-(1,1-difluoroethyl)-N-(6'-(2-hydroxyethoxy)-2-methyl-5-morpholino-[3,3'-bipyridin]-5-yl)picolinamide

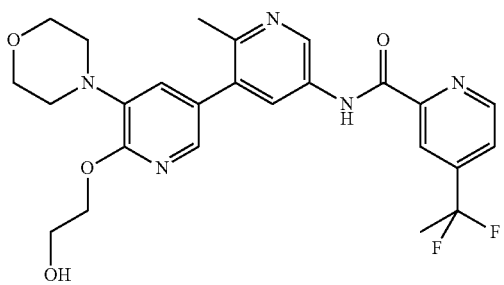 [SMILES: Cc1ncc(NC(=O)c2cc(C(C)(F)F)ccn2)cc1-c1cnc(OCCO)c(N2CCOCC2)c1]

¹H NMR (400 MHz, <cd3od>) δ ppm 2.01 (t, J=18.78 Hz, 3H) 2.65 (s, 3H) 3.16-3.24 (m, 4H) 3.84-3.91 (m, 4H) 3.93-4.01 (m, 2H) 4.47-4.57 (m, 2H) 7.33 (d, J=1.96 Hz, 1H) 7.82 (d, J=5.09 Hz, 1H) 7.86 (d, J=1.96 Hz, 1H) 8.37 (s, 1H) 8.57 (d, J=1.96 Hz, 1H) 8.88 (d, J=5.09 Hz, 1H) 9.33 (d, J=2.35 Hz, 1H). LCMS (m/z) (M+H)=500.1, Rt=0.66 min.

Example 975: N-(3-(6-ethoxy-5-morpholinopyridin-3-yl)-4-methylphenyl)-3-(S-methylsulfonimidoyl)benzamide

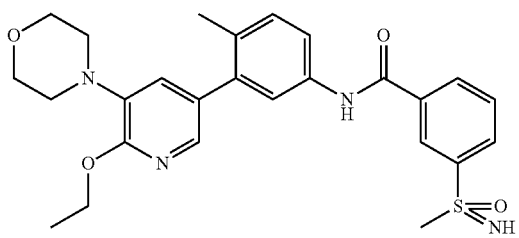 [SMILES: CCOc1ncc(-c2cc(NC(=O)c3cccc(S(C)(=N)=O)c3)ccc2C)cc1N1CCOCC1]

¹H NMR (500 MHz, CHLOROFORM-d) δ ppm 1.45 (t, J=7.09 Hz, 3H) 2.28 (s, 3H) 3.14 (br. s., 4H) 3.67 (s, 3H) 3.81-3.91 (m, 4H) 4.46 (q, J=7.15 Hz, 2H) 7.23 (d, J=1.89 Hz, 1H) 7.32 (d, J=8.51 Hz, 1H) 7.60 (d, J=2.21 Hz, 1H) 7.64 (dd, J=8.20, 2.21 Hz, 1H) 7.73 (d, J=2.21 Hz, 1H) 7.91 (t, J=7.88 Hz, 1H) 8.30-8.35 (m, 1H) 8.41 (d, J=7.88 Hz, 1H) 8.67 (t, J=1.73 Hz, 1H). LCMS (m/z) (M+H)=495.1, Rt=0.74 min.

Example 976: N-(6'-ethoxy-2-methyl-5'-morpholino-[3,3'-bipyridin]-5-yl)-3-(S-methylsulfonimidoyl)benzamide

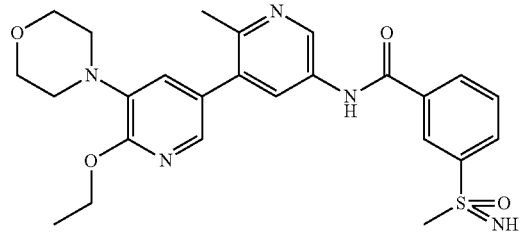 [SMILES: CCOc1ncc(-c2cc(NC(=O)c3cccc(S(C)(=N)=O)c3)cnc2C)cc1N1CCOCC1]

¹H NMR (500 MHz, CHLOROFORM-d) δ ppm 1.46 (t, J=7.09 Hz, 3H) 2.70 (s, 3H) 3.16 (dd, J=5.36, 3.78 Hz, 4H) 3.49 (s, 3H) 3.84-3.89 (m, 4H) 4.50 (q, J=7.04 Hz, 2H) 7.32 (d, J=2.21 Hz, 1H) 7.87 (d, J=2.21 Hz, 1H) 7.91 (t, J=7.88 Hz, 1H) 8.34 (ddd, J=7.88, 1.89, 0.95 Hz, 1H) 8.42 (dt, J=7.80, 1.30 Hz, 1H) 8.47 (d, J=2.21 Hz, 1H) 8.71 (t, J=1.89 Hz, 1H) 9.37 (d, J=2.21 Hz, 1H). LCMS (m/z) (M+H)=496.1, Rt=0.55 min Example 977: N-(2-methyl-5'-morpholino-6'-((tetrahydro-2H-pyran-4-yl)oxy)[3,3'-bipyridin]-5-yl)-3-(2,2,2-trifluoro-1-hydroxyethyl)benzamide

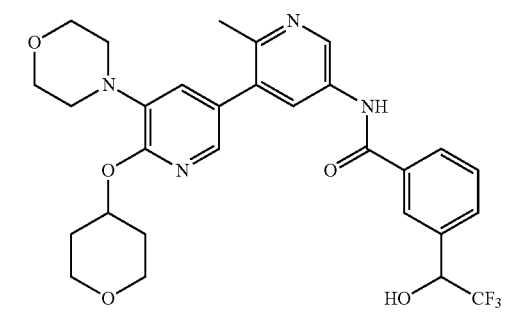 [SMILES: Cc1ncc(NC(=O)c2cccc(C(O)C(F)(F)F)c2)cc1-c1cnc(OC2CCOCC2)c(N2CCOCC2)c1]

LCMS (m/z) (M+H)=573.1, Rt=0.70 min.

Synthesis of 6'-(difluoromethoxy)-2-methyl-5-morpholino-[3,3'-bipyridin]-5-amine

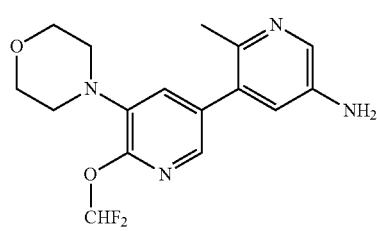 [SMILES: Cc1ncc(N)cc1-c1cnc(OC(F)F)c(N2CCOCC2)c1]

To a solution of 4-(5-bromo-2-(difluoromethoxy)pyridin-3-yl)morpholine (1.0 equiv.) and 6-methyl-5-(4,4,5,5-tetramethyl-1,3,2-dioxaborolan-2-yl)pyridin-3-amine (1.2 equiv.) in DME (0.4 M) was added sodium carbonate (2M, 1.0 equiv.) and PdCl₂(dppf)-DCM adduct (0.1 equiv.) and the mixture was heated in the microwave at 120° C. for 20 min. The reaction was partitioned between ethyl acetate and water, the organic layer was dried with sodium sulfate, filtered and concentrated. The residue was purified via silica gel chromatography (ISCO, 0-15% methanol in DCM) to give 6'-(difluoromethoxy)-2-methyl-5'-morpholino-[3,3'-bipyridin]-5-amine in 92% yield. LCMS (m/z) (M+H)=337.0, Rt=0.54 min.

Example 978: N-(6'-(difluoromethoxy)-2-methyl-5'-morpholino-[3,3'-bipyridin]-5-yl)-2-trifluoromethyl)isonicotinamide

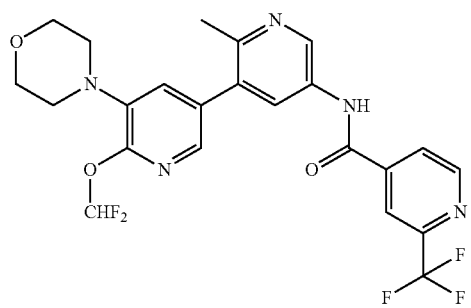 [SMILES: Cc1ncc(NC(=O)c2ccnc(C(F)(F)F)c2)cc1-c1cnc(OC(F)F)c(N2CCOCC2)c1]

1H NMR (400 MHz, <dmso>) δ ppm 3.05-3.13 (m, 4H) 3.74-3.75 (m, 3H) 7.43-7.50 (m, 1H) 7.76-7.81 (m, 1H) 7.85-7.98 (m, 1H) 8.08-8.11 (m, 1H) 8.18-8.24 (m, 1H) 8.36-8.41 (m, 1H) 8.86-8.92 (m, 1H) 8.99-9.05 (m, 1H) 10.96-10.99 (m, 1H). LCMS (m/z) (M+H)=510.1, Rt=0.74 min.

Example 979: N-(6'-(difluoromethoxy)-2-methyl-5'-morpholino-[3,3'-bipyridin]-5-yl)-2-(2-hydroxypropan-2-yl)isonicotinamide

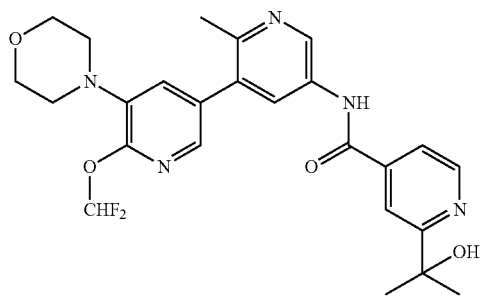

1H NMR (400 MHz, <dmso>) δ ppm 1.48 (s, 6H) 3.00-3.16 (m, 4H) 3.69-3.82 (m, 4H) 4.17-4.27 (m, 1H) 7.48-7.63 (m, 1H) 7.70-7.81 (m, 1H) 7.87-7.99 (m, 1H) 8.12-8.26 (m, 2H) 8.67-8.78 (m, 1H) 8.94-9.02 (m, 1H) 10.87-10.97 (m, 1H). LCMS (m/z) (M+H)=500.2, Rt=0.57 min.

Example 980: 2-(1,1-difluoroethyl)-N-(6'-(difluoromethoxy)-2-methyl-5'-morpholino-[3,3'-bipyridin]-5-yl)isonicotinamide

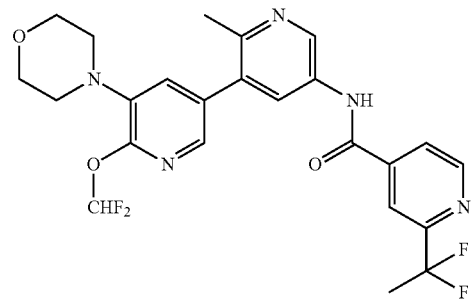 [SMILES: Cc1ncc(NC(=O)c2ccnc(C(C)(F)F)c2)cc1-c1cnc(OC(F)F)c(N2CCOCC2)c1]

LCMS (m/z) (M+H)=506.1 Rt=0.72 min.

Example 981: 4-(2-cyanopropan-2-yl)-N-(6'-(difluoromethoxy)-2-methyl-5'-morpholino-[3,3'-bipyridin]-5-yl)picolinamide

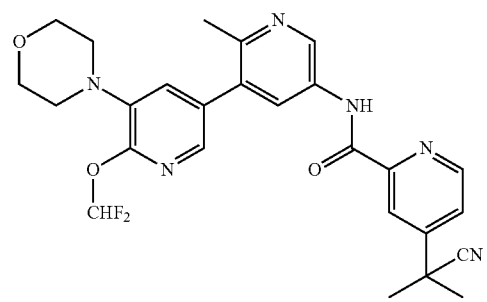 [SMILES: Cc1ncc(NC(=O)c2cc(C(C)(C)C#N)ccn2)cc1-c1cnc(OC(F)F)c(N2CCOCC2)c1]

1H NMR (400 MHz, <dmso>) δ ppm 1.75 (s, 6H) 3.04-3.16 (m, 4H) 3.66-3.87 (m, 4H) 7.45-7.55 (m, 1H) 7.75-7.79 (m, 1H) 7.82-7.98 (m, 2H) 8.23-8.30 (m, 2H) 8.75-8.83 (m, 1H) 9.04-9.12 (m, 1H) 11.01-11.13 (m, 1H). LCMS (m/z) (M+H)=509.2, Rt=0.74 min.

Example 982: N-(6'-(difluoromethoxy)-2-methyl-5'-morpholino-[3,3'-bipyridin]-5-yl)-2-(difluoromethyl)isonicotinamide

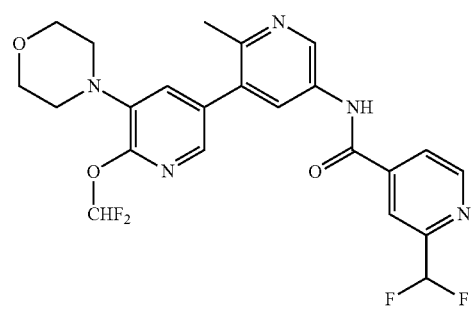 [SMILES: Cc1ncc(NC(=O)c2ccnc(C(F)F)c2)cc1-c1cnc(OC(F)F)c(N2CCOCC2)c1]

1H NMR (400 MHz, <dmso>) δ ppm 0.85-1.02 (m, 3H) 2.26-2.38 (m, 1H) 3.04-3.11 (m, 3H) 3.67-3.81 (m, 4H) 7.46-7.54 (m, 1H) 7.75-7.83 (m, 1H) 7.88-7.92 (m, 1H)

8.00-8.08 (m, 1H) 8.13-8.24 (m, 2H) 8.86-8.99 (m, 2H) 10.93-11.02 (m, 1H). LCMS (m/z) (M+H)=492.2, Rt=0.68 min.

Example 983: N-(6'-(difluoromethoxy)-2-methyl-5-morpholino-[3,3'-bipyridin]-5-yl)-2-(1,1-difluoropropyl)isonicotinamide

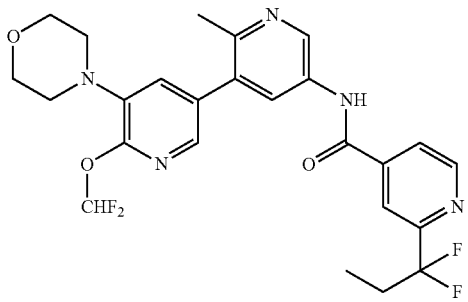 [SMILES: CCC(F)(F)c1cc(C(=O)Nc2cnc(C)c(-c3cnc(OC(F)F)c(N4CCOCC4)c3)c2)ccn1]

1H NMR (400 MHz, <dmso>) δ ppm 3.04-3.16 (m, 4H) 3.70-3.72 (m, 4H) 7.05-7.12 (m, 1H) 7.44-7.53 (m, 1H) 7.72-7.79 (m, 1H) 7.86-7.91 (m, 1H) 8.02-8.13 (m, 2H) 8.17-8.25 (m, 1H) 8.88-8.97 (m, 2H) 10.89-10.99 (m, 1H). LCMS (m/z) (M+H)=520.2, Rt=0.77 min.

Example 984: (R)—N-(6'-(2-hydroxypropoxy)-2-methyl-5'-morpholino-[3,3'-bipyridin]-5-yl)-3-(trifluoromethyl)benzamide

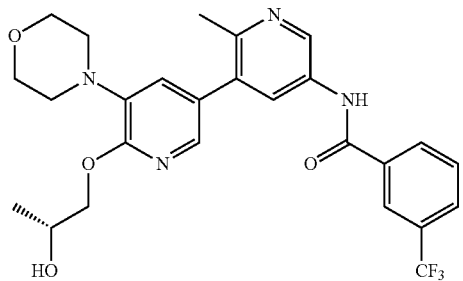 [SMILES: Cc1ncc(NC(=O)c2cccc(C(F)(F)F)c2)cc1-c1cnc(OC[C@@H](C)O)c(N2CCOCC2)c1]

To a solution of sodium hydride (4.2 equiv.) in DMA was added R-1,2-propanediol (4.0 equiv.) and the mixture was stirred for 15 min at rt. N-(6'-fluoro-2-methyl-5'-morpholino-[3,3'-bipyridin]-5-yl)-3-(trifluoromethyl)benzamide (1.0 equiv.) was added, and the reaction was heated to 100° C. and stirred for 16 hours. The cooled mixture was quenched with water and extracted with ethyl acetate (3×). The combined organics were washed with water, brine, dried over sodium sulfate, filtered and concentrated. The residue was purified via reverse phase prep-HPLC and the pure fractions were free based and lyophilized to give (R)—N-(6'-(2-hydroxypropoxy)-2-methyl-5'-morpholino-[3,3'-bipyridin]-5-yl)-3-(trifluoromethyl)benzamide as the major project in 10% yield. LCMS (m/z) (M+H)=517.1, Rt=0.69 min.

Example 985: (S)—N-(6'-((1-hydroxypropan-2-yl)oxy)-2-methyl-5'-morpholino-[3,3'-bipyridin]-5-yl)-3-(trifluoromethyl)benzamide

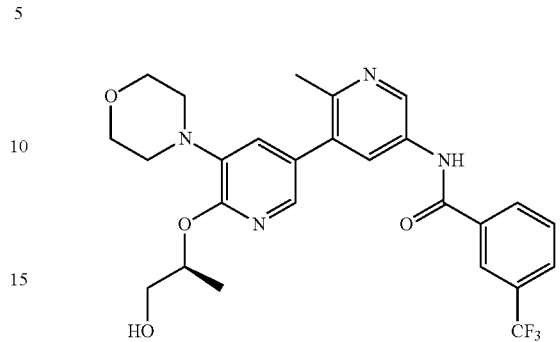

To a solution of (S)—N-(6'-((1-methoxypropan-2-yl)oxy)-2-methyl-5'-morpholino-[3,3'-bipyridin]-3-(trifluoromethyl)benzamide (1.0 equiv.) in DCM (0.04 M) at −78° C. was added 1M boron tribromide in DCM (1.2 equiv.) and the mixture was warmed to rt. The reaction was quenched with one drop of methanol and partitioned between DCM and water. The organic phase was dried with sodium sulfate, filtered and concentrated. The residue was purified via reverse phase HPLC to give (S)—N-(6'-((1-hydroxypropan-2-yl)oxy)-2-methyl-5'-morpholino-[3,3'-bipyridin]-5-yl)-3-(trifluoromethyl)benzamide in 17% yield. LCMS (m/z) (M+H)=517.1, Rt=0.69 min.

Example 986: N-(6'-((2-hydroxyethyl)(methyl)amino)-2-methyl-5'-morpholino-[3,3'-bipyridin]-5-yl)-3-(trifluoromethyl)benzamide

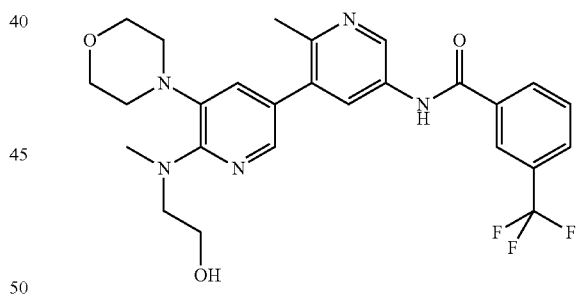

To a solution of N-(6'-fluoro-2-methyl-5'-morpholino-[3,3'-bipyridin]-5-yl)-3-(trifluoromethyl)benzamide (1.0 equiv.) in DMF (0.25 M) was added 2-(methylamino)ethanol (3.0 equiv.) and the mixture was stirred at 90° C. for 3 days. The cooled reaction mixture was diluted with DMSO, filtered and purified via reverse phase HPLC. The pure fractions were lyophilized to give N-(6'-((2-hydroxyethyl)(methyl)amino)-2-methyl-5-morpholino-[3,3'-bipyridin]-5-yl)-3-(trifluoromethyl)benzamide in 12% yield. $^1$H NMR (400 MHz, <cd3od>) δ ppm 2.63 (s, 3H) 3.05-3.13 (m, 4H) 3.35 (s, 3H) 3.84-3.89 (m, 2H) 3.90-3.95 (m, 4H) 3.96-4.03 (m, 2H) 7.70 (d, J=1.96 Hz, 1H) 7.79 (t, J=7.83 Hz, 1H) 7.92-8.00 (m, 2H) 8.28 (d, J=7.83 Hz, 1H) 8.34 (s, 1H) 8.44 (d, J=2.35 Hz, 1H) 9.07 (d, J=2.35 Hz, 1H). LCMS (m/z) (M+H)=516.1, Rt=0.59 min.

591
Synthesis of 5-bromo-N-methyl-3-morpholinopicolinamide

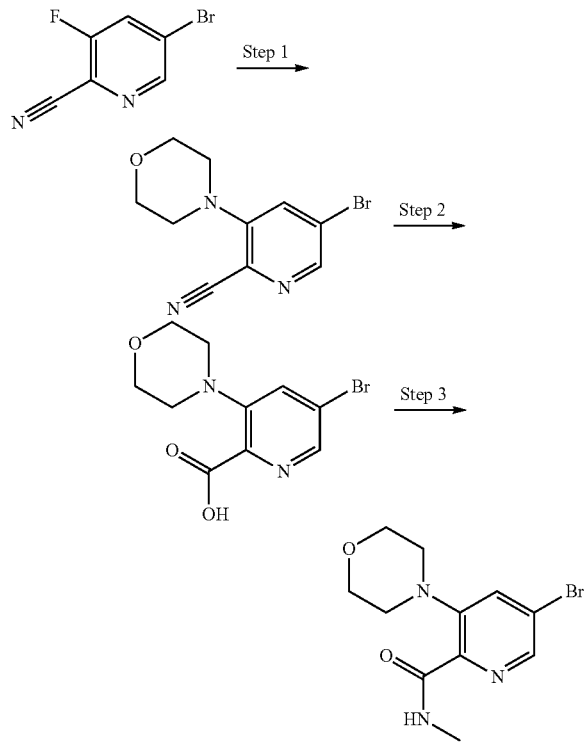

Step 1:

A solution of 5-bromo-3-fluoropicolinonitrile (1.0 equiv.), morpholine (1.1 equiv.) and DIEA (2.0 equiv.) in CAN (0.5 M) was heated to 90° C. overnight. The cooled reaction was diluted with water and filtered. The precipitate was dried to give 5-bromo-3-morpholinopicolinonitrile as a yellow crystalline solid in 87% yield. LCMS (m/z) (M+H)=267.9/269.9, Rt=0.79 min.

Step 2:

A solution of 5-bromo-3-morpholinopicolinonitrile (1.0 equiv.) in ethanol (1.0 M) was treated with 6M aqueous sodium hydroxide (10.0 equiv.) and stirred at 85° C. for 4 hours. The volatiles were removed under vacuo and the mixture was acidified to pH=4 with 2M HCl. Acetonitrile was added to this mixture and lyophilized to give 5-bromo-3-morpholinopicolinic acid as a yellow solid in 50% yield. LCMS (m/z) (M+H)=286.9/288.9, Rt=0.41 min.

Step 3:

To a solution of 5-bromo-3-morpholinopicolinic acid (1.0 equiv.), EDC (1.1 equiv.) and HOAt (1.1 equiv.) and methylamine hydrochloride (1.2 equiv.) in DMF (0.3M) was added DIEA (2.2 equiv.) and the mixture was stirred overnight at rt. The solution was diluted with water and extracted with ethyl acetate. The combined extracts were washed with sat. sodium bicarbonate, dried over sodium sulfate, filtered and concentrated to give 5-bromo-N-methyl-3-morpholinopicolinamide in 58% yield as a colorless residue. LCMS (m/z) (M+H)=299.9/301.9, Rt=0.47 min.

Note: the next several examples were made via a last-step Suzuki coupling.

592
Example 987: 5-(5-(2-(1,1-difluoroethyl)isonicotinamido)-2-methylphenyl)-N-methyl-3-morpholinopicolinamide

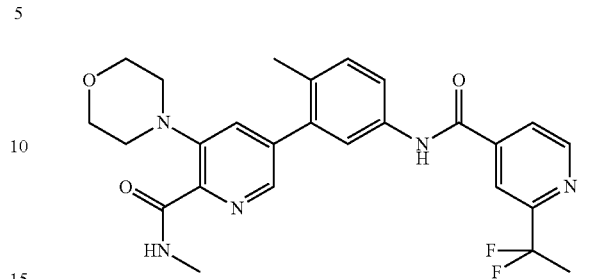

$^1$H NMR (400 MHz, <cd3od>) δ ppm 2.05 (t, J=18.78 Hz, 3H) 2.32 (s, 3H) 3.03 (s, 3H) 3.91-4.01 (m, 4H) 7.41 (d, J=8.22 Hz, 1H) 7.69 (dd, J=8.22, 1.96 Hz, 1H) 7.78 (d, J=2.35 Hz, 1H) 7.93 (s, 1H) 7.98 (d, J=4.70 Hz, 1H) 8.20 (s, 1H) 8.43 (s, 1H) 8.83 (d, J=5.09 Hz, 1H). LCMS (m/z) (M+H)=496.2, Rt=0.69 min.

Example 988: N-(2-methyl-5'-morpholino-6'-oxo-1',6'-dihydro-[3,3'-bipyridin]-5-yl)-3-(trifluoromethyl)benzamide

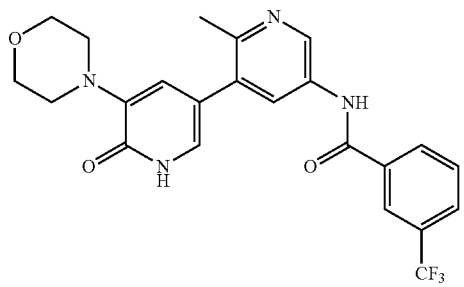 [SMILES: Cc1ncc(NC(=O)c2cccc(C(F)(F)F)c2)cc1-c1c[nH]c(=O)c(N2CCOCC2)c1]

LCMS (m/z) (M+H)=469.1, Rt=0.65 min.

Example 989: (S)—N-(3-(6-(2-hydroxypropoxy)-5-morpholinopyridin-3-yl)-4-methylphenyl)-2-(methylsulfonyl)isonicotinamide

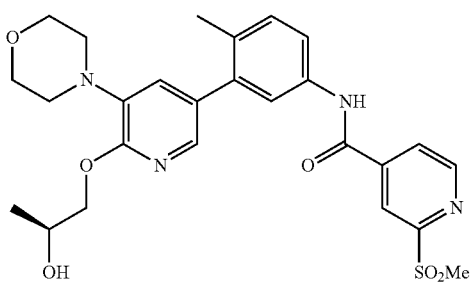 [SMILES: Cc1ccc(NC(=O)c2ccnc(S(C)(=O)=O)c2)cc1-c1cnc(OC[C@H](C)O)c(N2CCOCC2)c1]

1H NMR (400 MHz, <dmso>) δ ppm 1.10-1.21 (m, 3H) 2.17-2.27 (m, 4H) 3.03-3.11 (m, 4H) 3.67-3.79 (m, 4H) 7.07-7.13 (m, 1H) 7.26-7.34 (m, 1H) 7.57-7.77 (m, 4H) 8.16-8.25 (m, 1H) 8.47-8.53 (m, 1H) 8.93-9.01 (m, 1H) 10.71-10.77 (m, 1H). LCMS (m/z) (M+H)=527.1, Rt=0.71 min.

Example 990: (S)-2-(2-fluoropropan-2-yl)-N-(6'-(2-hydroxypropoxy)-2-methyl-5-morpholino-[3,3'-bipyridin]-5-yl)isonicotinamide

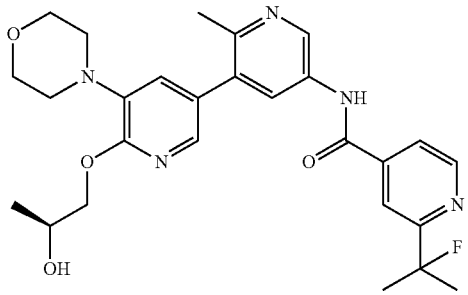 [SMILES: Cc1ncc(NC(=O)c2ccnc(C(C)(C)F)c2)cc1-c1cnc(OC[C@H](C)O)c(N2CCOCC2)c1]

1H NMR (500 MHz, DMSO-d6) δ ppm 1.14-1.25 (m, 3H) 1.65-1.77 (m, 6H) 2.45 (s, 3H) 3.04-3.16 (m, 4H) 3.69-3.80 (m, 4H) 3.98-4.08 (m, 1H) 4.11-4.17 (m, 1H) 4.20-4.28 (m, 2H) 4.76-4.91 (m, 2H) 7.15-7.28 (m, 2H) 7.73-7.80 (m, 2H) 7.83-7.89 (m, 2H) 8.00-8.12 (m, 4H) 8.74-8.79 (m, 1H) 8.85-8.93 (m, 1H) 10.72-10.80 (m, 1H). LCMS (m/z) (M+H)=510.2, Rt=0.62 min.

Example 991: (R)—N-(3-(2-((2-hydroxypropyl)amino)-6-morpholinopyridin-4-yl)-4-methylphenyl)-2-(trifluoromethyl)isonicotinamide

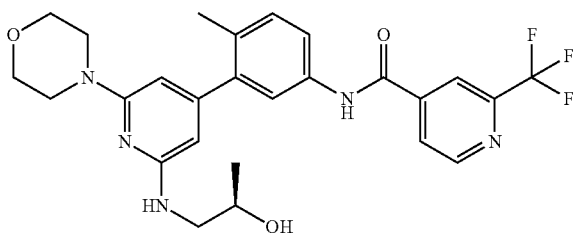 [SMILES: Cc1ccc(NC(=O)c2ccnc(C(F)(F)F)c2)cc1-c1cc(NC[C@@H](C)O)nc(N2CCOCC2)c1]

A solution of N-(3-(2-chloro-6-morpholinopyridin-4-yl)-4-methylphenyl)-2-(trifluoromethyl)isonicotinamide (1.0 equiv.), (R)-1-aminopropan-2-ol (2.0 equiv.), Pd-BrettPhos (0.1 equiv.) and cesium carbonate (1.5 equiv.) in t-BuOH (0.5M) was purged with Argon and heated to 90° C. overnight. The reaction was cooled to rt, diluted with aqueous sodium bicarbonate, extracted with ethyl acetate, dried over magnesium sulfate, filtered and concentrated. The residue was diluted with DMSO and purified via reverse phase HPLC to give (R)—N-(3-(2-((2-hydroxypropyl)amino)-6-morpholinopyridin-4-yl)-4-methylphenyl)-2-(trifluoromethyl)isonicotinamide in 37% yield. LCMS (m/z) (M+H)= 516.1, Rt=0.77 min.

Example 992: N-(6'-(1,4-dioxan-2-yl)methoxy)-2-methyl-5'-morpholino-[3,3'-bipyridin]-5-yl)-3-(trifluoromethyl)benzamide

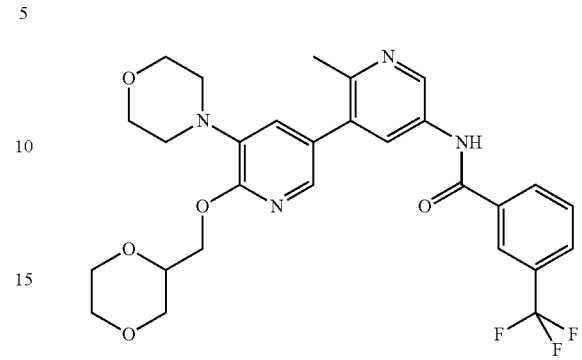

Sodium hydride (3.1 equiv.) was added to dioxane (0.15 M) at rt. (1,4-dioxan-2-yl)methanol (3.0 equiv.) was added and the mixture was stirred for 30 min. N-(6'-fluoro-2-methyl-5'-morpholino-[3,3'-bipyridin]-5-yl)-3-(trifluoromethyl)benzamide (1.0 equiv.) was added and the reaction was stirred at 105° C. for 3 hours. The cooled reaction mixture was poured into water and extracted with ethyl acetate. The combined organics were washed with brine, dried over sodium sulfate, filtered and concentrated. The mixture was purified via flash chromatography (0-10% methanol/DCM) to give N-(6'-((1,4-dioxan-2-yl)methoxy)-2-methyl-5'-morpholino-[3,3'-bipyridin]-5-yl)-3-(trifluoromethyl)benzamide in 49% yield. $^{1}$H NMR (400 MHz, Methanol-d4) δ 8.80 (d, J=2.5 Hz, 1H), 8.21 (dt, J=1.8, 1.1 Hz, 1H), 8.15 (ddd, J=8.0, 1.4, 0.7 Hz, 1H), 8.06 (d, J=2.5 Hz, 1H), 7.82 (ddt, J=7.8, 1.8, 1.0 Hz, 1H), 7.71-7.61 (m, 2H), 7.16 (d, J=2.1 Hz, 1H), 4.31 (d, J=4.9 Hz, 2H), 3.91 (dtd, J=9.9, 4.9, 2.6 Hz, 1H), 3.86-3.59 (m, 9H), 3.58-3.44 (m, 2H), 3.15-2.98 (m, 4H), 2.42 (s, 3H). LCMS (m/z) (M+H)=559.2, Rt=0.77 min.

Example 993: N-(6'-((4-hydroxytetrahydro-2H-pyran-4-yl)methyl)-2-methyl-5'-morpholino-[3,3'-bipyridin]-5-yl)-3-(trifluoromethyl)benzamide

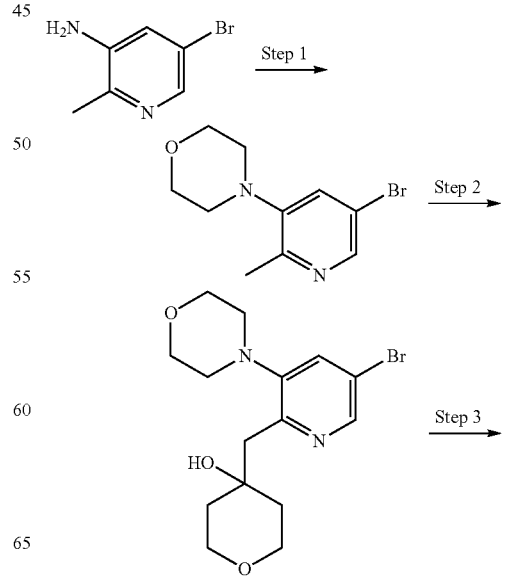

-continued

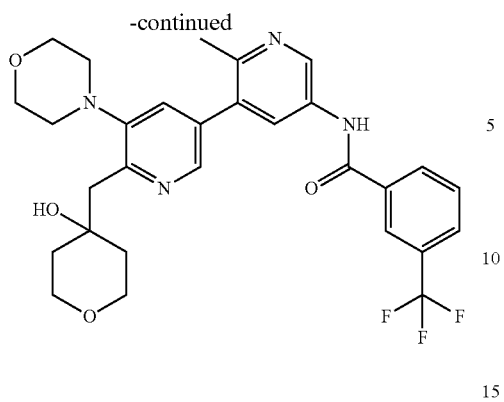

Step 1:

To a stirred solution of bis(2-bromoethyl) ether (2.0 equiv.) in DMF at 0° C. was slowly added sodium hydride (4.0 equiv.) and the mixture was allowed to warm to rt over 15 min followed by the addition of 5-bromo-2-methylpyridin-3-amine (1.0 equiv.) The mixture was heated to 90° C. and stirred for 48 hours. Upon cooling to rt, the mixture was poured onto ice water and extracted with ethyl acetate. The organic layer was dried over magnesium sulfate, filtered and concentrated. The residue was purified via silica gel chromatography to give 4-(5-bromo-2-methylpyridin-3-yl)morpholine in 63% yield. LCMS (m/z) (M+H)=258.9, Rt=0.43 min.

Step 2:

A solution of 4-(5-bromo-2-methylpyridin-3-yl)morpholine (1.0 equiv.) in THF under argon was cooled to −78° C. and treated with LDA (2.0 equiv.). The deep red solution was stirred for 1 hour at −78° C. at which time dihydro-2H-pyran-4(3H)-one (2.2 equiv.) was added dropwise. The mixture was stirred for 1 hour at −78° C., then warmed to rt and quenched with ammonium chloride (aq.), extracted with ethyl acetate (3×), dried, filtered and concentrated to give a crude oil. The residue was purified via silica gel chromatography (0-100% ethyl acetate/heptanes) to give 4-((5-bromo-3-morpholinopyridin-2-yl)methyl)tetrahydro-2H-pyran-4-ol in 94% yield. LCMS (m/z) (M+H)=357.0/359.0, Rt=0.53 min.

Step 3:

To a solution of N-(6-methyl-5-(4,4,5,5-tetramethyl-1,3,2-dioxaborolan-2-yl)pyridin-3-yl)-3-(trifluoromethyl)benzamide (1.5 equiv.) and 4-((5-bromo-3-morpholinopyridin-2-yl)methyl)tetrahydro-2H-pyran-4-ol (1.0 equiv.) in DME (0.1 M) was added PdCl$_2$(dppf)-DCM adduct (0.1 equiv.) and sodium carbonate (3.0 equiv., 2M aqueous sln) and the reaction was purged with nitrogen. The mixture was heated in the microwave at 120° C. for 30 mins, then quenched with sat. sodium bicarbonate, extracted with ethyl acetate (3×), dried over magnesium sulfate, filtered and concentrated. The residue was dissolved in DMSO and purified via reverse phase HPLC to give N-(6'-((4-hydroxytetrahydro-2H-pyran-4-yl)methyl)-2-methyl-5'-morpholino-[3,3'-bipyridin]-5-yl)-3-(trifluoromethyl)benzamide in 24% yield. $^1$H NMR (400 MHz, Methanol-d4) δ ppm 9.13 (d, J=2.4 Hz, 1H), 8.51 (dd, J=9.7, 2.2 Hz, 2H), 8.32 (dq, J=1.8, 0.9 Hz, 1H), 8.30-8.23 (m, 1H), 8.12 (d, J=1.9 Hz, 1H), 7.95 (ddt, J=7.8, 1.8, 1.0 Hz, 1H), 7.78 (ddt, J=7.9, 7.2, 0.8 Hz, 1H), 3.93-3.86 (m, 4H), 3.86-3.71 (m, 4H), 3.26 (s, 2H), 3.11-3.04 (m, 4H), 2.63 (s, 3H), 1.81 (ddd, J=14.4, 10.1, 4.8 Hz, 2H), 1.56 (d, J=13.8 Hz, 2H). LCMS (m/z) (M+H)=557.2, Rt=0.64 min.

Example 994: N-(6'-((dihydro-2H-pyran-4(3H)-ylidene)methyl)-2-methyl-5'-morpholino-[3,3'-bipyridin]-5-yl)-3-(trifluoromethyl)benzamide

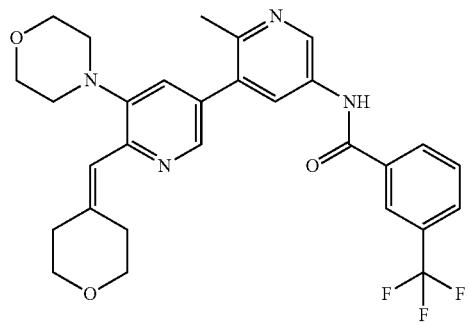 [SMILES: Cc1ncc(NC(=O)c2cccc(C(F)(F)F)c2)cc1-c1cnc(C=C2CCOCC2)c(N2CCOCC2)c1]

To a solution of N-(6'-((4-hydroxytetrahydro-2H-pyran-4-yl)methyl)-2-methyl-5'-morpholino-[3,3'-bipyridin]-5-yl)-3-(trifluoromethyl)benzamide (1.0 equiv.) in DCM (0.1 M) at −78° C. under argon was added DAST (1.3 equiv.) and the solution was stirred at −78° C. for 2 hours. Quenched by the addition of sat. sodium bicarbonate, extracted with DCM (3×), the organic layer was dried over magnesium sulfate, filtered and concentrated. The residue was purified via reverse phase prep-HPLC and the pure fractions were lyophilized to give N-(6'-((dihydro-2H-pyran-4(3H)-ylidene)methyl)-2-methyl-5'-morpholino-[3,3'-bipyridin]-5-yl)-3-(trifluoromethyl)benzamide in 42% yield. $^1$H NMR (400 MHz, Methanol-d4) δ 9.12 (t, J=1.9 Hz, 1H), 8.48-8.42 (m, 2H), 8.32 (dd, J=1.7, 0.9 Hz, 1H), 8.30-8.23 (m, 1H), 8.02-7.91 (m, 2H), 7.82-7.73 (m, 1H), 5.47 (t, J=1.5 Hz, 1H), 4.12 (q, J=2.4 Hz, 2H), 3.91-3.84 (m, 5H), 3.84-3.75 (m, 4H), 3.09-3.02 (m, 4H), 2.62 (s, 3H), 2.14 (s, 2H). LCMS (m/z) (M+H)=539.2, Rt=0.69 min.

Synthesis of 2-((5-(5-amino-2-methylphenyl)-3-morpholinopyridin-2-yl)oxy)ethanol

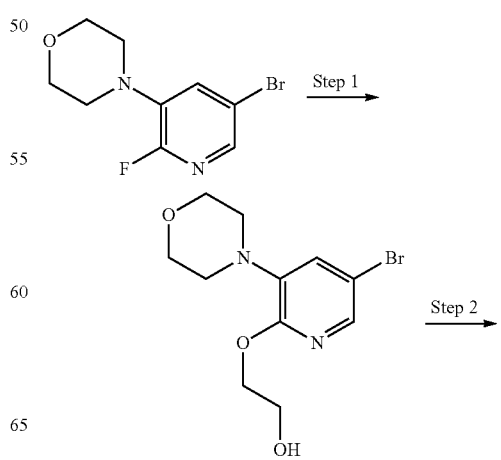

-continued

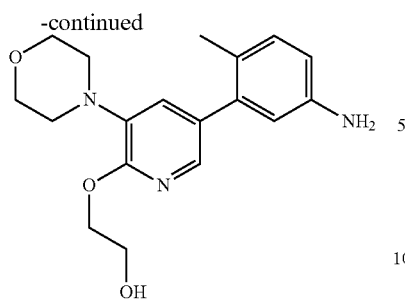

Step 1:

To a solution of ethylene glycol (5.0 equiv.) in dioxane and DMF (4:1, 0.08 M) was added sodium hydride (5.0 equiv.) and the mixture was stirred for 15 min at rt. 4-(5-bromo-2-fluoropyridin-3-yl)morpholine (1.0 equiv.) was then added, and the reaction was heated to 90° C. and stirred overnight. The mixture was carefully poured onto water and extracted three times with ethyl acetate. The combined organics were washed with water, brine, dried over magnesium sulfate, filtered and concentrated. The crude residue was purified via silica gel chromatography (0-100% ethyl acetate/heptanes) to give 2-((5-bromo-3-morpholinopyridin-2-yl)oxy)ethanol as a yellow oil in 54% yield. LCMS (m/z) (M+H)=302.9/304.9, Rt=0.63 min.

Step 2:

A solution of 2-((5-bromo-3-morpholinopyridin-2-yl)oxy)ethanol (1.0 equiv.), 4-methyl-3-(4,4,5,5-tetramethyl-1,3,2-dioxaborolan-2-yl)aniline (1.9 equiv.), PdCl$_2$(dppf)-DCM (0.1 equiv.), and sodium carbonate (4.0 equiv, 2M aqueous sln) was heated at 80° C. overnight. The cooled reaction was partitioned between water and ethyl acetate, the organic phase was dried with sodium sulfate, filtered and concentrated. The crude material was purified via silica gel chromatography (ISCO, eluting with 0-10% methanol in DCM) and the pure fractions were concentrated to give 2-((5-(5-amino-2-methylphenyl)-3-morpholinopyridin-2-yl)oxy)ethanol as a brown foam in 56% yield. LCMS (m/z) (M+H)=330.0, Rt=0.46 min.

The compounds listed below were prepared using methods similar to those described for the preparation of Example 919 above using the appropriate starting materials.

Example 997: 2-(2-fluoropropan-2-yl)-N-(3-(6-(2-hydroxyethoxy)-5-morpholinopyridin-3-yl)-4-methylphenyl)isonicotinamide

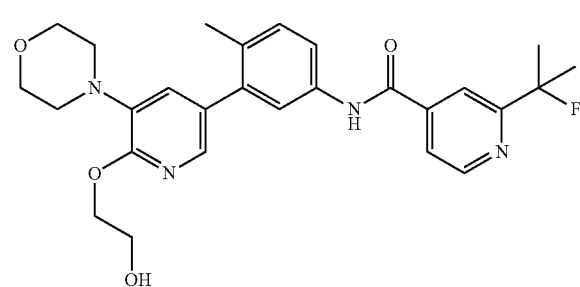 [SMILES: Cc1ccc(NC(=O)c2ccnc(C(C)(C)F)c2)cc1-c1cnc(OCCO)c(N2CCOCC2)c1]

LCMS (m/z) (M+H)=495.2, Rt=0.80 min.

Example 998: 2-(2-cyanopropan-2-yl)-N-(3-(6-(2-hydroxyethoxy)-5-morpholinopyridin-3-yl)-4-methylphenyl)isonicotinamide

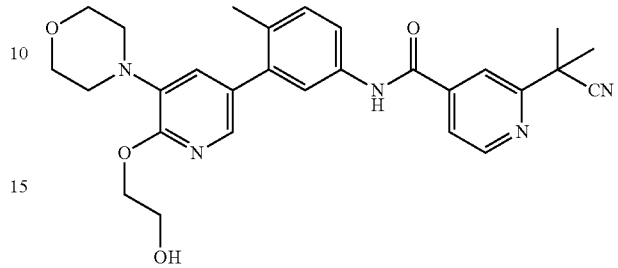

LCMS (m/z) (M+H)=502.2, Rt=0.79 min.

Example 999: 2-cyclopropyl-N-(3-(6-(2-hydroxyethoxy)-5-morpholinopyridin-3-yl)-4-methylphenyl)isonicotinamide

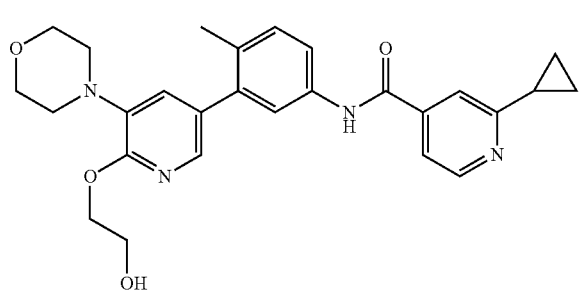 [SMILES: Cc1ccc(NC(=O)c2ccnc(C3CC3)c2)cc1-c1cnc(OCCO)c(N2CCOCC2)c1]

LCMS (m/z) (M+H)=475.2, Rt=0.63 min.

Example 1000: 2-(1,1-difluoroethyl)-N-(3-(6-(2-hydroxyethoxy)-5-morpholinopyridin-3-yl)-4-methylphenyl)isonicotinamide

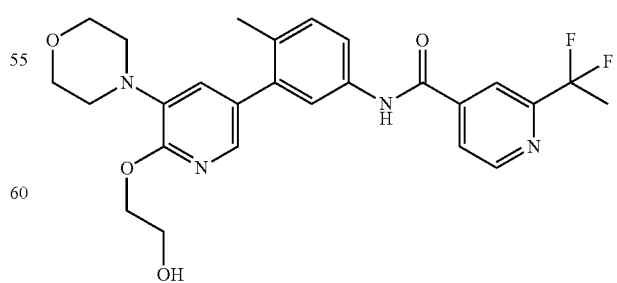

LCMS (m/z) (M+H)=499.2, Rt=0.82 min.

Example 1001: N-(3-(6-(2-hydroxyethoxy)-5-morpholinopyridin-3-yl)-4-methylphenyl)-5-(trifluoromethyl)nicotinamide

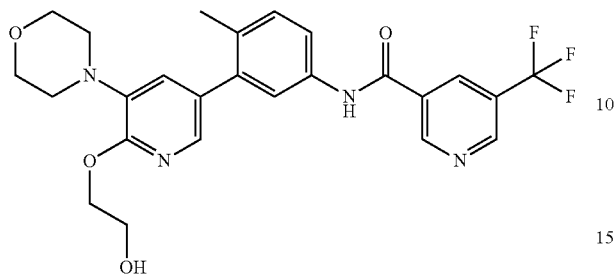

LCMS (m/z) (M+H)=503.2, Rt=0.83 min.

Example 1002: N-(3-(6-(2-hydroxyethoxy)-5-morpholinopyridin-3-yl)-4-methylphenyl)-2-(trifluoromethyl)isonicotinamide

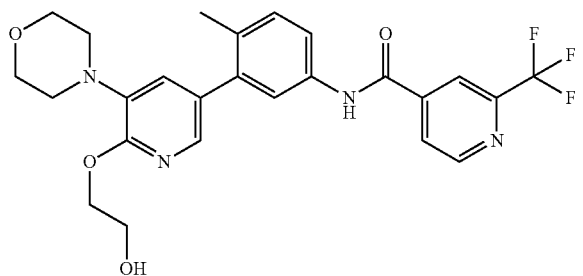 [SMILES: Cc1ccc(NC(=O)c2ccnc(C(C)(F)F)c2)cc1-c1cnc(OCCO)c(N2CCOCC2)c1]

LCMS (m/z) (M+H)=503.2, Rt=0.84 min.

Example 1003: (R)-methyl(2-((2'-methyl-5-morpholino-5'-(3-(trifluoromethyl)benzamido)-[3,3'-bipyridin]-6-yl)oxy)propyl)carbamate

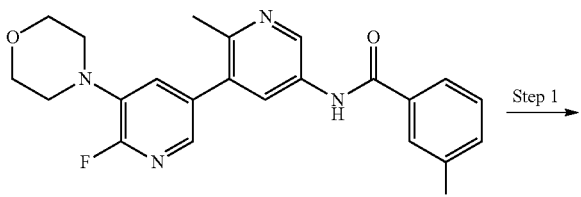

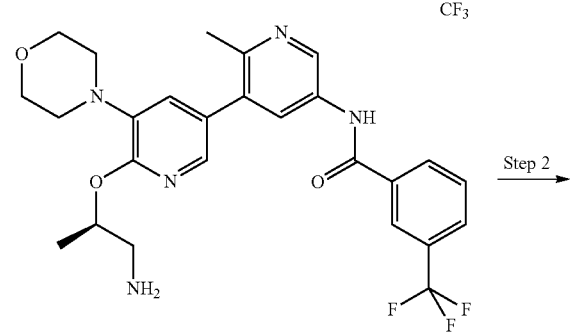

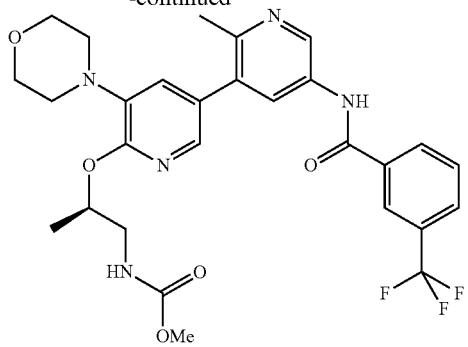

Step 1:

Sodium hydride (3.1 equiv.) was added to dioxane (0.09 M) at rt. (R)-1-aminopropan-2-ol (3.0 equiv.) was added, and the mixture was stirred for 30 min. N-(6'-fluoro-2-methyl-5'-morpholino-[3,3'-bipyridin]-5-yl)-3-(trifluoromethyl)benzamide (1.0 equiv.) was added and the reaction was stirred at rt for 18 hours. Upon overnight stirring at rt, the reaction was heated to 60° C. for 5 hours. The cooled reaction mixture was poured into water and extracted with ethyl acetate (3×). The combined organics were washed with brine, dried over sodium sulfate, filtered and concentrated. The mixture was purified by silica gel chromatography (0-10% methanol:DCM) and the pure fractions were concentrated to give (R)—N-(6'-((1-aminopropan-2-yl)oxy)-2-methyl-5'-morpholino-[3,3'-bipyridin]-5-yl)-3-(trifluoromethyl)benzamide in 20% yield. LCMS (m/z) (M+H)=516.1, Rt=0.64 min.

Step 2:

(R)—N-(6'-((1-aminopropan-2-yl)oxy)-2-methyl-5'-morpholino-[3,3'-bipyridin]-5-yl)-3-(trifluoromethyl)benzamide (1.0 equiv.) in DCM (0.03 M) followed by methyl chloroformate (1.2 equiv.) and the reaction was stirred at rt for 2 hours. Quenched by the addition of sat. sodium bicarbonate, extracted with DCM (3×), dried over magnesium sulfate, filtered and concentrated. The residue was redissolved in DMSO and purified via reverse phase prep-HPLC to give (R)-methyl(2-((2'-methyl-5-morpholino-5'-(3-(trifluoromethyl)benzamido)-[3,3'-bipyridin]-6-yl)oxy)propyl)carbamate in 32% yield. $^1$H NMR (400 MHz, Methanol-d4) δ 9.36 (d, J=2.4 Hz, 1H), 8.46 (d, J=2.4 Hz, 1H), 8.34 (dt, J=1.7, 1.0 Hz, 1H), 8.32-8.24 (m, 1H), 8.00-7.92 (m, 1H), 7.87 (d, J=2.2 Hz, 1H), 7.83-7.74 (m, 1H), 7.31 (d, J=2.2 Hz, 1H), 5.44 (td, J=6.6, 4.5 Hz, 1H), 3.86 (t, J=4.7 Hz, 4H), 3.62 (s, 3H), 3.53-3.36 (m, 2H), 3.21-3.07 (m, 4H), 2.70 (s, 3H), 1.37 (d, J=6.3 Hz, 3H). LCMS (m/z) (M+H)=574.2, Rt=0.77 min.

Synthesis of 6'-chloro-3'-fluoro-2-methyl-2'-morpholino-[3,4'-bipyridin]-5-amine

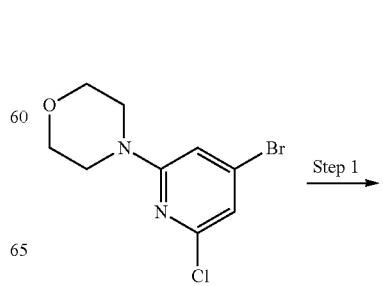

-continued

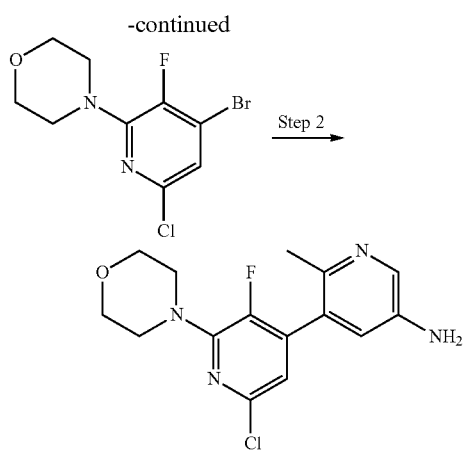

Step 1:
4-(4-bromo-6-chloropyridin-2-yl)morpholine (1.0 equiv.) was dissolved in acetonitrile (0.1 M). Selectfluor (1.1 equiv.) was added at rt and stirred for 18 hours. The reaction was diluted with ethyl acetate and washed with water, brine, dried over sodium sulfate, filtered and concentrated. The residue was purified by silica gel chromatography (ISCO, 0-10% ethyl acetate/heptanes) to give 4-(4-bromo-6-chloro-3-fluoropyridin-2-yl)morpholine in 42% yield and 4-(4-bromo-6-chloro-5-fluoropyridin-2-yl)morpholine in 14% yield. LCMS (m/z) (M+H)=294.7, Rt=0.95 and 0.99 min.

Step 2:
To a solution of 4-(4-bromo-6-chloro-3-fluoropyridin-2-yl)morpholine (1.0 equiv.) and 6-methyl-5-(4,4,5,5-tetramethyl-1,3,2-dioxaborolan-2-yl)pyridin-3-amine (1.7 equiv.) in DME (0.04 M) and sodium carbonate (2M, 3.0 equiv.) was added Pd(PPh$_3$)$_4$ (0.03 equiv.) and the reaction was heated at 100° C. for 2 hours. The mixture was poured onto ice water and extracted with ethyl acetate. The combined organics were washed with brine, dried over magnesium sulfate, filtered and concentrated. The mixture was purified via silica gel chromatography (10% methanol:ethyl acetate: heptanes) to give 6'-chloro-3'-fluoro-2-methyl-2'-morpholino-[3,4'-bipyridin]-5-amine as a yellow solid in 39% yield. $^1$H NMR (400 MHz, <cdcl3>) δ ppm 2.32 (s, 3H) 3.52-3.59 (m, 4H) 3.66 (br. s., 2H) 3.80-3.85 (m, 4H) 6.63 (d, J=3.91 Hz, 1H) 6.79-6.84 (m, 1H) 8.08 (d, J=2.74 Hz, 1H)

Synthesis of 2'-chloro-3'-fluoro-2-methyl-6'-morpholino-[3,4'-bipyridin]-5-amine

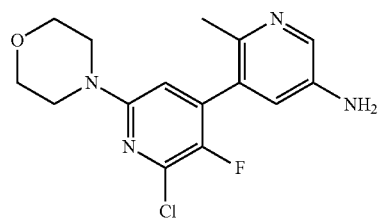 [SMILES: Cc1ncc(N)cc1-c1cc(N2CCOCC2)nc(Cl)c1F]

To a solution of 4-(4-bromo-6-chloro-5-fluoropyridin-2-yl)morpholine (1.0 equiv.) and 6-methyl-5-(4,4,5,5-tetramethyl-1,3,2-dioxaborolan-2-yl)pyridin-3-amine (1.4 equiv.) in DME (0.02 M)) and Na$_2$CO$_3$ (2 M aq.) (3.0 equiv.) was added Pd(PPh$_3$)$_4$ and heated (thermally) at 100° C. for 2 h. LCMS shows complete consumption of starting material with fairly clean conversion to desired product. The mixture was poured onto ice-water and extracted with EtOAc (3×). The combined organics were washed with brine, dried (MgSO$_4$) and concentrated. The mixture was adsorbed onto Celite and purified by ISCO flash column chromatography (silica gel, 10% methanol in EtOAc:heptane). Product fractions eluted around 40% EtOAc and were concentrated to give 2'-chloro-3'-fluoro-2-methyl-6'-morpholino-[3,4'-bipyridin]-5-amine in 77% yield as a pale yellow solid. LCMS (m/z) (M+H)=322.9, Rt=0.62 min.

Synthesis of 2-((4-(5-amino-2-methylphenyl)-3-fluoro-6-morpholinopyridin-2-yl)amino)ethanol

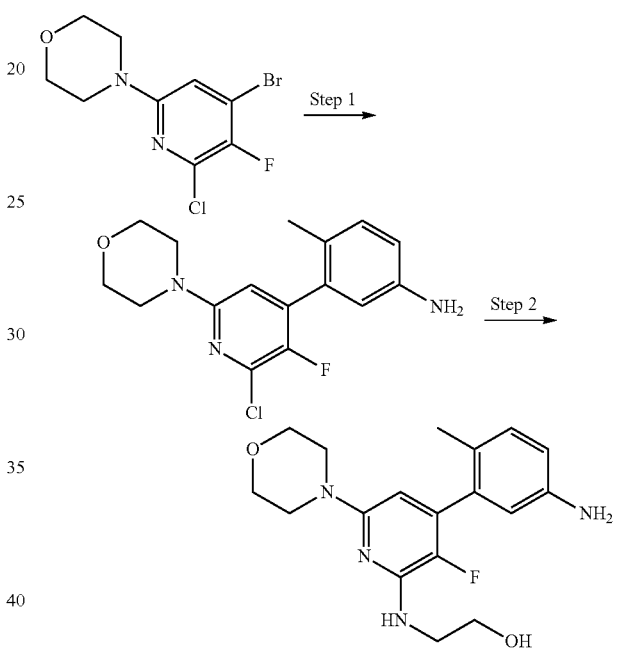

Step 1:
To a solution of 4-(4-bromo-6-chloro-5-fluoropyridin-2-yl)morpholine (1.0 equiv.) and 4-methyl-3-(4,4,5,5-tetramethyl-1,3,2-dioxaborolan-2-yl)aniline (1.2 equiv.) in DME (0.1 M) and Na$_2$CO$_3$ (2 M aq.) (3.0 equiv.) was added Pd(PPh$_3$)$_4$ and heated (thermally) at 100° C. for 2 h. LCMS shows complete consumption of starting material with fairly clean conversion to desired product. The mixture was poured onto ice-water and extracted with EtOAc (3×). The combined organics were washed with brine, dried (MgSO$_4$) and concentrated. The mixture was adsorbed onto Celite and purified by ISCO flash column chromatography (silica gel, 10% methanol in EtOAc:heptane). Product fractions eluted around 40% EtOAc and were concentrated to give 3-(2-chloro-3-fluoro-6-morpholinopyridin-4-yl)-4-methylaniline in 87% yield. LCMS (m/z) (M+H)=322, Rt=0.62 min.

Step 2:
In a microwave vial was added 3-(2-chloro-3-fluoro-6-morpholinopyridin-4-yl)-4-methylaniline (1.0 equiv.), 2-aminoethanol (50 equiv.), DIPEA (2.0 equiv.) in NMP (0.2). The vial was sealed with a crimp top. The reaction was then heated to 250° C. for 30 min heated by microwave. LC-MS showed completion of the reaction. The reaction mixture was diluted with ethyl acetate, washed with water, brine then dried over sodium sulfate. Concentrated to yield crude. Purified by 10% methanol in ethyl acetate to yield 2-((4-(5-amino-2-methylphenyl)-3-fluoro-6-morpholinopyridin-2-yl)amino)ethanol in 43% yield. LCMS (m/z) (M+H)=347.0, Rt=0.50 min.

Example 1004: N-(3'-fluoro-6'-((2-hydroxyethyl)amino)-2-methyl-2'-morpholino-[3,4'-bipyridin]-5-yl)-6-(trifluoromethyl)pyridazine-4-carboxamide

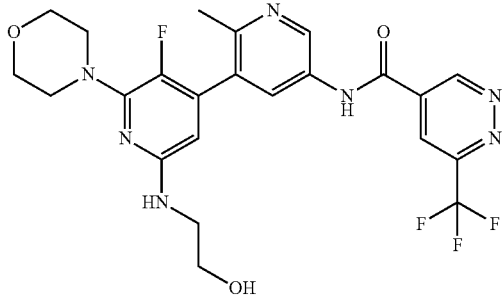 [SMILES: Cc1ncc(NC(=O)c2cnnc(C(F)(F)F)c2)cc1-c1cc(NCCO)nc(N2CCOCC2)c1F]

6-(trifluoromethyl)pyridazine-4-carboxylic acid (1.2 equiv.), 2-((5-amino-5'-fluoro-2-methyl-6'-morpholino-[3,4'-bipyridin]-2'-yl)amino)ethanol (1.0 equiv.) and DIPEA (1.5 equiv.) were added into DCM (0.09 M). 2,4,6-tripropyl-1,3,5,2,4,6-trioxatriphosphinane 2,4,6-trioxide (1.3 equiv.) was added and the mixture was stirred at rt over the weekend. The reaction mixture was purified directly via silica gel chromatography followed by neutral reverse phase prep-HPLC and the pure fractions were lyophilized to give N-(3'-fluoro-6'-((2-hydroxyethyl)amino)-2-methyl-2'-morpholino-[3,4'-bipyridin]-5-yl)-6-(trifluoromethyl)pyridazine-4-carboxamide in 8% yield. $^1$H NMR (400 MHz, <cdcl3>) δ ppm 2.48 (s, 3H) 3.39-3.54 (m, 7H) 3.73-3.88 (m, 7H) 4.61-4.71 (m, 1H) 5.76 (d, J=2.74 Hz, 1H) 8.08 (d, J=1.96 Hz, 1H) 8.29 (d, J=1.96 Hz, 1H) 8.70 (d, J=2.35 Hz, 1H) 9.83 (s, 1H). LCMS (m/z) (M+H)=522.1, Rt=0.62 min.

The compounds listed below were prepared using methods similar to those described for the preparation of Example 1004 above using the appropriate starting materials.

Example 1006: N-(3-(3-fluoro-2-((2-hydroxyethyl)amino)-6-morpholinopyridin-4-yl)-4-methylphenyl)-2-(trifluoromethyl)isonicotinamide

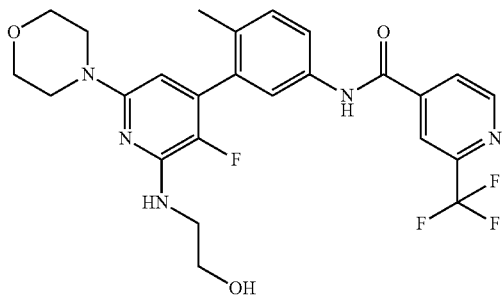

$^1$H NMR (500 MHz, CHLOROFORM-d) δ ppm 2.26 (s, 3H) 3.36-3.43 (m, 4H) 3.70 (m, 3H) 3.80-3.86 (m, 4H) 3.86-3.92 (m, 2H) 5.03 (br. s., 1H) 5.72 (br. s., 1H) 7.33 (d, J=8.20 Hz, 1H) 7.52 (br. s., 1H) 7.61 (d, J=8.20 Hz, 1H) 7.94 (d, J=2.84 Hz, 1H) 8.03 (br. s., 1H) 8.13 (s, 1H) 8.94 (d, J=4.73 Hz, 1H). LCMS (m/z) (M+H)=520.1, Rt=0.86 min.

Example 1007: N-(3-(3-fluoro-2-((2-hydroxyethyl)amino)-6-morpholinopyridin-4-yl)-4-methylphenyl)-6-(trifluoromethyl)pyridazine-4-carboxamide

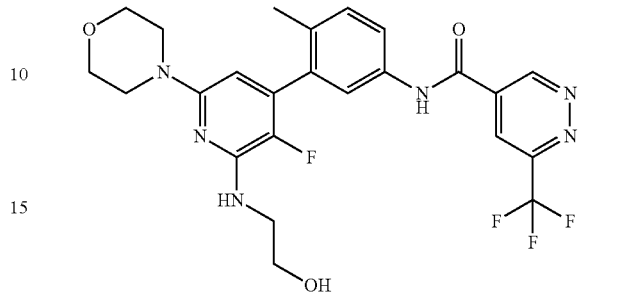

$^1$H NMR (400 MHz, <cdcl3>) δ ppm 2.23 (br. s., 3H) 3.35 (br. s., 4H) 3.66 (br. s., 2H) 3.76-3.88 (m, 8H) 5.01 (br. s., 1H) 5.66 (br. s., 1H) 7.30 (d, J=7.83 Hz, 1H) 7.45 (br. s., 1H) 7.62 (d, J=7.43 Hz, 1H) 8.28 (br. s., 1H) 8.64 (br. s., 1H) 9.78 (br. s., 1H). LCMS (m/z) (M+H)=521.1, Rt=0.81 min.

Example 1008: N-(3-(3-fluoro-6-((2-hydroxyethyl)amino)-2-morpholinopyridin-4-yl)-4-methylphenyl)-2-(trifluoromethyl)isonicotinamide

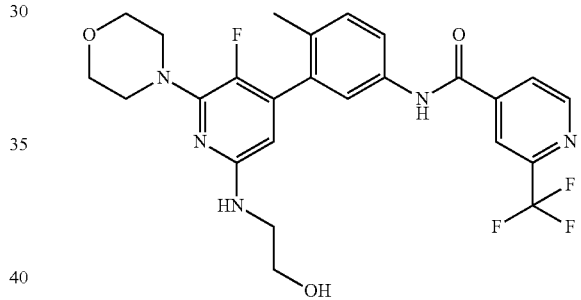

$^1$H NMR (500 MHz, CHLOROFORM-d) δ ppm 2.19-2.31 (m, 3H) 2.97-3.29 (m, 1H) 3.36-3.55 (m, 6H) 3.76-3.92 (m, 6H) 4.64 (br. s., 1H) 7.29-7.39 (m, 2H) 7.51 (br. s., 1H) 7.58 (d, J=8.20 Hz, 1H) 7.94 (d, J=3.47 Hz, 1H) 8.13 (br. s., 2H) 8.93 (d, J=4.41 Hz, 1H). LCMS (m/z) (M+H)=519.9, Rt=0.83 min.

Example 1009: 2-(difluoromethyl)-N-(3-(3-fluoro-6-((2-hydroxyethyl)amino)-2-morpholinopyridin-4-yl)-4-methylphenyl)isonicotinamide

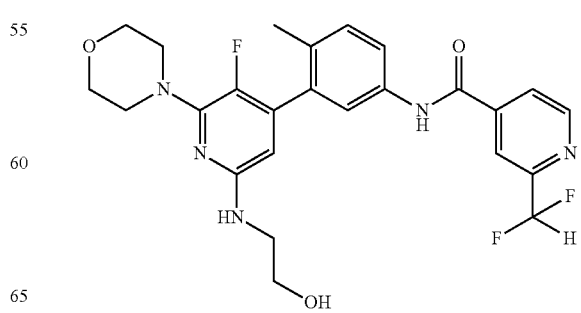

¹H NMR (500 MHz, CHLOROFORM-d) δ ppm 2.24 (s, 3H) 3.18 (br. s., 1H) 3.38-3.53 (m, 6H) 3.76-3.87 (m, 6H) 4.64 (br. s., 1H) 5.79 (d, J=2.84 Hz, 1H) 6.55-6.89 (m, 1H) 7.31 (s, 1H) 7.52 (s, 1H) 7.58 (d, J=8.20 Hz, 1H) 7.87 (d, J=4.41 Hz, 1H) 8.04 (s, 1H) 8.17 (s, 1H) 8.84 (d, J=5.04 Hz, 1H). LCMS (m/z) (M+H)=502.1, Rt=0.76 min.

Example 1010: N-(3-(3-fluoro-6-((2-hydroxyethyl) amino)-2-morpholinopyridin-4-yl)-4-methylphenyl)-2-(2-hydroxypropan-2-yl)isonicotinamide

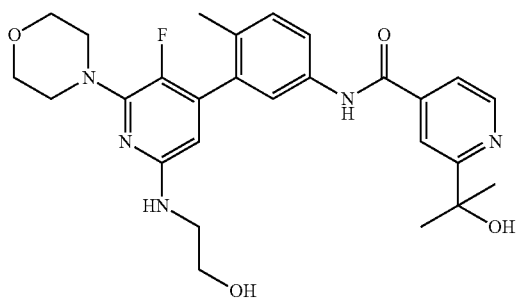 [SMILES: Cc1ccc(NC(=O)c2ccnc(C(C)(C)O)c2)cc1-c1cc(NCCO)nc(N2CCOCC2)c1F]

¹H NMR (500 MHz, CHLOROFORM-d) δ ppm 1.61 (s, 6H) 2.24 (s, 3H) 3.13-3.31 (m, 1H) 3.39-3.56 (m, 6H) 3.83 (d, J=2.84 Hz, 6H) 4.48-4.78 (m, 2H) 5.78 (br. s., 1H) 7.29-7.31 (m, 1H) 7.51 (s, 1H) 7.55-7.65 (m, 2H) 7.87 (s, 1H) 8.16 (s, 1H) 8.68 (d, J=5.04 Hz, 1H). LCMS (m/z) (M+H)=510.2, Rt=0.62 min.

Example 1011: 2-(1-cyanocyclopropyl)-N-(3-(3-fluoro-6-((2-hydroxyethyl)amino)-2-morpholinopyridin-4-yl)-4-methylphenyl)isonicotinamide

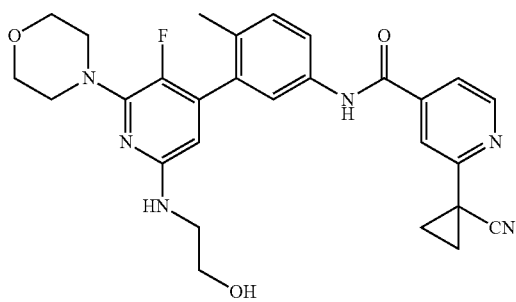 [SMILES: Cc1ccc(NC(=O)c2ccnc(C3(C#N)CC3)c2)cc1-c1cc(NCCO)nc(N2CCOCC2)c1F]

¹H NMR (500 MHz, CHLOROFORM-d) δ ppm 1.79-1.96 (m, 4H) 2.25 (d, J=2.84 Hz, 3H) 3.04 (br. s., 1H) 3.41-3.56 (m, 6H) 3.80-3.92 (m, 6H) 4.62 (br. s., 1H) 5.84 (d, J=3.15 Hz, 1H) 7.32 (d, J=3.15 Hz, 1H) 7.54 (br. s., 1H) 7.58-7.71 (m, 2H) 7.94 (br. s., 1H) 8.04 (br. s., 1H) 8.60-8.71 (m, 1H). LCMS (m/z) (M+H)=517.1, Rt=0.79 min.

Example 1012: 6-(2-cyanopropan-2-yl)-N-(3-(3-fluoro-6-((2-hydroxyethyl)amino)-2-morpholinopyridin-4-yl)-4-methylphenyl)pyridazine-4-carboxamide

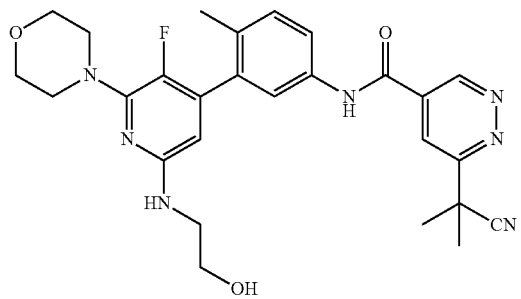 [SMILES: Cc1ccc(NC(=O)c2cnnc(C(C)(C)C#N)c2)cc1-c1cc(NCCO)nc(N2CCOCC2)c1F]

¹H NMR (500 MHz, CHLOROFORM-d) δ ppm 1.96 (s, 6H) 2.26 (s, 3H) 2.99-3.07 (m, 1H) 3.46-3.52 (m, 6H) 3.82-3.87 (m, 6H) 4.58-4.68 (m, 1H) 5.77-5.85 (m, 1H) 7.33 (d, J=8.20 Hz, 1H) 7.53 (s, 1H) 7.59-7.66 (m, 1H) 8.17 (s, 1H) 8.20-8.27 (m, 1H) 9.62 (s, 1H). LCMS (m/z) (M+H)=520.1, Rt=0.74 min.

Example 1013: N-(3-(3-fluoro-6-((2-hydroxyethyl) amino)-2-morpholinopyridin-4-yl)-4-methylphenyl)-6-(trifluoromethyl)pyridazine-4-carboxamide

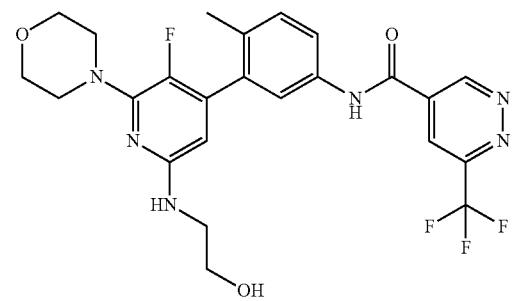 [SMILES: Cc1ccc(NC(=O)c2cnnc(C(F)(F)F)c2)cc1-c1cc(NCCO)nc(N2CCOCC2)c1F]

¹H NMR (400 MHz, <cdcl3>) δ ppm 2.23 (s, 3H) 3.43-3.50 (m, 7H) 3.76-3.88 (m, 7H) 5.76 (d, J=2.35 Hz, 1H) 7.30 (d, J=8.61 Hz, 1H) 7.47 (s, 1H) 7.60 (d, J=7.43 Hz, 1H) 8.26 (s, 1H) 8.40 (s, 1H) 9.78 (s, 1H). LCMS (m/z) (M+H)=521.1, Rt=0.84 min.

Example 1014: N-(3-(3,5-difluoro-2-((2-hydroxyethyl)amino)-6-morpholinopyridin-4-yl)-4-methylphenyl)-2-(trifluoromethyl)isonicotinamide

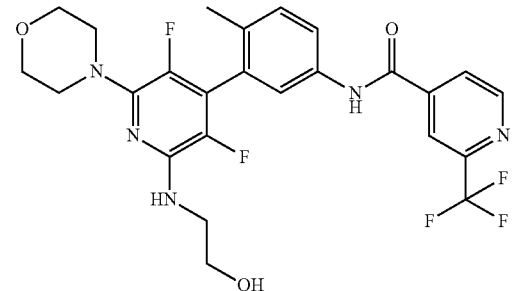 [SMILES: Cc1ccc(NC(=O)c2ccnc(C(F)(F)F)c2)cc1-c1c(F)c(NCCO)nc(N2CCOCC2)c1F]

¹H NMR (500 MHz, CHLOROFORM-d) δ ppm 2.20-2.32 (m, 3H) 3.04 (br. s., 1H) 3.33-3.46 (m, 4H) 3.60-3.73 (m, 2H) 3.81-3.93 (m, 6H) 4.84 (br. s., 1H) 7.34-7.42 (m, 1H) 7.57 (br. s., 1H) 7.63 (d, J=7.88 Hz, 1H) 7.94 (d, J=3.47

Hz, 1H) 8.04 (br. s., 1H) 8.12 (br. s., 1H) 8.94 (d, J=4.41 Hz, 1H). LCMS (m/z) (M+H)=538.1, Rt=0.94 min.

Example 1015: N-(3-(3,5-difluoro-2-((2-hydroxyethyl)amino)-6-morpholinopyridin-4-yl)-4-methylphenyl)-6-(trifluoromethyl)pyridazine-4-carboxamide

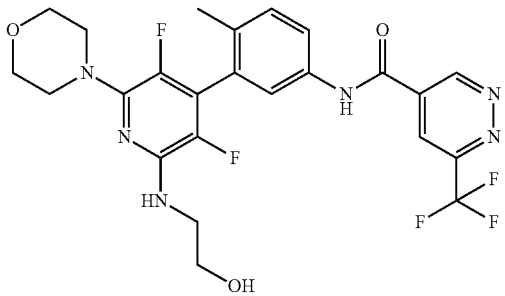 [SMILES: Cc1ccc(NC(=O)c2cnnc(C(F)(F)F)c2)cc1-c1c(F)c(NCCO)nc(N2CCOCC2)c1F]

$^1$H NMR (500 MHz, CHLOROFORM-d) δ ppm 2.17-2.30 (m, 3H) 3.19 (br. s., 1H) 3.37 (d, J=3.78 Hz, 4H) 3.55-3.73 (m, 2H) 3.80-3.90 (m, 6H) 4.84 (br. s., 1H) 7.32-7.41 (m, 1H) 7.47-7.56 (m, 1H) 7.60-7.71 (m, 1H) 8.23-8.34 (m, 1H) 8.55-8.66 (m, 1H) 9.75-9.84 (m, 1H). LCMS (m/z) (M+H)=539.1, Rt=0.90 min.

Example 1016: 2-(difluoromethyl)-N-(3-(3-fluoro-2-((2-hydroxyethyl)amino)-6-morpholinopyridin-4-yl)-4-methylphenyl)isonicotinamide

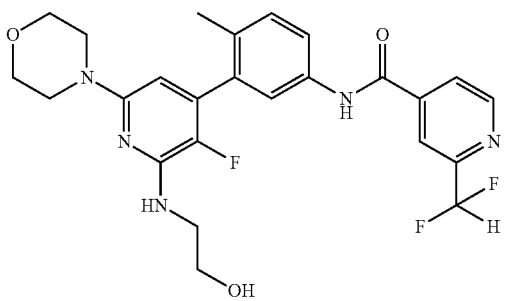 [SMILES: Cc1ccc(NC(=O)c2ccnc(C(F)F)c2)cc1-c1cc(N2CCOCC2)nc(NCCO)c1F]

$^1$H NMR (500 MHz, CHLOROFORM-d) δ ppm 2.26 (s, 3H) 3.35-3.44 (m, 4H) 3.70 (br. s., 2H) 3.80-3.86 (m, 4H) 3.87-3.93 (m, 2H) 4.96-5.11 (m, 1H) 5.73 (br. s., 1H) 6.60-6.89 (m, 1H) 7.32-7.36 (m, 1H) 7.54 (br. s., 1H) 7.62 (d, J=8.20 Hz, 1H) 7.88 (d, J=4.10 Hz, 1H) 7.95 (br. s., 1H) 8.04 (s, 1H) 8.87 (d, J=5.04 Hz, 1H). LCMS (m/z) (M+H)= 502.1, Rt=0.79 min.

Synthesis of 3-(6-methoxy-5-morpholinopyridazin-3-yl)-4-methylbenzoic acid

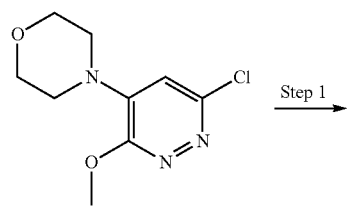

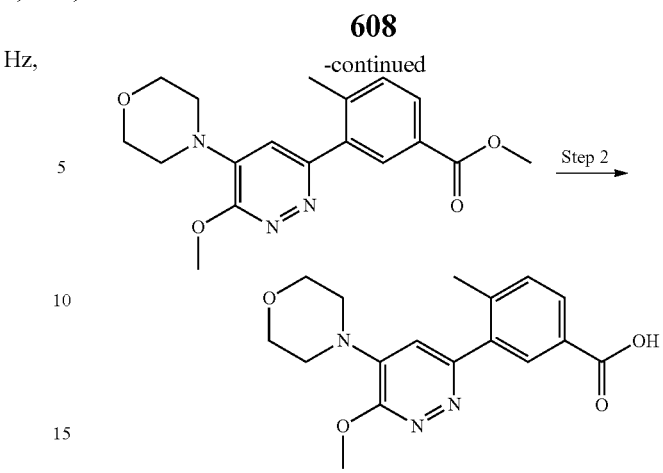

Step 1:
To a degassed solution of 4-(6-chloro-3-methoxypyridazin-4-yl)morpholine (1.0 equiv.), methyl 4-methyl-3-(4,4,5,5-tetramethyl-1,3,2-dioxaborolan-2-yl)benzoate (2.0 equiv.) and X-Phos (0.1 equiv.) in THF (0.3 M) was added K$_3$PO$_4$ (0.5 M, 2.0 equiv.). The reaction was heated at 40° C. overnight then partitioned between ethyl acetate and water. The aqueous phase was extracted with ethyl acetate (2×), the combined organics were dried over magnesium sulfate, filtered and concentrated. The crude was purified via silica gel chromatography (ISCO, 0-80% ethyl acetate/heptanes) and the pure fractions were concentrated to give methyl 3-(6-methoxy-5-morpholinopyridazin-3-yl)-4-methylbenzoate as a yellow oil in 55% yield. LCMS (m/z) (M+H)=344, Rt=0.58 min.

Step 2:
To a solution of methyl 3-(6-methoxy-5-morpholinopyridazin-3-yl)-4-methylbenzoate (1.0 equiv.) in THF (0.13 M) was added lithium hydroxide (2.5 equiv., 1M aqueous solution) and the reaction was stirred at rt overnight. The solution was neutralized with 1M HCl and the volatiles were removed under reduced pressure. The product was extracted with ethyl acetate, dried over magnesium sulfate, filtered and concentrated to give 3-(6-methoxy-5-morpholinopyridazin-3-yl)-4-methylbenzoic acid in 70% yield. LCMS (m/z) (M+H)=330.0, Rt=0.48 min.

Example 1017: 3-(6-methoxy-5-morpholinopyridazin-3-yl)-4-methyl-N-(2-(trifluoromethyl)pyridin-4-yl)benzamide

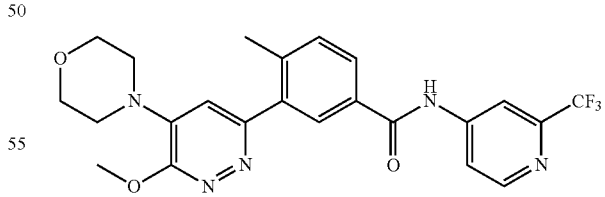

To a stirred solution of 3-(6-methoxy-5-morpholinopyridazin-3-yl)-4-methylbenzoic acid (1.0 equiv.) in DCM (0.06 M) at 0° C. was added 1-chloro-N,N,2-trimethylprop-1-en-1-amine (1.2 equiv.) and the mixture was allowed to stir at 0° C. for 1 hour. This solution was added to another solution containing 2-(trifluoromethyl)pyridin-4-amine (1.3 equiv.) and TEA (3.0 equiv.) in DCM and the reaction was allowed to warm to rt and stirred for 1 hour. The mixture was concentrated to dryness, dissolved in DMSO and purified via reverse phase prep-HPLC. The pure fractions were lyophilized to give 3-(6-methoxy-5-morpholinopyridazin-3-yl)-4-methyl-N-(2-(trifluoromethyl)pyridin-4-yl)benzamide in 23% yield. $^1$H NMR (400 MHz, <cd3od>) δ ppm 2.45 (s, 3H) 3.83-3.90 (m, 4H) 3.97 (br. s., 4H) 4.18 (s, 3H) 7.32 (s, 1H) 7.65 (d, J=8.22 Hz, 1H) 8.02 (dd, J=5.48, 1.96 Hz, 1H) 8.10 (d, J=1.57 Hz, 1H) 8.16 (dd, J=7.83, 1.96 Hz, 1H) 8.30 (d, J=1.56 Hz, 1H) 8.61 (d, J=5.87 Hz, 1H). LCMS (m/z) (M+H)=474.0, $R_t$=0.71 min.

The compounds listed below were prepared using methods similar to those described for the preparation of Example 1017 above using the appropriate starting materials.

Example 1019: N-(2-(1,1-difluoroethyl)pyridin-4-yl)-3-(6-methoxy-5-morpholinopyridazin-3-yl)-4-methylbenzamide

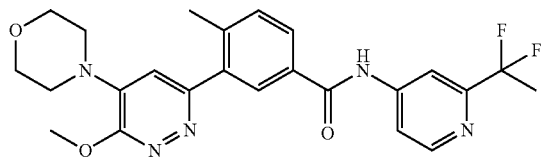 [SMILES: COc1nnc(-c2cc(C(=O)Nc3ccnc(C(C)(F)F)c3)ccc2C)cc1N1CCOCC1]

$^1$H NMR (400 MHz, <cd3od>) δ ppm 1.99 (t, J=18.59 Hz, 3H) 2.45 (s, 3H) 3.84-3.89 (m, 4H) 3.98 (br. s., 4H) 4.18 (s, 3H) 7.32 (s, 1H) 7.65 (d, J=8.22 Hz, 1H) 7.94 (dd, J=5.87, 1.96 Hz, 1H) 8.10 (d, J=1.96 Hz, 1H) 8.14 (d, J=1.96 Hz, 1H) 8.14-8.17 (m, 1H) 8.53 (d, J=5.48 Hz, 1H). LCMS (m/z) (M+H)=470.1, Rt=0.66 min.

Example 1020: N-(2-(1,1-difluoroethyl)pyridin-4-yl)-3-(6-ethoxy-5-morpholinopyridazin-3-yl)-4-methylbenzamide

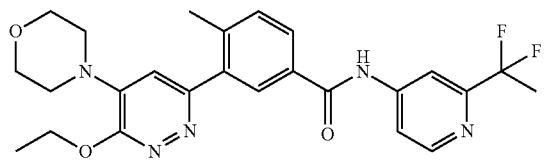 [SMILES: CCOc1nnc(-c2cc(C(=O)Nc3ccnc(C(C)(F)F)c3)ccc2C)cc1N1CCOCC1]

$^1$H NMR (400 MHz, <cd3od>) δ ppm 1.51-1.57 (m, 3H) 1.99 (t, J=18.78 Hz, 3H) 2.45 (s, 3H) 3.84-3.91 (m, 4H) 3.99 (br. s., 4H) 4.59 (q, J=7.04 Hz, 2H) 7.32 (s, 1H) 7.65 (d, J=8.22 Hz, 1H) 7.94 (dd, J=5.87, 1.96 Hz, 1H) 8.09 (d, J=1.56 Hz, 1H) 8.13-8.17 (m, 2H) 8.53 (d, J=5.87 Hz, 1H). LCMS (m/z) (M+H)=484.3, Rt=0.71 min.

Example 1021: (R)—N-(6'-((1-hydroxypropan-2-yl)oxy)-2-methyl-5'-morpholino-[3,3'-bipyridin]-5-yl)-3-(trifluoromethyl)benzamide

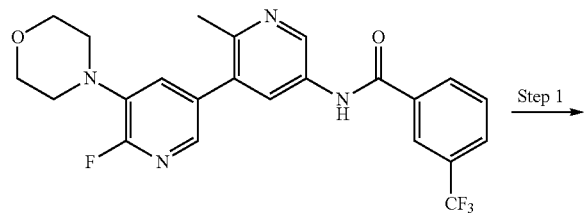

Step 1

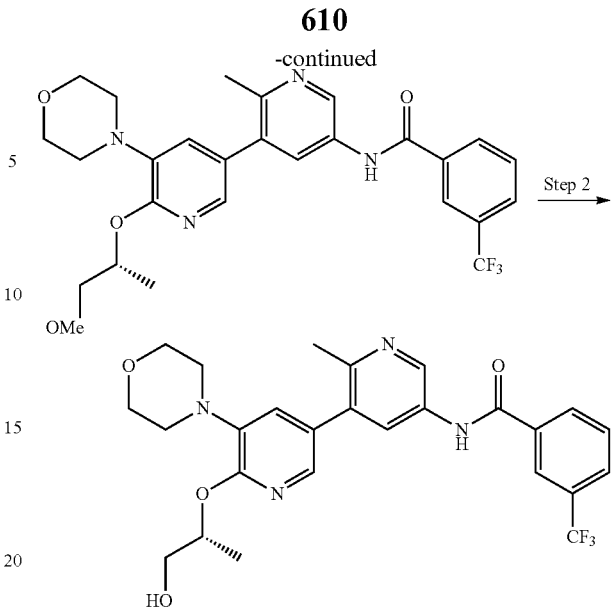

Step 2

Step 1:
To a solution of sodium hydride (4.2 equiv.) in DMAC at 90° C. was added R-1-methoxy-2-propanol (4.0 equiv.) and the mixture was stirred for 15 min. N-(6'-fluoro-2-methyl-5'-morpholino-[3,3'-bipyridin]-5-yl)-3-(trifluoromethyl)benzamide (1.0 equiv.) was added and the reaction was heated at 90° C. for 5 hours. The mixture was cooled and quenched with water and extracted with ethyl acetate. The combined organics were washed with water, brine, dried over sodium sulfate, filtered and concentrated. The crude residue was purified via silica gel chromatography eluting with 0-100% ethyl acetate in heptanes to give (R)—N-(6'-((1-methoxypropan-2-yl)oxy)-2-methyl-5'-morpholino-[3,3'-bipyridin]-5-yl)-3-(trifluoromethyl)benzamide as the desired product. LCMS (m/z) (M+H)=531.2 Rt=0.78 min.

Step 2:
To a solution of (R)—N-(6'-((1-methoxypropan-2-yl)oxy)-2-methyl-5'-morpholino-[3,3'-bipyridin]-5-yl)-3-(trifluoromethyl)benzamide (1.0 equiv.) in DCM (0.06 M) at 90° C. was added boron tribromide in DCM (1 M, 1.0 equiv.) and the mixture was stirred at 90° C. for 16 hours. Upon cooling to rt, the reaction was quenched with methanol and concentrated to dryness. The crude residue was purified via reverse phase prep-HPLC and the pure fractions were lyophilized to give (R)—N-(6'-((1-hydroxypropan-2-yl)oxy)-2-methyl-5'-morpholino-[3,3'-bipyridin]-5-yl)-3-(trifluoromethyl)benzamide. LCMS (m/z) (M+H)=517.3 Rt=0.71 min.

Example 1022: (S)—N-(6'-(2-hydroxypropoxy)-2-methyl-5'-morpholino-[3,3'-bipyridin]-5-yl)-3-(trifluoromethyl)benzamide

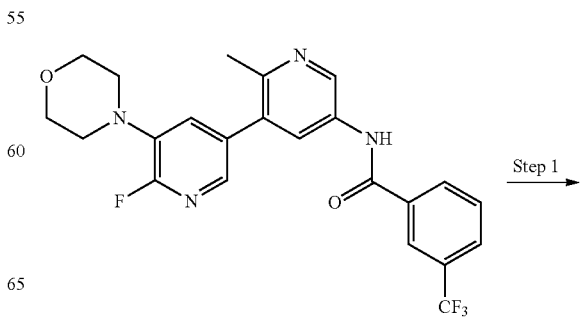

Step 1

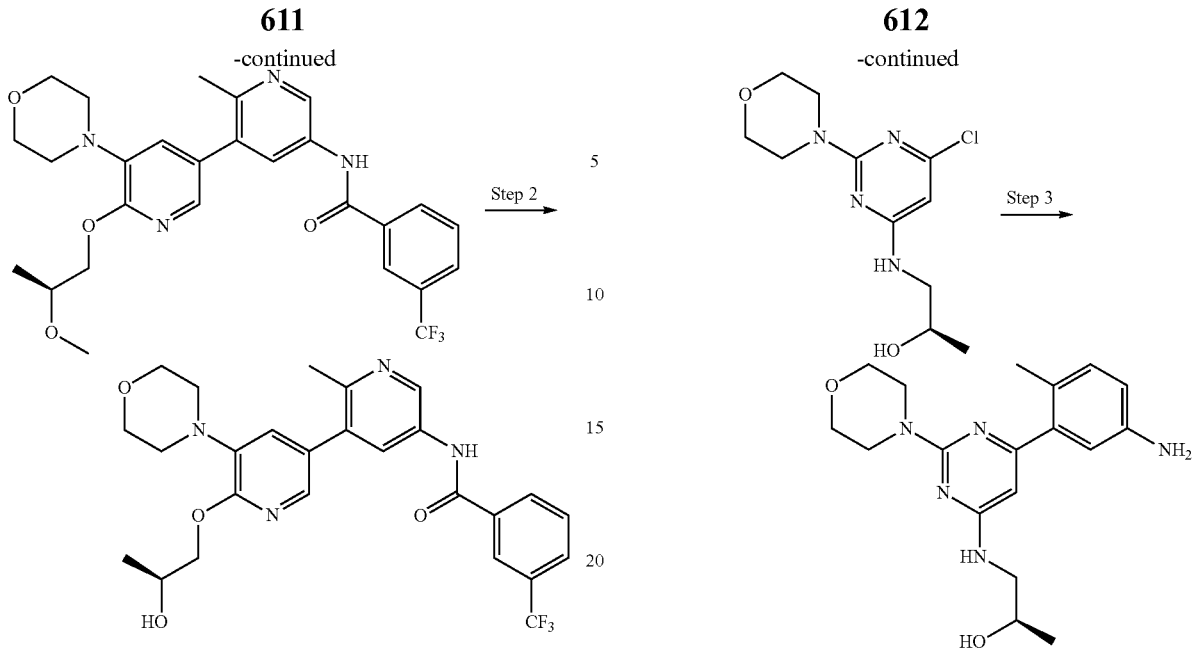

Step 1:
To a solution of sodium hydride (4.2 equiv.) in dioxane (0.02 M) at 100° C. was added (S)-2-methoxypropan-1-ol (4.0 equiv.) and the mixture was stirred for 15 min. N-(6'-fluoro-2-methyl-5'-morpholino-[3,3'-bipyridin]-5-yl)-3-(trifluoromethyl)benzamide (1.0 equiv.) was added and the reaction was heated at 100° C. for 4 hours. The mixture was cooled and quenched with water and extracted with ethyl acetate. The combined organics were washed with water, brine, dried over sodium sulfate, filtered and concentrated. The crude residue was purified via silica gel chromatography eluting with 0-100% ethyl acetate in heptanes to (S)—N-(6'-(2-methoxypropoxy)-2-methyl-5'-morpholino-[3,3'-bipyridin]-5-yl)-3-(trifluoromethyl)benzamide as the desired product in 44% yield. LCMS (m/z) (M+H)=531.2 Rt=0.77 min.

Step 2:
To a solution of (S)—N-(6'-(2-methoxypropoxy)-2-methyl-5'-morpholino-[3,3'-bipyridin]-5-yl)-3-(trifluoromethyl)benzamide (1.0 equiv.) in DCM (0.05 M) was added boron tribromide in DCM (1M, 1.2 equiv.) and the mixture was stirred at rt for 30 mins. The reaction was quenched with methanol and concentrated to dryness. The crude residue was purified via reverse phase prep-HPLC and the pure fractions were lyophilized to give (S)—N-(6'-(2-hydroxypropoxy)-2-methyl-5'-morpholino-[3,3'-bipyridin]-5-yl)-3-(trifluoromethyl)benzamide in 9% yield. 1H NMR (400 MHz, <dmso>) δ ppm 1.07-1.18 (m, 3H) 2.45-2.46 (m, 3H) 2.99-3.10 (m, 4H) 3.63-3.71 (m, 5H) 4.03-4.26 (m, 5H) 7.13-7.24 (m, 1H) 7.72-7.82 (m, 2H) 7.92-8.01 (m, 1H) 8.10-8.17 (m, 1H) 8.21-8.32 (m, 2H) 8.90-8.98 (m, 1H) 10.76-10.83 (m, 1H). LCMS (m/z) (M+H)=517.2, Rt=0.69 min.

Synthesis of (R)-1-((6-(5-amino-2-methylphenyl)-2-morpholinopyrimidin-4-yl)amino)propan-2-ol

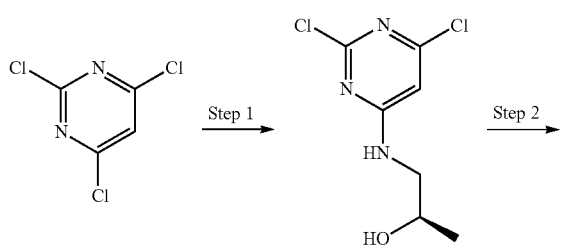

Step 1:
To a solution of 2,4,6-trichloropyrimidine (1.0 equiv.) in dioxane (0.36 M) at 0° C. was added DIEA (1.1 equiv.) and (R)-1-aminopropan-2-ol (1.1 equiv.) dropwise. The reaction was stirred at rt for 2 hours at which point, two isomeric products were observed by TLC. The dioxane was evaporated in vacuo and the residue was partitioned between water and DCM. The organic layer was separated and the aqueous layer was further extracted with DCM. The combined organics were dried over sodium sulfate, filtered and concentrated in vacuo. The crude was purified via silica gel chromatography (ISCO, 0-60% ethyl acetate in heptanes) to give (R)-1-((4,6-dichloropyrimidin-2-yl)amino)propan-2-ol and (R)-1-((4,6-dichloropyrimidin-2-yl)amino)propan-2-ol as white solids in 41% and 42% yields respectively. 1H NMR (400 MHz, <dmso>) δ ppm 1.05 (d, J=6.26 Hz, 3H) 3.08-3.27 (m, 2H) 3.76 (spt, J=6.00 Hz, 1H) 4.71 (d, J=5.09 Hz, 1H) 6.86 (s, 1H) 8.05 (t, J=5.67 Hz, 1H) and 1H NMR (400 MHz, <dmso>) δ ppm 1.07 (d, J=6.26 Hz, 3H) 3.05-3.30 (m, 2H) 3.75 (dq, J=11.44, 5.71 Hz, 1H) 4.84 (d, J=4.70 Hz, 1H) 6.60 (s, 1H) 8.22 (d, J=5.48 Hz, 1H).

Step 2:
To a solution of (R)-1-((2,6-dichloropyrimidin-4-yl)amino)propan-2-ol (1.0 equiv.) in dioxane (0.2 M) was added DIEA (1.5 equiv.) and morpholine (1.8 equiv.) and the reaction was heated to 70° C. for 5 hours. The precipitate was filtered and the dioxane was evaporated in vacuo. The crude solid was taken up in DCM and washed with water. The combined organics were dried over sodium sulfate, filtered and concentrated to give (R)-1-((6-chloro-2-morpholinopyrimidin-4-yl)amino)propan-2-ol in 93% yield. 1H NMR (400 MHz, <cdcl3>) δ ppm 1.24 (d, J=6.26 Hz, 3H) 3.26 (dt, J=13.21, 6.50 Hz, 1H) 3.44-3.57 (m, 1H) 3.69-3.79 (m, 9H) 4.01 (br. s., 1H) 5.04 (br. s., 1H) 5.75 (s, 1H). LCMS (m/z) (M+H)=273, 275; Rt=0.52 min.

Step 3:
To a degassed solution of (R)-1-((6-chloro-2-morpholinopyrimidin-4-yl)amino)propan-2-ol (1.0 equiv.) and 4-methyl-3-(4,4,5,5-tetramethyl-1,3,2-dioxaborolan-2-yl) aniline (1.3 equiv.) in DME and 2M sodium carbonate (3:1, 0.2 M) was added PdCl2(dppf)-DCM adduct (0.1 equiv.) and the reaction was heated to 70° C. for 4 hours. The cooled reaction was diluted with ethyl acetate and washed with water and brine. The organics were dried over magnesium sulfate, filtered and concentrated. The residue was purified via silica gel chromatography (ISCO, 0-100% ethyl acetate in heptanes, then 0-10% methanol in DCM) to give (R)-1-((6-(5-amino-2-methylphenyl)-2-morpholinopyrimidin-4-yl)amino)propan-2-ol as a light brown foam in 56% yield. LCMS (m/z) (M+H)=344, Rt=0.41 min.

Example 1023: (R)—N-(3-(6-((2-hydroxypropyl)amino)-2-morpholinopyrimidin-4-yl)-4-methylphenyl)-2-(trifluoromethyl)isonicotinamide

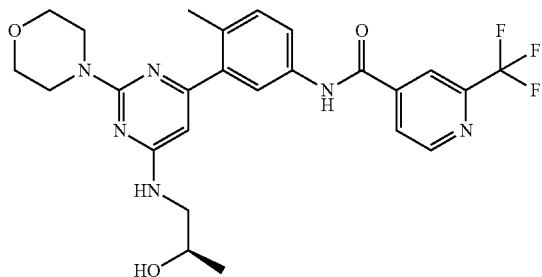 [SMILES: Cc1ccc(NC(=O)c2ccnc(C(F)(F)F)c2)cc1-c1cc(NC[C@@H](C)O)nc(N2CCOCC2)n1]

1H NMR (400 MHz, <cd3od>) δ ppm 1.24 (d, J=6.26 Hz, 3H) 2.37 (s, 3H) 3.46-3.62 (m, 2H) 3.81 (s, 8H) 3.98-4.04 (m, 1H) 6.17 (s, 1H) 7.43 (d, J=8.61 Hz, 1H) 7.67 (dd, J=8.22, 2.35 Hz, 1H) 7.97 (d, J=1.96 Hz, 1H) 8.12 (d, J=4.70 Hz, 1H) 8.30 (s, 1H) 8.92 (d, J=5.09 Hz, 1H). LCMS (m/z) (M+H)=517.3, Rt=0.68 min.

Example 1024: (R)-2-(1,1-difluoroethyl)-N-(3-(6-((2-hydroxypropylamino)-2-morpholinopyrimidin-4-yl)-4-methylphenyl)isonicotinamide

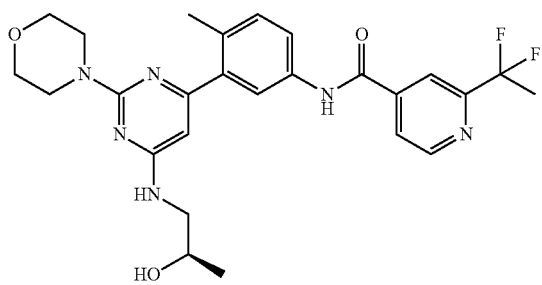 [SMILES: Cc1ccc(NC(=O)c2ccnc(C(C)(F)F)c2)cc1-c1cc(NC[C@@H](C)O)nc(N2CCOCC2)n1]

¹H NMR (400 MHz, <cd3od>) δ ppm 1.24 (d, J=6.26 Hz, 3H) 2.04 (t, J=18.78 Hz, 3H) 2.37 (s, 3H) 3.45-3.63 (m, 2H) 3.76-3.86 (m, 8H) 3.97-4.06 (m, 1H) 6.17 (s, 1H) 7.42 (d, J=8.61 Hz, 1H) 7.67 (dd, J=8.41, 2.15 Hz, 1H) 7.96 (d, J=2.35 Hz, 2H) 8.18 (s, 1H) 8.82 (d, J=5.09 Hz, 1H). LCMS (m/z) (M+H)=513.1, Rt=0.69 min.

Example 1025: (R)-2-(2-fluoropropan-2-yl)-N-(3-(6-((2-hydroxypropyl)amino)-2-morpholinopyrimidin-4-yl)-4-methylphenyl)isonicotinamide

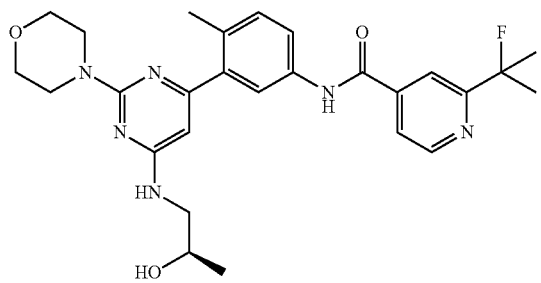 [SMILES: Cc1ccc(NC(=O)c2ccnc(C(C)(C)F)c2)cc1-c1cc(NC[C@@H](C)O)nc(N2CCOCC2)n1]

¹H NMR (400 MHz, <cd3od>) δ ppm 1.24 (d, J=6.26 Hz, 3H) 1.68-1.80 (m, 6H) 2.37 (s, 3H) 3.45-3.63 (m, 2H) 3.76-3.85 (m, 8H) 3.96-4.06 (m, 1H) 6.18 (s, 1H) 7.42 (d, J=8.22 Hz, 1H) 7.66 (dd, J=8.22, 1.96 Hz, 1H) 7.77 (dd, J=5.09, 1.57 Hz, 1H) 7.96 (d, J=2.35 Hz, 1H) 8.06 (s, 1H) 8.71 (d, J=5.09 Hz, 1H). LCMS (m/z) (M+H)=509.1, Rt=0.67 min.

Example 1026: (R)-2-(2-cyanopropan-2-yl)-N-(3-(6-((2-hydroxypropyl)amino)-2-morpholinopyrimidin-4-yl)-4-methylphenyl)isonicotinamide

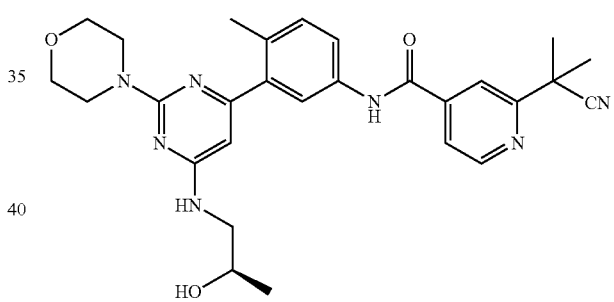

¹H NMR (400 MHz, <cd3od>) δ ppm 1.24 (d, J=6.26 Hz, 3H) 1.81 (s, 6H) 2.37 (s, 3H) 3.45-3.62 (m, 2H) 3.76-3.85 (m, 10H) 3.97-4.06 (m, 1H) 6.18 (s, 1H) 7.42 (d, J=8.22 Hz, 1H) 7.66 (dd, J=8.22, 1.96 Hz, 1H) 7.81 (dd, J=4.89, 1.37 Hz, 1H) 7.96 (d, J=1.96 Hz, 1H) 8.07 (s, 1H) 8.78 (d, J=4.70 Hz, 1H). LCMS (m/z) (M+H)=516.4, Rt=0.67 min.

Synthesis of 5-ethoxy-2'-methyl-6-morpholino-[2,3'-bipyridin]-5'-amine

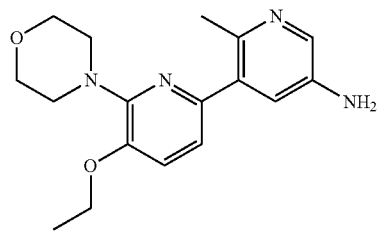 [SMILES: CCOc1ccc(-c2cc(N)cnc2C)nc1N1CCOCC1]

A solution of 2,6-dichloro-3-ethoxypyridine (1.0 equiv.) and morpholine (1.0 equiv.) in NMP (0.6 M) was heated at 150° C. in the microwave for 30 min. At this point, LC/MS indicated incompletion of the reaction, heated for 1 hour at 150° C. The cooled reaction mixture was purified via silica gel chromatography and the pure fractions were used for the next reaction. To a solution of 4-(6-bromo-3-ethoxypyridin-2-yl)morpholine (1.0 equiv.) in DME (0.4 M) was added sodium carbonate (3.0 equiv, 2M aqueous solution), 6-methyl-5-(4,4,5,5-tetramethyl-1,3,2-dioxaborolan-2-yl)pyridin-3-amine (1.0 equiv.), PdCl$_2$(dppf)-DCM (0.05 equiv.) and the reaction was heated at 130° C. in the microwave for 30 min. The cooled reaction mixture was partitioned between brine and ethyl acetate. The organic phase was dried with MgSO$_4$, filtered and concentrated. The crude material was purified via reverse phase prep-HPLC to give 5-ethoxy-2'-methyl-6-morpholino-[2,3'-bipyridin]-5'-amine in 14% yield. LCMS (m/z) (M+H)=315.1, Rt=0.58 min.

Example 1027: N-(5-ethoxy-2'-methyl-6-morpholino-[2,3'-bipyridin]-5'-yl)-2-(2-fluoropropan-2-yl)isonicotinamide

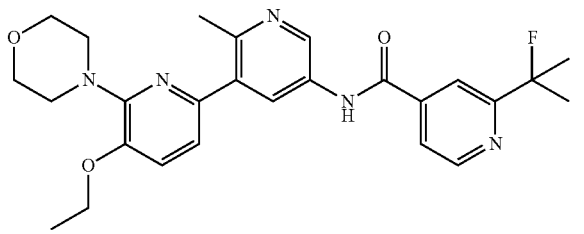 [SMILES: CCOc1ccc(-c2cc(NC(=O)c3ccnc(C(C)(C)F)c3)cnc2C)nc1N1CCOCC1]

1H NMR (400 MHz, <dmso>) δ ppm 1.37 (t, J=7.04 Hz, 2H) 1.64-1.80 (m, 4H) 2.60 (s, 2H) 3.30-3.43 (m, 2H) 3.54-3.78 (m, 5H) 4.11 (d, J=7.04 Hz, 1H) 7.15 (d, J=7.83 Hz, 1H) 7.38 (d, J=8.22 Hz, 1H) 7.84 (dd, J=4.89, 1.37 Hz, 1H) 8.05 (s, 1H) 8.35 (br. s., 1H) 8.78 (d, J=5.09 Hz, 1H) 8.87-8.96 (m, 1H) 10.88 (br. s., 1H). LCMS (m/z) (M+H)=480.1, Rt=0.73 min.

Example 1028: 2-(1,1-difluoroethyl)-N-(5-ethoxy-2'-methyl-6-morpholino-[2,3'-bipyridin]-5'-yl)isonicotinamide

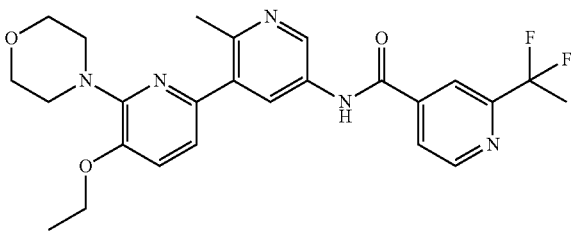 [SMILES: CCOc1ccc(-c2cc(NC(=O)c3ccnc(C(C)(F)F)c3)cnc2C)nc1N1CCOCC1]

1H NMR (400 MHz, <dmso>) δ ppm 1.37 (t, J=6.85 Hz, 1H) 2.05 (t, J=18.98 Hz, 1H) 2.62 (s, 1H) 3.29-3.46 (m, 2H) 3.66-3.82 (m, 2H) 4.03-4.22 (m, 1H) 7.16 (d, J=7.83 Hz, 1H) 7.39 (d, J=8.22 Hz, 1H) 8.05 (d, J=4.69 Hz, 1H) 8.20 (s, 1H) 8.38 (br. s., 1H) 8.84-9.02 (m, 1H) 11.00 (s, 1H). LCMS (m/z) (M+H)=484.1, Rt=0.73 min.

Example 1029: N-(6'-(((3R,4S)-3-fluorotetrahydro-2H-pyran-4-yl)oxy)-2-methyl-5'-morpholino-[3,3'-bipyridin]-5-yl)-3-(trifluoromethyl)benzamide and
Example 1030: N-(6'-(((3S,4R)-3-fluorotetrahydro-2H-pyran-4-yl)oxy)-2-methyl-5'-morpholino-[3,3'-bipyridin]-5-yl)-3-(trifluoromethyl)benzamide

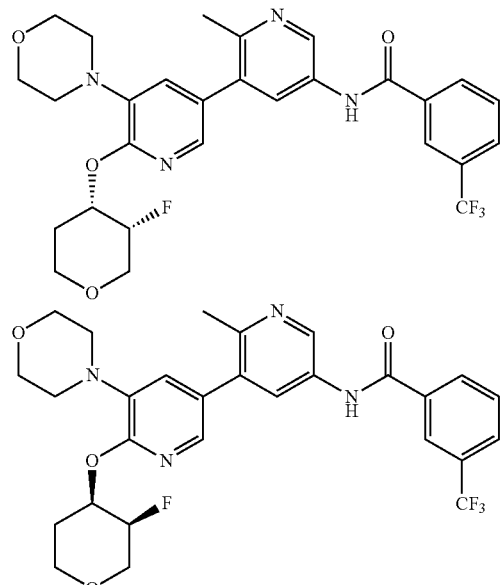

To a solution of N-(6-methyl-5-(4,4,5,5-tetramethyl-1,3,2-dioxaborolan-2-yl)pyridin-3-yl)-3-(trifluoromethyl)benzamide (1.0 equiv.), 4-(5-bromo-2-(((3R,4S)-3-fluorotetrahydro-2H-pyran-4-yl)oxy)pyridin-3-yl)morpholine (1.0 equiv.) and sodium carbonate (2M aqueous solution, 3.0 equiv.) in DME (0.15 M) was added PdCl$_2$(dppf)-DCM (0.05 equiv.) and the reaction was stirred at rt overnight. The mixture was purified via reverse phase prep-HPLC and the pure fractions were lyophilized to give racemic product. The two enantiomers were separated via chiral HPLC (heptanes/ethanol:85/15, AD-H column, HPLC:1 mL/min) to give peak 1 (6.889 min, 12 min run) and peak 2 (9.523 min, 12 min run). LCMS (m/z) (M+H)=561.2, Rt=0.78 min.

Example 1031: N-(6'-((4-deuterio-3-fluorotetrahydro-2H-pyran-4-yl)oxy)-2-methyl-5'-morpholino-[3,3'-bipyridin]-5-yl)-3-(trifluoromethyl)benzamide and Example 1032: N-(2-methyl-5'-morpholino-6'-(trideuteriomethoxy)-[3,3'-bipyridin]-5-yl)-3-(trifluoromethyl)benzamide

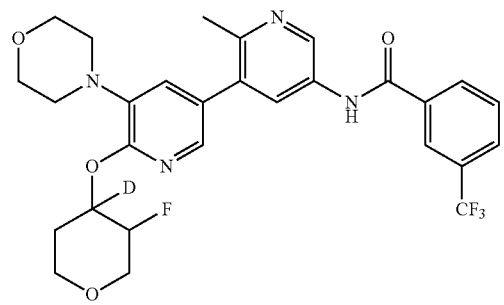

-continued

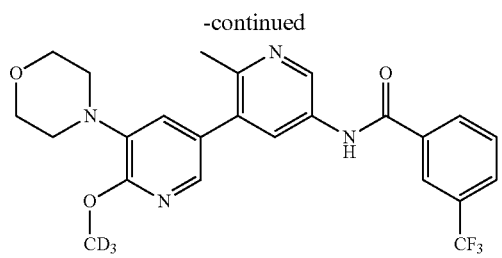

To a solution of dihydro-2H-pyran-4(3H)-one (1.0 equiv.) in CD3OD (0.1 M) was added NaBD4 at rt. The mixture was stirred at rt until no more bubbling. Quenched with saturated ammonium chloride and extracted twice with DCM. The organic phase was dried over sodium sulfate, filtered and concentrated. The crude was used directly for the next step. To a solution of N-(6'-fluoro-2-methyl-5'-morpholino-[3,3'-bipyridin]-5-yl)-3-(trifluoromethyl)benzamide (0.4 equiv.) and 4-deuterio-3-fluorotetrahydro-2H-pyran-4-ol (1.0 equiv., containing CD3ONa from previous reaction) in THF (0.6 M) was added sodium hydride (3.0 equiv.) and the mixture was heated to 90° C. for 2 hours. The solution was quenched with water and purified via reverse phase prep-HPLC to give N-(6'-((4-deuterio-3-fluorotetrahydro-2H-pyran-4-yl)oxy)-2-methyl-5'-morpholino-[3,3-bipyridin]-5-yl)-3-(trifluoromethyl)benzamide and N-(2-methyl-5'-morpholino-6-(trideuteriomethoxy)-[3,3-bipyridin]-5-yl)-3-(trifluoromethyl)benzamide. LCMS (m/z) (M+H)=562.0, Rt=0.79 min and LCMS (m/z) (M+H)=476.1 Rt=0.76 min respectively.

Example 1033: N-(6'-(2-(2-hydroxyethoxy)ethoxy)-2-methyl-5'-morpholino-[3,3-bipyridin]-5-yl)-3-(trifluoromethyl)benzamide

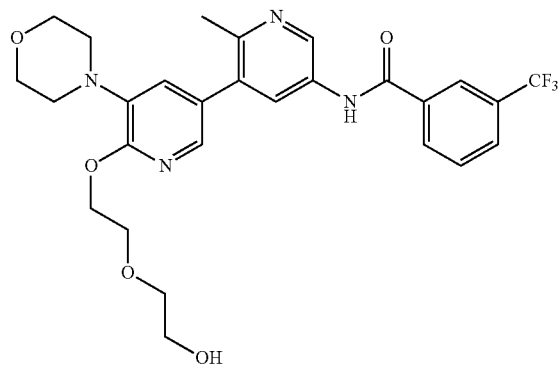 [SMILES: Cc1ncc(NC(=O)c2cccc(C(F)(F)F)c2)cc1-c1cnc(OCCOCCO)c(N2CCOCC2)c1]

To a solution of N-(6'-fluoro-2-methyl-5'-morpholino-[3,3'-bipyridin]-5-yl)-3-(trifluoromethyl)benzamide (1.0 equiv.) and 2,2'-oxydiethanol (4.0 equiv.) in THF (0.1 M) was added sodium hydride (4.0 equiv.) and the reaction was heated to 90° C. for two hours. The cooled reaction mixture was quenched with sat. ammonium chloride, the organic phase was concentrated to dryness and purified via reverse phase prep-HPLC to give N-(6'-(2-(2-hydroxyethoxy)ethoxy)-2-methyl-5'-morpholino-[3,3'-bipyridin]-5-yl)-3-(trifluoromethyl)benzamide in 27% yield. LCMS (m/z) (M+H)=547.1, Rt=0.69 min.

Example 1034: N-(6'-((1,1-dioxidotetrahydro-2H-thiopyran-4-yl)oxy)-2-methyl-5'-morpholino-[3,3'-bipyridin]-5-yl)-3-(trifluoromethyl)benzamide

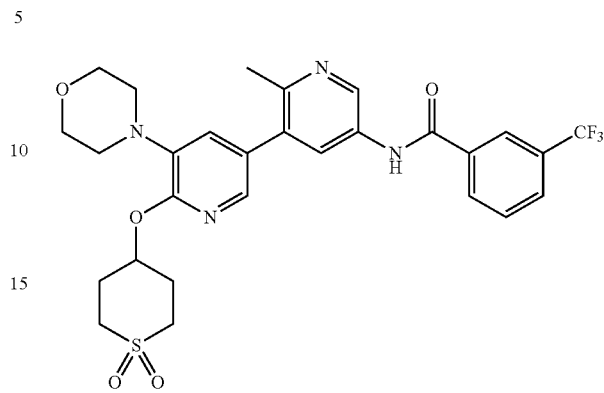

To a solution of N-(6'-fluoro-2-methyl-5'-morpholino-[3,3'-bipyridin]-5-yl)-3-(trifluoromethyl)benzamide (1.0 equiv.) and 4-hydroxytetrahydro-2H-thiopyran 1,1-dioxide (4.0 equiv.) in THF (0.1 M) was added sodium hydride (4.0 equiv.) and the reaction was heated to 90° C. for two hours. The cooled reaction mixture was quenched with sat. ammonium chloride, the organic phase was concentrated to dryness and purified via reverse phase prep-HPLC to give N-(6'-((1,1-dioxidotetrahydro-2H-thiopyran-4-yl)oxy)-2-methyl-5'-morpholino-[3,3'-bipyridin]-5-yl)-3-(trifluoromethyl)benzamide in 65% yield. LCMS (m/z) (M+H)=591.1, Rt=0.72 min.

Example 1035: N-(2-methyl-5'-morpholino-6'-((4-deuteriotetrahydro-2H-pyran-4-yl)oxy)-[3,3'-bipyridin]-5-yl)-3-(trifluoromethyl)benzamide

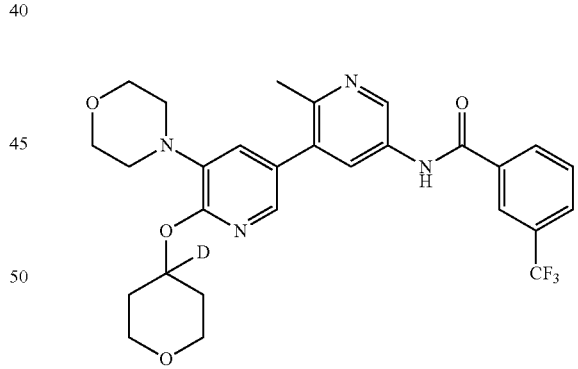

To a solution of N-(6'-fluoro-2-methyl-5'-morpholino-[3,3'-bipyridin]-5-yl)-3-(trifluoromethyl)benzamide (1.0 equiv.) and 4-deuteriotetrahydro-2H-pyran-4-ol (1.0 equiv.) in THF (0.7 M) was added sodium hydride (3.0 equiv.) and the reaction was heated to 90° C. for two hours. The cooled reaction mixture was quenched with water, the organic phase was concentrated to dryness and purified via reverse phase prep-HPLC to give N-(2-methyl-5'-morpholino-6'-((4-deuteriotetrahydro-2H-pyran-4-yl)oxy)-[3,3'-bipyridin]-5-yl)-3-(trifluoromethyl)benzamidein 65% yield. LCMS (m/z) (M+H)=544.1, Rt=0.79 min.

Example 1036: 3-(difluoromethyl)-N-(3-(2-((2-hydroxyethyl)amino)-6-morpholinopyridin-4-yl)-4-methylphenyl)benzamide

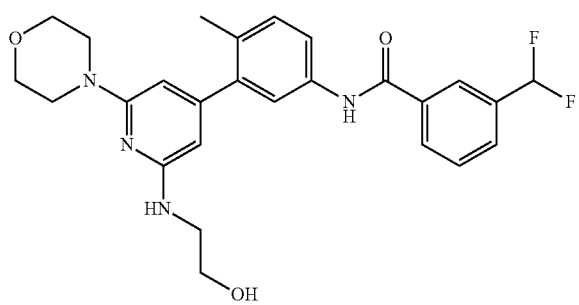 [SMILES: Cc1ccc(NC(=O)c2cccc(C(F)F)c2)cc1-c1cc(NCCO)nc(N2CCOCC2)c1]

¹H NMR (500 MHz, <cd3od>) δ ppm 2.34 (s, 3H) 3.54 (q, J=5.04 Hz, 6H) 3.85 (dt, J=10.48, 5.00 Hz, 6H) 6.25 (d, J=14.82 Hz, 2H) 6.90 (t, J=56.40 Hz, 1H) 7.35 (d, J=8.20 Hz, 1H) 7.56-7.61 (m, 1H) 7.66-7.70 (m, 1H) 7.77-7.81 (m, 2H) 8.10 (d, J=7.88 Hz, 1H) 8.15 (s, 1H). LCMS (m/z) (M+H)=483.1, Rt=0.72 min.

Example 1037: 2-(1,1-difluoroethyl)-N-(3-(2-((2-hydroxyethyl)amino)-6-morpholinopyridin-4-yl)-4-methylphenyl)isonicotinamide

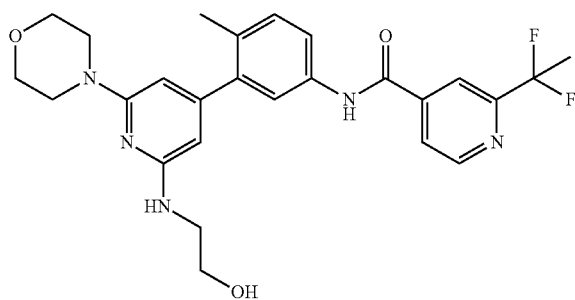 [SMILES: Cc1ccc(NC(=O)c2ccnc(C(C)(F)F)c2)cc1-c1cc(NCCO)nc(N2CCOCC2)c1]

¹H NMR (500 MHz, <cd3od>) δ ppm 2.06 (t, J=18.76 Hz, 3H) 2.35 (s, 3H) 3.51-3.58 (m, 6H) 3.85 (dt, J=9.54, 4.85 Hz, 6H) 6.26 (d, J=14.82 Hz, 2H) 7.37 (d, J=8.20 Hz, 1H) 7.62 (dd, J=8.20, 2.21 Hz, 1H) 7.81 (d, J=1.89 Hz, 1H) 7.98 (d, J=5.04 Hz, 1H) 8.20 (s, 1H) 8.84 (d, J=5.04 Hz, 1H). LCMS (m/z) (M+H)=498.1, Rt=0.72 min.

Example 1038: 3-(difluoromethyl)-N-(2'-((2-hydroxyethyl)amino)-2-methyl-6'-morpholino-[3,4'-bipyridin]-5-yl)benzamide

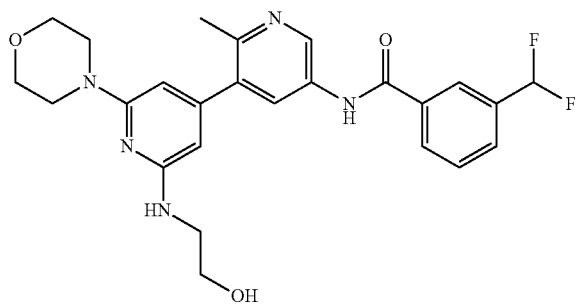 [SMILES: Cc1ncc(NC(=O)c2cccc(C(F)F)c2)cc1-c1cc(NCCO)nc(N2CCOCC2)c1]

¹H NMR (500 MHz, <cd3od>) δ ppm 2.63 (s, 3H) 3.51-3.59 (m, 6H) 3.79-3.87 (m, 6H) 6.17-6.24 (m, 1H) 6.92 (t, J=54.90 Hz, 1H) 7.69-7.75 (m, 1H) 7.84 (d, J=7.88 Hz, 1H) 8.16 (d, J=7.88 Hz, 1H) 8.21 (s, 1H) 8.41 (d, J=2.21 Hz, 1H) 9.09 (s, 1H). LCMS (m/z) (M+H)=484.2, Rt=0.54 min.

Example 1039: 2-(difluoromethyl)-N-(2'-((2-hydroxyethyl)amino)-2-methyl-6'-morpholino-[3,4'-bipyridin]-5-yl)isonicotinamide

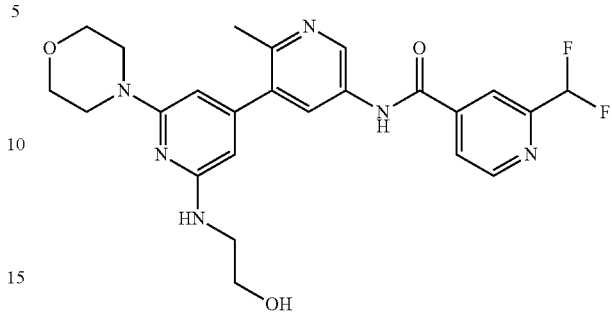

¹H NMR (500 MHz, <cd3od>) δ ppm 2.61 (s, 3H) 3.52-3.59 (m, 6H) 3.80-3.88 (m, 6H) 6.17-6.27 (m, 1H) 6.87 (t, J=54.90 Hz, 1H) 8.07 (d, J=5.04 Hz, 1H) 8.24 (s, 1H) 8.37 (d, J=2.21 Hz, 1H) 8.89 (d, J=5.04 Hz, 1H) 9.00 (br. s., 1H). LCMS (m/z) (M+H)=485.1, Rt=0.48 min.

Example 1040: N-(2'-((2-hydroxyethyl)amino)-2-methyl-6'-morpholino-[3,4'-bipyridin]-5-yl)-2-(trifluoromethyl)isonicotinamide

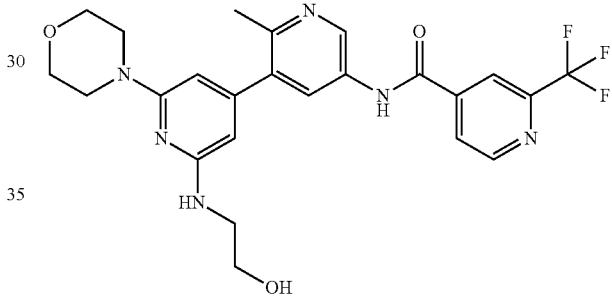

¹H NMR (500 MHz, <cd3od>) δ ppm 2.63 (s, 3H) 3.52-3.59 (m, 6H) 3.80-3.88 (m, 6H) 6.20-6.28 (m, 1H) 8.41 (d, J=2.52 Hz, 1H) 8.73 (s, 1H) 9.06 (s, 1H) 9.15 (s, 2H) 9.41 (d, J=1.89 Hz, 1H). LCMS (m/z) (M+H)=503.2, Rt=0.52 min.

Example 1041: 2-(1,1-difluoroethyl)-N-(2'-((2-hydroxyethyl)amino)-2-methyl-6'-morpholino-[3,4'-bipyridin]-5-yl)isonicotinamide

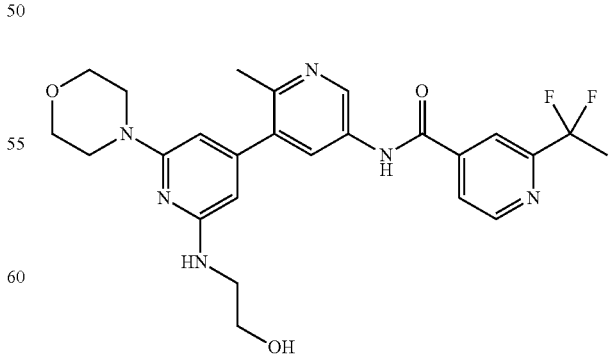

¹H NMR (500 MHz, <cd3od>) δ ppm 2.07 (t, J=18.76 Hz, 3H) 2.64 (s, 3H) 3.52-3.59 (m, 6H) 3.80-3.88 (m, 6H) 6.20-6.28 (m, 1H) 8.03 (d, J=5.04 Hz, 1H) 8.25 (s, 1H) 8.43

(d, J=2.52 Hz, 1H) 8.88 (d, J=4.73 Hz, 1H) 9.09 (d, J=1.58 Hz, 1H). LCMS (m/z) (M+H)=499.2, Rt=0.52 min.

Example 1042: 2-(2-cyanopropan-2-yl)-N-(2'-((2-hydroxyethyl)amino)-2-methyl-6'-morpholino-[3,4'-bipyridin]-5-yl)isonicotinamide

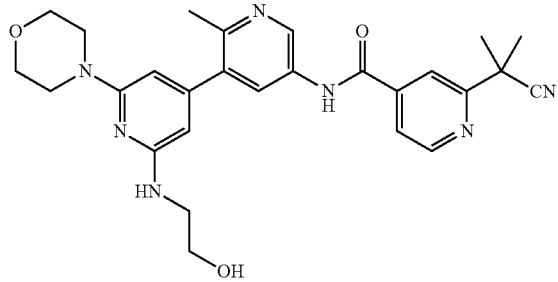 [SMILES: Cc1ncc(NC(=O)c2ccnc(C(C)(C)C#N)c2)cc1-c1cc(NCCO)nc(N2CCOCC2)c1]

LCMS (m/z) (M+H)=502.2, Rt=0.51 min.

Example 1043: N-(2'-((2-hydroxyethyl)amino)-2-methyl-6'-morpholino-[3,4'-bipyridin]-5-yl)-2-(methylsulfonyl)isonicotinamide

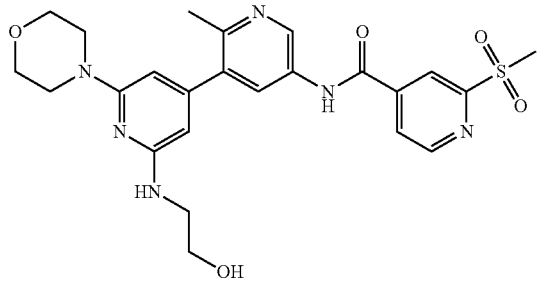 [SMILES: Cc1ncc(NC(=O)c2ccnc(S(C)(=O)=O)c2)cc1-c1cc(NCCO)nc(N2CCOCC2)c1]

LCMS (m/z) (M+H)=513.1, Rt=0.42 min.

Example 1044: 1-ethyl-N-(2'-((2-hydroxyethyl)amino)-2-methyl-6'-morpholino-[3,4'-bipyridin]-5-yl)-6-oxo-5-(trifluoromethyl)-1,6-dihydropyridine-3-carboxamide

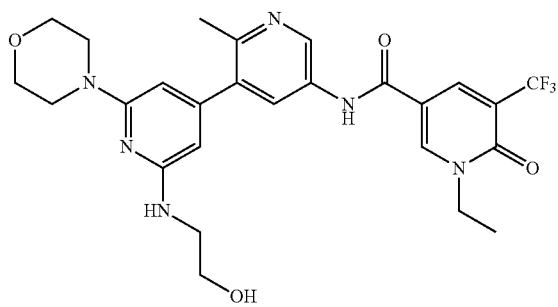 [SMILES: CCn1cc(C(=O)Nc2cnc(C)c(-c3cc(NCCO)nc(N4CCOCC4)c3)c2)cc(C(F)(F)F)c1=O]

$^1$H NMR (500 MHz, <cd3od>) δ ppm 1.44 (t, J=7.09 Hz, 3H) 2.62 (s, 3H) 3.51-3.58 (m, 6H) 3.80-3.87 (m, 6H) 4.19 (q, J=7.04 Hz, 2H) 8.35 (d, J=2.52 Hz, 1H) 8.53 (d, J=1.89 Hz, 1H) 8.80 (d, J=2.52 Hz, 1H) 9.02 (s, 1H). LCMS (m/z) (M+H)=547.2, Rt=0.52 min.

Example 1045: 3-(4-ethylpiperazin-1-yl)-N-(2'-((2-hydroxyethyl)amino)-2-methyl-6'-morpholino-[3,4'-bipyridin]-5-yl)-5-(trifluoromethyl)benzamide

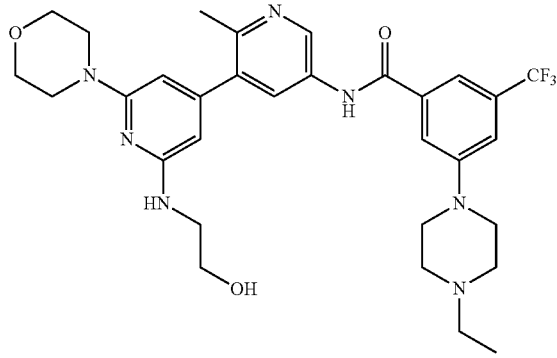 [SMILES: CCN1CCN(c2cc(C(=O)Nc3cnc(C)c(-c4cc(NCCO)nc(N5CCOCC5)c4)c3)cc(C(F)(F)F)c2)CC1]

LCMS (m/z) (M+H)=614.2, Rt=0.51 min

Example 1046: N-(2'-((2-hydroxyethyl)amino)-2-methyl-6'-morpholino-[3,4'-bipyridin]-5-yl)-2-(2-hydroxypropan-2-yl)isonicotinamide

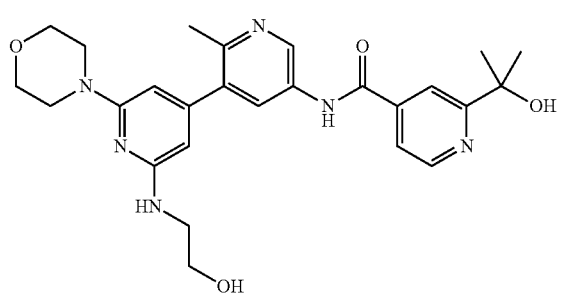

$^1$H NMR (500 MHz, <cd3od>) δ ppm 1.66 (s, 6H) 2.64 (s, 3H) 3.52-3.60 (m, 6H) 3.80-3.88 (m, 6H) 7.97 (dd, J=5.36, 1.58 Hz, 1H) 8.36 (d, J=0.95 Hz, 1H) 8.43 (d, J=2.21 Hz, 1H) 8.78 (d, J=5.36 Hz, 1H) 9.09 (d, J=2.21 Hz, 1H). LCMS (m/z) (M+H)=493.2, Rt=0.39 min.

Example 1047: N-(3-(2-((2-hydroxyethyl)amino)-6-morpholinopyridin-4-yl)-4-methylphenyl)-6-(trifluoromethyl)pyridazine-4-carboxamide

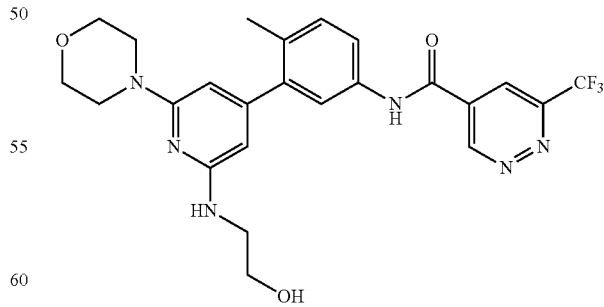

$^1$H NMR (500 MHz, <cd3od>) δ ppm 2.35 (s, 3H) 3.49-3.58 (m, 6H) 3.85 (dt, J=9.69, 4.77 Hz, 6H) 6.22-6.28 (m, 2H) 7.39 (d, J=8.51 Hz, 1H) 7.65 (dd, J=8.35, 2.05 Hz, 1H) 7.83 (d, J=2.21 Hz, 1H) 8.60 (d, J=1.89 Hz, 1H) 9.89 (d, J=1.58 Hz, 1H). LCMS (m/z) (M+H)=503.1, Rt=0.67 min.

Example 1048: 6-cyclopropyl-N-(3-(2-((2-hydroxy-ethyl)amino)-6-morpholinopyridin-4-yl)-4-methyl-phenyl)pyridazine-4-carboxamide

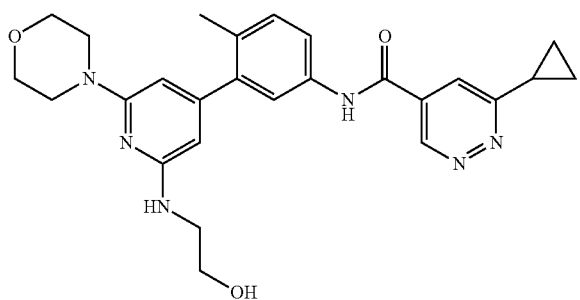 [SMILES: Cc1ccc(NC(=O)c2cnnc(C3CC3)c2)cc1-c1cc(NCCO)nc(N2CCOCC2)c1]

$^1$H NMR (500 MHz, <cd3od>) δ ppm 1.23-1.32 (m, 4H) 2.35 (s, 3H) 2.37-2.44 (m, 1H) 3.46-3.61 (m, 6H) 3.85 (dt, J=9.30, 4.81 Hz, 6H) 6.24-6.29 (m, 1H) 7.38 (d, J=8.51 Hz, 1H) 7.63 (dd, J=8.20, 2.21 Hz, 1H) 7.80 (d, J=2.21 Hz, 1H) 7.97 (d, J=1.89 Hz, 1H) 9.40 (d, J=1.89 Hz, 1H). LCMS (m/z) (M+H)=475.2, Rt=0.61 min.

Example 1049: 6-(2-cyanopropan-2-yl)-N-(3-(2-((2-hydroxyethyl)amino)-6-morpholinopyridin-4-yl)-4-methylphenyl)pyridazine-4-carboxamide

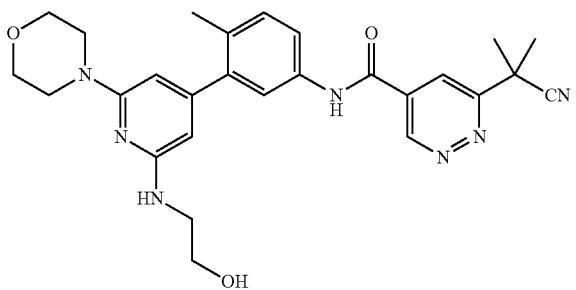 [SMILES: Cc1ccc(NC(=O)c2cnnc(C(C)(C)C#N)c2)cc1-c1cc(NCCO)nc(N2CCOCC2)c1]

$^1$H NMR (500 MHz, <cd3od>) d ppm 1.90-1.95 (m, 6H) 2.36 (s, 3H) 3.48-3.61 (m, 6H) 3.86 (dt, J=9.46, 4.73 Hz, 6H) 6.23-6.31 (m, 1H) 7.39 (d, J=8.51 Hz, 1H) 7.64 (dd, J=8.20, 2.21 Hz, 1H) 7.82 (d, J=2.21 Hz, 1H) 8.38 (d, J=1.89 Hz, 1H) 9.63 (d, J=1.89 Hz, 1H). LCMS (m/z) (M+H)=502.2, Rt=0.63 min.

Example 1050: 2-(1-cyanocyclopropyl)-N-(3-(2-((2-hydroxyethyl)amino)-6-morpholinopyridin-4-yl)-4-methylphenyl)isonicotinamide

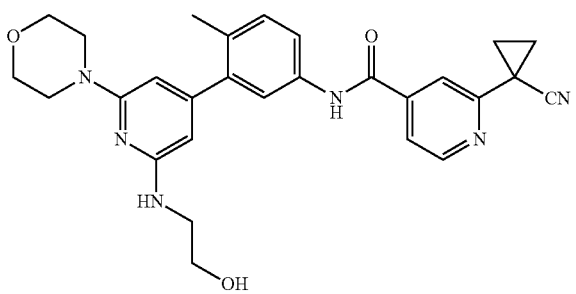 [SMILES: Cc1ccc(NC(=O)c2ccnc(C3(C#N)CC3)c2)cc1-c1cc(NCCO)nc(N2CCOCC2)c1]

$^1$H NMR (500 MHz, <cd3od>) δ ppm 1.81-1.90 (m, 4H) 2.35 (s, 3H) 3.46-3.61 (m, 7H) 3.85 (dt, J=9.54, 4.85 Hz, 7H) 6.24-6.30 (m, 1H) 7.37 (d, J=8.20 Hz, 1H) 7.61 (dd, J=8.20, 2.21 Hz, 1H) 7.71-7.75 (m, 1H) 7.81 (d, J=1.89 Hz, 1H) 8.10 (s, 1H) 8.68 (d, J=5.04 Hz, 1H). LCMS (m/z) (M+H)=499.2, Rt=0.69 min.

Example 1051: N-(2'-((2-hydroxyethyl)amino)-2-methyl-6'-morpholino-[3,4'-bipyridin]-5-yl)-6-(trifluoromethyl)pyridazine-4-carboxamide

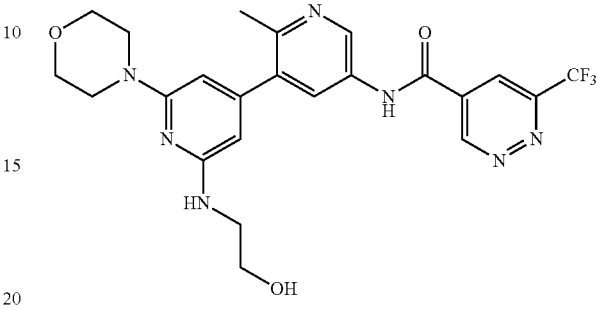

$^1$H NMR (500 MHz, <cd3od>) δ ppm 2.60 (s, 3H) 3.52-3.59 (m, 6H) 3.84 (dt, J=12.45, 4.97 Hz, 6H) 6.19-6.28 (m, 1H) 8.35 (d, J=2.21 Hz, 1H) 8.64 (d, J=1.89 Hz, 1H) 8.96 (s, 1H) 9.92 (d, J=1.89 Hz, 1H). LCMS (m/z) (M+H)=504.2, Rt=0.49 min.

Example 1052: 6-cyclopropyl-N-(2'-((2-hydroxyethyl)amino)-2-methyl-6'-morpholino-[3,4'-bipyridin]-5-yl)pyridazine-4-carboxamide

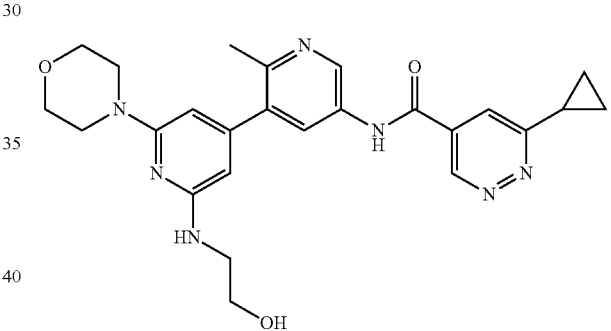

$^1$H NMR (500 MHz, <cd3od>) δ ppm 1.22-1.33 (m, 4H) 2.38-2.45 (m, 1H) 2.63 (s, 3H) 3.51-3.60 (m, 6H) 3.84 (dt, J=12.06, 4.85 Hz, 6H) 6.21-6.28 (m, 1H) 7.99 (d, J=2.21 Hz, 1H) 8.39 (d, J=2.21 Hz, 1H) 9.02 (d, J=2.21 Hz, 1H) 9.43 (d, J=1.89 Hz, 1H). LCMS (m/z) (M+H)=476.1, Rt=0.44 min.

Example 1053: 2-(difluoromethyl)-N-(3-(2-((2-hydroxyethyl)amino)-6-morpholinopyridin-4-yl)-4-methylphenyl)isonicotinamide

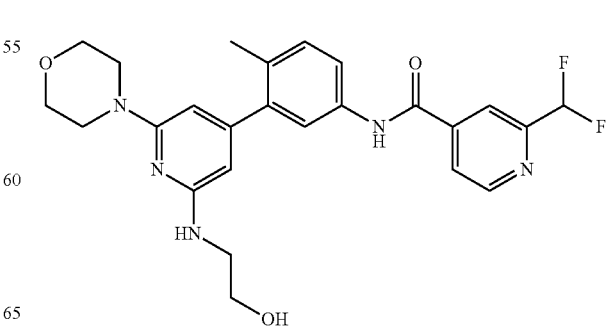

¹H NMR (500 MHz, METHANOL-d) δ ppm 2.30 (s, 5H) 3.43-3.55 (m, 10H) 3.69-3.85 (m, 10H) 5.85-5.99 (m, 1H) 6.65-7.03 (m, 1H) 7.30 (d, J=8.20 Hz, 1H) 7.57-7.68 (m, 2H) 8.03 (d, J=4.41 Hz, 1H) 8.19 (s, 1H) 8.85 (d, J=5.04 Hz, 1H). LC/MS (m/z): 484.3 (MH+), Rt=0.66 min.

Example 1054: N-(4-methyl-3-(2-morpholino-6-((tetrahydrofuran-3-yl)amino)pyridin-4-yl)phenyl)-2-(trifluoromethyl)isonicotinamide

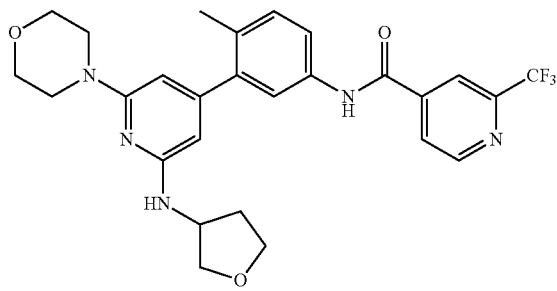 [SMILES: Cc1ccc(NC(=O)c2ccnc(C(F)(F)F)c2)cc1-c1cc(NC2CCOC2)nc(N2CCOCC2)c1]

1H NMR (400 MHz, <cd3od>) δ ppm 1.88-2.02 (m, 1H) 2.33 (s, 4H) 2.35-2.42 (m, 1H) 3.45-3.57 (m, 4H) 3.73-3.90 (m, 6H) 3.91-4.04 (m, 2H) 4.37 (br. s., 1H) 6.05-6.35 (m, 1H) 7.34 (d, J=8.22 Hz, 1H) 7.61 (dd, J=8.22, 2.35 Hz, 1H) 7.76 (br. s., 1H) 8.12 (d, J=4.30 Hz, 1H) 8.29 (s, 1H) 8.92 (d, J=5.09 Hz, 1H). LC/MS (m/z): 528.2 (MH+), Rt=0.78 min.

Example 1055: N-(4-methyl-3-(2-morpholino-6-(((tetrahydrofuran-3-yl)methyl)amino)pyridin-4-yl)phenyl)-2-(trifluoromethyl)isonicotinamide

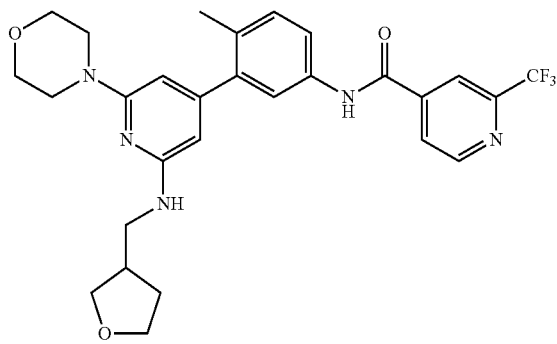 [SMILES: Cc1ccc(NC(=O)c2ccnc(C(F)(F)F)c2)cc1-c1cc(NCC2CCOC2)nc(N2CCOCC2)c1]

1H NMR (400 MHz, <cd3od>) δ ppm 1.53-1.70 (m, 1H) 2.04 (dtd, J=12.77, 7.90, 7.90, 5.48 Hz, 1H) 2.23 (s, 3H) 2.46-2.59 (m, 1H) 3.25 (d, J=7.43 Hz, 3H) 3.35-3.46 (m, 4H) 3.52 (dd, J=8.80, 5.28 Hz, 1H) 3.66 (q, J=7.83 Hz, 1H) 3.70-3.77 (m, 5H) 3.77-3.87 (m, 1H) 6.02-6.17 (m, 1H) 7.25 (d, J=8.22 Hz, 1H) 7.50 (dd, J=8.22, 2.35 Hz, 1H) 7.67 (s, 1H) 8.02 (d, J=3.91 Hz, 1H) 8.19 (s, 1H) 8.82 (d, J=5.09 Hz, 1H). LC/MS (m/z): 542.2 (MH+), Rt=0.79 min.

Example 1056: 2-(2-fluoropropan-2-yl)-N-(2'-((2-hydroxyethyl)amino)-2-methyl-6'-morpholino-[3,4'-bipyridin]-5-yl)isonicotinamide

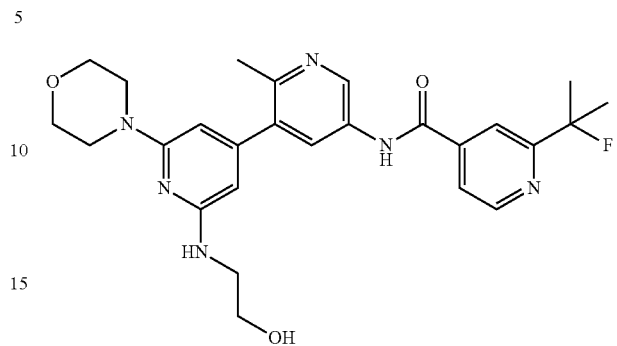

1H NMR (400 MHz, <cd3od>) δ ppm 1.71 (s, 3H) 1.77 (s, 4H) 2.62 (s, 3H) 3.43-3.62 (m, 7H) 3.82 (dt, J=10.08, 4.94 Hz, 7H) 6.13-6.30 (m, 1H) 7.81 (dd, J=5.09, 1.57 Hz, 1H) 8.11 (s, 1H) 8.41 (d, J=2.35 Hz, 1H) 8.74 (d, J=5.09 Hz, 1H) 9.07 (d, J=1.96 Hz, 1H). LC/MS (m/z): 495.2 (MH+), Rt=0.52 min.

Example 1057: 2-cyclopropyl-N-(2'-((2-hydroxyethyl)amino)-2-methyl-6'-morpholino-[3,4'-bipyridin]-5-yl)isonicotinamide

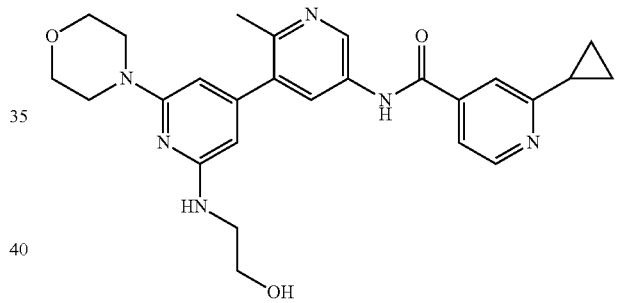

1H NMR (400 MHz, <cd3od>) δ ppm 1.06-1.34 (m, 4H) 2.23-2.35 (m, 1H) 2.61 (s, 3H) 3.42-3.60 (m, 6H) 3.81 (dt, J=9.78, 4.89 Hz, 6H) 6.14-6.29 (m, 1H) 7.71-7.91 (m, 2H) 8.39 (d, J=2.35 Hz, 1H) 8.64 (d, J=5.48 Hz, 1H) 9.05 (d, J=2.35 Hz, 1H). LC/MS (m/z): 475.2 (MH+), Rt=0.40 min.

Example 1058: 2-(1,1-difluoropropyl)-N-(2'-((2-hydroxyethyl)amino)-2-methyl-6'-morpholino-[3,4'-bipyridin]-5-yl)isonicotinamide

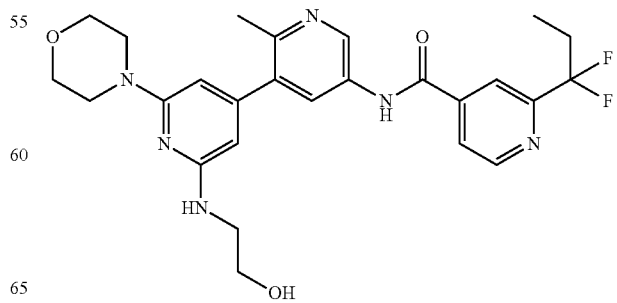

1H NMR (400 MHz, <cd3od>) δ ppm 1.01 (t, J=7.63 Hz, 3H) 2.39 (td, J=16.63, 7.43 Hz, 2H) 2.60 (s, 3H) 3.44-3.63 (m, 7H) 3.82 (dt, J=10.37, 4.99 Hz, 7H) 6.10-6.29 (m, 1H) 8.00 (d, J=5.09 Hz, 1H) 8.21 (s, 1H) 8.37 (d, J=2.35 Hz, 1H) 8.86 (d, J=5.09 Hz, 1H) 9.01 (s, 1H). LC/MS (m/z): 513.2 (MH+), Rt=0.57 min.

Example 1059: 2-(2-cyanopropan-2-yl)-N-(3-(2-(3-hydroxyazetidin-1-yl)-6-morpholinopyridin-4-yl)-4-methylphenyl)isonicotinamide

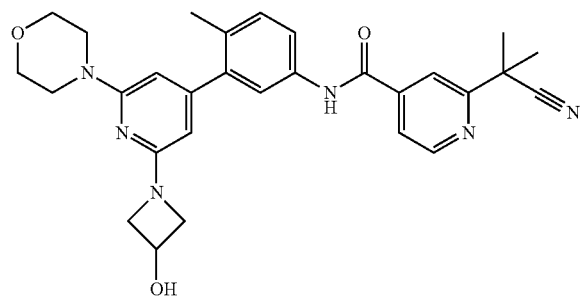 [SMILES: Cc1ccc(NC(=O)c2ccnc(C(C)(C)C#N)c2)cc1-c1cc(N2CCOCC2)nc(N2CC(O)C2)c1]

1H NMR (400 MHz, <cd3od>) δ ppm 1.81 (s, 6H) 2.32 (s, 3H) 3.40-3.53 (m, 5H) 3.80-3.89 (m, 4H) 4.05 (dd, J=9.39, 4.30 Hz, 2H) 4.42-4.51 (m, 2H) 4.70-4.79 (m, 1H) 5.94-6.24 (m, 1H) 7.34 (d, J=8.61 Hz, 1H) 7.59 (dd, J=8.22, 1.96 Hz, 1H) 7.75 (s, 1H) 7.81 (d, J=4.70 Hz, 1H) 8.06 (s, 1H) 8.77 (d, J=5.09 Hz, 1H). LC/MS (m/z): 513.2 (MH+), Rt=0.70 min.

Example 1060: N-(3-(2-(3-hydroxyazetidin-1-yl)-6-morpholinopyridin-4-yl)-4-methylphenyl)-2-(trifluoromethyl)isonicotinamide

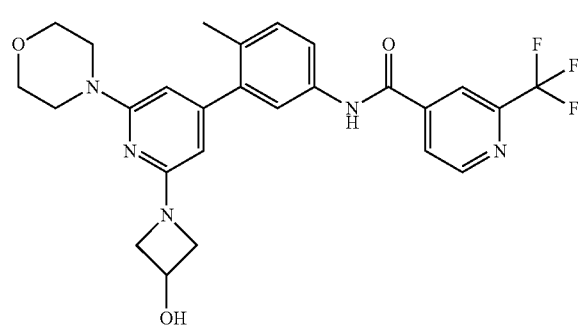 [SMILES: Cc1ccc(NC(=O)c2ccnc(C(F)(F)F)c2)cc1-c1cc(N2CCOCC2)nc(N2CC(O)C2)c1]

1H NMR (400 MHz, <cd3od>) δ ppm 2.31 (s, 3H) 3.38-3.54 (m, 4H) 3.69-3.89 (m, 4H) 3.98 (dd, J=9.39, 4.30 Hz, 2H) 4.31-4.49 (m, 2H) 4.66-4.78 (m, 1H) 5.85-6.20 (m, 1H) 7.33 (d, J=8.61 Hz, 1H) 7.61 (dd, J=8.22, 1.96 Hz, 1H) 7.72 (s, 1H) 8.11 (d, J=5.09 Hz, 1H) 8.29 (s, 1H) 8.91 (d, J=5.09 Hz, 1H). LC/MS (m/z): 514.1 (MH+), Rt=0.74 min.

Example 1061: 1-ethyl-N-(3-(2-(3-hydroxyazetidin-1-yl)-6-morpholinopyridin-4-yl)-4-methylphenyl)-6-oxo-5-(trifluoromethyl)-1,6-dihydropyridine-3-carboxamide

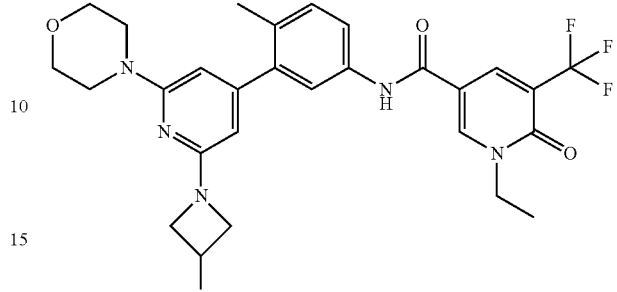

1H NMR (400 MHz, <cd3od>) δ ppm 1.42 (t, J=7.04 Hz, 3H) 2.30 (s, 3H) 3.37-3.52 (m, 4H) 3.75-3.88 (m, 4H) 3.99 (dd, J=9.00, 4.30 Hz, 2H) 4.16 (q, J=7.17 Hz, 2H) 4.34-4.49 (m, 2H) 4.68-4.78 (m, 1H) 5.86-6.21 (m, 1H) 7.30 (d, J=8.22 Hz, 1H) 7.53 (dd, J=8.22, 1.96 Hz, 1H) 7.65 (s, 1H) 8.47 (s, 1H) 8.70 (d, J=2.35 Hz, 1H). LC/MS (m/z): 558.2 (MH+), Rt=0.72 min.

Example 1062: N-(3-(2-((2-hydroxy-2-methylpropyl)amino)-6-morpholinopyridin-4-yl)-4-methylphenyl)-3-(trifluoromethyl)benzamide

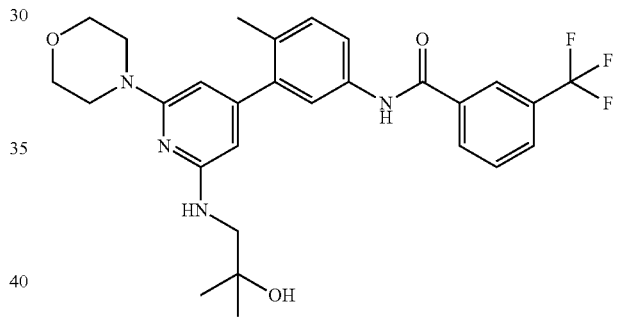

1H NMR (400 MHz, <cd3od>) δ ppm 1.33 (s, 6H) 2.32 (s, 3H) 3.37 (s, 2H) 3.46-3.58 (m, 4H) 3.76-3.89 (m, 4H) 6.22 (d, J=6.26 Hz, 1H) 7.33 (d, J=8.22 Hz, 1H) 7.57 (dd, J=8.22, 1.96 Hz, 1H) 7.68-7.80 (m, 2H) 7.90 (d, J=7.83 Hz, 1H) 8.20 (d, J=7.83 Hz, 1H) 8.25 (s, 1H). LC/MS (m/z): 529.2 (MH+), Rt=0.87 min.

Example 1063: N-(4-methyl-3-(2-morpholino-6-((3,3,3-trifluoro-2-hydroxypropyl)amino)pyridin-4-yl)phenyl)-3-(trifluoromethyl)benzamide

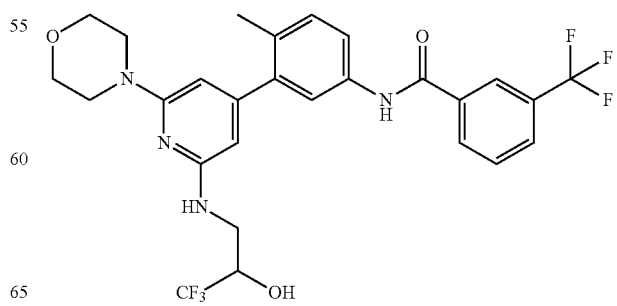

1H NMR (400 MHz, <cd3od>) δ ppm 2.31 (s, 3H) 3.45-3.62 (m, 5H) 3.71-3.90 (m, 5H) 4.28 (td, J=7.14, 3.33 Hz, 1H) 6.09-6.25 (m, 1H) 7.32 (d, J=8.22 Hz, 1H) 7.57 (dd, J=8.22, 2.35 Hz, 1H) 7.66-7.79 (m, 2H) 7.90 (d, J=7.83 Hz, 1H) 8.20 (d, J=7.83 Hz, 1H) 8.25 (s, 1H). LC/MS (m/z): 569.1 (MH+), Rt=0.91 min.

Example 1064: (R)—N-(3-(2-(4-hydroxy-2-oxopyrrolidin-1-yl)-6-morpholinopyridin-4-yl)-4-methylphenyl)-3-(trifluoromethyl)benzamide

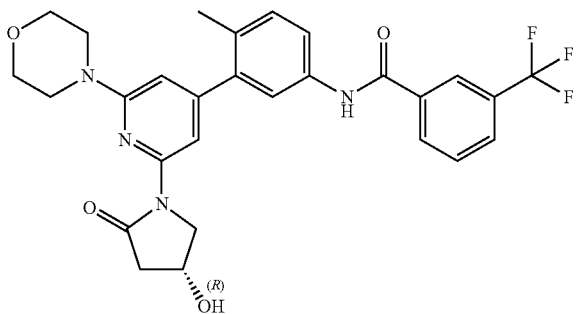

1H NMR (400 MHz, <cd3od>) δ ppm 2.28 (s, 3H) 2.52 (d, J=17.22 Hz, 1H) 3.01 (dd, J=17.41, 6.06 Hz, 1H) 3.49-3.63 (m, 4H) 3.74-3.89 (m, 4H) 4.07-4.17 (m, 1H) 4.18-4.29 (m, 1H) 4.52 (t, J=5.28 Hz, 1H) 6.56 (s, 1H) 7.31 (d, J=7.83 Hz, 1H) 7.56 (br. s., 1H) 7.59-7.68 (m, 2H) 7.68-7.77 (m, 1H) 7.89 (d, J=7.83 Hz, 1H) 8.20 (d, J=8.22 Hz, 1H) 8.26 (s, 1H). LC/MS (m/z): 541.2 (MH+), Rt=0.91 min.

Example 1065: (R)—N-(3-(2-(3-hydroxy-2-oxopyrrolidin-1-yl)-6-morpholinopyridin-4-yl)-4-methylphenyl)-3-(trifluoromethyl)benzamide

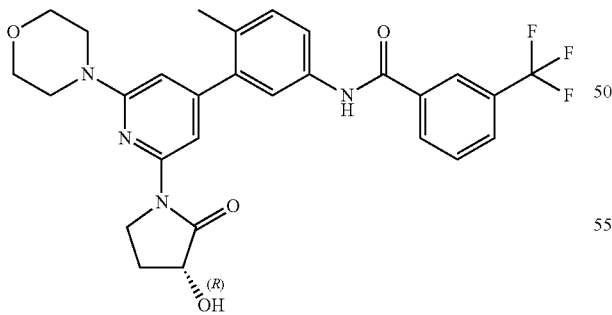

1H NMR (400 MHz, <cd3od>) δ ppm 1.86-2.06 (m, 1H) 2.28 (s, 3H) 2.46-2.61 (m, 1H) 3.49-3.64 (m, 4H) 3.70-3.93 (m, 5H) 4.21 (t, J=9.39 Hz, 1H) 4.49 (t, J=8.80 Hz, 1H) 6.57 (s, 1H) 7.31 (d, J=9.00 Hz, 1H) 7.59 (s, 1H) 7.61-7.67 (m, 2H) 7.68-7.76 (m, 1H) 7.89 (d, J=7.83 Hz, 1H) 8.20 (d, J=7.83 Hz, 1H) 8.26 (s, 1H). LC/MS (m/z): 541.2 (MH+), Rt=0.94 min.

Example 1066: N-(3-(2-(2-hydroxypropanamido)-6-morpholinopyridin-4-yl)-4-methylphenyl)-3-(trifluoromethyl)benzamide

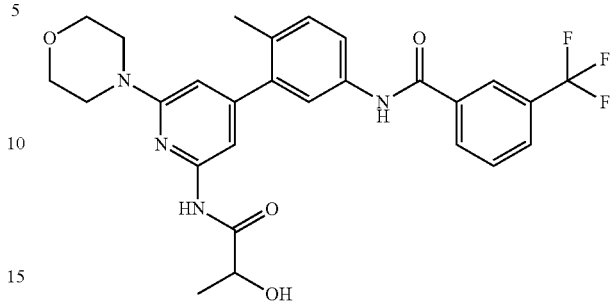

1H NMR (400 MHz, <cd3od>) δ ppm 1.44 (d, J=6.65 Hz, 3H) 2.30 (s, 3H) 3.50-3.62 (m, 4H) 3.74-3.87 (m, 4H) 4.30 (q, J=7.04 Hz, 1H) 6.63 (s, 1H) 7.32 (d, J=8.61 Hz, 1H) 7.37 (s, 1H) 7.59-7.69 (m, 2H) 7.69-7.78 (m, 1H) 7.89 (d, J=7.43 Hz, 1H) 8.20 (d, J=7.83 Hz, 1H) 8.26 (s, 1H). LC/MS (m/z): 529.2 (MH+), Rt=0.91 min.

Example 1067: 2-(difluoromethyl)-N-(3-(2-(3-hydroxyazetidin-1-yl)-6-morpholinopyridin-4-yl)-4-methylphenyl)isonicotinamide

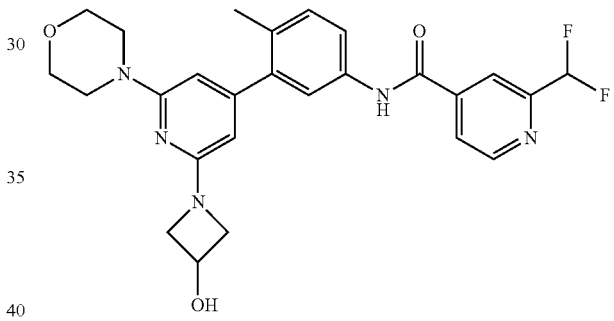

1H NMR (400 MHz, <cd3od>) δ ppm 2.26 (s, 3H) 3.40-3.52 (m, 4H) 3.67-3.85 (m, 6H) 4.09-4.28 (m, 2H) 4.66 (t, J=5.48 Hz, 1H) 5.73 (s, 1H) 6.00 (s, 1H) 6.59-7.02 (m, 1H) 7.28 (d, J=8.22 Hz, 1H) 7.51-7.67 (m, 2H) 8.00 (d, J=4.70 Hz, 1H) 8.17 (s, 1H) 8.82 (d, J=5.09 Hz, 1H). LC/MS (m/z): 496.1 (MH+), $R_t$=0.68 min.

Example 1068: 2-cyclopropyl-N-(3-(2-(3-hydroxyazetidin-1-yl)-6-morpholinopyridin-4-yl)-4-methylphenyl)isonicotinamide

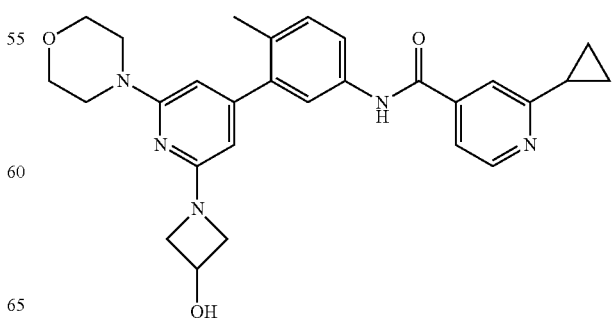

1H NMR (400 MHz, <cd3od>) vppm 0.98-1.15 (m, 4H) 2.12-2.23 (m, 1H) 2.26 (s, 3H) 3.12 (d, J=6.65 Hz, 1H) 3.42-3.53 (m, 5H) 3.67-3.85 (m, 6H) 4.12-4.28 (m, 2H) 4.58 (s, 2H) 4.66 (t, J=5.28 Hz, 1H) 5.73 (s, 1H) 6.00 (s, 1H) 7.27 (d, J=8.22 Hz, 1H) 7.51-7.73 (m, 4H) 8.52 (d, J=5.09 Hz, 1H). LC/MS (m/z): 486.1 (MH+), Rt=0.57 min.

Example 1069: N-(3-(2-(3-hydroxyazetidin-1-yl)-6-morpholinopyridin-4-yl)-4-methylphenyl)-2-isopropylisonicotinamide

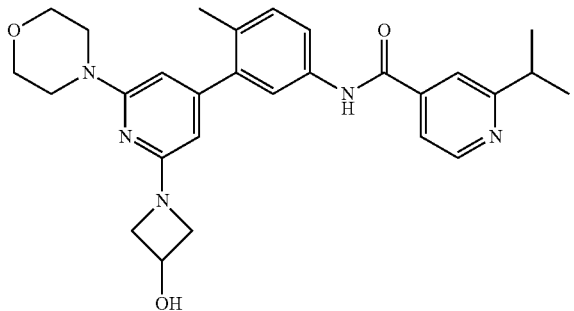 [SMILES: Cc1ccc(NC(=O)c2ccnc(C(C)C)c2)cc1-c1cc(N2CCOCC2)nc(N2CC(O)C2)c1]

1H NMR (400 MHz, <cd3od>) δ ppm 1.40 (d, J=7.04 Hz, 6H) 2.31 (s, 3H) 3.16-3.27 (m, 1H) 3.39-3.51 (m, 4H) 3.73-3.88 (m, 4H) 3.97 (dd, J=9.39, 4.30 Hz, 2H) 4.41 (t, J=7.83 Hz, 2H) 4.63-4.78 (m, 1H) 5.86-6.19 (m, 1H) 7.33 (d, J=8.22 Hz, 1H) 7.42-7.51 (m, 1H) 7.61 (dd, J=8.22, 1.96 Hz, 1H) 7.71 (s, 1H) 7.86 (d, J=4.70 Hz, 1H) 7.97 (s, 1H) 8.02 (d, J=7.04 Hz, 1H) 8.69 (d, J=5.09 Hz, 1H). LC/MS (m/z): 488.2 (MH+), Rt=0.57 min.

Example 1070: N-(3-(2-(3-hydroxyazetidin-1-yl)-6-morpholinopyridin-4-yl)-4-methylphenyl)-6-(trifluoromethyl)pyridazine-4-carboxamide

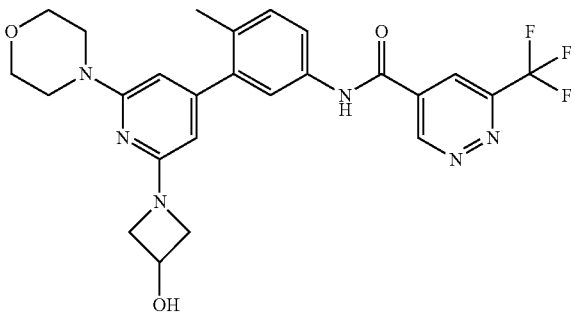 [SMILES: Cc1ccc(NC(=O)c2cnnc(C(F)(F)F)c2)cc1-c1cc(N2CCOCC2)nc(N2CC(O)C2)c1]

1H NMR (400 MHz, <cd3od>) δ ppm 2.29 (s, 3H) 2.59-2.76 (m, 1H) 3.08-3.21 (m, 3H) 3.42-3.51 (m, 6H) 3.69-3.93 (m, 6H) 4.29 (t, J=7.83 Hz, 2H) 4.64-4.73 (m, 1H) 5.81 (s, 1H) 6.06 (s, 1H) 7.31 (d, J=9.00 Hz, 1H) 7.42-7.50 (m, 1H) 7.65 (d, J=6.26 Hz, 2H) 8.02 (d, J=7.04 Hz, 1H) 8.58 (d, J=1.96 Hz, 1H) 9.87 (d, J=1.96 Hz, 1H). LC/MS (m/z): 515.1 (MH+), Rt=0.70 min.

Example 1071: 2-(1-cyanocyclopropyl)-N-(3-(2-(3-hydroxyazetidin-1-yl)-6-morpholinopyridin-4-yl)-4-methylphenyl)isonicotinamide

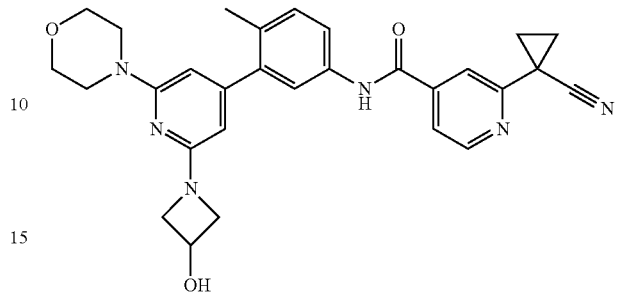

1H NMR (400 MHz, <cd3od>) δ ppm 1.82 (d, J=12.52 Hz, 4H) 2.26 (s, 3H) 3.12 (d, J=9.00 Hz, 5H) 3.43-3.53 (m, 8H) 3.69-3.85 (m, 6H) 4.20 (t, J=7.63 Hz, 2H) 5.73 (s, 1H) 6.00 (s, 1H) 7.27 (d, J=8.61 Hz, 1H) 7.55 (s, 1H) 7.61 (d, J=8.22 Hz, 1H) 7.71 (d, J=5.09 Hz, 1H) 8.06 (s, 1H) 8.64 (d, J=5.09 Hz, 1H). LC/MS (m/z): 511.1 (MH+), Rt=0.71 min.

Example 1072: 2-(difluoromethyl)-N-(3-(2-(3-hydroxy-3-methylazetidin-1-yl)-6-morpholinopyridin-4-yl)-4-methylphenyl)isonicotinamide

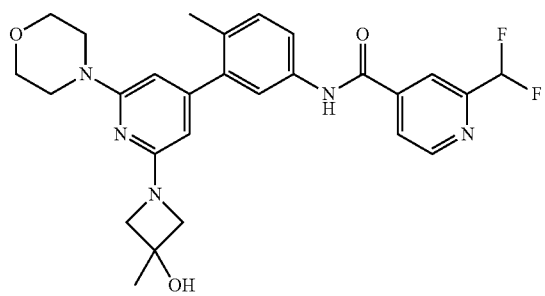 [SMILES: Cc1ccc(NC(=O)c2ccnc(C(F)F)c2)cc1-c1cc(N2CCOCC2)nc(N2CC(C)(O)C2)c1]

1H NMR (400 MHz, <cd3od>) δ ppm 1.54 (s, 3H) 2.27 (s, 3H) 3.41-3.51 (m, 4H) 3.68-3.81 (m, 4H) 3.81-3.96 (m, 4H) 5.74 (s, 1H) 6.01 (s, 1H) 6.59-7.01 (m, 1H) 7.28 (d, J=8.22 Hz, 1H) 7.53-7.69 (m, 2H) 8.00 (d, J=4.70 Hz, 1H) 8.17 (s, 1H) 8.82 (d, J=5.09 Hz, 1H). LC/MS (m/z): 510.1 (MH+), Rt=0.70 min.

Example 1073: N-(3-(2-(3-hydroxy-3-methylazetidin-1-yl)-6-morpholinopyridin-4-yl)-4-methylphenyl)-6-(trifluoromethyl)pyridazine-4-carboxamide

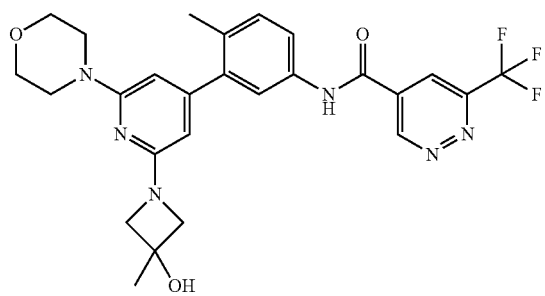 [SMILES: Cc1ccc(NC(=O)c2cnnc(C(F)(F)F)c2)cc1-c1cc(N2CCOCC2)nc(N2CC(C)(O)C2)c1]

1H NMR (400 MHz, <cd3od>) δ ppm 1.54 (s, 3H) 2.16 (s, 4H) 2.27 (s, 3H) 3.40-3.52 (m, 6H) 3.70-3.81 (m, 4H) 3.81-3.92 (m, 4H) 4.58 (s, 2H) 5.73 (s, 1H) 6.00 (s, 1H) 7.29 (d, J=8.22 Hz, 1H) 7.56-7.73 (m, 1H) 8.58 (d, J=1.96 Hz, 1H) 9.87 (d, J=1.57 Hz, 1H). LC/MS (m/z): 529.1 (MH+), Rt=0.72 min.

Example 1074: N-(3-(2-(3-hydroxy-3-methylazetidin-1-yl)-6-morpholinopyridin-4-yl)-4-methylphenyl)-3-(methylsulfonyl)benzamide

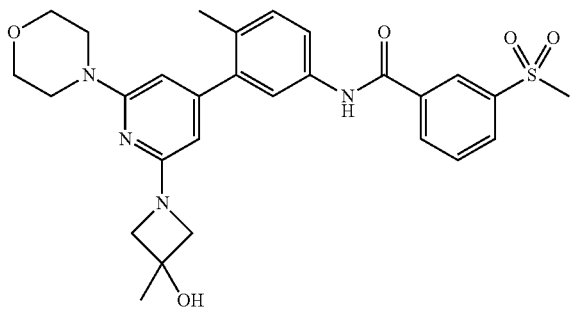 [SMILES: Cc1ccc(NC(=O)c2cccc(S(C)(=O)=O)c2)cc1-c1cc(N2CCOCC2)nc(N2CC(C)(O)C2)c1]

1H NMR (400 MHz, <cd3od>) δ ppm 1.54 (s, 3H) 2.27 (s, 3H) 3.19 (s, 3H) 3.41-3.53 (m, 4H) 3.71-3.81 (m, 4H) 3.81-3.97 (m, 4H) 5.75 (s, 1H) 6.01 (s, 1H) 7.27 (d, J=8.61 Hz, 1H) 7.52-7.65 (m, 2H) 7.79 (t, J=7.83 Hz, 1H) 8.16 (d, J=8.22 Hz, 1H) 8.26 (d, J=7.83 Hz, 1H) 8.50 (s, 1H). LC/MS (m/z): 537.1 (MH+), Rt=0.66 min.

Example 1075: 5-(difluoromethyl)-N-(3-(2-(3-hydroxyazetidin-1-yl)-6-morpholinopyridin-4-yl)-4-methylphenyl)pyridazine-4-carboxamide

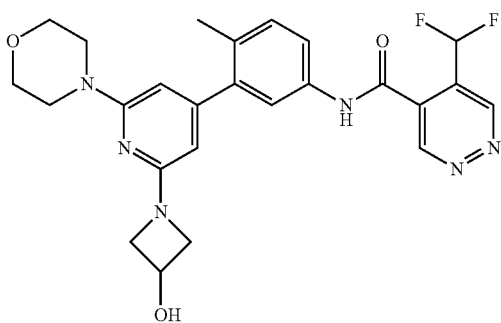 [SMILES: Cc1ccc(NC(=O)c2cnncc2C(F)F)cc1-c1cc(N2CCOCC2)nc(N2CC(O)C2)c1]

1H NMR (400 MHz, <cd3od>) δ ppm 2.26 (s, 3H) 3.41-3.52 (m, 4H) 3.70-3.84 (m, 6H) 4.15-4.26 (m, 2H) 4.58 (s, 1H) 4.62-4.70 (m, 1H) 5.71 (s, 1H) 5.99 (s, 1H) 7.19-7.65 (m, 1H) 7.25 (s, 1H) 7.28 (d, J=8.22 Hz, 1H) 7.38 (s, 1H) 7.49-7.55 (m, 1H) 7.59 (dd, J=8.22, 1.96 Hz, 1H) 9.58 (s, 2H). LC/MS (m/z): 497.1 (MH+), Rt=0.61 min.

Example 1076: 6-cyclopropyl-N-(3-(2-(3-hydroxy-3-methylazetidin-1-yl)-6-morpholinopyridin-4-yl)-4-methylphenyl)pyridazine-4-carboxamide

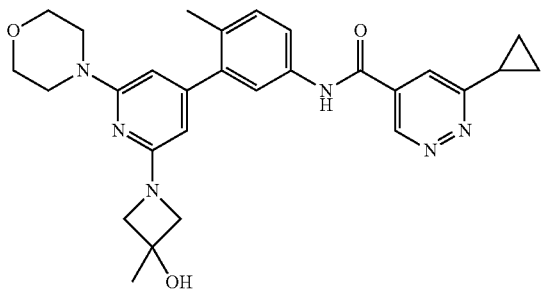 [SMILES: Cc1ccc(NC(=O)c2cnnc(C3CC3)c2)cc1-c1cc(N2CCOCC2)nc(N2CC(C)(O)C2)c1]

1H NMR (500 MHz, cd3od) δ ppm 1.10-1.37 (m, 4H) 1.56 (s, 3H) 2.30 (s, 3H) 2.33-2.42 (m, 1H) 3.38-3.51 (m, 4H) 3.74-3.86 (m, 4H) 3.96-4.13 (m, 4H) 5.94 (s, 1H) 6.14 (s, 1H) 7.32 (d, J=8.51 Hz, 1H) 7.60 (dd, J=8.20, 2.21 Hz, 1H) 7.70 (s, 1H) 7.91 (d, J=1.89 Hz, 1H) 9.37 (d, J=1.58 Hz, 1H). LC/MS (m/z): 501.3 (MH+), Rt=0.64 min.

Example 1077: 3-(difluoromethyl)-N-(3-(2-(3-hydroxyazetidin-1-yl)-6-morpholinopyridin-4-yl)-4-methylphenyl)benzamide

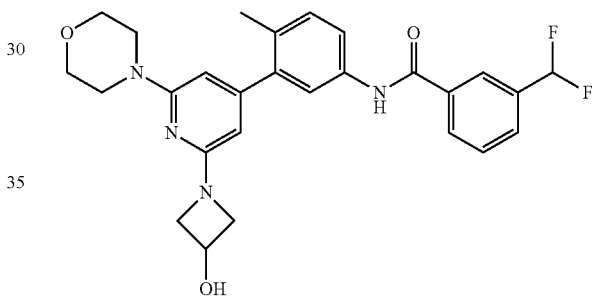

¹H NMR (400 MHz, <cd3od>) δ ppm 2.31 (s, 3H) 3.41-3.51 (m, 4H) 3.79-3.87 (m, 4H) 4.03 (dd, J=9.59, 4.11 Hz, 2H) 4.43-4.49 (m, 2H) 4.71-4.78 (m, 1H) 6.00-6.20 (m, 1H) 6.87 (t, J=56.00 Hz, 1H) 7.32 (d, J=8.22 Hz, 1H) 7.57 (dd, J=8.22, 2.35 Hz, 1H) 7.65 (t, J=7.83 Hz, 1H) 7.73 (s, 1H) 7.77 (d, J=7.83 Hz, 1H) 8.08 (d, J=7.83 Hz, 1H) 8.12 (s, 1H). LCMS (m/z) (M+H)=495.1, Rt=0.75 min.

Example 1078: 2-(1,1-difluoroethyl)-N-(3-(2-(3-hydroxyazetidin-1-yl)-6-morpholinopyridin-4-yl)-4-methylphenyl)isonicotinamide

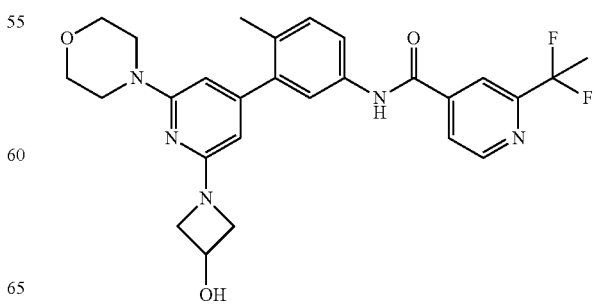

¹H NMR (400 MHz, <cd3od>) δ ppm 2.03 (t, J=18.78 Hz, 3H) 2.31 (s, 3H) 3.41-3.49 (m, 4H) 3.79-3.85 (m, 4H) 4.03 (dd, J=9.59, 4.11 Hz, 2H) 4.42-4.50 (m, 2H) 4.71-4.78 (m, 1H) 6.00-6.20 (m, 1H) 7.33 (d, J=8.22 Hz, 1H) 7.59 (dd, J=8.41, 2.15 Hz, 1H) 7.75 (s, 1H) 7.95 (d, J=4.70 Hz, 1H) 8.17 (s, 1H) 8.80 (d, J=5.09 Hz, 1H). LCMS (m/z) (M+H)=510.2, Rt=0.72 min.

Example 1079: 3-(difluoromethyl)-N-(2'-(3-hydroxyazetidin-1-yl)-2-methyl-6'-morpholino-[3,4'-bipyridin]-5-yl)benzamide

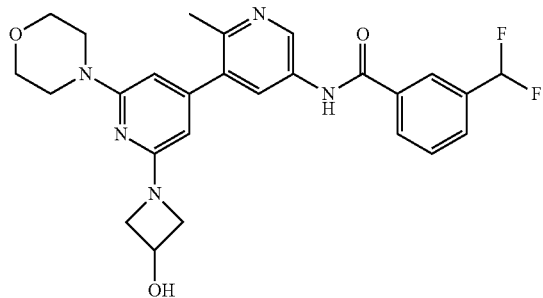 [SMILES: Cc1ncc(NC(=O)c2cccc(C(F)F)c2)cc1-c1cc(N2CCOCC2)nc(N2CC(O)C2)c1]

¹H NMR (400 MHz, <cd3od>) δ ppm 2.68 (s, 3H) 3.48-3.53 (m, 4H) 3.76-3.82 (m, 4H) 3.85 (dd, J=9.19, 4.50 Hz, 2H) 4.25-4.34 (m, 2H) 4.66-4.74 (m, 1H) 6.90 (t, J=56.00 Hz, 1H) 7.67-7.74 (m, 1H) 7.83 (d, J=7.83 Hz, 1H) 8.16 (d, J=7.43 Hz, 1H) 8.21 (s, 1H) 8.47 (d, J=2.35 Hz, 1H) 9.36 (d, J=2.35 Hz, 1H). LCMS (m/z) (M+H)=496.1, Rt=0.61 min.

Example 1080: 2-(1,1-difluoroethyl)-N-(2'-(3-hydroxyazetidin-1-yl)-2-methyl-6'-morpholino-[3,4'-bipyridin]-5-yl)isonicotinamide

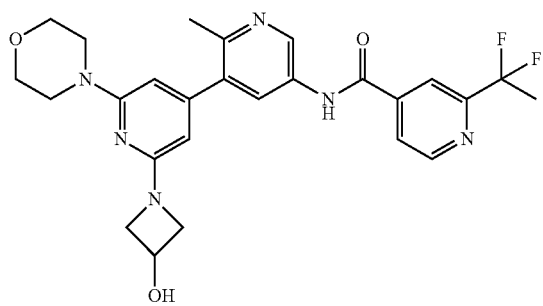 [SMILES: Cc1ncc(NC(=O)c2ccnc(C(C)(F)F)c2)cc1-c1cc(N2CCOCC2)nc(N2CC(O)C2)c1]

¹H NMR (400 MHz, <cd3od>) δ ppm 2.05 (t, J=18.78 Hz, 3H) 2.67 (s, 3H) 3.48-3.53 (m, 4H) 3.75-3.82 (m, 4H) 3.85 (dd, J=9.00, 4.30 Hz, 2H) 4.27-4.33 (m, 2H) 4.67-4.75 (m, 1H) 8.02 (d, J=4.69 Hz, 1H) 8.25 (s, 1H) 8.44 (d, J=2.35 Hz, 1H) 8.86 (d, J=5.09 Hz, 1H) 9.31 (d, J=2.35 Hz, 1H). LCMS (m/z) (M+H)=511.1, Rt=0.57 min.

Example 1081: N-(2'-(3-hydroxyazetidin-1-yl)-2-methyl-6'-morpholino-[3,4'-bipyridin]-5-yl)-2-isopropylisonicotinamide

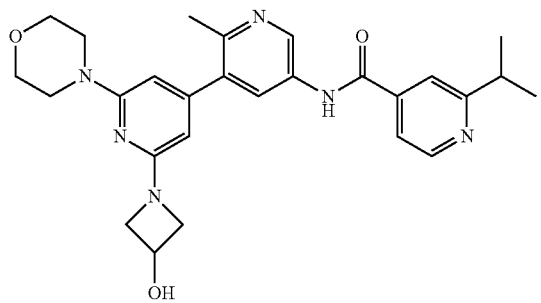 [SMILES: Cc1ncc(NC(=O)c2ccnc(C(C)C)c2)cc1-c1cc(N2CCOCC2)nc(N2CC(O)C2)c1]

¹H NMR (400 MHz, <cd3od>) δ ppm 1.41 (d, J=7.04 Hz, 7H) 2.66 (s, 3H) 3.48-3.53 (m, 4H) 3.76-3.82 (m, 4H) 3.85 (dd, J=9.00, 4.70 Hz, 2H) 4.26-4.33 (m, 2H) 4.67-4.74 (m, 1H) 7.93 (dd, J=5.48, 1.57 Hz, 1H) 8.04 (s, 1H) 8.41 (d, J=2.35 Hz, 1H) 8.76 (d, J=5.48 Hz, 1H) 9.27 (d, J=2.35 Hz, 1H). LCMS (m/z) (M+H)=489.1, Rt=0.46 min.

Example 1082: N-(2'-(3-hydroxyazetidin-1-yl)-2-methyl-6'-morpholino-[3,4'-bipyridin]-5-yl)-2-(2-hydroxypropan-2-yl)isonicotinamide

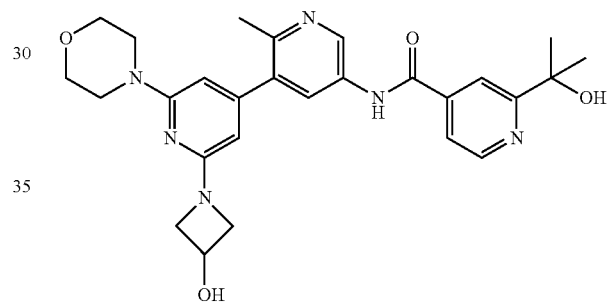

¹H NMR (400 MHz, <cd3od>) δ ppm 1.63 (s, 6H) 2.67 (s, 3H) 3.47-3.53 (m, 4H) 3.76-3.82 (m, 4H) 3.85 (dd, J=9.00, 4.70 Hz, 2H) 4.27-4.33 (m, 2H) 4.67-4.74 (m, 1H) 7.94 (dd, J=5.48, 1.57 Hz, 1H) 8.34 (s, 1H) 8.43 (d, J=2.35 Hz, 1H) 8.76 (d, J=5.48 Hz, 1H) 9.29 (d, J=2.35 Hz, 1H). LCMS (m/z) (M+H)=505.2, Rt=0.43 min.

Example 1083: 2-(2-cyanopropan-2-yl)-N-(2'-(3-hydroxyazetidin-1-yl)-2-methyl-6'-morpholino-[3,4'-bipyridin]-5-yl)isonicotinamide

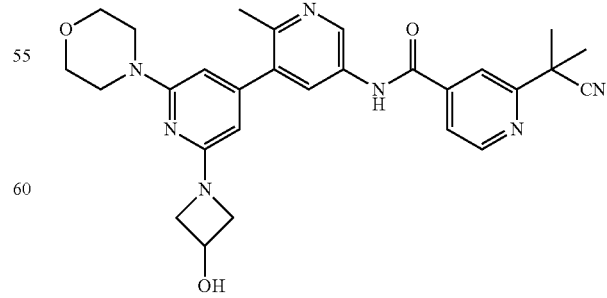

¹H NMR (400 MHz, <cd3od>) δ ppm 1.82 (s, 6H) 2.68 (s, 3H) 3.47-3.53 (m, 4H) 3.75-3.82 (m, 4H) 3.85 (dd, J=9.19, 4.50 Hz, 2H) 4.27-4.33 (m, 2H) 4.67-4.75 (m, 1H) 7.87 (dd, J=4.89, 1.37 Hz, 1H) 8.13 (s, 1H) 8.44 (d, J=1.96 Hz, 1H) 8.82 (d, J=5.09 Hz, 1H) 9.31 (d, J=1.96 Hz, 1H). LCMS (m/z) (M+H)=514.2, Rt=0.66 min.

Example 1084: N-(2'-(3-hydroxyazetidin-1-yl)-2-methyl-6'-morpholino-[3,4'-bipyridin]-5-yl)-3-(methylsulfonyl)benzamide

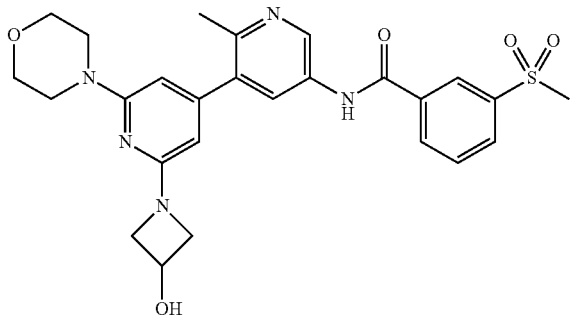

$^1$H NMR (400 MHz, <cd3od>) δ ppm 2.67 (s, 3H) 3.20 (s, 3H) 3.47-3.54 (m, 4H) 3.76-3.81 (m, 4H) 3.83 (dd, J=9.00, 4.30 Hz, 2H) 4.24-4.31 (m, 2H) 4.67-4.74 (m, 1H) 7.85 (t, J=8.02 Hz, 1H) 8.23 (d, J=7.83 Hz, 1H) 8.34 (d, J=7.83 Hz, 1H) 8.43 (d, J=2.35 Hz, 1H) 8.59 (s, 1H) 9.32 (d, J=2.35 Hz, 1H). LCMS (m/z) (M+H)=524.2, Rt=0.52 min.

Example 1085: 3-((dimethylamino)methyl)-N-(2'-(3-hydroxyazetidin-1-yl)-2-methyl-6'-morpholino-[3,4'-bipyridin]-5-yl)-5-(trifluoromethyl)benzamide

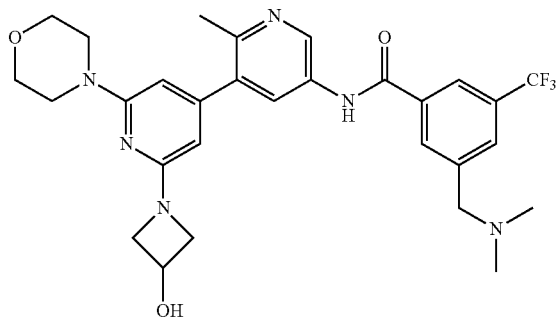 [SMILES: Cc1ncc(NC(=O)c2cc(CN(C)C)cc(C(F)(F)F)c2)cc1-c1cc(N2CCOCC2)nc(N2CC(O)C2)c1]

$^1$H NMR (400 MHz, <cd3od>) δ ppm 2.64 (s, 3H) 2.93 (s, 6H) 3.47-3.53 (m, 4H) 3.76-3.80 (m, 4H) 3.83 (dd, J=9.00, 4.30 Hz, 2H) 4.24-4.31 (m, 2H) 4.53 (s, 2H) 4.66-4.74 (m, 1H) 8.16 (s, 1H) 8.38 (d, J=2.35 Hz, 1H) 8.46 (s, 1H) 8.50 (s, 1H) 9.22 (d, J=2.35 Hz, 1H). LCMS (m/z) (M+H)=571.2, Rt=0.50 min.

Example 1086: 1-ethyl-N-(2'-(3-hydroxyazetidin-1-yl)-2-methyl-6'-morpholino-[3,4'-bipyridin]-5-yl)-6-oxo-5-(trifluoromethyl)-1,6-dihydropyridine-3-carboxamide

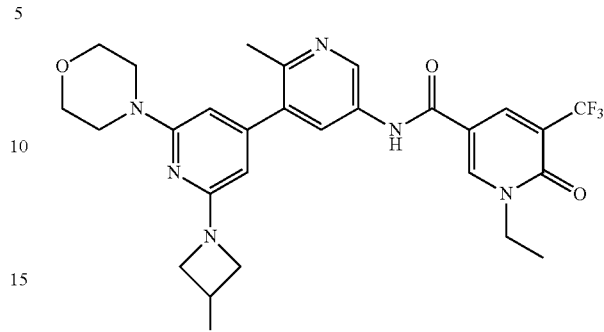

$^1$H NMR (400 MHz, <cd3od>) δ ppm 1.42 (t, J=7.24 Hz, 3H) 2.66 (s, 3H) 3.47-3.53 (m, 4H) 3.75-3.80 (m, 4H) 3.83 (dd, J=9.00, 4.70 Hz, 2H) 4.18 (q, J=7.04 Hz, 2H) 4.25-4.31 (m, 2H) 4.67-4.73 (m, 1H) 8.36 (d, J=2.35 Hz, 1H) 8.52 (d, J=1.96 Hz, 1H) 8.79 (d, J=2.35 Hz, 1H) 9.25 (d, J=1.96 Hz, 1H). LCMS (m/z) (M+H)=559.2, Rt=0.54 min.

Example 1087: 3-(4-ethylpiperazin-1-yl)-N-(2'-(3-hydroxyazetidin-1-yl)-2-methyl-6'-morpholino-[3,4'-bipyridin]-5-yl)-5-(trifluoromethyl)benzamide

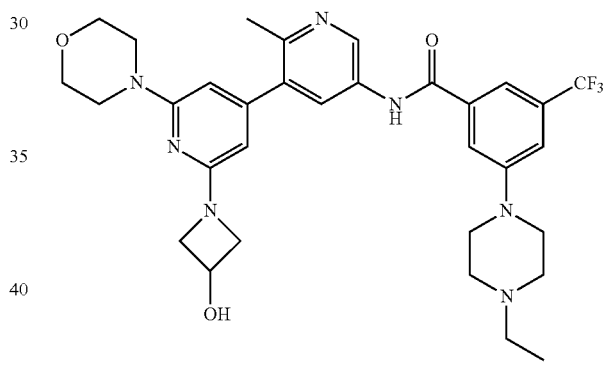

$^1$H NMR (400 MHz, <cd3od>) δ ppm 1.41 (t, J=7.24 Hz, 3H) 2.65 (s, 3H) 3.15-3.27 (m, 2H) 3.47-3.54 (m, 4H) 3.64-3.86 (m, 8H) 4.09 (br. s., 2H) 4.24-4.31 (m, 2H) 4.66-4.74 (m, 1H) 7.56 (s, 1H) 7.87 (d, J=10.56 Hz, 2H) 8.40 (d, J=2.35 Hz, 1H) 9.26 (d, J=2.35 Hz, 1H). LCMS (m/z) (M+H)=626.2, Rt=0.61 min.

Example 1088: N-(2'-(3-hydroxyazetidin-1-yl)-2-methyl-6'-morpholino-[3,4'-bipyridin]-5-yl)-2-(trifluoromethyl)isonicotinamide

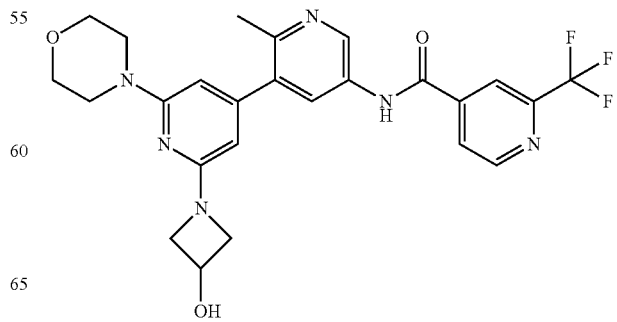

¹H NMR (400 MHz, <cd3od>) δ ppm 2.66 (s, 3H) 3.47-3.53 (m, 4H) 3.76-3.81 (m, 4H) 3.85 (dd, J=9.19, 4.50 Hz, 2H) 4.26-4.32 (m, 2H) 4.67-4.74 (m, 1H) 8.17 (d, J=4.30 Hz, 1H) 8.36 (s, 1H) 8.40 (d, J=2.35 Hz, 1H) 8.97 (d, J=5.09 Hz, 1H) 9.26 (d, J=2.35 Hz, 1H). LCMS (m/z) (M+H)=515.2, Rt=0.57 min.

Example 1089: 2-(tert-butyl)-N-(2'-(3-hydroxyazetidin-1-yl)-2-methyl-6'-morpholino-[3,4'-bipyridin]-5-yl)isonicotinamide

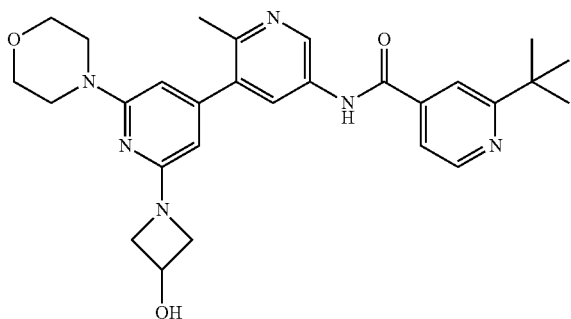 [SMILES: Cc1ncc(NC(=O)c2ccnc(C(C)(C)C)c2)cc1-c1cc(N2CCOCC2)nc(N2CC(O)C2)c1]

¹H NMR (400 MHz, <cd3od>) δ ppm 1.45 (s, 9H) 2.66 (s, 3H) 3.48-3.53 (m, 4H) 3.76-3.81 (m, 4H) 3.84 (dd, J=9.00, 4.70 Hz, 2H) 4.25-4.32 (m, 2H) 4.67-4.74 (m, 1H) 7.81 (dd, J=5.09, 1.57 Hz, 1H) 8.06 (s, 1H) 8.41 (d, J=2.35 Hz, 1H) 8.74 (d, J=5.09 Hz, 1H) 9.28 (d, J=2.35 Hz, 1H). LCMS (m/z) (M+H)=503.3, Rt=0.50 min.

Example 1090: N-(2'-(3-hydroxyazetidin-1-yl)-2-methyl-6'-morpholino-[3,4'-bipyridin]-5-yl)-2-(methylsulfonyl)isonicotinamide

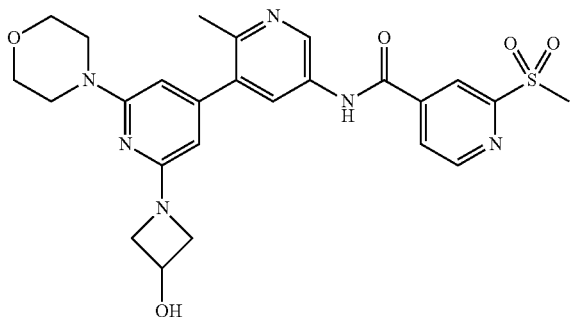 [SMILES: Cc1ncc(NC(=O)c2ccnc(S(C)(=O)=O)c2)cc1-c1cc(N2CCOCC2)nc(N2CC(O)C2)c1]

¹H NMR (400 MHz, <cd3od>) δ ppm 2.66 (s, 3H) 3.47-3.53 (m, 4H) 3.76-3.81 (m, 4H) 3.84 (dd, J=9.00, 4.30 Hz, 2H) 4.26-4.32 (m, 2H) 4.67-4.74 (m, 1H) 8.20 (dd, J=4.89, 1.37 Hz, 1H) 8.40 (d, J=2.35 Hz, 1H) 8.61 (s, 1H) 8.99 (d, J=4.69 Hz, 1H) 9.25 (d, J=1.96 Hz, 1H). LCMS (m/z) (M+H)=525.2, Rt=0.45 min.

Example 1091: N-(2'-(3-hydroxyazetidin-1-yl)-2-methyl-6'-morpholino-[3,4'-bipyridin]-5-yl)-3-(2-(methylsulfonyl)propan-2-yl)benzamide

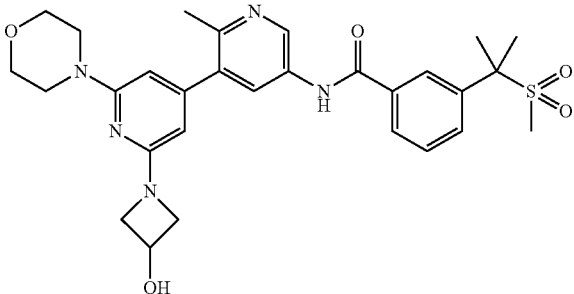 [SMILES: Cc1ncc(NC(=O)c2cccc(C(C)(C)S(C)(=O)=O)c2)cc1-c1cc(N2CCOCC2)nc(N2CC(O)C2)c1]

¹H NMR (400 MHz, <cd3od>) δ ppm 1.92 (s, 6H) 2.66 (s, 3H) 2.72 (s, 3H) 3.47-3.55 (m, 4H) 3.76-3.81 (m, 4H) 3.81-3.84 (m, 2H) 4.23-4.30 (m, 2H) 4.66-4.73 (m, 1H) 5.82 (s, 1H) 6.09 (s, 1H) 7.63 (t, J=7.83 Hz, 1H) 7.97 (d, J=8.22 Hz, 1H) 8.03 (d, J=7.83 Hz, 1H) 8.28 (s, 1H) 8.41 (d, J=1.96 Hz, 1H) 9.32 (d, J=1.96 Hz, 1H). LCMS (m/z) (M+H)=566.2, Rt=0.52 min.

Example 1092: N-(2'-(3-hydroxyazetidin-1-yl)-2-methyl-6'-morpholino-[3,4'-bipyridin]-5-yl)-3-(1,3,4-oxadiazol-2-yl)benzamide

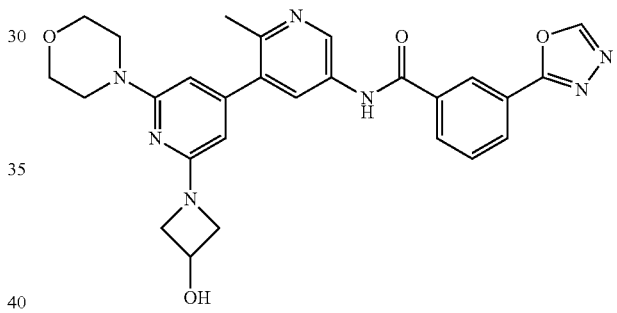

¹H NMR (400 MHz, <cd3od>) δ ppm 2.66 (s, 3H) 3.49-3.54 (m, 4H) 3.76-3.85 (m, 6H) 4.24-4.31 (m, 2H) 4.69 (d, J=6.26 Hz, 1H) 5.83 (s, 1H) 6.10 (s, 1H) 7.80 (t, J=7.83 Hz, 1H) 8.25 (d, J=7.83 Hz, 1H) 8.35 (d, J=7.83 Hz, 1H) 8.42 (d, J=2.35 Hz, 1H) 8.73 (s, 1H) 9.10 (s, 1H) 9.31 (s, 1H). LCMS (m/z) (M+H)=514.2, Rt=0.50 min.

Example 1093: 5-cyclopropyl-N-(2'-(3-hydroxyazetidin-1-yl)-2-methyl-6'-morpholino-[3,4'-bipyridin]-5-yl)isoxazole-3-carboxamide

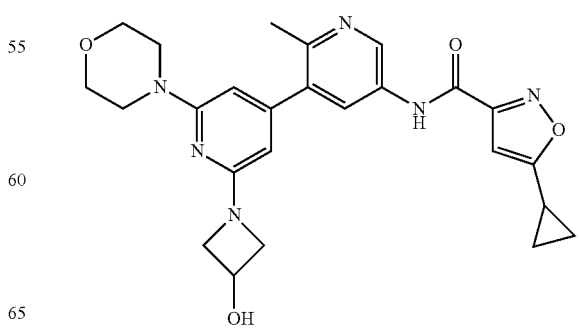

¹H NMR (400 MHz, <cd3od>) δ ppm 0.97-1.04 (m, 2H) 1.14-1.21 (m, 2H) 2.17-2.26 (m, 1H) 2.63 (s, 3H) 3.46-3.53 (m, 4H) 3.74-3.85 (m, 6H) 4.24-4.30 (m, 2H) 4.67-4.72 (m, 1H) 5.81 (s, 1H) 6.07 (s, 1H) 6.53 (s, 1H) 8.39 (d, J=2.35 Hz, 1H) 9.19 (d, J=1.96 Hz, 1H). LCMS (m/z) (M+H)=477.2 Rt=0.57 min.

Example 1094: N-(2'-(3-hydroxyazetidin-1-yl)-2-methyl-6'-morpholino-[3,4'-bipyridin]-5-yl)-3-(trifluoromethyl)benzamide

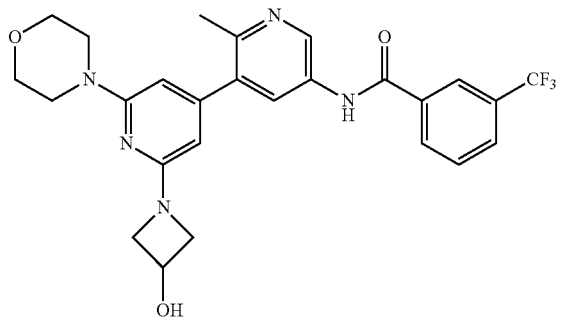 [SMILES: Cc1ncc(NC(=O)c2cccc(C(F)(F)F)c2)cc1-c1cc(N2CCOCC2)nc(N2CC(O)C2)c1]

¹H NMR (400 MHz, <cd3od>) δ ppm 2.63 (s, 3H) 3.47-3.54 (m, 4H) 3.75-3.84 (m, 6H) 4.23-4.30 (m, 2H) 4.66-4.72 (m, 1H) 5.81 (s, 1H) 6.08 (s, 1H) 7.78 (t, J=7.83 Hz, 1H) 7.96 (d, J=7.43 Hz, 1H) 8.27 (d, J=7.83 Hz, 1H) 8.31-8.36 (m, 2H) 9.22 (s, 1H). LCMS (m/z) (M+H)=514.2, Rt=0.64 min Example 1095: 5-cyclopropyl-N-(3-(2-(3-hydroxyazetidin-1-yl)-6-morpholinopyridin-4-yl)-4-methylphenyl)isoxazole-3-carboxamide

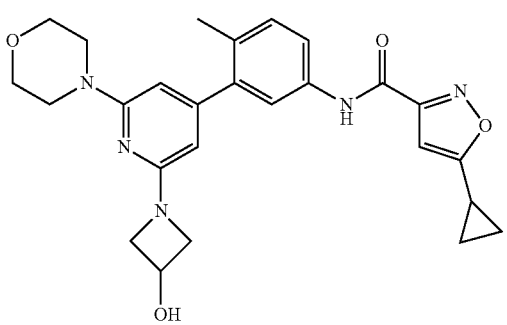 [SMILES: Cc1ccc(NC(=O)c2cc(C3CC3)on2)cc1-c1cc(N2CCOCC2)nc(N2CC(O)C2)c1]

¹H NMR (400 MHz, <cd3od>) δ ppm 0.96-1.03 (m, 2H) 1.12-1.19 (m, 2H) 2.15-2.23 (m, 1H) 2.29 (s, 3H) 3.41-3.48 (m, 4H) 3.78-3.85 (m, 4H) 3.99 (dd, J=9.39, 4.30 Hz, 2H) 4.42 (t, J=8.02 Hz, 2H) 4.69-4.77 (m, 1H) 5.96 (s, 1H) 6.14 (s, 1H) 6.46 (s, 1H) 7.30 (d, J=8.22 Hz, 1H) 7.59 (dd, J=8.22, 1.96 Hz, 1H) 7.66 (s, 1H). LCMS (m/z) (M+H)=476.2, Rt=0.73 min.

Example 1096: N-(3-(2-(3-hydroxyazetidin-1-yl)-6-morpholinopyridin-4-yl)-4-methylphenyl)-3-(methylsulfonyl)benzamide

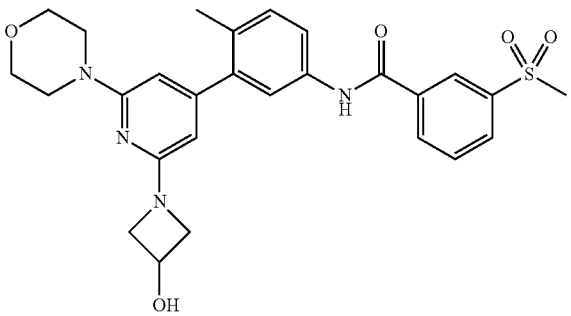 [SMILES: Cc1ccc(NC(=O)c2cccc(S(C)(=O)=O)c2)cc1-c1cc(N2CCOCC2)nc(N2CC(O)C2)c1]

¹H NMR (400 MHz, <cd3od>) δ ppm 2.32 (s, 3H) 3.19 (s, 3H) 3.41-3.50 (m, 4H) 3.79-3.86 (m, 4H) 4.03 (dd, J=9.39, 4.30 Hz, 2H) 4.41-4.50 (m, 2H) 4.71-4.79 (m, 1H) 5.99-6.20 (m, 1H) 7.33 (d, J=8.22 Hz, 1H) 7.59 (dd, J=8.22, 2.35 Hz, 1H) 7.74 (s, 1H) 7.80 (t, J=7.83 Hz, 1H) 8.17 (d, J=7.83 Hz, 1H) 8.26 (d, J=7.83 Hz, 1H) 8.51 (s, 1H). LCMS (m/z) (M+H)=523.2, Rt=0.62 min.

Example 1097: N-(3-(2-(3-hydroxyazetidin-1-yl)-6-morpholinopyridin-4-yl)-4-methylphenyl)-2-(methylsulfonyl)isonicotinamide

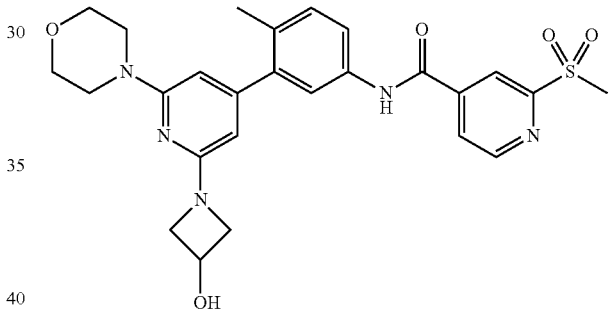

¹H NMR (400 MHz, <cd3od>) δ ppm 2.31 (s, 3H) 3.42-3.49 (m, 4H) 3.79-3.86 (m, 4H) 4.01 (dd, J=9.39, 3.91 Hz, 2H) 4.40-4.47 (m, 2H) 4.70-4.78 (m, 1H) 5.97-6.19 (m, 1H) 7.34 (d, J=8.61 Hz, 1H) 7.62 (dd, J=8.22, 1.96 Hz, 1H) 7.74 (s, 1H) 8.15 (dd, J=4.89, 1.37 Hz, 1H) 8.54 (s, 1H) 8.94 (d, J=5.09 Hz, 1H). LCMS (m/z) (M+H)=524.2, Rt=0.59 min.

Example 1098: N-(3-(2-(3-hydroxyazetidin-1-yl)-6-morpholinopyridin-4-yl)-4-methylphenyl)-2-(2-hydroxypropan-2-yl)isonicotinamide

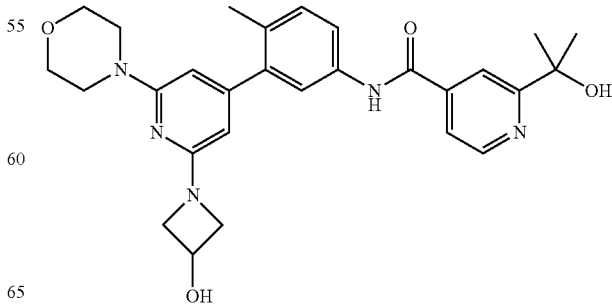

¹H NMR (400 MHz, <cd3od>) δ ppm 1.64 (s, 6H) 2.32 (s, 3H) 3.41-3.50 (m, 4H) 3.79-3.86 (m, 4H) 4.02 (dd, J=9.39, 4.30 Hz, 2H) 4.41-4.49 (m, 2H) 4.70-4.78 (m, 1H) 5.99-6.18 (m, 1H) 7.34 (d, J=8.22 Hz, 1H) 7.61 (dd, J=8.22, 1.96 Hz, 1H) 7.74 (s, 1H) 7.94 (d, J=4.30 Hz, 1H) 8.30 (s, 1H) 8.73 (d, J=5.48 Hz, 1H). LCMS (m/z) (M+H)=504.2, Rt=0.53 min.

Example 1099: N-(3-(2-(3-hydroxyazetidin-1-yl)-6-morpholinopyridin-4-yl)-4-methylphenyl)-3-(2-(methylsulfonyl)propan-2-yl)benzamide

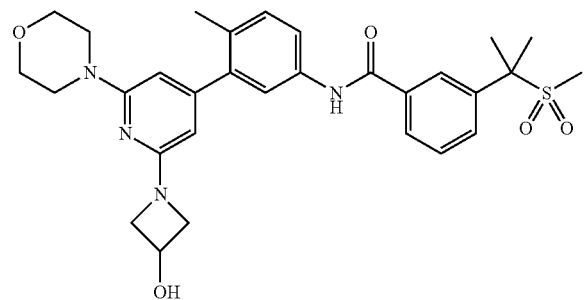 [SMILES: Cc1ccc(NC(=O)c2cccc(C(C)(C)S(C)(=O)=O)c2)cc1-c1cc(N2CCOCC2)nc(N2CC(O)C2)c1]

¹H NMR (400 MHz, <cd3od>) δ ppm 1.91 (s, 6H) 2.31 (s, 3H) 2.69 (s, 3H) 3.42-3.49 (m, 4H) 3.80-3.86 (m, 4H) 4.03 (dd, J=9.59, 4.11 Hz, 2H) 4.42-4.49 (m, 2H) 4.71-4.78 (m, 1H) 6.00-6.20 (m, 1H) 7.32 (d, J=8.22 Hz, 1H) 7.54-7.61 (m, 2H) 7.72 (s, 1H) 7.94 (dd, J=13.30, 8.22 Hz, 2H) 8.20 (s, 1H). LCMS (m/z) (M+H)=565.3, Rt=0.66 min.

Example 1100: N-(3-(2-(3-hydroxyazetidin-1-yl)-6-morpholinopyridin-4-yl)-4-methylphenyl)-3-(1,3,4-oxadiazol-2-yl)benzamide

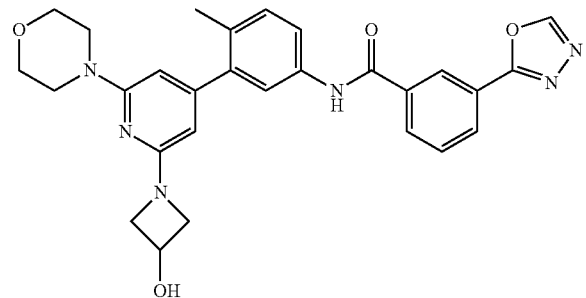 [SMILES: Cc1ccc(NC(=O)c2cccc(-c3nnco3)c2)cc1-c1cc(N2CCOCC2)nc(N2CC(O)C2)c1]

¹H NMR (400 MHz, <cd3od>) δ ppm 2.31 (s, 3H) 3.42-3.49 (m, 4H) 3.79-3.86 (m, 4H) 4.01 (dd, J=9.19, 4.11 Hz, 2H) 4.40-4.48 (m, 2H) 4.70-4.78 (m, 1H) 5.98-6.19 (m, 1H) 7.33 (d, J=8.22 Hz, 1H) 7.60 (dd, J=8.22, 1.96 Hz, 1H) 7.71-7.79 (m, 2H) 8.17 (d, J=8.22 Hz, 1H) 8.29 (d, J=7.83 Hz, 1H) 8.65 (s, 1H) 9.08 (s, 1H). LCMS (m/z) (M+H)=513.2, Rt=0.64 min.

Example 1101: 6-cyclopropyl-N-(2'-(3-hydroxy-3-methylazetidin-1-yl)-2-methyl-6'-morpholino-[3,4'-bipyridin]-5-yl)pyridazine-4-carboxamide

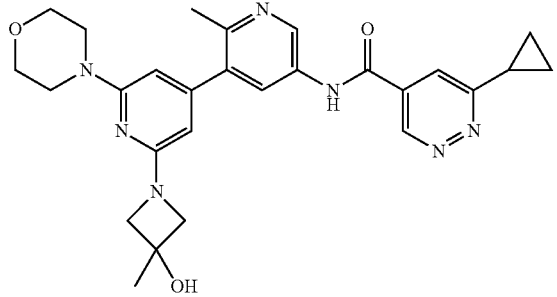 [SMILES: Cc1ncc(NC(=O)c2cnnc(C3CC3)c2)cc1-c1cc(N2CCOCC2)nc(N2CC(C)(O)C2)c1]

¹H NMR (500 MHz, <cd3od>) δ ppm 1.22-1.33 (m, 4H) 1.57 (s, 3H) 2.38-2.45 (m, 1H) 2.68 (s, 3H) 3.50-3.55 (m, 4H) 3.78-3.84 (m, 4H) 3.91-4.01 (m, 4H) 5.85-6.14 (m, 1H) 8.00 (d, J=2.21 Hz, 1H) 8.40 (d, J=2.21 Hz, 1H) 9.26 (d, J=2.21 Hz, 1H) 9.44 (d, J=2.21 Hz, 1H). LCMS (m/z) (M+H)=502.2, Rt=0.51 min.

Example 1102: 2-cyclopropyl-N-(2'-(3-hydroxy-3-methylazetidin-1-yl)-2-methyl-6'-morpholino-[3,4'-bipyridin]-5-yl)isonicotinamide

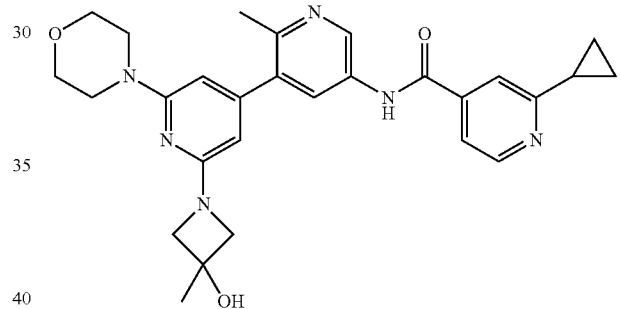

¹H NMR (500 MHz, <cd3od>) δ ppm 1.13-1.26 (m, 4H) 1.57 (s, 3H) 2.26-2.33 (m, 1H) 2.68 (s, 3H) 3.50-3.55 (m, 4H) 3.77-3.83 (m, 4H) 3.91-4.00 (m, 4H) 5.85-6.13 (m, 1H) 7.79 (dd, J=5.36, 1.58 Hz, 1H) 7.85 (s, 1H) 8.42 (d, J=2.52 Hz, 1H) 8.65 (d, J=5.36 Hz, 1H) 9.30 (d, J=2.21 Hz, 1H). LCMS (m/z) (M+H)=501.2, Rt=0.46 min.

Example 1103: 2-(difluoromethyl)-N-(2'-(3-hydroxy-3-methylazetidin-1-yl)-2-methyl-6'-morpholino-[3,4'-bipyridin]-5-yl)isonicotinamide

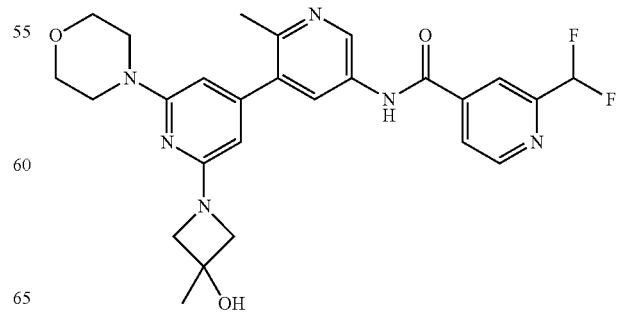

¹H NMR (400 MHz, <cd3od>) δ ppm 1.55 (s, 3H) 2.67 (s, 3H) 3.47-3.55 (m, 4H) 3.75-3.83 (m, 4H) 3.89-3.99 (m, 4H) 6.85 (t, J=55.60 Hz, 1H) 8.06 (d, J=5.09 Hz, 1H) 8.24 (s, 1H) 8.43 (d, J=2.35 Hz, 1H) 8.89 (d, J=5.09 Hz, 1H) 9.29 (d, J=2.35 Hz, 1H). LCMS (m/z) (M+H)=511.2, Rt=0.54 min.

Example 1104: N-(2'-(3-hydroxy-3-methylazetidin-1-yl)-2-methyl-6'-morpholino-[3,4'-bipyridin]-5-yl)-2-(trifluoromethyl)isonicotinamide

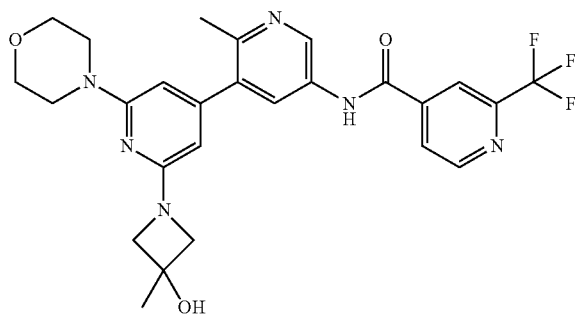 [SMILES: Cc1ncc(NC(=O)c2ccnc(C(F)(F)F)c2)cc1-c1cc(N2CCOCC2)nc(N2CC(C)(O)C2)c1]

¹H NMR (500 MHz, <cd3od>) δ ppm 1.57 (s, 3H) 2.68 (s, 3H) 3.50-3.55 (m, 4H) 3.78-3.83 (m, 4H) 3.91-4.00 (m, 4H) 5.85-6.13 (m, 1H) 8.20 (d, J=5.67 Hz, 1H) 8.36-8.39 (m, 1H) 8.41 (d, J=2.21 Hz, 1H) 8.99 (d, J=5.04 Hz, 1H) 9.27 (d, J=1.89 Hz, 1H). LCMS (m/z) (M+H)=529.2, Rt=0.60 min.

Example 1105: 2-(1,1-difluoroethyl)-N-(2'-(3-hydroxy-3-methylazetidin-1-yl)-2-methyl-6'-morpholino-[3,4'-bipyridin]-5-yl)isonicotinamide

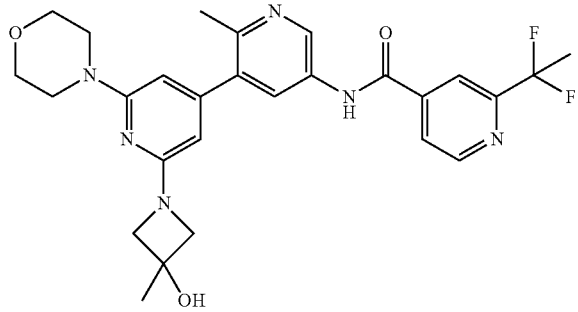 [SMILES: Cc1ncc(NC(=O)c2ccnc(C(C)(F)F)c2)cc1-c1cc(N2CCOCC2)nc(N2CC(C)(O)C2)c1]

¹H NMR (500 MHz, <cd3od>) δ ppm 1.57 (s, 3H) 2.02-2.12 (m, 3H) 2.70 (s, 3H) 3.51-3.55 (m, 4H) 3.79-3.83 (m, 4H) 3.92-4.00 (m, 4H) 5.87-6.14 (m, 1H) 8.04 (d, J=5.36 Hz, 1H) 8.27 (s, 1H) 8.46 (d, J=2.21 Hz, 1H) 8.89 (d, J=5.04 Hz, 1H) 9.33 (d, J=2.21 Hz, 1H). LCMS (m/z) (M+H)= 525.2, Rt=0.59 min.

Example 1106: 2-(2-fluoropropan-2-yl)-N-(2'-(3-hydroxy-3-methylazetidin-1-yl)-2-methyl-6'-morpholino-[3,4'-bipyridin]-5-yl)isonicotinamide

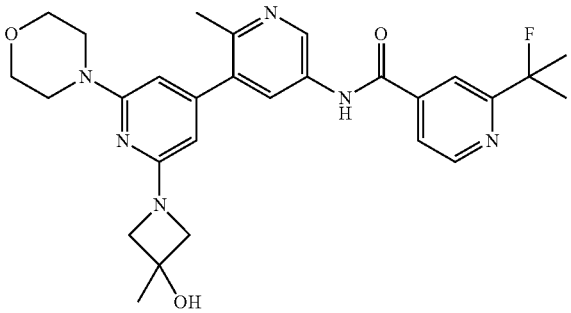 [SMILES: Cc1ncc(NC(=O)c2ccnc(C(C)(C)F)c2)cc1-c1cc(N2CCOCC2)nc(N2CC(C)(O)C2)c1]

¹H NMR (500 MHz, <cd3od>) δ ppm 1.58 (s, 3H) 1.74 (s, 3H) 1.78 (s, 3H) 2.70 (s, 3H) 3.50-3.55 (m, 4H) 3.78-3.83 (m, 4H) 3.92-4.01 (m, 4H) 7.83-7.88 (m, 1H) 8.16 (s, 1H) 8.49 (d, J=2.52 Hz, 1H) 8.78 (dd, J=5.04, 0.63 Hz, 1H) 9.36 (d, J=2.52 Hz, 1H). LCMS (m/z) (M+H)=521.2, Rt=0.60 min.

Example 1107: N-(2'-(3-hydroxy-3-methylazetidin-1-yl)-2-methyl-6'-morpholino-[3,4'-bipyridin]-5-yl)-6-(trifluoromethyl)pyridazine-4-carboxamide

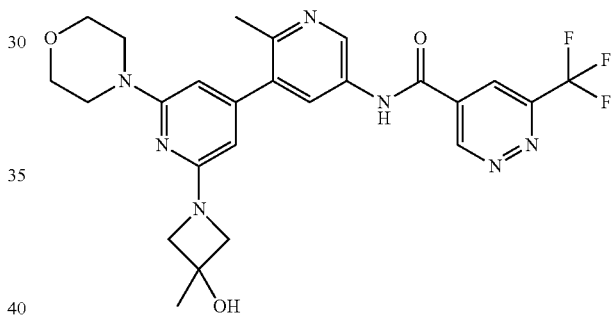

¹H NMR (500 MHz, <cd3od>) δ ppm 1.58 (s, 3H) 2.67 (s, 3H) 3.50-3.55 (m, 4H) 3.79-3.83 (m, 4H) 3.93-4.02 (m, 4H) 8.39 (d, J=2.21 Hz, 1H) 8.65 (d, J=1.89 Hz, 1H) 9.23 (d, J=2.21 Hz, 1H) 9.93 (d, J=1.89 Hz, 1H). LCMS (m/z) (M+H)=530.2, Rt=0.56 min.

Example 1108: 2-(2-cyanopropan-2-yl)-N-(2'-(3-hydroxy-3-methylazetidin-1-yl)-2-methyl-6'-morpholino-[3,4'-bipyridin]-5-yl)isonicotinamide

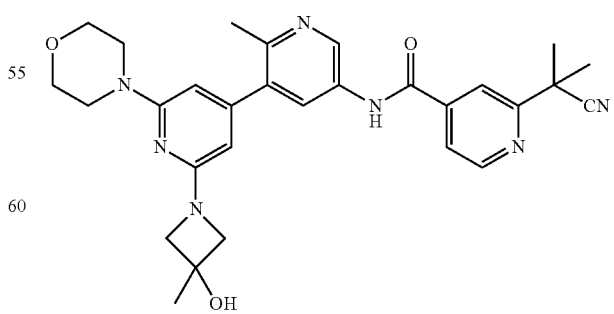

¹H NMR (500 MHz, <cd3od>) δ ppm 1.57 (s, 3H) 1.84 (s, 6H) 2.70 (s, 3H) 3.50-3.55 (m, 4H) 3.78-3.83 (m, 4H)

3.93-4.02 (m, 4H) 7.90 (dd, J=4.89, 1.42 Hz, 1H) 8.16 (d, J=0.63 Hz, 1H) 8.47 (d, J=2.21 Hz, 1H) 8.85 (d, J=5.04 Hz, 1H) 9.35 (d, J=2.21 Hz, 1H). LCMS (m/z) (M+H)=528.2, Rt=0.58 min.

Example 1109: 2-(1-cyanocyclopropyl)-N-(2'-(3-hydroxy-3-methylazetidin-1-yl)-2-methyl-6'-morpholino-[3,4'-bipyridin]-5-yl)isonicotinamide

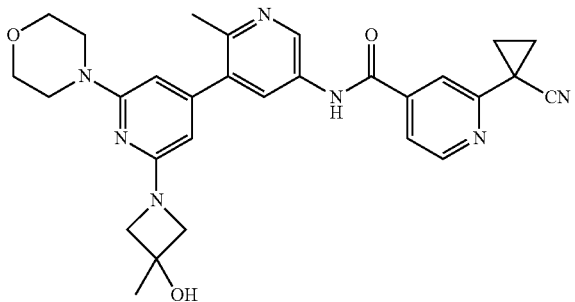 [SMILES: Cc1ncc(NC(=O)c2ccnc(C3(C#N)CC3)c2)cc1-c1cc(N2CCOCC2)nc(N2CC(C)(O)C2)c1]

¹H NMR (500 MHz, <cd3od>) δ ppm 1.57 (s, 3H) 1.79-1.91 (m, 4H) 2.70 (s, 3H) 3.50-3.55 (m, 4H) 3.78-3.83 (m, 4H) 3.92-4.01 (m, 4H) 7.79 (dd, J=4.89, 1.10 Hz, 1H) 8.18 (s, 1H) 8.45 (d, J=2.52 Hz, 1H) 8.73 (d, J=5.04 Hz, 1H) 9.34 (d, J=2.21 Hz, 1H). LCMS (m/z) (M+H)=526.2, Rt=0.58 min.

Example 1110: 2-(2-cyanopropan-2-yl)-N-(3-(2-(3-hydroxy-3-methylazetidin-1-yl)-6-morpholinopyridin-4-yl)-4-methylphenyl)isonicotinamide

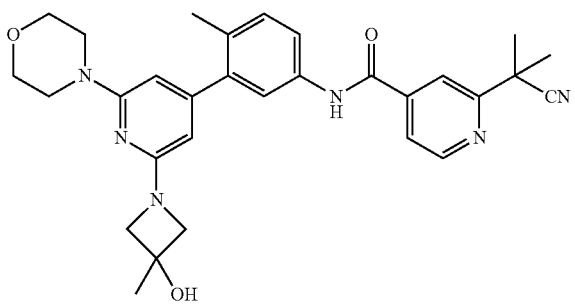 [SMILES: Cc1ccc(NC(=O)c2ccnc(C(C)(C)C#N)c2)cc1-c1cc(N2CCOCC2)nc(N2CC(C)(O)C2)c1]

¹H NMR (500 MHz, <cd3od>) δ ppm 1.59 (s, 3H) 1.84 (s, 6H) 2.34 (s, 3H) 3.45-3.50 (m, 4H) 3.82-3.87 (m, 4H) 4.08-4.17 (m, 4H) 7.36 (d, J=8.51 Hz, 1H) 7.61 (dd, J=8.51, 2.21 Hz, 1H) 7.77 (d, J=1.89 Hz, 1H) 7.83 (dd, J=5.04, 1.58 Hz, 1H) 8.09 (s, 1H) 8.79 (d, J=5.04 Hz, 1H). LCMS (m/z) (M+H)=527.2, Rt=0.72 min.

Example 1111: 2-(1-cyanocyclopropyl)-N-(3-(2-(3-hydroxy-3-methylazetidin-1-yl)-6-morpholinopyridin-4-yl)-4-methylphenyl)isonicotinamide

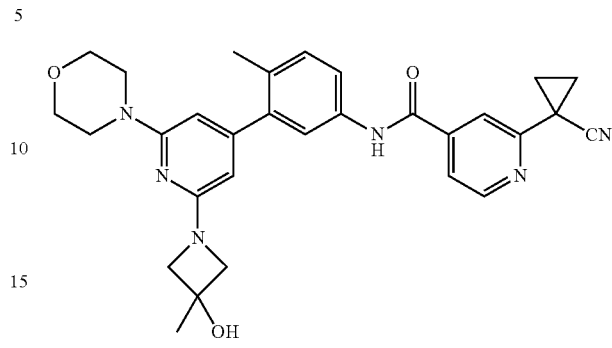

¹H NMR (500 MHz, <cd3od>) δ ppm 1.59 (s, 3H) 1.81-1.90 (m, 4H) 2.34 (s, 3H) 3.45-3.50 (m, 4H) 3.83-3.87 (m, 4H) 4.09-4.19 (m, 4H) 7.36 (d, J=8.51 Hz, 1H) 7.61 (dd, J=8.20, 1.89 Hz, 1H) 7.73 (d, J=5.04 Hz, 1H) 7.77 (s, 1H) 8.10 (s, 1H) 8.67 (d, J=5.04 Hz, 1H). LCMS (m/z) (M+H)=525.2, Rt=0.72 min.

Example 1112: N-(3-(2,6-dimorpholinopyridin-4-yl)-4-methylphenyl)-2-(trifluoromethyl)isonicotinamide

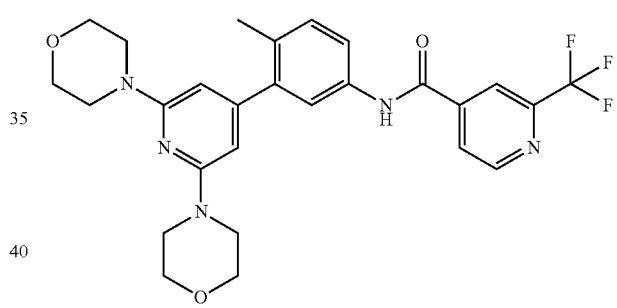

1H NMR (400 MHz, <cd3od>) δ ppm 2.28 (s, 3H) 3.42-3.58 (m, 8H) 3.72-3.87 (m, 8H) 7.30 (d, J=8.22 Hz, 1H) 7.55-7.69 (m, 2H) 8.11 (d, J=4.30 Hz, 1H) 8.29 (s, 1H) 8.90 (d, J=5.09 Hz, 1H). LC/MS (m/z): 528.1 (MH+), Rt=0.93 min.

Example 1113: 2-(2-cyanopropan-2-yl)-N-(3-(2,6-dimorpholinopyridin-4-yl)-4-methylphenyl)isonicotinamide

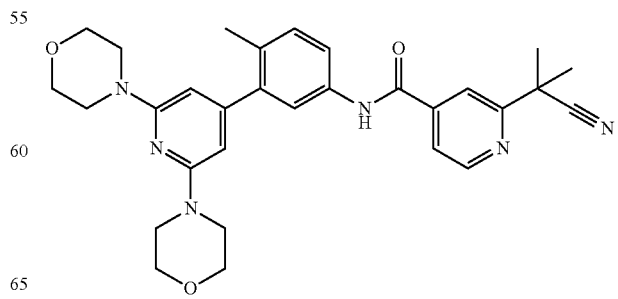

1H NMR (400 MHz, <cd3od>) δ ppm 1.81 (s, 6H) 2.29 (s, 3H) 3.39-3.55 (m, 8H) 3.72-3.87 (m, 8H) 7.31 (d, J=8.22 Hz, 1H) 7.60 (dd, J=8.22, 1.96 Hz, 1H) 7.67 (d, J=1.96 Hz, 1H) 7.81 (dd, J=4.89, 0.98 Hz, 1H) 8.06 (s, 1H) 8.76 (d, J=5.09 Hz, 1H). LC/MS (m/z): 527.2 (MH+), Rt=0.88 min.

Example 1114: N-(3-(2,6-dimorpholinopyridin-4-yl)-4-methylphenyl)-1-ethyl-6-oxo-5-(trifluoromethyl)-1,6-dihydropyridine-3-carboxamide

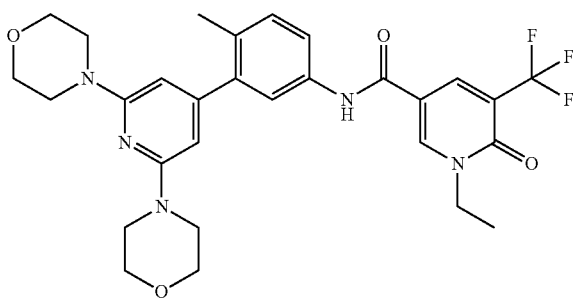

1H NMR (400 MHz, <cd3od>) δ ppm 1.41 (t, J=7.04 Hz, 3H) 2.27 (s, 3H) 3.41-3.59 (m, 8H) 3.74-3.90 (m, 8H) 4.15 (q, J=7.30 Hz, 2H) 7.27 (d, J=8.22 Hz, 1H) 7.46-7.64 (m, 2H) 8.47 (d, J=1.57 Hz, 1H) 8.69 (d, J=2.35 Hz, 1H). LC/MS (m/z): 572.2 (MH+), Rt=0.89 min.

Example 1115: 2-(difluoromethyl)-N-(3-(2,6-dimorpholinopyridin-4-yl)-4-methylphenyl)isonicotinamide

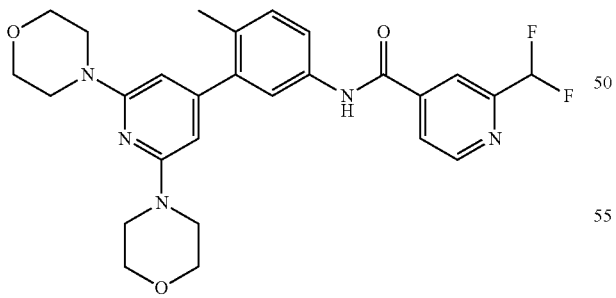 [SMILES: Cc1ccc(NC(=O)c2ccnc(C(C)(C)C#N)c2)cc1-c1cc(N2CCOCC2)nc(N2CCOCC2)c1]

1H NMR (400 MHz, <cd3od>) δ ppm 2.28 (s, 3H) 3.39-3.57 (m, 9H) 3.69-3.90 (m, 8H) 6.13 (s, 1H) 6.60-7.01 (m, 1H) 7.29 (d, J=9.00 Hz, 1H) 7.62 (d, J=5.87 Hz, 2H) 8.00 (d, J=4.70 Hz, 1H) 8.17 (s, 1H) 8.83 (d, J=4.70 Hz, 1H). LC/MS (m/z): 510.1 (MH+), Rt=0.85 min.

Example 1116: 3-(difluoromethyl)-N-(3-(2,6-dimorpholinopyridin-4-yl)-4-methylphenyl)benzamide

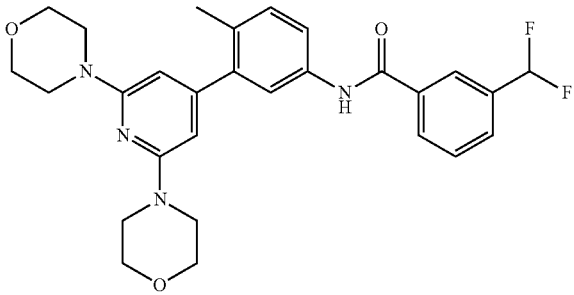 [SMILES: Cc1ccc(NC(=O)c2cccc(C(F)F)c2)cc1-c1cc(N2CCOCC2)nc(N2CCOCC2)c1]

1H NMR (400 MHz, <cd3od>) δ ppm 2.28 (s, 3H) 3.41-3.60 (m, 9H) 3.69-3.89 (m, 9H) 6.64-7.07 (m, 1H) 7.29 (d, J=8.22 Hz, 1H) 7.57 (dd, J=8.22, 1.96 Hz, 1H) 7.60-7.70 (m, 2H) 7.76 (d, J=7.43 Hz, 1H) 7.98-8.16 (m, 1H). LC/MS (m/z): 509.2 (MH+), Rt=0.92 min.

Example 1117: N-(3-(2,6-dimorpholinopyridin-4-yl)-4-methylphenyl)-2-isopropylisonicotinamide

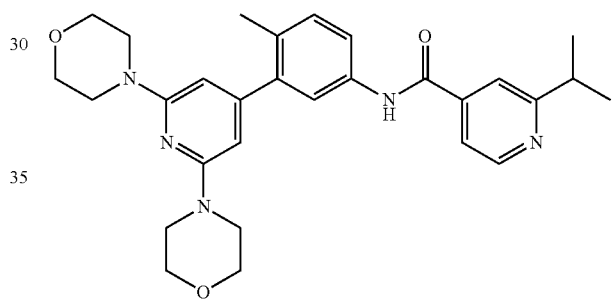

1H NMR (400 MHz, <cd3od>) δ ppm 1.34 (d, J=7.04 Hz, 6H) 2.18 (s, 3H) 3.30-3.49 (m, 8H) 3.60-3.78 (m, 8H) 7.20 (d, J=8.22 Hz, 1H) 7.43-7.61 (m, 2H) 7.95 (d, J=5.09 Hz, 1H) 8.07 (s, 1H) 8.67 (d, J=5.87 Hz, 1H). LC/MS (m/z): 502.2 (MH+), Rt=0.72 min.

Example 1118: N-(3-(2,6-dimorpholinopyridin-4-yl)-4-methylphenyl)-2-(methylsulfonyl)isonicotinamide

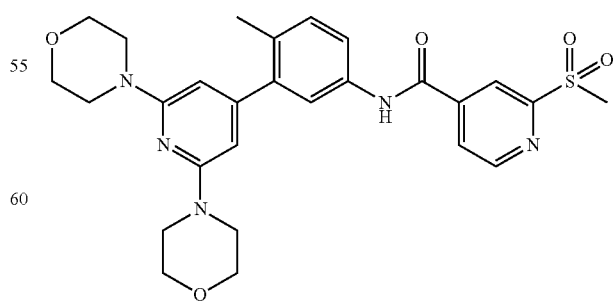

1H NMR (400 MHz, <dmso>) ppm 2.21 (s, 3H) 3.33 (br. s., 5H) 3.40 (br. s., 17H) 3.54-3.78 (m, 8H) 6.03 (s, 1H) 7.28

(d, J=8.22 Hz, 1H) 7.60 (d, J=1.96 Hz, 1H) 7.66-7.76 (m, 1H) 8.07-8.27 (m, 1H) 8.51 (s, 1H) 8.98 (d, J=4.69 Hz, 1H) 10.74 (s, 1H). LC/MS (m/z): 538.2 (MH+), Rt=0.77 min.

Example 1119: 2-isopropyl-N-(2-methyl-2',6'-dimorpholino-[3,4'-bipyridin]-5-yl)isonicotinamide

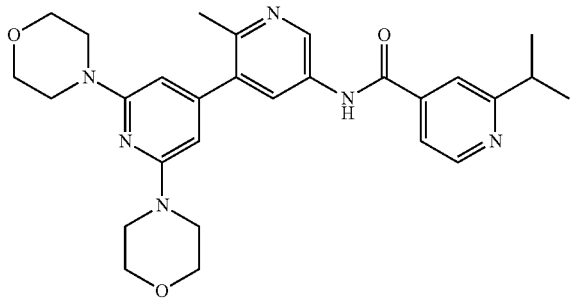 [SMILES: Cc1ncc(NC(=O)c2ccnc(C(C)C)c2)cc1-c1cc(N2CCOCC2)nc(N2CCOCC2)c1]

1H NMR (400 MHz, <cd3od>) δ ppm 1.42 (d, J=7.04 Hz, 6H) 2.69 (s, 3H) 3.49-3.55 (m, 8H) 3.75-3.82 (m, 8H) 7.97 (dd, J=5.48, 1.57 Hz, 1H) 8.08 (s, 1H) 8.45 (d, J=1.96 Hz, 1H) 8.77 (d, J=5.48 Hz, 1H) 9.36 (d, J=2.35 Hz, 1H). LC/MS (m/z): 503.2 (MH+), Rt=0.60 min.

Example 1120: N-(2-methyl-2',6'-dimorpholino-[3,4'-bipyridin]-5-yl)-2-(trifluoromethyl)isonicotinamide

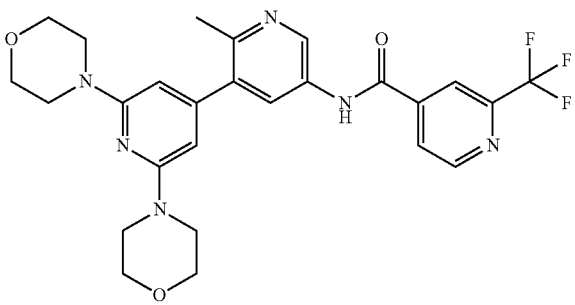 [SMILES: Cc1ncc(NC(=O)c2ccnc(C(F)(F)F)c2)cc1-c1cc(N2CCOCC2)nc(N2CCOCC2)c1]

1H NMR (400 MHz, <cd3od>) δ ppm 2.68 (s, 3H) 3.49-3.56 (m, 8H) 3.75-3.82 (m, 8H) 6.13 (s, 1H) 8.18 (d, J=4.30 Hz, 1H) 8.36 (s, 1H) 8.4 (d, J=2.35 Hz, 1H) 8.97 (d, J=5.09 Hz, 1H) 9.33 (d, J=2.35 Hz, 1H). LC/MS (m/z): 529.2 (MH+), Rt=0.75 min.

Example 1121: 3-(difluoromethyl)-N-(2-methyl-2',6'-dimorpholino-[3,4'-bipyridin]-5-yl)benzamide

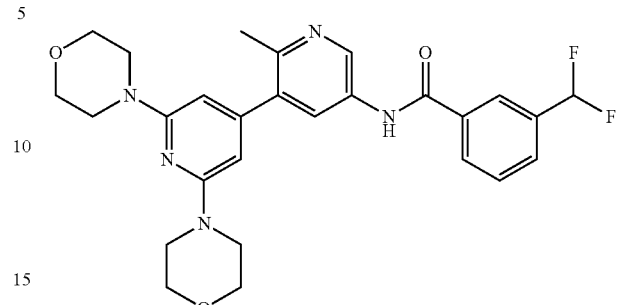

¹H NMR (400 MHz, <cd3od>) δ ppm 2.68 (s, 3H) 3.49-3.56 (m, 8H) 3.75-3.82 (m, 8H) 6.14 (s, 1H) 6.90 (t, J=56.30 Hz, 1H) 7.67-7.73 (m, 1H) 7.83 (d, J=7.83 Hz, 1H) 8.16 (d, J=7.83 Hz, 1H) 8.22 (s, 1H) 8.45 (d, J=2.35 Hz, 1H) 9.39 (d, J=2.35 Hz, 1H). LCMS (m/z) (M+H)=510.2, Rt=0.76 min.

Example 1122: 2-(difluoromethyl)-N-(2-methyl-2',6'-dimorpholino-[3,4'-bipyridin]-5-yl)isonicotinamide

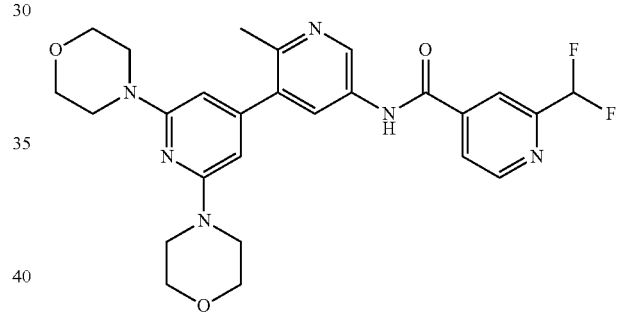

¹H NMR (400 MHz, <cd3od>) δ ppm 2.69 (s, 3H) 3.49-3.55 (m, 8H) 3.76-3.81 (m, 8H) 6.14 (s, 1H) 6.85 (t, J=54.80 Hz, 1H) 8.07 (d, J=5.09 Hz, 1H) 8.25 (s, 1H) 8.44 (d, J=2.35 Hz, 1H) 8.89 (d, J=5.09 Hz, 1H) 9.37 (d, J=2.35 Hz, 1H). LCMS (m/z) (M+H)=511.1, Rt=0.69 min.

Example 1123: 2-(2-cyanopropan-2-yl)-N-(2-methyl-2',6'-dimorpholino-[3,4'-bipyridin]-5-yl)isonicotinamide

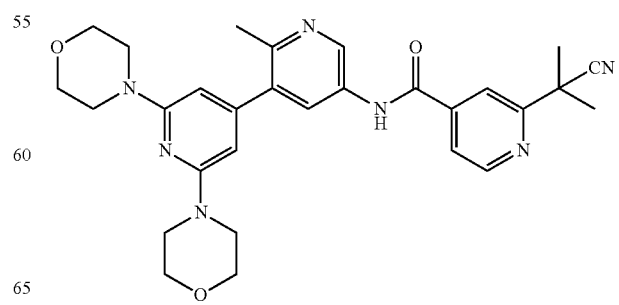

¹H NMR (400 MHz, <cd3od>) δ ppm 1.82 (s, 6H) 2.68 (s, 3H) 3.49-3.56 (m, 8H) 3.74-3.82 (m, 8H) 6.14 (s, 1H) 7.87 (dd, J=4.89, 1.37 Hz, 1H) 8.14 (s, 1H) 8.43 (d, J=2.35 Hz, 1H) 8.82 (d, J=5.09 Hz, 1H) 9.36 (d, J=2.35 Hz, 1H). LCMS (m/z) (M+H)=528.1, Rt=0.72 min.

Example 1124: N-(2-methyl-2',6'-dimorpholino-[3,4'-bipyridin]-5-yl)-2-(methylsulfonyl)isonicotinamide

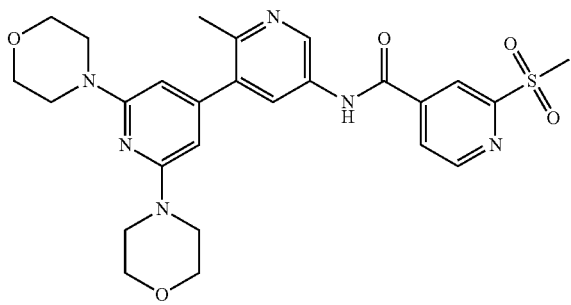 [SMILES: Cc1ncc(NC(=O)c2ccnc(S(C)(=O)=O)c2)cc1-c1cc(N2CCOCC2)nc(N2CCOCC2)c1]

¹H NMR (400 MHz, <cd3od>) δ ppm 2.68 (s, 3H) 3.48-3.55 (m, 8H) 3.75-3.82 (m, 8H) 6.13 (s, 1H) 8.21 (dd, J=4.70, 1.57 Hz, 1H) 8.43 (d, J=1.96 Hz, 1H) 8.62 (s, 1H) 8.99 (d, J=4.70 Hz, 1H) 9.33 (d, J=2.35 Hz, 1H). LCMS (m/z) (M+H)=539.0, Rt=0.62 min.

Example 1125: 1-ethyl-N-(2-methyl-2',6'-dimorpholino-[3,4'-bipyridin]-5-yl)-6-oxo-5-(trifluoromethyl)-1,6-dihydropyridine-3-carboxamide

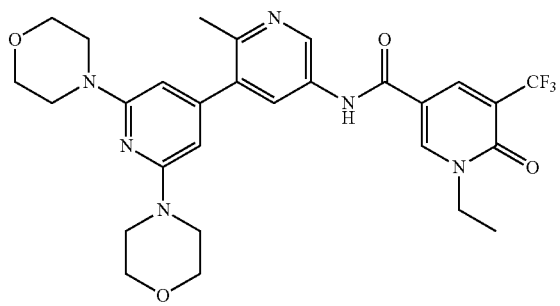 [SMILES: CCn1cc(C(=O)Nc2cnc(C)c(-c3cc(N4CCOCC4)nc(N4CCOCC4)c3)c2)cc(C(F)(F)F)c1=O]

¹H NMR (400 MHz, <cd3od>) δ ppm 1.42 (t, J=7.24 Hz, 3H) 2.67 (s, 3H) 3.51 (t, J=4.89 Hz, 8H) 3.74-3.83 (m, 8H) 4.18 (q, J=7.30 Hz, 2H) 6.13 (s, 1H) 8.37 (d, J=2.35 Hz, 1H) 8.52 (d, J=1.96 Hz, 1H) 8.80 (d, J=2.35 Hz, 1H) 9.30 (d, J=2.35 Hz, 1H). LCMS (m/z) (M+H)=573.1, Rt=0.73 min.

Example 1126: N-(4-methyl-3-(2-(1-methyl-1H-pyrazol-4-yl)-6-morpholinopyridin-4-yl)phenyl)-2-(trifluoromethyl)isonicotinamide

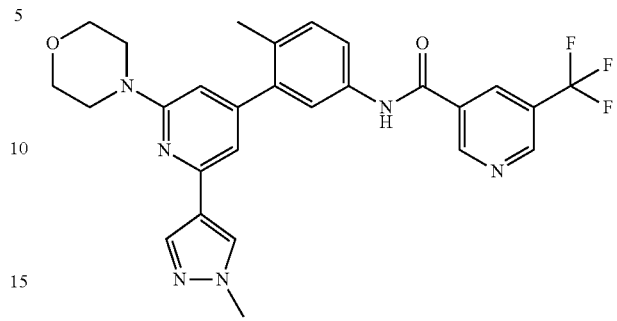

¹H NMR (400 MHz, <cd3od>) δ ppm 2.33 (s, 3H) 3.67 (t, J=4.70 Hz, 4H) 3.82-3.89 (m, 4H) 3.96 (s, 3H) 6.81 (s, 1H) 7.09 (s, 1H) 7.36 (d, J=8.22 Hz, 1H) 7.65 (dd, J=8.41, 2.15 Hz, 1H) 7.76 (d, J=1.96 Hz, 1H) 8.04 (s, 1H) 8.12 (d, J=4.30 Hz, 1H) 8.23 (s, 1H) 8.30 (s, 1H) 8.91 (d, J=5.09 Hz, 1H). LCMS (m/z) (M+H)=523.1, Rt=0.84 min.

Example 1127: N-(3-(2-(3,5-dimethyl-1H-pyrazol-4-yl)-6-morpholinopyridin-4-yl)-4-methylphenyl)-2-(trifluoromethyl)isonicotinamide

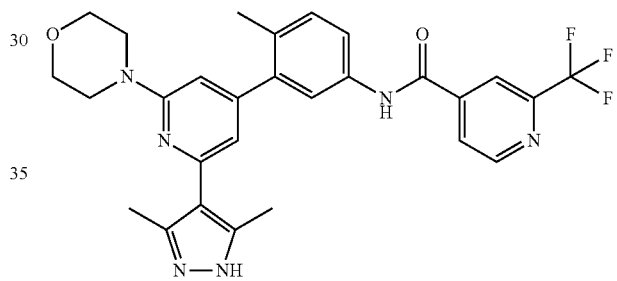

¹H NMR (400 MHz, <cd3od>) δ ppm 2.38 (s, 3H) 2.45 (s, 6H) 3.64-3.70 (m, 4H) 3.83-3.89 (m, 4H) 6.92 (s, 1H) 6.99 (s, 1H) 7.38 (d, J=8.22 Hz, 1H) 7.64 (dd, J=8.22, 2.35 Hz, 1H) 7.83 (d, J=1.96 Hz, 1H) 8.12 (d, J=4.70 Hz, 1H) 8.30 (s, 1H) 8.92 (d, J=5.09 Hz, 1H). LCMS (m/z) (M+H)=537.2, Rt=0.74 min.

Example 1128: N-(4-methyl-3-(2-morpholino-6-(piperazin-1-yl)pyridin-4-yl)phenyl)-2-(trifluoromethyl)isonicotinamide

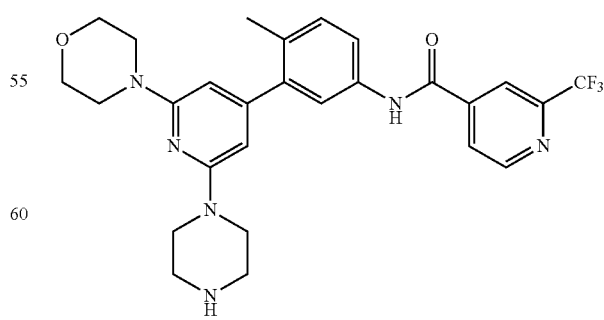

¹H NMR (400 MHz, <cd3od>) δ ppm 2.27 (s, 3H) 3.47-3.53 (m, 6H) 3.79 (q, J=4.83 Hz, 10H) 6.18 (d, J=13.69

Hz, 2H) 7.30 (d, J=8.22 Hz, 1H) 7.55 (dd, J=8.22, 1.96 Hz, 1H) 7.67 (d, J=2.35 Hz, 1H) 8.11 (d, J=5.09 Hz, 1H) 8.29 (s, 1H) 8.91 (d, J=5.09 Hz, 1H).). LCMS (m/z) (M+H)=527.2, Rt=0.78 min.

Example 1129: N-(2-methyl-2'-morpholino-6'-(piperazin-1-yl)-[3,4'-bipyridin]-5-yl)-3-(trifluoromethyl)benzamide

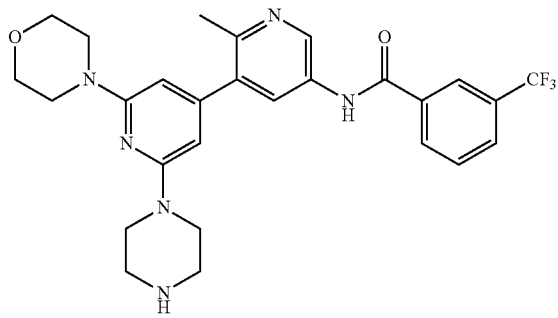 [SMILES: Cc1ncc(NC(=O)c2cccc(C(F)(F)F)c2)cc1-c1cc(N2CCNCC2)nc(N2CCOCC2)c1]

$^1$H NMR (400 MHz, <cd3od>) δ ppm 2.56 (s, 3H) 3.50-3.56 (m, 6H) 3.81 (dt, J=14.97, 5.04 Hz, 10H) 6.23 (d, J=10.17 Hz, 2H) 7.74-7.80 (m, 1H) 7.95 (d, J=7.83 Hz, 1H) 8.25 (d, J=7.83 Hz, 1H) 8.31 (d, J=2.35 Hz, 2H) 8.98 (d, J=2.35 Hz, 1H). LCMS (m/z) (M+H)=527.3, Rt=0.64 min.

Example 1130: N-(3-(2-(3-hydroxypyrrolidin-1-yl)-6-morpholinopyridin-4-yl)-4-methylphenyl)-2-(trifluoromethyl)isonicotinamide

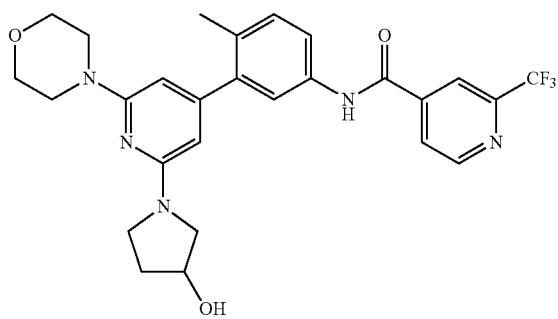 [SMILES: Cc1ccc(NC(=O)c2ccnc(C(F)(F)F)c2)cc1-c1cc(N2CCOCC2)nc(N2CCC(O)C2)c1]

$^1$H NMR (500 MHz, <cd3od>) δ ppm 2.13 (br. s., 1H) 2.17-2.25 (m, 1H) 2.35 (s, 3H) 3.44-3.58 (m, 5H) 3.66-3.76 (m, 3H) 3.86 (t, J=4.73 Hz, 4H) 4.60 (br. s., 1H) 6.15 (s, 1H) 7.36 (d, J=8.51 Hz, 1H) 7.64 (dt, J=8.20, 2.52 Hz, 1H) 7.76 (br. s., 1H) 8.14 (d, J=4.73 Hz, 1H) 8.32 (s, 1H) 8.94 (d, J=5.04 Hz, 1H). LCMS (m/z) (M+H)=528.2, Rt=0.75 min.

Example 1131: N-(2'-(3-hydroxypyrrolidin-1-yl)-2-methyl-6'-morpholino-[3,4'-bipyridin]-5-yl)-3-(trifluoromethyl)benzamide

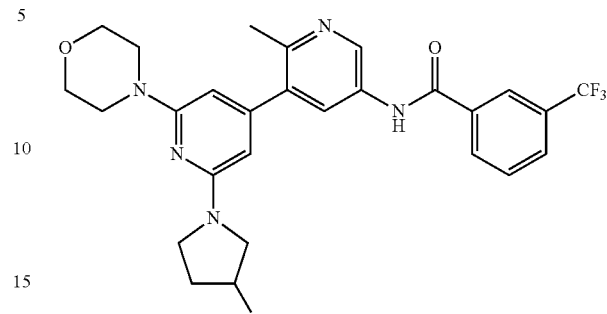

$^1$H NMR (500 MHz, <cd3od>) δ ppm 2.13 (d, J=3.78 Hz, 1H) 2.17-2.26 (m, 1H) 2.35 (s, 3H) 3.43-3.57 (m, 5H) 3.66-3.76 (m, 3H) 3.86 (t, J=4.73 Hz, 4H) 4.59 (d, J=1.89 Hz, 1H) 6.15 (br. s., 1H) 7.36 (d, J=8.20 Hz, 1H) 7.65 (dd, J=8.35, 2.36 Hz, 1H) 7.76 (br. s., 1H) 8.14 (d, J=4.73 Hz, 1H) 8.32 (s, 1H) 8.94 (d, J=4.73 Hz, 1H). LCMS (m/z) (M+H)=528.2, Rt=0.75 min.

Example 1132: N-(3-(2-(1,4-dioxan-2-yl)-6-morpholinopyridin-4-yl)-4-methylphenyl)-2-(trifluoromethyl)piperidine-4-carboxamide

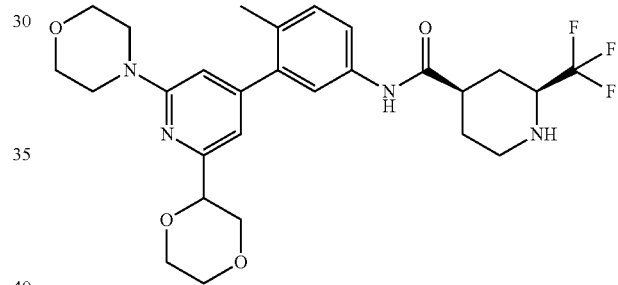

$^1$H NMR (500 MHz, <cd3od>) δ ppm 1.90-2.04 (m, 2H) 2.23 (s, 3H) 2.38 (d, J=12.93 Hz, 1H) 2.76-2.86 (m, 1H) 3.49-3.57 (m, 5H) 3.62-3.71 (m, 2H) 3.75-3.83 (m, 5H) 3.84-3.97 (m, 2H) 4.14 (dd, J=11.51, 2.68 Hz, 1H) 4.30 (ddd, J=9.62, 6.46, 3.15 Hz, 1H) 4.61 (dd, J=9.93, 2.68 Hz, 1H) 6.66 (s, 1H) 6.81 (s, 1H) 7.26 (d, J=8.20 Hz, 1H) 7.45 (dd, J=8.20, 2.21 Hz, 1H) 7.47 (d, J=2.21 Hz, 1H) 9.95 (s, 1H). LCMS (m/z) (M+H)=535.3, Rt=0.61 min.

Example 1133: N-(3-(2-ethoxy-6-morpholinopyridin-4-yl)-4-methylphenyl)-2-(trifluoromethyl)isonicotinamide

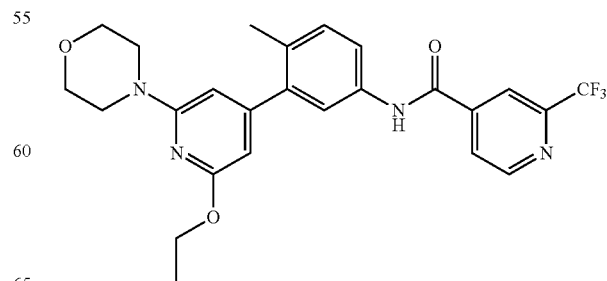

LC/MS (m/z): 487.1 (MH+), Rt=1.09 min.

Synthesis of
4-(4-bromopyridin-2-yl)morpholin-3-one

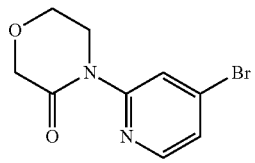 [SMILES: O=C1COCCN1c1cc(Br)ccn1]

To a suspension of 3-morpholinone (1.50 equiv.) in toluene was added potassium tert-butoxide, 1.0M in THF (1.40 equiv.). The mixture was stirred for 10 min. 4-bromo-2-fluoropyridine (1.00 equiv.) was added. The mixture was stirred at 110° C. for 5 hr. The cooled reaction mixture was diluted with ethyl acetate and washed with saturated aqueous sodium bicarbonate. The separated organic phase was dried over sodium sulfate, filtered, and concentrated to give 4-(4-bromopyridin-2-yl)morpholin-3-one. LCMS (m/z) (M+H)=256.9/258.8, Rt=0.59 min.

Example 1134: N-(4-methyl-3-(2-(3-oxomorpholino)pyridin-4-yl)phenyl)-3-trifluoromethyl)benzamide

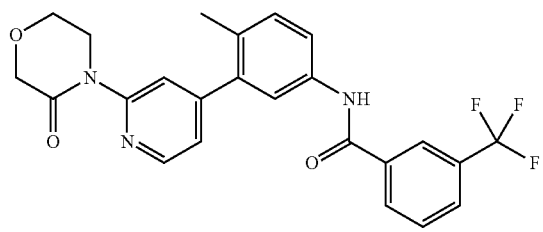 [SMILES: Cc1ccc(NC(=O)c2cccc(C(F)(F)F)c2)cc1-c1ccnc(N2CCOCC2=O)c1]

$^1$H NMR (400 MHz, <cd3od>) δ ppm 2.33 (s, 3H) 4.10 (s, 4H) 4.35 (s, 2H) 7.32-7.40 (m, 2H) 7.66-7.78 (m, 3H) 7.90 (d, J=7.83 Hz, 1H) 7.95 (s, 1H) 8.22 (d, J=7.83 Hz, 1H) 8.27 (s, 1H) 8.53 (d, J=5.09 Hz, 1H) LCMS (m/z) (M+H)= 456.1, Rt=0.97 min.

Example 1135: N-(2-methyl-2'-(3-oxomorpholino)-[3,4'-bipyridin]-5-yl)-3-(trifluoromethyl)benzamide

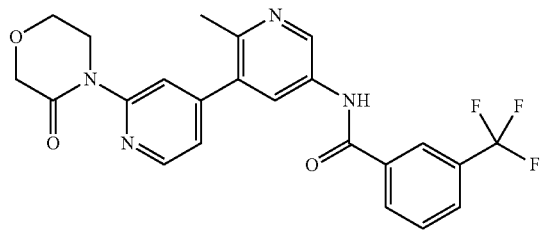 [SMILES: Cc1ncc(NC(=O)c2cccc(C(F)(F)F)c2)cc1-c1ccnc(N2CCOCC2=O)c1]

$^1$H NMR (400 MHz, <cd3od>) δ ppm 2.70 (s, 3H) 4.06-4.20 (m, 4H) 4.36 (s, 2H) 7.40 (dd, J=5.09, 1.57 Hz, 1H) 7.74-7.84 (m, 1H) 7.97 (d, J=7.83 Hz, 1H) 8.18 (s, 1H) 8.29 (d, J=8.22 Hz, 1H) 8.36 (s, 1H) 8.50 (d, J=1.96 Hz, 1H) 8.66 (d, J=5.09 Hz, 1H) 9.36 (d, J=2.35 Hz, 1H). LCMS (m/z) (M+H)=457.1, Rt=0.72 min.

Example 1136: 2-isopropyl-N-(2-methyl-2'-morpholino-[3,4'-bipyridin]-5-yl)isonicotinamide

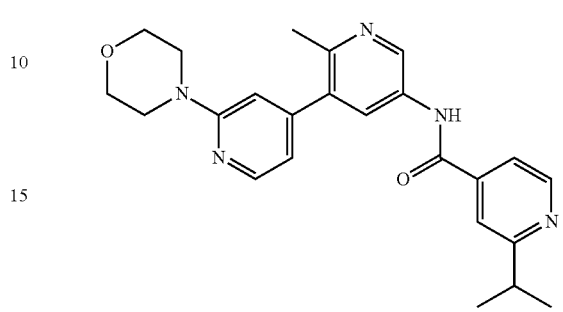

$^1$H NMR (400 MHz, <cd3od>) δ ppm 1.43 (d, J=6.65 Hz, 6H) 2.60 (s, 3H) 3.24-3.31 (m, 1H) 3.66-3.76 (m, 4H) 3.83-3.93 (m, 4H) 7.06 (d, J=6.26 Hz, 1H) 7.36 (s, 1H) 7.96 (dd, J=5.67, 1.37 Hz, 1H) 8.08 (s, 1H) 8.14 (d, J=6.26 Hz, 1H) 8.43 (d, J=2.35 Hz, 1H) 8.77 (d, J=5.48 Hz, 1H) 9.01 (d, J=1.96 Hz, 1H). LCMS (m/z) (M+H)=418.2, Rt=0.41 min.

Example 1137: 2-(1,1-difluoroethyl)-N-(4-methyl-3-(2-morpholinopyridin-4-yl)phenyl)isonicotinamide

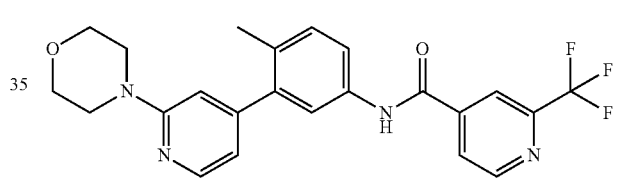

LC/MS (m/z): 439.1 (MH+), Rt=0.68 min.

Example 1138: (R)-2-(2-fluoropropan-2-yl)-N-(2'-((2-hydroxyethyl)amino)-2-methyl-6'-(3-methylmorpholino)-[3,4'-bipyridin]-5-yl)isonicotinamide

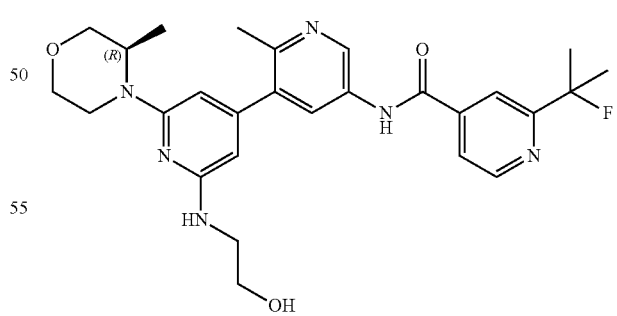

1H NMR (400 MHz, <cd3od>) δ ppm 1.35 (d, J=6.65 Hz, 3H) 1.60-1.85 (m, 7H) 2.63 (s, 3H) 3.36-3.72 (m, 6H) 3.72-3.87 (m, 5H) 4.03 (d, J=10.96 Hz, 1H) 4.17 (d, J=6.65 Hz, 1H) 6.07-6.32 (m, 1H) 7.81 (dd, J=5.09, 1.57 Hz, 1H) 8.11 (s, 1H) 8.42 (d, J=2.35 Hz, 1H) 8.74 (d, J=5.09 Hz, 1H) 9.07 (d, J=1.96 Hz, 1H). LC/MS (m/z): 509.4 (MH+), Rt=0.57 min.

Example 1139: (R)-2-(1,1-difluoroethyl)-N-(2'-((2-hydroxyethyl)amino)-2-methyl-6'-(3-methylmorpholino)-[3,4'-bipyridin]-5-yl)isonicotinamide

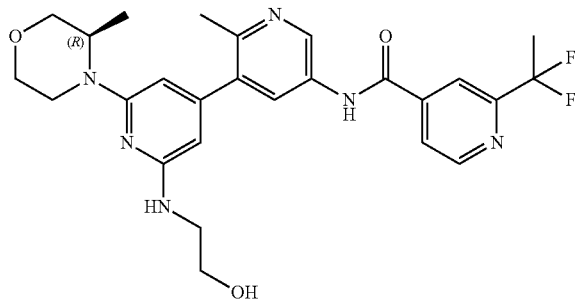

1H NMR (400 MHz, <cd3od>) δ ppm 1.34 (d, J=6.65 Hz, 3H) 2.05 (t, J=18.59 Hz, 3H) 2.60 (s, 3H) 3.36-3.55 (m, 3H) 3.57-3.72 (m, 2H) 3.73-3.89 (m, 4H) 4.02 (d, J=11.35 Hz, 1H) 4.18 (d, J=5.87 Hz, 1H) 6.05-6.33 (m, 1H) 8.00 (d, J=4.70 Hz, 1H) 8.22 (s, 1H) 8.37 (d, J=2.35 Hz, 1H) 8.85 (d, J=5.09 Hz, 1H) 9.00 (s, 1H). LC/MS (m/z): 513.4 (MH+), Rt=0.56 min.

Example 1140: (R)—N-(2'-((2-hydroxyethyl)amino)-2-methyl-6'-(3-methylmorpholino)-[3,4'-bipyridin]-5-yl)-2-(trifluoromethyl)isonicotinamide

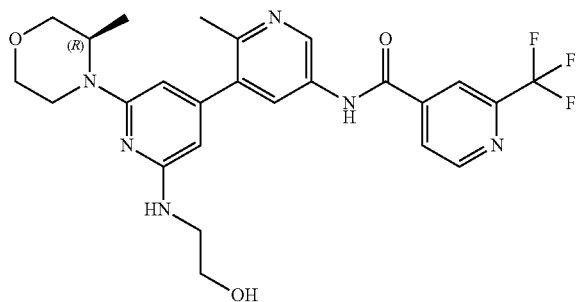

1H NMR (400 MHz, <cd3od>) δ ppm 1.34 (d, J=6.65 Hz, 3H) 2.59 (s, 3H) 3.36-3.55 (m, 3H) 3.58-3.71 (m, 2H) 3.74-3.89 (m, 4H) 3.92-4.08 (m, 1H) 4.17 (d, J=6.26 Hz, 1H) 6.04-6.29 (m, 1H) 8.15 (d, J=4.30 Hz, 1H) 8.28-8.41 (m, 1H) 8.87-9.06 (m, 1H). LC/MS (m/z): 517.3 (MH+), Rt=0.58 min.

Example 1141: (R)-2-(difluoromethyl)-N-(2'-((2-hydroxyethyl)amino)-2-methyl-6'-(3-methylmorpholino)-[3,4'-bipyridin]-5-yl)isonicotinamide

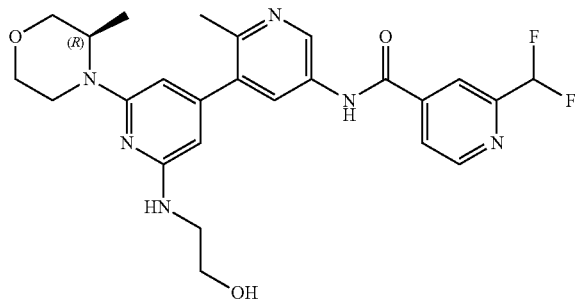

1H NMR (400 MHz, <cd3od>) δ ppm 1.35 (d, J=6.65 Hz, 3H) 2.61 (s, 3H) 3.36-3.71 (m, 6H) 3.71-3.87 (m, 5H) 3.93-4.09 (m, 1H) 4.17 (d, J=6.65 Hz, 1H) 6.08-6.32 (m, 1H) 6.66-7.09 (m, 1H) 8.05 (d, J=5.09 Hz, 1H) 8.16-8.28 (m, 1H) 8.32-8.48 (m, 1H) 8.84-8.94 (m, 1H) 9.04 (d, J=1.96 Hz, 1H). LC/MS (m/z): 499.4 (MH+), Rt=0.51 min.

Example 1142: N-(2'-ethoxy-2-methyl-6'-morpholino-[3,4'-bipyridin]-5-yl)-2-(2-fluoropropan-2-yl)isonicotinamide

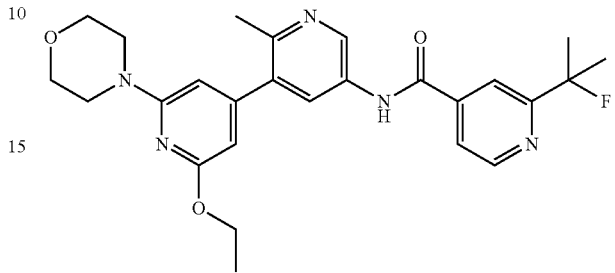

1H NMR (400 MHz, <cd3od>) δ ppm 1.38 (t, J=7.04 Hz, 4H) 1.62-1.86 (m, 6H) 2.68 (s, 3H) 3.45-3.63 (m, 4H) 3.70-3.87 (m, 4H) 4.37 (q, J=7.04 Hz, 2H) 6.14 (s, 1H) 6.31 (s, 1H) 7.83 (dd, J=5.09, 1.57 Hz, 1H) 8.13 (s, 1H) 8.45 (d, J=2.35 Hz, 1H) 8.76 (d, J=5.09 Hz, 1H) 9.38 (d, J=2.35 Hz, 1H). LC/MS (m/z): 480.2 (MH+), Rt=0.82 min.

Example 1143: 2-(1,1-difluoroethyl)-N-(2'-ethoxy-2-methyl-6'-morpholino-[3,4'-bipyridin]-5-yl)isonicotinamide

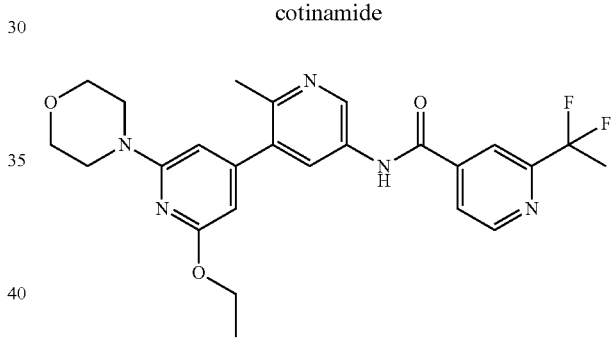

1H NMR (400 MHz, <cd3od>) δ ppm 1.24-1.46 (m, 5H) 2.05 (t, J=18.78 Hz, 3H) 2.66 (s, 3H) 3.46-3.62 (m, 4H) 3.71-3.88 (m, 4H) 4.37 (q, J=7.04 Hz, 2H) 6.14 (s, 1H) 6.30 (s, 1H) 8.02 (d, J=4.30 Hz, 1H) 8.25 (s, 1H) 8.40 (d, J=2.35 Hz, 1H) 8.86 (d, J=5.09 Hz, 1H) 9.31 (d, J=2.35 Hz, 1H). LC/MS (m/z): 484.2 (MH+), Rt=0.82 min.

Example 1144: N-(3-(2-(1,4-dioxan-2-yl)-6-morpholinopyridin-4-yl)-4-methylphenyl)-2-(2-fluoropropan-2-yl)isonicotinamide

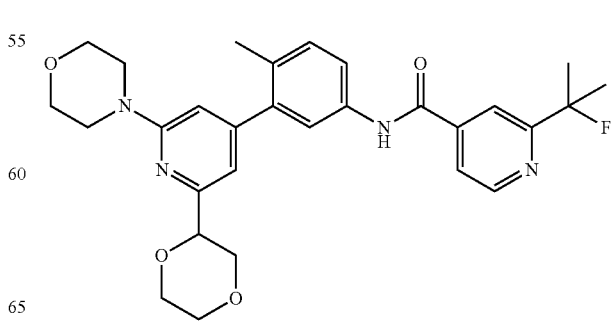

1H NMR (400 MHz, <cd3od>) δ ppm 1.62-1.83 (m, 6H) 2.29 (s, 3H) 3.46-4.02 (m, 14H) 4.13 (dd, J=11.54, 2.54 Hz, 1H) 4.74 (dd, J=9.78, 2.35 Hz, 1H) 6.95 (d, J=4.30 Hz, 2H) 7.34 (d, J=8.22 Hz, 1H) 7.63 (dd, J=8.22, 2.35 Hz, 1H) 7.71 (d, J=1.96 Hz, 1H) 7.78 (dd, J=5.09, 1.57 Hz, 1H) 8.07 (s, 1H) 8.70 (d, J=5.09 Hz, 1H). LC/MS (m/z): 521.2 (MH+), Rt=0.85 min.

Example 1145: N-(3-(2-(1,4-dioxan-2-yl)-6-morpholinopyridin-4-yl)-4-methylphenyl)-2-1,1-difluoroethyl)isonicotinamide

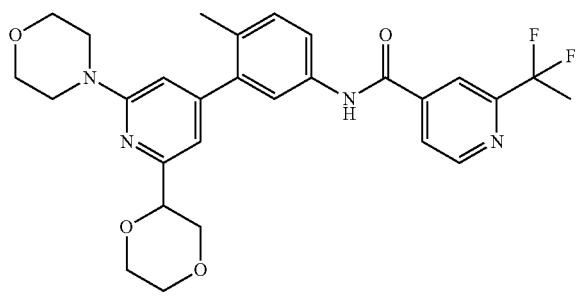 [SMILES: Cc1ccc(NC(=O)c2ccnc(C(C)(F)F)c2)cc1-c1cc(C2COCCO2)nc(N2CCOCC2)c1]

1H NMR (400 MHz, <cd3od>) δ ppm 1.32 (d, J=6.65 Hz, 3H) 2.03 (t, J=18.59 Hz, 3H) 2.30 (s, 3H) 3.46-4.02 (m, 14H) 4.14 (dd, J=11.54, 2.54 Hz, 1H) 4.76 (dd, J=9.78, 2.74 Hz, 1H) 6.98 (d, J=1.96 Hz, 2H) 7.35 (d, J=8.22 Hz, 1H) 7.64 (dd, J=8.22, 2.35 Hz, 1H) 7.74 (d, J=1.96 Hz, 1H) 7.96 (d, J=4.30 Hz, 1H) 8.18 (s, 1H) 8.81 (d, J=5.09 Hz, 1H). LC/MS (m/z): 525.2 (MH+), Rt=0.85 min.

Example 1146: 2-(difluoromethyl)-N-(2'-ethoxy-2-methyl-6'-morpholino-[3,4'-bipyridin]-5-yl)isonicotinamide

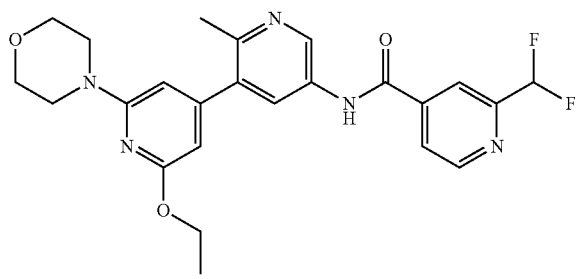 [SMILES: CCOc1cc(-c2cc(NC(=O)c3ccnc(C(F)F)c3)cnc2C)cc(N2CCOCC2)n1]

1H NMR (400 MHz, <cd3od>) δ ppm 1.38 (t, J=7.04 Hz, 3H) 2.68 (s, 3H) 3.47-3.63 (m, 4H) 3.71-3.85 (m, 4H) 4.37 (q, J=7.04 Hz, 2H) 6.14 (s, 1H) 6.31 (s, 1H) 6.61-7.04 (m, 1H) 8.07 (d, J=5.09 Hz, 1H) 8.25 (s, 1H) 8.44 (d, J=2.35 Hz, 1H) 8.89 (d, J=5.09 Hz, 1H) 9.36 (d, J=2.35 Hz, 1H). LC/MS (m/z): 470.2 (MH+), Rt=0.78 min.

Example 1147: 2-(2-cyanopropan-2-yl)-N-(2'-ethoxy-2-methyl-6'-morpholino-[3,4'-bipyridin]-5-yl)isonicotinamide

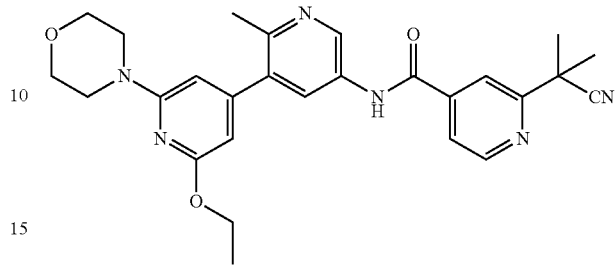

1H NMR (400 MHz, <cd3od>) δ ppm 1.38 (t, J=7.04 Hz, 3H) 1.82 (s, 6H) 2.67 (s, 3H) 3.46-3.62 (m, 4H) 3.70-3.87 (m, 4H) 4.37 (q, J=7.17 Hz, 2H) 6.15 (s, 1H) 6.31 (s, 1H) 7.87 (dd, J=5.09, 1.17 Hz, 1H) 8.13 (s, 1H) 8.42 (d, J=2.35 Hz, 1H) 8.82 (d, J=4.70 Hz, 1H) 9.36 (d, J=2.35 Hz, 1H). LC/MS (m/z): 487.2 (MH+), Rt=0.81 min.

Example 1148: N-(2'-ethoxy-2-methyl-6'-morpholino-[3,4'-bipyridin]-5-yl)-2-(2-hydroxypropan-2-yl)isonicotinamide

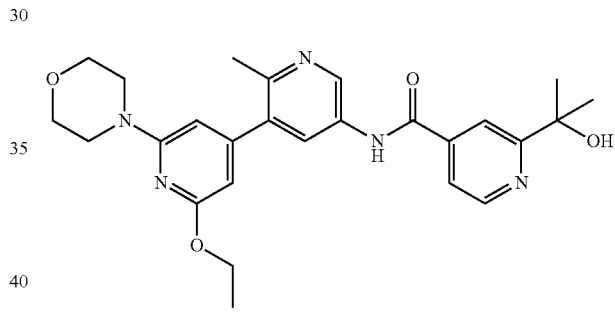

1H NMR (400 MHz, <cd3od>) δ ppm 1.38 (t, J=7.04 Hz, 3H) 1.64 (s, 6H) 2.67 (s, 3H) 3.45-3.62 (m, 4H) 3.68-3.88 (m, 4H) 4.37 (q, J=7.04 Hz, 2H) 6.14 (s, 1H) 6.31 (s, 1H) 7.95 (dd, J=5.28, 1.76 Hz, 1H) 8.34 (d, J=0.78 Hz, 1H) 8.44 (d, J=2.35 Hz, 1H) 8.77 (d, J=5.48 Hz, 1H) 9.35 (d, J=2.35 Hz, 1H). LC/MS (m/z): 478.3 (MH+), Rt=0.64 min.

Example 1149: 2-cyclopropyl-N-(2'-ethoxy-2-methyl-6'-morpholino-[3,4'-bipyridin]-5-yl)isonicotinamide

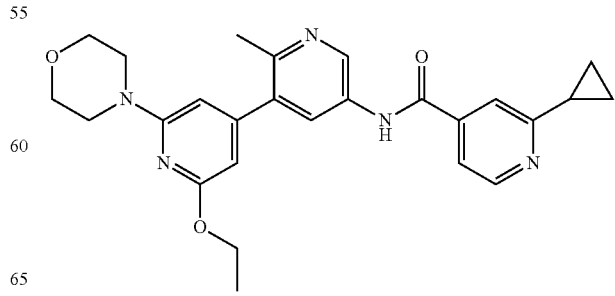

1H NMR (400 MHz, <cd3od>) δ ppm 1.06-1.27 (m, 4H) 1.38 (t, J=7.04 Hz, 3H) 2.20-2.33 (m, 1H) 2.66 (s, 3H) 3.42-3.64 (m, 4H) 3.67-3.94 (m, 4H) 4.37 (q, J=7.04 Hz, 2H) 6.14 (s, 1H) 6.30 (s, 1H) 7.78 (dd, J=5.48, 1.57 Hz, 1H) 7.84 (s, 1H) 8.40 (d, J=1.96 Hz, 1H) 8.64 (d, J=5.09 Hz, 1H) 9.33 (d, J=2.35 Hz, 1H). LC/MS (m/z): 460.3 (MH+), Rt=0.67 min.

Example 1150: 2-(2-hydroxypropan-2-yl)-N-(4-methyl-3-(2-morpholino-6-((tetrahydro-2H-pyran-4-yl)oxy)pyridin-4-yl)phenyl)isonicotinamide

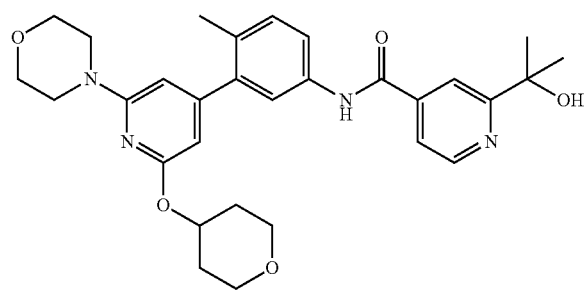 [SMILES: Cc1ccc(NC(=O)c2ccnc(C(C)(C)O)c2)cc1-c1cc(OC2CCOCC2)nc(N2CCOCC2)c1]

1H NMR (400 MHz, Methanol-d4) δ 8.76 (dd, J=5.8, 0.8 Hz, 1H), 8.41 (dd, J=1.7, 0.8 Hz, 1H), 8.13 (dd, J=5.8, 1.7 Hz, 1H), 7.69-7.57 (m, 2H), 7.34-7.27 (m, 1H), 6.22 (d, J=0.9 Hz, 1H), 6.06 (d, J=0.9 Hz, 1H), 5.26-5.15 (m, 1H), 3.96 (dt, J=11.7, 4.5 Hz, 2H), 3.83-3.75 (m, 4H), 3.62 (ddd, J=11.8, 8.9, 3.0 Hz, 2H), 3.52-3.44 (m, 4H), 2.27 (s, 3H), 2.13-2.03 (m, 2H), 1.78 (ddd, J=13.0, 8.6, 4.0 Hz, 2H), 1.67 (s, 6H). LC/MS (m/z): 533.2 (MH+), Rt=0.81 min.

Example 1151: 2-(difluoromethyl)-N-(4-methyl-3-(2-morpholino-6-((tetrahydro-2H-pyran-4-yl)oxy)pyridin-4-yl)phenyl)isonicotinamide

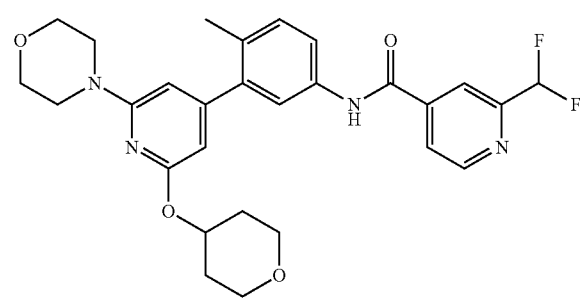 [SMILES: Cc1ccc(NC(=O)c2ccnc(C(F)F)c2)cc1-c1cc(OC2CCOCC2)nc(N2CCOCC2)c1]

1H NMR (400 MHz, Methanol-d4) δ 8.83 (dd, J=5.1, 0.7 Hz, 1H), 8.17 (d, J=1.7 Hz, 1H), 8.00 (ddd, J=4.4, 1.7, 0.9 Hz, 1H), 7.63 (dd, J=4.5, 2.1 Hz, 2H), 7.34-7.26 (m, 1H), 6.82 (t, J=55.1 Hz, 1H), 6.32-6.26 (m, 1H), 6.13 (d, J=1.0 Hz, 1H), 5.24-5.14 (m, 1H), 4.02-3.92 (m, 2H), 3.84-3.76 (m, 4H), 3.62 (ddd, J=11.8, 8.9, 3.0 Hz, 2H), 3.51 (dd, J=5.7, 4.1 Hz, 4H), 2.27 (s, 3H), 2.14-2.05 (m, 2H), 1.78 (dtd, J=12.8, 8.7, 4.0 Hz, 2H). LC/MS (m/z): 525.2 (MH+), Rt=0.97 min.

Example 1152: 2-(2-cyanopropan-2-yl)-N-(4-methyl-3-(2-morpholino-6-((tetrahydro-2H-pyran-4-yl)oxy)pyridin-4-yl)phenyl)isonicotinamide

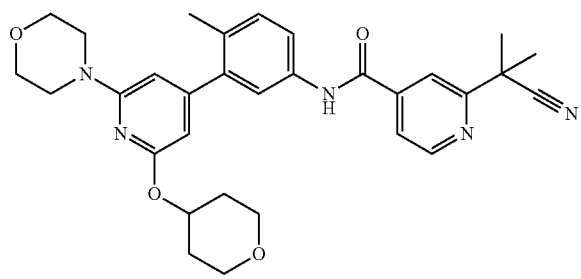 [SMILES: Cc1ccc(NC(=O)c2ccnc(C(C)(C)C#N)c2)cc1-c1cc(OC2CCOCC2)nc(N2CCOCC2)c1]

1H NMR (400 MHz, Methanol-d4) δ 8.76 (dd, J=5.0, 0.9 Hz, 1H), 8.06 (dd, J=1.6, 0.9 Hz, 1H), 7.81 (dd, J=5.1, 1.6 Hz, 1H), 7.62 (d, J=8.2 Hz, 2H), 7.30 (dd, J=8.0, 1.0 Hz, 1H), 6.29 (d, J=1.3 Hz, 1H), 6.13 (d, J=1.0 Hz, 1H), 5.25-5.13 (m, 1H), 4.02-3.92 (m, 2H), 3.84-3.76 (m, 4H), 3.62 (ddd, J=11.8, 8.9, 3.0 Hz, 2H), 3.54-3.47 (m, 4H), 2.27 (s, 3H), 2.09 (ddd, J=11.7, 6.1, 3.0 Hz, 2H), 1.81 (s, 8H). LC/MS (m/z): 542.2 (MH+), Rt=0.99 min.

Example 1153: 6-(2-cyanopropan-2-yl)-N-(4-methyl-3-(2-morpholino-6-((tetrahydro-2H-pyran-4-yl)oxy)pyridin-4-yl)phenyl)pyridazine-4-carboxamide

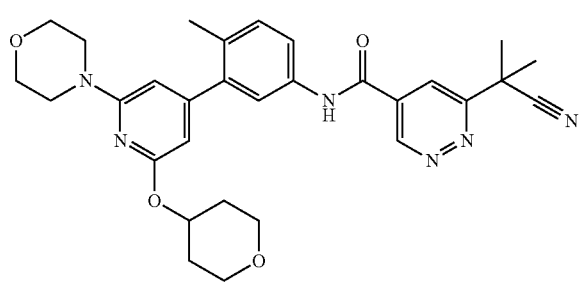 [SMILES: Cc1ccc(NC(=O)c2cnnc(C(C)(C)C#N)c2)cc1-c1cc(OC2CCOCC2)nc(N2CCOCC2)c1]

1H NMR (400 MHz, Methanol-d4) δ 9.61 (d, J=2.0 Hz, 1H), 8.35 (d, J=2.0 Hz, 1H), 7.65 (dd, J=8.3, 2.3 Hz, 1H), 7.60 (d, J=2.4 Hz, 1H), 7.34-7.27 (m, 1H), 6.23 (d, J=0.9 Hz, 1H), 6.07 (d, J=0.9 Hz, 1H), 5.25-5.16 (m, 2H), 4.01-3.91 (m, 2H), 3.83-3.75 (m, 4H), 3.62 (ddd, J=11.8, 8.9, 3.1 Hz, 2H), 3.52-3.45 (m, 5H), 2.27 (s, 3H), 2.12-2.04 (m, 2H), 1.91 (s, 5H), 1.77 (dt, J=8.6, 4.2 Hz, 2H). LC/MS (m/z): 543.2 (MH+), Rt=0.93 min.

Example 1154: 6-cyclopropyl-N-(4-methyl-3-(2-morpholino-6-((tetrahydro-2H-pyran-4-yl)oxy)pyridin-4-yl)phenyl)pyridazine-4-carboxamide

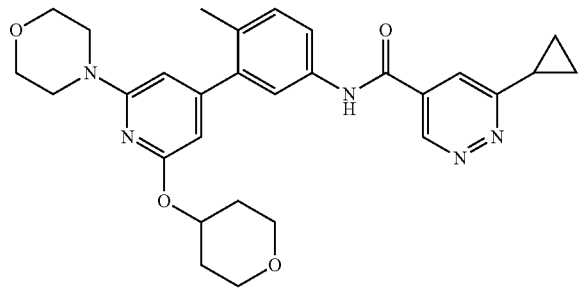 [SMILES: Cc1ccc(NC(=O)c2cnnc(C3CC3)c2)cc1-c1cc(OC2CCOCC2)nc(N2CCOCC2)c1]

1H NMR (400 MHz, Methanol-d4) δ 9.43 (d, J=2.0 Hz, 1H), 8.05 (d, J=2.0 Hz, 1H), 7.67-7.57 (m, 2H), 7.30 (d, J=8.2 Hz, 1H), 6.25 (d, J=1.2 Hz, 1H), 6.09 (d, J=1.0 Hz, 1H), 5.19 (dddt, J=7.8, 4.9, 3.9, 0.5 Hz, 1H), 4.01-3.91 (m, 2H), 3.83-3.75 (m, 4H), 3.61 (ddd, J=11.8, 8.9, 3.0 Hz, 2H), 3.49 (dd, J=5.4, 4.4 Hz, 4H), 2.45-2.36 (m, 1H), 2.26 (s, 3H), 2.13-2.04 (m, 2H), 1.77 (dt, J=8.6, 4.1 Hz, 2H), 1.37-1.23 (m, 4H). LC/MS (m/z): 516.2 (MH+), Rt=0.91 min.

Example 1155: N-(4-methyl-3-(2-morpholino-6-((tetrahydro-2H-pyran-4-yl)oxy)pyridin-4-yl)phenyl)-6-(trifluoromethyl)pyridazine-4-carboxamide

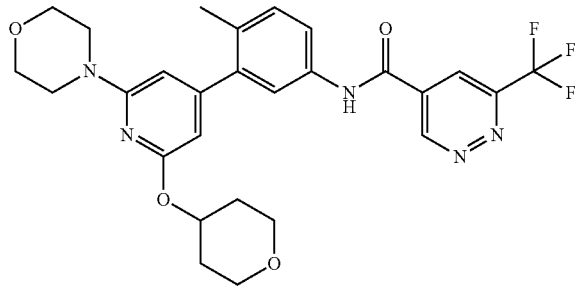 [SMILES: Cc1ccc(NC(=O)c2cnnc(C(F)(F)F)c2)cc1-c1cc(OC2CCOCC2)nc(N2CCOCC2)c1]

1H NMR (400 MHz, Methanol-d4) δ 9.86 (d, J=2.0 Hz, 1H), 8.57 (d, J=2.0 Hz, 1H), 7.69-7.61 (m, 2H), 7.34-7.27 (m, 1H), 6.27 (d, J=1.3 Hz, 1H), 6.11 (d, J=1.0 Hz, 1H), 5.24-5.14 (m, 1H), 3.96 (dt, J=11.6, 4.5 Hz, 2H), 3.83-3.76 (m, 4H), 3.61 (ddd, J=11.8, 8.9, 3.0 Hz, 2H), 3.53-3.46 (m, 4H), 2.27 (s, 3H), 2.08 (ddt, J=11.7, 5.7, 2.8 Hz, 2H), 1.77 (dtd, J=12.8, 8.7, 4.0 Hz, 2H). LC/MS (m/z): 544.2 (MH+), Rt=0.99 min.

Example 1156: N-(3-(2-(2-hydroxyethoxy)-6-morpholinopyridin-4-yl)-4-methylphenyl)-2-(trifluoromethyl)isonicotinamide

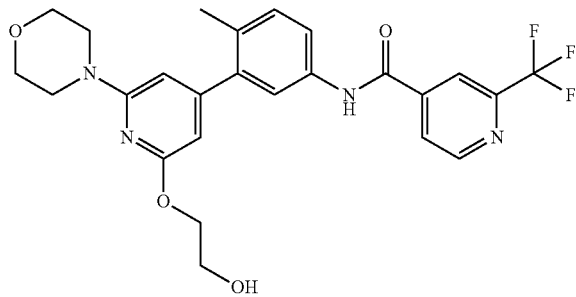 [SMILES: Cc1ccc(NC(=O)c2ccnc(C(F)(F)F)c2)cc1-c1cc(OCCO)nc(N2CCOCC2)c1]

Step 1:
2,6-difluoro-4-(4,4,5,5-tetramethyl-1,3,2-dioxaborolan-2-yl)pyridine (1.0 equiv.), 3-bromo-4-methylaniline (1.04 equiv.) and Pd-Xphos precat (0.005 equiv.) were stirred in a solution of THF (0.5 M) under nitrogen. Potassium phosphate (2.0 equiv, 0.5 M solution) was added and the mixture was heated to 35° C. overnight. Upon overnight stirring, another 0.005 equiv. of catalyst was added and the mixture was warmed to 60° C. for 18 hours. The mixture was carefully poured onto water and extracted with ethyl acetate (3×). The combined organics were washed with water, brine, dried over magnesium sulfate, filtered and concentrated. The crude residue was purified via silica gel chromatography (ISCO, 0-100% ethyl acetate in heptanes) to give 3-(2,6-difluoropyridin-4-yl)-4-methylaniline in 64% yield. LCMS (m/z) (M+H)=220.9, Rt=0.54 min.

Step 2:
To a solution of 3-(2,6-difluoropyridin-4-yl)-4-methylaniline (1.0 equiv.) in DMSO (1 M) was added morpholine (3.0 equiv.) and potassium carbonate (2.0 equiv.) to give a yellow suspension. The mixture was heated to 40° C. for 3 hours and upon cooling to rt, diluted with water and sodium bicarbonate, extracted with ethyl acetate (3×), dried, filtered and concentrated to give 3-(2-fluoro-6-morpholinopyridin-4-yl)-4-methylaniline in quantitative yield. LCMS (m/z) (M+H)=288.0, Rt=0.60 min.

Step 3:
To a solution of 3-(2-fluoro-6-morpholinopyridin-4-yl)-4-methylaniline (1.0 equiv.) in dioxane (0.2 M) was added 2-((tetrahydro-2H-pyran-2-yl)oxy)ethanol (2.0 equiv.) to give an orange solution. Sodium hydride (60% dispersion, 2.0 equiv.) was added carefully and the reaction was stirred at rt for 30 min, then warmed to 60° C. for 2 hours. At this point, about 75% conversion to product, so the mixture was heated to 70° C. for another one hour. The reaction was cooled to rt, quenched with aqueous sodium bicarbonate, extracted with ethyl acetate (3×), dried over magnesium sulfate, filtered and concentrated. The crude material was purified via silica gel chromatography (ISCO, 0-5% methanol in DCM then 0-100% ethyl acetate in heptanes to give 4-methyl-3-(2-morpholino-6-(2-((tetrahydro-2H-pyran-2-yl)oxy)ethoxy)pyridin-4-yl)aniline in 72% yield. LCMS (m/z) (M+H)=414.1, Rt=0.73 min.

Step 4:
A solution of 4-methyl-3-(2-morpholino-6-(2-((tetrahydro-2H-pyran-2-yl)oxy)ethoxy)pyridin-4-yl)aniline (1.0 equiv.), 2-(trifluoromethyl)isonicotinic acid (1.7 equiv.), N1-((ethylimino)methylene)-N3,N3-dimethylpropane-1,3-diamine hydrochloride (1.7 equiv.), 3H-[1,2,3]triazolo[4,5-b]pyridin-3-ol hydrate (1.7 equiv.) and Huenig's base (2.0 equiv.) in DMF (0.1 M) was stirred at rt overnight. HCl (5.0 equiv., 2.0 M aqueous solution) was added and the reaction was stirred for 90 min, at which point LC/MS indicated about 90% conversion to product. Additional 2.5 equiv. of HCl was added and stirred for 30 min at rt. The solution was diluted with water and solid sodium bicarbonate was carefully added until pH=5 was reached. The solution was extracted with ethyl acetate (3×), dried over magnesium sulfate, filtered and concentrated. The crude material was purified via silica gel chromatography (ISCO, 0-100% ethyl acetate in heptanes to give N-(3-(2-(2-hydroxyethoxy)-6-morpholinopyridin-4-yl)-4-methylphenyl)-2-(trifluoromethyl)isonicotinamide in 81% yield. 1H NMR (400 MHz, Methanol-d4) δ 8.93-8.86 (m, 1H), 8.31-8.26 (m, 1H), 8.14-8.07 (m, 1H), 7.68-7.56 (m, 2H), 7.33-7.25 (m, 1H), 6.32-6.24 (m, 1H), 6.13 (dd, J=28.4, 0.9 Hz, 1H), 4.76-4.59 (m, 2H), 4.41-4.33 (m, 1H), 3.91-3.84 (m, 1H), 3.79 (ddd, J=6.7, 4.0, 1.8 Hz, 4H), 3.51 (q, J=4.8 Hz, 4H), 2.26 (d, J=4.9 Hz, 3H). LC/MS (m/z): 503.2 (MH+), Rt=0.88 min.

Example 1157: 2-cyclopropyl-N-(3-(2-(2-hydroxyethoxy)-6-morpholinopyridin-4-yl)-4-methylphenyl)isonicotinamide

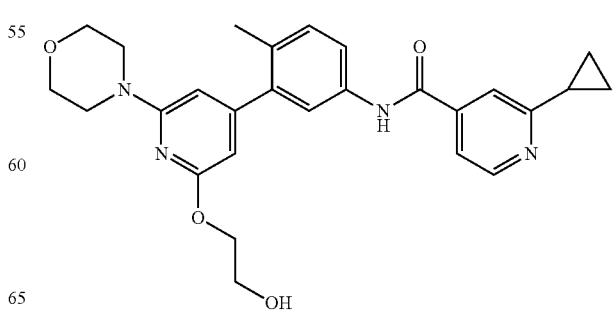

1H NMR (400 MHz, Methanol-d4) δ 8.64 (dd, J=5.8, 0.8 Hz, 1H), 7.94-7.85 (m, 2H), 7.63 (dd, J=8.2, 2.4 Hz, 1H), 7.57 (d, J=2.3 Hz, 1H), 7.29 (dd, J=8.3, 0.7 Hz, 1H), 6.22 (d, J=0.9 Hz, 1H), 6.10 (d, J=0.9 Hz, 1H), 4.40-4.33 (m, 2H), 3.90-3.83 (m, 2H), 3.83-3.75 (m, 5H), 3.54-3.46 (m, 5H), 2.38-2.26 (m, 1H), 2.26 (s, 3H), 1.38-1.17 (m, 5H). LC/MS (m/z): 475.2 (MH+), Rt=0.69 min.

Example 1158: 2-(2-fluoropropan-2-yl)-N-(3-(2-(2-hydroxyethoxy)-6-morpholinopyridin-4-yl)-4-methylphenyl)isonicotinamide

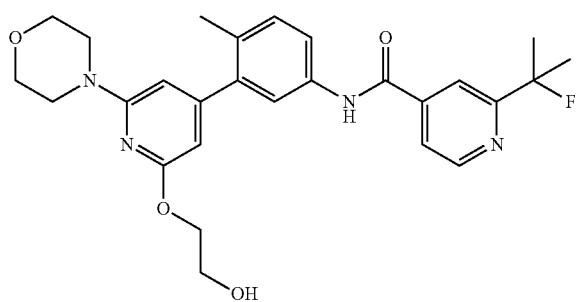 [SMILES: Cc1ccc(NC(=O)c2ccnc(C(C)(C)F)c2)cc1-c1cc(OCCO)nc(N2CCOCC2)c1]

1H NMR (400 MHz, Methanol-d4) δ 8.71 (dd, J=5.2, 0.9 Hz, 1H), 8.10 (dt, J=2.0, 1.0 Hz, 1H), 7.82 (ddd, J=5.2, 2.7, 1.7 Hz, 1H), 7.67-7.55 (m, 2H), 7.33-7.25 (m, 1H), 6.34-6.25 (m, 1H), 6.14 (dd, J=32.5, 0.9 Hz, 1H), 4.76-4.59 (m, 2H), 4.41-4.34 (m, 1H), 3.92-3.84 (m, 1H), 3.79 (ddd, J=5.1, 4.2, 2.3 Hz, 4H), 3.56-3.47 (m, 4H), 2.26 (d, J=5.7 Hz, 3H), 1.74 (dd, J=22.0, 0.6 Hz, 6H). LC/MS (m/z): 495.2 (MH+), Rt=0.84 min.

Example 1159: 2-(1,1-difluoroethyl)-N-(3-(2-(2-hydroxyethoxy)-6-morpholinopyridin-4-yl)-4-methylphenyl)isonicotinamide

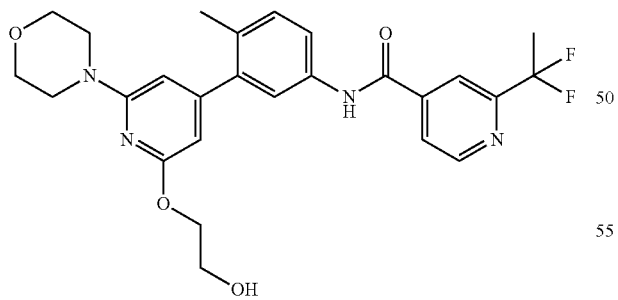

1H NMR (400 MHz, Methanol-d4) δ 8.79 (dt, J=5.1, 0.8 Hz, 1H), 8.17 (dd, J=1.6, 0.9 Hz, 1H), 7.95 (ddd, J=5.1, 1.5, 0.8 Hz, 1H), 7.67-7.55 (m, 2H), 7.33-7.25 (m, 1H), 6.32-6.24 (m, 1H), 6.13 (dd, J=26.2, 0.9 Hz, 1H), 4.76-4.59 (m, 2H), 4.41-4.33 (m, 2H), 3.91-3.84 (m, 2H), 3.83-3.75 (m, 5H), 3.51 (dt, J=6.2, 3.9 Hz, 5H), 2.26 (d, J=4.6 Hz, 3H), 2.03 (t, J=18.7 Hz, 3H). LC/MS (m/z): 499.2 (MH+), Rt=0.85 min.

Example 1160: 2-(difluoromethyl)-N-(3-(2-(2-hydroxyethoxy)-6-morpholinopyridin-4-yl)-4-methylphenyl)isonicotinamide

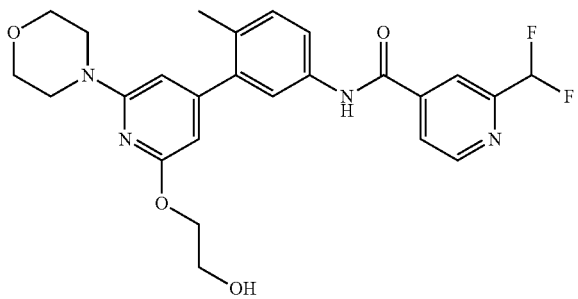 [SMILES: Cc1ccc(NC(=O)c2ccnc(C(F)F)c2)cc1-c1cc(OCCO)nc(N2CCOCC2)c1]

1H NMR (400 MHz, Methanol-d4) δ 8.82 (dt, J=5.2, 0.8 Hz, 1H), 8.16 (d, J=1.6 Hz, 1H), 8.00 (ddt, J=5.2, 1.8, 0.9 Hz, 1H), 7.67-7.55 (m, 2H), 7.33-7.25 (m, 1H), 6.81 (t, J=55.1 Hz, 1H), 6.32-6.24 (m, 1H), 6.13 (dd, J=26.0, 0.9 Hz, 1H), 4.76-4.59 (m, 2H), 4.41-4.33 (m, 1H), 3.91-3.84 (m, 1H), 3.79 (ddd, J=6.5, 3.7, 1.6 Hz, 4H), 3.52 (dd, J=5.5, 4.0 Hz, 4H), 2.26 (d, J=4.5 Hz, 3H). LC/MS (m/z): 485.2 (MH+), Rt=0.81 min.

Example 1161: 2-(2-cyanopropan-2-yl)-N-(3-(2-(2-hydroxyethoxy)-6-morpholinopyridin-4-yl)-4-methylphenyl)isonicotinamide

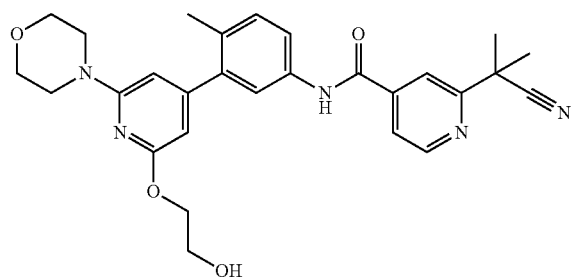 [SMILES: Cc1ccc(NC(=O)c2ccnc(C(C)(C)C#N)c2)cc1-c1cc(OCCO)nc(N2CCOCC2)c1]

1H NMR (400 MHz, Methanol-d4) δ 8.75 (dd, J=5.1, 1.0 Hz, 1H), 8.05 (dt, J=1.5, 0.8 Hz, 1H), 7.80 (dd, J=5.1, 1.6 Hz, 1H), 7.67-7.54 (m, 2H), 7.33-7.25 (m, 1H), 6.35-6.25 (m, 1H), 6.14 (dd, J=33.3, 0.9 Hz, 1H), 4.76-4.59 (m, 2H), 4.41-4.34 (m, 1H), 3.92-3.84 (m, 1H), 3.84-3.75 (m, 4H), 3.56-3.47 (m, 4H), 2.26 (d, J=5.9 Hz, 3H), 1.80 (s, 6H). LC/MS (m/z): 502.2 (MH+), Rt=0.83 min.

Example 1162: 6-cyclopropyl-N-(3-(2-(2-hydroxyethoxy)-6-morpholinopyridin-4-yl)-4-methylphenyl)pyridazine-4-carboxamide

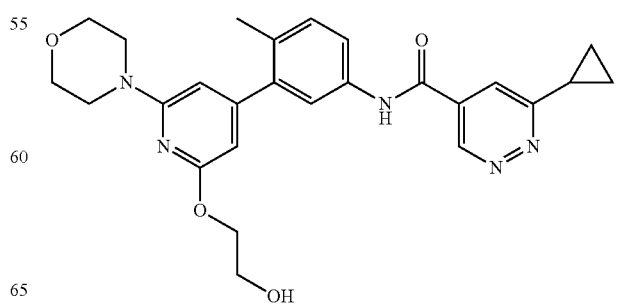

1H NMR (400 MHz, Methanol-d4) δ 9.41 (d, J=2.1 Hz, 1H), 8.00 (d, J=2.0 Hz, 1H), 7.67-7.54 (m, 2H), 7.33-7.26 (m, 1H), 6.25 (d, J=1.1 Hz, 1H), 6.13 (d, J=0.9 Hz, 1H), 4.76-4.61 (m, 1H), 4.41-4.33 (m, 2H), 3.91-3.83 (m, 2H), 3.83-3.76 (m, 5H), 3.55-3.47 (m, 5H), 2.39 (tt, J=8.2, 4.9 Hz, 1H), 2.26 (d, J=3.0 Hz, 3H), 1.35-1.21 (m, 5H). LC/MS (m/z): 476.2 (MH+), Rt=0.75 min.

Example 1163: N-(3-(2-(2-hydroxyethoxy)-6-morpholinopyridin-4-yl)-4-methylphenyl)-4-(trifluoromethyl)picolinamide

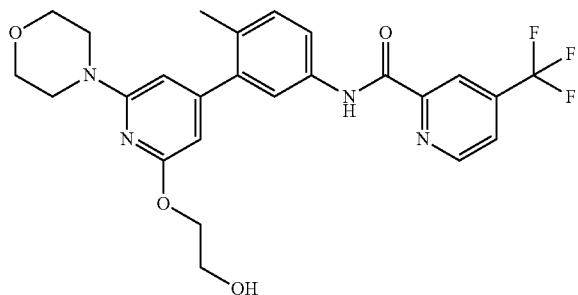 [SMILES: Cc1ccc(NC(=O)c2cc(C(F)(F)F)ccn2)cc1-c1cc(OCCO)nc(N2CCOCC2)c1]

1H NMR (400 MHz, Methanol-d4) δ 8.95 (dt, J=5.1, 0.7 Hz, 1H), 8.42 (dt, J=1.6, 0.7 Hz, 1H), 7.91 (ddd, J=5.1, 1.8, 0.8 Hz, 1H), 7.71 (dd, J=6.2, 2.4 Hz, 2H), 7.30 (dd, J=8.9, 0.8 Hz, 1H), 6.27 (d, J=1.0 Hz, 1H), 6.15 (d, J=0.9 Hz, 1H), 4.41-4.33 (m, 2H), 3.91-3.84 (m, 2H), 3.83-3.76 (m, 4H), 3.56-3.48 (m, 5H), 2.26 (d, J=0.6 Hz, 3H). LC/MS (m/z): 503.2 (MH+), Rt=0.96 min.

Example 1164: N-(3-(2-(2-hydroxyethoxy)-6-morpholinopyridin-4-yl)-4-methylphenyl)-6-(trifluoromethyl)pyridazine-4-carboxamide

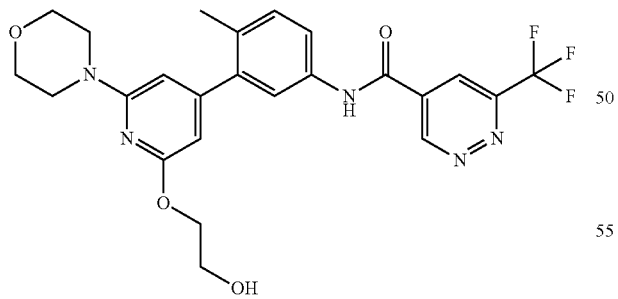

1H NMR (400 MHz, Methanol-d4) δ 9.86 (d, J=2.0 Hz, 1H), 8.57 (d, J=2.0 Hz, 1H), 7.70-7.57 (m, 2H), 7.34-7.27 (m, 1H), 6.27 (dd, J=6.5, 1.0 Hz, 1H), 6.12 (dd, J=24.2, 0.9 Hz, 1H), 4.76-4.60 (m, 1H), 4.41-4.33 (m, 2H), 3.91-3.84 (m, 2H), 3.79 (ddd, J=6.2, 3.6, 1.2 Hz, 5H), 3.55-3.48 (m, 4H), 2.26 (d, J=3.8 Hz, 3H). LC/MS (m/z): 504.2 (MH+), Rt=0.83 min.

Example 1165: N-(2'-(1,4-dioxan-2-yl)-2-methyl-6'-morpholino-[3,4'-bipyridin]-5-yl)-2-(trifluoromethyl)isonicotinamide

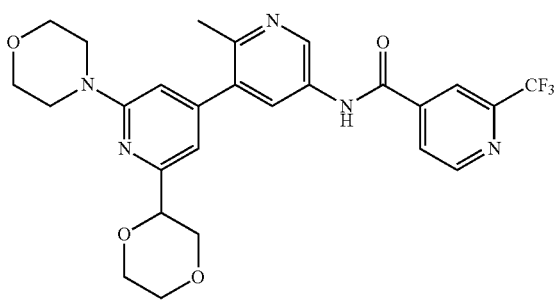 [SMILES: Cc1ncc(NC(=O)c2ccnc(C(F)(F)F)c2)cc1-c1cc(C2COCCO2)nc(N2CCOCC2)c1]

1H NMR (400 MHz, <cd3od>) ppm 2.64 (s, 3H) 3.47-3.54 (m, 1H) 3.55-3.61 (m, 4H) 3.63-3.71 (m, 1H) 3.75-3.83 (m, 5H) 3.85-3.97 (m, 2H) 4.18 (dd, J=11.35, 2.74 Hz, 1H) 4.62 (dd, J=9.98, 2.54 Hz, 1H) 6.77 (s, 1H) 6.92 (s, 1H) 8.18 (d, J=3.91 Hz, 1H) 8.36 (s, 1H) 8.40 (d, J=2.35 Hz, 1H) 8.97 (d, J=5.09 Hz, 1H) 9.28 (d, J=2.35 Hz, 1H). LC/MS (m/z): 530.1 (MH+), Rt=0.72 min.

Example 1166: N-(2'-(1,4-dioxan-2-yl)-2-methyl-6'-morpholino-[3,4'-bipyridin]-5-yl)-2-(1,1-difluoroethyl)isonicotinamide

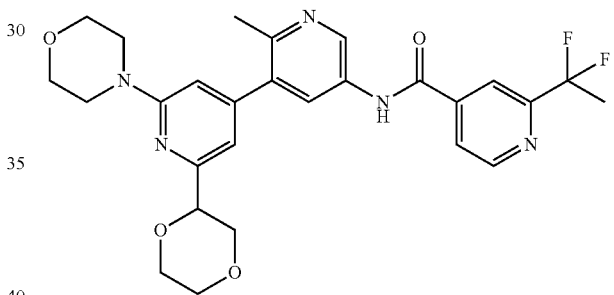

1H NMR (400 MHz, <cd3od>) ppm 2.05 (t, J=18.78 Hz, 3H) 2.64 (s, 3H) 3.46-3.54 (m, 1H) 3.55-3.61 (m, 4H) 3.63-3.71 (m, 1H) 3.75-3.83 (m, 5H) 3.85-3.96 (m, 2H) 4.18 (dd, J=11.74, 2.74 Hz, 1H) 4.62 (dd, J=9.78, 2.74 Hz, 1H) 6.77 (s, 1H) 6.92 (s, 1H) 8.02 (d, J=4.70 Hz, 1H) 8.25 (s, 1H) 8.40 (d, J=2.35 Hz, 1H) 8.86 (d, J=5.09 Hz, 1H) 9.29 (d, J=2.35 Hz, 1H). LC/MS (m/z): 526.2 (MH+), Rt=0.70 min.

Example 1167: N-(2'-(1,4-dioxan-2-yl)-2-methyl-6'-morpholino-[3,4'-bipyridin]-5-yl)-2-(2-fluoropropan-2-yl)isonicotinamide

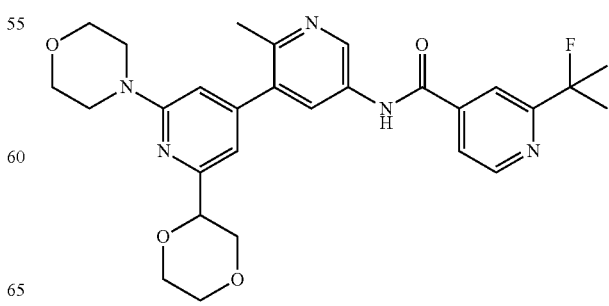

1H NMR (400 MHz, <cd3od>) ppm 1.67-1.80 (m, 6H) 2.66 (s, 3H) 3.50 (dd, J=11.54, 9.98 Hz, 1H) 3.55-3.61 (m, 4H) 3.63-3.70 (m, 1H) 3.75-3.83 (m, 5H) 3.85-3.98 (m, 2H) 4.18 (dd, J=11.35, 2.74 Hz, 1H) 4.63 (dd, J=9.78, 2.74 Hz, 1H) 6.78 (s, 1H) 6.93 (s, 1H) 7.83 (dd, J=5.09, 1.96 Hz, 1H) 8.14 (s, 1H) 8.45 (d, J=2.35 Hz, 1H) 8.76 (d, J=5.09 Hz, 1H) 9.35 (d, J=2.35 Hz, 1H). LC/MS (m/z): 522.2 (MH+), Rt=0.71 min.

Example 1168: N-(2'-(1,4-dioxan-2-yl)-2-methyl-6'-morpholino-[3,4'-bipyridin]-5-yl)-2-(1,1-difluoropropyl)isonicotinamide

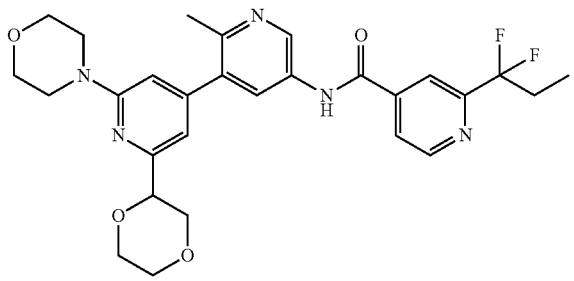 [SMILES: CCC(F)(F)c1cc(C(=O)Nc2cnc(C)c(-c3cc(C4COCCO4)nc(N4CCOCC4)c3)c2)ccn1]

1H NMR (400 MHz, <cd3od>) δ ppm 1.01 (t, J=7.63 Hz, 3H) 2.31-2.47 (m, 2H) 2.65 (s, 3H) 3.50 (dd, J=11.35, 10.17 Hz, 1H) 3.55-3.61 (m, 4H) 3.62-3.71 (m, 1H) 3.75-3.84 (m, 5H) 3.85-3.97 (m, 2H) 4.18 (dd, J=11.74, 2.74 Hz, 1H) 4.62 (dd, J=9.78, 2.74 Hz, 1H) 6.77 (s, 1H) 6.92 (s, 1H) 8.02 (d, J=5.09 Hz, 1H) 8.23 (s, 1H) 8.42 (d, J=2.35 Hz, 1H) 8.88 (d, J=5.09 Hz, 1H) 9.31 (d, J=2.35 Hz, 1H). LC/MS (m/z): 540.2 (MH+), Rt=0.76 min.

Example 1169: N-(2'-(1,4-dioxan-2-yl)-2-methyl-6'-morpholino-[3,4'-bipyridin]-5-yl)-2-cyclopropylisonicotinamide

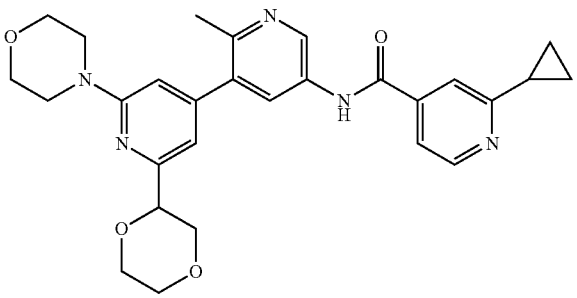 [SMILES: Cc1ncc(NC(=O)c2ccnc(C3CC3)c2)cc1-c1cc(C2COCCO2)nc(N2CCOCC2)c1]

1H NMR (400 MHz, <cd3od>) d ppm 1.10-1.24 (m, 4H) 2.23-2.31 (m, 1H) 2.63 (s, 3H) 3.50 (dd, J=11.35, 10.17 Hz, 1H) 3.54-3.61 (m, 4H) 3.62-3.71 (m, 1H) 3.76-3.84 (m, 5H) 3.84-3.96 (m, 2H) 4.18 (dd, J=11.35, 2.74 Hz, 1H) 4.62 (dd, J=10.17, 2.74 Hz, 1H) 6.77 (s, 1H) 6.91 (s, 1H) 7.76 (dd, J=5.09, 1.57 Hz, 1H) 7.82 (s, 1H) 8.38 (d, J=2.35 Hz, 1H) 8.63 (d, J=5.09 Hz, 1H) 9.27 (d, J=2.35 Hz, 1H). LC/MS (m/z): 502.2 (MH+), Rt=0.58 min.

5-amino-2'-morpholino-[3,4'-bipyridin]-2(1H)-one

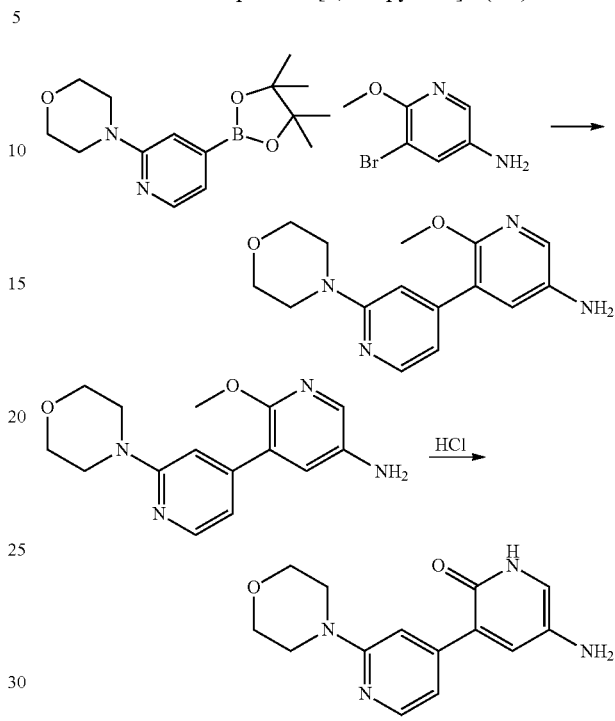

Step 1:
A mixture of 4-(4-(4,4,5,5-tetramethyl-1,3,2-dioxaborolan-2-yl)pyridin-2-yl)morpholine (1.0 equiv.), 5-bromo-6-methoxypyridin-3-amine (1.0 equiv.), sodium carbonate (2 M, 8 equiv.) and PdCl$_2$(dppf) (0.5 equiv.) in DME (0.1 M) were heated to 110° C. for 15 min in the microwave. After removing the DME soluble portion and concentrating, the resulting solid was partitioned between EtOAc and water. The organic phase was washed with brine and then dried over sodium sulfate. After concentration, the crude material was purified via normal phase chromatography. 2-methoxy-2'-morpholino-[3,4'-bipyridin]-5-amine was isolated in 64% yield. LCMS (m/z) (M+H)=287.1, Rt=0.46 min.

Step 2:
2-methoxy-2'-morpholino-[3,4'-bipyridin]-5-amine (1.0 equiv.) was dissolved in a solution of 4 M HCl in dioxane (2.0 equiv.) and heated to 110° C. for 1.5 h in the microwave. The dioxane soluble portion was concentrated and semi-crude 5-amino-2'-morpholino-[3,4'-bipyridin]-2(1H)-one was used in the next step without further purification. LCMS (m/z) (M+H)=273.0, Rt=0.23 min.

6-methyl-2'-morpholino-4-oxo-4H-[1,4'-bipyridine]-3-carboxylic acid

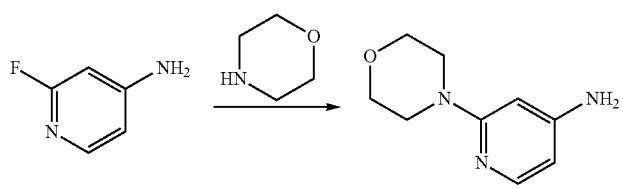

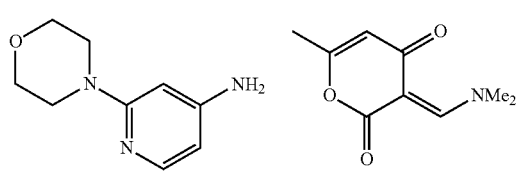 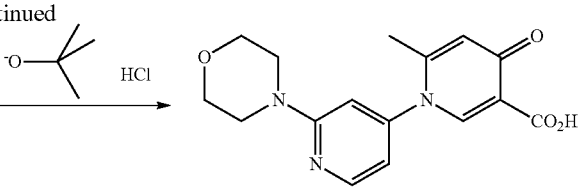

Step 1:

2-fluoropyridin-4-amine (1.0 equiv.) and morpholine (1.4 equiv.) in THF (6 M) were heated to 110° C. for 17 h in an oil bath. The reaction mixture was concentrated and semi-crude 2-morpholinopyridin-4-amine was used in the next step without further purification. LCMS (m/z) (M+H)=180.2, Rt=0.26 min.

Step 2:

To a suspension of 2-morpholinopyridin-4-amine (1.0 equiv.) and (E)-3-((dimethylamino)methylene)-6-methyl-2H-pyran-2,4(3H)-dione (1.0 equiv.) in isopropanol (0.1 M) under an Ar atmosphere was added potassium 2-methylpropan-2-olate. The reaction mixture was heated to reflux for 17 h in an oil bath. The resulting thick orange mixture was concentrated and partitioned between EtOAc and water. The aqueous phase was acidified with 6 N HCl and then extracted twice with EtOAc. The resulting organic phase was dried over sodium sulfate and concentrated to give 6-methyl-2'-morpholino-4-oxo-4H-[1,4'-bipyridine]-3-carboxylic acid in 58% yield. LCMS (m/z) (M+H)=316.0, Rt=0.38 min.

Example 1170: 2-(2-cyanopropan-2-yl)-N-(2-methoxy-2'-morpholino-[3,4'-bipyridin]-5-yl)isonicotinamide

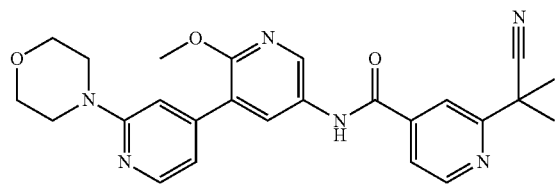 [SMILES: COc1ncc(NC(=O)c2ccnc(C(C)(C)C#N)c2)cc1-c1ccnc(N2CCOCC2)c1]

$^1$H NMR (400 MHz, <dmso>) δ ppm 1.75 (s, 6H) 3.53 (t, J=4.30 Hz, 4H) 3.67-3.76 (m, 4H) 3.90 (s, 3H) 6.98 (d, J=5.48 Hz, 1H) 7.15 (br. s., 1H) 7.88 (dd, J=4.89, 1.37 Hz, 1H) 8.02 (s, 1H) 8.11-8.23 (m, 2H) 8.58 (d, J=2.35 Hz, 1H) 8.82 (d, J=5.09 Hz, 1H) 10.73 (s, 1H). LCMS (m/z) (M+H)=459.3, Rt=0.69 min.

Example 1171: 2-(1,1-difluoroethyl)-N-(2'-morpholino-2-oxo-1,2-dihydro-[3,4'-bipyridin]-5-yl)isonicotinamide

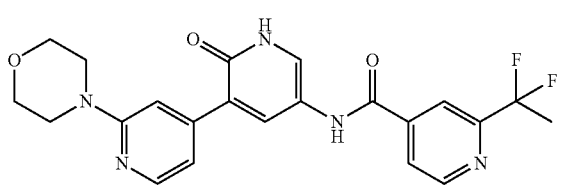 [SMILES: CC(F)(F)c1cc(C(=O)Nc2c[nH]c(=O)c(-c3ccnc(N4CCOCC4)c3)c2)ccn1]

$^1$H NMR (400 MHz, <dmso>) δ ppm 1.94-2.12 (m, 3H) 3.54 (d, J=4.70 Hz, 4H) 3.68-3.79 (m, 4H) 7.19 (d, J=5.48 Hz, 1H) 7.56 (br. s., 1H) 8.00 (d, J=4.70 Hz, 1H) 8.04-8.15 (m, 3H) 8.17 (s, 1H) 8.88 (d, J=5.09 Hz, 1H) 10.54 (s, 1H). LCMS (m/z) (M+H)=442.2, Rt=0.60 min.

Example 1172: N-(2'-morpholino-2-oxo-1,2-dihydro-[3,4'-bipyridin]-5-yl)-2-(trifluoromethyl)isonicotinamide

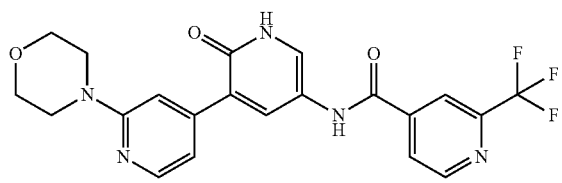 [SMILES: O=C(Nc1c[nH]c(=O)c(-c2ccnc(N3CCOCC3)c2)c1)c1ccnc(C(F)(F)F)c1]

$^1$H NMR (400 MHz, <dmso>) δ ppm 3.53 (d, J=4.30 Hz, 4H) 3.68-3.77 (m, 4H) 7.17 (d, J=4.70 Hz, 1H) 7.52 (br. s., 1H) 8.00-8.14 (m, 3H) 8.17 (d, J=4.70 Hz, 1H) 8.34 (s, 1H) 9.00 (d, J=5.09 Hz, 1H) 10.59 (s, 1H). LCMS (m/z) (M+H)=446.2, Rt=0.61 min.

Example 1173: 2-(2-cyanopropan-2-yl)-N-(2'-morpholino-2-oxo-1,2-dihydro-[3,4'-bipyridin]-5-yl)isonicotinamide

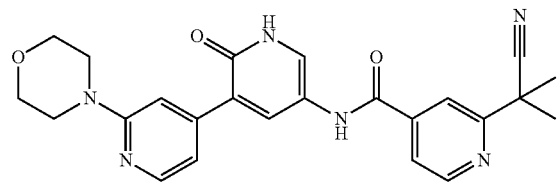 [SMILES: CC(C)(C#N)c1cc(C(=O)Nc2c[nH]c(=O)c(-c3ccnc(N4CCOCC4)c3)c2)ccn1]

$^1$H NMR (400 MHz, <dmso>) δ ppm 1.75 (s, 6H) 3.60 (m, 4H) 3.69-3.79 (m, 4H) 7.05-7.21 (m, 1H) 7.50 (br. s., 1H) 7.84 (dd, J=5.09, 1.57 Hz, 1H) 7.99 (s, 1H) 8.03 (br. s., 1H) 8.06-8.15 (m, 2H) 8.81 (d, J=5.09 Hz, 1H) 10.45 (s, 1H). LCMS (m/z) (M+H)=445.2, Rt=0.59 min.

Example 1174: 3-(difluoromethyl)-N-(2'-morpholino-2-oxo-1,2-dihydro-[3,4'-bipyridin]-5-yl)benzamide

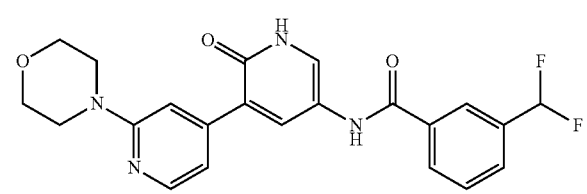 [SMILES: O=C(Nc1c[nH]c(=O)c(-c2ccnc(N3CCOCC3)c2)c1)c1cccc(C(F)F)c1]

$^1$H NMR (400 MHz, <dmso>) δ ppm 3.53 (d, J=4.70 Hz, 4H) 3.65-3.83 (m, 4H) 6.91-7.37 (m, 2H) 7.54 (br. s., 1H) 7.63-7.73 (m, 1H) 7.79 (d, J=7.43 Hz, 1H) 7.98-8.24 (m, 5H) 10.28 (s, 1H). LCMS (m/z) (M+H)=427.1, Rt=0.54 min.

Example 1175: 6-methyl-2'-morpholino-4-oxo-N-(3-(trifluoromethyl)phenyl)-4H-[1,4'-bipyridine]-3-carboxamide
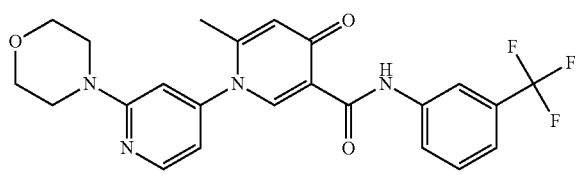 [SMILES: Cc1cc(=O)c(C(=O)Nc2cccc(C(F)(F)F)c2)cn1-c1ccnc(N2CCOCC2)c1]
$^1$H NMR (400 MHz, <dmso>) δ ppm 2.15 (s, 3H) 3.51-3.54 (m, 4H) 3.65-3.73 (m, 4H) 6.66 (s, 1H) 6.85-6.93 (m, 1H) 7.10 (s, 1H) 7.44 (d, J=7.83 Hz, 1H) 7.58 (t, J=8.02 Hz, 1H) 7.78 (d, J=8.22 Hz, 1H) 8.23 (s, 1H) 8.31 (d, J=5.09 Hz, 1H) 8.38 (s, 1H) 12.92 (s, 1H). LCMS (m/z) (M+H)= 459.0, Rt=0.80 min.
The following additional compounds have been made by the methods described herein.
TABLE A
1176
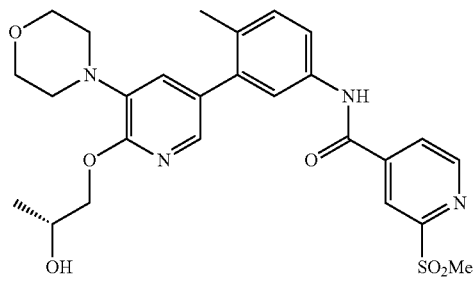 [SMILES: Cc1ccc(NC(=O)c2ccnc(S(C)(=O)=O)c2)cc1-c1cnc(OC[C@@H](C)O)c(N2CCOCC2)c1]
1177
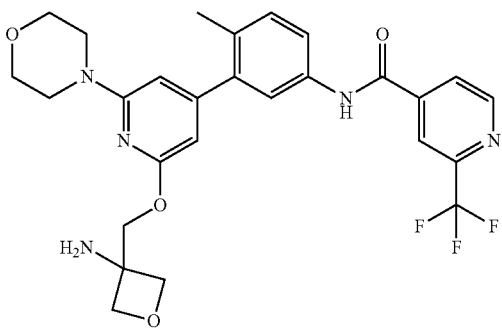 [SMILES: Cc1ccc(NC(=O)c2ccnc(C(F)(F)F)c2)cc1-c1cc(OCC2(N)COC2)nc(N2CCOCC2)c1]
1178
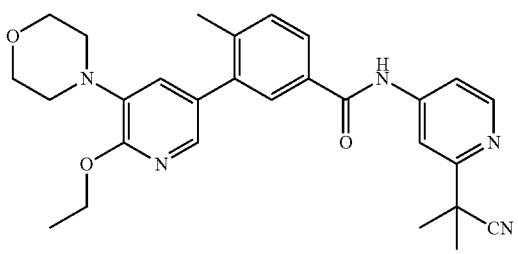 [SMILES: CCOc1ncc(-c2cc(C(=O)Nc3ccnc(C(C)(C)C#N)c3)ccc2C)cc1N1CCOCC1]
1179
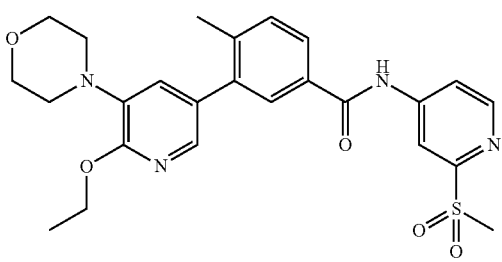 [SMILES: CCOc1ncc(-c2cc(C(=O)Nc3ccnc(S(C)(=O)=O)c3)ccc2C)cc1N1CCOCC1]

TABLE A-continued
1180 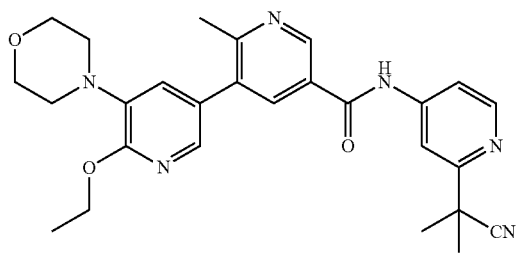 [SMILES: CCOc1ncc(-c2cc(C(=O)Nc3ccnc(C(C)(C)C#N)c3)cnc2C)cc1N1CCOCC1]
1181 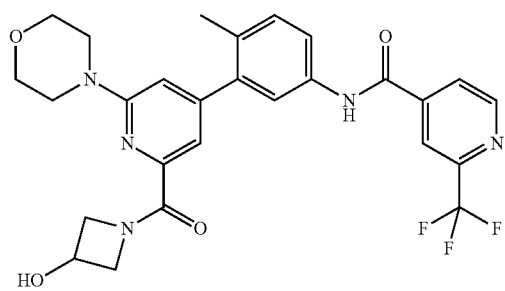 [SMILES: Cc1ccc(NC(=O)c2ccnc(C(F)(F)F)c2)cc1-c1cc(C(=O)N2CC(O)C2)nc(N2CCOCC2)c1]
1182 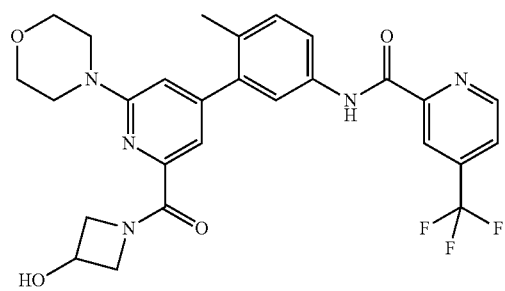 [SMILES: Cc1ccc(NC(=O)c2cc(C(F)(F)F)ccn2)cc1-c1cc(C(=O)N2CC(O)C2)nc(N2CCOCC2)c1]
1183 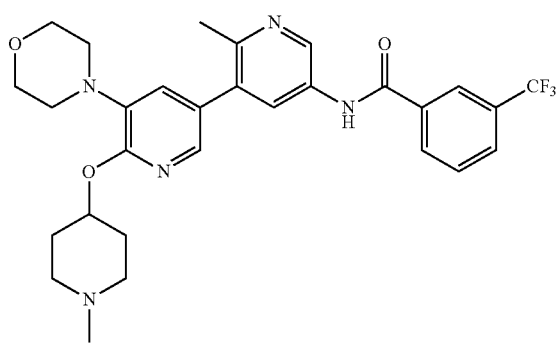 [SMILES: Cc1ncc(NC(=O)c2cccc(C(F)(F)F)c2)cc1-c1cnc(OC2CCN(C)CC2)c(N2CCOCC2)c1]
1184 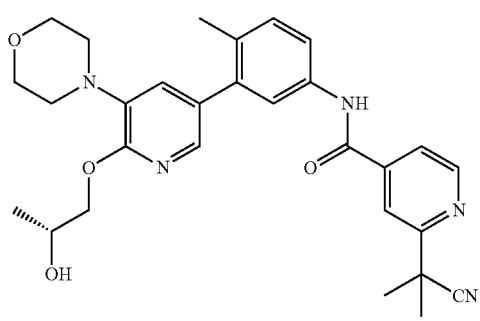 [SMILES: Cc1ccc(NC(=O)c2ccnc(C(C)(C)C#N)c2)cc1-c1cnc(OC[C@@H](C)O)c(N2CCOCC2)c1]

TABLE A-continued
1185
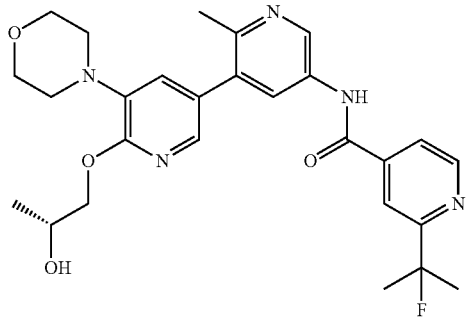 [SMILES: Cc1ncc(NC(=O)c2ccnc(C(C)(C)F)c2)cc1-c1cnc(OC[C@@H](C)O)c(N2CCOCC2)c1]
1186
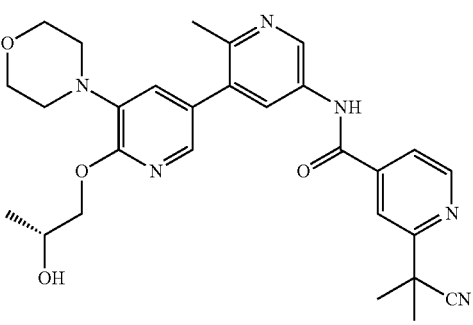 [SMILES: Cc1ncc(NC(=O)c2ccnc(C(C)(C)C#N)c2)cc1-c1cnc(OC[C@@H](C)O)c(N2CCOCC2)c1]
1187
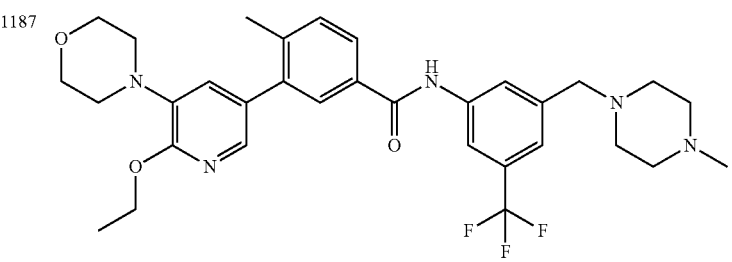
1188
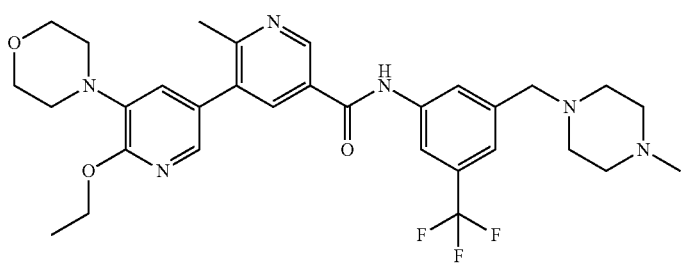 [SMILES: CCOc1ncc(-c2cc(C(=O)Nc3cc(CN4CCN(C)CC4)cc(C(F)(F)F)c3)cnc2C)cc1N1CCOCC1]
1189
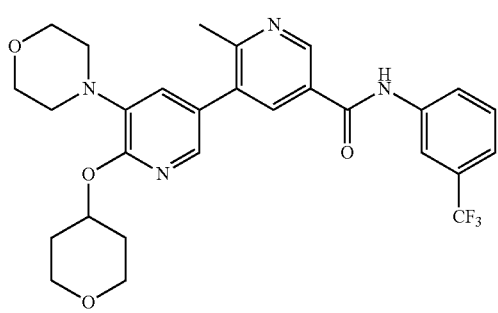 [SMILES: Cc1ncc(C(=O)Nc2cccc(C(F)(F)F)c2)cc1-c1cnc(OC2CCOCC2)c(N2CCOCC2)c1]

TABLE A-continued
1190 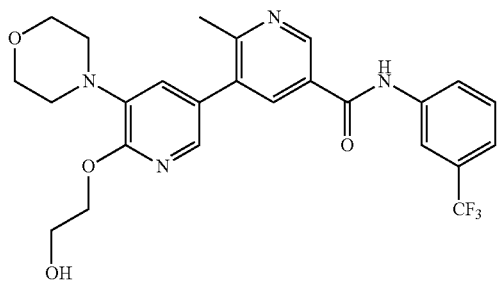 [SMILES: Cc1ncc(C(=O)Nc2cccc(C(F)(F)F)c2)cc1-c1cnc(OCCO)c(N2CCOCC2)c1]
1191 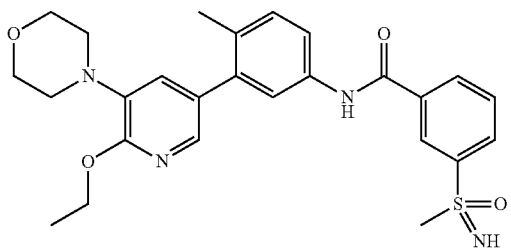 [SMILES: CCOc1ncc(-c2cc(NC(=O)c3cccc(S(C)(=N)=O)c3)ccc2C)cc1N1CCOCC1]
1192 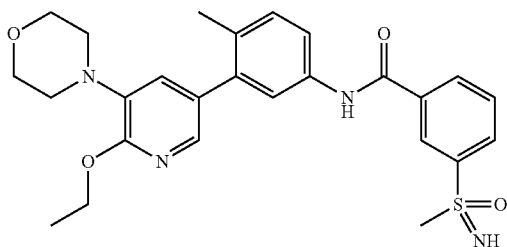 [SMILES: CCOc1ncc(-c2cc(NC(=O)c3cccc(S(C)(=N)=O)c3)ccc2C)cc1N1CCOCC1]
1193 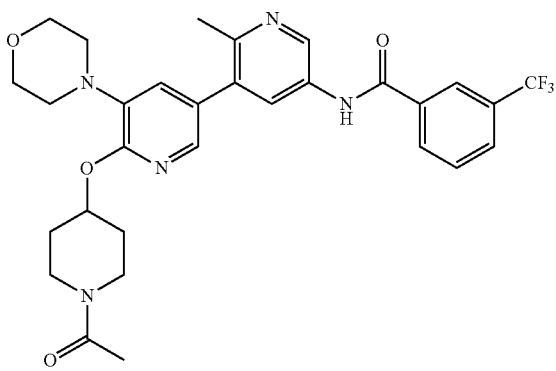 [SMILES: CC(=O)N1CCC(Oc2ncc(-c3cc(NC(=O)c4cccc(C(F)(F)F)c4)cnc3C)cc2N2CCOCC2)CC1]
1194 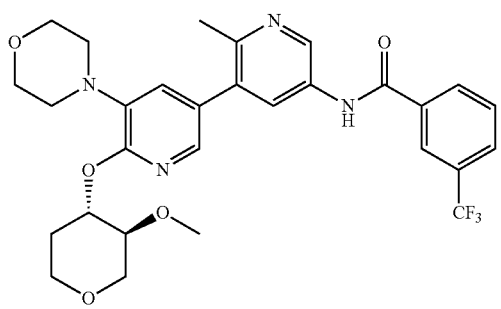 [SMILES: CO[C@H]1COCC[C@@H]1Oc1ncc(-c2cc(NC(=O)c3cccc(C(F)(F)F)c3)cnc2C)cc1N1CCOCC1]

TABLE A-continued
| 1195 | 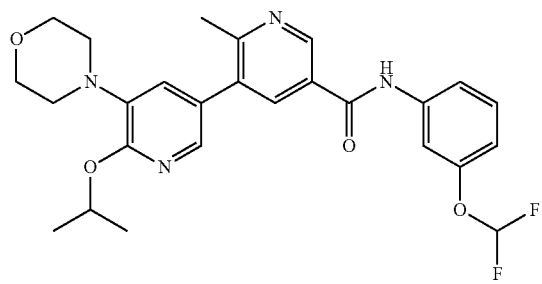 [SMILES: Cc1ncc(C(=O)Nc2cccc(OC(F)F)c2)cc1-c1cnc(OC(C)C)c(N2CCOCC2)c1] |
| 1196 | 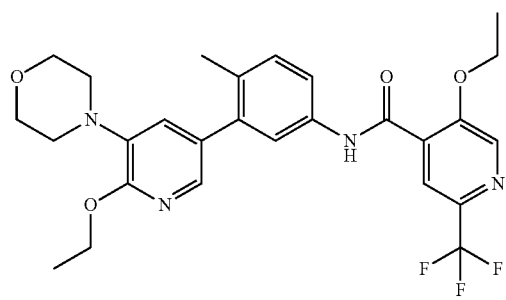 [SMILES: CCOc1cnc(C(F)(F)F)cc1C(=O)Nc1ccc(C)c(-c2cnc(OCC)c(N3CCOCC3)c2)c1] |
| 1197 | 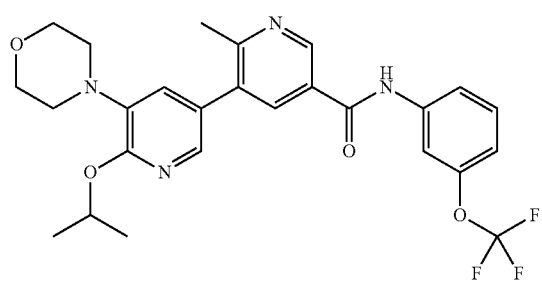 [SMILES: Cc1ncc(C(=O)Nc2cccc(OC(F)(F)F)c2)cc1-c1cnc(OC(C)C)c(N2CCOCC2)c1] |
| 1198 | 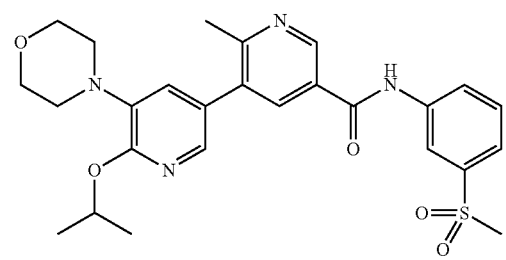 [SMILES: Cc1ncc(C(=O)Nc2cccc(S(C)(=O)=O)c2)cc1-c1cnc(OC(C)C)c(N2CCOCC2)c1] |
| 1199 | 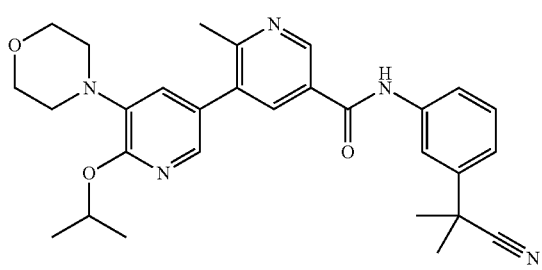 [SMILES: Cc1ncc(C(=O)Nc2cccc(C(C)(C)C#N)c2)cc1-c1cnc(OC(C)C)c(N2CCOCC2)c1] |
| 1200 | 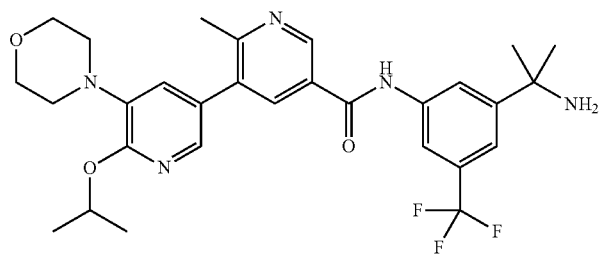 [SMILES: Cc1ncc(C(=O)Nc2cc(C(C)(C)N)cc(C(F)(F)F)c2)cc1-c1cnc(OC(C)C)c(N2CCOCC2)c1] |

TABLE A-continued
| | |
|---|---|
| 1201 | 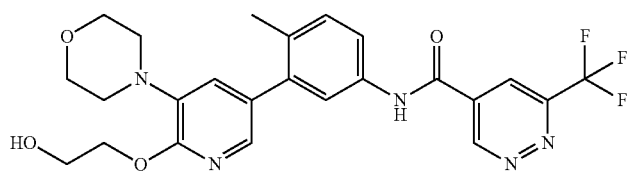 [SMILES: Cc1ccc(NC(=O)c2cnnc(C(F)(F)F)c2)cc1-c1cnc(OCCO)c(N2CCOCC2)c1] |
| 1202 | 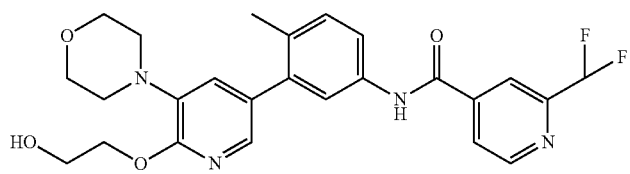 [SMILES: Cc1ccc(NC(=O)c2ccnc(C(F)F)c2)cc1-c1cnc(OCCO)c(N2CCOCC2)c1] |
| 1203 | 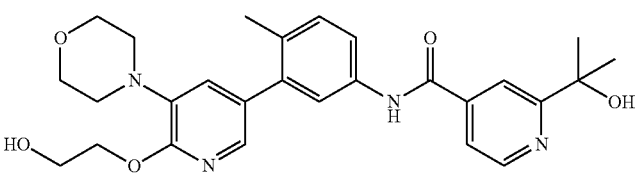 [SMILES: Cc1ccc(NC(=O)c2ccnc(C(C)(C)O)c2)cc1-c1cnc(OCCO)c(N2CCOCC2)c1] |
| 1204 | 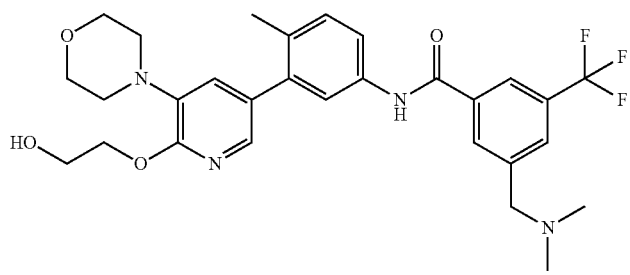 [SMILES: Cc1ccc(NC(=O)c2cc(CN(C)C)cc(C(F)(F)F)c2)cc1-c1cnc(OCCO)c(N2CCOCC2)c1] |
| 1205 | 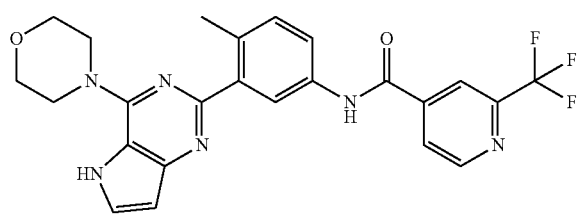 |
| 1206 | 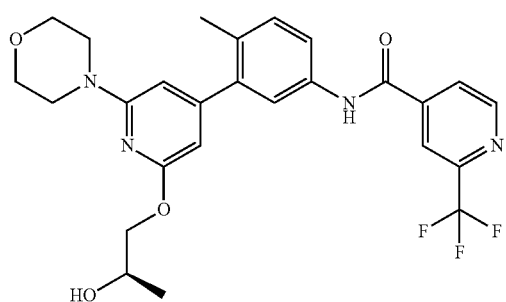 [SMILES: Cc1ccc(NC(=O)c2ccnc(C(F)(F)F)c2)cc1-c1cc(OC[C@@H](C)O)nc(N2CCOCC2)c1] |
| 1207 | 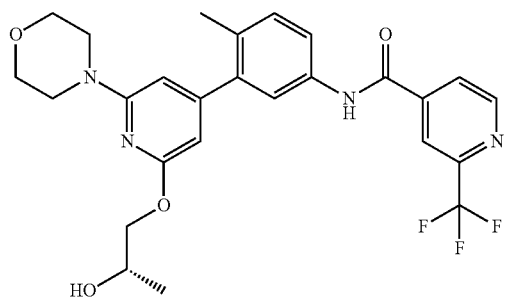 [SMILES: Cc1ccc(NC(=O)c2ccnc(C(F)(F)F)c2)cc1-c1cc(OC[C@H](C)O)nc(N2CCOCC2)c1] |

TABLE A-continued
1208 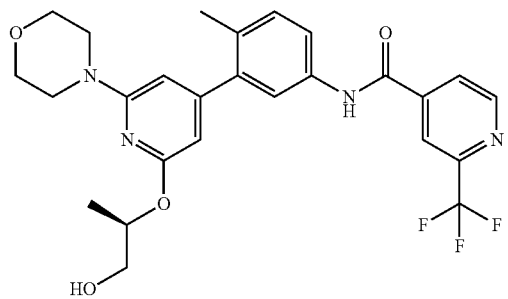 [SMILES: Cc1ccc(NC(=O)c2ccnc(C(F)(F)F)c2)cc1-c1cc(O[C@H](C)CO)nc(N2CCOCC2)c1]
1209 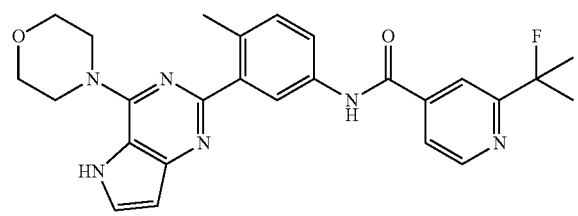 [SMILES: Cc1ccc(NC(=O)c2ccnc(C(C)(C)F)c2)cc1-c1nc(N2CCOCC2)c2[nH]ccc2n1]
1210 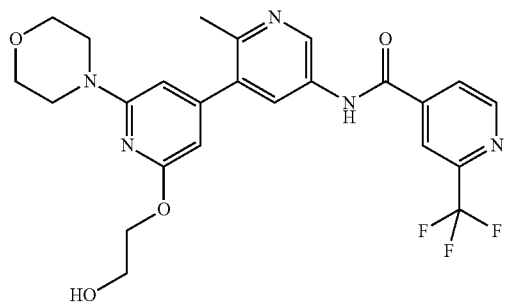 [SMILES: Cc1ncc(NC(=O)c2ccnc(C(F)(F)F)c2)cc1-c1cc(OCCO)nc(N2CCOCC2)c1]
1211 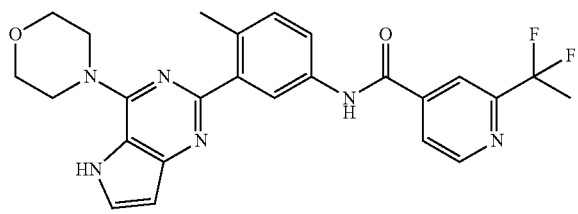
1212 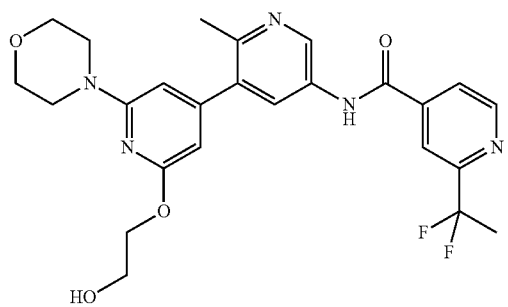 [SMILES: Cc1ncc(NC(=O)c2ccnc(C(C)(F)F)c2)cc1-c1cc(OCCO)nc(N2CCOCC2)c1]

TABLE A-continued
1213 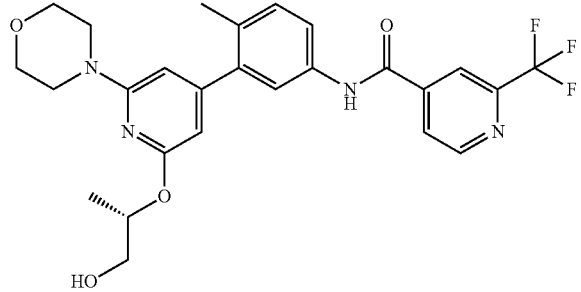 [SMILES: Cc1ccc(NC(=O)c2ccnc(C(F)(F)F)c2)cc1-c1cc(O[C@@H](C)CO)nc(N2CCOCC2)c1]
1214 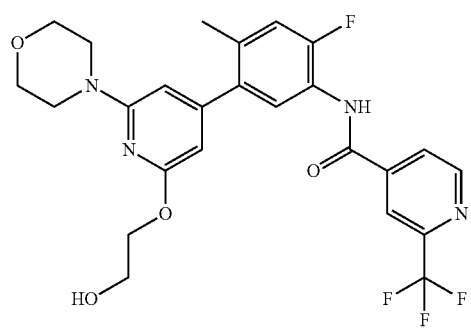 [SMILES: Cc1cc(F)c(NC(=O)c2ccnc(C(F)(F)F)c2)cc1-c1cc(OCCO)nc(N2CCOCC2)c1]
1215 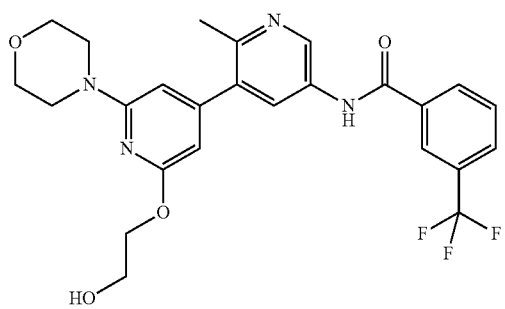 [SMILES: Cc1ncc(NC(=O)c2cccc(C(F)(F)F)c2)cc1-c1cc(OCCO)nc(N2CCOCC2)c1]
1216 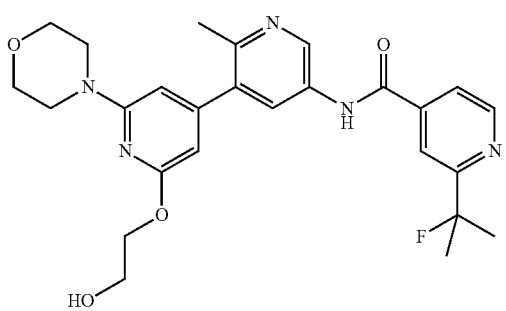 [SMILES: Cc1ncc(NC(=O)c2ccnc(C(C)(C)F)c2)cc1-c1cc(OCCO)nc(N2CCOCC2)c1]
1217 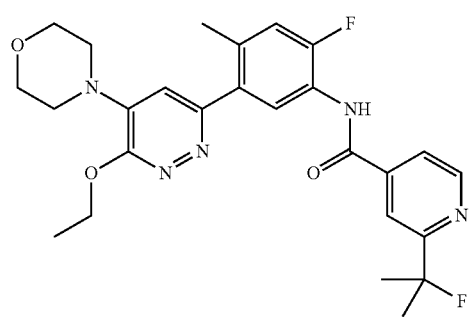 [SMILES: CCOc1nnc(-c2cc(NC(=O)c3ccnc(C(C)(C)F)c3)c(F)cc2C)cc1N1CCOCC1]

TABLE A-continued
1218 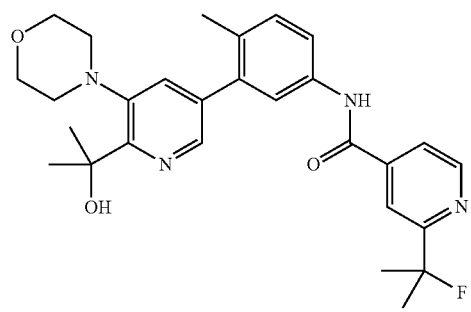 [SMILES: Cc1ccc(NC(=O)c2ccnc(C(C)(C)F)c2)cc1-c1cnc(C(C)(C)O)c(N2CCOCC2)c1]
1219 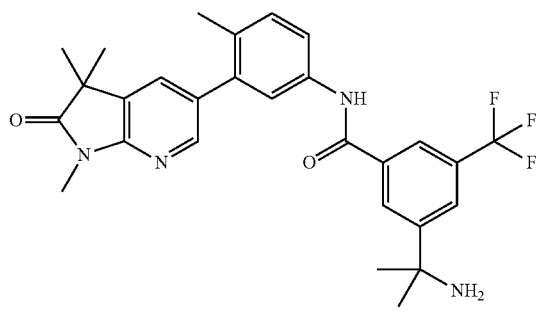 [SMILES: Cc1ccc(NC(=O)c2cc(C(C)(C)N)cc(C(F)(F)F)c2)cc1-c1cnc2c(c1)C(C)(C)C(=O)N2C]
1220 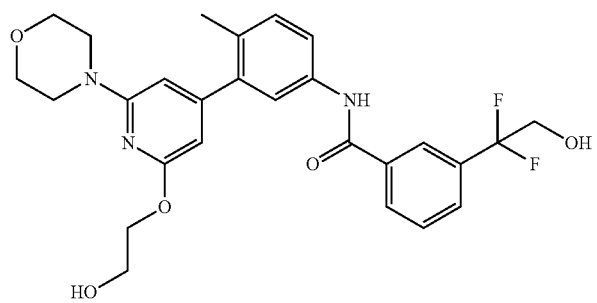 [SMILES: Cc1ccc(NC(=O)c2cccc(C(F)(F)CO)c2)cc1-c1cc(OCCO)nc(N2CCOCC2)c1]
1221 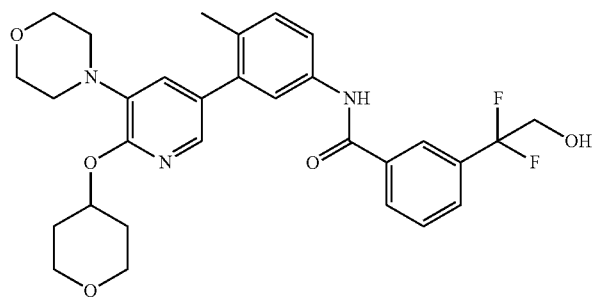 [SMILES: Cc1ccc(NC(=O)c2cccc(C(F)(F)CO)c2)cc1-c1cnc(OC2CCOCC2)c(N2CCOCC2)c1]
1222 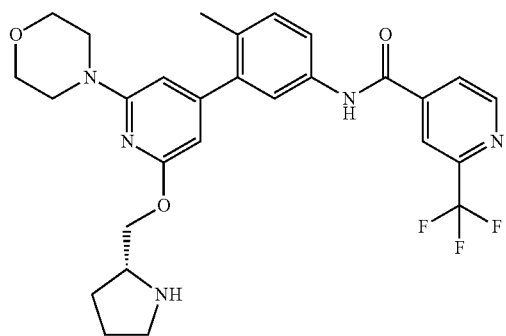 [SMILES: Cc1ccc(NC(=O)c2ccnc(C(F)(F)F)c2)cc1-c1cc(OC[C@H]2CCCN2)nc(N2CCOCC2)c1]

TABLE A-continued
1223 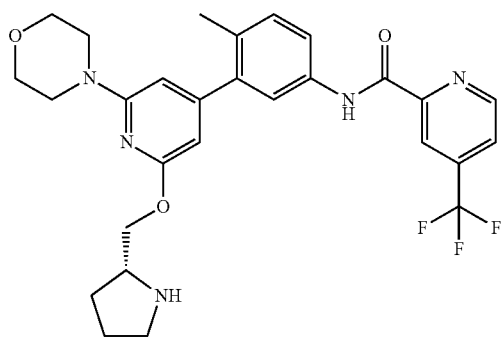 [SMILES: Cc1ccc(NC(=O)c2cc(C(F)(F)F)ccn2)cc1-c1cc(OC[C@H]2CCCN2)nc(N2CCOCC2)c1]
1224 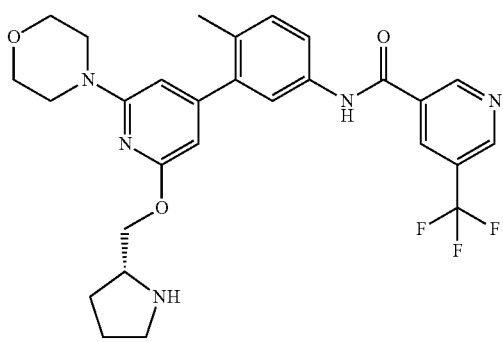 [SMILES: Cc1ccc(NC(=O)c2cncc(C(F)(F)F)c2)cc1-c1cc(OC[C@H]2CCCN2)nc(N2CCOCC2)c1]
1225 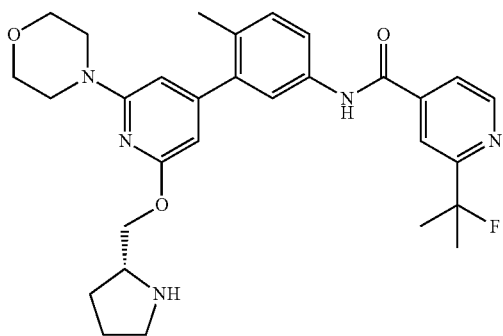 [SMILES: Cc1ccc(NC(=O)c2ccnc(C(C)(C)F)c2)cc1-c1cc(OC[C@H]2CCCN2)nc(N2CCOCC2)c1]
1226 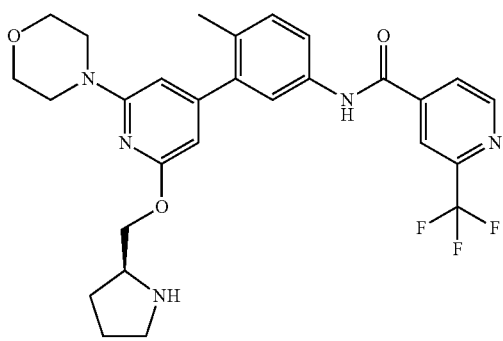 [SMILES: Cc1ccc(NC(=O)c2ccnc(C(F)(F)F)c2)cc1-c1cc(OC[C@@H]2CCCN2)nc(N2CCOCC2)c1]

TABLE A-continued
| 1227 | 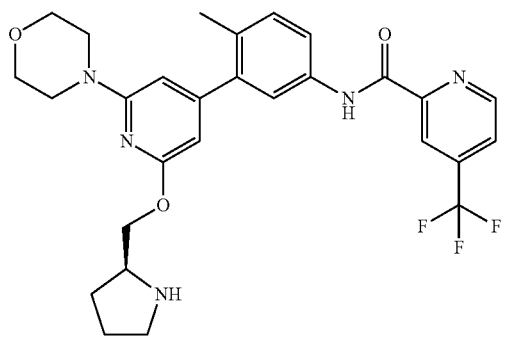 [SMILES: Cc1ccc(NC(=O)c2cc(C(F)(F)F)ccn2)cc1-c1cc(OC[C@@H]2CCCN2)nc(N2CCOCC2)c1] |
| 1228 | 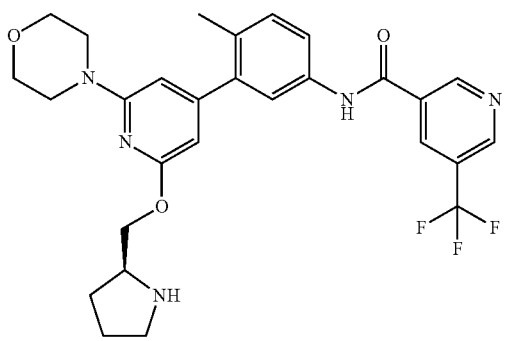 [SMILES: Cc1ccc(NC(=O)c2cncc(C(F)(F)F)c2)cc1-c1cc(OC[C@@H]2CCCN2)nc(N2CCOCC2)c1] |
| 1229 | 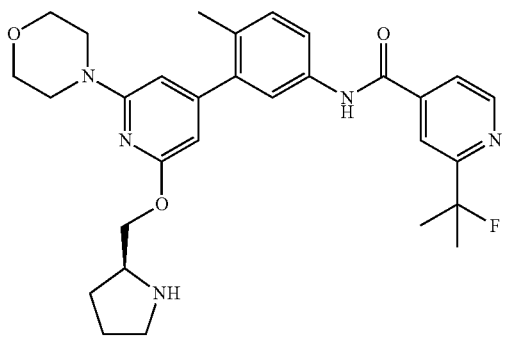 [SMILES: Cc1ccc(NC(=O)c2ccnc(C(C)(C)F)c2)cc1-c1cc(OC[C@@H]2CCCN2)nc(N2CCOCC2)c1] |
| 1230 | 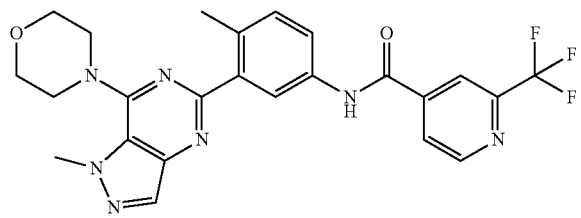 [SMILES: Cc1ccc(NC(=O)c2ccnc(C(F)(F)F)c2)cc1-c1nc(N2CCOCC2)c2c(cnn2C)n1] |
| 1231 | 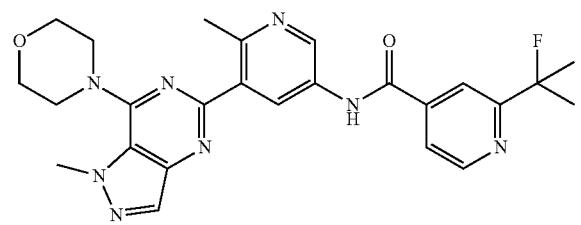 [SMILES: Cc1ncc(NC(=O)c2ccnc(C(C)(C)F)c2)cc1-c1nc(N2CCOCC2)c2c(cnn2C)n1] |

TABLE A-continued

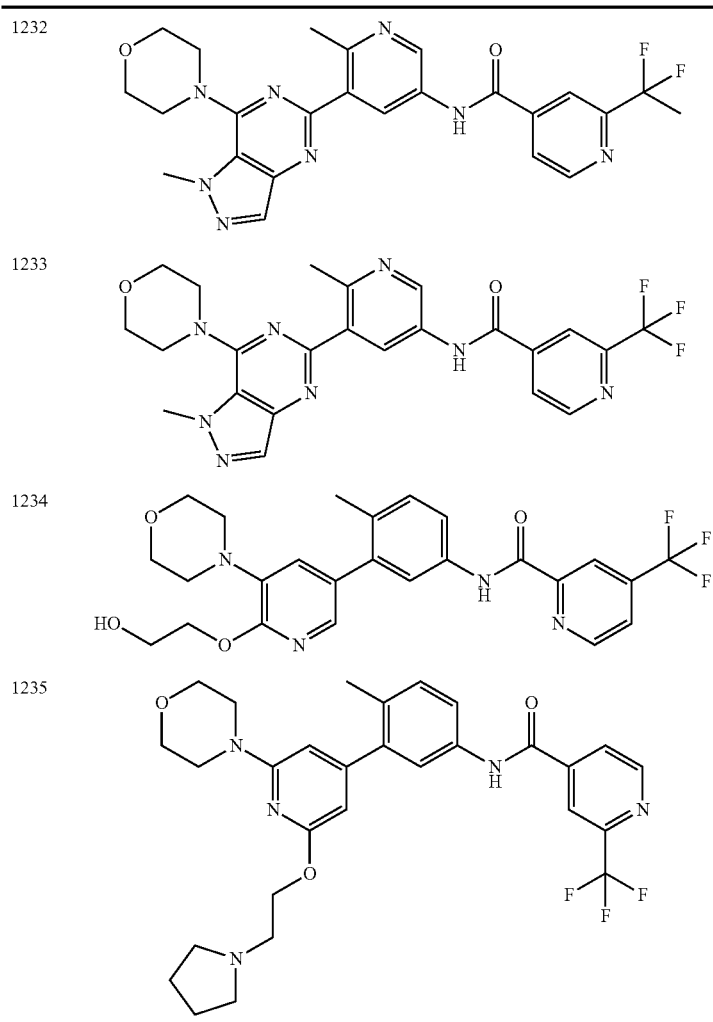

The activity of a compound according to the present invention can be assessed by well-known in vitro & in vivo methods. Raf inhibition data provided herein was obtained using the following procedures.

Example 1236: In Vitro Raf Activity Determination

The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf TR refers to a truncated C-Raf protein, a Δ1-324 deletion mutant.

C-Raf FL refers to the full-length C-Raf protein.

Full length MEK1 with an inactivating K97R ATP binding site mutation is utilized as a RAF substrate. The MEK1 cDNA was subcloned with an N-terminal (his)$_6$ tag into a vector for E. Coli expression. The MEK1 substrate was purified from E. Coli lysate by nickel affinity chromatography followed by anion exchange. The final MEK1 preparation was biotinylated (Pierce EZ-Link Sulfo-NHS-LC-Biotin) and concentrated.

Assay Materials

Assay buffer: 50 mM Tris, pH 7.5, 15 mM MgCl$_2$, 0.01% Bovine Serum Albumin (BSA), 1 mM dithiothreitol (DTT)

Stop buffer: 60 mM ethylenediaminetetraacetic acid (EDTA), 0.01% Tween® 20 b-Raf (V600E), active biotinylated Mek, kinase dead

Alpha Screen detection kit (available from PerkinElmer™, #6760617R)

Anti phospho-MEK1/2 (available from Cell Signaling Technology, Inc. #9121)

384 well low volume assay plates (White Greiner® plates)

Assay Conditions b-Raf (V600E) approximately 4 pM c-Raf approximately 4 nM biotinylated Mek, Kinase dead approximately 10 nM ATP 10 μM for BRAF (V600E) and 1 uM for CRAF Pre-incubation time with compounds 60 minutes at room temperature Reaction time 1 or 3 hours at room temperature Assay Protocol Raf and biotinylated Mek, kinase dead, were combined at 2× final concentrations in assay buffer (50 mM Tris, pH 7.5, 15 mM MgCl$_2$, 0.01% BSA and 1 mM DTT) and dispensed 5 ml per well in assay plates (Greiner white 384 well assay plates #781207) containing 0.25 ml of 40× of a Raf kinase inhibitor test compound diluted in 100% DMSO. The plate was incubated for 60 minutes at room temperature.

The Raf kinase activity reaction was started by the addition of 5 mL per well of 2×ATP diluted in assay buffer. After 3 hours (b-Raf(V600E)) or 1 hour (c-Raf). The reactions were stopped and the phosphorylated product was measured using a rabbit anti-p-MEK (Cell Signaling, #9121) antibody and the Alpha Screen IgG (ProteinA) detection Kit (PerkinElmer #6760617R), by the addition of 10 mL to the well of a mixture of the antibody (1:2000 dilution) and detection beads (1:2000 dilution of both beads) in Stop/bead buffer (25 mM EDTA, 50 mM Tris, pH 7.5, 0.01% Tween20). The additions were carried out under dark conditions to protect the detection beads from light. A lid was placed on top of the plate and incubated for 1 hour at room temperature, then the luminescence was read on a PerkinElmer Envision instrument. The concentration of each compound for 50% inhibition (IC$_{50}$) was calculated by non-linear regression using XL Fit data analysis software.

Using the assays described above, compounds of the invention exhibit inhibitory efficacy as reported in Table 1.

TABLE 1

Selected compound structures and Raf inhibition data: numbering corresponds to the Examples above, most structures are found in the Examples. IC50's are micromolar.

| Ex. No. | Structure | B-Raf IC50 | C-Raf FL IC50 | C-Raf TR IC50 |
|---|---|---|---|---|
| 1 | -structure and name are in the Example- | | 0.000145 | 0.000144 |
| 2 | -structure and name are in the Example- | | 0.001416 | 0.002953 |
| 3 | -structure and name are in the Example- | | 0.000148 | |
| 4 | -structure and name are in the Example- | | 0.000431 | |
| 5 | -structure and name are in the Example- | 0.002996 | 0.000713 | |
| 6 | -structure and name are in the Example- | | | 0.000408 |
| 7 | -structure and name are in the Example- | 0.003146 | 0.001183 | 0.001114 |
| 8 | -structure and name are in the Example- | 0.000837 | 0.000389 | 0.000514 |
| 9 | -structure and name are in the Example- | 0.001587 | 0.000949 | 0.000899 |
| 10 | -structure and name are in the Example- | 0.00033 | 0.000103 | 0.000118 |
| 11 | -structure and name are in the Example- | 0.001481 | 0.000542 | 0.00058 |
| 12 | -structure and name are in the Example- | 0.00182 | 0.000353 | |
| 13 | -structure and name are in the Example- | 0.002168 | 0.000474 | 0.000533 |
| 14 | -structure and name are in the Example- | 0.002007 | 0.000616 | 0.000803 |
| 15 | -structure and name are in the Example- | 0.002224 | 0.00065 | |
| 16 | -structure and name are in the Example- | 0.001521 | 0.000299 | |
| 17 | -structure and name are in the Example- | 0.00305 | 0.000785 | |
| 18 | -structure and name are in the Example- | 0.000456 | 0.000137 | |
| 19 | -structure and name are in the Example- | 0.001851 | 0.000562 | |
| 20 | -structure and name are in the Example- | 0.001967 | 0.000516 | |
| 21 | -structure and name are in the Example- | 0.003433 | 0.000905 | |
| 22 | -structure and name are in the Example- | 0.000652 | 0.000202 | |
| 23 | -structure and name are in the Example- | 0.002416 | 0.00086 | |
| 24 | -structure and name are in the Example- | 0.001356 | 0.000328 | |
| 25 | -structure and name are in the Example- | 0.001197 | 0.000352 | |
| 26 | -structure and name are in the Example- | 0.002177 | 0.000514 | |
| 27 | -structure and name are in the Example- | 0.00086 | 0.00011 | |
| 28 | -structure and name are in the Example- | 0.000585 | 0.000214 | |
| 29 | -structure and name are in the Example- | 0.001306 | 0.000421 | |
| 30 | -structure and name are in the Example- | 0.00083 | 0.000322 | |
| 31 | -structure and name are in the Example- | 0.000737 | 0.00021 | |
| 32 | -structure and name are in the Example- | 0.001695 | 0.00051 | |
| 33 | -structure and name are in the Example- | 0.000455 | 0.000134 | |
| 34 | -structure and name are in the Example- | 0.001853 | 0.000304 | |
| 35 | -structure and name are in the Example- | 0.003454 | 0.000634 | |
| 36 | -structure and name are in the Example- | 0.001277 | 0.000456 | |
| 37 | -structure and name are in the Example- | 0.000773 | 0.000198 | |
| 38 | -structure and name are in the Example- | 0.001429 | 0.000344 | |
| 39 | -structure and name are in the Example- | 0.000816 | 0.000322 | |
| 40 | -structure and name are in the Example- | 0.000601 | 0.000132 | |
| 42 | -structure and name are in the Example- | 0.000422 | 0.00009 | 0.000137 |
| 43 | -structure and name are in the Example- | 0.001648 | 0.000388 | 0.000376 |
| 44 | -structure and name are in the Example- | 0.002875 | 0.000637 | 0.000714 |
| 45 | -structure and name are in the Example- | 0.005678 | 0.001392 | 0.001018 |
| 46 | -structure and name are in the Example- | 0.002118 | 0.000433 | |
| 47 | -structure and name are in the Example- | 0.002454 | 0.000356 | |
| 48 | -structure and name are in the Example- | 0.00143 | 0.000347 | |
| 49 | -structure and name are in the Example- | 0.001495 | 0.000376 | |
| 50 | -structure and name are in the Example- | 0.001131 | 0.00025 | |
| 51 | -structure and name are in the Example- | 0.003162 | 0.000661 | |
| 52 | -structure and name are in the Example- | 0.000884 | 0.000282 | |
| 53 | -structure and name are in the Example- | 0.002499 | 0.000651 | |
| 54 | -structure and name are in the Example- | 0.00314 | 0.000625 | |
| 55 | -structure and name are in the Example- | | | |
| 56 | -structure and name are in the Example- | 0.001001 | 0.000191 | |

TABLE 1-continued

Selected compound structures and Raf inhibition data: numbering corresponds to the Examples above, most structures are found in the Examples. IC50's are micromolar.

| Ex. No. | Structure | B-Raf IC50 | C-Raf FL IC50 | C-Raf TR IC50 |
|---|---|---|---|---|
| 57 | -structure and name are in the Example- | 0.000994 | 0.000179 | |
| 58 | -structure and name are in the Example- | 0.008715 | 0.00103 | |
| 59 | -structure and name are in the Example- | 0.002655 | 0.000432 | |
| 60 | -structure and name are in the Example- | 0.006966 | 0.001007 | |
| 61 | -structure and name are in the Example- | 0.002273 | 0.000314 | |
| 62 | -structure and name are in the Example- | 0.00108 | 0.000161 | |
| 63 | -structure and name are in the Example- | 0.002553 | 0.000436 | 0.000508 |
| 64 | -structure and name are in the Example- | | | 0.000847 |
| 65 | -structure and name are in the Example- | 0.001142 | 0.000187 | |
| 66 | -structure and name are in the Example- | 0.003002 | 0.000711 | |
| 67 | -structure and name are in the Example- | 0.458152 | 0.077922 | |
| 68 | -structure and name are in the Example- | 0.00064 | 0.000124 | |
| 69 | -structure and name are in the Example- | 0.002054 | 0.000396 | |
| 70 | -structure and name are in the Example- | 0.157 | 0.024002 | |
| 71 | -structure and name are in the Example- | 0.599193 | 0.083265 | |
| 72 | -structure and name are in the Example- | 0.639127 | 0.078004 | |
| 73 | -structure and name are in the Example- | 0.001499 | 0.00025 | |
| 74 | -structure and name are in the Example- | | | |
| 75 | -structure and name are in the Example- | 0.000385 | 0.000056 | |
| 76 | -structure and name are in the Example- | 0.003222 | 0.000765 | |
| 77 | -structure and name are in the Example- | 0.000632 | 0.00013 | |
| 78 | -structure and name are in the Example- | 0.00149 | 0.000199 | |
| 79 | -structure and name are in the Example- | 0.101957 | 0.028001 | |
| 80 | -structure and name are in the Example- | 0.030653 | 0.010123 | |
| 81 | -structure and name are in the Example- | 0.014017 | 0.001449 | |
| 82 | -structure and name are in the Example- | 0.014469 | 0.001768 | |
| 83 | -structure and name are in the Example- | 0.002533 | 0.00029 | |
| 84 | -structure and name are in the Example- | 0.002927 | 0.001218 | |
| 85 | -structure and name are in the Example- | 0.010918 | 0.001343 | |
| 86 | -structure and name are in the Example- | 0.00843 | 0.001099 | |
| 87 | -structure and name are in the Example- | 0.012091 | 0.001495 | |
| 88 | -structure and name are in the Example- | 0.037439 | 0.003837 | |
| 89 | -structure and name are in the Example- | >25 | 7.685426 | |
| 90 | -structure and name are in the Example- | >25 | >25 | |
| 91 | -structure and name are in the Example- | 18.594788 | 1.925371 | |
| 92 | -structure and name are in the Example- | | | |
| 93 | -structure and name are in the Example- | 0.000802 | 0.000117 | |
| 94 | -structure and name are in the Example- | 0.005788 | 0.000489 | |
| 95 | -structure and name are in the Example- | 0.013459 | 0.001829 | |
| 96 | -structure and name are in the Example- | 0.001241 | 0.000182 | |
| 97 | -structure and name are in the Example- | 0.009087 | 0.000998 | |
| 98 | -structure and name are in the Example- | 0.025693 | 0.001993 | |
| 99 | -structure and name are in the Example- | 0.00117 | 0.00016 | |
| 100 | -structure and name are in the Example- | 0.004089 | 0.000522 | |
| 101 | -structure and name are in the Example- | 0.002183 | 0.000253 | |
| 102 | -structure and name are in the Example- | 0.028046 | 0.003089 | |
| 103 | -structure and name are in the Example- | 0.018432 | 0.001947 | |
| 104 | -structure and name are in the Example- | 0.038535 | 0.005505 | |
| 106 | -structure and name are in the Example- | 0.001708 | 0.000359 | |
| 107 | -structure and name are in the Example- | 0.001688 | 0.000363 | |
| 108 | -structure and name are in the Example- | 0.006113 | 0.000778 | |
| 109 | -structure and name are in the Example- | 0.005035 | 0.000719 | |
| 110 | -structure and name are in the Example- | 0.002185 | 0.000332 | |
| 111 | -structure and name are in the Example- | | | 0.000403 |
| 112 | -structure and name are in the Example- | 0.002384 | 0.0005 | |
| 113 | -structure and name are in the Example- | 0.001137 | 0.000465 | |
| 114 | -structure and name are in the Example- | 0.001626 | 0.000285 | |
| 115 | -structure and name are in the Example- | 0.012797 | 0.000872 | |
| 116 | -structure and name are in the Example- | 0.010923 | 0.000735 | |
| 117 | -structure and name are in the Example- | 0.002035 | 0.000265 | |
| 118 | -structure and name are in the Example- | 0.001003 | 0.000156 | 0.000308 |
| 119 | -structure and name are in the Example- | | | 0.00027 |
| 120 | -structure and name are in the Example- | 0.001214 | 0.000187 | |
| 121 | -structure and name are in the Example- | 0.004451 | 0.000599 | |
| 122 | -structure and name are in the Example- | 0.003877 | 0.000606 | |
| 123 | -structure and name are in the Example- | 0.023164 | 0.004813 | |
| 124 | -structure and name are in the Example- | 0.082672 | 0.017977 | |
| 125 | -structure and name are in the Example- | 0.022327 | 0.006383 | |
| 126 | -structure and name are in the Example- | 0.00107 | 0.000299 | |
| 127 | -structure and name are in the Example- | 0.001667 | 0.00031 | |
| 128 | -structure and name are in the Example- | 0.003782 | 0.000873 | |
| 129 | -structure and name are in the Example- | 0.013441 | 0.002331 | |
| 130 | -structure and name are in the Example- | 0.00577 | 0.001005 | |

TABLE 1-continued

Selected compound structures and Raf inhibition data: numbering corresponds to the Examples above, most structures are found in the Examples. IC50's are micromolar.

| Ex. No. | Structure | B-Raf IC50 | C-Raf FL IC50 | C-Raf TR IC50 |
|---|---|---|---|---|
| 131 | -structure and name are in the Example- | 0.000483 | 0.000119 | |
| 132 | -structure and name are in the Example- | 0.002708 | 0.000457 | |
| 133 | -structure and name are in the Example- | 0.028875 | 0.001937 | |
| 134 | -structure and name are in the Example- | 0.00364 | 0.000471 | |
| 135 | -structure and name are in the Example- | 0.003957 | 0.000322 | |
| 136 | -structure and name are in the Example- | 0.004173 | 0.000503 | |
| 137 | -structure and name are in the Example- | 0.003792 | 0.000527 | |
| 138 | -structure and name are in the Example- | 0.003112 | 0.000652 | |
| 139 | -structure and name are in the Example- | 0.002454 | 0.000491 | |
| 140 | -structure and name are in the Example- | 0.0025 | 0.000483 | |
| 141 | -structure and name are in the Example- | 0.034633 | 0.005762 | |
| 142 | -structure and name are in the Example- | 0.00223 | 0.000341 | |
| 143 | -structure and name are in the Example- | 0.00998 | 0.002261 | |
| 144 | -structure and name are in the Example- | 0.013851 | 0.002686 | |
| 145 | -structure and name are in the Example- | 0.003786 | 0.000676 | |
| 146 | -structure and name are in the Example- | 0.001918 | 0.000219 | |
| 147 | -structure and name are in the Example- | 0.000756 | 0.000103 | |
| 148 | -structure and name are in the Example- | 0.001889 | 0.000285 | |
| 149 | -structure and name are in the Example- | 0.002181 | 0.000273 | |
| 150 | -structure and name are in the Example- | 0.003933 | 0.000562 | |
| 151 | -structure and name are in the Example- | 0.019733 | 0.002897 | |
| 152 | -structure and name are in the Example- | 0.003295 | 0.000474 | |
| 153 | -structure and name are in the Example- | 0.001023 | 0.000196 | |
| 154 | -structure and name are in the Example- | 0.007186 | 0.001095 | |
| 155 | -structure and name are in the Example- | 0.003831 | 0.000361 | |
| 156 | -structure and name are in the Example- | 0.002484 | 0.000415 | |
| 157 | -structure and name are in the Example- | 0.015761 | 0.002134 | |
| 158 | -structure and name are in the Example- | 0.008383 | 0.000835 | |
| 159 | -structure and name are in the Example- | 0.002618 | 0.000366 | |
| 160 | -structure and name are in the Example- | 0.009738 | 0.00089 | |
| 161 | -structure and name are in the Example- | 0.002648 | 0.000393 | |
| 162 | -structure and name are in the Example- | 0.001835 | 0.000215 | |
| 163 | -structure and name are in the Example- | 0.00769 | 0.000818 | |
| 164 | -structure and name are in the Example- | 0.001575 | 0.000255 | |
| 165 | -structure and name are in the Example- | 0.003127 | 0.000416 | |
| 166 | -structure and name are in the Example- | 0.006933 | 0.000665 | |
| 167 | -structure and name are in the Example- | 0.106629 | 0.007674 | |
| 168 | -structure and name are in the Example- | 0.003139 | 0.000245 | |
| 169 | -structure and name are in the Example- | 0.000775 | 0.00018 | |
| 170 | -structure and name are in the Example- | 0.001278 | 0.000263 | |
| 171 | -structure and name are in the Example- | 0.001254 | 0.000213 | |
| 172 | -structure and name are in the Example- | 0.002908 | 0.000386 | |
| 173 | -structure and name are in the Example- | 0.0118 | 0.000853 | |
| 174 | -structure and name are in the Example- | 0.010049 | 0.002238 | |
| 175 | -structure and name are in the Example- | 0.001542 | 0.00023 | |
| 176 | -structure and name are in the Example- | 0.002474 | 0.000398 | |
| 177 | -structure and name are in the Example- | 0.000706 | 0.000122 | |
| 178 | -structure and name are in the Example- | 0.000862 | 0.000172 | |
| 179 | -structure and name are in the Example- | 0.000905 | 0.00016 | |
| 181 | -structure and name are in the Example- | 0.002664 | 0.000493 | |
| 182 | -structure and name are in the Example- | 0.021222 | 0.002263 | |
| 184 | -structure and name are in the Example- | 0.002202 | 0.000479 | |
| 185 | -structure and name are in the Example- | 0.001819 | 0.000269 | |
| 186 | -structure and name are in the Example- | 0.002242 | 0.000278 | |
| 189 | -structure and name are in the Example- | 0.004735 | 0.000678 | |
| 191 | -structure and name are in the Example- | 0.009525 | 0.001426 | |
| 192 | -structure and name are in the Example- | 0.033857 | 0.002507 | |
| 193 | -structure and name are in the Example- | 0.105813 | 0.011051 | |
| 194 | -structure and name are in the Example- | 0.012407 | 0.002225 | |
| 196 | -structure and name are in the Example- | 0.002191 | 0.000403 | 0.000621 |
| 197 | -structure and name are in the Example- | 0.006733 | 0.001062 | |
| 198 | -structure and name are in the Example- | | | 0.000455 |
| 199 | -structure and name are in the Example- | | | 0.001292 |

TABLE 1-continued

Selected compound structures and Raf inhibition data: numbering corresponds to the Examples above, most structures are found in the Examples. IC50's are micromolar.

| Ex. No. | Structure | B-Raf IC50 | C-Raf FL IC50 | C-Raf TR IC50 |
|---|---|---|---|---|
| 200 | 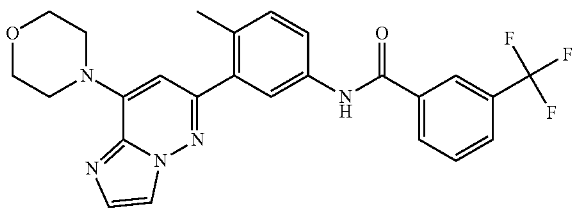 | 0.001538 | 0.000205 | |
| 201 | 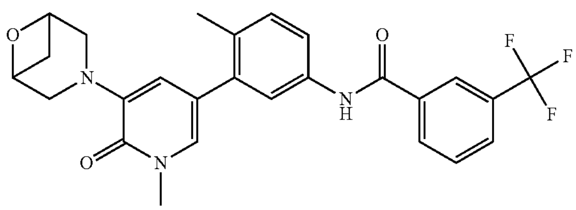 [SMILES: Cc1ccc(NC(=O)c2cccc(C(F)(F)F)c2)cc1-c1cc(N2CC3CC(C2)O3)c(=O)n(C)c1] | 0.014467 | 0.001991 | |
| 202 | 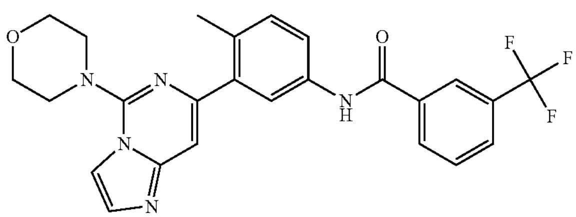 [SMILES: Cc1ccc(NC(=O)c2cccc(C(F)(F)F)c2)cc1-c1cc2nccn2c(N2CCOCC2)n1] | 0.000941 | 0.000155 | |
| 203 | 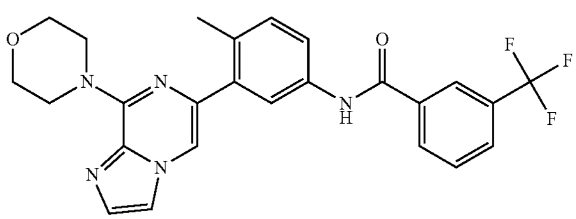 [SMILES: Cc1ccc(NC(=O)c2cccc(C(F)(F)F)c2)cc1-c1cn2ccnc2c(N2CCOCC2)n1] | 0.000389 | 0.000065 | |
| 204 | 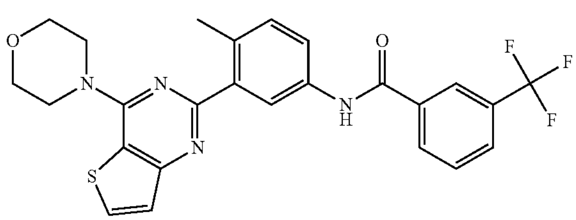 [SMILES: Cc1ccc(NC(=O)c2cccc(C(F)(F)F)c2)cc1-c1nc(N2CCOCC2)c2sccc2n1] | 0.000152 | 0.000039 | |
| 205 | 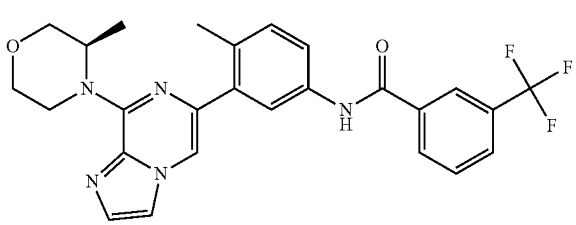 [SMILES: Cc1ccc(NC(=O)c2cccc(C(F)(F)F)c2)cc1-c1cn2ccnc2c(N2CCOC[C@H]2C)n1] | 0.001286 | 0.000185 | |

TABLE 1-continued

Selected compound structures and Raf inhibition data: numbering corresponds to the Examples above, most structures are found in the Examples. IC50's are micromolar.

| Ex. No. | Structure | B-Raf IC50 | C-Raf FL IC50 | C-Raf TR IC50 |
|---|---|---|---|---|
| 206 | 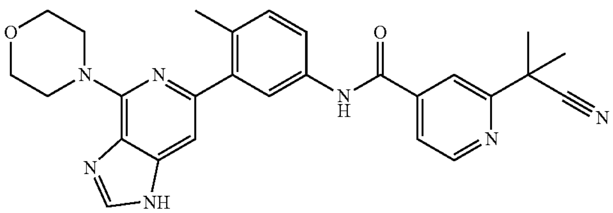 [SMILES: Cc1ccc(NC(=O)c2ccnc(C(C)(C)C#N)c2)cc1-c1cc2[nH]cnc2c(N2CCOCC2)n1] | 0.009218 | 0.001619 | |
| 207 | 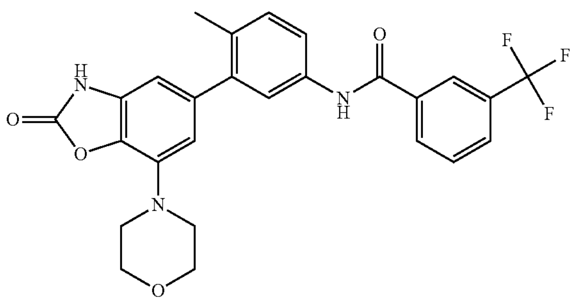 [SMILES: Cc1ccc(NC(=O)c2cccc(C(F)(F)F)c2)cc1-c1cc(N2CCOCC2)c2oc(=O)[nH]c2c1] | 0.001399 | 0.000225 | |
| 208 | 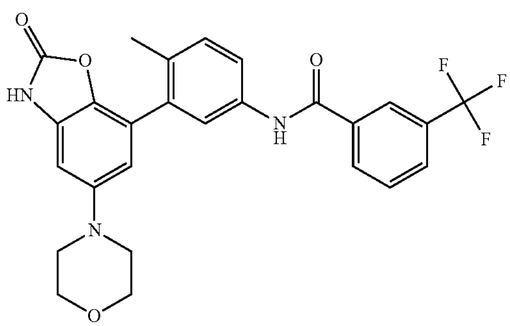 [SMILES: Cc1ccc(NC(=O)c2cccc(C(F)(F)F)c2)cc1-c1cc(N2CCOCC2)cc2[nH]c(=O)oc12] | 0.005048 | 0.001099 | |
| 209 | 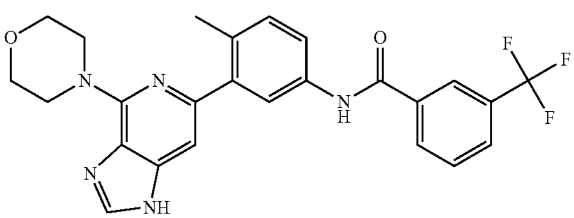 [SMILES: Cc1ccc(NC(=O)c2cccc(C(F)(F)F)c2)cc1-c1cc2[nH]cnc2c(N2CCOCC2)n1] | 0.001067 | 0.000171 | |
| 210 | 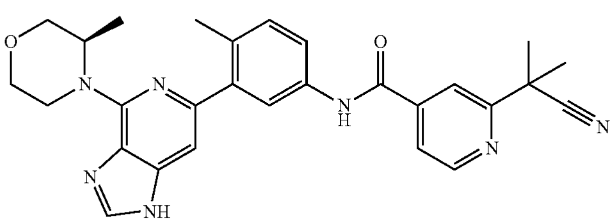 [SMILES: Cc1ccc(NC(=O)c2ccnc(C(C)(C)C#N)c2)cc1-c1cc2[nH]cnc2c(N2CCOC[C@H]2C)n1] | 0.022094 | 0.002729 | |
| 211 | 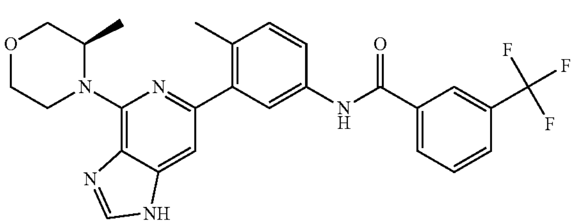 [SMILES: Cc1ccc(NC(=O)c2cccc(C(F)(F)F)c2)cc1-c1cc2[nH]cnc2c(N2CCOC[C@H]2C)n1] | 0.006261 | 0.000873 | |

TABLE 1-continued
Selected compound structures and Raf inhibition data: numbering corresponds to the Examples above, most structures are found in the Examples. IC50's are micromolar.
| Ex. No. | Structure | B-Raf IC50 | C-Raf FL IC50 | C-Raf TR IC50 |
|---|---|---|---|---|
| 212 | 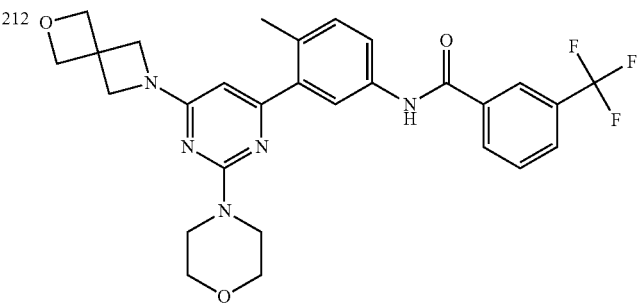 | | | |
| 214 | 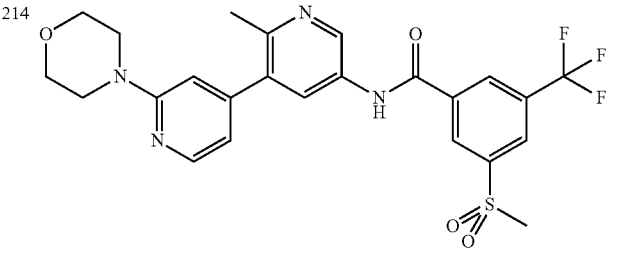 | 0.00483 | 0.000547 | |
| 215 | 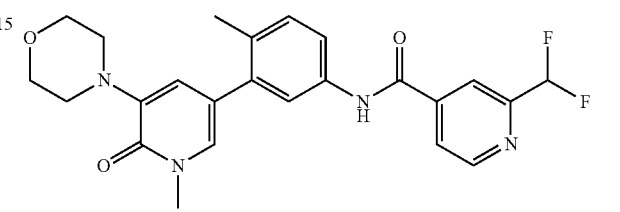 | 0.007267 | 0.000785 | |
| 216 | 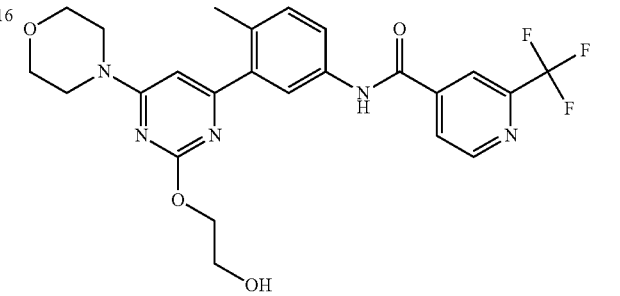 | | | |
| 217 | 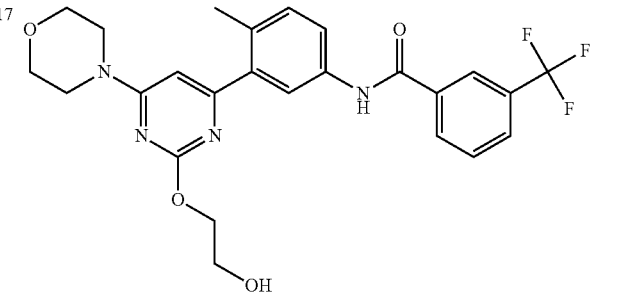 | | | |

TABLE 1-continued

Selected compound structures and Raf inhibition data: numbering corresponds to the Examples above, most structures are found in the Examples. IC50's are micromolar.

| Ex. No. | Structure | B-Raf IC50 | C-Raf FL IC50 | C-Raf TR IC50 |
|---|---|---|---|---|
| 218 | 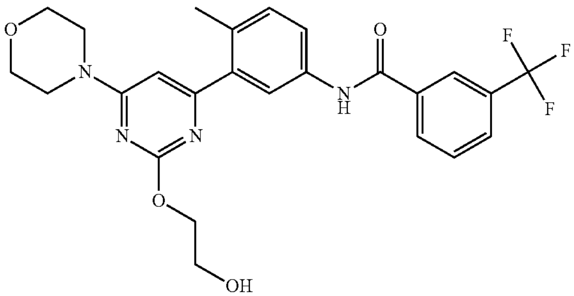 [SMILES: Cc1ccc(NC(=O)c2cccc(C(F)(F)F)c2)cc1-c1cc(N2CCOCC2)nc(OCCO)n1] | | | |
| 219 | 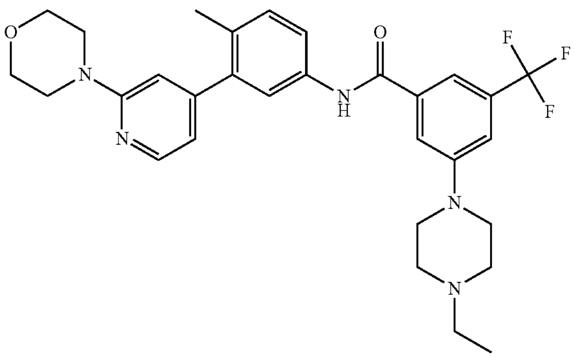 [SMILES: CCN1CCN(c2cc(C(=O)Nc3ccc(C)c(-c4ccnc(N5CCOCC5)c4)c3)cc(C(F)(F)F)c2)CC1] | | 0.002834 | 0.000362 |
| 220 | 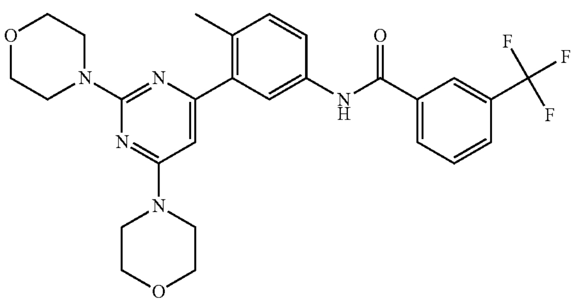 [SMILES: Cc1ccc(NC(=O)c2cccc(C(F)(F)F)c2)cc1-c1cc(N2CCOCC2)nc(N2CCOCC2)n1] | | | |

Additional in vitro Raf inhibition data is provided in the following Table for compounds shown in the synthesis Examples above-compound names and structures are in the Examples. Some of the compounds in the preceding table are also included here, and the associated data in the following table may be from a different repetition of the corresponding assay.

TABLE 2

| Cmpd | b-Raf IC-50 (µM) | c-Raf FL IC-50 (µM) |
|---|---|---|
| Example 1 | 0.00030 | 0.00010 |
| Example 2 | 0.00480 | 0.00180 |
| Example 3 | 0.00050 | 0.00010 |
| Example 4 | 0.00130 | 0.00040 |
| Example 5 | 0.00300 | 0.00070 |
| Example 6 | 0.00130 | 0.00040 |
| Example 7 | 0.00250 | 0.00110 |
| Example 8 | 0.00090 | 0.00050 |
| Example 9 | 0.00150 | 0.00090 |
| Example 10 | 0.00030 | 0.00050 |
| Example 11 | 0.00150 | 0.00060 |
| Example 12 | 0.00180 | 0.00040 |
| Example 13 | 0.00220 | 0.00050 |
| Example 14 | 0.00200 | 0.00070 |
| Example 15 | 0.00220 | 0.00060 |
| Example 16 | 0.00150 | 0.00030 |
| Example 17 | 0.00310 | 0.00080 |
| Example 18 | 0.00050 | 0.00010 |
| Example 19 | 0.00190 | 0.00060 |
| Example 20 | 0.00200 | 0.00050 |
| Example 21 | 0.00400 | 0.00090 |
| Example 22 | 0.00070 | 0.00020 |
| Example 23 | 0.00240 | 0.00060 |
| Example 24 | 0.00140 | 0.00030 |
| Example 25 | 0.00120 | 0.00040 |
| Example 26 | 0.00220 | 0.00050 |
| Example 27 | 0.00090 | 0.00010 |
| Example 28 | 0.00060 | 0.00020 |
| Example 29 | 0.00130 | 0.00040 |

TABLE 2-continued

| Cmpd | b-Raf IC-50 (μM) | c-Raf FL IC-50 (μM) |
|---|---|---|
| Example 30 | 0.00080 | 0.00030 |
| Example 31 | 0.00070 | 0.00020 |
| Example 32 | 0.00170 | 0.00050 |
| Example 33 | 0.00050 | 0.00010 |
| Example 34 | 0.00190 | 0.00030 |
| Example 35 | 0.00350 | 0.00060 |
| Example 36 | 0.00130 | 0.00050 |
| Example 37 | 0.00080 | 0.00020 |
| Example 38 | 0.00140 | 0.00030 |
| Example 39 | 0.00080 | 0.00030 |
| Example 40 | 0.00080 | 0.00020 |
| Example 42 | 0.00160 | 0.00040 |
| Example 43 | 0.00050 | 0.00010 |
| Example 44 | 0.00290 | 0.00070 |
| Example 45 | 0.00570 | 0.00120 |
| Example 46 | 0.00210 | 0.00040 |
| Example 47 | 0.00250 | 0.00040 |
| Example 48 | 0.00140 | 0.00030 |
| Example 49 | 0.00150 | 0.00040 |
| Example 50 | 0.00110 | 0.00030 |
| Example 51 | 0.00320 | 0.00070 |
| Example 52 | 0.00090 | 0.00030 |
| Example 53 | 0.00250 | 0.00070 |
| Example 54 | 0.00310 | 0.00060 |
| Example 55 | 0.00150 | 0.00040 |
| Example 56 | 0.00100 | 0.00020 |
| Example 57 | 0.00100 | 0.00020 |
| Example 58 | 0.00890 | 0.00110 |
| Example 59 | 0.00280 | 0.00040 |
| Example 60 | 0.00730 | 0.00100 |
| Example 61 | 0.00230 | 0.00030 |
| Example 62 | 0.00110 | 0.00020 |
| Example 63 | 0.00210 | 0.00050 |
| Example 64 | 0.00090 | 0.00080 |
| Example 65 | 0.00110 | 0.00020 |
| Example 66 | 0.00300 | 0.00070 |
| Example 67 | 0.50000 | 0.07790 |
| Example 68 | 0.00060 | 0.00010 |
| Example 69 | 0.00210 | 0.00040 |
| Example 70 | 0.20000 | 0.02400 |
| Example 71 | 0.60000 | 0.08330 |
| Example 72 | 0.60000 | 0.07800 |
| Example 73 | 0.00190 | 0.00030 |
| Example 74 | 0.00280 | 0.00040 |
| Example 75 | 0.00040 | 0.00006 |
| Example 76 | 0.00320 | 0.00080 |
| Example 77 | 0.00060 | 0.00010 |
| Example 78 | 0.00150 | 0.00020 |
| Example 79 | 0.10000 | 0.02800 |
| Example 80 | 0.03070 | 0.01010 |
| Example 81 | 0.01400 | 0.00140 |
| Example 82 | 0.01450 | 0.00180 |
| Example 83 | 0.00250 | 0.00030 |
| Example 84 | 0.00290 | 0.00120 |
| Example 85 | 0.01090 | 0.00130 |
| Example 86 | 0.00840 | 0.00110 |
| Example 87 | 0.01270 | 0.00150 |
| Example 88 | 0.03740 | 0.00380 |
| Example 89 | 25.00034 | 7.70000 |
| Example 90 | 25.00034 | 25.00034 |
| Example 91 | 18.60000 | 1.90000 |
| Example 92 | 0.00060 | 0.00060 |
| Example 93 | 0.00080 | 0.00030 |
| Example 94 | 0.00580 | 0.00050 |
| Example 95 | 0.01350 | 0.00180 |
| Example 96 | 0.00120 | 0.00020 |
| Example 97 | 0.00910 | 0.00100 |
| Example 98 | 0.02570 | 0.00200 |
| Example 99 | 0.00120 | 0.00020 |
| Example 100 | 0.00410 | 0.00050 |
| Example 101 | 0.00220 | 0.00030 |
| Example 102 | 0.02800 | 0.00310 |
| Example 103 | 0.01840 | 0.00190 |
| Example 104 | 0.03850 | 0.00550 |
| Example 106 | 0.00170 | 0.00040 |
| Example 107 | 0.00170 | 0.00040 |
| Example 108 | 0.00610 | 0.00080 |
| Example 109 | 0.00500 | 0.00070 |
| Example 110 | 0.00220 | 0.00030 |
| Example 111 | 0.00050 | 0.00040 |
| Example 112 | 0.00240 | 0.00050 |
| Example 113 | 0.00110 | 0.00050 |
| Example 114 | 0.00160 | 0.00030 |
| Example 115 | 0.01280 | 0.00090 |
| Example 116 | 0.01090 | 0.00070 |
| Example 117 | 0.00230 | 0.00040 |
| Example 118 | 0.00070 | 0.00020 |
| Example 119 | 0.00040 | 0.00030 |
| Example 120 | 0.00120 | 0.00020 |
| Example 121 | 0.00450 | 0.00060 |
| Example 122 | 0.00390 | 0.00060 |
| Example 123 | 0.02320 | 0.00480 |
| Example 124 | 0.08270 | 0.01800 |
| Example 125 | 0.02230 | 0.00640 |
| Example 126 | 0.00110 | 0.00030 |
| Example 127 | 0.00190 | 0.00040 |
| Example 128 | 0.00380 | 0.00090 |
| Example 129 | 0.01490 | 0.00360 |
| Example 130 | 0.00580 | 0.00100 |
| Example 131 | 0.00180 | 0.00050 |
| Example 132 | 0.00270 | 0.00050 |
| Example 133 | 0.02890 | 0.00190 |
| Example 134 | 0.00240 | 0.00070 |
| Example 135 | 0.00400 | 0.00030 |
| Example 136 | 0.00420 | 0.00050 |
| Example 137 | 0.00710 | 0.00070 |
| Example 138 | 0.00470 | 0.00080 |
| Example 139 | 0.00250 | 0.00050 |
| Example 140 | 0.00250 | 0.00050 |
| Example 141 | 0.04750 | 0.01020 |
| Example 142 | 0.00220 | 0.00030 |
| Example 143 | 0.01000 | 0.00230 |
| Example 144 | 0.01390 | 0.00270 |
| Example 145 | 0.00300 | 0.00060 |
| Example 146 | 0.00190 | 0.00020 |
| Example 147 | 0.00100 | 0.00010 |
| Example 148 | 0.00190 | 0.00030 |
| Example 149 | 0.00220 | 0.00030 |
| Example 150 | 0.00400 | 0.00060 |
| Example 151 | 0.02000 | 0.00290 |
| Example 152 | 0.00330 | 0.00050 |
| Example 153 | 0.00100 | 0.00020 |
| Example 154 | 0.00730 | 0.00110 |
| Example 155 | 0.00390 | 0.00040 |
| Example 156 | 0.00250 | 0.00040 |
| Example 157 | 0.01580 | 0.00210 |
| Example 158 | 0.00840 | 0.00080 |
| Example 159 | 0.00260 | 0.00040 |
| Example 160 | 0.01060 | 0.00090 |
| Example 161 | 0.00290 | 0.00040 |
| Example 162 | 0.00180 | 0.00020 |
| Example 163 | 0.00570 | 0.00070 |
| Example 164 | 0.00170 | 0.00030 |
| Example 165 | 0.00310 | 0.00040 |
| Example 166 | 0.00690 | 0.00070 |
| Example 167 | 0.05340 | 0.00790 |
| Example 168 | 0.00310 | 0.00020 |
| Example 169 | 0.00080 | 0.00020 |
| Example 170 | 0.00130 | 0.00030 |
| Example 171 | 0.00130 | 0.00020 |
| Example 172 | 0.00290 | 0.00040 |
| Example 173 | 0.00920 | 0.00180 |
| Example 174 | 0.00690 | 0.00150 |
| Example 175 | 0.00150 | 0.00020 |
| Example 176 | 0.00250 | 0.00040 |
| Example 177 | 0.00070 | 0.00010 |
| Example 178 | 0.00090 | 0.00020 |
| Example 179 | 0.00090 | 0.00020 |
| Example 181 | 0.00270 | 0.00050 |
| Example 182 | 0.02120 | 0.00230 |
| Example 184 | 0.00310 | 0.00080 |
| Example 185 | 0.00180 | 0.00030 |
| Example 189 | 0.00470 | 0.00070 |
| Example 190 | 0.00220 | 0.00030 |
| Example 191 | 0.00540 | 0.00110 |
| Example 192 | 0.03390 | 0.00250 |

TABLE 2-continued

| Cmpd | b-Raf IC-50 (μM) | c-Raf FL IC-50 (μM) |
|---|---|---|
| Example 193 | 0.10000 | 0.01120 |
| Example 194 | 0.01320 | 0.00220 |
| Example 196 | 0.00150 | 0.00050 |
| Example 197 | 0.00670 | 0.00110 |
| Example 198 | 0.00080 | 0.00050 |
| Example 199 | 0.00360 | 0.00130 |
| Example 215 | 0.00730 | 0.00080 |
| Example 222 | 0.00380 | 0.00040 |
| Example 223 | 0.00220 | 0.00090 |
| Example 224 | 0.00270 | 0.00090 |
| Example 225 | 0.01230 | 0.00390 |
| Example 226 | 0.00190 | 0.00070 |
| Example 227 | 0.00180 | 0.00040 |
| Example 228 | 0.00470 | 0.00110 |
| Example 229 | 0.00070 | 0.00030 |
| Example 230 | 0.00140 | 0.00040 |
| Example 231 | 0.00040 | 0.00010 |
| Example 232 | 0.00080 | 0.00030 |
| Example 233 | 0.00060 | 0.00020 |
| Example 234 | 0.00100 | 0.00050 |
| Example 235 | 0.00100 | 0.00030 |
| Example 236 | 0.00160 | 0.00060 |
| Example 237 | 0.00040 | 0.00020 |
| Example 238 | 0.00090 | 0.00040 |
| Example 239 | 0.00560 | 0.00210 |
| Example 240 | 0.01530 | 0.00510 |
| Example 241 | 0.00570 | 0.00200 |
| Example 242 | 0.00390 | 0.00180 |
| Example 243 | 0.00530 | 0.00270 |
| Example 244 | 0.00760 | 0.00360 |
| Example 245 | 0.00130 | 0.00060 |
| Example 246 | 0.00120 | 0.00060 |
| Example 247 | 0.00110 | 0.00060 |
| Example 248 | 0.00120 | 0.00040 |
| Example 249 | 0.03650 | 0.00360 |
| Example 250 | 0.00310 | 0.00080 |
| Example 251 | 0.00310 | 0.00050 |
| Example 252 | 0.00310 | 0.00080 |
| Example 253 | 0.00260 | 0.00070 |
| Example 254 | 0.00180 | 0.00050 |
| Example 255 | 0.00560 | 0.00200 |
| Example 256 | 0.00180 | 0.00040 |
| Example 257 | 0.01000 | 0.00350 |
| Example 258 | 0.00830 | 0.00220 |
| Example 259 | 0.00310 | 0.00150 |
| Example 260 | 0.00290 | 0.00080 |
| Example 261 | 0.00180 | 0.00050 |
| Example 262 | 0.00340 | 0.00100 |
| Example 263 | 0.00900 | 0.00330 |
| Example 264 | 0.00860 | 0.00240 |
| Example 265 | 0.00450 | 0.00110 |
| Example 266 | 0.00190 | 0.00050 |
| Example 267 | 0.00110 | 0.00030 |
| Example 268 | 0.00160 | 0.00060 |
| Example 269 | 0.00240 | 0.00090 |
| Example 270 | 0.00050 | 0.00020 |
| Example 271 | 0.00070 | 0.00030 |
| Example 272 | 0.00630 | 0.00270 |
| Example 273 | 0.00270 | 0.00110 |
| Example 274 | 0.00080 | 0.00040 |
| Example 275 | 0.00050 | 0.00020 |
| Example 276 | 0.00040 | 0.00020 |
| Example 277 | 0.00100 | 0.00050 |
| Example 278 | 0.00840 | 0.00240 |
| Example 279 | 3.20000 | 0.80000 |
| Example 280 | 0.00110 | 0.00040 |
| Example 281 | 0.00630 | 0.00160 |
| Example 282 | 0.05300 | 0.01780 |
| Example 283 | 0.00600 | 0.00120 |
| Example 284 | 0.00110 | 0.00040 |
| Example 285 | 0.20000 | 0.05190 |
| Example 286 | 0.20000 | 0.05190 |
| Example 287 | 0.01650 | 0.00400 |
| Example 288 | 0.00600 | 0.00120 |
| Example 289 | 0.01560 | 0.00380 |
| Example 290 | 0.00600 | 0.00140 |
| Example 291 | 0.00230 | 0.00040 |
| Example 292 | 0.00380 | 0.00140 |
| Example 293 | 0.03230 | 0.00660 |
| Example 294 | 0.01080 | 0.00270 |
| Example 295 | 0.00360 | 0.00060 |
| Example 296 | 0.02470 | 0.00490 |
| Example 297 | 0.01880 | 0.00360 |
| Example 298 | 0.00390 | 0.00190 |
| Example 299 | 0.00690 | 0.00270 |
| Example 300 | 0.01460 | 0.00470 |
| Example 301 | 0.00320 | 0.00090 |
| Example 302 | 0.00060 | 0.00020 |
| Example 303 | 0.10000 | 0.01440 |
| Example 304 | 0.00090 | 0.00030 |
| Example 306 | 0.00110 | 0.00060 |
| Example 307 | 0.00060 | 0.00010 |
| Example 308 | 0.00080 | 0.00020 |
| Example 309 | 0.00920 | 0.00460 |
| Example 310 | 0.00180 | 0.00070 |
| Example 311 | 0.00240 | 0.00090 |
| Example 312 | 0.00400 | 0.00110 |
| Example 313 | 0.00700 | 0.00170 |
| Example 314 | 0.00600 | 0.00160 |
| Example 315 | 0.00080 | 0.00030 |
| Example 316 | 0.00310 | 0.00080 |
| Example 317 | 0.00160 | 0.00050 |
| Example 318 | 0.00330 | 0.00080 |
| Example 319 | 0.00120 | 0.00040 |
| Example 320 | 0.00170 | 0.00040 |
| Example 321 | 0.02480 | 0.00850 |
| Example 322 | 0.00110 | 0.00050 |
| Example 323 | 0.01290 | 0.00280 |
| Example 324 | 0.00740 | 0.00140 |
| Example 325 | 0.30000 | 0.06230 |
| Example 326 | 0.00370 | 0.00110 |
| Example 327 | 0.00390 | 0.00100 |
| Example 328 | 0.06240 | 0.01730 |
| Example 329 | 1.10000 | 0.30000 |
| Example 330 | 2.40000 | 1.30000 |
| Example 331 | 0.00390 | 0.00040 |
| Example 332 | 0.02320 | 0.00750 |
| Example 333 | 0.01140 | 0.00150 |
| Example 334 | 0.00230 | 0.00070 |
| Example 335 | 0.00440 | 0.00200 |
| Example 336 | 0.00550 | 0.00130 |
| Example 337 | 0.01250 | 0.00610 |
| Example 338 | 9.00000 | 6.40000 |
| Example 339 | 0.00180 | 0.00070 |
| Example 340 | 0.03640 | 0.00840 |
| Example 341 | 0.00200 | 0.00050 |
| Example 344 | 0.00310 | 0.00050 |
| Example 345 | 0.00160 | 0.00030 |
| Example 346 | 0.00870 | 0.00160 |
| Example 347 | 0.01870 | 0.00330 |
| Example 348 | 0.00270 | 0.00080 |
| Example 349 | 0.00620 | 0.00130 |
| Example 350 | 0.00350 | 0.00040 |
| Example 351 | 0.01950 | 0.00380 |
| Example 352 | 0.00220 | 0.00040 |
| Example 353 | 0.00120 | 0.00020 |
| Example 354 | 0.00100 | 0.00020 |
| Example 355 | 0.00250 | 0.00060 |
| Example 356 | 0.00390 | 0.00080 |
| Example 357 | 0.00340 | 0.00080 |
| Example 358 | 0.00730 | 0.00080 |
| Example 359 | 0.00550 | 0.00040 |
| Example 360 | 0.00600 | 0.00130 |
| Example 361 | 0.00280 | 0.00040 |
| Example 362 | 0.00290 | 0.00040 |
| Example 363 | 0.00380 | 0.00080 |
| Example 364 | 0.00210 | 0.00050 |
| Example 365 | 0.08590 | 0.01330 |
| Example 366 | 0.10000 | 0.01670 |
| Example 367 | 0.01260 | 0.00300 |
| Example 368 | 0.01220 | 0.00250 |
| Example 369 | 0.05310 | 0.01270 |
| Example 371 | 0.00080 | 0.00020 |
| Example 372 | 0.00070 | 0.00020 |
| Example 373 | 1.10000 | 0.20000 |
| Example 374 | 3.40000 | 0.60000 |

TABLE 2-continued

| Cmpd | b-Raf IC-50 (μM) | c-Raf FL IC-50 (μM) |
|---|---|---|
| Example 375 | 0.20000 | 0.04340 |
| Example 376 | 2.80000 | 0.70000 |
| Example 377 | 0.20000 | 0.06190 |
| Example 379 | 0.00590 | 0.00140 |
| Example 380 | 0.01250 | 0.00260 |
| Example 381 | 0.10000 | 0.02550 |
| Example 382 | 0.90000 | 0.30000 |
| Example 383 | 2.80000 | 0.20000 |
| Example 384 | 2.80000 | 0.20000 |
| Example 389 | 0.06420 | 0.01410 |
| Example 390 | 0.00540 | 0.00140 |
| Example 391 | 0.01230 | 0.00450 |
| Example 392 | 0.01530 | 0.00390 |
| Example 393 | 0.00460 | 0.00130 |
| Example 394 | 0.00360 | 0.00100 |
| Example 395 | 0.00980 | 0.00220 |
| Example 396 | 0.01080 | 0.00500 |
| Example 397 | 0.01000 | 0.00340 |
| Example 398 | 0.00840 | 0.00310 |
| Example 399 | 0.04270 | 0.01480 |
| Example 400 | 0.03510 | 0.00330 |
| Example 401 | 0.10000 | 0.01150 |
| Example 402 | 0.10000 | 0.01230 |
| Example 403 | 0.06200 | 0.01020 |
| Example 404 | 0.00430 | 0.00120 |
| Example 405 | 0.00450 | 0.00130 |
| Example 406 | 0.00130 | 0.00040 |
| Example 407 | 0.00140 | 0.00050 |
| Example 408 | 0.00680 | 0.00260 |
| Example 409 | 0.00170 | 0.00030 |
| Example 410 | 0.00200 | 0.00040 |
| Example 411 | 3.10000 | 4.70000 |
| Example 412 | 0.00080 | 0.00020 |
| Example 413 | 0.00040 | 0.00009 |
| Example 414 | 0.00140 | 0.00030 |
| Example 415 | 10.10000 | 6.20000 |
| Example 416 | 1.10000 | 0.20000 |
| Example 417 | 0.00310 | 0.00060 |
| Example 418 | 0.00350 | 0.00090 |
| Example 419 | 0.00430 | 0.00120 |
| Example 420 | 3.60000 | 5.50000 |
| Example 421 | 0.00100 | 0.00020 |
| Example 422 | 0.00370 | 0.00090 |
| Example 423 | 0.00600 | 0.00190 |
| Example 424 | 0.05040 | 0.01430 |
| Example 425 | 0.00260 | 0.00040 |
| Example 426 | 0.00240 | 0.00070 |
| Example 427 | 0.00600 | 0.00120 |
| Example 428 | 0.01010 | 0.00330 |
| Example 429 | 0.03370 | 0.00670 |
| Example 430 | 0.00160 | 0.00060 |
| Example 431 | 0.00370 | 0.00110 |
| Example 432 | 0.09900 | 0.02320 |
| Example 433 | 0.20000 | 0.05580 |
| Example 435 | 0.00240 | 0.00070 |
| Example 436 | 0.00380 | 0.00090 |
| Example 437 | 0.01540 | 0.00490 |
| Example 438 | 0.02760 | 0.00570 |
| Example 439 | 0.00630 | 0.00270 |
| Example 440 | 0.09390 | 0.02250 |
| Example 441 | 0.03320 | 0.00930 |
| Example 442 | 0.06870 | 0.02020 |
| Example 443 | 0.00620 | 0.00170 |
| Example 444 | 0.04480 | 0.01460 |
| Example 445 | 0.01200 | 0.00570 |
| Example 446 | 0.10000 | 0.02910 |
| Example 451 | 0.08370 | 0.01410 |
| Example 452 | 0.00230 | 0.00050 |
| Example 453 | 0.00430 | 0.00110 |
| Example 454 | 0.00190 | 0.00050 |
| Example 455 | 0.00280 | 0.00070 |
| Example 456 | 0.00330 | 0.00080 |
| Example 457 | 0.03050 | 0.00630 |
| Example 460 | 0.01590 | 0.00310 |
| Example 461 | 0.01100 | 0.00210 |
| Example 462 | 0.00370 | 0.00070 |
| Example 464 | 0.01680 | 0.00210 |
| Example 465 | 0.10000 | 0.01500 |
| Example 466 | 0.00550 | 0.00140 |
| Example 467 | 0.01210 | 0.00240 |
| Example 469 | 0.00310 | 0.00060 |
| Example 470 | 0.00450 | 0.00100 |
| Example 471 | 0.00100 | 0.00020 |
| Example 472 | 0.00210 | 0.00050 |
| Example 473 | 0.01210 | 0.00370 |
| Example 474 | 0.00220 | 0.00060 |
| Example 475 | 0.00080 | 0.00010 |
| Example 476 | 0.00060 | 0.00010 |
| Example 477 | 0.00040 | 0.00020 |
| Example 478 | 0.00250 | 0.00040 |
| Example 479 | 0.00180 | 0.00030 |
| Example 480 | 0.00060 | 0.00010 |
| Example 481 | 0.00120 | 0.00030 |
| Example 482 | 0.00060 | 0.00020 |
| Example 483 | 0.00350 | 0.00090 |
| Example 484 | 0.00040 | 0.00010 |
| Example 485 | 0.00110 | 0.00040 |
| Example 486 | 0.00110 | 0.00030 |
| Example 487 | 0.00280 | 0.00080 |
| Example 488 | 0.00190 | 0.00040 |
| Example 489 | 0.00240 | 0.00080 |
| Example 490 | 0.00250 | 0.00040 |
| Example 491 | 0.00210 | 0.00040 |
| Example 492 | 0.00300 | 0.00050 |
| Example 493 | 0.00410 | 0.00080 |
| Example 494 | 0.01680 | 0.00370 |
| Example 495 | 0.00450 | 0.00100 |
| Example 496 | 0.00090 | 0.00020 |
| Example 497 | 0.00280 | 0.00050 |
| Example 498 | 0.00570 | 0.00070 |
| Example 499 | 0.02190 | 0.00350 |
| Example 500 | 0.00560 | 0.00130 |
| Example 501 | 0.03220 | 0.00830 |
| Example 502 | 0.02000 | 0.00540 |
| Example 503 | 0.20000 | 0.06250 |
| Example 504 | 0.02100 | 0.00530 |
| Example 505 | 0.00580 | 0.00140 |
| Example 506 | 0.00180 | 0.00040 |
| Example 507 | 0.02060 | 0.00420 |
| Example 508 | 0.00780 | 0.00270 |
| Example 509 | 0.01730 | 0.00380 |
| Example 510 | 0.00750 | 0.00140 |
| Example 511 | 0.00640 | 0.00130 |
| Example 512 | 0.05980 | 0.01560 |
| Example 513 | 0.00240 | 0.00070 |
| Example 514 | 0.00110 | 0.00040 |
| Example 515 | 0.00450 | 0.00110 |
| Example 516 | 0.01770 | 0.00650 |
| Example 517 | 0.00120 | 0.00040 |
| Example 518 | 0.07900 | 0.03710 |
| Example 519 | 0.00060 | 0.00010 |
| Example 520 | 0.00210 | 0.00050 |
| Example 521 | | |
| Example 522 | 0.00250 | 0.00060 |
| Example 523 | 0.00370 | 0.00080 |
| Example 524 | 0.04120 | 0.01360 |
| Example 525 | 0.00380 | 0.00070 |
| Example 526 | 0.04970 | 0.00940 |
| Example 527 | 0.00560 | 0.00100 |
| Example 528 | 0.01520 | 0.00400 |
| Example 529 | 0.07610 | 0.02620 |
| Example 530 | 0.05130 | 0.01650 |
| Example 531 | 0.00500 | 0.00080 |
| Example 532 | 0.00770 | 0.00120 |
| Example 533 | 0.00440 | 0.00060 |
| Example 534 | 0.00600 | 0.00110 |
| Example 535 | 0.04550 | 0.00410 |
| Example 536 | | |
| Example 537 | 0.00440 | 0.00060 |
| Example 538 | 0.00120 | 0.00030 |
| Example 539 | 0.00280 | 0.00080 |
| Example 540 | 0.01260 | 0.00220 |
| Example 541 | 0.00550 | 0.00090 |
| Example 542 | 0.00770 | 0.00170 |
| Example 543 | 0.01690 | 0.00310 |
| Example 544 | 0.00640 | 0.00130 |

TABLE 2-continued

| Cmpd | b-Raf IC-50 (μM) | c-Raf FL IC-50 (μM) |
|---|---|---|
| Example 540 | 0.01250 | 0.00210 |
| Example 541 | 0.00290 | 0.00070 |
| Example 542 | 0.00360 | 0.00070 |
| Example 543 | 0.00740 | 0.00130 |
| Example 544 | 0.00310 | 0.00050 |
| Example 545 | 0.01650 | 0.00390 |
| Example 546 | 0.00500 | 0.00080 |
| Example 547 | 0.00100 | 0.00030 |
| Example 548 | 0.00110 | 0.00030 |
| Example 549 | 0.00210 | 0.00050 |
| Example 550 | 0.00120 | 0.00040 |
| Example 551 | 0.00120 | 0.00050 |
| Example 552 | 0.00300 | 0.00080 |
| Example 553 | 0.00120 | 0.00040 |
| Example 554 | 0.00120 | 0.00050 |
| Example 555 | 0.00300 | 0.00080 |
| Example 556 | 0.00390 | 0.00150 |
| Example 557 | 0.00540 | 0.00220 |
| Example 558 | 0.00210 | 0.00070 |
| Example 559 | 0.00090 | 0.00030 |
| Example 560 | 0.00100 | 0.00030 |
| Example 561 | 0.00030 | 0.00010 |
| Example 562 | 0.00060 | 0.00020 |
| Example 563 | 0.00060 | 0.00020 |
| Example 564 | 0.00130 | 0.00040 |
| Example 565 | 0.00130 | 0.00040 |
| Example 566 | 0.00070 | 0.00020 |
| Example 567 | 0.00200 | 0.00080 |
| Example 568 | 0.00070 | 0.00020 |
| Example 569 | 0.00280 | 0.00080 |
| Example 570 | 0.00080 | 0.00030 |
| Example 571 | 0.00250 | 0.00080 |
| Example 572 | 0.00380 | 0.00100 |
| Example 573 | 0.00080 | 0.00020 |
| Example 574 | 0.00220 | 0.00080 |
| Example 575 | 0.00290 | 0.00090 |
| Example 576 | 0.00350 | 0.00110 |
| Example 577 | 0.00060 | 0.00020 |
| Example 578 | 0.00080 | 0.00020 |
| Example 579 | 0.00060 | 0.00020 |
| Example 580 | 0.00050 | 0.00010 |
| Example 581 | 0.00220 | 0.00070 |
| Example 582 | 0.00080 | 0.00020 |
| Example 583 | 0.00130 | 0.00030 |
| Example 584 | 0.00120 | 0.00030 |
| Example 585 | 0.00140 | 0.00040 |
| Example 586 | 0.00100 | 0.00020 |
| Example 587 | 0.00110 | 0.00030 |
| Example 588 | 0.00220 | 0.00070 |
| Example 589 | 0.00150 | 0.00040 |
| Example 590 | 0.00090 | 0.00020 |
| Example 591 | 0.00210 | 0.00060 |
| Example 592 | 0.00070 | 0.00020 |
| Example 593 | 0.00060 | 0.00020 |
| Example 594 | 0.00080 | 0.00020 |
| Example 595 | 0.00060 | 0.00020 |
| Example 596 | 0.00130 | 0.00030 |
| Example 597 | 0.00050 | 0.00020 |
| Example 598 | 0.00110 | 0.00050 |
| Example 599 | 0.00050 | 0.00020 |
| Example 600 | 0.00080 | 0.00030 |
| Example 601 | 0.00110 | 0.00030 |
| Example 602 | 0.00120 | 0.00030 |
| Example 603 | 0.00270 | 0.00090 |
| Example 604 | 0.00230 | 0.00060 |
| Example 605 | 0.00270 | 0.00100 |
| Example 606 | 0.00350 | 0.00130 |
| Example 607 | 0.00470 | 0.00150 |
| Example 608 | 0.00490 | 0.00200 |
| Example 609 | 0.00090 | 0.00030 |
| Example 610 | 0.00450 | 0.00150 |
| Example 611 | 0.00130 | 0.00050 |
| Example 612 | 0.00180 | 0.00070 |
| Example 613 | 0.01000 | 0.00360 |
| Example 614 | 0.00420 | 0.00290 |
| Example 615 | 0.01230 | 0.00860 |
| Example 616 | 0.00160 | 0.00040 |
| Example 617 | 0.00350 | 0.00100 |
| Example 618 | 0.00500 | 0.00440 |
| Example 619 | 0.00160 | 0.00050 |
| Example 620 | 0.00190 | 0.00050 |
| Example 621 | 0.00260 | 0.00070 |
| Example 622 | 0.00490 | 0.00120 |
| Example 623 | 0.05670 | 0.00930 |
| Example 624 | 0.00470 | 0.00150 |
| Example 625 | 0.07680 | 0.01260 |
| Example 626 | 0.01400 | 0.00380 |
| Example 627 | 0.00370 | 0.00110 |
| Example 628 | 0.00180 | 0.00040 |
| Example 629 | 0.00120 | 0.00040 |
| Example 630 | 0.00290 | 0.00080 |
| Example 631 | 0.00270 | 0.00080 |
| Example 632 | 0.00750 | 0.00180 |
| Example 633 | 0.00720 | 0.00220 |
| Example 634 | 0.01710 | 0.00360 |
| Example 635 | 0.01880 | 0.00660 |
| Example 636 | 0.00130 | 0.00040 |
| Example 637 | 0.02490 | 0.00550 |
| Example 638 | 0.00960 | 0.00210 |
| Example 639 | 0.00730 | 0.00140 |
| Example 640 | 0.00540 | 0.00110 |
| Example 641 | 0.00270 | 0.00070 |
| Example 642 | 0.00140 | 0.00040 |
| Example 643 | 0.00130 | 0.00030 |
| Example 644 | 0.00290 | 0.00090 |
| Example 645 | 0.05340 | 0.00790 |
| Example 646 | 0.00840 | 0.00310 |
| Example 647 | 0.00530 | 0.00150 |
| Example 648 | 0.00450 | 0.00120 |
| Example 649 | 0.00460 | 0.00120 |
| Example 650 | 0.00470 | 0.00070 |
| Example 651 | 0.00690 | 0.00070 |
| Example 652 | 0.00670 | 0.00050 |
| Example 653 | 0.00310 | 0.00040 |
| Example 654 | 0.00170 | 0.00040 |
| Example 655 | 0.00220 | 0.00030 |
| Example 656 | 0.00100 | 0.00030 |
| Example 657 | 0.00110 | 0.00030 |
| Example 658 | 0.00310 | 0.00020 |
| Example 659 | 0.00070 | 0.00010 |
| Example 660 | | |
| Example 661 | 0.00430 | 0.00090 |
| Example 662 | 0.00390 | 0.00130 |
| Example 663 | 0.00920 | 0.00210 |
| Example 664 | 0.00290 | 0.00060 |
| Example 665 | 0.00670 | 0.00210 |
| Example 666 | 0.00780 | 0.00240 |
| Example 667 | 0.00340 | 0.00110 |
| Example 668 | 0.00410 | 0.00120 |
| Example 669 | 0.01000 | 0.00250 |
| Example 670 | 0.00280 | 0.00090 |
| Example 671 | 0.02550 | 0.00680 |
| Example 672 | 0.01580 | 0.00350 |
| Example 673 | 0.00630 | 0.00270 |
| Example 674 | 0.00370 | 0.00100 |
| Example 675 | 0.00490 | 0.00140 |
| Example 676 | 0.00240 | 0.00070 |
| Example 677 | 0.01270 | 0.00460 |
| Example 678 | 0.00640 | 0.00210 |
| Example 679 | 0.00810 | 0.00270 |
| Example 680 | 0.01460 | 0.00400 |
| Example 681 | 0.00310 | 0.00100 |
| Example 682 | 0.00690 | 0.00220 |
| Example 683 | 0.01120 | 0.00300 |
| Example 684 | 0.00290 | 0.00030 |
| Example 685 | 0.02140 | 0.00190 |
| Example 686 | 0.00170 | 0.00020 |
| Example 687 | 0.00080 | 0.00020 |
| Example 691 | 0.02380 | 0.00320 |
| Example 694 | 0.00100 | 0.00040 |
| Example 695 | 0.00400 | 0.00160 |
| Example 696 | 0.00240 | 0.00100 |
| Example 697 | 0.00100 | 0.00040 |
| Example 698 | 0.00070 | 0.00020 |
| Example 699 | 0.00170 | 0.00070 |
| Example 700 | 0.00120 | 0.00040 |

TABLE 2-continued

| Cmpd | b-Raf IC-50 (µM) | c-Raf FL IC-50 (µM) |
|---|---|---|
| Example 701 | 0.00130 | 0.00030 |
| Example 702 | 0.00300 | 0.00130 |
| Example 703 | 0.00130 | 0.00040 |
| Example 704 | 0.00002 | 0.00008 |
| Example 705 | 0.00410 | 0.00140 |
| Example 706 | 0.00080 | 0.00030 |
| Example 707 | 0.00190 | 0.00070 |
| Example 708 | 0.00050 | 0.00010 |
| Example 709 | 0.00340 | 0.00130 |
| Example 710 | 0.00400 | 0.00160 |
| Example 711 | 0.00560 | 0.00260 |
| Example 712 | 0.01210 | 0.00640 |
| Example 713 | 0.00250 | 0.00140 |
| Example 714 | 0.00250 | 0.00090 |
| Example 716 | 0.00130 | 0.00060 |
| Example 717 | 0.00290 | 0.00080 |
| Example 718 | 0.00840 | 0.00230 |
| Example 719 | 0.00200 | 0.00050 |
| Example 720 | 0.02320 | 0.00490 |
| Example 721 | 0.00330 | 0.00090 |
| Example 722 | 0.00160 | 0.00040 |
| Example 723 | 0.03480 | 0.00680 |
| Example 724 | 0.02050 | 0.00480 |
| Example 725 | 0.00420 | 0.00120 |
| Example 726 | 0.00900 | 0.00220 |
| Example 727 | 0.00850 | 0.00270 |
| Example 728 | 0.00440 | 0.00080 |
| Example 729 | 0.01770 | 0.00290 |
| Example 730 | 0.02720 | 0.00750 |
| Example 731 | 0.00440 | 0.00150 |
| Example 732 | 0.00220 | 0.00060 |
| Example 733 | 0.00080 | 0.00030 |
| Example 734 | 0.00690 | 0.00180 |
| Example 735 | 0.00430 | 0.00050 |
| Example 736 | 0.04780 | 0.00730 |
| Example 737 | 0.01790 | 0.00540 |
| Example 738 | 0.03320 | 0.01070 |
| Example 739 | 0.00410 | 0.00140 |
| Example 740 | 0.00210 | 0.00030 |
| Example 741 | 0.00510 | 0.00120 |
| Example 742 | 0.03860 | 0.00460 |
| Example 743 | 0.00370 | 0.00080 |
| Example 744 | 0.04270 | 0.00620 |
| Example 745 | 0.00360 | 0.00070 |
| Example 746 | 0.00460 | 0.00120 |
| Example 747 | 0.01900 | 0.00300 |
| Example 748 | 0.00190 | 0.00040 |
| Example 749 | 0.00190 | 0.00050 |
| Example 750 | 0.02240 | 0.00380 |
| Example 751 | 0.00140 | 0.00040 |
| Example 752 | 0.00180 | 0.00040 |
| Example 753 | 0.03090 | 0.00670 |
| Example 754 | 0.00340 | 0.00100 |
| Example 755 | 0.01780 | 0.00720 |
| Example 756 | 0.00420 | 0.00150 |
| Example 757 | 0.00140 | 0.00040 |
| Example 758 | 0.00280 | 0.00120 |
| Example 759 | 0.01150 | 0.00470 |
| Example 760 | 0.01130 | 0.00330 |
| Example 761 | 0.00090 | 0.00020 |
| Example 762 | 0.00070 | 0.00020 |
| Example 763 | 0.00110 | 0.00020 |
| Example 764 | 0.00340 | 0.00080 |
| Example 765 | 0.00100 | 0.00020 |
| Example 766 | 0.00180 | 0.00050 |
| Example 767 | 0.04740 | 0.01210 |
| Example 768 | 0.01110 | 0.00280 |
| Example 769 | 0.01020 | 8.00000 |
| Example 770 | 0.00530 | 0.00130 |
| Example 771 | 0.00250 | 0.00080 |
| Example 772 | 0.00190 | 0.00060 |
| Example 773 | 0.00170 | 0.00040 |
| Example 774 |  |  |
| Example 775 | 0.02000 | 0.00460 |
| Example 776 | 25.00034 | 10.60000 |
| Example 777 | 0.00020 | 0.00008 |
| Example 778 | 0.00230 | 0.00090 |
| Example 779 | 0.00220 | 0.00070 |
| Example 780 | 0.00210 | 0.00080 |
| Example 781 | 0.01080 | 0.00270 |
| Example 782 | 0.02230 | 0.00650 |
| Example 783 | 0.00630 | 0.00210 |
| Example 784 | 0.20000 | 0.05100 |
| Example 785 | 0.00750 | 0.00310 |
| Example 786 | 0.01490 | 0.00340 |
| Example 787 | 0.00550 | 0.00170 |
| Example 788 | 0.20000 | 0.03800 |
| Example 789 |  |  |
| Example 790 | 0.00350 | 0.00130 |
| Example 791 | 0.01140 | 0.00260 |
| Example 792 | 0.00170 | 0.00030 |
| Example 793 | 0.00130 | 0.00030 |
| Example 794 | 0.00260 | 0.00080 |
| Example 795 | 0.00180 | 0.00090 |
| Example 796 | 0.00070 | 0.00020 |
| Example 797 | 0.02470 | 0.00790 |
| Example 798 | 0.00110 | 0.00050 |
| Example 799 | 0.00150 | 0.00040 |
| Example 800 | 0.00200 | 0.00080 |
| Example 801 | 0.00300 | 0.00090 |
| Example 802 | 0.00310 | 0.00100 |
| Example 803 | 0.00190 | 0.00090 |
| Example 804 | 0.00080 | 0.00030 |
| Example 805 | 0.00040 | 0.00020 |
| Example 806 | 0.00110 | 0.00060 |
| Example 807 | 0.00880 | 0.00280 |
| Example 810 | 0.00140 | 0.00030 |
| Example 811 | 0.00630 | 0.00090 |
| Example 813 | 0.00270 | 0.00030 |
| Example 814 | 0.03210 | 0.00310 |
| Example 815 | 0.10000 | 0.00900 |
| Example 816 | 0.01740 | 0.00160 |
| Example 817 | 0.20000 | 0.01320 |
| Example 818 | 0.01840 | 0.00110 |
| Example 820 | 0.00140 | 0.00010 |
| Example 821 | 0.00380 | 0.00040 |
| Example 822 | 0.00770 | 0.00070 |
| Example 823 | 0.00940 | 0.00090 |
| Example 824 | 0.00040 | 0.00007 |
| Example 825 | 0.00130 | 0.00020 |
| Example 826 | 0.00500 | 0.00110 |
| Example 827 | 0.00140 | 0.00020 |
| Example 828 | 0.00100 | 0.00020 |
| Example 829 | 0.00020 | 0.00004 |
| Example 830 | 0.00060 | 0.00010 |
| Example 831 | 0.00150 | 0.00020 |
| Example 832 | 1.40000 | 0.20000 |
| Example 833 | 0.00170 | 0.00020 |
| Example 834 | 0.00060 | 0.00020 |
| Example 835 | 0.00210 | 0.00060 |
| Example 836 | 0.00310 | 0.00040 |
| Example 837 | 0.00020 | 0.00010 |
| Example 838 | 0.00090 | 0.00030 |
| Example 839 | 0.00090 | 0.00030 |
| Example 840 | 0.00060 | 0.00020 |
| Example 841 | 0.00170 | 0.00040 |
| Example 842 | 0.00130 | 0.00030 |
| Example 843 | 0.00080 | 0.00020 |
| Example 844 | 0.00170 | 0.00020 |
| Example 845 | 0.00090 | 0.00030 |
| Example 846 | 0.00060 | 0.00020 |
| Example 847 | 0.00020 | 0.00004 |
| Example 848 | 0.00040 | 0.00010 |
| Example 849 | 0.00380 | 0.00090 |
| Example 850 | 0.00060 | 0.00020 |
| Example 851 | 0.00090 | 0.00030 |
| Example 852 | 0.00070 | 0.00020 |
| Example 853 | 0.00240 | 0.00070 |
| Example 854 | 0.00080 | 0.00010 |
| Example 855 | 0.00230 | 0.00040 |
| Example 856 | 0.00550 | 0.00100 |
| Example 857 | 0.00040 | 0.00008 |
| Example 858 | 0.02210 | 0.00270 |
| Example 860 | 0.01160 | 0.00070 |
| Example 861 | 0.00250 | 0.00060 |
| Example 862 | 0.00090 | 0.00030 |

TABLE 2-continued

| Cmpd | b-Raf IC-50 (µM) | c-Raf FL IC-50 (µM) |
|---|---|---|
| Example 863 | 0.00280 | 0.00060 |
| Example 864 | 0.07020 | 0.02400 |
| Example 865 | 3.70000 | 7.90000 |
| Example 866 | 0.00760 | 0.00200 |
| Example 867 | 0.00140 | 0.00020 |
| Example 868 | 0.00130 | 0.00030 |
| Example 869 | 0.00130 | 0.00020 |
| Example 870 | 0.00750 | 0.00150 |
| Example 871 | 0.00060 | 0.00010 |
| Example 873 | 0.00280 | 0.00050 |
| Example 874 | 0.01970 | 0.00340 |
| Example 875 | 0.00660 | 0.00160 |
| Example 876 | 0.00240 | 0.00040 |
| Example 877 | 0.00650 | 0.00140 |
| Example 878 | 0.10000 | 0.01960 |
| Example 879 | 0.00610 | 0.00120 |
| Example 880 | 0.00320 | 0.00060 |
| Example 881 | 0.03260 | 0.00570 |
| Example 882 | 0.00810 | 0.00150 |
| Example 883 | 0.00170 | 0.00040 |
| Example 884 | 0.01970 | 0.00340 |
| Example 885 | 0.01230 | 0.00270 |
| Example 886 | 0.00760 | 0.00060 |
| Example 887 | 1.30000 | 0.10000 |
| Example 888 | 0.00160 | 0.00040 |
| Example 889 | 0.00330 | 0.00060 |
| Example 899 | 0.00187 | 0.00048 |
| Example 900 | 0.00317 | 0.00078 |
| Example 901 | 0.00085 | 0.00021 |
| Example 902 | 0.00337 | 0.00070 |
| Example 903 | 0.00364 | 0.00082 |
| Example 904 | 0.00201 | 0.00047 |
| Example 905 | 0.00233 | 0.00058 |
| Example 906 | 0.00945 | 0.00238 |
| Example 907 | 0.00443 | 0.00094 |
| Example 908 | 0.00688 | 0.00253 |
| Example 909 | 0.00156 | 0.00032 |
| Example 910 | 0.00509 | 0.00102 |
| Example 911 | 0.00358 | 0.00120 |
| Example 912 | 0.00225 | 0.00065 |
| Example 913 | 0.00216 | 0.00069 |
| Example 914 | 0.00195 | 0.00070 |
| Example 915 | 0.00111 | 0.00045 |
| Example 916 | 0.00131 | 0.00039 |
| Example 917 | 0.00080 | 0.00091 |
| Example 918 | 0.00117 | 0.00037 |
| Example 919 | 0.00411 | 0.00088 |
| Example 920 | 0.00885 | 0.00199 |
| Example 921 | 0.00773 | 0.00182 |
| Example 923 | 0.00546 | 0.00107 |
| Example 924 | 0.05773 | 0.01099 |
| Example 925 | 0.01218 | 0.00223 |
| Example 926 | 0.00213 | 0.00047 |
| Example 927 | 0.00791 | 0.00353 |
| Example 928 | 0.00190 | 0.00055 |
| Example 929 | 0.00105 | 0.00033 |
| Example 930 | 0.00103 | 0.00031 |
| Example 931 | 0.00270 | 0.00077 |
| Example 932 | 0.00689 | 0.00183 |
| Example 933 | 0.00078 | 0.00022 |
| Example 934 | 0.00420 | 0.00120 |
| Example 935 | 0.00204 | 0.00058 |
| Example 936 | 0.00755 | 0.00169 |
| Example 937 | 0.00453 | 0.00197 |
| Example 938 | 0.00236 | 0.00077 |
| Example 939 | 0.01532 | 0.00684 |
| Example 940 | 0.00481 | 0.00133 |
| Example 941 | 0.00228 | 0.00067 |
| Example 942 | 0.00217 | 0.00059 |
| Example 943 | 0.00951 | 0.00269 |
| Example 944 | 0.00389 | 0.00153 |
| Example 945 | 0.00135 | 0.00053 |
| Example 946 | 0.00236 | 0.00096 |
| Example 947 | 0.00176 | 0.00061 |
| Example 948 | 0.00233 | 0.00064 |
| Example 949 | 0.00363 | 0.00138 |
| Example 950 | 0.00047 | 0.00021 |
| Example 951 | 0.00031 | 0.00011 |
| Example 952 | 0.00198 | 0.00071 |
| Example 953 | 0.00333 | 0.00136 |
| Example 954 | 0.00730 | 0.00243 |
| Example 955 | 0.01815 | 0.00801 |
| Example 956 | 0.00294 | 0.00116 |
| Example 957 | 0.00623 | 0.00241 |
| Example 958 | 0.00915 | 0.00345 |
| Example 959 | 0.01940 | 0.00629 |
| Example 960 | 0.00266 | 0.00118 |
| Example 961 | 0.00183 | 0.00070 |
| Example 962 | 0.01543 | 0.00392 |
| Example 963 | 0.00288 | 0.00104 |
| Example 964 | 0.00813 | 0.00317 |
| Example 965 | 0.00187 | 0.00071 |
| Example 966 | 0.00135 | 0.00052 |
| Example 967 | 0.00574 | 0.00215 |
| Example 968 | 0.00372 | 0.00098 |
| Example 969 | 0.01803 | 0.00498 |
| Example 970 | 0.00879 | 0.00234 |
| Example 971 | 0.00827 | 0.00255 |
| Example 972 | 0.03704 | 0.01184 |
| Example 973 | 0.01575 | 0.00560 |
| Example 974 | 0.00278 | 0.00095 |
| Example 975 | 0.00181 | 0.00078 |
| Example 976 | | |
| Example 977 | 0.00421 | 0.00177 |
| Example 978 | 0.00186 | 0.00074 |
| Example 979 | 0.01358 | 0.00624 |
| Example 980 | 0.00199 | 0.00078 |
| Example 981 | 0.00765 | 0.00317 |
| Example 982 | 0.00244 | 0.00110 |
| Example 983 | 0.00299 | 0.00143 |
| Example 984 | 0.00228 | 0.00051 |
| Example 985 | 0.00201 | 0.00060 |
| Example 986 | 0.00083 | 0.00028 |
| Example 987 | 0.00263 | 0.00080 |
| Example 988 | 0.00583 | 0.00097 |
| Example 989 | 0.00196 | 0.00056 |
| Example 990 | 0.00541 | 0.00200 |
| Example 991 | 0.00236 | 0.00076 |
| Example 992 | 0.00163 | 0.00097 |
| Example 993 | 0.00966 | 0.00249 |
| Example 994 | 0.00193 | 0.00066 |
| Example 997 | 0.00200 | 0.00044 |
| Example 998 | 0.00300 | 0.00070 |
| Example 999 | 0.00091 | 0.00019 |
| Example 1000 | 0.00215 | 0.00051 |
| Example 1001 | 0.00136 | 0.00031 |
| Example 1002 | 0.00175 | 0.00041 |
| Example 1003 | 0.00412 | 0.00116 |
| Example 1004 | 0.08356 | 0.01395 |
| Example 1006 | 0.00397 | 0.00114 |
| Example 1007 | 0.00538 | 0.00114 |
| Example 1008 | 0.01330 | 0.00277 |
| Example 1009 | 0.01482 | 0.00263 |
| Example 1010 | 0.02889 | 0.00447 |
| Example 1011 | 0.02447 | 0.00381 |
| Example 1012 | 0.07063 | 0.01867 |
| Example 1013 | 0.00979 | 0.00199 |
| Example 1014 | 0.01277 | 0.00243 |
| Example 1015 | 0.02946 | 0.00497 |
| Example 1016 | 0.00227 | 0.00070 |
| Example 1017 | 0.00098 | 0.00035 |
| Example 1018 | 0.00176 | 0.00057 |
| Example 1019 | 0.00111 | 0.00038 |
| Example 1020 | 0.00772 | 0.00220 |
| Example 1021 | 0.00260 | 0.00069 |
| Example 1022 | 0.00149 | 0.00037 |
| Example 1023 | 0.00232 | 0.00118 |
| Example 1024 | 0.00510 | 0.00104 |
| Example 1025 | 0.01273 | 0.00197 |
| Example 1026 | 0.01294 | 0.00290 |
| Example 1027 | 0.00848 | 0.00179 |
| Example 1028 | 0.00411 | 0.00160 |
| Example 1029 | 0.00327 | 0.00156 |
| Example 1030 | 0.00249 | 0.00091 |
| Example 1031 | 0.00092 | 0.00023 |
| Example 1032 | 0.00275 | 0.00076 |

TABLE 2-continued

| Cmpd | b-Raf IC-50 (µM) | c-Raf FL IC-50 (µM) |
|---|---|---|
| Example 1033 | 0.00208 | 0.00059 |
| Example 1034 | 0.00159 | 0.00046 |
| Example 1036 | 0.00054 | 0.00015 |
| Example 1037 | 0.00107 | 0.00030 |
| Example 1038 | 0.00286 | 0.00045 |
| Example 1039 | 0.00504 | 0.00096 |
| Example 1040 | 0.00435 | 0.00068 |
| Example 1041 | 0.00572 | 0.00074 |
| Example 1042 | 0.04056 | 0.00504 |
| Example 1043 | 0.02279 | 0.00371 |
| Example 1044 | 0.03061 | 0.00467 |
| Example 1045 | 0.03291 | 0.00818 |
| Example 1046 | 0.06840 | 0.01062 |
| Example 1047 | 0.00395 | 0.00051 |
| Example 1048 | 0.00155 | 0.00028 |
| Example 1049 | 0.00769 | 0.00114 |
| Example 1050 | 0.00131 | 0.00026 |
| Example 1051 | 0.00819 | 0.00104 |
| Example 1052 | 0.00824 | 0.00148 |
| Example 1053 | 0.00086 | 0.00020 |
| Example 1054 | 0.00118 | 0.00033 |
| Example 1055 | 0.00117 | 0.00038 |
| Example 1056 | 0.01118 | 0.00219 |
| Example 1057 | 0.00412 | 0.00081 |
| Example 1058 | 0.01075 | 0.00177 |
| Example 1059 | 0.00384 | 0.00085 |
| Example 1060 | 0.00393 | 0.00095 |
| Example 1061 | 0.00305 | 0.00065 |
| Example 1062 | 0.00098 | 0.00025 |
| Example 1063 | 0.00148 | 0.00025 |
| Example 1064 | 0.00065 | 0.00018 |
| Example 1065 | 0.00053 | 0.00018 |
| Example 1066 | 0.00058 | 0.00021 |
| Example 1067 | 0.00060 | 0.00027 |
| Example 1068 | 0.00072 | 0.00014 |
| Example 1069 | 0.00264 | 0.00053 |
| Example 1070 | 0.00241 | 0.00073 |
| Example 1071 | 0.00208 | 0.00086 |
| Example 1072 | 0.00174 | 0.00041 |
| Example 1073 | 0.00299 | 0.00055 |
| Example 1074 | 0.00186 | 0.00057 |
| Example 1075 | 0.68224 | 0.12035 |
| Example 1076 | 0.00231 | 0.00039 |
| Example 1077 | 0.00085 | 0.00046 |
| Example 1078 | 0.00067 | 0.00079 |
| Example 1079 | 0.00464 | 0.00117 |
| Example 1080 | 0.01286 | 0.00242 |
| Example 1081 | 0.00643 | 0.00201 |
| Example 1082 | 0.05816 | 0.01047 |
| Example 1083 | 0.03519 | 0.00540 |
| Example 1084 | 0.02330 | 0.00339 |
| Example 1085 | 0.10763 | 0.02762 |
| Example 1086 | 0.02068 | 0.00329 |
| Example 1087 | 0.02651 | 0.00523 |
| Example 1088 | 0.00406 | 0.00112 |
| Example 1089 | 0.07138 | 0.02035 |
| Example 1090 | 0.05109 | 0.01271 |
| Example 1091 | 1.11486 | 0.29498 |
| Example 1092 | 0.03491 | 0.00506 |
| Example 1093 | 0.00658 | 0.00090 |
| Example 1094 | 0.00384 | 0.00082 |
| Example 1095 | 0.00111 | 0.00027 |
| Example 1096 | 0.00200 | 0.00045 |
| Example 1097 | 0.00332 | 0.00096 |
| Example 1098 | 0.00575 | 0.00117 |
| Example 1099 | 0.01883 | 0.00317 |
| Example 1100 | 0.00389 | 0.00068 |
| Example 1101 | 0.01370 | 0.00264 |
| Example 1102 | 0.00445 | 0.00085 |
| Example 1103 | 0.00670 | 0.00144 |
| Example 1104 | 0.00764 | 0.00143 |
| Example 1105 | 0.00562 | 0.00119 |
| Example 1106 | 0.00859 | 0.00182 |
| Example 1107 | 0.01345 | 0.00175 |
| Example 1108 | 0.02035 | 0.00278 |
| Example 1109 | 0.00802 | 0.00145 |
| Example 1110 | 0.00482 | 0.00075 |
| Example 1111 | 0.00209 | 0.00036 |
| Example 1112 | 0.00083 | 0.00024 |
| Example 1113 | 0.00132 | 0.00037 |
| Example 1114 | 0.00314 | 0.00068 |
| Example 1115 | 0.00065 | 0.00019 |
| Example 1116 | 0.00082 | 0.00022 |
| Example 1117 | 0.00131 | 0.00030 |
| Example 1118 | 0.00102 | 0.00030 |
| Example 1119 | 0.00200 | 0.00035 |
| Example 1120 | 0.00163 | 0.00028 |
| Example 1121 | 0.00193 | 0.00026 |
| Example 1122 | 0.00331 | 0.00037 |
| Example 1123 | 0.01085 | 0.00134 |
| Example 1124 | 0.01211 | 0.00158 |
| Example 1125 | 0.01000 | 0.00093 |
| Example 1126 | 0.00185 | 0.00050 |
| Example 1127 | 0.00148 | 0.00038 |
| Example 1128 | 0.00216 | 0.00074 |
| Example 1129 | 0.00464 | 0.00126 |
| Example 1130 | 0.00224 | 0.00067 |
| Example 1131 | 0.00234 | 0.00072 |
| Example 1132 | 0.26960 | 0.06134 |
| Example 1133 | 0.00129 | 0.00030 |
| Example 1134 | 0.00499 | 0.00082 |
| Example 1135 | 0.04295 | 0.00735 |
| Example 1136 | 0.00503 | 0.00058 |
| Example 1137 | 0.00062 | 0.00012 |
| Example 1138 | 0.02778 | 0.00476 |
| Example 1139 | 0.01434 | 0.00280 |
| Example 1140 | 0.01345 | 0.00289 |
| Example 1141 | 0.01574 | 0.00371 |
| Example 1142 | 0.00318 | 0.00110 |
| Example 1143 | 0.00181 | 0.00054 |
| Example 1144 | 0.00156 | 0.00046 |
| Example 1145 | 0.00130 | 0.00040 |
| Example 1146 | 0.00187 | 0.00032 |
| Example 1147 | 0.00831 | 0.00152 |
| Example 1148 | 0.01192 | 0.00229 |
| Example 1149 | 0.00313 | 0.00056 |
| Example 1150 | 0.00160 | 0.00050 |
| Example 1151 | 0.00060 | 0.00018 |
| Example 1152 | 0.00125 | 0.00033 |
| Example 1153 | 0.00215 | 0.00049 |
| Example 1154 | 0.00060 | 0.00012 |
| Example 1155 | 0.00066 | 0.00014 |
| Example 1156 | 0.00073 | 0.00020 |
| Example 1157 | 0.00043 | 0.00009 |
| Example 1158 | 0.00163 | 0.00037 |
| Example 1159 | 0.00075 | 0.00015 |
| Example 1160 | 0.00055 | 0.00016 |
| Example 1161 | 0.00150 | 0.00030 |
| Example 1162 | 0.00038 | 0.00007 |
| Example 1163 | 0.00112 | 0.00020 |
| Example 1164 | 0.00057 | 0.00012 |
| Example 1165 | 0.00282 | 0.00072 |
| Example 1166 | 0.00328 | 0.00074 |
| Example 1167 | 0.00762 | 0.00212 |
| Example 1168 | 0.00456 | 0.00121 |
| Example 1169 | 0.00301 | 0.00060 |
| Example 1170 | 0.03744 | 0.00384 |
| Example 1171 | 25.00034 | 7.68543 |
| Example 1172 | 25.00034 | 25.00034 |
| Example 1173 | 18.59479 | 1.92537 |
| Example 1174 | 25.00034 | 22.05985 |
| Example 1175 | 0.08001 | 0.02036 |

The invention claimed is:
1. A compound, or a pharmaceutically acceptable salt thereof, selected from:
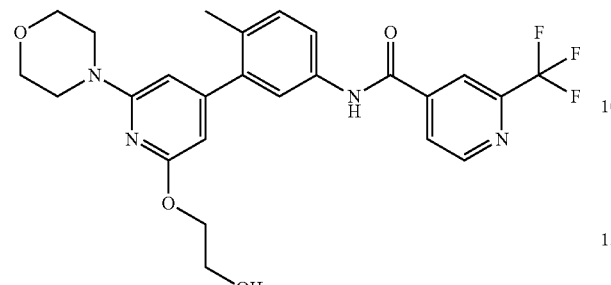
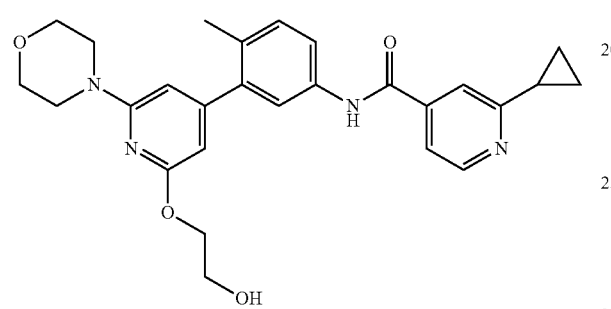
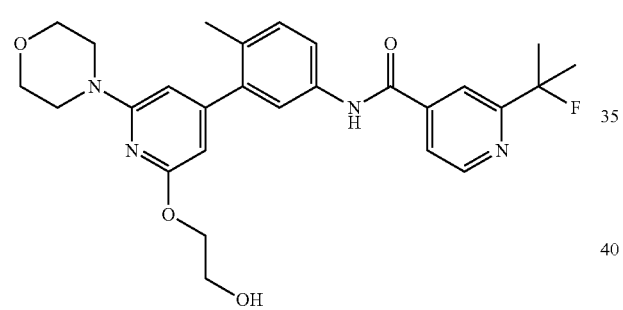
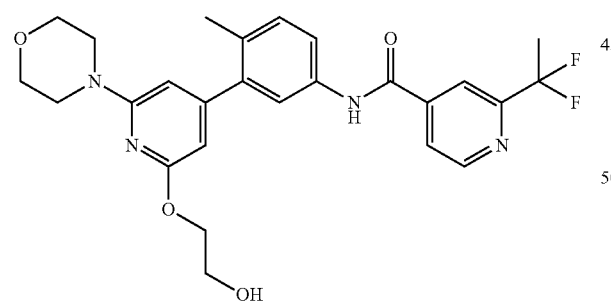
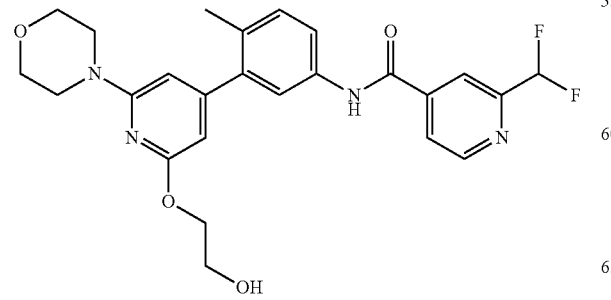
-continued
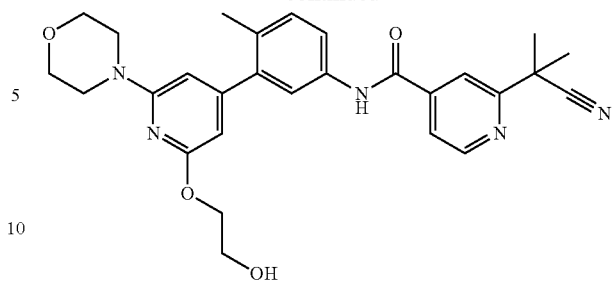
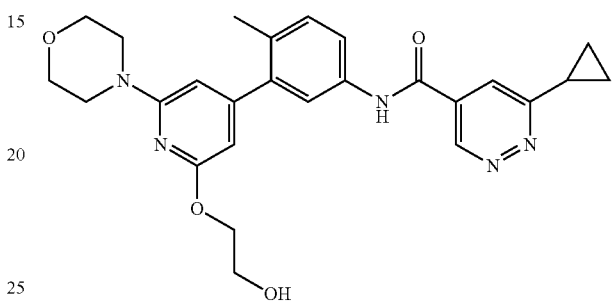
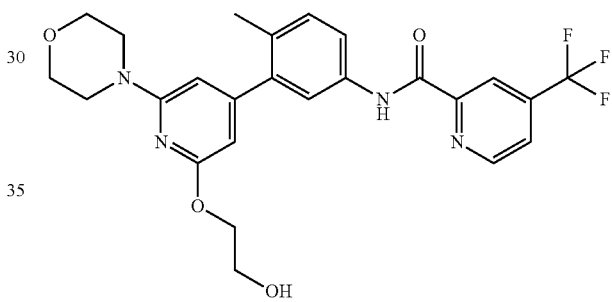
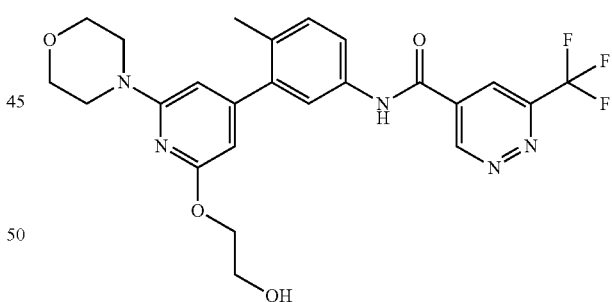
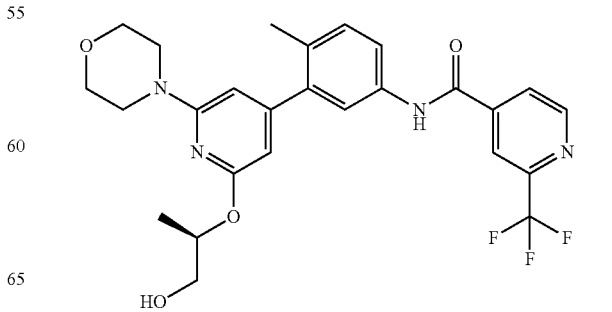

729
-continued

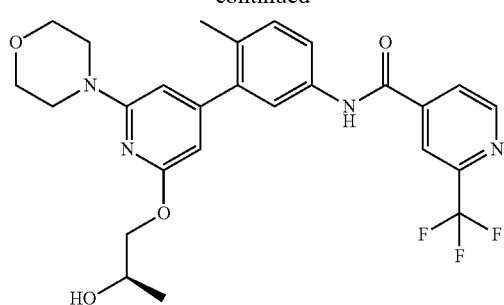

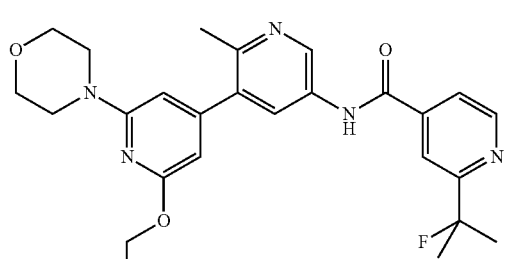

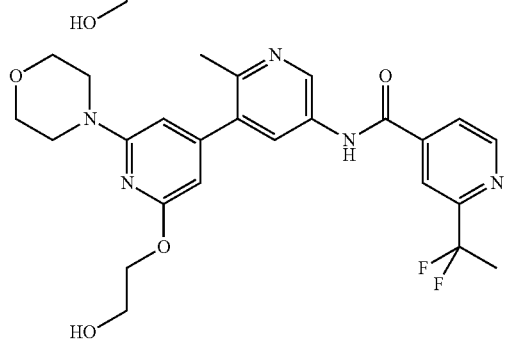

730
-continued

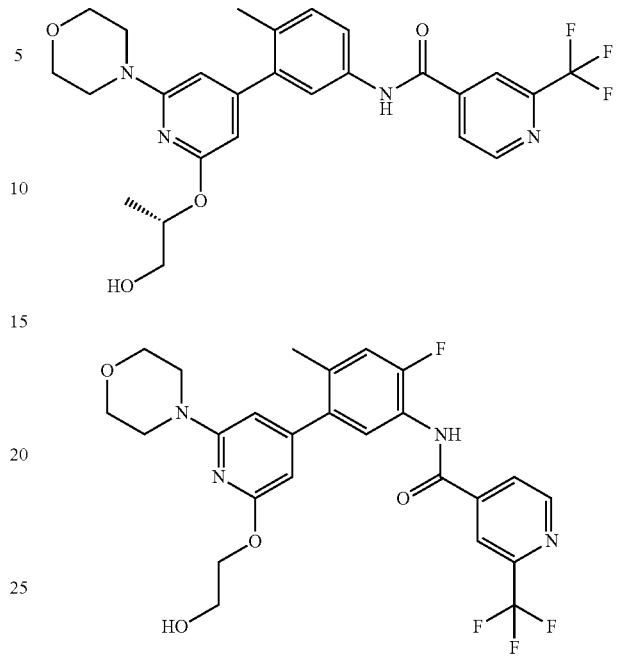

2. A pharmaceutical composition comprising a compound of claim 1 or a pharmaceutically acceptable salt thereof and one or more pharmaceutically acceptable carriers.

3. A combination comprising a therapeutically effective amount of a compound according to claim 1 or a pharmaceutically acceptable salt thereof and one or more therapeutically active co-agents.

4. The compound according to claim 1 that is:

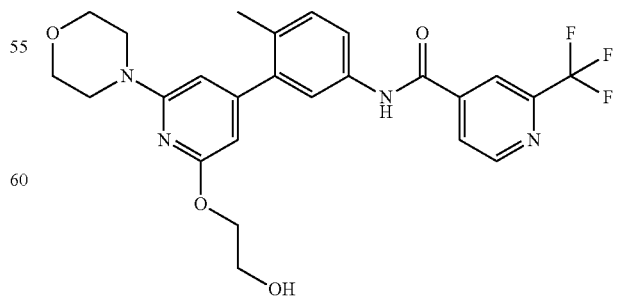

or a pharmaceutically acceptable salt thereof.

5. The compound according to claim 1 that is:
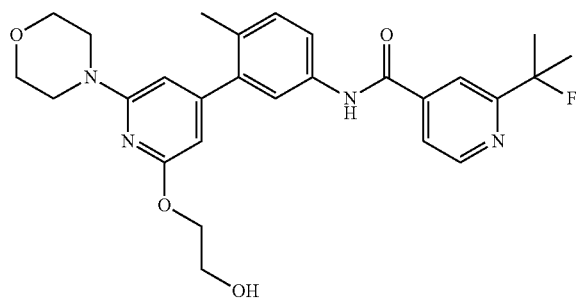 [SMILES: Cc1ccc(NC(=O)c2ccnc(C(C)(C)F)c2)cc1-c1cc(OCCO)nc(N2CCOCC2)c1]
or a pharmaceutically acceptable salt thereof.
6. The compound according to claim 1 that is:
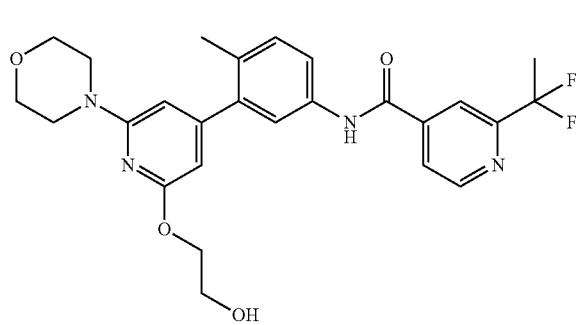
or a pharmaceutically acceptable salt thereof.
7. The compound according to claim 1 that is:
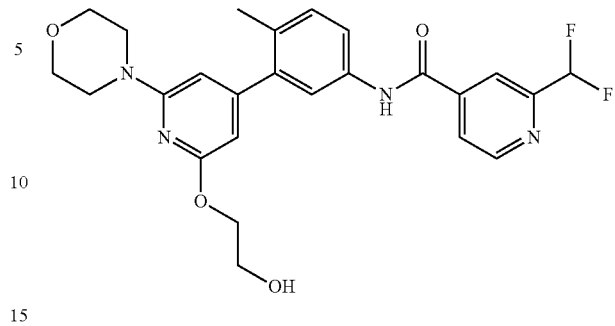
or a pharmaceutically acceptable salt thereof.
8. The compound according to claim 1 that is:
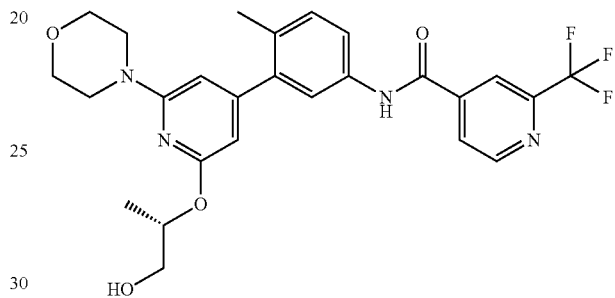
or a pharmaceutically acceptable salt thereof.
* * * * *